United States Patent
Tasaki et al.

(10) Patent No.: US 11,552,259 B1
(45) Date of Patent: Jan. 10, 2023

(54) ORGANIC ELECTROLUMINESCENT ELEMENT AND ELECTRONIC DEVICE

(71) Applicant: IDEMITSU KOSAN CO., LTD., Tokyo (JP)

(72) Inventors: Satomi Tasaki, Sodegaura (JP); Kazuki Nishimura, Sodegaura (JP); Hiroaki Toyoshima, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 0 days.

(21) Appl. No.: 17/463,266

(22) Filed: Aug. 31, 2021

Related U.S. Application Data

(63) Continuation of application No. PCT/JP2021/005077, filed on Feb. 10, 2021.

(30) Foreign Application Priority Data

Feb. 14, 2020 (JP) .............................. JP2020-023551

(51) Int. Cl.
  H01L 51/00 (2006.01)
  H01L 51/50 (2006.01)
  H01L 27/32 (2006.01)

(52) U.S. Cl.
  CPC ...... H01L 51/0072 (2013.01); H01L 51/0052 (2013.01); H01L 51/0054 (2013.01);
  (Continued)

(58) Field of Classification Search
  CPC ............. H01L 51/0072; H01L 51/0054; H01L 51/0055; H01L 51/0056; H01L 51/0058; H01L 51/0059; H01L 51/0073
  (Continued)

(56) References Cited

U.S. PATENT DOCUMENTS 10,622,576 B2   4/2020   Peng et al.
10,700,303 B1   6/2020   Lee et al.
(Continued)

FOREIGN PATENT DOCUMENTS

JP    2007-294261 A    11/2007
JP    2013-157552 A    8/2013
(Continued)

OTHER PUBLICATIONS

International Searching Authority, "International Search Report," issued in connection with International Patent Application No. PCT/JP2021/005077, dated Apr. 6, 2021.
(Continued)

*Primary Examiner* — Dzung Tran
(74) *Attorney, Agent, or Firm* — Foley & Lardner LLP

(57) ABSTRACT

An organic electroluminescence device includes two or more emitting units disposed between an anode and a cathode, and an intermediate layer, in which the intermediate layer contains a phenanthroline compound, the laminated emitting unit includes a first emitting layer containing a first host material and a second emitting layer containing a second host material, and a triplet energy $T_1(H1)$ of the first host material and a triplet energy $T_1(H2)$ of the second host material satisfy a relationship of a numerical formula (Numerical Formula 3), $T_1(H1) > T_1(H2)$    (Numerical Formula 3).

27 Claims, 1 Drawing Sheet

(52) U.S. Cl.
    CPC ...... *H01L 51/0058* (2013.01); *H01L 51/0059* (2013.01); *H01L 51/0073* (2013.01); *H01L 51/0074* (2013.01); H01L 27/3209 (2013.01); H01L 51/006 (2013.01); H01L 51/008 (2013.01); H01L 51/0071 (2013.01); H01L 51/5012 (2013.01); H01L 51/5016 (2013.01); H01L 2251/5376 (2013.01); H01L 2251/5384 (2013.01)

(58) Field of Classification Search
    USPC .......................................................... 257/40
    See application file for complete search history.

(56) References Cited

U.S. PATENT DOCUMENTS

| | | | |
|---|---|---|---|
| 2006/0043858 | A1 | 3/2006 | Ikeda et al. |
| 2006/0154107 | A1 | 7/2006 | Kubota et al. |
| 2008/0074047 | A1* | 3/2008 | Lee .................... H01L 51/5278 313/506 |
| 2010/0295444 | A1 | 11/2010 | Kuma et al. |
| 2010/0301318 | A1 | 12/2010 | Kuma et al. |
| 2010/0308718 | A1 | 12/2010 | Kubota et al. |
| 2010/0327266 | A1 | 12/2010 | Kawamura |
| 2011/0034744 | A1 | 2/2011 | Ikeda et al. |
| 2012/0119197 | A1 | 5/2012 | Nishimura et al. |
| 2012/0187826 | A1 | 7/2012 | Kawamura et al. |
| 2012/0235561 | A1 | 9/2012 | Ikeda et al. |
| 2013/0270539 | A1 | 10/2013 | Kuma et al. |
| 2014/0291653 | A1 | 10/2014 | Ikeda et al. |
| 2017/0125687 | A1 | 5/2017 | Ikeda et al. |
| 2017/0271609 | A1 | 9/2017 | Imai et al. |
| 2017/0324043 | A1* | 11/2017 | Ikeda .................... C07D 307/91 |
| 2019/0280209 | A1* | 9/2019 | Fujita .................. H01L 51/0054 |
| 2019/0296090 | A1* | 9/2019 | Jang ...................... H01L 51/504 |

FOREIGN PATENT DOCUMENTS

| | | |
|---|---|---|
| JP | 2016-111134 A | 6/2016 |
| JP | 2018-125504 A | 8/2018 |
| JP | 2019-161218 A | 9/2019 |
| WO | WO-2004/018587 A1 | 3/2004 |
| WO | WO-2005/115950 A1 | 12/2005 |
| WO | WO-2009/066600 A1 | 5/2009 |
| WO | WO-2010/134350 A1 | 11/2010 |
| WO | WO-2011/077691 A1 | 6/2011 |
| WO | WO-2011/148909 A1 | 12/2011 |
| WO | WO-2014/104144 A1 | 7/2014 |

OTHER PUBLICATIONS

International Searching Authority, "Written Opinion," issued in connection with International Patent Application No. PCT/JP2021/005077, dated Apr. 6, 2021.

Alex S. Ionkin, et al., "A tetra-substituted chrysene: orientation of multiple electrophilic substitution and use of a tetra-substituted chrysene as a blue emitter for OLEDs", Chem. Commun. Apr. 9, 2008.

Habiba Guedouar, et al., "Benzo[c]phenanthrene derivatives: Synthesis, optical properties and cytotoxic activity", Journal of Advances in Chemistry, Apr. 2016.

Hiromu Kubo, et al., "Control over the Emission Properties of [5]Helicenes Based on the Symmetry and Energy Levels of Their Molecular Orbitals", Organic Letters, 2017.

Shiv Kumar, et al., "Fluoranthene derivatives as blue fluorescent materials for non-doped organic light-emitting diodes", Journal of Materials Chemistry C, 2016.

Suhee Song, et al. "Novel cyclopenta[def]phenanthrene based blue emitting oligomers for OLEDs", Tetrahedron Letters, Apr. 7, 2008.

Third Party Observation on PCT Appl. Ser. No. PCT/JP2021/005077 dated Jun. 13, 2022 with English translation (14 pages).

Tomas Serevicius, et al., "Impact of non-symmetric 2,9,10-aryl substitution on charge transport and optical properties of anthracene derivatives", Dyes and Pigments, Jun. 19, 2015.

Xu Qiu, et al., "Novel 9,9-dimethylfluorene-bridged D-p-A-type fluorophores with a hybridized local and charge-transfer excited state for deep-blue electroluminescence with ClEy ~0.05", Journal of Materials Chemistry C, 2019.

Youngeup Jin, et al., "Novel efficient blue materials with 4H-cyclopenta[def]phenanthrene for OLEDs", Synthetic Metals, Apr. 24, 2008.

* cited by examiner

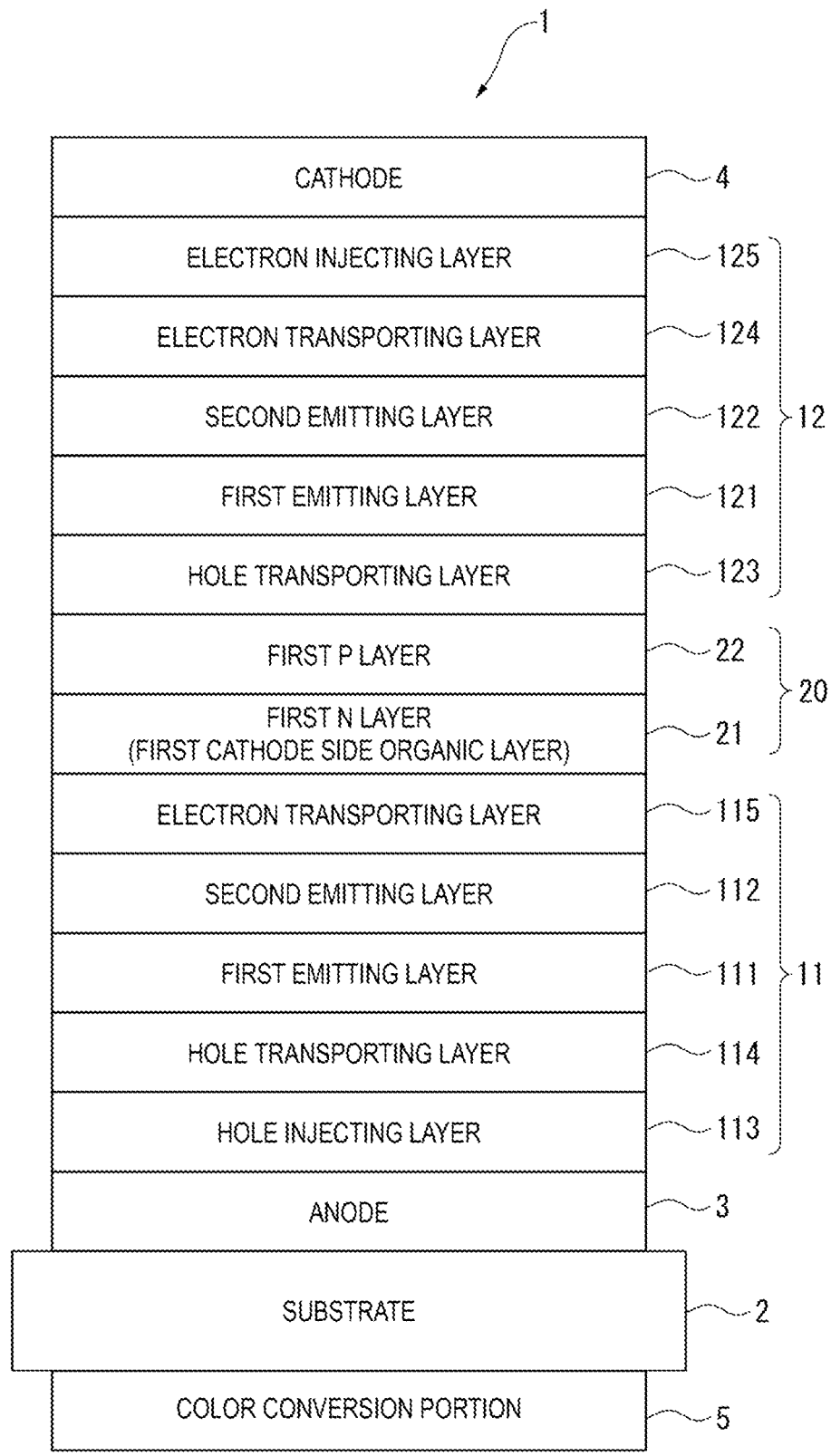

ORGANIC ELECTROLUMINESCENT ELEMENT AND ELECTRONIC DEVICE

CROSS-REFERENCE TO RELATED APPLICATIONS

This application claims priority to Application No. PCT/JP2021/005077 filed on Feb. 10, 2021, which application claims priority to Japanese Application No. 2020-023551, filed on Feb. 14, 2020. The entire contents of the above applications are incorporated herein by reference in their entireties.

TECHNICAL FIELD

The present invention relates to an organic electroluminescence device and an electronic device.

BACKGROUND ART

An organic electroluminescence device (hereinafter, occasionally referred to as "organic EL device") has found its application in a full-color display for mobile phones, televisions and the like. When a voltage is applied to an organic EL device, holes and electrons are injected from an anode and a cathode, respectively, into an emitting layer. The injected holes and electrons are recombined in the emitting layer to form excitons. Specifically, according to the electron spin statistics theory, singlet excitons and triplet excitons are generated at a ratio of 25%:75%.

Various studies have been made for compounds to be used for the organic EL device in order to enhance the performance of the organic EL device (see, for instance, Patent Literatures 1 to 6). For instance, Patent Literatures 6 and 7 have studied on laminating a plurality of emitting layers. In addition, Patent Literature 8 describes a phenomenon where singlet excitons are generated by collision and fusion of two triplet excitons (hereinafter, sometimes referred to as a Triplet-Triplet Fusion (TTF) phenomenon) in order to enhance the performance of the organic EL device. The performance of the organic EL device is evaluatable in terms of, for instance, luminance, emission wavelength, chromaticity, emission efficiency, drive voltage, and lifetime.

CITATION LIST

Patent Literatures

Patent Literature 1: JP 2013-157552 A
Patent Literature 2: International Publication No. WO2004/018587
Patent Literature 3: International Publication No. WO2005/115950
Patent Literature 4: International Publication No. WO2011/077691
Patent Literature 5: JP 2018-125504 A
Patent Literature 6: US Patent Application Publication No. 2019/280209
Patent Literature 7: JP 2007-294261 A
Patent Literature 8: International Publication No. WO2010/134350

SUMMARY OF THE INVENTION

Problems to be Solved by the Invention

For instance, Patent Literature 7 describes an organic EL device in which bathophenanthroline (BCP) as a phenanthroline compound having a phenanthroline skeleton is vapor-deposited on an emitting layer to form an electron transporting layer, BCP and Cs (cesium) are further co-deposited thereon to form an electron injecting layer, and aluminum is further vapor-deposited thereon to form a cathode.

A tandem organic EL device including a plurality of emitting units tends to have a short lifetime when the phenanthroline compound is used for an intermediate layer disposed between the emitting units.

An object of the invention is to provide an organic electroluminescence device with enhanced performance. Another object of the invention is to provide an organic electroluminescence device having improved luminous efficiency and a longer lifetime, and an electronic device including the organic electroluminescence device.

Means for Solving the Problem(s)

According to an aspect of the invention, an organic electroluminescence device includes:
an anode;
a cathode;
two or more emitting units disposed between the anode and the cathode; and
an intermediate layer disposed between the anode and the cathode, in which
at least one emitting unit of the two or more emitting units is a laminated emitting unit,
the intermediate layer contains a phenanthroline compound having a phenanthroline skeleton,
the laminated emitting unit includes a first emitting layer and a second emitting layer,
the first emitting layer contains a first host material,
the second emitting layer contains a second host material,
the first host material and the second host material are mutually different,
the first emitting layer at least contains a first emitting compound that emits light having a maximum peak wavelength of 500 nm or less,
the second emitting layer at least contains a second emitting compound that emits light having a maximum peak wavelength of 500 nm or less,
the first emitting compound and the second emitting compound are mutually the same or different, and
a triplet energy $T_1(H1)$ of the first host material and a triplet energy $T_1(H2)$ of the second host material satisfy a relationship of a numerical formula (Numerical Formula 3) below.

$$T_1(H1) > T_1(H2) \quad \text{(Numerical Formula 3)}$$

According to another aspect of the invention, an organic electroluminescence device includes:
an anode;
a cathode;
two or more emitting units disposed between the anode and the cathode; and
an intermediate layer disposed between the anode and the cathode, in which
at least one emitting unit of the two or more emitting units is a laminated emitting unit,
the intermediate layer contains a phenanthroline compound having a phenanthroline skeleton,
the laminated emitting unit includes a first emitting layer and a second emitting layer,
the first emitting layer contains a first host material,
the second emitting layer contains a second host material, the first host material has a structure of Condition (i) or a structure of Condition (ii) below in a molecule, the second host material is an anthracene derivative, the first host material and the second host material are mutually different, a triplet energy $T_1(H1)$ of the first host material and a triplet energy $T_1(H2)$ of the second host material satisfy a relationship of a numerical formula (Numerical Formula 3) below, $$T_1(H1) > T_1(H2) \qquad \text{(Numerical Formula 3)},$$

the first emitting layer at least contains a first emitting compound that emits light having a maximum peak wavelength of 500 nm or less, the second emitting layer at least contains a second emitting compound that emits light having a maximum peak wavelength of 500 nm or less, and the first emitting compound and the second emitting compound are mutually the same or different, Condition (i): a biphenyl structure including a first benzene ring and a second benzene ring that are linked to each other with a single bond, the first benzene ring and the second benzene ring in the biphenyl structure being further linked to each other by cross-linking at at least one site other than the single bond, Condition (ii): a linking structure including a benzene ring and a naphthalene ring that are linked to each other with a single bond, the benzene ring and the naphthalene ring in the linking structure being each independently further fused or not fused with a monocyclic ring or fused ring, the benzene ring and the naphthalene ring in the linking structure being further linked to each other by cross-linking at at least one site other than the single bond.

According to still another aspect of the invention, an electronic device including the organic electroluminescence device according to the above aspects of the invention is provided.

According to the above aspects of the invention, an organic electroluminescence device with enhanced performance can be provided. According to the above aspects of the invention, an organic electroluminescence device having improved luminous efficiency and a longer lifetime can be provided. According to a further aspect of the invention, an electronic device installed with the organic electroluminescence device can be provided.

BRIEF DESCRIPTION OF DRAWINGS

The FIGURE schematically shows an exemplary arrangement of an organic electroluminescence device according to an exemplary embodiment of the invention.

DESCRIPTION OF EMBODIMENT(S)

Definitions

Herein, a hydrogen atom includes isotope having different numbers of neutrons, specifically, protium, deuterium and tritium.

In chemical formulae herein, it is assumed that a hydrogen atom (i.e. protium, deuterium and tritium) is bonded to each of bondable positions that are not annexed with signs "R" or the like or "D" representing a deuterium.

Herein, the ring carbon atoms refer to the number of carbon atoms among atoms forming a ring of a compound (e.g., a monocyclic compound, fused-ring compound, cross-linking compound, carbon ring compound, and heterocyclic compound) in which the atoms are bonded to each other to form the ring. When the ring is substituted by a substituent (s), carbon atom(s) contained in the substituent(s) is not counted in the ring carbon atoms. Unless otherwise specified, the same applies to the "ring carbon atoms" described later. For instance, a benzene ring has 6 ring carbon atoms, a naphthalene ring has 10 ring carbon atoms, a pyridine ring has 5 ring carbon atoms, and a furan ring has 4 ring carbon atoms. Further, for instance, 9,9-diphenylfluorenyl group has 13 ring carbon atoms and 9,9'-spirobifluorenyl group has 25 ring carbon atoms.

When a benzene ring is substituted by a substituent in a form of, for instance, an alkyl group, the number of carbon atoms of the alkyl group is not counted in the number of the ring carbon atoms of the benzene ring. Accordingly, the benzene ring substituted by an alkyl group has 6 ring carbon atoms. When a naphthalene ring is substituted by a substituent in a form of, for instance, an alkyl group, the number of carbon atoms of the alkyl group is not counted in the number of the ring carbon atoms of the naphthalene ring. Accordingly, the naphthalene ring substituted by an alkyl group has 10 ring carbon atoms.

Herein, the ring atoms refer to the number of atoms forming a ring of a compound (e.g., a monocyclic compound, fused-ring compound, cross-linking compound, carbon ring compound, and heterocyclic compound) in which the atoms are bonded to each other to form the ring (e.g., monocyclic ring, fused ring, and ring assembly). Atom(s) not forming the ring (e.g., hydrogen atom(s) for saturating the valence of the atom which forms the ring) and atom(s) in a substituent by which the ring is substituted are not counted as the ring atoms. Unless otherwise specified, the same applies to the "ring atoms" described later. For instance, a pyridine ring has 6 ring atoms, a quinazoline ring has 10 ring atoms, and a furan ring has 5 ring atoms. For instance, the number of hydrogen atom(s) bonded to a pyridine ring or the number of atoms forming a substituent are not counted as the pyridine ring atoms. Accordingly, a pyridine ring bonded to a hydrogen atom(s) or a substituent (s) has 6 ring atoms. For instance, the hydrogen atom(s) bonded to a quinazoline ring or the atoms forming a substituent are not counted as the quinazoline ring atoms. Accordingly, a quinazoline ring bonded to hydrogen atom(s) or a substituent(s) has 10 ring atoms.

Herein, "XX to YY carbon atoms" in the description of "substituted or unsubstituted ZZ group having XX to YY carbon atoms" represent carbon atoms of an unsubstituted ZZ group and do not include carbon atoms of a substituent(s) of the substituted ZZ group. Herein, "YY" is larger than "XX," "XX" representing an integer of 1 or more and "YY" representing an integer of 2 or more.

Herein, "XX to YY atoms" in the description of "substituted or unsubstituted ZZ group having XX to YY atoms" represent atoms of an unsubstituted ZZ group and does not include atoms of a substituent(s) of the substituted ZZ group. Herein, "YY" is larger than "XX," "XX" representing an integer of 1 or more and "YY" representing an integer of 2 or more.

Herein, an unsubstituted ZZ group refers to an "unsubstituted ZZ group" in a "substituted or unsubstituted ZZ group," and a substituted ZZ group refers to a "substituted ZZ group" in a "substituted or unsubstituted ZZ group."

Herein, the term "unsubstituted" used in a "substituted or unsubstituted ZZ group" means that a hydrogen atom(s) in the ZZ group is not substituted with a substituent(s). The hydrogen atom(s) in the "unsubstituted ZZ group" is protium, deuterium, or tritium.

Herein, the term "substituted" used in a "substituted or unsubstituted ZZ group" means that at least one hydrogen atom in the ZZ group is substituted with a substituent. Similarly, the term "substituted" used in a "BB group substituted by AA group" means that at least one hydrogen atom in the BB group is substituted with the AA group.

Substituent Mentioned Herein

Substituents mentioned herein will be described below.

An "unsubstituted aryl group" mentioned herein has, unless otherwise specified herein, 6 to 50, preferably 6 to 30, more preferably 6 to 18 ring carbon atoms.

An "unsubstituted heterocyclic group" mentioned herein has, unless otherwise specified herein, 5 to 50, preferably 5 to 30, more preferably 5 to 18 ring atoms.

An "unsubstituted alkyl group" mentioned herein has, unless otherwise specified herein, 1 to 50, preferably 1 to 20, more preferably 1 to 6 carbon atoms.

An "unsubstituted alkenyl group" mentioned herein has, unless otherwise specified herein, 2 to 50, preferably 2 to 20, more preferably 2 to 6 carbon atoms.

An "unsubstituted alkynyl group" mentioned herein has, unless otherwise specified herein, 2 to 50, preferably 2 to 20, more preferably 2 to 6 carbon atoms.

An "unsubstituted cycloalkyl group" mentioned herein has, unless otherwise specified herein, 3 to 50, preferably 3 to 20, more preferably 3 to 6 ring carbon atoms.

An "unsubstituted arylene group" mentioned herein has, unless otherwise specified herein, 6 to 50, preferably 6 to 30, more preferably 6 to 18 ring carbon atoms.

An "unsubstituted divalent heterocyclic group" mentioned herein has, unless otherwise specified herein, 5 to 50, preferably 5 to 30, more preferably 5 to 18 ring atoms.

An "unsubstituted alkylene group" mentioned herein has, unless otherwise specified herein, 1 to 50, preferably 1 to 20, more preferably 1 to 6 carbon atoms.

Substituted or Unsubstituted Aryl Group

Specific examples (specific example group G1) of the "substituted or unsubstituted aryl group" mentioned herein include unsubstituted aryl groups (specific example group G1A) below and substituted aryl groups (specific example group G1B). (Herein, an unsubstituted aryl group refers to an "unsubstituted aryl group" in a "substituted or unsubstituted aryl group," and a substituted aryl group refers to a "substituted aryl group" in a "substituted or unsubstituted aryl group.") A simply termed "aryl group" herein includes both of "unsubstituted aryl group" and "substituted aryl group."

The "substituted aryl group" refers to a group derived by substituting at least one hydrogen atom in an "unsubstituted aryl group" with a substituent. Examples of the "substituted aryl group" include a group derived by substituting at least one hydrogen atom in the "unsubstituted aryl group" in the specific example group G1A below with a substituent, and examples of the substituted aryl group in the specific example group G1B below. It should be noted that the examples of the "unsubstituted aryl group" and the "substituted aryl group" mentioned herein are merely exemplary, and the "substituted aryl group" mentioned herein includes a group derived by further substituting a hydrogen atom bonded to a carbon atom of a skeleton of a "substituted aryl group" in the specific example group G1B below, and a group derived by further substituting a hydrogen atom of a substituent of the "substituted aryl group" in the specific example group G1B below.

Unsubstituted Aryl Group (Specific Example Group G1A): phenyl group, p-biphenyl group, m-biphenyl group, o-biphenyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-terphenyl-4-yl group, o-terphenyl-3-yl group, o-terphenyl-2-yl group, 1-naphthyl group, 2-naphthyl group, anthryl group, benzanthryl group, phenanthryl group, benzophenanthryl group, phenalenyl group, pyrenyl group, chrysenyl group, benzochrysenyl group, triphenylenyl group, benzotriphenylenyl group, tetracenyl group, pentacenyl group, fluorenyl group, 9,9'-spirobifluorenyl group, benzofluorenyl group, dibenzofluorenyl group, fluoranthenyl group, benzofluoranthenyl group, perylenyl group, and a monovalent aryl group derived by removing one hydrogen atom from cyclic structures represented by formulae (TEMP-1) to (TEMP-15) below.

[Formula 1]

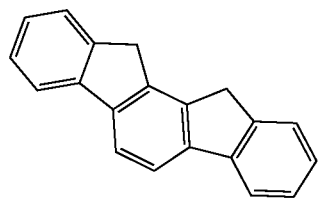

(TEMP-1)

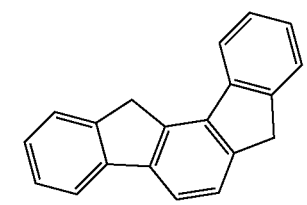

(TEMP-2)

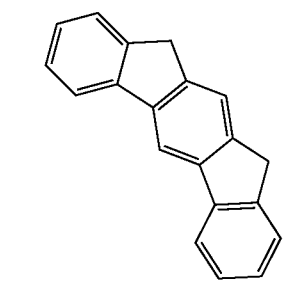

(TEMP-3)

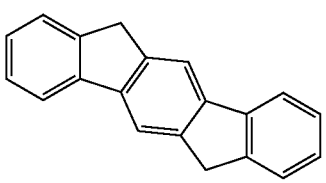

(TEMP-4)

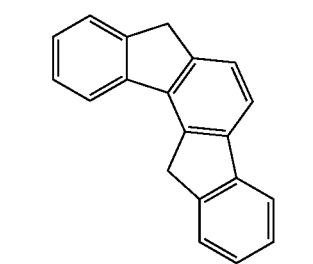

(TEMP-5)

[Formula 2]

(TEMP-6)
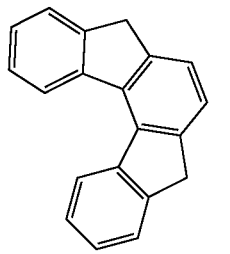

(TEMP-7)
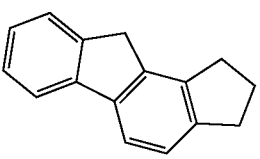

(TEMP-8)
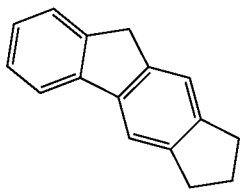

(TEMP-9)
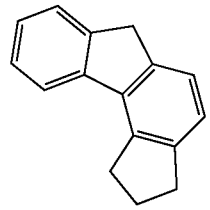

(TEMP-10)
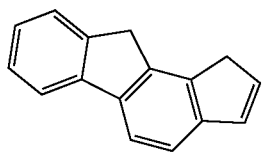

(TEMP-11)
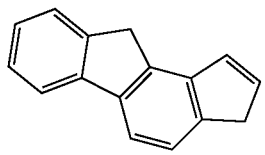

(TEMP-12)
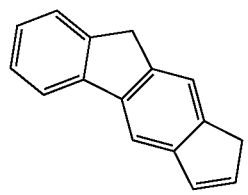

(TEMP-13)
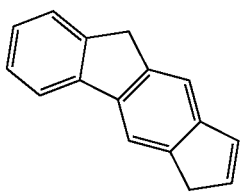

(TEMP-14)
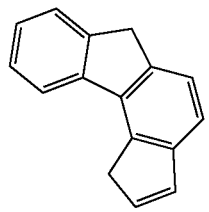

(TEMP-15)
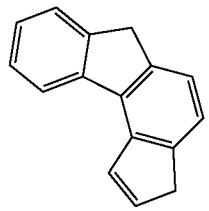

Substituted Aryl Group (Specific Example Group G1B):

o-tolyl group, m-tolyl group, p-tolyl group, para-xylyl group, meta-xylyl group, ortho-xylyl group, para-isopropylphenyl group, meta-isopropylphenyl group, ortho-isopropylphenyl group, para-t-butylphenyl group, meta-t-butylphenyl group, ortho-t-butylphenyl group, 3,4,5-trimethylphenyl group, 9,9-dimethylfluorenyl group, 9,9-diphenylfluorenyl group, 9,9-bis(4-methylphenyl)fluorenyl group, 9,9-bis(4-isopropylphenyl)fluorenyl group, 9,9-bis(4-t-butylphenyl)fluorenyl group, cyanophenyl group, triphenylsilylphenyl group, trimethylsilylphenyl group, phenylnaphthyl group, naphthylphenyl group, and a group derived by substituting at least one hydrogen atom of a monovalent group derived from one of the cyclic structures represented by the formulae (TEMP-1) to (TEMP-15) with a substituent.

Substituted or Unsubstituted Heterocyclic Group

The "heterocyclic group" mentioned herein refers to a cyclic group having at least one hetero atom in the ring atoms. Specific examples of the hetero atom include a nitrogen atom, oxygen atom, sulfur atom, silicon atom, phosphorus atom, and boron atom.

The "heterocyclic group" mentioned herein is a monocyclic group or a fused-ring group.

The "heterocyclic group" mentioned herein is an aromatic heterocyclic group or a non-aromatic heterocyclic group.

Specific examples (specific example group G2) of the "substituted or unsubstituted heterocyclic group" mentioned herein include unsubstituted heterocyclic groups (specific example group G2A) and substituted heterocyclic groups (specific example group G2B). (Herein, an unsubstituted heterocyclic group refers to an "unsubstituted heterocyclic group" in a "substituted or unsubstituted heterocyclic group," and a substituted heterocyclic group refers to a "substituted heterocyclic group" in a "substituted or unsubstituted heterocyclic group.") A simply termed "heterocyclic group" herein includes both of "unsubstituted heterocyclic group" and "substituted heterocyclic group."

The "substituted heterocyclic group" refers to a group derived by substituting at least one hydrogen atom in an "unsubstituted heterocyclic group" with a substituent. Specific examples of the "substituted heterocyclic group" include a group derived by substituting at least one hydrogen atom in the "unsubstituted heterocyclic group" in the specific example group G2A below with a substituent, and examples of the substituted heterocyclic group in the specific example group G2B below. It should be noted that the examples of the "unsubstituted heterocyclic group" and the "substituted heterocyclic group" mentioned herein are merely exemplary, and the "substituted heterocyclic group" mentioned herein includes a group derived by further substituting a hydrogen atom bonded to a ring atom of a skeleton of a "substituted heterocyclic group" in the specific example group G2B below, and a group derived by further substituting a hydrogen atom of a substituent of the "substituted heterocyclic group" in the specific example group G2B below.

The specific example group G2A includes, for instance, unsubstituted heterocyclic groups including a nitrogen atom (specific example group G2A1) below, unsubstituted heterocyclic groups including an oxygen atom (specific example group G2A2) below, unsubstituted heterocyclic groups including a sulfur atom (specific example group G2A3) below, and monovalent heterocyclic groups (specific example group G2A4) derived by removing a hydrogen atom from cyclic structures represented by formulae (TEMP-16) to (TEMP-33) below.

The specific example group G2B includes, for instance, substituted heterocyclic groups including a nitrogen atom (specific example group G2B1) below, substituted heterocyclic groups including an oxygen atom (specific example group G2B2) below, substituted heterocyclic groups including a sulfur atom (specific example group G2B3) below, and groups derived by substituting at least one hydrogen atom of the monovalent heterocyclic groups (specific example group G2B4) derived from the cyclic structures represented by formulae (TEMP-16) to (TEMP-33) below.

Unsubstituted Heterocyclic Groups Including Nitrogen Atom (Specific Example Group G2A1):
pyrrolyl group, imidazolyl group, pyrazolyl group, triazolyl group, tetrazolyl group, oxazolyl group, isoxazolyl group, oxadiazolyl group, thiazolyl group, isothiazolyl group, thiadiazolyl group, pyridyl group, pyridazynyl group, pyrimidinyl group, pyrazinyl group, triazinyl group, indolyl group, isoindolyl group, indolizinyl group, quinolizinyl group, quinolyl group, isoquinolyl group, cinnolyl group, phthalazinyl group, quinazolinyl group, quinoxalinyl group, benzimidazolyl group, indazolyl group, phenanthrolinyl group, phenanthridinyl group, acridinyl group, phenazinyl group, carbazolyl group, benzocarbazolyl group, morpholino group, phenoxazinyl group, phenothiazinyl group, azacarbazolyl group, and diazacarbazolyl group.

Unsubstituted Heterocyclic Groups Including Oxygen Atom (Specific Example Group G2A2):
furyl group, oxazolyl group, isoxazolyl group, oxadiazolyl group, xanthenyl group, benzofuranyl group, isobenzofuranyl group, dibenzofuranyl group, naphthobenzofuranyl group, benzoxazolyl group, benzisoxazolyl group, phenoxazinyl group, morpholino group, dinaphthofuranyl group, azadibenzofuranyl group, diazadibenzofuranyl group, azanaphthobenzofuranyl group, and diazanaphthobenzofuranyl group.

Unsubstituted Heterocyclic Groups Including Sulfur Atom (Specific Example Group G2A3):
thienyl group, thiazolyl group, isothiazolyl group, thiadiazolyl group, benzothiophenyl group (benzothienyl group), isobenzothiophenyl group (isobenzothienyl group), dibenzothiophenyl group (dibenzothienyl group), naphthobenzothiophenyl group (nahthobenzothienyl group), benzothiazolyl group, benzisothiazolyl group, phenothiazinyl group, dinaphthothiophenyl group (dinaphthothienyl group), azadibenzothiophenyl group (azadibenzothienyl group), diazadibenzothiophenyl group (diazadibenzothienyl group), azanaphthobenzothiophenyl group (azanaphthobenzothienyl group), and diazanaphthobenzothiophenyl group (diazanaphthobenzothienyl group).

Monovalent Heterocyclic Groups Derived by Removing One Hydrogen Atom from Cyclic Structures Represented by Formulae (TEMP-16) to (TEMP-33) below (Specific Example Group G2A4):

[Formula 3]

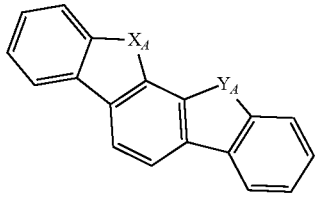

(TEMP-16)

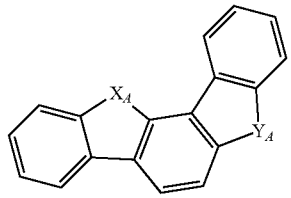

(TEMP-17)

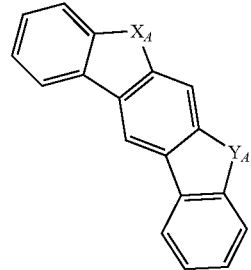

(TEMP-18)

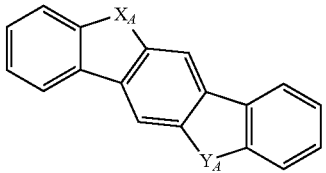

(TEMP-19)

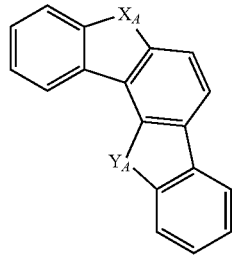

(TEMP-20)

-continued (TEMP-21)
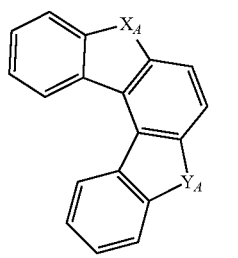

(TEMP-22)
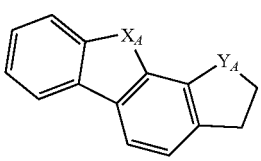

(TEMP-23)
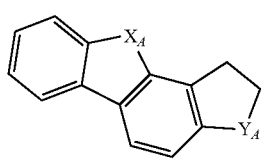

(TEMP-24)
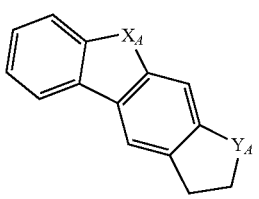

[Formula 4]

(TEMP-25)
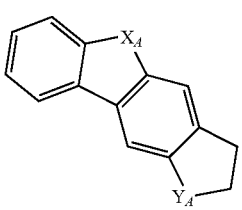

(TEMP-26)
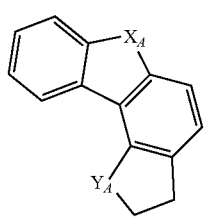

(TEMP-27)
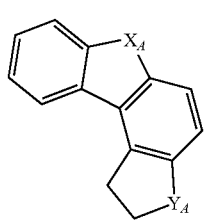

-continued (TEMP-28)
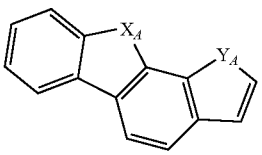

(TEMP-29)
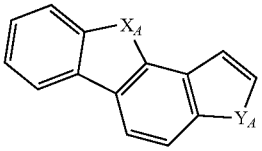

(TEMP-30)
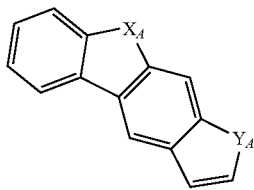

(TEMP-31)
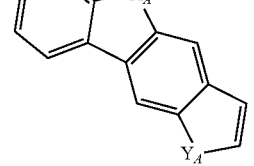

(TEMP-32)
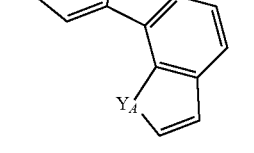

(TEMP-33)
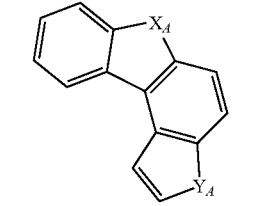

In the formulae (TEMP-16) to (TEMP-33), $X_A$ and $Y_A$ are each independently an oxygen atom, a sulfur atom, NH or $CH_2$, with a proviso that at least one of $X_A$ or $Y_A$ is an oxygen atom, a sulfur atom, or NH.

When at least one of $X_A$ or $Y_A$ in the formulae (TEMP-16) to (TEMP-33) is NH or $CH_2$, the monovalent heterocyclic groups derived from the cyclic structures represented by the formulae (TEMP-16) to (TEMP-33) include a monovalent group derived by removing one hydrogen atom from NH or $CH_2$.

Substituted Heterocyclic Groups Including Nitrogen Atom (Specific Example Group G2B1):

(9-phenyl)carbazolyl group, (9-biphenylyl)carbazolyl group, (9-phenyl)phenylcarbazolyl group, (9-naphthyl)carbazolyl group, diphenylcarbazole-9-yl group, phenylcarbazole-9-yl group, methylbenzimidazolyl group, ethylbenzimidazolyl group, phenyltriazinyl group, biphenylyltriazinyl group, diphenyltriazinyl group, phenylquinazolinyl group, and biphenylylquinazolinyl group.

Substituted Heterocyclic Groups Including Oxygen Atom (Specific Example Group G2B2):
phenyldibenzofuranyl group, methyldibenzofuranyl group, t-butyldibenzofuranyl group, and monovalent residue of spiro[9H-xanthene-9,9'-[9H]fluorene].
Substituted Heterocyclic Groups Including Sulfur Atom (Specific Example Group G2B3):
phenyldibenzothiophenyl group, methyldibenzothiophenyl group, t-butyldibenzothiophenyl group, and monovalent residue of spiro[9H-thioxanthene-9, 9'-[9H]fluorene].
Groups Derived by Substituting at Least One Hydrogen Atom of Monovalent Heterocyclic Group Derived from Cyclic Structures Represented by Formulae (TEMP-16) to (TEMP-33) with Substituent (Specific Example Group G2B4):

The "at least one hydrogen atom of a monovalent heterocyclic group" means at least one hydrogen atom selected from a hydrogen atom bonded to a ring carbon atom of the monovalent heterocyclic group, a hydrogen atom bonded to a nitrogen atom of at least one of $X_A$ or $Y_A$ in a form of NH, and a hydrogen atom of one of $X_A$ and $Y_A$ in a form of a methylene group ($CH_2$).

Substituted or Unsubstituted Alkyl Group

Specific examples (specific example group G3) of the "substituted or unsubstituted alkyl group" mentioned herein include unsubstituted alkyl groups (specific example group G3A) and substituted alkyl groups (specific example group G3B) below. (Herein, an unsubstituted alkyl group refers to an "unsubstituted alkyl group" in a "substituted or unsubstituted alkyl group," and a substituted alkyl group refers to a "substituted alkyl group" in a "substituted or unsubstituted alkyl group.") A simply termed "alkyl group" herein includes both of "unsubstituted alkyl group" and "substituted alkyl group."

The "substituted alkyl group" refers to a group derived by substituting at least one hydrogen atom in an "unsubstituted alkyl group" with a substituent. Specific examples of the "substituted alkyl group" include a group derived by substituting at least one hydrogen atom of an "unsubstituted alkyl group" (specific example group G3A) below with a substituent, and examples of the substituted alkyl group (specific example group G3B) below. Herein, the alkyl group for the "unsubstituted alkyl group" refers to a chain alkyl group. Accordingly, the "unsubstituted alkyl group" include linear "unsubstituted alkyl group" and branched "unsubstituted alkyl group." It should be noted that the examples of the "unsubstituted alkyl group" and the "substituted alkyl group" mentioned herein are merely exemplary, and the "substituted alkyl group" mentioned herein includes a group derived by further substituting a hydrogen atom bonded to a carbon atom of a skeleton of the "substituted alkyl group" in the specific example group G3B, and a group derived by further substituting a hydrogen atom of a substituent of the "substituted alkyl group" in the specific example group G3B.

Unsubstituted Alkyl Group (Specific Example Group G3A):
methyl group, ethyl group, n-propyl group, isopropyl group, n-butyl group, isobutyl group, s-butyl group, and t-butyl group.
Substituted Alkyl Group (Specific Example Group G3B):
heptafluoropropyl group (including isomer thereof), pentafluoroethyl group, 2,2,2-trifluoroethyl group, and trifluoromethyl group.
Substituted or Unsubstituted Alkenyl Group Specific examples (specific example group G4) of the "substituted or unsubstituted alkenyl group" mentioned herein include unsubstituted alkenyl groups (specific example group G4A) and substituted alkenyl groups (specific example group G4B). (Herein, an unsubstituted alkenyl group refers to an "unsubstituted alkenyl group" in a "substituted or unsubstituted alkenyl group," and a substituted alkenyl group refers to a "substituted alkenyl group" in a "substituted or unsubstituted alkenyl group.") A simply termed "alkenyl group" herein includes both of "unsubstituted alkenyl group" and "substituted alkenyl group."

The "substituted alkenyl group" refers to a group derived by substituting at least one hydrogen atom in an "unsubstituted alkenyl group" with a substituent. Specific examples of the "substituted alkenyl group" include an "unsubstituted alkenyl group" (specific example group G4A) substituted by a substituent, and examples of the substituted alkenyl group (specific example group G4B) below. It should be noted that the examples of the "unsubstituted alkenyl group" and the "substituted alkenyl group" mentioned herein are merely exemplary, and the "substituted alkenyl group" mentioned herein includes a group derived by further substituting a hydrogen atom of a skeleton of the "substituted alkenyl group" in the specific example group G4B with a substituent, and a group derived by further substituting a hydrogen atom of a substituent of the "substituted alkenyl group" in the specific example group G4B with a substituent.

Unsubstituted Alkenyl Group (Specific Example Group G4A):
vinyl group, allyl group, 1-butenyl group, 2-butenyl group, and 3-butenyl group.
Substituted Alkenyl Group (Specific Example Group G4B):
1,3-butanedienyl group, 1-methylvinyl group, 1-methylallyl group, 1,1-dimethylallyl group, 2-methylallyl group, and 1,2-dimethylallyl group.
Substituted or Unsubstituted Alkynyl Group Specific examples (specific example group G5) of the "substituted or unsubstituted alkynyl group" mentioned herein include unsubstituted alkynyl groups (specific example group G5A) below (Herein, an unsubstituted alkynyl group refers to an "unsubstituted alkynyl group" in the "substituted or unsubstituted alkynyl group.") A simply termed "alkynyl group" herein includes both of "unsubstituted alkynyl group" and "substituted alkynyl group."

The "substituted alkynyl group" refers to a group derived by substituting at least one hydrogen atom in an "unsubstituted alkynyl group" with a substituent. Specific examples of the "substituted alkynyl group" include a group derived by substituting at least one hydrogen atom of the "unsubstituted alkynyl group" (specific example group G5A) below with a substituent.

Unsubstituted Alkynyl Group (Specific Example Group G5A): ethynyl group.
Substituted or Unsubstituted Cycloalkyl Group Specific examples (specific example group G6) of the "substituted or unsubstituted cycloalkyl group" mentioned herein include unsubstituted cycloalkyl groups (specific example group G6A) and substituted cycloalkyl groups (specific example group G6B). (Herein, an unsubstituted cycloalkyl group refers to an "unsubstituted cycloalkyl group" in the "substituted or unsubstituted cycloalkyl group," and a substituted cycloalkyl group refers to the "substituted cycloalkyl group" in a "substituted or unsubstituted cycloalkyl group.") A simply termed "cycloalkyl group" herein includes both of "unsubstituted cycloalkyl group" and "substituted cycloalkyl group."

The "substituted cycloalkyl group" refers to a group derived by substituting at least one hydrogen atom of an "unsubstituted cycloalkyl group" with a substituent. Specific examples of the "substituted cycloalkyl group" include a group derived by substituting at least one hydrogen atom of the "unsubstituted cycloalkyl group" (specific example group G6A) below with a substituent, and examples of the substituted cycloalkyl group (specific example group G6B) below. It should be noted that the examples of the "unsubstituted cycloalkyl group" and the "substituted cycloalkyl group" mentioned herein are merely exemplary, and the "substituted cycloalkyl group" mentioned herein includes a group derived by substituting at least one hydrogen atom bonded to a carbon atom of a skeleton of the "substituted cycloalkyl group" in the specific example group G6B with a substituent, and a group derived by further substituting a hydrogen atom of a substituent of the "substituted cycloalkyl group" in the specific example group G6B with a substituent.

Unsubstituted Cycloalkyl Group (Specific Example Group G6A):
cyclopropyl group, cyclobutyl group, cyclopentyl group, cyclohexyl group, 1-adamantyl group, 2-adamantyl group, 1-norbornyl group, and 2-norbornyl group.

Substituted Cycloalkyl Group (Specific Example Group G6B):
4-methylcyclohexyl group.

Group Represented by "—Si($R_{901}$)($R_{902}$)($R_{903}$)"
Specific examples (specific example group G7) of the group represented herein by —Si($R_{901}$)($R_{902}$)($R_{903}$) include: —Si(G1)(G1)(G1); —Si(G1)(G2)(G2); —Si(G1)(G1)(G2); —Si(G2)(G2)(G2); —Si(G3)(G3)(G3); and —Si(G6)(G6)(G6), where:
G1 represents a "substituted or unsubstituted aryl group" in the specific example group G1;
G2 represents a "substituted or unsubstituted heterocyclic group" in the specific example group G2;
G3 represents a "substituted or unsubstituted alkyl group" in the specific example group G3;
G6 represents a "substituted or unsubstituted cycloalkyl group" in the specific example group G6;
a plurality of G1 in —Si(G1)(G1)(G1) are mutually the same or different;
a plurality of G2 in —Si(G1)(G2)(G2) are mutually the same or different;
a plurality of G1 in —Si(G1)(G1)(G2) are mutually the same or different;
a plurality of G2 in —Si(G2)(G2)(G2) are mutually the same or different;
a plurality of G3 in —Si(G3)(G3)(G3) are mutually the same or different; and
a plurality of G6 in —Si(G6)(G6)(G6) are mutually the same or different.

Group Represented by —O—($R_{904}$)
Specific examples (specific example group G8) of a group represented by —O—($R_{904}$) herein include: —O(G1); —O(G2); —O(G3); and —O(G6), where:
G1 represents a "substituted or unsubstituted aryl group" in the specific example group G1;
G2 represents a "substituted or unsubstituted heterocyclic group" in the specific example group G2;
G3 represents a "substituted or unsubstituted alkyl group" in the specific example group G3; and
G6 represents a "substituted or unsubstituted cycloalkyl group" in the specific example group G6.

Group Represented by —S—($R_{905}$)
Specific examples (specific example group G9) of a group represented herein by —S—($R_{905}$) include: —S(G1); —S(G2); —S(G3); and —S(G6), where:
G1 represents a "substituted or unsubstituted aryl group" in the specific example group G1;
G2 represents a "substituted or unsubstituted heterocyclic group" in the specific example group G2;
G3 represents a "substituted or unsubstituted alkyl group" in the specific example group G3;
G6 represents a "substituted or unsubstituted cycloalkyl group" in the specific example group G6.

Group Represented by —N($R_{906}$)($R_{907}$)
Specific examples (specific example group G10) of a group represented herein by —N($R_{906}$)($R_{907}$) include: —N(G1)(G1); —N(G2)(G2); —N(G1)(G2); —N(G3)(G3); and —N(G6)(G6), where:
G1 represents a "substituted or unsubstituted aryl group" in the specific example group G1;
G2 represents a "substituted or unsubstituted heterocyclic group" in the specific example group G2;
G3 represents a "substituted or unsubstituted alkyl group" in the specific example group G3;
G6 represents a "substituted or unsubstituted cycloalkyl group" in the specific example group G6;
a plurality of G1 in —N(G1)(G1) are mutually the same or different;
a plurality of G2 in —N(G2)(G2) are mutually the same or different;
a plurality of G3 in —N(G3)(G3) are mutually the same or different; and
a plurality of G6 in —N(G6)(G6) are mutually the same or different.

Halogen Atom
Specific examples (specific example group G11) of "halogen atom" mentioned herein include a fluorine atom, chlorine atom, bromine atom, and iodine atom.

Substituted or Unsubstituted Fluoroalkyl Group
The "substituted or unsubstituted fluoroalkyl group" mentioned herein refers to a group derived by substituting at least one hydrogen atom of the "substituted or unsubstituted alkyl group" with a fluorine atom, and also includes a group (perfluoro group) derived by substituting all of the hydrogen atoms bonded to a carbon atom(s) of the alkyl group in the "substituted or unsubstituted alkyl group" with fluorine atoms. An "unsubstituted fluoroalkyl group" has, unless otherwise specified herein, 1 to 50, preferably 1 to 30, more preferably 1 to 18 carbon atoms. The "substituted fluoroalkyl group" refers to a group derived by substituting at least one hydrogen atom in a "fluoroalkyl group" with a substituent. It should be noted that the examples of the "substituted fluoroalkyl group" mentioned herein include a group derived by further substituting at least one hydrogen atom bonded to a carbon atom of an alkyl chain of a "substituted fluoroalkyl group" with a substituent, and a group derived by further substituting at least one hydrogen atom of a substituent of the "substituted fluoroalkyl group" with a substituent. Specific examples of the "substituted fluoroalkyl group" include a group derived by substituting at least one hydrogen atom of the "alkyl group" (specific example group G3) with a fluorine atom.

Substituted or Unsubstituted Haloalkyl Group The "substituted or unsubstituted haloalkyl group" mentioned herein refers to a group derived by substituting at least one hydrogen atom of the "substituted or unsubstituted alkyl group" with a halogen atom, and also includes a group derived by substituting all of the hydrogen atoms bonded to a carbon atom(s) of the alkyl group in the "substituted or unsubstituted alkyl group" with halogen atoms. An "unsubstituted haloalkyl group" has, unless otherwise specified herein, 1 to 50, preferably 1 to 30, more preferably 1 to 18 carbon atoms. The "substituted haloalkyl group" refers to a group derived by substituting at least one hydrogen atom in a "haloalkyl group" with a substituent. It should be noted that the examples of the "substituted haloalkyl group" mentioned herein include a group derived by further substituting at least one hydrogen atom bonded to a carbon atom of an alkyl chain of a "substituted haloalkyl group" with a substituent, and a group derived by further substituting at least one hydrogen atom of a substituent of the "substituted haloalkyl group" with a substituent. Specific examples of the "substituted haloalkyl group" include a group derived by substituting at least one hydrogen atom of the "alkyl group" (specific example group G3) with a halogen atom. The haloalkyl group is sometimes referred to as a halogenated alkyl group.

Substituted or Unsubstituted Alkoxy Group

Specific examples of a "substituted or unsubstituted alkoxy group" mentioned herein include a group represented by —O(G3), G3 being the "substituted or unsubstituted alkyl group" in the specific example group G3. An "unsubstituted alkoxy group" has, unless otherwise specified herein, 1 to 50, preferably 1 to 30, more preferably 1 to 18 carbon atoms.

Substituted or Unsubstituted Alkylthio Group

Specific examples of a "substituted or unsubstituted alkylthio group" mentioned herein include a group represented by —S(G3), G3 being the "substituted or unsubstituted alkyl group" in the specific example group G3. An "unsubstituted alkylthio group" has, unless otherwise specified herein, 1 to 50, preferably 1 to 30, more preferably 1 to 18 carbon atoms.

Substituted or Unsubstituted Aryloxy Group

Specific examples of a "substituted or unsubstituted aryloxy group" mentioned herein include a group represented by —O(G1), G1 being the "substituted or unsubstituted aryl group" in the specific example group G1. An "unsubstituted aryloxy group" has, unless otherwise specified herein, 6 to 50, preferably 6 to 30, more preferably 6 to 18 ring carbon atoms.

Substituted or Unsubstituted Arylthio Group

Specific examples of a "substituted or unsubstituted arylthio group" mentioned herein include a group represented by —S(G1), G1 being the "substituted or unsubstituted aryl group" in the specific example group G1. An "unsubstituted arylthio group" has, unless otherwise specified herein, 6 to 50, preferably 6 to 30, more preferably 6 to 18 ring carbon atoms.

Substituted or Unsubstituted Trialkylsilyl Group

Specific examples of a "trialkylsilyl group" mentioned herein include a group represented by —Si(G3)(G3)(G3), G3 being the "substituted or unsubstituted alkyl group" in the specific example group G3. The plurality of G3 in —Si(G3)(G3)(G3) are mutually the same or different. Each of the alkyl groups in the "trialkylsilyl group" has, unless otherwise specified herein, 1 to 50, preferably 1 to 20, more preferably 1 to 6 carbon atoms.

Substituted or Unsubstituted Aralkyl Group

Specific examples of a "substituted or unsubstituted aralkyl group" mentioned herein include a group represented by (G3)-(G1), G3 being the "substituted or unsubstituted alkyl group" in the specific example group G3, G1 being the "substituted or unsubstituted aryl group" in the specific example group G1. Accordingly, the "aralkyl group" is a group derived by substituting a hydrogen atom of the "alkyl group" with a substituent in a form of the "aryl group," which is an example of the "substituted alkyl group." An "unsubstituted aralkyl group," which is an "unsubstituted alkyl group" substituted by an "unsubstituted aryl group," has, unless otherwise specified herein, 7 to 50 carbon atoms, preferably 7 to 30 carbon atoms, more preferably 7 to 18 carbon atoms.

Specific examples of the "substituted or unsubstituted aralkyl group" include a benzyl group, 1-phenylethyl group, 2-phenylethyl group, 1-phenylisopropyl group, 2-phenylisopropyl group, phenyl-t-butyl group, a-naphthylmethyl group, 1-a-naphthylethyl group, 2-α-naphthylethyl group, 1-a-naphthylisopropyl group, 2-a-naphthylisopropyl group, β-naphthylmethyl group, 1-β-naphthylethyl group, 2-β-naphthylethyl group, 1-β-naphthylisopropyl group, and 2-β-naphthylisopropyl group.

Preferable examples of the substituted or unsubstituted aryl group mentioned herein include, unless otherwise specified herein, a phenyl group, p-biphenyl group, m-biphenyl group, o-biphenyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-terphenyl-4-yl group, o-terphenyl-3-yl group, o-terphenyl-2-yl group, 1-naphthyl group, 2-naphthyl group, anthryl group, phenanthryl group, pyrenyl group, chrysenyl group, triphenylenyl group, fluorenyl group, 9,9'-spirobifluorenyl group, 9,9-dimethylfluorenyl group, and 9,9-diphenylfluorenyl group.

Preferable examples of the substituted or unsubstituted heterocyclic group mentioned herein include, unless otherwise specified herein, a pyridyl group, pyrimidinyl group, triazinyl group, quinolyl group, isoquinolyl group, quinazolinyl group, benzimidazolyl group, phenanthrolinyl group, carbazolyl group (1-carbazolyl group, 2-carbazolyl group, 3-carbazolyl group, 4-carbazolyl group, or 9-carbazolyl group), benzocarbazolyl group, azacarbazolyl group, diazacarbazolyl group, dibenzofuranyl group, naphthobenzofuranyl group, azadibenzofuranyl group, diazadibenzofuranyl group, dibenzothiophenyl group, naphthobenzothiophenyl group, azadibenzothiophenyl group, diazadibenzothiophenyl group, (9-phenyl)carbazolyl group ((9-phenyl)carbazole-1-yl group, (9-phenyl)carbazole-2-yl group, (9-phenyl)carbazole-3-yl group, or (9-phenyl)carbazole-4-yl group), (9-biphenylyl)carbazolyl group, (9-phenyl)phenylcarbazolyl group, diphenylcarbazole-9-yl group, phenylcarbazole-9-yl group, phenyltriazinyl group, biphenylyltriazinyl group, diphenyltriazinyl group, phenyldibenzofuranyl group, and phenyldibenzothiophenyl group.

The carbazolyl group mentioned herein is, unless otherwise specified herein, specifically a group represented by one of formulae below.

[Formula 5]

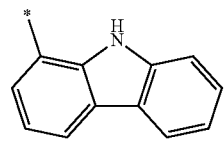

(TEMP-Cz1)

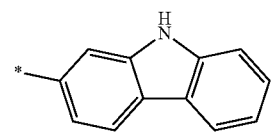

(TEMP-Cz2)

(TEMP-Cz3)
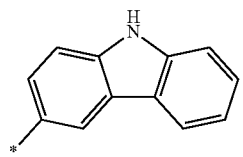

(TEMP-Cz4)
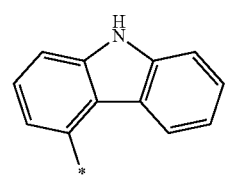

(TEMP-Cz5)
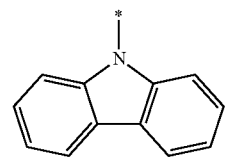

The (9-phenyl)carbazolyl group mentioned herein is, unless otherwise specified herein, specifically a group represented by one of formulae below.

[Formula 6]

(TEMP-Cz6)
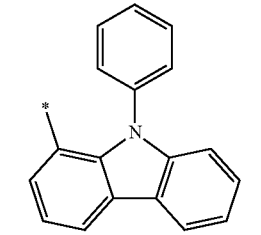

(TEMP-Cz7)
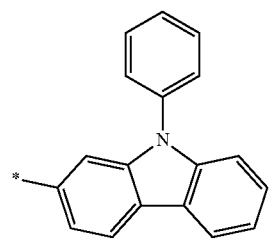

(TEMP-Cz8)
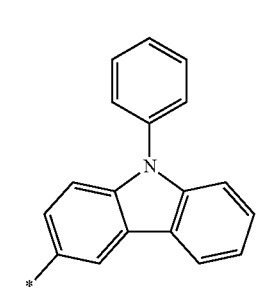

(TEMP-Cz9)
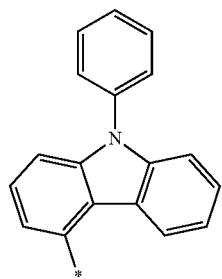

In the formulae (TEMP-Cz1) to (TEMP-Cz9), * represents a bonding position.

The dibenzofuranyl group and dibenzothiophenyl group mentioned herein are, unless otherwise specified herein, each specifically represented by one of formulae below.

[Formula 7]

(TEMP-34)
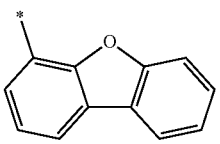

(TEMP-35)
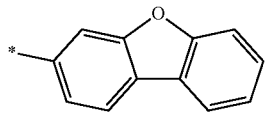

(TEMP-36)
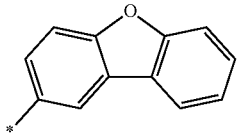

(TEMP-37)
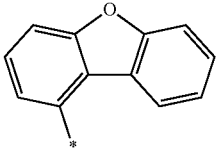

(TEMP-38)
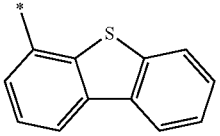

(TEMP-39)
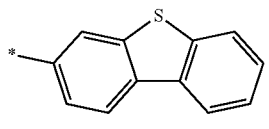

(TEMP-40)
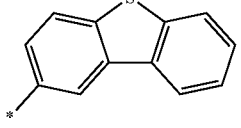

-continued (TEMP-41)

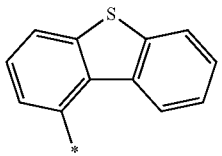

In the formulae (TEMP-34) to (TEMP-41), * represents a bonding position.

Preferable examples of the substituted or unsubstituted alkyl group mentioned herein include, unless otherwise specified herein, a methyl group, ethyl group, propyl group, isopropyl group, n-butyl group, isobutyl group, and t-butyl group.

Substituted or Unsubstituted Arylene Group

The "substituted or unsubstituted arylene group" mentioned herein is, unless otherwise specified herein, a divalent group derived by removing one hydrogen atom on an aryl ring of the "substituted or unsubstituted aryl group." Specific examples of the "substituted or unsubstituted arylene group" (specific example group G12) include a divalent group derived by removing one hydrogen atom on an aryl ring of the "substituted or unsubstituted aryl group" in the specific example group G1.

Substituted or Unsubstituted Divalent Heterocyclic Group

The "substituted or unsubstituted divalent heterocyclic group" mentioned herein is, unless otherwise specified herein, a divalent group derived by removing one hydrogen atom on a heterocycle of the "substituted or unsubstituted heterocyclic group." Specific examples of the "substituted or unsubstituted divalent heterocyclic group" (specific example group G13) include a divalent group derived by removing one hydrogen atom on a heterocyclic ring of the "substituted or unsubstituted heterocyclic group" in the specific example group G2.

Substituted or Unsubstituted Alkylene Group

The "substituted or unsubstituted alkylene group" mentioned herein is, unless otherwise specified herein, a divalent group derived by removing one hydrogen atom on an alkyl chain of the "substituted or unsubstituted alkyl group." Specific examples of the "substituted or unsubstituted alkylene group" (specific example group G14) include a divalent group derived by removing one hydrogen atom on an alkyl chain of the "substituted or unsubstituted alkyl group" in the specific example group G3.

The substituted or unsubstituted arylene group mentioned herein is, unless otherwise specified herein, preferably any one of groups represented by formulae (TEMP-42) to (TEMP-68) below.

[Formula 8]

(TEMP-42)

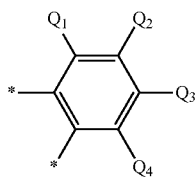

-continued (TEMP-43)

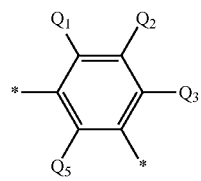

(TEMP-44)

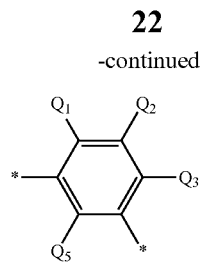

(TEMP-45)

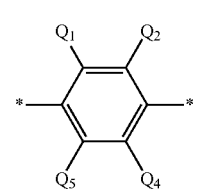

(TEMP-46)

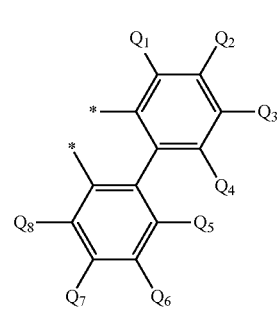

(TEMP-47)

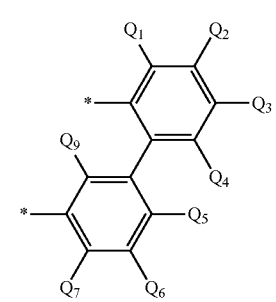

[Formula 9]
(TEMP-48)
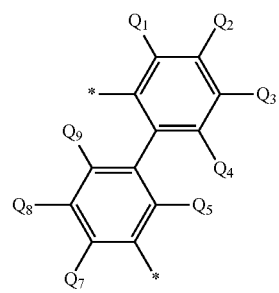
(TEMP-49)
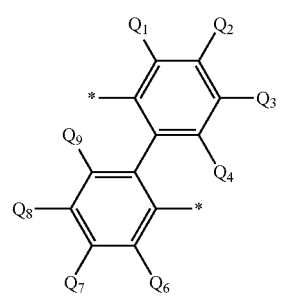
(TEMP-50)
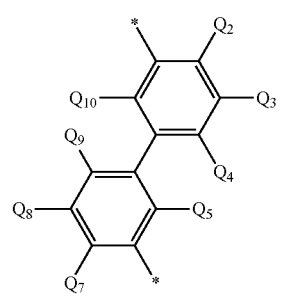
(TEMP-51)
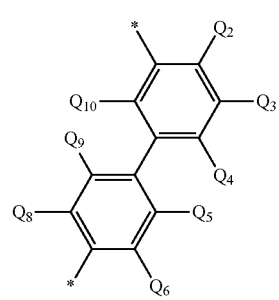
(TEMP-52)
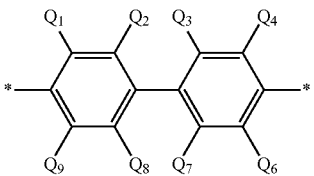
In the formulae (TEMP-42) to (TEMP-52), $Q_1$ to $Q_{10}$ each independently are a hydrogen atom or a substituent.
In the formulae (TEMP-42) to (TEMP-52), * represents a bonding position.
[Formula 10]
(TEMP-53)

(TEMP-54)
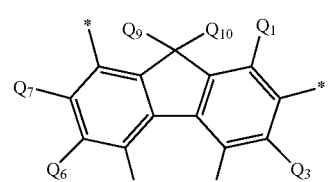
(TEMP-55)
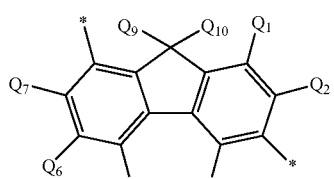
(TEMP-56)
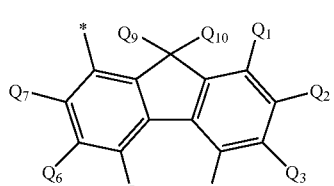
(TEMP-57)
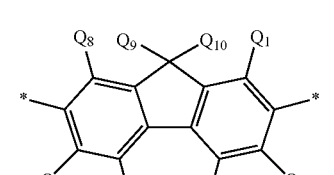
(TEMP-58)
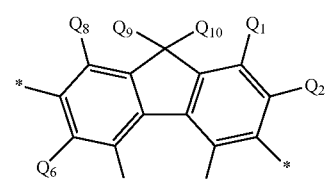
(TEMP-59)
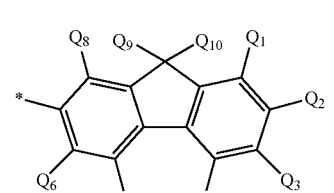
(TEMP-60)
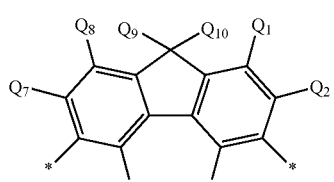

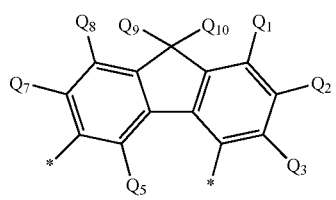
(TEMP-61)

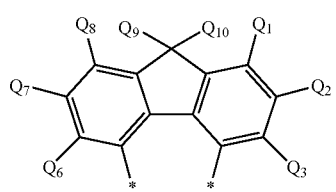
(TEMP-62)

In the formulae (TEMP-53) to (TEMP-62), $Q_1$ to $Q_{10}$ each independently are a hydrogen atom or a substituent.

In the formulae, $Q_9$ and $Q_{10}$ may be mutually bonded through a single bond to form a ring.

In the formulae (TEMP-53) to (TEMP-62), * represents a bonding position.

[Formula 11]

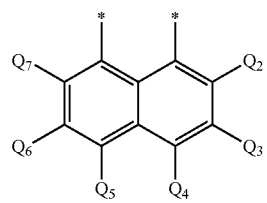
(TEMP-63)

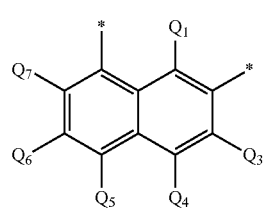
(TEMP-64)

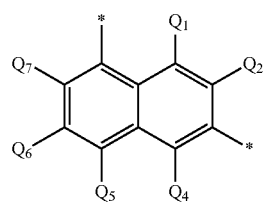
(TEMP-65)

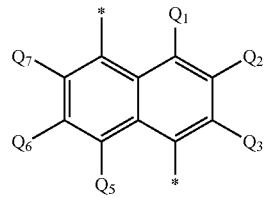
(TEMP-66)

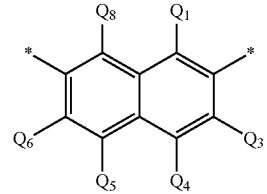
(TEMP-67)

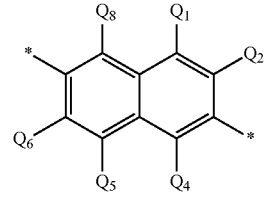
(TEMP-68)

In the formulae (TEMP-63) to (TEMP-68), $Q_1$ to $Q_8$ each independently are a hydrogen atom or a substituent.

In the formulae (TEMP-63) to (TEMP-68), * represents a bonding position.

The substituted or unsubstituted divalent heterocyclic group mentioned herein is, unless otherwise specified herein, preferably a group represented by any one of formulae (TEMP-69) to (TEMP-102) below.

[Formula 12]

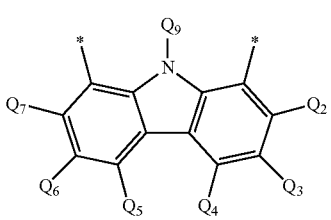
(TEMP-69)

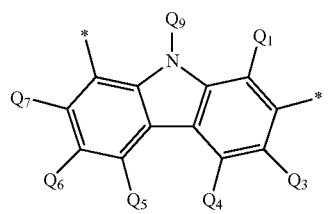
(TEMP-70)

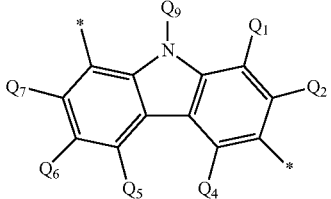
(TEMP-71)

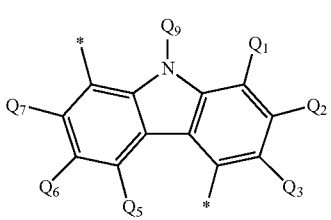
(TEMP-72)

27
-continued
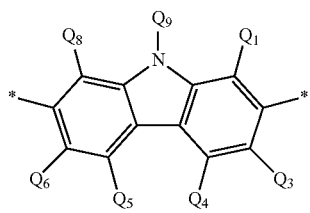
(TEMP-73)
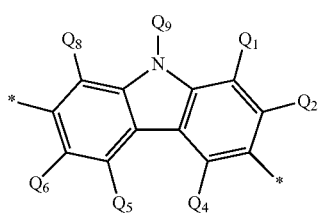
(TEMP-74)
[Formula 13]
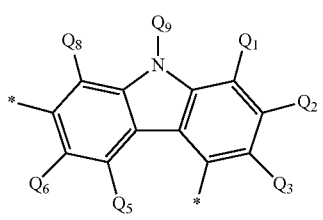
(TEMP-75)
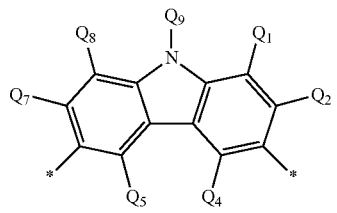
(TEMP-76)
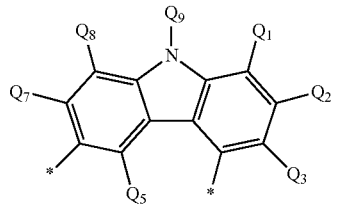
(TEMP-77)
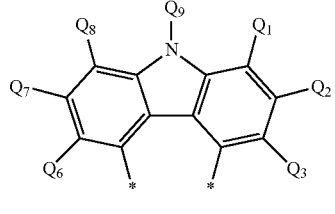
(TEMP-78)
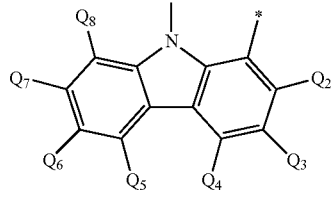
(TEMP-79)
28
-continued
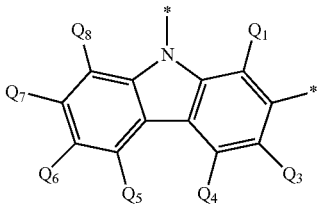
(TEMP-80)
[Formula 14]
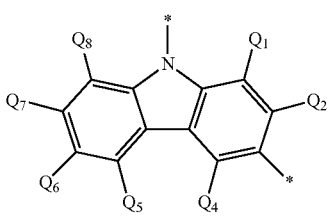
(TEMP-81)
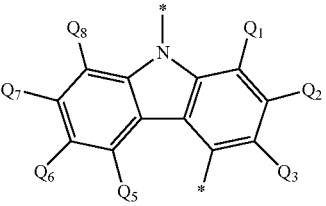
(TEMP-82)
In the formulae (TEMP-69) to (TEMP-82), $Q_1$ to $Q_9$ each independently are a hydrogen atom or a substituent.
[Formula 15]
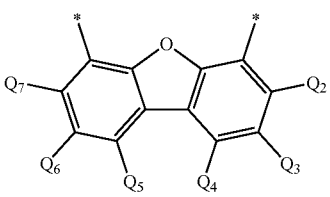
(TEMP-83)
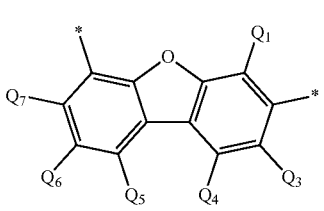
(TEMP-84)
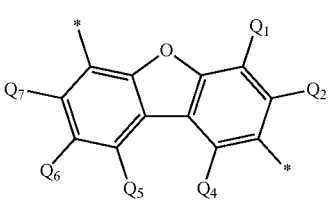
(TEMP-85)

-continued
(TEMP-86)
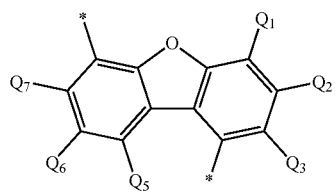
(TEMP-87)
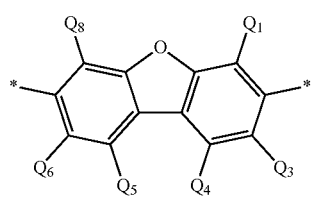
(TEMP-88)
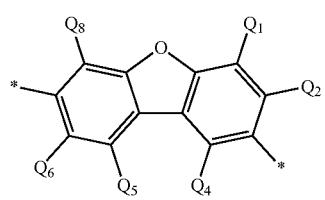
[Formula 16]
(TEMP-89)
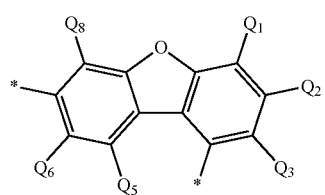
(TEMP-90)
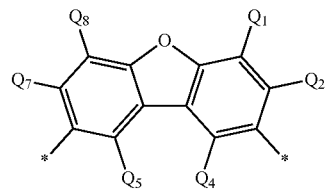
(TEMP-91)
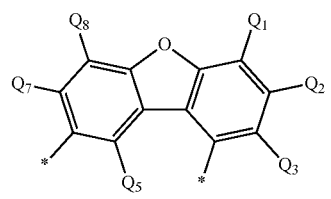
(TEMP-92)
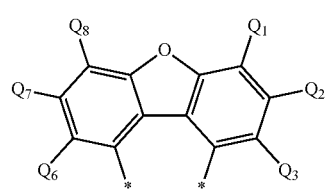
[Formula 17]
(TEMP-93)
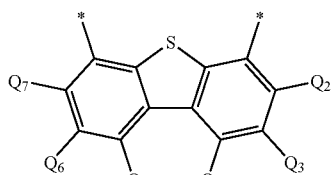
(TEMP-94)
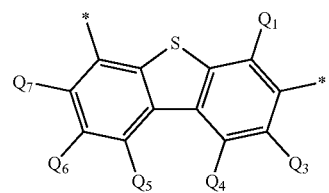
(TEMP-95)
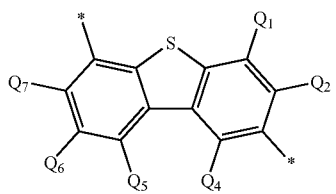
(TEMP-96)
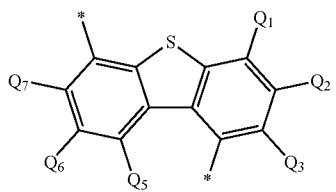
(TEMP-97)
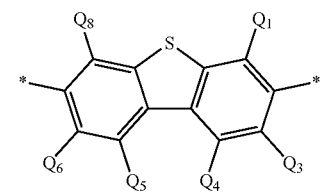
(TEMP-98)
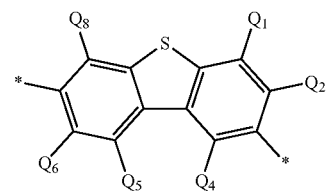
[Formula 18]
(TEMP-99)

-continued

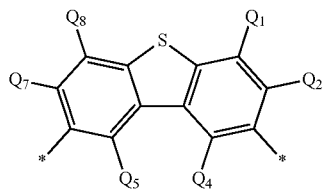
(TEMP-100)

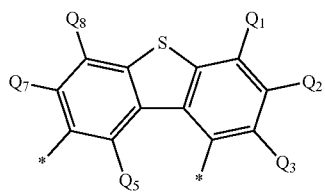
(TEMP-101)

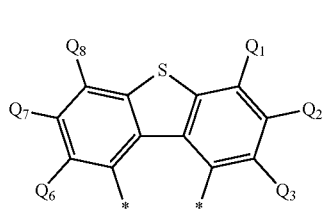
(TEMP-102)

In the formulae (TEMP-83) to (TEMP-102), $Q_1$ to $Q_8$ each independently are a hydrogen atom or a substituent.

The substituent mentioned herein has been described above.

Instance of "Bonded to Form a Ring"

Instances where "at least one combination of adjacent two or more (of . . . ) are mutually bonded to form a substituted or unsubstituted monocyclic ring, mutually bonded to form a substituted or unsubstituted fused ring, or not mutually bonded" mentioned herein refer to instances where "at least one combination of adjacent two or more (of . . . ) are mutually bonded to form a substituted or unsubstituted monocyclic ring, "at least one combination of adjacent two or more (of . . . ) are mutually bonded to form a substituted or unsubstituted fused ring," and "at least one combination of adjacent two or more (of . . . ) are not mutually bonded."

Instances where "at least one combination of adjacent two or more (of . . . ) are mutually bonded to form a substituted or unsubstituted monocyclic ring" and "at least one combination of adjacent two or more (of . . . ) are mutually bonded to form a substituted or unsubstituted fused ring" mentioned herein (these instances will be sometimes collectively referred to as an instance of "bonded to form a ring" hereinafter) will be described below. An anthracene compound having a basic skeleton in a form of an anthracene ring and represented by a formula (TEMP-103) below will be used as an example for the description.

[Formula 19]

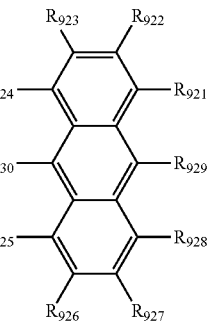
(TEMP-103)

For instance, when "at least one combination of adjacent two or more of" $R_{921}$ to $R_{930}$ "are mutually bonded to form a ring," the combination of adjacent ones of $R_{921}$ to $R_{930}$ (i.e. the combination at issue) is a combination of $R_{921}$ and $R_{922}$, a combination of $R_{922}$ and $R_{923}$, a combination of $R_{923}$ and $R_{924}$, a combination of $R_{924}$ and $R_{930}$, a combination of $R_{930}$ and $R_{925}$, a combination of $R_{925}$ and $R_{926}$, a combination of $R_{926}$ and $R_{927}$, a combination of $R_{927}$ and $R_{928}$, a combination of $R_{928}$ and $R_{929}$, or a combination of $R_{929}$ and $R_{921}$.

The term "at least one combination" means that two or more of the above combinations of adjacent two or more of $R_{921}$ to $R_{930}$ may simultaneously form rings. For instance, when $R_{921}$ and $R_{922}$ are mutually bonded to form a ring $Q_A$ and $R_{925}$ and $R_{926}$ are simultaneously mutually bonded to form a ring $Q_B$, the anthracene compound represented by the formula (TEMP-103) is represented by a formula (TEMP-104) below.

[Formula 20]

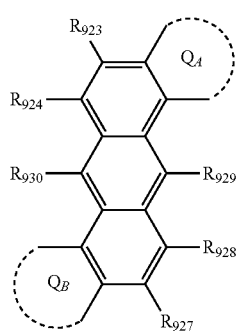
(TEMP-104)

The instance where the "combination of adjacent two or more" form a ring means not only an instance where the "two" adjacent components are bonded but also an instance where adjacent "three or more" are bonded. For instance, $R_{921}$ and $R_{922}$ are mutually bonded to form a ring $Q_A$ and $R_{922}$ and $R_{923}$ are mutually bonded to form a ring $Q_C$, and mutually adjacent three components ($R_{921}$, $R_{922}$ and $R_{923}$) are mutually bonded to form a ring fused to the anthracene basic skeleton. In this case, the anthracene compound represented by the formula (TEMP-103) is represented by a formula (TEMP-105) below. In the formula (TEMP-105) below, the ring $Q_A$ and the ring $Q_C$ share $R_{922}$.

[Formula 21]

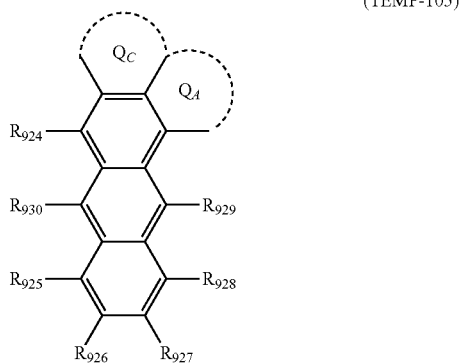

(TEMP-105)

The formed "monocyclic ring" or "fused ring" may be, in terms of the formed ring in itself, a saturated ring or an unsaturated ring. When the "combination of adjacent two" form a "monocyclic ring" or a "fused ring," the "monocyclic ring" or "fused ring" may be a saturated ring or an unsaturated ring. For instance, the ring $Q_A$ and the ring $Q_B$ formed in the formula (TEMP-104) are each independently a "monocyclic ring" or a "fused ring." Further, the ring $Q_A$ and the ring $Q_C$ formed in the formula (TEMP-105) are each a "fused ring." The ring $Q_A$ and the ring $Q_C$ in the formula (TEMP-105) are fused to form a fused ring. When the ring $Q_A$ in the formula (TMEP-104) is a benzene ring, the ring $Q_A$ is a monocyclic ring. When the ring $Q_A$ in the formula (TMEP-104) is a naphthalene ring, the ring $Q_A$ is a fused ring.

The "unsaturated ring" represents an aromatic hydrocarbon ring or an aromatic heterocycle. The "saturated ring" represents an aliphatic hydrocarbon ring or a non-aromatic heterocycle.

Specific examples of the aromatic hydrocarbon ring include a ring formed by terminating a bond of a group in the specific example of the specific example group G1 with a hydrogen atom.

Specific examples of the aromatic heterocycle include a ring formed by terminating a bond of an aromatic heterocyclic group in the specific example of the specific example group G2 with a hydrogen atom.

Specific examples of the aliphatic hydrocarbon ring include a ring formed by terminating a bond of a group in the specific example of the specific example group G6 with a hydrogen atom.

The phrase "to form a ring" herein means that a ring is formed only by a plurality of atoms of a basic skeleton, or by a combination of a plurality of atoms of the basic skeleton and one or more optional atoms. For instance, the ring $Q_A$ formed by mutually bonding $R_{921}$ and $R_{922}$ shown in the formula (TEMP-104) is a ring formed by a carbon atom of the anthracene skeleton bonded to $R_{921}$, a carbon atom of the anthracene skeleton bonded to $R_{922}$, and one or more optional atoms. Specifically, when the ring $Q_A$ is a monocyclic unsaturated ring formed by $R_{921}$ and $R_{922}$, the ring formed by a carbon atom of the anthracene skeleton bonded to $R_{921}$, a carbon atom of the anthracene skeleton bonded to $R_{922}$, and four carbon atoms is a benzene ring.

The "optional atom" is, unless otherwise specified herein, preferably at least one atom selected from the group consisting of a carbon atom, nitrogen atom, oxygen atom, and sulfur atom. A bond of the optional atom (e.g. a carbon atom and a nitrogen atom) not forming a ring may be terminated by a hydrogen atom or the like or may be substituted by an "optional substituent" described later. When the ring includes an optional element other than carbon atom, the resultant ring is a heterocycle.

The number of "one or more optional atoms" forming the monocyclic ring or fused ring is, unless otherwise specified herein, preferably in a range from 2 to 15, more preferably in a range from 3 to 12, further preferably in a range from 3 to 5.

Unless otherwise specified herein, the ring, which may be a "monocyclic ring" or "fused ring," is preferably a "monocyclic ring."

Unless otherwise specified herein, the ring, which may be a "saturated ring" or "unsaturated ring," is preferably an "unsaturated ring."

Unless otherwise specified herein, the "monocyclic ring" is preferably a benzene ring.

Unless otherwise specified herein, the "unsaturated ring" is preferably a benzene ring.

When "at least one combination of adjacent two or more" (of . . . ) are "mutually bonded to form a substituted or unsubstituted monocyclic ring" or "mutually bonded to form a substituted or unsubstituted fused ring," unless otherwise specified herein, at least one combination of adjacent two or more of components are preferably mutually bonded to form a substituted or unsubstituted "unsaturated ring" formed of a plurality of atoms of the basic skeleton, and 1 to 15 atoms of at least one element selected from the group consisting of carbon, nitrogen, oxygen and sulfur.

When the "monocyclic ring" or the "fused ring" has a substituent, the substituent is the substituent described in later-described "optional substituent." When the "monocyclic ring" or the "fused ring" has a substituent, specific examples of the substituent are the substituents described in the above under the subtitle "Substituent Mentioned Herein."

When the "saturated ring" or the "unsaturated ring" has a substituent, the substituent is the substituent described in later-described "optional substituent." When the "monocyclic ring" or the "fused ring" has a substituent, specific examples of the substituent are the substituents described in the above under the subtitle "Substituent Mentioned Herein."

The above is the description for the instances where "at least one combination of adjacent two or more (of . . . ) are mutually bonded to form a substituted or unsubstituted monocyclic ring" and "at least one combination of adjacent two or more (of . . . ) are mutually bonded to form a substituted or unsubstituted fused ring" mentioned herein (sometimes referred to as an instance of "bonded to form a ring").

Substituent for Substituted or Unsubstituted Group

In an exemplary embodiment herein: a substituent for the substituted or unsubstituted group (sometimes referred to as an "optional substituent" hereinafter) is, for instance, a group selected from the group consisting of an unsubstituted alkyl group having 1 to 50 carbon atoms, an unsubstituted alkenyl group having 2 to 50 carbon atoms, an unsubstituted alkynyl group having 2 to 50 carbon atoms, an unsubstituted cycloalkyl group having 3 to 50 ring carbon atoms, —Si($R_{901}$)($R_{902}$)($R_{903}$), —O—($R_{904}$), —S—($R_{905}$), —N($R_{906}$)($R_{907}$), a halogen atom, a cyano group, a nitro group, an unsubstituted aryl group having 6 to 50 ring carbon atoms, and an unsubstituted heterocyclic group having 5 to 50 ring atoms; $R_{901}$ to $R_{907}$ each independently are a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms; when two or more $R_{901}$ are present, the two or more $R_{901}$ are mutually the same or different; when two or more $R_{902}$ are present, the two or more $R_{902}$ are mutually the same or different;

when two or more $R_{903}$ are present, the two or more $R_{903}$ are mutually the same or different;

when two or more $R_{904}$ are present, the two or more $R_{904}$ are mutually the same or different;

when two or more $R_{905}$ are present, the two or more $R_{905}$ are mutually the same or different;

when two or more $R_{906}$ are present, the two or more $R_{906}$ are mutually the same or different; and when two or more $R_{907}$ are present, the two or more $R_{907}$ are mutually the same or different.

In an exemplary embodiment, a substituent for the substituted or unsubstituted group is selected from the group consisting of an alkyl group having 1 to 50 carbon atoms, an aryl group having 6 to 50 ring carbon atoms, and a heterocyclic group having 5 to 50 ring atoms.

In an exemplary embodiment, a substituent for the substituted or unsubstituted group is selected from the group consisting of an alkyl group having 1 to 18 carbon atoms, an aryl group having 6 to 18 ring carbon atoms, and a heterocyclic group having 5 to 18 ring atoms.

Specific examples of the above optional substituent are the same as the specific examples of the substituent described in the above under the subtitle "Substituent Mentioned Herein."

Unless otherwise specified herein, adjacent ones of the optional substituents may form a "saturated ring" or an "unsaturated ring," preferably a substituted or unsubstituted saturated five-membered ring, a substituted or unsubstituted saturated six-membered ring, a substituted or unsubstituted unsaturated five-membered ring, or a substituted or unsubstituted unsaturated six-membered ring, more preferably a benzene ring.

Unless otherwise specified herein, the optional substituent may further include a substituent. Examples of the substituent for the optional substituent are the same as the examples of the optional substituent.

Herein, numerical ranges represented by "AA to BB" represents a range whose lower limit is the value (AA) recited before "to" and whose upper limit is the value (BB) recited after "to."

First Exemplary Embodiment

Organic Electroluminescence Device

An organic electroluminescence device according to a first exemplary embodiment has the following basic arrangement.

Basic Arrangement

An organic electroluminescence device according to the exemplary embodiment includes: an anode; a cathode; two or more emitting units disposed between the anode and the cathode; and a first cathode side organic layer disposed between the anode and the cathode, in which at least one emitting unit of the two or more emitting units is a laminated emitting unit, the first cathode side organic layer is disposed close to the cathode with respect to the at least one laminated emitting unit, the first cathode side organic layer contains a phenanthroline compound having a phenanthroline skeleton, the laminated emitting unit includes a first emitting layer and a second emitting layer, the first emitting layer contains a first host material, the second emitting layer contains a second host material, the first host material and the second host material are mutually different, the first emitting layer at least contains a first emitting compound that emits light having a maximum peak wavelength of 500 nm or less, the second emitting layer at least contains a second emitting compound that emits light having a maximum peak wavelength of 500 nm or less, and the first emitting compound and the second emitting compound are mutually the same or different.

The organic EL device according to the exemplary embodiment has at least one of Element 1 or Element 2 below in addition to the above basic arrangement.

Element 1

In Element 1, a triplet energy $T_1(H1)$ of the first host material and a triplet energy $T_1(H2)$ of the second host material satisfy a relationship of a numerical formula (Numerical Formula 3) below.

$$T_1(H1) > T_1(H2) \qquad \text{(Numerical Formula 3)}$$

Element 2

In Element 2, the first host material has a structure of Condition (i) or a structure of Condition (ii) below in a molecule, the first benzene ring and the second benzene ring in the biphenyl structure are further linked to each other by cross-linking at at least one site other than the single bond, and the second host material is an anthracene derivative.

Condition (i): a biphenyl structure including a first benzene ring and a second benzene ring that are linked to each other with a single bond, the first benzene ring and the second benzene ring in the biphenyl structure being further linked to each other by cross-linking at at least one site other than the single bond.

Condition (ii): a linking structure including a benzene ring and a naphthalene ring that are linked to each other with a single bond, the benzene ring and the naphthalene ring in the linking structure being each independently further fused or not fused with a monocyclic ring or fused ring, the benzene ring and the naphthalene ring in the linking structure being further linked to each other by cross-linking at at least one site other than the single bond.

Hereinafter, the organic EL device according to the exemplary embodiment having the above basic arrangement and at least one of Element 1 or Element 2 will be described.

Herein, an organic electroluminescence device including two or more emitting units disposed between an anode and a cathode is referred to as a tandem organic electroluminescence device (tandem organic EL device).

According to the exemplary embodiment, an organic electroluminescence device with improved luminous efficiency can be provided.

Conventionally, Triplet-Triplet-Annihilation (sometimes referred to as TTA) is known as a technique for improving the luminous efficiency of the organic electroluminescence device. TTA is a mechanism in which triplet excitons collide with one another to generate singlet excitons. It should be noted that the TTA mechanism is also sometimes referred to as a TTF mechanism as described in Patent Literature 8.

The TTF phenomenon will be described. Holes injected from an anode and electrons injected from a cathode are recombined in an emitting layer to generate excitons. As for the spin state, as is conventionally known, singlet excitons account for 25% and triplet excitons account for 75%. In a conventionally known fluorescent device, light is emitted when singlet excitons of 25% are relaxed to the ground state. The remaining triplet excitons of 75% are returned to the ground state without emitting light through a thermal deactivation process. Accordingly, the theoretical limit value of the internal quantum efficiency of a conventional fluorescent device is believed to be 25%.

The behavior of triplet excitons generated within an organic substance has been theoretically examined. According to S. M. Bachilo et al. (J. Phys. Chem. A, 104, 7711 (2000)), assuming that high-order excitons such as quintet excitons are quickly returned to triplet excitons, triplet excitons (hereinafter abbreviated as $^3A^*$) collide with one another with an increase in the density thereof, whereby a reaction shown by the following formula occurs. In the formula, $^1A$ represents the ground state and $^1A^*$ represents the lowest singlet excitons.

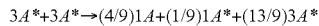

$$3A^* + 3A^* \rightarrow (4/9)1A + (1/9)1A^* + (13/9)3A^*$$

In other words, $5\,^3A^* \rightarrow 4\,^1A + 1A^*$ is satisfied, and it is expected that, among triplet excitons initially generated, which account for 75%, one fifth thereof (i.e., 20%) is changed to singlet excitons. Accordingly, the amount of singlet excitons which contribute to emission is 40%, which is a value obtained by adding 15% (75% x (1/5)=15%) to 25%, which is the amount ratio of initially generated singlet excitons. At this time, a ratio of luminous intensity derived from TTF (TTF ratio) relative to the total luminous intensity is 15/40, i.e., 37.5%. Assuming that singlet excitons are generated by collision of initially generated triplet excitons accounting for 75% (i.e., one siglet exciton is generated from two triplet excitons), a significantly high internal quantum efficiency of 62.5% is obtained, which is a value obtained by adding 37.5% (75% x (1/2)=37.5%) to 25% (the amount ratio of initially generated singlet excitons). At this time, the TTF ratio is 37.5/62.5=60%.

In the organic electroluminescence device according to the exemplary embodiment, it is considered that triplet excitons generated by recombination of holes and electrons in the first emitting layer in a laminated emitting unit and present on an interface between the first emitting layer and organic layer(s) in direct contact therewith are not likely to be quenched even under the presence of excessive carriers on the interface between the first emitting layer and the organic layer(s). For instance, the presence of a recombination region locally on an interface between the first emitting layer and a hole transporting layer or an electron blocking layer is considered to cause quenching by excessive electrons. Meanwhile, the presence of a recombination region locally on an interface between the first emitting layer and an electron transporting layer or a hole blocking layer is considered to cause quenching by excessive holes.

The organic electroluminescence device according to the exemplary embodiment includes a laminated emitting unit including at least two emitting layers (i.e., the first emitting layer and a second emitting layer), which satisfy a predetermined relationship. A triplet energy $T_1(H1)$ of a first host material in the first emitting layer and a triplet energy $T_1(H2)$ of a second host material in the second emitting layer satisfy a relationship of the numerical formula (Numerical Formula 3).

By including the laminated emitting unit including the first emitting layer and the second emitting layer so as to satisfy the numerical formula (Numerical Formula 3), triplet excitons generated in the first emitting layer can transfer to the second emitting layer without being quenched by excessive carriers and be prevented from back-transferring from the second emitting layer to the first emitting layer. Consequently, the second emitting layer exhibits the TTF mechanism to efficiently generate singlet excitons, thereby improving luminous efficiency.

Accordingly, the laminated emitting unit in the organic electroluminescence device includes, as different regions, the first emitting layer mainly generating triplet excitons and the second emitting layer mainly exhibiting the TTF mechanism using triplet excitons having transferred from the first emitting layer. A difference in triplet energy is provided by using, as the second host material in the second emitting layer, a compound having a smaller triplet energy than that of the first host material in the first emitting layer, thereby improving luminous efficiency.

The phenanthroline compound having a phenanthroline skeleton is likely to generate charges, and thus is suitably usable as an electron transporting material in the so-called tandem organic EL device including a plurality of emitting units. However, due to low resistance of the phenanthroline compound to holes, when holes transfer from an emitting layer to an organic layer (for instance, the electron transporting layer) containing a phenanthroline compound, the phenanthroline compound deteriorates, so that a device lifetime tends to be reduced.

In the organic EL device according to the exemplary embodiment, a first cathode side organic layer containing a phenanthroline compound is disposed close to the cathode with respect to the laminated emitting unit including the first emitting layer and the second emitting layer. This laminated emitting unit includes, as different regions, the first emitting layer mainly generating triplet excitons and the second emitting layer mainly exhibiting the TTF mechanism using triplet excitons having transferred from the first emitting layer. Accordingly, it is considered that the first cathode side organic layer containing a phenanthroline compound, which is likely to deteriorate, can be disposed apart from the first emitting layer (recombination layer) to reduce an amount of holes transferring from the laminated emitting unit to the first cathode side organic layer, resulting in the organic EL device with a longer lifetime.

The first cathode side organic layer is an organic layer disposed close to the cathode with respect to at least one laminated emitting unit. The first cathode side organic layer is sometimes referred to as an intermediate layer.

The intermediate layer is generally also referred to as an intermediate electrode, intermediate conductive layer, charge generating layer, electron drawing layer, connection layer or intermediate insulative layer.

The intermediate layer is a layer configured to supply electrons to a layer located close to the anode with respect to the intermediate layer and supply holes to a layer located close to the cathode with respect to the intermediate layer. The intermediate layer can be made of a known material. The intermediate layer may be a single layer, or may be provided by two or more layers. A unit made of two or more intermediate layers is sometimes referred to as an intermediate unit. The compositions of the plurality of intermediate layers of the intermediate unit are mutually the same or different.

Further, a plurality of layers including the emitting layer, which are disposed between the intermediate layer/intermediate unit and the anode/cathode, is sometimes collectively referred to as an emitting unit. Examples of the device arrangement of the organic EL device including a plurality of emitting units include (TND1) to (TND4) below.

(TND1) anode/first emitting unit/intermediate layer/second emitting unit/cathode (TND2) anode/first emitting unit/intermediate unit/second emitting unit/cathode (TND3) anode/first emitting unit/first intermediate layer/second emitting unit/second intermediate layer/third emitting unit/cathode (TND4) anode/first emitting unit/first intermediate unit/second emitting unit/second intermediate unit/third emitting unit/cathode In the organic EL device according to the exemplary embodiment, the number of the emitting units and the intermediate layers (or the intermediate units) is not limited to the examples (TND1) to (TND4) shown above.

In the device arrangements (TND1) to (TND4), the first cathode side organic layer is also preferably included as at least one of the intermediate layers or as an intermediate layer in at least one of the intermediate units.

The first emitting layer and the second emitting layer are preferably included in at least one of the first emitting unit, the second emitting unit or the third emitting unit.

The first emitting layer and the second emitting layer are also preferably included in all of the emitting units of the organic EL device.

In the device arrangements (TND1) to (TND4), it is preferable that the emitting unit disposed close to the anode with respect to the intermediate layer in a form of the first cathode side organic layer or the emitting unit disposed close to the anode with respect to the intermediate unit including the first cathode side organic layer is the laminated emitting unit according to the exemplary embodiment.

The laminated emitting unit of the organic EL device according to the exemplary embodiment may include one or more organic layer(s) in addition to the first emitting layer and the second emitting layer. Examples of the organic layer include at least one layer selected from the group consisting of a hole injecting layer, a hole transporting layer, an emitting layer, an electron injecting layer, an electron transporting layer, a hole blocking layer, and an electron blocking layer.

In the organic EL device according to the exemplary embodiment, the organic layer of the laminated emitting unit may consist of the first emitting layer and the second emitting layer. Alternatively, the organic layer may further include, for instance, at least one layer selected from the group consisting of the hole injecting layer, the hole transporting layer, the electron injecting layer, the electron transporting layer, the hole blocking layer, and the electron blocking layer.

A zone disposed close to the anode with respect to the emitting layers in each emitting unit is sometimes referred to as a hole transporting zone. The hole transporting zone may be provided by a single layer or a plurality of layers. Examples of layers forming the hole transporting zone include a hole transporting layer, hole injecting layer, and electron blocking layer.

A zone disposed close to the cathode with respect to the emitting layers in each emitting unit is sometimes referred to as an electron transporting zone. The electron transporting zone may be provided by a single layer or a plurality of layers. Examples of layers forming the electron transporting zone include an electron transporting layer, electron injecting layer, and hole blocking layer.

The organic EL device according to the exemplary embodiment may include an emitting unit including at least one emitting layer as an emitting unit other than the laminated emitting unit. The emitting unit other than the laminated emitting unit may include, in addition to the emitting layer, for instance, at least one layer selected from the group consisting of the hole injecting layer, the hole transporting layer, the electron injecting layer, the electron transporting layer, the hole blocking layer, and the electron blocking layer as an organic layer(s).

In the organic EL device according to the exemplary embodiment, two or more emitting units also preferably include the laminated emitting unit and at least one phosphorescent emitting unit, which is different from the laminated emitting unit. The phosphorescent emitting unit preferably contains a phosphorescent compound that exhibits phosphorescence. The phosphorescent compound is preferably a metal complex The metal complex as a phosphorescent compound is preferably an iridium complex, a copper complex, a platinum complex, an osmium complex, or a gold complex.

The phosphorescent emitting unit preferably includes at least one phosphorescent layer containing a phosphorescent compound. The phosphorescent emitting unit may include two or more phosphorescent layers. When the phosphorescent emitting unit includes two or more phosphorescent layers, the phosphorescent layers may be in direct contact with each other or may not be in contact with each other.

In addition, the phosphorescent emitting unit preferably includes: a green phosphorescent layer containing a phosphorescent compound that emits green light; and a red phosphorescent layer containing a phosphorescent compound that emits red light. Herein, the green light emission refers to a light emission in which a maximum peak wavelength of emission spectrum is in a range from 500 nm to 550 nm. Herein, the red light emission refers to a light emission in which a maximum peak wavelength of emission spectrum is in a range from 600 nm to 640 nm.

When the organic EL device according to the exemplary embodiment includes the phosphorescent emitting unit, the organic EL device also preferably includes two or more laminated emitting units. In addition, the organic EL device according to the exemplary embodiment also preferably includes one laminated emitting unit and one phosphorescent emitting unit.

Moreover, the organic EL device according to the exemplary embodiment also preferably does not include the phosphorescent emitting unit.

The FIGURE schematically shows an arrangement of an organic EL device 1 as an example of the organic EL device according to the exemplary embodiment. The organic EL device 1 is a tandem organic EL device. The organic EL device 1 includes a substrate 2, a cathode 4, an anode 3, an intermediate unit 20 provided between the cathode 4 and the anode 3, a first emitting unit 11 provided between the intermediate unit 20 and the anode 3, and a second emitting unit 12 provided between the intermediate unit 20 and the cathode 4.

In the organic EL device 1, the first emitting unit 11 is connected in series with the second emitting unit 12 via the intermediate unit 20.

The organic EL device 1 includes the first emitting unit 11 and the second emitting unit 12 as two emitting units. The first emitting unit 11 and the second emitting unit 12 in the organic EL device 1 are each the laminated emitting unit according to the exemplary embodiment. The first emitting unit 11 is sometimes referred to as a first laminated emitting unit. The second emitting unit 12 is sometimes referred to as a second laminated emitting unit.

The first emitting unit 11 includes a hole injecting layer 113, a hole transporting layer 114, a first emitting layer 111, a second emitting layer 112 and an electron transporting layer 115, which are sequentially laminated from the anode 3.

The second emitting unit 12 includes a hole transporting layer 123, a first emitting layer 121, a second emitting layer 122, an electron transporting layer 124 and an electron injecting layer 125, which are sequentially laminated from the anode 3.

The intermediate unit 20 includes a first cathode side organic layer 21 (sometimes referred to as a first N layer) and a first P layer 22, which are sequentially laminated from the anode 3.

It should be noted that the invention is not limited to the arrangement of the organic EL device shown in the FIGURE. Other arrangements of the organic EL device are exemplified by an embodiment of the emitting unit including the second emitting layer and the first emitting layer, which are sequentially laminated from the anode. It should be noted that the number of the emitting units and the intermediate units is also not limited to the arrangement of the organic EL device shown in the FIGURE. In addition, the other arrangements of the organic EL device are also exemplified by an embodiment in which the first cathode side organic layer serving as the intermediate layer not as the intermediate unit is provided between the first emitting unit and the second emitting unit.

The organic EL device according to the exemplary embodiment may be a bottom emission type organic EL device. In addition, the organic EL device according to the exemplary embodiment may be a top emission type organic EL device.

In addition, examples of the the device arrangement of the organic EL device including the laminated emitting unit and the phosphorescent emitting unit as a plurality of emitting units include (TND5) to (TND8) below.

(TND5) anode/first emitting unit (laminated emitting unit)/intermediate layer/second emitting unit (phosphorescent emitting unit)/cathode (TND6) anode/first emitting unit (laminated emitting unit)/intermediate unit/second emitting unit (phosphorescent emitting unit)/cathode (TND7) anode/first emitting unit (laminated emitting unit)/first intermediate layer/second emitting unit (phosphorescent emitting unit)/second intermediate layer/third emitting unit (laminated emitting unit)/cathode (TND8) anode/first emitting unit (laminated emitting unit)/first intermediate unit/second emitting unit (phosphorescent emitting unit)/second intermediate unit/third emitting unit (laminated emitting unit)/cathode The number of the emitting units and the intermediate layers (or the intermediate units) is not limited to the examples (TND5) to (TND8) shown above. The order of disposing the laminated emitting unit and the phosphorescent emitting unit is also not limited to the examples (TND5) to (TND8) shown above.

First Cathode Side Organic Layer

The first cathode side organic layer contains a phenanthroline compound having a phenanthroline skeleton.

The first cathode side organic layer preferably contains a phenanthroline compound and an electron donating material.

The electron donating material is preferably at least one selected from the group consisting of an electron donating metal element, metal compound and metal complex. Specifically, the electron donating material is preferably at least one selected from the group consisting of alkali metal, alkali metal compound, organic metal complex containing alkali metal, alkaline earth metal, alkaline earth metal compound, organic metal complex containing alkaline earth metal, rare earth metal, rare earth metal compound, and organic metal complex containing rare earth metal. Among these substances, the electron donating material is more preferably at least one selected from the group of alkali metal, alkaline earth metal, rare earth metal element, rare earth metal compound and rare earth metal complex. For instance, the first cathode side organic layer also preferably contains the phenanthroline compound and at least one metal selected from the group consisting of Li, Yb and Cs.

Intermediate Unit

The organic EL device according to the exemplary embodiment may include the intermediate unit between the emitting units. The intermediate unit includes a plurality of organic layers. The first cathode side organic layer may be an organic layer forming the intermediate unit.

In the organic EL device according to the exemplary embodiment, it is also preferable that the intermediate unit is disposed close to the cathode with respect to at least one laminated emitting unit and the intermediate unit includes the first cathode side organic layer.

The intermediate unit preferably includes at least one N layer and at least one P layer. The N layer is disposed closer to the anode than the P layer. In the organic EL device according to the exemplary embodiment, the intermediate unit preferably contains the first cathode side organic layer as the N layer. The intermediate unit may include, as a plurality of N layers, the first N layer disposed close to the anode and a second N layer disposed closer to the cathode than the first N layer. The first cathode side organic layer may be the first N layer or the second N layer. When the second N layer is the first cathode side organic layer, it is easy to dispose the first cathode side organic layer apart from the first emitting layer.

The N layer preferably contains a π electron-deficient compound and an electron donating material. The π electron-deficient compound is exemplified by a compound capable of coordinating with a metal atom. The π electron-deficient compound is exemplified by a phenanthroline compound, a benzimidazole compound, an azine compound, and quinolinol.

The P layer is a layer containing an acceptor material. The P layer may be a layer doped with the acceptor material (i.e., P-doped layer). The acceptor material also can be selected for use as needed from the "high hole injectable substance" exemplarily listed in the description of the hole injecting layer.

In the organic EL device according to the exemplary embodiment, a second cathode side organic layer also can be disposed between the first emitting layer and the first cathode side organic layer.

For instance, the organic EL device according to the exemplary embodiment may include the second emitting layer, the first emitting layer, the second cathode side organic layer and the first cathode side organic layer in this order from the anode. Accordingly, when the second emitting layer and the first emitting layer are provided in this order from the anode, the first emitting layer can be disposed apart from the first cathode side organic layer via the second cathode side organic layer.

In addition, for instance, the organic EL device according to the exemplary embodiment may include the first emitting layer, the second emitting layer, the second cathode side organic layer and the first cathode side organic layer in this order from the anode. It should be noted that when the first emitting layer and the second emitting layer are provided in this order from the anode, the first emitting layer can be disposed apart from the first cathode side organic layer containing a phenanthroline compound even if the second cathode side organic layer is not disposed.

In the organic EL device according to the exemplary embodiment, the second cathode side organic layer preferably does not contain a phenanthroline compound having a phenanthroline skeleton.

The second cathode side organic layer may be an N layer different from the first cathode side organic layer in the intermediate unit. For instance, the second cathode side organic layer may be the first N layer and the first cathode side organic layer may be the second N layer.

In addition, the second cathode side organic layer may be the electron transporting layer or the hole blocking layer in the emitting unit.

In the organic EL device according to the exemplary embodiment, the first emitting layer is preferably disposed 30 nm or more apart from the first cathode side organic layer. It is considered that disposing the first cathode side organic layer 30 nm or more apart from the first emitting layer makes it easy to reduce an amount of holes transferring from the laminated emitting unit to the first cathode side organic layer, resulting in the organic EL device with a longer lifetime.

In the organic EL device according to the exemplary embodiment, at least one emitting unit may be disposed between the first cathode side organic layer and the cathode.

In the organic EL device according to the exemplary embodiment, the first cathode side organic layer containing a phenanthroline compound may be disposed between the laminated emitting unit and another emitting unit different from the laminated emitting unit.

When the organic layer containing a phenanthroline compound is disposed at a position that allows for easily receiving electron injection from the cathode (for instance, in direct contact with the cathode or the electron injecting layer), the organic layer containing a phenanthroline compound easily receives electron injection and thus deterioration due to injection of holes having transferred from the emitting layer is alleviated.

Meanwhile, when the organic layer containing a phenanthroline compound is disposed between the emitting units not to undergo an activation effect by the cathode (metal electrode) and be unlikely to receive electron injection, the phenanthroline compound is likely to deteriorate due to holes.

In the organic EL device according to the exemplary embodiment, the laminated emitting unit is disposed close to the anode with respect to the first cathode side organic layer. It is thus considered that an amount of holes transferring from the laminated emitting unit to the first cathode side organic layer is reduced even when the first cathode side organic layer containing a phenanthroline compound is unlikely to receive electron injection by being disposed between the emitting units, which results in the organic EL device with a longer lifetime.

In the organic EL device according to the exemplary embodiment, the organic layer containing a phenanthroline compound may or may not be disposed closer to the cathode than the emitting unit, which is disposed closest to the cathode among the two or more emitting units.

Emitting Unit

The organic EL device according to the exemplary embodiment includes two or more emitting units. The emitting units include the respective emitting layers. The organic EL device according to the exemplary embodiment includes at least one laminated emitting unit. The laminated emitting unit includes the first emitting layer and the second emitting layer as described above.

The organic EL device according to the exemplary embodiment may include two or more laminated emitting units. Another emitting unit, which is not a laminated emitting unit, may include a single emitting layer or may include a plurality of emitting layers.

In the organic EL device according to the exemplary embodiment, the second emitting layer of the laminated emitting unit is also preferably disposed between the first emitting layer and the first cathode side organic layer. Since the second emitting layer is disposed between the first emitting layer as a recombination layer and the first cathode side organic layer containing a phenanthroline compound, even when another organic layer is not disposed between the first emitting layer and the first cathode side organic layer, the first emitting layer can be disposed apart from the first cathode side organic layer via the second emitting layer.

In the organic EL device according to the exemplary embodiment, the first emitting layer of the laminated emitting unit is also preferably disposed between the second emitting layer and the first cathode side organic layer.

The organic EL device according to the exemplary embodiment may include the first emitting layer and the second emitting layer in this order from the anode, or may include the second emitting layer and the first emitting layer in this order from the anode. In either of the orders of including the first emitting layer and the second emitting layer, the effect of the laminate arrangement of the emitting layers can be expected by selecting a combination of materials that satisfy the relationship of the numerical formula (Numerical Formula 3).

In the organic EL device according to the exemplary embodiment, when the first emitting layer and the second emitting layer are laminated in this order from the anode, it is also preferable that a hole mobility $\mu h(H1)$ of the first host material and a hole mobility $\mu h(H2)$ of the second host material satisfy a relationship of a numerical formula (Numerical Formula 31) below. When the first host material and the second host material satisfy the relationship of the numerical formula (Numerical Formula 31), the deterioration of the phenanthroline compound can be further inhibited.

$$\mu h(H1) > \mu h(H2) \qquad \text{(Numerical Formula 31)}$$

In the organic EL device according to the exemplary embodiment, when the first emitting layer and the second emitting layer are laminated in this order from the anode, it is also preferable that the hole mobility $\mu h(H1)$ of the first host material, an electron mobility $\mu e(H1)$ of the first host material, the hole mobility $\mu h(H2)$ of the second host material and an electron mobility $\mu e(H2)$ of the second host material satisfy a relationship of a numerical formula (Numerical Formula 32) below. When the first host material and the second host material satisfy the relationship of the numerical formula (Numerical Formula 32), the deterioration of the phenanthroline compound can be further inhibited.

$$(\mu e(H1)/\mu h(H1)) < (\mu e(H2)/\mu h(H2)) \qquad \text{(Numerical Formula 32)}$$

In the organic EL device according to the exemplary embodiment, when the first emitting layer and the second emitting layer are laminated in this order from the anode, it is also preferable that the electron mobility $\mu e(H1)$ of the first host material and the electron mobility $\mu e(H2)$ of the second host material satisfy a relationship of a numerical formula (Numerical Formula 33) below. When the first host material and the second host material satisfy the relationship of the numerical formula (Numerical Formula 33), a recombination ability between holes and electrons in the first emitting layer is improved.

$$\mu e(H1) < \mu e(H2) \quad \text{(Numerical Formula 33)}$$

The electron mobility can be measured according to an impedance measurement using a mobility evaluation device manufactured by the following steps. The mobility evaluation device is, for instance, manufactured by the following steps.

A compound Target, which is to be measured for an electron mobility, is vapor-deposited on a glass substrate having an aluminum electrode (anode) so as to cover the aluminum electrode, thereby forming a measurement target layer. A compound ET-A below is vapor-deposited on this measurement target layer to form an electron transporting layer. LiF is vapor-deposited on this formed electron transporting layer to form an electron injecting layer. Metal aluminum (Al) is vapor-deposited on this formed electron injecting layer to form a metal cathode.

An arrangement of the mobility evaluation device above is roughly shown as follows.

glass/Al(50)/Target(200)/ET-A(10)/LiF(1)/Al(50)

Numerals in parentheses represent a film thickness (nm).

[Formula 22]

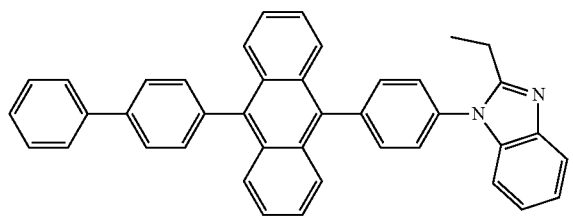

ET-A

The mobility evaluation device for an electron mobility is set in an impedance measurement device to perform an impedance measurement. In the impedance measurement, a measurement frequency is swept from 1 Hz to 1 MHz. At this time, an alternating current amplitude of 0.1 V and a direct current voltage V are applied to the device. A modulus M is calculated from a measured impedance Z using a relationship of a calculation formula (C1) below.

$$M = j\omega Z \quad \text{Calculation formula (C1):}$$

In the calculation formula (C1), j is an imaginary unit whose square is −1 and ω is an angular frequency [rad/s].

In a bode plot in which an imaginary part of the modulus M is represented by an ordinate axis and the frequency [Hz] is represented by an abscissa axis, an electrical time constant τ of the mobility evaluation device is obtained from a frequency fmax showing a peak using a calculation formula (C2) below.

$$\tau = 1/(2\pi f \text{max}) \quad \text{Calculation formula (C2):}$$

π in the calculation formula (C2) is a symbol representing a circumference ratio.

An electron mobility μe is calculated from a relationship of a calculation formula (C3-1) below using τ.

$$\mu e = d^2/(V\tau) \quad \text{Calculation formula (C3-1):}$$

d in the calculation formula (C3-1) is a total film thickness of organic thin film(s) forming the device. In a case of the arrangement of the mobility evaluation device for an electron mobility, d=210 [nm] is satisfied.

The hole mobility can be measured according to an impedance measurement using a mobility evaluation device manufactured by the following steps. The mobility evaluation device is, for instance, manufactured by the following steps.

A compound HA-2 below is vapor-deposited on a glass substrate having an ITO transparent electrode (anode) so as to cover the transparent electrode, thereby forming a hole injecting layer. A compound HT-A below is vapor-deposited on this formed hole injecting layer to form a hole transporting layer. Subsequently, a compound Target, which is to be measured for a hole mobility, is vapor-deposited to form a measurement target layer. Metal aluminum (Al) is vapor-deposited on this measurement target layer to form a metal cathode.

An arrangement of the mobility evaluation device above is roughly shown as follows.

ITO(130)/HA-2(5)/HT-A(10)/Target(200)/Al(80)

Numerals in parentheses represent a film thickness (nm).

[Formula 23]

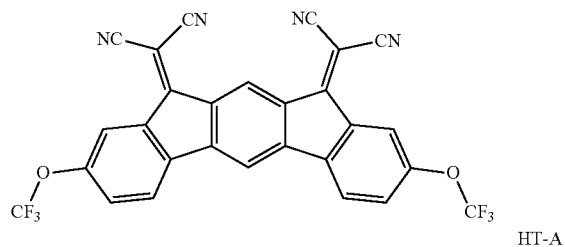

HA-2

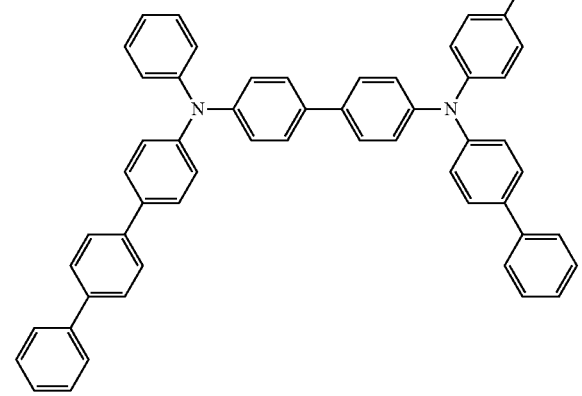

HT-A

The mobility evaluation device for a hole mobility is set in an impedance measurement device to perform an impedance measurement. In the impedance measurement, a measurement frequency is swept from 1 Hz to 1 MHz. At this time, an alternating current amplitude of 0.1 V and a direct current voltage V are applied to the device. A modulus M is calculated from a measured impedance Z using the relationship of the calculation formula (C1).

In a bode plot in which an imaginary part of the modulus M is represented by an ordinate axis and the frequency [Hz]

is represented by an abscissa axis, an electrical time constant τ of the mobility evaluation device is obtained from a frequency fmax showing a peak using the calculation formula (C2).

A hole mobility μh is calculated from a relationship of a calculation formula (C3-2) below using T obtained from the calculation formula (C2).

$$\mu h = d^2/(V\tau) \qquad \text{Calculation formula (C3-2):}$$

d in the calculation formula (C3-2) is a total film thickness of organic thin film(s) forming the device. In a case of the arrangement of the mobility evaluation device for a hole mobility, d=215 [nm] is satisfied.

The electron mobility and the hole mobility herein are each a value obtained in a case where a square root of an electric field intensity meets $E^{1/2}=500$ [$V^{1/2}/cm^{1/2}$]. The square root of an electric field intensity, $E^{1/2}$, can be calculated from a relationship of a calculation formula (C4) below.

$$E^{1/2}=V^{1/2}/d^{1/2} \qquad \text{Calculation formula (C4):}$$

For the impedance measurement, a 1260 type by Solartron Analytical is used as the impedance measurement device, and for a higher accuracy, a 1296 type dielectric constant measurement interface by Solartron Analytical can be used together therewith.

In the organic EL device according to the exemplary embodiment, the triplet energy $T_1(H1)$ of the first host material and the triplet energy $T_1(H2)$ of the second host material preferably satisfy a relationship of a numerical formula (Numerical Formula 5) below.

$$T_1(H1)-T_1(H2)>0.03 \text{ eV} \qquad \text{(Numerical Formula 5)}$$

First Emitting Layer

The first emitting layer contains the first host material. The first host material is a compound different from the second host material contained in the second emitting layer.

The first emitting layer at least contains a first emitting compound that emits light having a maximum peak wavelength of 500 nm or less. The first emitting compound is preferably a fluorescent compound that exhibits fluorescence having a maximum peak wavelength of 500 nm or less.

In the organic EL device according to the exemplary embodiment, the first emitting compound is preferably a compound containing no azine ring structure in a molecule thereof.

In the organic EL device according to the exemplary embodiment, the first emitting compound is preferably not a boron-containing complex, more preferably not a complex.

In the organic EL device according to the exemplary embodiment, the first emitting layer preferably does not contain a metal complex. Moreover, in the organic EL device according to the exemplary embodiment, the first emitting layer also preferably does not contain a boron-containing complex.

In the organic EL device according to the exemplary embodiment, the first emitting layer preferably does not contain a phosphorescent material (dopant material).

In addition, the first emitting layer preferably does not contain a heavy-metal complex and a phosphorescent rare earth metal complex. Examples of the heavy-metal complex herein include iridium complex, osmium complex, and platinum complex.

In an emission spectrum of the first emitting compound, where a peak exhibiting a maximum luminous intensity is defined as a maximum peak and a height of the maximum peak is defined as 1, heights of other peaks appearing in the emission spectrum are preferably less than 0.6. It should be noted that the peaks in the emission spectrum are defined as local maximum values.

Moreover, in the emission spectrum of the first emitting compound, the number of peaks is preferably less than three.

In the organic EL device according to the exemplary embodiment, the first emitting layer preferably emits light having a maximum peak wavelength of 500 nm or less when being driven.

The maximum peak wavelength of the light emitted from the emitting layer when being driven can be measured by the following method.

Maximum Peak Wavelength λp of Light Emitted from Emitting Layer When Organic EL Device is Driven For a maximum peak wavelength $\lambda p_1$ of light emitted from the first emitting layer when the organic EL device is driven, the organic EL device is manufactured by using the same material for the first emitting layer and the second emitting layer, and voltage is applied on the organic EL device so that a current density becomes 10 mA/cm², where spectral radiance spectrum is measured by a spectroradiometer CS-2000 (manufactured by Konica Minolta, Inc.). The maximum peak wavelength $\lambda p_1$ (unit: nm) is calculated from the obtained spectral radiance spectrum.

For a maximum peak wavelength $\lambda p_2$ of light emitted from the second emitting layer when the organic EL device is driven, the organic EL device is manufactured by using the same material for the first emitting layer and the second emitting layer, and voltage is applied on the organic EL device so that a current density becomes 10 mA/cm², where spectral radiance spectrum is measured by a spectroradiometer CS-2000 (manufactured by Konica Minolta, Inc.). The maximum peak wavelength $\lambda p_2$ (unit: nm) is calculated from the obtained spectral radiance spectrum.

In the organic EL device according to the exemplary embodiment, a singlet energy $S_1(H1)$ of the first host material and a singlet energy $S_1(D1)$ of the first emitting compound preferably satisfy a relationship of a numerical formula (Numerical Formula 20) below.

$$S_1(H1)>S_1(D1) \qquad \text{(Numerical Formula 20)}$$

The singlet energy Si means an energy difference between the lowest singlet state and the ground state.

When the first host material and the first emitting compound satisfy the relationship of the numerical formula (Numerical Formula 20), singlet excitons generated on the first host material easily transfer energy thereof from the first host material to the first emitting compound, thereby contributing to fluorescence of the first emitting compound.

In the organic EL device according to the exemplary embodiment, the triplet energy $T_1(H1)$ of the first host material and a triplet energy $T_1(D1)$ of the first emitting compound preferably satisfy a relationship of a numerical formula (Numerical Formula 20A) below.

$$T_1(D1)>T_1(H1) \qquad \text{(Numerical Formula 20A)}$$

When the first host material and the first emitting compound satisfy the relationship of the numerical formula (Numerical Formula 20A), triplet excitons generated in the first emitting layer are transferred not onto the the first emitting compound having higher triplet energy but onto the first host material, thereby being easily transferred to the second emitting layer.

The organic EL device according to the exemplary embodiment preferably satisfies a relationship of a numerical formula (Numerical Formula 20B) below.

$$T_1(D1)>T_1(H1)>T_1(H2) \qquad \text{(Numerical Formula 20B)}$$

In the organic EL device according to the exemplary embodiment, the first emitting compound is preferably contained at more than 1.1 mass % in the first emitting layer. Specifically, the first emitting layer preferably contains the first emitting compound at more than 1.1 mass % relative to a total mass amount of the first emitting layer, more preferably at 1.2 mass % or more relative to the total mass amount of the first emitting layer, further preferably at 1.5 mass % or more relative to the total mass amount of the first emitting layer.

The first emitting layer preferably contains the first emitting compound at 10 mass % or less relative to the total mass amount of the first emitting layer, more preferably at 7 mass % or less relative to the total mass amount of the first emitting layer, further preferably at 5 mass % or less relative to the total mass amount of the first emitting layer.

In the organic EL device according to the exemplary embodiment, the first emitting layer preferably contains a first compound as the first host material at 60 mass % or more relative to the total mass amount of the first emitting layer, more preferably at 70 mass % or more relative to the total mass amount of the first emitting layer, further preferably at 80 mass % or more relative to the total mass amount of the first emitting layer, further more preferably at 90 mass % or more relative to the total mass amount of the first emitting layer, still further preferably at 95 mass % or more relative to the total mass amount of the first emitting layer.

The first emitting layer preferably contains the first host material at 99 mass % or less relative to the total mass amount of the first emitting layer.

It should be noted that when the first emitting layer contains the first host material and the first emitting compound, an upper limit of the total of the respective content ratios of the first host material and the first emitting compound is 100 mass %.

It is not excluded that the first emitting layer according to the exemplary embodiment further contains a material(s) other than the first host material and the first emitting compound.

The first emitting layer may include a single type of the first host material or may include two or more types of the first host material. The first emitting layer may include a single type of the first emitting compound or may include two or more types of the first emitting compound.

In the organic EL device according to the exemplary embodiment, the film thickness of the first emitting layer is preferably 3 nm or more, more preferably 5 nm or more. When the film thickness of the first emitting layer is 3 nm or more, the film thickness is sufficient to cause recombination of holes and electrons in the first emitting layer.

In the organic EL device according to the exemplary embodiment, the film thickness of the first emitting layer is preferably 15 nm or less, more preferably 10 nm or less. When the film thickness of the first emitting layer is 15 nm or less, the film thickness is sufficiently thin to allow for transfer of triplet excitons to the second emitting layer.

In the organic EL device according to the exemplary embodiment, the film thickness of the first emitting layer is more preferably in a range from 3 nm to 15 nm.

Second Emitting Layer

The second emitting layer contains the second host material. The second host material is a compound different from the first host material contained in the first emitting layer.

The second emitting layer at least contains a second emitting compound that emits light having a maximum peak wavelength of 500 nm or less. The second emitting compound is preferably a fluorescent compound that exhibits fluorescence having a maximum peak wavelength of 500 nm or less.

A measurement method of the maximum peak wavelength of a compound is as follows.

In the organic EL device according to the exemplary embodiment, the second emitting layer preferably emits light having a maximum peak wavelength of 500 nm or less when being driven.

In the organic EL device according to the exemplary embodiment, a half bandwidth of a maximum peak of the second emitting compound is preferably in a range from 1 nm to 20 nm.

In the organic EL device according to the exemplary embodiment, a Stokes shift of the second emitting compound preferably exceeds 7 nm.

When the Stokes shift of the second emitting compound is more than 7 nm, a reduction in luminous efficiency due to self-absorption is likely to be prevented.

The self-absorption is a phenomenon that emitted light is absorbed by the same compound to reduce luminous efficiency. The self-absorption is notably observed in a compound having a small Stokes shift (i.e., a large overlap between an absorption spectrum and a fluorescence spectrum). Accordingly, in order to inhibit the self-absorption, it is preferable to use a compound having a large Stokes shift (i.e., a small overlap between the absorption spectrum and the fluorescence spectrum). The Stokes shift can be measured by the following method.

A measurement target compound is dissolved in toluene at a concentration of $2.0 \times 10^{-5}$ mol/L to prepare a measurement sample. The measurement sample is put into a quartz cell and is irradiated with continuous light falling within an ultraviolet-to-visible region at a room temperature (300K) to measure an absorption spectrum (ordinate axis: absorbance, abscissa axis: wavelength). A spectrophotometer such as a spectrophotometer U-3900/3900H manufactured by Hitachi High-Tech Science Corporation can be used for the absorption spectrum measurement. Moreover, a measurement target compound is dissolved in toluene at a concentration of $4.9 \times 10^{-6}$ mol/L to prepare a measurement sample. The measurement sample is put into a quartz cell and is irradiated with excited light at a room temperature (300K) to measure fluorescence spectrum (ordinate axis: fluorescence intensity, abscissa axis: wavelength). A spectrophotometer can be used for the fluorescence spectrum measurement. For instance, a spectrophotofluorometer F-7000 manufactured by Hitachi High-Tech Science Corporation can be used for the measurement.

A difference between an absorption local maximum wavelength and a fluorescence local maximum wavelength is calculated from the absorption spectrum and the fluorescence spectrum to obtain a Stokes shift (SS). A unit of the Stokes shift (SS) is denoted by nm.

In the organic EL device according to the exemplary embodiment, a triplet energy $T_1(D2)$ of the second emitting compound and the triplet energy $T_1(H2)$ of the second host material preferably satisfy a relationship of a numerical formula (Numerical Formula 3A) below.

$$T_1(D2) > T_1(H2) \qquad \text{(Numerical Formula 3A)}$$

In the organic EL device according to the exemplary embodiment, when the second emitting compound and the second host material satisfy the relationship of the numerical formula (Numerical Formula 3A), in transfer of triplet excitons generated in the first emitting layer to the second emitting layer, the triplet excitons transfer energy thereof not onto the second emitting compound having higher triplet energy but onto molecules of the second host material. In addition, triplet excitons generated by recombination of holes and electrons on the second host material do not transfer to the second emitting compound having higher triplet energy. Triplet excitons generated by recombination on molecules of the second emitting compound quickly transfer energy thereof to molecules of the second host material.

Triplet excitons in the second host material do not transfer to the second emitting compound but efficiently collide with one another on the second host material to generate singlet excitons by the TTF phenomenon.

In the organic EL device according to the exemplary embodiment, a singlet energy $S_1$ (H2) of the second host material and a singlet energy $S_1$(D2) of the second emitting compound preferably satisfy a relationship of a numerical formula (Numerical Formula 4) below.

$$S_1(H2) > S_1(D2) \quad \text{(Numerical Formula 4)}$$

In the organic EL device according to the exemplary embodiment, when the second emitting compound and the second host material satisfy the relationship of the numerical formula (Numerical formula 4), due to the singlet energy of the second emitting compound being smaller than the singlet energy of the second host material, singlet excitons generated by the TTF phenomenon transfer energy thereof from the second host material to the second emitting compound, thereby contributing to fluorescence of the second emitting compound.

In the organic EL device according to the exemplary embodiment, the second emitting compound is preferably a compound containing no azine ring structure in a molecule thereof.

In the organic EL device according to the exemplary embodiment, the second emitting compound is preferably not a boron-containing complex, more preferably not a complex.

In the organic EL device according to the exemplary embodiment, the second emitting layer preferably does not contain a metal complex. Moreover, in the organic EL device according to the exemplary embodiment, the second emitting layer also preferably does not contain a boron-containing complex.

In the organic EL device according to the exemplary embodiment, the second emitting layer preferably does not contain a phosphorescent material (dopant material).

In addition, the second emitting layer preferably does not contain a heavy-metal complex and a phosphorescent rare earth metal complex. Examples of the heavy-metal complex herein include iridium complex, osmium complex, and platinum complex.

In the organic EL device according to the exemplary embodiment, the second emitting compound is preferably contained at more than 1.1 mass % in the second emitting layer. Specifically, the second emitting layer preferably contains the second emitting compound at more than 1.1 mass % relative to a total mass amount of the second emitting layer, more preferably at 1.2 mass % or more relative to the total mass amount of the second emitting layer, further preferably at 1.5 mass % or more relative to the total mass amount of the second emitting layer.

The second emitting layer preferably contains the second emitting compound at 10 mass % or less relative to the total mass amount of the second emitting layer, more preferably at 7 mass % or less relative to the total mass amount of the second emitting layer, further preferably at 5 mass % or less relative to the total mass amount of the second emitting layer.

The second emitting layer preferably contains a second compound as the second host material at 60 mass % or more relative to the total mass amount of the second emitting layer, more preferably at 70 mass % or more relative to the total mass amount of the second emitting layer, further preferably at 80 mass % or more relative to the total mass amount of the second emitting layer, further more preferably at 90 mass % or more relative to the total mass amount of the second emitting layer, still further preferably at 95 mass % or more relative to the total mass amount of the second emitting layer.

The second emitting layer preferably contains the second host material at 99 mass % or less relative to the total mass amount of the second emitting layer.

When the second emitting layer contains the second host material and the second emitting compound, an upper limit of the total of the respective content ratios of the second host material and the second emitting compound is 100 mass %.

It is not excluded that the second emitting layer according to the exemplary embodiment further contains a material(s) other than the second host material and the second emitting compound.

The second emitting layer may include a single type of the second host material or may include two or more types of the second host material. The second emitting layer may include a single type of the second emitting compound or may include two or more types of the second emitting compound.

In the organic EL device according to the exemplary embodiment, the film thickness of the second emitting layer is preferably 5 nm or more, more preferably 15 nm or more. When the film thickness of the second emitting layer is 5 nm or more, it is easy to inhibit triplet excitons having transferred from the first emitting layer to the second emitting layer from returning to the first emitting layer. Further, when the film thickness of the second emitting layer is 5 nm or more, triplet excitons can be sufficiently separated from the recombination portion in the first emitting layer.

In the organic EL device according to the exemplary embodiment, the film thickness of the second emitting layer is preferably 25 nm or less, more preferably 20 nm or less. When the film thickness of the second emitting layer is 25 nm or less, a density of the triplet excitons in the second emitting layer is improved to cause the TTF phenomenon more easily.

In the organic EL device according to the exemplary embodiment, the film thickness of the second emitting layer is preferably in a range from 5 nm to 25 nm.

In the organic EL device according to the exemplary embodiment, a triplet energy $T_1$(DX) of the first emitting compound or the second emitting compound, the triplet energy $T_1$(H1) of the first host material and the triplet energy $T_1$(H2) of the second host material preferably satisfy a relationship of a numerical formula (Numerical Formula 10) below.

$$2.6 \text{ eV} > T_1(DX) > T_1(H1) > T_1(H2) \quad \text{(Numerical Formula 10)}$$

The triplet energy $T_1$(D1) of the first emitting compound preferably satisfies a relationship of a numerical formula (Numerical Formula 10A) below.

$$2.6 \text{ eV} > T_1(D1) > T_1(H1) > T_1(H2) \quad \text{(Numerical Formula 10A)}$$

The triplet energy $T_1$(D2) of the second emitting compound preferably satisfies a relationship of a numerical formula (Numerical Formula 10B) below.

$$2.6 \text{ eV} > T_1(D2) > T_1(H1) > T_1(H2) \quad \text{(Numerical Formula 10B)}$$

In the organic EL device according to the exemplary embodiment, the triplet energy $T_1(DX)$ of the first emitting compound or the second emitting compound and the triplet energy $T_1(H1)$ of the first host material preferably satisfy a relationship of a numerical formula (Numerical Formula 11) below.

$$0\text{ eV} < T_1(DX) - T_1(H1) < 0.6\text{ eV} \quad \text{(Numerical Formula 11)}$$

The triplet energy $T_1(D1)$ of the first emitting compound preferably satisfies a relationship of a numerical formula (Numerical Formula 11A) below.

$$0\text{ eV} < T_1(D1) - T_1(H1) < 0.6\text{ eV} \quad \text{(Numerical Formula 11A)}$$

The triplet energy $T_1(D2)$ of the second emitting compound preferably satisfies a relationship of a numerical formula (Numerical Formula 11B) below.

$$0\text{ eV} < T_1(D2) - T_1(H2) < 0.8\text{ eV} \quad \text{(Numerical Formula 11B)}$$

In the organic EL device according to the exemplary embodiment, the triplet energy $T_1(H1)$ of the first host material preferably satisfies a relationship of a numerical formula (Numerical Formula 12) below.

$$T_1(H1) > 2.0\text{ eV} \quad \text{(Numerical Formula 12)}$$

In the organic EL device according to the exemplary embodiment, the triplet energy $T_1(H1)$ of the first host material also preferably satisfies a relationship of a numerical formula (Numerical Formula 12A) below, or also preferably satisfies a relationship of a numerical formula (Numerical Formula 12B) below.

$$T_1(H1) > 2.10\text{ eV} \quad \text{(Numerical Formula 12A)}$$

$$T_1(H1) > 2.15\text{ eV} \quad \text{(Numerical Formula 12B)}$$

In the organic EL device according to the exemplary embodiment, when the triplet energy $T_1(H1)$ of the first host material satisfies the relationship of the numerical formula (Numerical Formula 12A) or the numerical formula (Numerical Formula 12B), triplet excitons generated in the first emitting layer are easily transferred to the second emitting layer, and also easily inhibited from back-transferring from the second emitting layer to the first emitting layer. Consequently, singlet excitons are efficiently generated in the second emitting layer, thereby improving luminous efficiency.

In the organic EL device according to the exemplary embodiment, the triplet energy $T_1(H1)$ of the first host material also preferably satisfies a relationship of a numerical formula (Numerical Formula 12C) below, or also preferably satisfies a relationship of a numerical formula (Numerical Formula 12D) below.

$$2.08\text{ eV} > T_1(H1) > 1.87\text{ eV} \quad \text{(Numerical Formula 12C)}$$

$$2.05\text{ eV} > T_1(H1) > 1.90\text{ eV} \quad \text{(Numerical Formula 12D)}$$

In the organic EL device according to the exemplary embodiment, when the triplet energy $T_1(H1)$ of the first host material satisfies the relationship of the numerical formula (Numerical Formula 12C) or the numerical formula (Numerical Formula 12D), energy of the triplet excitons generated in the first emitting layer is reduced, so that the organic EL device can be expected to have a longer lifetime.

In the organic EL device according to the exemplary embodiment, the triplet energy $T_1(D1)$ of the first emitting compound also preferably satisfies a relationship of a numerical formula (Numerical Formula 14A) below, or also preferably satisfies a relationship of a numerical formula (Numerical Formula 14B) below.

$$2.60\text{ eV} > T_1(D1) \quad \text{(Numerical Formula 14A)}$$

$$2.50\text{ eV} > T_1(D1) \quad \text{(Numerical Formula 14B)}$$

When the first emitting layer contains the first emitting compound that satisfies the relationship of the numerical formula (Numerical Formula 14A) or (Numerical Formula 14B), the organic EL device has a longer lifetime.

In the organic EL device according to the exemplary embodiment, the triplet energy $T_1(D2)$ of the second emitting compound also preferably satisfies a relationship of a numerical formula (Numerical Formula 14C) below, or also preferably satisfies a relationship of a numerical formula (Numerical Formula 14D) below.

$$2.60\text{ eV} > T_1(D2) \quad \text{(Numerical Formula 14C)}$$

$$2.50\text{ eV} > T_1(D2) \quad \text{(Numerical Formula 14D)}$$

When the second emitting layer contains the compound that satisfies the relationship of the numerical formula (Numerical Formula 14C) or (Numerical Formula 14D), the organic EL device has a longer lifetime.

In the organic EL device according to the exemplary embodiment, the triplet energy $T_1(H2)$ of the second host material preferably satisfies a relationship of a numerical formula (Numerical Formula 13) below.

$$T_1(H2) \geq 1.9\text{ eV} \quad \text{(Numerical Formula 13)}$$

Third Emitting Layer

The organic EL device according to the exemplary embodiment may include a third emitting layer.

It is preferable that: the third emitting layer contains a third host material; the first host material, the second host material and the third host material are different from one another; the third emitting layer at least contains a third emitting compound that emits light having a maximum peak wavelength of 500 nm or less; the first emitting compound, the second emitting compound and the third emitting compound are mutually the same or different; and the triplet energy $T_1(H1)$ of the first host material and a triplet energy $T_1(H3)$ of the third host material satisfy a relationship of a numerical formula (Numerical Formula 1A) below.

$$T_1(H1) > T_1(H3) \quad \text{(Numerical Formula 1A)}$$

When the organic EL device according to the exemplary embodiment includes the third emitting layer, the triplet energy $T_1(H2)$ of the second host material and the triplet energy $T_1(H3)$ of the third host material preferably satisfy a relationship of a numerical formula (Numerical Formula 1B) below.

$$T_1(H2) > T_1(H3) \quad \text{(Numerical Formula 1B)}$$

In the organic EL device according to the exemplary embodiment, the first emitting layer and the second emitting layer are preferably in direct contact with each other.

Herein, a layer arrangement that the first emitting layer and the second emitting layer are in direct contact with each other can include one of embodiments (LS1), (LS2) and (LS3) below.

(LS1) An embodiment in which a region containing both the first host material and the second host material is generated in a process of vapor-depositing the compound of the first emitting layer and vapor-depositing the compound of the second emitting layer, and is present on the interface between the first emitting layer and the second emitting layer.

(LS2) An embodiment in which in a case of containing an emitting compound in the first emitting layer and the second emitting layer, a region containing all of the first host material, the second host material and the emitting compound is generated in a process of vapor-depositing the compound of the first emitting layer and vapor-depositing the compound of the second emitting layer, and is present on the interface between the first emitting layer and the second emitting layer.

(LS3) An embodiment in which in a case of containing an emitting compound in the first emitting layer and the second emitting layer, a region containing the emitting compound, a region containing the first host material or a region containing the second host material is generated in a process of vapor-depositing the compound of the first emitting layer and vapor-depositing the compound of the second emitting layer, and is present on the interface between the first emitting layer and the second emitting layer.

When the organic EL device according to the exemplary embodiment contains the third emitting layer, it is preferable that the first emitting layer and the second emitting layer are in direct contact with each other and the second emitting layer and the third emitting layer are in direct contact with each other.

Herein, a layer arrangement that the second emitting layer and the third emitting layer are in direct contact with each other can include one of embodiments (LS4), (LS5) and (LS6) below.

(LS4) An embodiment in which a region containing both the second host material and the third host material is generated in a process of vapor-depositing the compound of the second emitting layer and vapor-depositing the compound of the third emitting layer, and is present on the interface between the second emitting layer and the third emitting layer.

(LS5) An embodiment in which in a case of containing an emitting compound in the second emitting layer and the third emitting layer, a region containing all of the second host material, the third host material and the emitting compound is generated in a process of vapor-depositing the compound of the second emitting layer and vapor-depositing the compound of the third emitting layer, and is present on the interface between the second emitting layer and the third emitting layer.

(LS6) An embodiment in which in a case of containing an emitting compound in the second emitting layer and the third emitting layer, a region containing the emitting compound, a region containing the second host material or a region containing the third host material is generated in a process of vapor-depositing the compound of the second emitting layer and vapor-depositing the compound of the third emitting layer, and is present on the interface between the second emitting layer and the third emitting layer.

For instance, in the organic EL device according to the exemplary embodiment, the first emitting layer containing the first compound represented by a formula (1) and the like as the first host material may be in direct contact with the second emitting layer containing the the second compound represented by a formula (2) and the like as the second host material. By thus layering the first emitting layer and the second emitting layer, the generated singlet excitons and the triplet excitons can be efficiently used and, consequently, the luminous efficiency of the organic EL device can be improved.

Layer Containing No Emitting Compound

In addition, it is also preferable that the laminated emitting unit of the organic EL device according to the exemplary embodiment is disposed between the organic layers, and further includes a layer containing no emitting compound (sometimes referred to as an interposed layer).

When the laminated emitting unit of the organic EL device according to the exemplary embodiment includes the layer containing no emitting compound (interposed layer), the layer containing no emitting compound (interposed layer) is preferably disposed between the first emitting layer and the second emitting layer.

The interposed layer preferably does not contain a metal atom.

The interposed layer contains an organic material. The organic material contained in the interposed layer is preferably not an emitting compound.

Examples of the organic material contained in the interposed layer include: 1) a heterocyclic compound such as an oxadiazole derivative, benzimidazole derivative, or phenanthroline derivative; 2) a fused aromatic compound such as a carbazole derivative, anthracene derivative, phenanthrene derivative, pyrene derivative or chrysene derivative; and 3) an aromatic amine compound such as a triarylamine derivative or a fused polycyclic aromatic amine derivative.

The organic material contained in the interposed layer may be one or both of the first host material contained in the first emitting layer and the second host material contained in the second emitting layer.

When the interposed layer contains a plurality of organic materials, the content ratios thereof are each preferably at 10 mass % or more relative to the total mass amount of the interposed layer.

The interposed layer preferably contains the organic material at 60 mass % or more relative to the total mass amount of the interposed layer, more preferably at 70 mass % or more relative to the total mass amount of the interposed layer, further preferably at 80 mass % or more relative to the total mass amount of the interposed layer, further more preferably at 90 mass % or more relative to the total mass amount of the interposed layer, still further preferably at 95 mass % or more relative to the total mass amount of the interposed layer.

The interposed layer may include a single type of the organic material or may include two or more types of the organic material.

When the interposed layer contains two or more types of the organic material, an upper limit of the total of the respective content ratios of the two or more types of the organic material is 100 mass %.

It is not excluded that the interposed layer according to the exemplary embodiment further contains a material(s) other than the organic material.

The interposed layer may be provided in the form of a single layer or a laminate of two or more layers.

A film thickness of the interposed layer is not particularly limited but each layer in the interposed layer is preferably in a range from 3 nm to 15 nm, more preferably in a range from 5 nm to 10 nm.

In the first compound and the second compound, it is preferable that all groups described as "substituted or unsubstituted" groups are "unsubstituted" groups.

Herein, the "host material" refers to, for instance, a material that accounts for "50 mass % or more of the layer." Accordingly, for instance, the first emitting layer contains 50 mass % or more first compound represented by the formula (1) below with respect to a total mass of the first emitting layer. The second emitting layer contains 50 mass % or more second compound represented by the formula (2) below with respect to a total mass of the second emitting layer.
Phenanthroline Compound It is preferable that the phenanthroline compound is a compound that has at least one group represented by a formula (21) below and is represented by a formula (20) below.

[Formula 24]

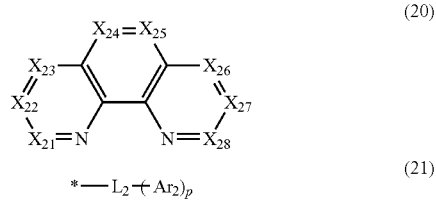

(20)

$$*—L_2\!\!-\!\!(Ar_2)_p \quad (21)$$

In the formula (20):

$X_{21}$ to $X_{28}$ are each independently a nitrogen atom, $CR_{21}$, or a carbon atom bonded to a group represented by the formula (21);

at least one of $X_{21}$ to $X_{28}$ is a carbon atom bonded to a group represented by the formula (21);

when a plurality of groups represented by the formula (21) are present, the plurality of groups represented by the formula (21) are mutually the same or different;

at least one combination of adjacent two or more of the plurality of $R_{21}$ are mutually bonded to form a substituted or unsubstituted monocyclic ring, mutually bonded to form a substituted or unsubstituted fused ring, or not mutually bonded; and $R_{21}$ not forming the substituted or unsubstituted monocyclic ring and not forming the substituted or unsubstituted fused ring are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a substituted or unsubstituted aralkyl group having 7 to 50 carbon atoms, a group represented by —C(=O)$R_{931}$, a group represented by —COO$R_{932}$, a group represented by —S(=O)$_2R_{933}$, a group represented by —B($R_{934}$)($R_{935}$), a group represented by —P(=O)($R_{936}$)($R_{937}$), a halogen atom, a cyano group, a nitro group, a substituted or unsubstituted aryl group having 6 to 50 ring carbon atoms, or a substituted or unsubstituted heterocyclic group having 5 to 50 ring atoms.

In the formula (21):

$Ar_2$ is a substituted or unsubstituted aryl group having 6 to 50 ring carbon atoms, or a substituted or unsubstituted heterocyclic group having 5 to 50 ring atoms;

p is 1, 2, 3, 4 or 5;

when two or more $Ar_2$ are present, the two or more $Ar_2$ are mutually the same or different;

$L_2$ is a single bond or a linking group;

$L_2$ as the linking group is a substituted or unsubstituted polyvalent linear, branched or cyclic aliphatic hydrocarbon group having 1 to 50 carbon atoms, a substituted or unsubstituted polyvalent aromatic hydrocarbon group having 6 to 50 ring carbon atoms, a substituted or unsubstituted polyvalent heterocyclic group having 5 to 50 ring atoms, or a polyvalent multiple linking group provided by bonding two or three groups selected from the polyvalent aromatic hydrocarbon ring group and the polyvalent heterocyclic group;

the aromatic hydrocarbon ring group and the heterocyclic group forming the multiple linking group are mutually the same or different, and adjacent ones thereof are mutually bonded to form a ring, or not mutually bonded;

$Ar_2$ and $L_2$ as the linking group are mutually bonded to form a ring, or not mutually bonded;

$L_2$ as the linking group, and a carbon atom in one of $X_{21}$ to $X_{28}$ adjacent to a carbon atom bonded to $L_2$, or $R_{21}$ in $CR_{21}$ are mutually bonded to form a ring, or not mutually bonded; and

* in the formula (21) represents a bonding position to the ring represented by the formula (20).

In the phenanthroline compound: $R_{901}$, $R_{902}$, $R_{903}$, $R_{904}$, $R_{905}$, $R_{906}$, $R_{907}$, $R_{931}$, $R_{932}$, $R_{933}$, $R_{934}$, $R_{935}$, $R_{936}$ and $R_{937}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when a plurality of $R_{901}$ are present, the plurality of $R_{901}$ are mutually the same or different;

when a plurality of $R_{902}$ are present, the plurality of $R_{902}$ are mutually the same or different;

when a plurality of $R_{903}$ are present, the plurality of $R_{903}$ are mutually the same or different;

when a plurality of $R_{904}$ are present, the plurality of $R_{904}$ are mutually the same or different;

when a plurality of $R_{905}$ are present, the plurality of $R_{905}$ are mutually the same or different;

when a plurality of $R_{906}$ are present, the plurality of $R_{906}$ are mutually the same or different;

when a plurality of $R_{907}$ are present, the plurality of $R_{907}$ are mutually the same or different;

when a plurality of $R_{931}$ are present, the plurality of $R_{931}$ are mutually the same or different;

when a plurality of $R_{932}$ are present, the plurality of $R_{932}$ are mutually the same or different;

when a plurality of $R_{933}$ are present, the plurality of $R_{933}$ are mutually the same or different;

when a plurality of $R_{934}$ are present, the plurality of $R_{934}$ are mutually the same or different;

when a plurality of $R_{935}$ are present, the plurality of $R_{935}$ are mutually the same or different;

when a plurality of $R_{936}$ are present, the plurality of $R_{936}$ are mutually the same or different; and when a plurality of $R_{937}$ are present, the plurality of $R_{937}$ are mutually the same or different.

Herein, a group represented by —O—($R_{904}$) is a hydroxy group when $R_{904}$ is a hydrogen atom.

Herein, a group represented by —S—($R_{905}$) is a thiol group when $R_{905}$ is a hydrogen atom.

Herein, a group represented by —S(=O)$_2R_{933}$ is a substituted sulfo group when $R_{933}$ is a substituent.

Herein, a group represented by —B($R_{934}$)($R_{935}$) is a substituted boryl group when $R_{934}$ and $R_{935}$ are substituents.

Herein, a group represented by —P(=O)($R_{936}$)($R_{937}$) is a substituted phosphine oxide group when $R_{936}$ and $R_{937}$ are substituents, and is an arylphosphoryl group when $R_{936}$ and $R_{937}$ are aryl groups.

An "unsubstituted polyvalent linear, branched or cyclic aliphatic hydrocarbon group" mentioned herein has, unless otherwise specified herein, 1 to 50, preferably 1 to 20, more preferably 1 to 6 carbon atoms.

An "unsubstituted polyvalent aromatic hydrocarbon group" mentioned herein has, unless otherwise specified herein, 6 to 50, preferably 6 to 30, more preferably 6 to 18 ring carbon atoms.

An "unsubstituted polyvalent heterocyclic group" mentioned herein has, unless otherwise specified herein, 5 to 50, preferably 5 to 30, more preferably 5 to 18 ring atoms.

A substituted or unsubstituted group derived from a cyclic structure represented by the formula (20) is preferably included as a heterocyclic group having 5 to 50 ring atoms in $Ar_2$ of the formula (21).

$X_{21}$ and $X_{28}$ in the formula (20) are also preferably a carbon atom bonded to a group represented by the formula (21).

In the formula (20), it is also preferable that one of $X_{21}$ and $X_{28}$ is a carbon atom bonded to a group represented by the formula (21), and the other of $X_{21}$ and $X_{28}$ is a carbon atom bonded to a hydrogen atom.

$X_{21}$ to $X_{28}$ in the formula (20) are preferably each independently $CR_{21}$ or a carbon atom bonded to a group represented by the formula (21).

$X_{21}$ to $X_{28}$ in the formula (20) not being a carbon atom bonded to a group represented by the formula (21) are preferably $CR_{21}$. In other words, the compound represented by the formula (20) is preferably a 1,10-phenanthroline derivative.

$Ar_2$ in the formula (21) is also preferably a substituted or unsubstituted fused aromatic hydrocarbon group having 8 to 20 ring carbon atoms.

The fused aromatic hydrocarbon group having 8 to 20 ring carbon atoms is also preferably a group derived from aromatic hydrocarbon selected from the group consisting of, for instance, naphthalene, anthracene, acephenanthrylene, aceanthrylene, benzanthracene, triphenylene, pyrene, chrysene, naphthacene, fluorene, phenanthrene, fluoranthene and benzofluoranthene.

$Ar_2$ in the formula (21) is also preferably a substituted or unsubstituted anthryl group.

$Ar_2$ in the formula (21) is also preferably a substituted or unsubstituted heterocyclic group having 5 to 40 ring carbon atoms.

$Ar_2$ in the formula (21) is also preferably a substituted or unsubstituted group derived from a cyclic structure represented by the formula (20).

$Ar_2$ in the formula (21) is also preferably a group represented by a formula (23) below.

[Formula 25]

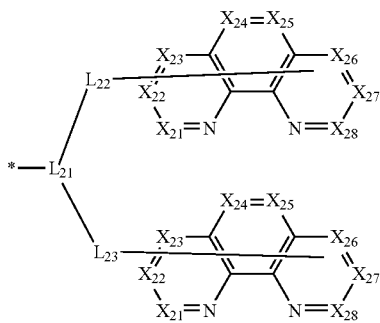

(23)

In the formula (23):

$X_{21}$ to $X_{28}$ are each independently a nitrogen atom, $CR_{21}$, a group represented by the formula (21), or a carbon atom bonded to $L_{22}$ or $L_{23}$, $L_{21}$ is a linking group, and $L_{21}$ as the linking group is a substituted or unsubstituted trivalent linear, branched or cyclic aliphatic hydrocarbon group having 1 to 50 carbon atoms, a substituted or unsubstituted trivalent aromatic hydrocarbon group having 6 to 50 ring carbon atoms, or a substituted or unsubstituted trivalent heterocyclic group having 5 to 50 ring atoms; and $L_{22}$ and $L_{23}$ are each independently a single bond or a linking group, and $L_{22}$ and $L_{23}$ as the linking group are each independently a substituted or unsubstituted divalent linear, branched or cyclic aliphatic hydrocarbon group having 1 to 50 carbon atoms, a substituted or unsubstituted arylene group having 6 to 50 ring carbon atoms, or a substituted or unsubstituted divalent heterocyclic group having 5 to 50 ring atoms.

In the formula of the phenanthroline compound:
when a plurality of $X_{21}$ are present, the plurality of $X_{21}$ are mutually the same or different;
when a plurality of $X_{22}$ are present, the plurality of $X_{22}$ are mutually the same or different;
when a plurality of $X_{23}$ are present, the plurality of $X_{23}$ are mutually the same or different;
when a plurality of $X_{24}$ are present, the plurality of $X_{24}$ are mutually the same or different;
when a plurality of $X_{25}$ are present, the plurality of $X_{25}$ are mutually the same or different;
when a plurality of $X_{26}$ are present, the plurality of $X_{26}$ are mutually the same or different;
when a plurality of $X_{27}$ are present, the plurality of $X_{27}$ are mutually the same or different; and
when a plurality of $X_{28}$ are present, the plurality of $X_{28}$ are mutually the same or different.

$X_{21}$ to $X_{28}$ in the formula (23) are preferably each independently a nitrogen atom, $CR_{21}$, or a carbon atom bonded to $L_{22}$ or $L_{23}$, more preferably $CR_{21}$, or a carbon atom bonded to $L_{22}$ or $L_{23}$.

The phenanthroline compound is also preferably a compound represented by a formula (24) below.

[Formula 26]

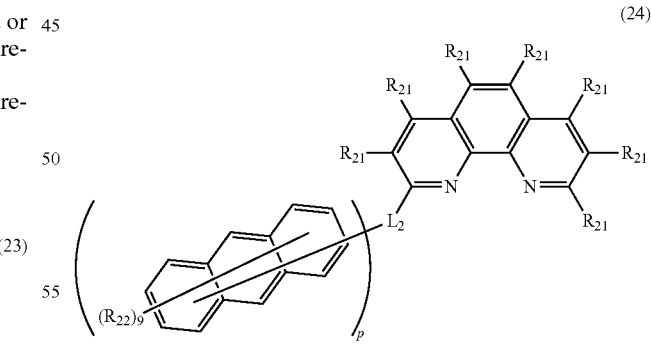

(24)

In the formula (24):
a plurality of $R_{21}$ each independently represent the same as $R_{21}$ in the formula (20);
a plurality of $R_{22}$ each independently represent the same as $R_{21}$ in the formula (20);
$L_2$ represents the same as $L_2$ in the formula (21);
p is 1, 2, 3, 4 or 5; and
the plurality of $R_{22}$ and $L_2$ are each bonded to a carbon atom at one of positions 1 to 10 of an anthracene ring.

The phenanthroline compound is also preferably a compound represented by a formula (24A) below.

[Formula 27]

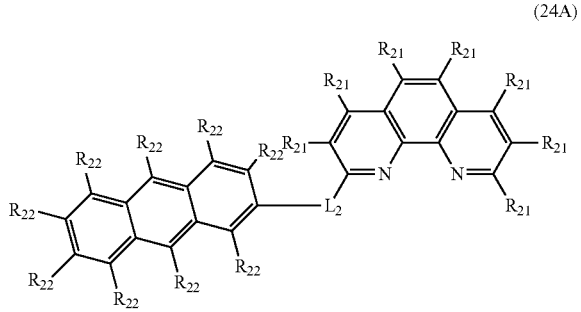

(24A)

In the formula (24A):

a plurality of $R_{21}$ each independently represent the same as $R_{21}$ in the formula (20);

a plurality of $R_{22}$ each independently represent the same as $R_{21}$ in the formula (20); and $L_2$ represents the same as $L_2$ in the formula (21).

The phenanthroline compound is also preferably a compound represented by a formula (24B) below.

[Formula 28]

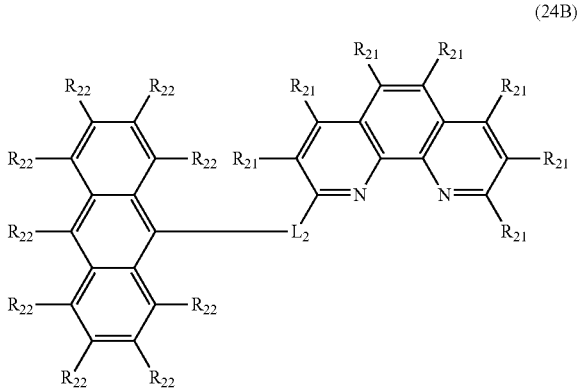

(24B)

In the formula (24B):

a plurality of $R_{21}$ each independently represent the same as $R_{21}$ in the formula (20);

a plurality of $R_{22}$ each independently represent the same as $R_{21}$ in the formula (20); and $L_2$ represents the same as $L_2$ in the formula (21).

The phenanthroline compound is also preferably a compound represented by a formula (25) below.

[Formula 29]

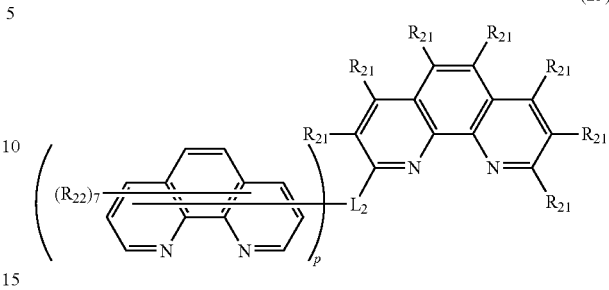

(25)

In the formula (25):

a plurality of $R_{21}$ each independently represent the same as $R_{21}$ in the formula (20);

a plurality of $R_{22}$ each independently represent the same as $R_{21}$ in the formula (20);

$L_2$ represents the same as $L_2$ in the formula (21);

p is 1, 2, 3, 4 or 5; and the plurality of $R_{22}$ and $L_2$ are each bonded to a carbon atom at one of positions 2 to 9 of a phenanthroline ring.

The phenanthroline compound is also preferably a compound represented by a formula (25A) below.

[Formula 30]

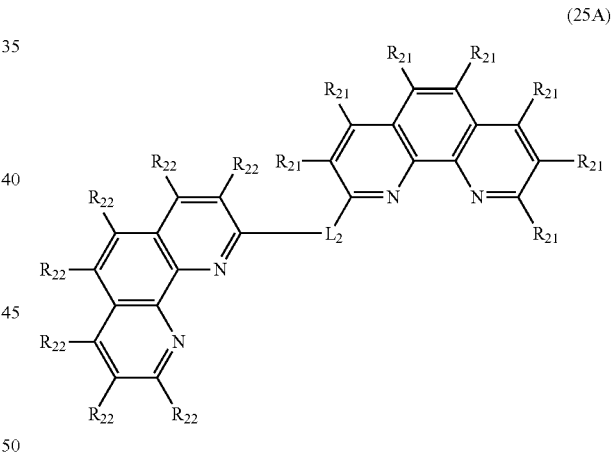

(25A)

In the formula (25A):

a plurality of $R_{21}$ each independently represent the same as $R_{21}$ in the formula (20);

a plurality of $R_{22}$ each independently represent the same as $R_{21}$ in the formula (20); and $L_2$ represents the same as $L_2$ in the formula (21).

$L_2$ in the formulae (24), (24A), (24B), (25) and (25A) is also preferably a single bond, a substituted or unsubstituted arylene group having 6 to 50 ring carbon atoms, or a substituted or unsubstituted divalent heterocyclic group having 5 to 50 ring atoms.

The phenanthroline compound is also preferably a compound represented by a formula (25B) below.

[Formula 31]

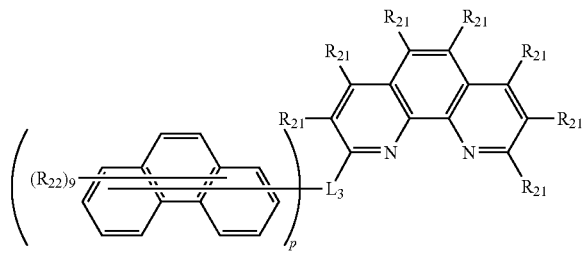

(25B)

In the formula (25B):

a plurality of $R_{21}$ each independently represent the same as $R_{21}$ in the formula (20);

a plurality of $R_{22}$ each independently represent the same as $R_{21}$ in the formula (20);

$L_3$ is a linking group, and $L_3$ as the linking group is a substituted or unsubstituted polyvalent linear, branched or cyclic aliphatic hydrocarbon group having 1 to 50 carbon atoms, a substituted or unsubstituted polyvalent amino group, a substituted or unsubstituted polyvalent aromatic hydrocarbon ring group having 6 to 50 ring carbon atoms, a substituted or unsubstituted polyvalent heterocyclic group having 5 to 50 ring atoms, or a polyvalent multiple linking group provided by bonding two or three groups selected from the polyvalent aromatic hydrocarbon ring group and the polyvalent heterocyclic group;

the aromatic hydrocarbon ring group and the heterocyclic group forming $L_3$ as the multiple linking group are mutually the same or different, and adjacent ones thereof are mutually bonded to form a ring, or not mutually bonded;

p is 1, 2, 3, 4 or 5; and the plurality of $R_{22}$ and $L_3$ are each bonded to a carbon atom at one of positions 1 to 10 of a phenanthrene ring.

The phenanthroline compound is also preferably a compound represented by a formula (25C) below.

[Formula 32]

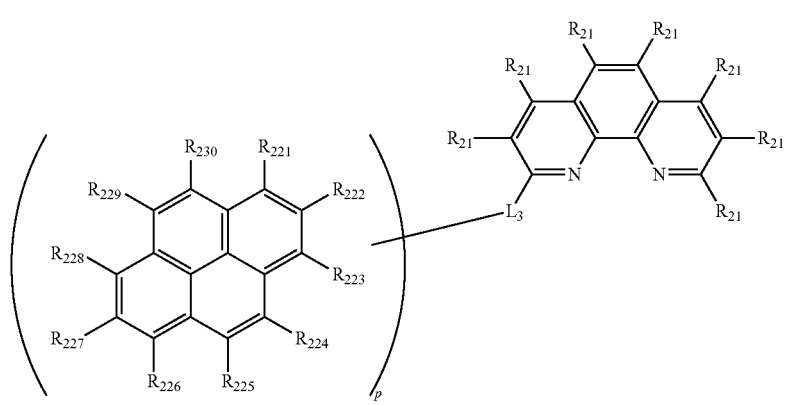

(25C)

In the formula (25C):

a plurality of $R_{21}$ each independently represent the same as $R_{21}$ in the formula (20);

one of $R_{221}$ to $R_{230}$ is a single bond bonded to $L_3$, and $R_{221}$ to $R_{230}$ not being the single bond bonded to $L_3$ each independently represent the same as $R_{21}$ in the formula (20);

$L_3$ is a linking group, and $L_3$ as the linking group represents the same as $L_3$ as the linking group in the formula (25B); and p is 1, 2, 3, 4 or 5.

The phenanthroline compound is also preferably a compound represented by a formula (25D) below.

[Formula 33]

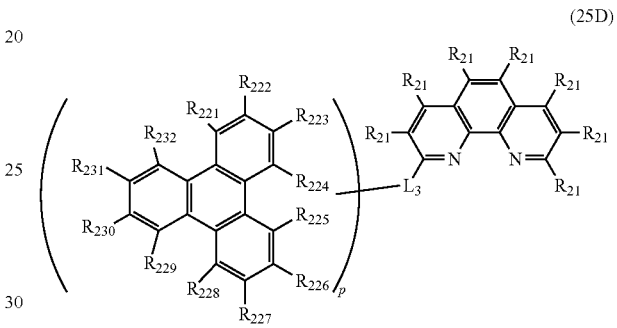

(25D)

In the formula (25D):

a plurality of $R_{21}$ each independently represent the same as $R_{21}$ in the formula (20);

one of $R_{221}$ to $R_{232}$ is a single bond bonded to $L_3$, and $R_{221}$ to $R_{232}$ not being the single bond bonded to $L_3$ each independently represent the same as $R_{21}$ in the formula (20);

$L_3$ is a linking group, and $L_3$ as the linking group represents the same as $L_3$ as the linking group in the formula (25B); and p is 1, 2, 3, 4 or 5.

The phenanthroline compound is also preferably a compound represented by a formula (25E) below.

[Formula 34]

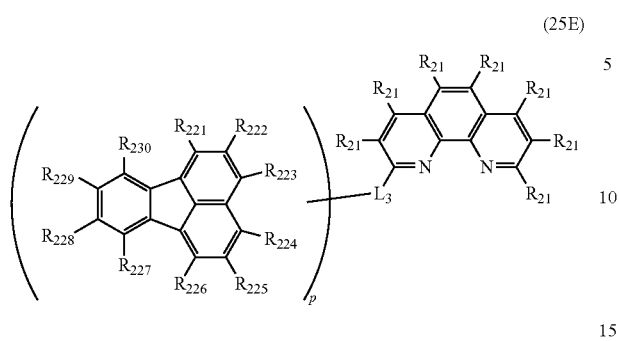

(25E)

In the formula (25E):

a plurality of $R_{21}$ each independently represent the same as $R_{21}$ in the formula (20);

one of $R_{221}$ to $R_{230}$ is a single bond bonded to $L_3$, and $R_{221}$ to $R_{230}$ not being the single bond bonded to $L_3$ each independently represent the same as $R_{21}$ in the formula (20);

$L_3$ is a linking group, and $L_3$ as the linking group represents the same as $L_3$ as the linking group in the formula (25B); and p is 1, 2, 3, 4 or 5.

$L_3$ in the formulae (25B), (25C), (25D) and (25E) is also preferably a substituted or unsubstituted arylene group having 6 to 50 ring carbon atoms, or a substituted or unsubstituted divalent heterocyclic group having 5 to 50 ring atoms.

Method of Manufacturing Phenanthroline Compound

The phenanthroline compound can be manufactured by a known method. The phenanthroline compound also can be manufactured based on a known method through a known alternative reaction using a known material(s) tailored for the target compound.

Specific Examples of Phenanthroline Compound

Specific examples of the phenanthroline compound include the following compounds. It should however be noted that the invention is not limited by the specific examples of the phenanthroline compound.

[Formula 35]

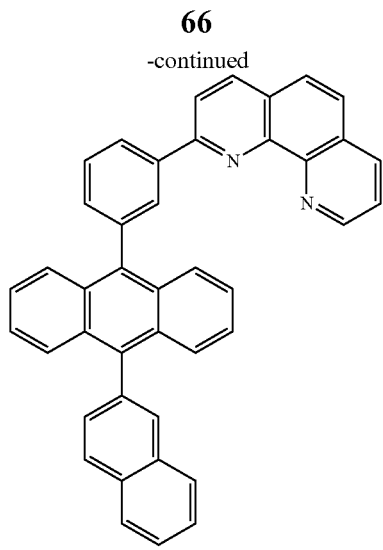

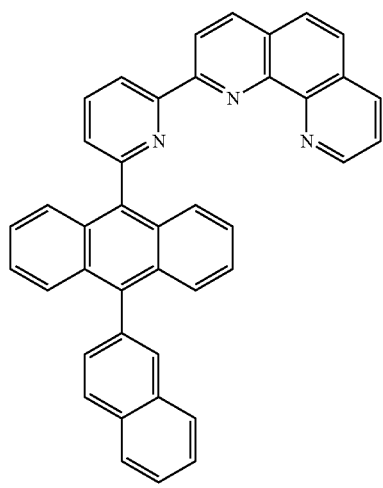

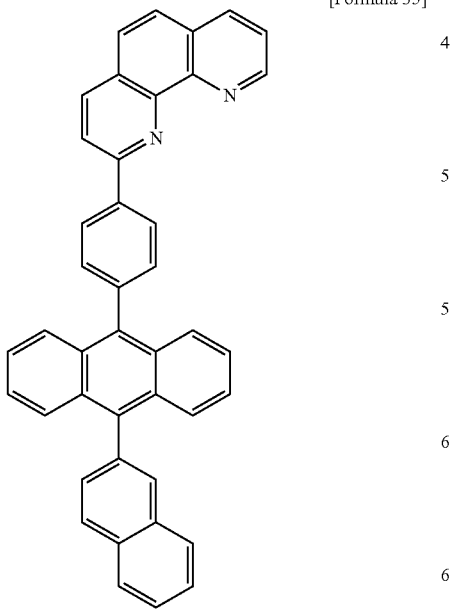

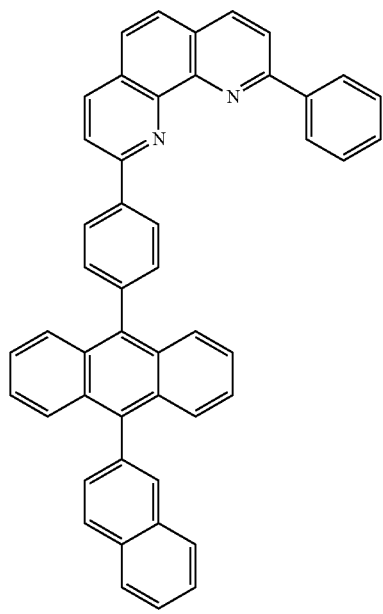

-continued
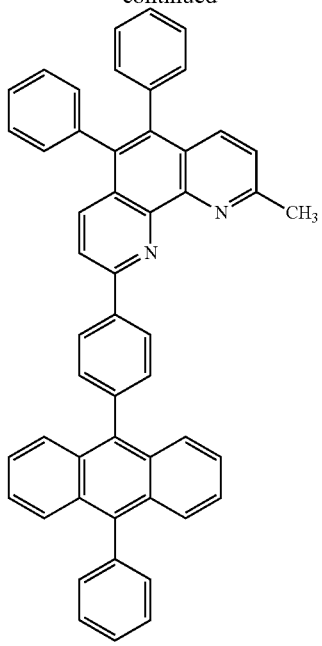
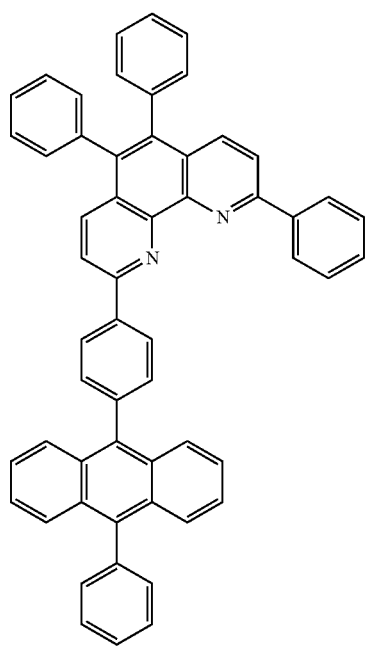
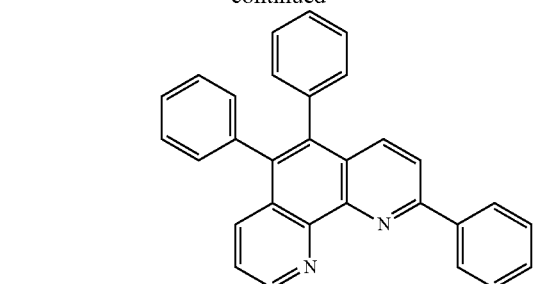
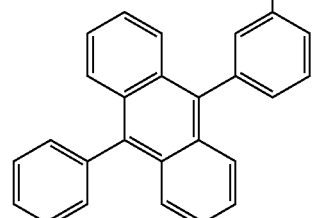
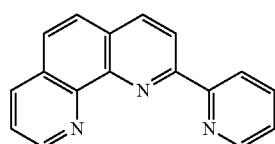
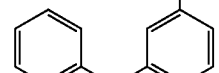
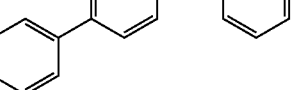
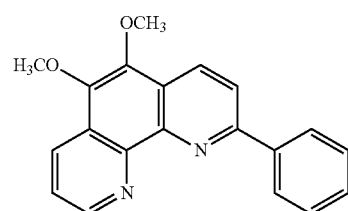
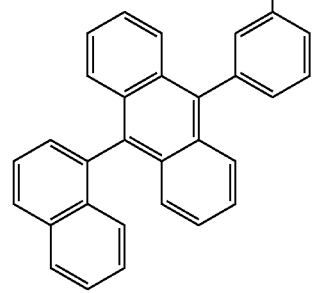

69
-continued
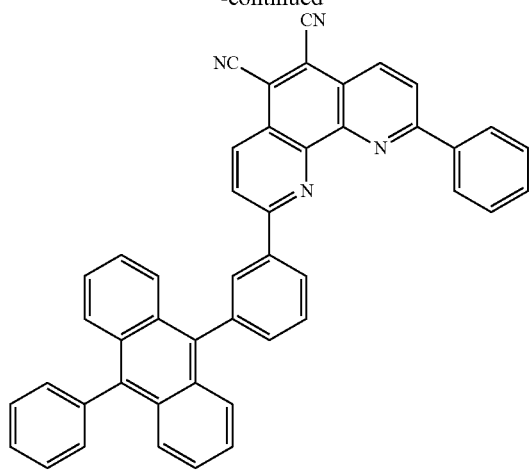
70
-continued
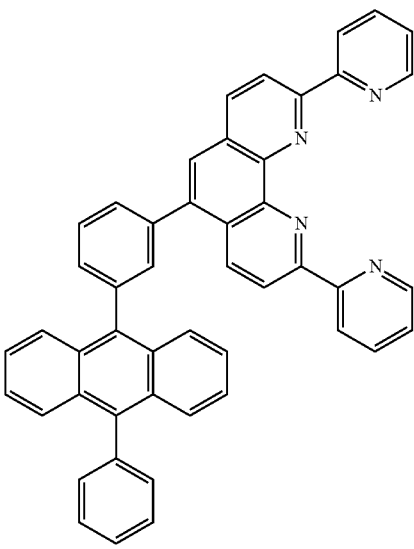
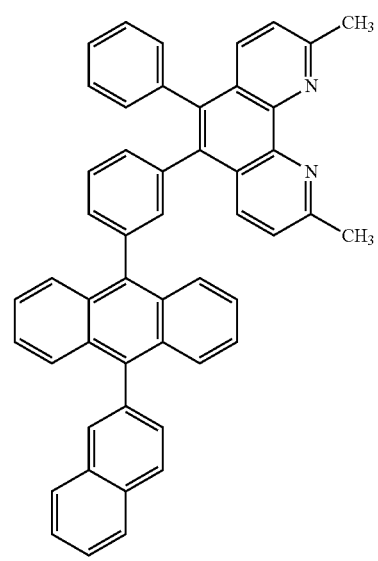
[Formula 36]
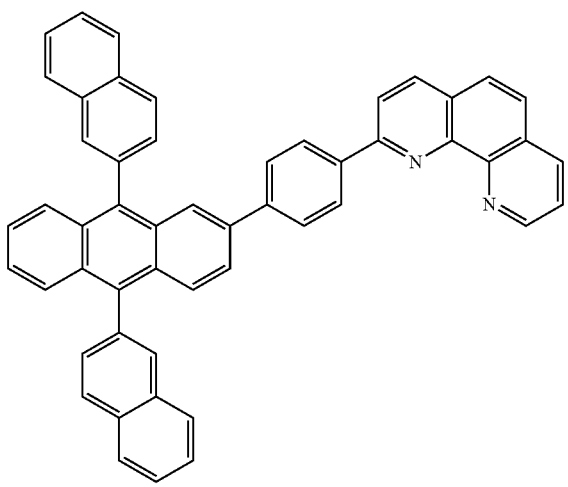
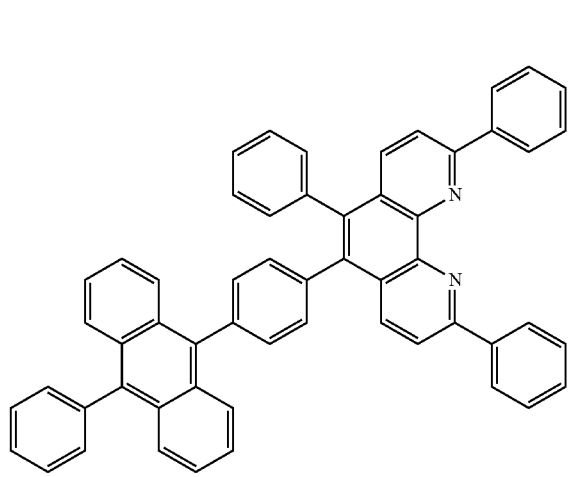
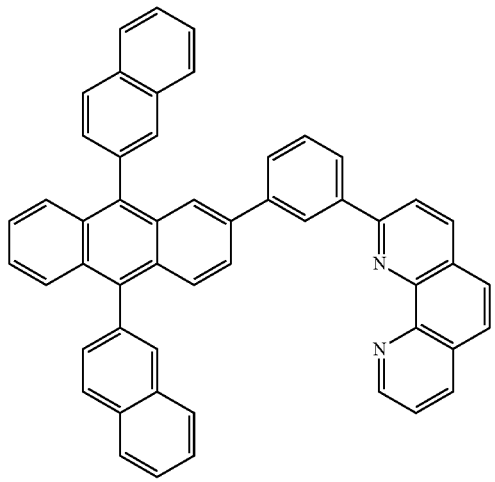

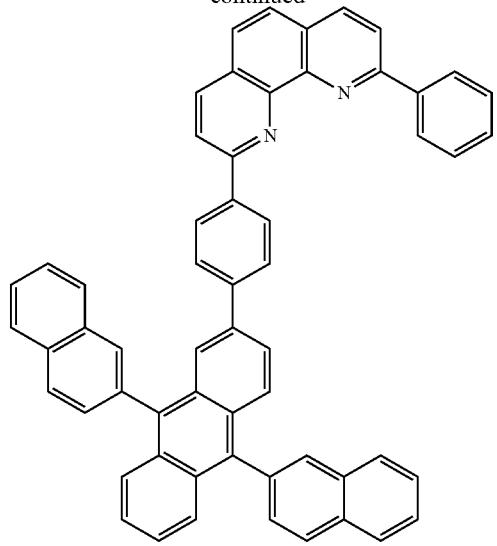
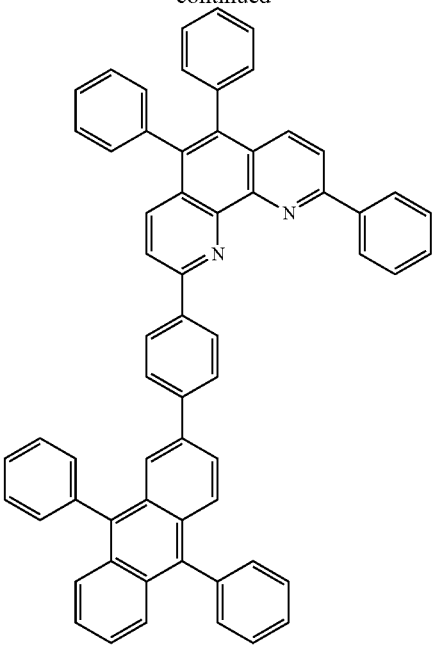
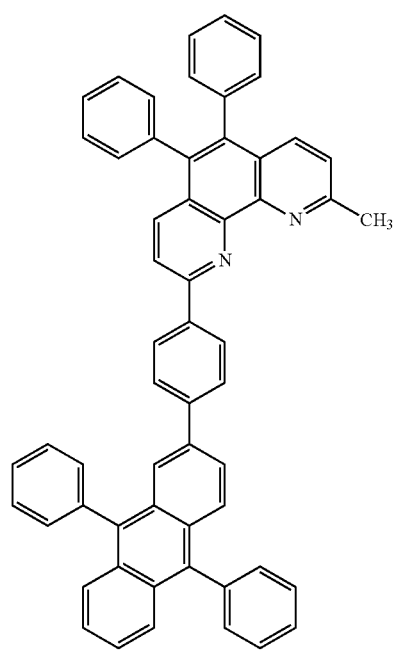
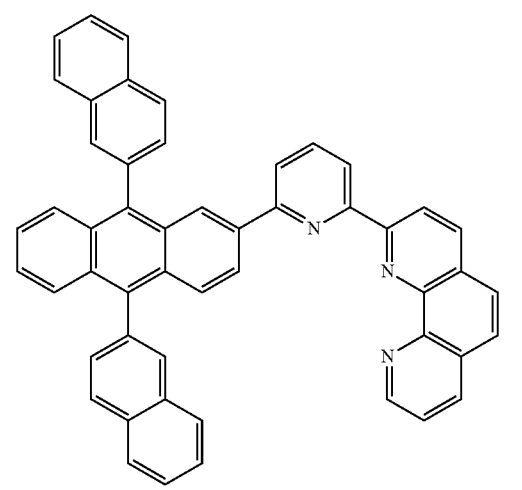
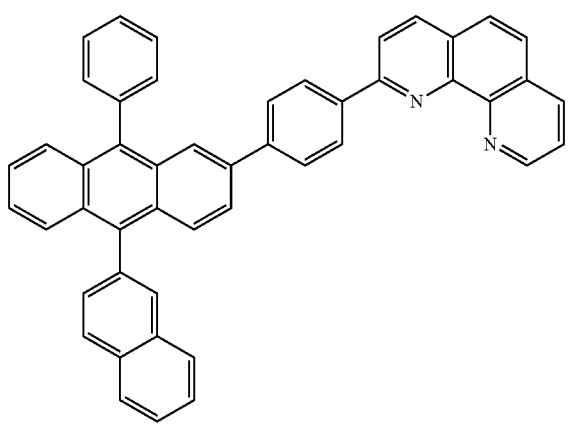

73
-continued
74
[Formula 37]
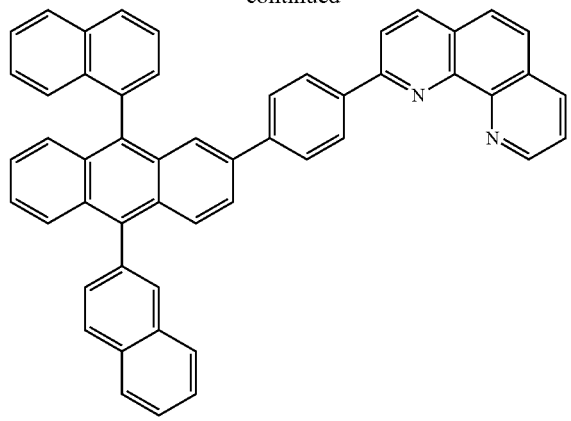
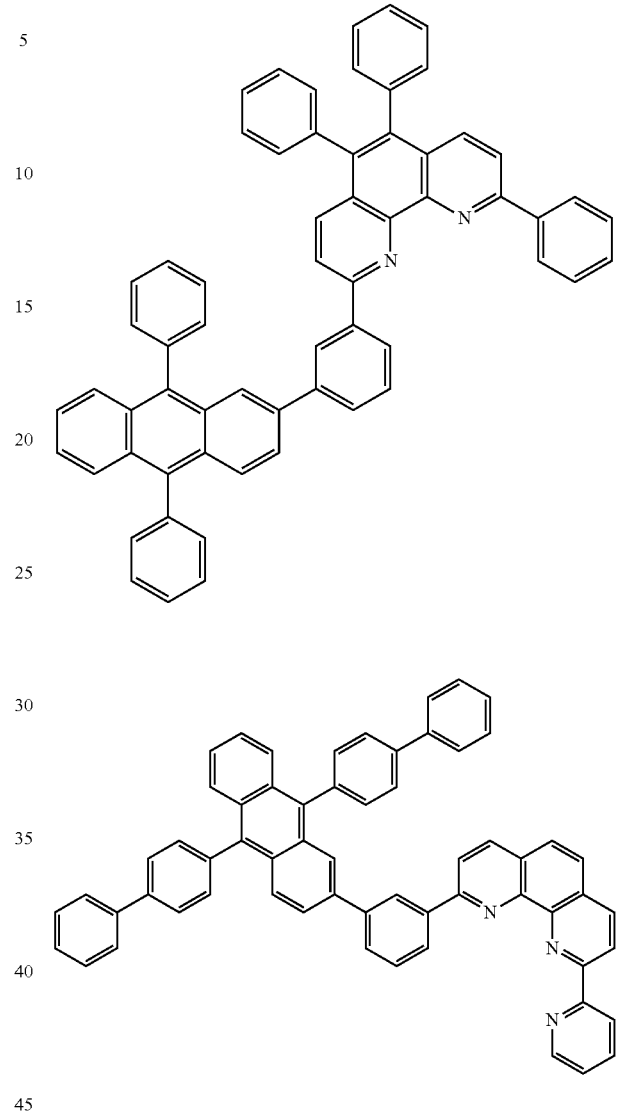
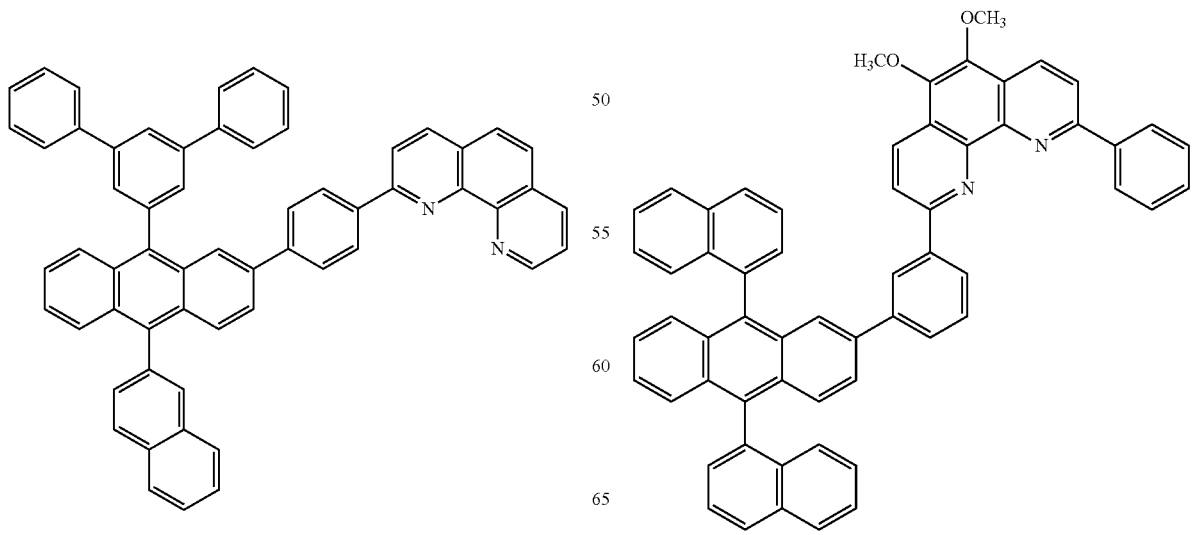

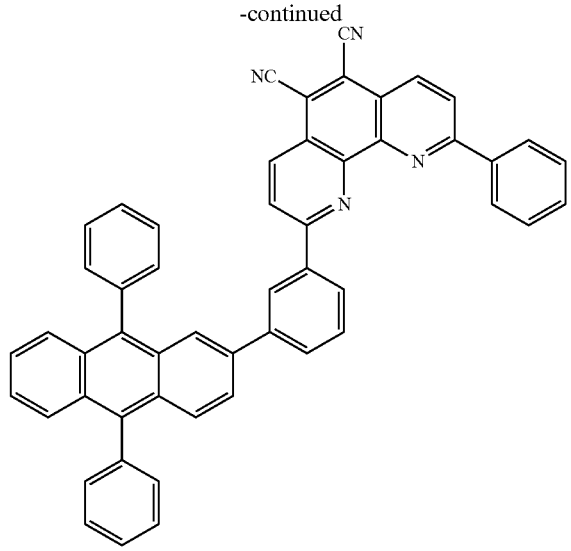
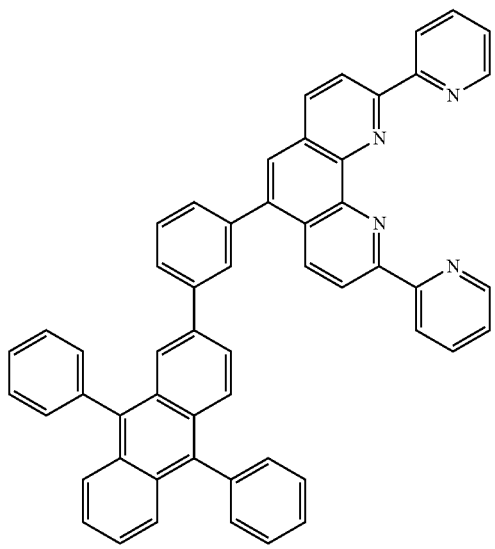 [SMILES: c1ccc(-c2c3ccccc3c(-c3ccccc3)c3cc(-c4cccc(-c5cc6ccc(-c7ccccn7)nc6c6nc(-c7ccccn7)ccc56)c4)ccc23)cc1]
[Formula 38]
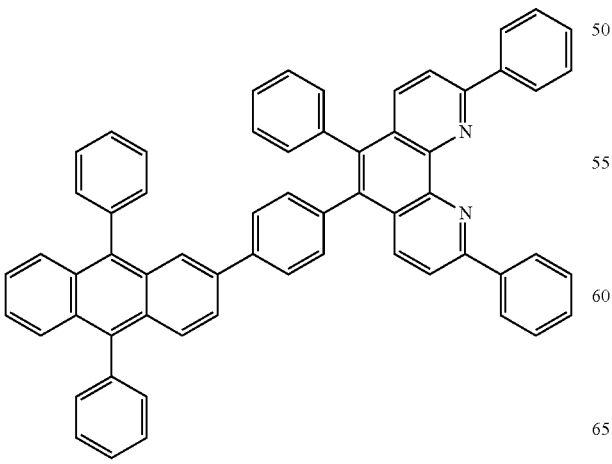
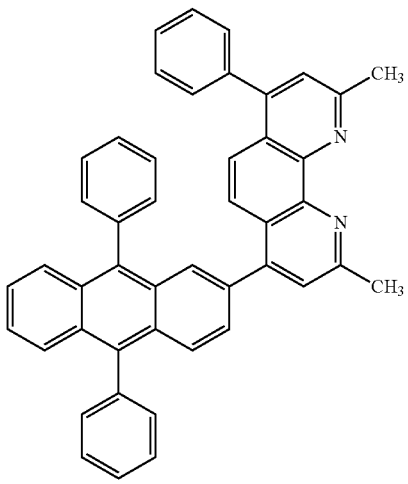

-continued
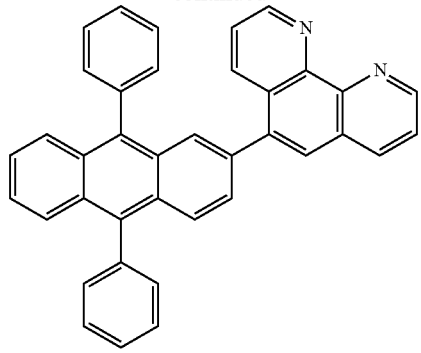
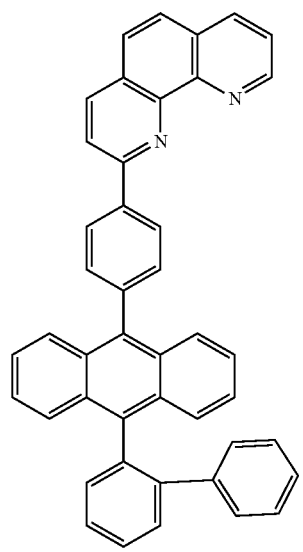
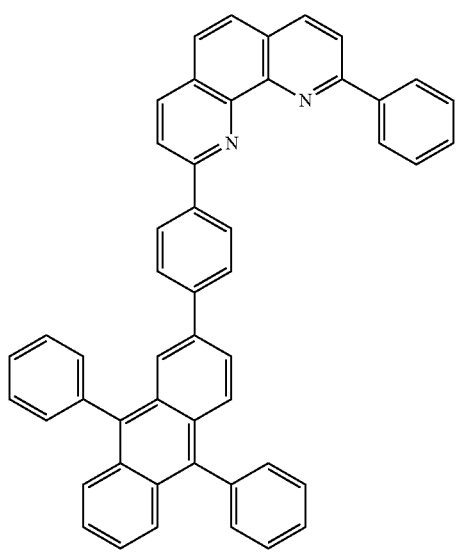
-continued
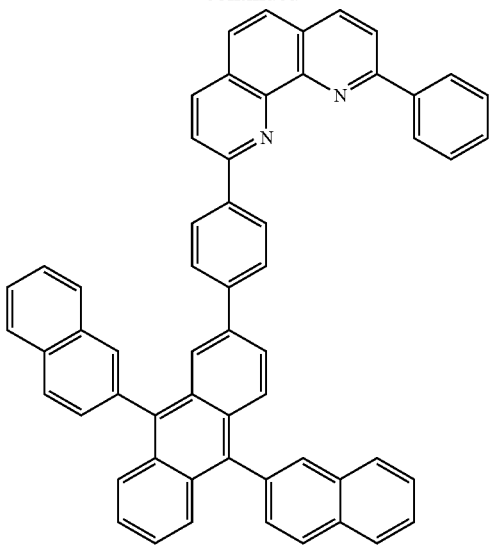
[Formula 39]
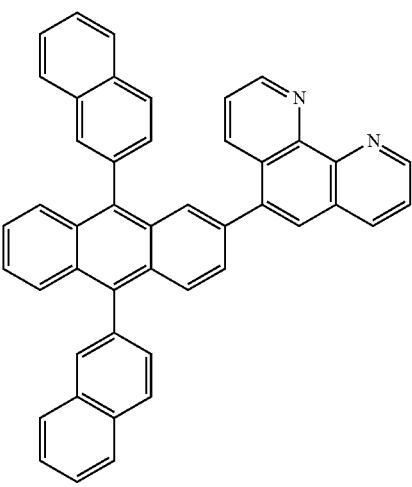
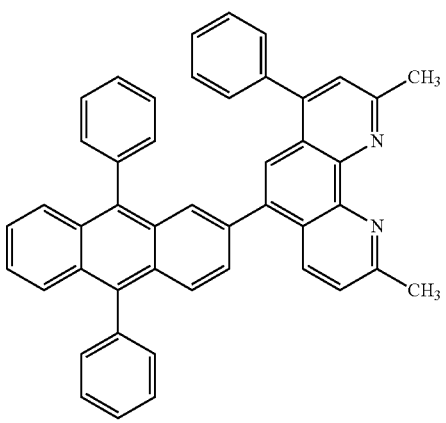

79
-continued
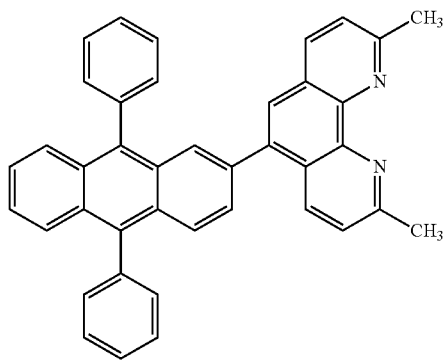
80
-continued
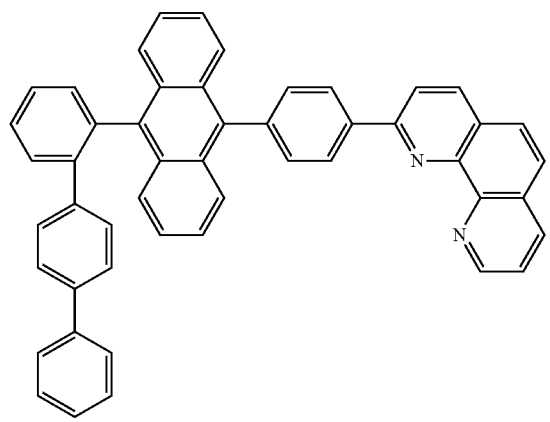
[Formula 40]
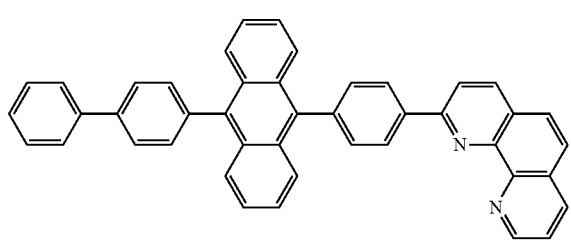
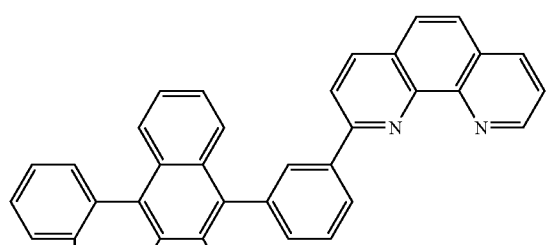
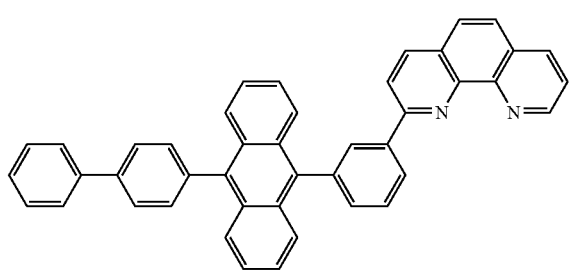
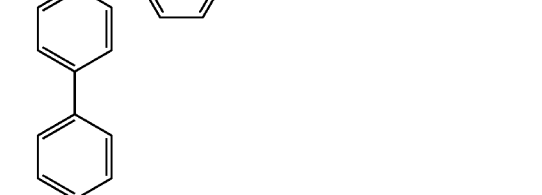
[Formula 41]
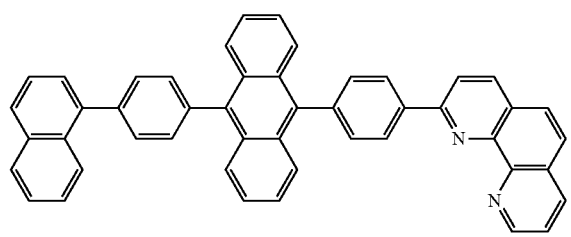
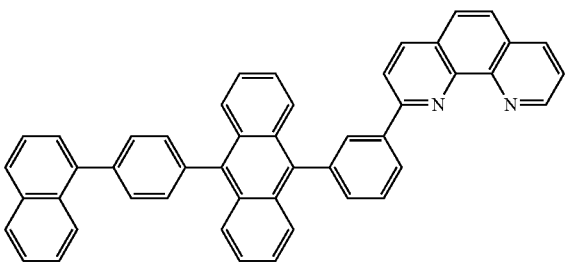

[Formula 42]
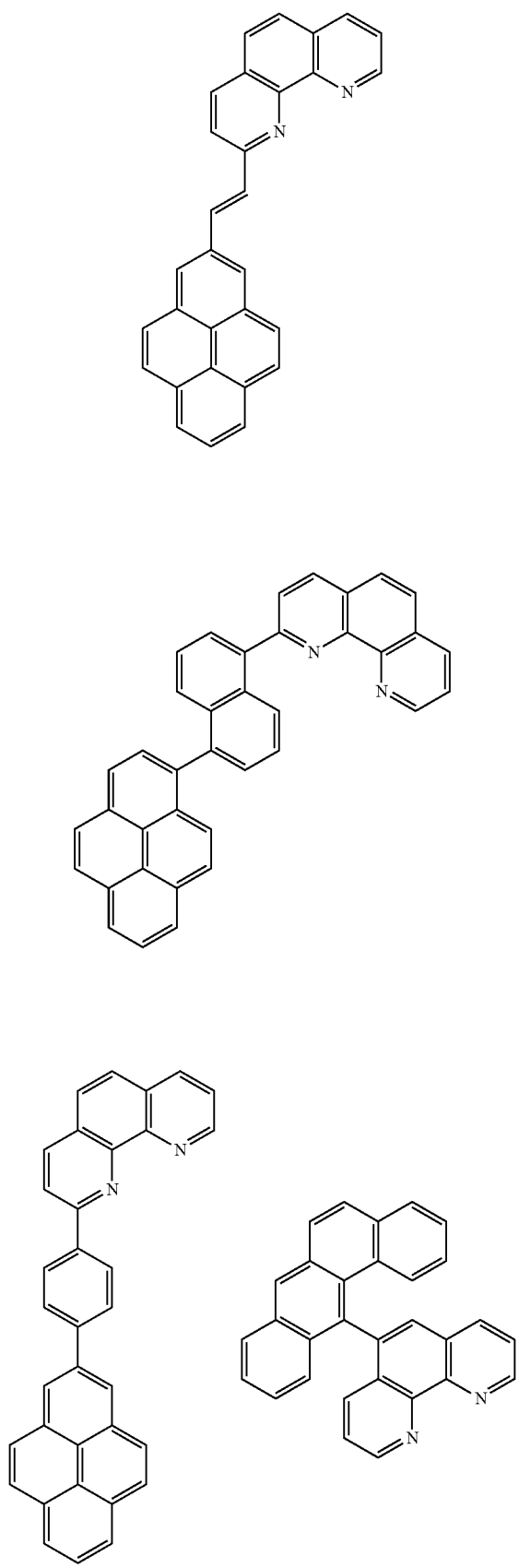
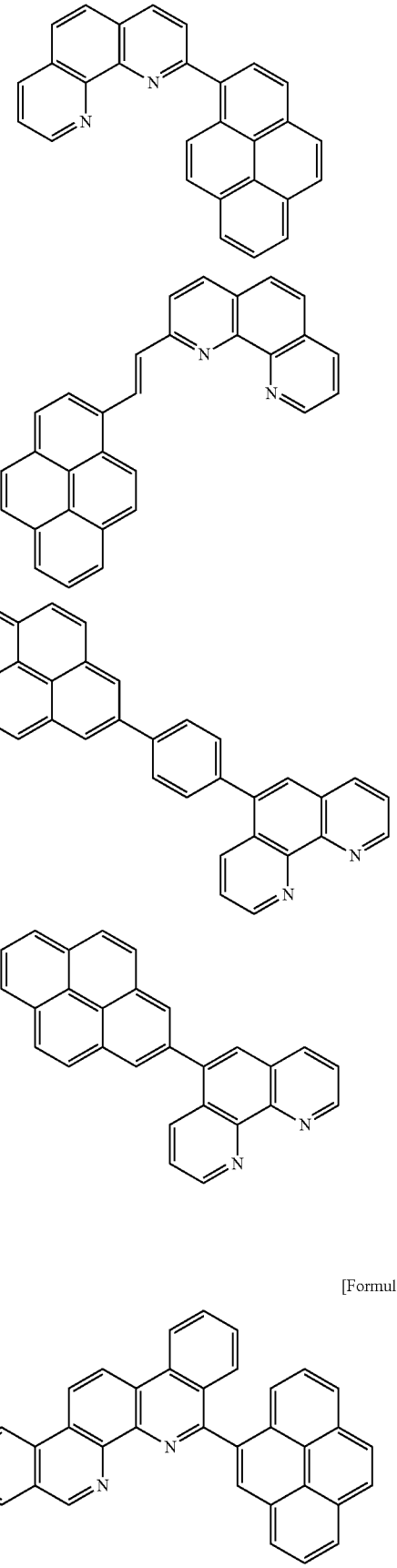
[Formula 43]

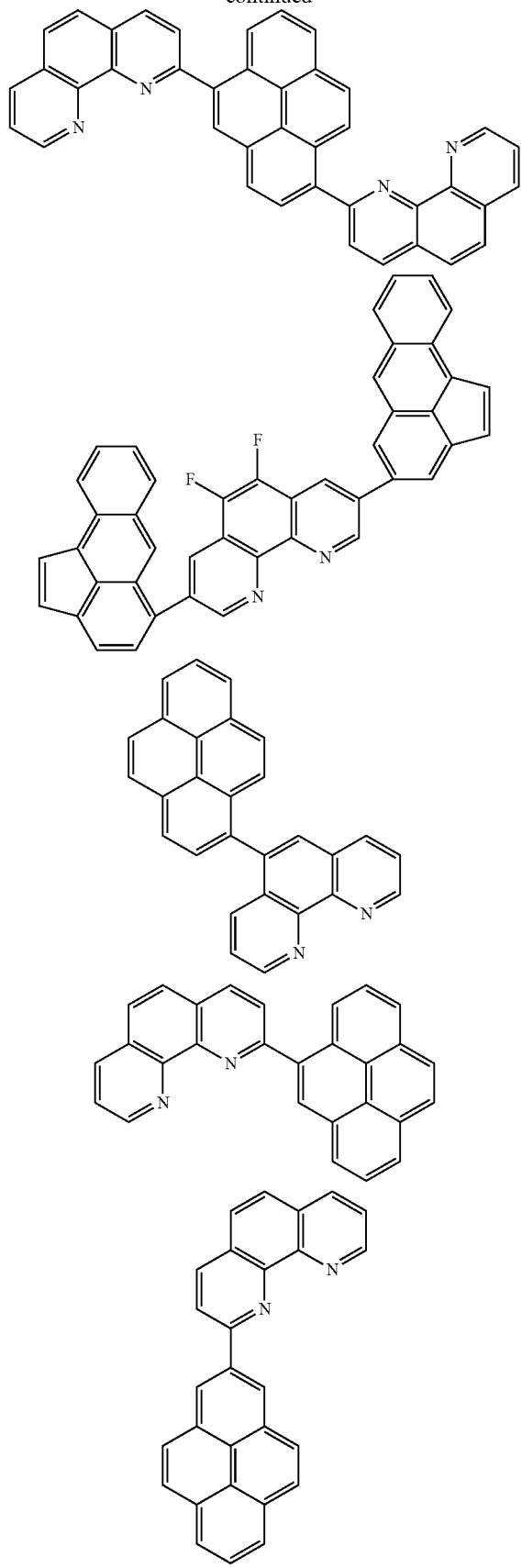
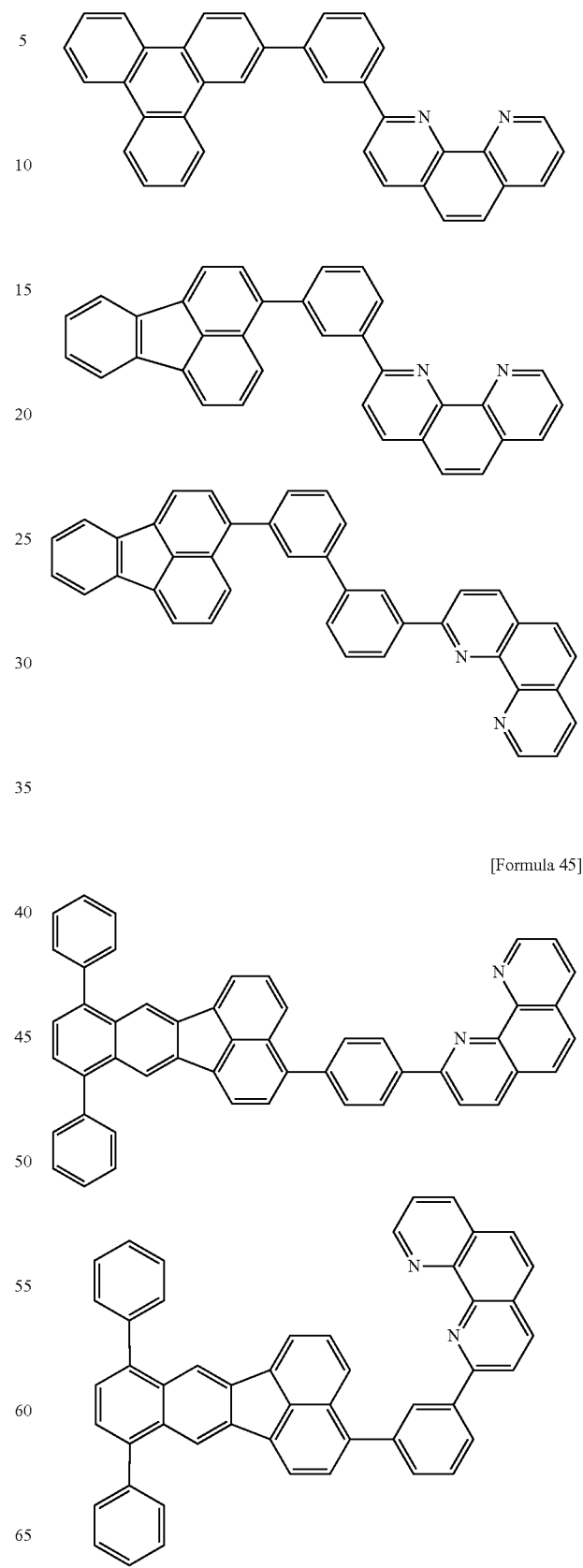
[Formula 44]
[Formula 45]

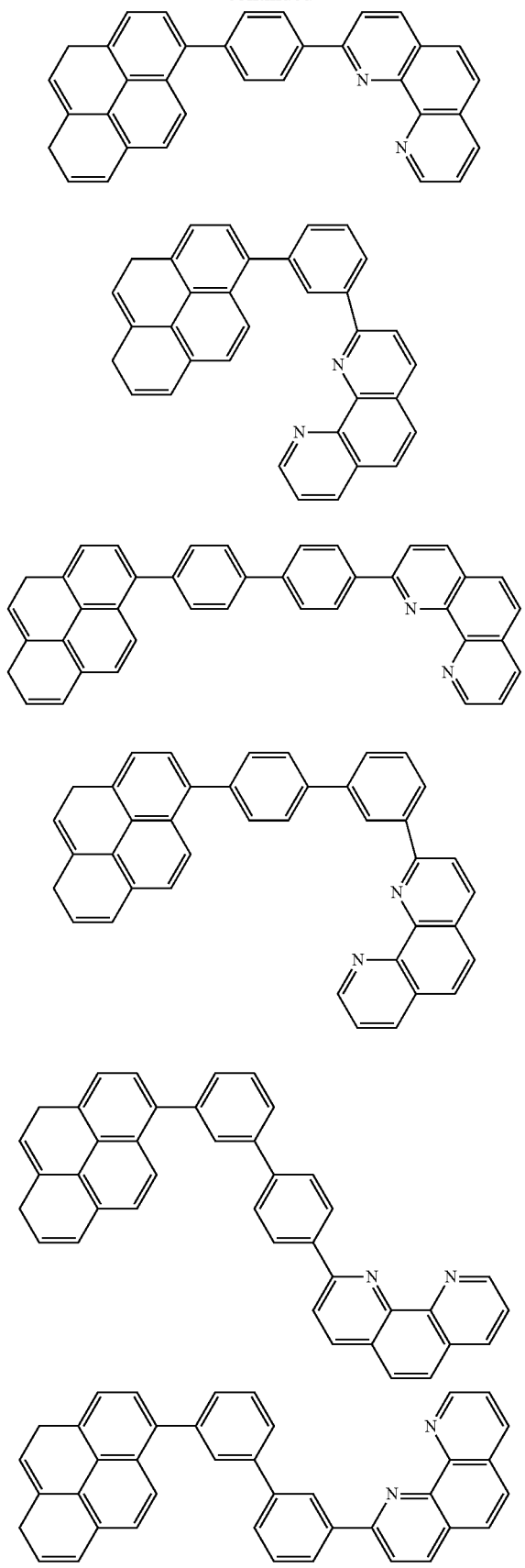
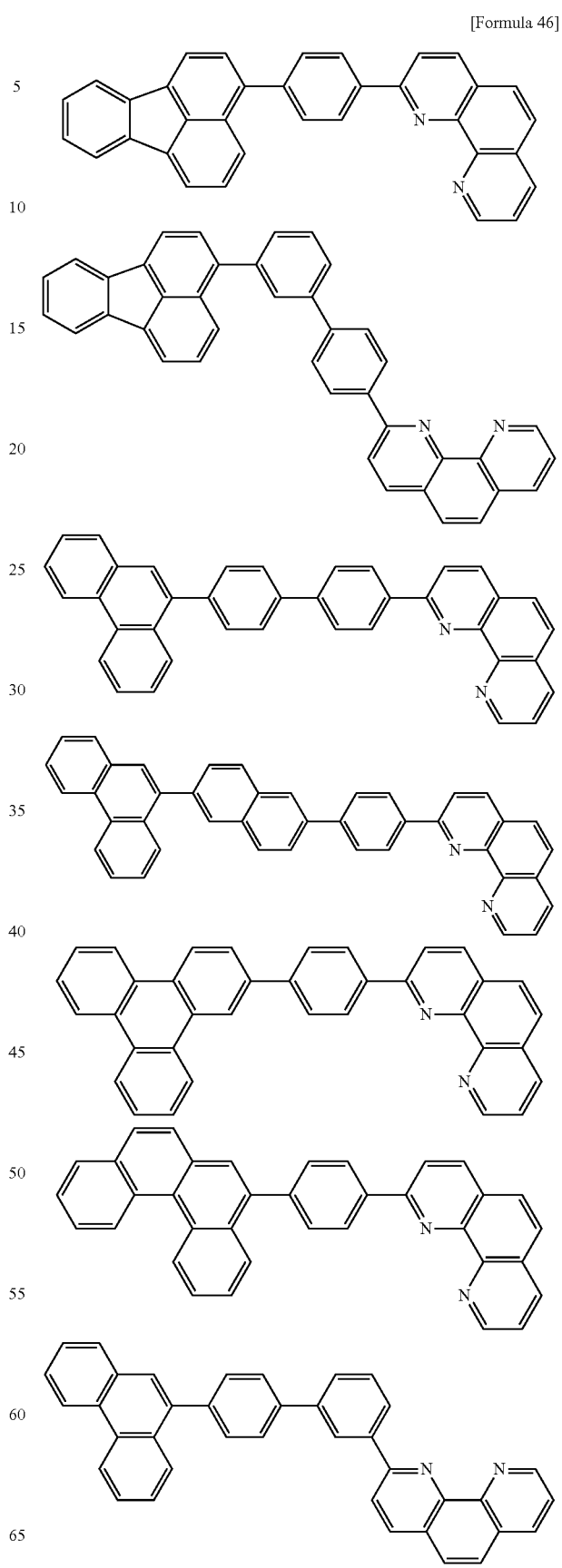
[Formula 46]

-continued
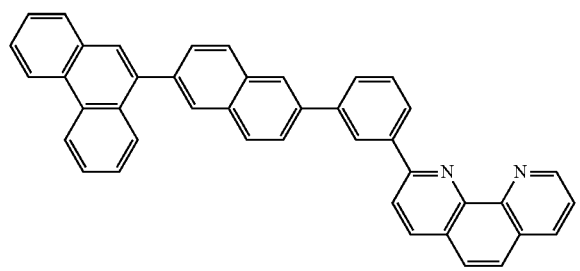
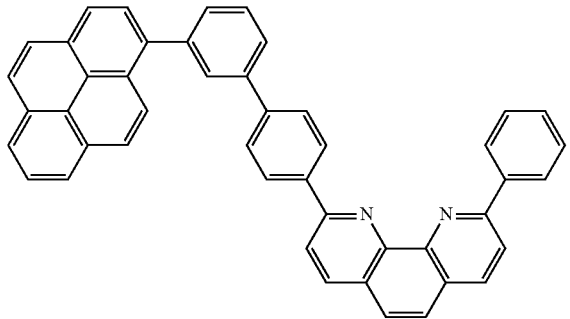
[Formula 47]
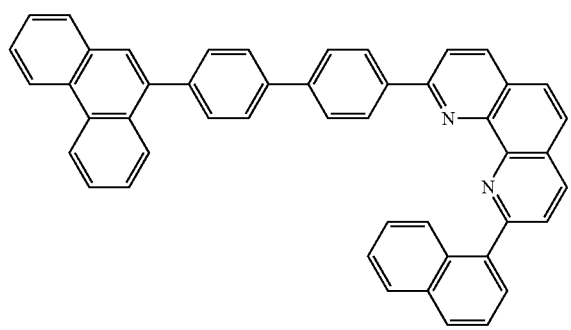
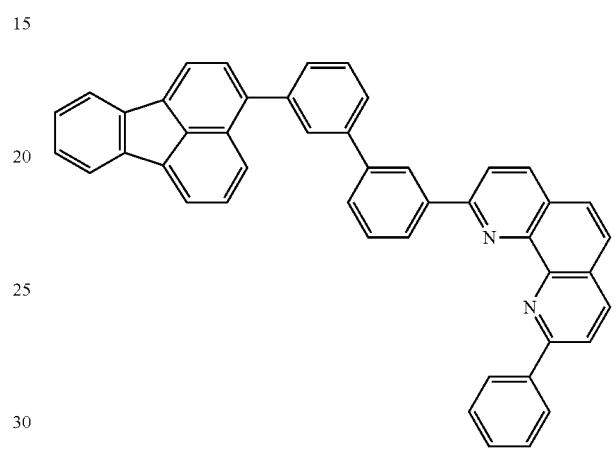
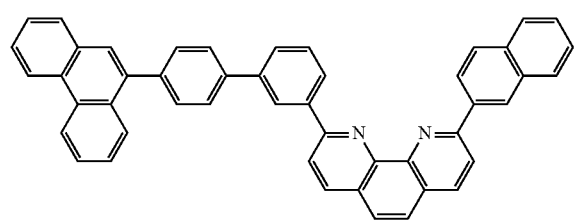
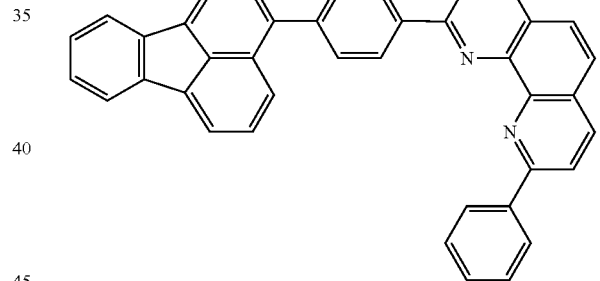
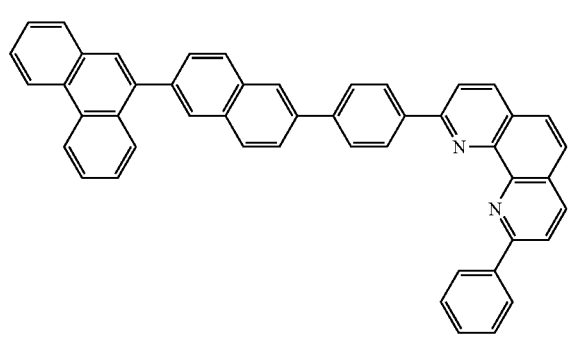
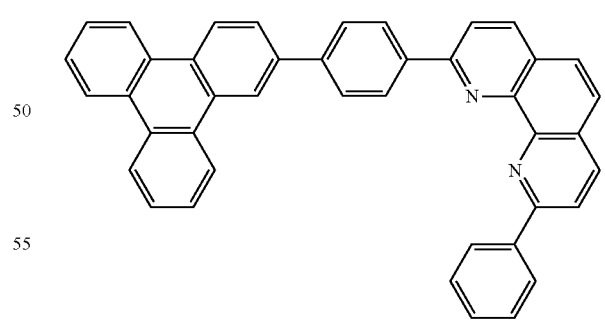
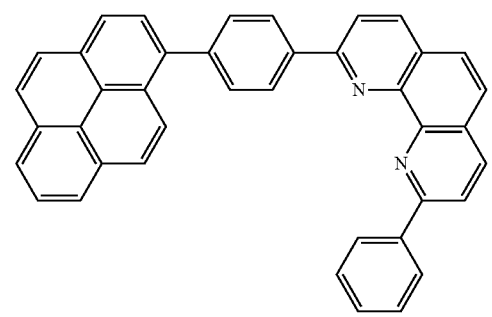
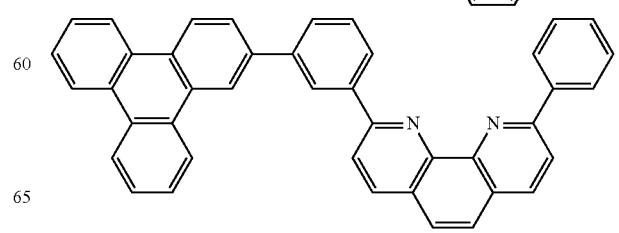

89
-continued
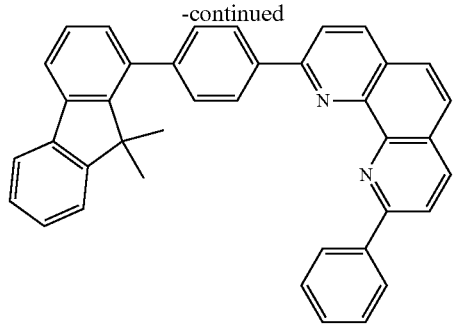
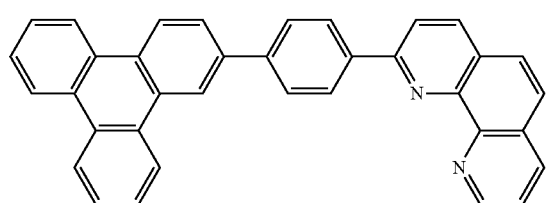
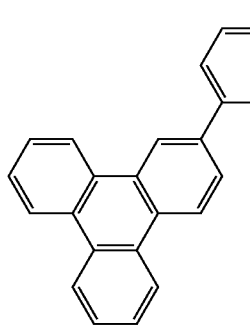
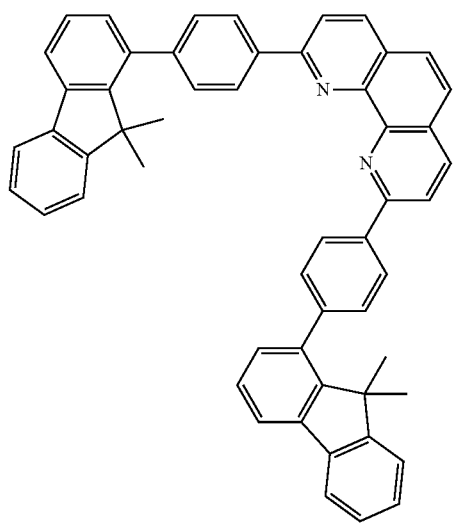
90
-continued
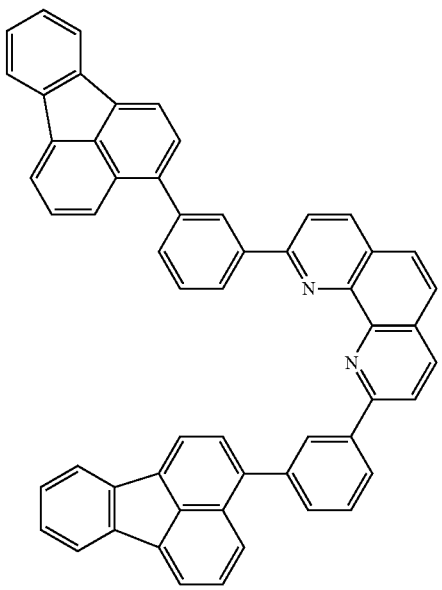 [SMILES: c1cc(-c2ccc3ccc4ccc(-c5cccc(-c6ccc7c8c(cccc68)-c6ccccc6-7)c5)nc4c3n2)cc(-c2ccc3c4c(cccc24)-c2ccccc2-3)c1]
[Formula 48]
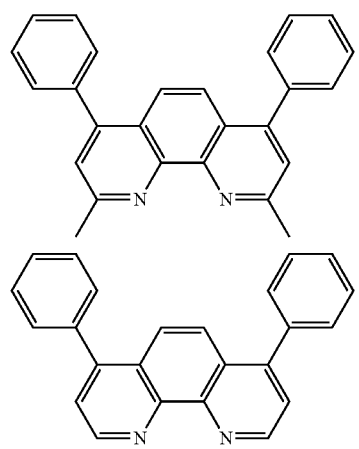
[Formula 49]
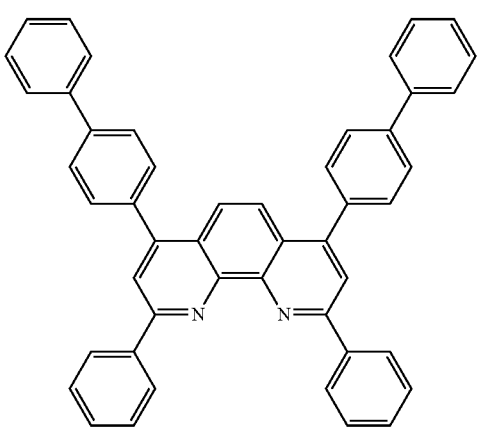

91
-continued
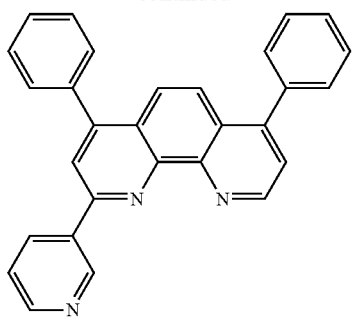
[Formula 50]
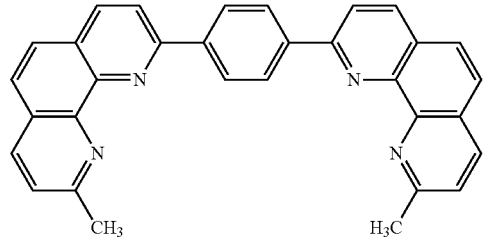
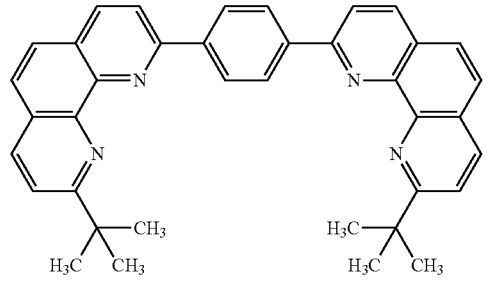
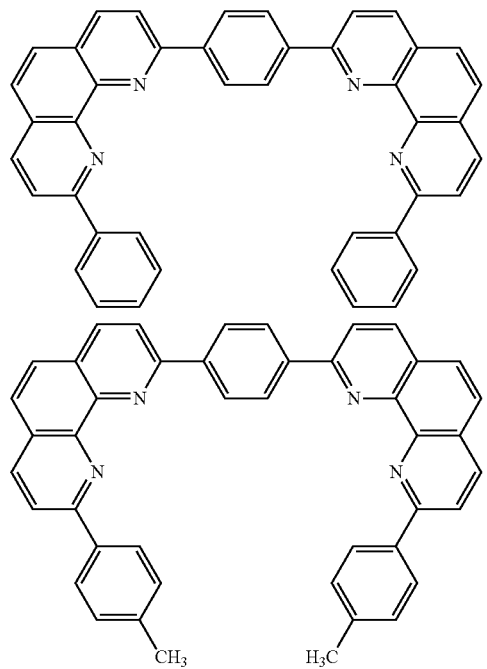
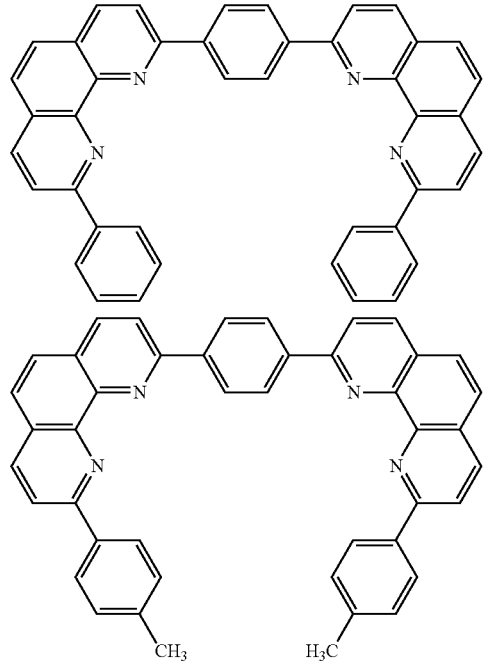
92
-continued
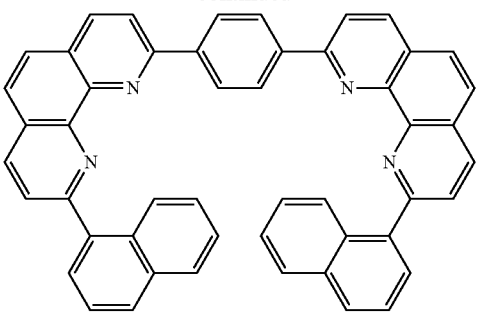
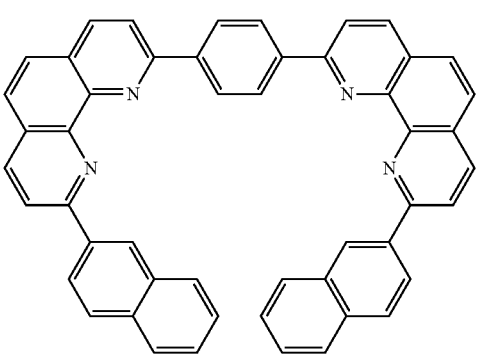 [SMILES: c1ccc2cc(-c3ccc4ccc5ccc(-c6ccc(-c7ccc8ccc9ccc(-c%10ccc%11ccccc%11c%10)nc9c8n7)cc6)nc5c4n3)ccc2c1]
[Formula 51]
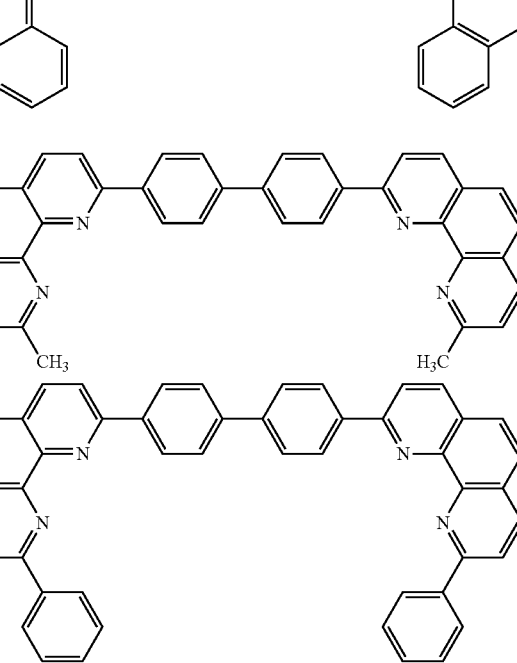

[Formula 52]
[Formula 53]
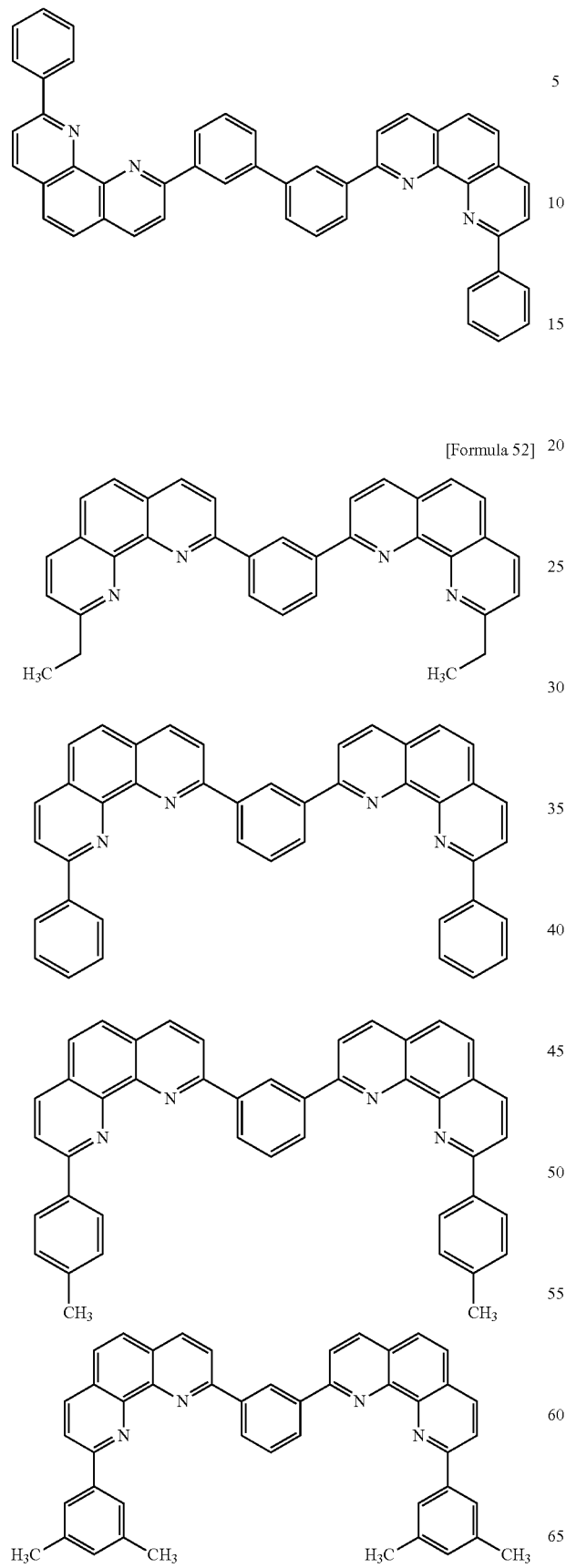
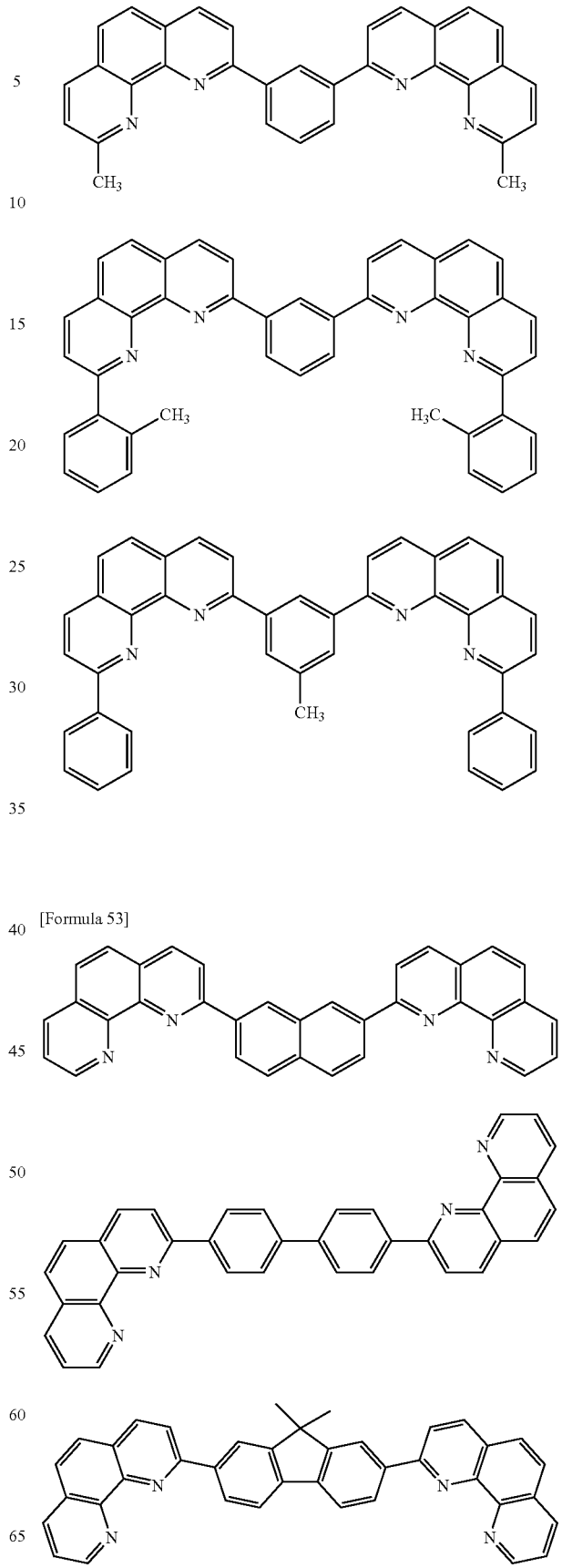

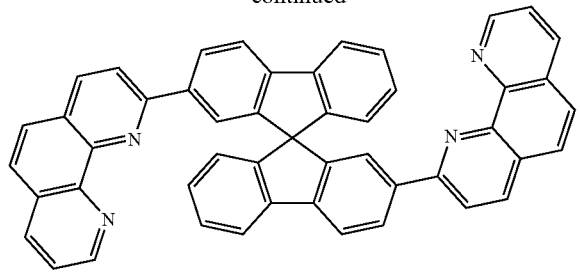

First Host Material, Second Host Material and Third Host Material

In the organic EL device according to the exemplary embodiment, examples of the first host material, the second host material and the third host material include the first compound represented by the formula (1), a formula (1X), (12X), (13X), (14X), (15X), or (16X) below, and the second compound represented by the formula (2). Moreover, the first compound also can be used as the first host material and the second host material. In this case, the compound represented by the formula (1), (1X), (12X), (13X), (14X), (15X), or (16X) used as the second host material is sometimes referred to as the second compound for convenience.

First Host Material

In the organic EL device according to the exemplary embodiment, it is also preferable that the first host material has, in a molecule, the structure of Condition (ii), i.e., a linking structure including a benzene ring and a naphthalene ring that are linked to each other with a single bond, in which the benzene ring and the naphthalene ring in the linking structure are each independently further fused or not fused with a monocyclic ring or fused ring, and the benzene ring and the naphthalene ring in the linking structure are further linked to each other by cross-linking at at least one site other than the single bond.

Since the first host material has the linking structure including such cross-linking, it can be expected to inhibit the deterioration in the chromaticity of the organic EL device.

The first host material in the above case is only required to have a linking structure as the minimum unit in a molecule, the linking structure including a benzene ring and a naphthalene ring linked to each other with a single bond (sometimes referred to as a benzene-naphthalene linking structure), the linking structure being as represented by a formula (X1) or a formula (X2) below. The benzene ring may be further fused with a monocyclic ring or fused ring, and the naphthalene ring may be further fused with a monocyclic ring or fused ring. For instance, also in a case where the first host material has, in a molecule, a linking structure including a naphthalene ring and a naphthalene ring linked to each other with a single bond (sometimes referred to as a naphthalene-naphthalene linking structure) and being as represented by a formula (X3), a formula (X4), or a formula (X5) below, the naphthalene-naphthalene linking structure is regarded as including the benzene-naphthalene linking structure since one of the naphthalene rings includes a benzene ring.

[Formula 54]

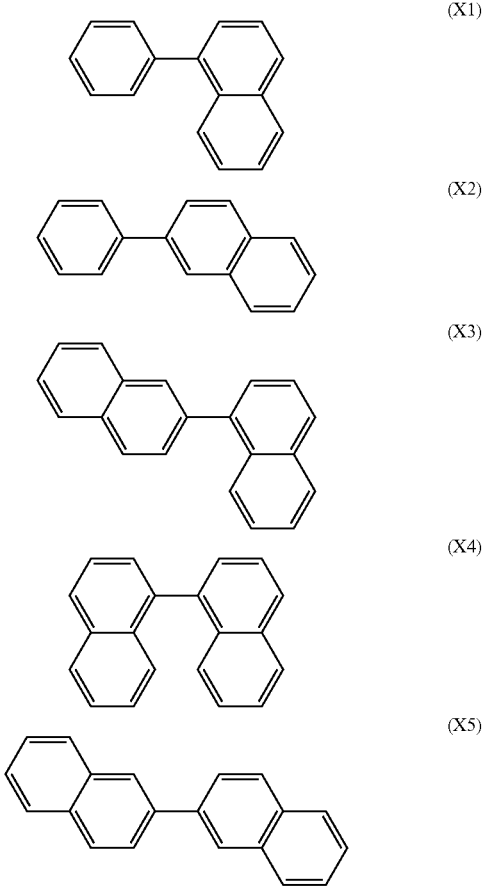

In the organic EL device according to the exemplary embodiment, the cross-linking also preferably includes a double bond. Specifically, the first host material also preferably has a linking structure in which the benzene ring and the naphthalene ring are further linked to each other at any other site than the single bond by a cross-linking structure including a double bond.

Assuming that the benzene ring and the naphthalene ring in the benzene-naphthalene linking structure are further linked to each other at at least one site other than the single bond by cross-linking, for instance, a linking structure (fused ring) represented by a formula (X11) below is obtained in a case of the formula (X1), and a linking structure (fused ring) represented by a formula (X31) below is obtained in a case of the formula (X3).

Assuming that the benzene ring and the naphthalene ring in the benzene-naphthalene linking structure are further linked to each other at any other site than the single bond by cross-linking including a double bond, for instance, a linking structure (fused ring) represented by a formula (X12) below is obtained in a case of the formula (X1), a linking structure (fused ring) represented by a formula (X21), a formula (X22) or a formula (X23) below is obtained in a case of the formula (X2), a linking structure (fused ring) represented by a formula (X41) below is obtained in a case of the formula (X4), and a linking structure (fused ring) represented by a formula (X51) below is obtained in a case of the formula (X5).

Assuming that the benzene ring and the naphthalene ring in the benzene-naphthalene linking structure are further linked to each other at at least one site other than the single bond by cross-linking including a hetero atom (e.g., an oxygen atom), for instance, a linking structure (fused ring) represented by a formula (X13) below is obtained in a case of the formula (X1).

[Formula 55]

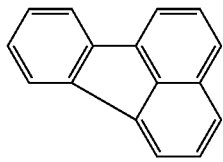 (X11)

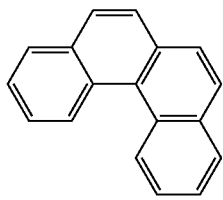 (X12)

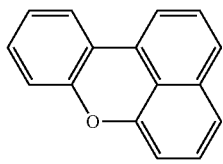 (X13)

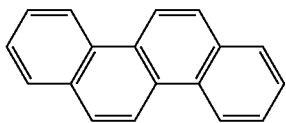 (X21)

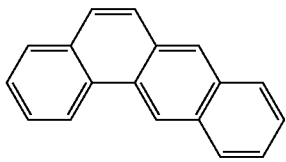 (X22)

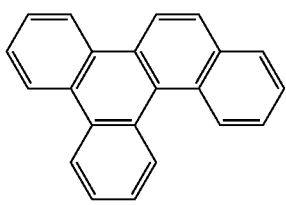 (X23)

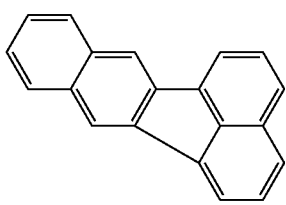 (X31)

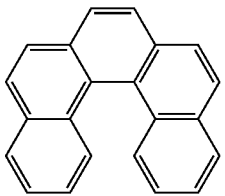 (X41)

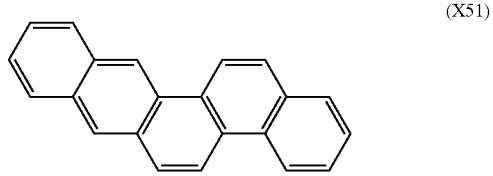 (X51)

In the organic EL device according to the exemplary embodiment, it is also preferable that the first host material has the structure of Condition (i), i.e., has in a molecule, a biphenyl structure including a first benzene ring and a second benzene ring linked to each other with a single bond, and the first benzene ring and the second benzene ring in the biphenyl structure are further linked to each other by cross-linking at at least one site other than the single bond.

In the organic EL device according to the exemplary embodiment, it is also preferable that: the first host material has the structure of Condition (i) in a molecule; and the first benzene ring and the second benzene ring in the biphenyl structure are further linked to each other by the cross-linking at one site other than the single bond. Since the first host material has the biphenyl structure including such cross-linking, it can be expected to inhibit the deterioration in the chromaticity of the organic EL device.

In the organic EL device according to the exemplary embodiment, it is also preferable that: the first host material has the structure of Condition (i) in a molecule; and the first benzene ring and the second benzene ring in the biphenyl structure are further linked to each other by the cross-linking at two sites other than the single bond.

In the organic EL device according to the exemplary embodiment, it is also preferable that the first host material has the structure of Condition (i) in a molecule and the cross-linking includes a double bond.

In the organic EL device according to the exemplary embodiment, it is also preferable that the first host material has the structure of Condition (i) in a molecule and the cross-linking includes no double bond.

In the organic EL device according to the exemplary embodiment, it is also preferable that: the first host material has the structure of Condition (i) in a molecule; the first benzene ring and the second benzene ring in the biphenyl structure are further linked to each other by the cross-linking at two sites other than the single bond; and the cross-linking includes no double bond. Since the first host material has the biphenyl structure including such cross-linking, it can be expected to inhibit the deterioration in the chromaticity of the organic EL device.

For instance, assuming that the first benzene ring and the second benzene ring in the biphenyl structure represented by a formula (BP1) below are further linked to each other by cross-linking at at least one site other than the single bond, the biphenyl structure is exemplified by linking structures (fused rings) represented by formulae (BP11) to (BP15) below.

[Formula 56]

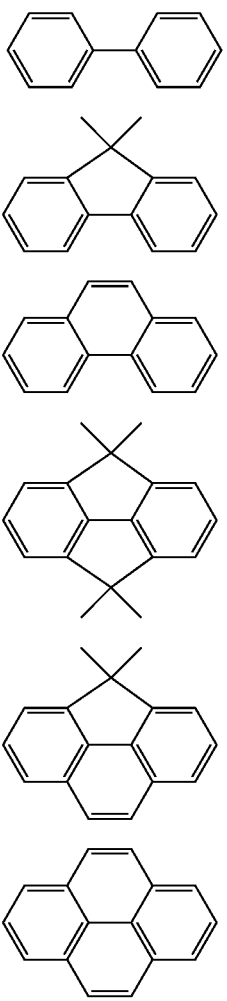

(BP1)

(BP11)

(BP12)

(BP13)

(BP14)

(BP15)

The formula (BP11) represents a linking structure in which the first benzene ring and the second benzene ring are linked to each other at one site other than the single bond by cross-linking including no double bond.

The formula (BP12) represents a linking structure in which the first benzene ring and the second benzene ring are linked to each other at one site other than the single bond by cross-linking including a double bond.

The formula (BP13) represents a linking structure in which the first benzene ring and the second benzene ring are linked to each other by cross-linking including no double bond at two sites other than the single bond.

The formula (BP14) represents a linking structure in which the first benzene ring and the second benzene ring are linked to each other by cross-linking including no double bond at one of two sites other than the single bond, and the first benzene ring and the second benzene ring are linked to each other by cross-linking including a double bond at the other of the two sites other than the single bond.

The formula (BP15) represents a linking structure in which the first benzene ring and the second benzene ring are linked to each other at two sites other than the single bond by cross-linking including a double bond.

First Compound

In the organic EL device according to the exemplary embodiment, the first host material is also preferably the first compound that has at least one group represented by a formula (11) below and is represented by the formula (1).

[Formula 57]

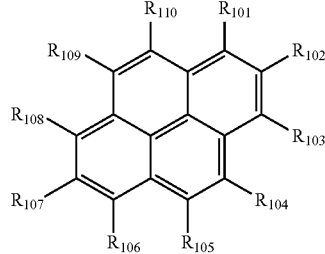

(1)

$$*\!-\!(\mathrm{L}_{101})_{\overline{mx}}\mathrm{Ar}_{101}$$ (11)

In the formula (1):

$R_{101}$ to $R_{110}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(=O)$R_{801}$, a group represented by —COO$R_{802}$, a halogen atom, a cyano group, a nitro group, a substituted or unsubstituted aryl group having 6 to 50 ring carbon atoms, a substituted or unsubstituted heterocyclic group having 5 to 50 ring atoms, or a group represented by the formula (11);

at least one of $R_{101}$ to $R_{110}$ is a group represented by the formula (11);

when a plurality of groups represented by the formula (11) are present, the plurality of groups represented by the formula (11) are mutually the same or different;

$L_{101}$ is a single bond, a substituted or unsubstituted arylene group having 6 to 50 ring carbon atoms, or a substituted or unsubstituted divalent heterocyclic group having 5 to 50 ring atoms;

$Ar_{101}$ is a substituted or unsubstituted aryl group having 6 to 50 ring carbon atoms, or a substituted or unsubstituted heterocyclic group having 5 to 50 ring atoms;

mx is 0, 1, 2, 3, 4, or 5;

when two or more $L_{101}$ are present, the two or more $L_{101}$ are mutually the same or different;

when two or more $Ar_{101}$ are present, the two or more $Ar_{101}$ are mutually the same or different; and

* in the formula (11) represents a bonding position to a pyrene ring in the formula (1).

In the first compound according to the exemplary embodiment: $R_{901}$, $R_{902}$, $R_{903}$, $R_{904}$, $R_{905}$, $R_{906}$, $R_{907}$, $R_{801}$, and $R_{802}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when a plurality of $R_{901}$ are present, the plurality of $R_{901}$ are mutually the same or different;

when a plurality of $R_{902}$ are present, the plurality of $R_{902}$ are mutually the same or different;

when a plurality of $R_{903}$ are present, the plurality of $R_{903}$ are mutually the same or different;

when a plurality of $R_{904}$ are present, the plurality of $R_{904}$ are mutually the same or different;

when a plurality of $R_{905}$ are present, the plurality of $R_{905}$ are mutually the same or different;

when a plurality of $R_{906}$ are present, the plurality of $R_{906}$ are mutually the same or different;

when a plurality of $R_{907}$ are present, the plurality of $R_{907}$ are mutually the same or different;

when a plurality of $R_{801}$ are present, the plurality of $R_{801}$ are mutually the same or different; and when a plurality of $R_{802}$ are present, the plurality of $R_{802}$ are mutually the same or different.

In the organic EL device according to the exemplary embodiment, the group represented by the formula (11) is preferably a group represented by a formula (111) below.

[Formula 58]

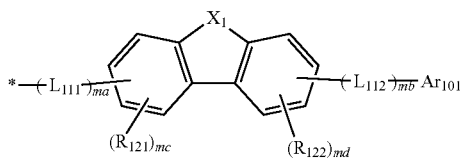

(111)

In the formula (111):

$X_1$ is $CR_{123}R_{124}$, an oxygen atom, a sulfur atom, or $NR_{125}$;

$L_{111}$ and $L_{112}$ are each independently a single bond, a substituted or unsubstituted arylene group having 6 to 50 ring carbon atoms, or a substituted or unsubstituted divalent heterocyclic group having 5 to 50 ring atoms;

ma is 0, 1, 2, 3, or 4;

mb is 0, 1, 2, 3, or 4;

ma+mb is 0, 1, 2, 3, or 4;

$Ar_{101}$ represents the same as $Ar_{101}$ in the formula (11);

$R_{121}$, $R_{122}$, $R_{123}$, $R_{124}$, and $R_{125}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si$(R_{901})(R_{902})(R_{903})$, a group represented by —O—$(R_{904})$, a group represented by —S—$(R_{905})$, a substituted or unsubstituted aralkyl group having 7 to 50 carbon atoms, a group represented by —C(=O)$R_{801}$, a group represented by —COO$R_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

mc is 3;

three $R_{121}$ are mutually the same or different; and is 3; and three $R_{122}$ are mutually the same or different.

Among positions *1 to *8 of carbon atoms in the cyclic structure represented by a formula (111a) below in the group represented by the formula (111), $L_{111}$ is bonded to one of positions *1 to *4, $R_{121}$ is bonded to three positions of the rest of *1 to *4, $L_{112}$ is bonded to one of positions *5 to *8, and $R_{122}$ is bonded to three positions of the rest of *5 to *8.

[Formula 59]

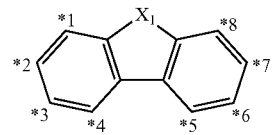

(111a)

For instance, in the group represented by the formula (111), when $L_{111}$ is bonded to a carbon atom at *2 in the cyclic structure represented by the formula (111a) and $L_{112}$ is bonded to a carbon atom at *7 in the cyclic structure represented by the formula (111a), the group represented by the formula (111) is represented by a formula (111b) below.

[Formula 60]

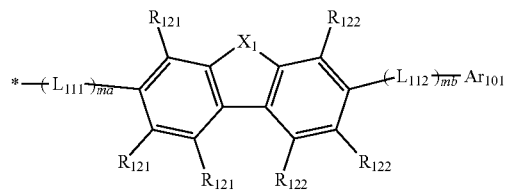

(111b)

In the formula (111b):

$X_1$, $L_{111}$, $L_{112}$, ma, mb, $Ar_{101}$, $R_{121}$, $R_{122}$, $R_{123}$, $R_{124}$, and $R_{125}$ each independently represent the same as $X_1$, $L_{111}$, $L_{112}$, ma, mb, $Ar_{101}$, $R_{121}$, $R_{122}$, $R_{123}$, $R_{124}$, and $R_{125}$ in the formula (111);

a plurality of $R_{121}$ are mutually the same or different; and a plurality of $R_{122}$ are mutually the same or different.

In the organic EL device according to the exemplary embodiment, the group represented by the formula (111) is preferably a group represented by the formula (111b).

In the organic EL device according to the exemplary embodiment, it is preferable that: ma is 0, 1, or 2; and mb is 0, 1, or 2.

In the organic EL device according to the exemplary embodiment, it is preferable that: ma is 0 or 1; and mb is 0 or 1.

In the organic EL device according to the exemplary embodiment, $Ar_{101}$ is preferably a substituted or unsubstituted aryl group having 6 to 50 ring carbon atoms.

In the organic EL device according to the exemplary embodiment, it is preferable that $Ar_{101}$ is a substituted or unsubstituted phenyl group, a substituted or unsubstituted naphthyl group, a substituted or unsubstituted biphenyl group, a substituted or unsubstituted terphenyl group, a substituted or unsubstituted pyrenyl group, a substituted or unsubstituted phenanthryl group, or a substituted or unsubstituted fluorenyl group.

In the organic EL device according to the exemplary embodiment, $Ar_{101}$ is also preferably a group represented by a formula (12), a formula (13), or a formula (14) below.

[Formula 61]

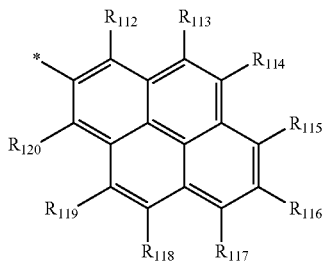
(12)

[Formula 62]

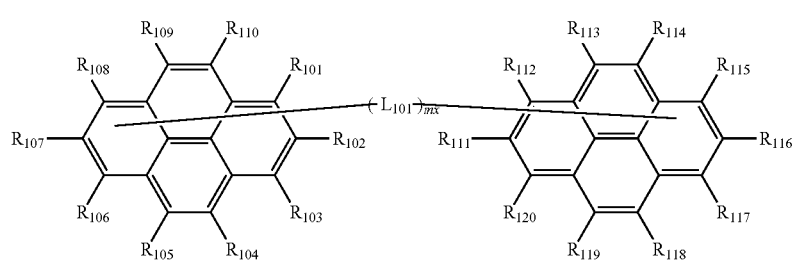
(101)

-continued

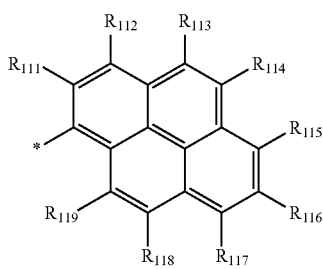
(13)

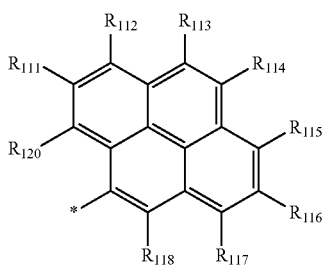
(14)

In the formulae (12), (13), and (14):

$R_{111}$ to $R_{120}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a substituted or unsubstituted aralkyl group having 7 to 50 carbon atoms, a group represented by —C(=O)$R_{124}$, a group represented by —COO$R_{125}$, a halogen atom, a cyano group, a nitro group, a substituted or unsubstituted aryl group having 6 to 50 ring carbon atoms, or a substituted or unsubstituted heterocyclic group having 5 to 50 ring atoms; and

* in each of the formulae (12), (13) and (14) represents a bonding position to $L_{101}$ in the formula (11), a bonding position to $L_{112}$ in the formula (111) or the formula (111b).

The first compound of the organic EL device according to the exemplary embodiment is preferably represented by a formula (101) below.

In the formula (101):

$R_{101}$ to $R_{120}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(=O)$R_{801}$, a group represented by —COO$R_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

one of $R_{101}$ to $R_{110}$ represents a bonding position to $L_{101}$, and one of $R_{111}$ to $R_{120}$ represents a bonding position to $L_{101}$;

$L_{101}$ is a single bond, a substituted or unsubstituted arylene group having 6 to 50 ring carbon atoms, or a substituted or unsubstituted divalent heterocyclic group having 5 to 50 ring atoms;

mx is 0, 1, 2, 3, 4, or 5; and when two or more $L_{101}$ are present, the two or more $L_{101}$ are mutually the same or different.

In the first compound represented by the formula (101), it is preferable that: $R_{101}$ to $R_{110}$, and $R_{111}$ to $R_{120}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si(R$_{901}$)(R$_{902}$)(R$_{903}$), a group represented by —O—(R$_{904}$), a group represented by —S—(R$_{905}$), a substituted or unsubstituted aralkyl group having 7 to 50 carbon atoms, a group represented by —C(=O)R$_{801}$, a group represented by —COOR$_{802}$, a halogen atom, a cyano group, a nitro group, a substituted or unsubstituted aryl group having 6 to 50 ring carbon atoms, or a substituted or unsubstituted heterocyclic group having 5 to 50 ring atoms; one of R$_{101}$ to R$_{110}$ represents a bonding position to L$_{101}$, and one of R$_{111}$ to R$_{120}$ represents a bonding position to L$_{101}$; L$_{101}$ is a single bond, a substituted or unsubstituted arylene group having 6 to 24 ring carbon atoms, or a substituted or unsubstituted divalent heterocyclic group having 5 to 24 ring atoms; mx is 1, 2, 3, 4, or 5; and when two or more L$_{101}$ are present, the two or more L$_{101}$ are mutually the same or different.

In the organic EL device according to the exemplary embodiment, the first compound is preferably represented by a formula (1010), a formula (1011), a formula (1012), a formula (1013), a formula (1014), or a formula (1015) below.

[Formula 63]

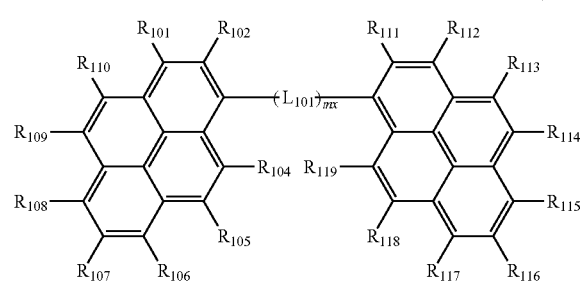

(1010)

[Formula 64]

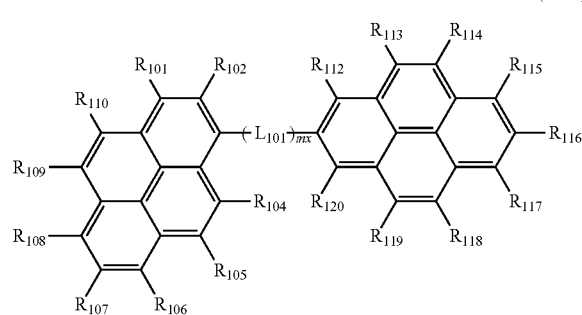

(1011)

[Formula 65]

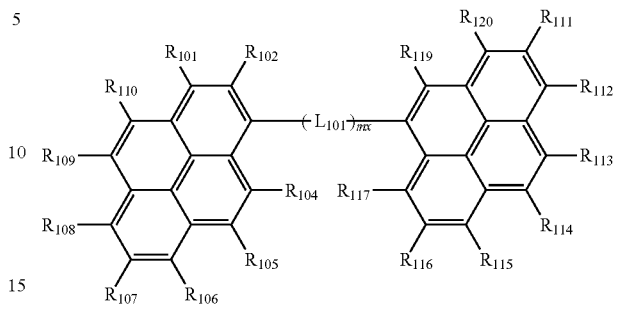

(1012)

[Formula 66]

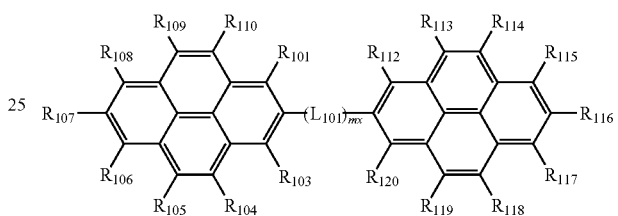

(1013)

[Formula 67]

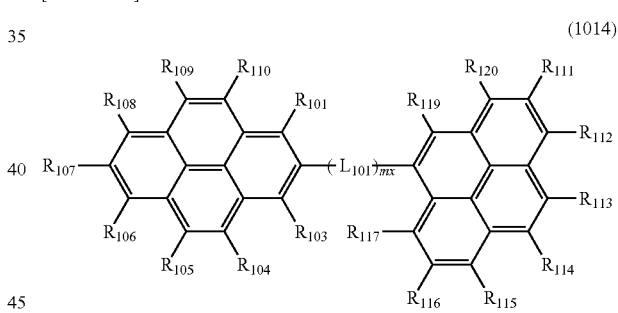

(1014)

[Formula 68]

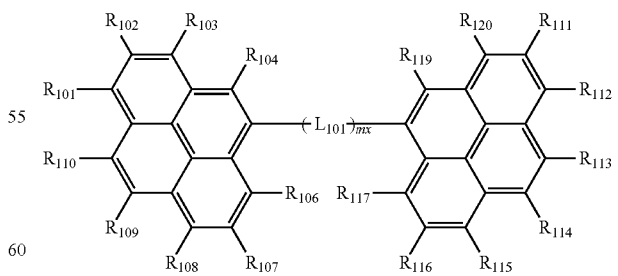

(1015)

In the formulae (1010) to (1015):

R$_{101}$ to R$_{120}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(=O)$R_{801}$, a group represented by —COO$R_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

$L_{101}$ is a single bond, a substituted or unsubstituted arylene group having 6 to 50 ring carbon atoms, or a substituted or unsubstituted divalent heterocyclic group having 5 to 50 ring atoms;

mx is 0, 1, 2, 3, 4, or 5; and when two or more $L_{101}$ are present, the two or more $L_{101}$ are mutually the same or different.

The compound represented by the formula (1010) corresponds to a compound, in which $R_{103}$ represents a bonding position to $L_{101}$ and $R_{120}$ represents a bonding position to $L_{101}$.

The compound represented by the formula (1011) corresponds to a compound, in which $R_{103}$ represents a bonding position to $L_{101}$ and $R_{111}$ represents a bonding position to $L_{101}$.

The compound represented by the formula (1012) corresponds to a compound, in which $R_{103}$ represents a bonding position to $L_{101}$ and $R_{111}$ represents a bonding position to $L_{101}$.

The compound represented by the formula (1013) corresponds to a compound, in which $R_{102}$ represents a bonding position to $L_{101}$ and $R_{111}$ represents a bonding position to $L_{101}$.

The compound represented by the formula (1014) corresponds to a compound, in which $R_{102}$ represents a bonding position to $L_{101}$ and $R_{111}$ represents a bonding position to $L_{101}$.

The compound represented by the formula (1015) corresponds to a compound, in which $R_{105}$ represents a bonding position to $L_{101}$ and $R_{111}$ represents a bonding position to $L_{101}$.

The first compound of the organic EL device according to the exemplary embodiment is preferably represented by the formula (1010).

In the organic EL device according to the exemplary embodiment, $R_{101}$ to $R_{110}$ not being the bonding position to $L_{101}$ are preferably each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

In the organic EL device according to the exemplary embodiment, $R_{101}$ to $R_{110}$ not being the bonding position to $L_{101}$ are preferably each independently a hydrogen atom, a substituted or unsubstituted alkyl group having 1 to 50 carbon atoms, or a substituted or unsubstituted cycloalkyl group having 3 to 50 ring carbon atoms.

In the organic EL device according to the exemplary embodiment, $R_{101}$ to $R_{110}$ not being the bonding position to $L_{101}$ are each preferably a hydrogen atom.

In the organic EL device according to the exemplary embodiment, $R_{111}$ to $R_{120}$ not being the bonding position to $L_{101}$ are preferably each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

In the organic EL device according to the exemplary embodiment, $R_{111}$ to $R_{120}$ not being the bonding position to $L_{101}$ are preferably each independently a hydrogen atom, a substituted or unsubstituted alkyl group having 1 to 50 carbon atoms, or a substituted or unsubstituted cycloalkyl group having 3 to 50 ring carbon atoms.

In the organic EL device according to the exemplary embodiment, $R_{111}$ to $R_{120}$ not being the bonding position to $L_{101}$ are each preferably a hydrogen atom.

In the organic EL device according to the exemplary embodiment, $L_{101}$ is preferably a single bond, or a substituted or unsubstituted arylene group having 6 to 50 ring carbon atoms.

In the organic EL device according to the exemplary embodiment, it is also preferable that $L_{101}$ is a single bond, a substituted or unsubstituted arylene group having 6 to 18 ring carbon atoms, or a substituted or unsubstituted divalent heterocyclic group having 5 to 18 ring atoms.

In the organic EL device according to the exemplary embodiment, it is also preferable that $L_{101}$ is a single bond, or a substituted or unsubstituted arylene group having 6 to 18 ring carbon atoms.

In the organic EL device according to the exemplary embodiment, it is also preferable that $L_{101}$ is a substituted or unsubstituted arylene group having 6 to 18 ring carbon atoms.

In the organic EL device according to the exemplary embodiment, it is also preferable that $L_{101}$ is a single bond, a substituted or unsubstituted arylene group having 6 to 13 ring carbon atoms, or a substituted or unsubstituted divalent heterocyclic group having 5 to 13 ring atoms.

In the organic EL device according to the exemplary embodiment, it is also preferable that $L_{101}$ is a single bond, or a substituted or unsubstituted arylene group having 6 to 13 ring carbon atoms.

In the organic EL device according to the exemplary embodiment, it is also preferable that $L_{101}$ is a substituted or unsubstituted arylene group having 6 to 13 ring carbon atoms.

In the organic EL device according to the exemplary embodiment, mx is also preferably 1, 2, or 3.

In the organic EL device according to the exemplary embodiment, mx is also preferably 1 or 2.

In the organic EL device according to the exemplary embodiment, it is also preferable that: mx is 1, 2, or 3; and $L_{101}$ is a substituted or unsubstituted arylene group having 6 to 18 ring carbon atoms, or a substituted or unsubstituted divalent heterocyclic group having 5 to 18 ring atoms.

In the organic EL device according to the exemplary embodiment, it is also preferable that: mx is 1 or 2; and $L_{101}$ is a substituted or unsubstituted arylene group having 6 to 18 ring carbon atoms, or a substituted or unsubstituted divalent heterocyclic group having 5 to 18 ring atoms.

In the organic EL device according to the exemplary embodiment, it is also preferable that: mx is 1 or 2; and $L_{101}$ is a substituted or unsubstituted arylene group having 6 to 18 ring carbon atoms.

In the organic EL device according to the exemplary embodiment, the first compound is preferably represented by a formula (102) below.

[Formula 69]

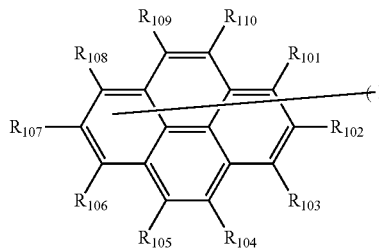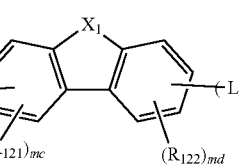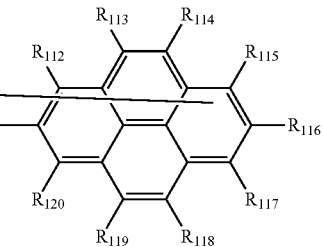

(102)

In the formula (102):

$R_{101}$ to $R_{120}$ each independently represent the same as $R_{101}$ to $R_{120}$ in the formula (101);

one of $R_{101}$ to $R_{110}$ represents a bonding position to $L_{111}$, and one of $R_{111}$ to $R_{120}$ represents a bonding position to $L_{112}$;

$X_1$ is $CR_{123}R_{124}$, an oxygen atom, a sulfur atom, or $NR_{125}$;

$L_{111}$ and $L_{112}$ are each independently a single bond, a substituted or unsubstituted arylene group having 6 to 50 ring carbon atoms, or a substituted or unsubstituted divalent heterocyclic group having 5 to 50 ring atoms;

ma is 0, 1, 2, 3, or 4;

mb is 0, 1, 2, 3, or 4;

ma+mb is 0, 1, 2, 3, or 4;

$R_{121}$, $R_{122}$, $R_{123}$, $R_{124}$, and $R_{125}$ are each dependently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a substituted or unsubstituted aralkyl group having 7 to 50 carbon atoms, a group represented by $-C(=O)R_{801}$, a group represented by $-COOR_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

mc is 3;

three $R_{121}$ are mutually the same or different;

md is 3; and three $R_{122}$ are mutually the same or different.

In the compound represented by the formula (102), it is preferable that: ma is 0, 1, or 2; and mb is 0, 1, or 2.

In the compound represented by the formula (102), it is preferable that: ma is 0 or 1; and mb is 0 or 1.

In the compound represented by the formula (102), it is preferable that $L_{111}$ and $L_{112}$ are each independently a single bond, a substituted or unsubstituted arylene group having 6 to 24 ring carbon atoms, or a substituted or unsubstituted divalent heterocyclic group having 5 to 24 ring atoms.

In the compound represented by the formula (102), it is preferable that: ma is 1, 2, or 3; mb is 1, 2, or 3; and ma+mb is 2, 3, or 4.

In the compound represented by the formula (102), it is preferable that: ma is 1 or 2; and mb is 1 or 2.

In the compound represented by the formula (102), it is preferable that: ma is 1; and mb is 1.

In the organic EL device according to the exemplary embodiment, $R_{101}$ to $R_{110}$ not being the bonding position to $L_{111}$ are preferably each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

In the organic EL device according to the exemplary embodiment, $R_{101}$ to $R_{110}$ not being the bonding position to $L_{111}$ are preferably each independently a hydrogen atom, a substituted or unsubstituted alkyl group having 1 to 50 carbon atoms, or a substituted or unsubstituted cycloalkyl group having 3 to 50 ring carbon atoms.

In the organic EL device according to the exemplary embodiment, $R_{101}$ to $R_{110}$ not being the bonding position to $L_{111}$ are each preferably a hydrogen atom.

In the organic EL device according to the exemplary embodiment, $R_{111}$ to $R_{120}$ not being the bonding position to $L_{112}$ are preferably each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

In the organic EL device according to the exemplary embodiment, $R_{111}$ to $R_{120}$ not being the bonding position to $L_{112}$ are preferably each independently a hydrogen atom, a substituted or unsubstituted alkyl group having 1 to 50 carbon atoms, or a substituted or unsubstituted cycloalkyl group having 3 to 50 ring carbon atoms.

In the organic EL device according to the exemplary embodiment, $R_{111}$ to $R_{120}$ not being the bonding position to $L_{112}$ are each preferably a hydrogen atom.

In the organic EL device according to the exemplary embodiment, two or more of $R_{101}$ to $R_{110}$ are preferably groups represented by the formula (11).

In the organic EL device according to the exemplary embodiment, it is preferable that two or more of $R_{101}$ to $R_{110}$ are groups represented by the formula (11), and $Ar_{101}$ is a substituted or unsubstituted aryl group having 6 to 50 ring carbon atoms.

In the organic EL device according to the exemplary embodiment, it is preferable that: $Ar_{101}$ is not a substituted or unsubstituted pyrenyl group; $L_{101}$ is not a substituted or unsubstituted pyrenylene group; and the substituted or unsubstituted aryl group having 6 to 50 ring carbon atoms as $R_{101}$ to $R_{110}$ not being the group represented by the formula (11) is not a substituted or unsubstituted pyrenyl group.

In the organic EL device according to the exemplary embodiment, it is preferable that $R_{101}$ to $R_{110}$ not being the group represented by the formula (11) are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

In the organic EL device according to the exemplary embodiment, it is preferable that $R_{101}$ to $R_{110}$ not being the group represented by the formula (11) are each independently a hydrogen atom, a substituted or unsubstituted alkyl group having 1 to 50 carbon atoms, or a substituted or unsubstituted cycloalkyl group having 3 to 50 ring carbon atoms.

In the organic EL device according to the exemplary embodiment, $R_{101}$ to $R_{110}$ not being the group represented by the formula (11) are each preferably a hydrogen atom.

In the first compound and the second compound, the groups specified to be "substituted or unsubstituted" are each preferably an "unsubstituted" group.

In the organic EL device according to the exemplary embodiment, for instance, two of $R_{101}$ to $R_{110}$ in the first compound represented by the formula (1) are groups represented by the formula (11).

In the organic EL device according to the exemplary embodiment, for instance, three of $R_{101}$ to $R_{110}$ in the first compound represented by the formula (1) are groups represented by the formula (11).

In the organic EL device according to the exemplary embodiment, for instance, four of $R_{101}$ to $R_{110}$ in the first compound represented by the formula (1) are groups represented by the formula (11).

In the organic EL device according to the exemplary embodiment, for instance, one of $R_{101}$ to $R_{110}$ in the first compound represented by the formula (1) is a group represented by the formula (11) and mx is 1 or more.

In the organic EL device according to the exemplary embodiment, for instance, one of $R_{101}$ to $R_{110}$ in the first compound represented by the formula (1) is a group represented by the formula (11), mx is 0, and $Ar_{101}$ is a substituted or unsubstituted aryl group.

In the organic EL device according to the exemplary embodiment, for instance, one of $R_{101}$ to $R_{110}$ in the first compound represented by the formula (1) is a group represented by the formula (11), mx is 0, and $Ar_{101}$ is a substituted or unsubstituted heterocyclic group including a nitrogen atom.

In the organic EL device according to the exemplary embodiment, for instance, one of $R_{101}$ to $R_{110}$ in the first compound represented by the formula (1) is a group represented by the formula (11), mx is 0, and $Ar_{101}$ is a substituted or unsubstituted heterocyclic group including a sulfur atom.

In the organic EL device according to the exemplary embodiment, for instance, one of $R_{101}$ to $R_{110}$ in the first compound represented by the formula (1) is a group represented by the formula (11), mx is 0, and $Ar_{101}$ is a substituted or unsubstituted furyl group, oxazolyl group, isoxazolyl group, oxadiazolyl group, xanthenyl group, benzofuranyl group, isobenzofuranyl group, dibenzofuranyl group, benzoxazolyl group, benzisoxazolyl group, phenoxazinyl group, morpholino group, dinaphthofuranyl group, azadibenzofuranyl group, diazadibenzofuranyl group, azanaphthobenzofuranyl group, and diazanaphthobenzofuranyl group.

In the organic EL device according to the exemplary embodiment, for instance, one of $R_{101}$ to $R_{110}$ in the first compound represented by the formula (1) is a group represented by the formula (11), mx is 0, and $Ar_{101}$ is at least one group selected from the group consisting of unsubstituted furyl group, oxazolyl group, isoxazolyl group, oxadiazolyl group, xanthenyl group, benzofuranyl group, isobenzofuranyl group, dibenzofuranyl group, benzoxazolyl group, benzisoxazolyl group, phenoxazinyl group, morpholino group, dinaphthofuranyl group, azadibenzofuranyl group, diazadibenzofuranyl group, azanaphthobenzofuranyl group, and diazanaphthobenzofuranyl group.

In the organic EL device according to the exemplary embodiment, for instance, one of $R_{101}$ to $R_{110}$ in the first compound represented by the formula (1) is a group represented by the formula (11), mx is 0, and $Ar_{101}$ is a substituted or unsubstituted dibenzofuranyl group.

In the organic EL device according to the exemplary embodiment, for instance, one of $R_{101}$ to $R_{110}$ in the first compound represented by the formula (1) is a group represented by the formula (11), mx is 0, and $Ar_{101}$ is an unsubstituted dibenzofuranyl group.

In the organic EL device according to the exemplary embodiment, for instance, mx in the first compound represented by the formula (101) is 2 or more.

In the organic EL device according to the exemplary embodiment, for instance, mx in the first compound represented by the formula (101) is 1 or more, and $L_{101}$ is an arylene group having 6 to 24 ring carbon atoms or a divalent heterocyclic group having 5 to 24 ring atoms.

In the organic EL device according to the exemplary embodiment, for instance, mx in the first compound represented by the formula (101) is 1 or more, and $L_{101}$ is an arylene group having 6 to 18 ring carbon atoms or a divalent heterocyclic group having 5 to 18 ring atoms.

Compound Represented by Formula (1X)

In the organic EL device according to the exemplary embodiment, the first compound is also preferably a compound represented by the formula (1X).

[Formula 70]

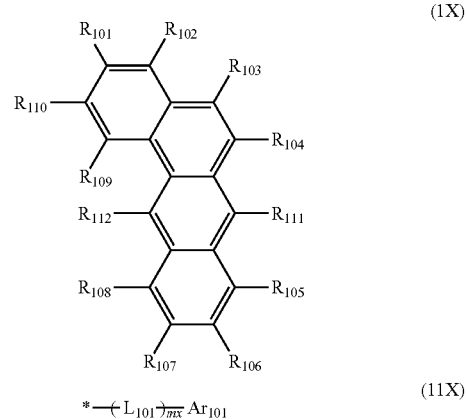

In the formula (1X):

$R_{101}$ to $R_{112}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(=O)$R_{801}$, a group represented by —COO$R_{802}$, a halogen atom, a cyano group, a nitro group, a substituted or unsubstituted aryl group having 6 to 50 ring carbon atoms, a substituted or unsubstituted heterocyclic group having 5 to 50 ring atoms, or a group represented by the formula (11X);

at least one of $R_{101}$ to $R_{112}$ is the group represented by the formula (11X);

when a plurality of groups represented by the formula (11X) are present, the plurality of groups represented by the formula (11X) are mutually the same or different;

$L_{101}$ is a single bond, a substituted or unsubstituted arylene group having 6 to 50 ring carbon atoms, or a substituted or unsubstituted divalent heterocyclic group having 5 to 50 ring atoms;

$Ar_{101}$ is a substituted or unsubstituted aryl group having 6 to 50 ring carbon atoms, or a substituted or unsubstituted heterocyclic group having 5 to 50 ring atoms;

mx is 1, 2, 3, 4, or 5;

when two or more $L_{101}$ are present, the two or more $L_{101}$ are mutually the same or different;

when two or more $Ar_{101}$ are present, the two or more $Ar_{101}$ are mutually the same or different; and

* in the formula (11X) represents a bonding position to a benz[a]anthracene ring in the formula (1X).

In the organic EL device according to the exemplary embodiment, the group represented by the formula (11X) is preferably a group represented by a formula (111X) below.

[Formula 71]

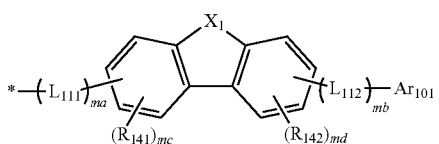

(111X)

In the formula (111X):

$X_1$ is $CR_{143}R_{144}$, an oxygen atom, a sulfur atom, or $NR_{145}$;

$L_{111}$ and $L_{112}$ are each independently a single bond, a substituted or unsubstituted arylene group having 6 to 50 ring carbon atoms, or a substituted or unsubstituted divalent heterocyclic group having 5 to 50 ring atoms;

ma is 1, 2, 3, or 4;

mb is 1, 2, 3, or 4;

ma+mb is 2, 3, or 4;

$Ar_{101}$ represents the same as $Ar_{101}$ in the formula (11);

$R_{141}$, $R_{142}$, $R_{143}$, $R_{144}$ and $R_{145}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(=O)$R_{801}$, a group represented by —COO$R_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

mc is 3;

three $R_{141}$ are mutually the same or different;

md is 3; and three $R_{142}$ are mutually the same or different.

Among positions *1 to *8 of carbon atoms in a cyclic structure represented by a formula (111aX) below in the group represented by the formula (111X), $L_{111}$ is bonded to one of the positions *1 to *4, $R_{141}$ is bonded to each of three positions of the rest of *1 to *4, $L_{112}$ is bonded to one of the positions *5 to *8, and $R_{142}$ is bonded to each of three positions of the rest of *5 to *8.

[Formula 72]

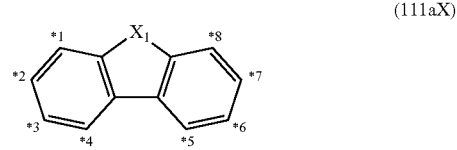

(111aX)

For instance, when $L_{111}$ is bonded to a carbon atom at position *2 in the cyclic structure represented by the formula (111aX) and $L_{112}$ is bonded to a carbon atom at position *7 in the cyclic structure represented by the formula (111aX) in the group represented by the formula (111X), the group represented by the formula (111X) is represented by a formula (111bX) below.

[Formula 73]

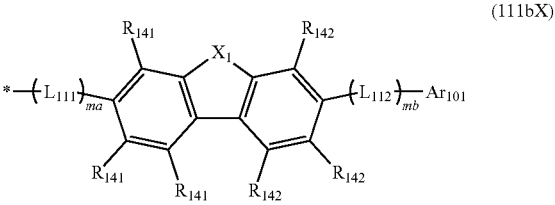

(111bX)

In the formula (111bX):

$X_1$, $L_{111}$, $L_{112}$, ma, mb, $Ar_{101}$, $R_{141}$, $R_{142}$, $R_{143}$, $R_{144}$ and $R_{145}$ each independently represent the same as $X_1$, $L_{111}$, $L_{112}$, ma, mb, $Ar_{101}$, $R_{141}$, $R_{142}$, $R_{143}$, $R_{144}$ and $R_{145}$ in the formula (111X);

a plurality of $R_{141}$ are mutually the same or different; and a plurality of $R_{142}$ are mutually the same or different.

In the organic EL device according to the exemplary embodiment, the group represented by the formula (111X) is preferably the group represented by the formula (111bX).

In the compound represented by the formula (1X), it is preferable that ma is 1 or 2 and mb is 1 or 2.

In the compound represented by the formula (1X), it is preferable that ma is 1 and mb is 1.

In the compound represented by the formula (1X), $Ar_{101}$ is preferably a substituted or unsubstituted aryl group having 6 to 50 ring carbon atoms.

In the compound represented by the formula (1X), $Ar_{101}$ is preferably a substituted or unsubstituted phenyl group, a substituted or unsubstituted naphthyl group, a substituted or unsubstituted biphenyl group, a substituted or unsubstituted terphenyl group, a substituted or unsubstituted benz[a]anthryl group, a substituted or unsubstituted pyrenyl group, a substituted or unsubstituted phenanthryl group, or a substituted or unsubstituted fluorenyl group.

The compound represented by the formula (1X) is also preferably represented by a formula (101X) below.

[Formula 74]

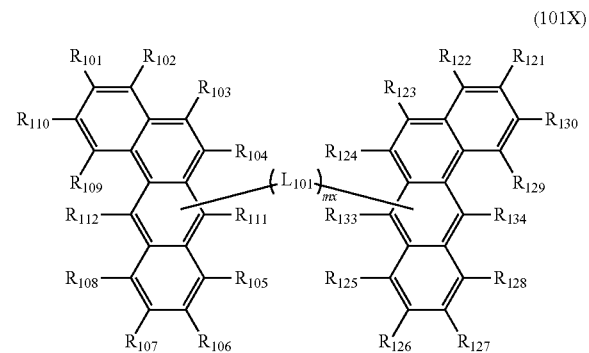

(101X)

In the formula (101X):

one of $R_{111}$ and $R_{112}$ represents a bonding position to $L_{101}$ and one of $R_{133}$ and $R_{134}$ represents a bonding position to $L_{101}$;

$R_{111}$ or $R_{112}$ that is not a bonding position to $R_{101}$ to $R_{110}$, $R_{121}$ to $R_{130}$, and $L_{101}$, and $R_{133}$ or $R_{134}$ that is not a bonding position to $L_{101}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(=O)$R_{801}$, a group represented by —COO$R_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

$L_{101}$ is a single bond, a substituted or unsubstituted arylene group having 6 to 50 ring carbon atoms, or a substituted or unsubstituted divalent heterocyclic group having 5 to 50 ring atoms;

mx is 1, 2, 3, 4, or 5; and when two or more $L_{101}$ are present, the two or more $L_{101}$ are mutually the same or different.

In the compound represented by the formula (1X), $L_{101}$ is preferably a single bond or a substituted or unsubstituted arylene group having 6 to 50 ring carbon atoms.

The compound represented by the formula (1X) is also preferably represented by a formula (102X) below.

[Formula 75]

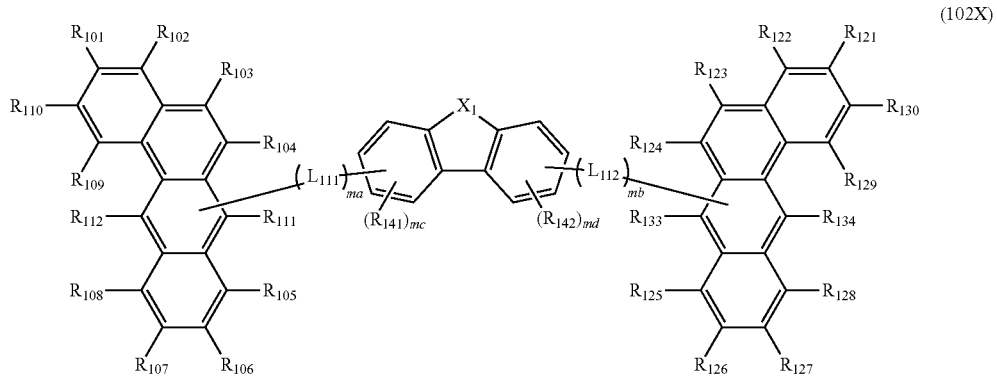

(102X)

In the formula (102X):

one of $R_{111}$ and $R_{112}$ represents a bonding position to $L_{111}$ and one of $R_{133}$ and $R_{134}$ represents a bonding position to $L_{112}$;

$R_{111}$ or $R_{112}$ that is not a bonding position to $R_{101}$ to $R_{110}$, $R_{121}$ to $R_{130}$ and $L_{111}$, and $R_{133}$ or $R_{134}$ that is not a bonding position to $L_{112}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(=O)$R_{180}$, a group represented by —COOR$_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

$X_1$ is $CR_{143}R_{144}$, an oxygen atom, a sulfur atom, or $NR_{145}$;

$L_{111}$ and $L_{112}$ are each independently a single bond, a substituted or unsubstituted arylene group having 6 to 50 ring carbon atoms, or a substituted or unsubstituted divalent heterocyclic group having 5 to 50 ring atoms; ma is 1, 2, 3, or 4;

mb is 1, 2, 3, or 4;

ma+mb is 2, 3, 4 or 5;

$R_{141}$, $R_{142}$, $R_{143}$, $R_{144}$ and $R_{145}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(=O)$R_{801}$, a group represented by —COOR$_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

mc is 3;

three $R_{141}$ are mutually the same or different;

md is 3; and three $R_{142}$ are mutually the same or different.

In the compound represented by the formula (1X), it is preferable that ma is 1 or 2 and mb is 1 or 2 in the formula (102X).

In the compound represented by the formula (1X), it is preferable that ma is 1 and mb is 1 in the formula (102X).

In the compound represented by the formula (1X), the group represented by the formula (11X) is also preferably a group represented by a formula (11AX) below or a group represented by a formula (11BX) below.

[Formula 76]

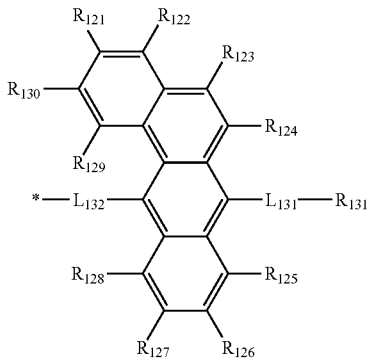

(11AX)

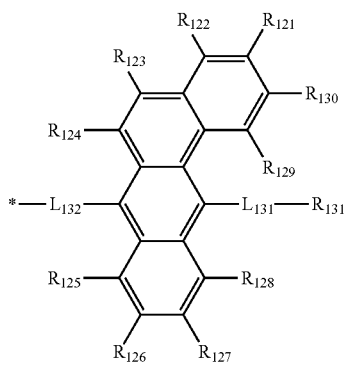

(11BX)

In the formulae (11AX) and (11BX):

$R_{121}$ to $R_{131}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(=O)$R_{801}$, a group represented by —COOR$_{802}$, a halogen atom, a cyano group, a nitro group, a substituted or unsubstituted aryl group having 6 to 50 ring carbon atoms, or a substituted or unsubstituted heterocyclic group having 5 to 50 ring atoms, when a plurality of groups represented by the formula (11AX) are present, the plurality of groups represented by the formula (11AX) are mutually the same or different;

when a plurality of groups represented by the formula (11BX) are present, the plurality of groups represented by the formula (11BX) are mutually the same or different;

$L_{131}$ and $L_{132}$ are each independently a single bond, a substituted or unsubstituted arylene group having 6 to 50 ring carbon atoms, or a substituted or unsubstituted divalent heterocyclic group having 5 to 50 ring atoms; and

* in each of the formulae (11AX) and (11BX) represents a bonding position to a benz[a]anthracene ring in the formula (1X).

The compound represented by the formula (1X) is also preferably represented by a formula (103X) below.

[Formula 77]

(103X)

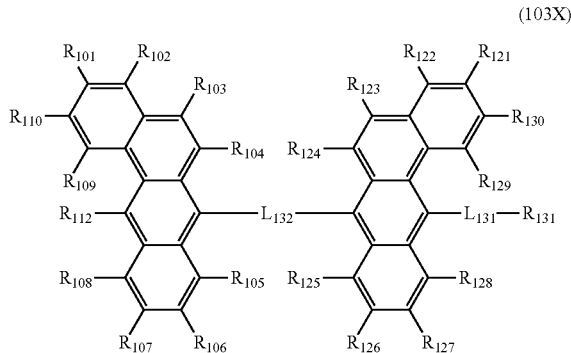

In the formula (103X):

$R_{101}$ to $R_{110}$ and $R_{112}$ respectively represent the same as $R_{101}$ to $R_{110}$ and $R_{112}$ in the formula (1X); and $R_{121}$ to $R_{131}$, $L_{131}$, and $L_{132}$ respectively represent the same as $R_{121}$ to $R_{131}$, $L_{131}$, and $L_{132}$ in the formula (11BX).

In the compound represented by the formula (1X), $L_{131}$ is also preferably a substituted or unsubstituted arylene group having 6 to 50 ring carbon atoms.

In the compound represented by the formula (1X), $L_{132}$ is also preferably a substituted or unsubstituted arylene group having 6 to 50 ring carbon atoms.

In the compound represented by the formula (1X), two or more of $R_{101}$ to $R_{112}$ are also preferably the groups represented by the formula (11).

In the compound represented by the formula (1X), it is preferable that two or more of $R_{101}$ to $R_{112}$ are the groups represented by the formula (11X) and $Ar_{101}$ in the formula (11X) is a substituted or unsubstituted aryl group having 6 to 50 ring carbon atoms.

In the compound represented by the formula (1X): it is also preferable that $Ar_{101}$ is not a substituted or unsubstituted benz[a]anthryl group, $L_{101}$ is not a substituted or unsubstituted benz[a]anthrylene group, and a substituted or unsubstituted aryl group having 6 to 50 ring carbon atoms as $R_{101}$ to $R_{110}$ that are not the groups represented by the formula (11X) is not a substituted or unsubstituted benz[a]anthryl group.

In the compound represented by the formula (1X), $R_{101}$ to $R_{112}$ not being the groups represented by the formula (11X) are preferably each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms, In the compound represented by the formula (1X), $R_{101}$ to $R_{112}$ not being the groups represented by the formula (11X) are preferably each independently a hydrogen atom, a substituted or unsubstituted alkyl group having 1 to 50 carbon atoms, or a substituted or unsubstituted cycloalkyl group having 3 to 50 ring carbon atoms.

In the compound represented by the formula (1X), $R_{101}$ to $R_{112}$ not being the groups represented by the formula (11X) are each preferably a hydrogen atom.

Compound Represented by Formula (12X)

In the organic EL device according to the exemplary embodiment, the first compound is also preferably a compound represented by the formula (12X).

[Formula 78]

(12X)

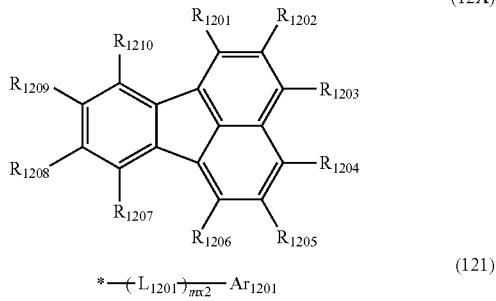

(121)

$*\!-\!(L_{1201})_{\overline{mx2}}\!-\!Ar_{1201}$

In the formula (12X):

at least one combination of adjacent two or more of $R_{1201}$ to $R_{1210}$ are mutually bonded to form a substituted or unsubstituted monocyclic ring, or mutually bonded to form a substituted or unsubstituted fused ring;

$R_{1201}$ to $R_{1210}$ not forming the substituted or unsubstituted monocyclic ring and not forming the substituted or unsubstituted fused ring are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(=O)$R_{801}$, a group represented by —COOR$_{802}$, a halogen atom, a cyano group, a nitro group, a substituted or unsubstituted aryl group having 6 to 50 ring carbon atoms, a substituted or unsubstituted heterocyclic group having 5 to 50 ring atoms, or a group represented by the formula (121);

a substituent for substituting the substituted or unsubstituted monocyclic ring, a substituent for substituting the substituted or unsubstituted fused ring, and at least one of $R_{1201}$ to $R_{1210}$ are each the group represented by the formula (121);

when a plurality of groups represented by the formula (121) are present, the plurality of groups represented by the formula (121) are mutually the same or different;

$L_{1201}$ is a single bond, a substituted or unsubstituted arylene group having 6 to 50 ring carbon atoms, or a substituted or unsubstituted divalent heterocyclic group having 5 to 50 ring atoms;

$Ar_{1201}$ is a substituted or unsubstituted aryl group having 6 to 50 ring carbon atoms, or a substituted or unsubstituted heterocyclic group having 5 to 50 ring atoms;

mx2 is 0, 2, 3, 4 or 5;

when two or more $L_{1201}$ are present, the two or more $L_{1201}$ are mutually the same or different;

when two or more $Ar_{1201}$ are present, the two or more $Ar_{1201}$ are mutually the same or different; and

* in the formula (121) represents a bonding position to the ring represented by the formula (12X).

In the formula (12X), combinations of adjacent two of $R_{1201}$ to $R_{1210}$ refer to a combination of $R_{1201}$ and $R_{1202}$, a combination of $R_{1202}$ and $R_{1203}$, a combination of $R_{1203}$ and $R_{1204}$, a combination of $R_{1204}$ and $R_{1205}$, a combination of $R_{1205}$ and $R_{1206}$, a combination of $R_{1207}$ and $R_{1208}$, a combination of $R_{1208}$ and $R_{1209}$, and a combination of $R_{1209}$ and $R_{1210}$.

Compound Represented by Formula (13X)

In the organic EL device according to the exemplary embodiment, the first compound is also preferably a compound represented by the formula (13X).

[Formula 79]

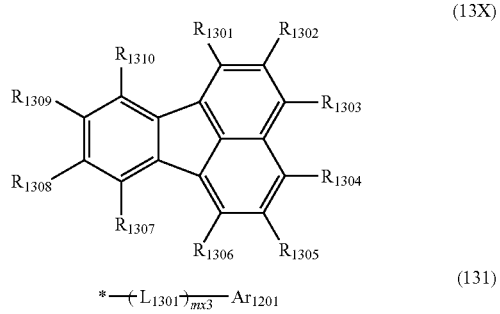

(13X)

$$*-(L_{1301})_{\overline{mx3}}-Ar_{1201}$$ (131)

In the formula (13X):

$R_{1301}$ to $R_{1310}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(=O)$R_{801}$, a group represented by —COO$R_{802}$, a halogen atom, a cyano group, a nitro group, a substituted or unsubstituted aryl group having 6 to 50 ring carbon atoms, a substituted or unsubstituted heterocyclic group having 5 to 50 ring atoms, or a group represented by the formula (131);

at least one of $R_{1301}$ to $R_{1310}$ is the group represented by the formula (131);

when a plurality of groups represented by the formula (131) are present, the plurality of groups represented by the formula (131) are mutually the same or different;

$L_{1301}$ is a single bond, a substituted or unsubstituted arylene group having 6 to 50 ring carbon atoms, or a substituted or unsubstituted divalent heterocyclic group having 5 to 50 ring atoms;

$Ar_{1301}$ is a substituted or unsubstituted aryl group having 6 to 50 ring carbon atoms, or a substituted or unsubstituted heterocyclic group having 5 to 50 ring atoms;

mx3 is 0, 1, 2, 3, 4 or 5;

when two or more $L_{1301}$ are present, the two or more $L_{1301}$ are mutually the same or different;

when two or more $Ar_{1301}$ are present, the two or more $Ar_{1301}$ are mutually the same or different; and

* in the formula (131) represents a bonding position to the fluoranthene ring in the formula (13X).

In the organic EL device according to the exemplary embodiment, combinations of adjacent two or more of $R_{1301}$ to $R_{1310}$ that are not the group represented by the formula (131) are not mutually bonded. In the formula (13X), combinations of adjacent two of $R_{1301}$ to $R_{1310}$ refer to a combination of $R_{1301}$ and $R_{1302}$, a combination of $R_{1302}$ and $R_{1303}$, a combination of $R_{1303}$ and $R_{1304}$, a combination of $R_{1304}$ and $R_{1305}$, a combination of $R_{1305}$ and $R_{1306}$, a combination of $R_{1307}$ and $R_{1308}$, a combination of $R_{1308}$ and $R_{1309}$, and a combination of $R_{1309}$ and $R_{1310}$.

Compound Represented by Formula (14X)

In the organic EL device according to the exemplary embodiment, the first compound is also preferably a compound represented by the formula (14X).

[Formula 80]

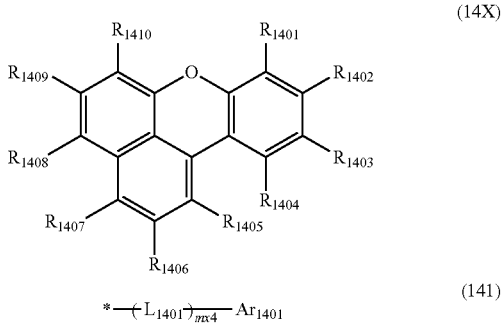

(14X)

$$*-(L_{1401})_{\overline{mx4}}-Ar_{1401}$$ (141)

In the formula (14X):

$R_{1401}$ to $R_{1410}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(=O)$R_{801}$, a group represented by —COO$R_{802}$, a halogen atom, a cyano group, a nitro group, a substituted or unsubstituted aryl group having 6 to 50 ring carbon atoms, a substituted or unsubstituted heterocyclic group having 5 to 50 ring atoms, or a group represented by the formula (141);

at least one of $R_{1401}$ to $R_{1410}$ is the group represented by the formula (141);

when a plurality of groups represented by the formula (141) are present, the plurality of groups represented by the formula (141) are mutually the same or different;

$L_{1401}$ is a single bond, a substituted or unsubstituted arylene group having 6 to 50 ring carbon atoms, or a substituted or unsubstituted divalent heterocyclic group having 5 to 50 ring atoms;

$Ar_{1401}$ is a substituted or unsubstituted aryl group having 6 to 50 ring carbon atoms, or a substituted or unsubstituted heterocyclic group having 5 to 50 ring atoms; mx4 is 0, 1, 2, 3, 4 or 5;

when two or more $L_{1401}$ are present, the two or more $L_{1401}$ are mutually the same or different;

when two or more $Ar_{1401}$ are present, the two or more $Ar_{1401}$ are mutually the same or different; and

* in the formula (141) represents a bonding position to the ring represented by the formula (14X).

Compound Represented by Formula (15X)

In the organic EL device according to the exemplary embodiment, the first compound is also preferably a compound represented by the formula (15X).

[Formula 81]

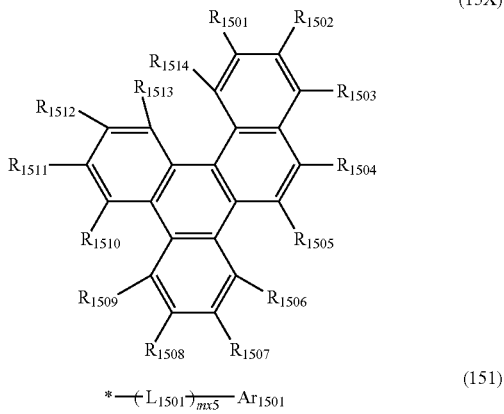

(15X)

*―(L₁₅₀₁)ₘₓ₅―Ar₁₅₀₁  (151)

In the formula (15X):

$R_{1501}$ to $R_{1514}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(=O)$R_{801}$, a group represented by —COOR$_{802}$, a halogen atom, a cyano group, a nitro group, a substituted or unsubstituted aryl group having 6 to 50 ring carbon atoms, a substituted or unsubstituted heterocyclic group having 5 to 50 ring atoms, or a group represented by the formula (151);

at least one of $R_{1501}$ to $R_{1514}$ is the group represented by the formula (151);

when a plurality of groups represented by the formula (151) are present, the plurality of groups represented by the formula (151) are mutually the same or different;

$L_{1501}$ is a single bond, a substituted or unsubstituted arylene group having 6 to 50 ring carbon atoms, or a substituted or unsubstituted divalent heterocyclic group having 5 to 50 ring atoms;

$Ar_{1501}$ is a substituted or unsubstituted aryl group having 6 to 50 ring carbon atoms, or a substituted or unsubstituted heterocyclic group having 5 to 50 ring atoms;

mx5 is 0, 1, 2, 3, 4 or 5;

when two or more $L_{1501}$ are present, the two or more $L_{1501}$ are mutually the same or different;

when two or more $Ar_{1501}$ are present, the two or more $Ar_{1501}$ are mutually the same or different; and

* in the formula (151) represents a bonding position to the ring represented by the formula (15X).

Compound Represented by Formula (16X)

In the organic EL device according to the exemplary embodiment, the first compound is also preferably a compound represented by the formula (16X).

[Formula 82]

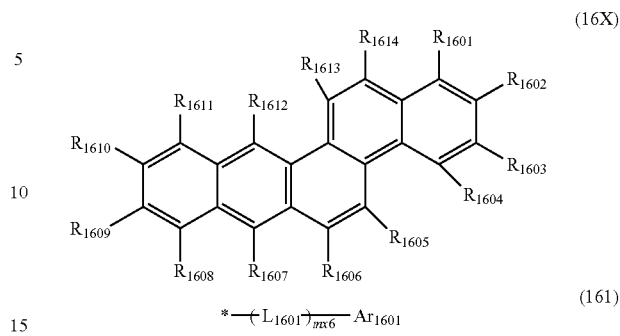

(16X)

*―(L₁₆₀₁)ₘₓ₆―Ar₁₆₀₁  (161)

In the formula (16X):

$R_{1601}$ to $R_{1614}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(=O)$R_{801}$, a group represented by —COOR$_{802}$, a halogen atom, a cyano group, a nitro group, a substituted or unsubstituted aryl group having 6 to 50 ring carbon atoms, a substituted or unsubstituted heterocyclic group having 5 to 50 ring atoms, or a group represented by the formula (161);

at least one of $R_{1601}$ to $R_{1614}$ is the group represented by the formula (161);

when a plurality of groups represented by the formula (161) are present, the plurality of groups represented by the formula (161) are mutually the same or different;

$L_{1601}$ is a single bond, a substituted or unsubstituted arylene group having 6 to 50 ring carbon atoms, or a substituted or unsubstituted divalent heterocyclic group having 5 to 50 ring atoms;

$Ar_{1601}$ is a substituted or unsubstituted aryl group having 6 to 50 ring carbon atoms, or a substituted or unsubstituted heterocyclic group having 5 to 50 ring atoms;

mx6 is 0, 1, 2, 3, 4 or 5;

when two or more $L_{1601}$ are present, the two or more $L_{1601}$ are mutually the same or different;

when two or more $Ar_{1601}$ are present, the two or more $Ar_{1601}$ are mutually the same or different; and

* in the formula (161) represents a bonding position to the ring represented by the formula (16X).

In the first compound and the second compound, all groups described as "substituted or unsubstituted" groups are preferably "unsubstituted" groups.

Method of Manufacturing First Compound

The first compound can be manufactured by a known method. The first compound can also be manufactured based on a known method through a known alternative reaction using a known material(s) tailored for the target compound.

Specific Examples of First Compound

Specific examples of the first compound include the following compounds. It should however be noted that the invention is not limited by the specific examples of the first compound.

In the specific examples of the compound herein, D represents a deuterium atom, Me represents a methyl group, and tBu represents a tert-butyl group.

[Formula 83]
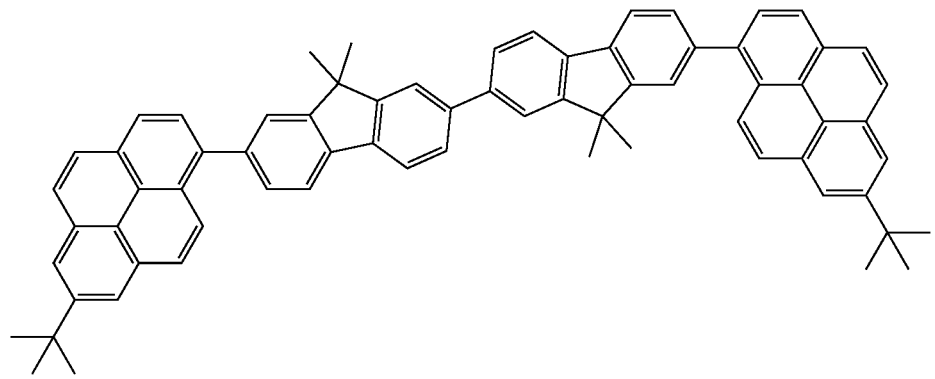
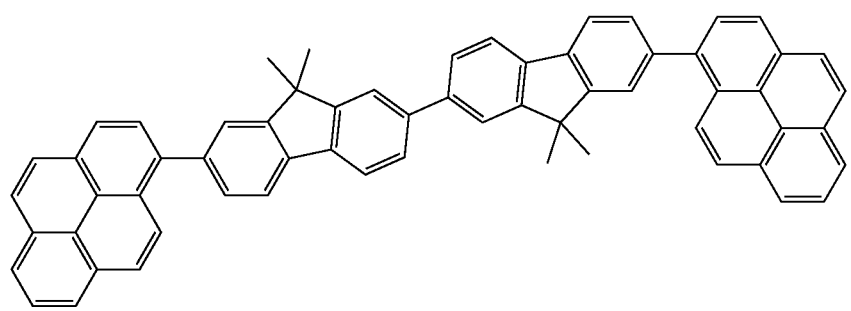
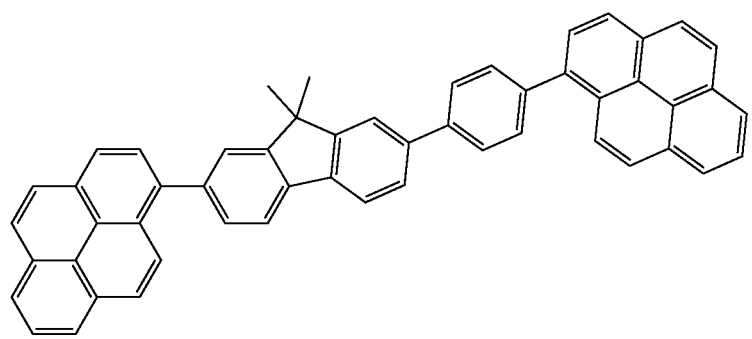
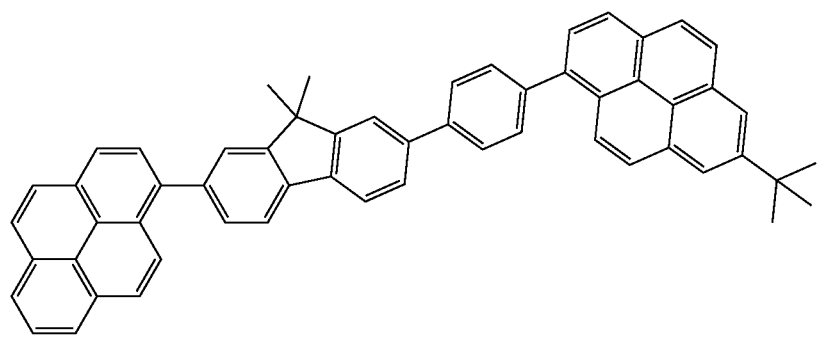
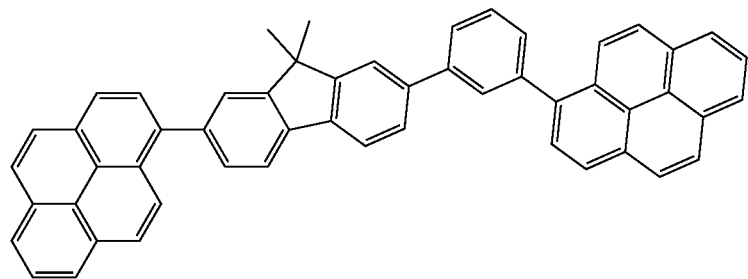

-continued
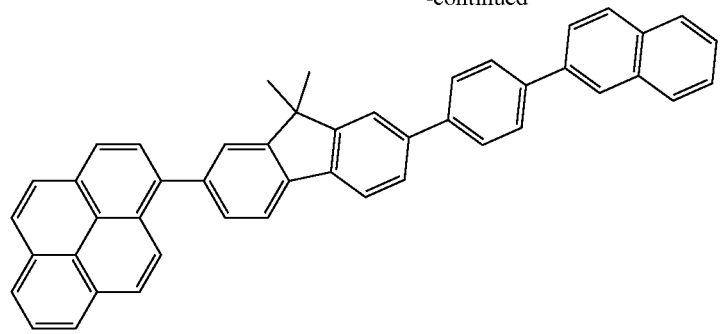
[Formula 84]
-continued
[Formula 85]

-continued
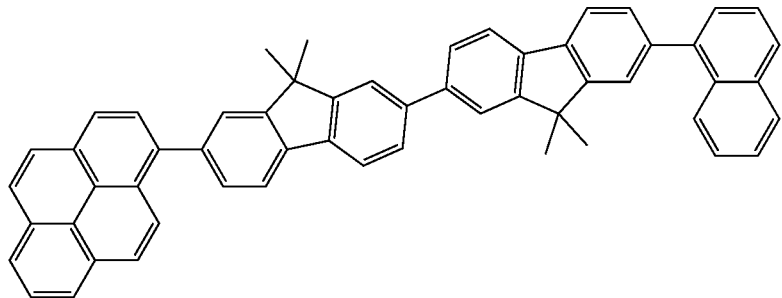

[Formula 86]
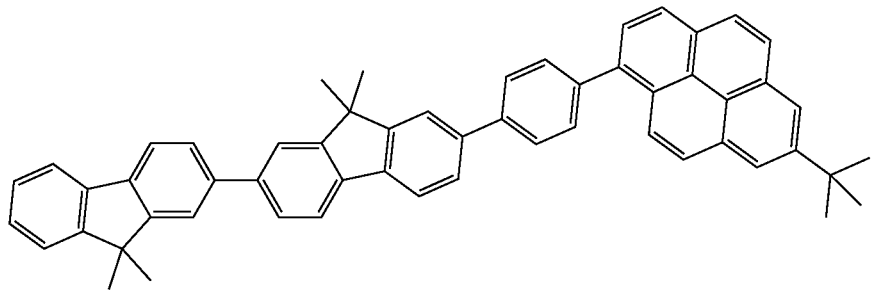
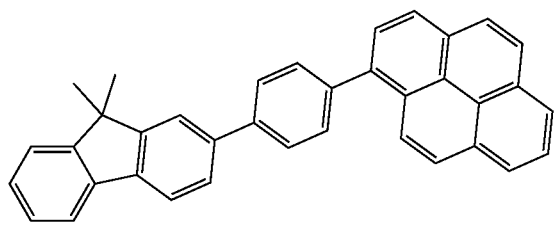
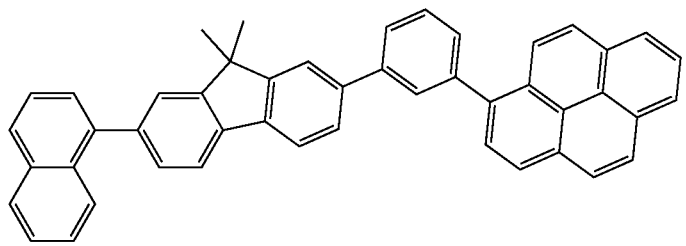
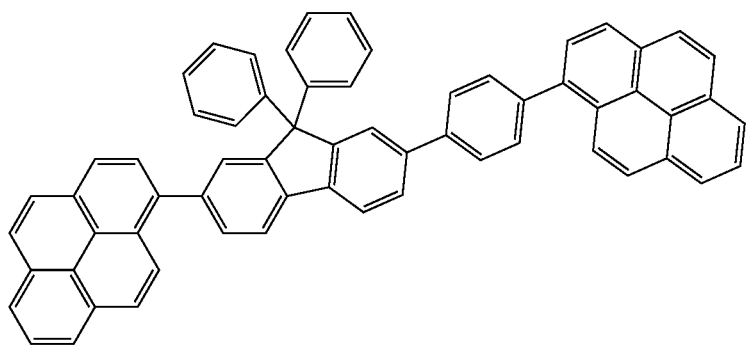
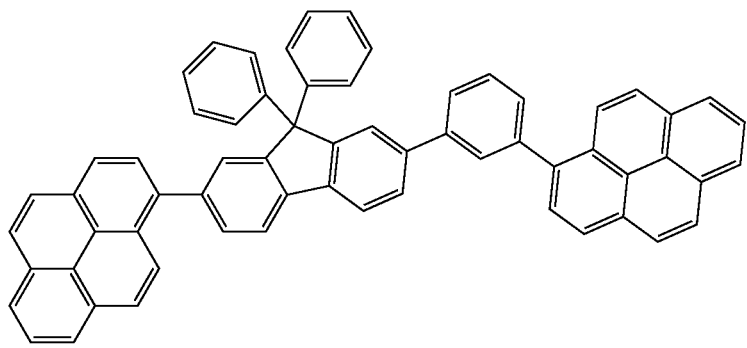

-continued
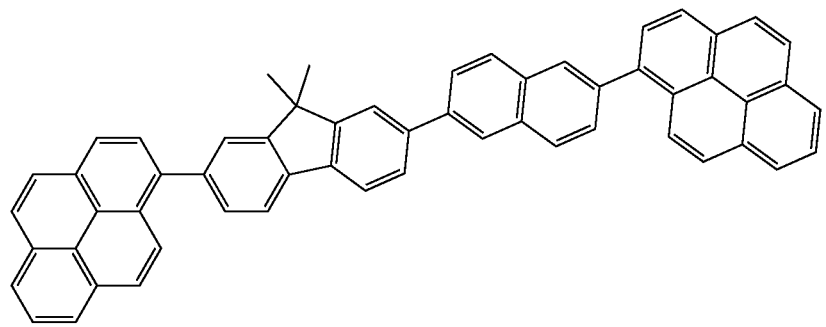
[Formula 87]
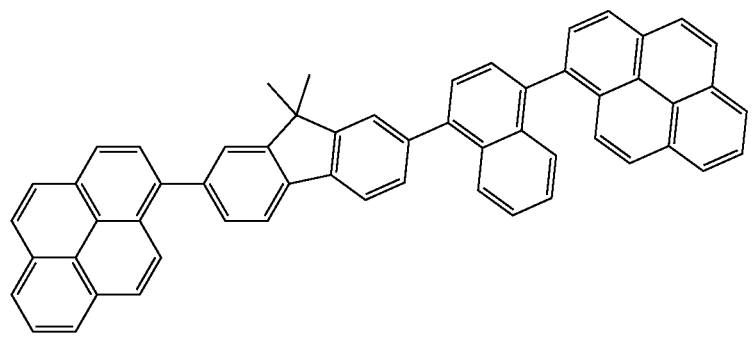
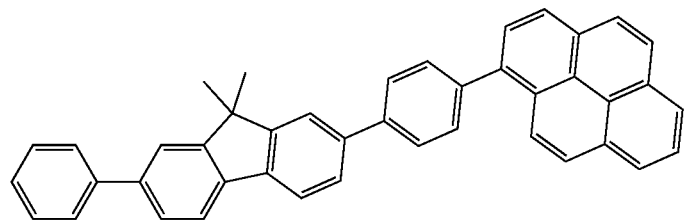
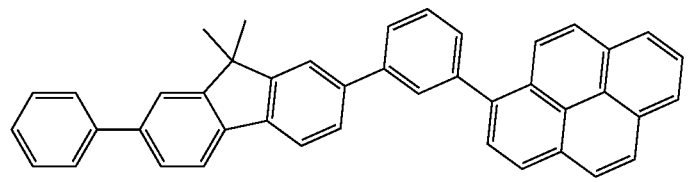
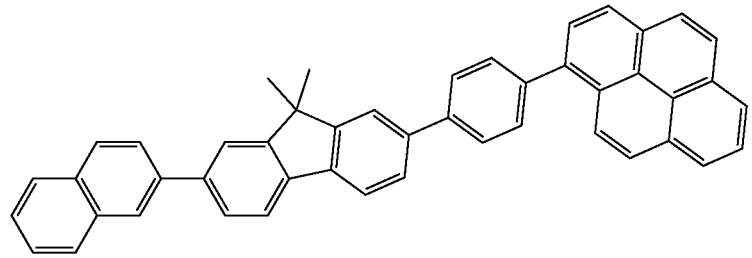
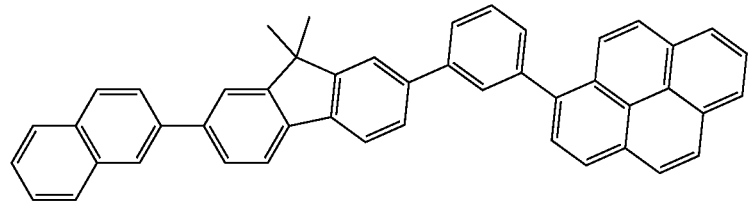

-continued
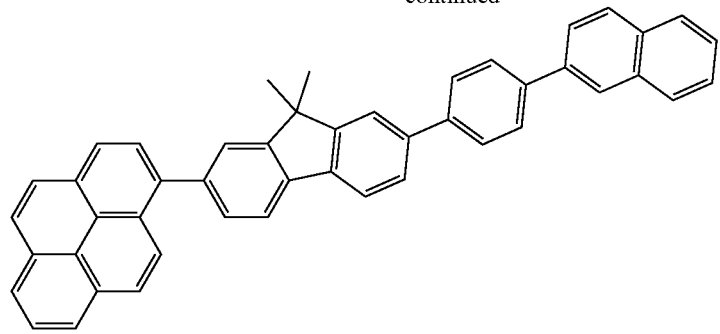
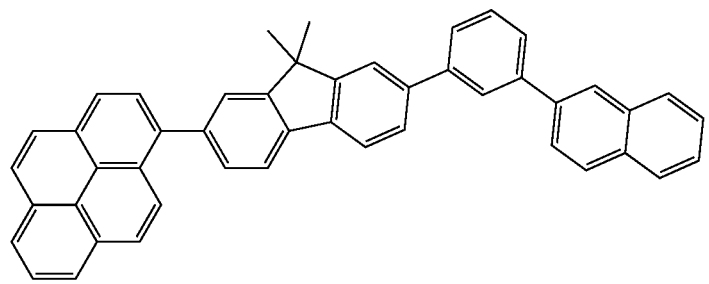
[Formula 88]
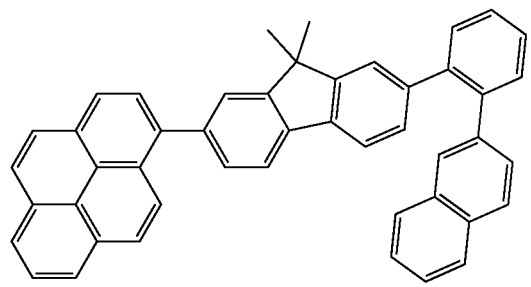
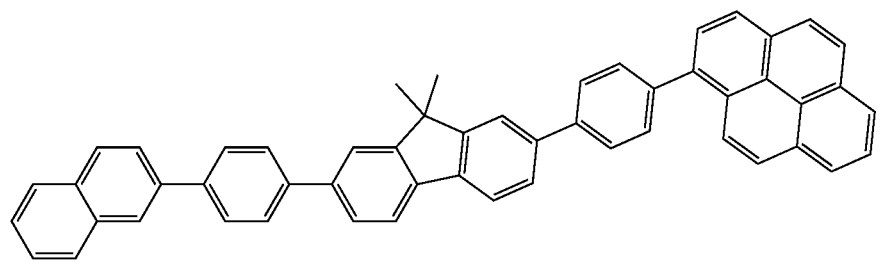
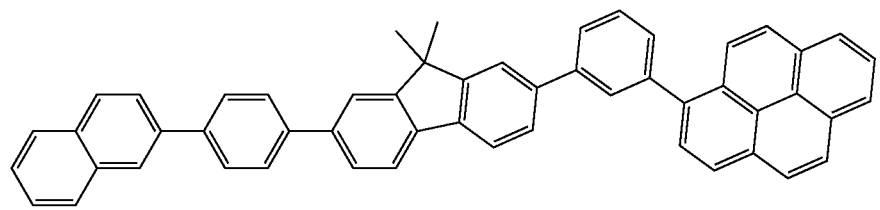

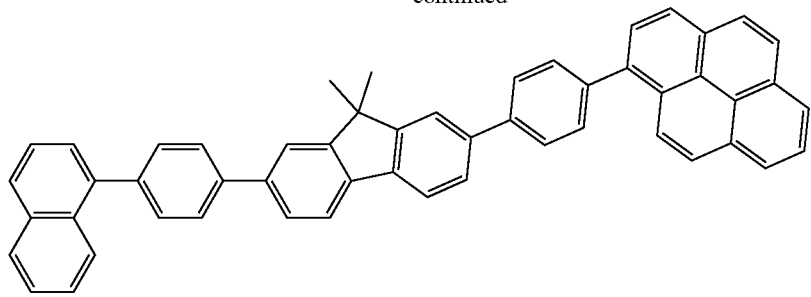
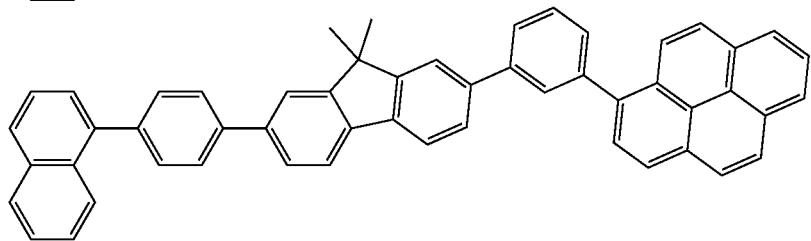
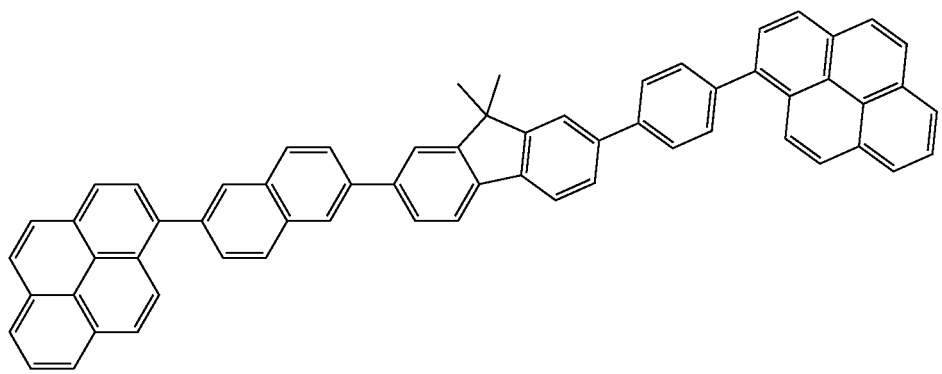
[Formula 89]
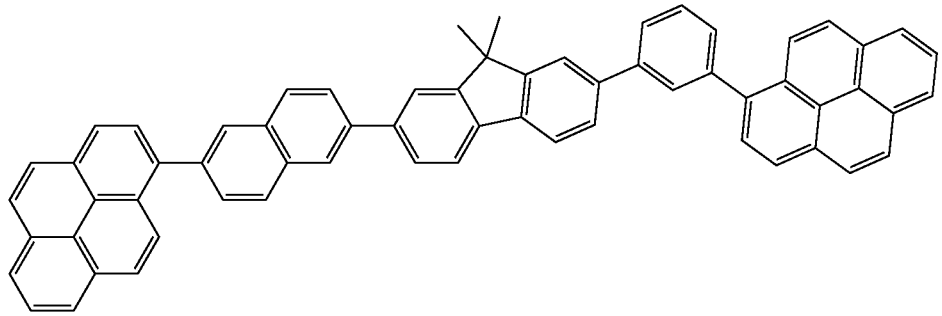
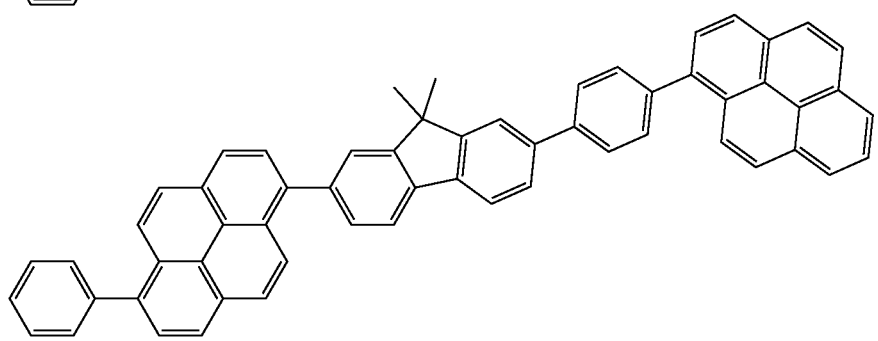

-continued
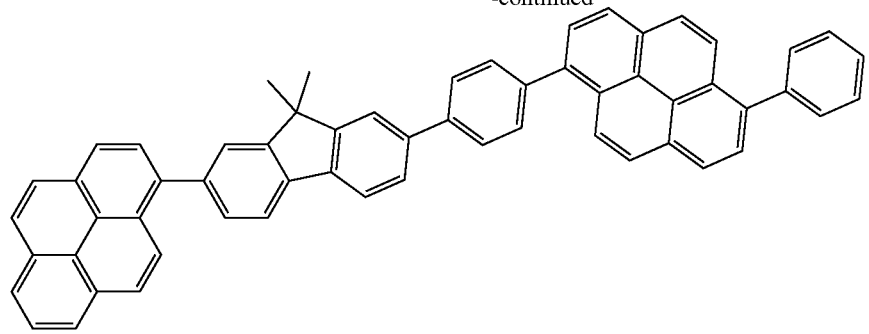
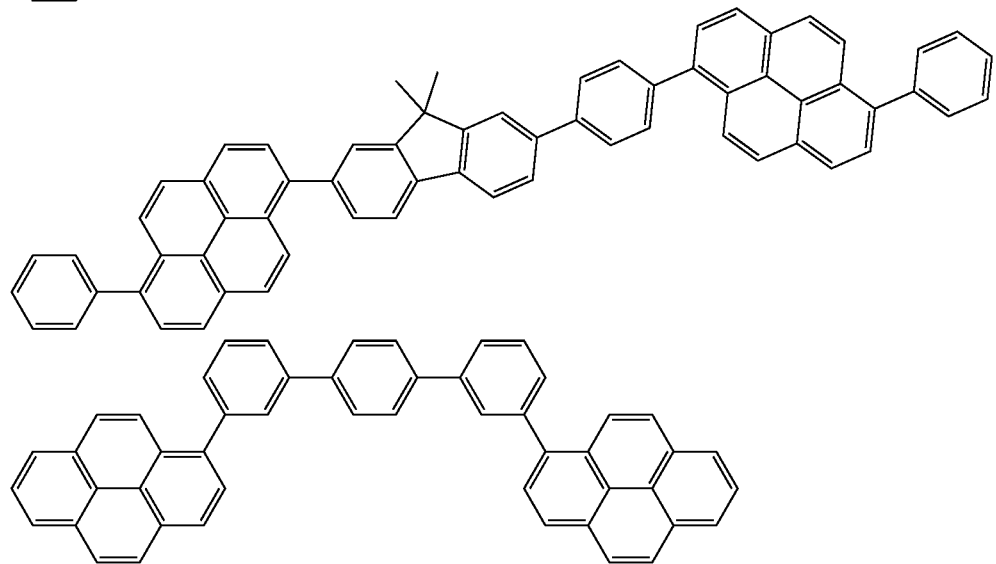
[Formula 90]
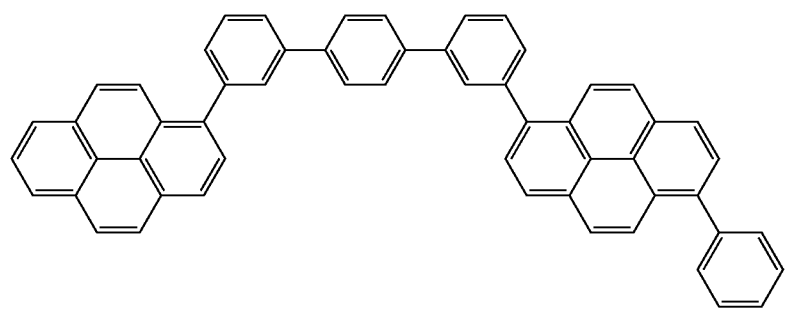
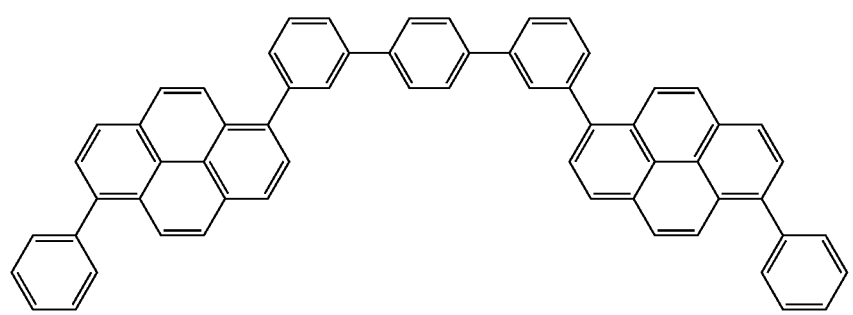

-continued
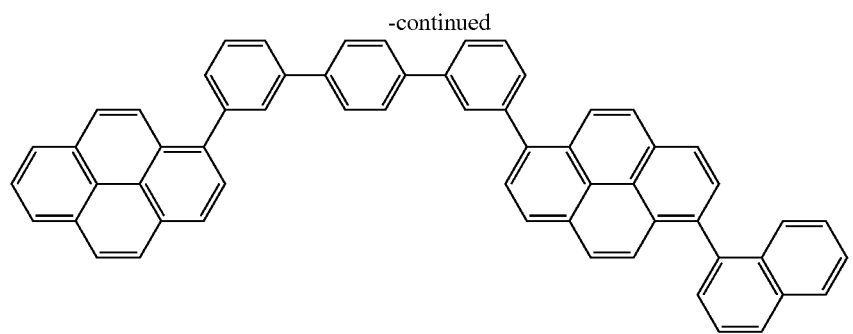
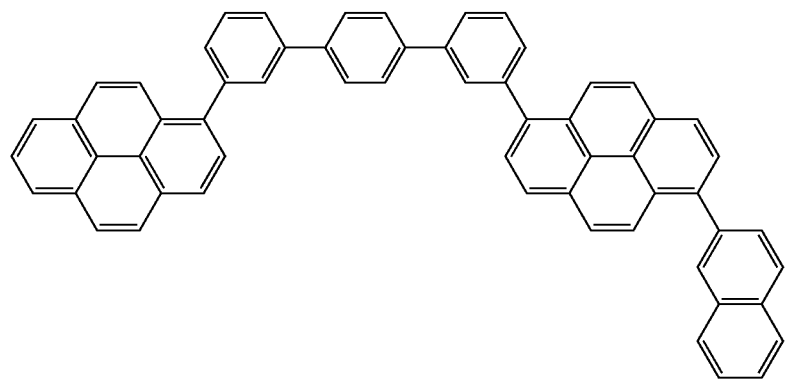
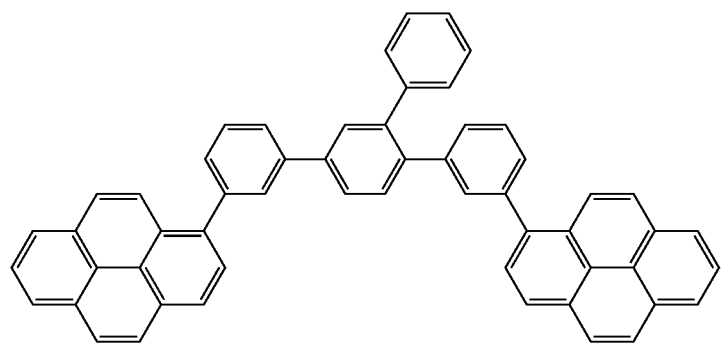
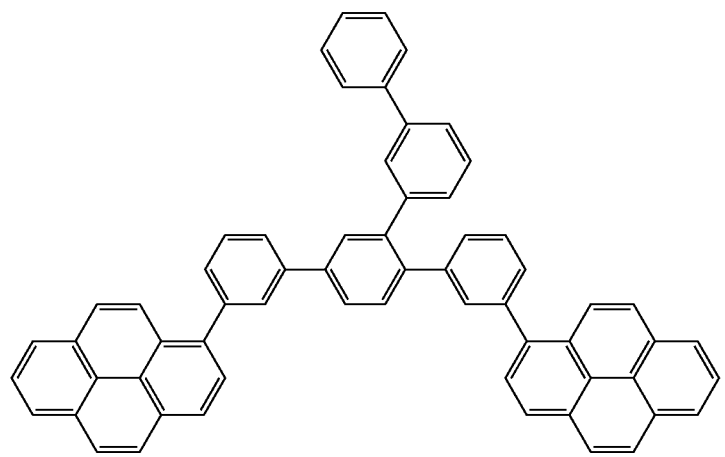 [SMILES: c1ccc(-c2cccc(-c3cc(-c4cccc(-c5ccc6ccc7cccc8ccc5c6c78)c4)ccc3-c3cccc(-c4ccc5ccc6cccc7ccc4c5c67)c3)c2)cc1]

[Formula 91]
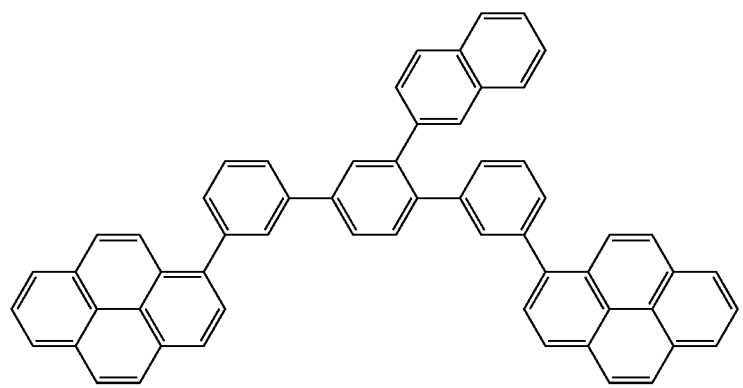
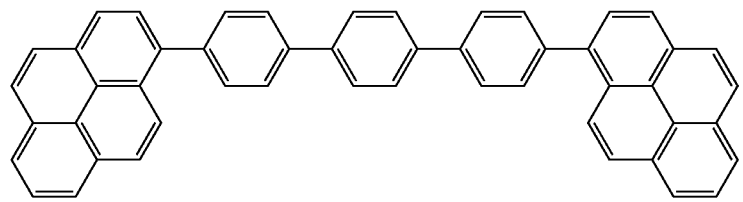
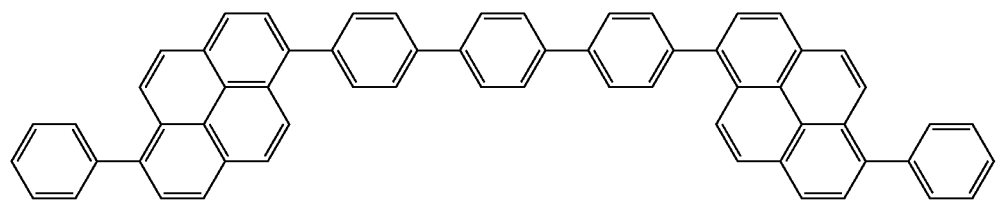
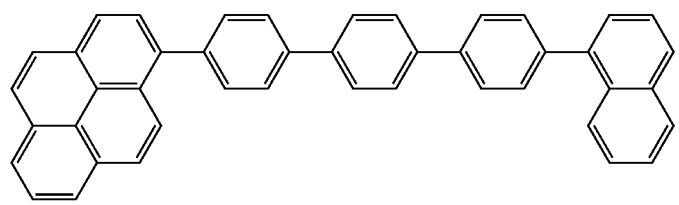
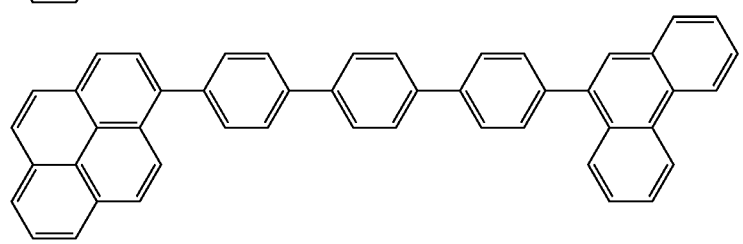
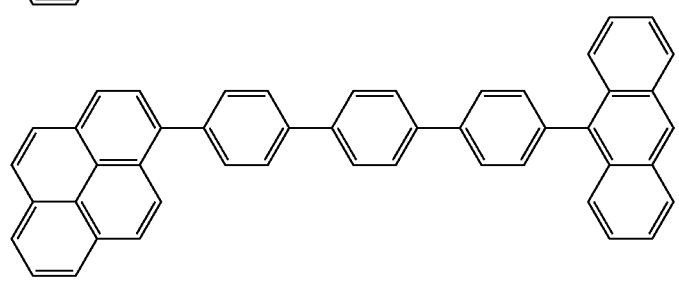

[Formula 92]
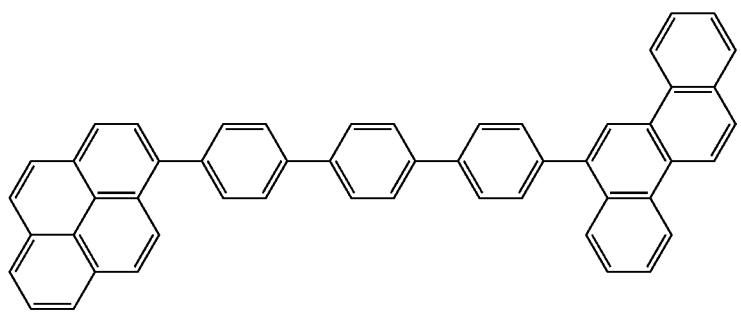
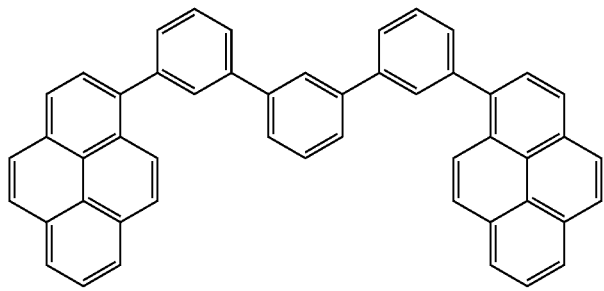
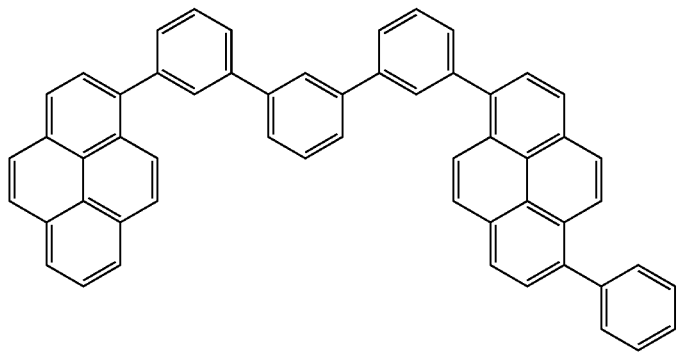
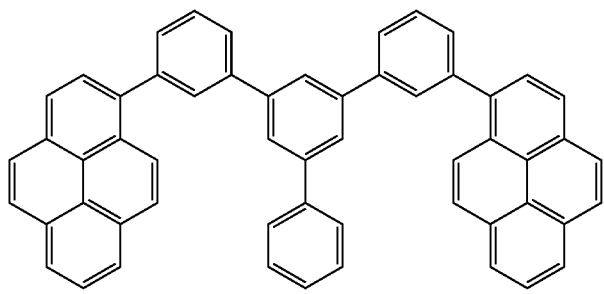
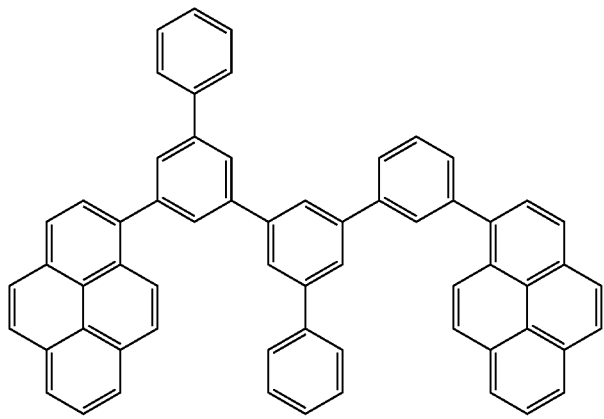

-continued
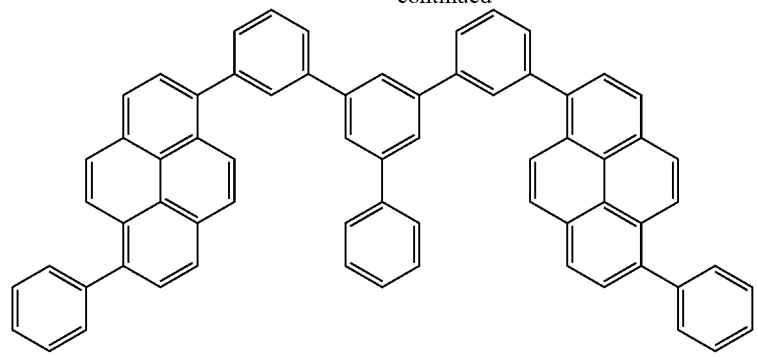
[Formula 93]
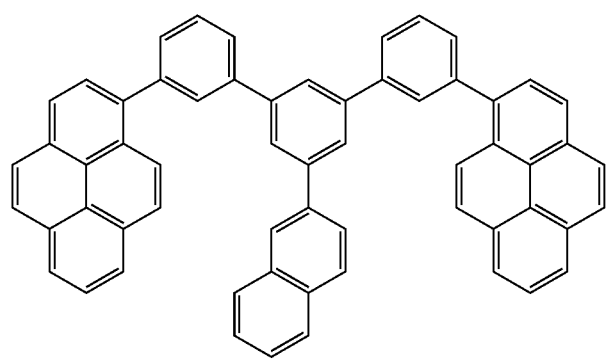
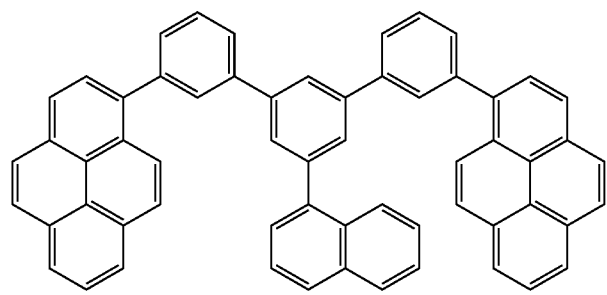
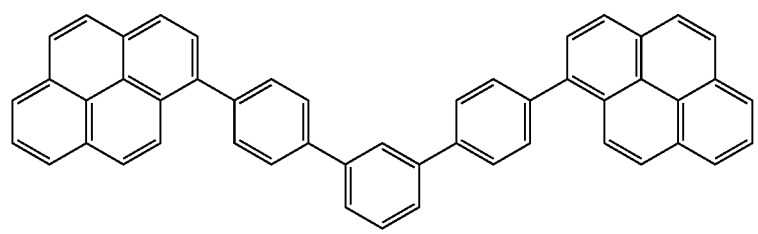
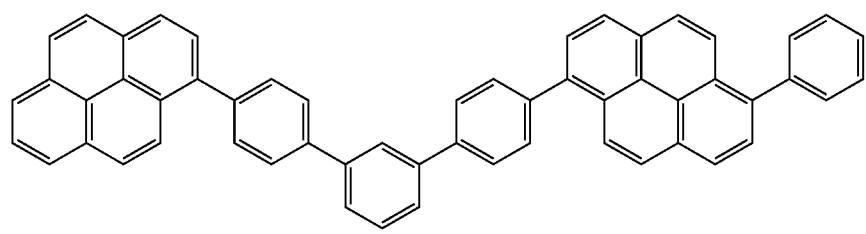

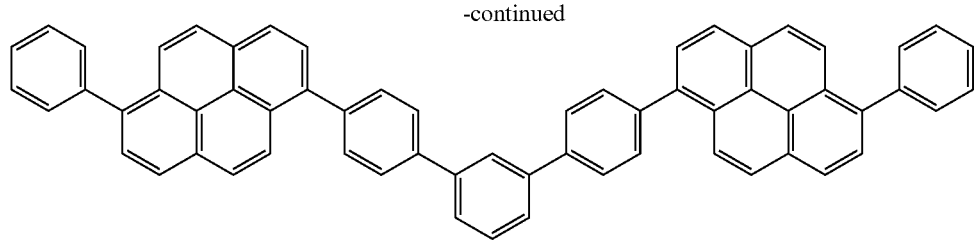
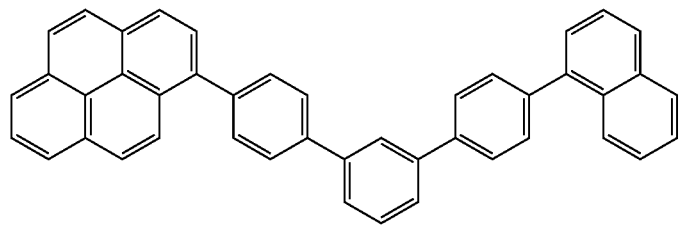
[Formula 94]
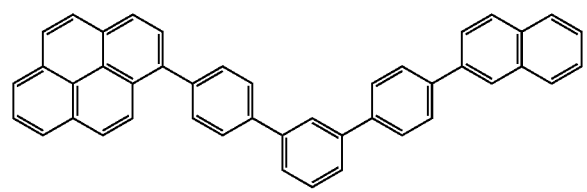
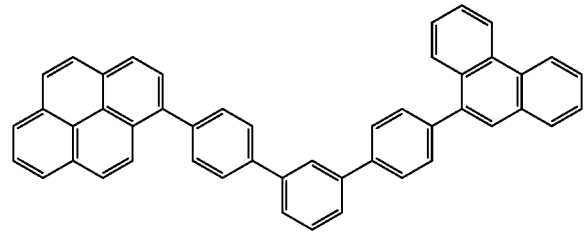
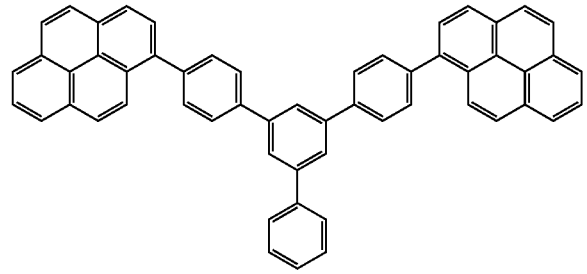
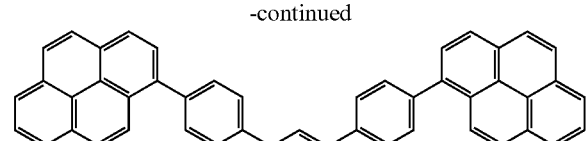
[Formula 95]
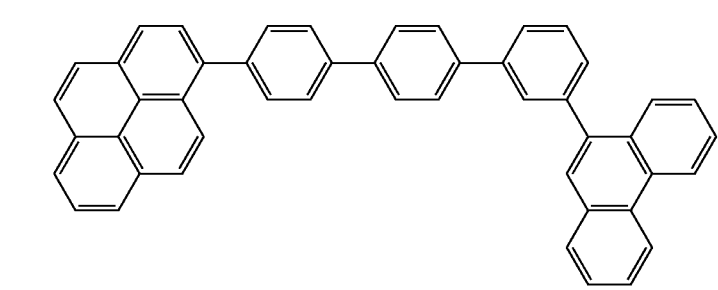

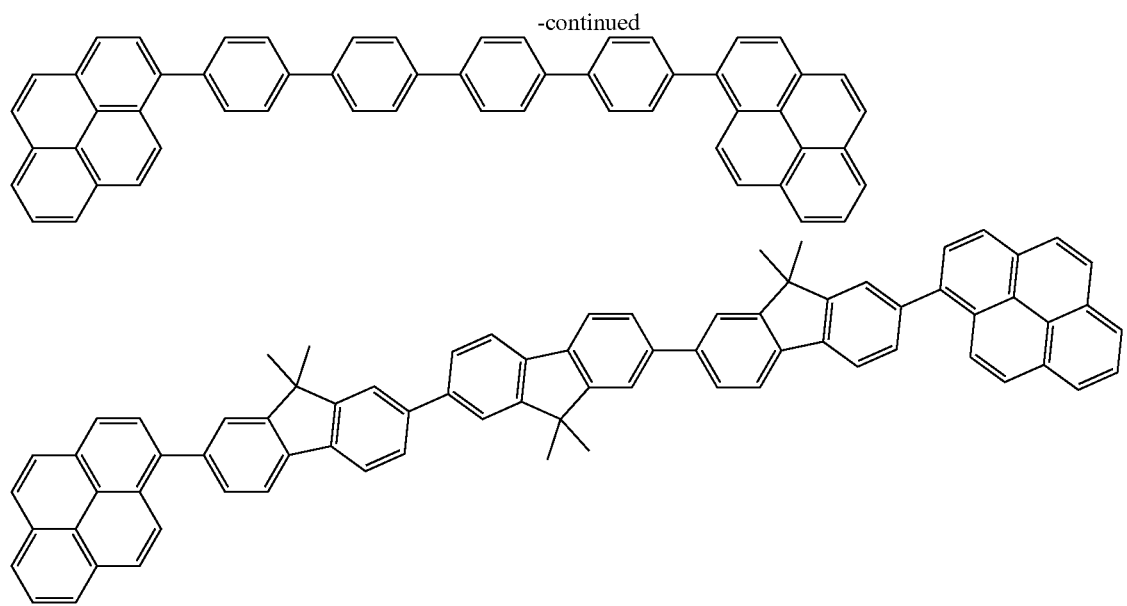
[Formula 96]
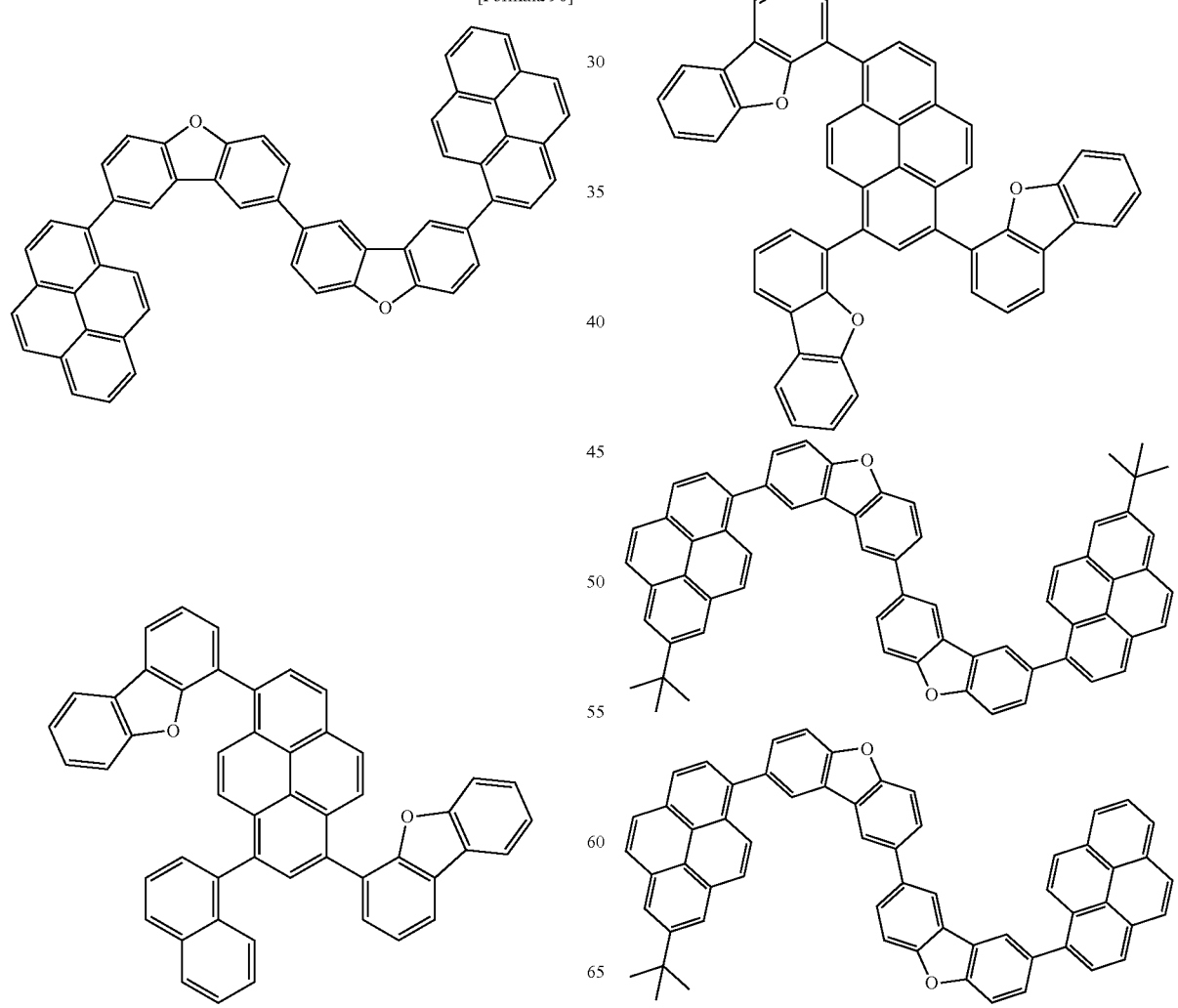

153
-continued
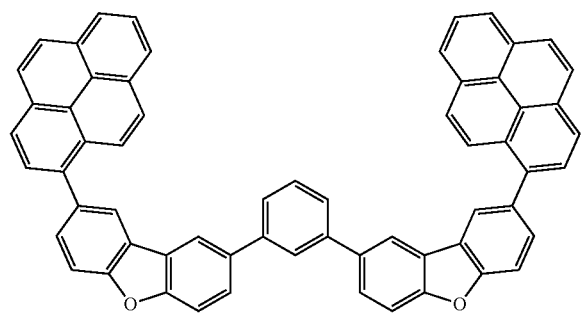
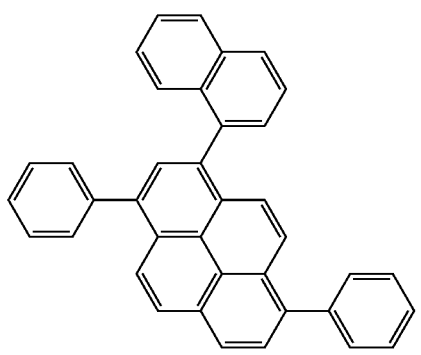
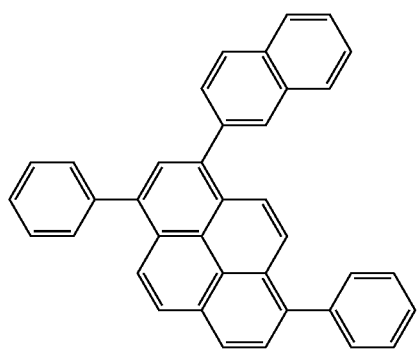
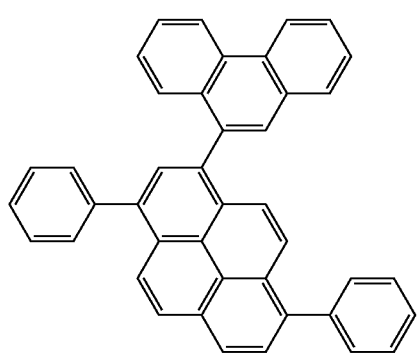
154
-continued
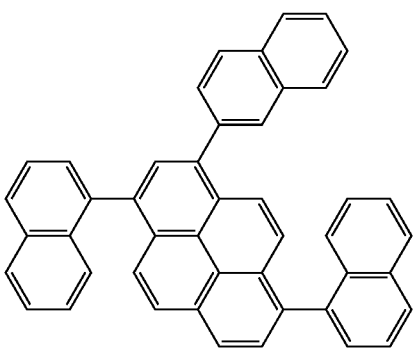
[Formula 97]
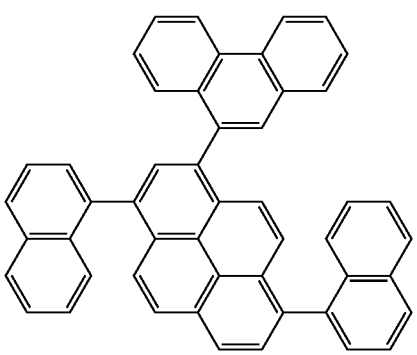
[Formula 98]
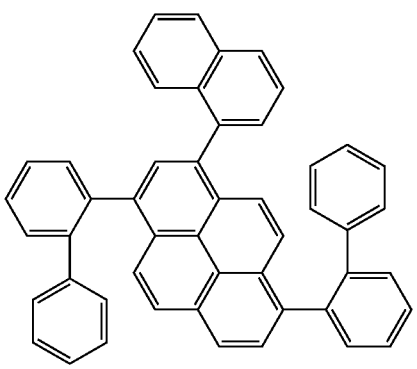 [SMILES: c1ccc(-c2ccccc2-c2ccc3ccc4c(-c5ccccc5-c5ccccc5)cc(-c5cccc6ccccc56)c5ccc2c3c45)cc1]
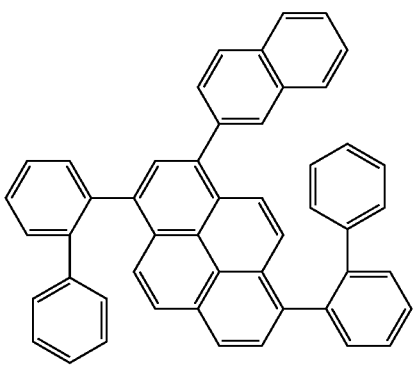

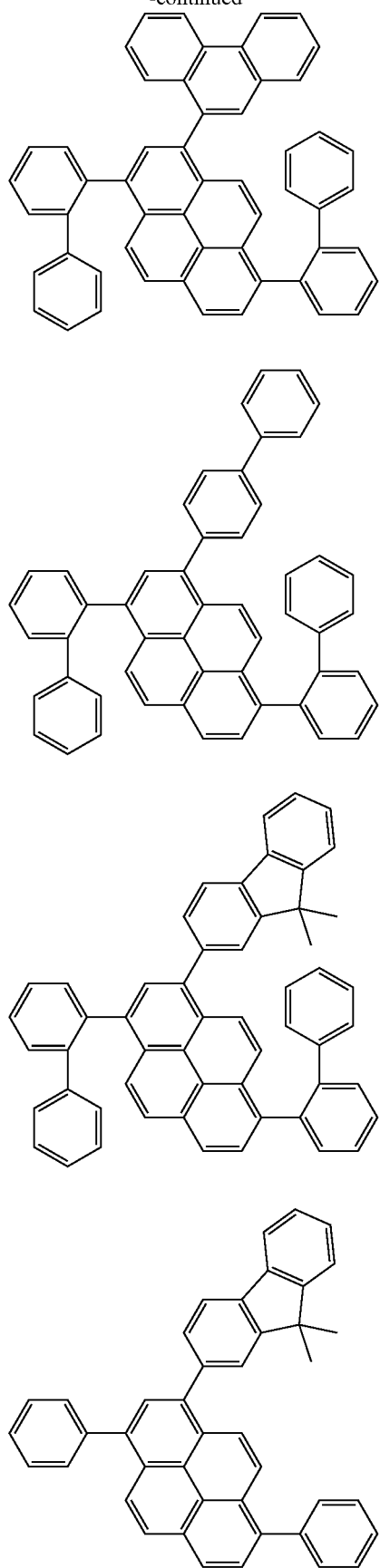
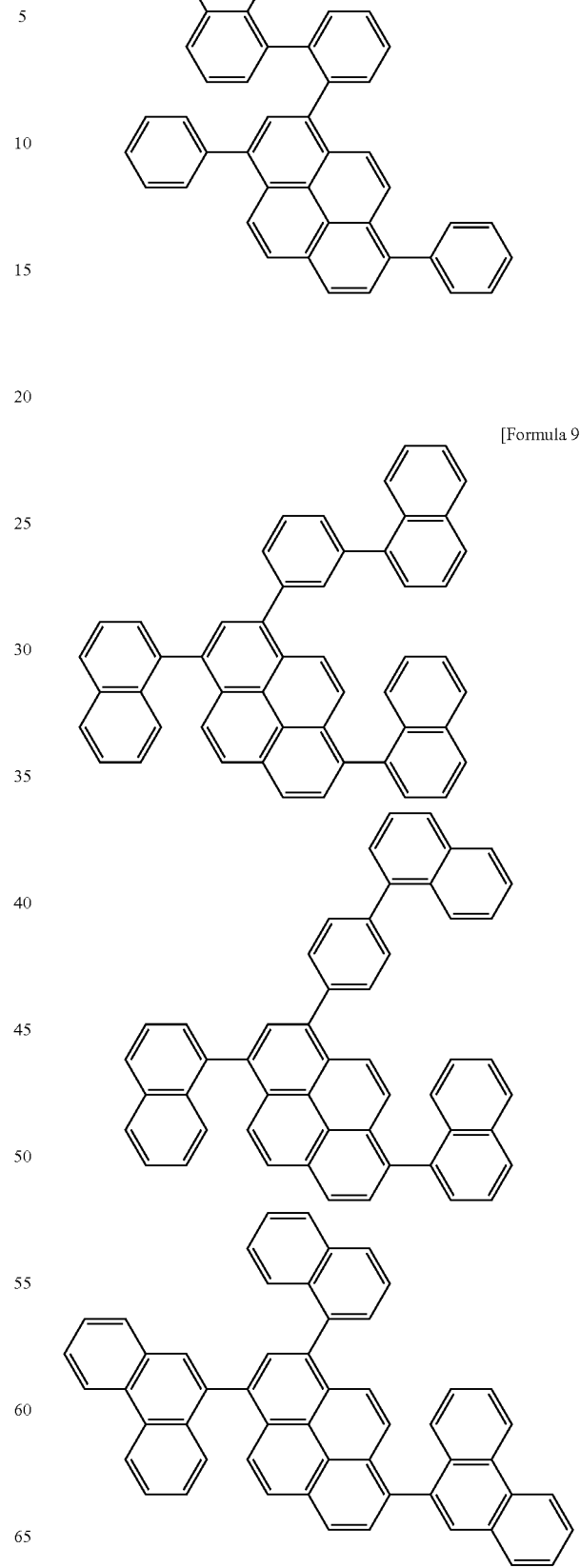
[Formula 99]

[Formula 100]
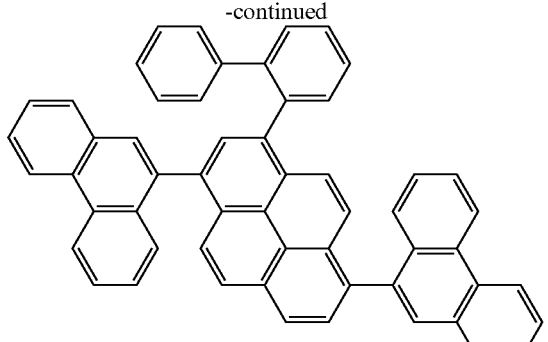
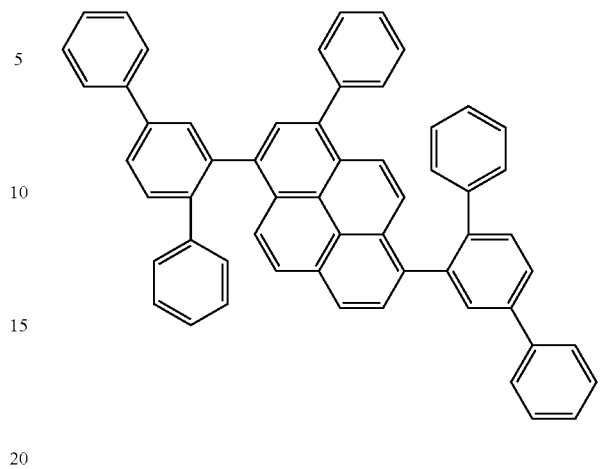
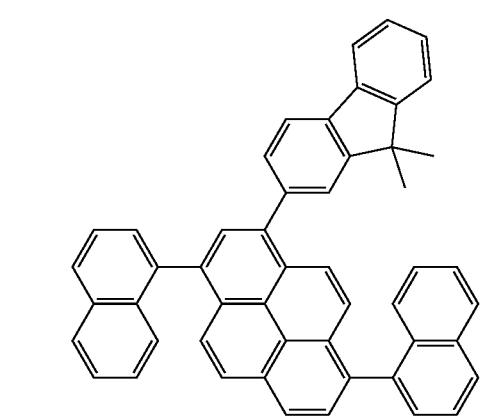
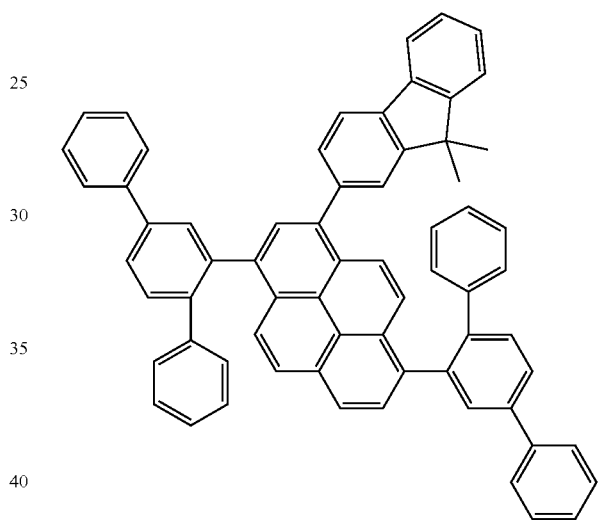
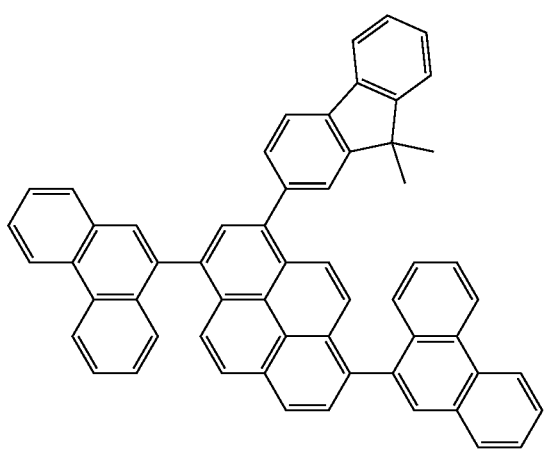
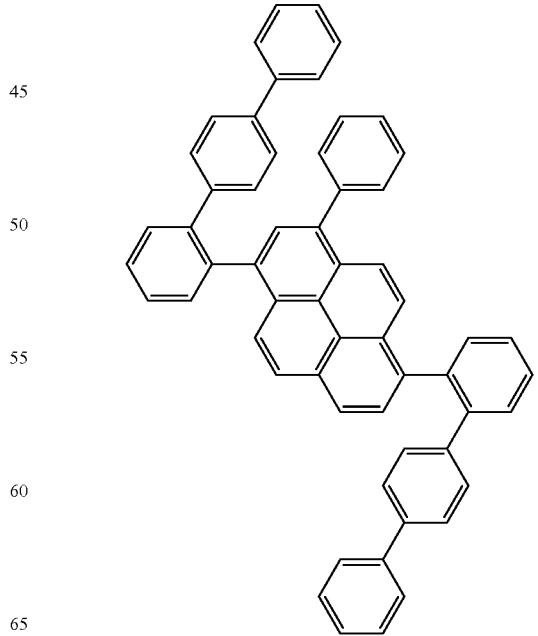

[Formula 101]
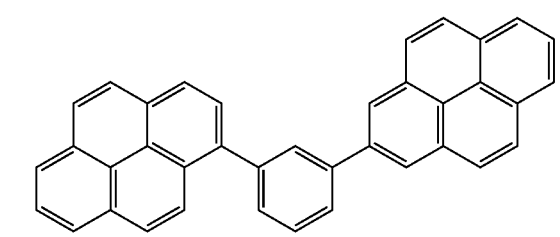
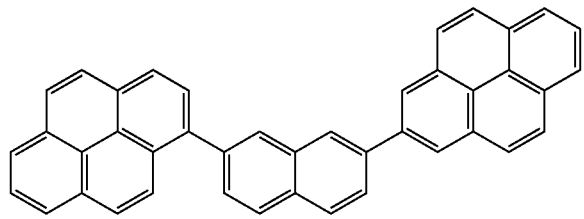
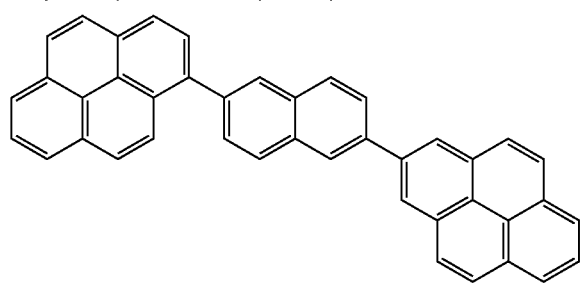
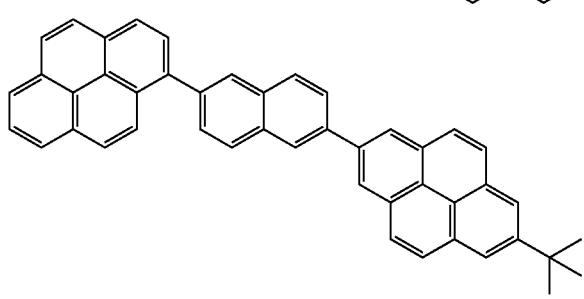
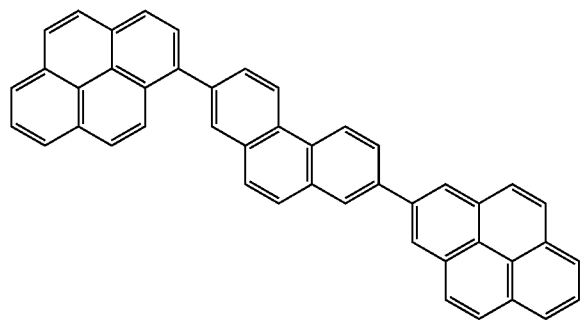
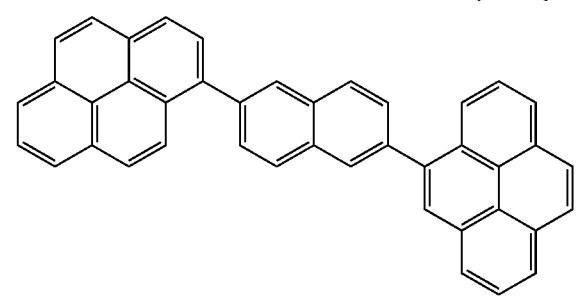
-continued
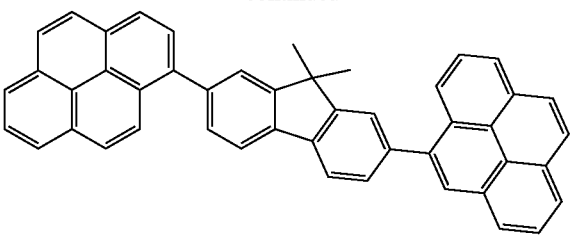
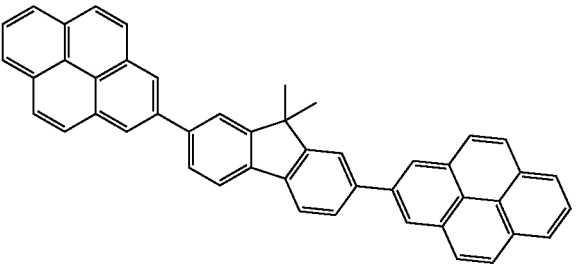
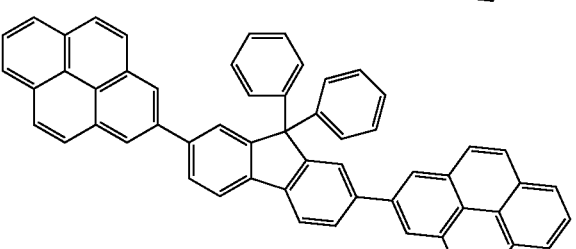
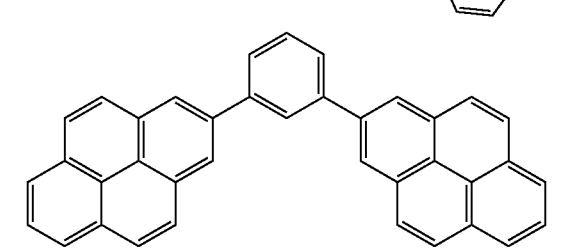

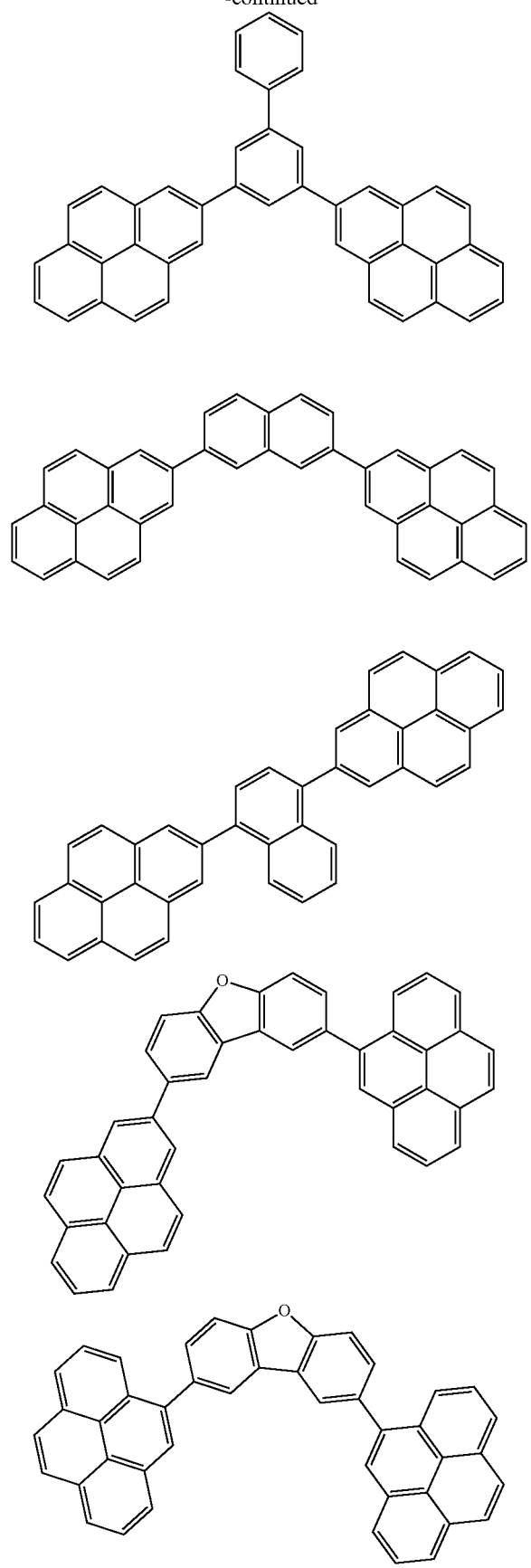
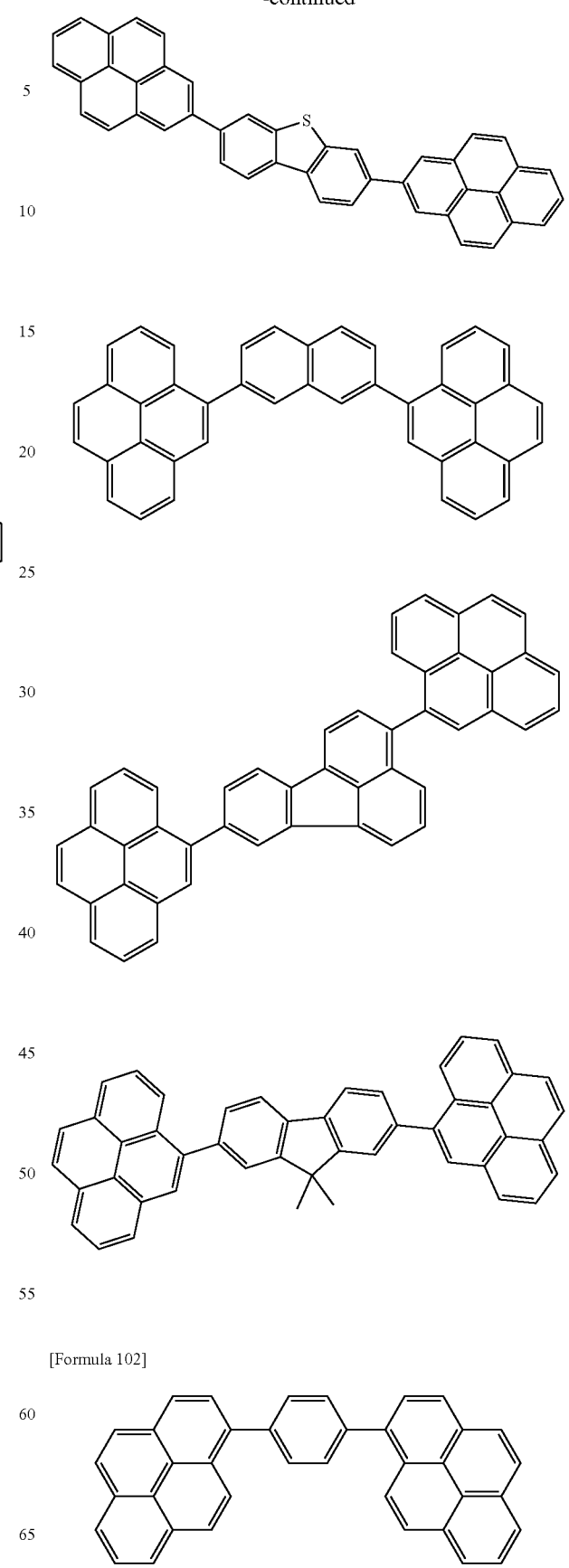
[Formula 102]

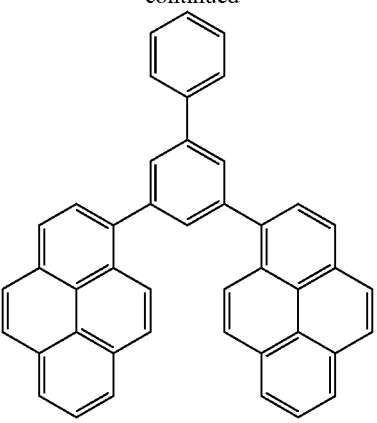
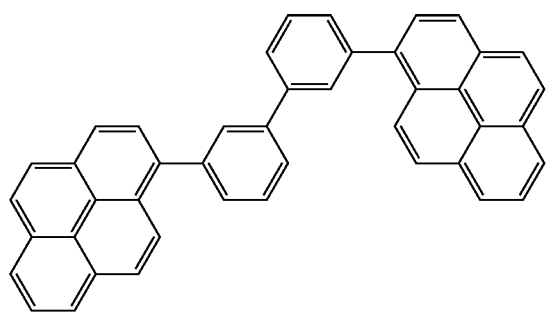
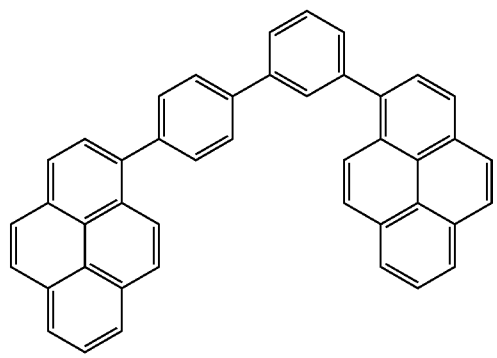
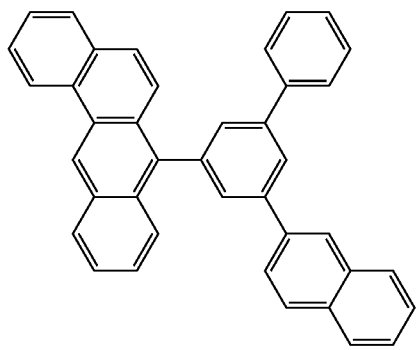
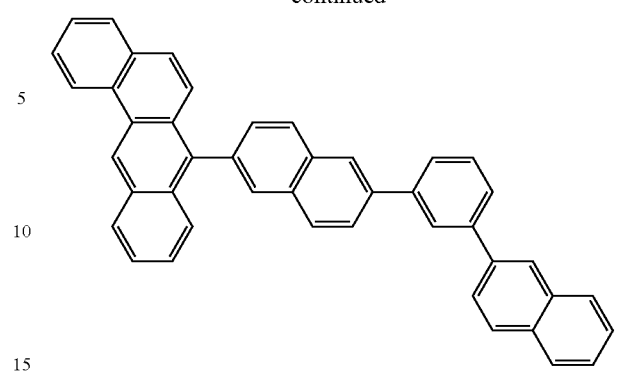
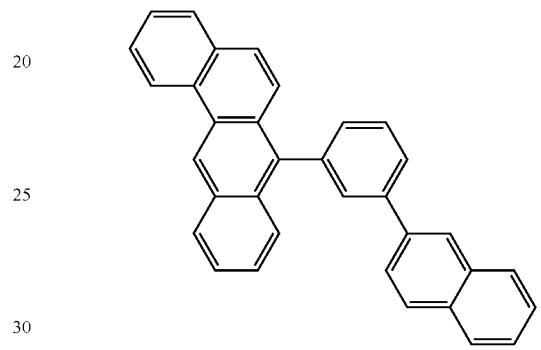
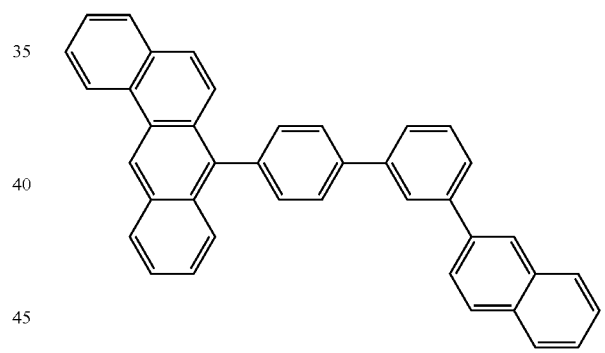
[Formula 103]
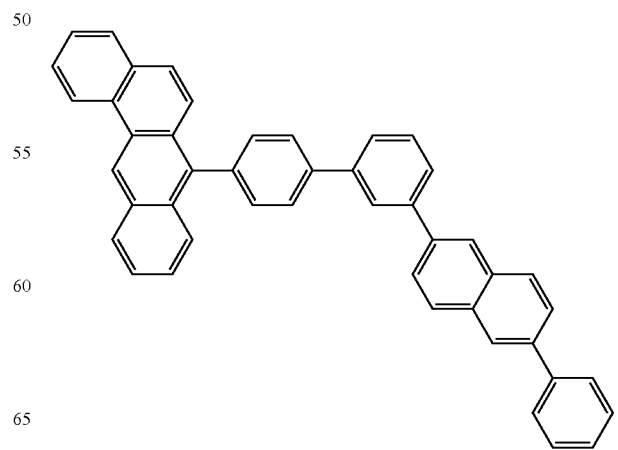

165
-continued
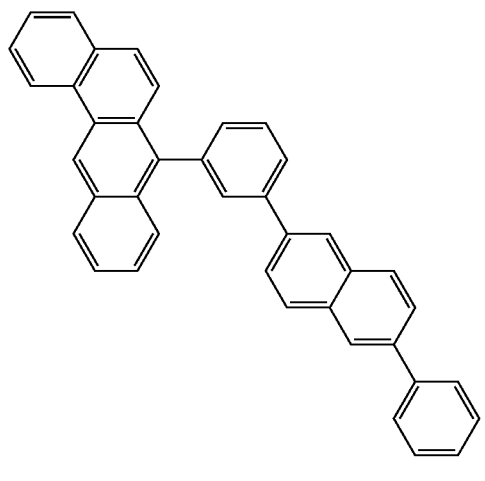 [SMILES: c1ccc(-c2ccc3cc(-c4cccc(-c5c6ccccc6cc6c5ccc5ccccc56)c4)ccc3c2)cc1]
[Formula 104]
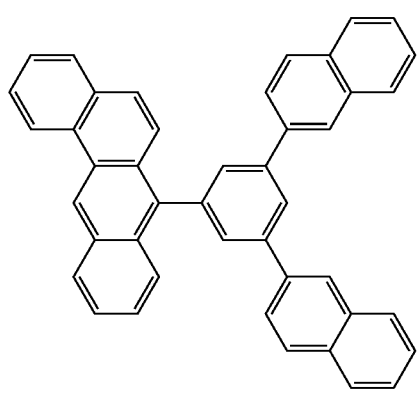
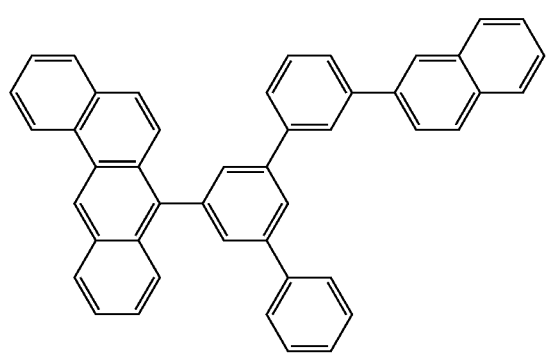
166
-continued
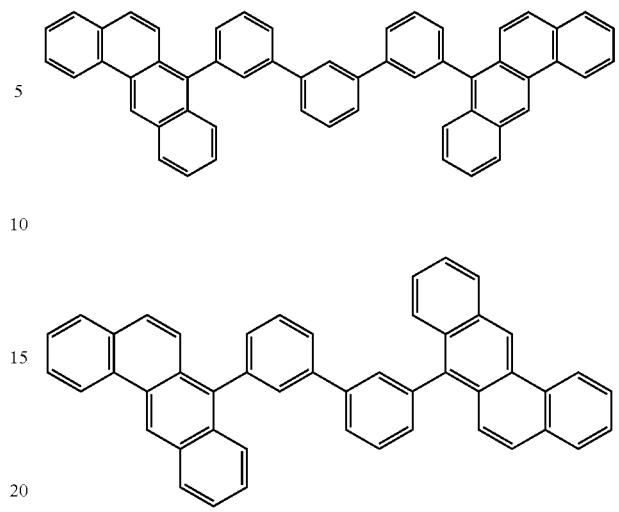
[Formula 105]
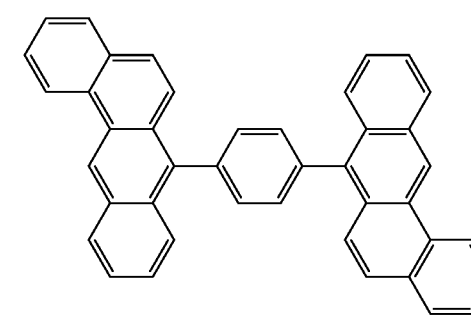
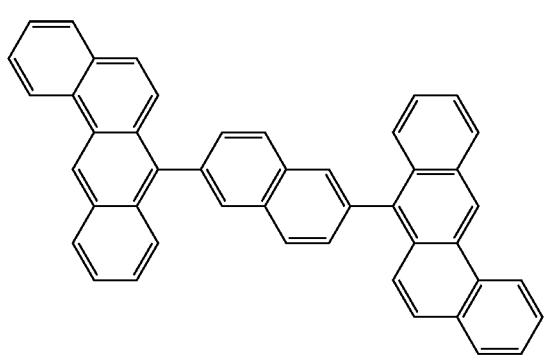
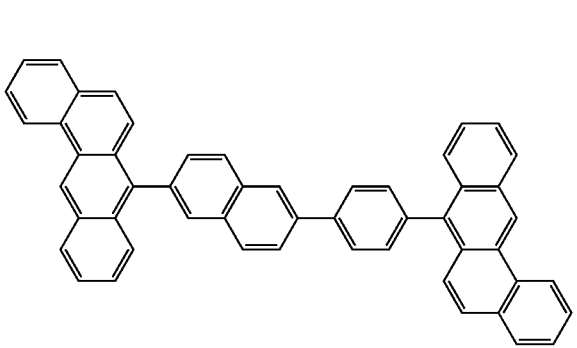

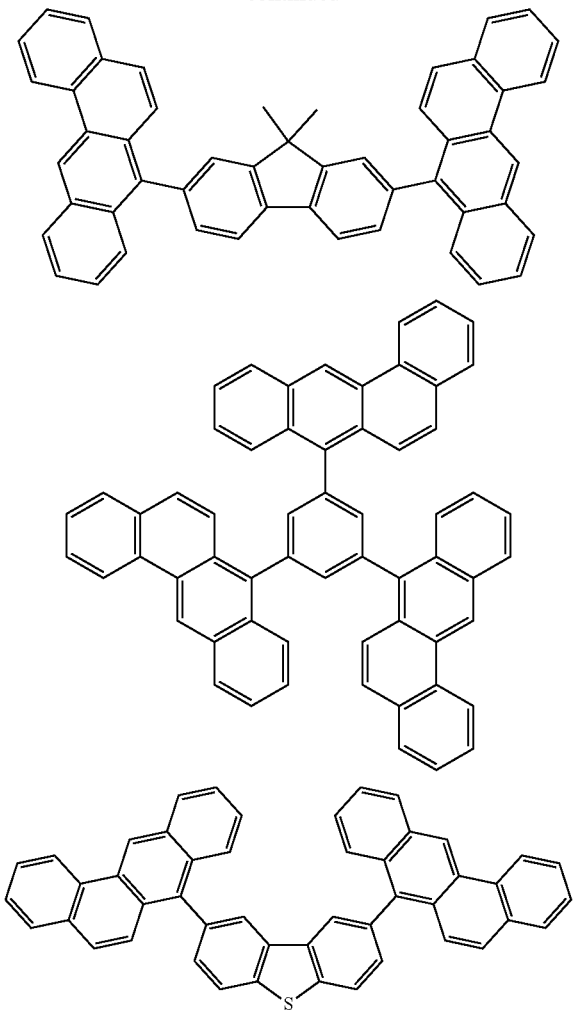
[Formula 106]
[Formula 107]
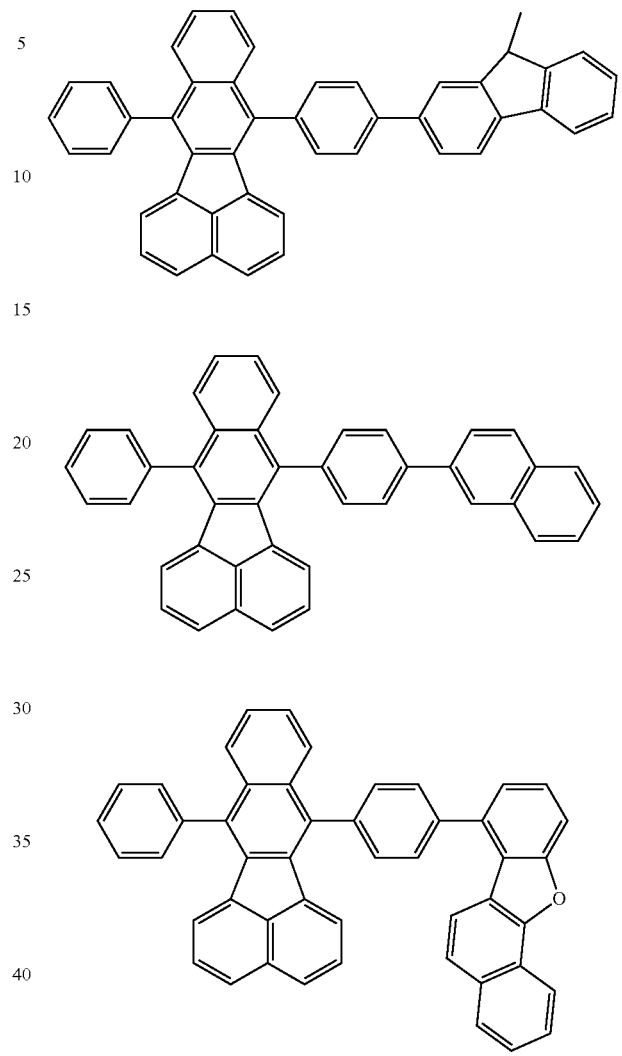
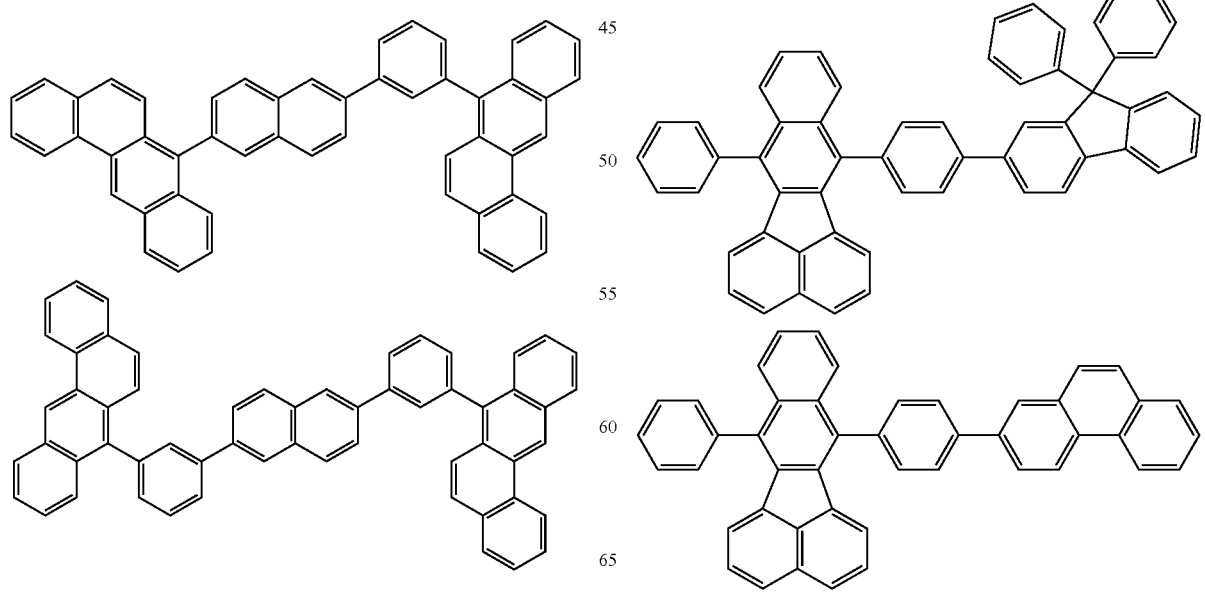

169
-continued
170
-continued
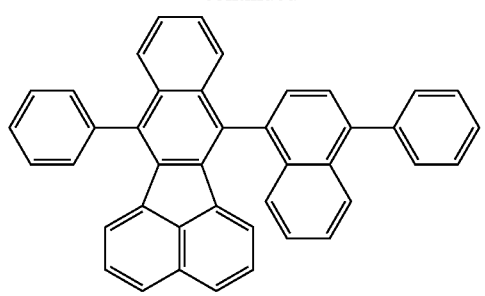
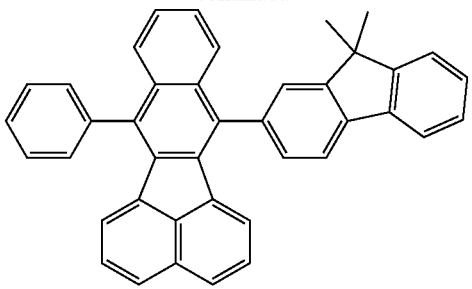
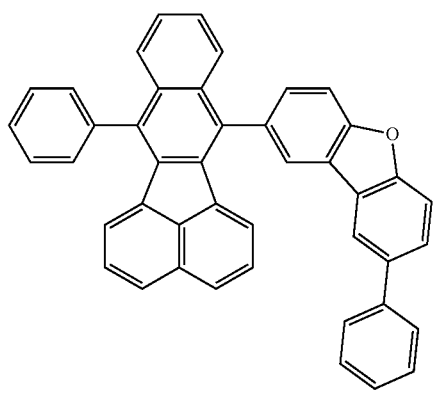
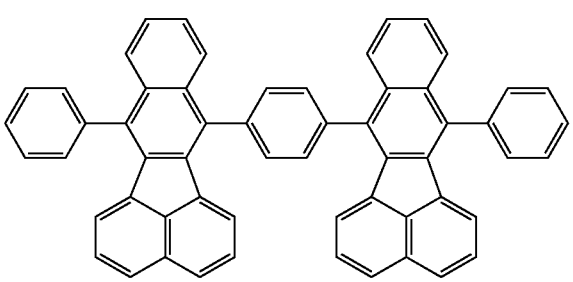
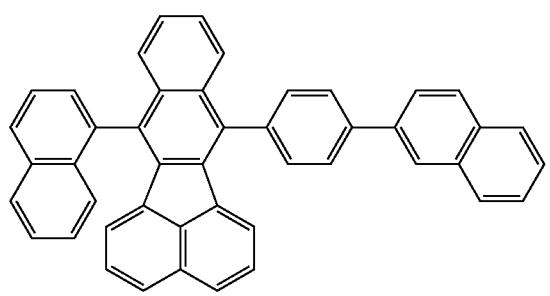
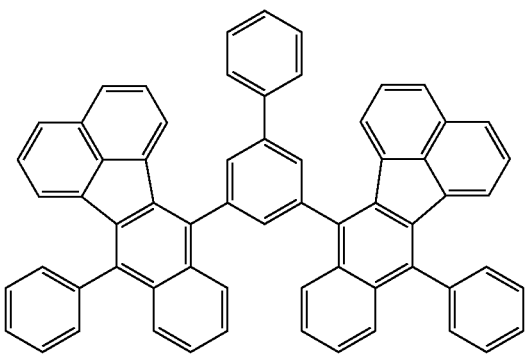
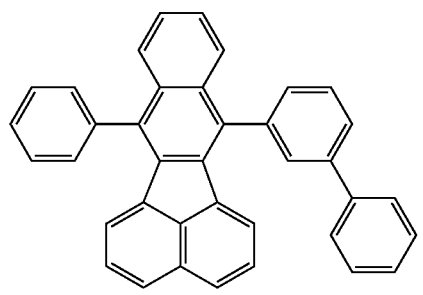
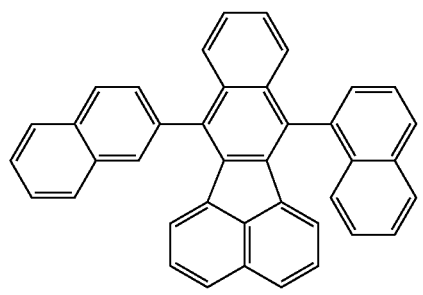
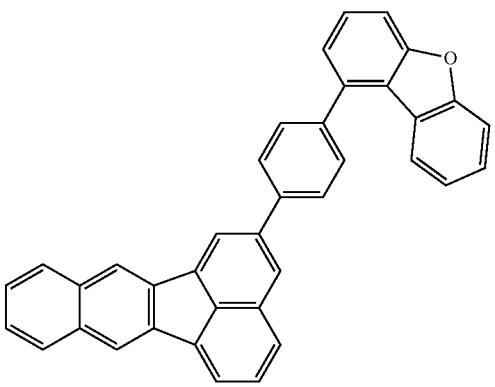

171
-continued
172
-continued
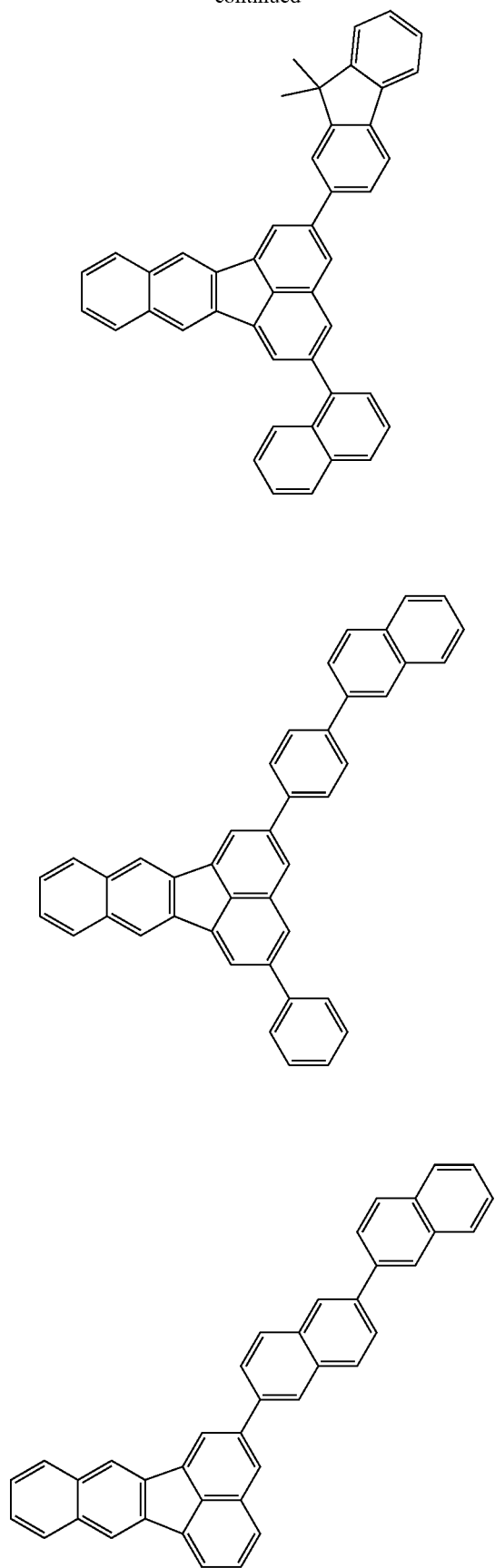
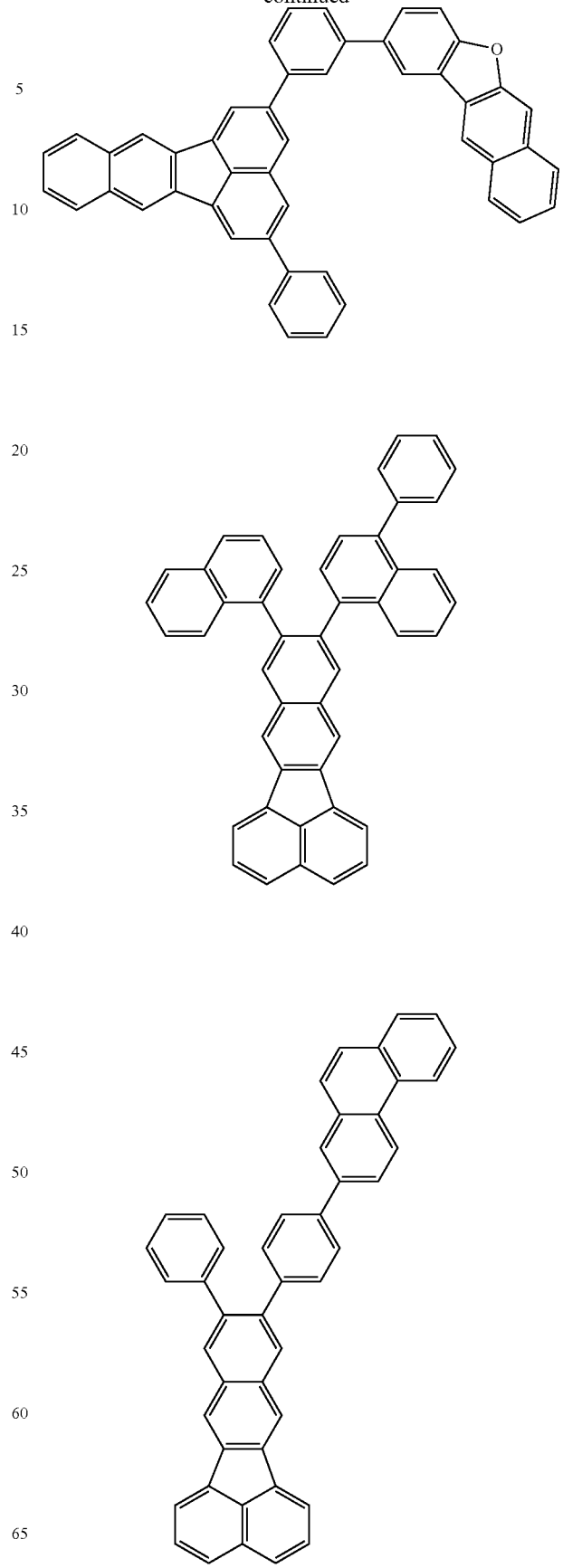

173
-continued
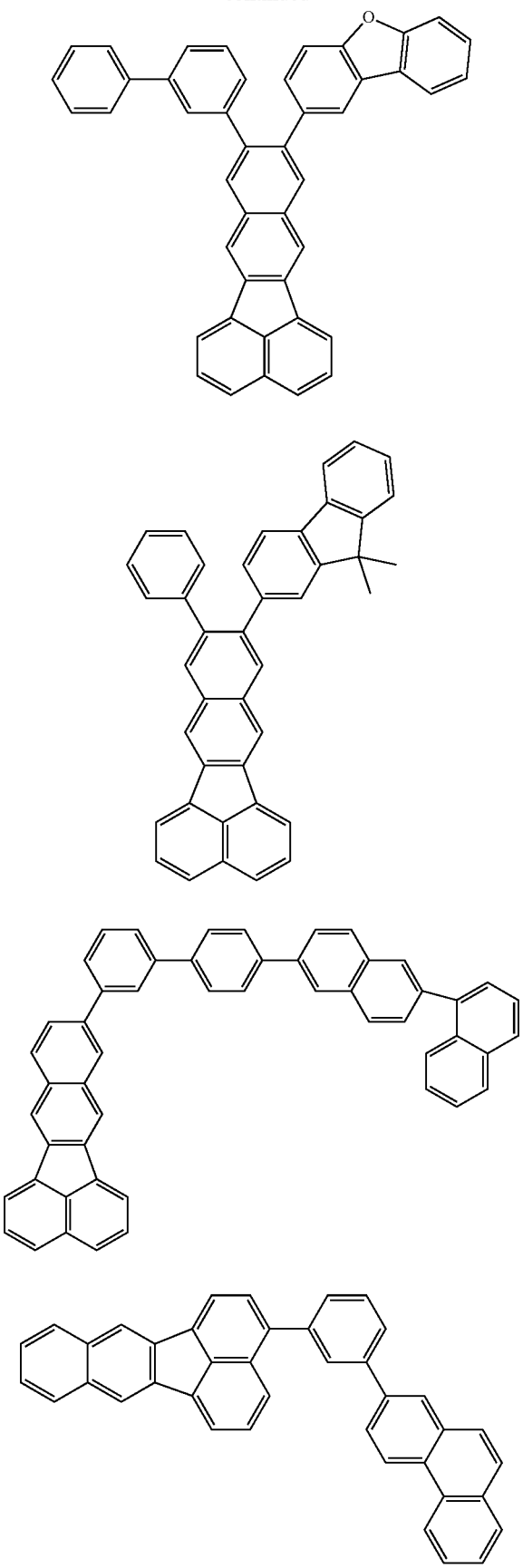
174
-continued
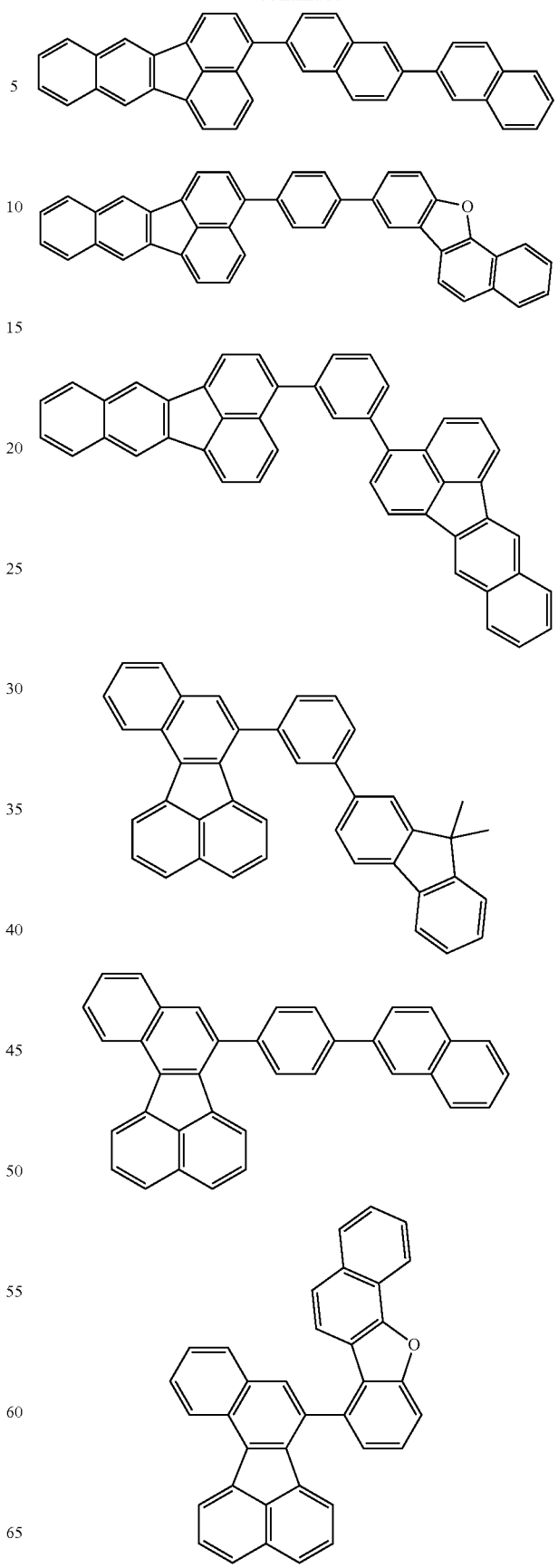

175
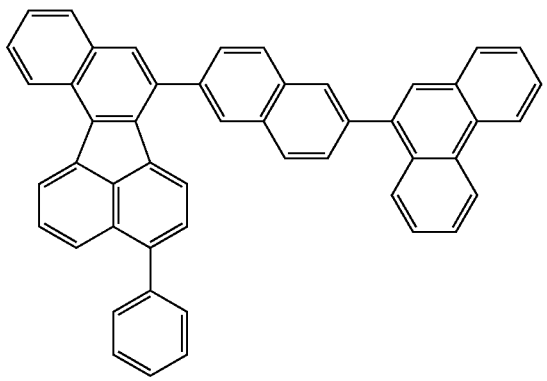
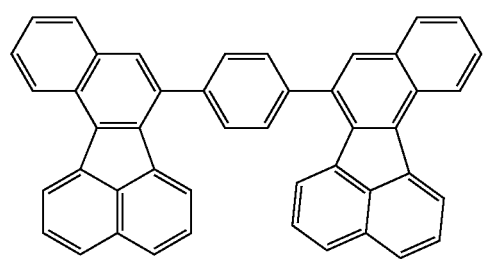
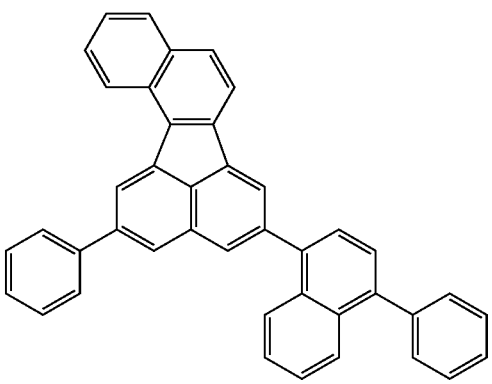
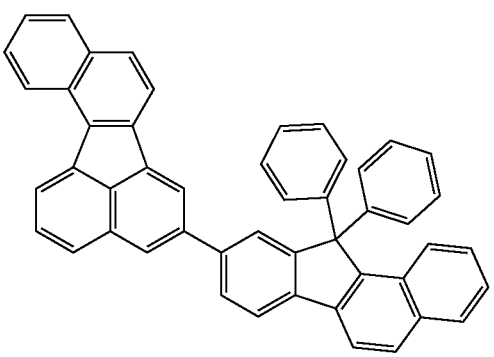
176
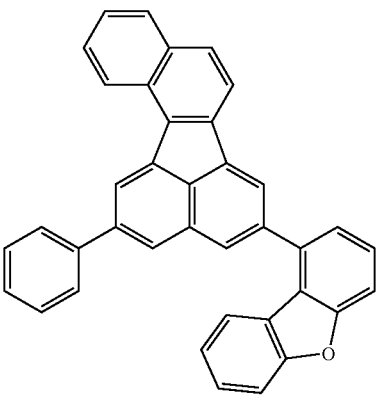
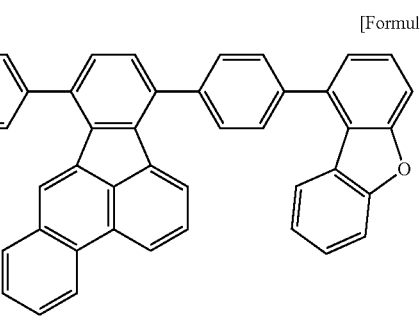
[Formula 108]

177
-continued
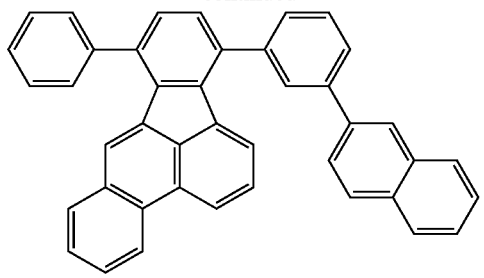
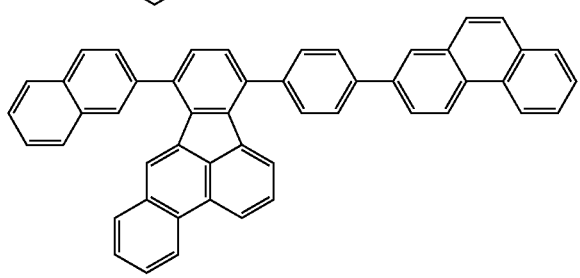
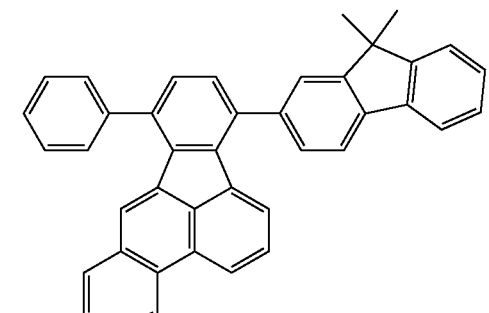
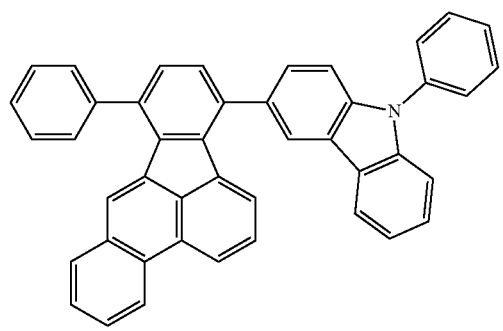
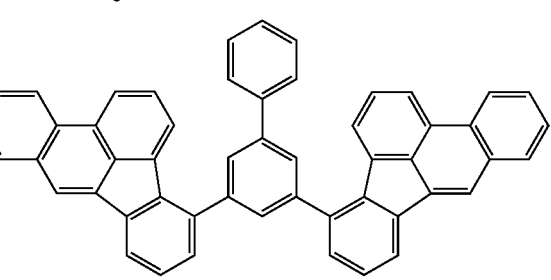
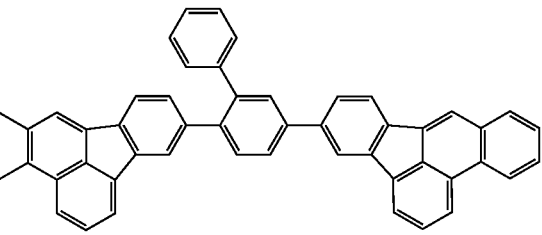
178
-continued
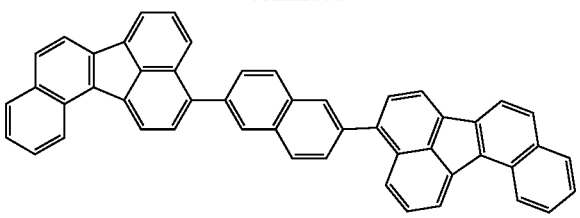
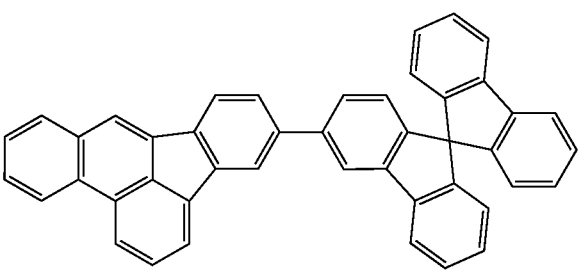
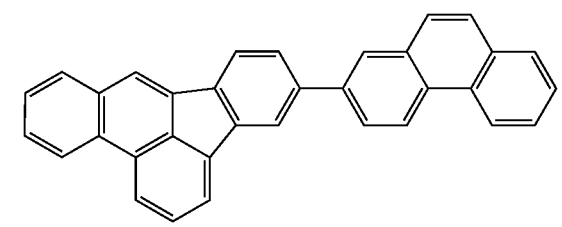
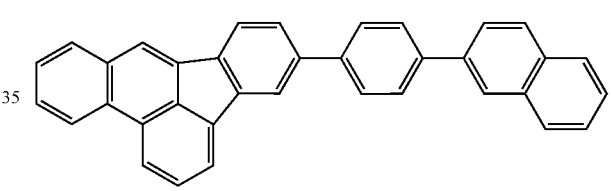
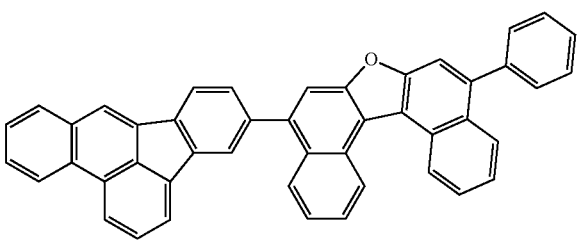
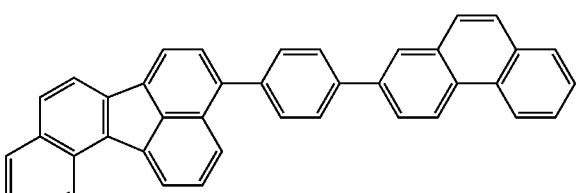
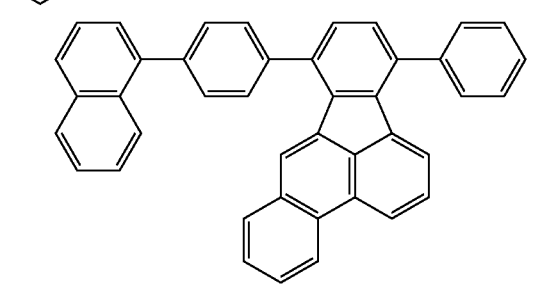

179
-continued
180
-continued
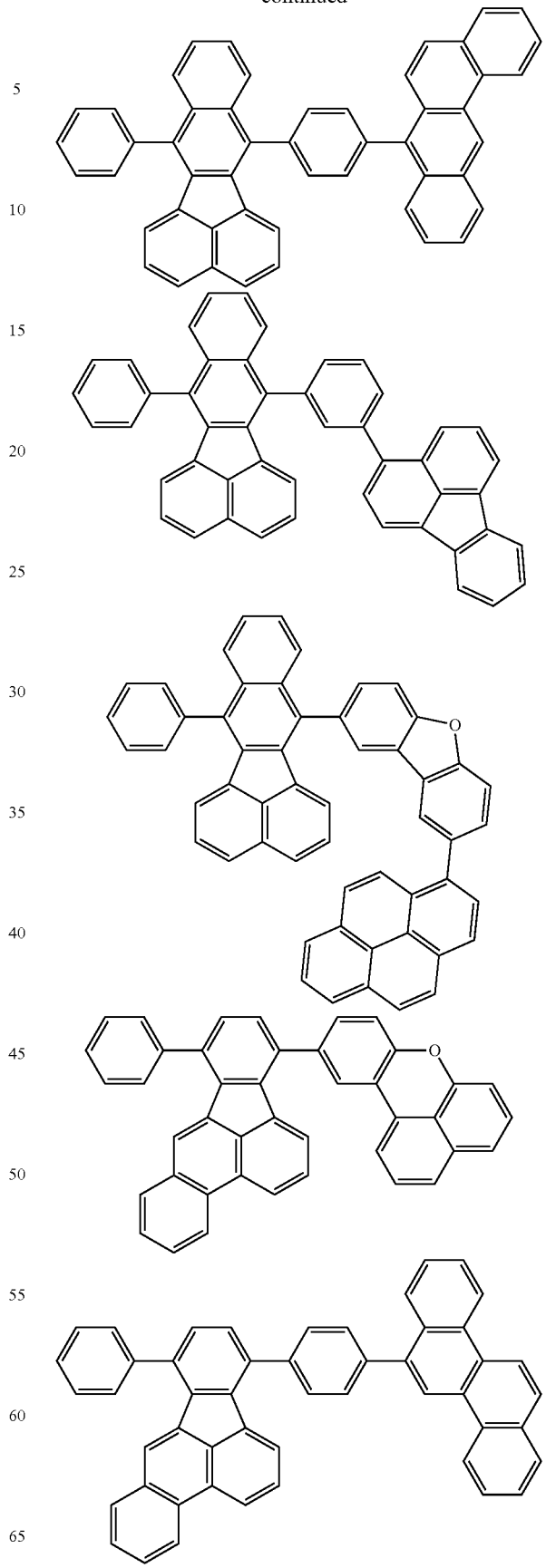

-continued
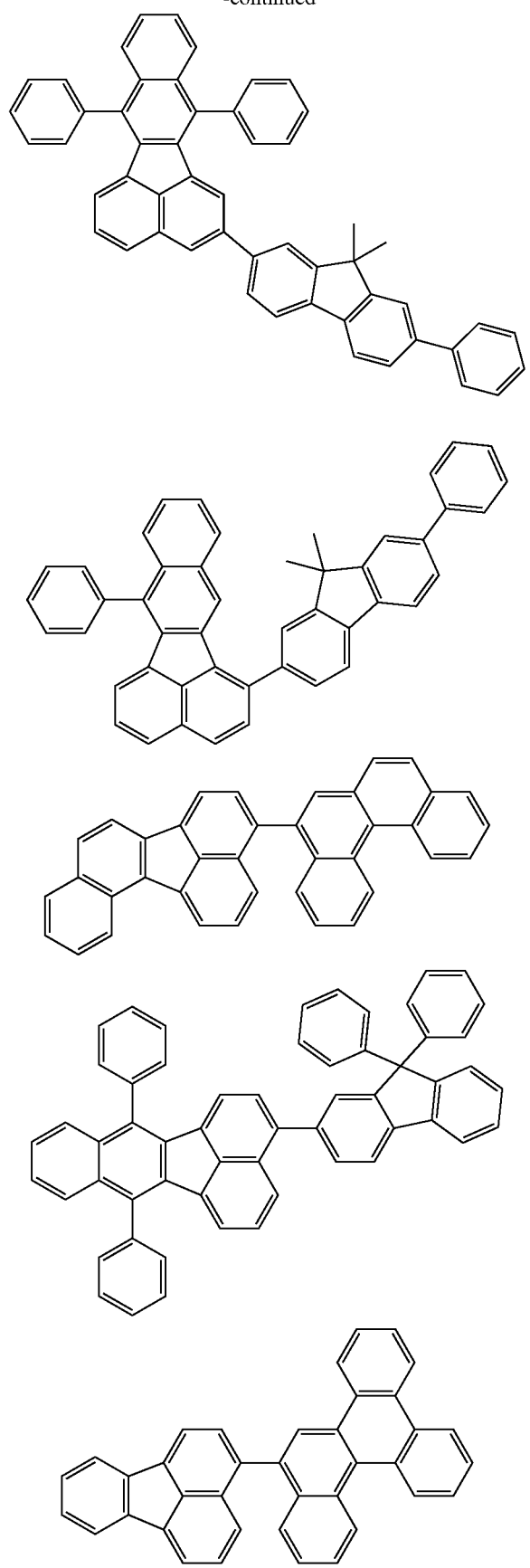
-continued
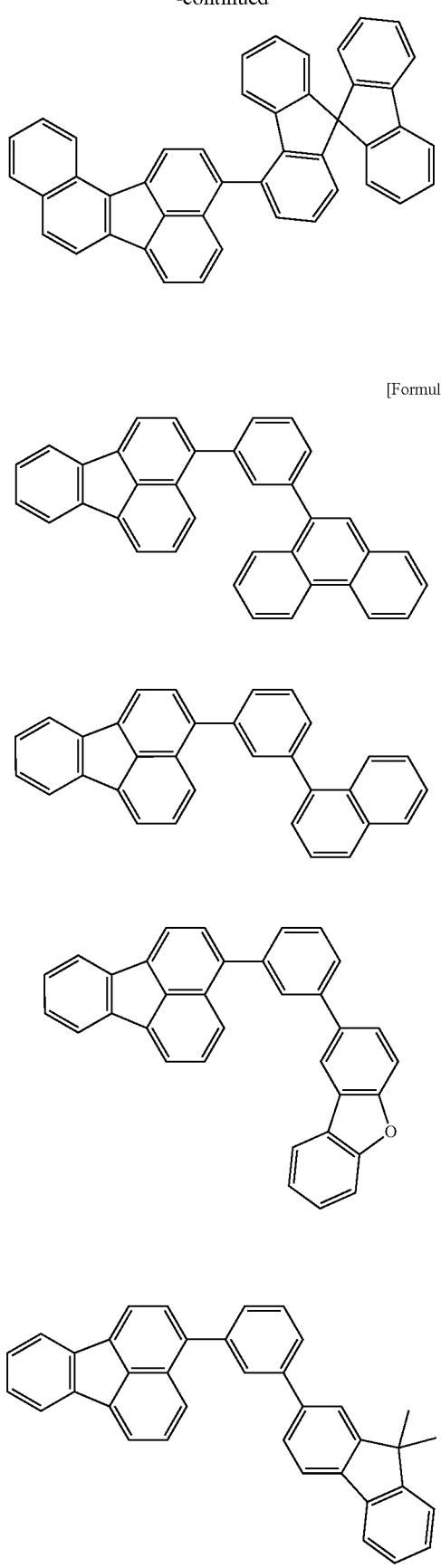
[Formula 109]

-continued
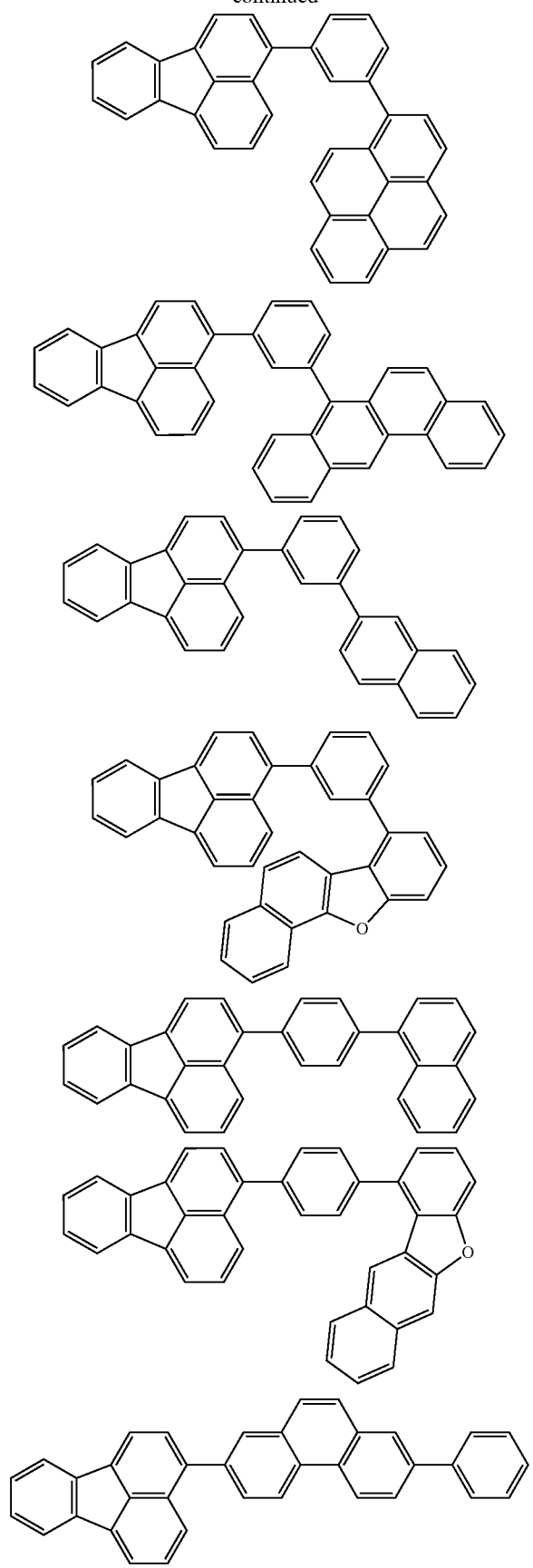
-continued
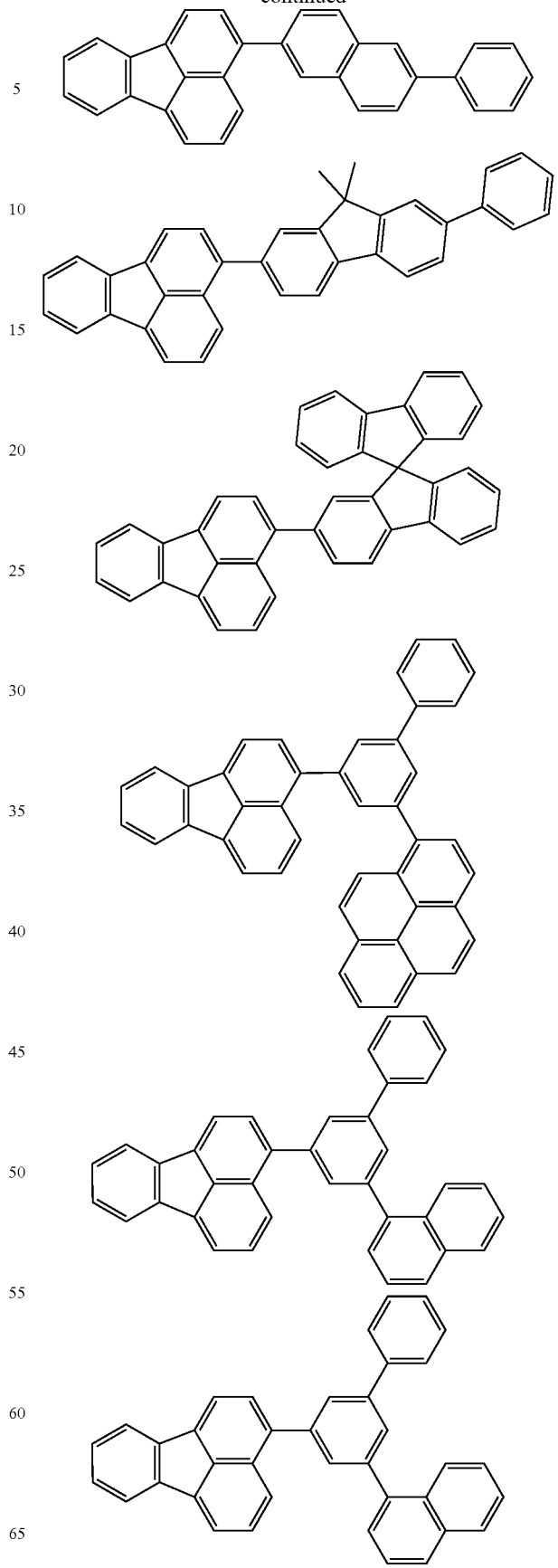

185
-continued
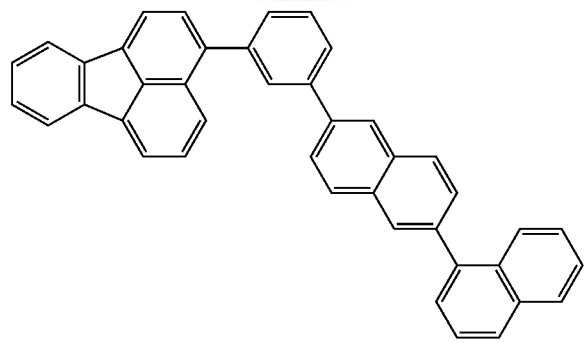
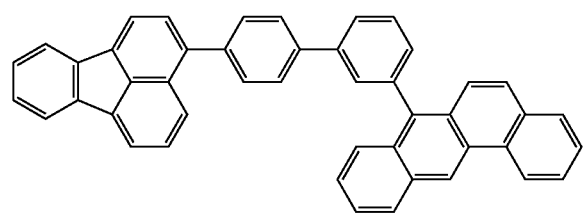
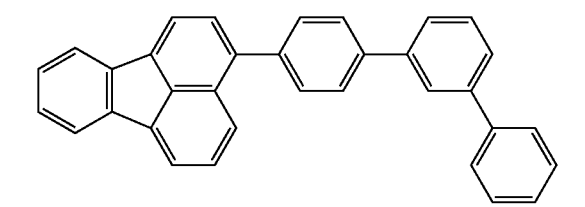
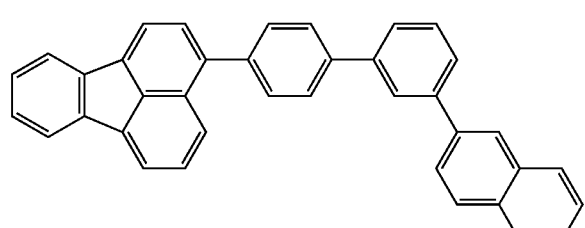
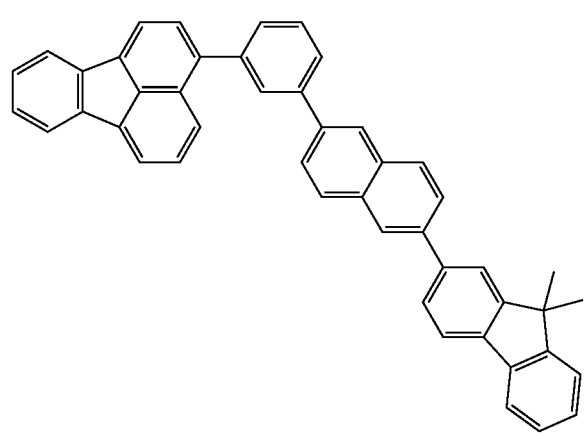
186
-continued
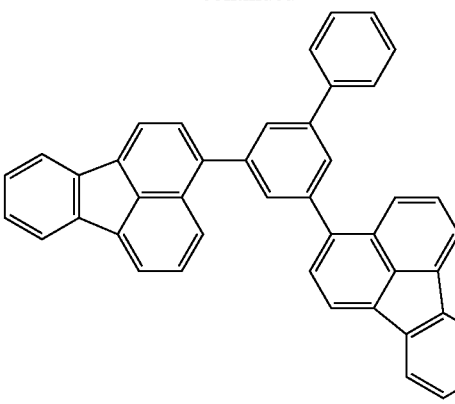
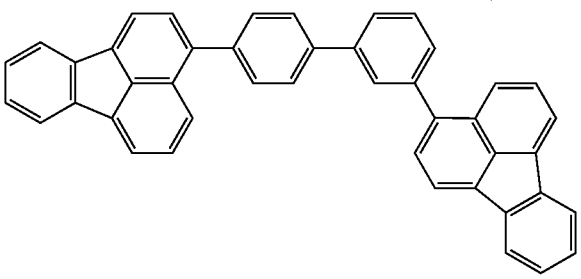
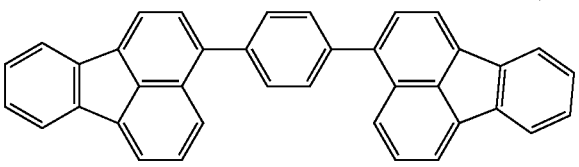
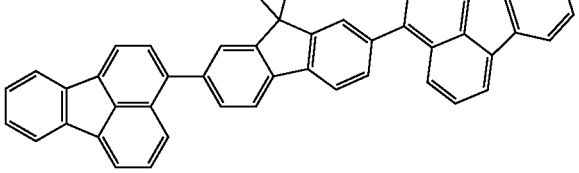
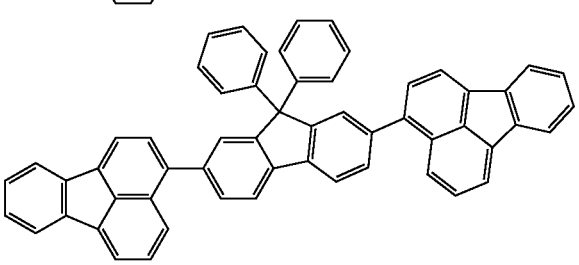
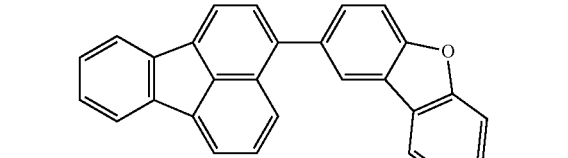
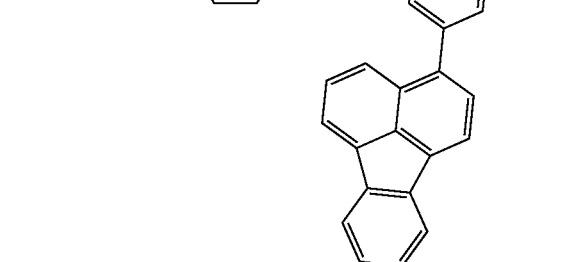

187
-continued
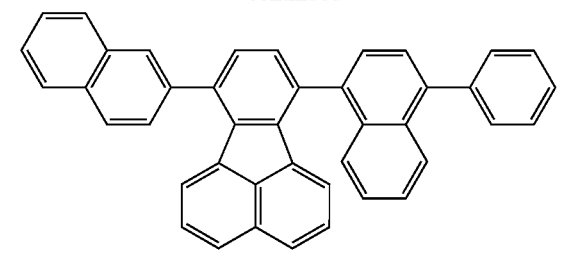
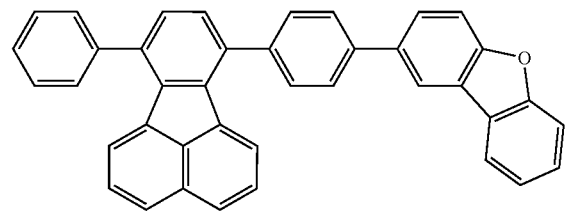
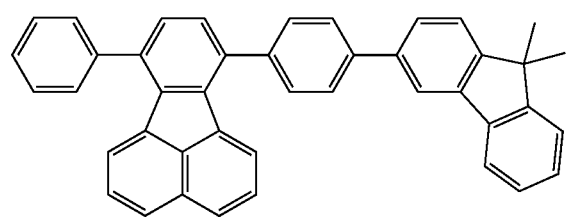
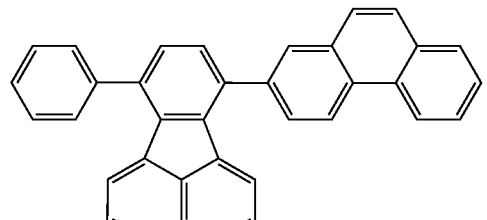
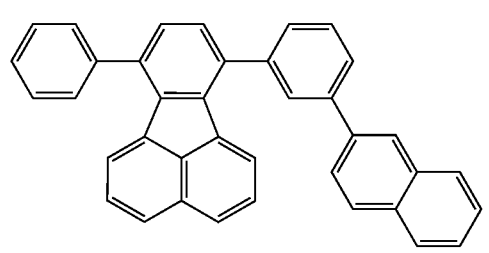
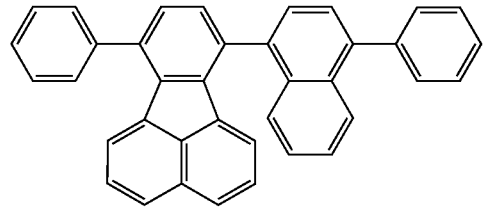
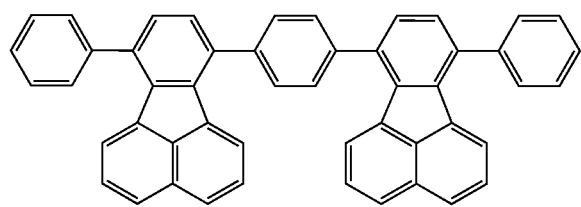
188
-continued
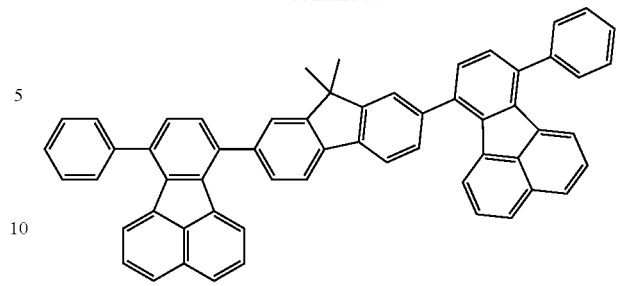
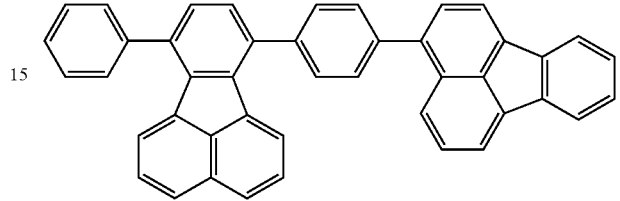
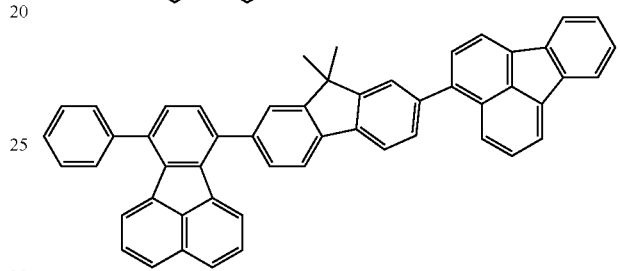
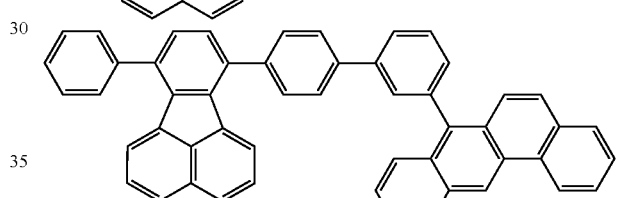
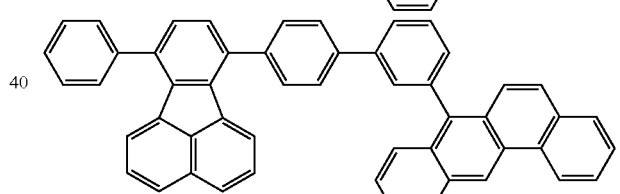
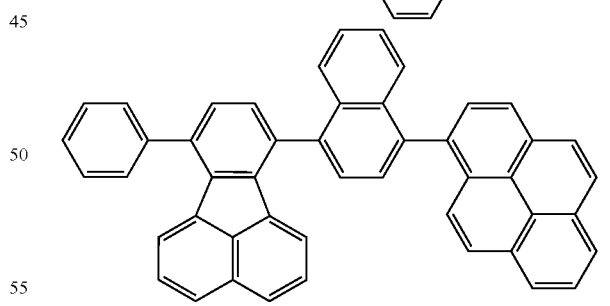
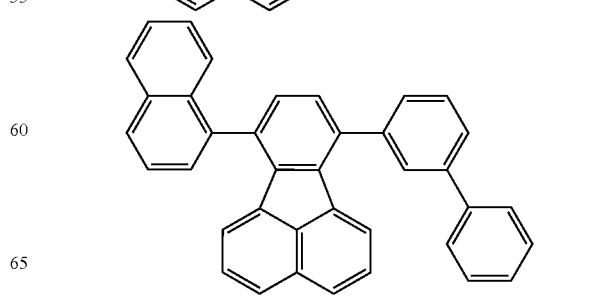

189
-continued
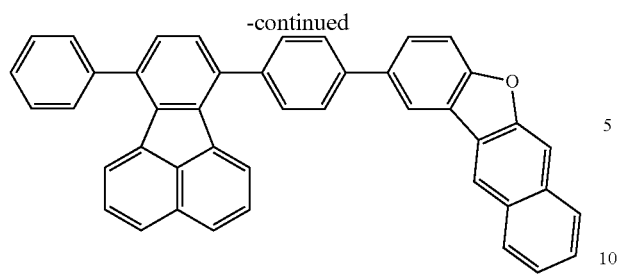
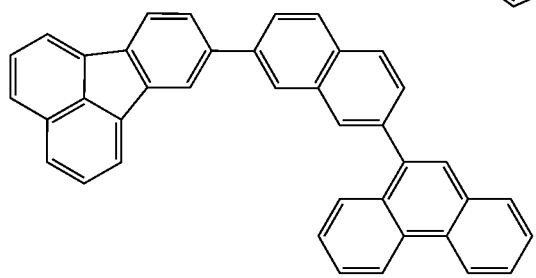
190
-continued
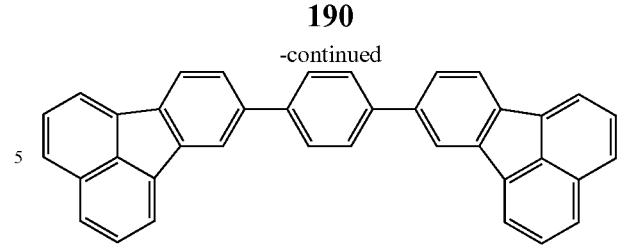
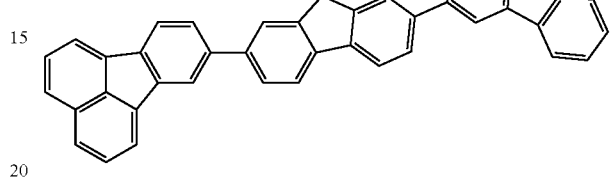
[Formula 110]
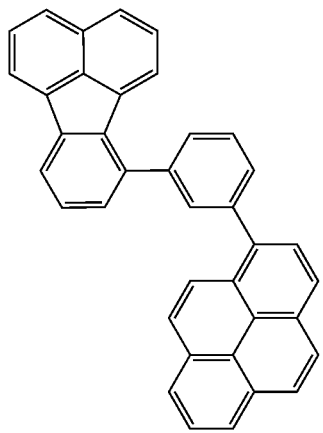 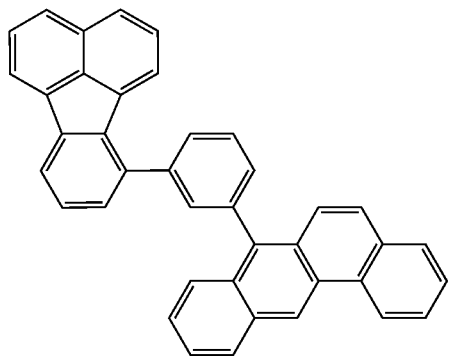 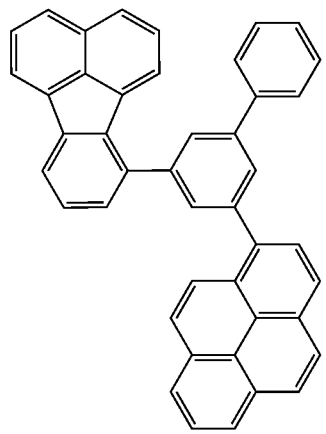
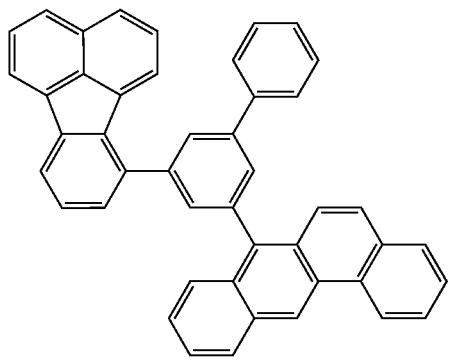 

-continued
| 191 | 192 |
|---|---|
| 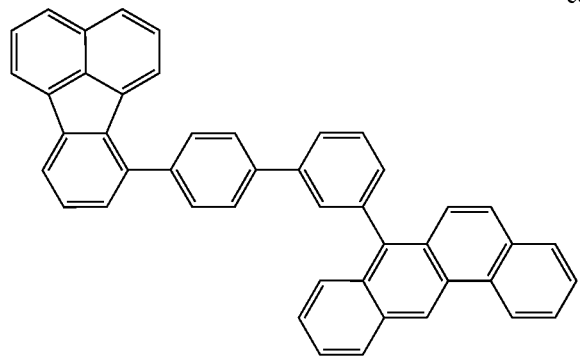 | 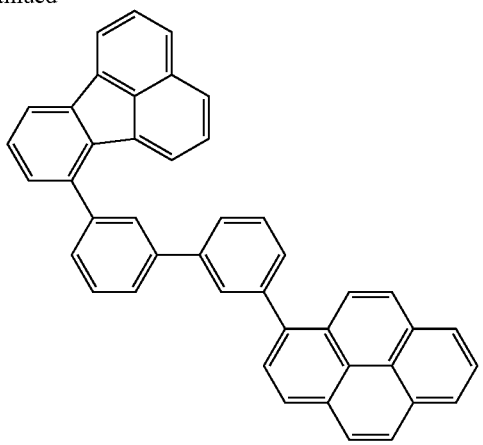 |
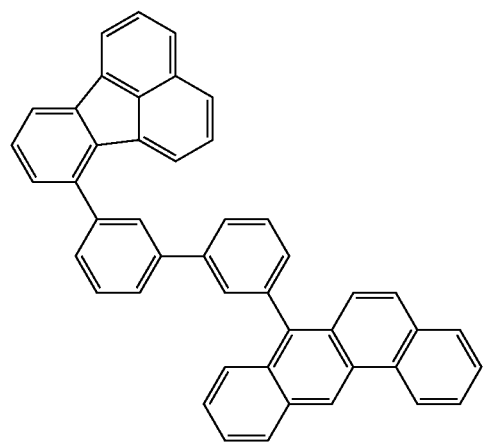
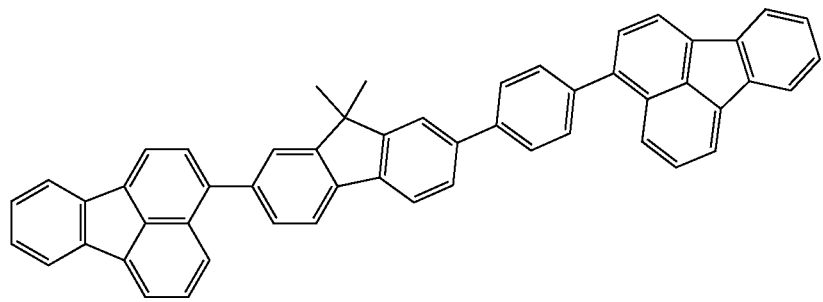
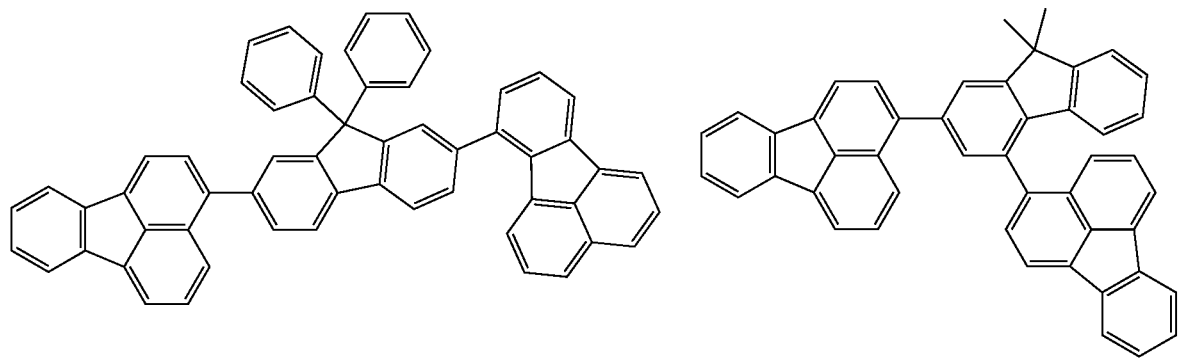

193
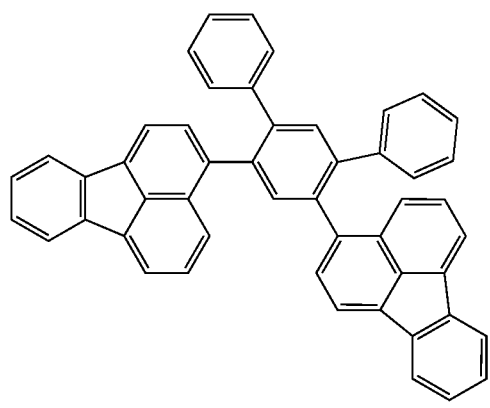
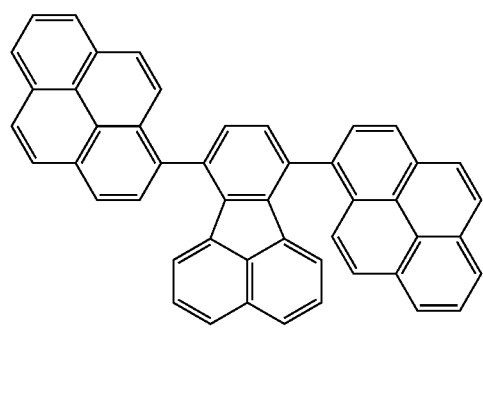
194
-continued
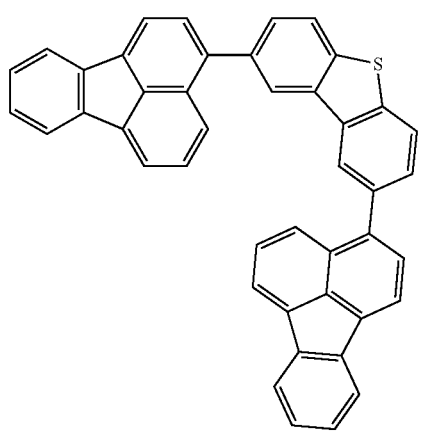
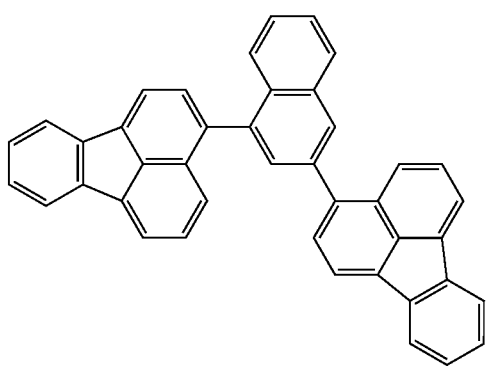
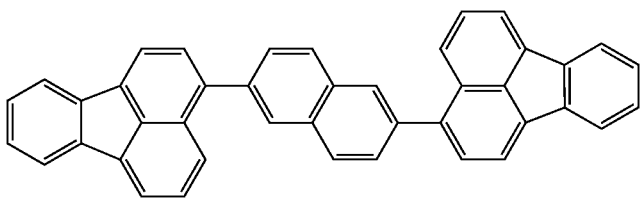
[Formula 111]
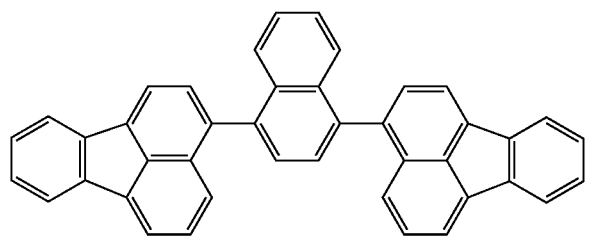
-continued
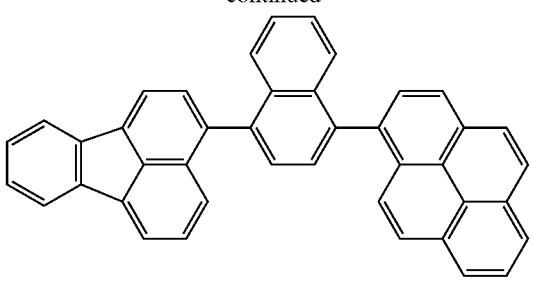

195
-continued
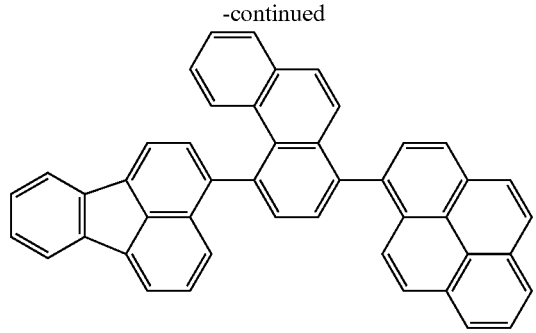
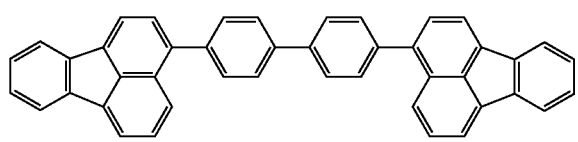
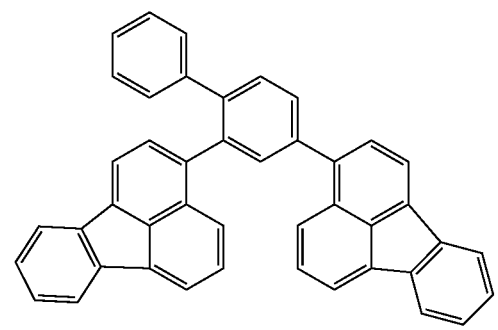
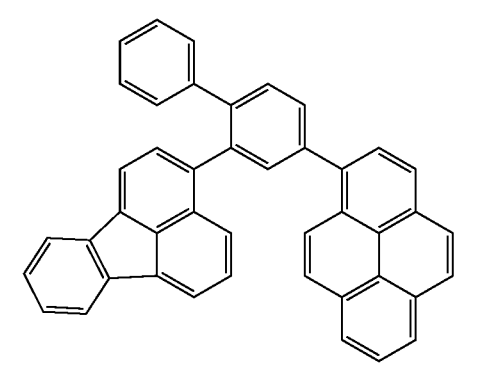
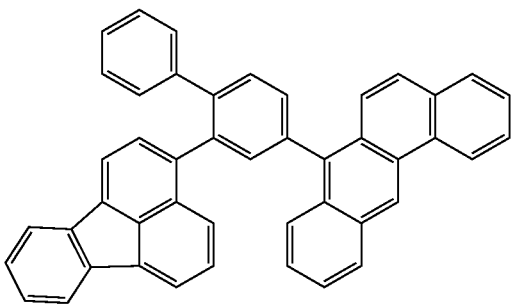
196
-continued
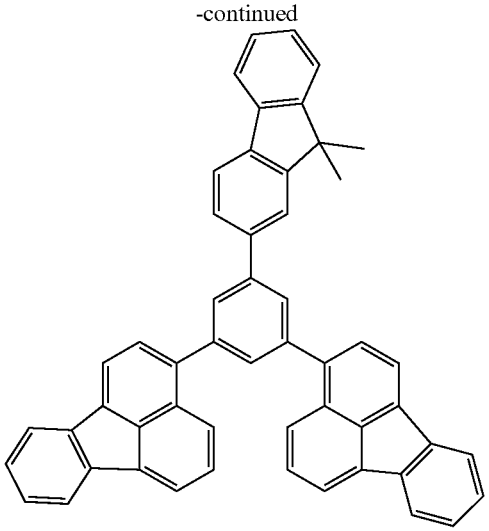

197
-continued
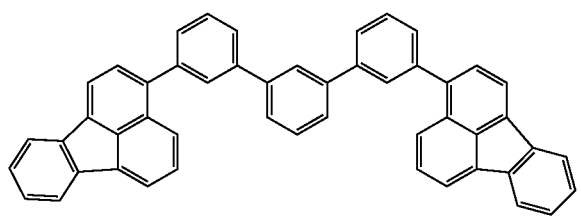
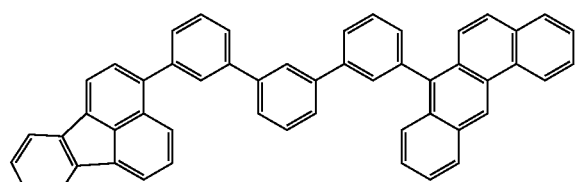
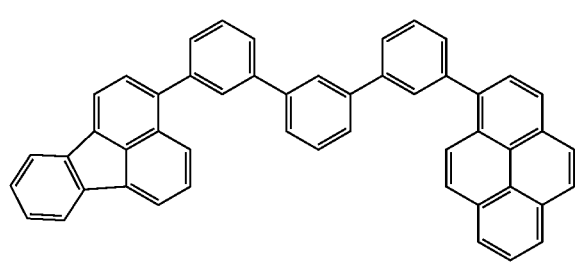
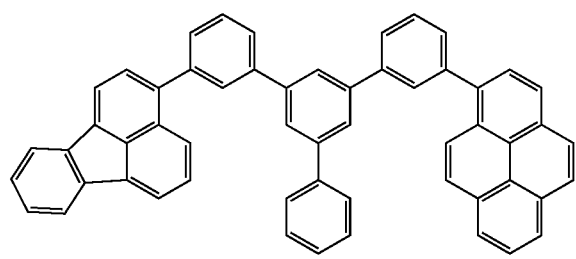 [SMILES: c1ccc(-c2cc(-c3cccc(-c4ccc5c6c(cccc46)-c4ccccc4-5)c3)cc(-c3cccc(-c4ccc5ccc6cccc7ccc4c5c67)c3)c2)cc1]
[Formula 112]
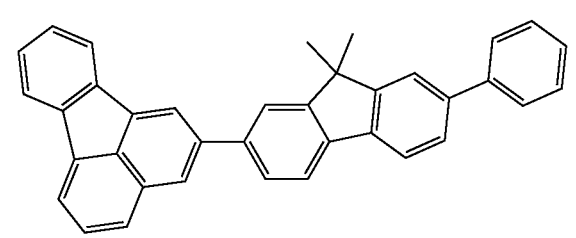
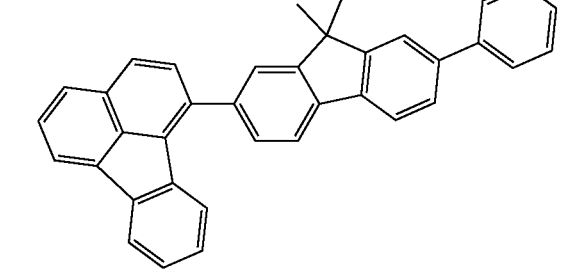
198
-continued
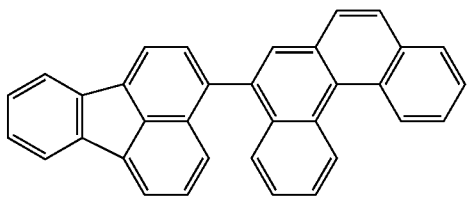
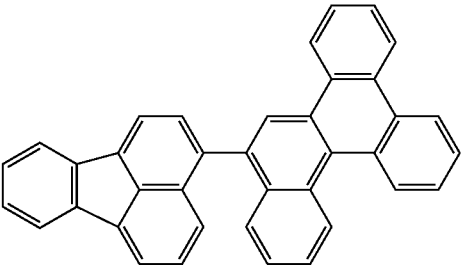
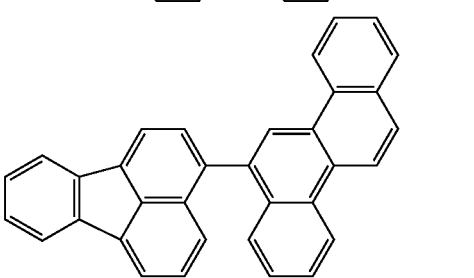
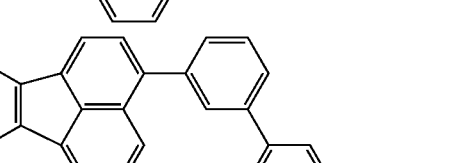
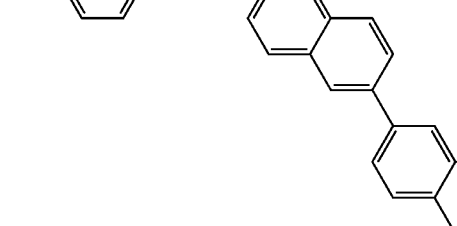

199
-continued
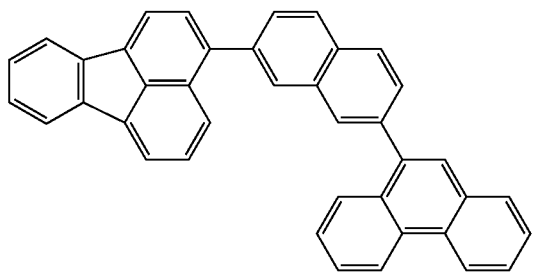
200
-continued
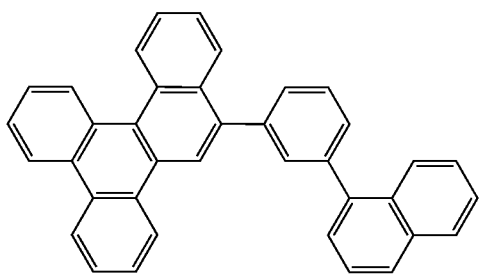
[Formula 113]
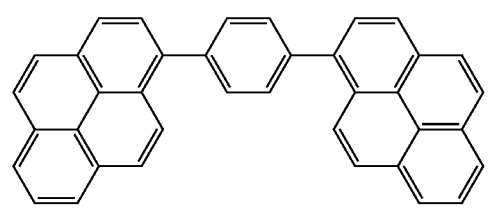
[Formula 114]
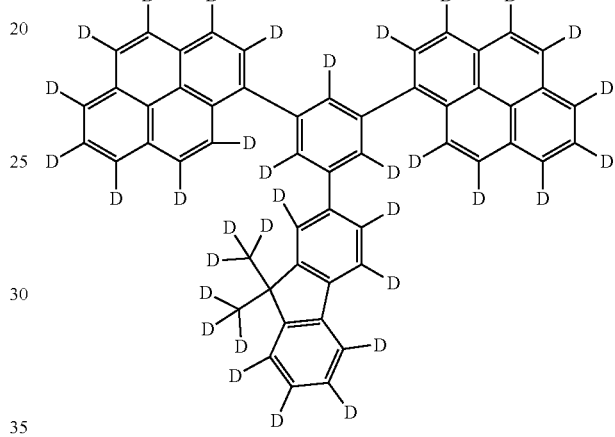
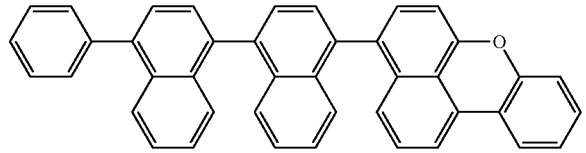
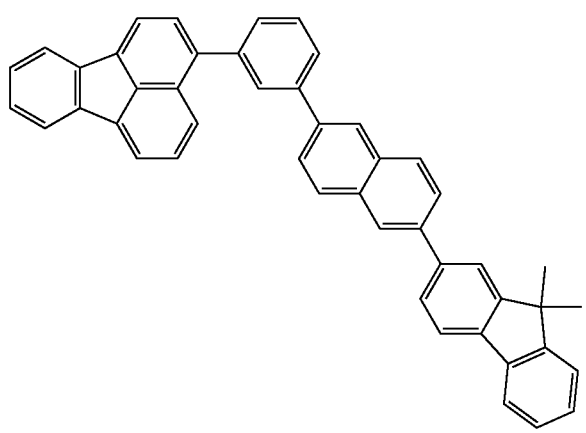
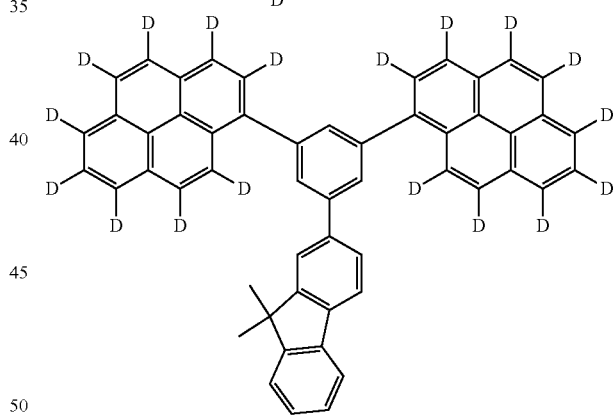
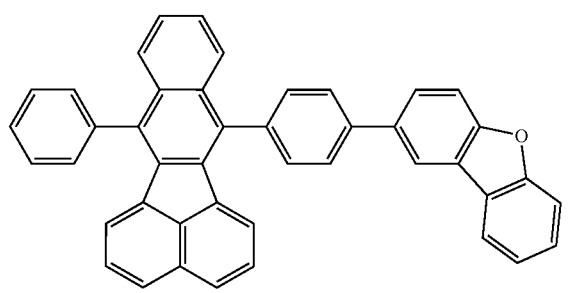
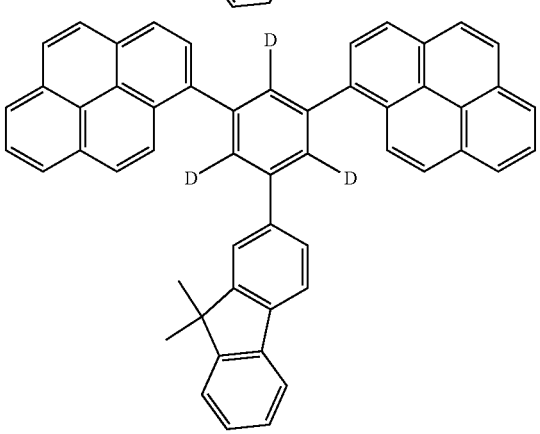

201
-continued
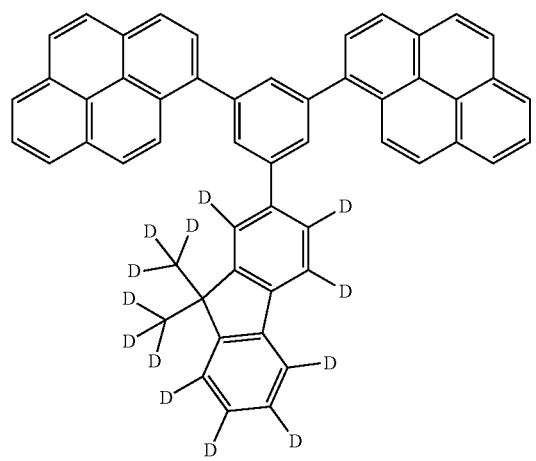
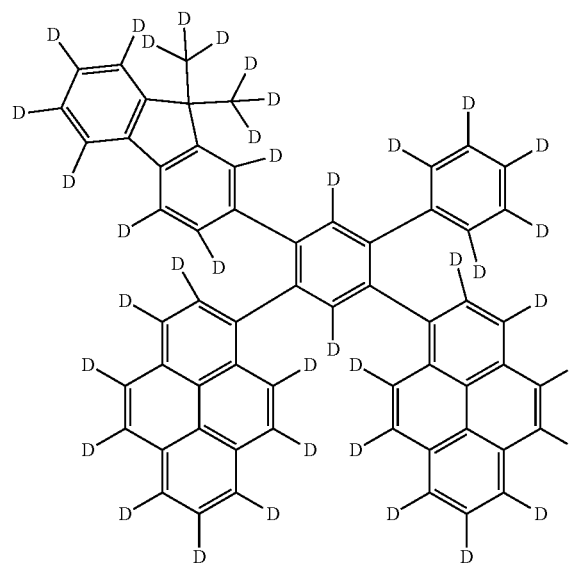
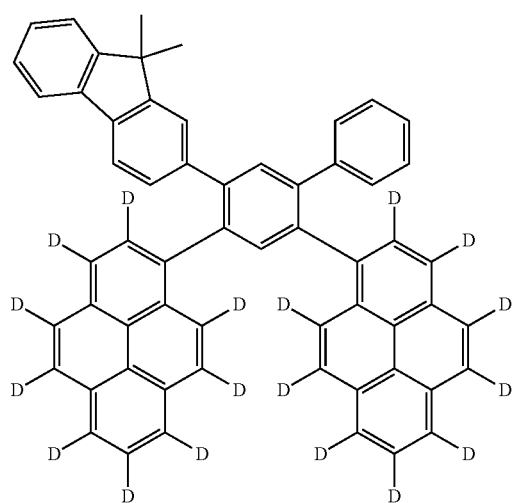
202
-continued
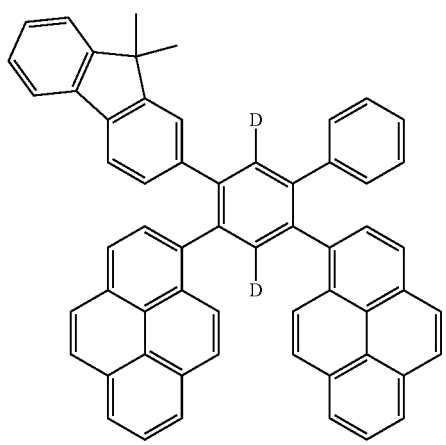
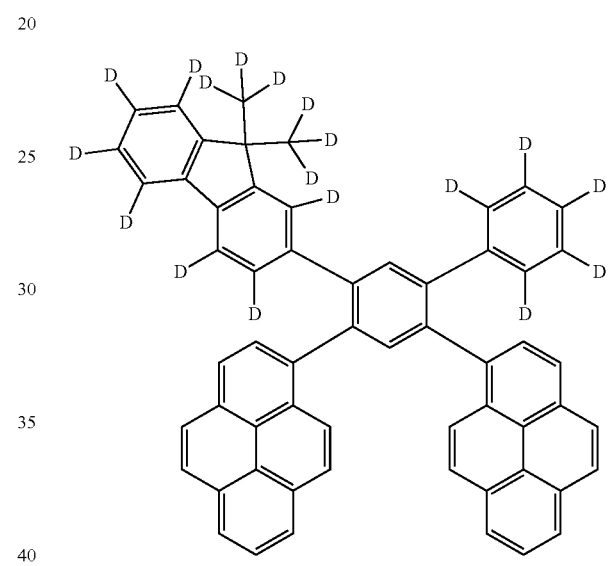
[Formula 115]
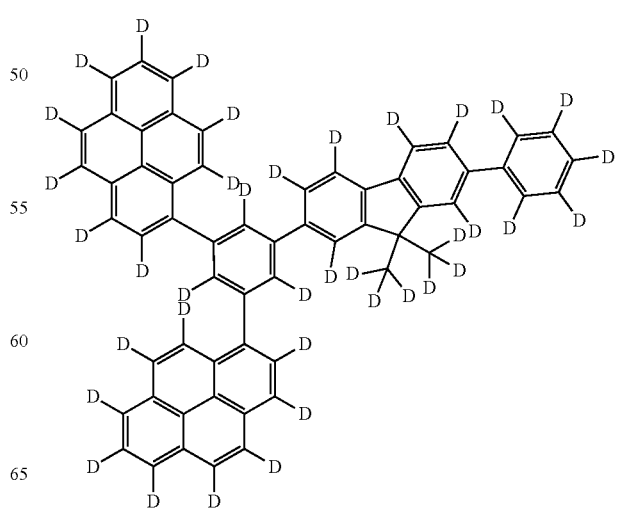

203
-continued
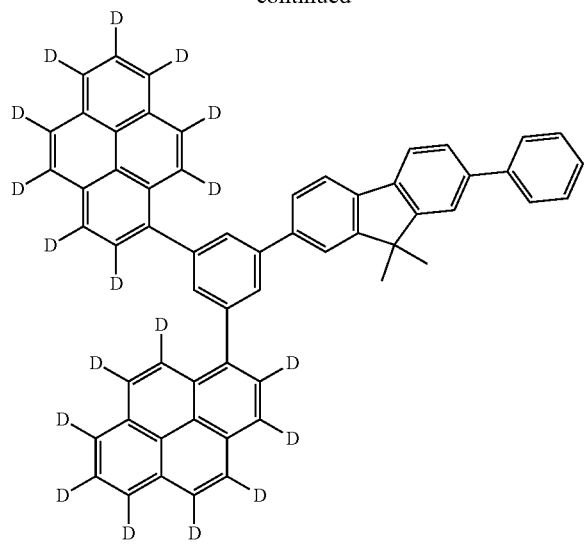
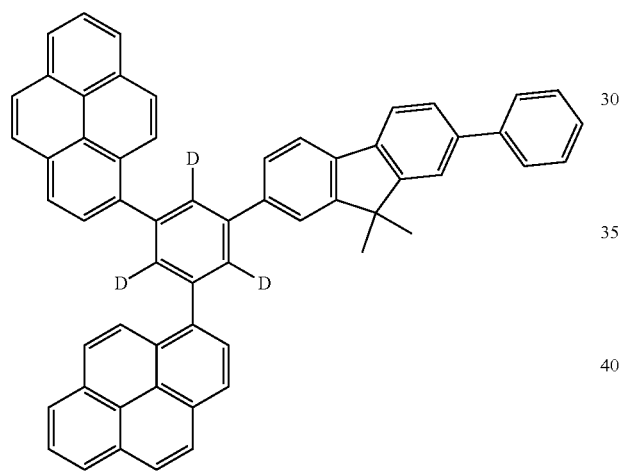
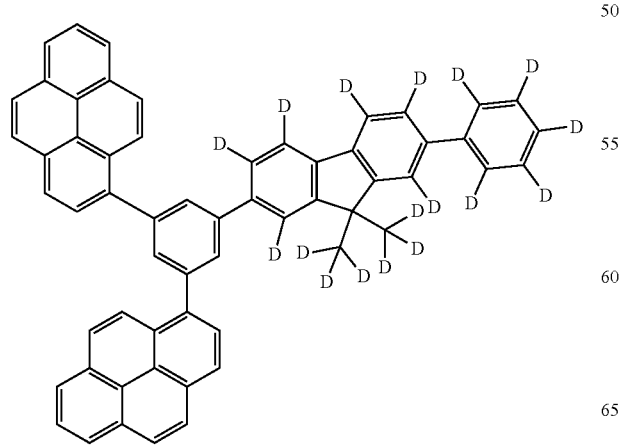
204
-continued
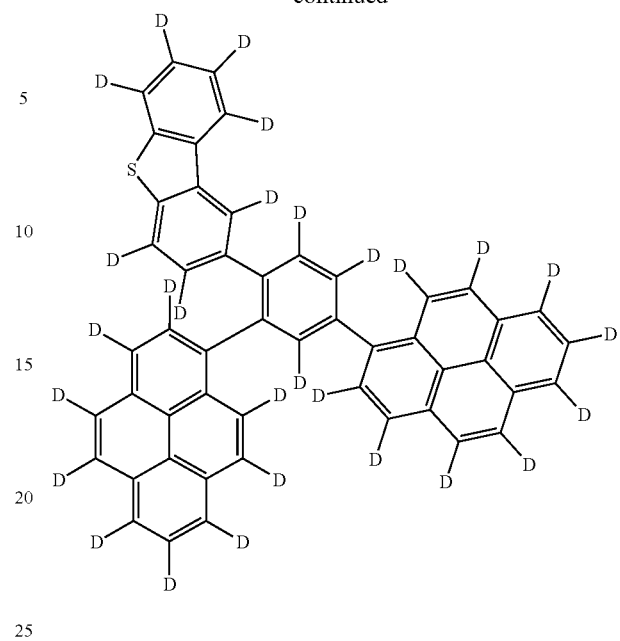
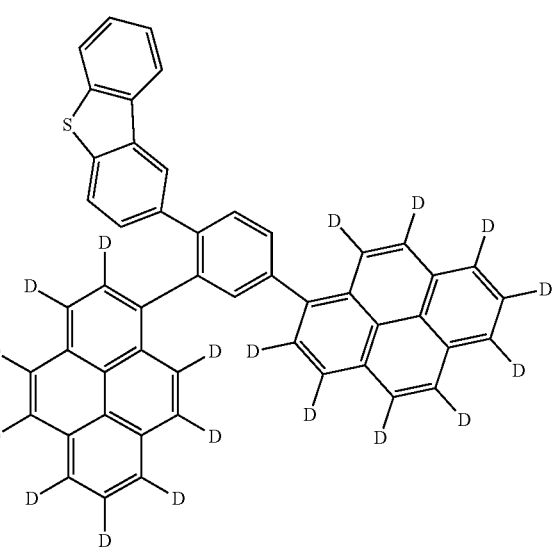
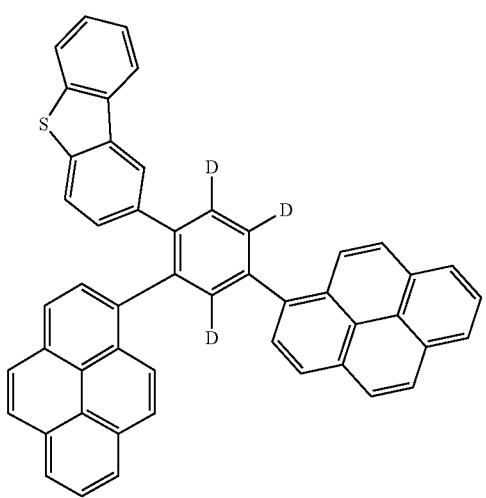

205
-continued
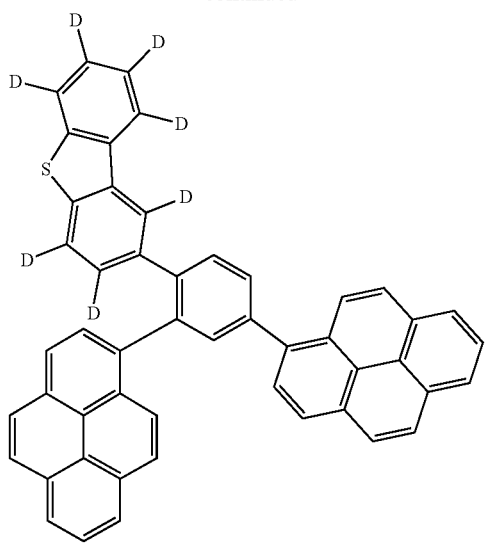
[Formula 116]
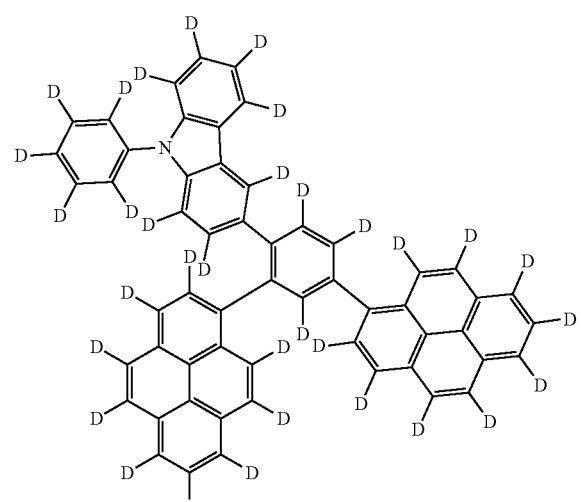
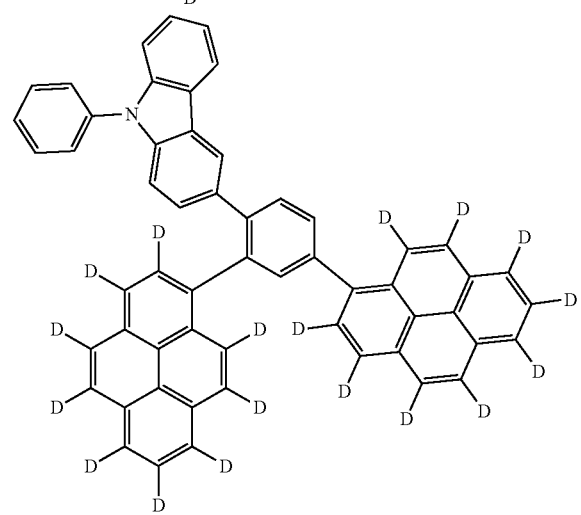
206
-continued
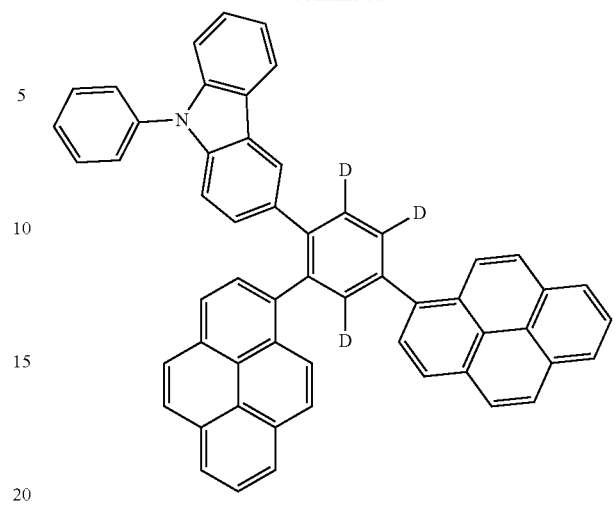
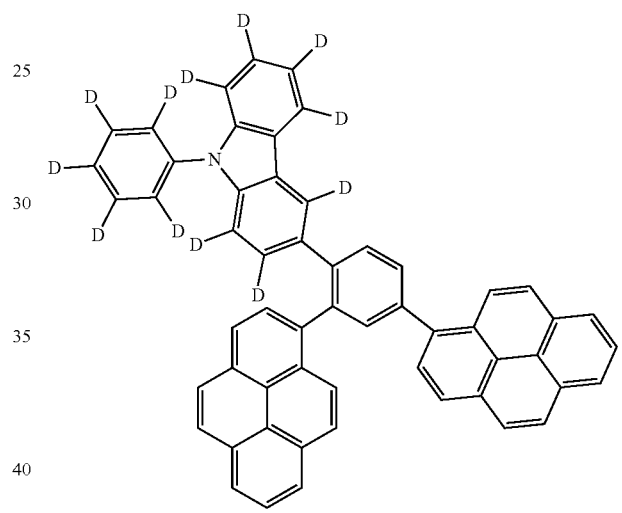
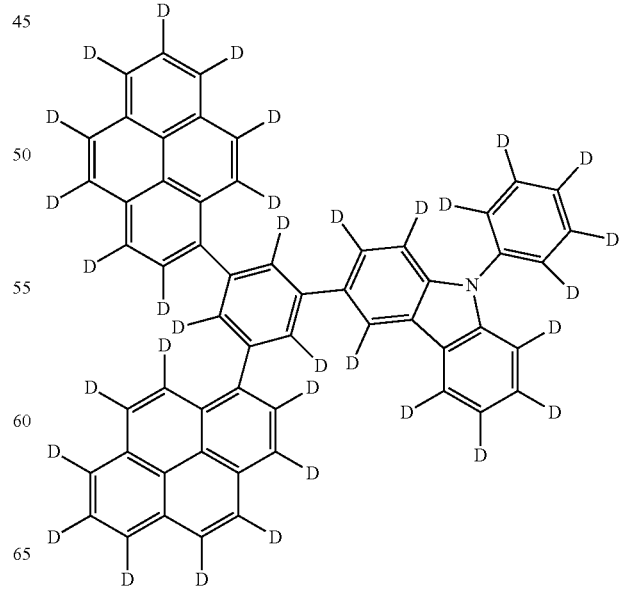

207
-continued
208
[Formula 117]
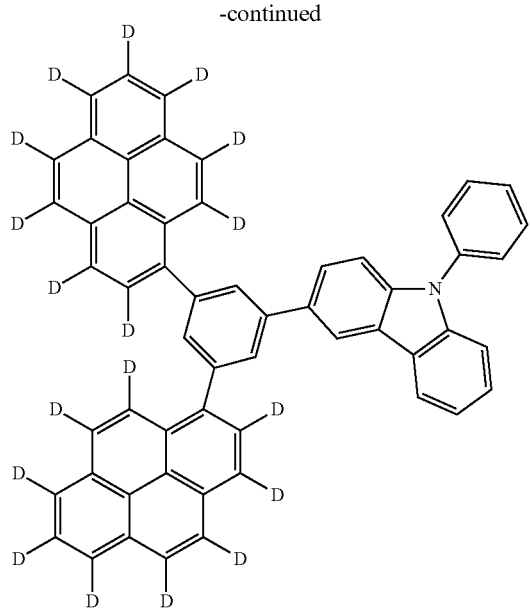
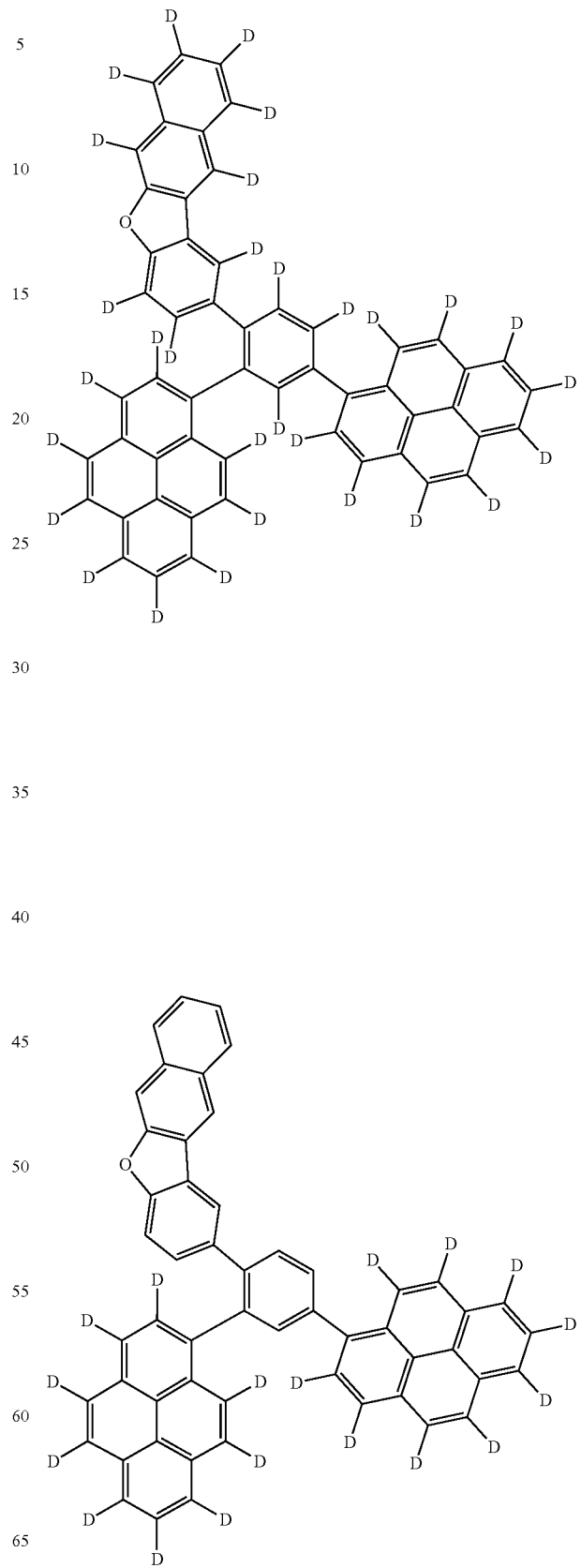

209
-continued
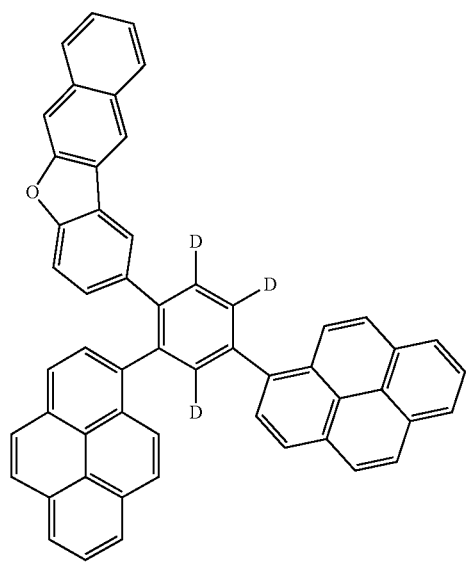
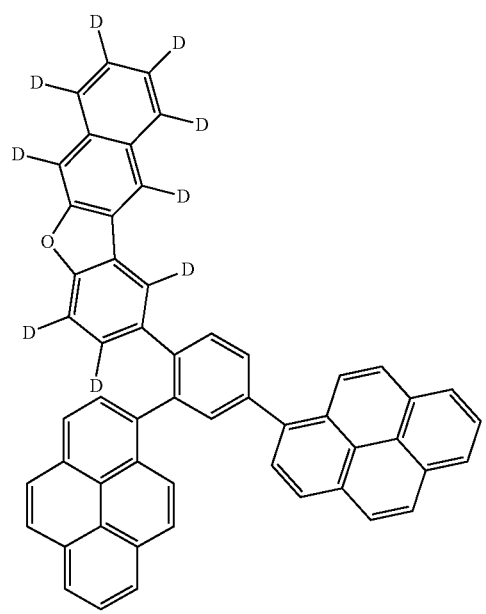
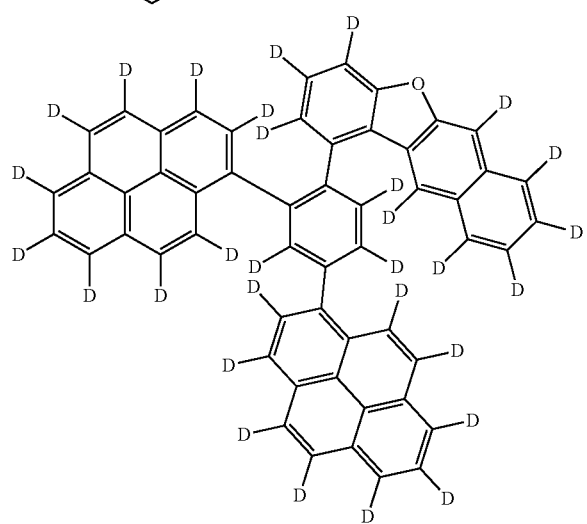
210
-continued
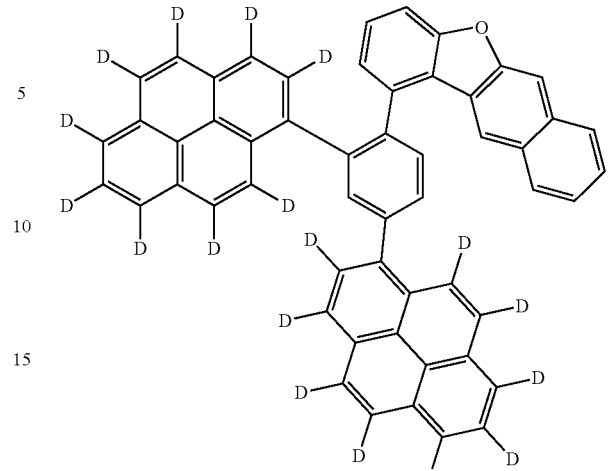
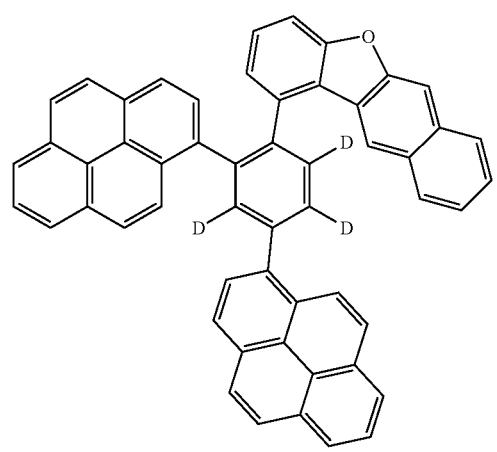
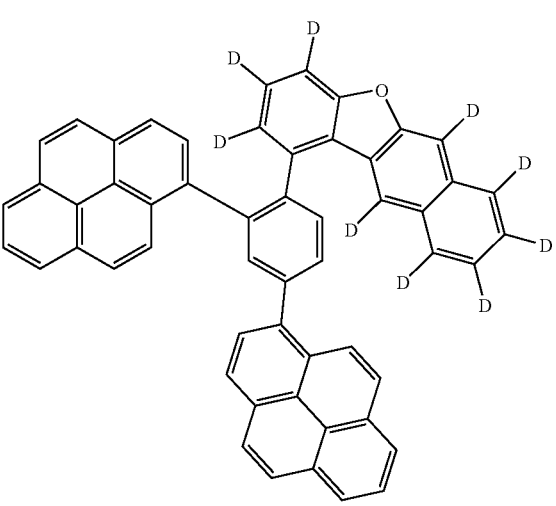

211
[Formula 118]
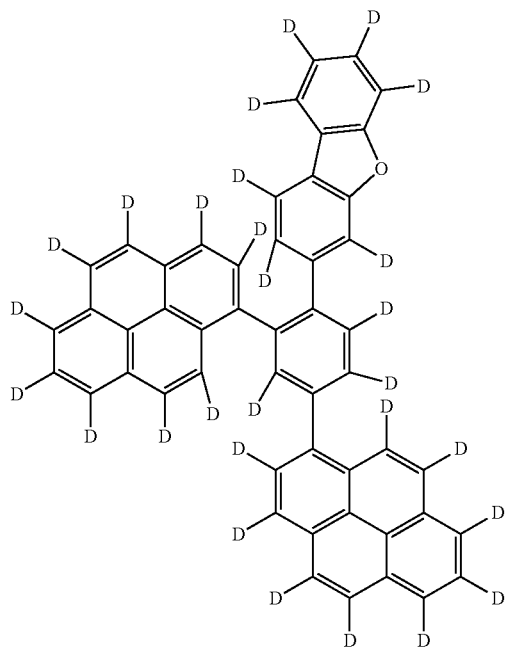
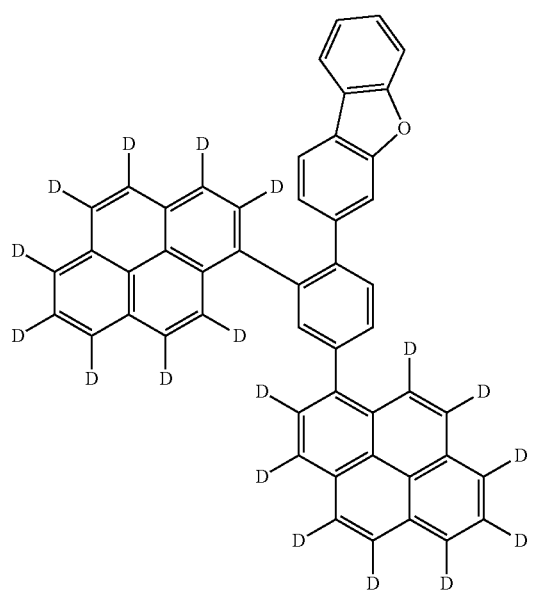
212
-continued
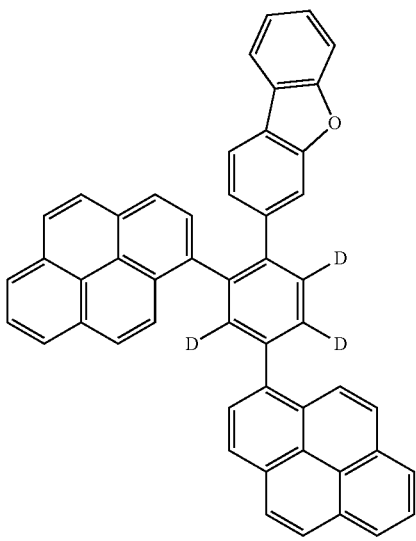
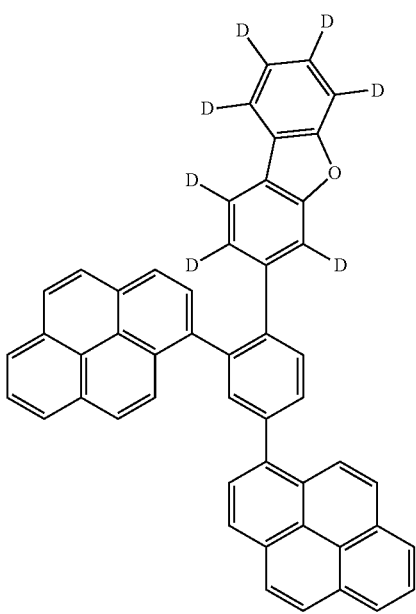

213
-continued
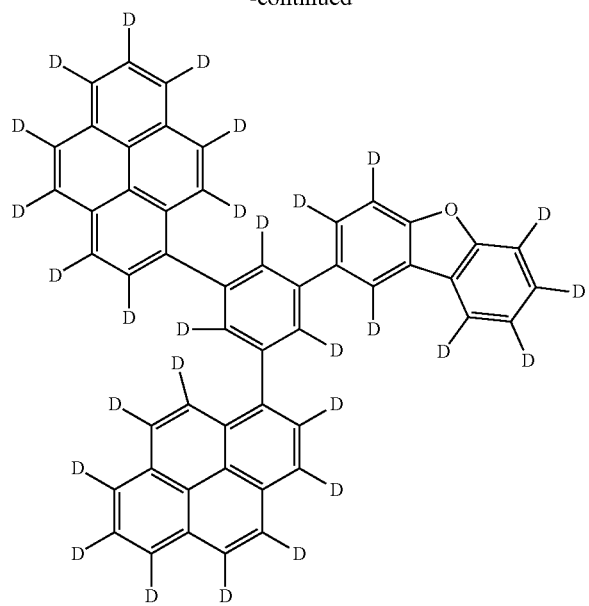
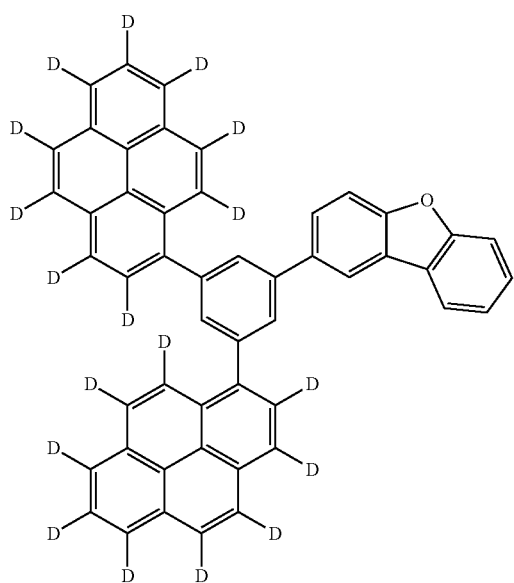
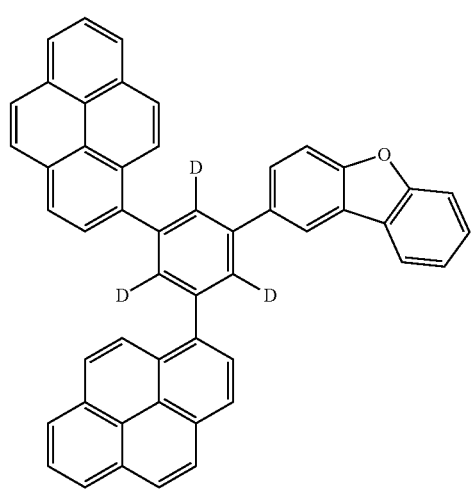
214
-continued
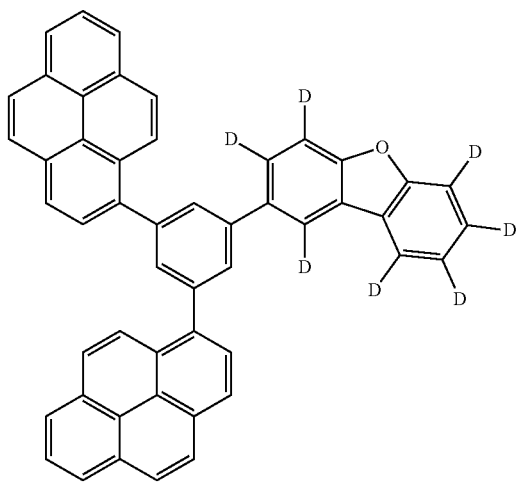
[Formula 119]
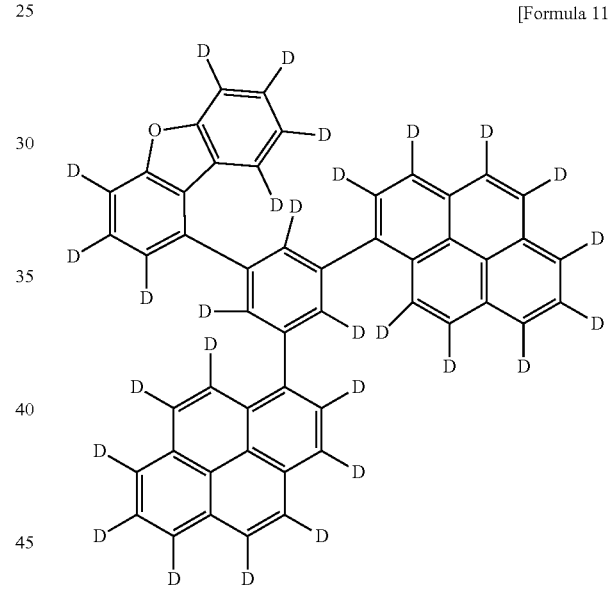
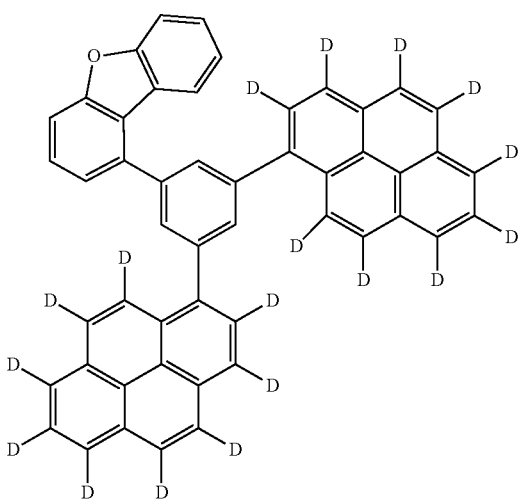

215
-continued
216
-continued
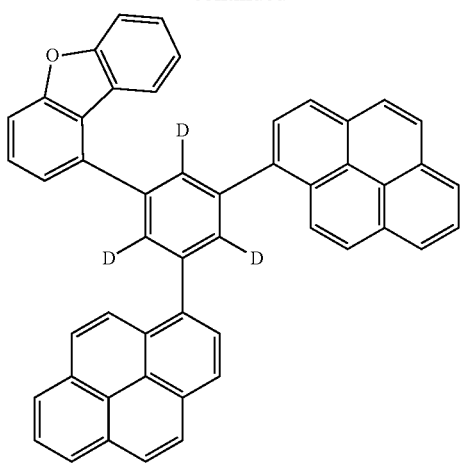
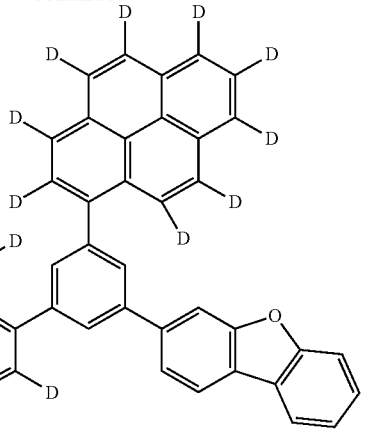
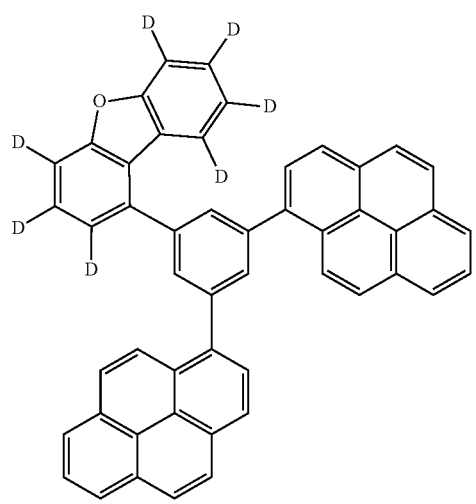
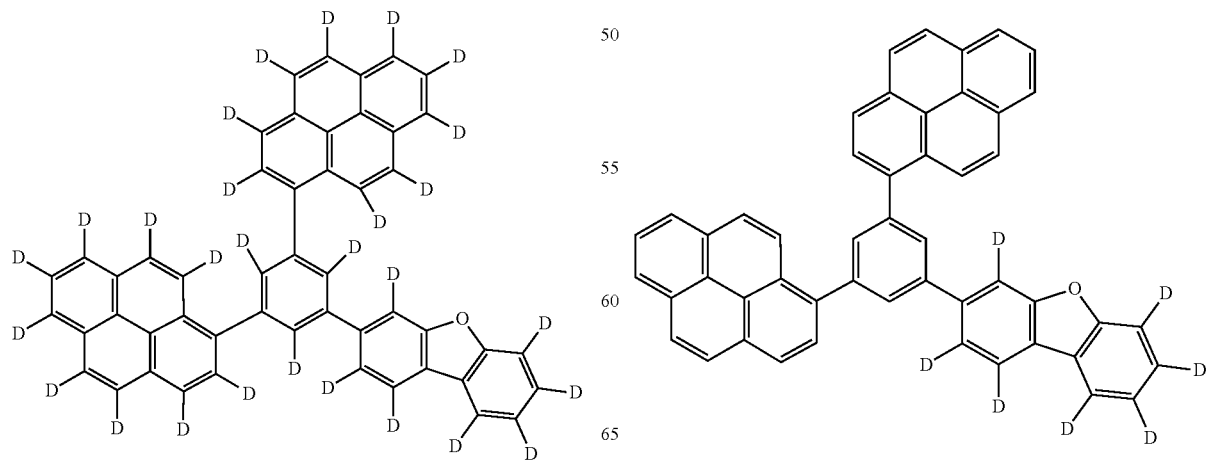

[Formula 120]
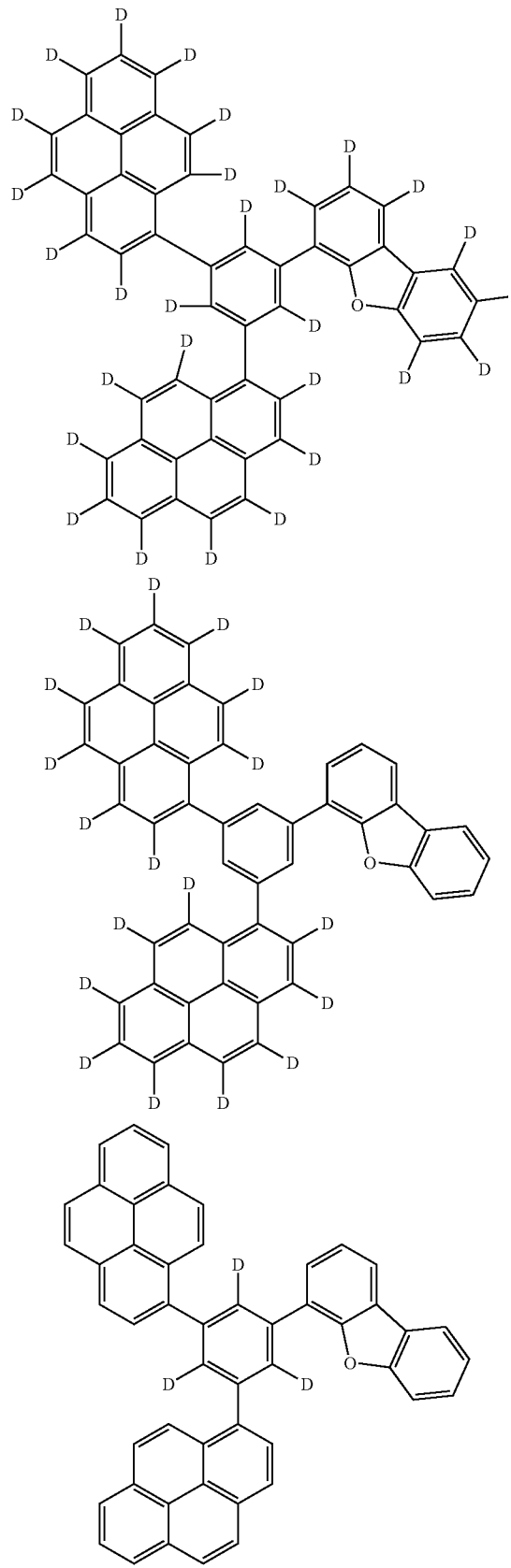
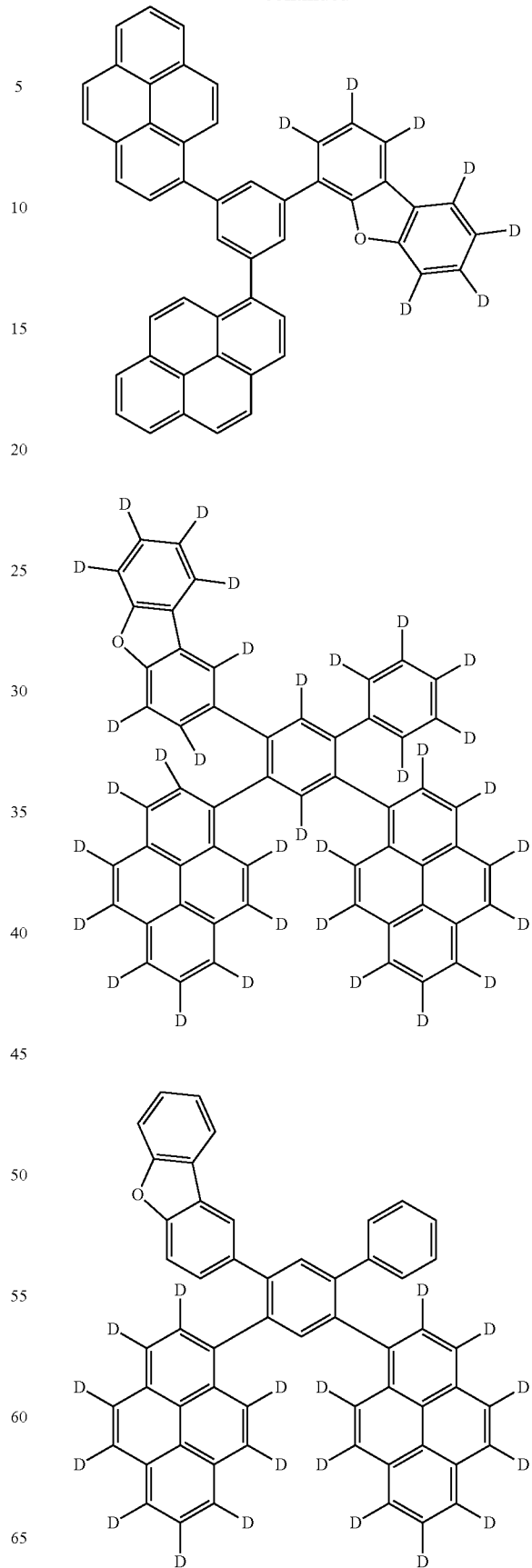

219
-continued
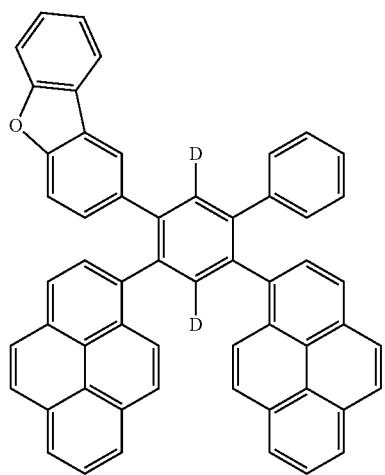
220
[Formula 121]
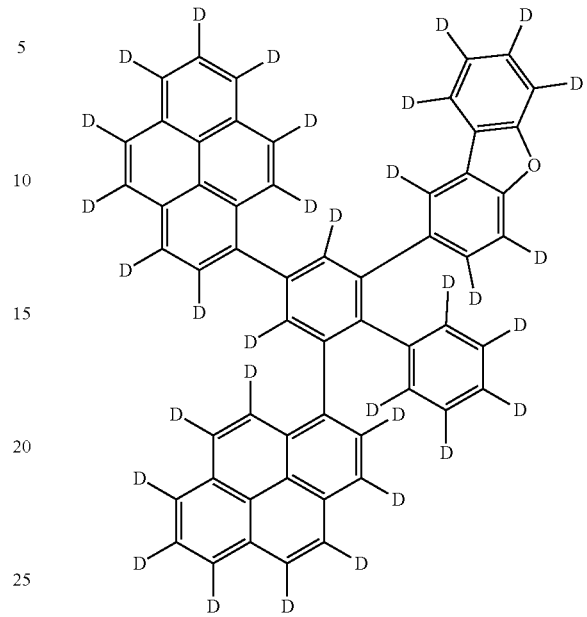
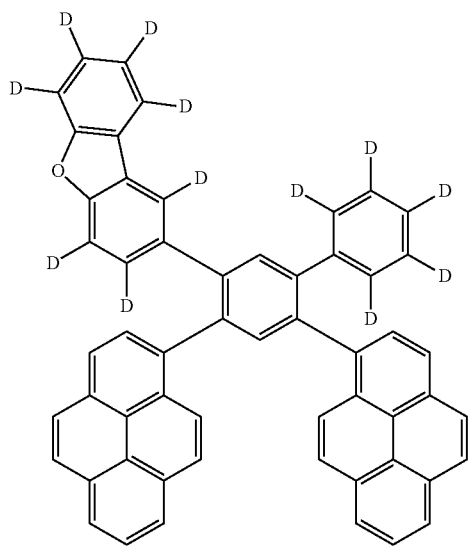
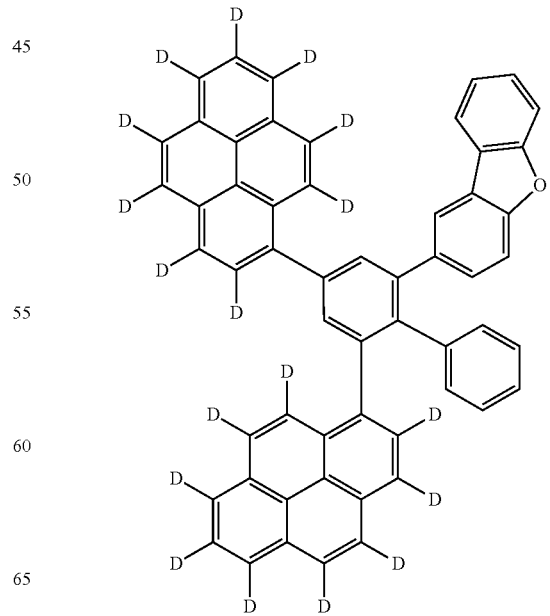

221
-continued
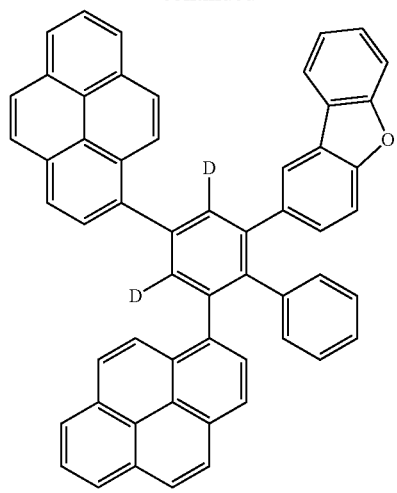
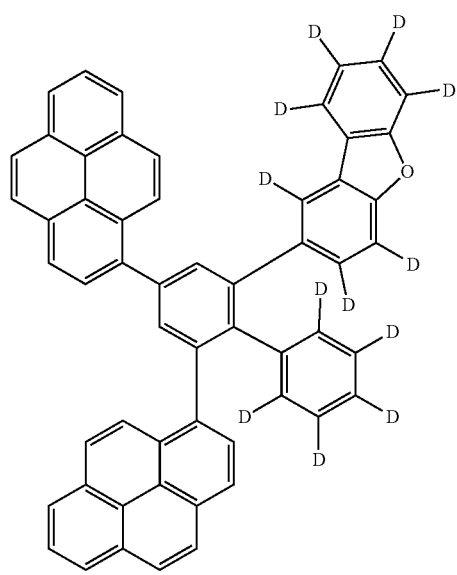
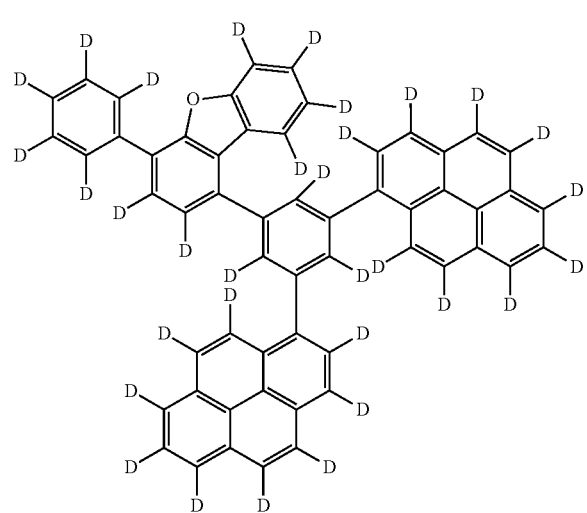
222
-continued
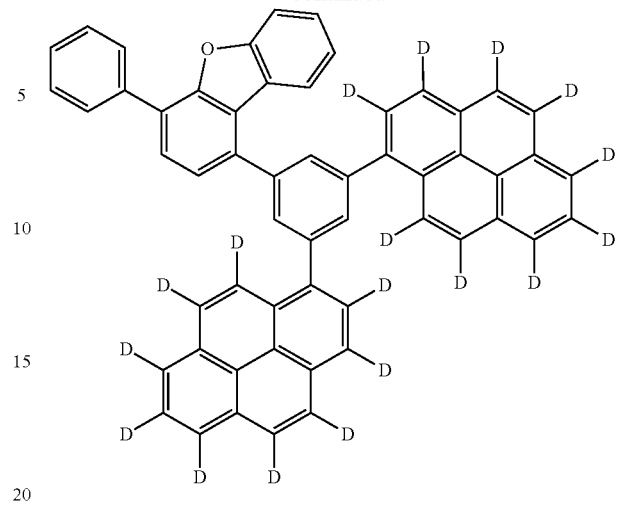
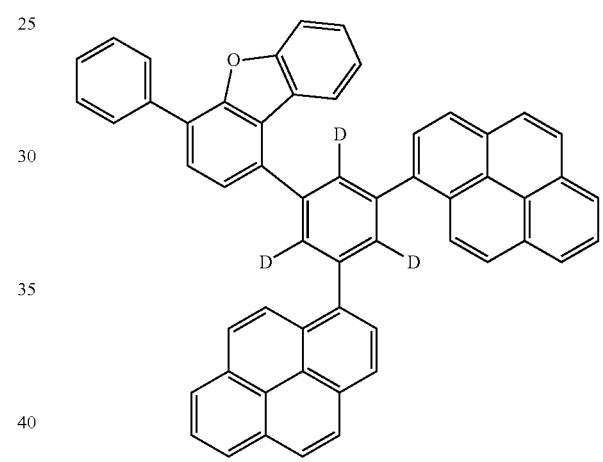
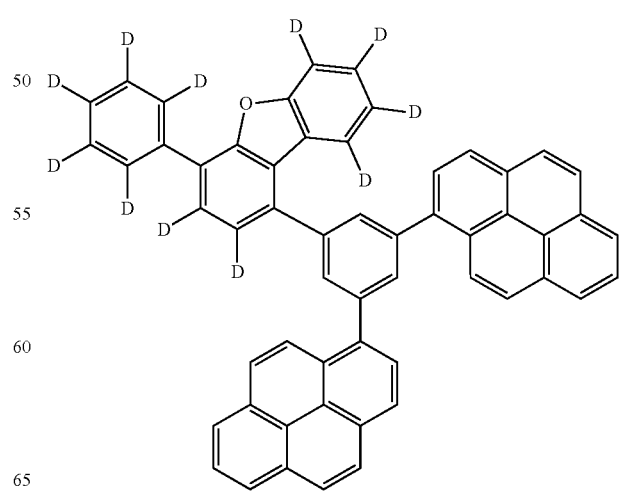

[Formula 122]
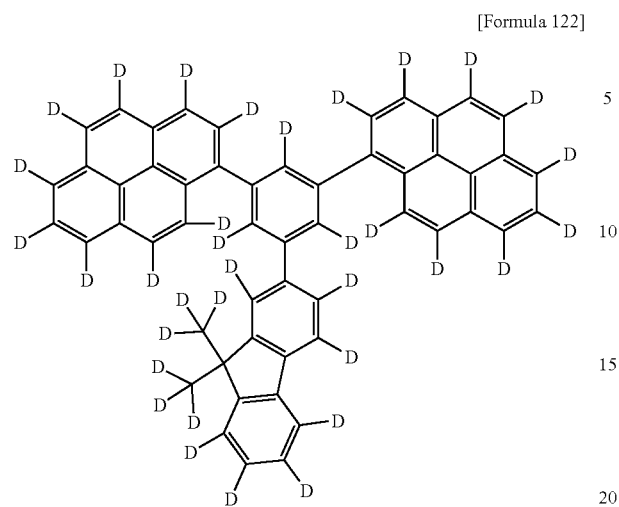
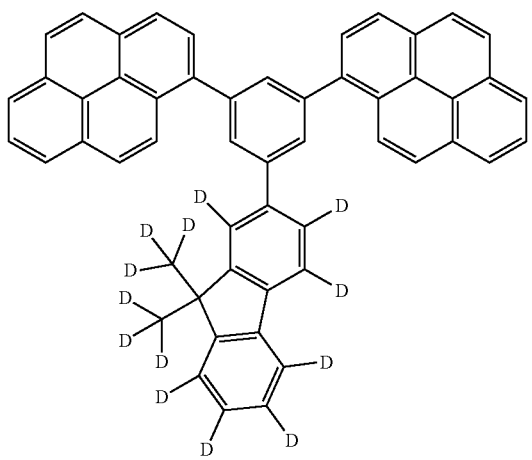
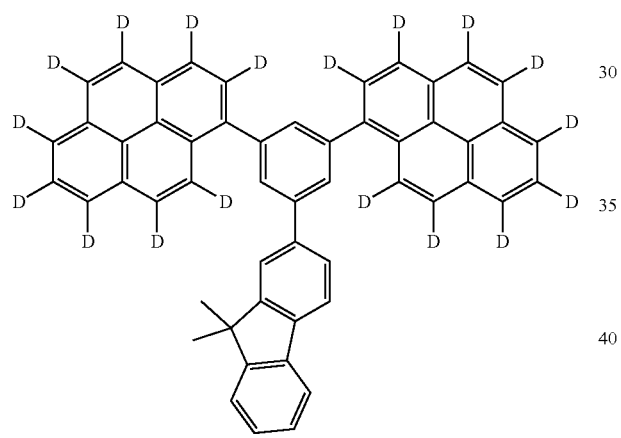
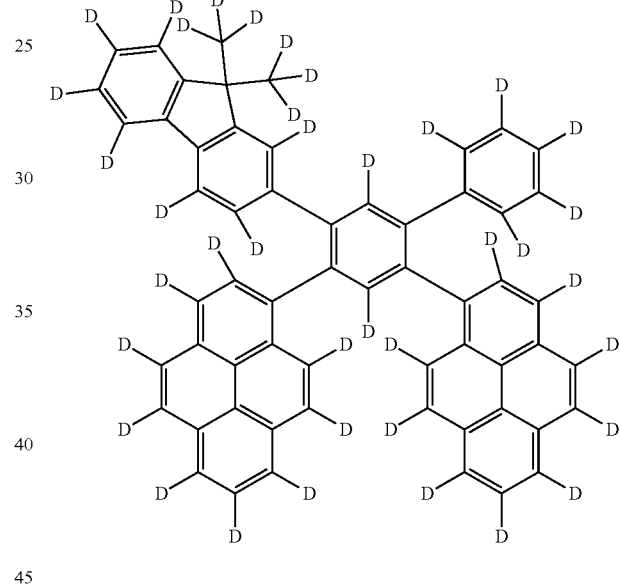
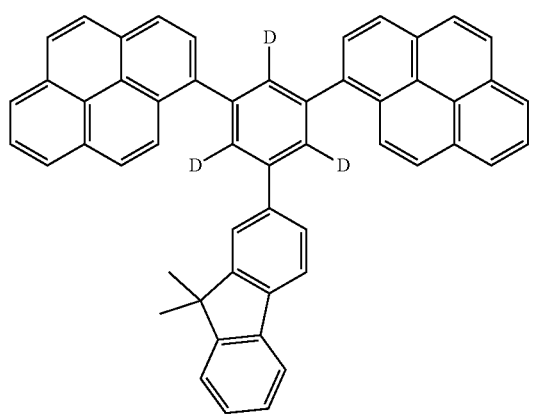
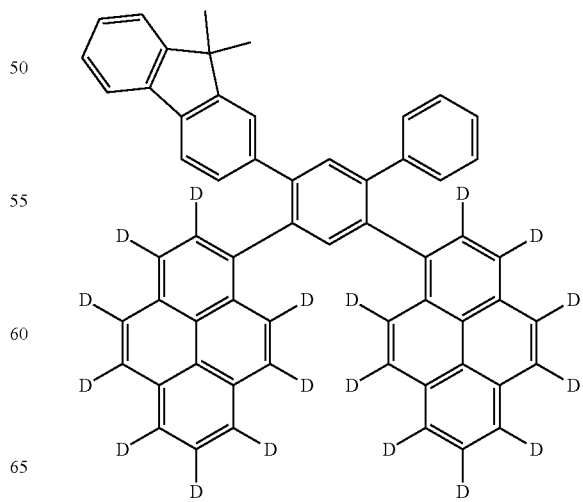

225
226
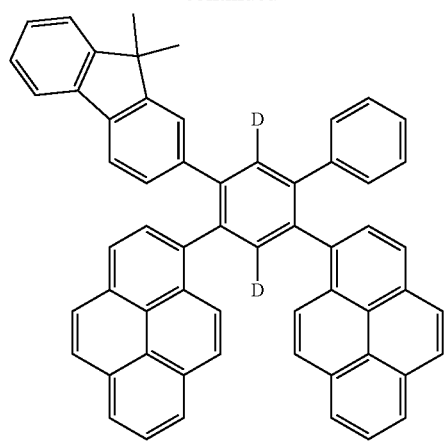
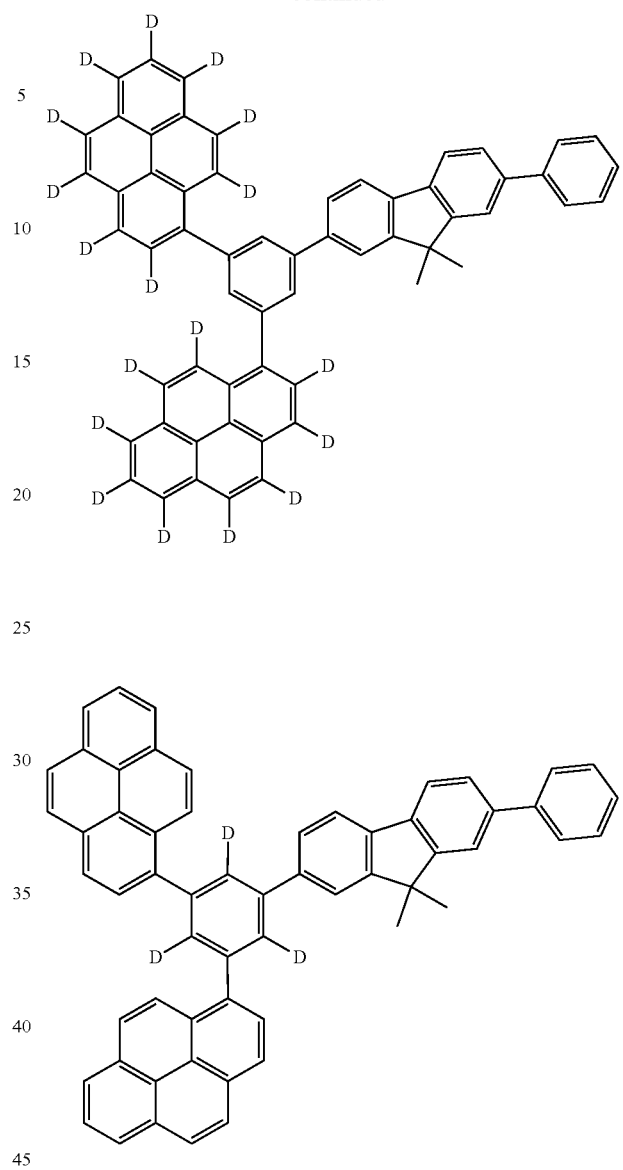
[Formula 123]
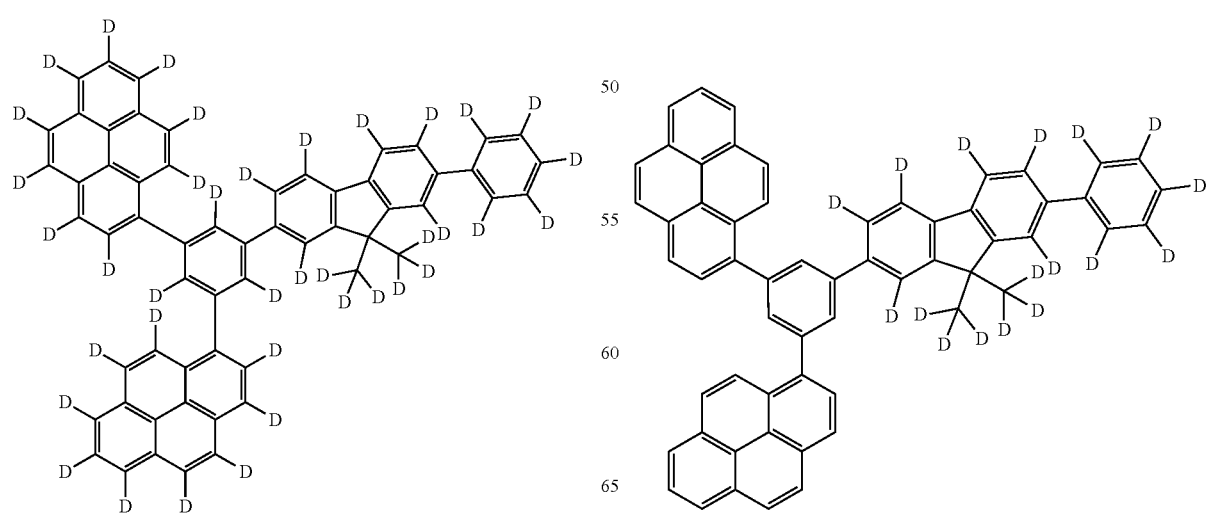

227
-continued
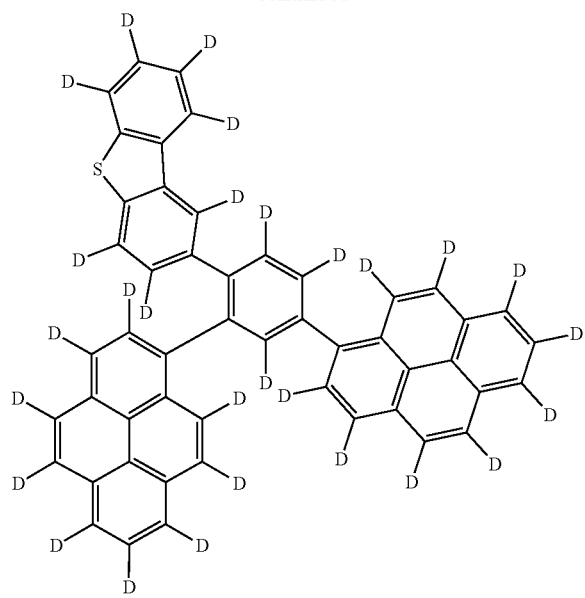
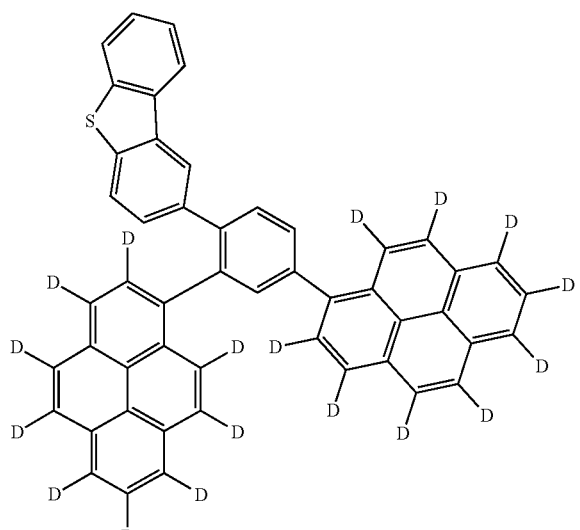
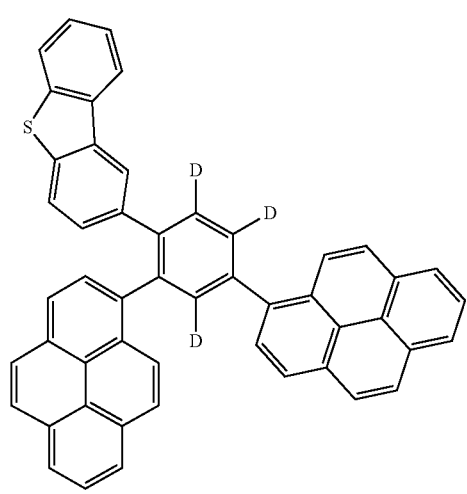
228
-continued
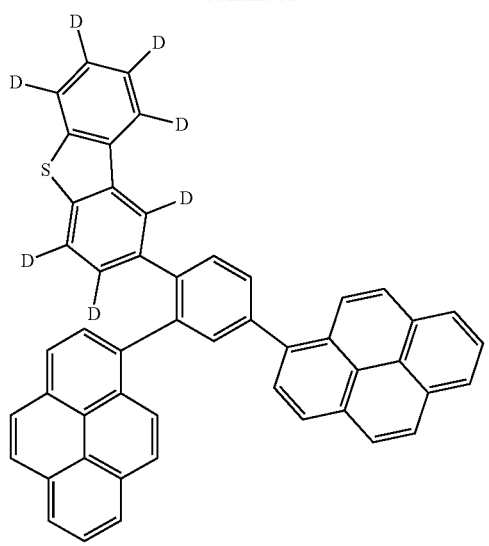
[Formula 124]
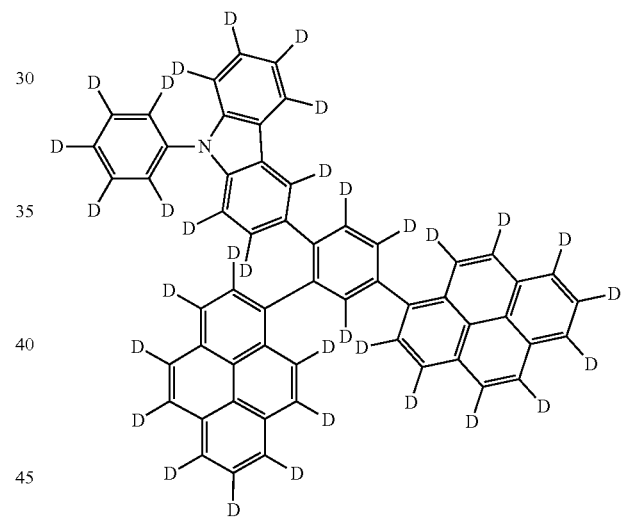
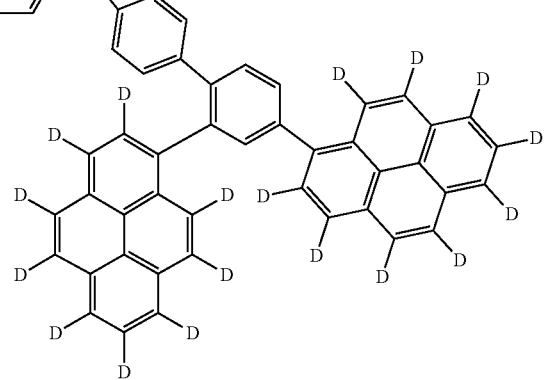

229
-continued
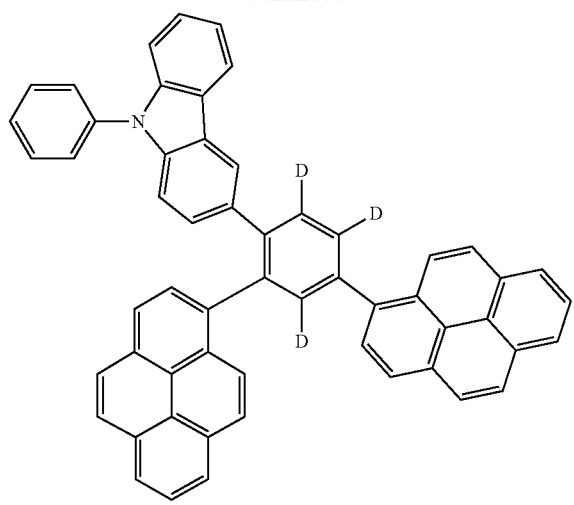
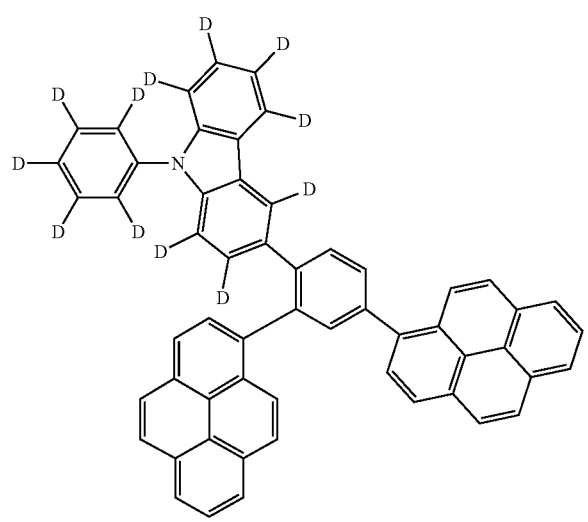
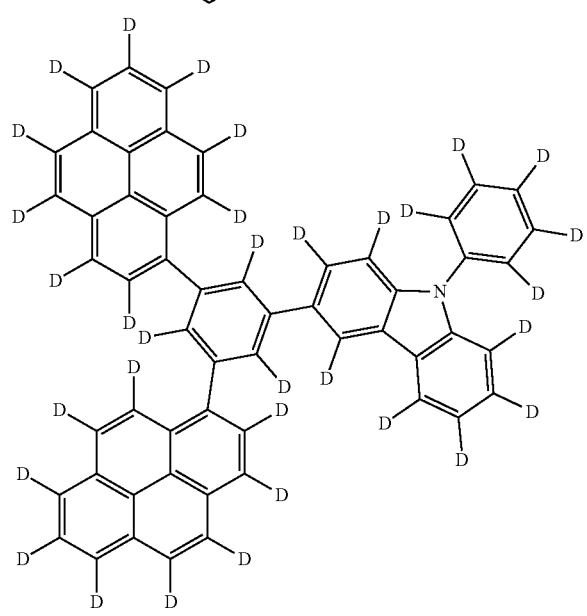
230
-continued
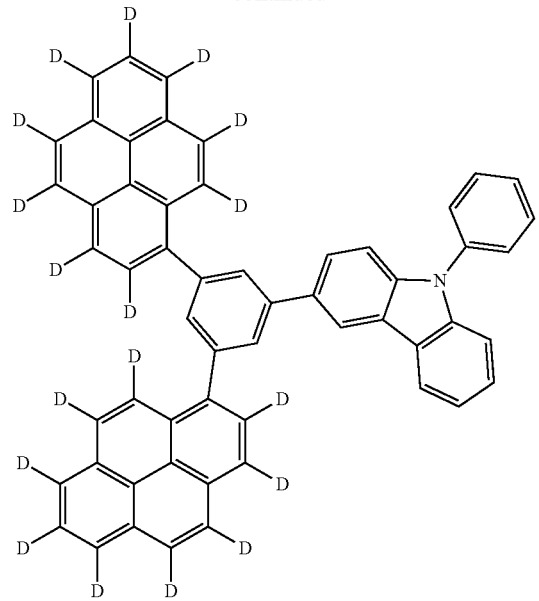
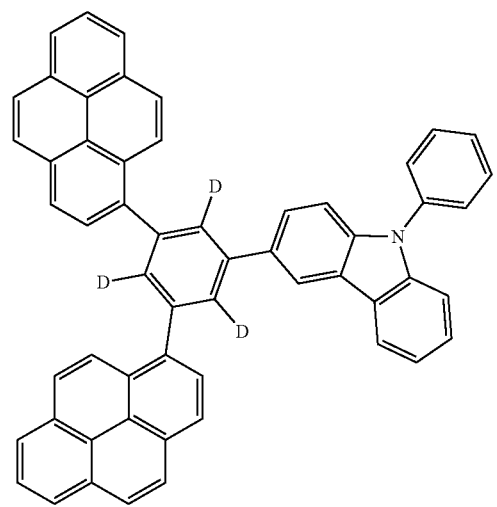
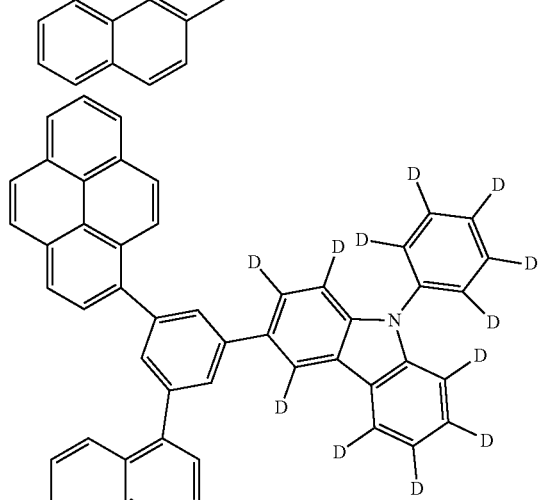

[Formula 125]
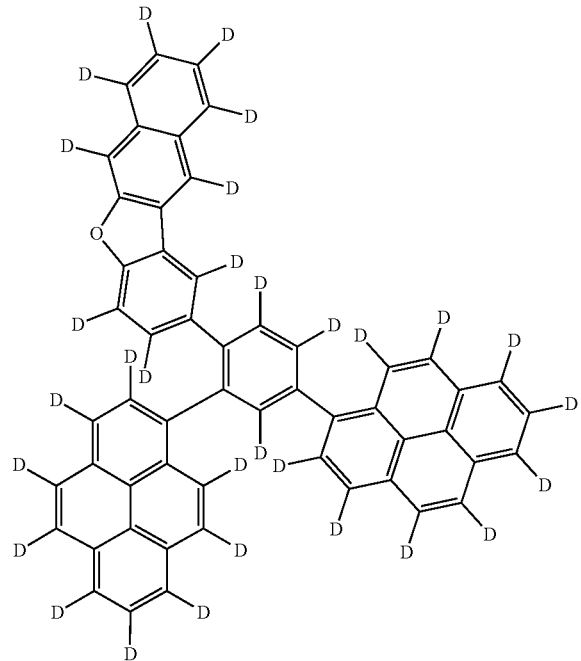
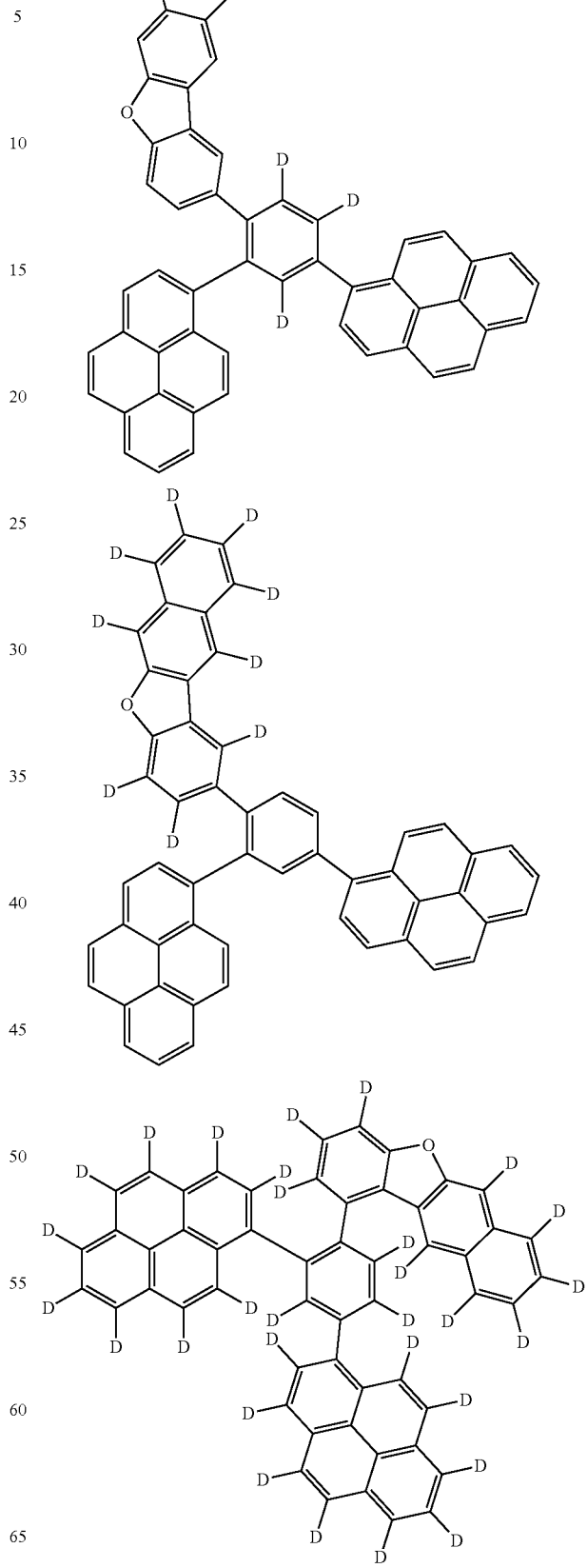

233
-continued
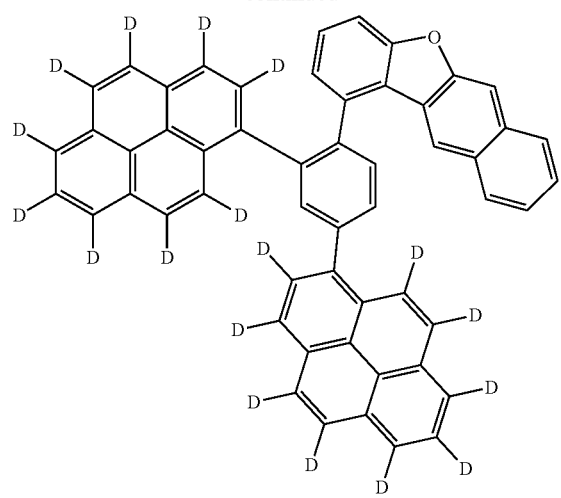
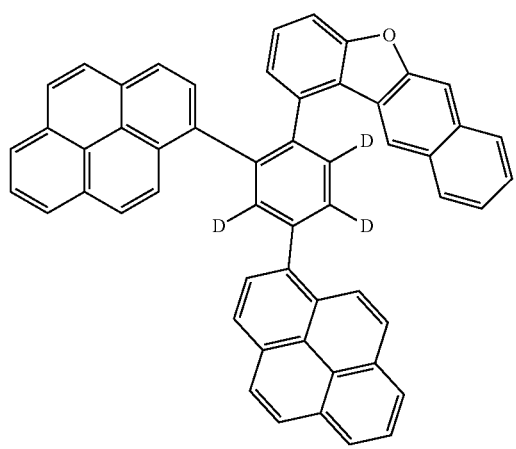
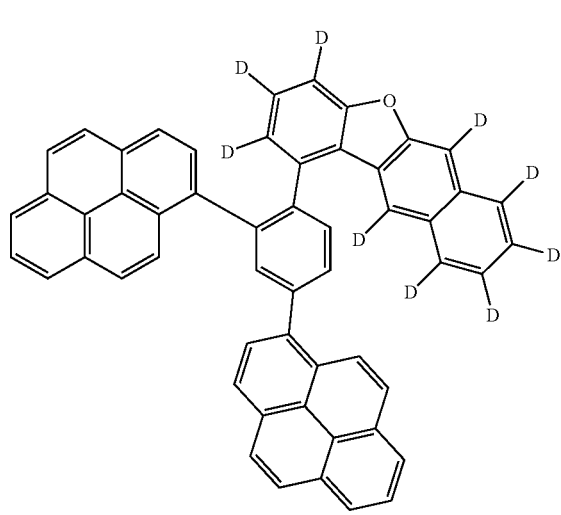
234
[Formula 126]
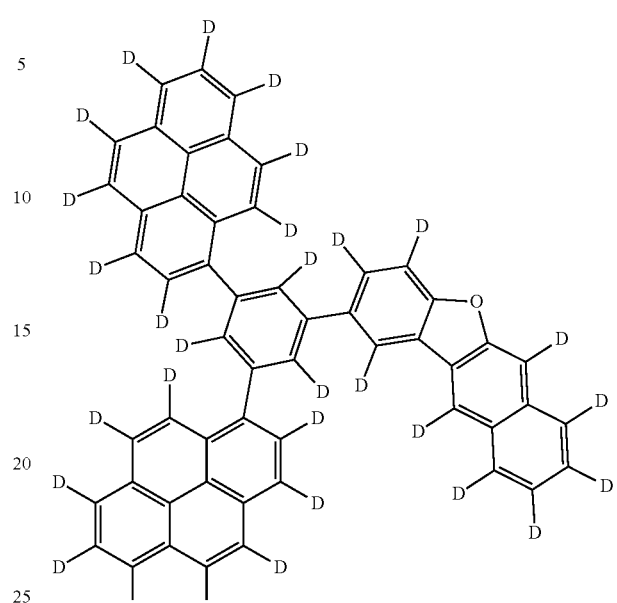
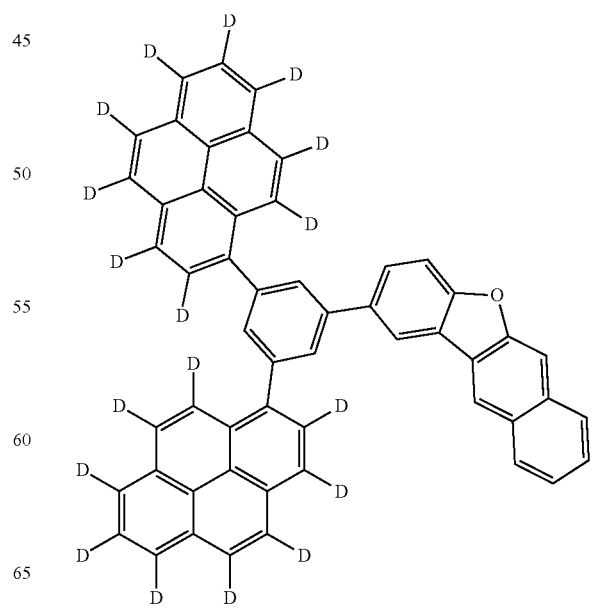

235
-continued
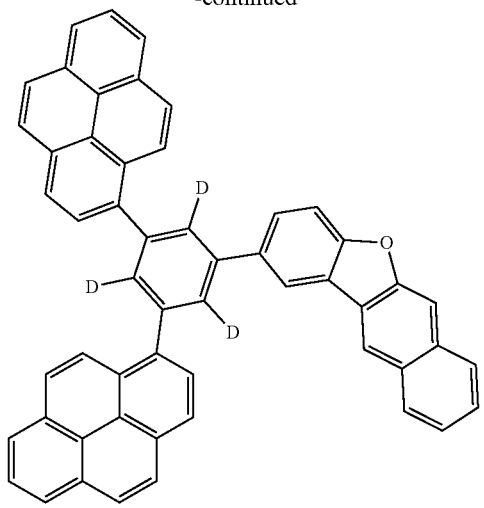
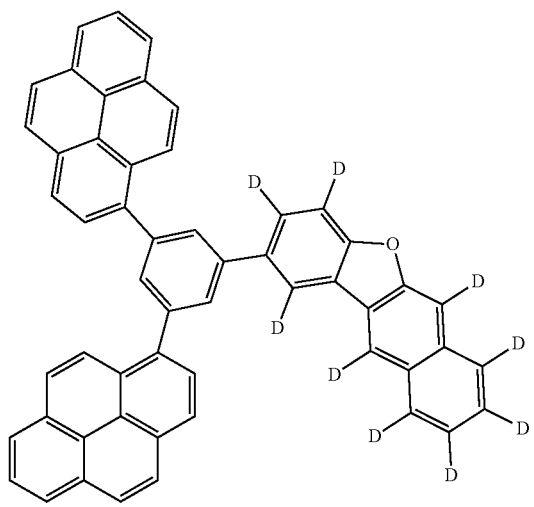
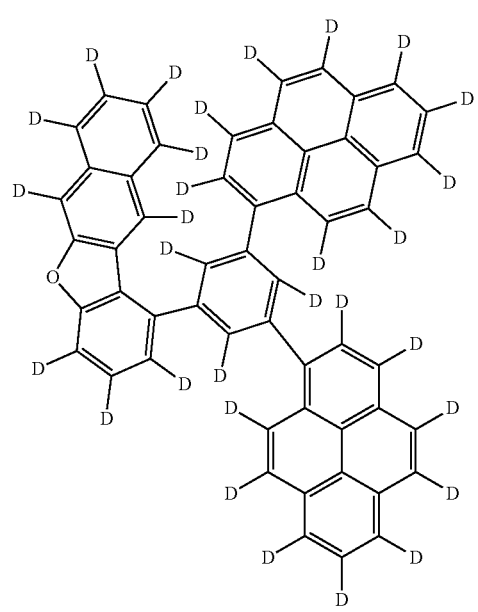
236
-continued
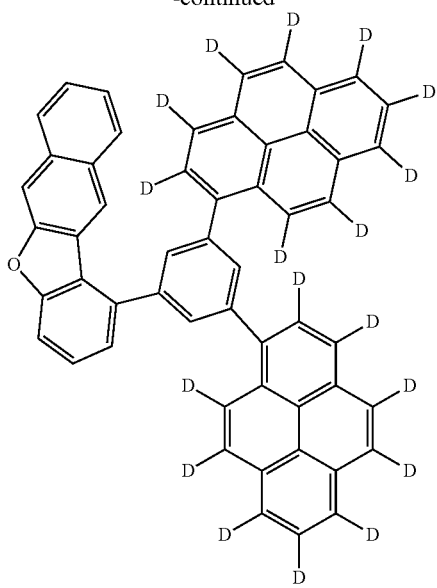
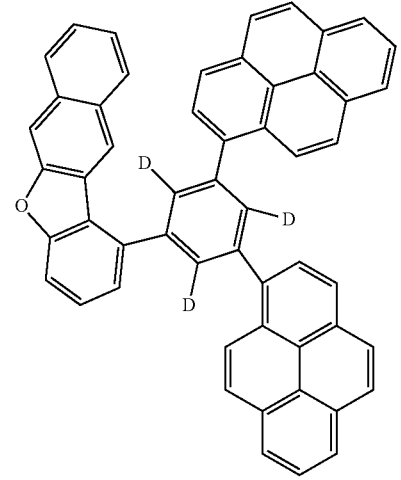
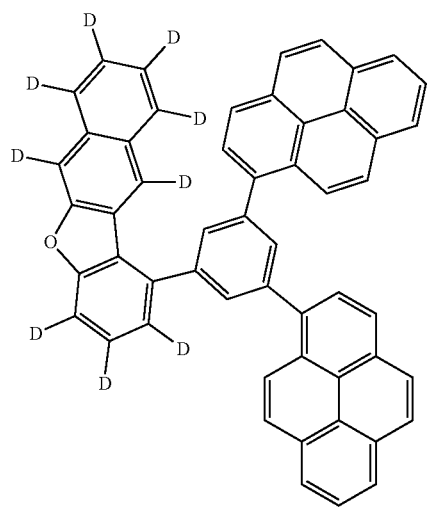

237
[Formula 127]
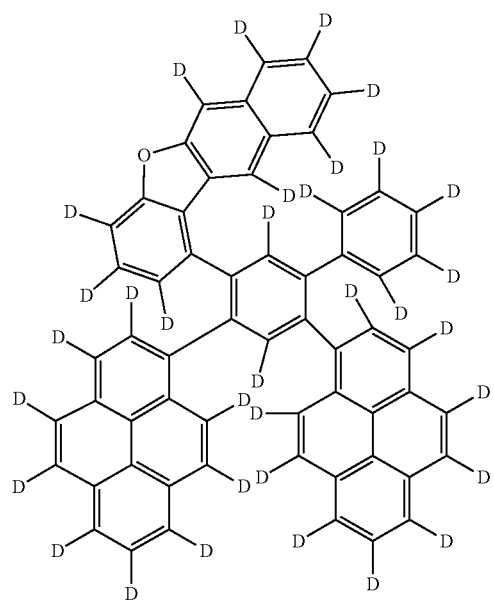
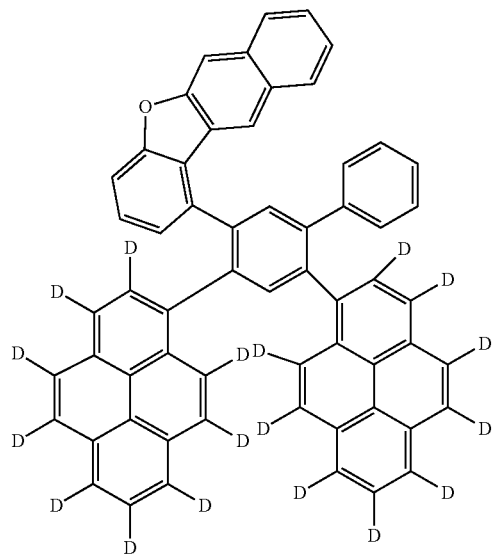
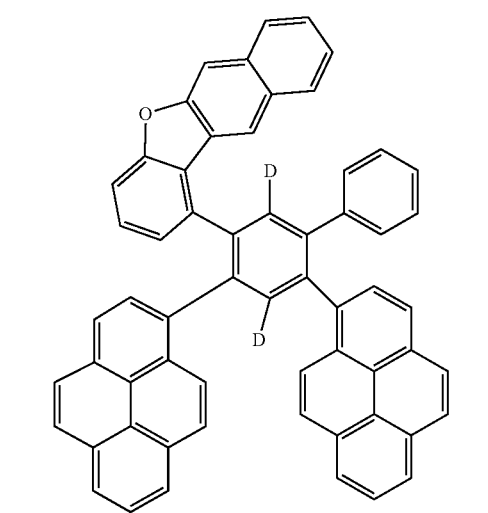
238
-continued
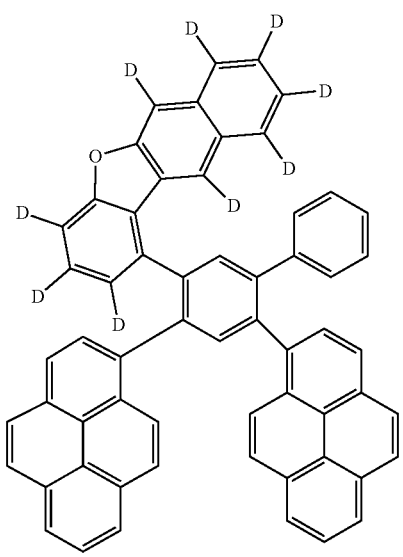
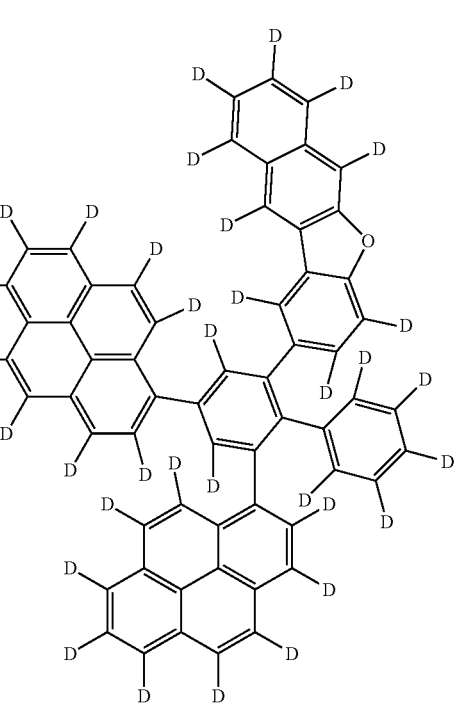

239
-continued
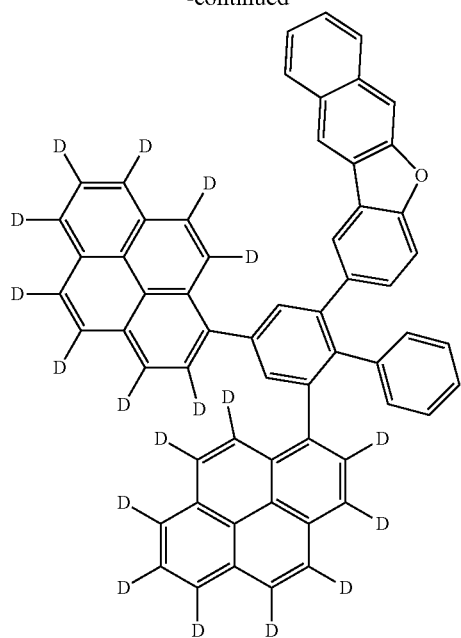
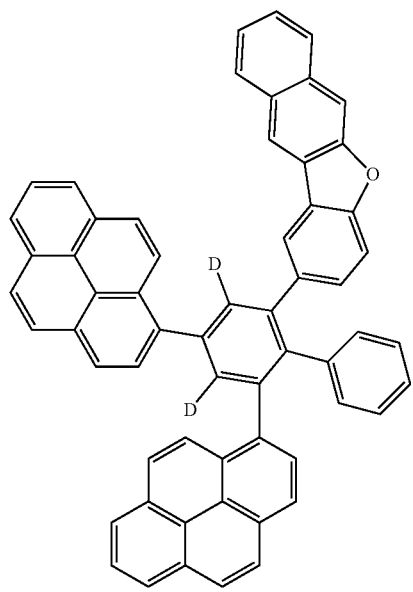
240
-continued
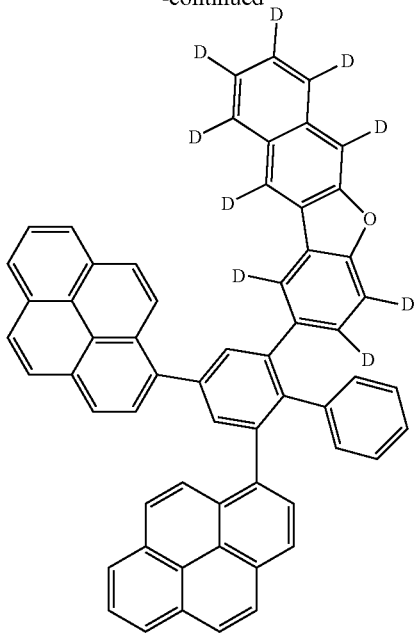
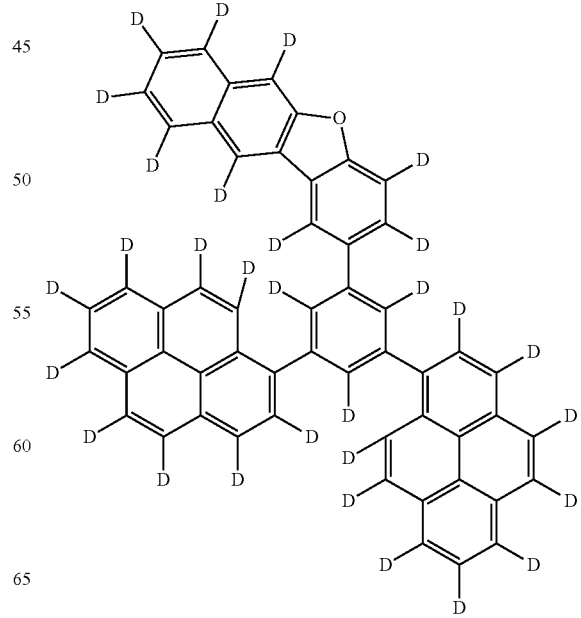

241
-continued
242
[Formula 128]
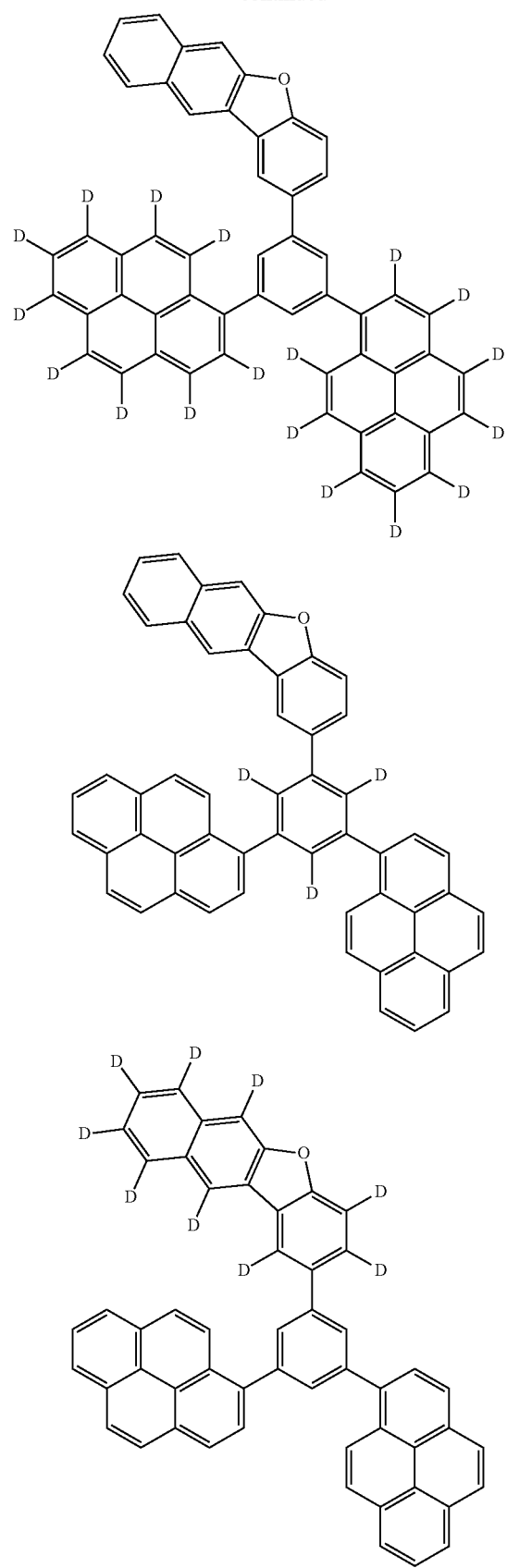
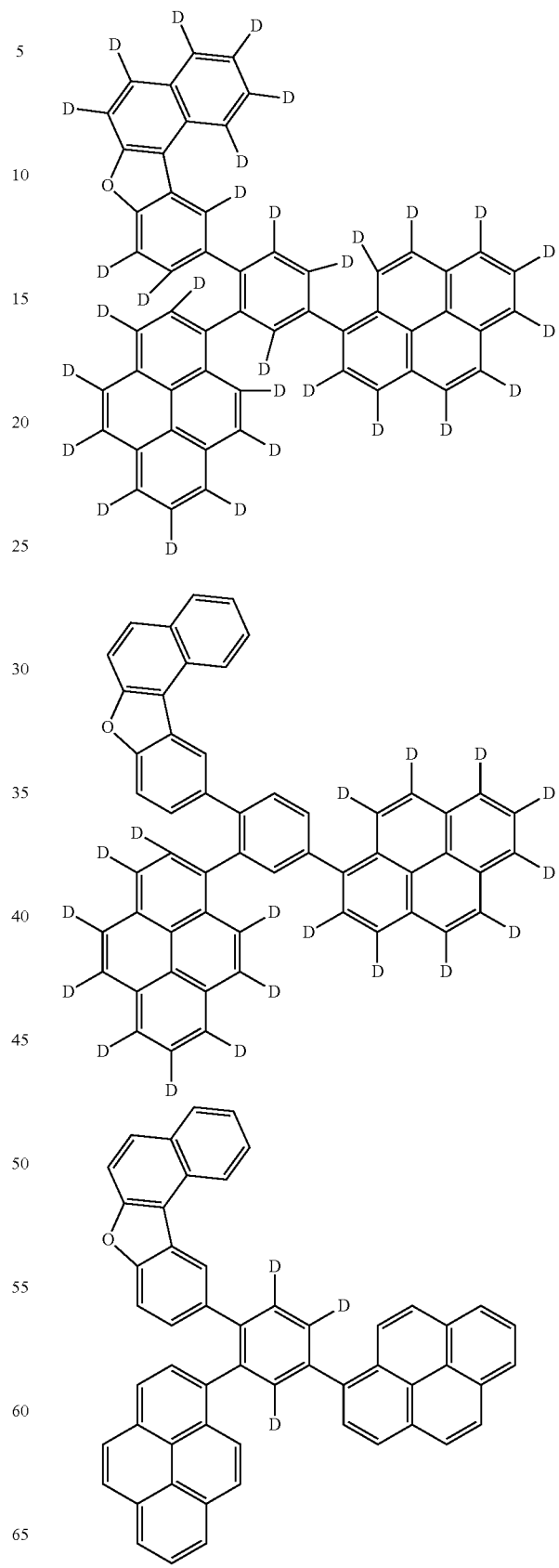

243
-continued
244
-continued
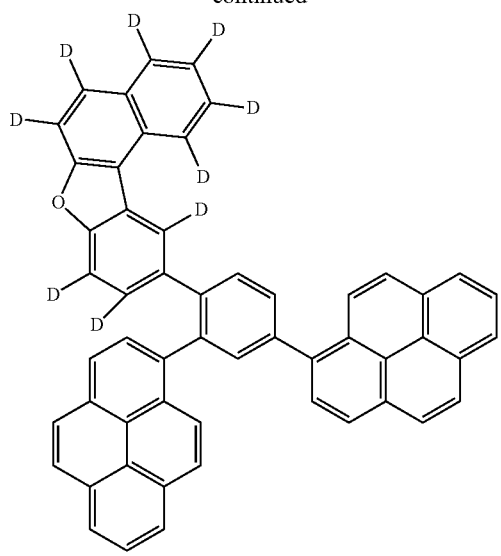
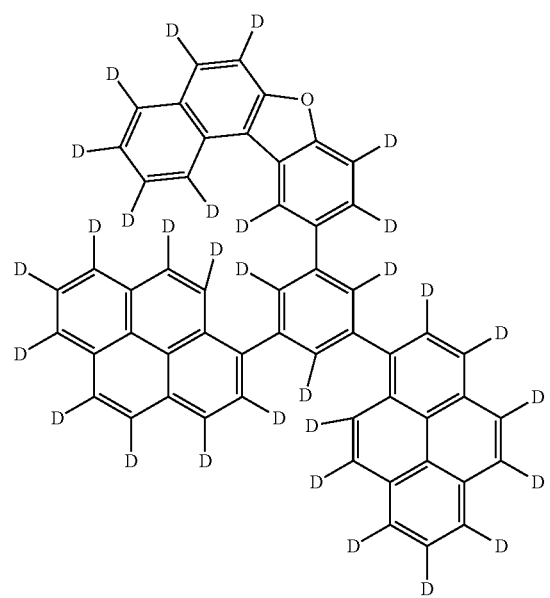
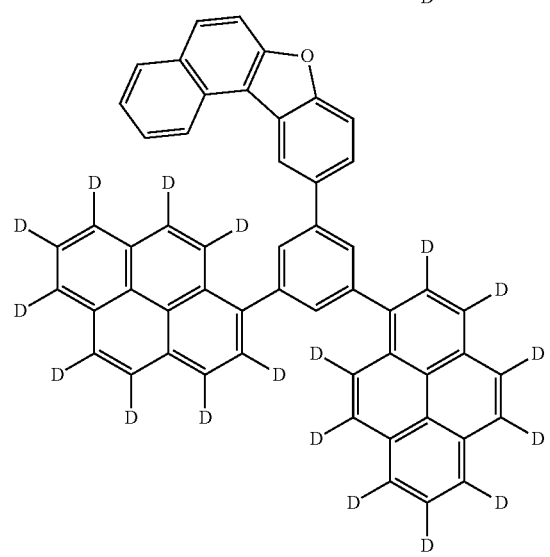
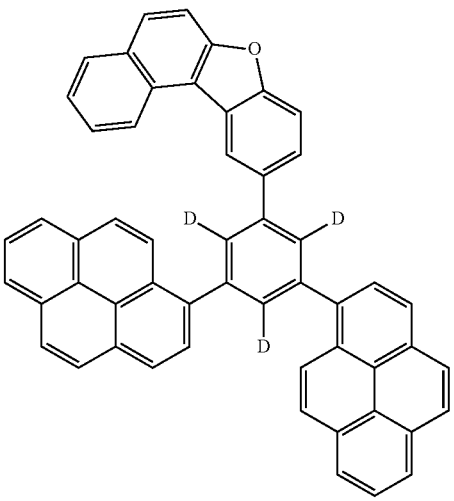
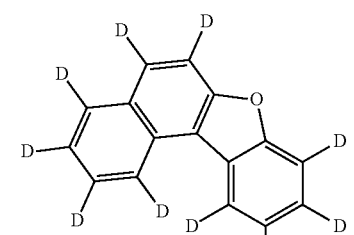
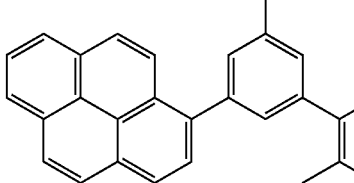

[Formula 129]
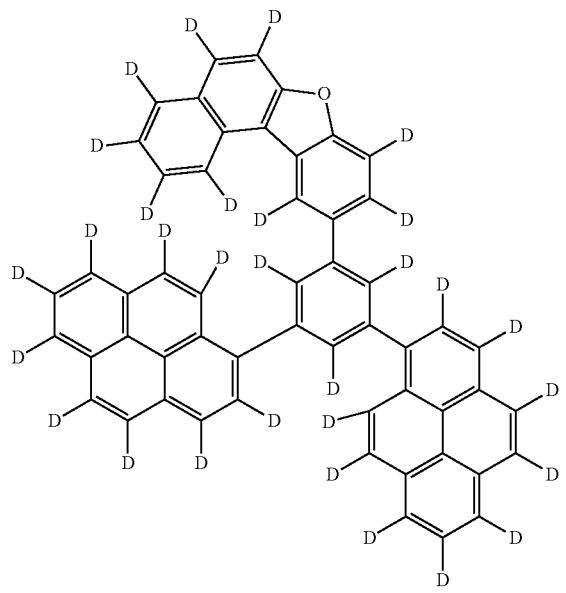
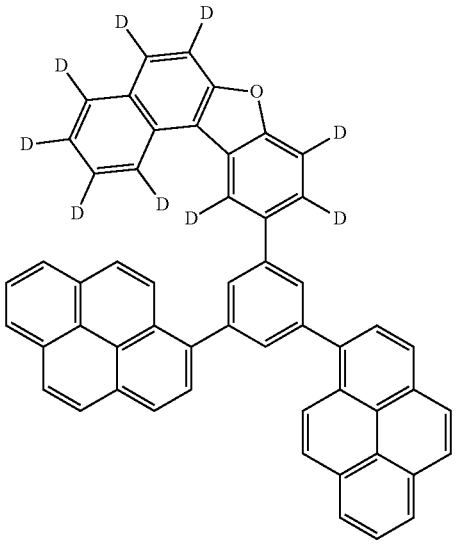 [SMILES: [2H]c1c(-c2cc(-c3ccc4ccc5cccc6ccc3c4c56)cc(-c3ccc4ccc5cccc6ccc3c4c56)c2)c([2H])c2c(oc3c([2H])c([2H])c4c([2H])c([2H])c([2H])c([2H])c4c32)c1[2H]]
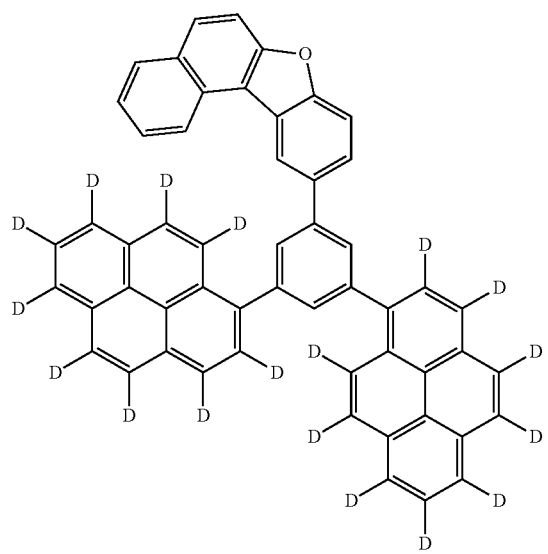
[Formula 130]
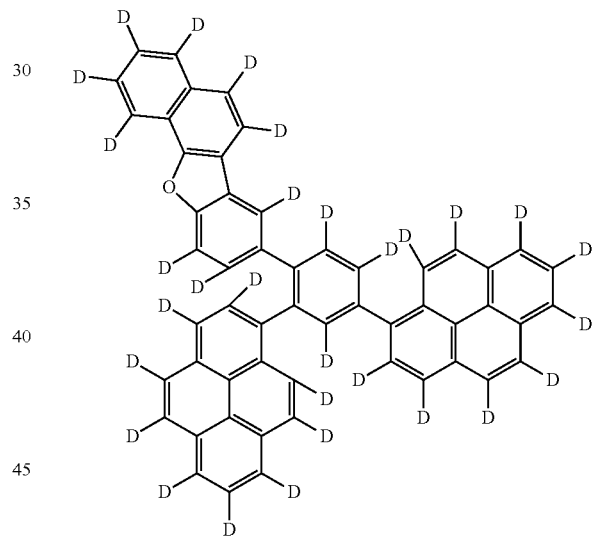
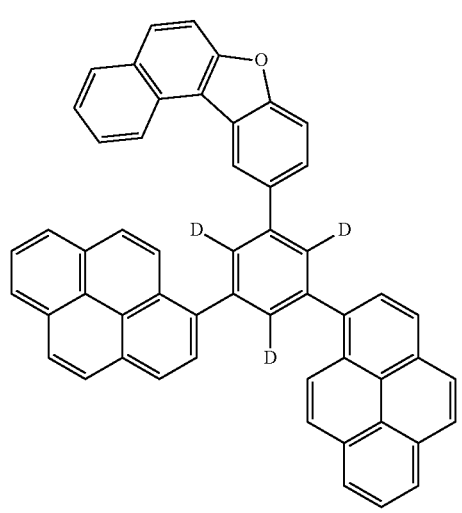
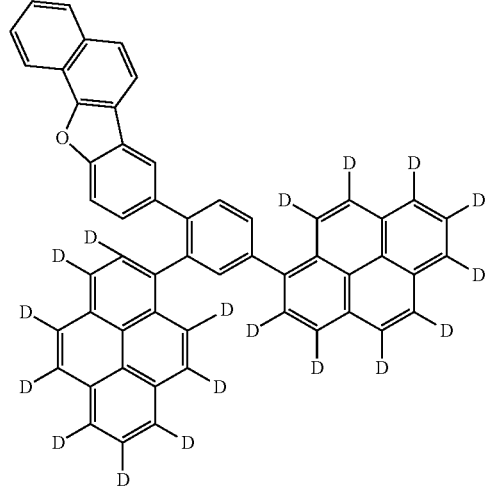

247
-continued
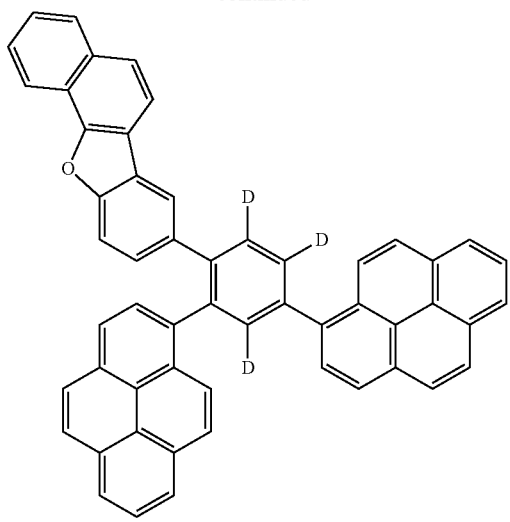
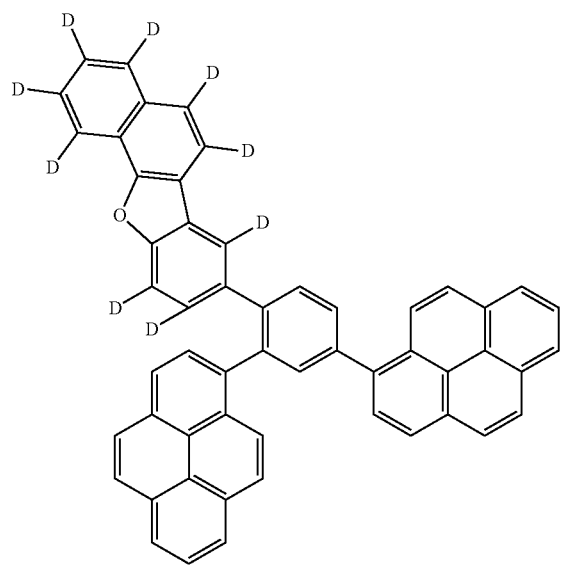
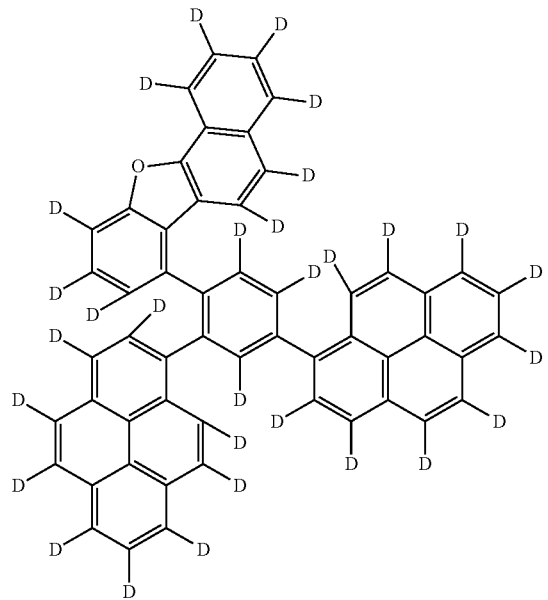
248
-continued
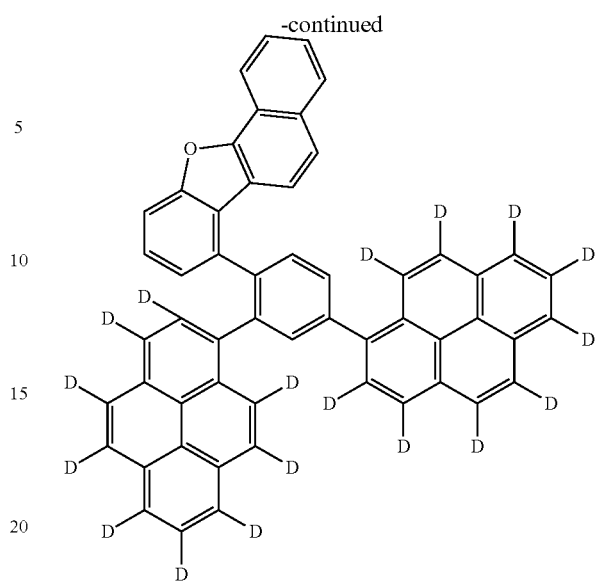
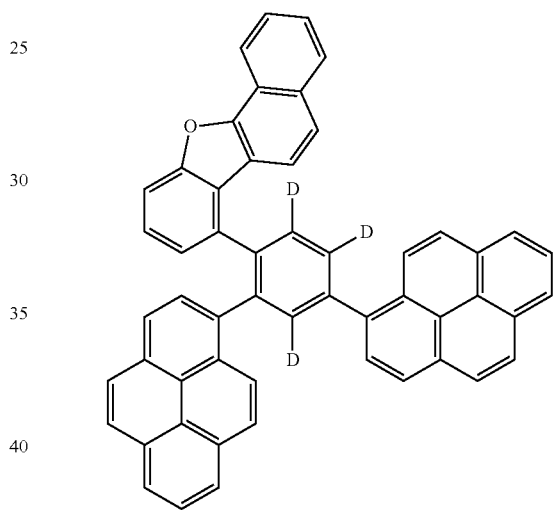
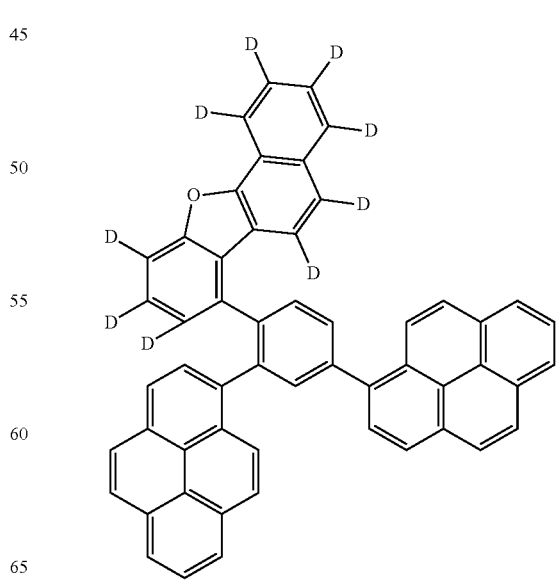

[Formula 131]
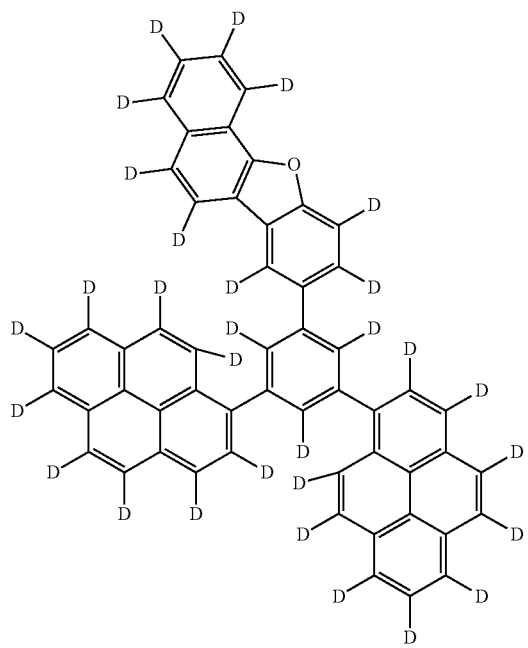
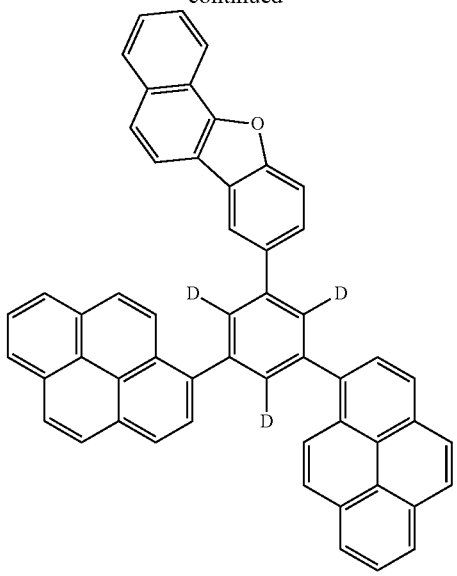
-continued
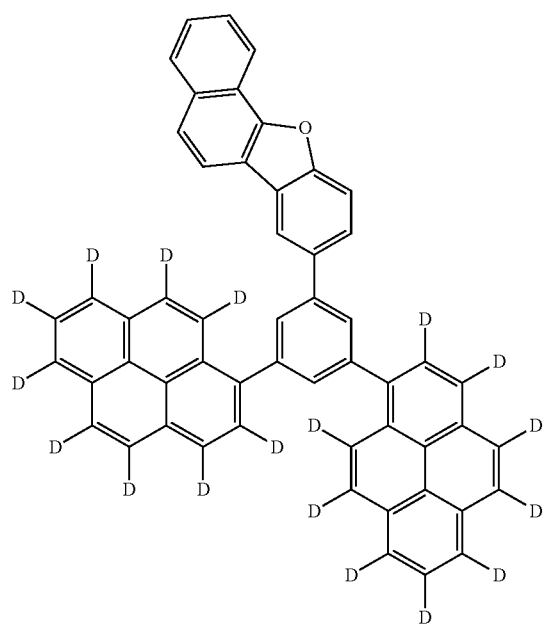
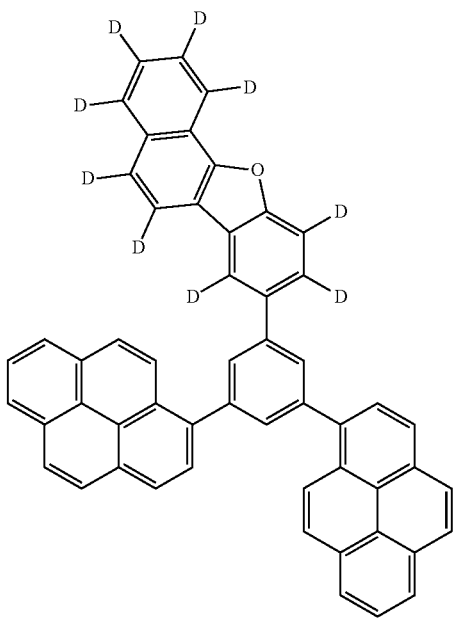

251
-continued
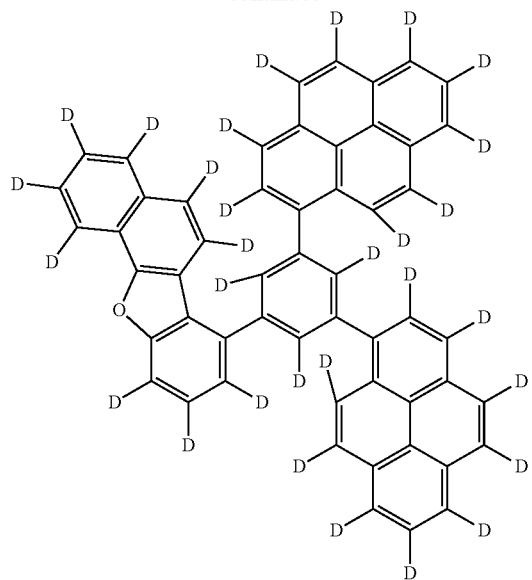
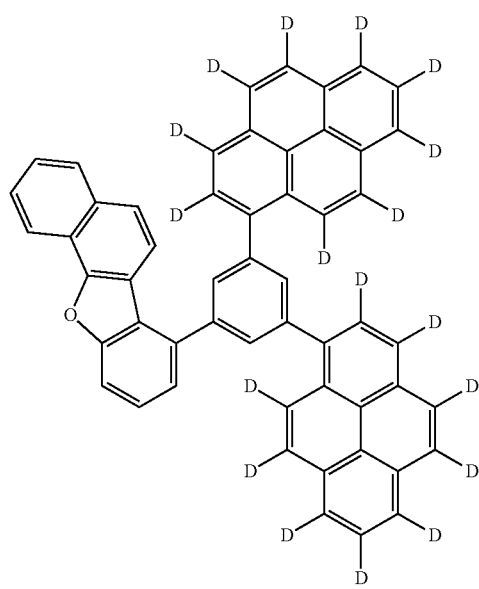
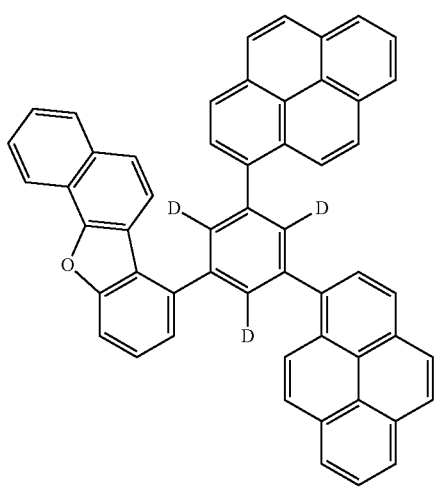
252
-continued
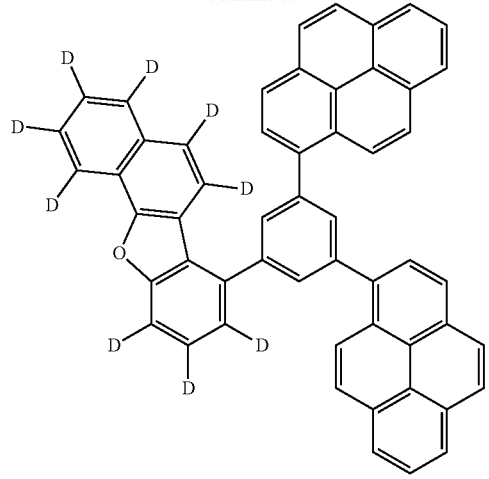
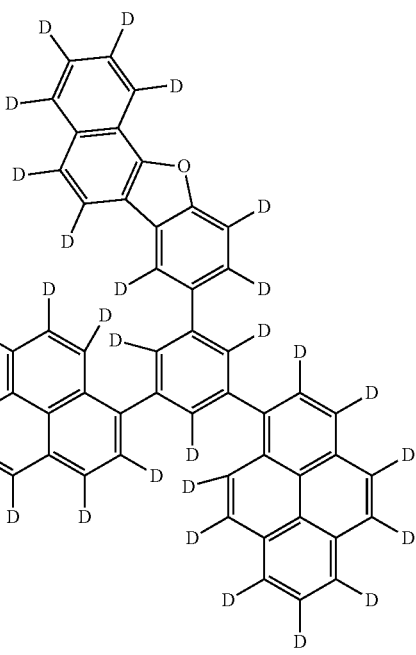

253
-continued
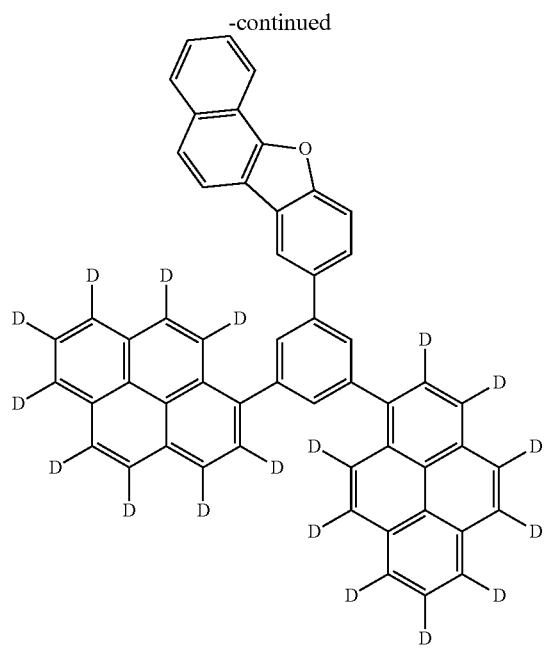
254
-continued
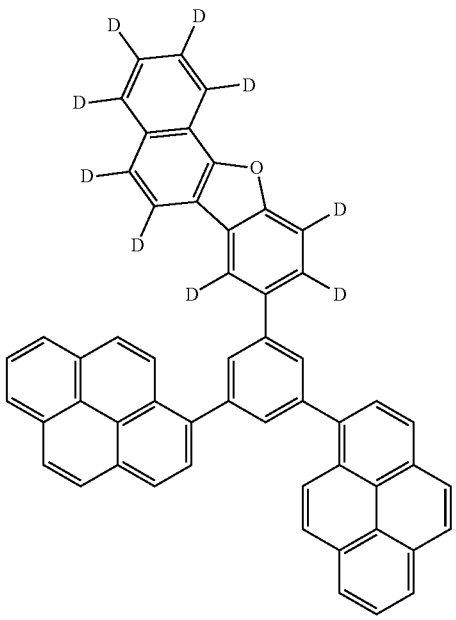
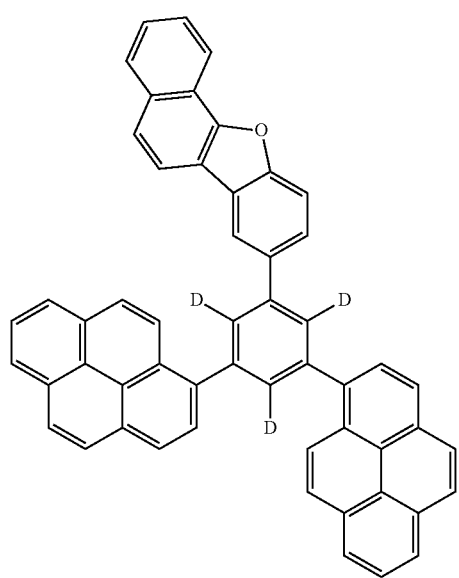
[Formula 132]
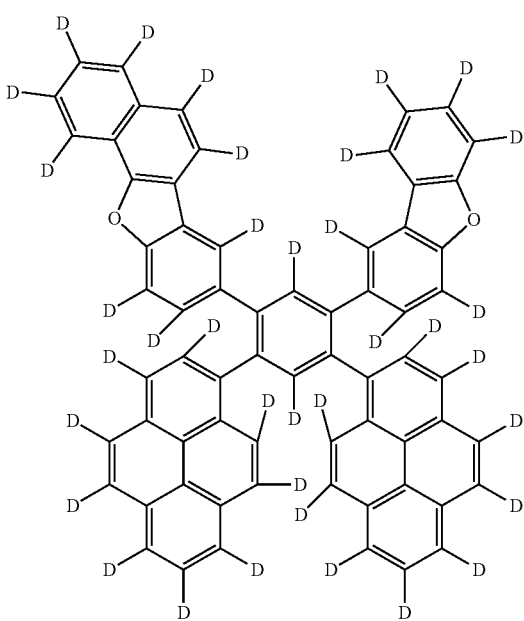

255
-continued
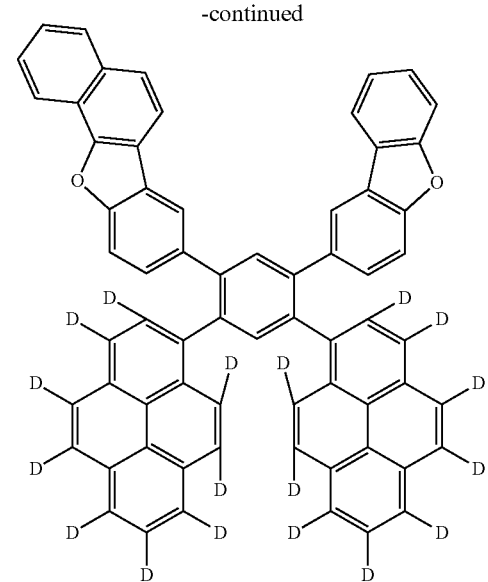
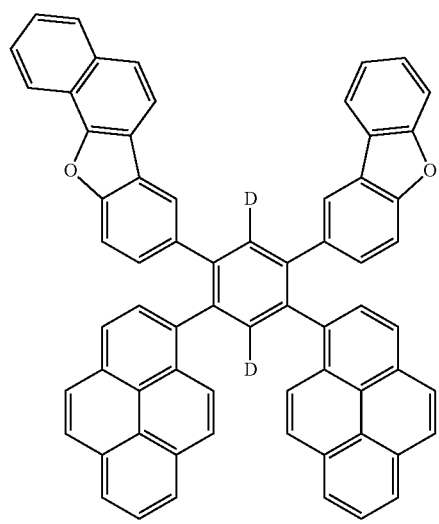
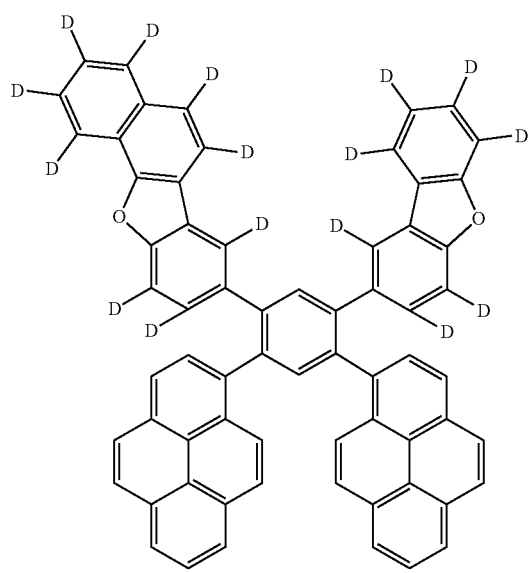 [SMILES: [2H]c1c([2H])c([2H])c2c(oc3c([2H])c([2H])c(-c4cc(-c5c([2H])c([2H])c6oc7c8c([2H])c([2H])c([2H])c([2H])c8c([2H])c([2H])c7c6c5[2H])c(-c5ccc6ccc7cccc8ccc5c6c78)cc4-c4ccc5ccc6cccc7ccc4c5c67)c([2H])c32)c1[2H]]
256
[Formula 133]
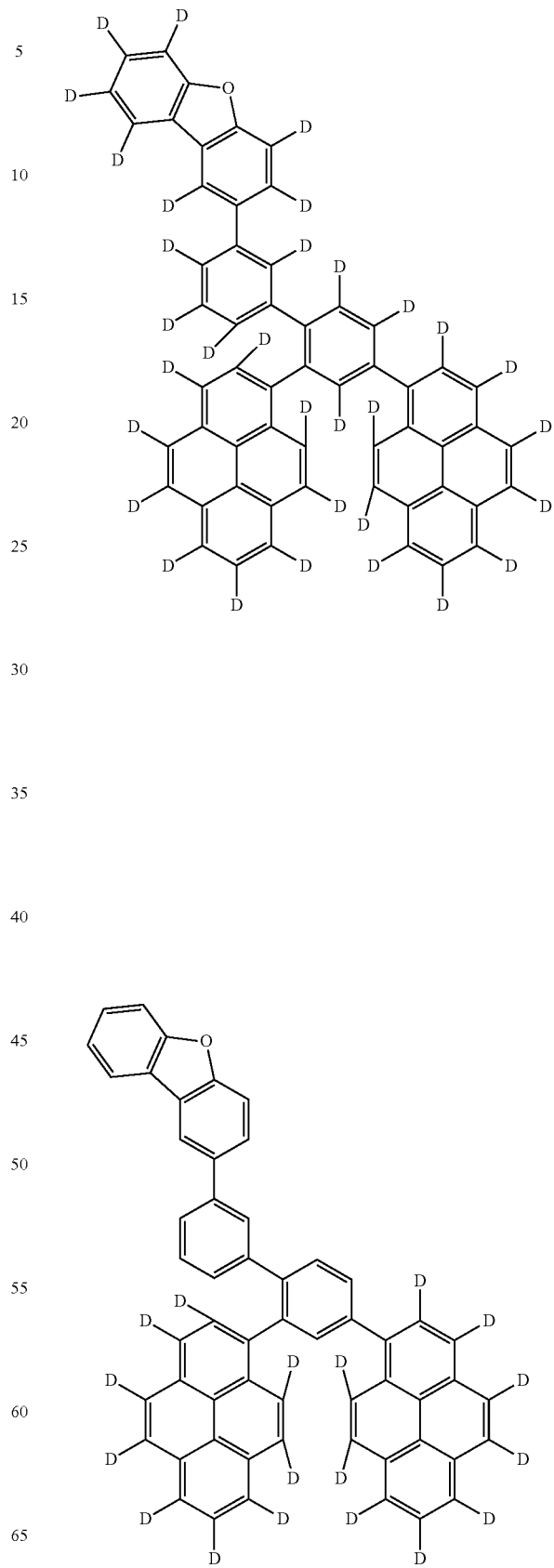

257
-continued
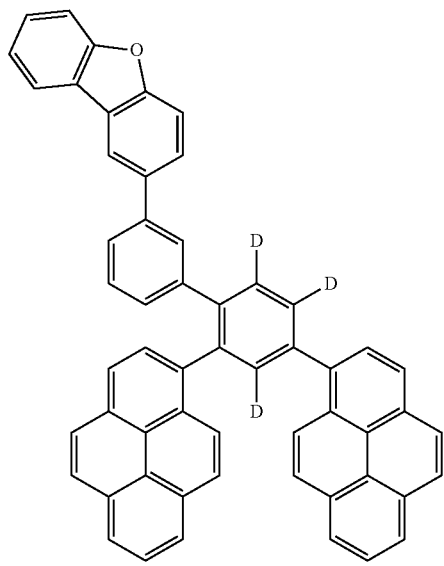
258
-continued
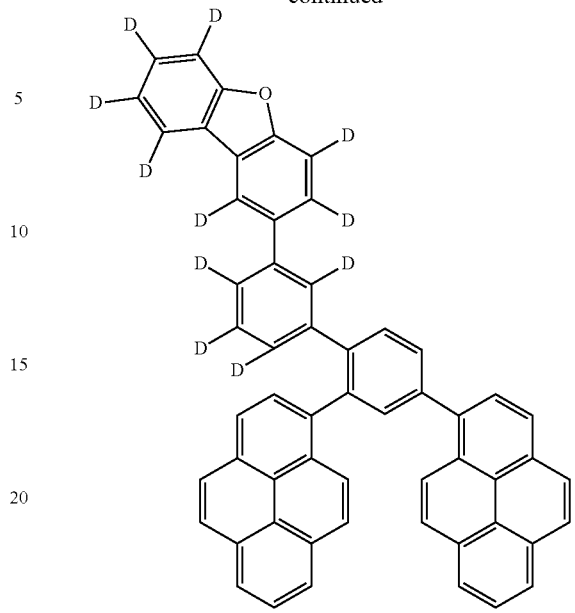
[Formula 134]
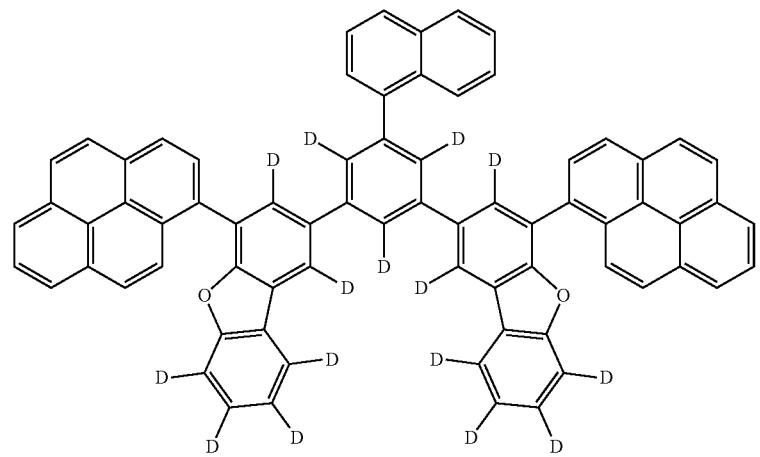
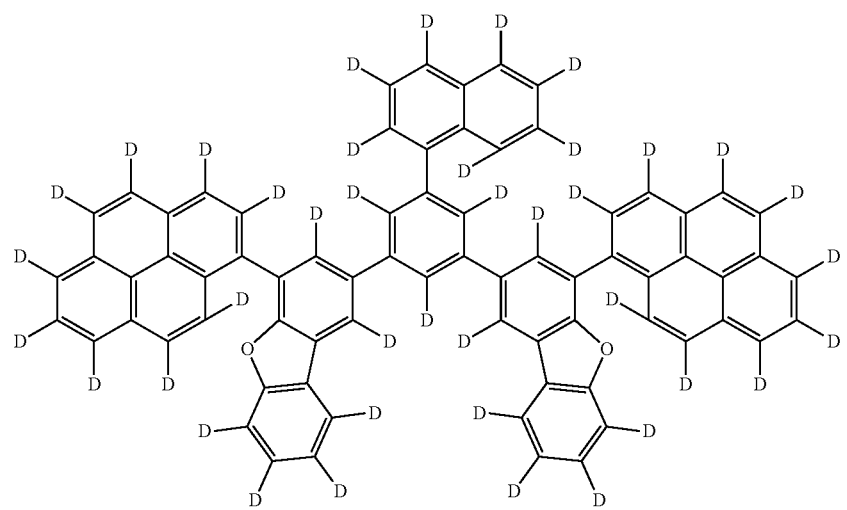

-continued
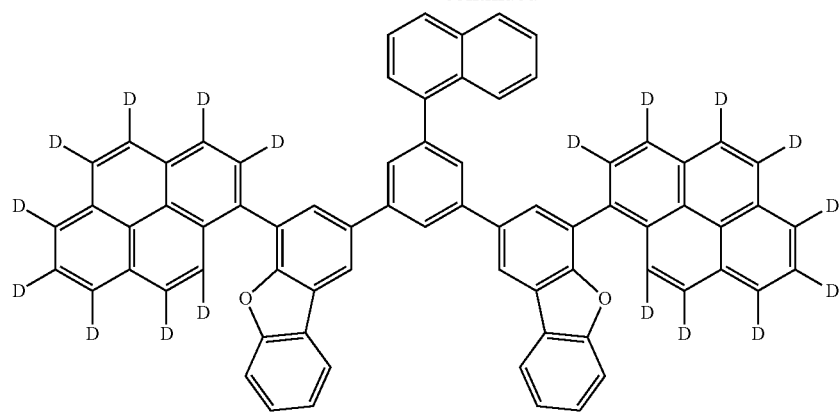
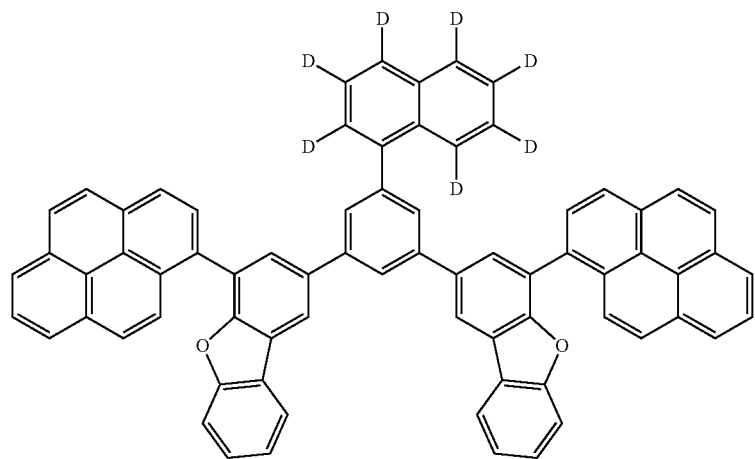
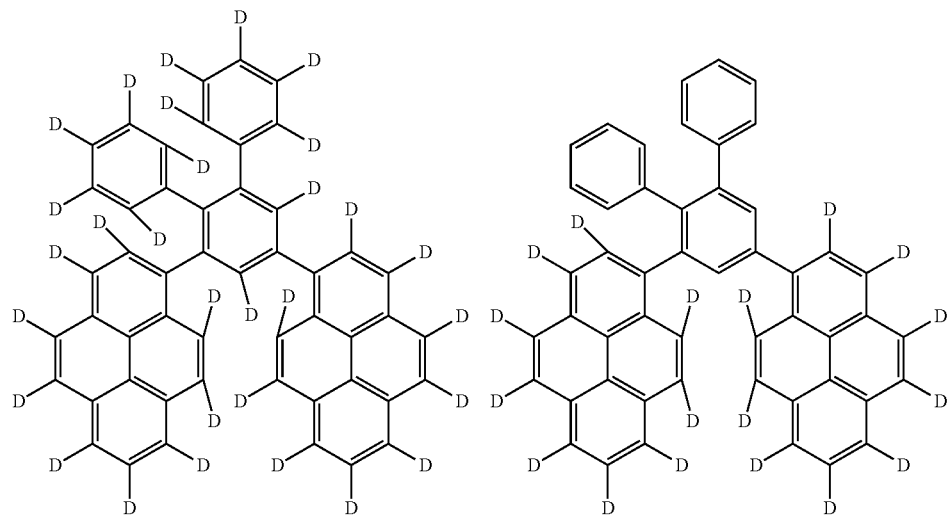

-continued
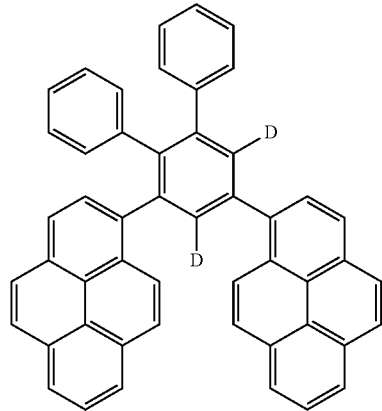
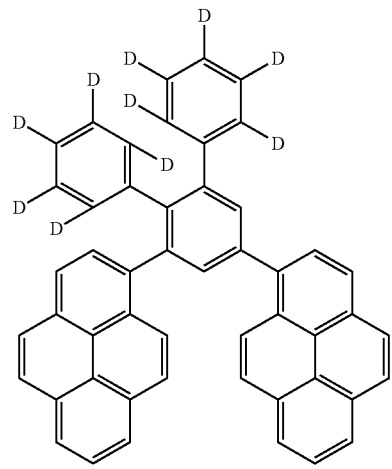
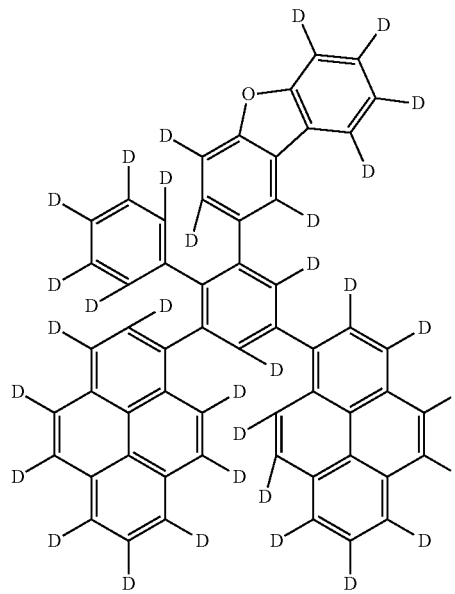
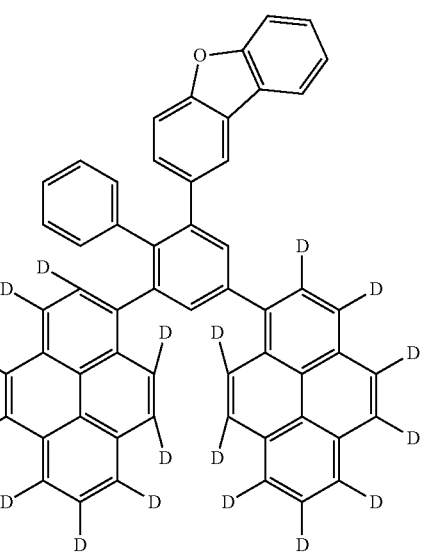
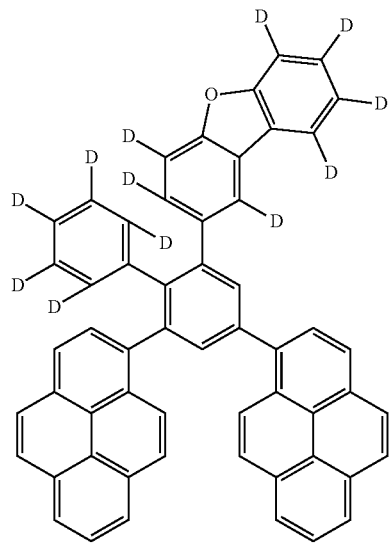

[Formula 135]
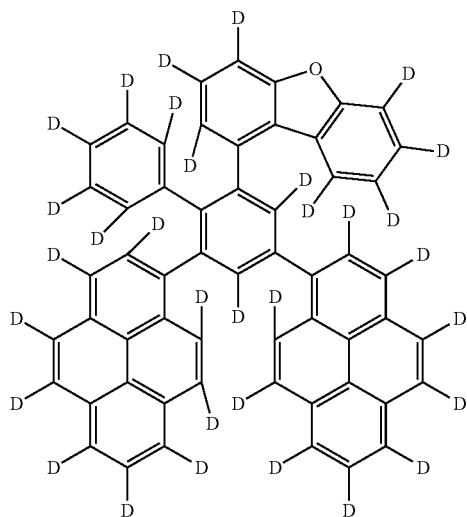
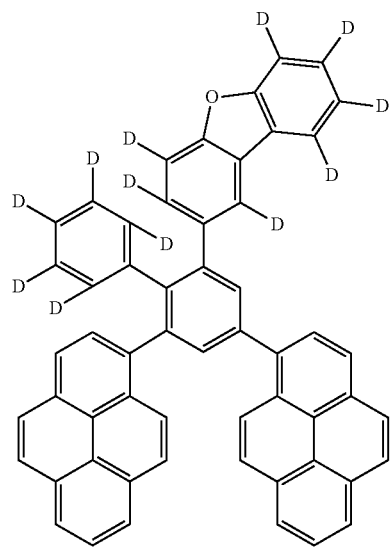 [SMILES: [2H]c1c([2H])c([2H])c(-c2c(-c3c([2H])c([2H])c4oc5c([2H])c([2H])c([2H])c([2H])c5c4c3[2H])cc(-c3ccc4ccc5cccc6ccc3c4c56)cc2-c2ccc3ccc4cccc5ccc2c3c45)c([2H])c1[2H]]
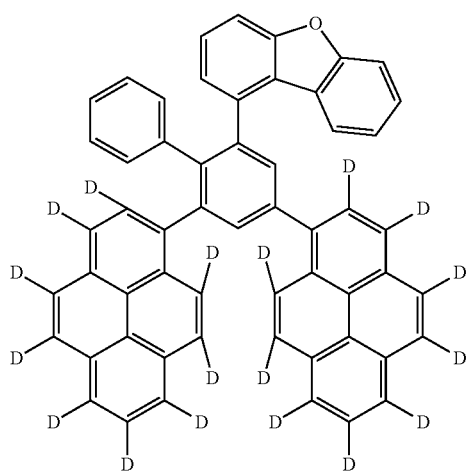
[Formula 136]
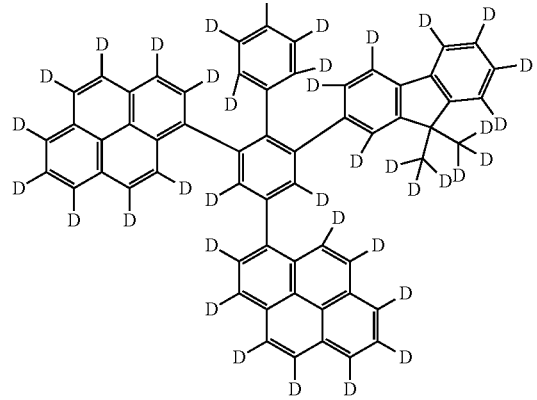
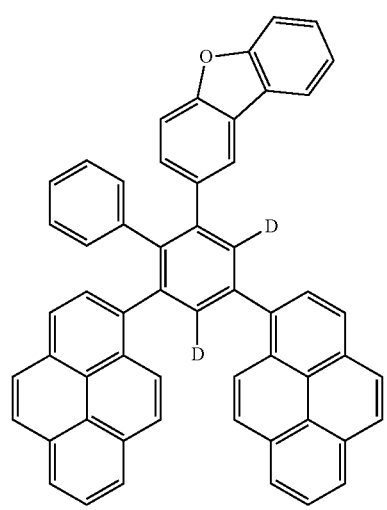
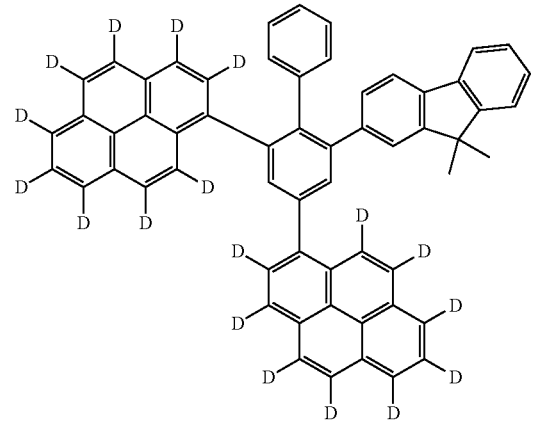

265
-continued
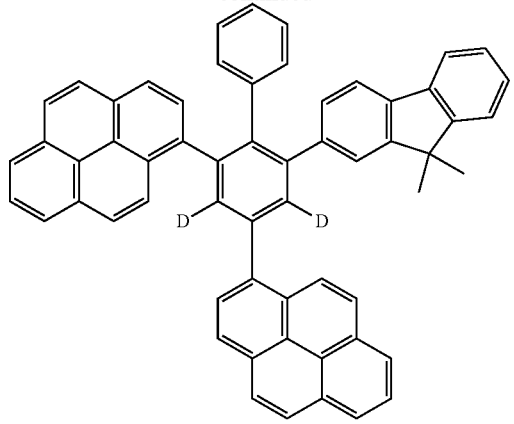
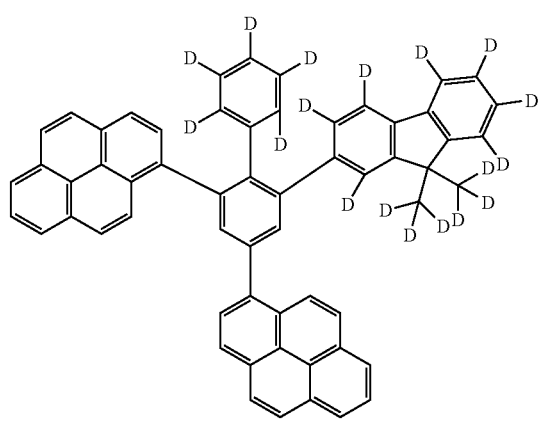
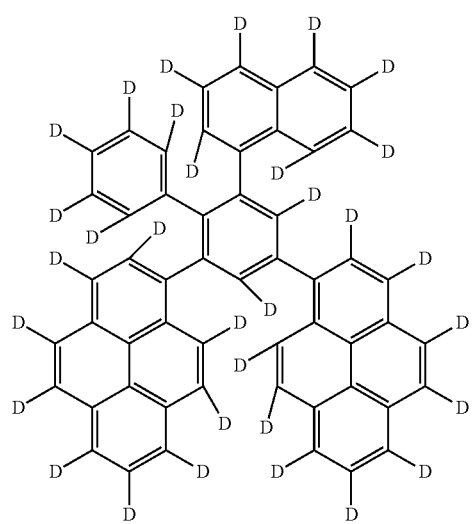
266
-continued
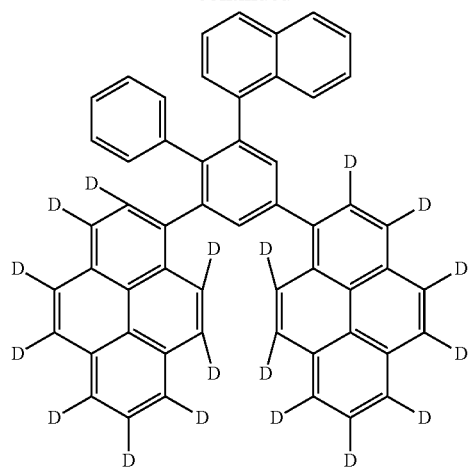
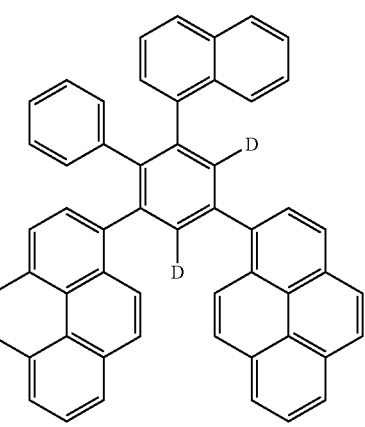
[Formula 137]
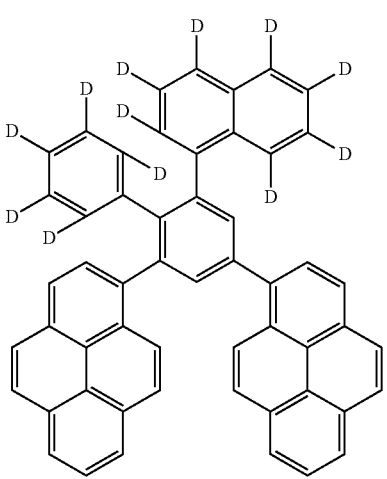

267
-continued
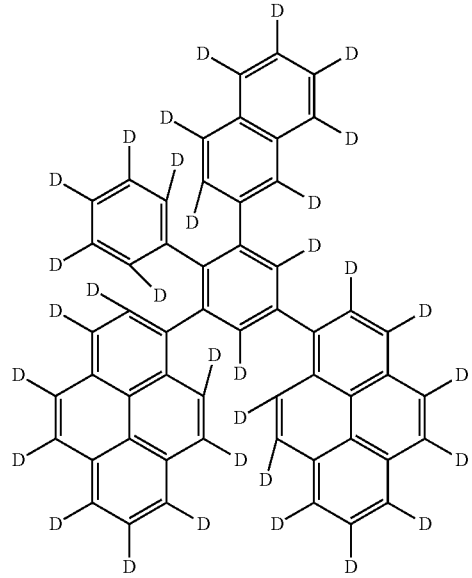
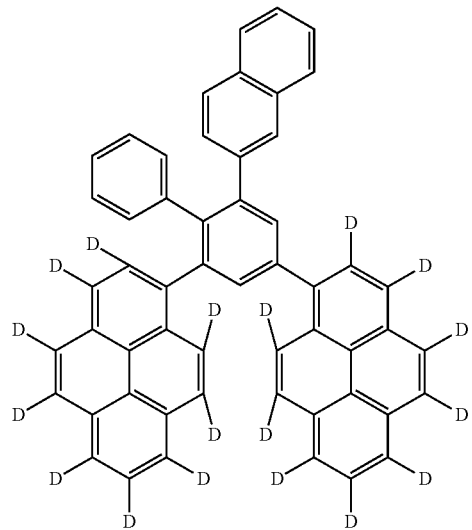
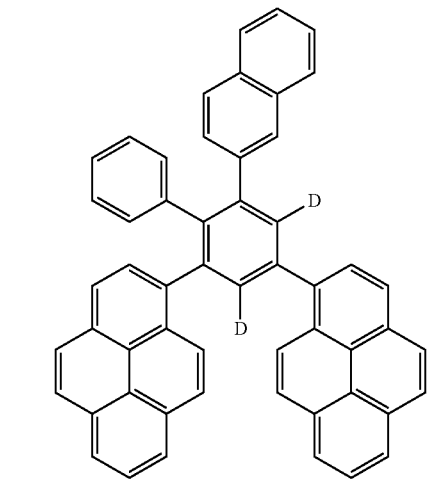
268
-continued
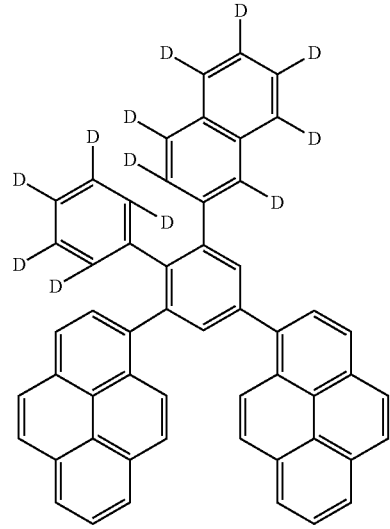
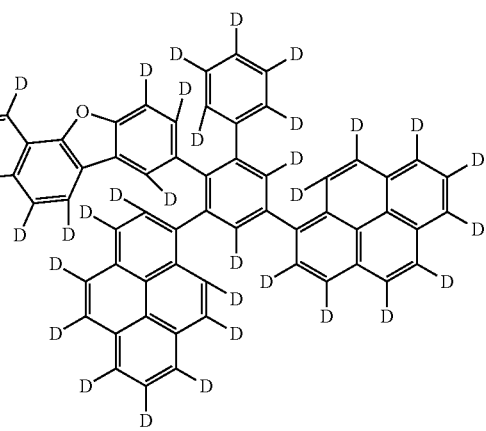
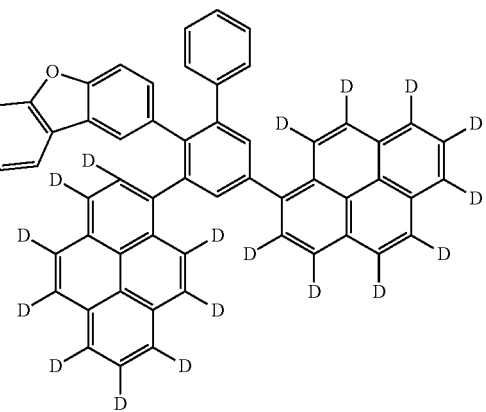

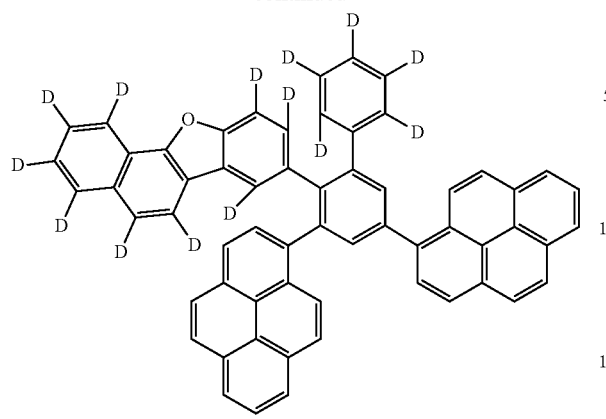
[Formula 138]
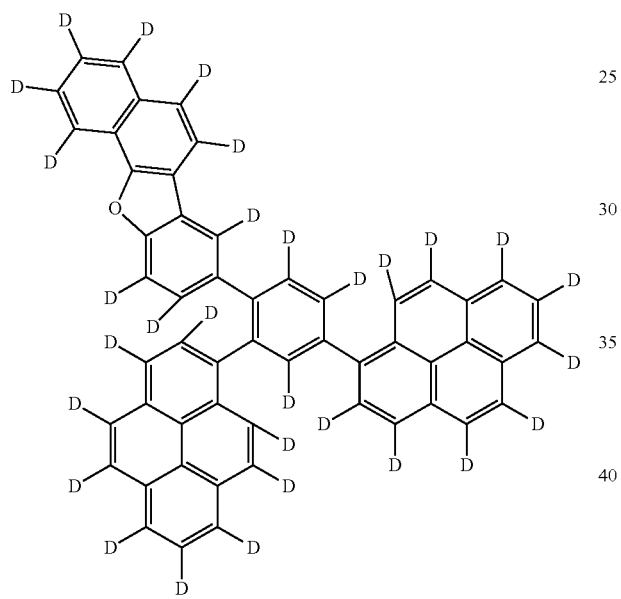
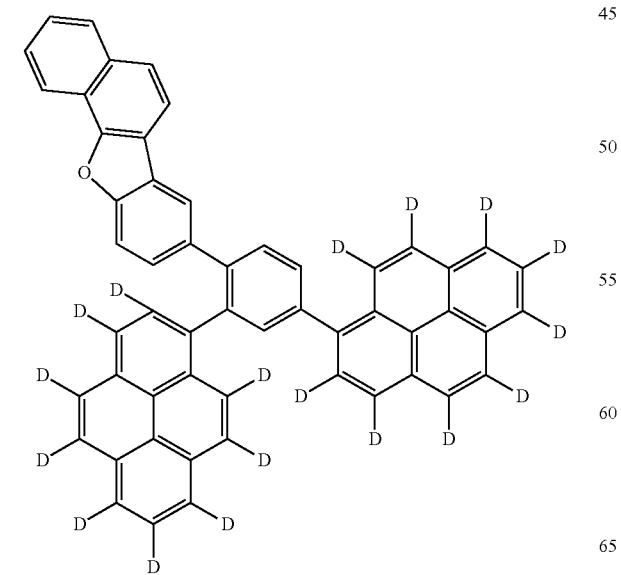
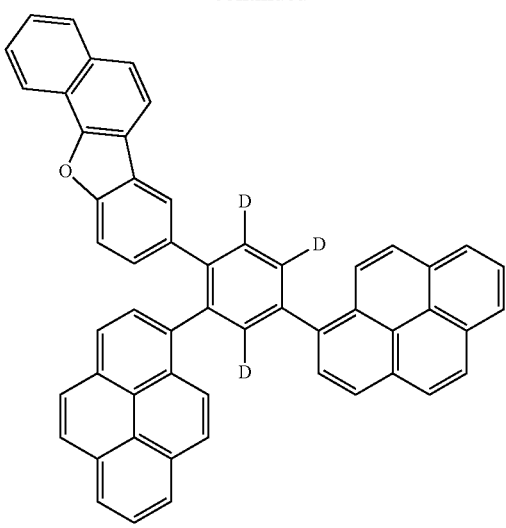
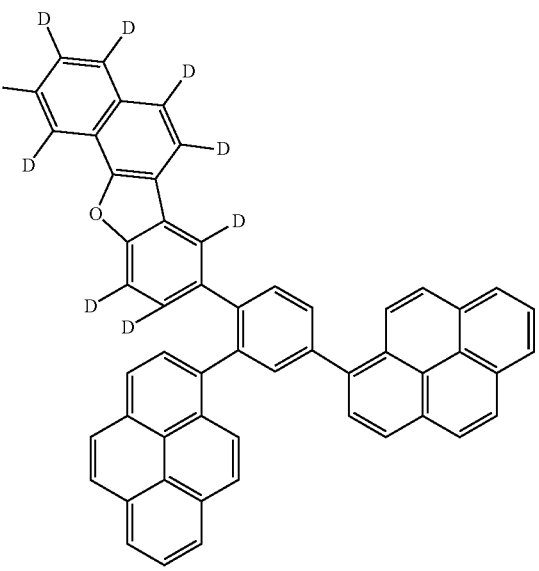

[Formula 139]
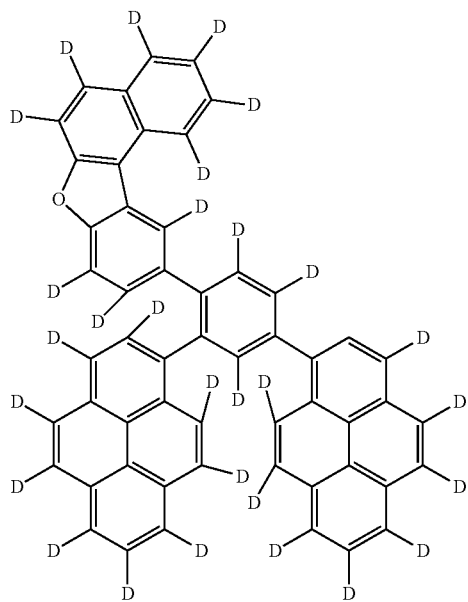
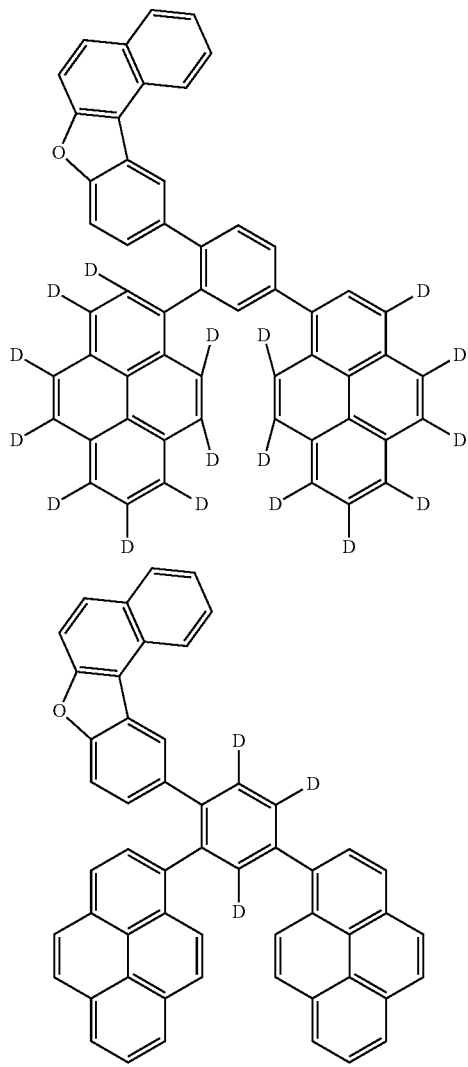
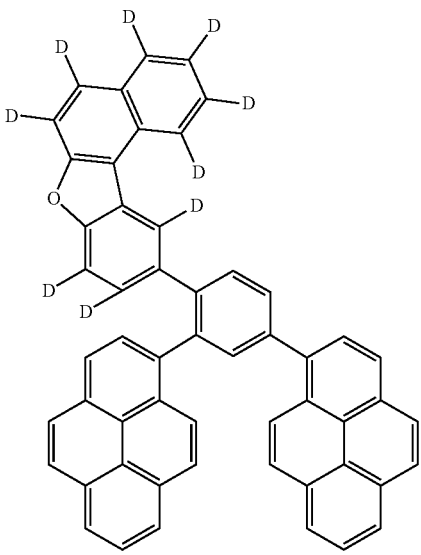
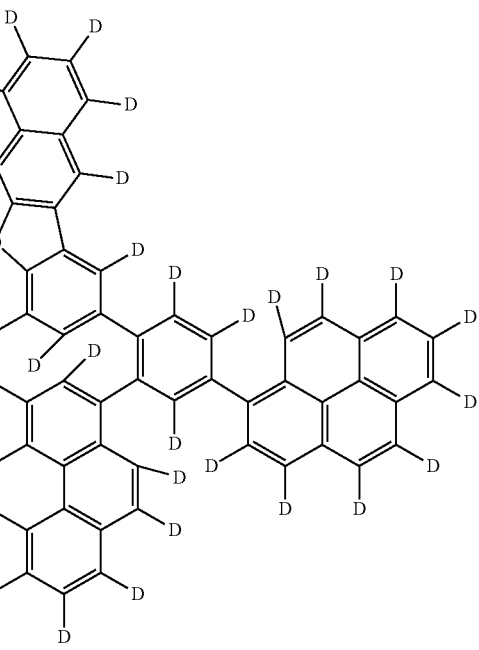

273
-continued
274
-continued
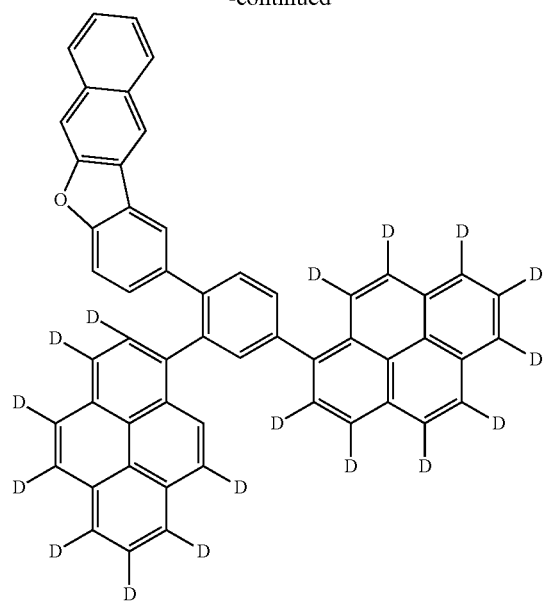
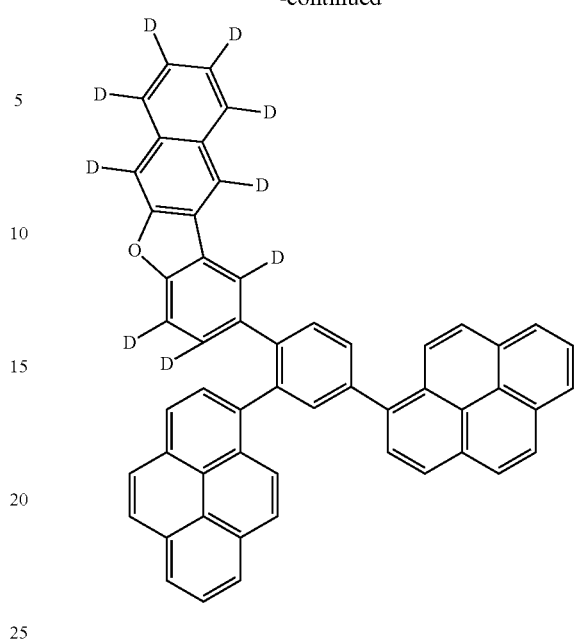
[Formula 140]
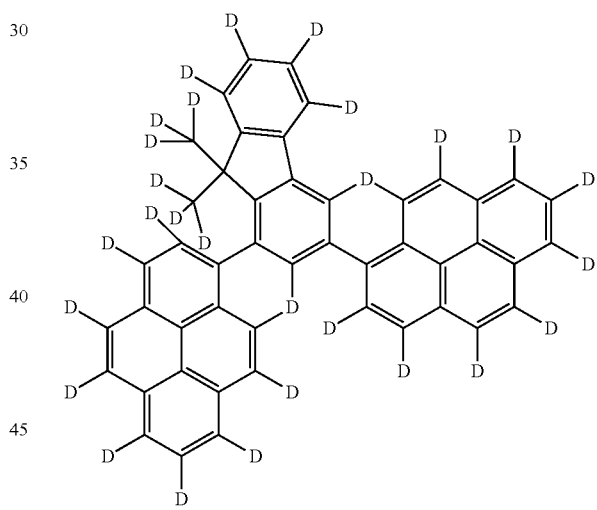
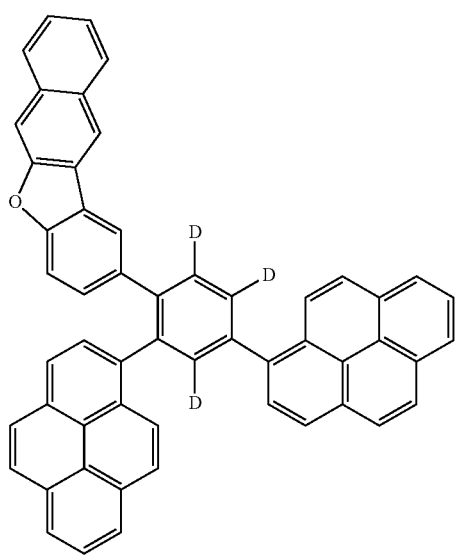

275
-continued
276
-continued
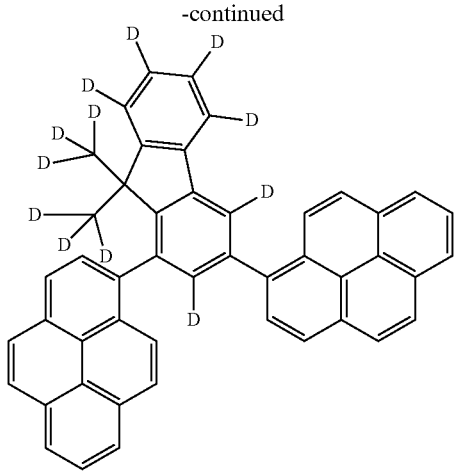
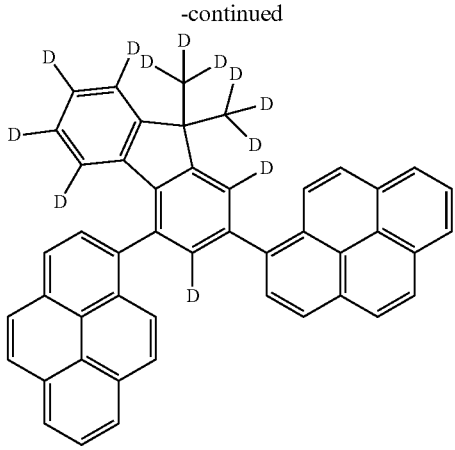
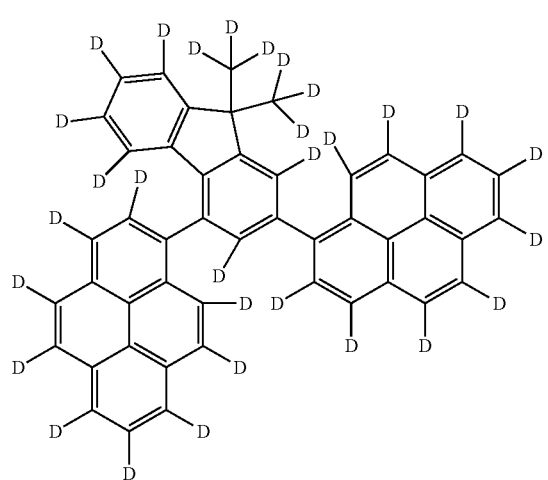
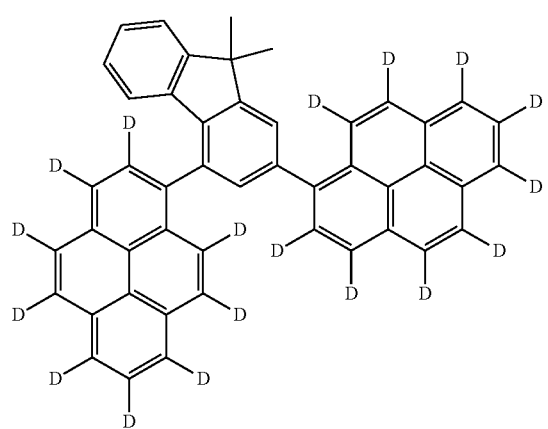
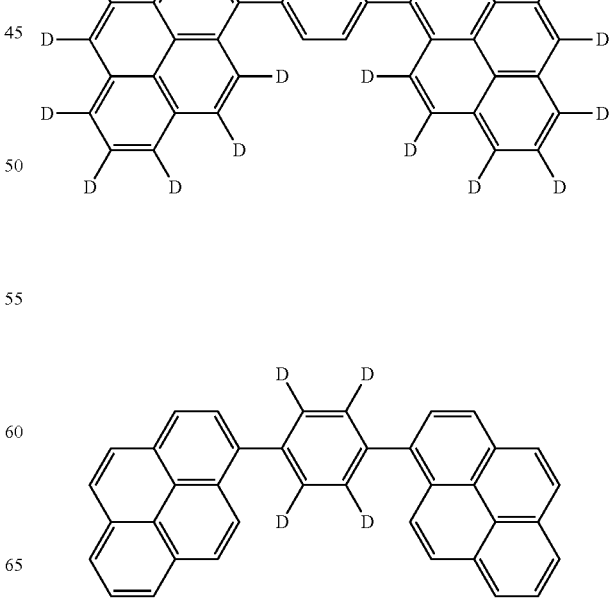

-continued
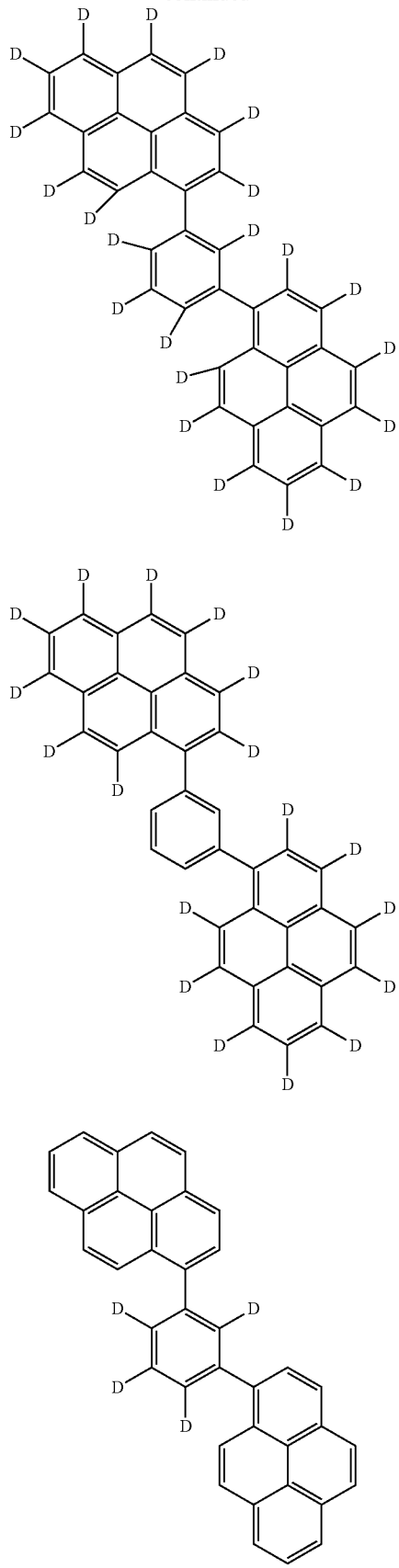
[Formula 141]
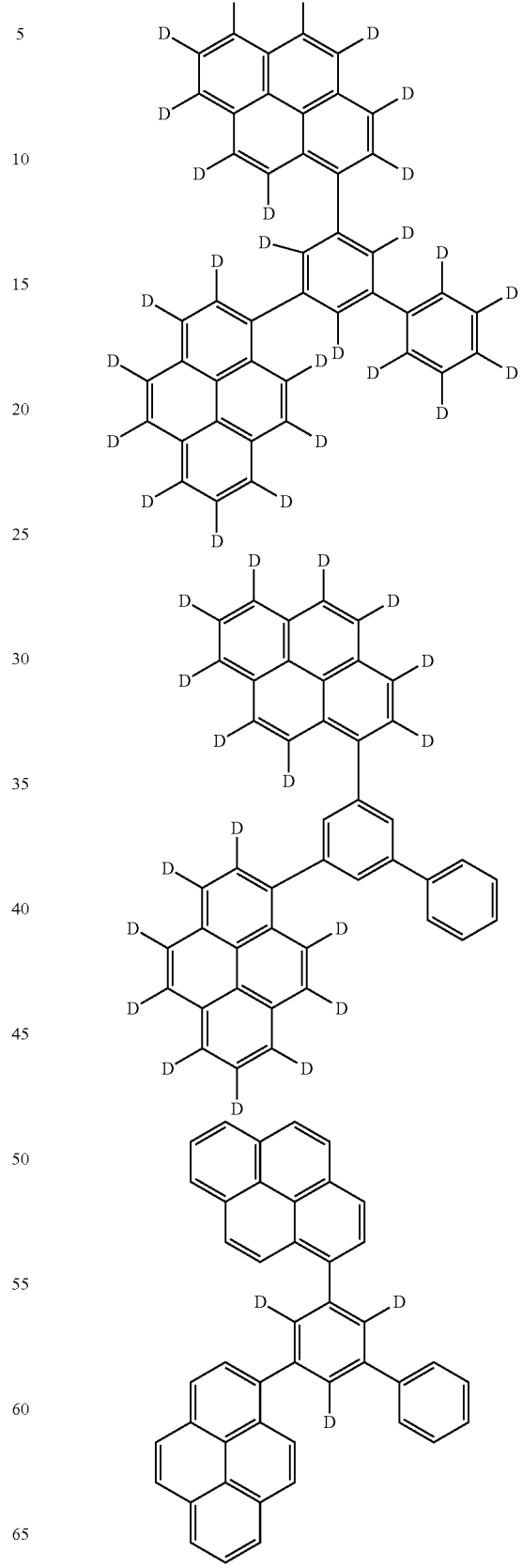

279
-continued
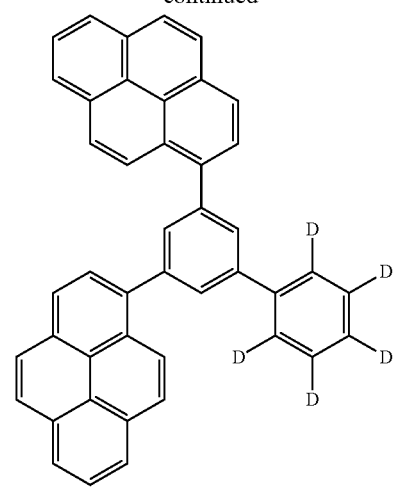
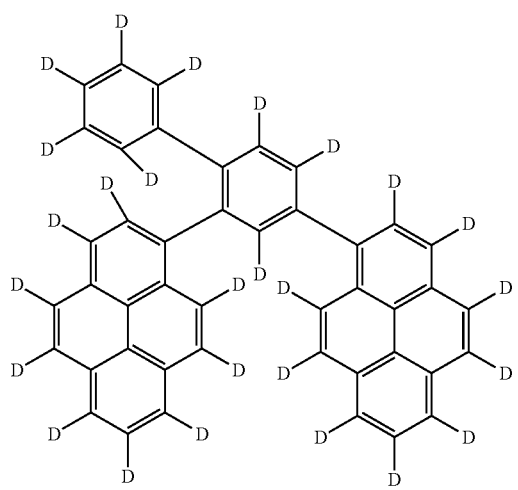
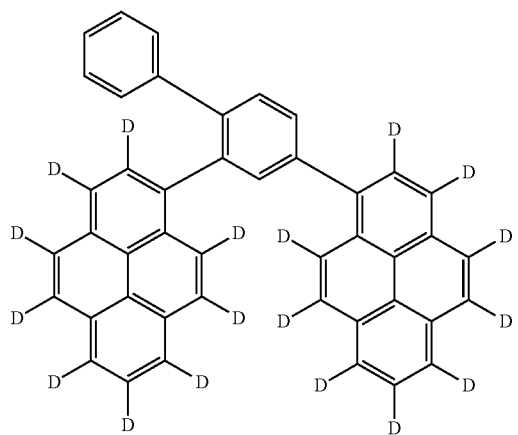
280
-continued
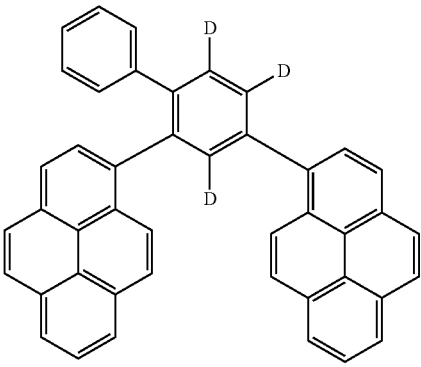
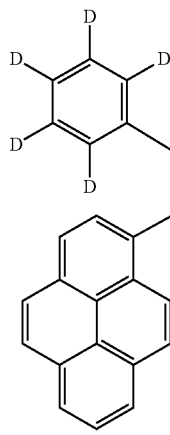
[Formula 142]
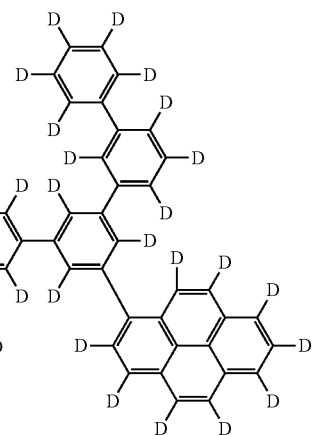

281
-continued
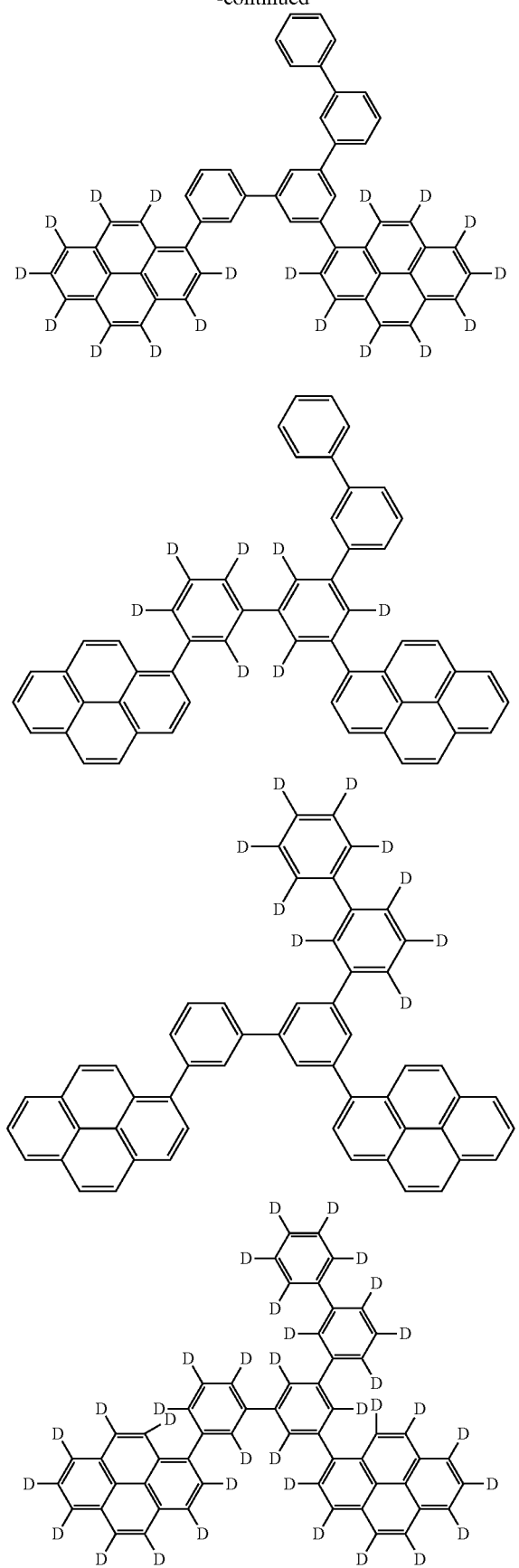
282
-continued
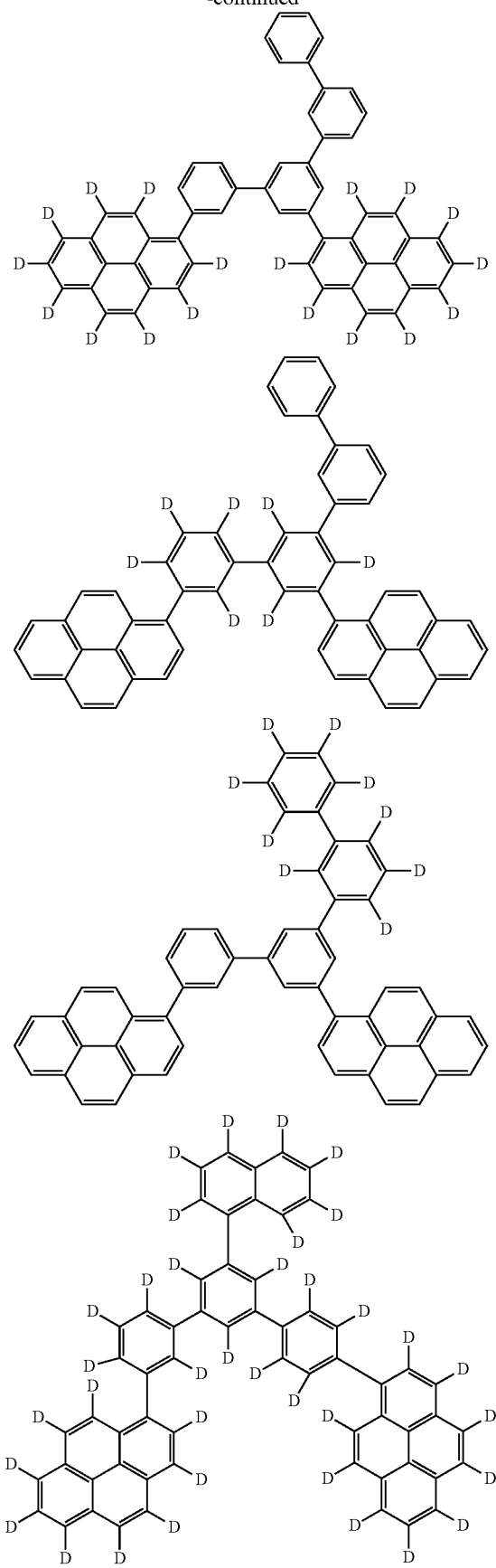

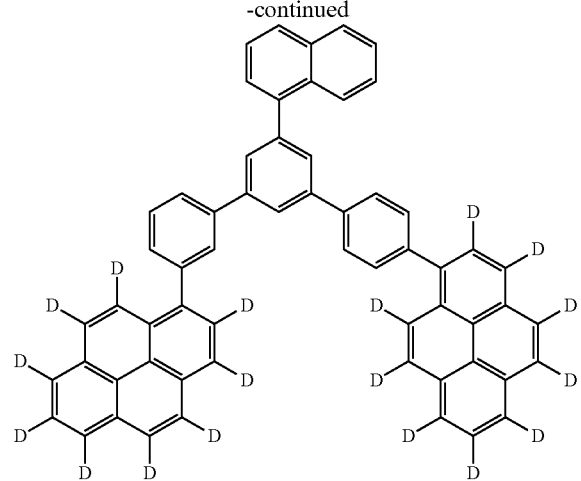
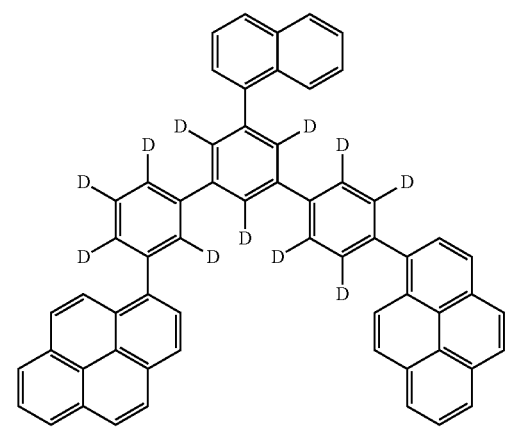
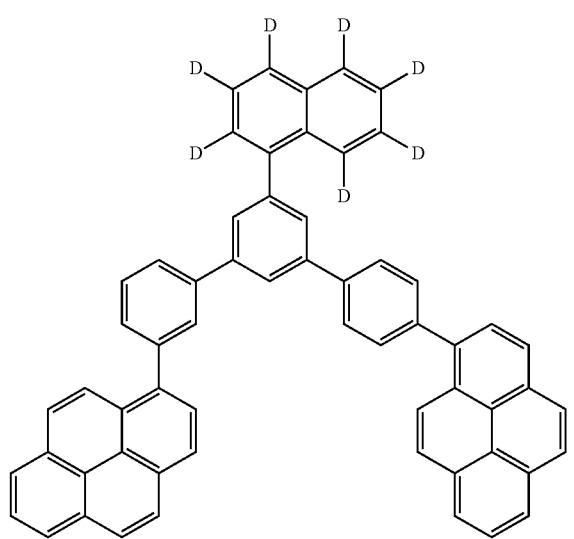
[Formula 143]
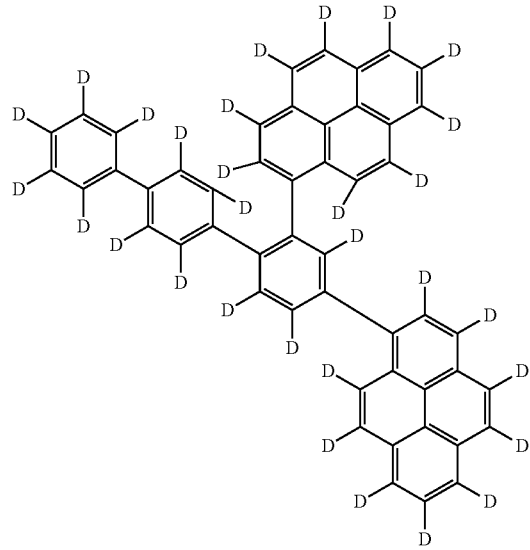
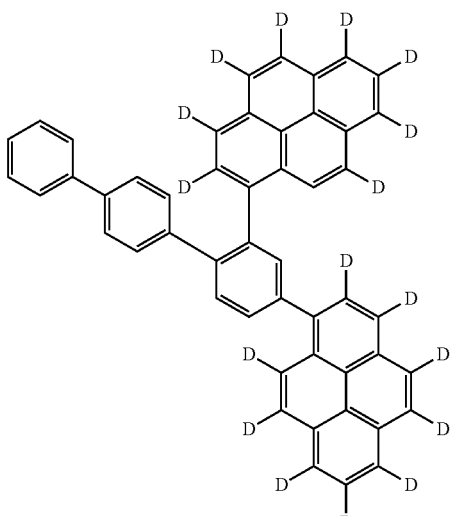
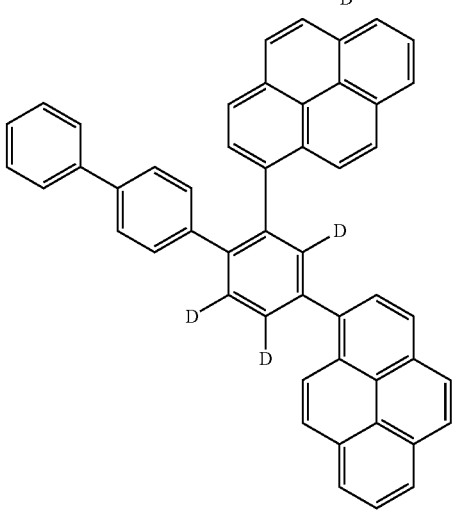

285
-continued
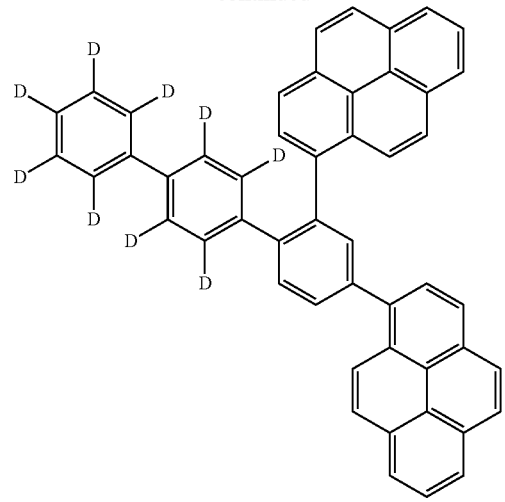
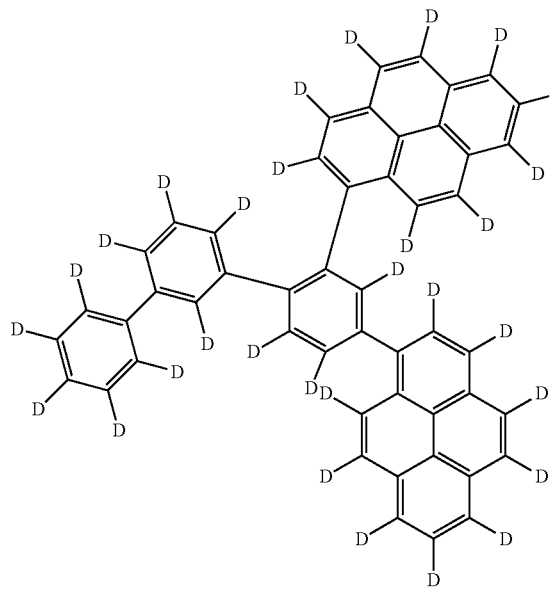
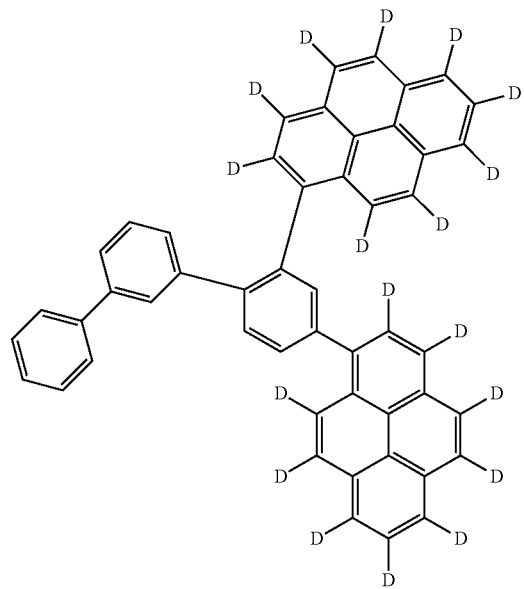
286
-continued
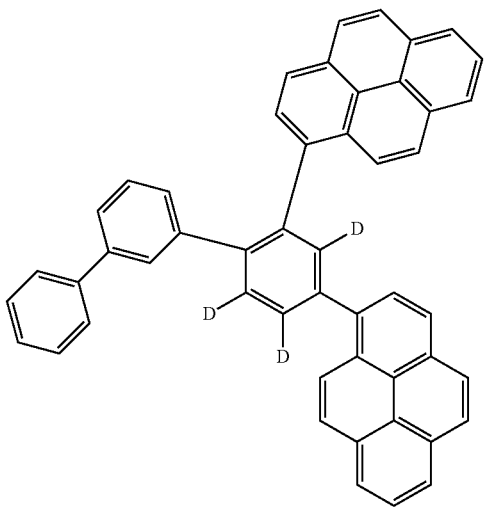
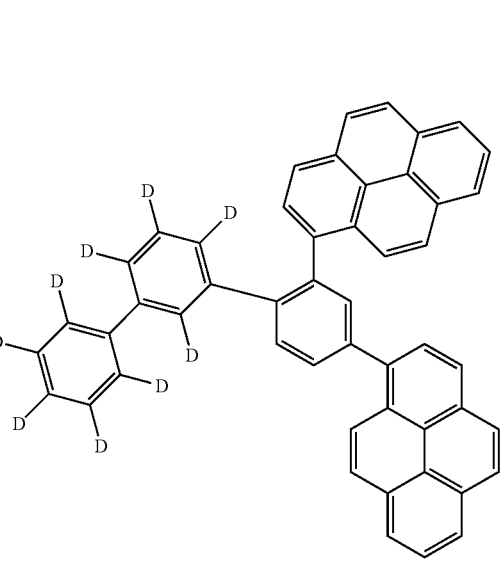
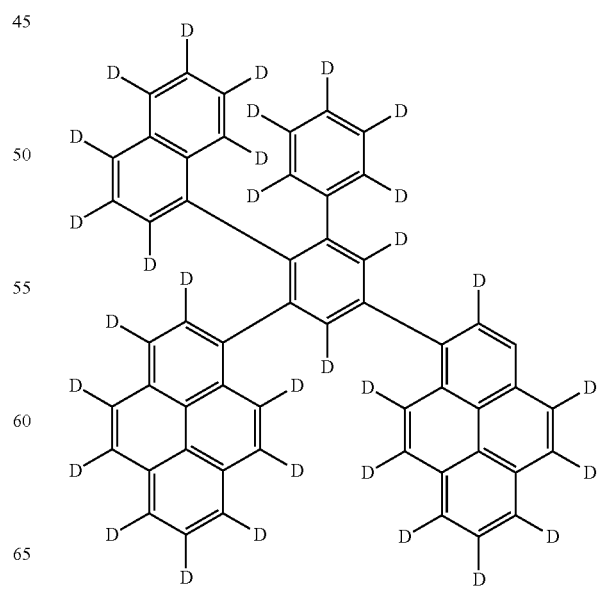

287
-continued
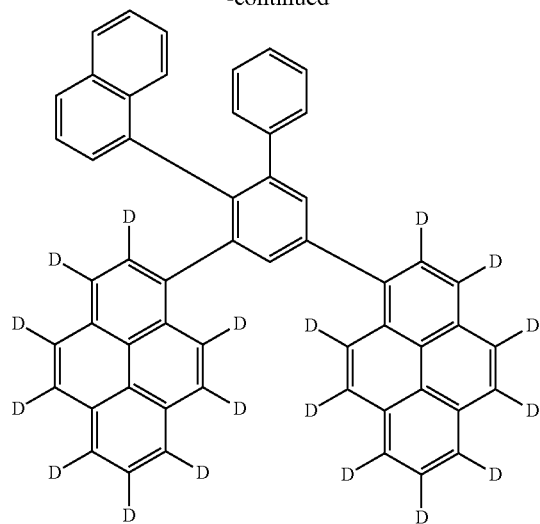
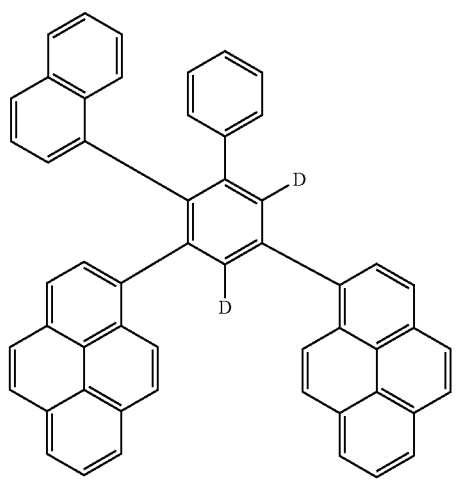
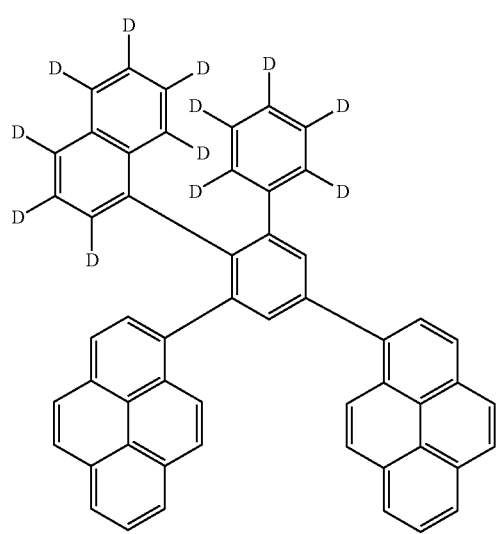
288
[Formula 144]
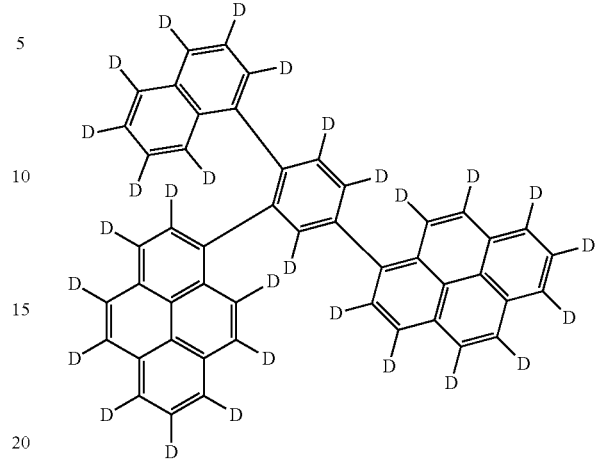
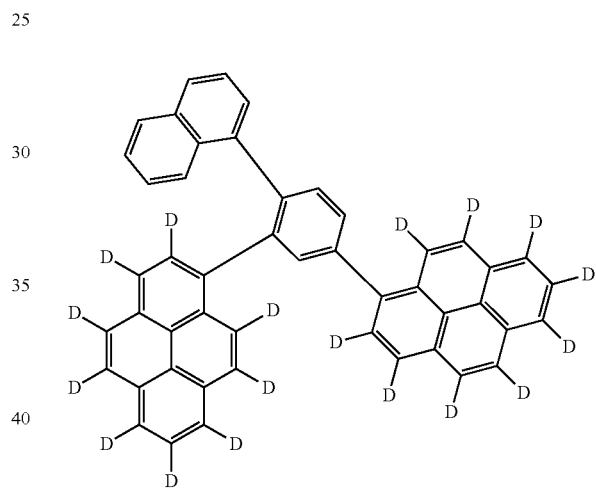
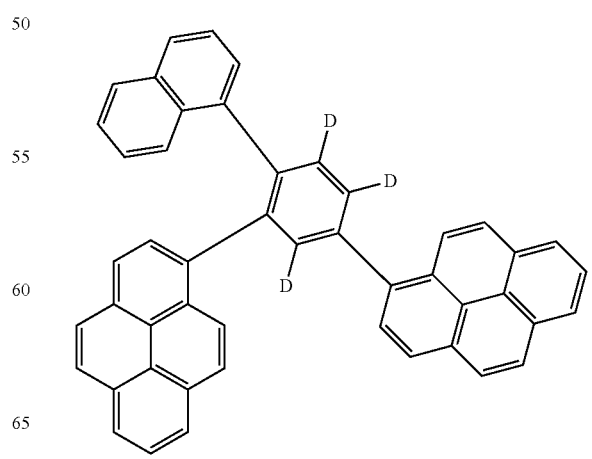

289
-continued
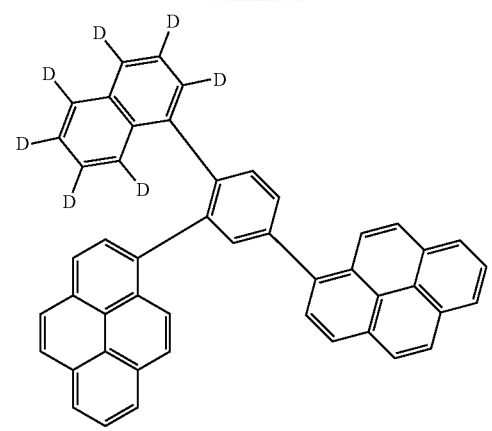
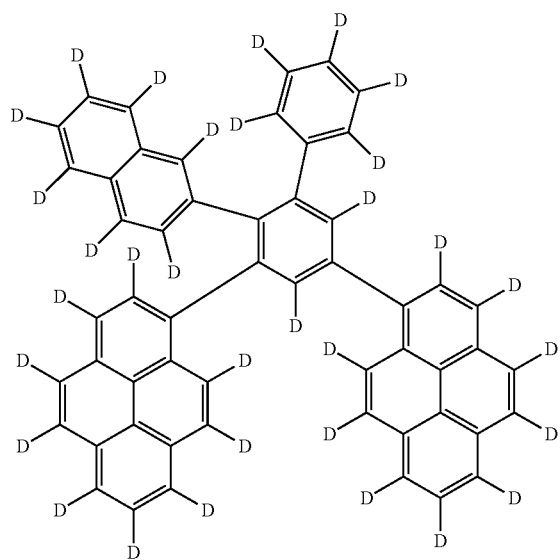
290
-continued
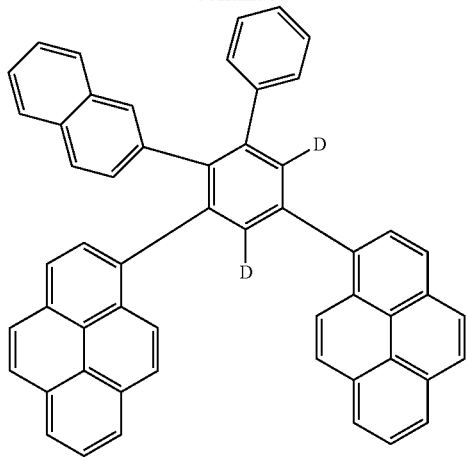
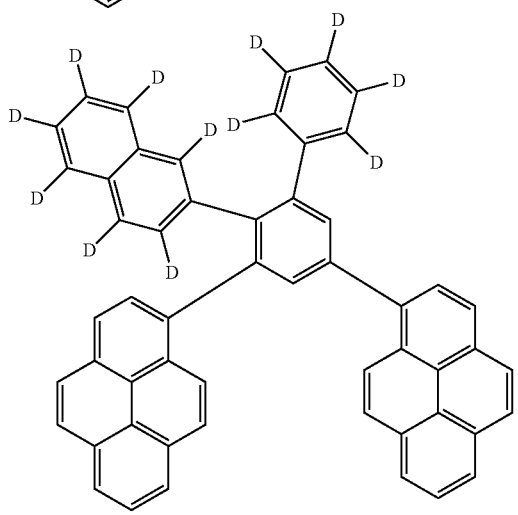
[Formula 145]
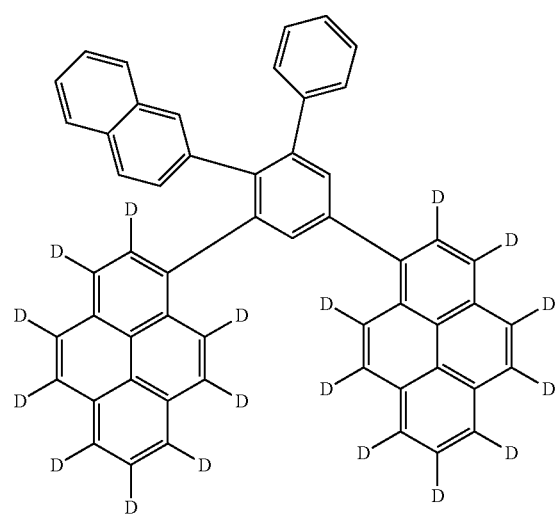
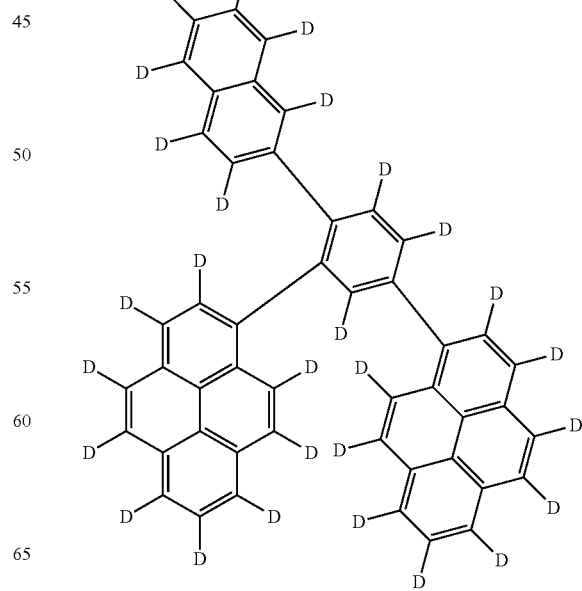

291
-continued
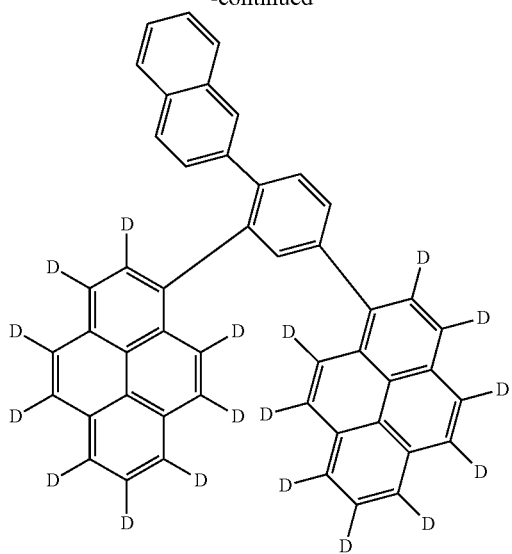
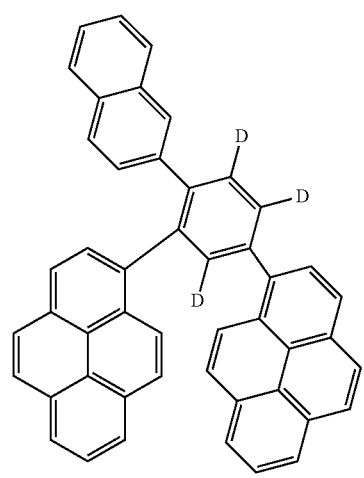
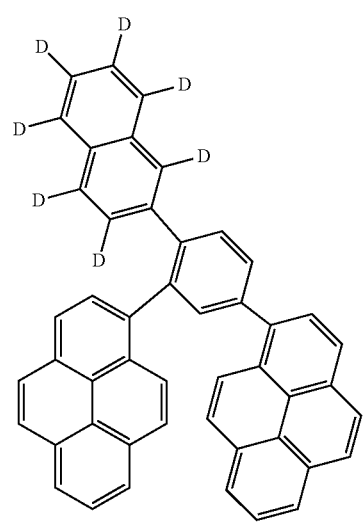
292
-continued
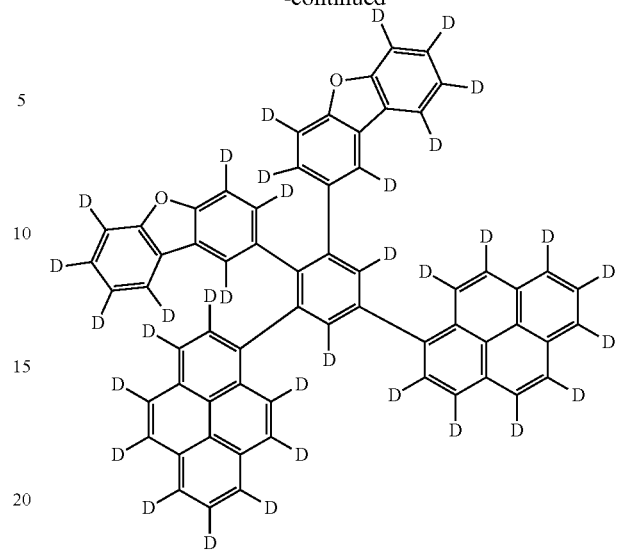
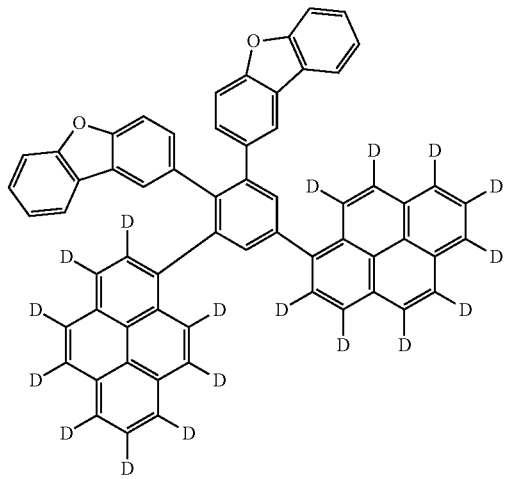
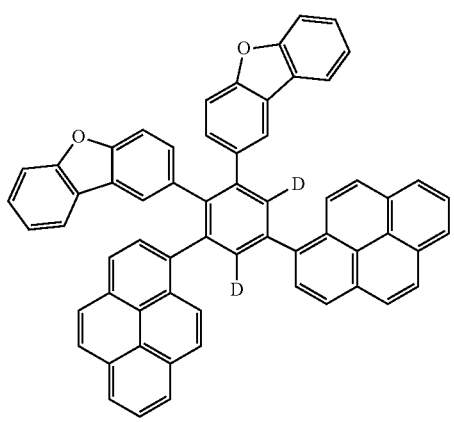

293
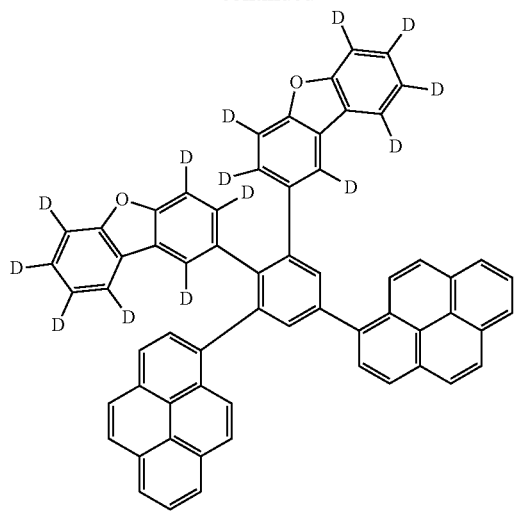
294
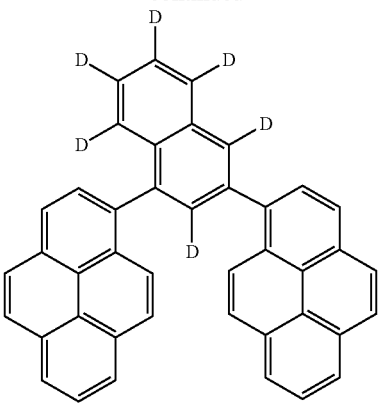
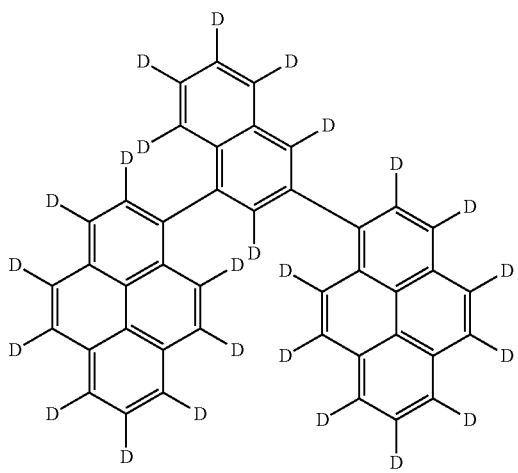
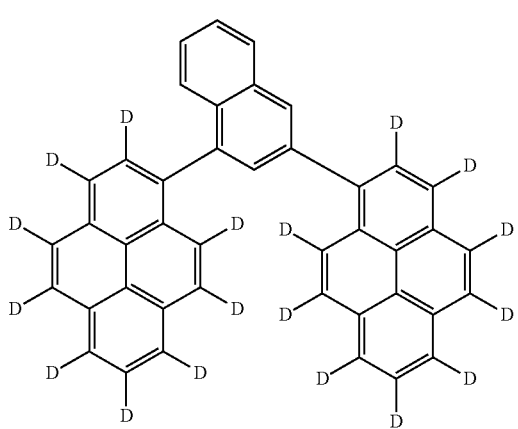
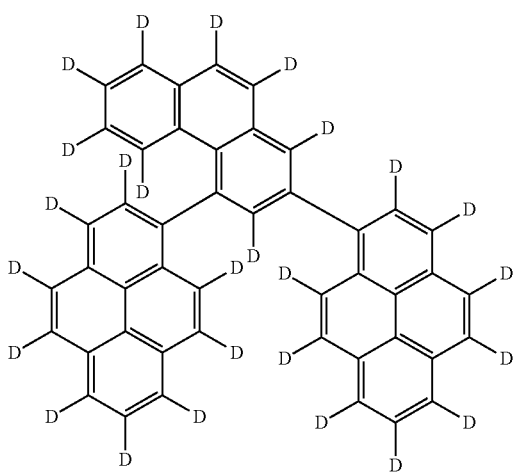

[Formula 146]
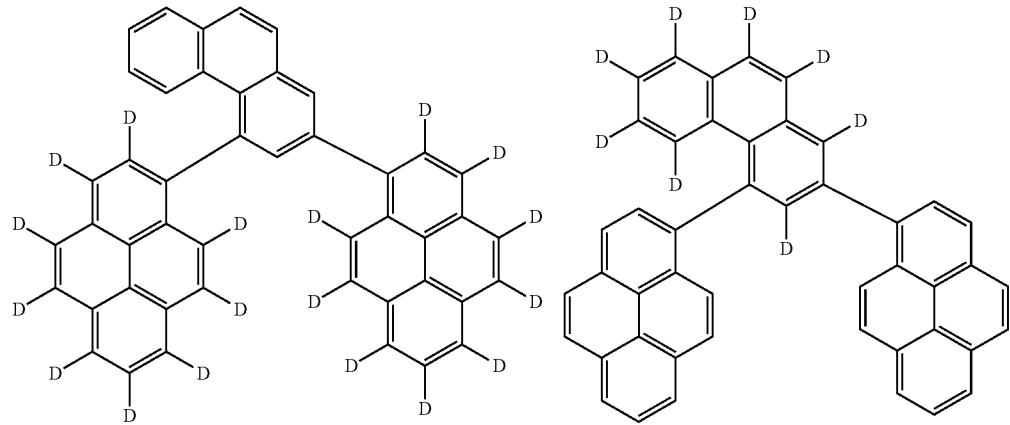
295
296
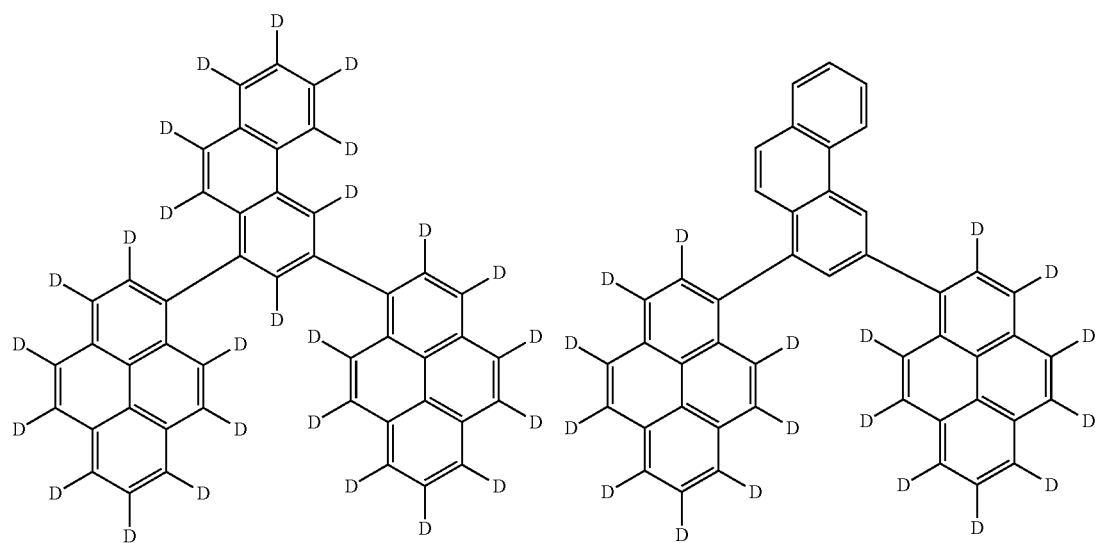
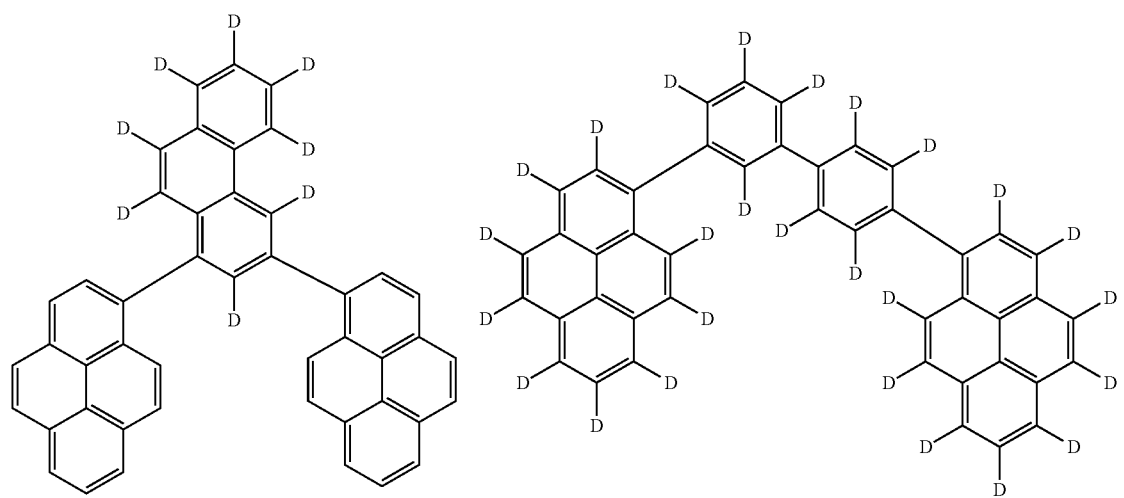

297 298
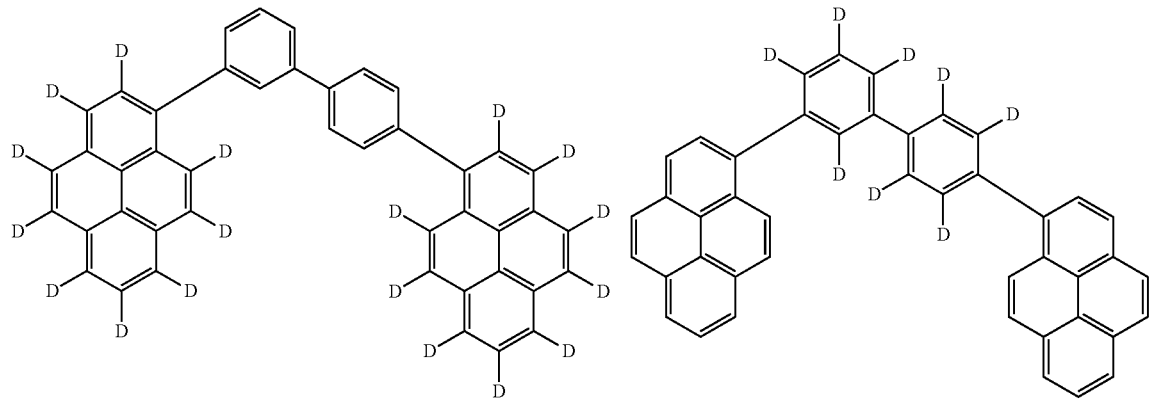
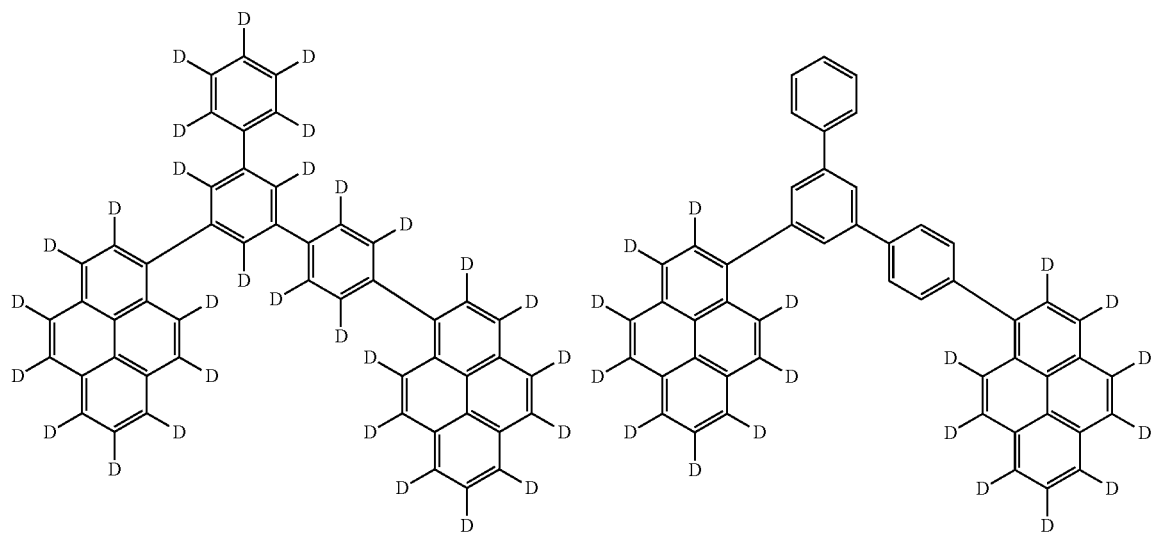
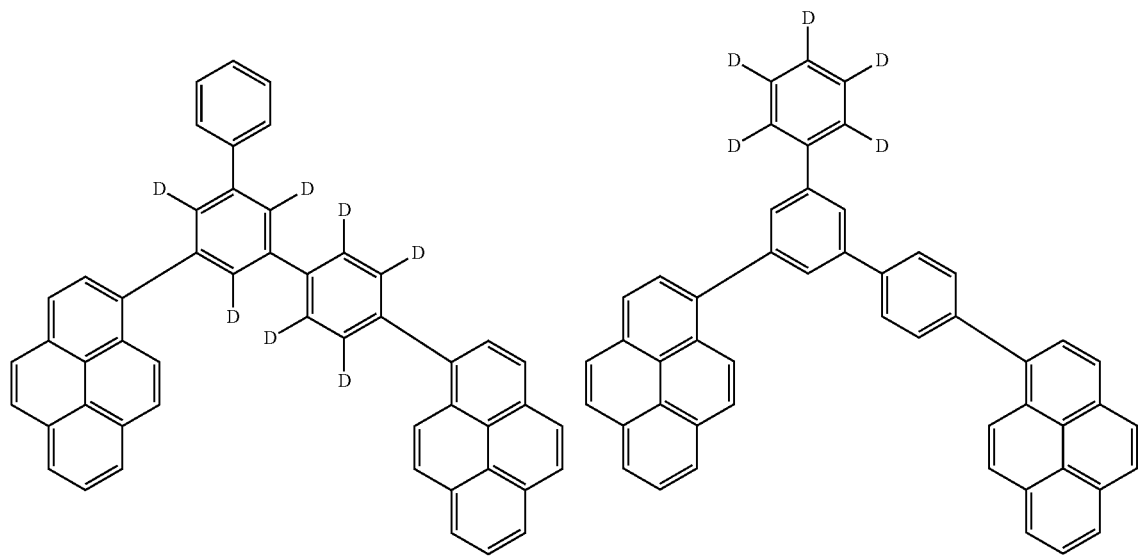

[Formula 147]
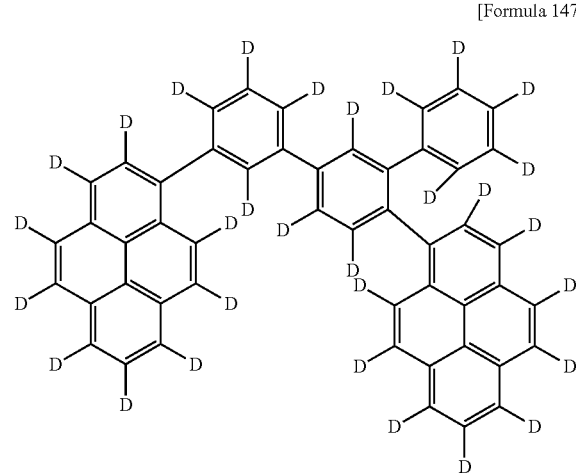
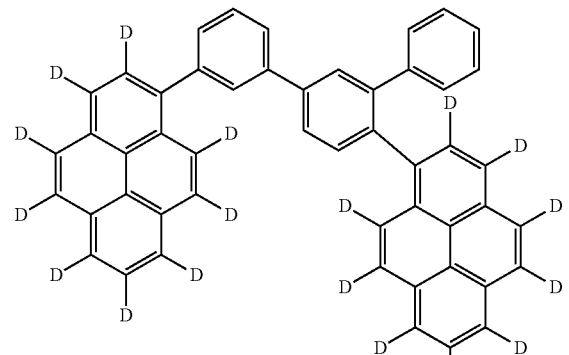
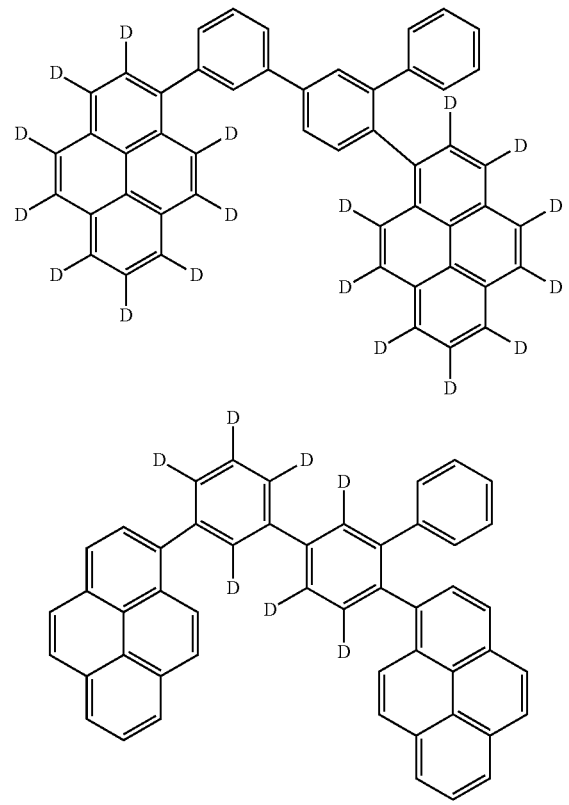
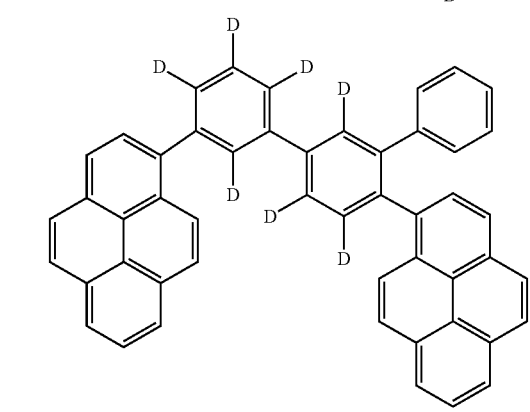

301
-continued
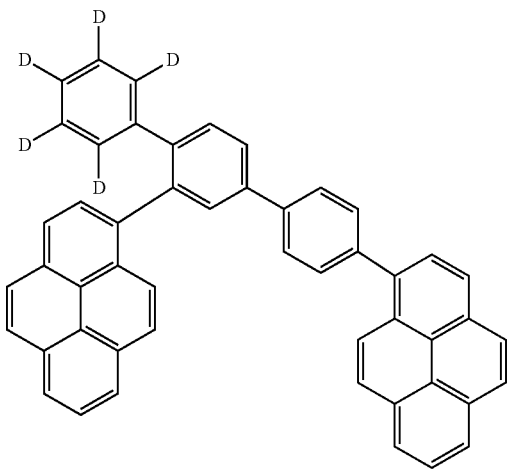
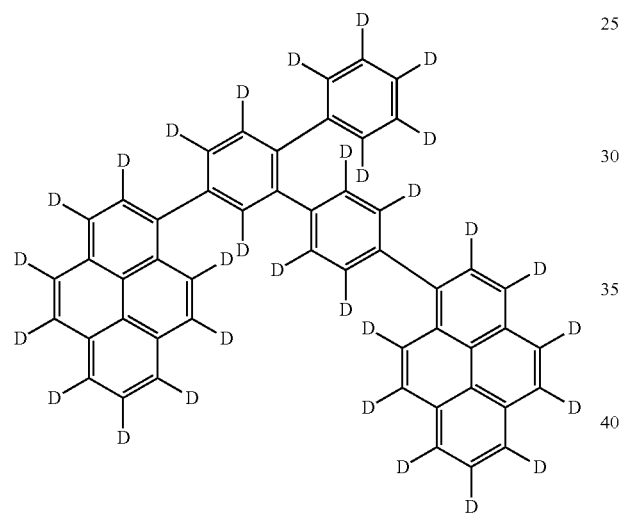
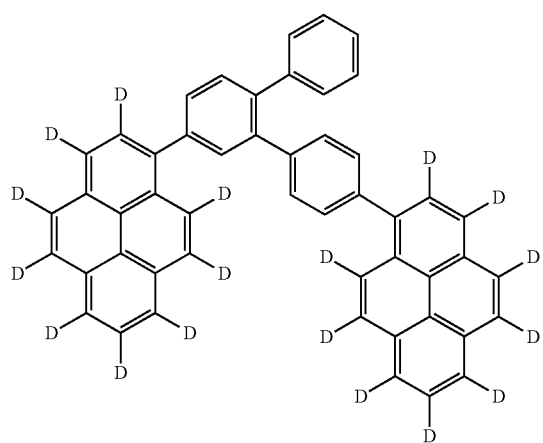
302
-continued
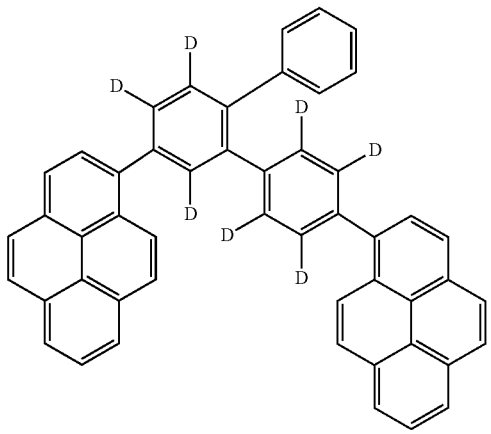
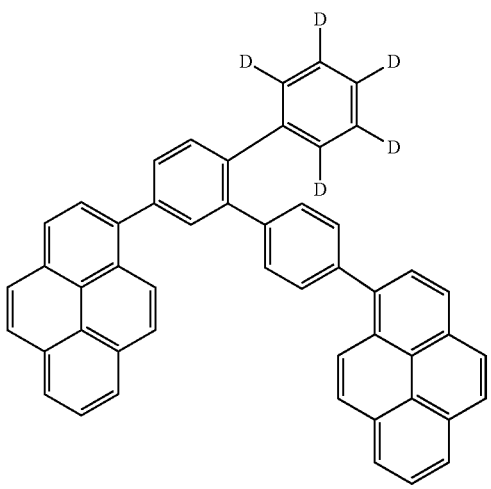
[Formula 148]
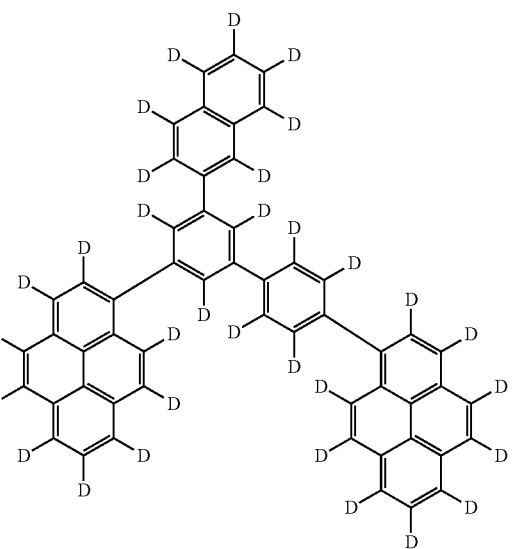

303
-continued
304
-continued
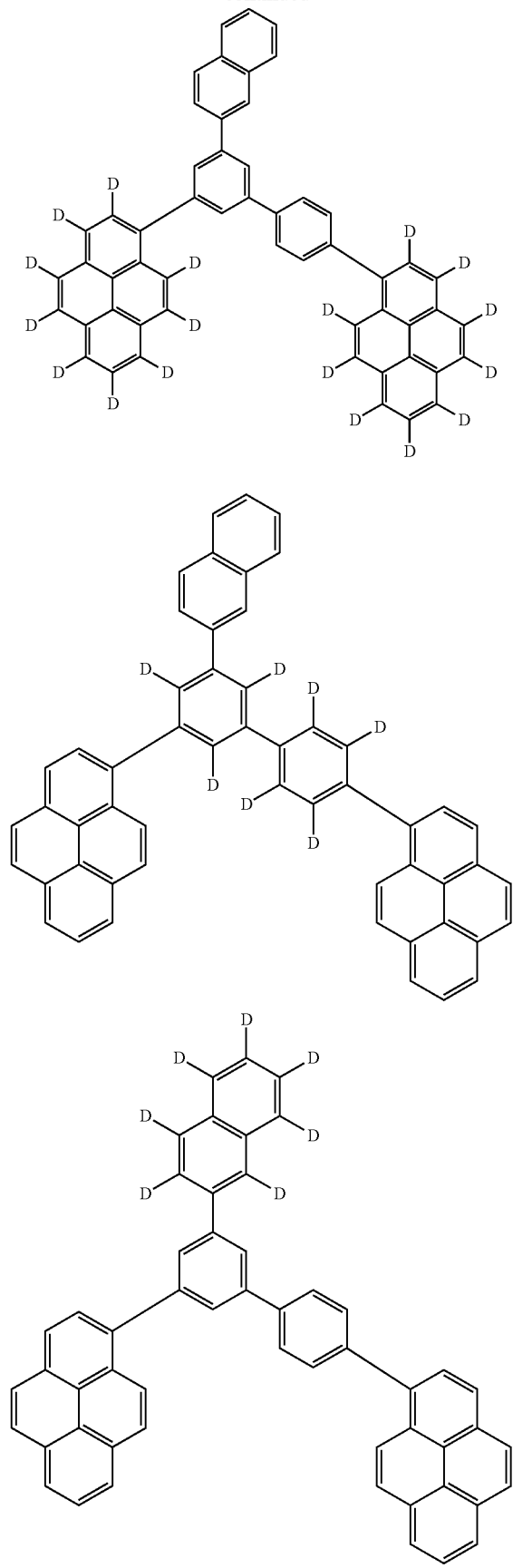
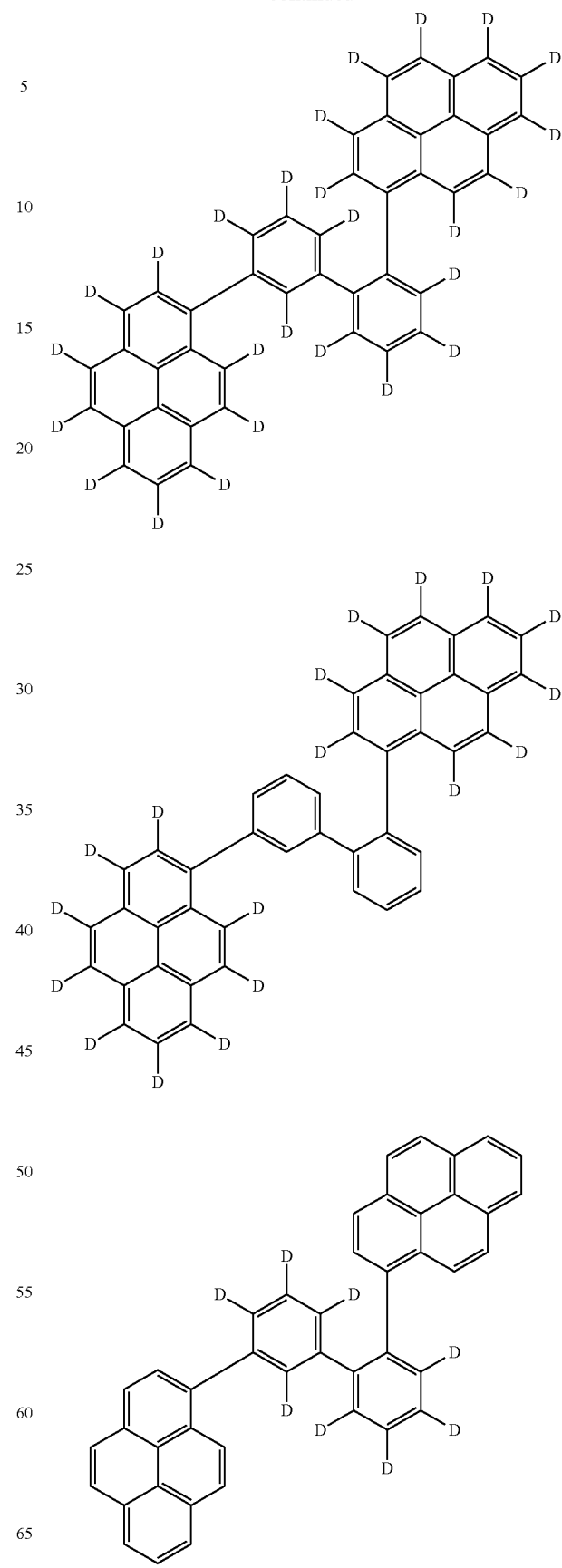

305
-continued
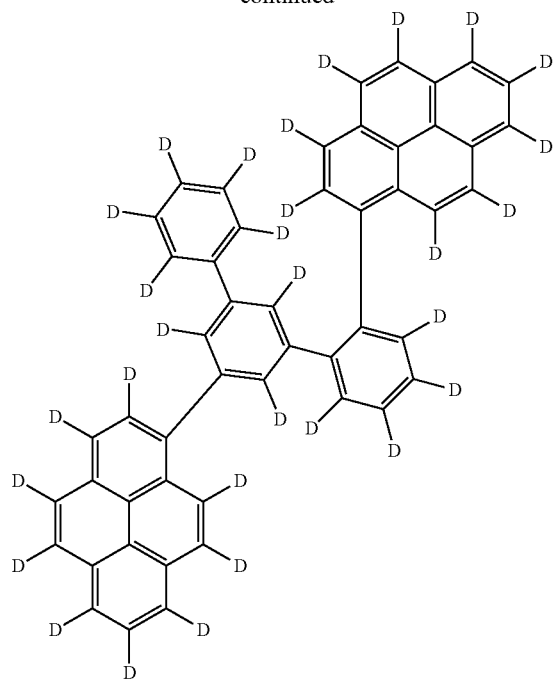
[Formula 149]
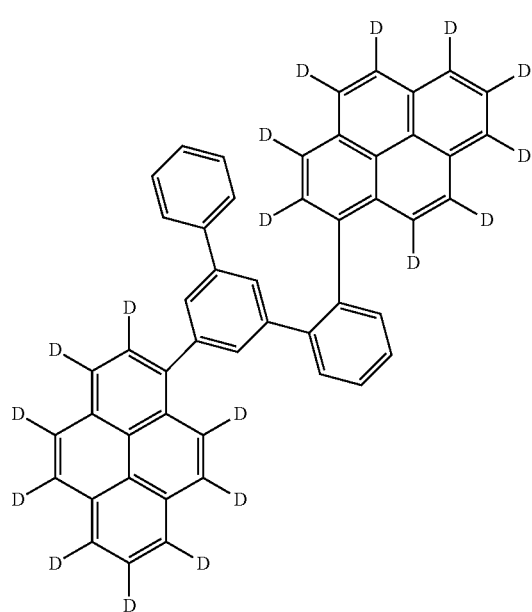
306
-continued
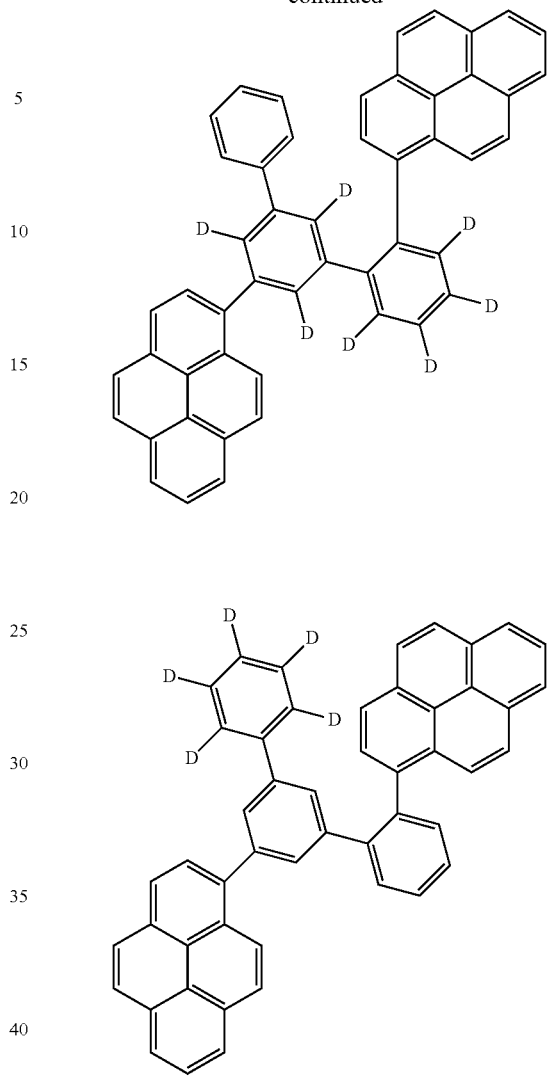
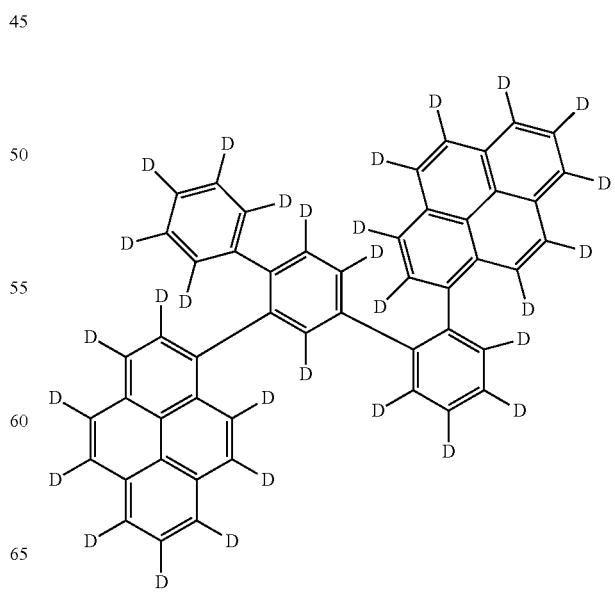

307
-continued
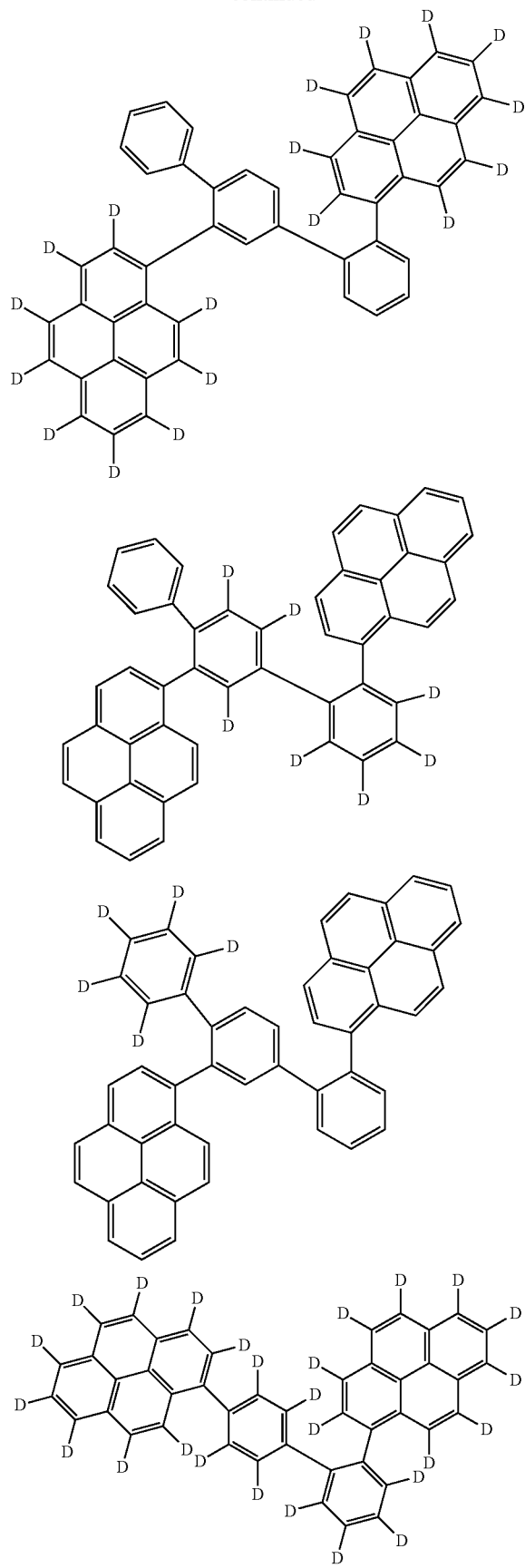
308
-continued
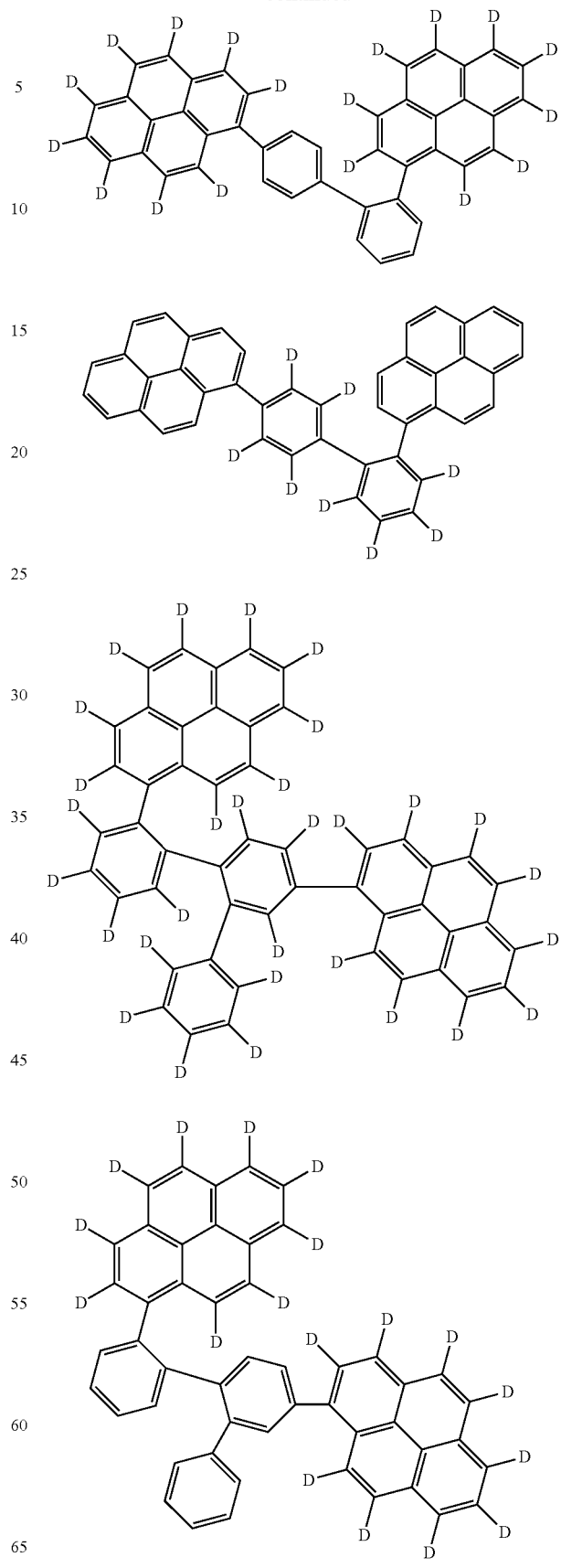

[Formula 150]
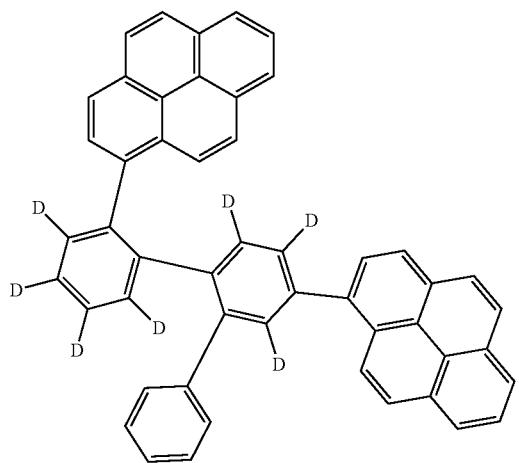
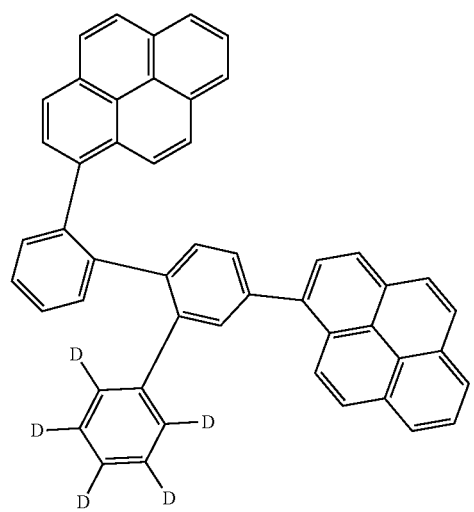
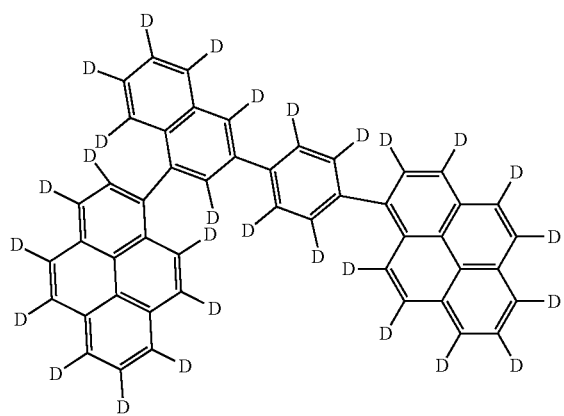
-continued
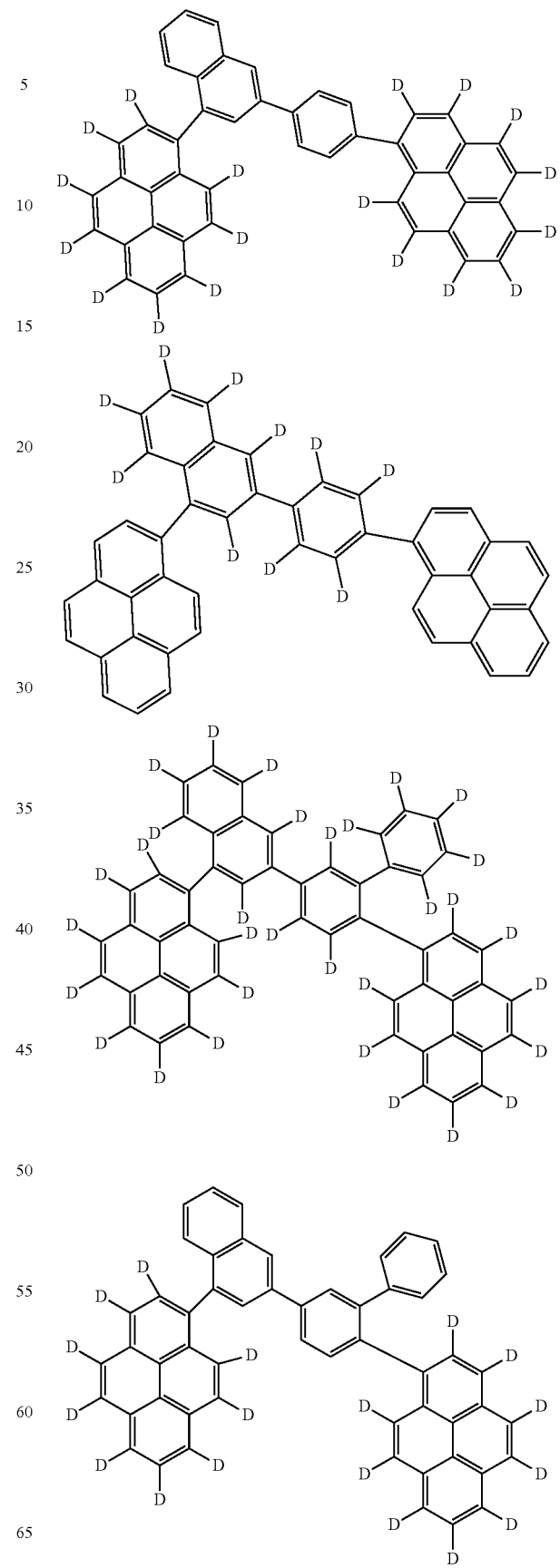

311
-continued
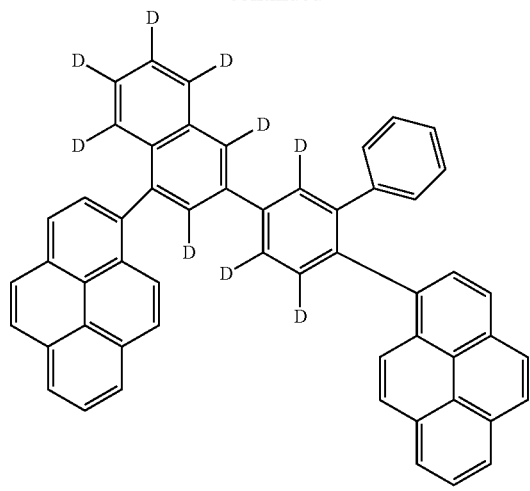
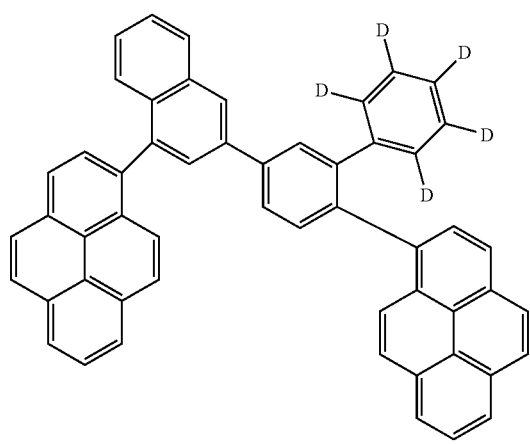
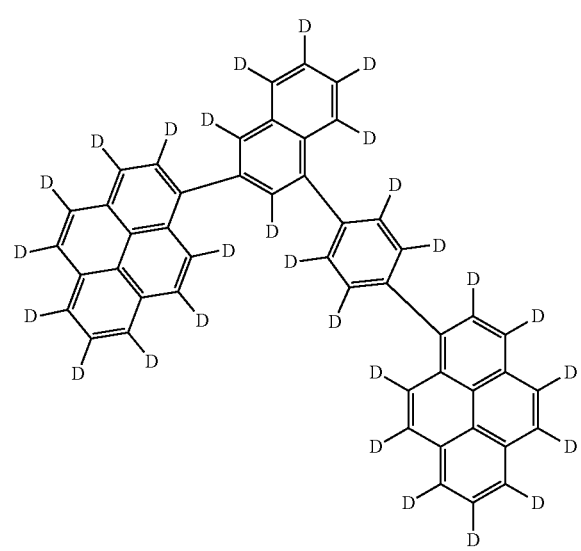
312
-continued
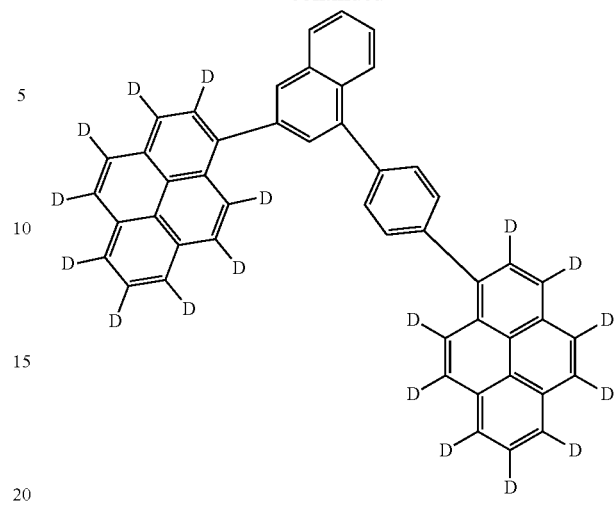
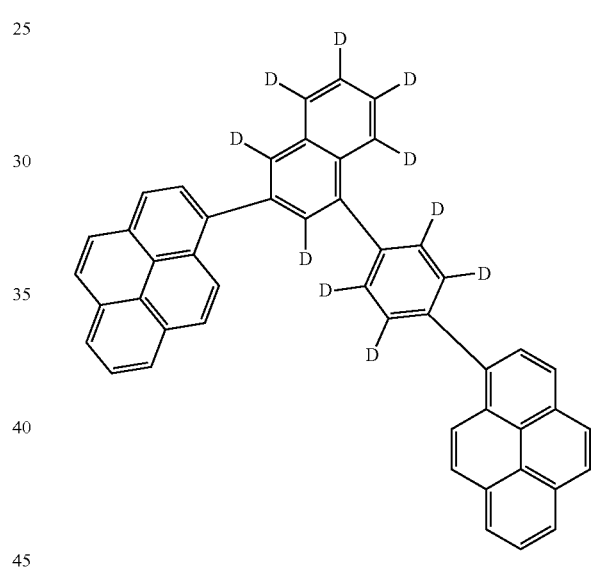
[Formula 151]
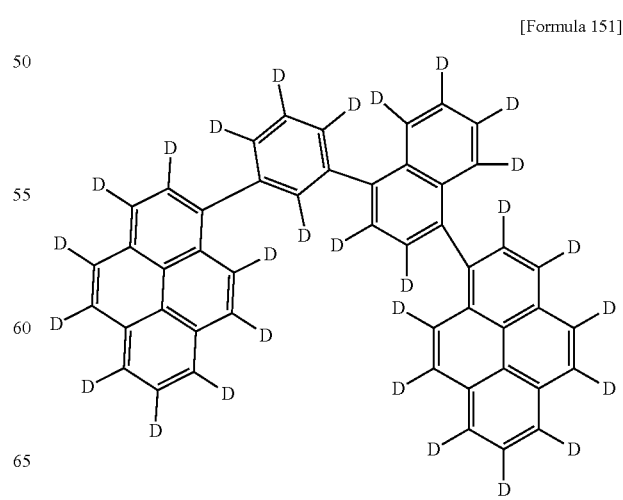

313
-continued
314
[Formula 152]
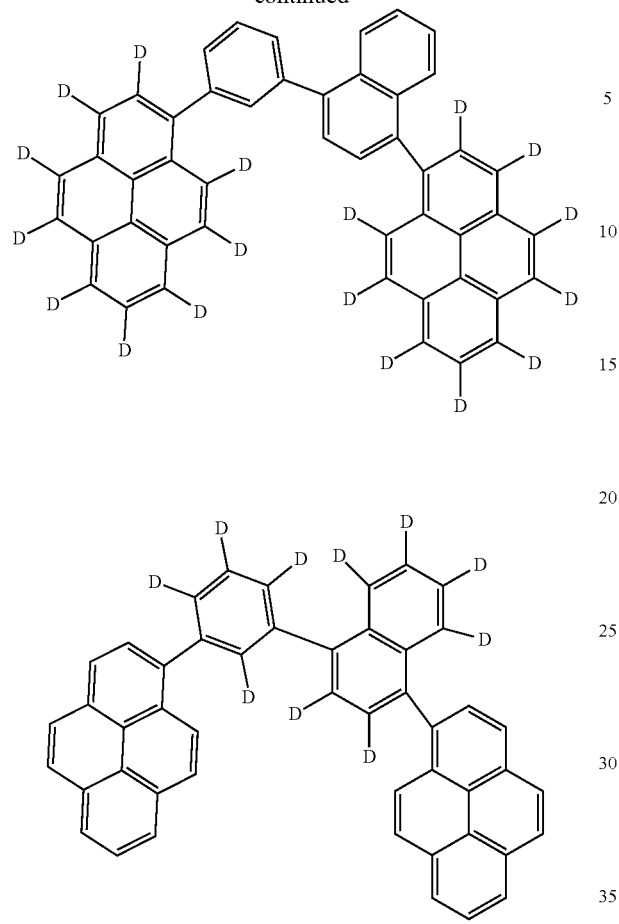
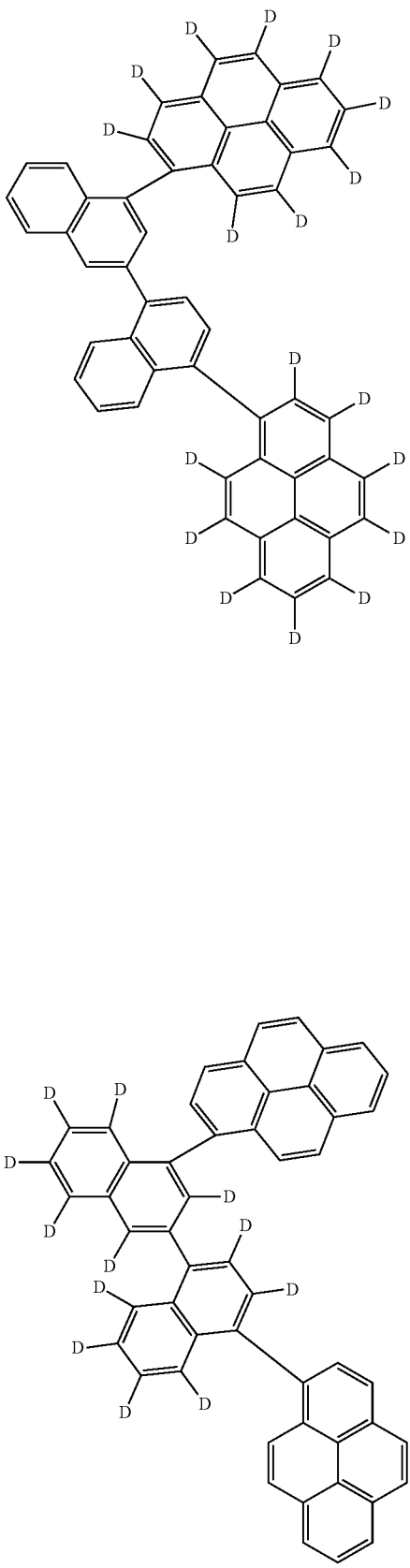

315
-continued
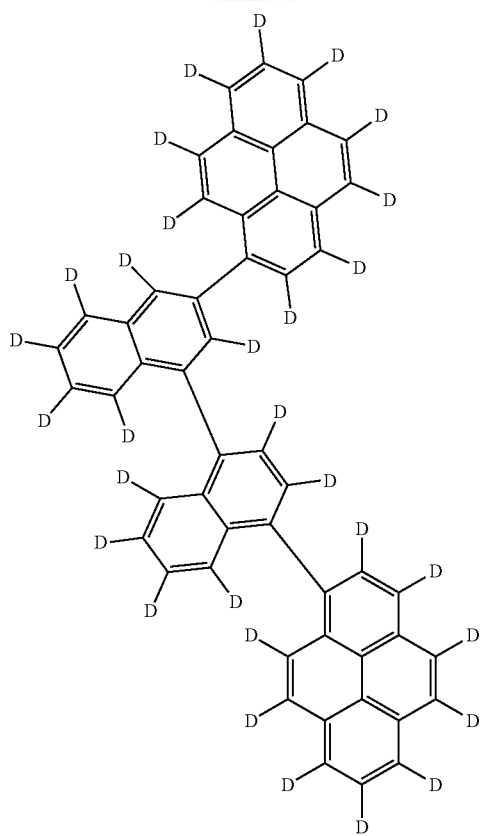
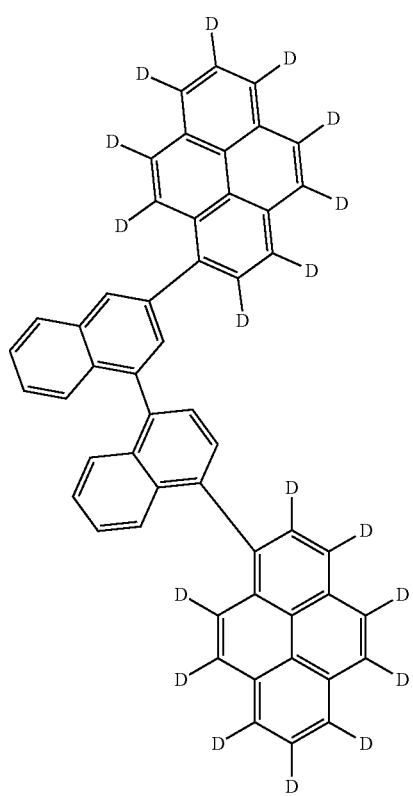
316
-continued
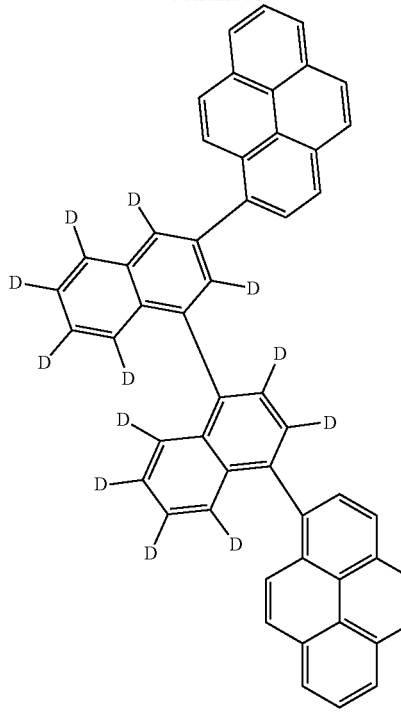
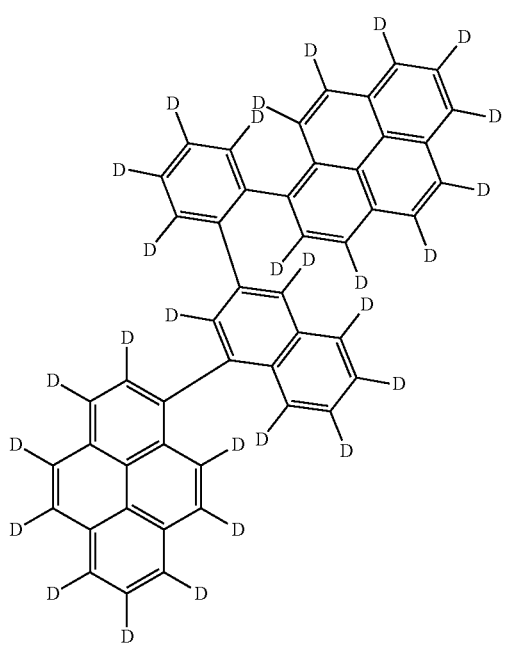

317
-continued
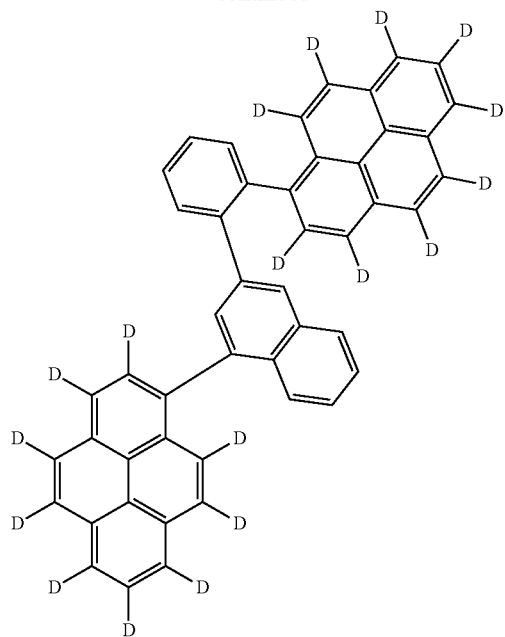
318
-continued
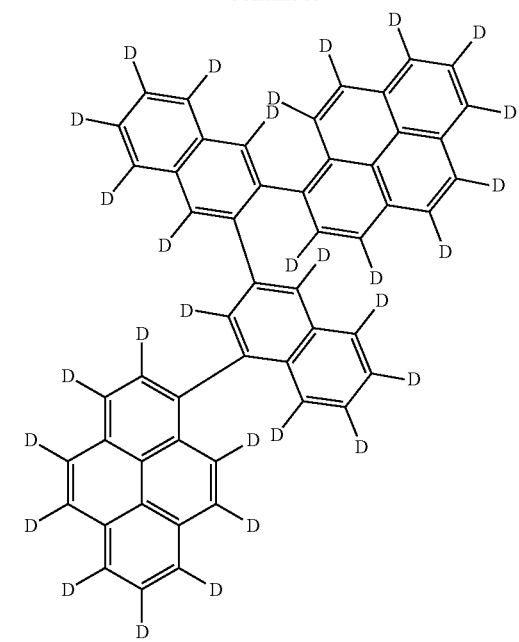
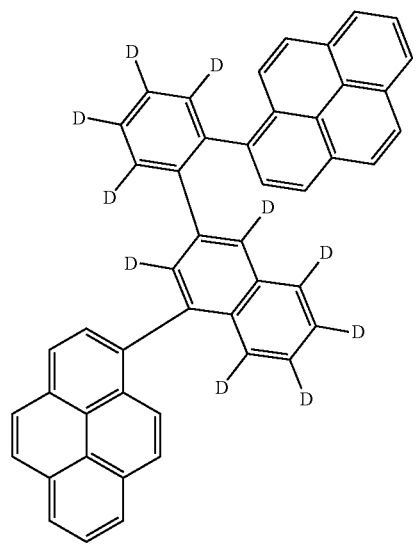
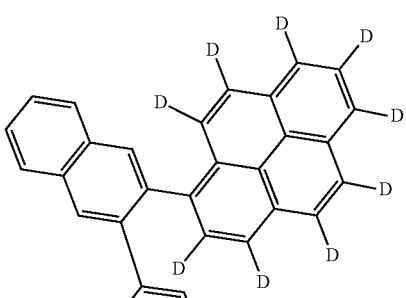
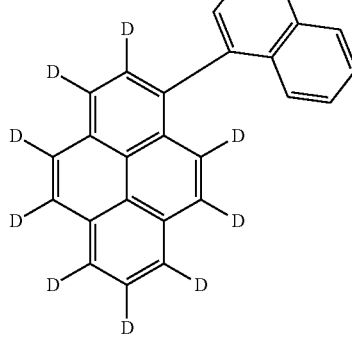

319
-continued
320
-continued
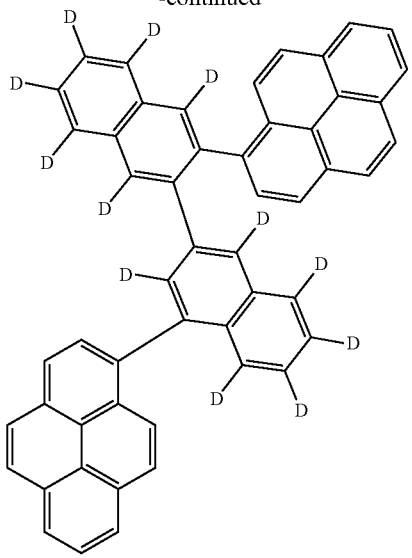
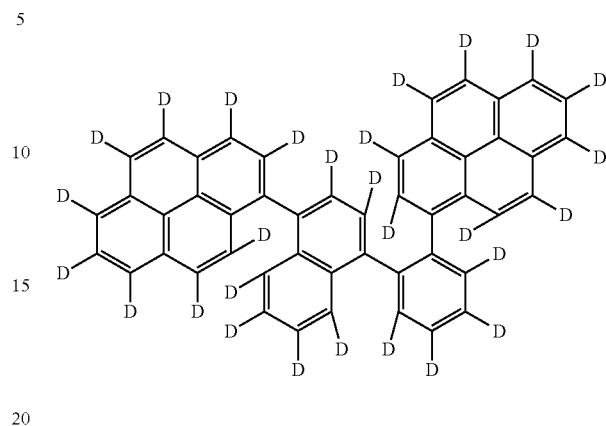
[Formula 153]
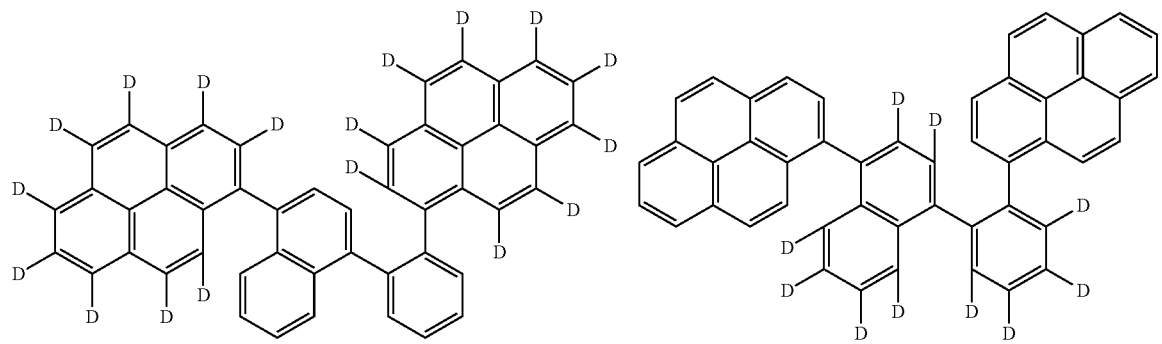
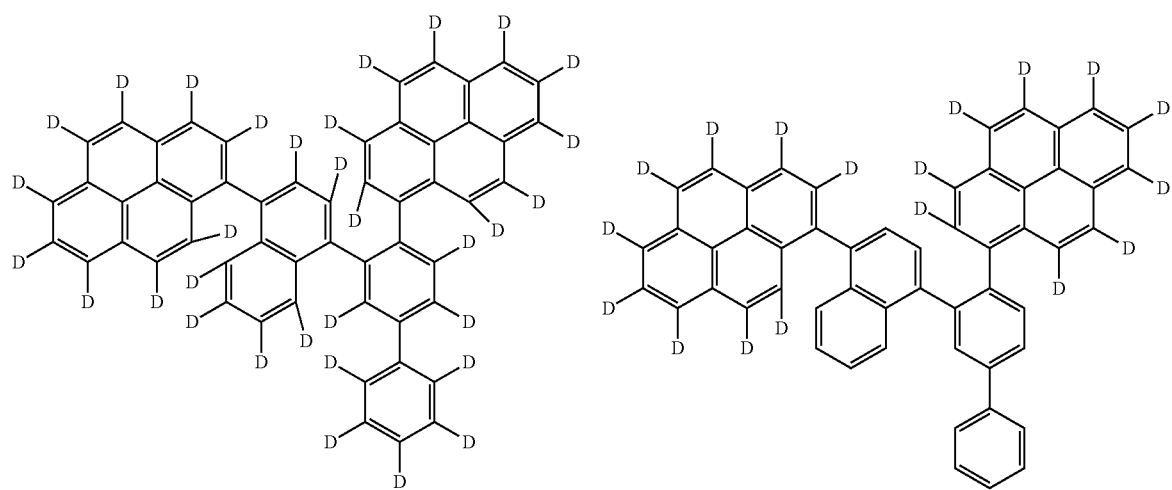

321 322
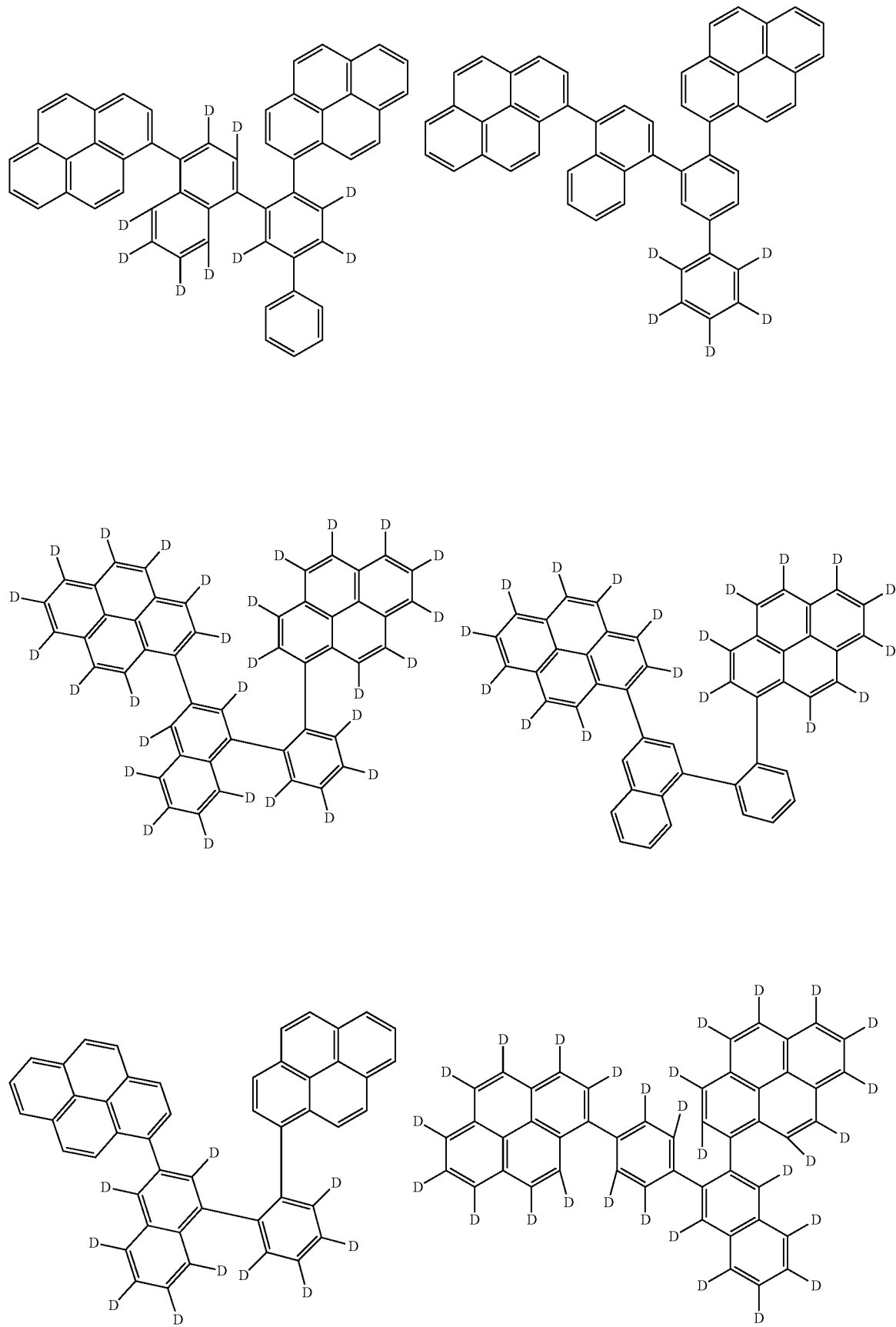

323
-continued
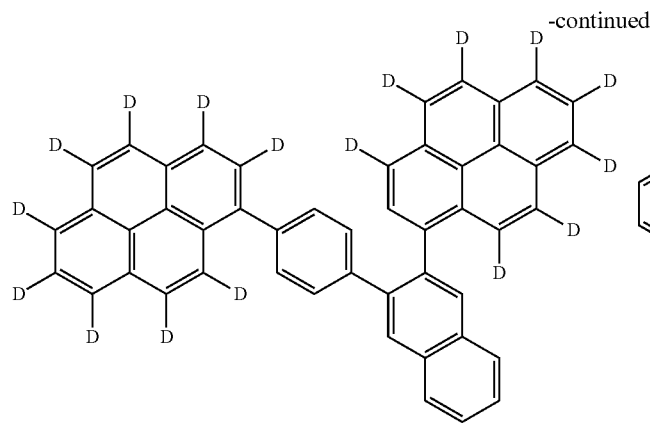
[Formula 154]
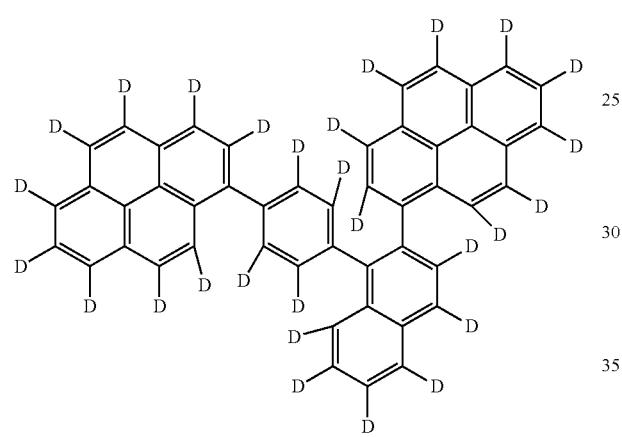
324
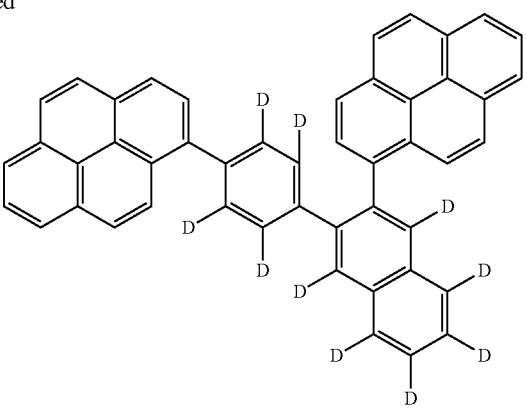
-continued
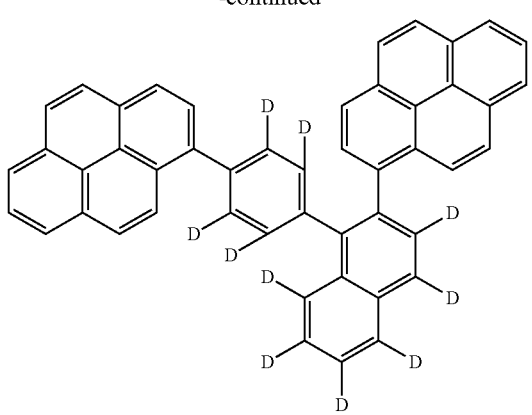
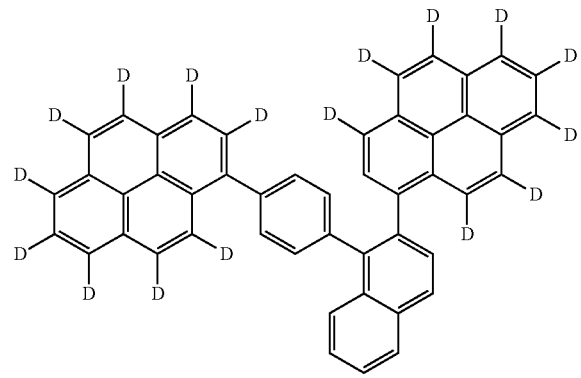
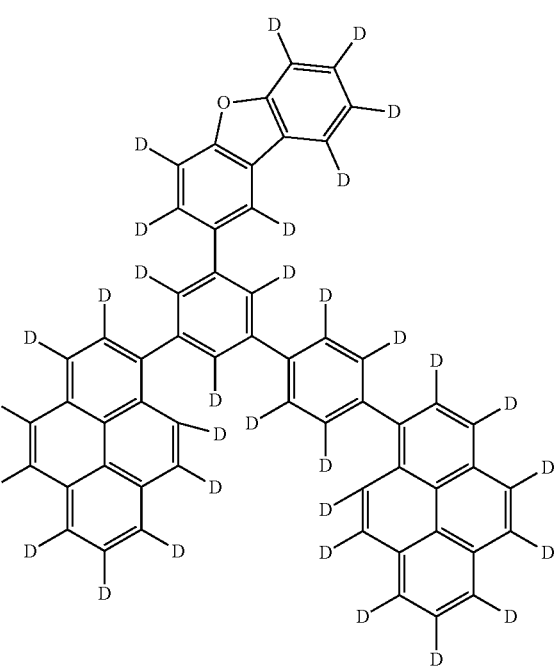

325
-continued
326
-continued
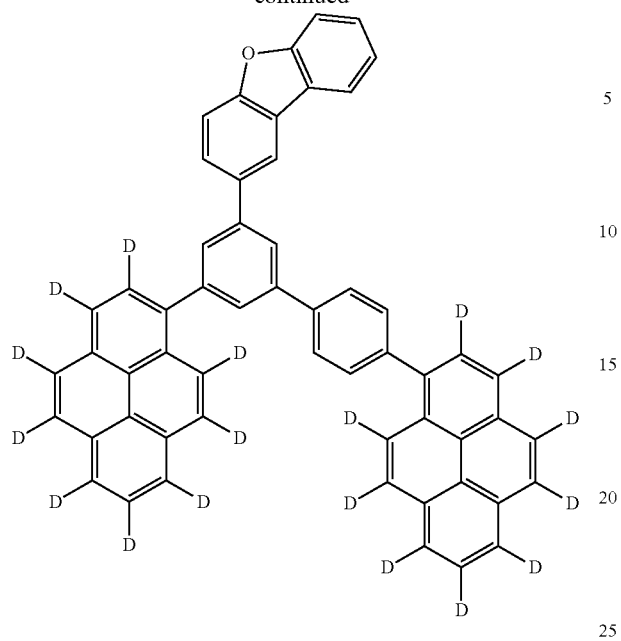
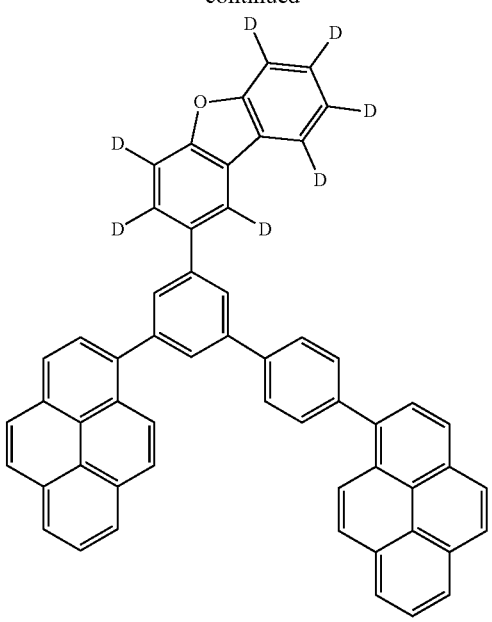
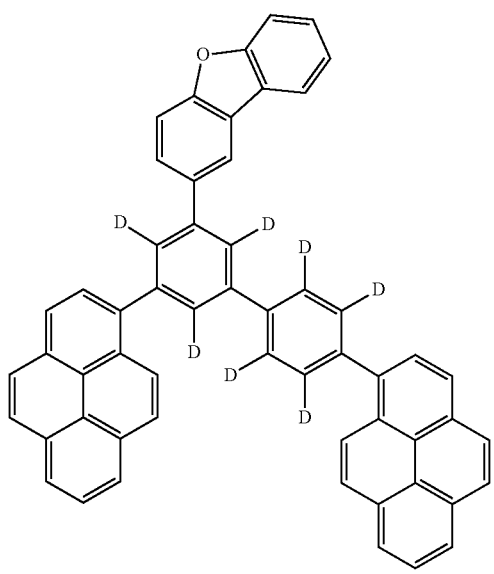

[Formula 155]
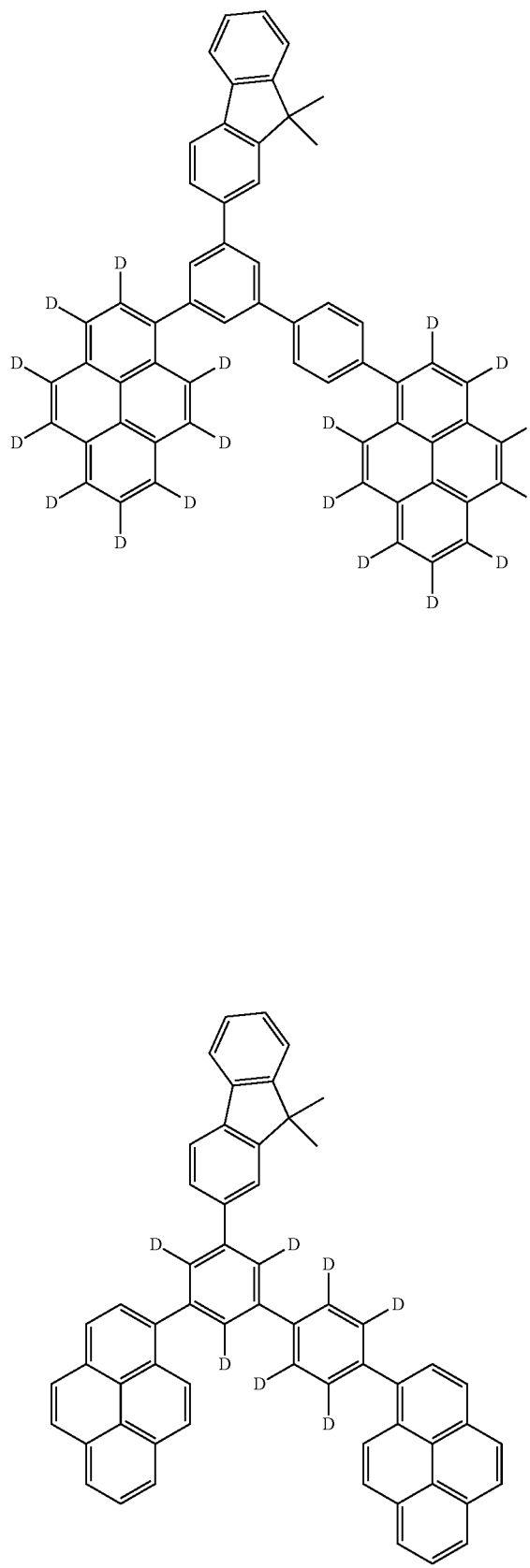
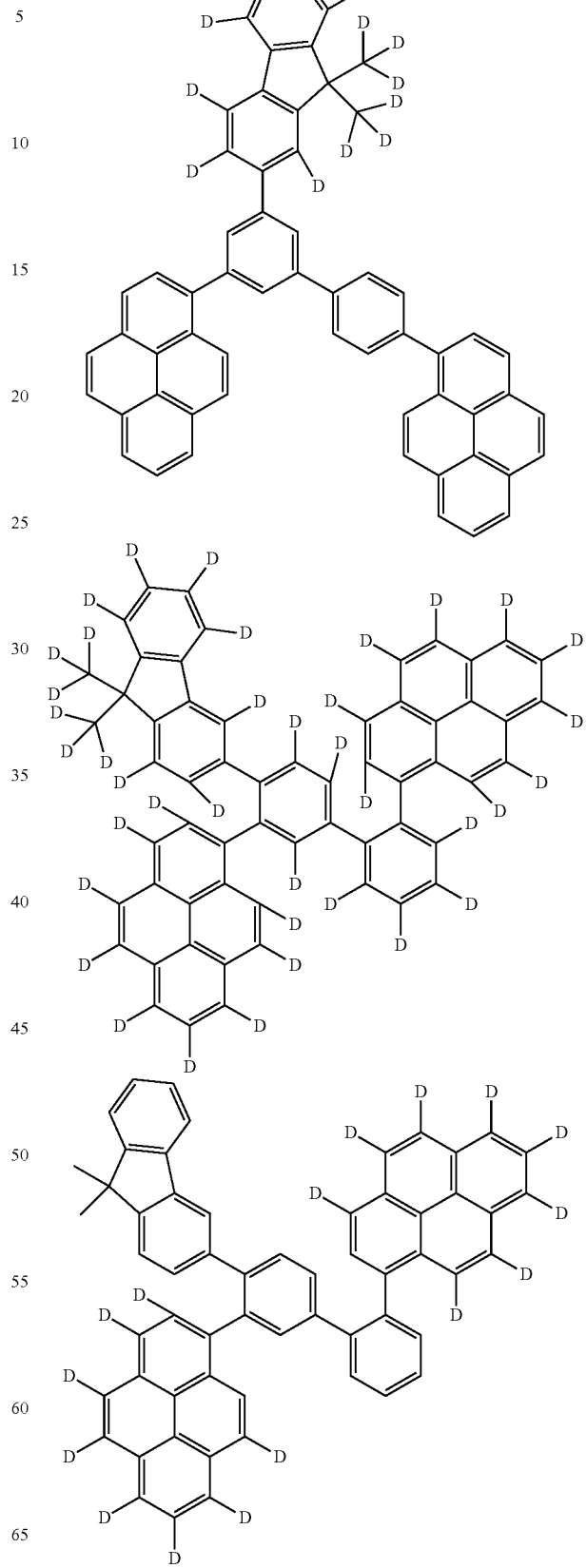

329
-continued
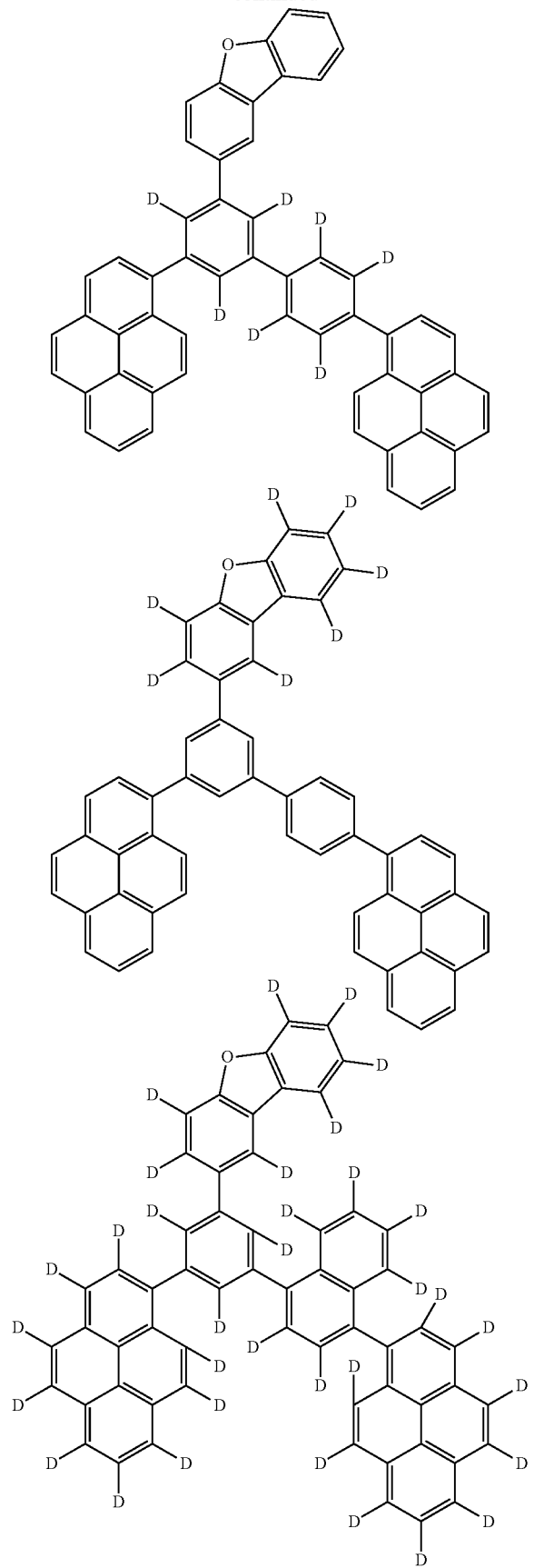
330
-continued
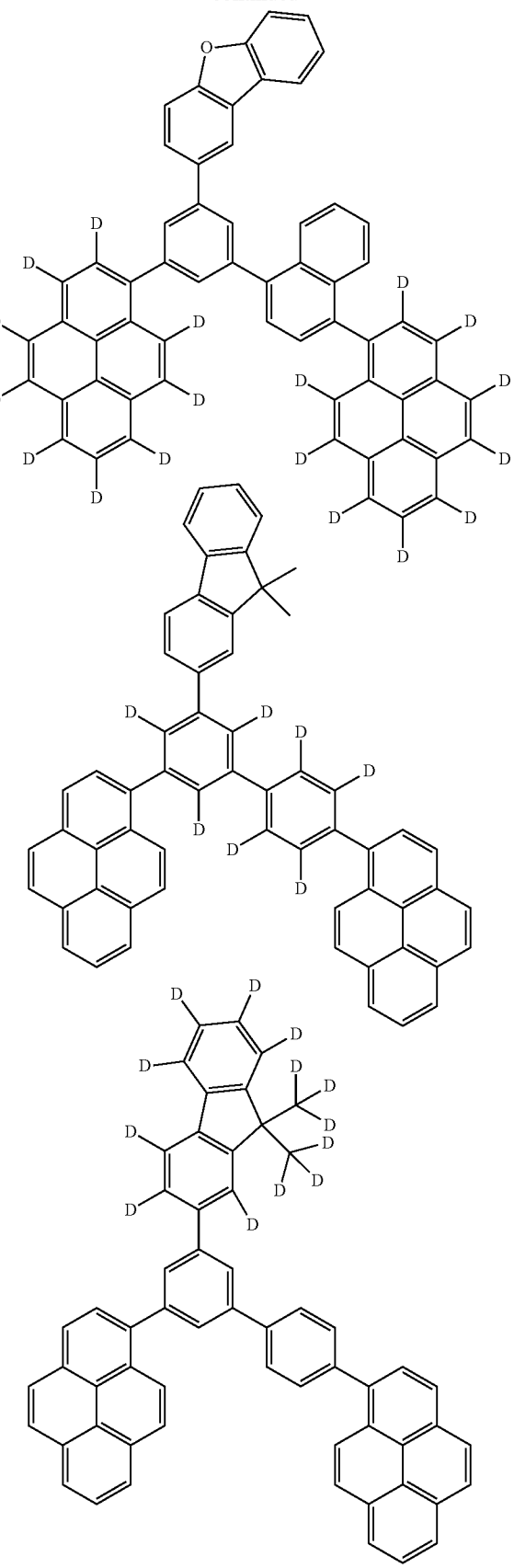

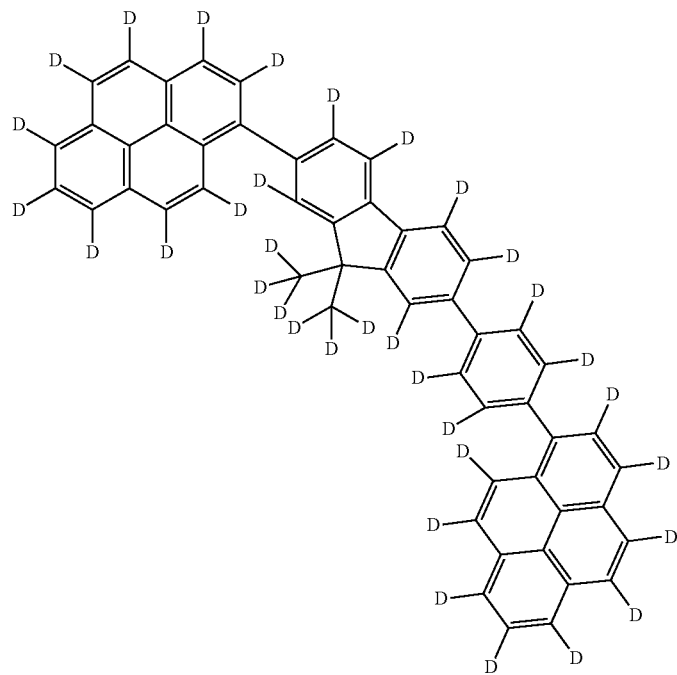
[Formula 156]
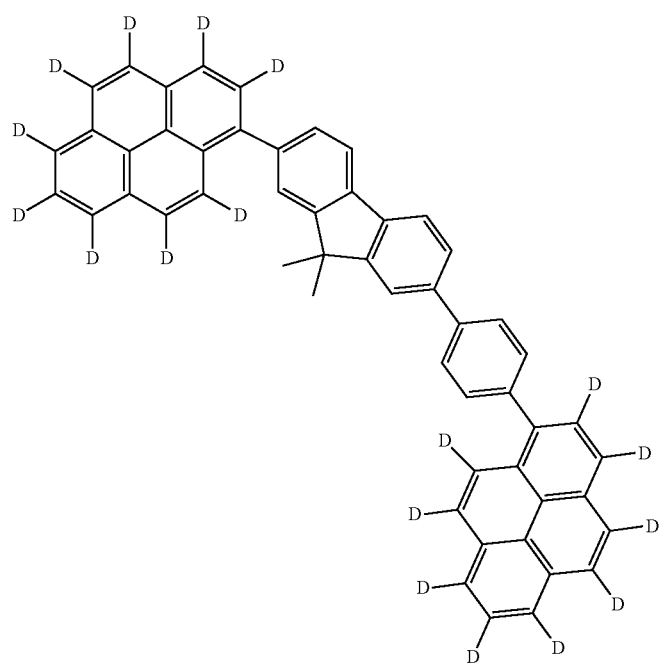

-continued
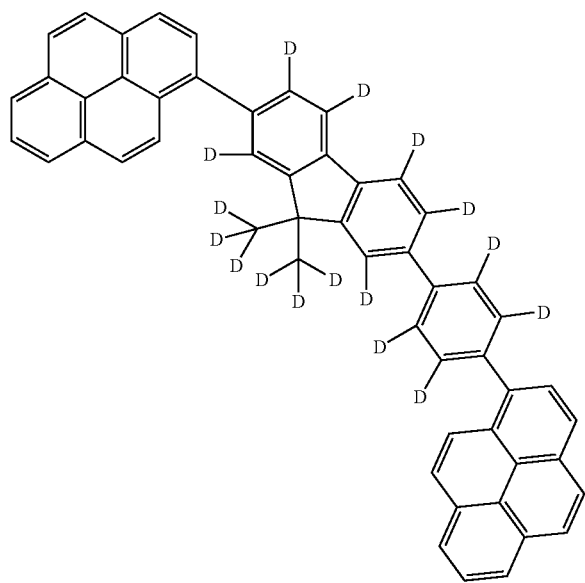
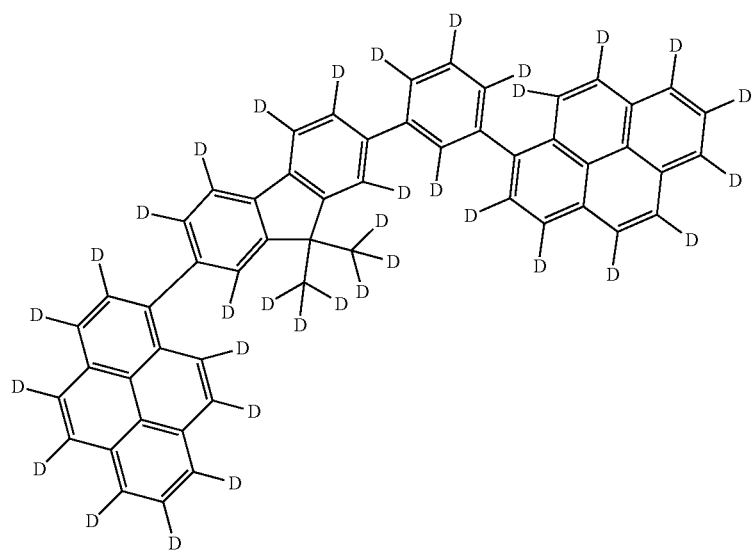
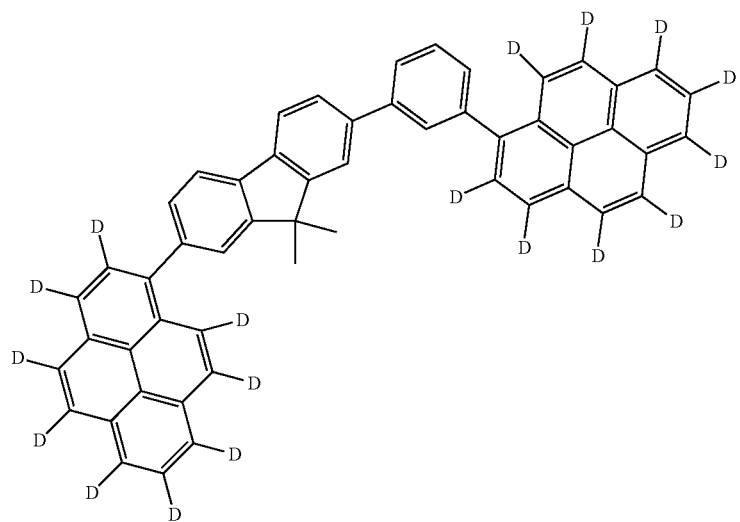

-continued
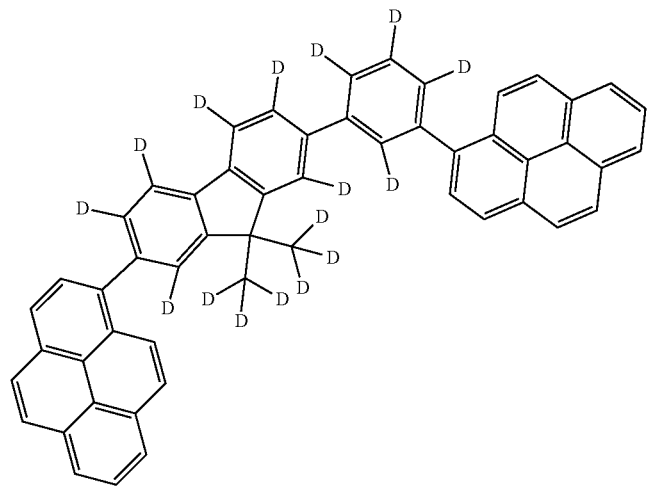
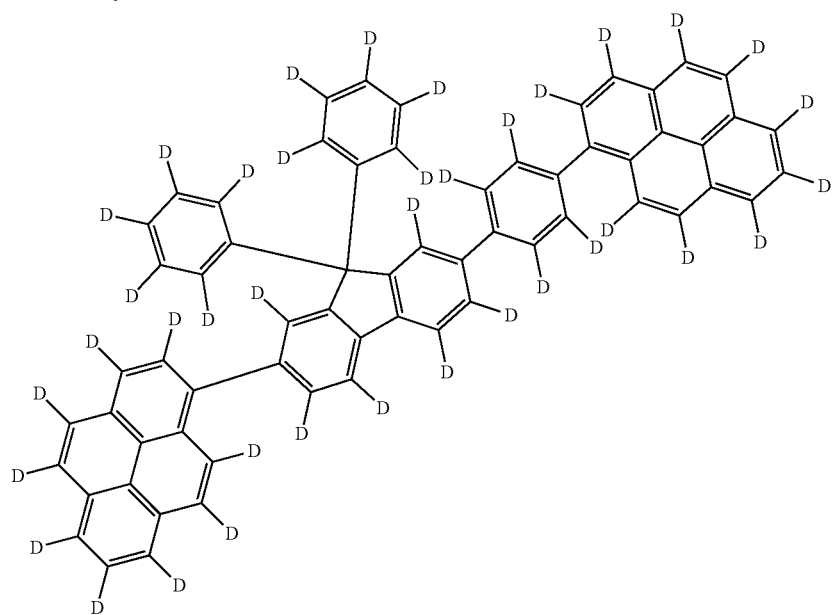
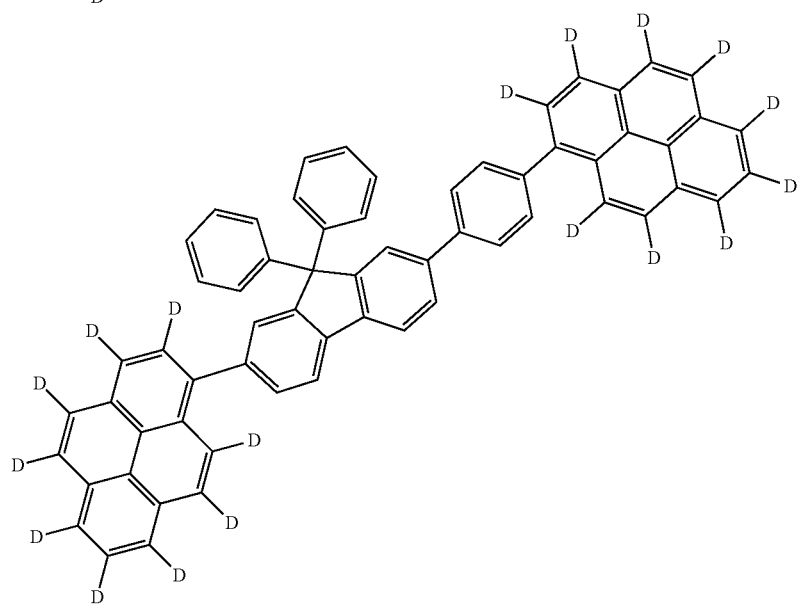

[Formula 157]
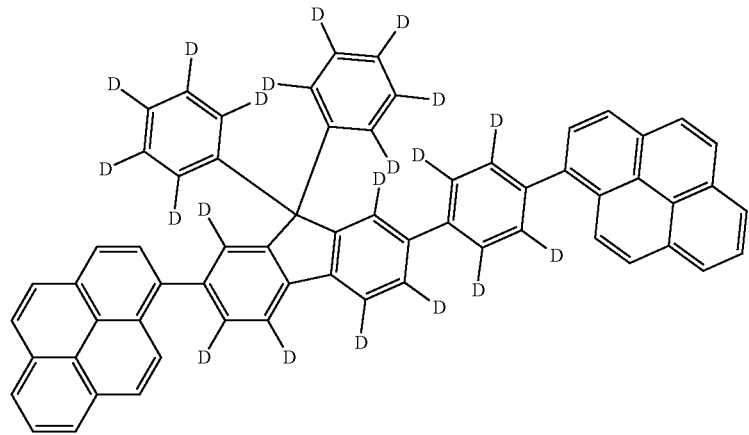
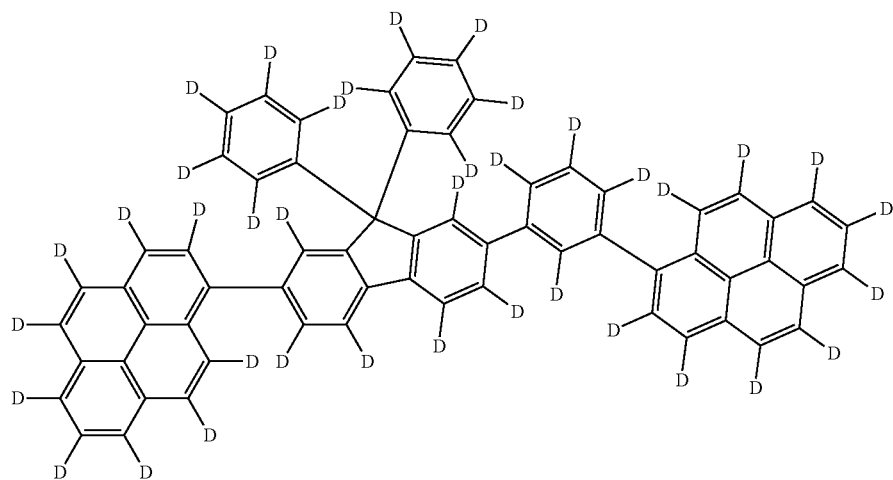
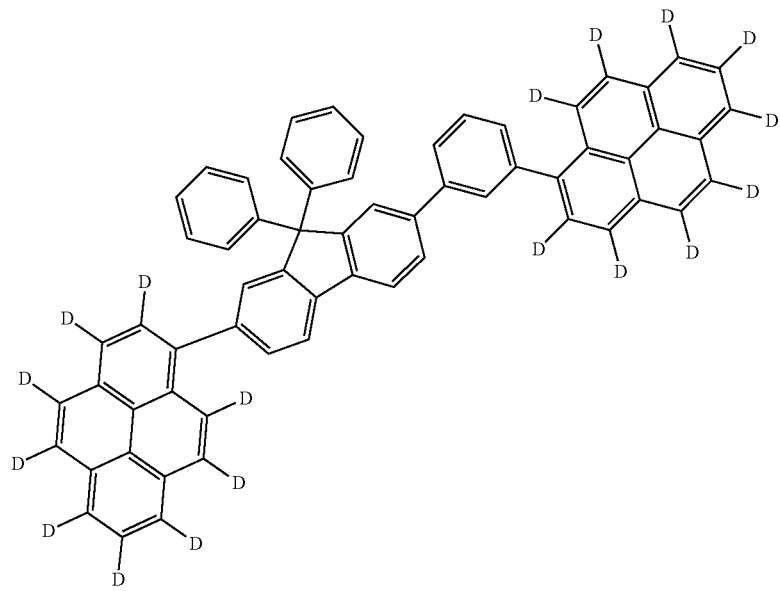

-continued
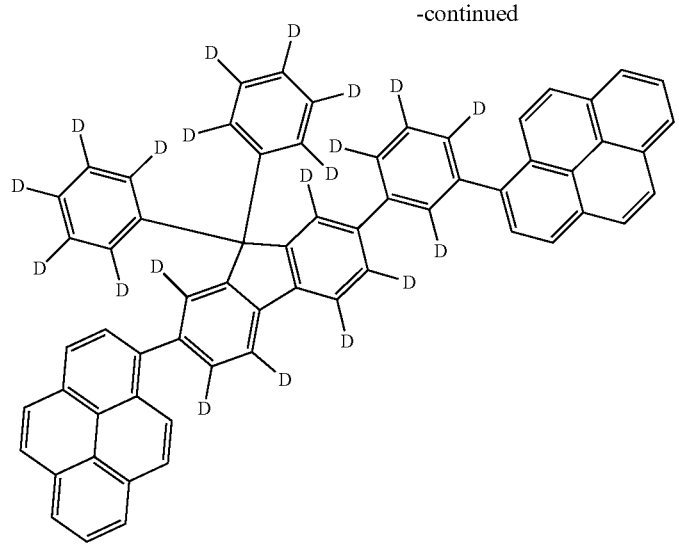
[Formula 158]
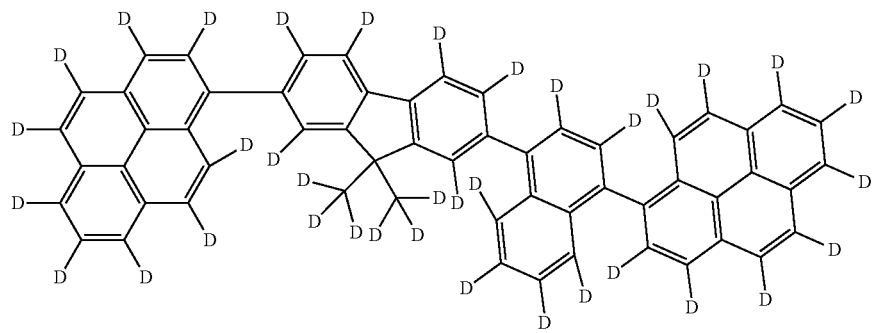
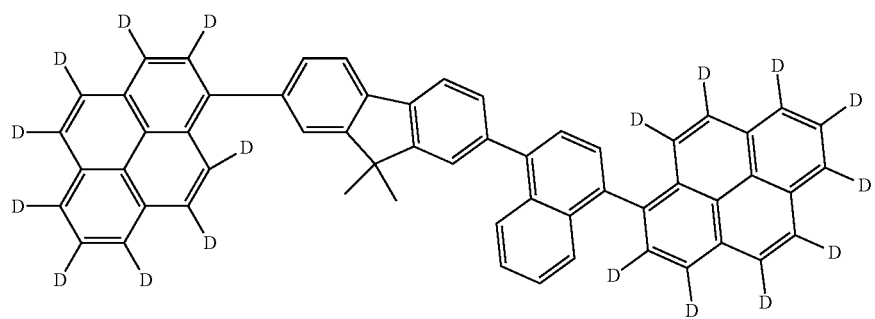

-continued
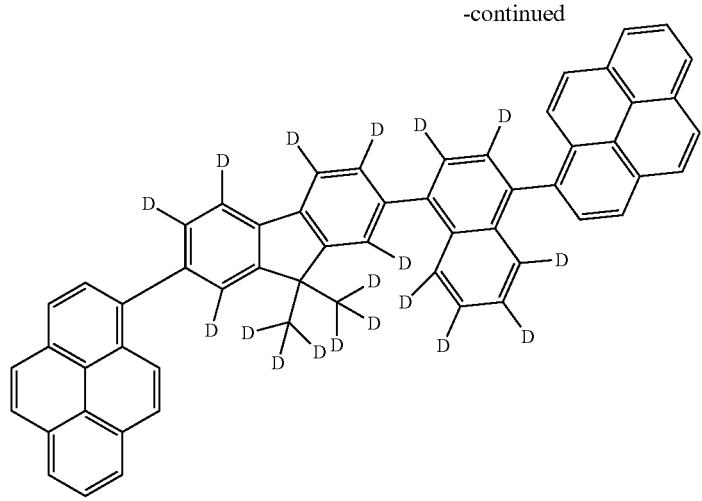
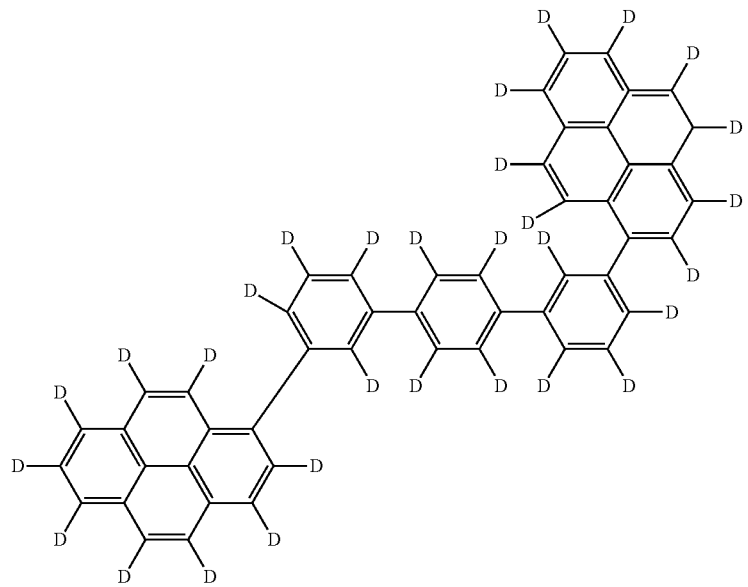
[Formula 159]
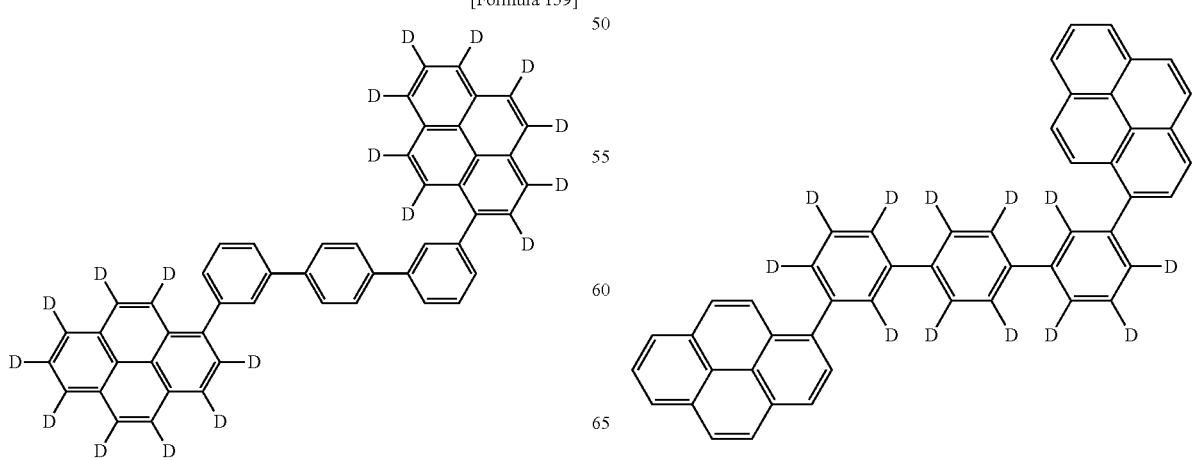
-continued

343
-continued
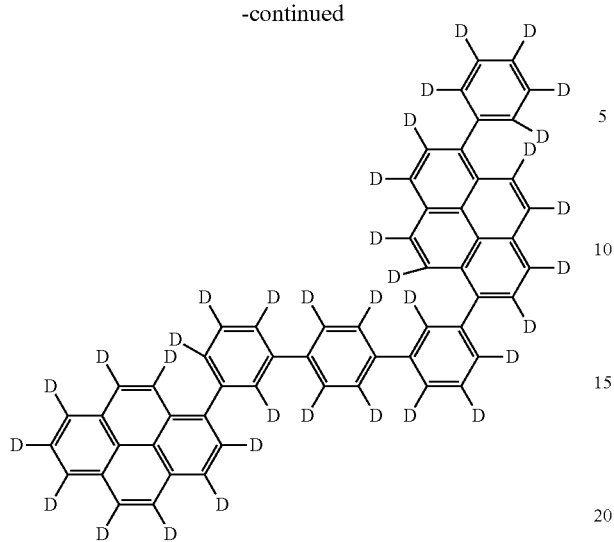
344
-continued
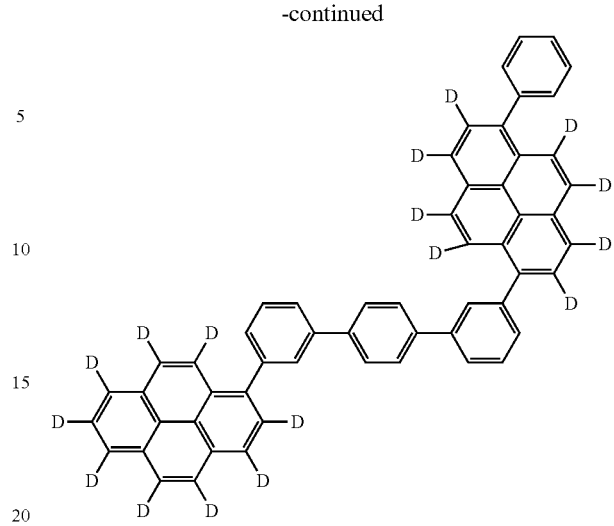
[Formula 160]
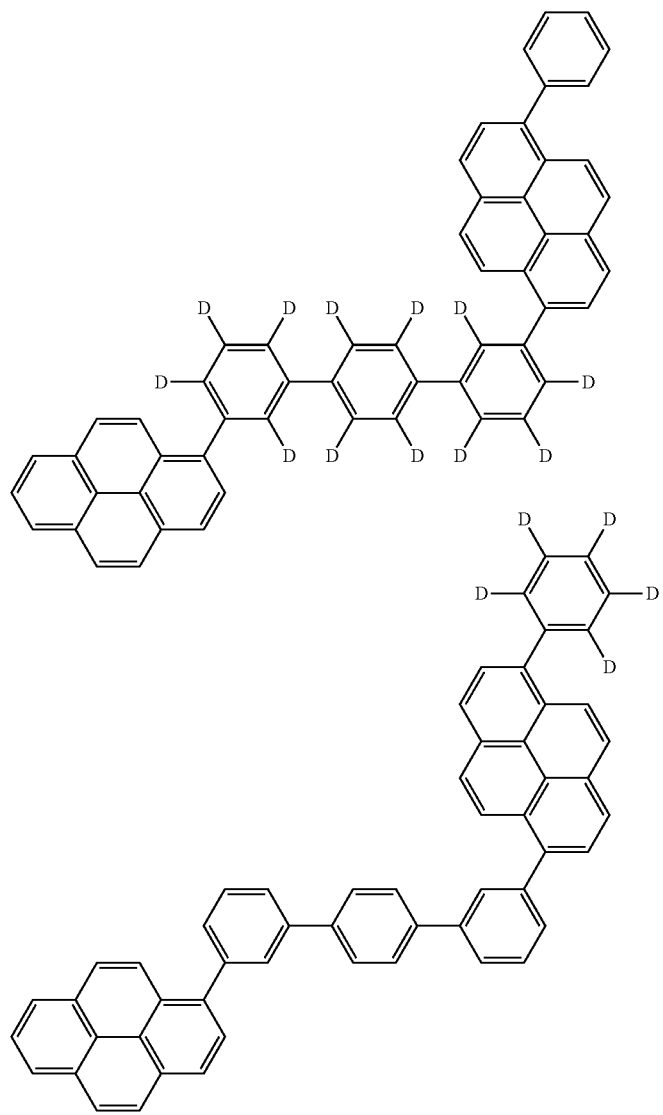

345
-continued
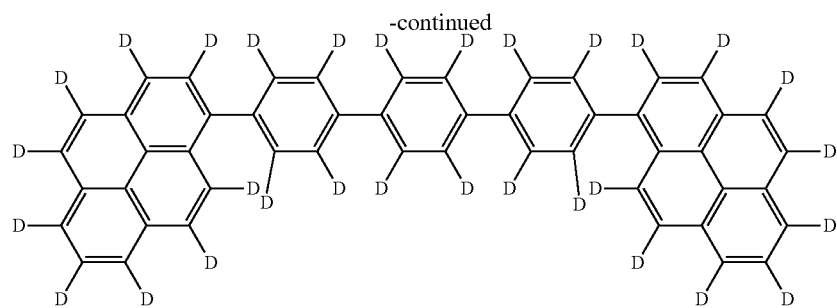
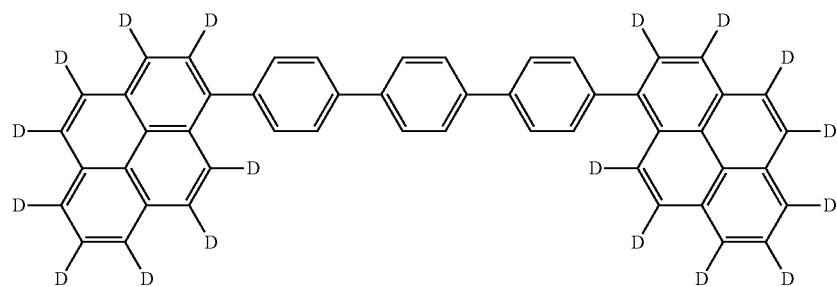 [SMILES: [2H]c1c([2H])c2c([2H])c([2H])c3c([2H])c([2H])c(-c4ccc(-c5ccc(-c6ccc(-c7c([2H])c([2H])c8c([2H])c([2H])c9c([2H])c([2H])c([2H])c%10c([2H])c([2H])c7c8c9%10)cc6)cc5)cc4)c4c([2H])c([2H])c(c1[2H])c2c34]
[Formula 161]
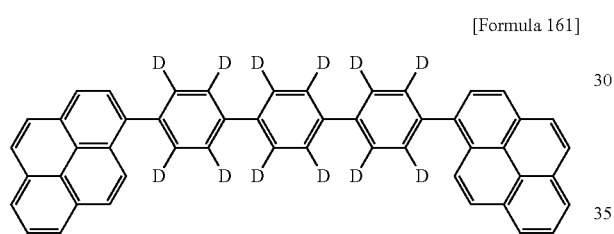
346
-continued
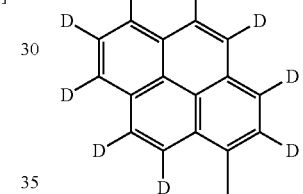
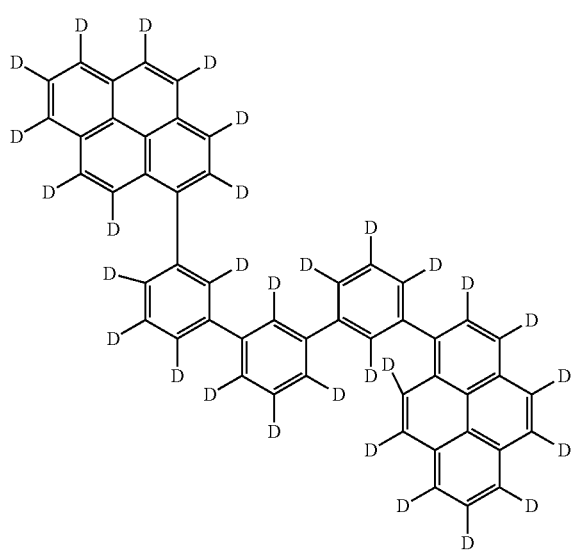
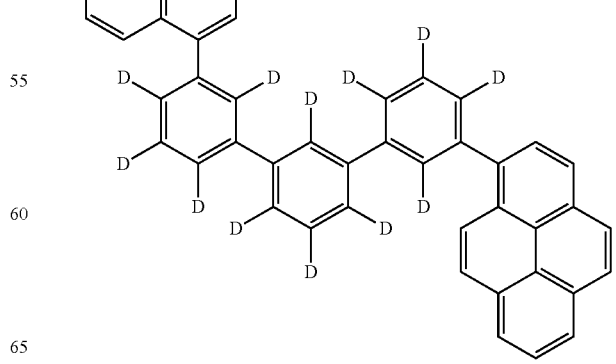

[Formula 162]
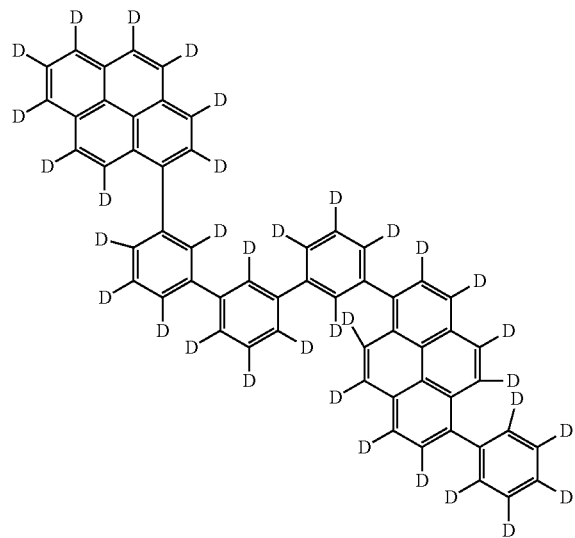
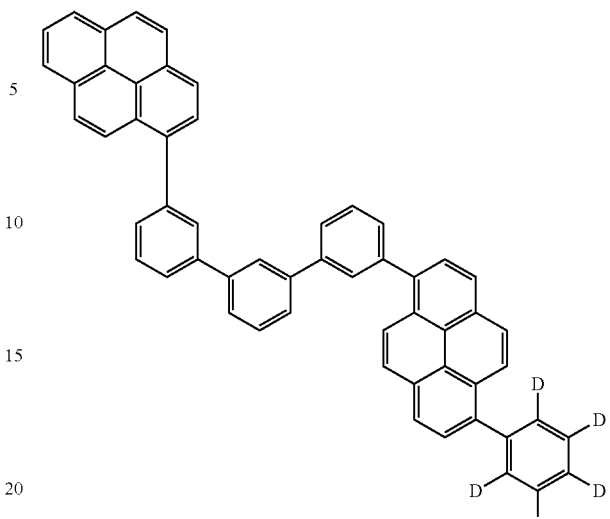
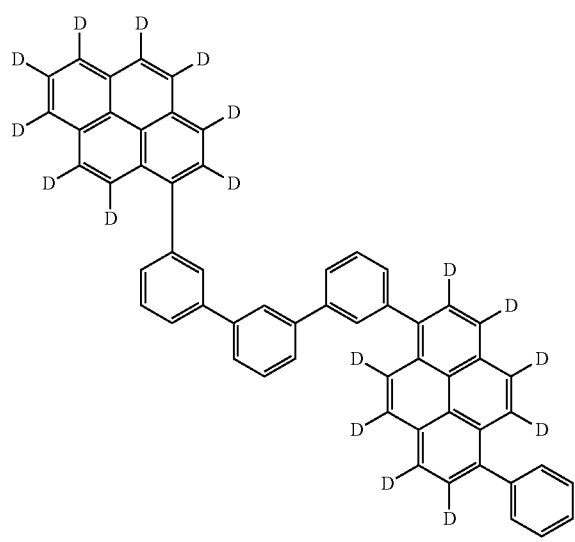
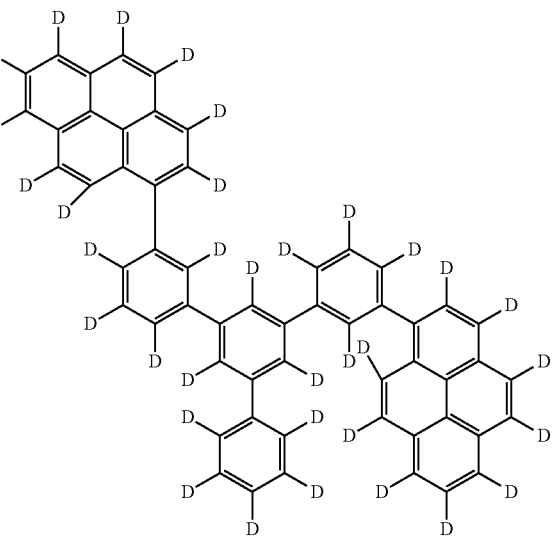
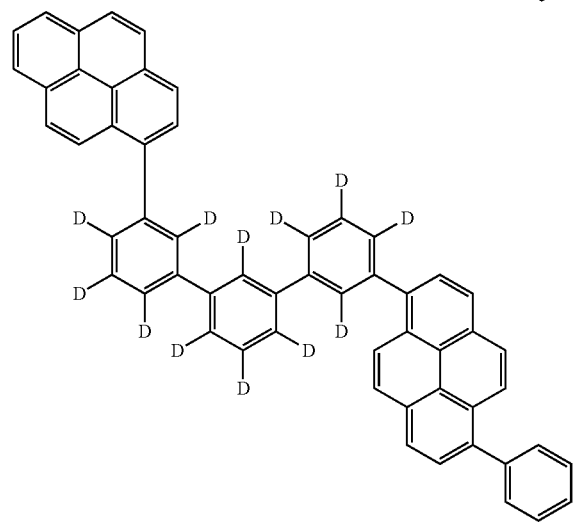
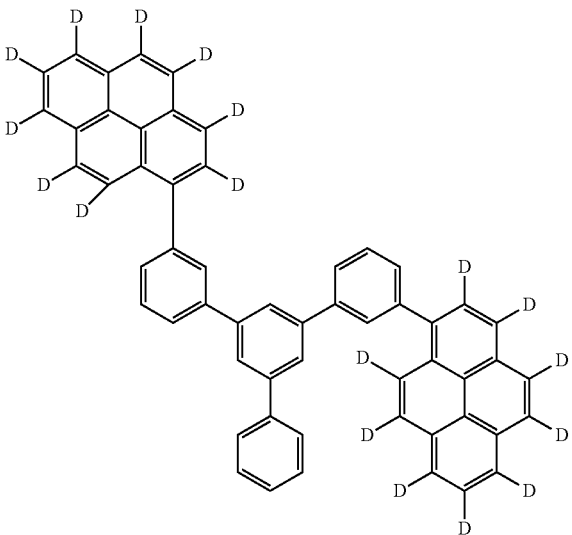

349
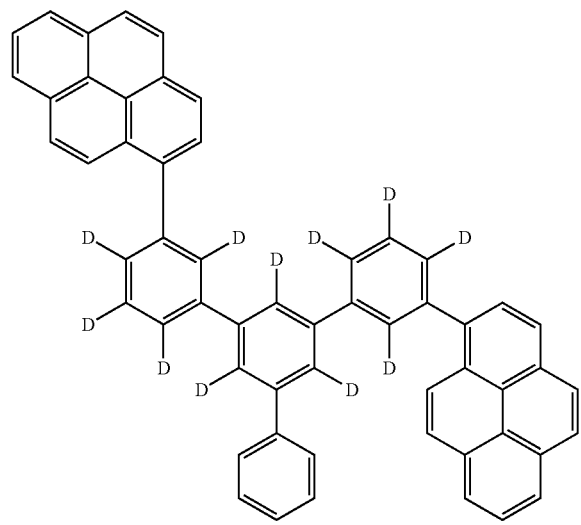
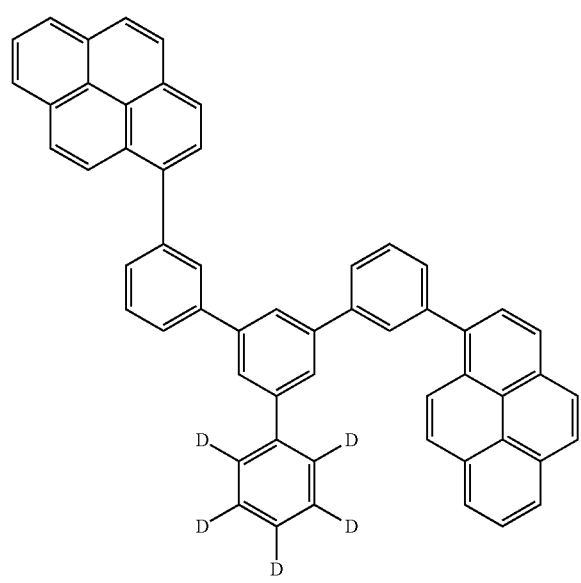
350
[Formula 163]
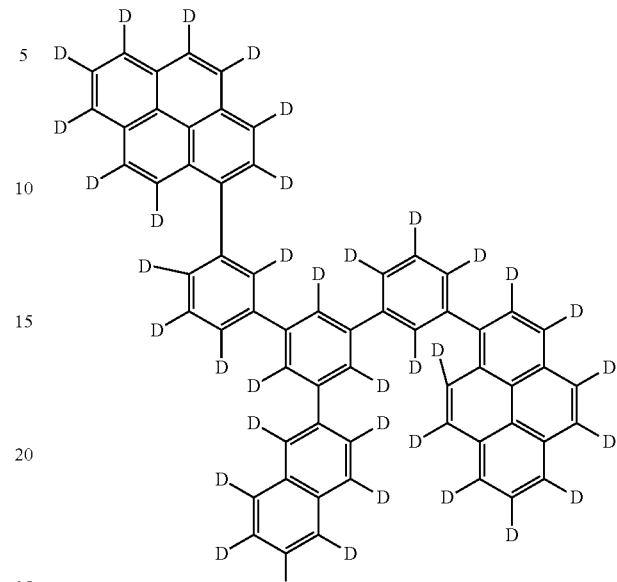
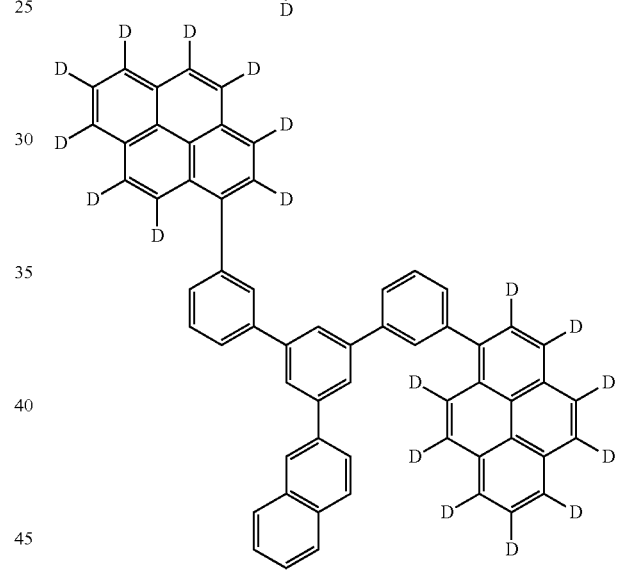

351
-continued
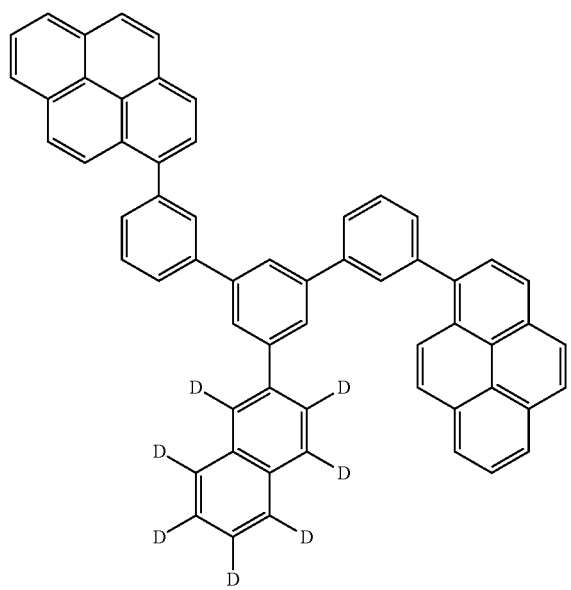
352
-continued
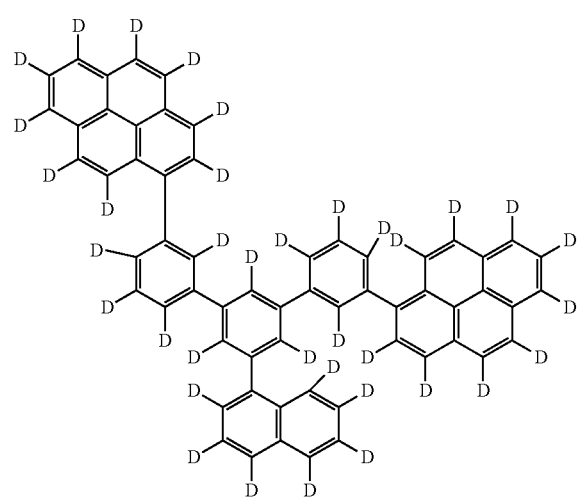

353 354
[Formula 164]
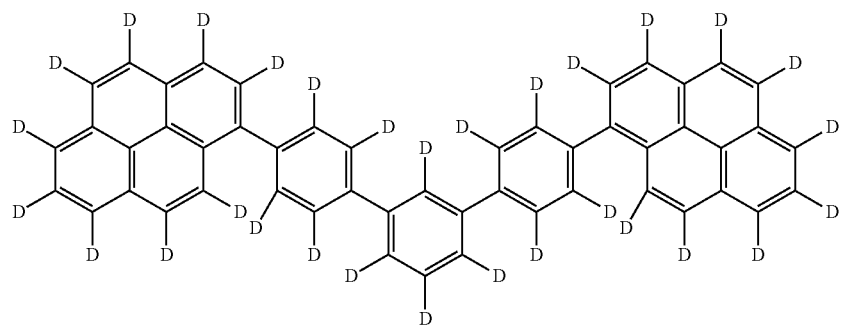
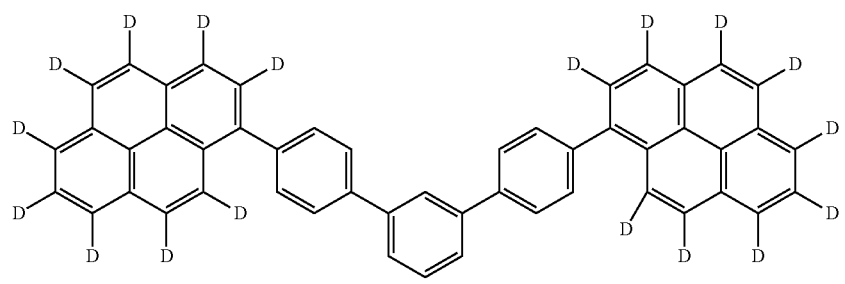
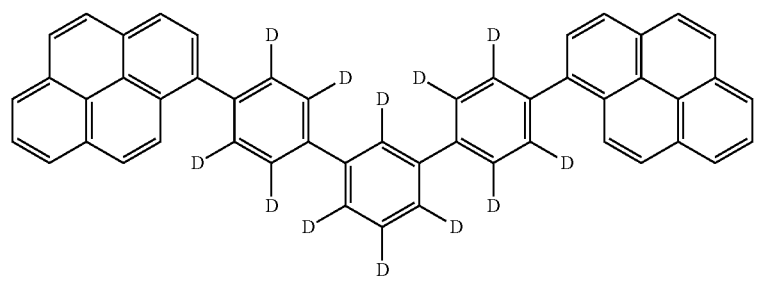
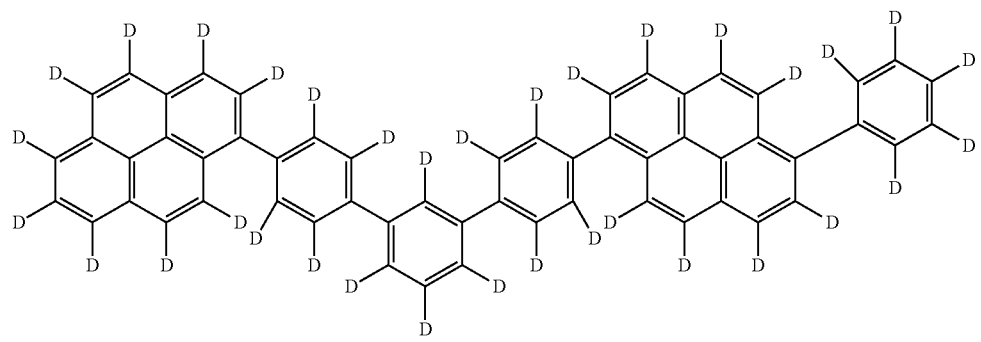
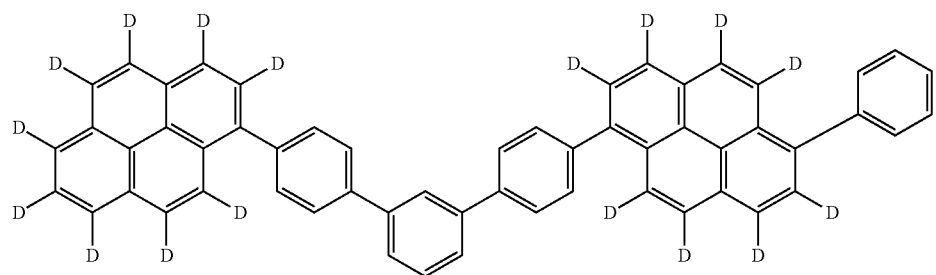

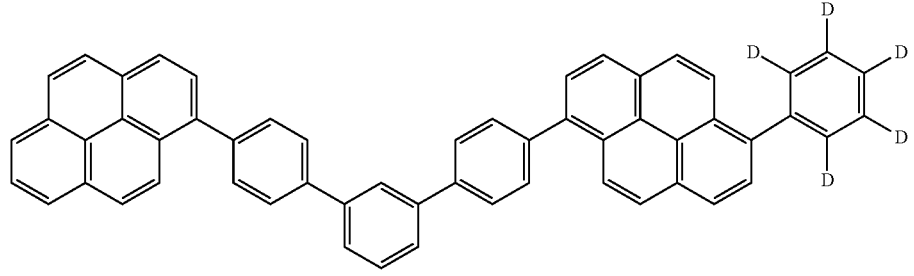 [SMILES: [2H]c1c([2H])c([2H])c(-c2ccc3ccc4c(-c5ccc(-c6cccc(-c7ccc(-c8ccc9ccc%10cccc%11ccc8c9c%10%11)cc7)c6)cc5)ccc5ccc2c3c54)c([2H])c1[2H]]
[Formula 165]
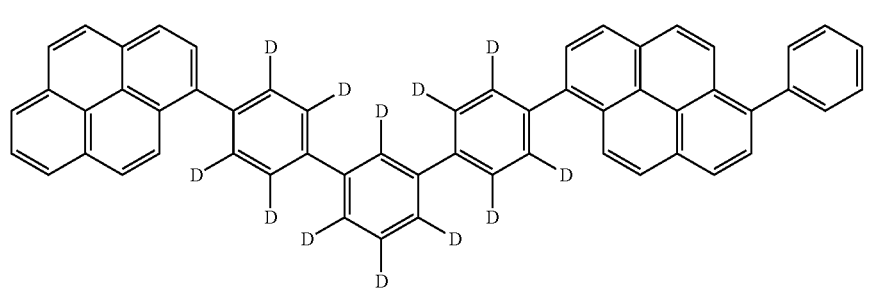
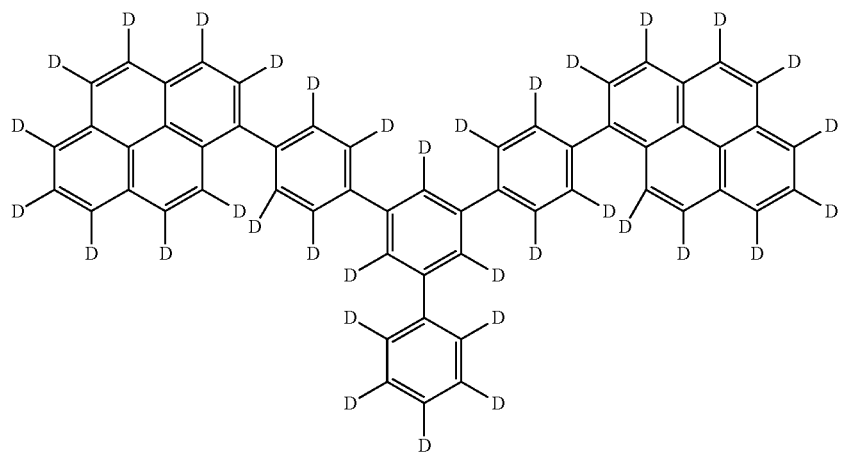
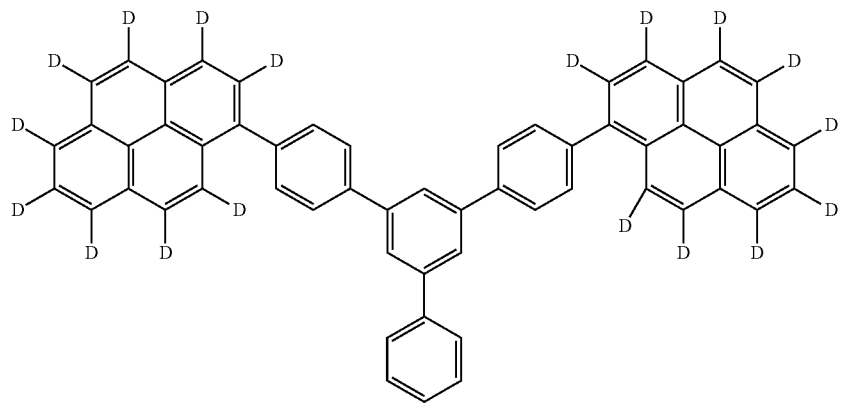

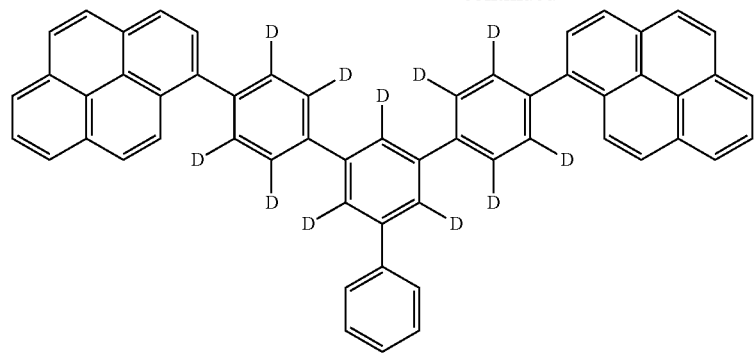
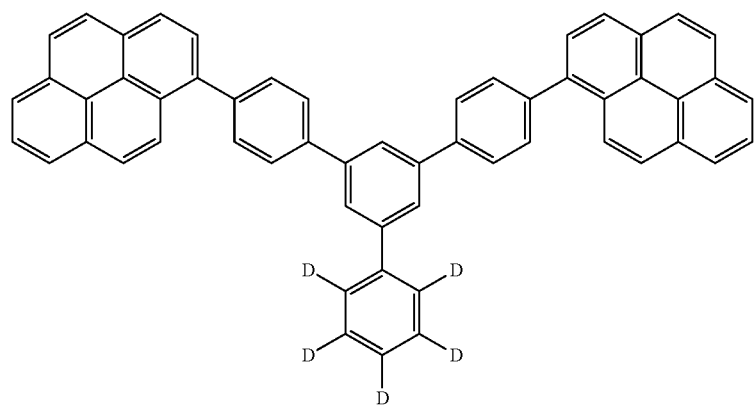
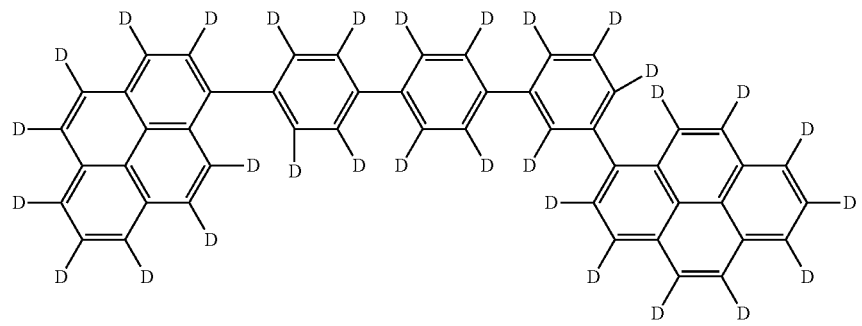
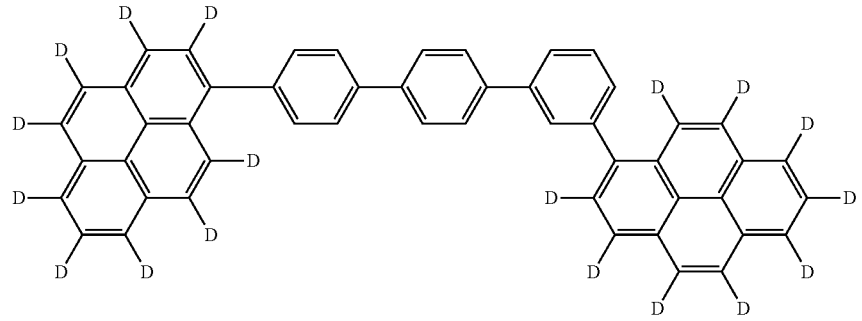
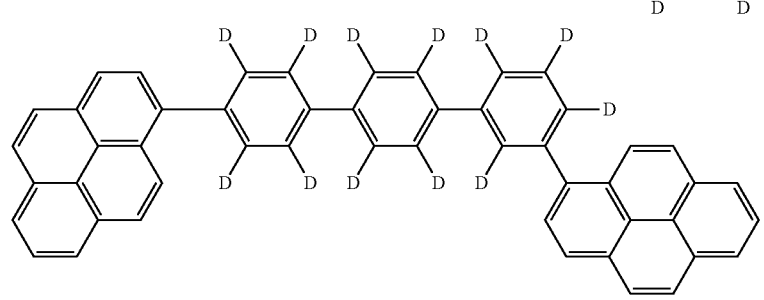

-continued
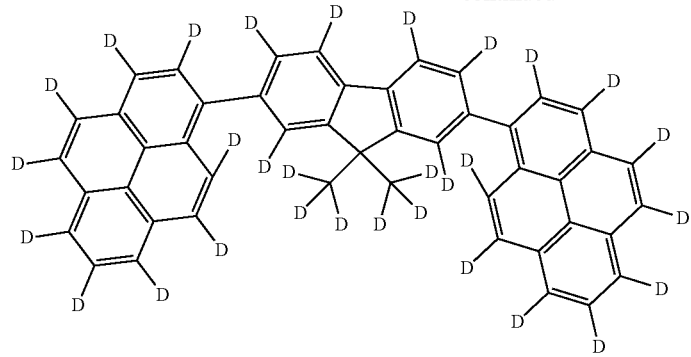 [SMILES: [2H]c1c([2H])c2c(c([2H])c1-c1c([2H])c([2H])c3c([2H])c([2H])c4c([2H])c([2H])c([2H])c5c([2H])c([2H])c1c3c45)C(C([2H])([2H])[2H])(C([2H])([2H])[2H])c1c([2H])c(-c3c([2H])c([2H])c4c([2H])c([2H])c5c([2H])c([2H])c([2H])c6c([2H])c([2H])c3c4c56)c([2H])c([2H])c1-2]
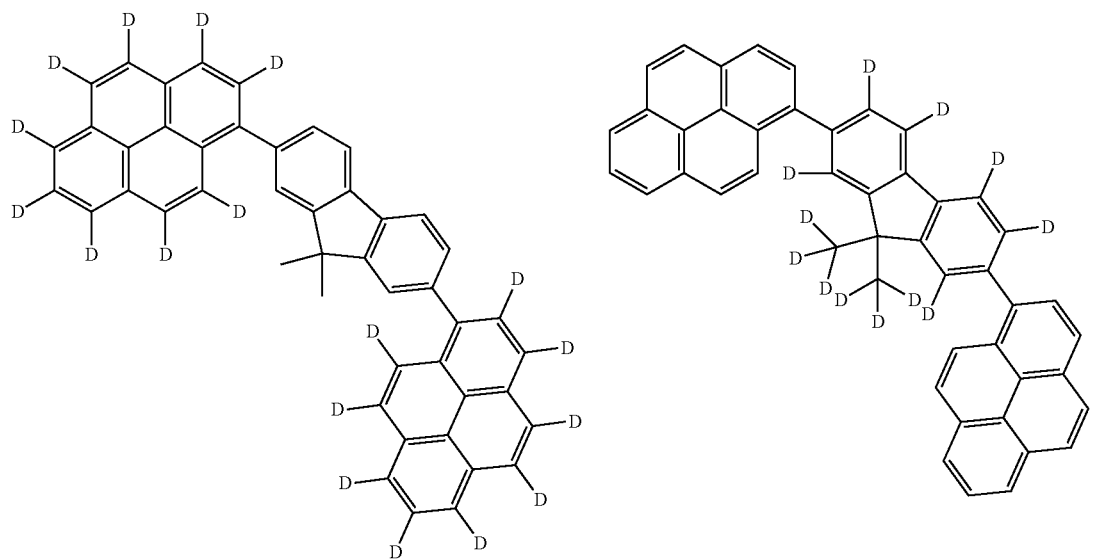
[Formula 166]
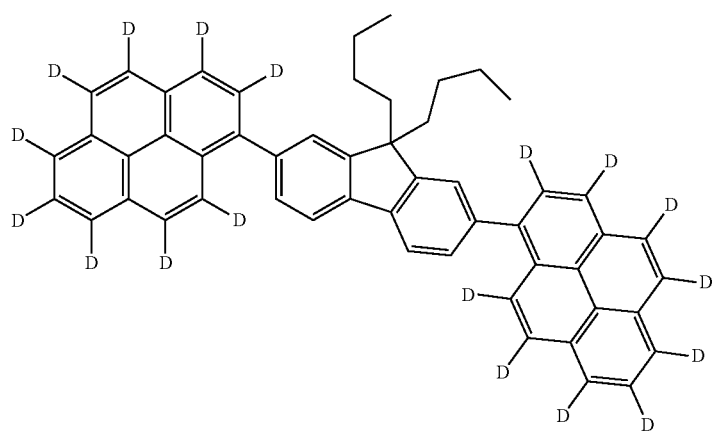

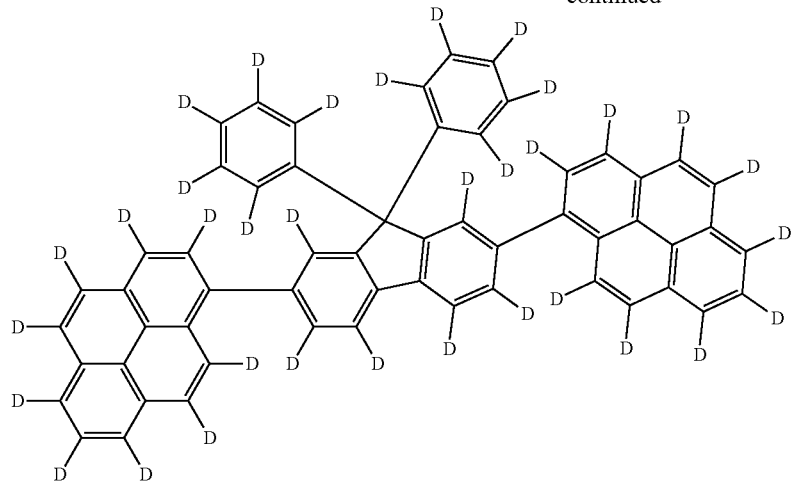
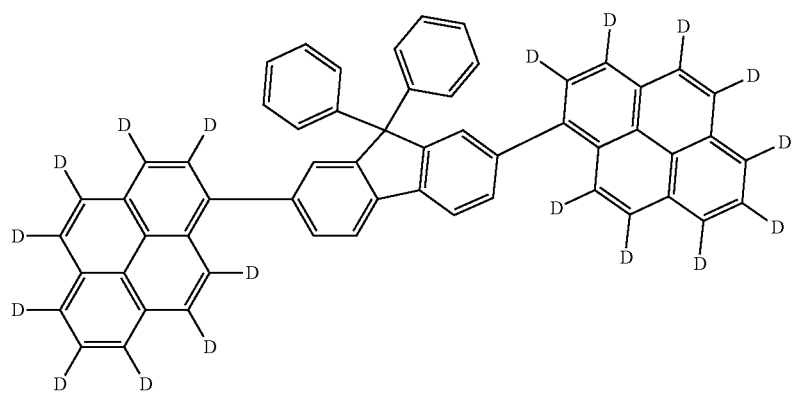
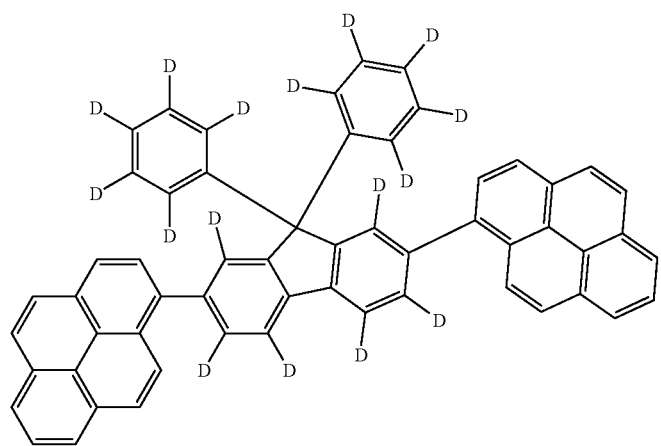

-continued
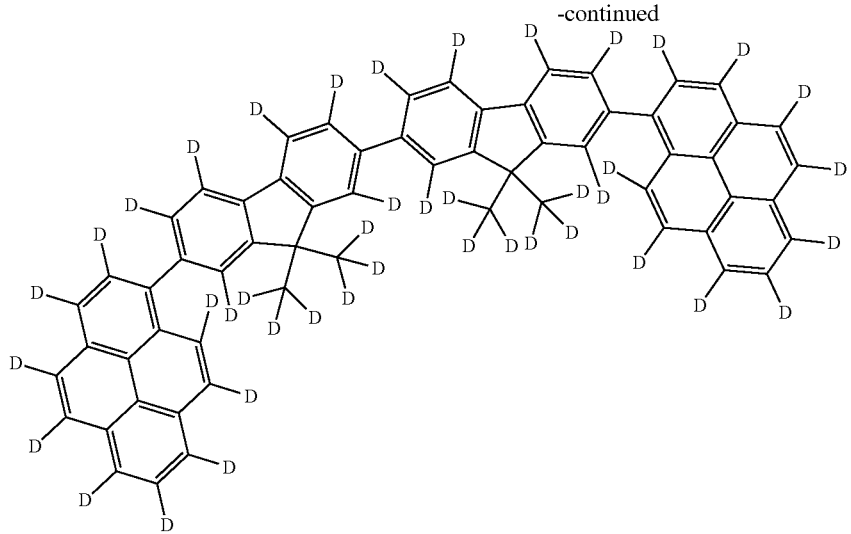
[Formula 167]
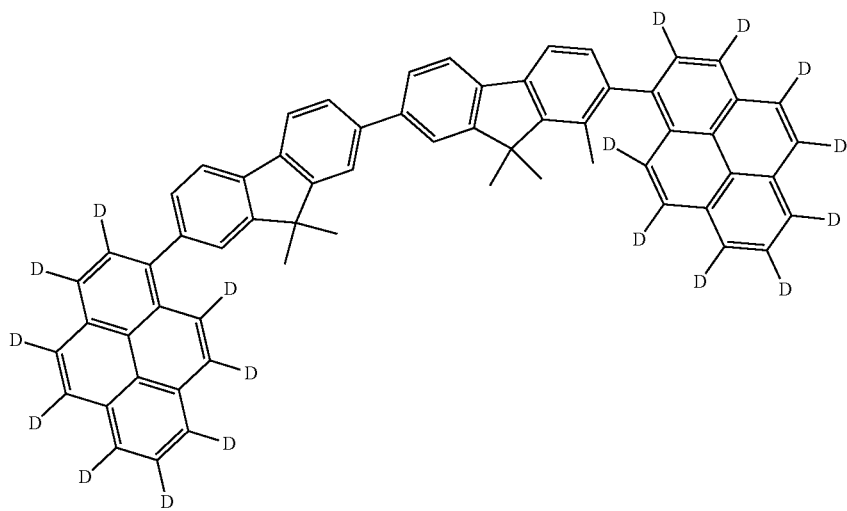
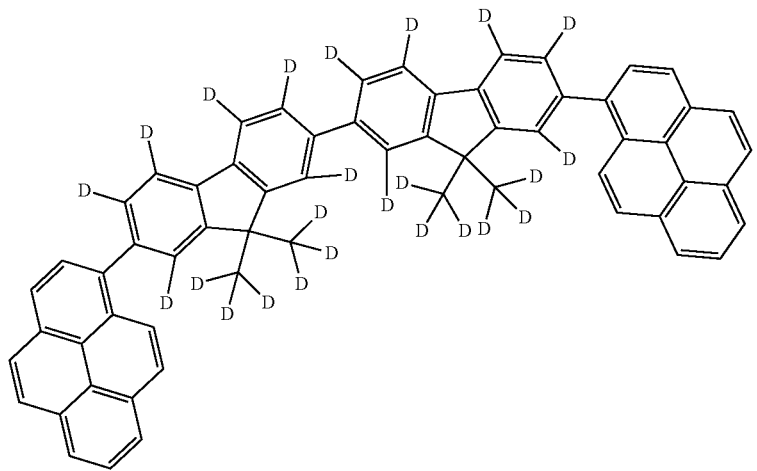

-continued
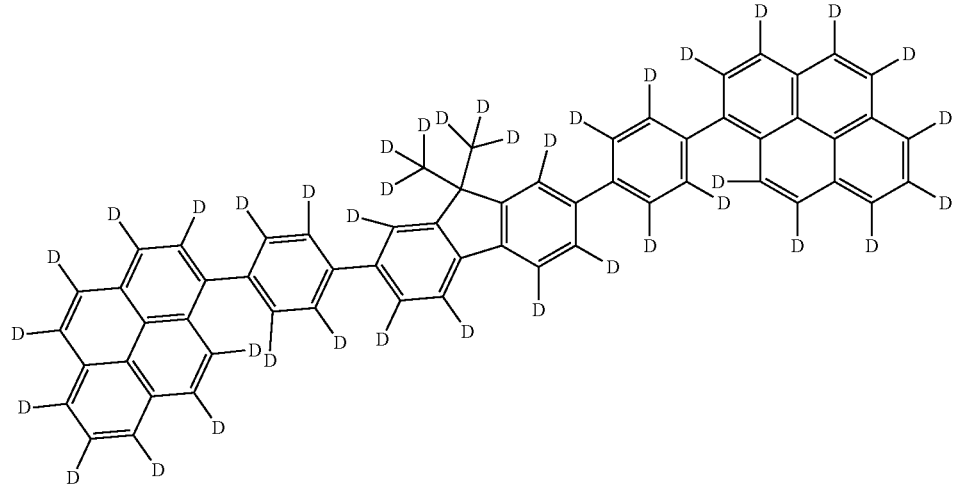
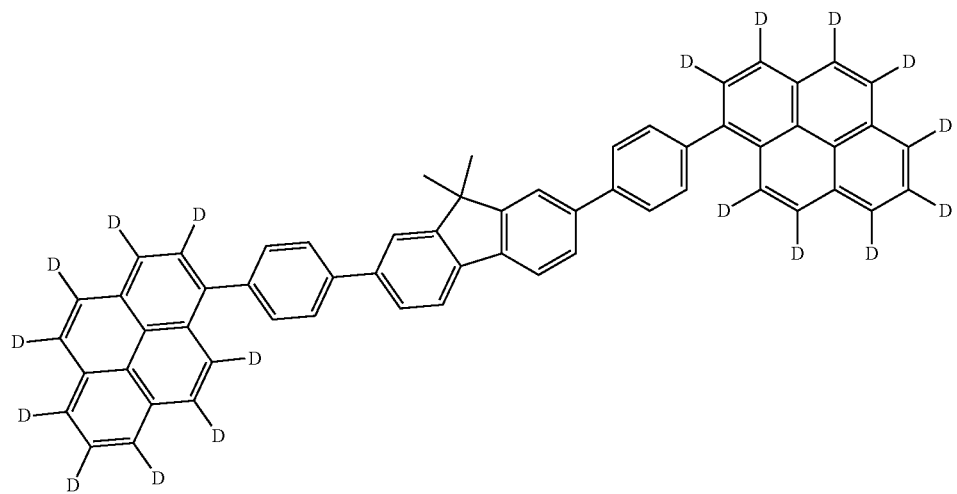
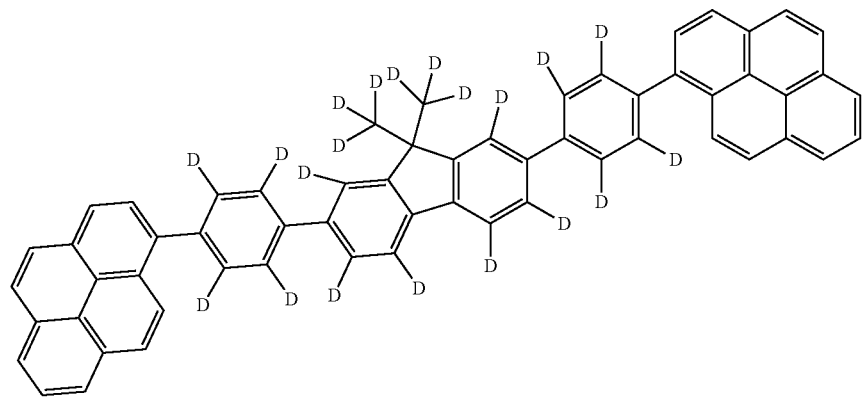

-continued
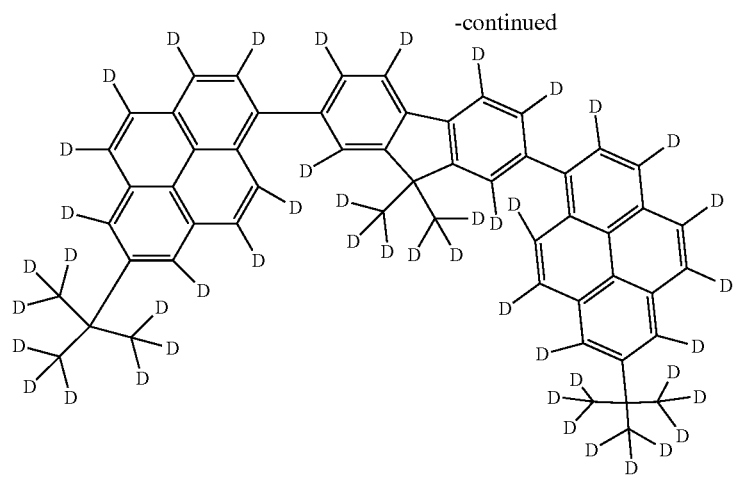
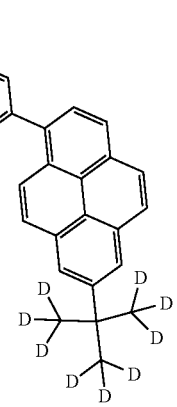
[Formula 168]
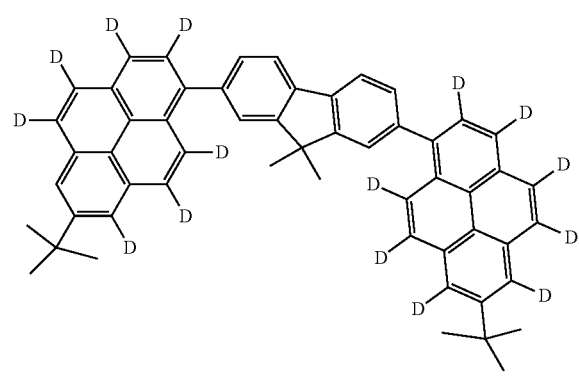
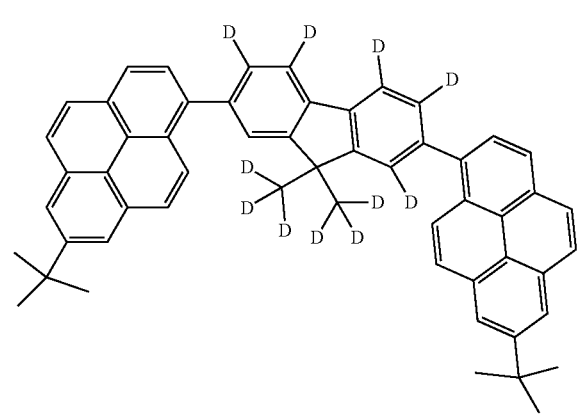
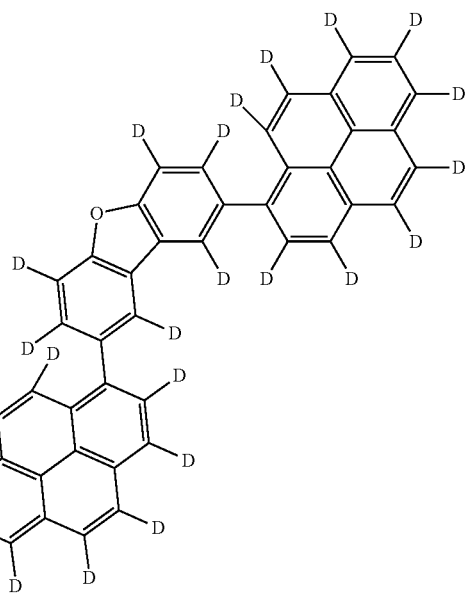

369
-continued
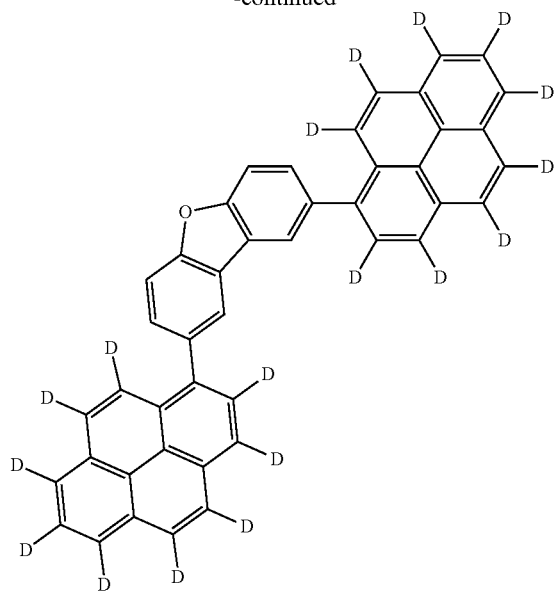
370
-continued
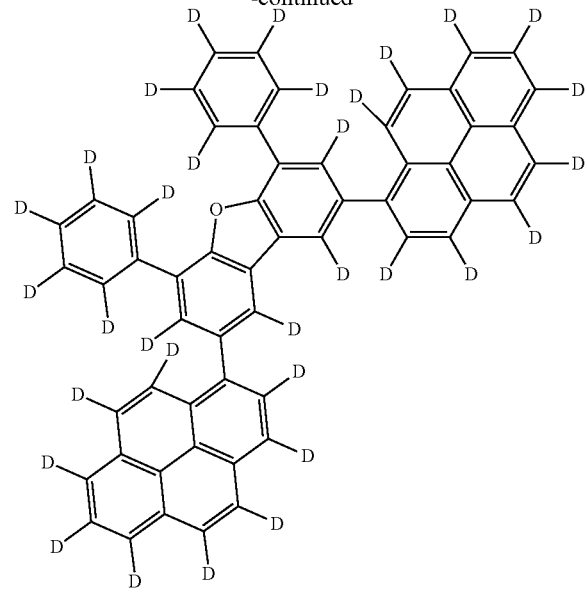
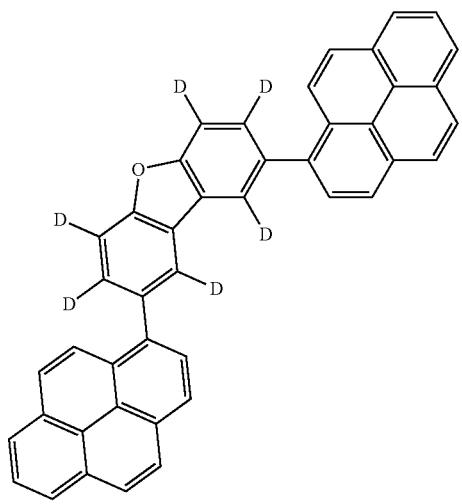

371 372
[Formula 169]
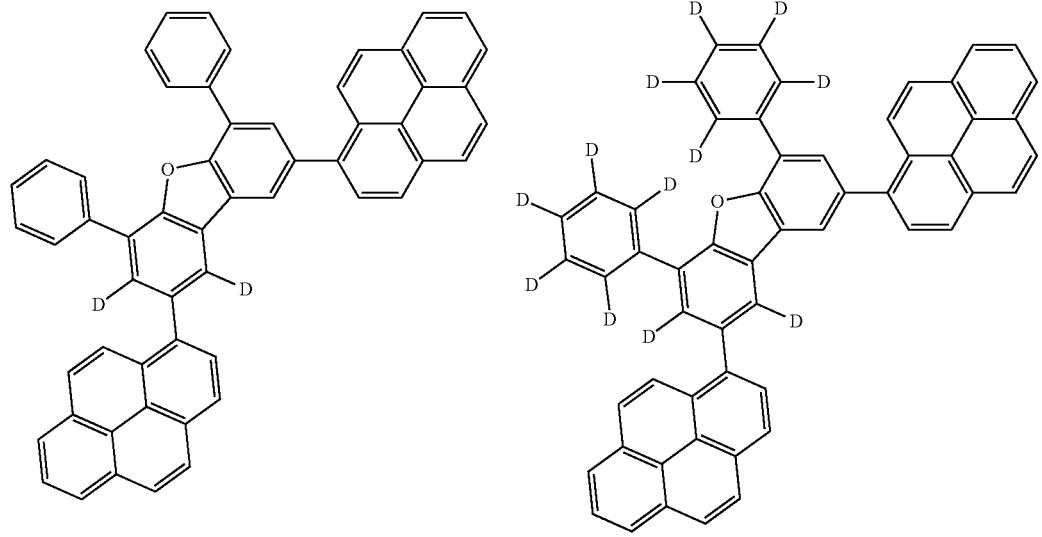
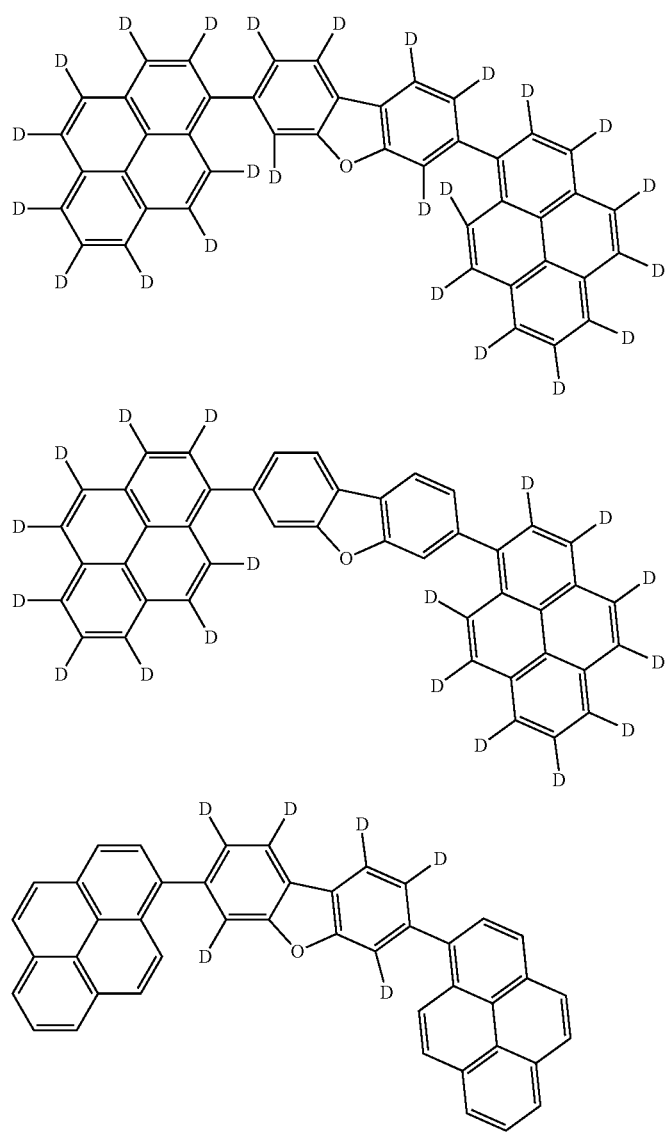

-continued
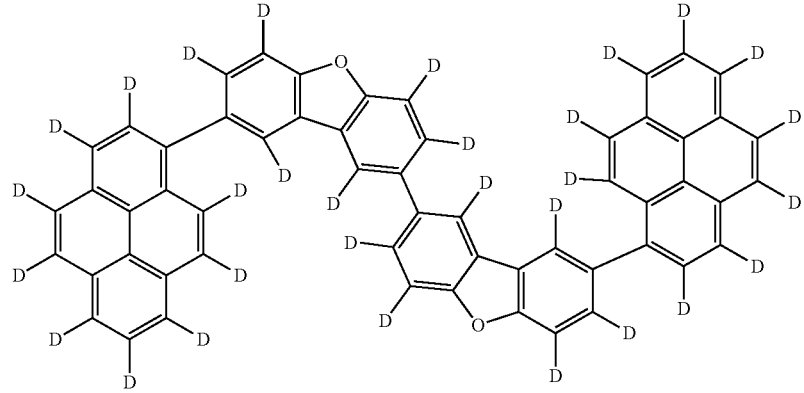
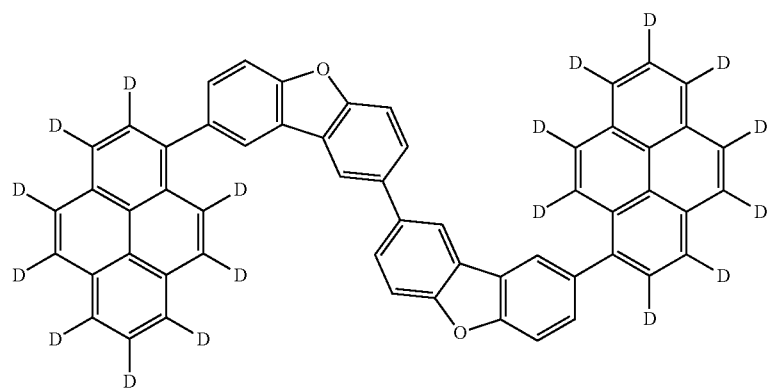
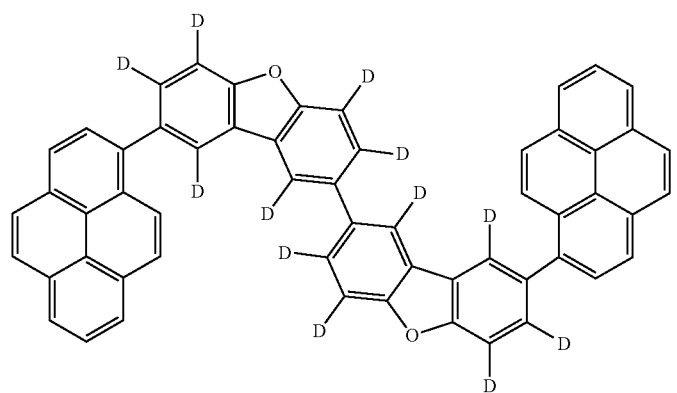

[Formula 170]
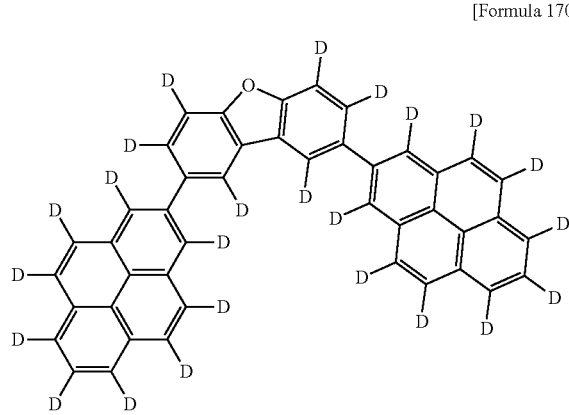
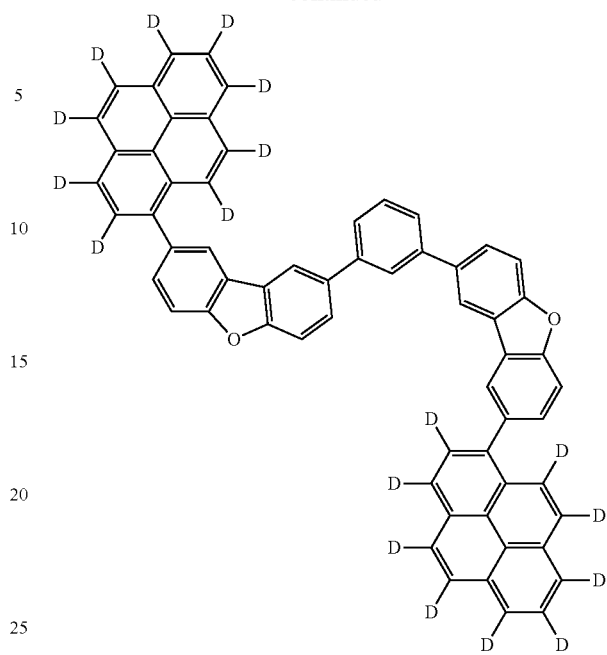
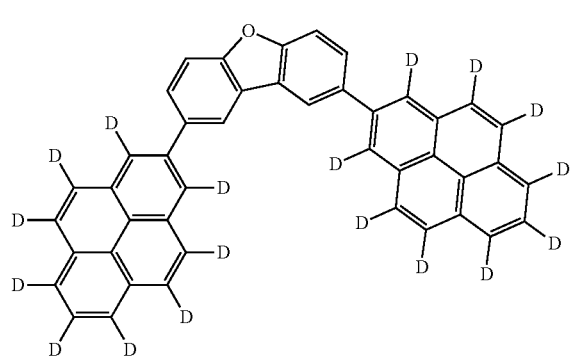
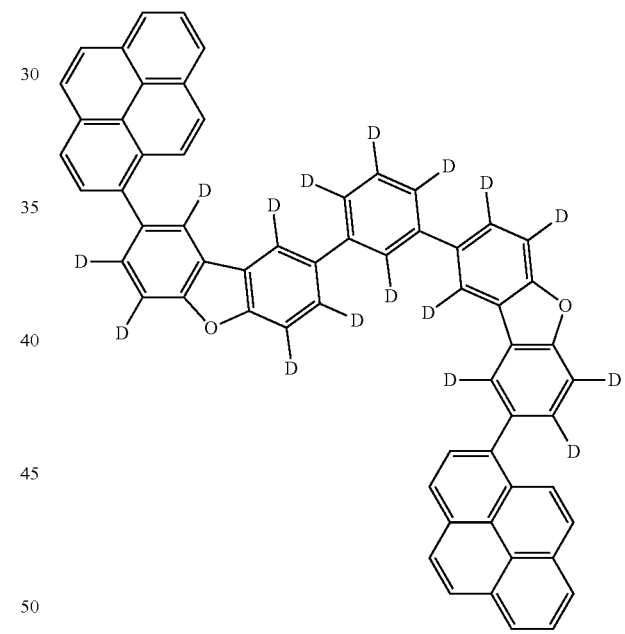
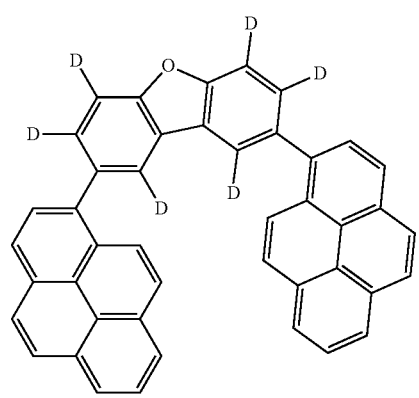
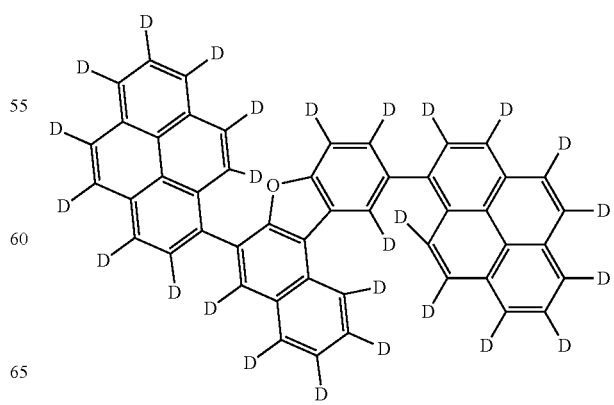

US 11,552,259 B1
377
-continued
378
-continued
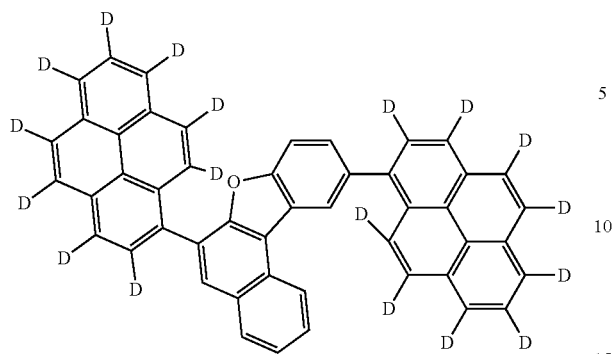
[Formula 171]

[Formula 172]

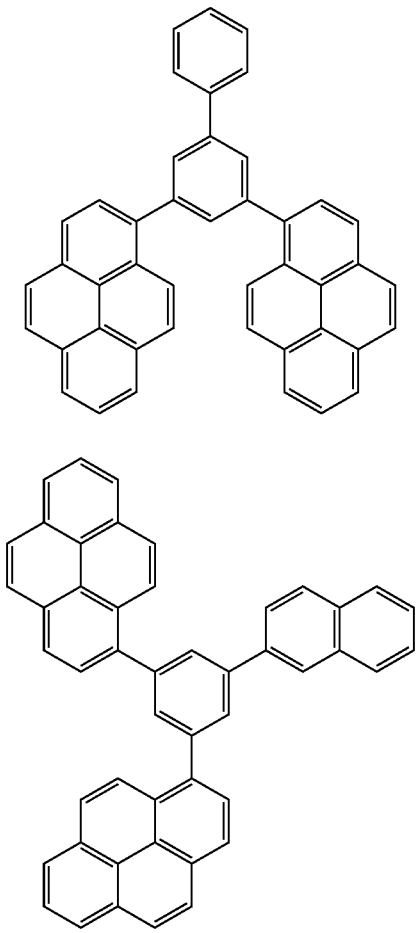

[Formula 173]

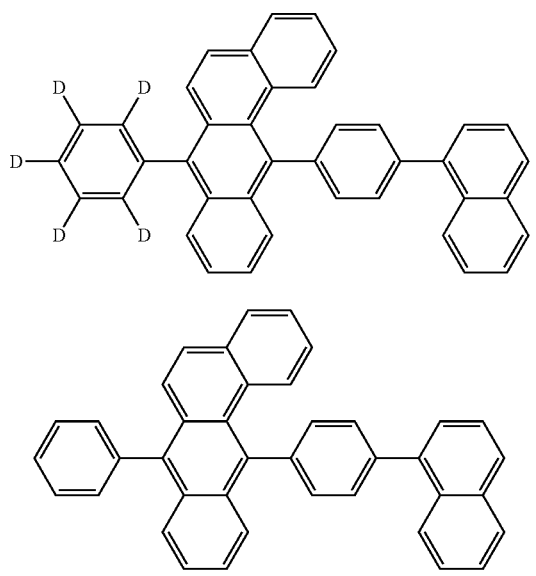

[Formula 174]


Second Host Material

In the organic EL device according to the exemplary embodiment, the second host material is also preferably an anthracene derivative.

In the organic EL device according to the exemplary embodiment, the second host material is also preferably the second compound represented by the formula (2).

[Formula 175]

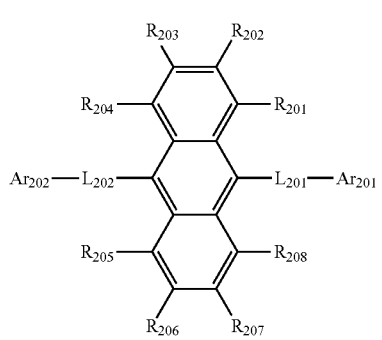

(2)

In the formula (2):

$R_{201}$ to $R_{208}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a substituted or unsubstituted aralkyl group having 7 to 50 carbon atoms, a group represented by —C(=O)$R_{801}$, a group represented by —COO$R_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

$L_{201}$ and $L_{202}$ are each independently a single bond, a substituted or unsubstituted arylene group having 6 to 50 ring carbon atoms, or a substituted or unsubstituted divalent heterocyclic group having 5 to 50 ring atoms; and $Ar_{201}$ and $Ar_{202}$ are each independently a substituted or unsubstituted aryl group having 6 to 50 ring carbon atoms, or a substituted or unsubstituted heterocyclic group having 5 to 50 ring atoms.

In the second compound according to the exemplary embodiment: $R_{901}$, $R_{902}$, $R_{903}$, $R_{904}$, $R_{905}$, $R_{906}$, $R_{907}$, $R_{801}$, and $R_{802}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when a plurality of $R_{901}$ are present, the plurality of $R_{901}$ are mutually the same or different;

when a plurality of $R_{902}$ are present, the plurality of $R_{902}$ are mutually the same or different;

when a plurality of $R_{903}$ are present, the plurality of $R_{903}$ are mutually the same or different;

when a plurality of $R_{904}$ are present, the plurality of $R_{904}$ are mutually the same or different;

when a plurality of $R_{905}$ are present, the plurality of $R_{905}$ are mutually the same or different;

when a plurality of $R_{906}$ are present, the plurality of $R_{906}$ are mutually the same or different;

when a plurality of $R_{907}$ are present, the plurality of $R_{907}$ are mutually the same or different;

when a plurality of $R_{801}$ are present, the plurality of $R_{801}$ are mutually the same or different; and when a plurality of $R_{802}$ are present, the plurality of $R_{802}$ are mutually the same or different.

In the organic EL device according to the exemplary embodiment, $R_{201}$ to $R_{208}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a substituted or unsubstituted aralkyl group having 7 to 50 carbon atoms, a group represented by —C(=O)$R_{801}$, a group represented by —COO$R_{802}$, a halogen atom, a cyano group, or a nitro group;

$L_{201}$ and $L_{202}$ are each independently a single bond, a substituted or unsubstituted arylene group having 6 to 50 ring carbon atoms, or a substituted or unsubstituted divalent heterocyclic group having 5 to 50 ring atoms; and $Ar_{201}$ and $Ar_{202}$ are each independently a substituted or unsubstituted aryl group having 6 to 50 ring carbon atoms, or a substituted or unsubstituted heterocyclic group having 5 to 50 ring atoms.

In the organic EL device according to the exemplary embodiment, it is preferable that: $L_{201}$ and $L_{202}$ are each independently a single bond, or a substituted or unsubstituted arylene group having 6 to 50 ring carbon atoms; and $Ar_{201}$ and $Ar_{202}$ are each independently a substituted or unsubstituted aryl group having 6 to 50 ring carbon atoms.

In the organic EL device according to the exemplary embodiment, $Ar_{201}$ and $Ar_{202}$ are preferably each independently a phenyl group, a naphthyl group, a phenanthryl group, a biphenyl group, a terphenyl group, a diphenylfluorenyl group, a dimethylfluorenyl group, a benzodiphenylfluorenyl group, a benzodimethylfluorenyl group, a dibenzofuranyl group, a dibenzothienyl group, a naphthobenzofuranyl group, or a naphthobenzothienyl group.

In the organic EL device according to the exemplary embodiment, the second compound represented by the formula (2) is preferably a compound represented by a formula (201), a formula (202), a formula (203), a formula (204), a formula (205), a formula (206), a formula (207), a formula (208), or a formula (209) below.

[Formula 176]

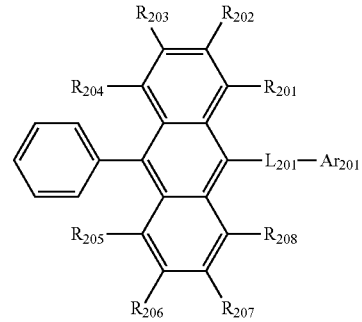

(201)

[Formula 177]

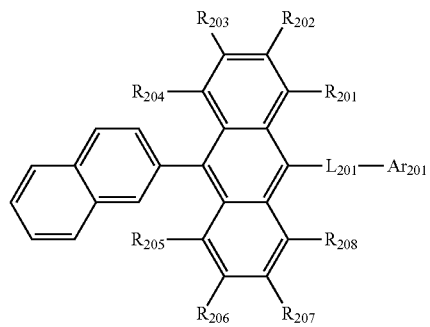

(202)

[Formula 178] (203)
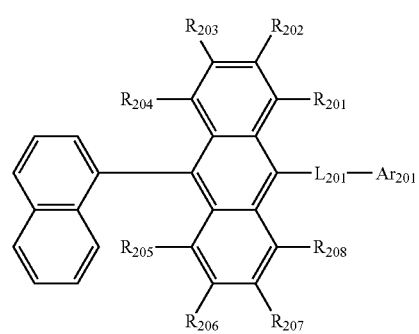
[Formula 181] (206)
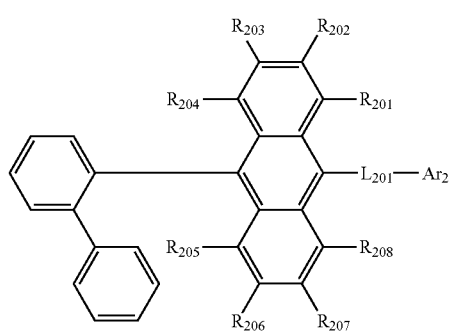
[Formula 179] (204)
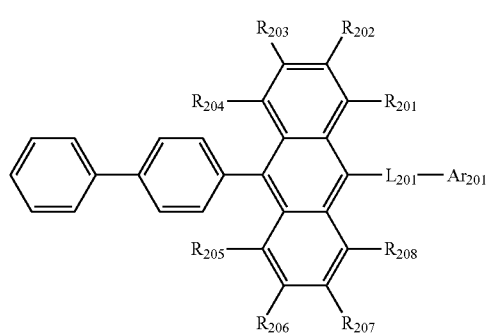
[Formula 182] (207)
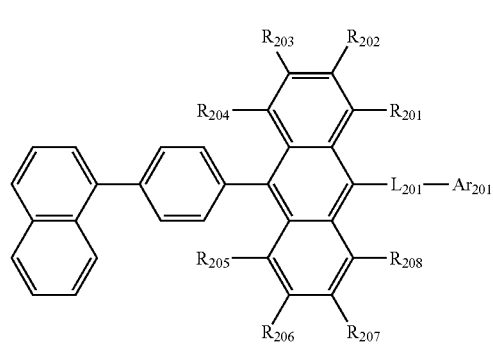
[Formula 180] (205)
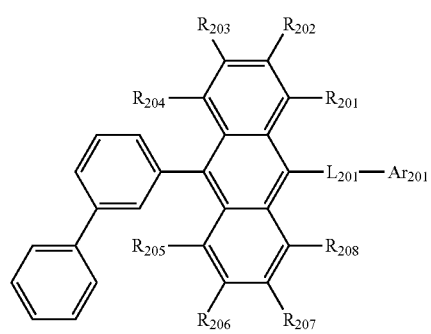
[Formula 183] (208)
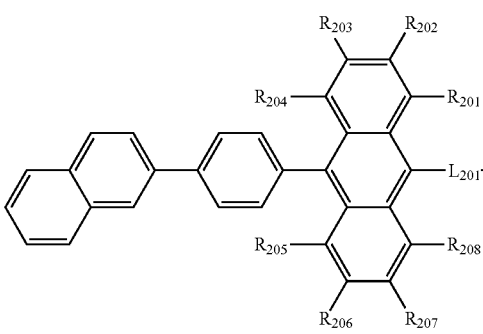

[Formula 184]

(209)

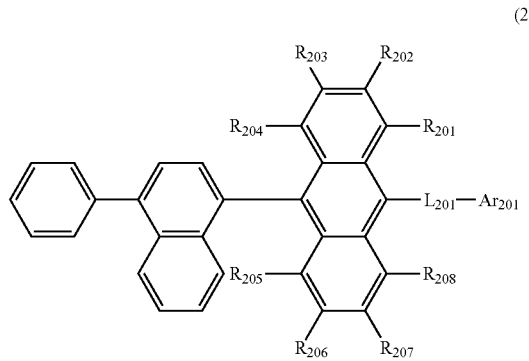

[Formula 187]

(223)

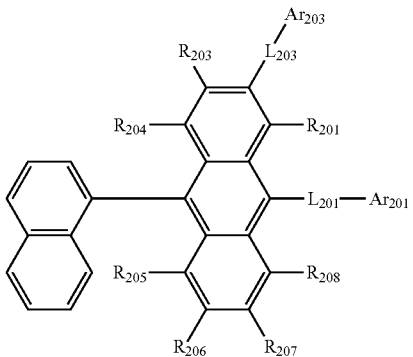

In the formulae (201) to (209):

$L_{201}$ and $Ar_{201}$ represent the same as $L_{201}$ and $Ar_{201}$ in the formula (2); and $R_{201}$ to $R_{208}$ each independently represent the same as $R_{201}$ to $R_{208}$ in the formula (2).

The second compound represented by the formula (2) is also preferably a compound represented by a formula (221), a formula (222), a formula (223), a formula (224), a formula (225), a formula (226), a formula (227), a formula (228), or a formula (229) below.

[Formula 185]

(221)

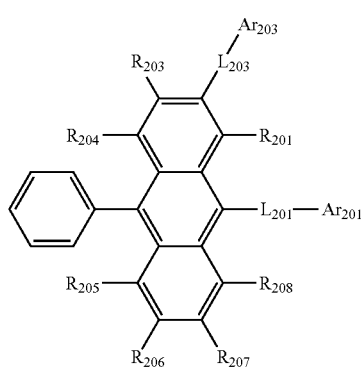

[Formula 188]

(224)

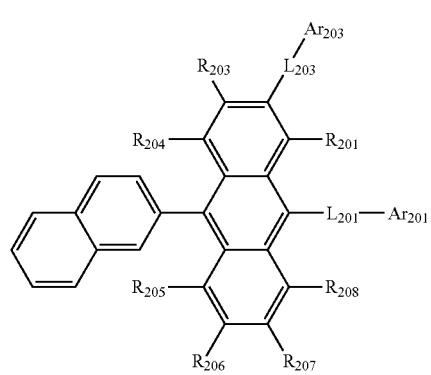

[Formula 186]

(222)

[Formula 189]

(225)

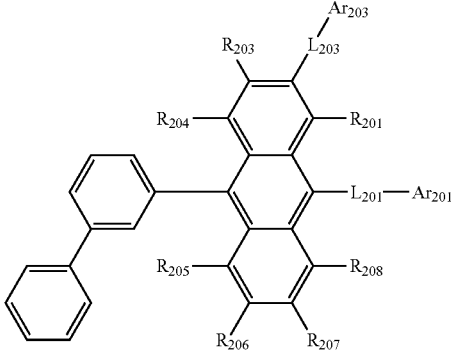

[Formula 190]

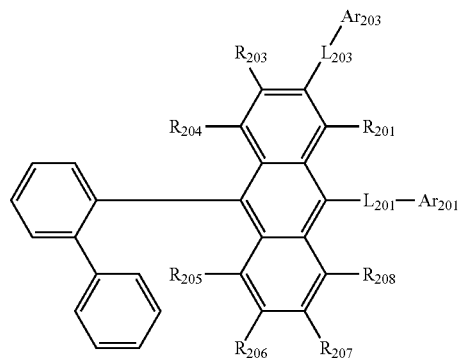

(226)

[Formula 191]

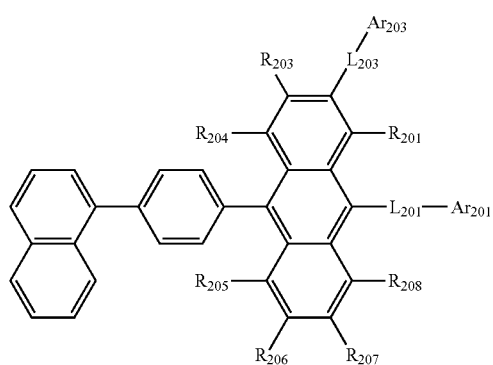

(227)

[Formula 192]

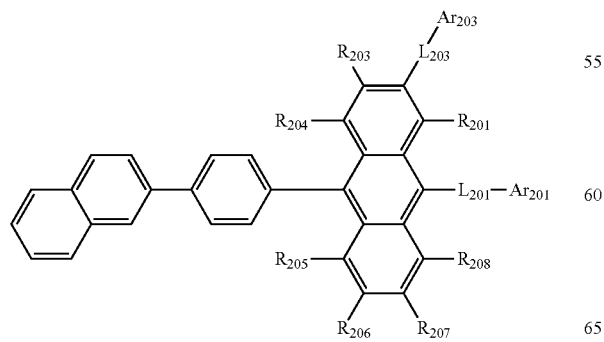

(228)

[Formula 193]

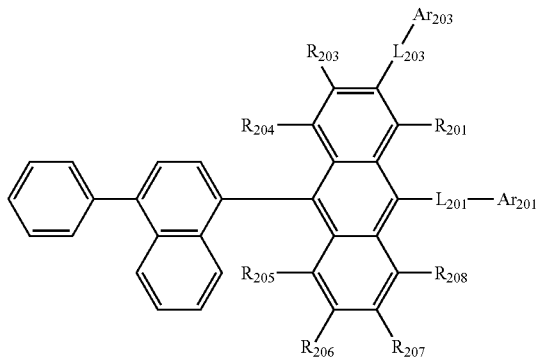

(229)

In the formulae (221), (222), (223), (224), (225), (226), (227), (228), and (229):

$R_{201}$ and $R_{203}$ to $R_{208}$ each independently represent the same as $R_{201}$ and $R_{203}$ to $R_{208}$ in the formula (2);

$L_{201}$ and $Ar_{201}$ respectively represent the same as $L_{201}$ and $Ar_{201}$ in the formula (2);

$L_{203}$ represents the same as $L_{201}$ in the formula (2);

$L_{203}$ and $L_{201}$ are mutually the same or different;

$Ar_{203}$ represents the same as $Ar_{201}$ in the formula (2); and $Ar_{203}$ and $Ar_{201}$ are mutually the same or different.

The second compound represented by the formula (2) is also preferably a compound represented by a formula (241), a formula (242), a formula (243), a formula (244), a formula (245), a formula (246), a formula (247), a formula (248), or a formula (249) below.

[Formula 194]

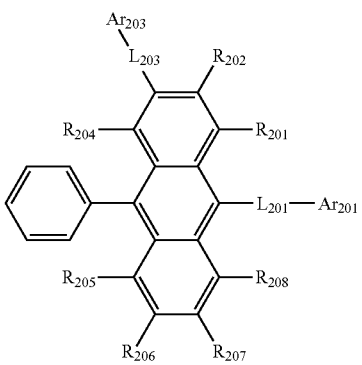

(241)

[Formula 195]
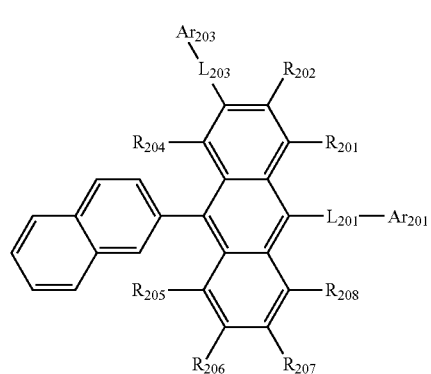
(242)
[Formula 196]
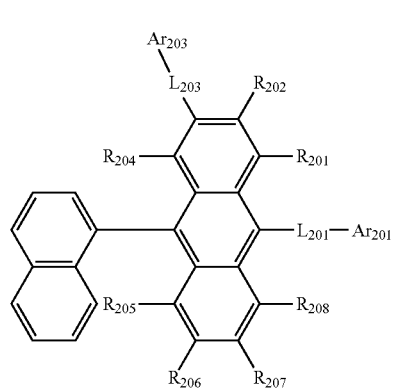
(243)
[Formula 197]
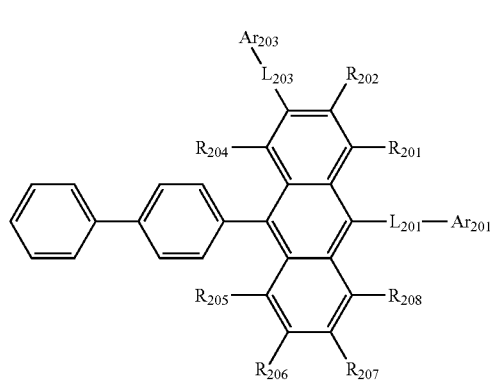
(244)
[Formula 198]
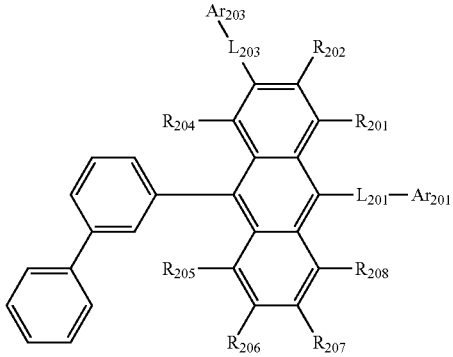
(245)
[Formula 199]
(246)
[Formula 200]
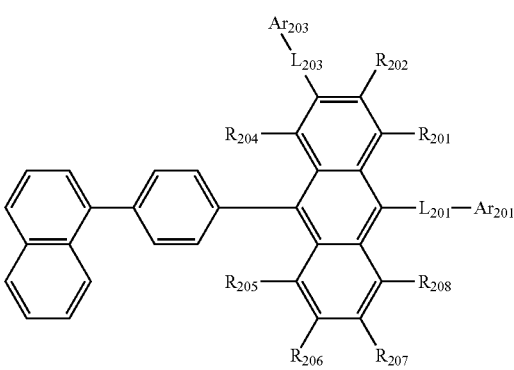
(247)

[Formula 201]

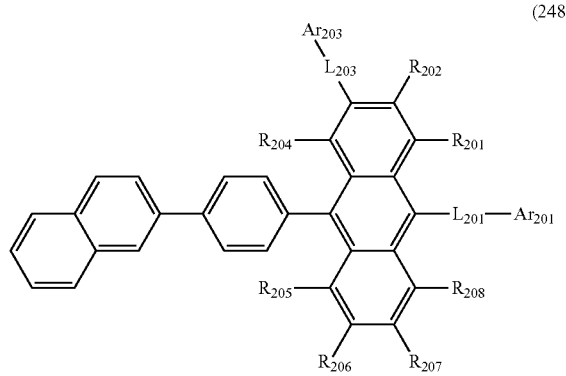

(248)

[Formula 202]

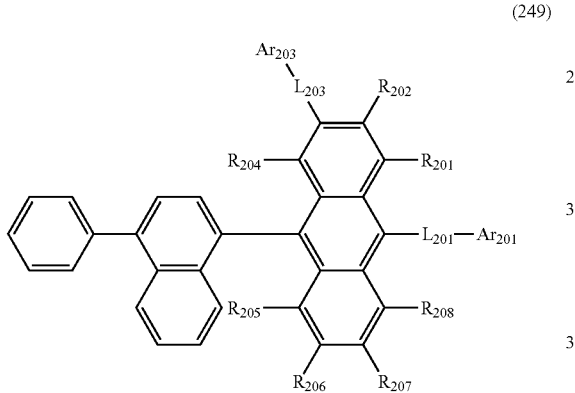

(249)

In the formulae (241), (242), (243), (244), (245), (246), (247), (248), and (249):

$R_{201}$, $R_{202}$, and $R_{204}$ to $R_{208}$ each independently represent the same as $R_{201}$, $R_{202}$, and $R_{204}$ to $R_{208}$ in the formula (2);

$L_{201}$ and $Ar_{201}$ respectively represent the same as $L_{201}$ and $Ar_{201}$ in the formula (2);

$L_{203}$ represents the same as $L_{201}$ in the formula (2);

$L_{203}$ and $L_{201}$ are mutually the same or different;

$Ar_{203}$ represents the same as $Ar_{201}$ in the formula (2); and $Ar_{203}$ and $Ar_{201}$ are mutually the same or different.

In the second compound represented by the formula (2), $R_{201}$ to $R_{208}$ not being the group represented by the formula (21) are preferably each independently a hydrogen atom, a substituted or unsubstituted alkyl group having 1 to 50 carbon atoms, a substituted or unsubstituted cycloalkyl group having 3 to 50 ring carbon atoms, or a group represented by —Si($R_{901}$)($R_{902}$)($R_{903}$).

$L_{101}$ is preferably a single bond, or an unsubstituted arylene group having 6 to 22 ring carbon atoms, and $Ar_{101}$ is a substituted or unsubstituted aryl group having 6 to 22 ring carbon atoms.

In the organic EL device according to the exemplary embodiment, $R_{201}$ to $R_{208}$ that are substituents of an anthracene skeleton in the second compound represented by the formula (2) are preferably hydrogen atoms in terms of preventing inhibition of intermolecular interaction and inhibiting decrease in electron mobility. However, $R_{201}$ to $R_{208}$ may be a substituted or unsubstituted aryl group having 6 to 50 ring carbon atoms or a substituted or unsubstituted heterocyclic group having 5 to 50 ring atoms.

Assuming that $R_{201}$ to $R_{208}$ each are a bulky substituent such as an alkyl group and a cycloalkyl group, intermolecular interaction may be inhibited to decrease the electron mobility of the second compound relative to that of the first host material, so that a relationship of µe(H1)<µe(H2) shown by the numerical formula (Numerical Formula 33) may not be satisfied. When the second compound is used in the second emitting layer, it can be expected that satisfying the relationship of µe(H1)<µe(H2) inhibits a decrease in a recombination ability between holes and electrons in the first emitting layer and a decrease in a luminous efficiency. It should be noted that substituents, namely, a haloalkyl group, alkenyl group, alkynyl group, group represented by —Si($R_{901}$)($R_{902}$)($R_{903}$), group represented by —O—($R_{904}$), group represented by —S—($R_{905}$), group represented by —N($R_{906}$)($R_{907}$), aralkyl group, group represented by —C(=O)$R_{801}$, group represented by —COO$R_{802}$, halogen atom, cyano group, and nitro group are likely to be bulky, and an alkyl group and cycloalkyl group are likely to be further bulky.

In the second compound represented by the formula (2), $R_{201}$ to $R_{208}$, which are the substituents on the anthracene skeleton, are each preferably not a bulky substituent and preferably not an alkyl group and cycloalkyl group. More preferably, $R_{201}$ to $R_{208}$ are each not an alkyl group, cycloalkyl group, haloalkyl group, alkenyl group, alkynyl group, group represented by —Si($R_{901}$)($R_{902}$)($R_{903}$), group represented by —O—($R_{904}$), group represented by —S—($R_{905}$), group represented by —N($R_{906}$)($R_{907}$), aralkyl group, group represented by —C(=O)$R_{801}$, group represented by —COO$R_{802}$, halogen atom, cyano group, and nitro group.

In the organic EL device according to the exemplary embodiment, it is preferable that in the second compound represented by the formula (2), $R_{201}$ to $R_{208}$ are each independently a hydrogen atom, a substituted or unsubstituted alkyl group having 1 to 50 carbon atoms, a substituted or unsubstituted cycloalkyl group having 3 to 50 ring carbon atoms, or a group represented by —Si($R_{901}$)($R_{902}$)($R_{903}$).

In the organic EL device according to the exemplary embodiment, $R_{201}$ to $R_{208}$ in the second compound represented by the formula (2) are each preferably a hydrogen atom.

In the second compound, examples of the substituent for a "substituted or unsubstituted" group on $R_{201}$ to $R_{208}$ also preferably do not include the above-described substituent that is likely to be bulky, especially a substituted or unsubstituted alkyl group and a substituted or unsubstituted cycloalkyl group. Since examples of the substituent for a "substituted or unsubstituted" group on $R_{201}$ to $R_{208}$ do not include a substituted or unsubstituted alkyl group and a substituted or unsubstituted cycloalkyl group, inhibition of intermolecular interaction to be caused by presence of a bulky substituent such as an alkyl group and a cycloalkyl group can be prevented, thereby preventing a decrease in the electron mobility. Moreover, when the second compound described above is used in the second emitting layer, a decrease in a recombination ability between holes and electrons in the first emitting layer and a decrease in the luminous efficiency can be inhibited.

It is more preferable that: $R_{201}$ to $R_{208}$, which are the substituents on the anthracene skeleton, are not bulky substituents; and $R_{201}$ to $R_{208}$ as substituents are unsubstituted. Assuming that $R_{201}$ to $R_{208}$, which are the substituents on the anthracene skeleton, are not bulky substituents and substituents are bonded to $R_{201}$ to $R_{208}$ which are the not-bulky substituents: the substituents bonded to $R_{201}$ to $R_{208}$ are preferably not the bulky substituents; and the substituents bonded to $R_{201}$ to $R_{208}$ serving as substituents are preferably not an alkyl group and cycloalkyl group, more preferably not an alkyl group, cycloalkyl group, haloalkyl group, alkenyl group, alkynyl group, group represented by —Si($R_{901}$)($R_{902}$)($R_{903}$), group represented by —O—($R_{904}$), group represented by —S—($R_{905}$), group represented by —N($R_{906}$)($R_{907}$), aralkyl group, group represented by —C(=O)$R_{801}$, group represented by —COO$R_{802}$, halogen atom, cyano group, and nitro group.

In the second compound, the groups specified to be "substituted or unsubstituted" are each preferably an "unsubstituted" group.

In the organic EL device according to the exemplary embodiment, for instance, $Ar_{201}$ in the second compound represented by the formula (2) is a substituted or unsubstituted dibenzofuranyl group.

In the organic EL device according to the exemplary embodiment, for instance, $Ar_{201}$ in the second compound represented by the formula (2) is an unsubstituted dibenzofuranyl group.

In the organic EL device according to the exemplary embodiment, for instance, at least one hydrogen atom is included in the second compound represented by the formula (2), the hydrogen atom including at least one deuterium atom.

In the organic EL device according to the exemplary embodiment, for instance, $L_{201}$ in the second compound represented by the formula (2) is one of TEMP-63 to TEMP-68.

[Formula 203]

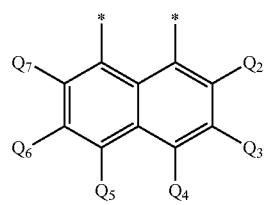
(TEMP-63)

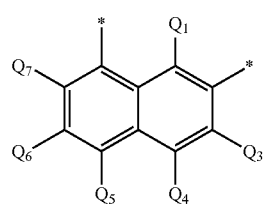
(TEMP-64)

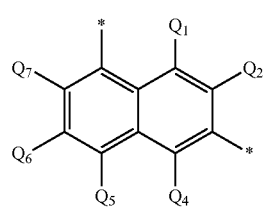
(TEMP-65)

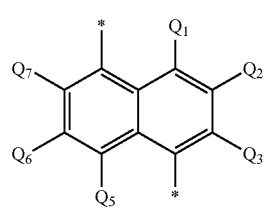
(TEMP-66)

-continued

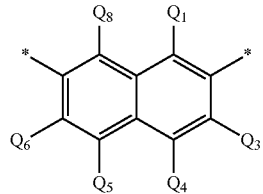
(TEMP-67)

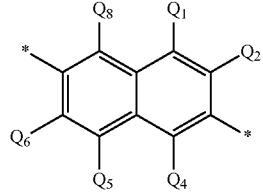
(TEMP-68)

In the organic EL device according to the exemplary embodiment, for instance, $Ar_{201}$ in the second compound represented by the formula (2) is at least one substituted or unsubstituted group selected from the group consisting of anthryl group, benzanthryl group, phenanthryl group, benzophenanthryl group, phenalenyl group, pyrenyl group, chrysenyl group, benzochrysenyl group, triphenylenyl group, benzotriphenylenyl group, tetracenyl group, pentacenyl group, fluoranthenyl group, benzofluoranthenyl group, and perylenyl group.

In the organic EL device according to the exemplary embodiment, for instance, $Ar_{201}$ in the second compound represented by the formula (2) is a substituted or unsubstituted fluorenyl group.

In the organic EL device according to the exemplary embodiment, for instance, $Ar_{201}$ in the second compound represented by the formula (2) is a substituted or unsubstituted xanthenyl group.

In the organic EL device according to the exemplary embodiment, for instance, $Ar_{201}$ in the second compound represented by the formula (2) is a benzoxanthenyl group.

Method of Manufacturing Second Compound

The second compound can be manufactured by a known method. The second compound can also be manufactured based on a known method through a known alternative reaction using a known material(s) tailored for the target compound.

Specific Examples of Second Compound

Specific examples of the second compound include the following compounds. It should however be noted that the invention is not limited by the specific examples of the second compound.

[Formula 204]

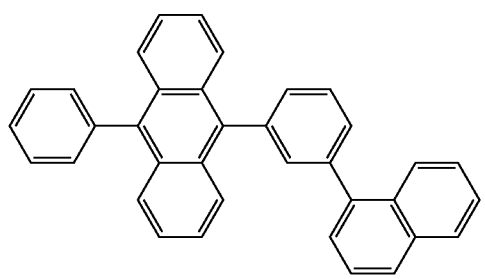

395
-continued
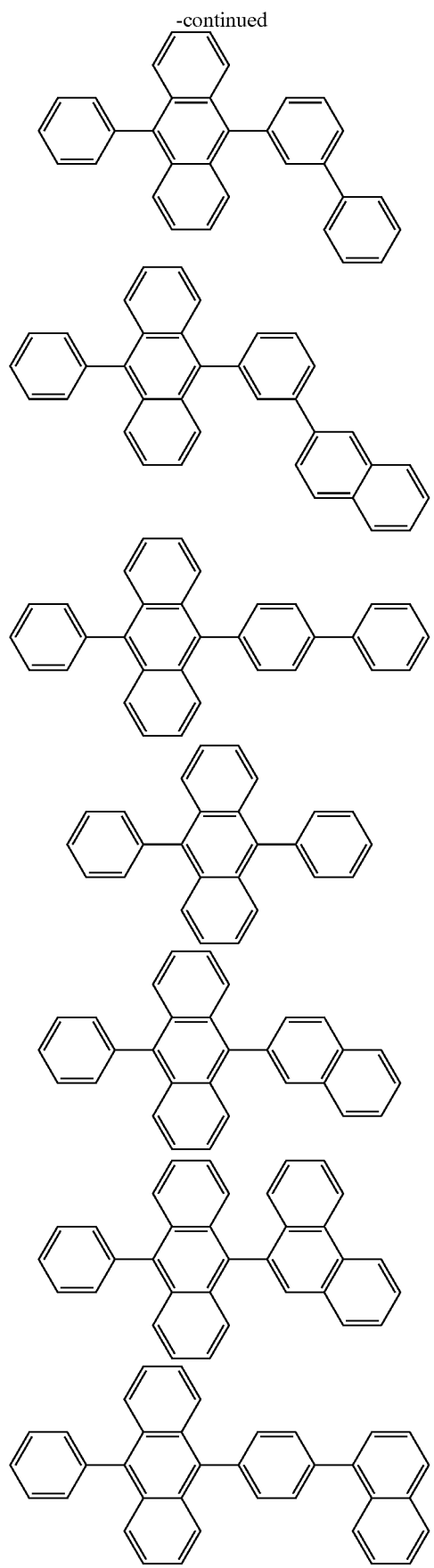
396
-continued
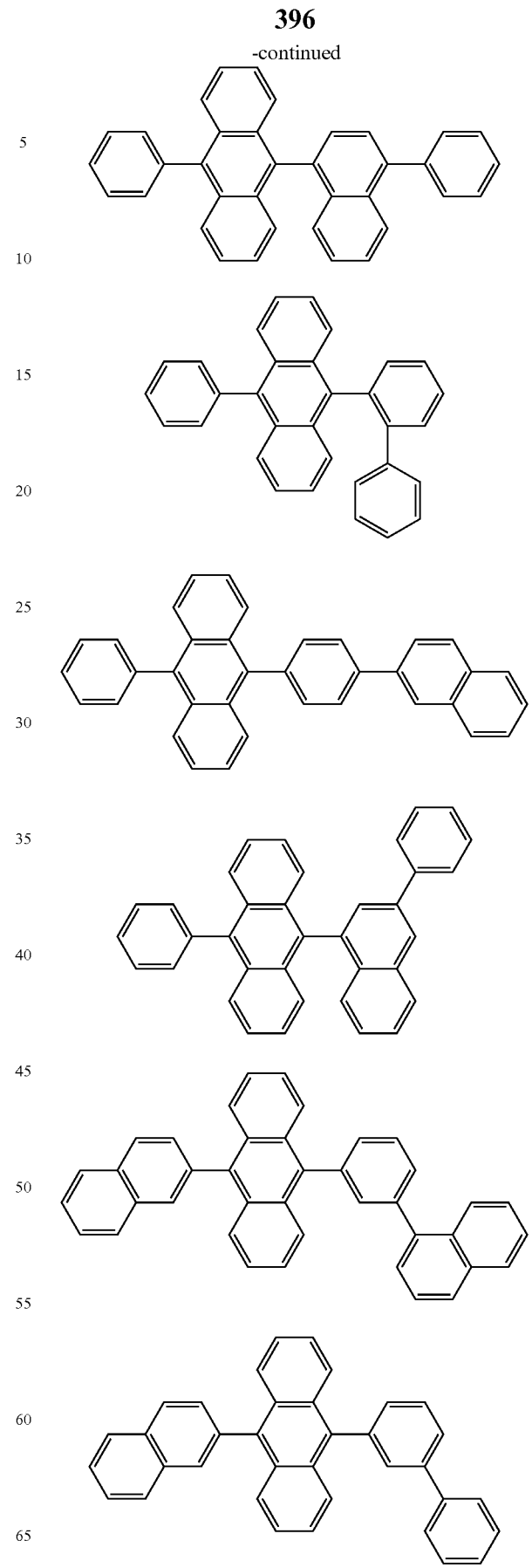

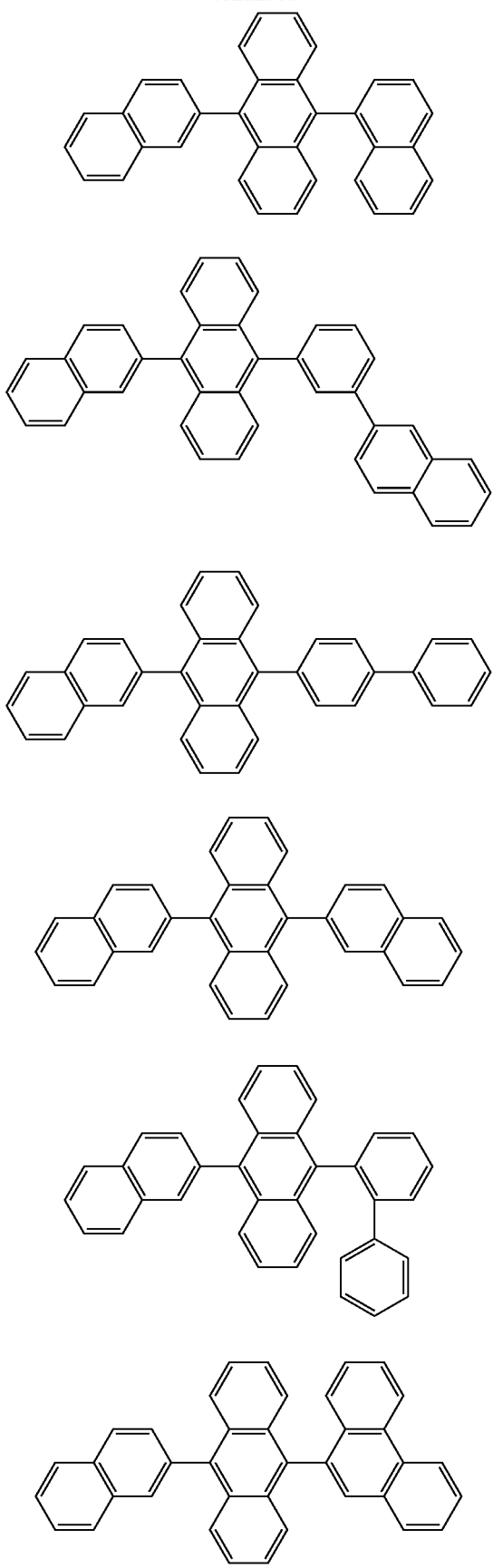
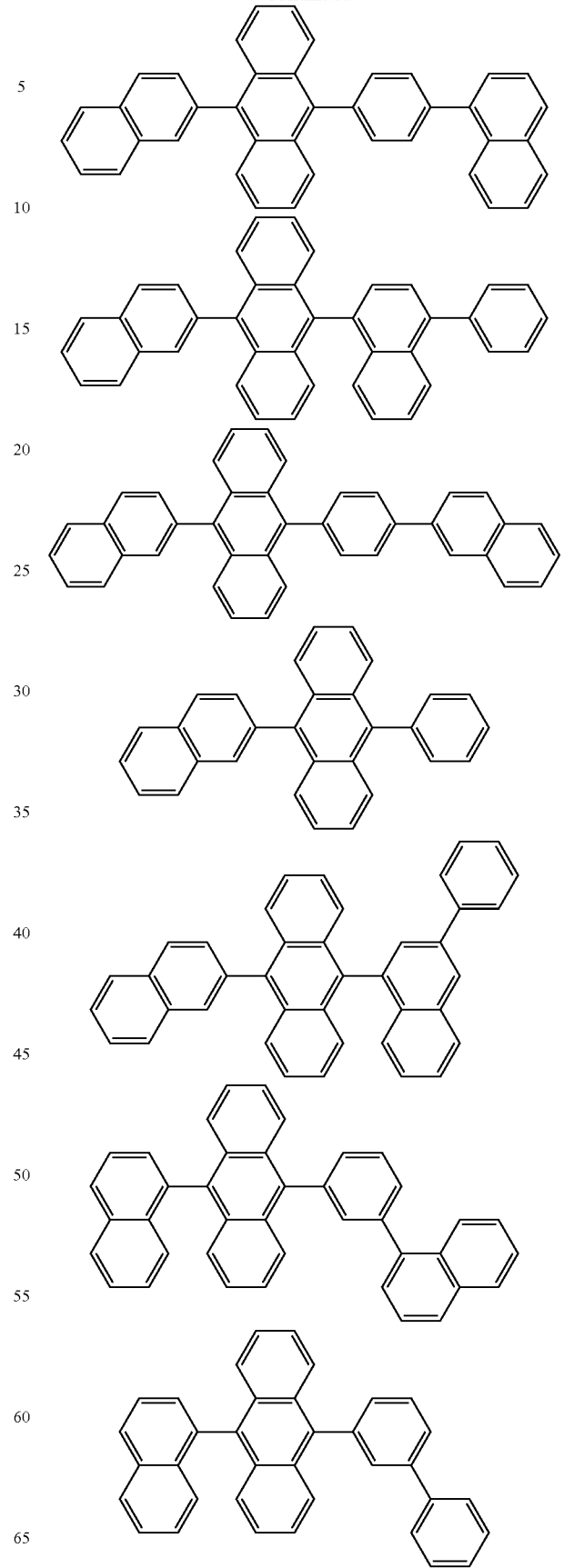

399
-continued
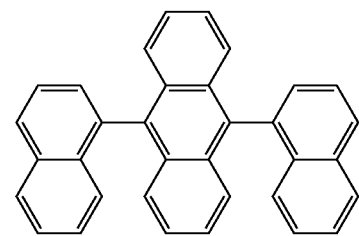
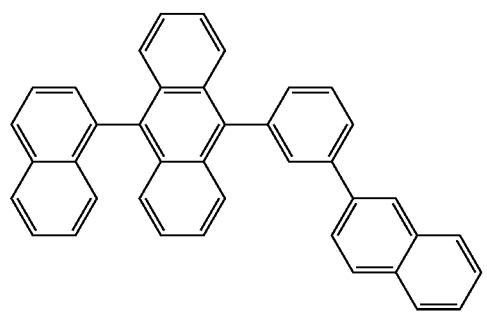
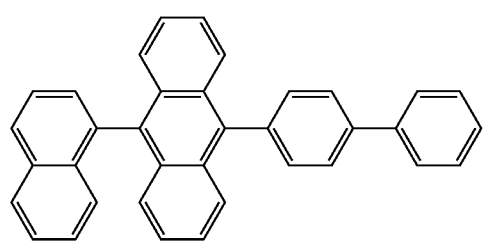
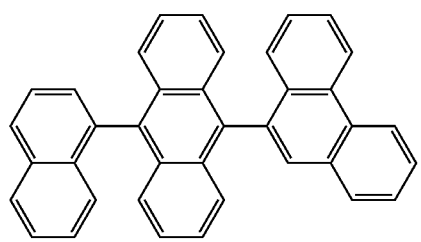
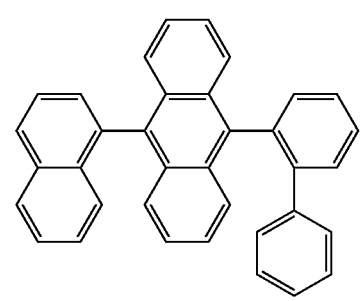
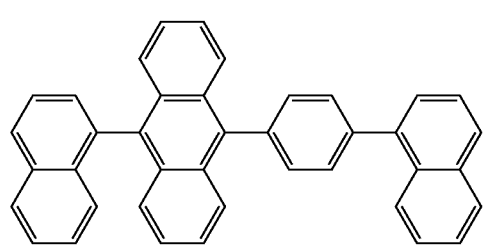
400
-continued
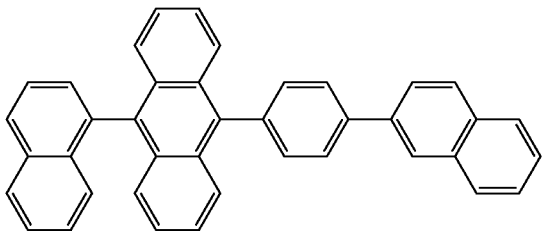
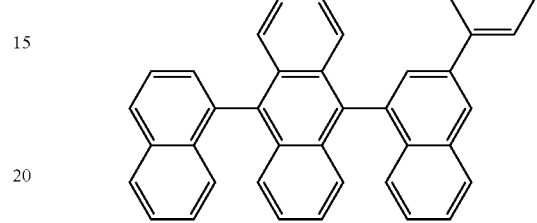
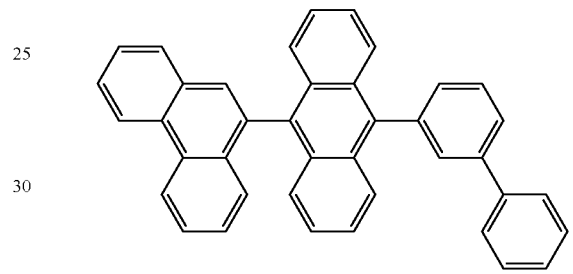
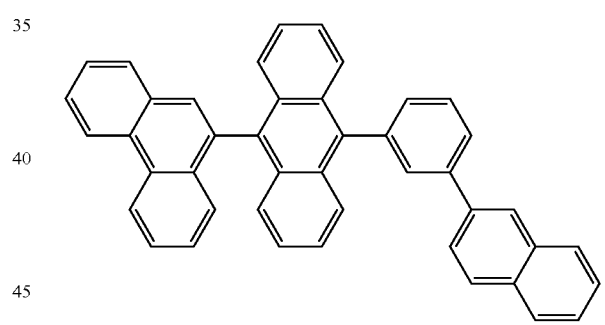
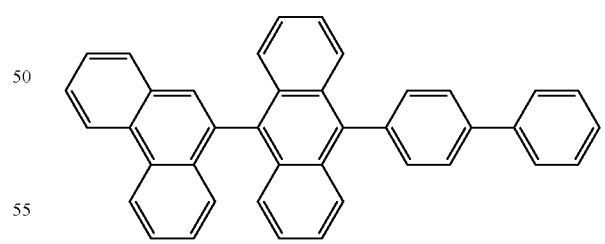
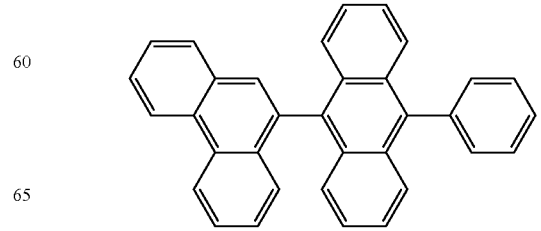

401
-continued
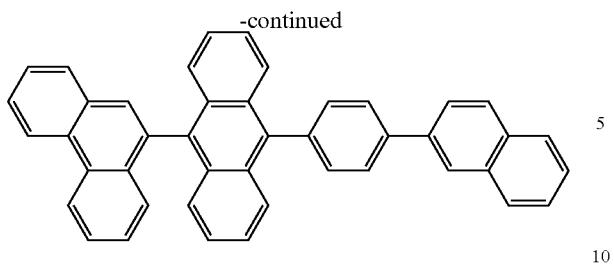
[Formula 205]
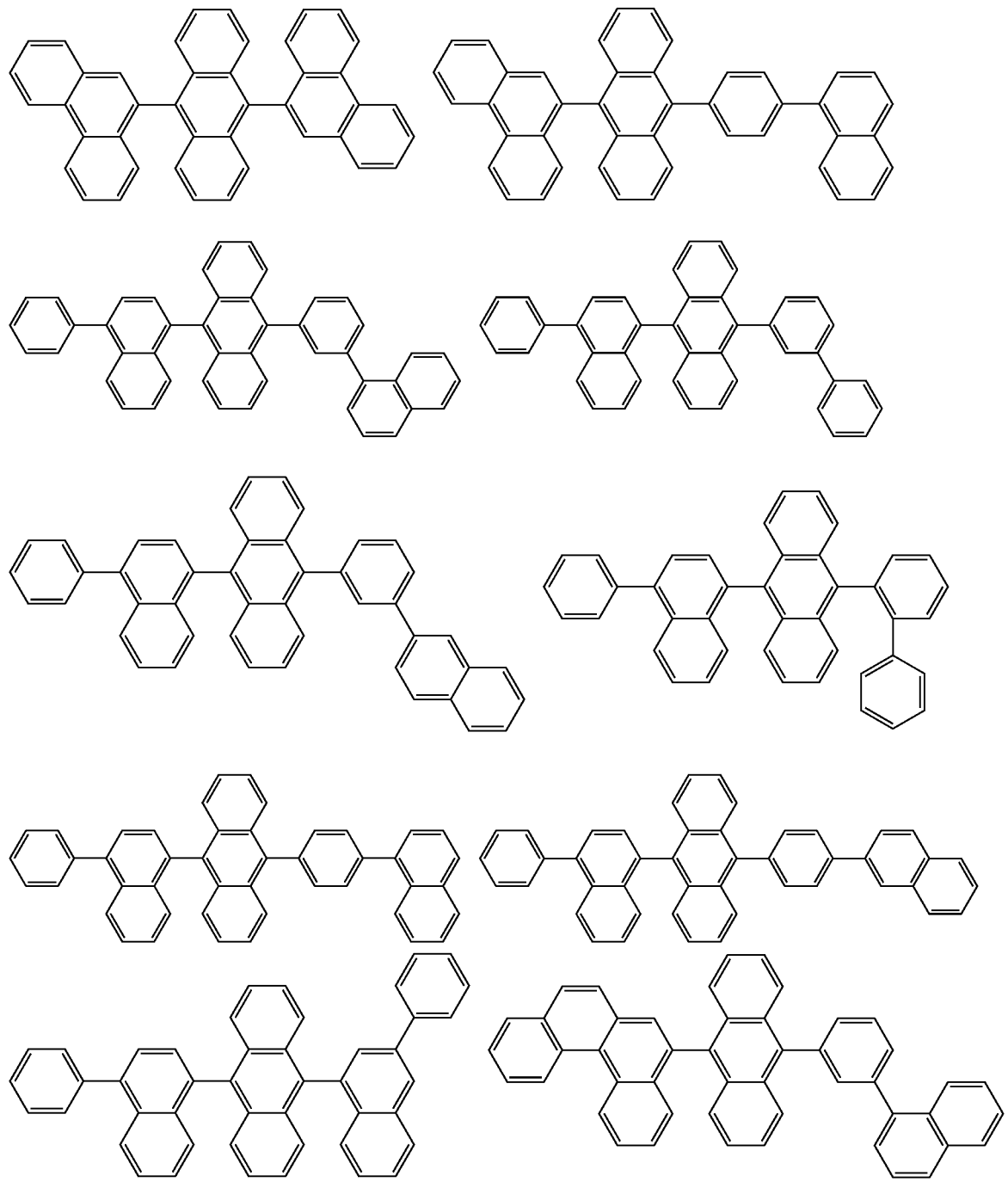
402

403 404
-continued
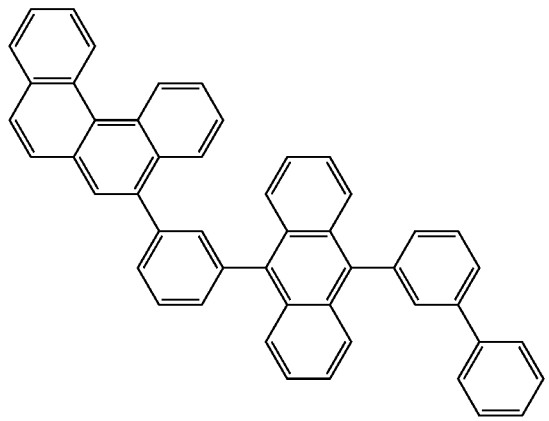
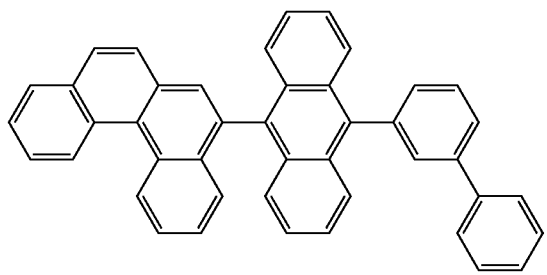
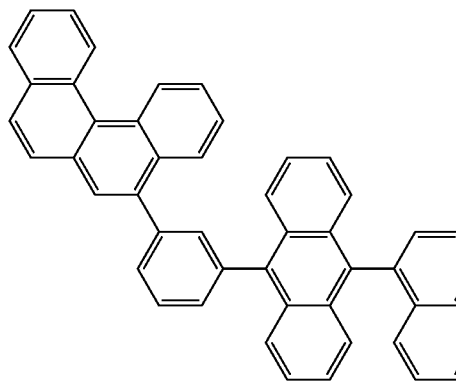
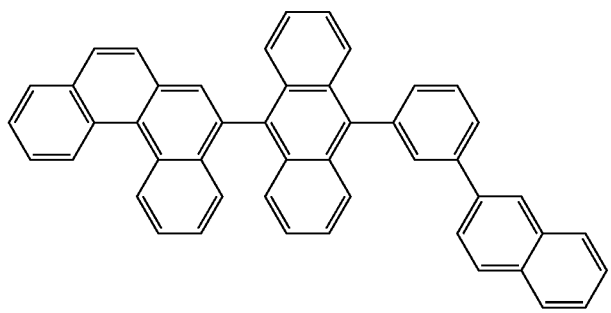
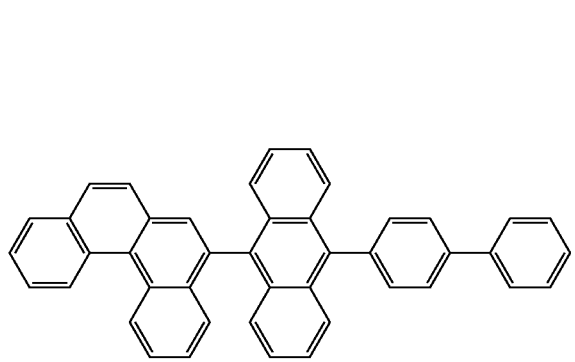
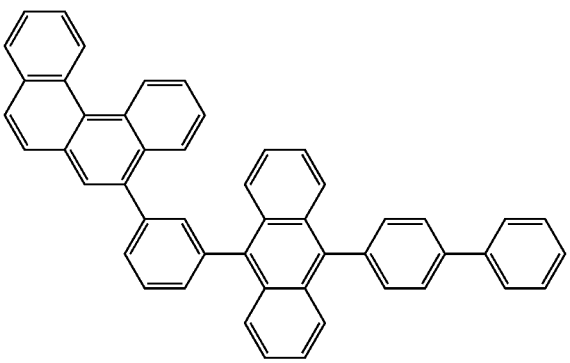
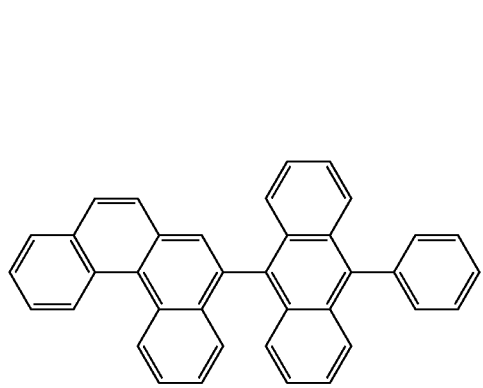
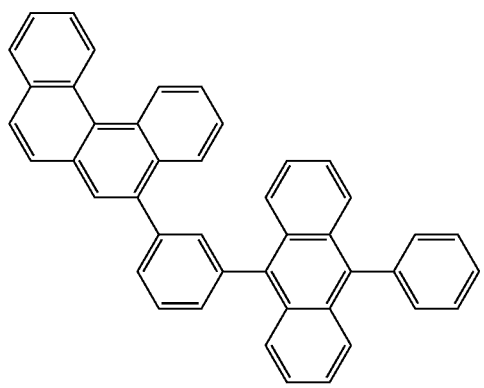

-continued
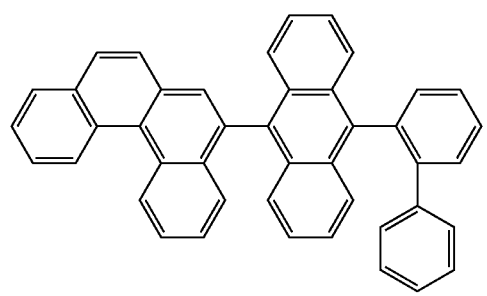
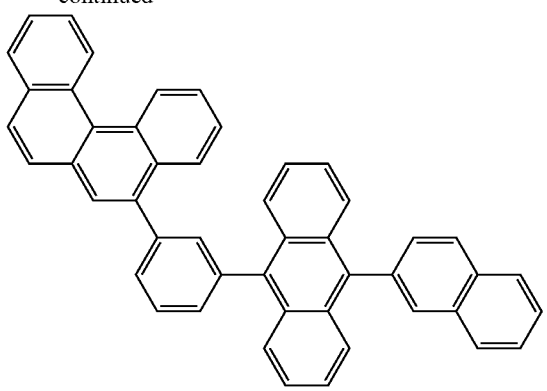
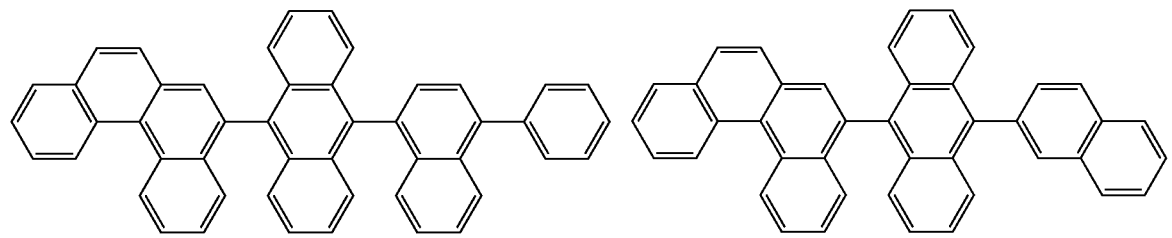
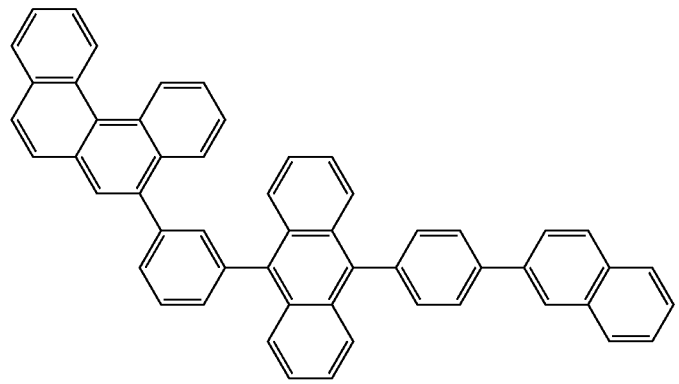
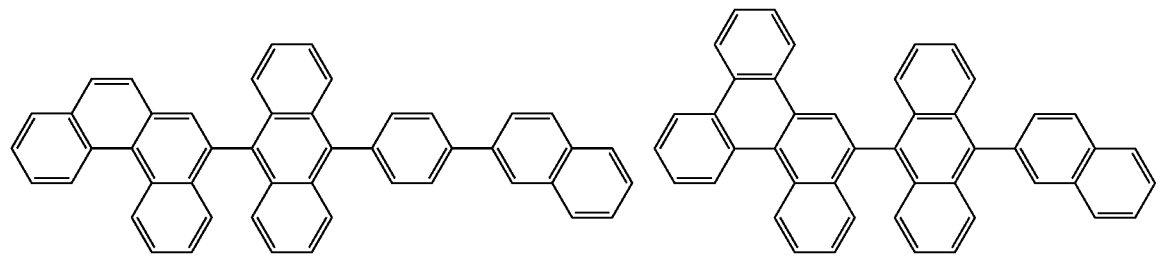
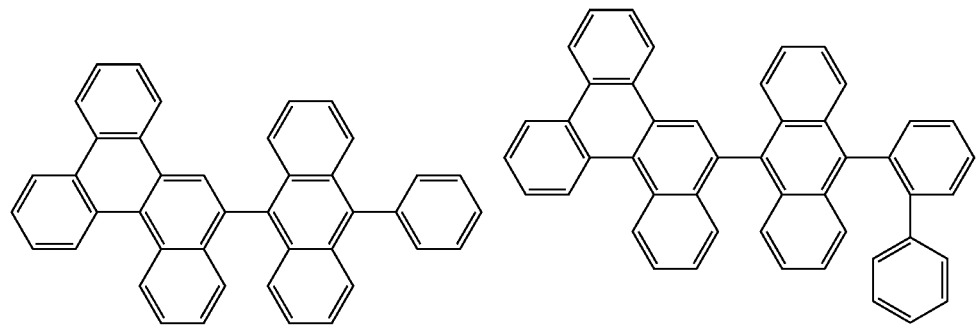

407
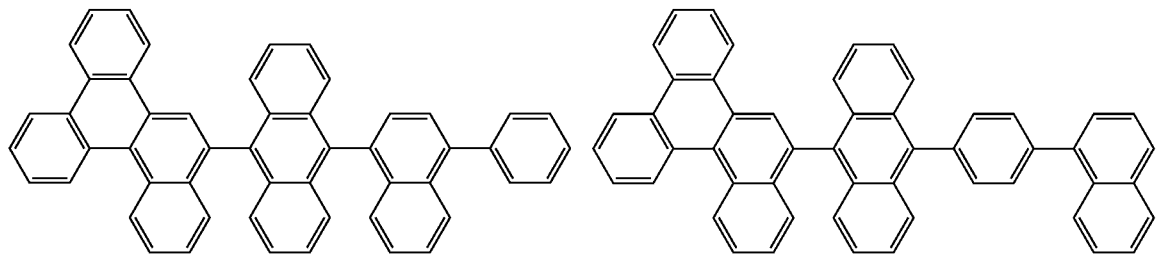
-continued
408
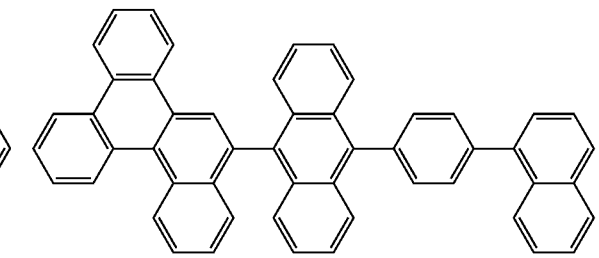
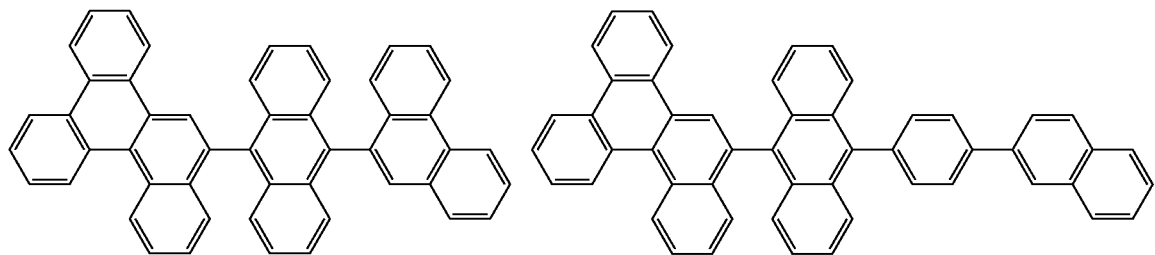
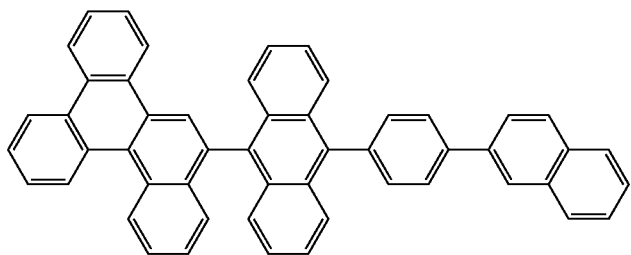
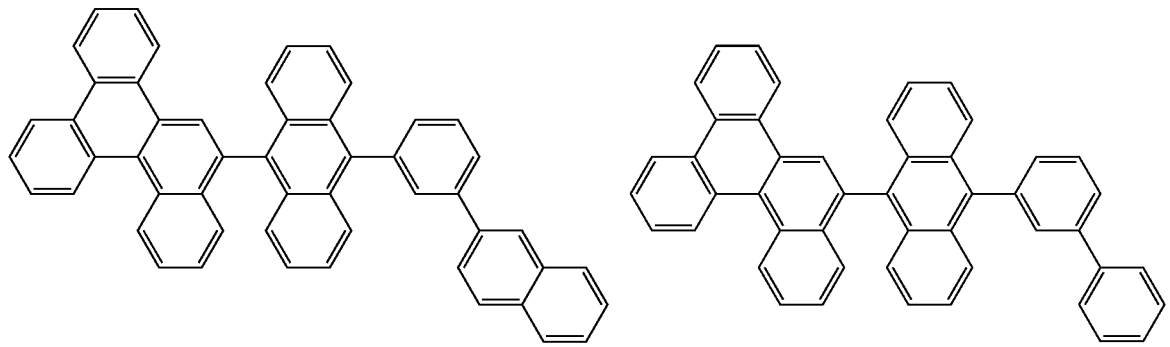
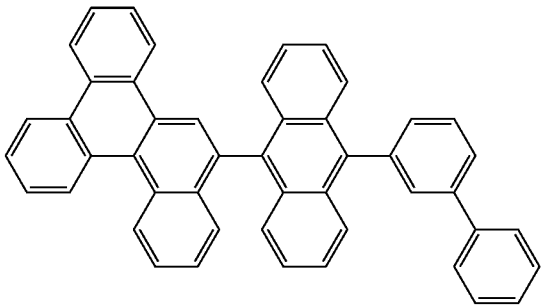
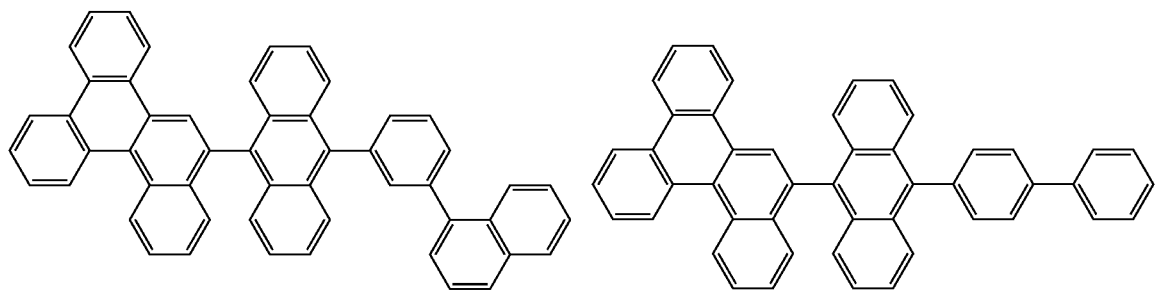
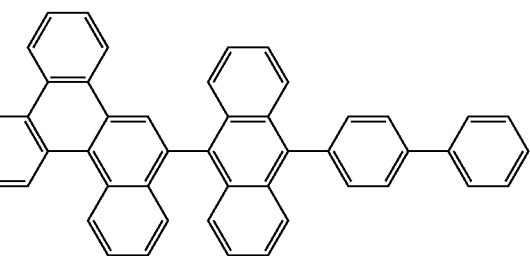
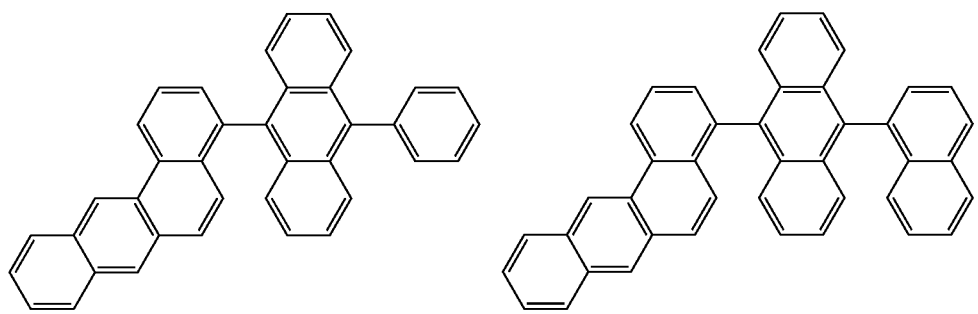
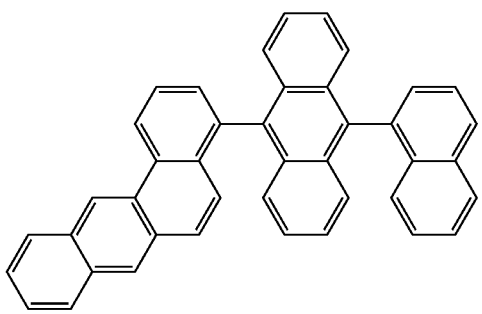

409 410
-continued
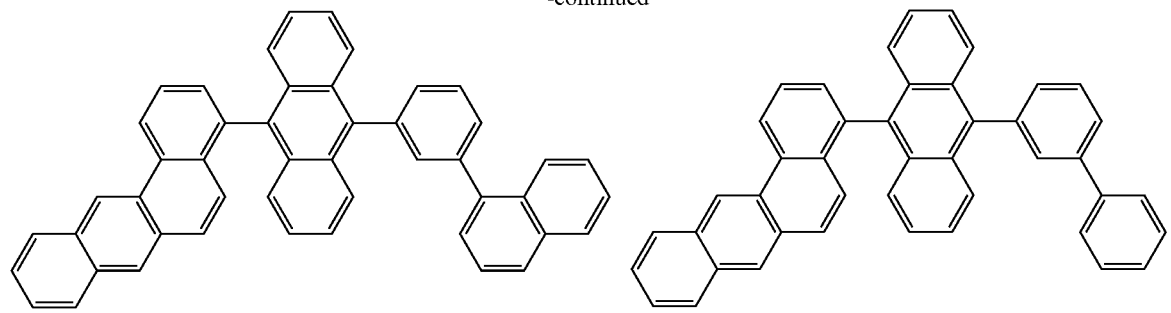
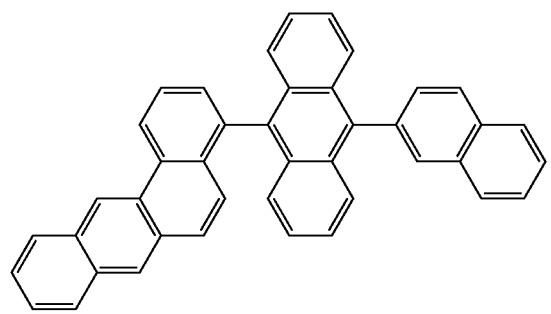
[Formula 206]
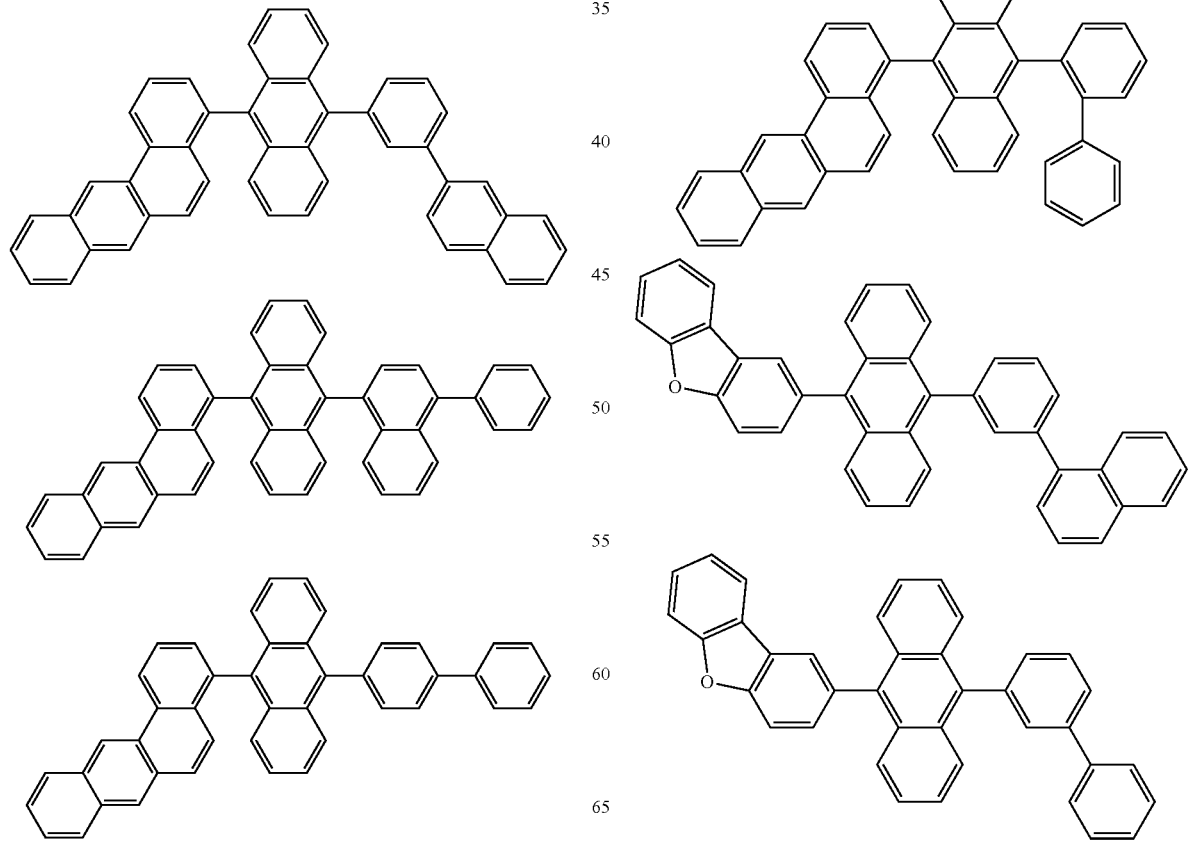

| 411 -continued | 412 -continued |
|---|---|
| 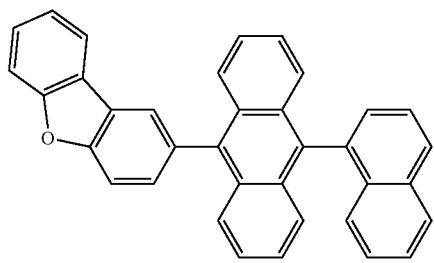 | 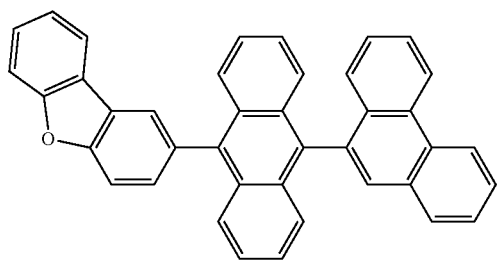 |
| 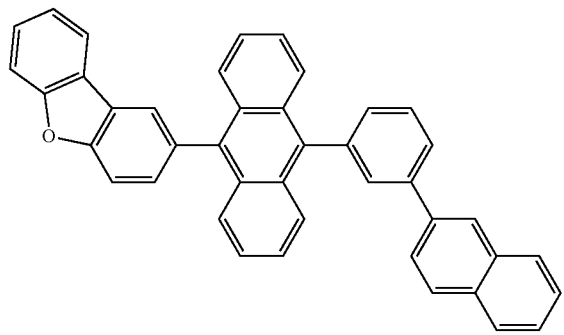 | 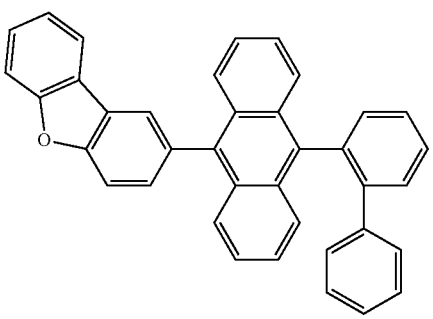 |
| 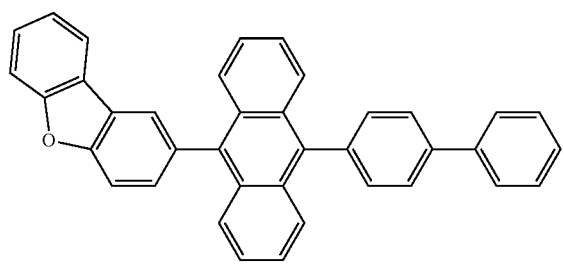 | 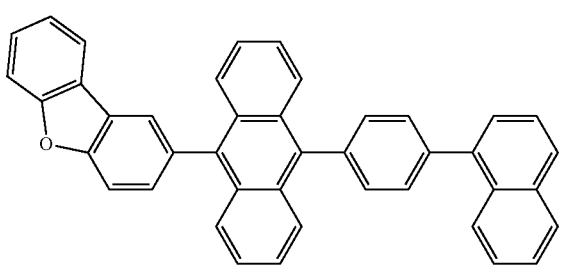 |
| 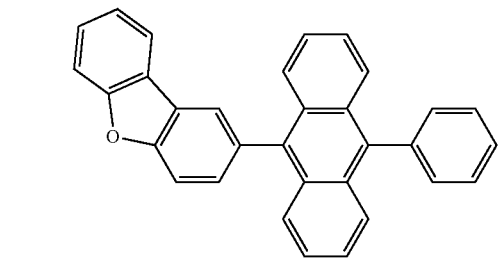 | 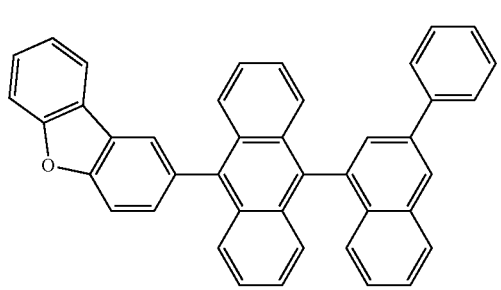 |
| 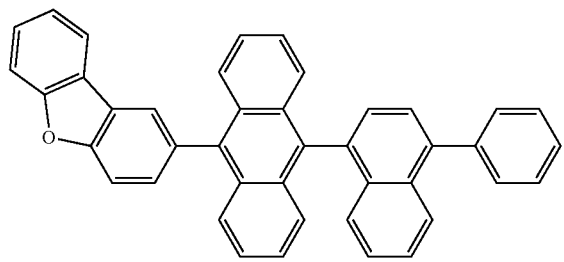 | 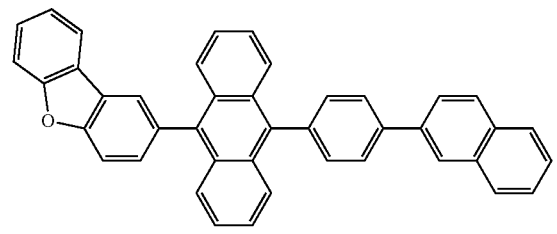 |
| 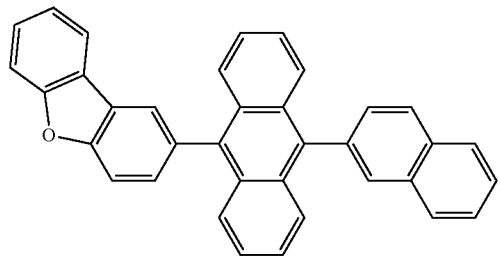 | 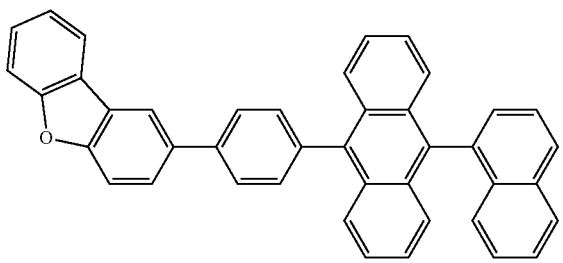 |

413
-continued
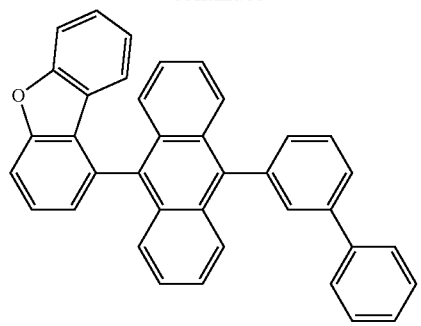
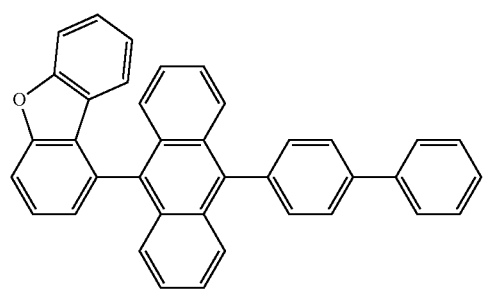
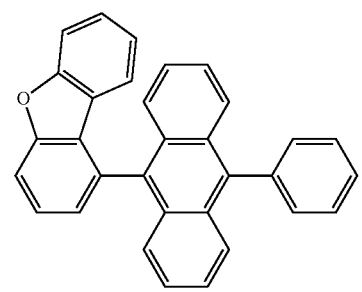
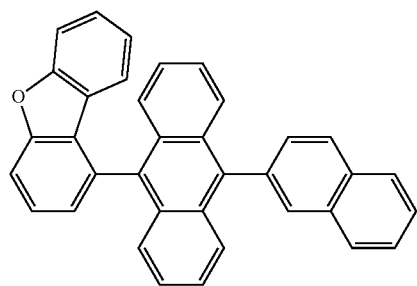
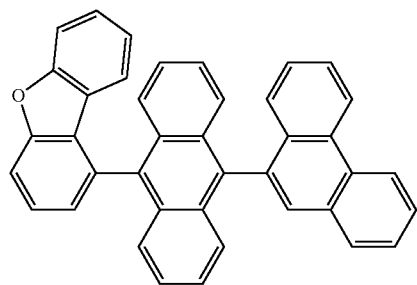
414
-continued
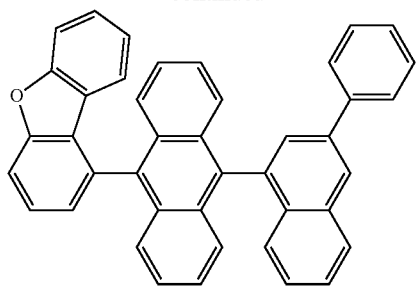
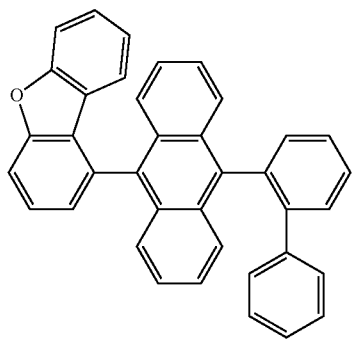
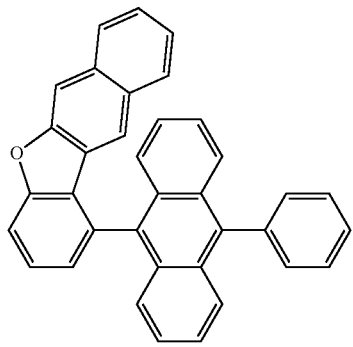
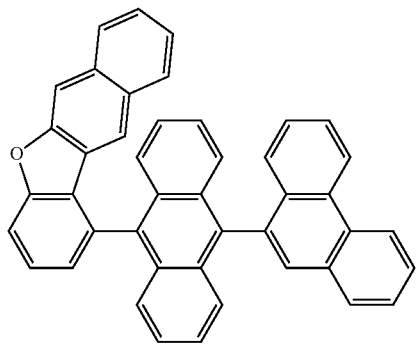
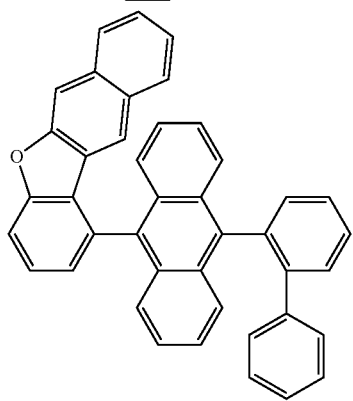

415
-continued

416
-continued

-continued
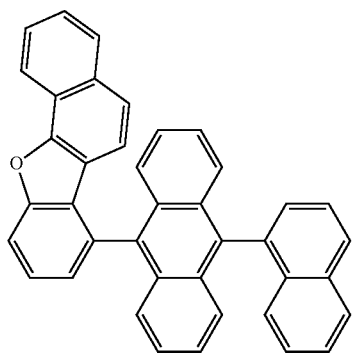
[Formula 207]
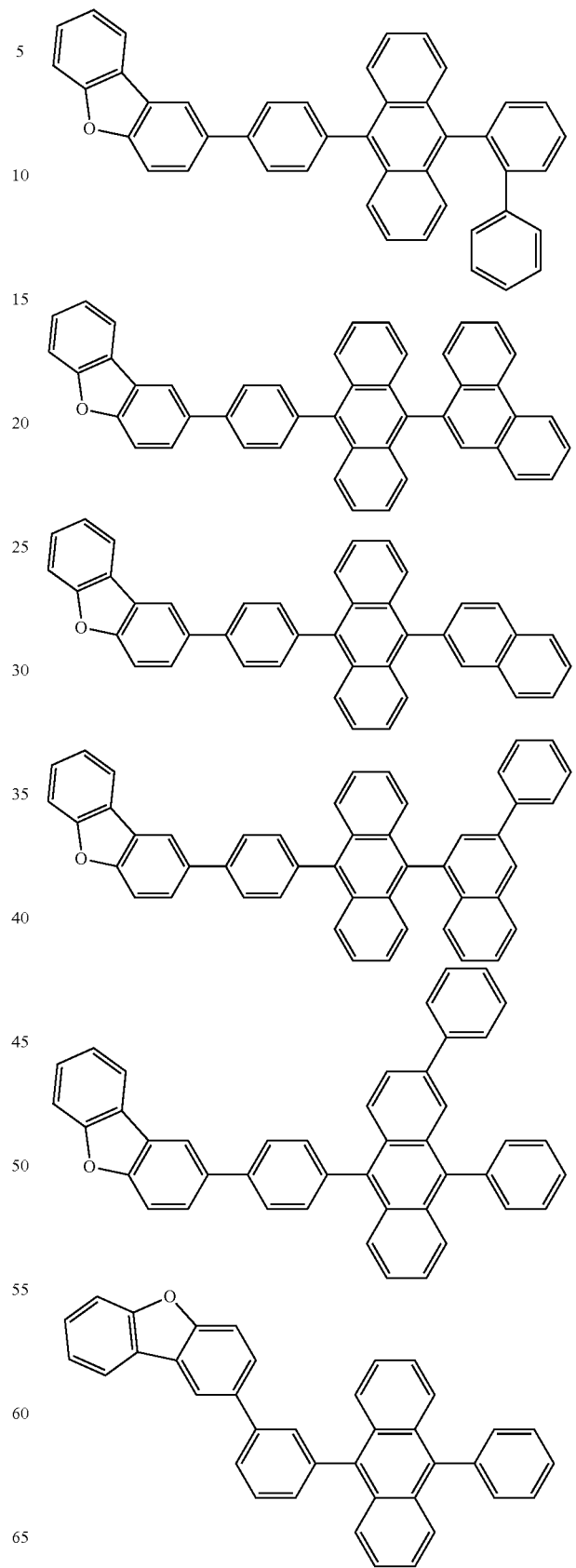

419
-continued
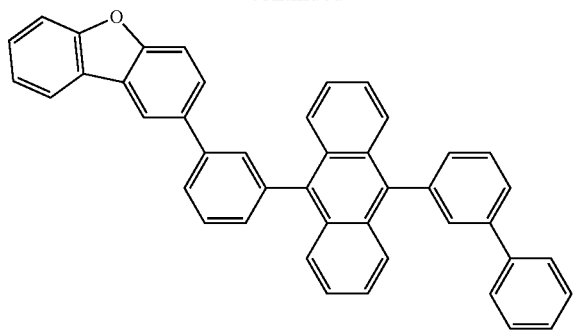
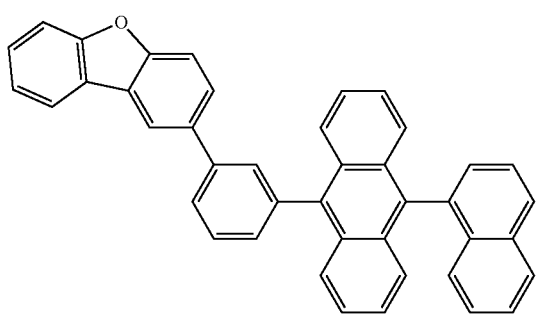
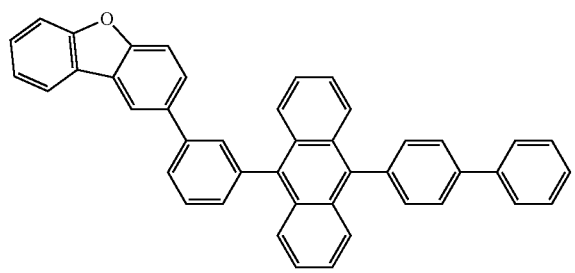
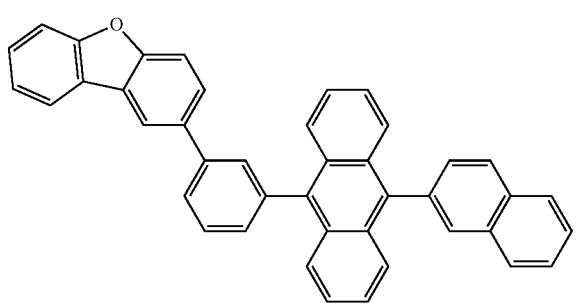
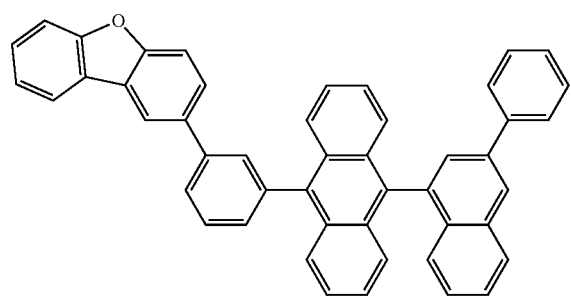
420
-continued
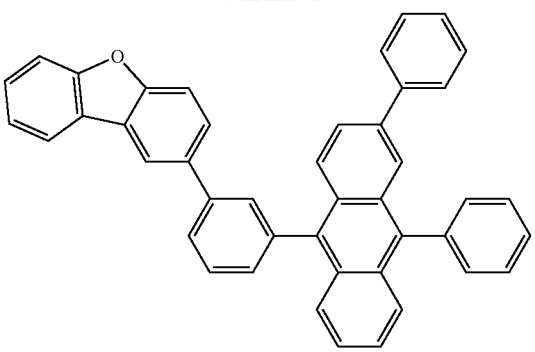
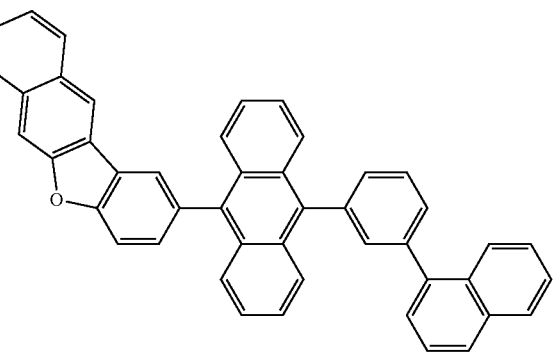
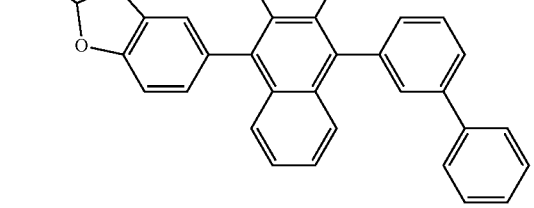
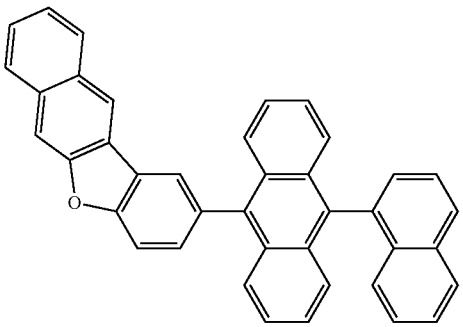

421
-continued
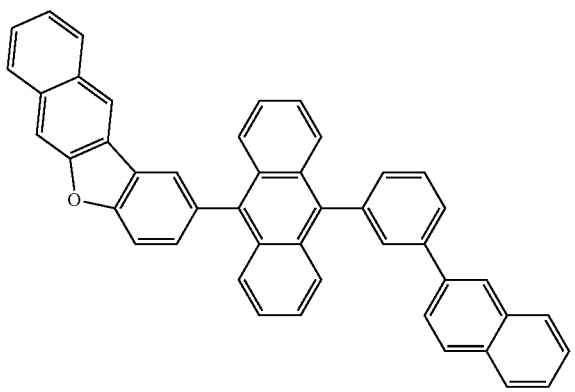
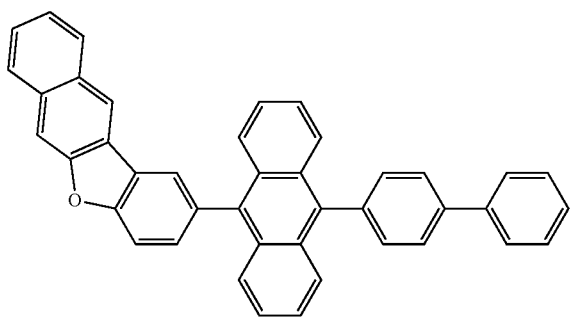
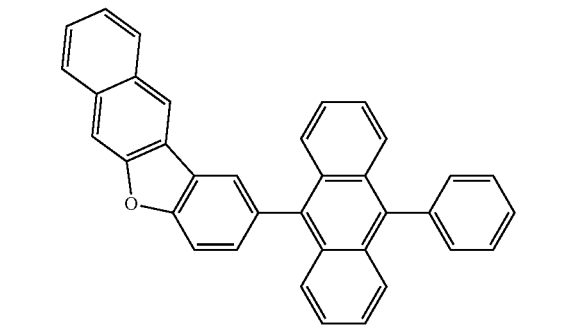
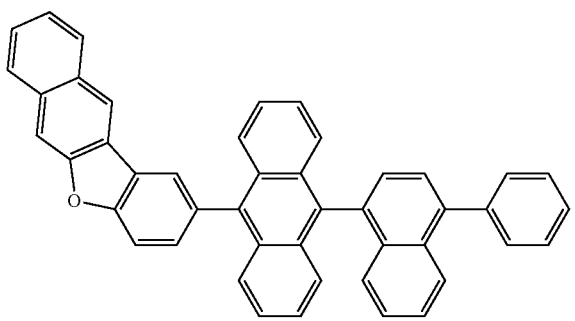
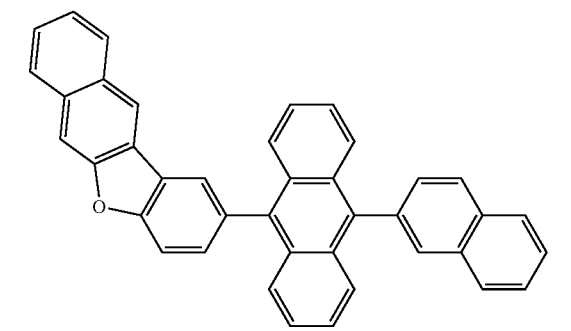
422
-continued
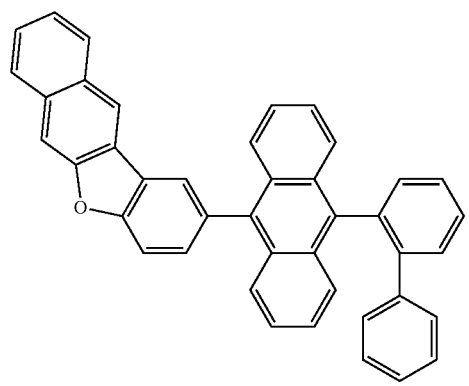
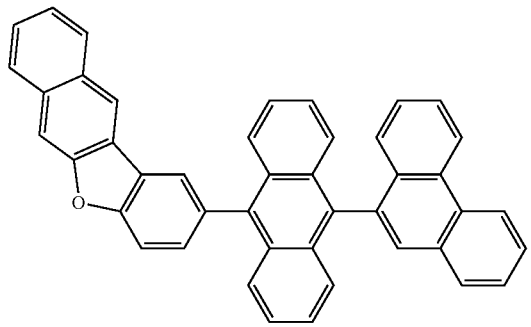
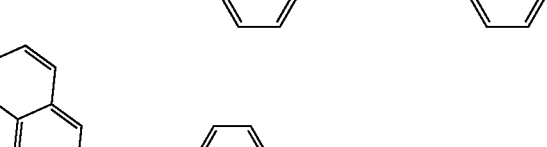
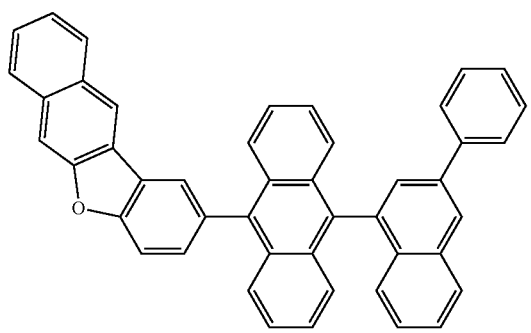

423
-continued
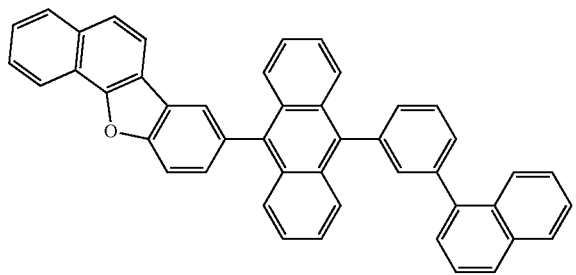
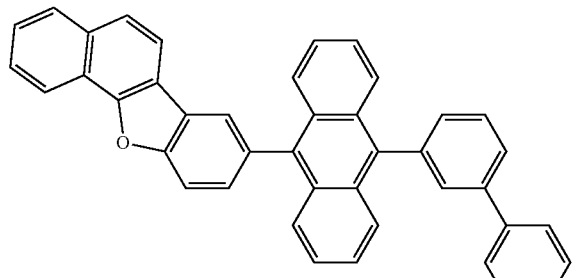
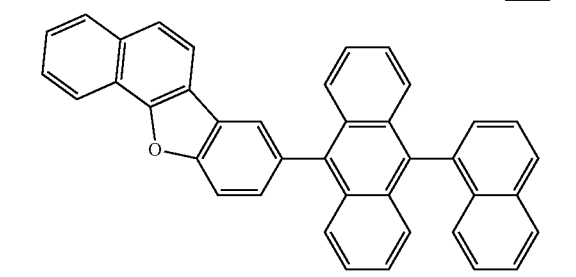
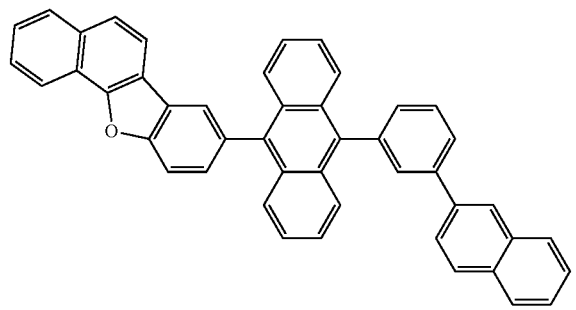
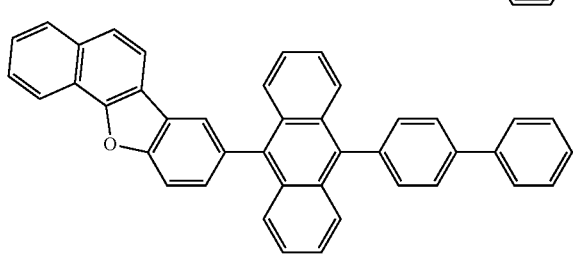
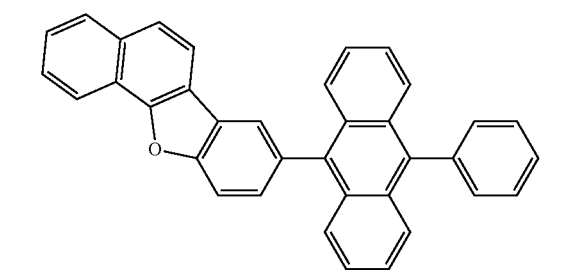
424
-continued
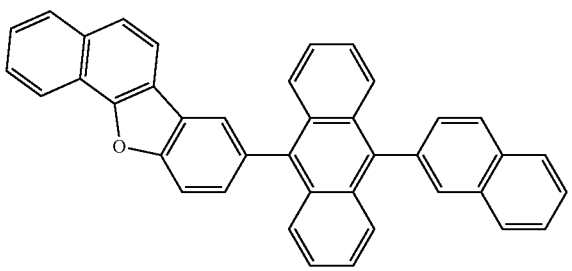
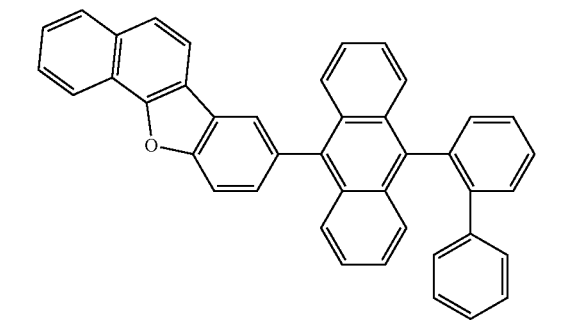
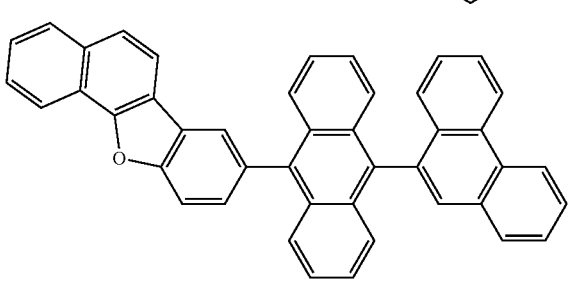
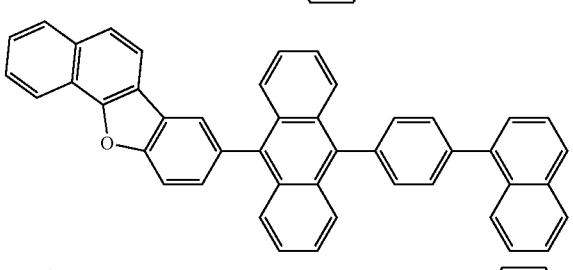
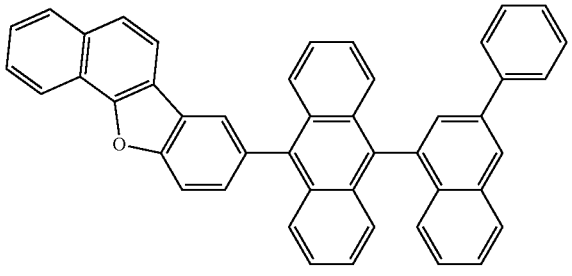
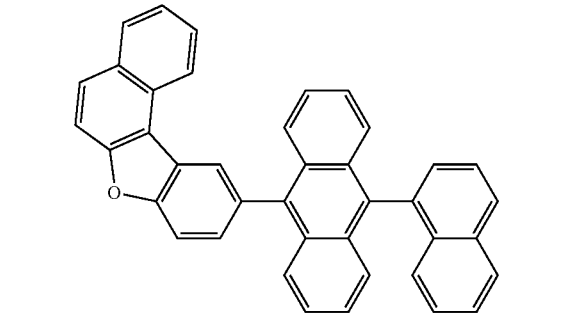

425
-continued
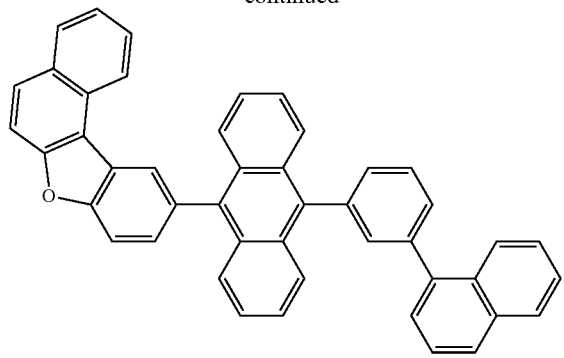
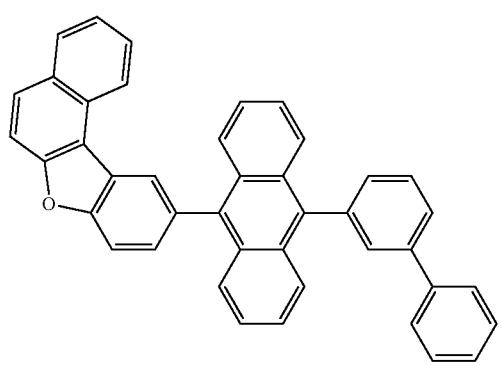
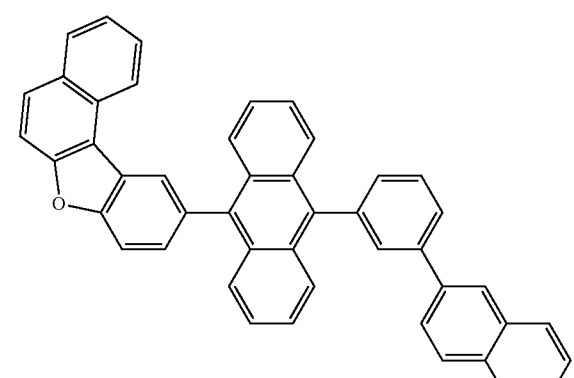
[Formula 208]
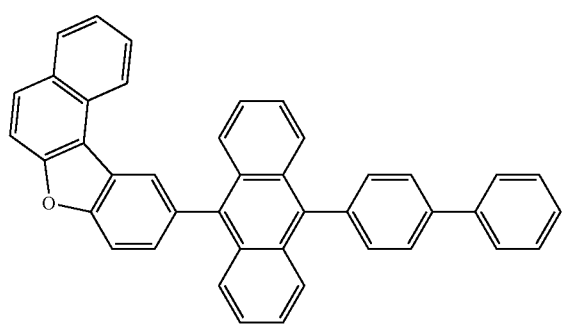
426
-continued
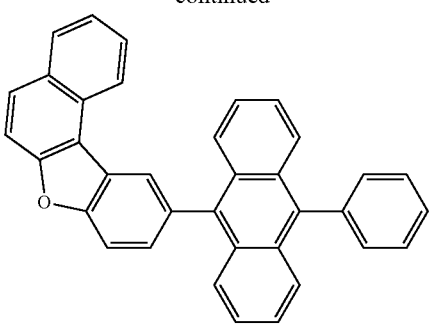
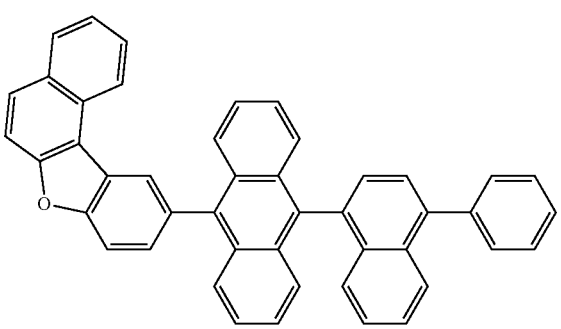
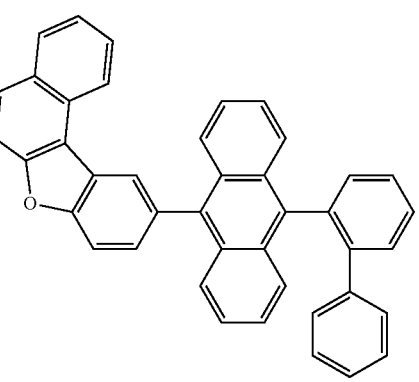
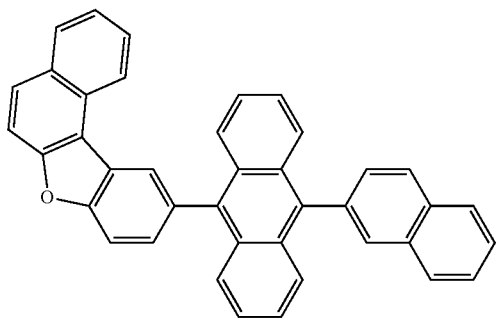
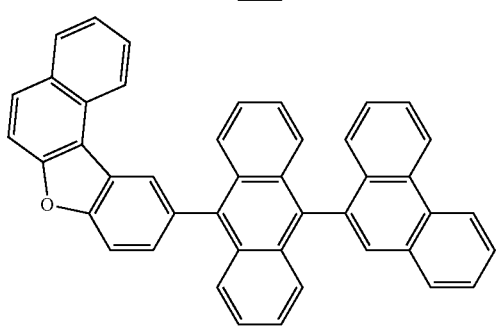

427
-continued
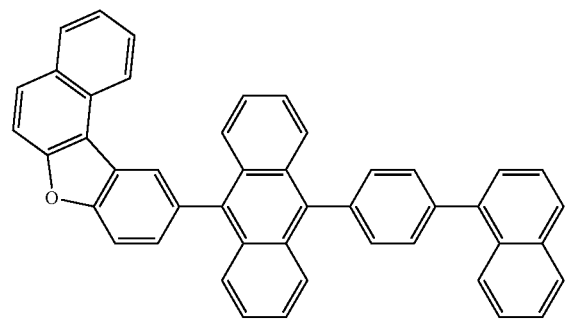
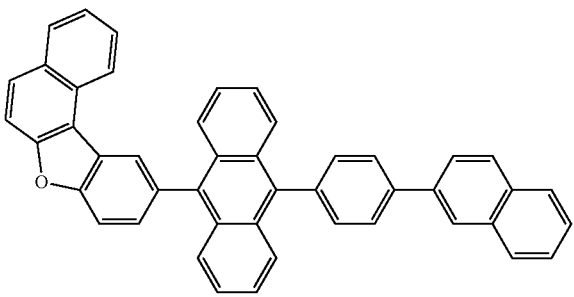
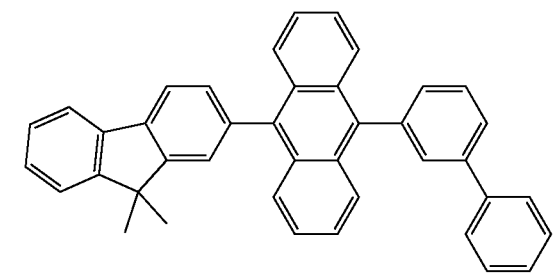
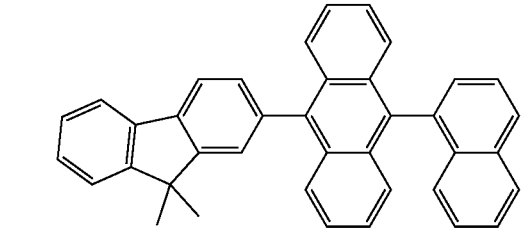
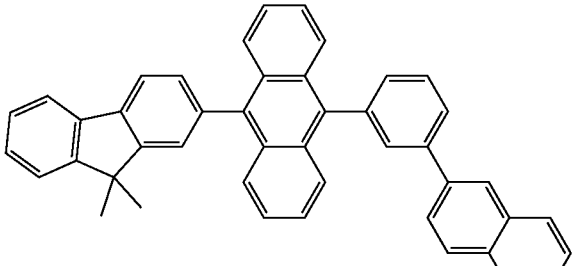
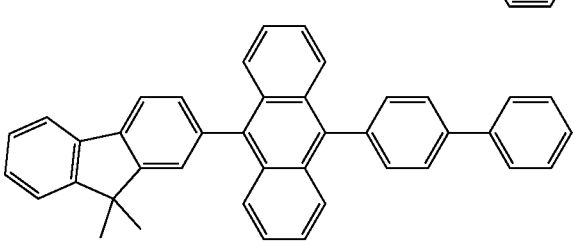
428
-continued
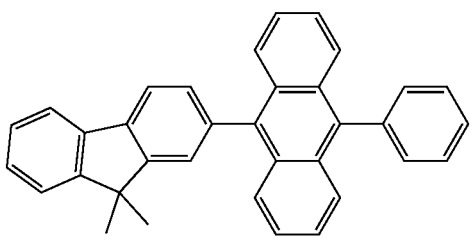
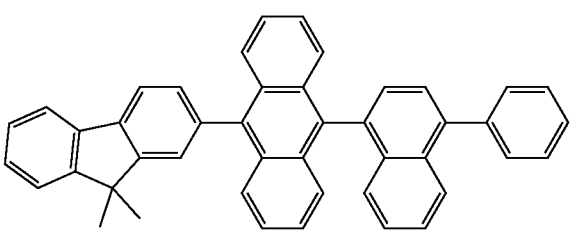
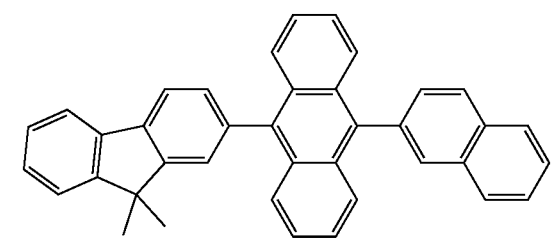
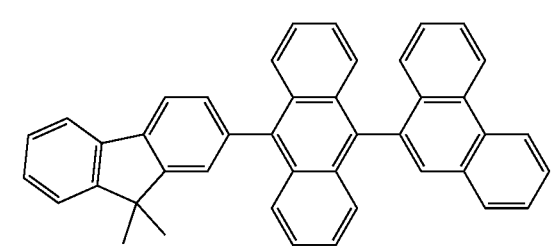
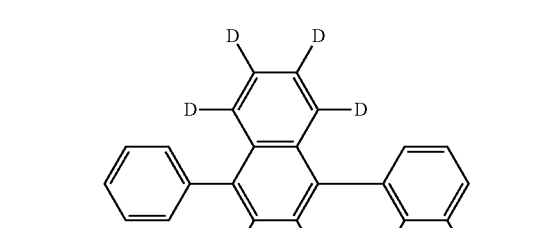

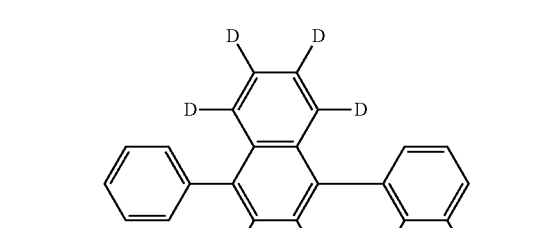

429
-continued
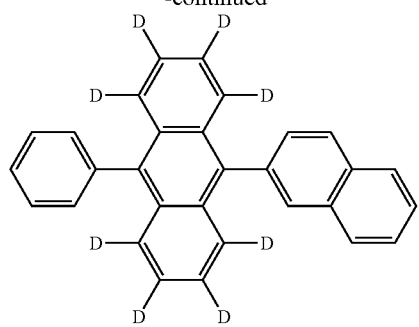
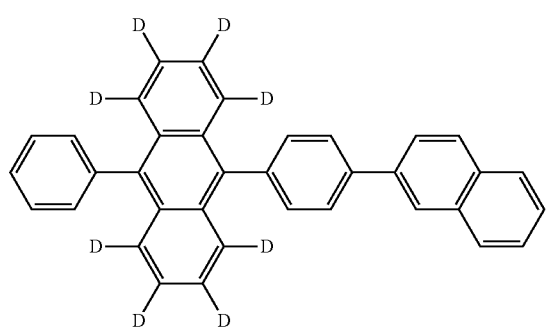
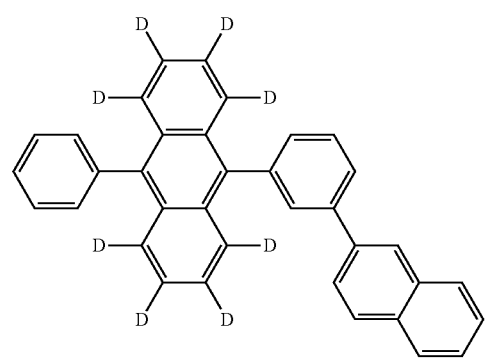
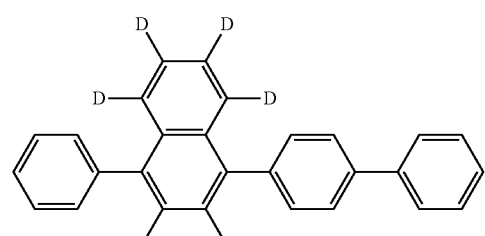
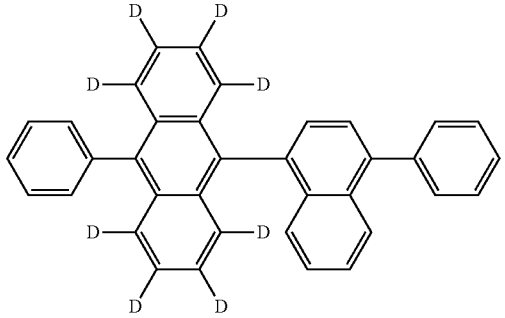
430
-continued
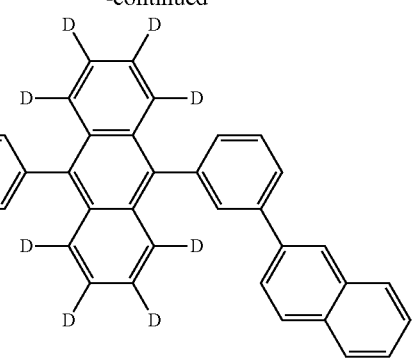
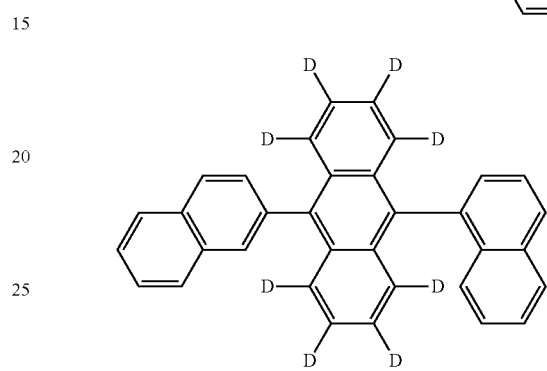
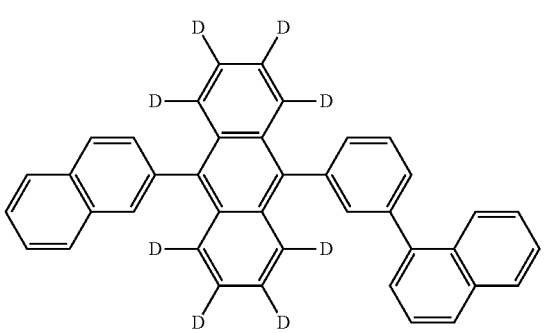
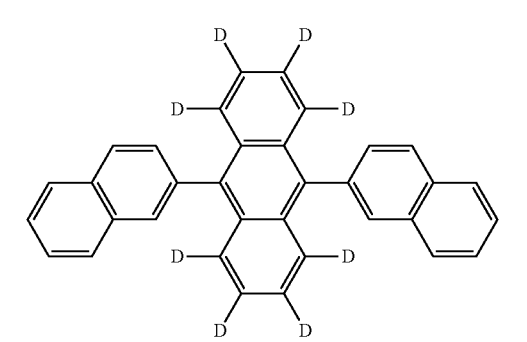

431
-continued
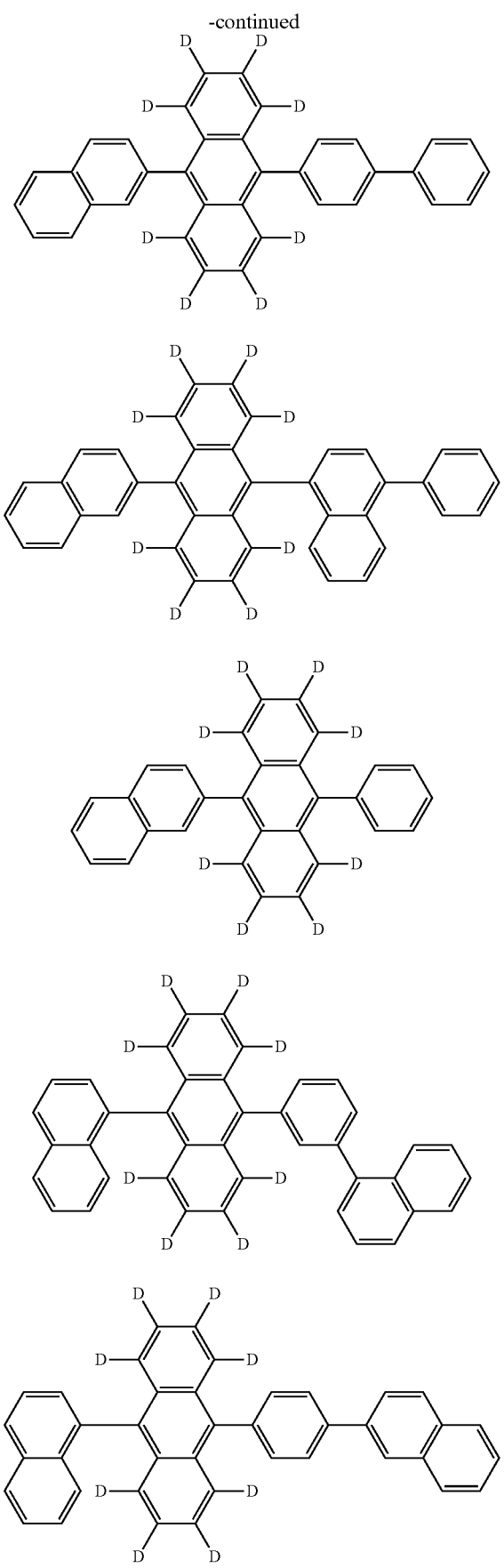
432
-continued
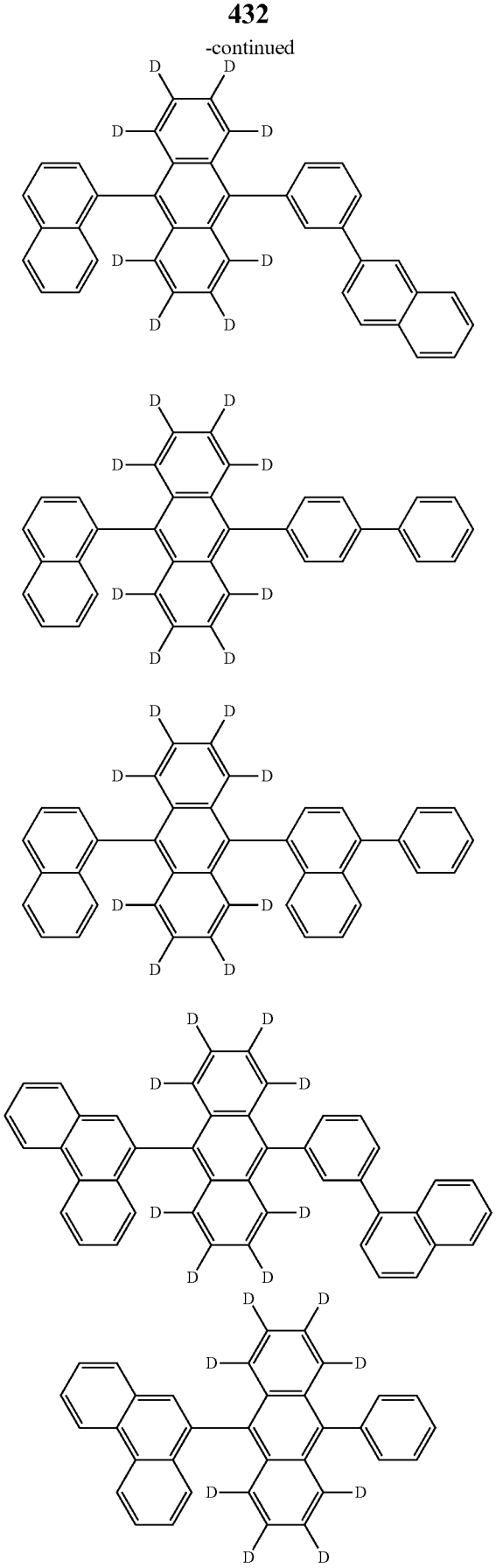

433
-continued
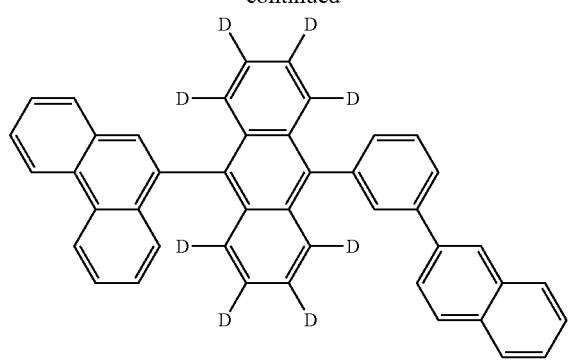
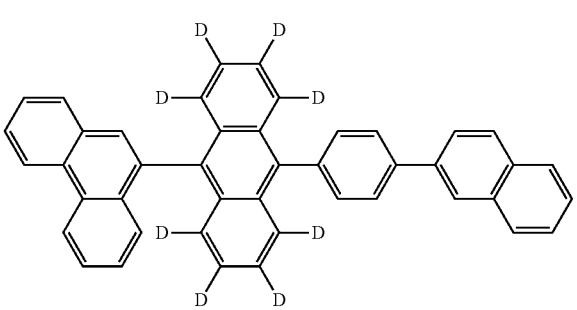
[Formula 209]
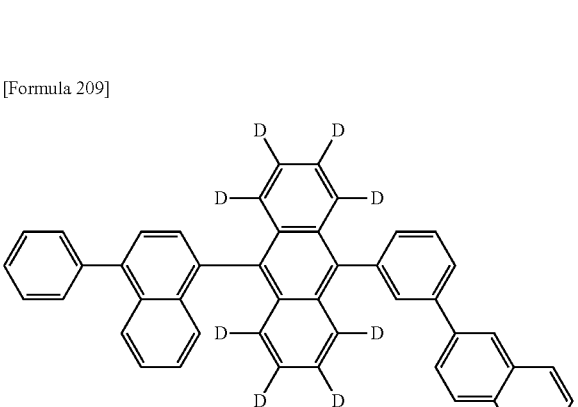
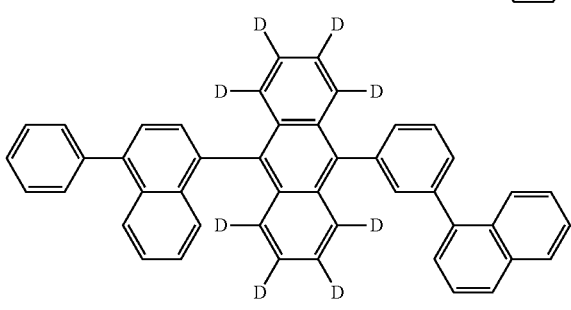
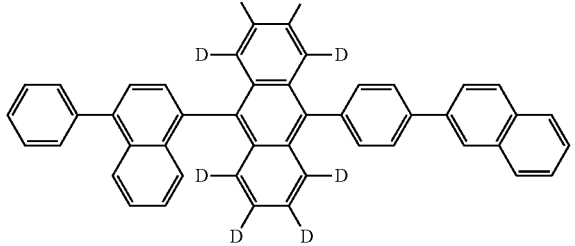
434
-continued
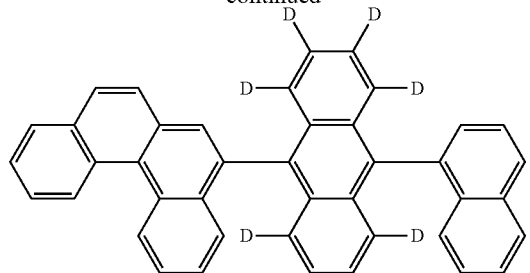
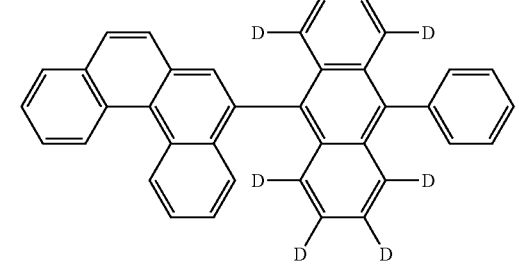
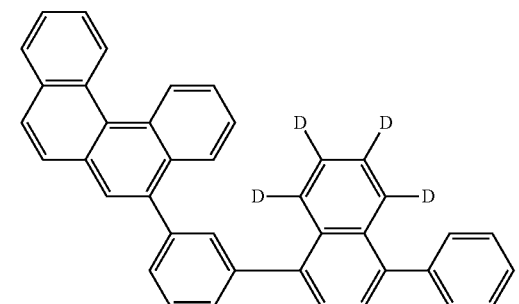
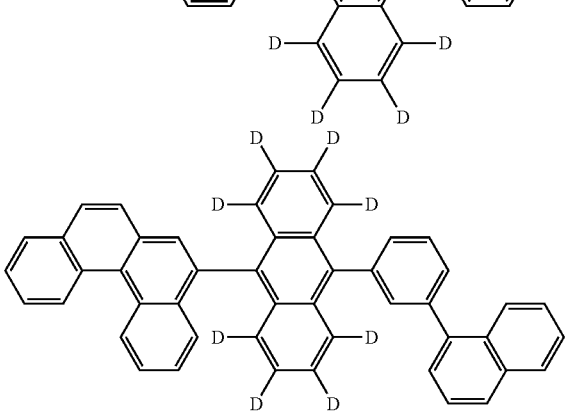
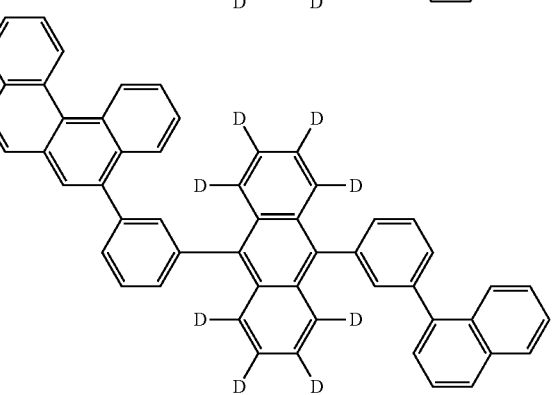

435
-continued
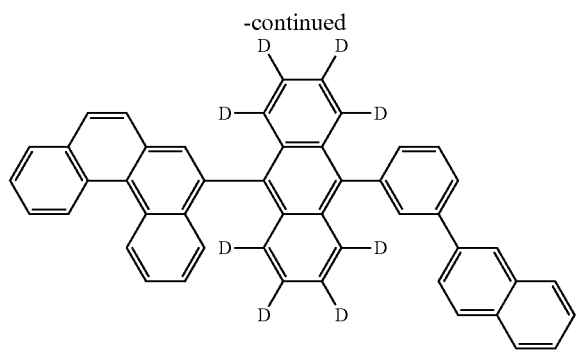
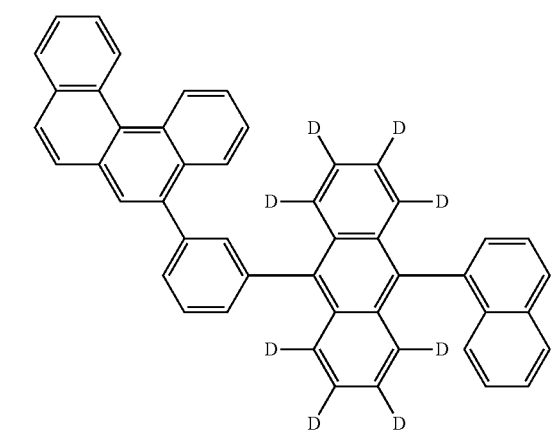
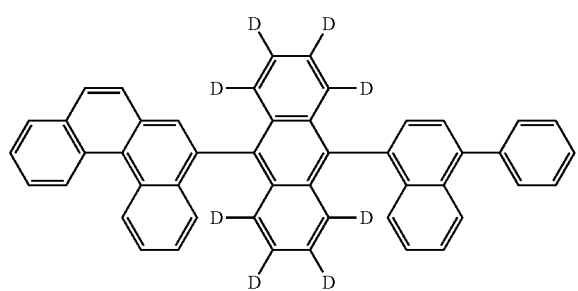
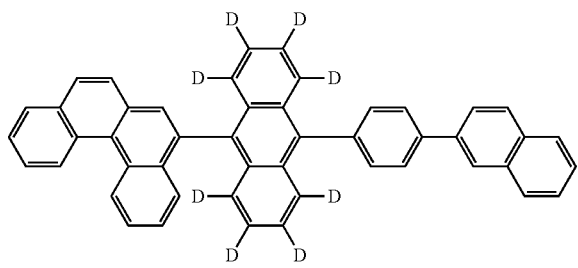
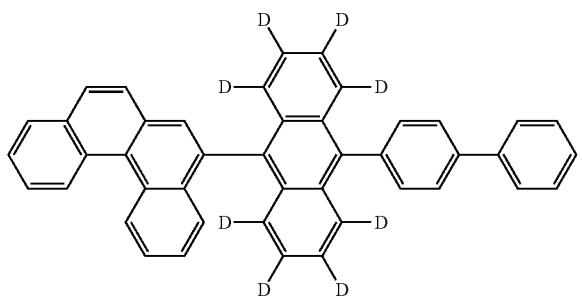
436
-continued
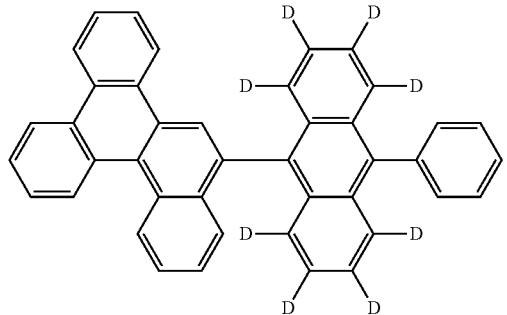
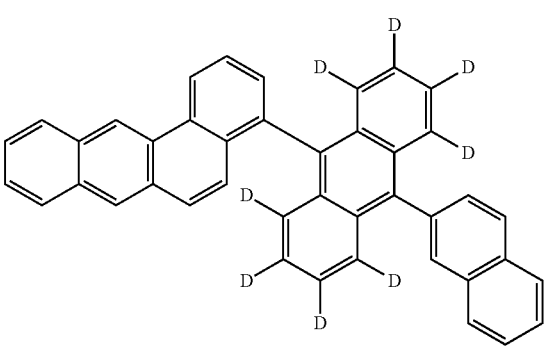
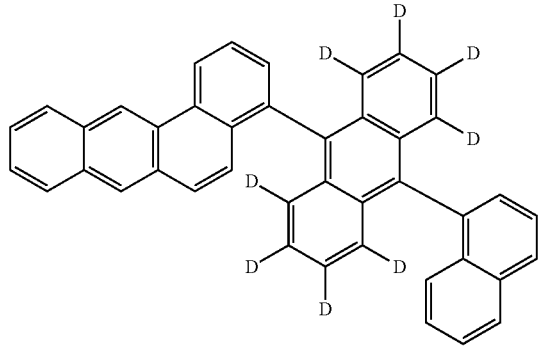
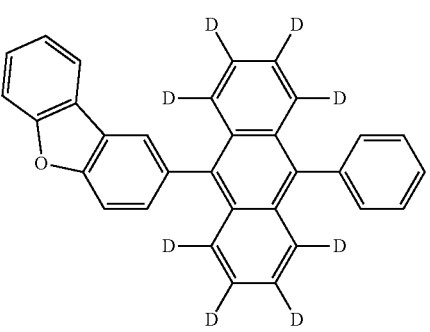
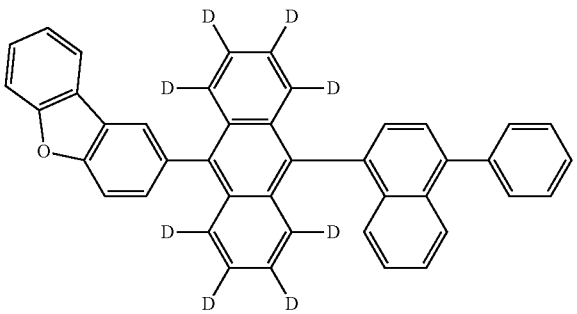

437
-continued
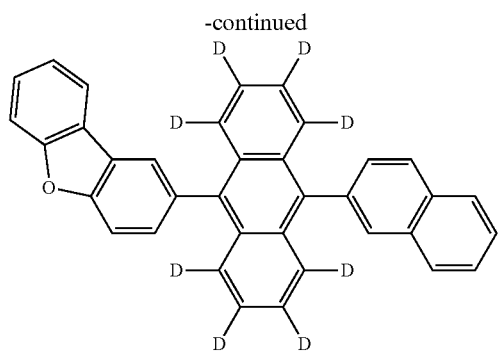
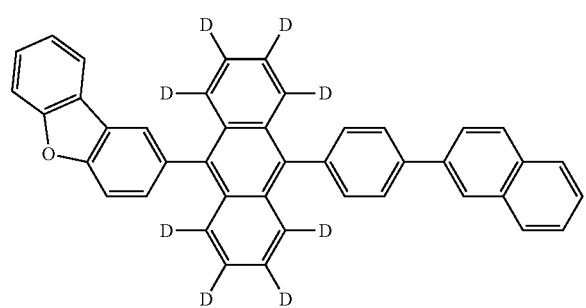
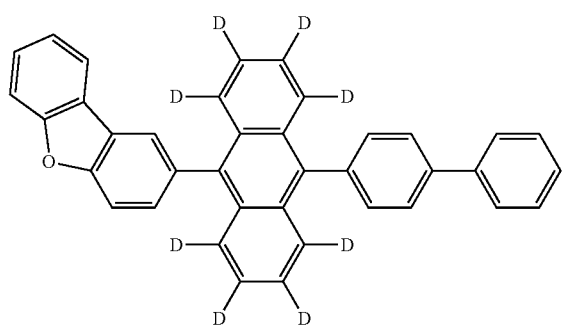
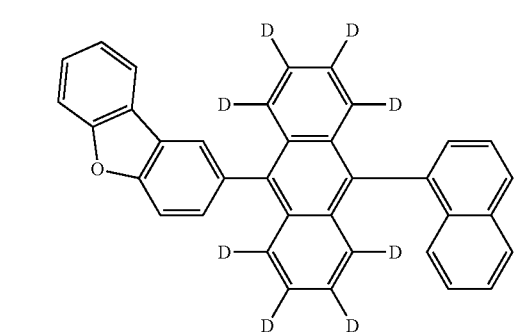
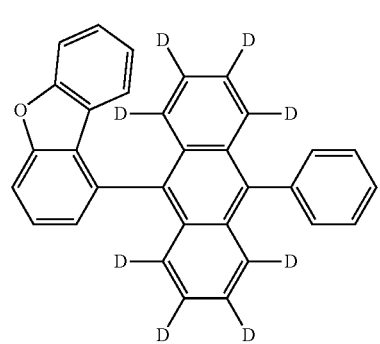
438
-continued
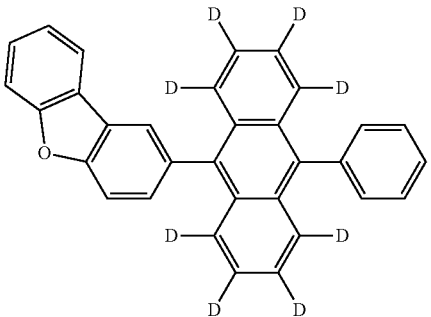
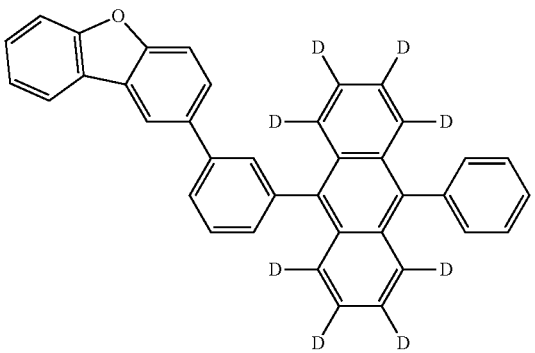
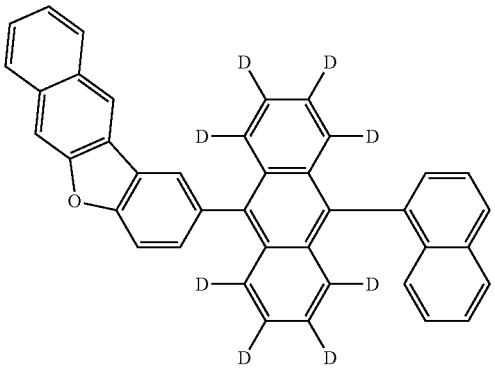
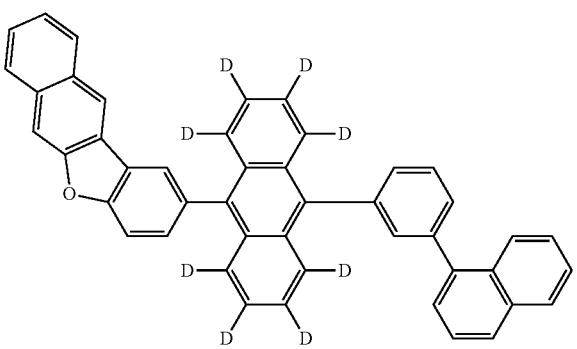

439
-continued
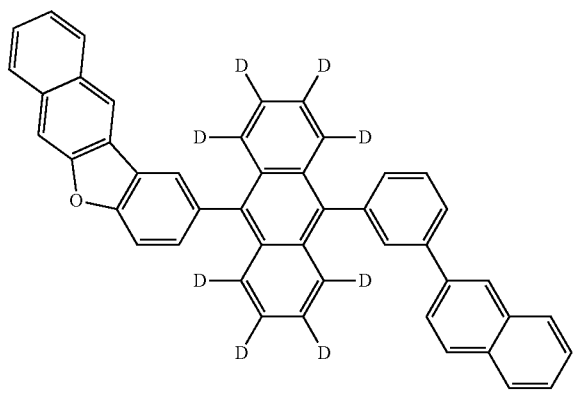
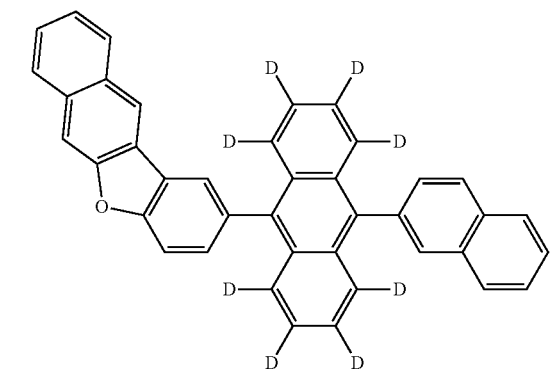
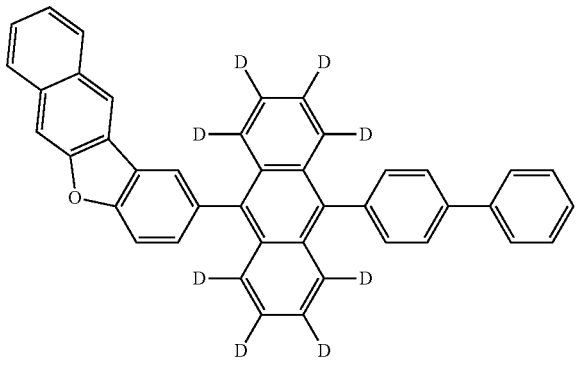
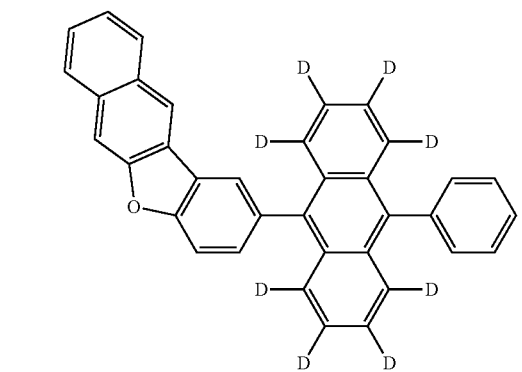
440
-continued
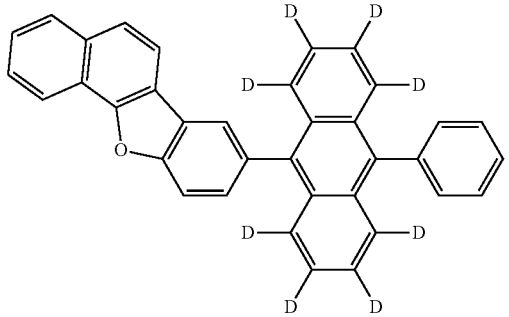
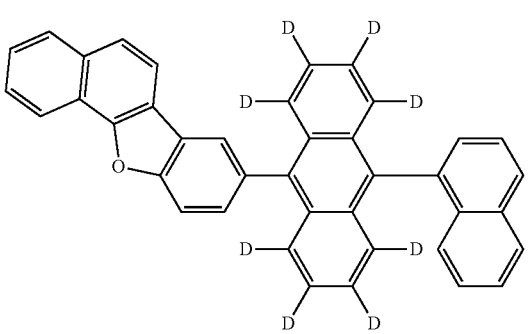
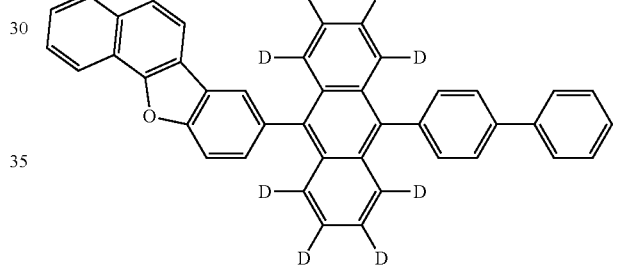
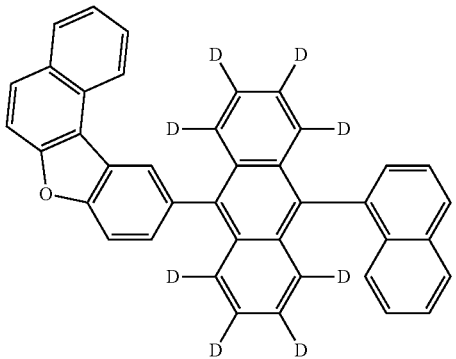
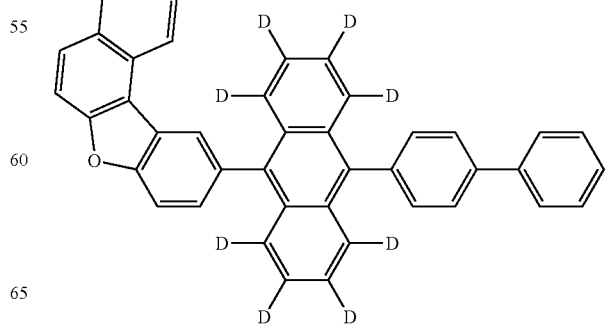

441
-continued
442
-continued
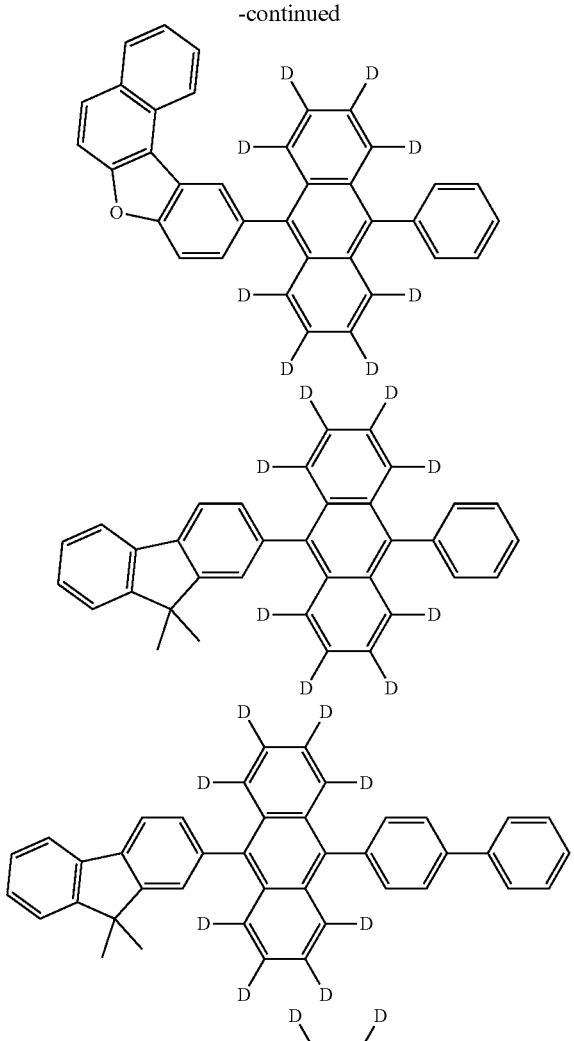
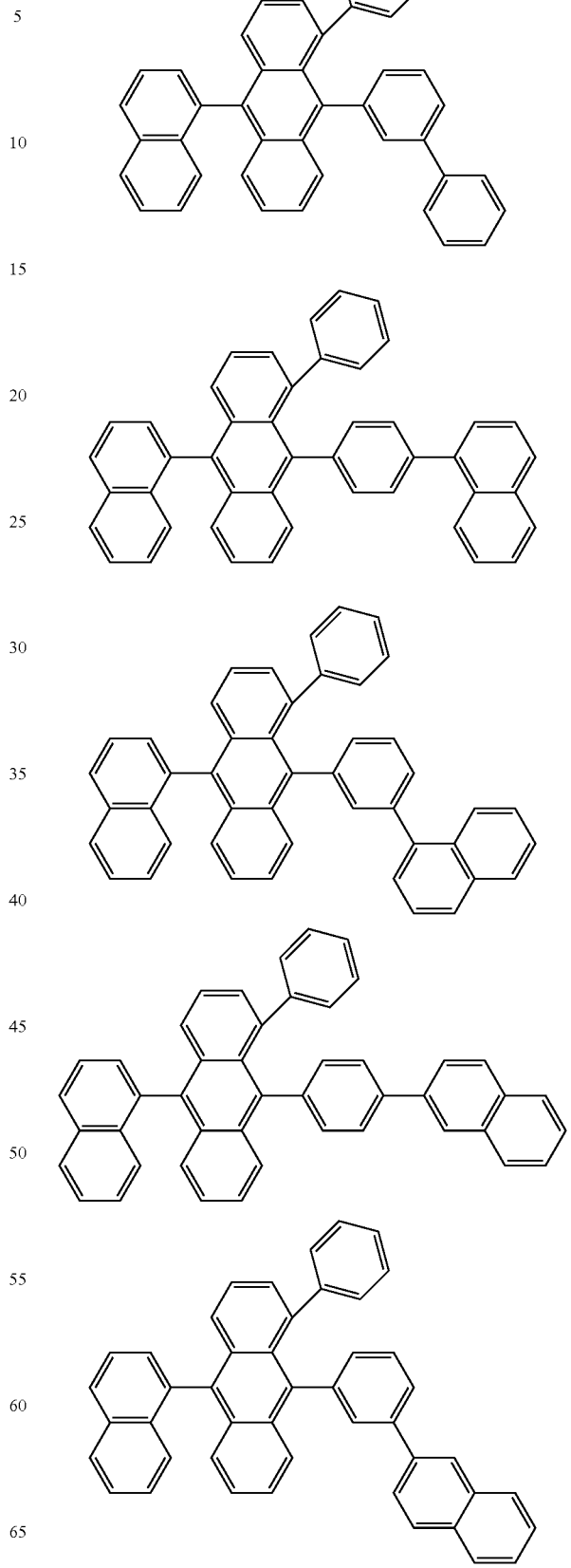
[Formula 210]

443
-continued
444
-continued
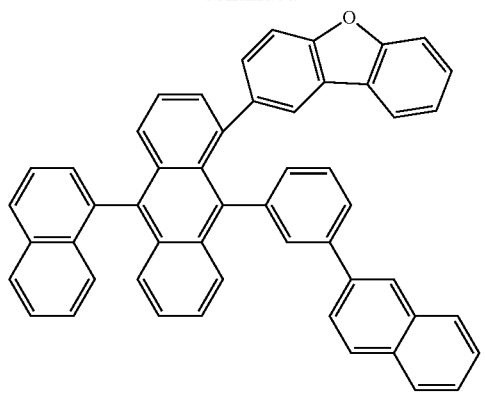
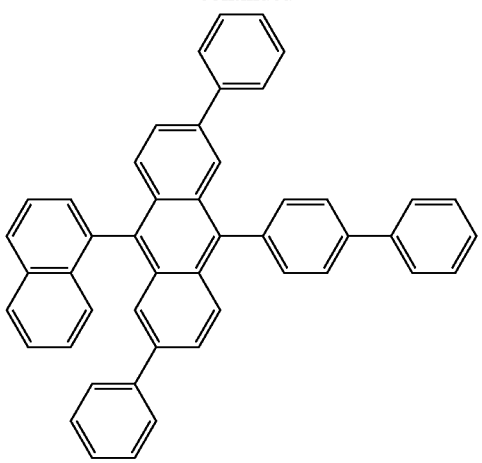
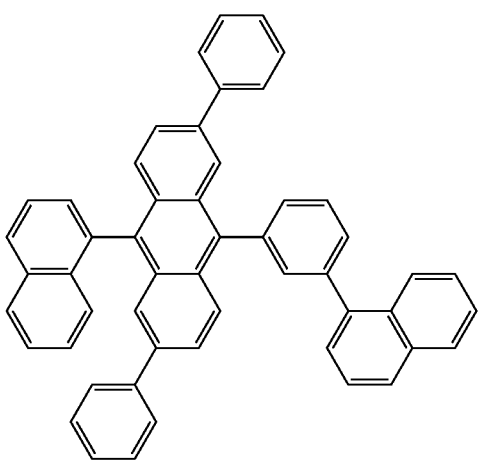
[Formula 211]
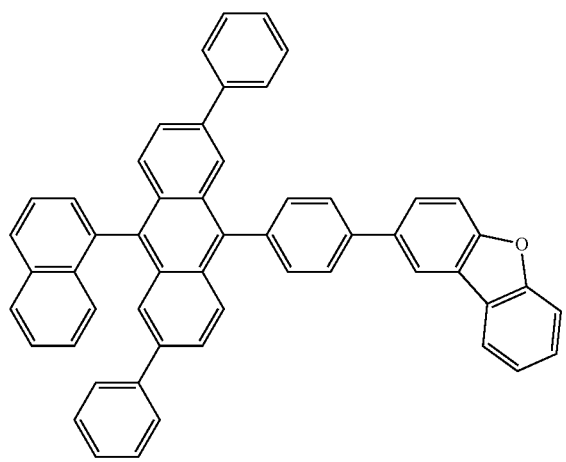

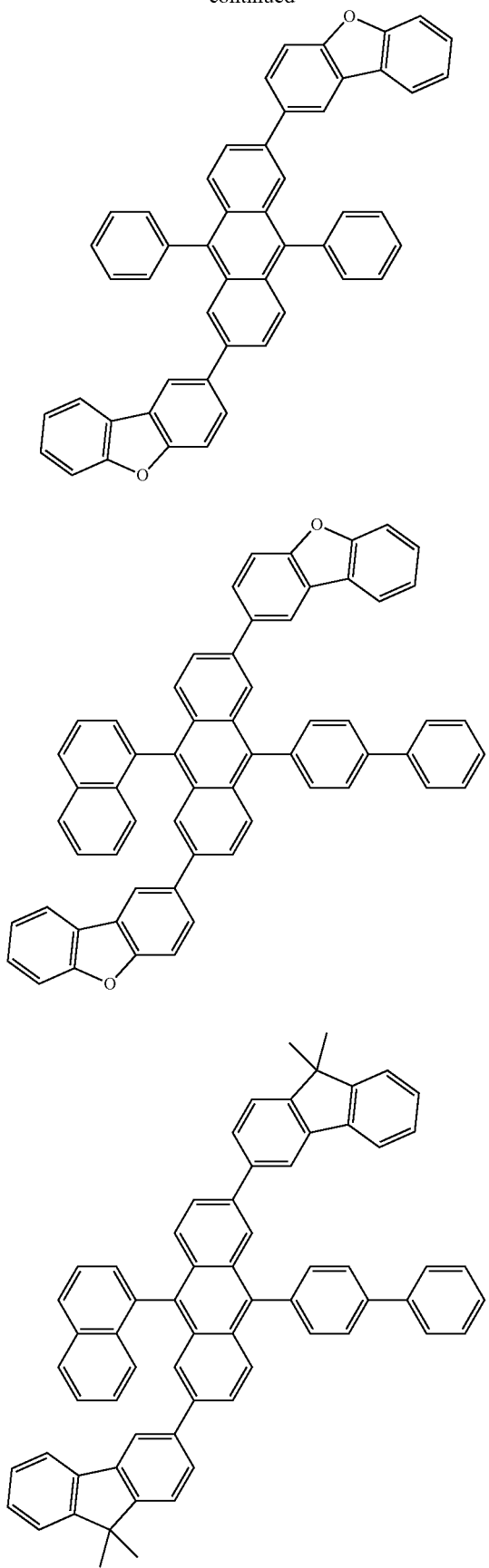
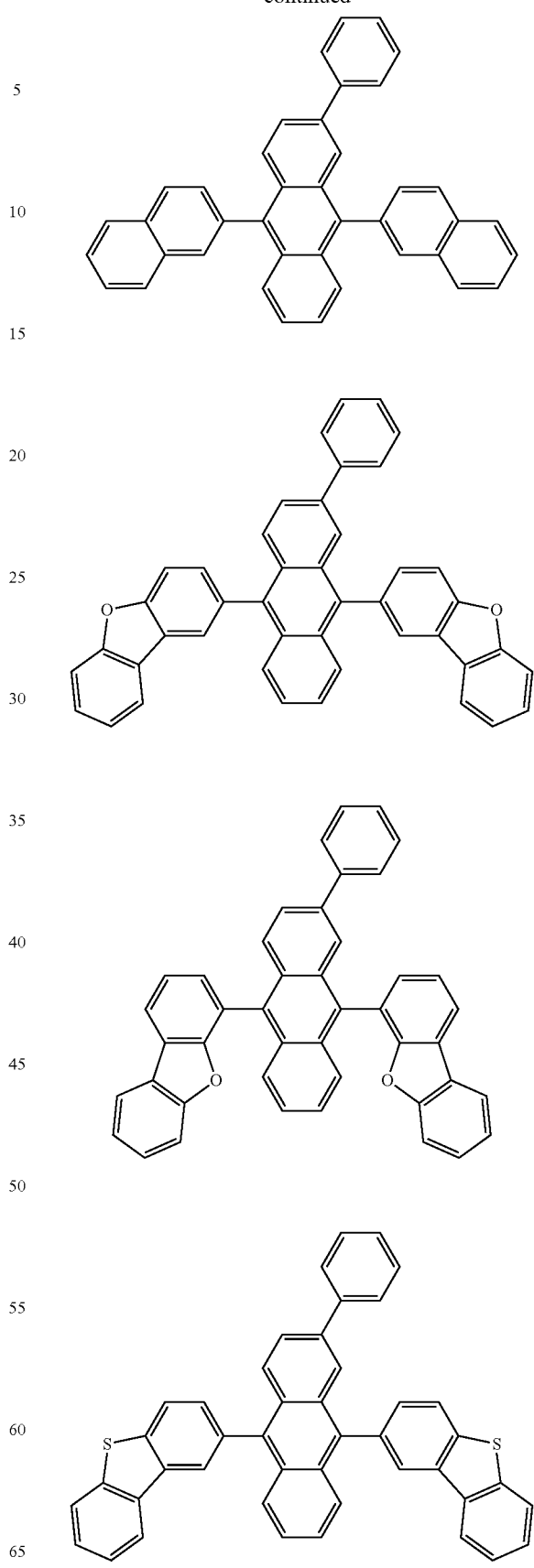

[Formula 212]
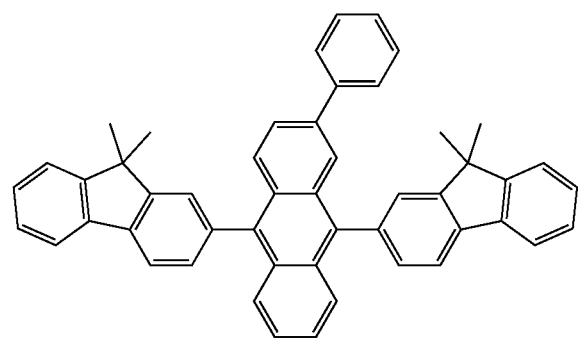
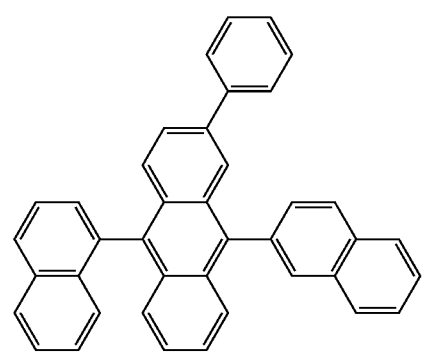
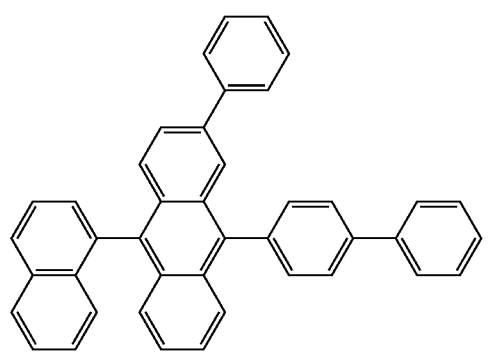
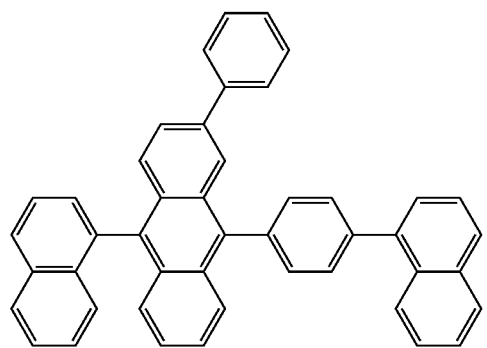
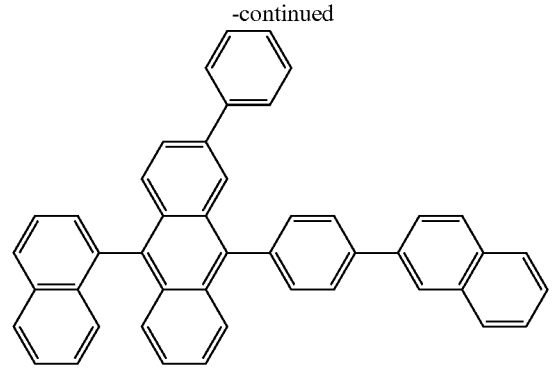
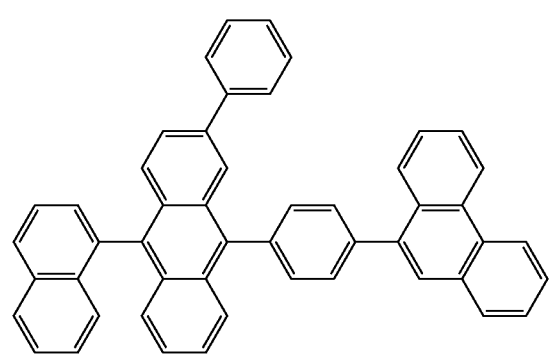
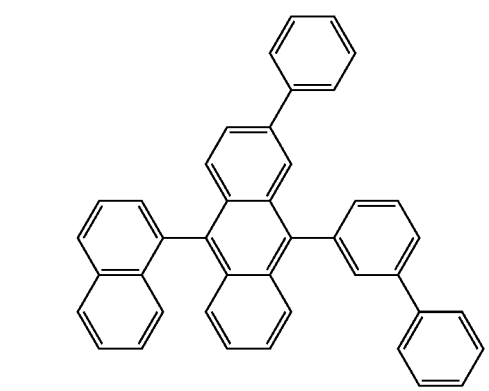
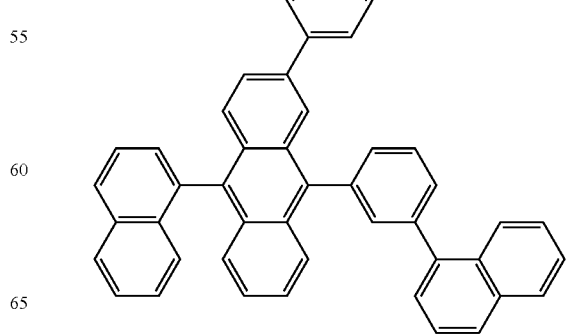

[Formula 213]
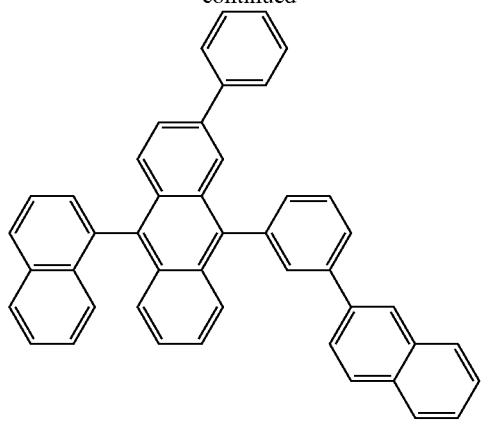 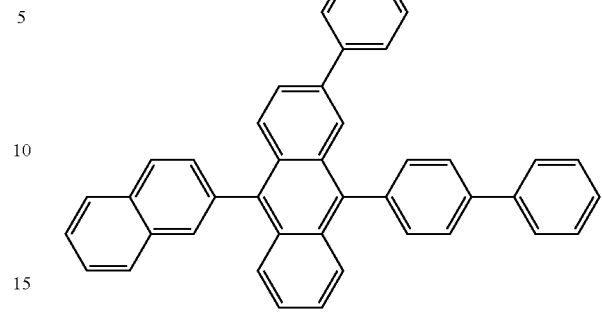
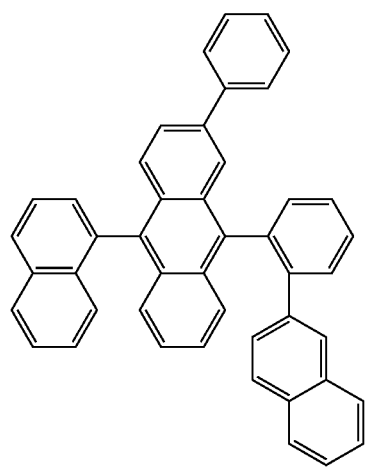 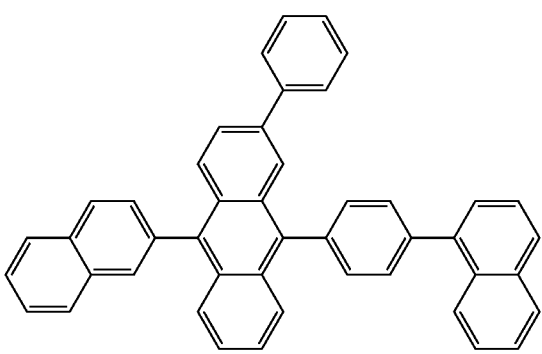
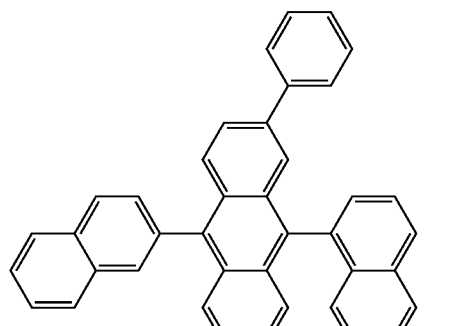 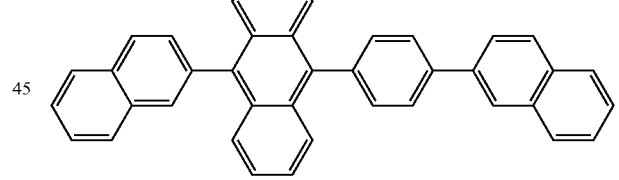
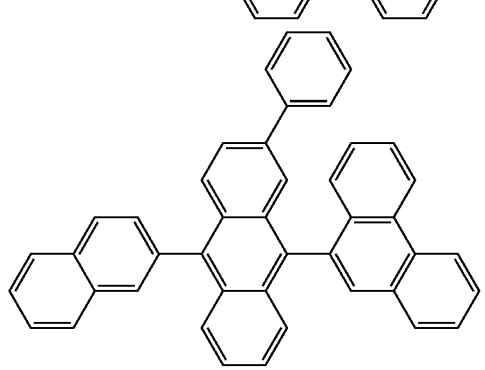 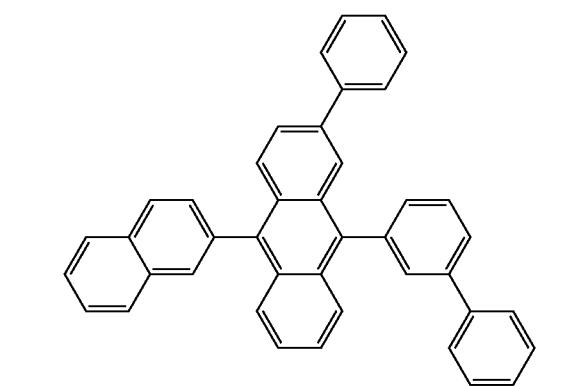

-continued
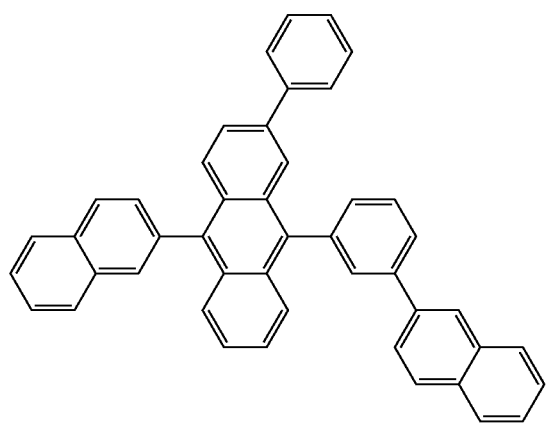
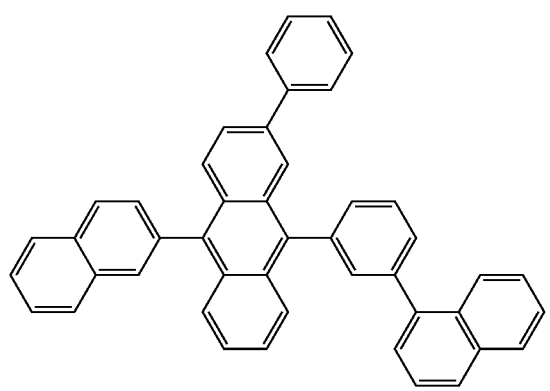
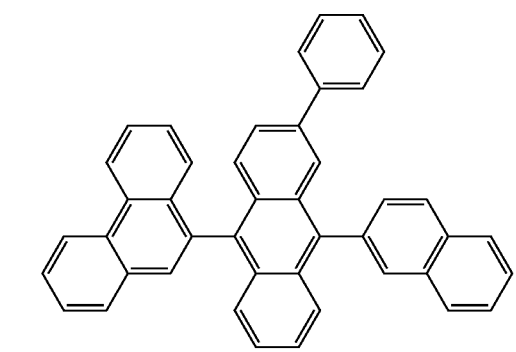
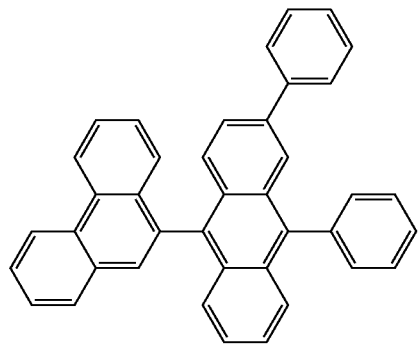
[Formula 214]
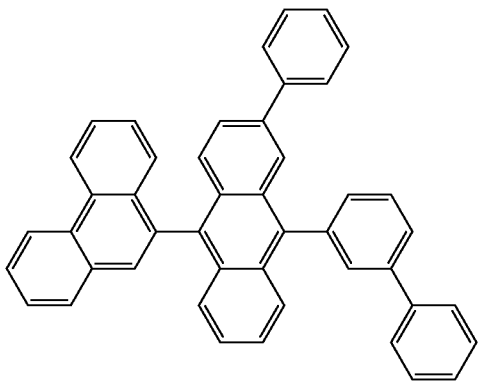
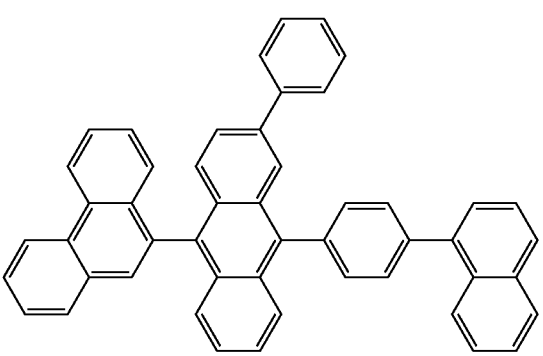
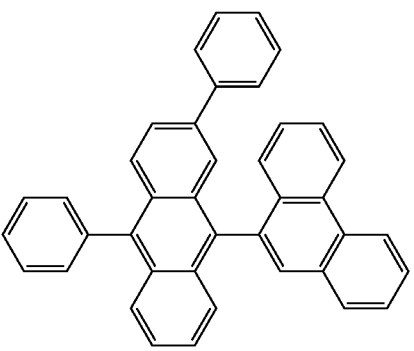
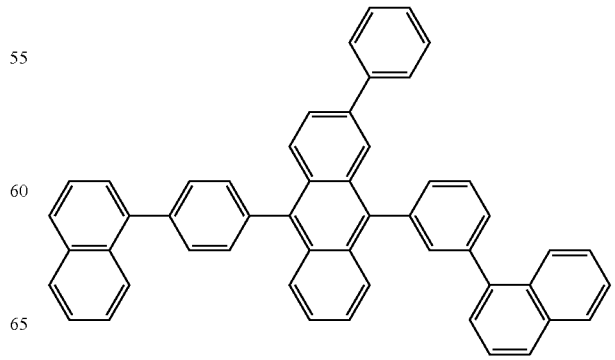

-continued
[Formula 215]
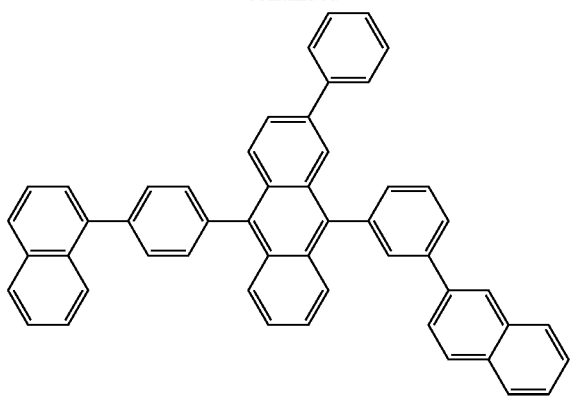
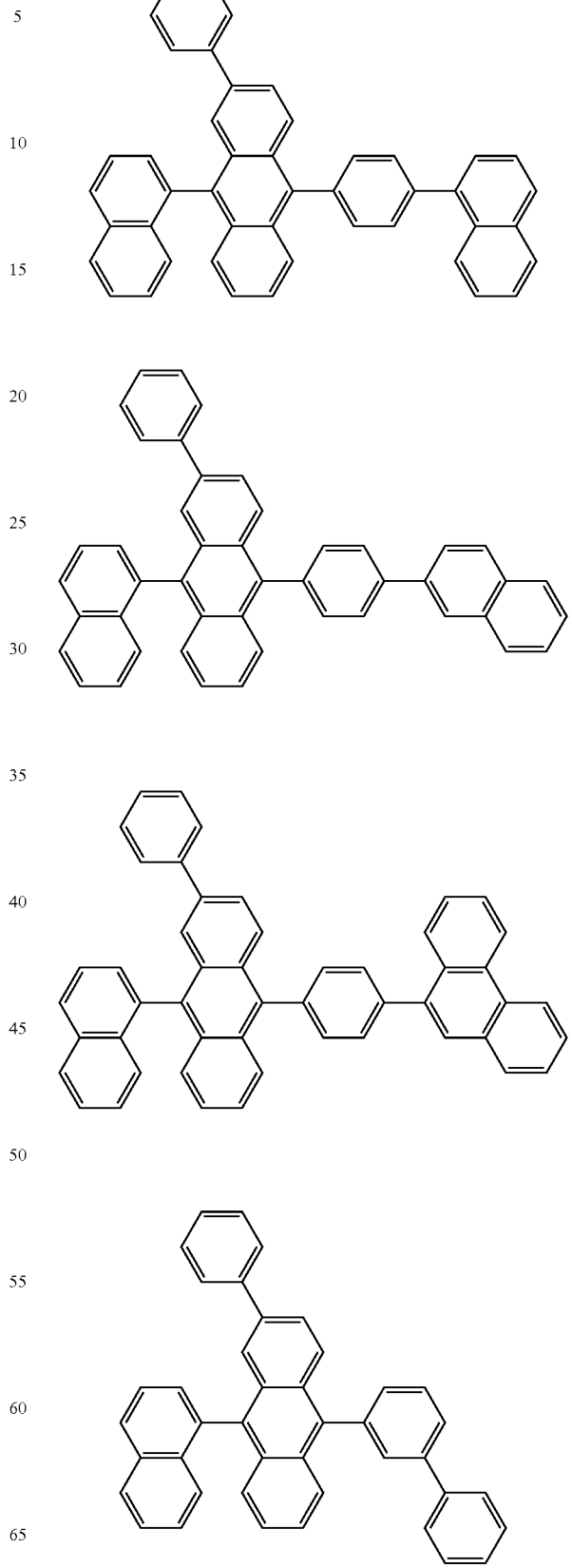

[Formula 216]
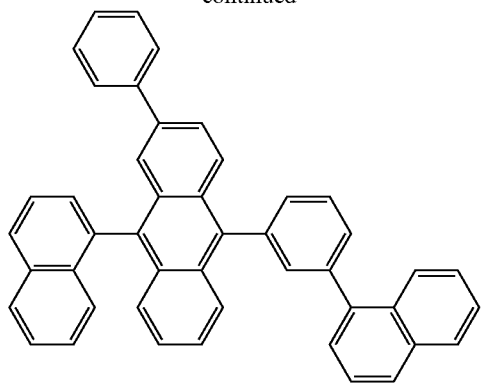
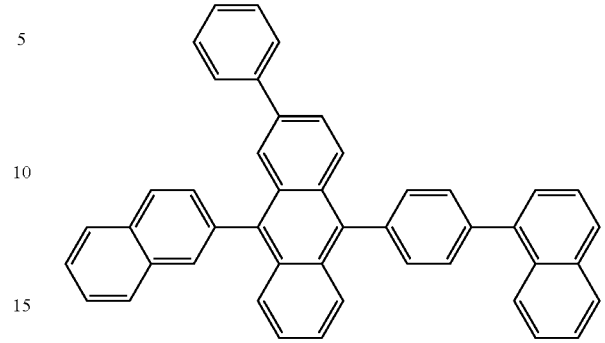
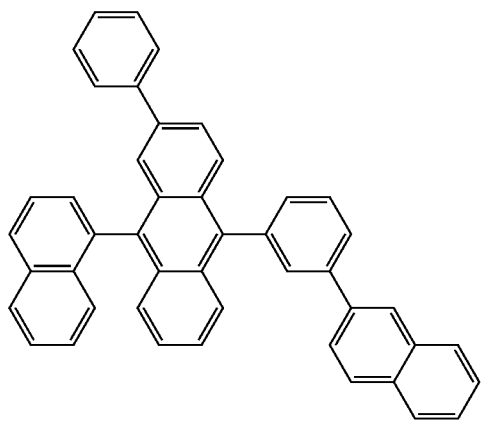
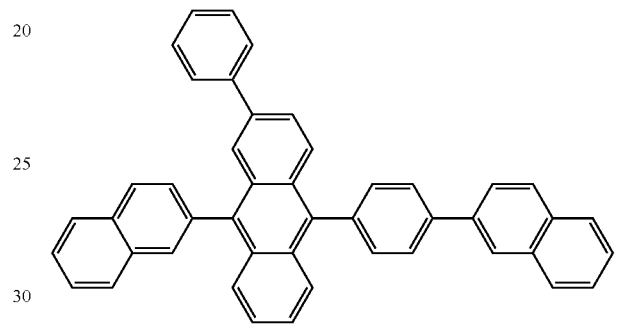
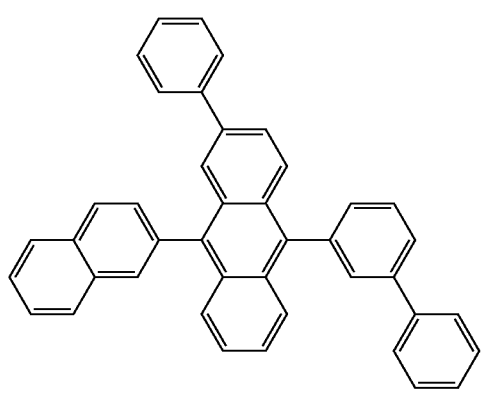
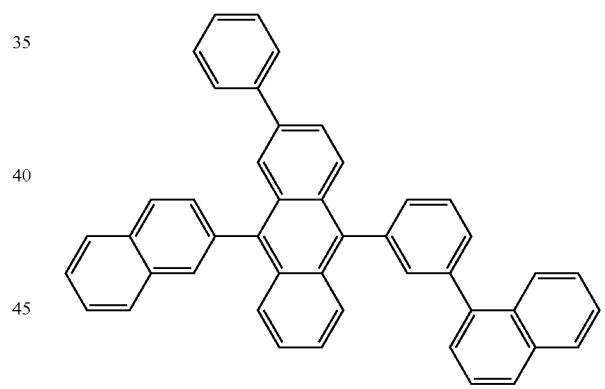
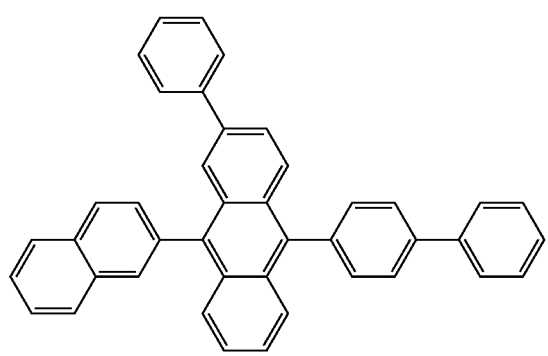
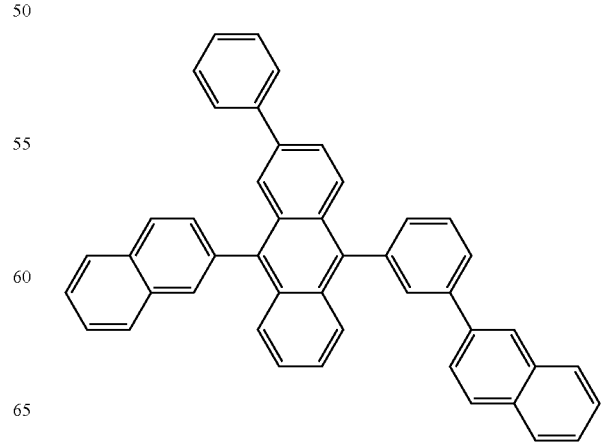

457
-continued
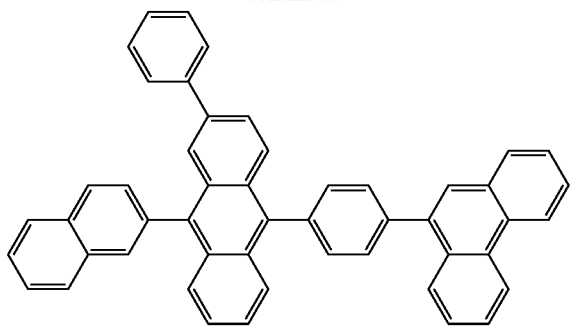
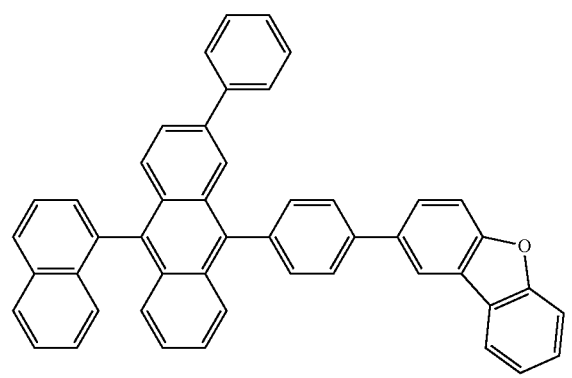
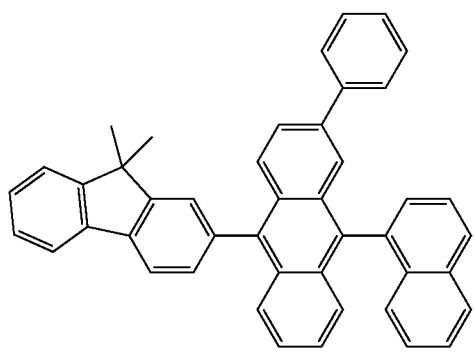
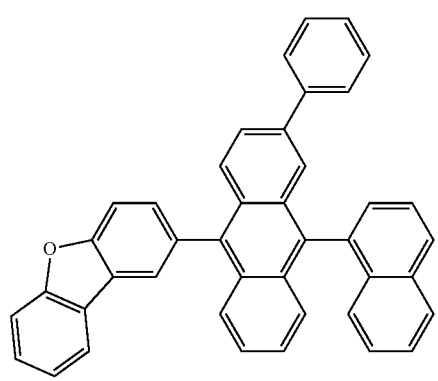
458
[Formula 217]
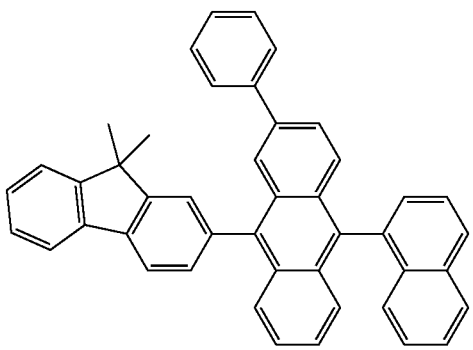
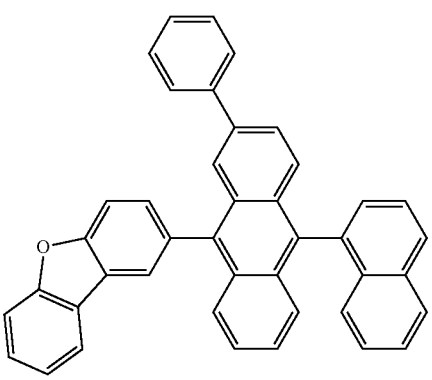
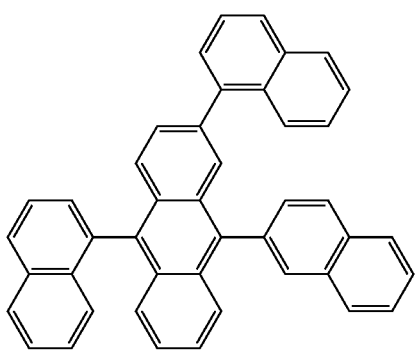
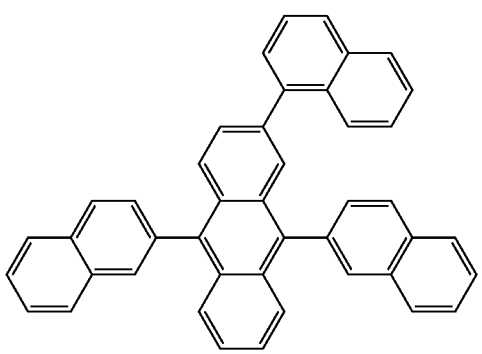

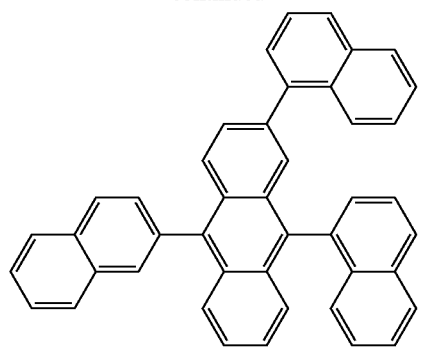
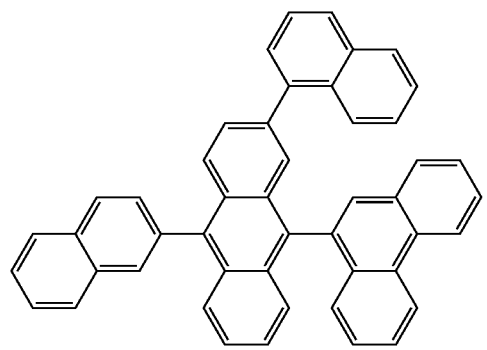
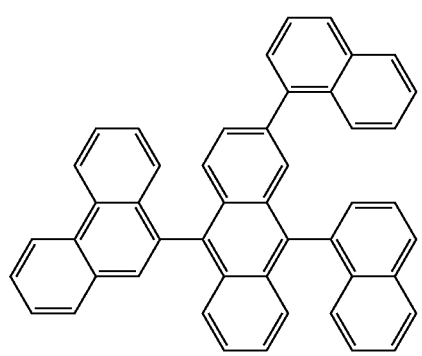
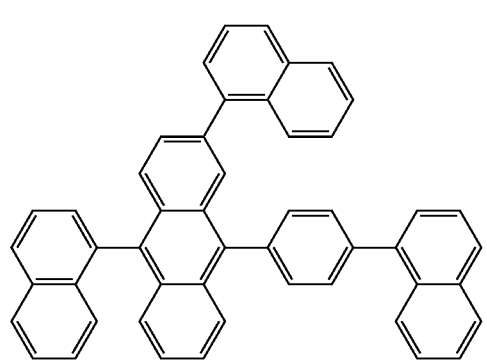
[Formula 218]
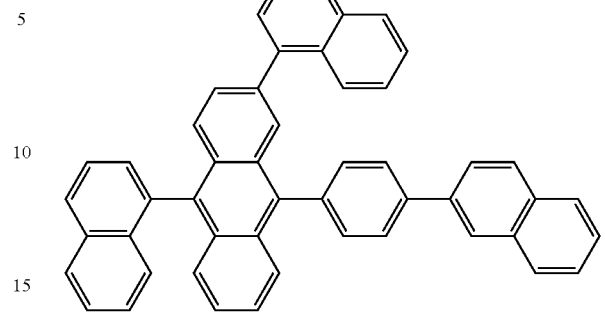
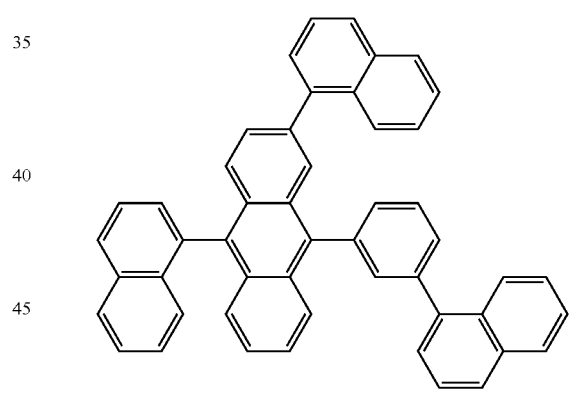

461
-continued
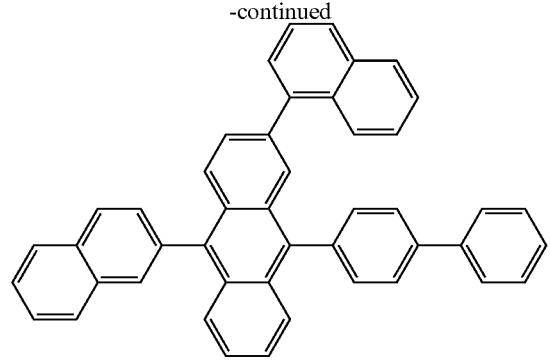
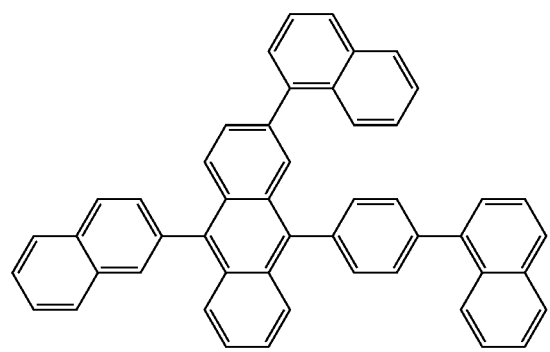
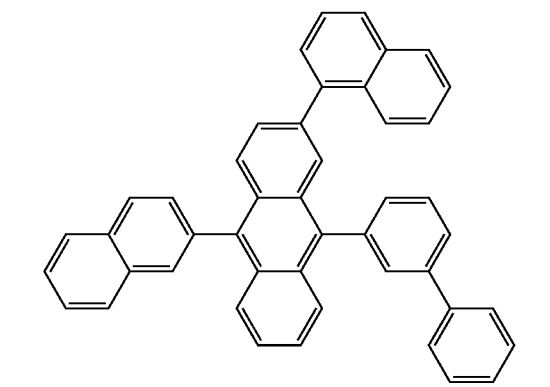
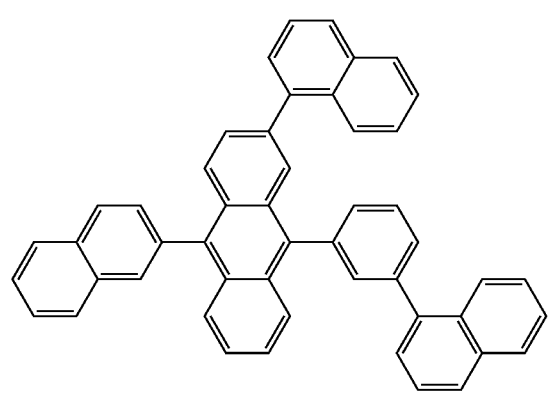
462
[Formula 219]
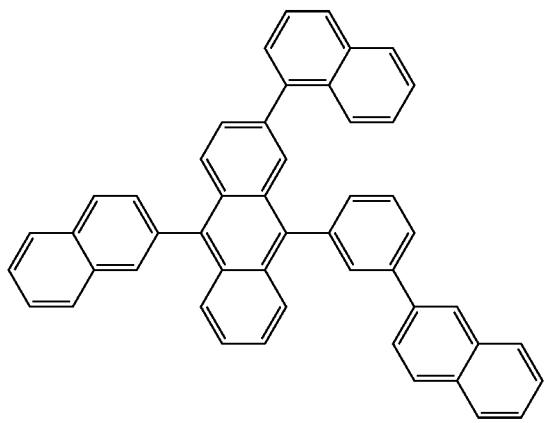
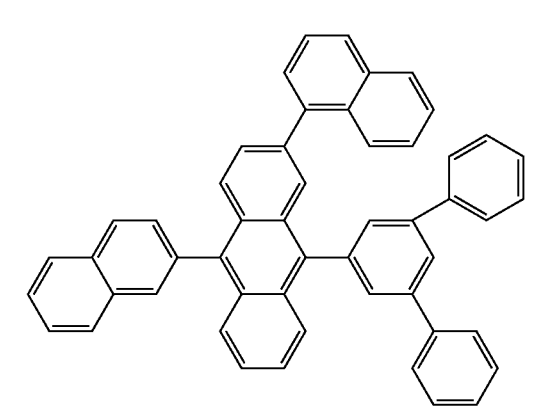
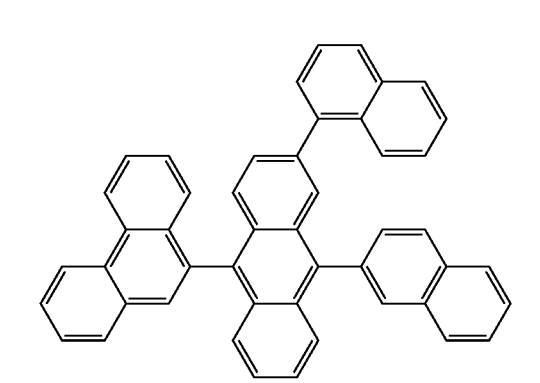
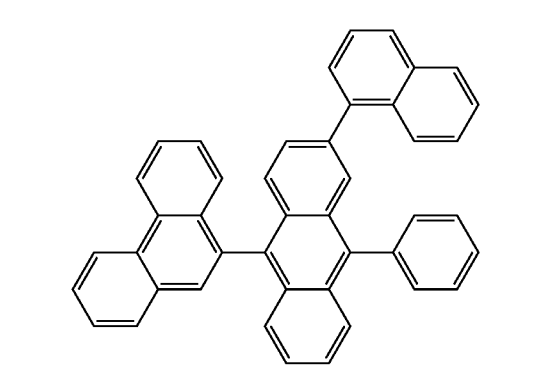

463
-continued
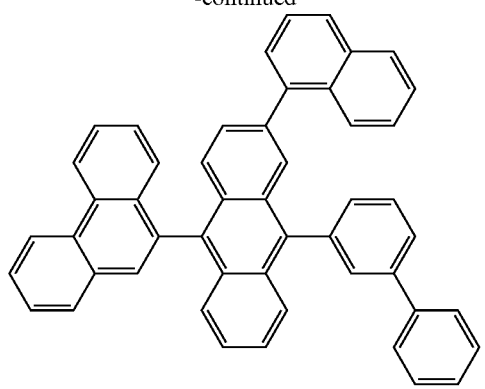
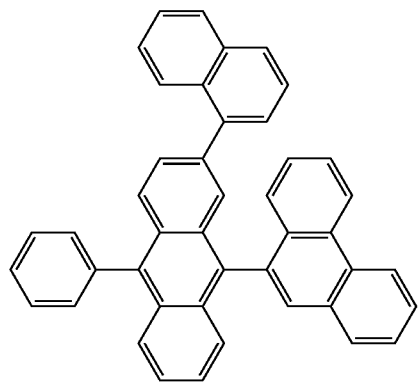
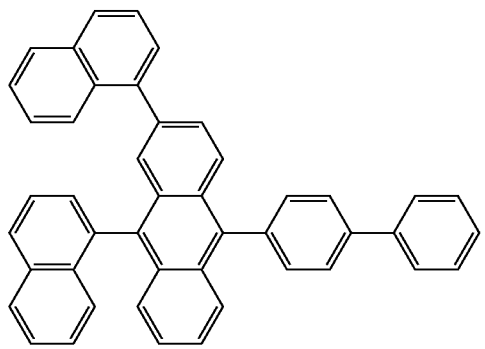
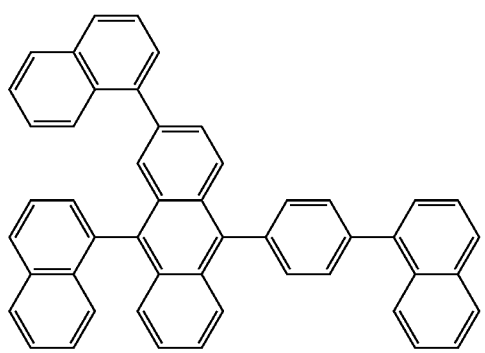
464
[Formula 220]
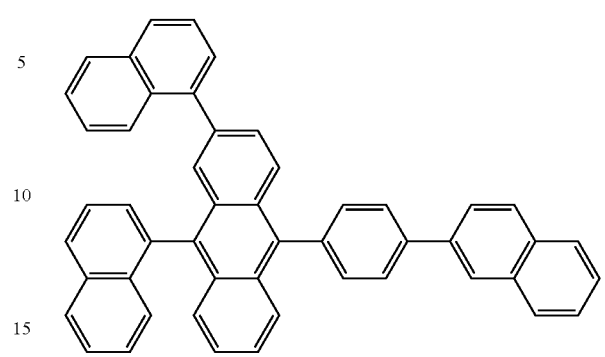
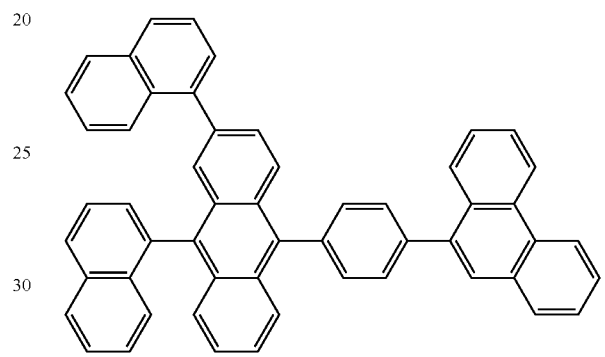
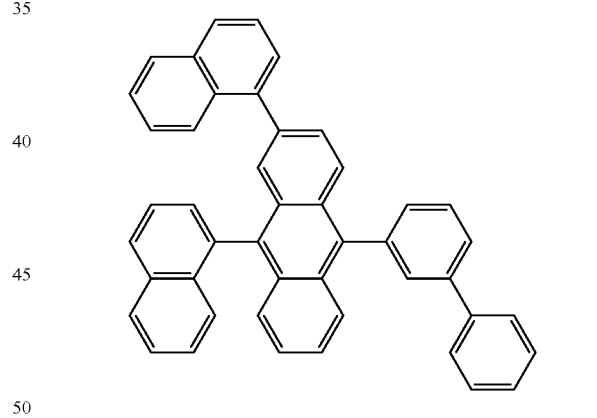
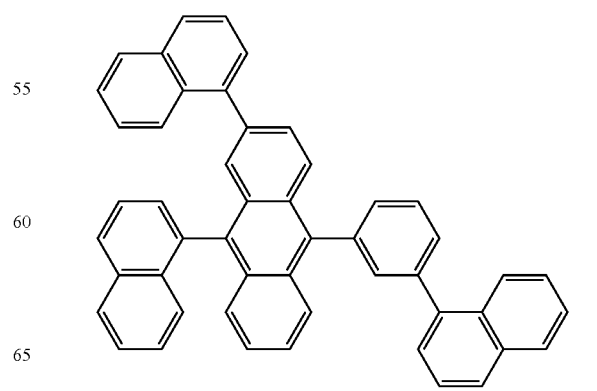

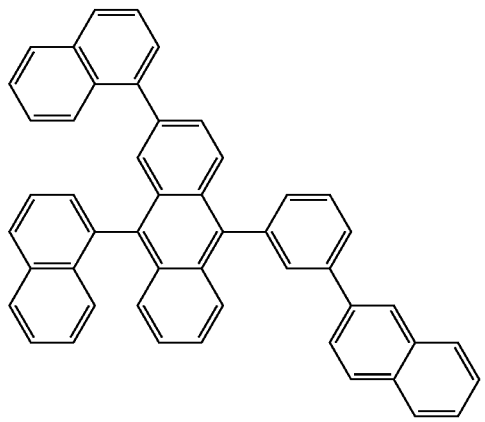
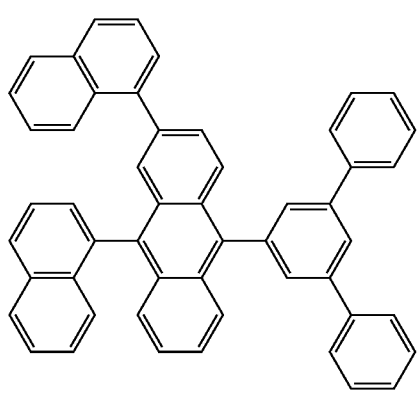
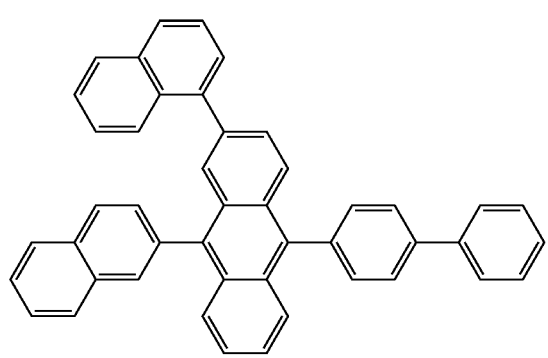
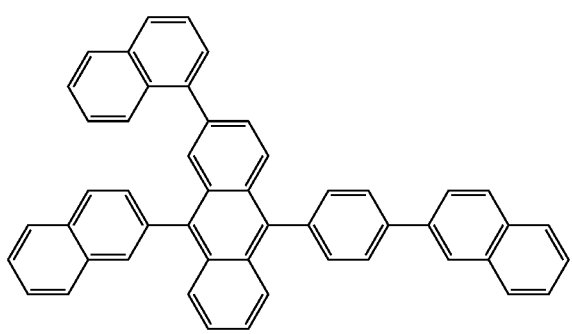
[Formula 221]
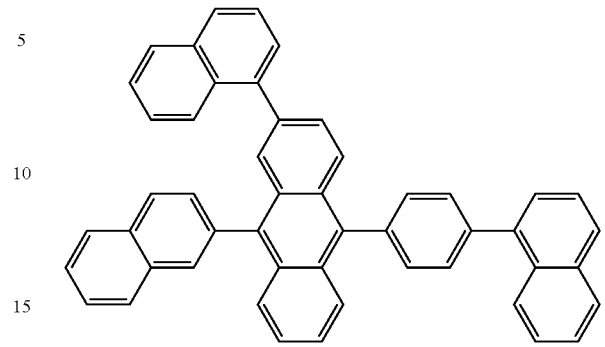
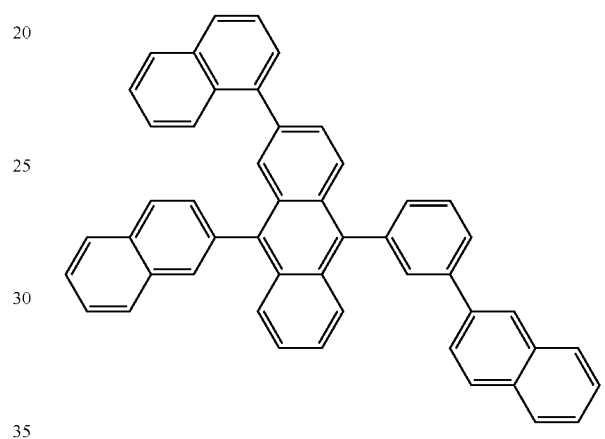
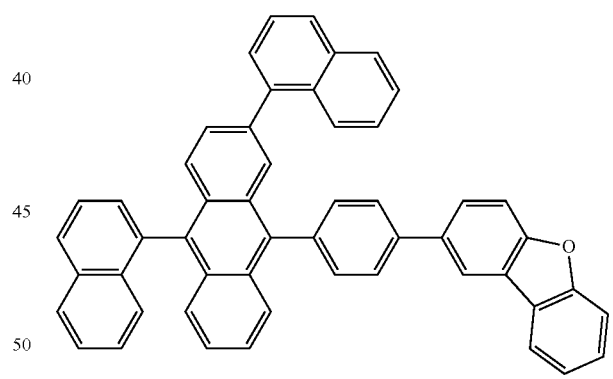
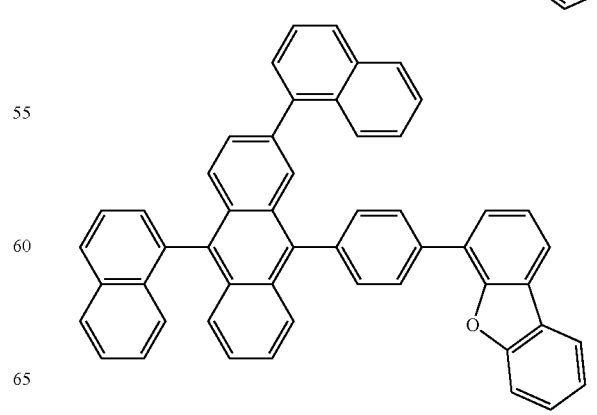

467
-continued
468
[Formula 222]
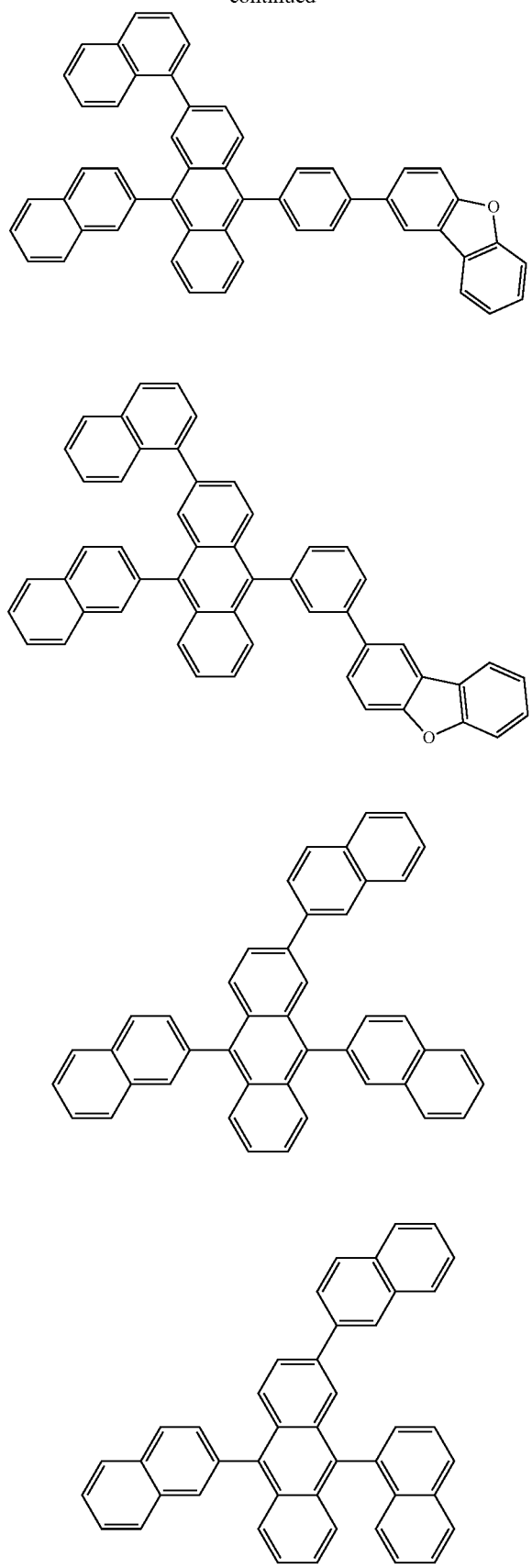

469
-continued
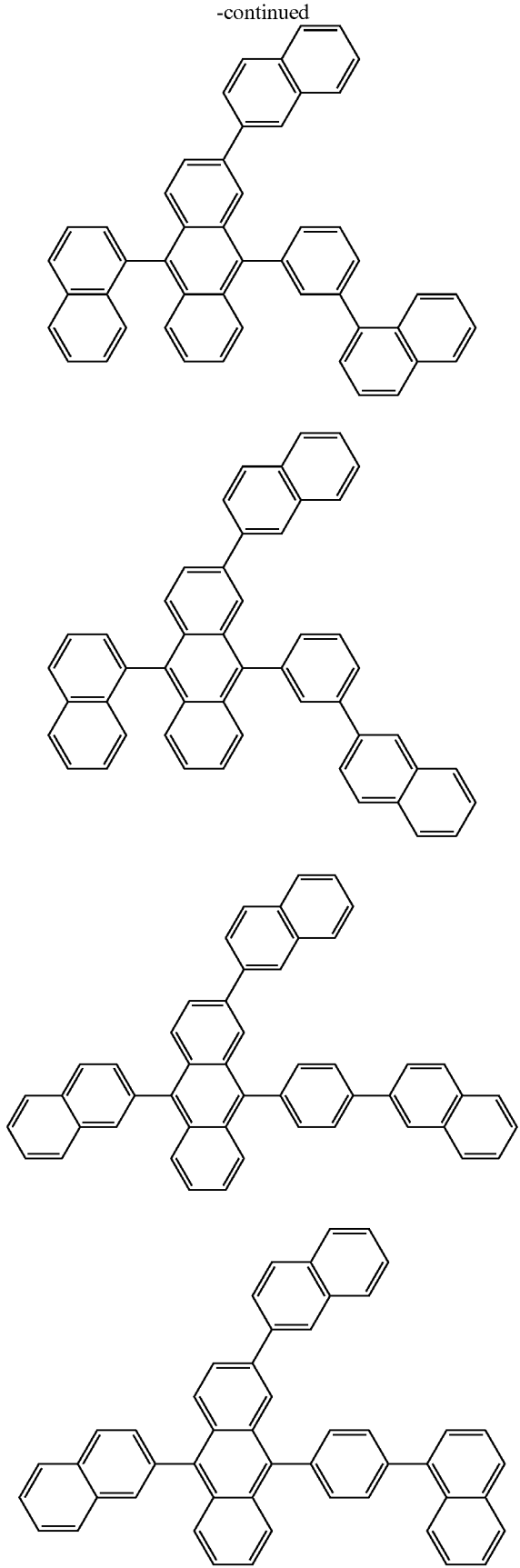
470
[Formula 223]
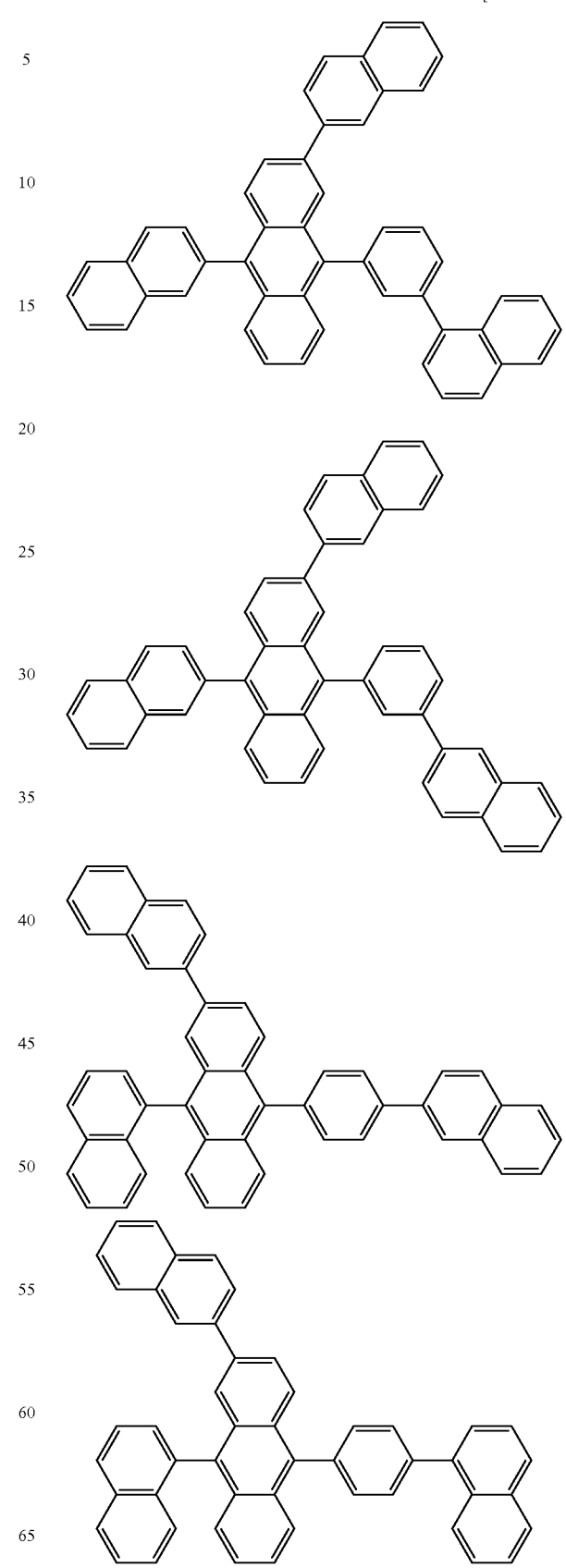

471
-continued
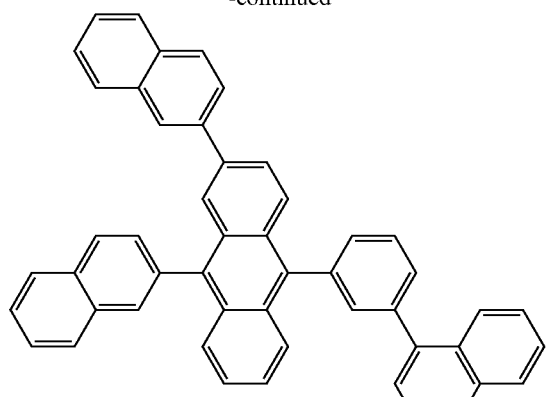
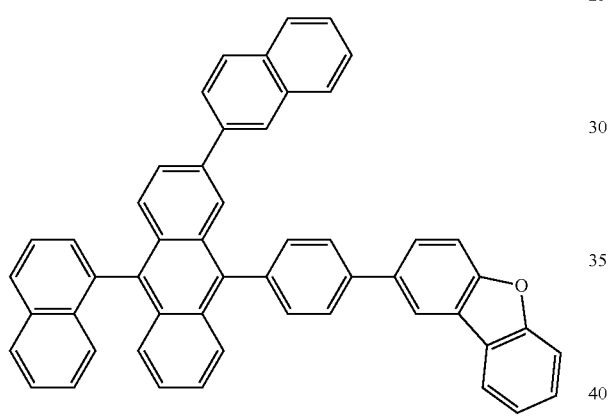
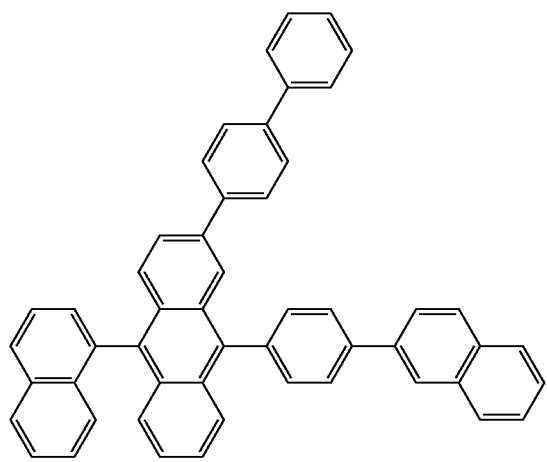
472
-continued
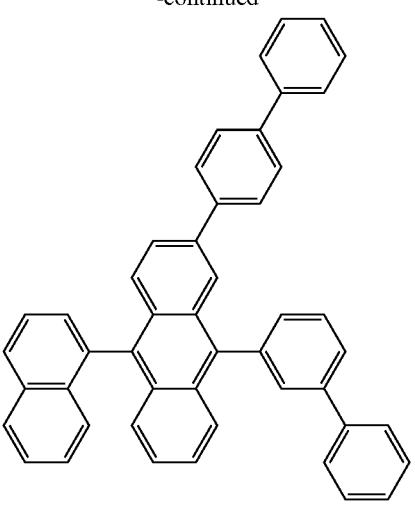
[Formula 224]
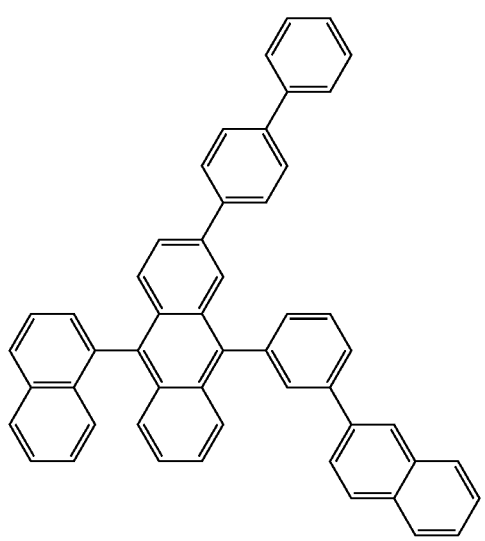
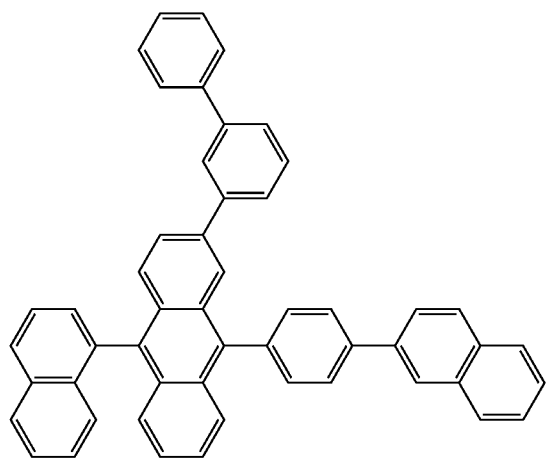

473
-continued
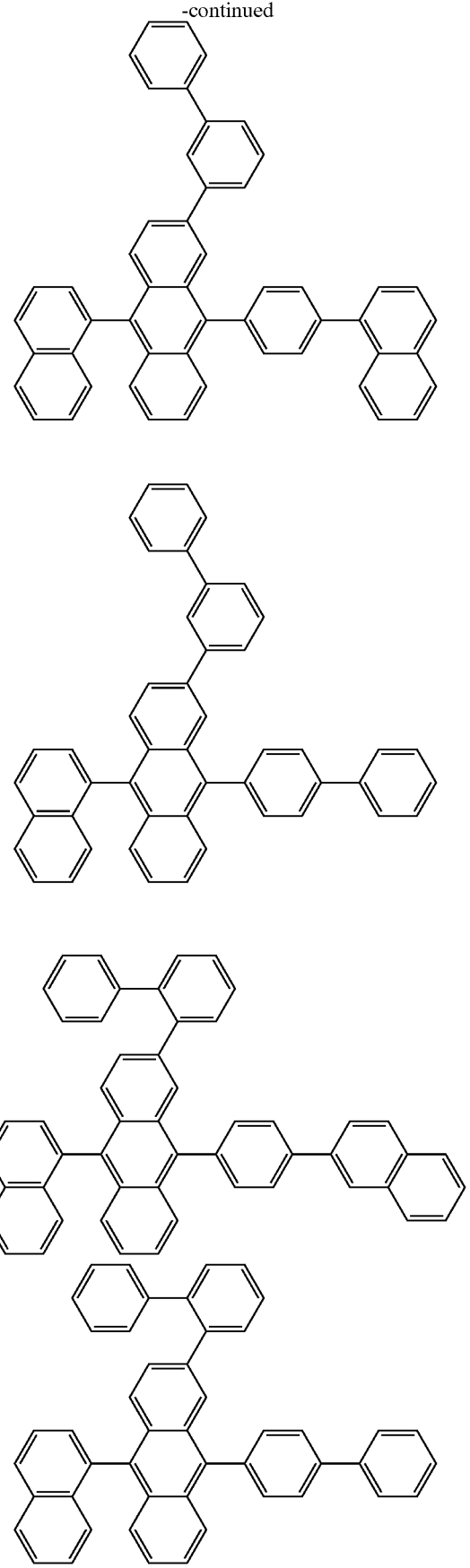
474
-continued
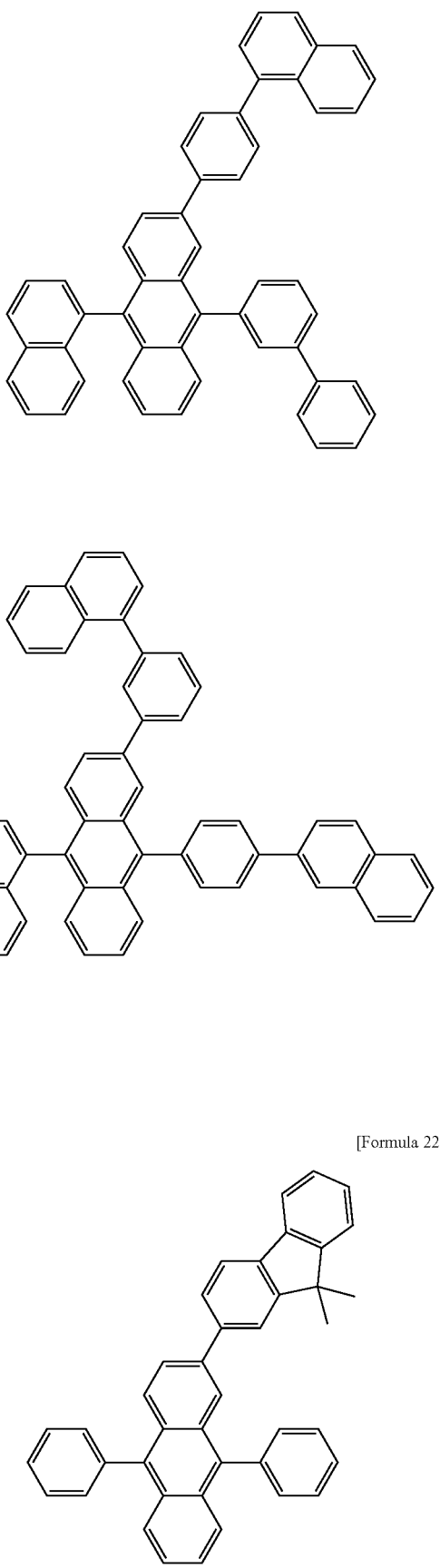
[Formula 225]

475
-continued
476
-continued
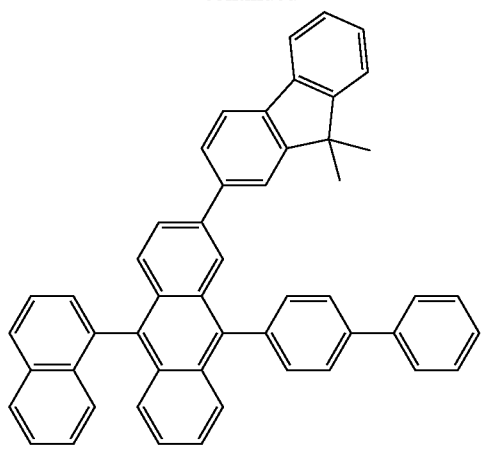
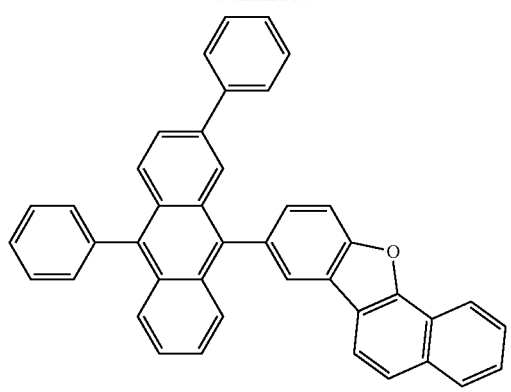
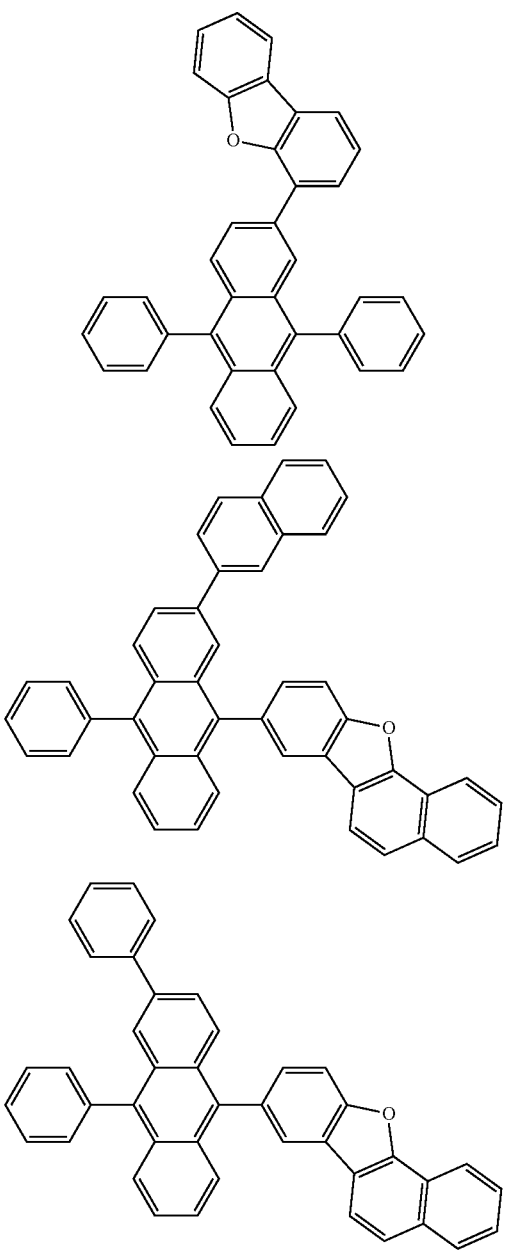
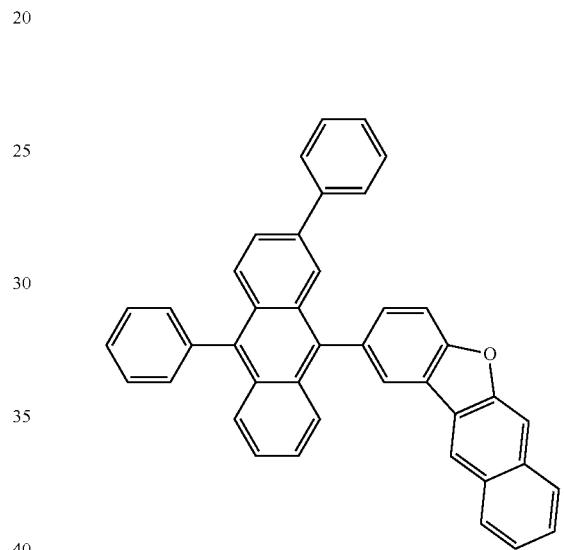
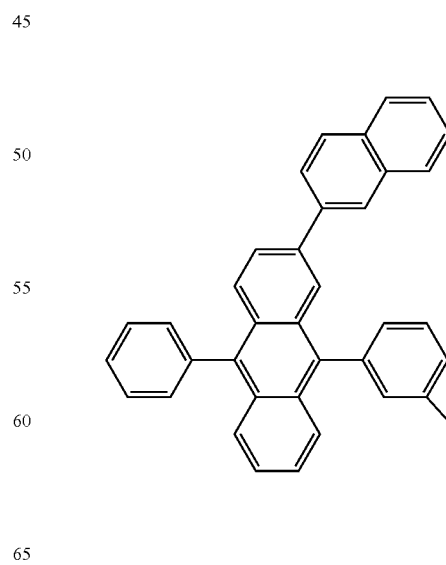

[Formula 226]
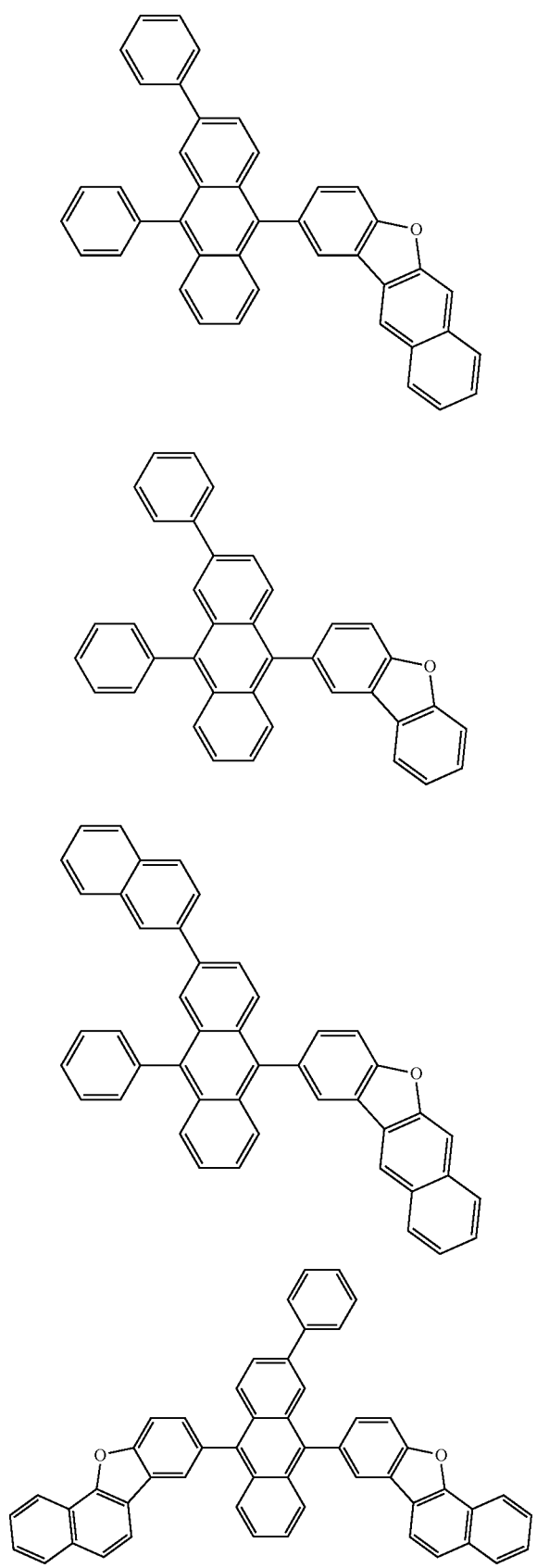
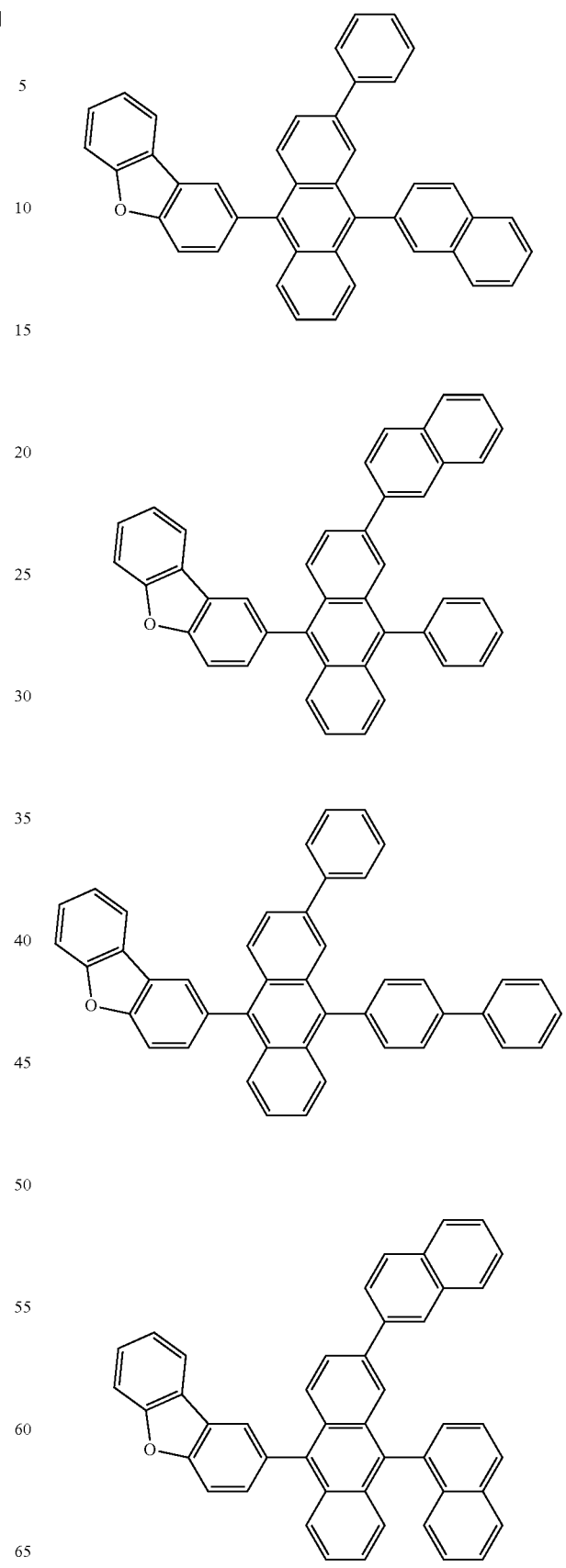

479
[Formula 227]
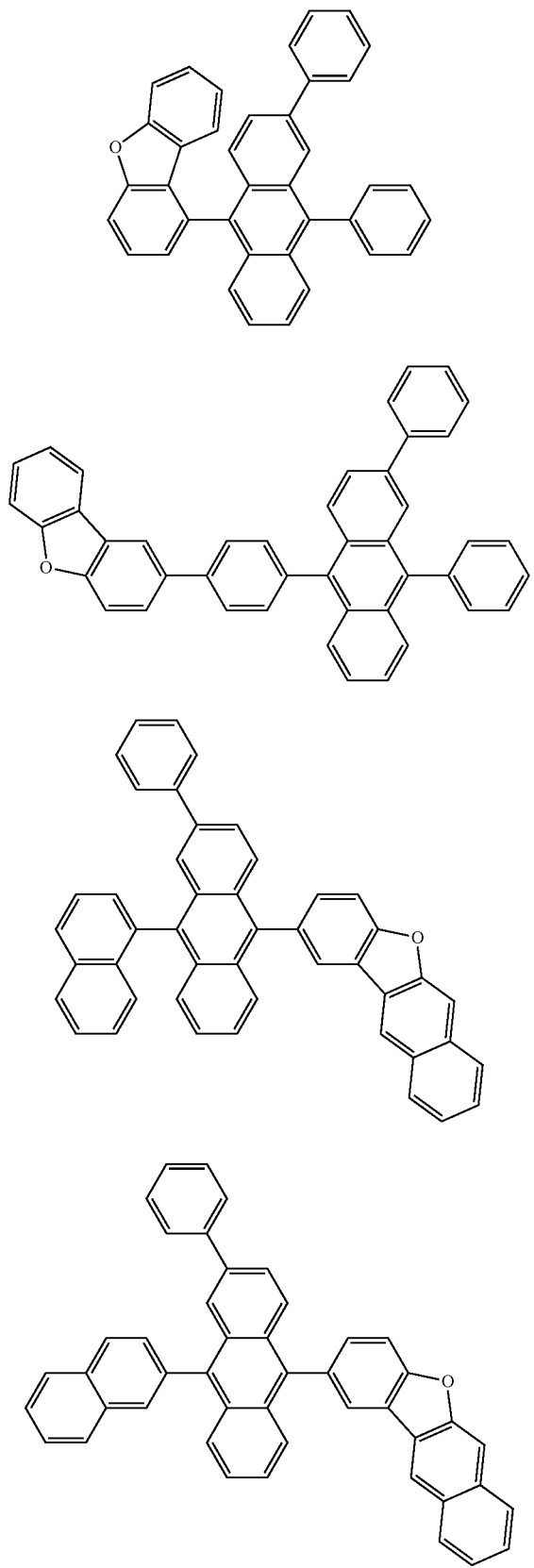
480
[Formula 228]
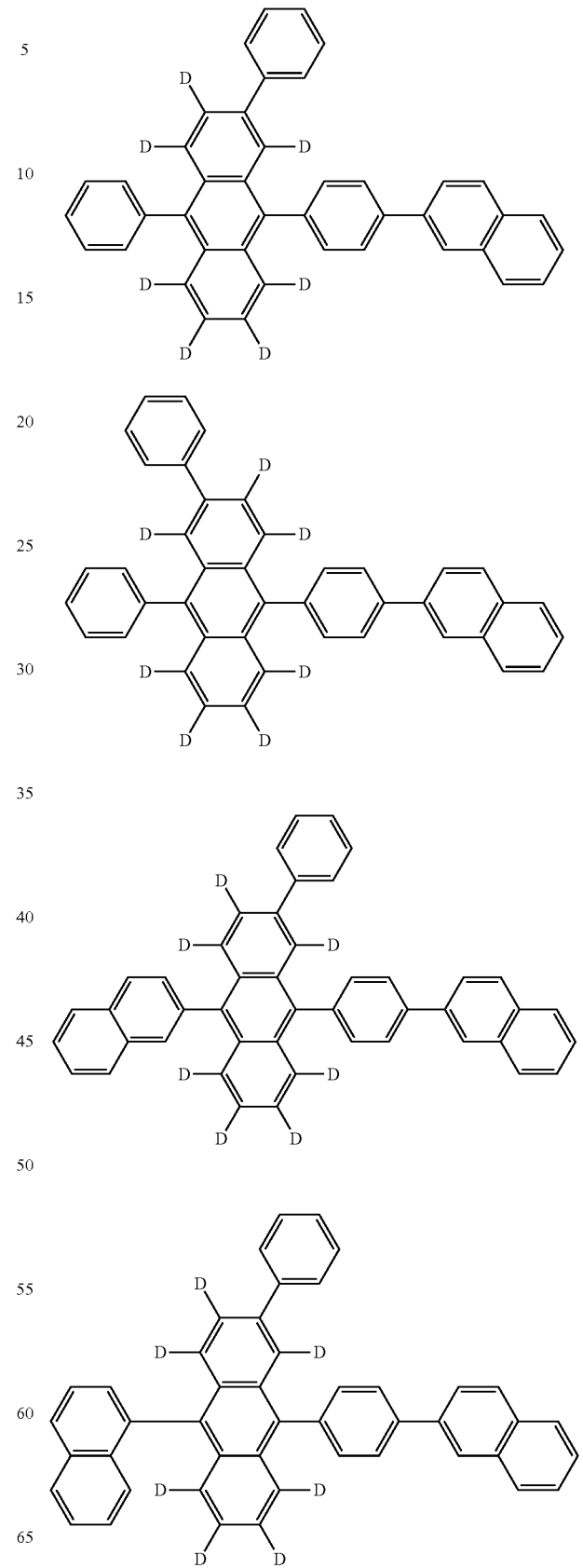

481
-continued
482
-continued
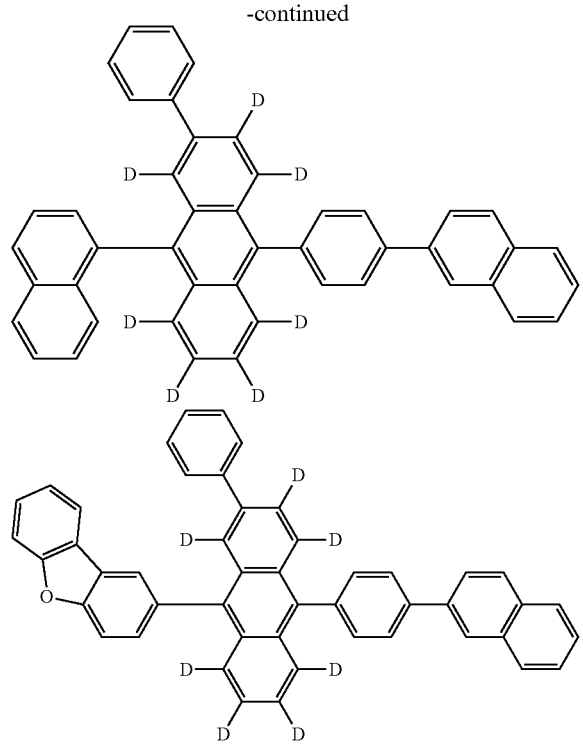
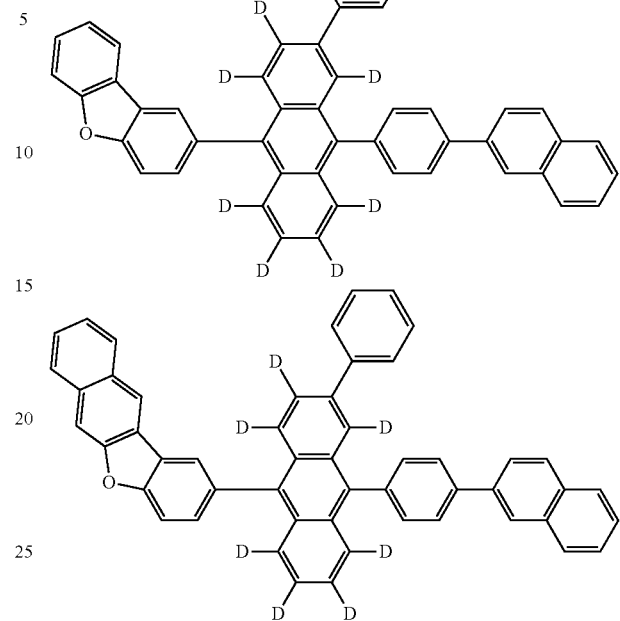
[Formula 229]
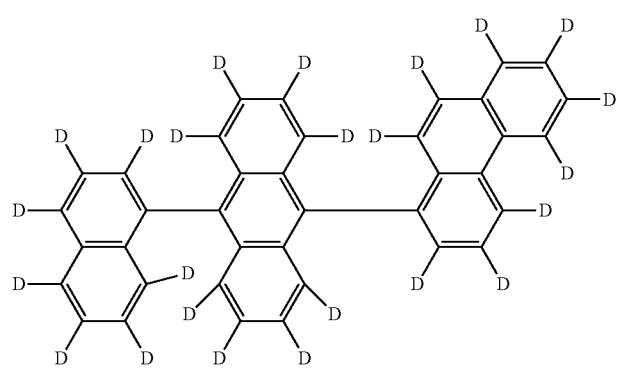
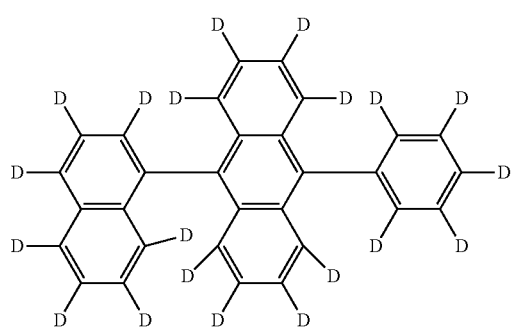
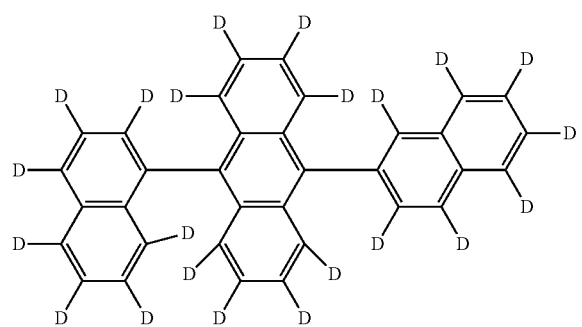

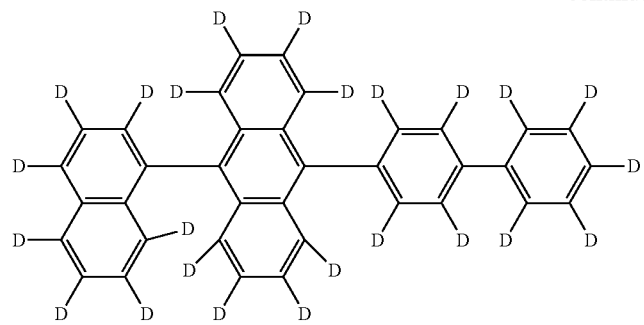

485
-continued
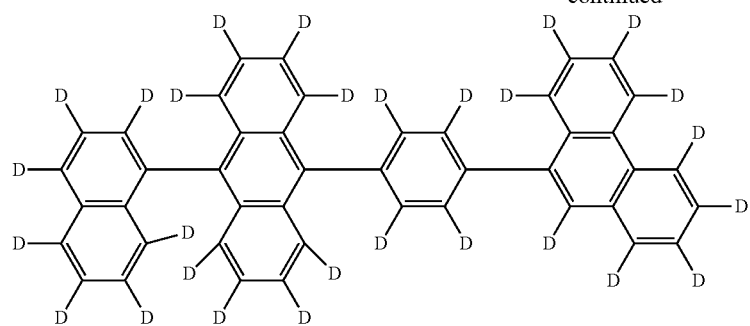
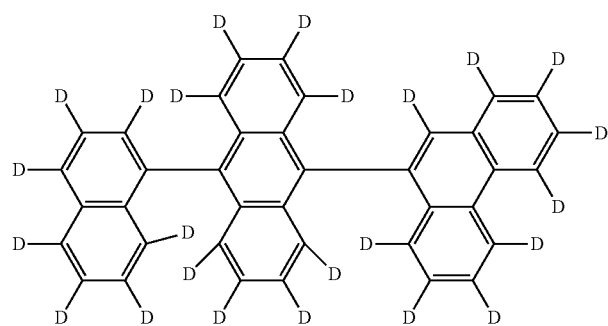
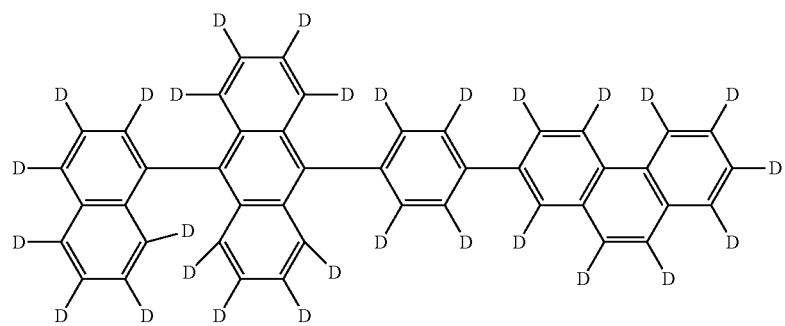
486
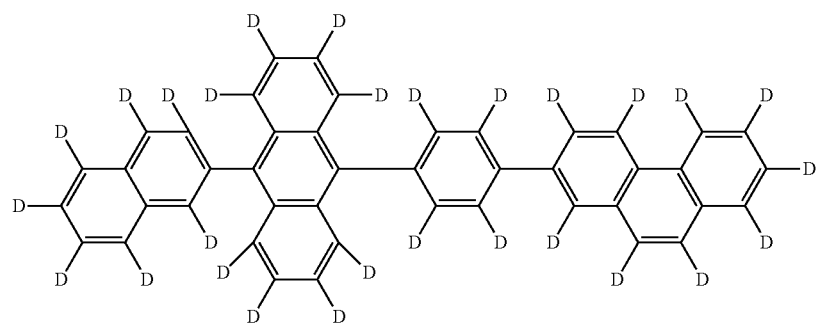

[Formula 230]
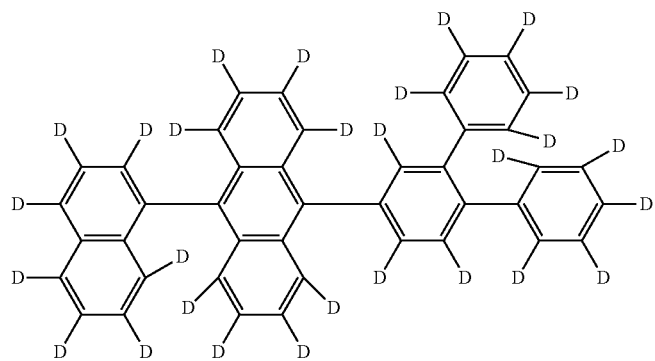
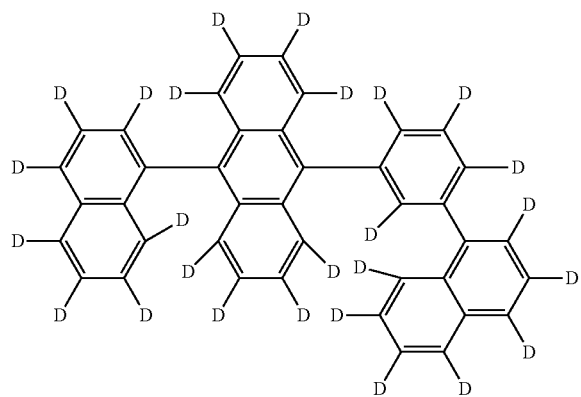
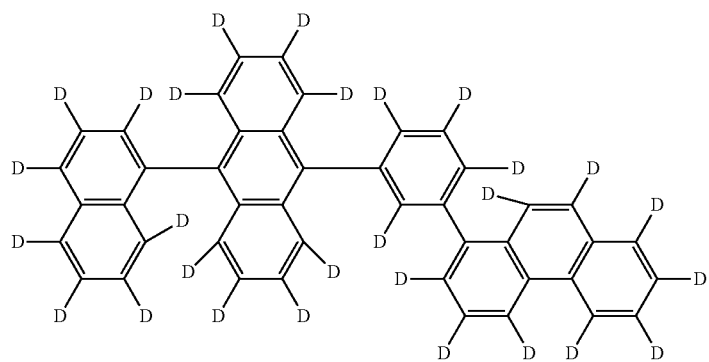
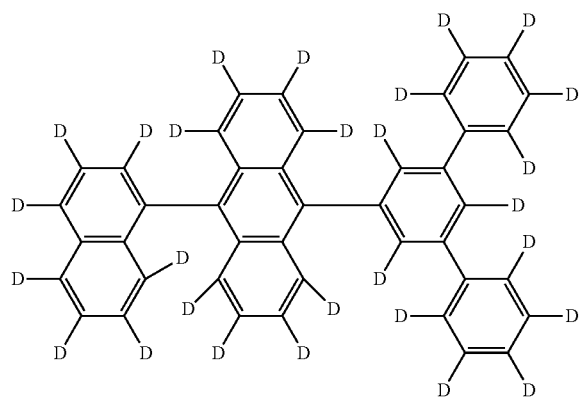

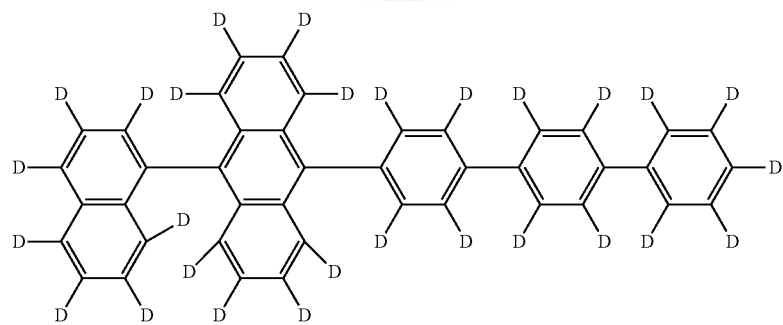
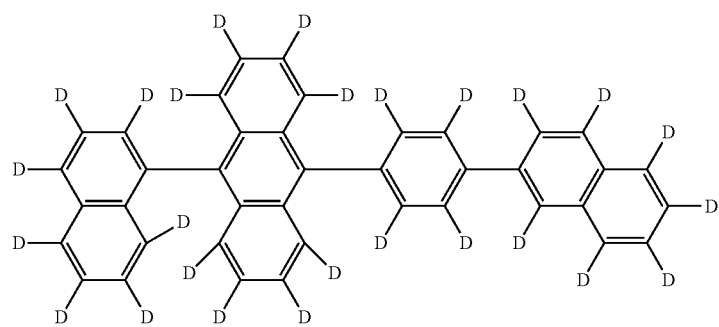
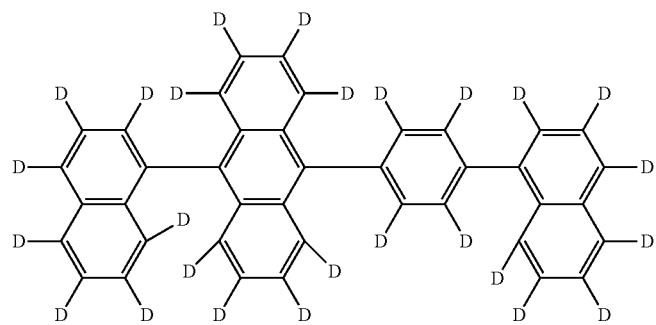
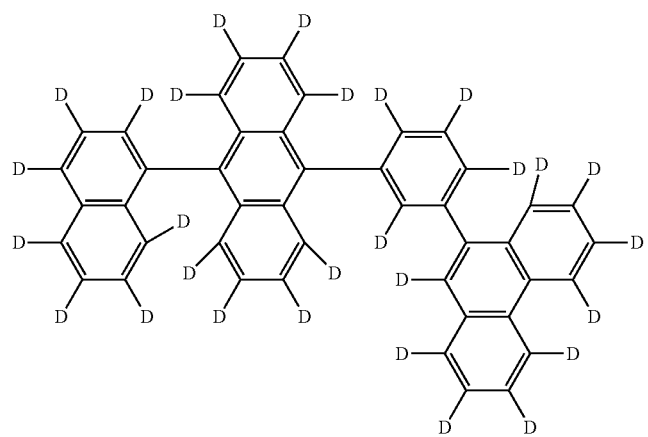

-continued
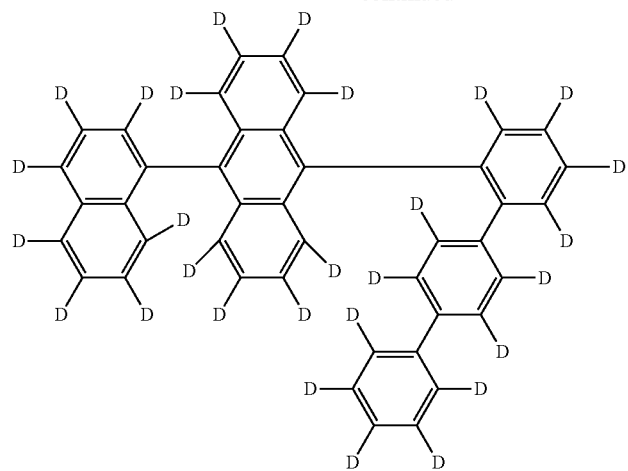
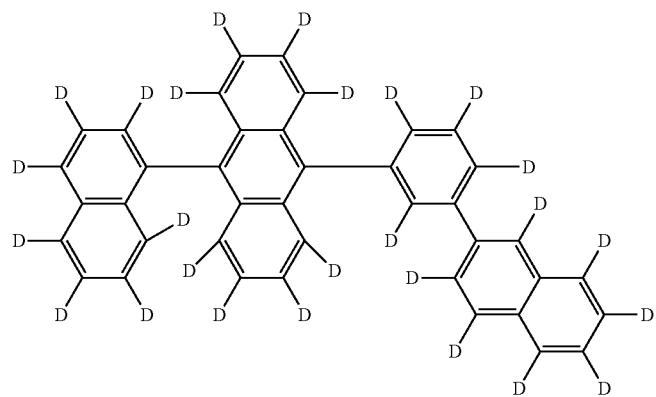
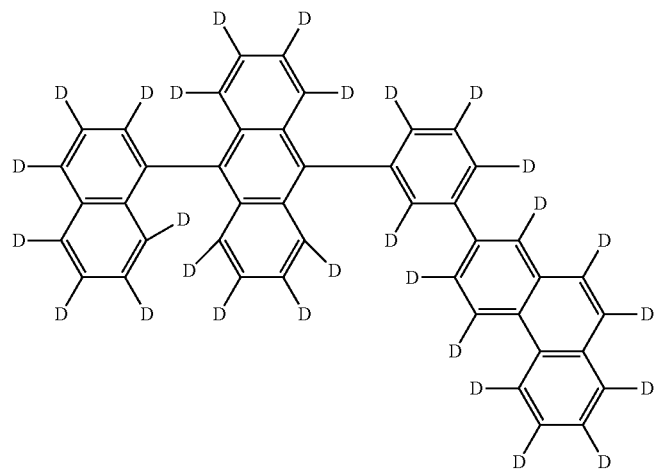
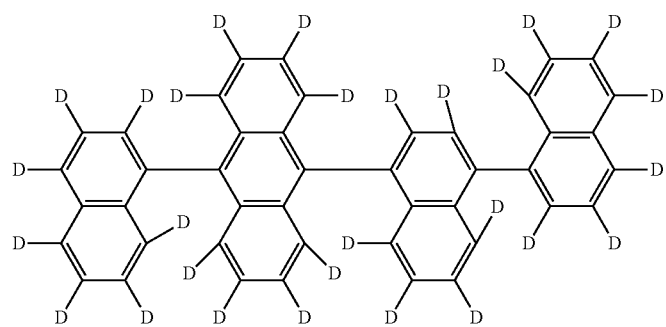

493 494
-continued
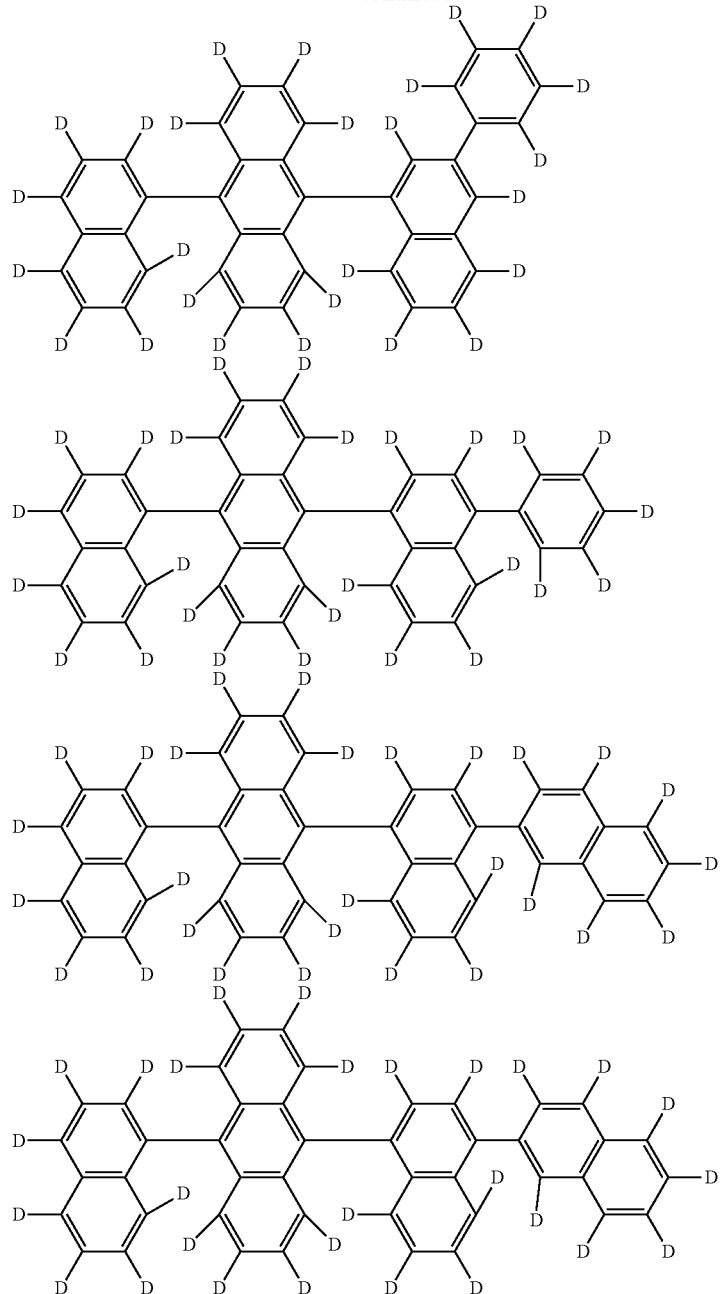
[Formula 231]
-continued
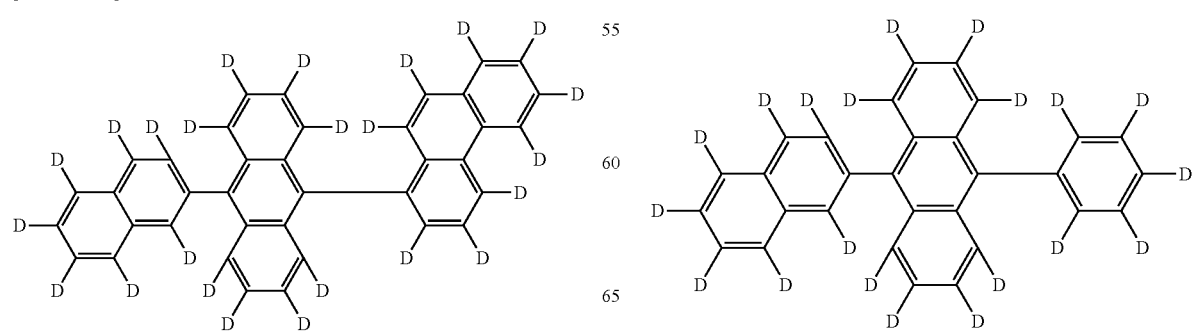

495
-continued
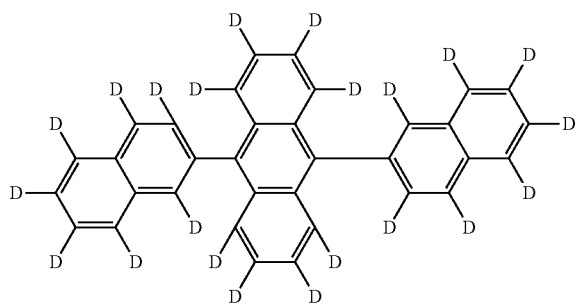
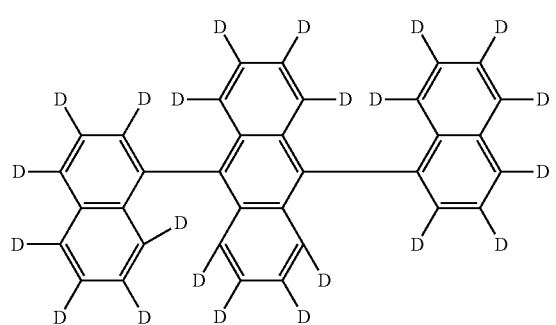
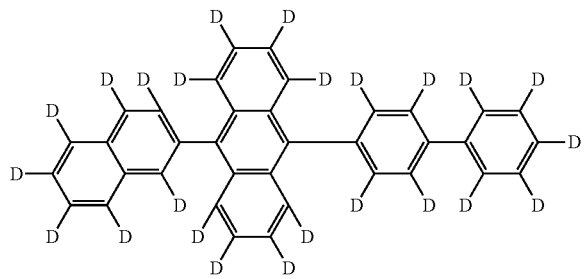
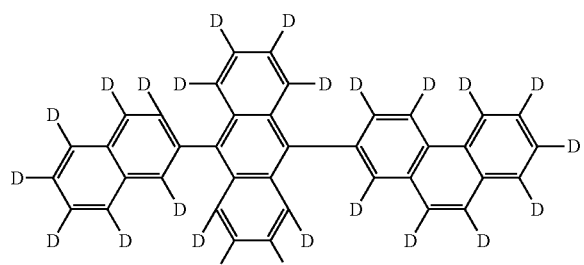
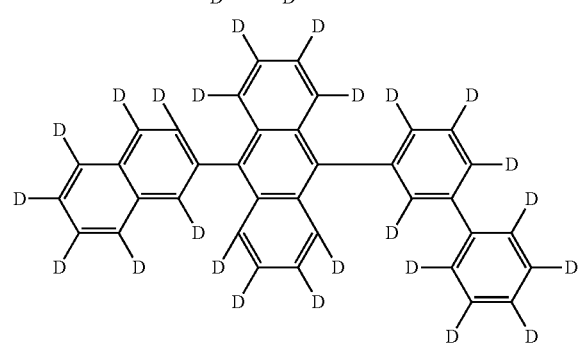
496
-continued
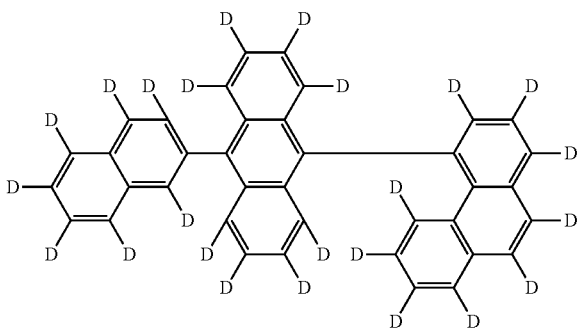
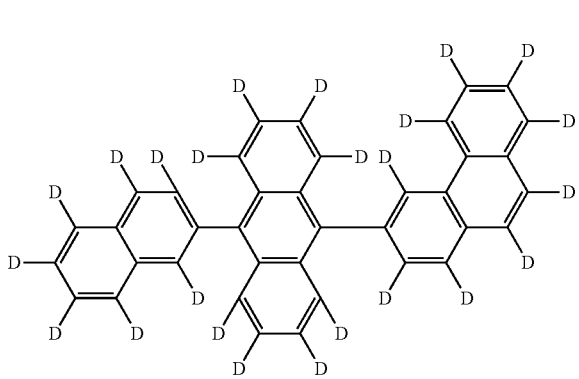
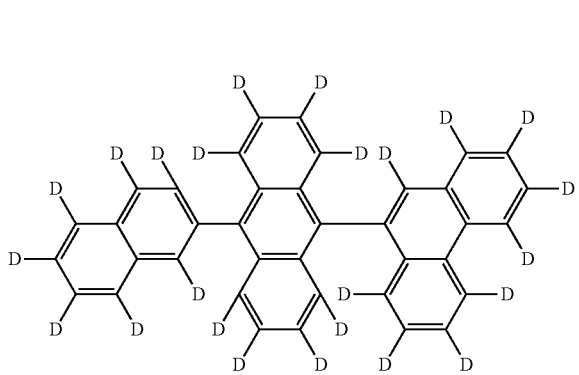
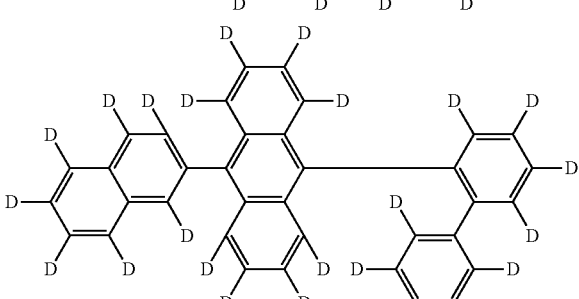
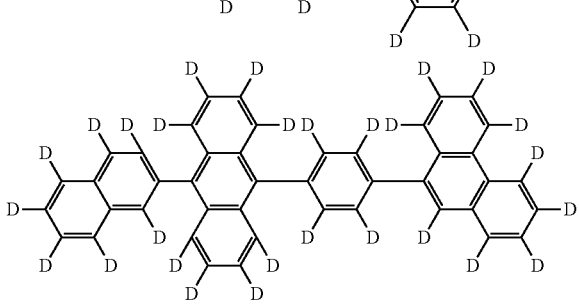

[Formula 232]
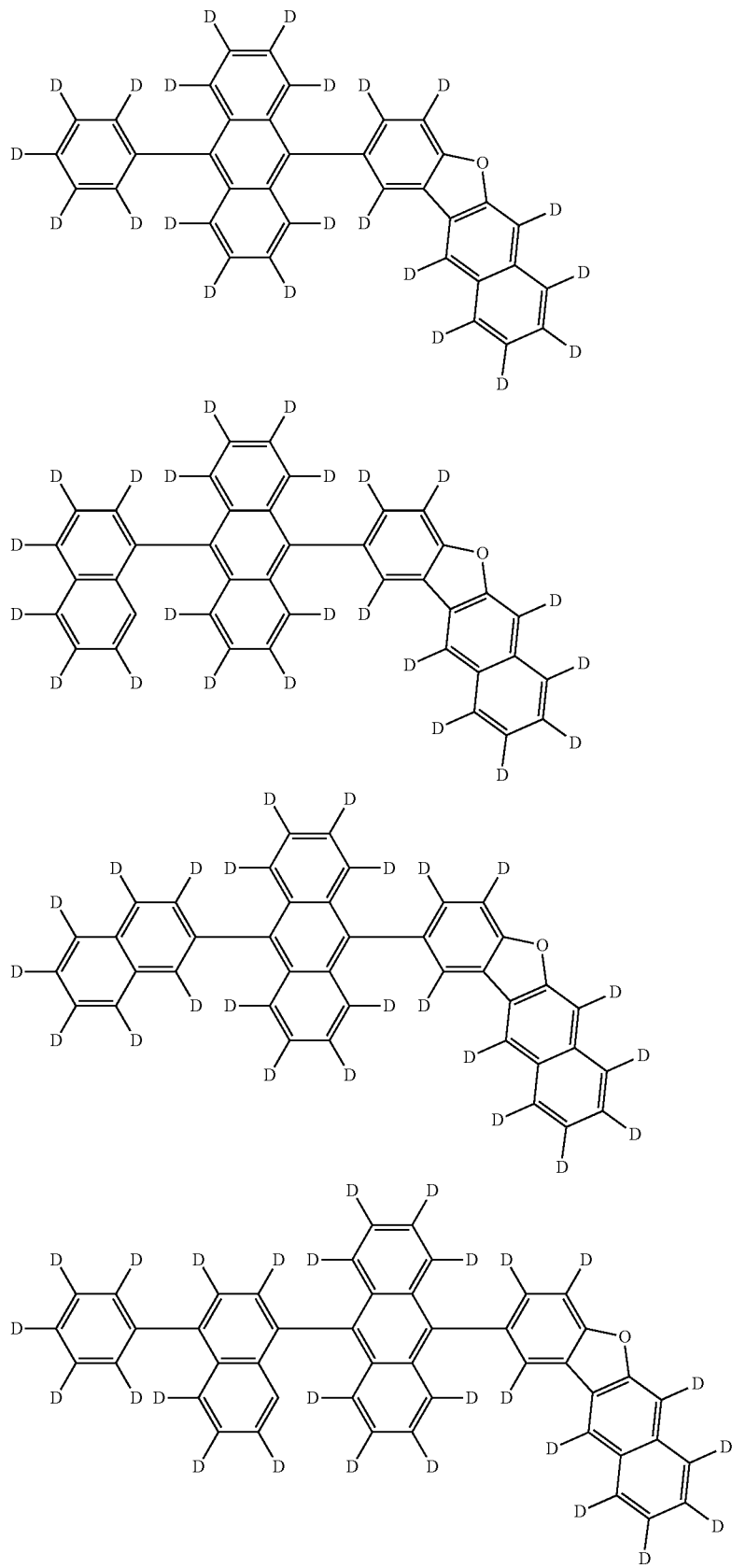

-continued
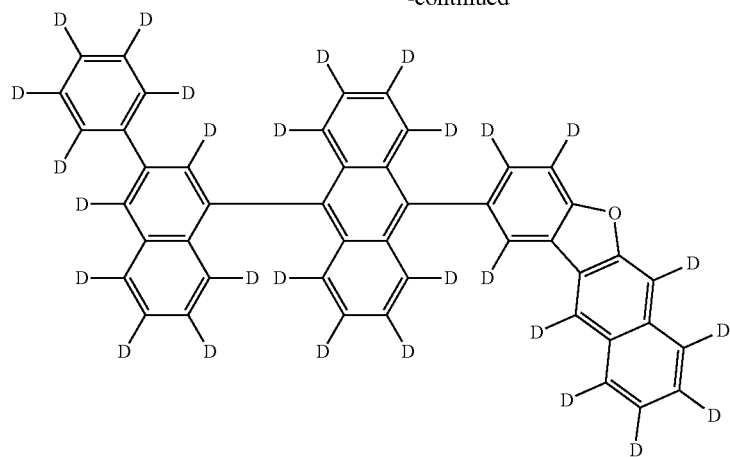
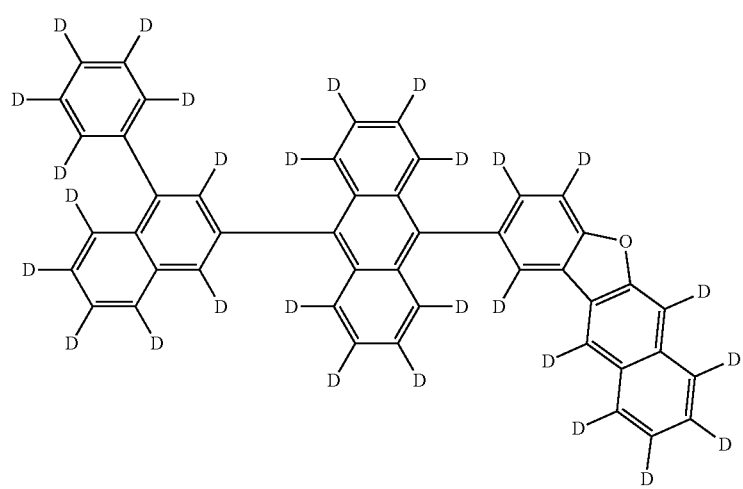
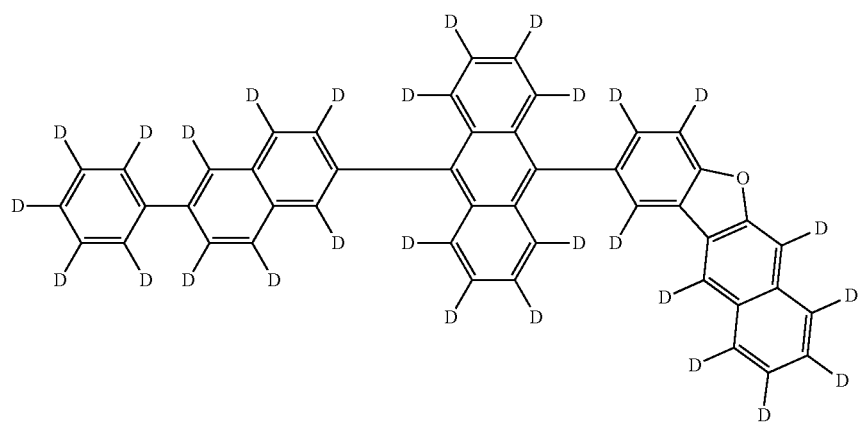

-continued
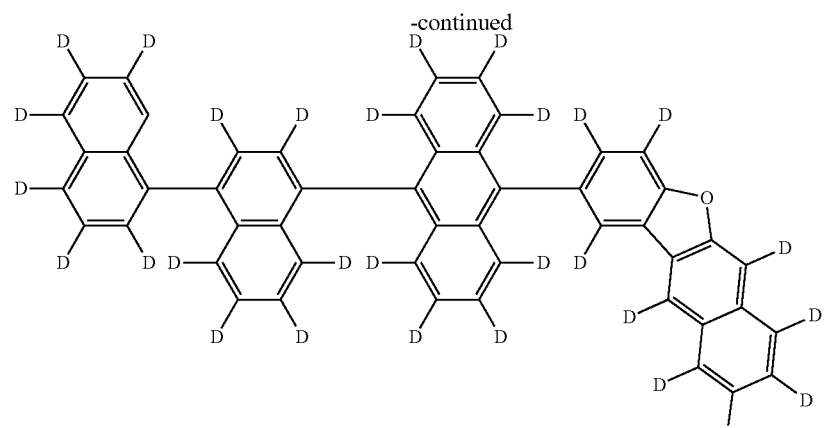
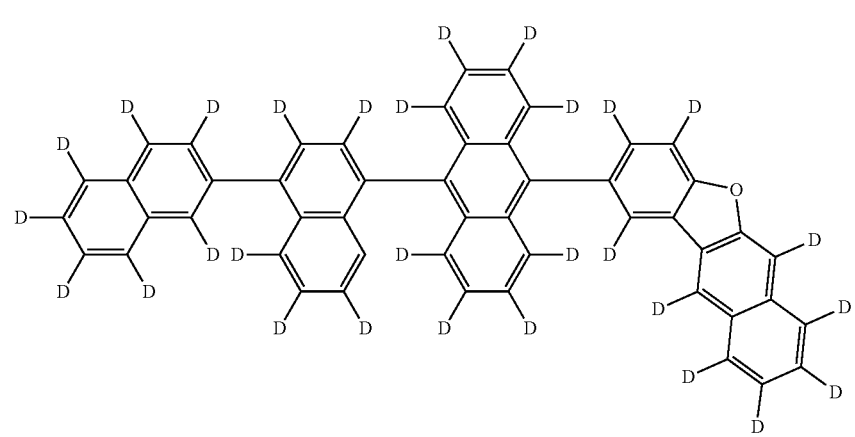
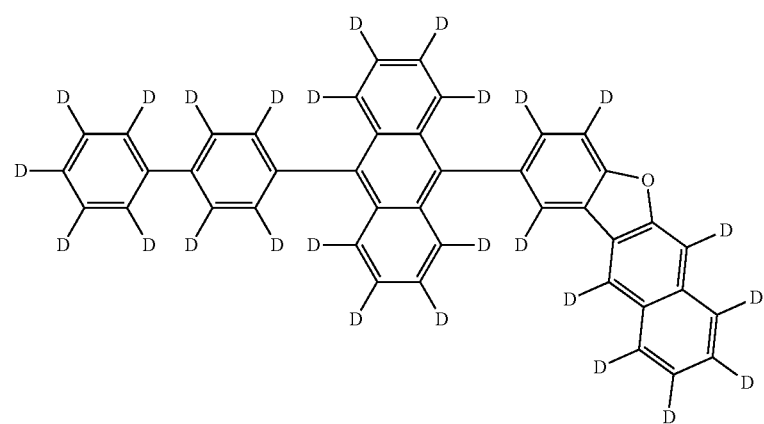
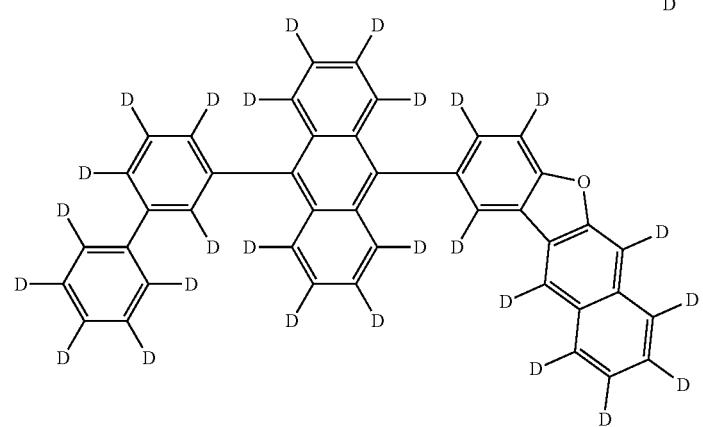

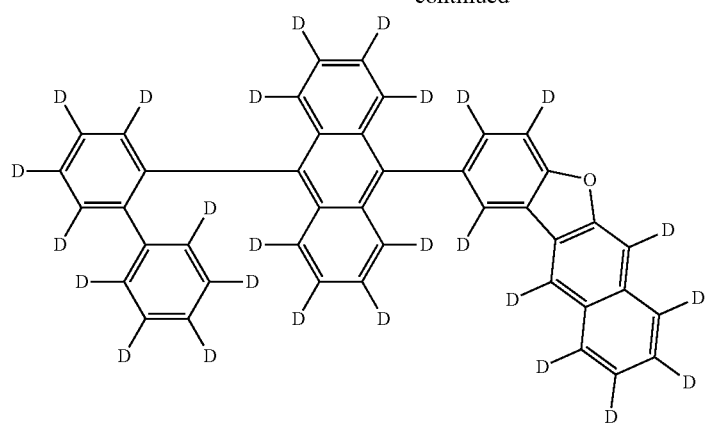

-continued
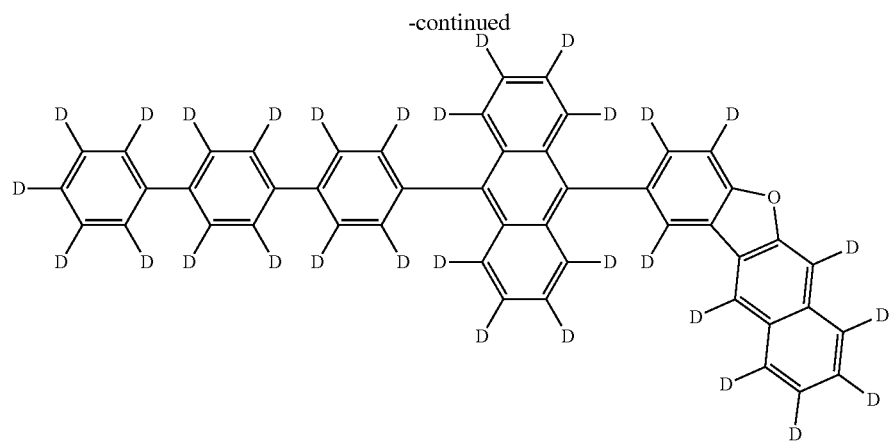
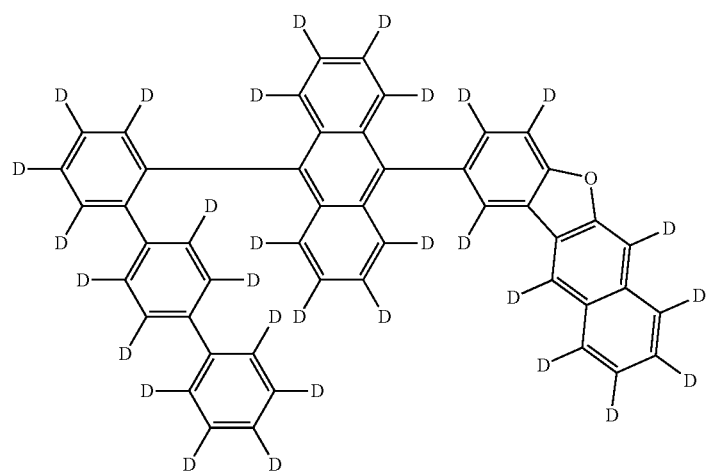
[Formula 233]
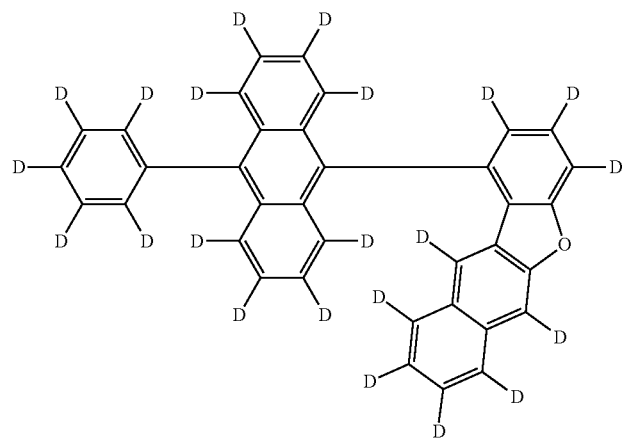

-continued
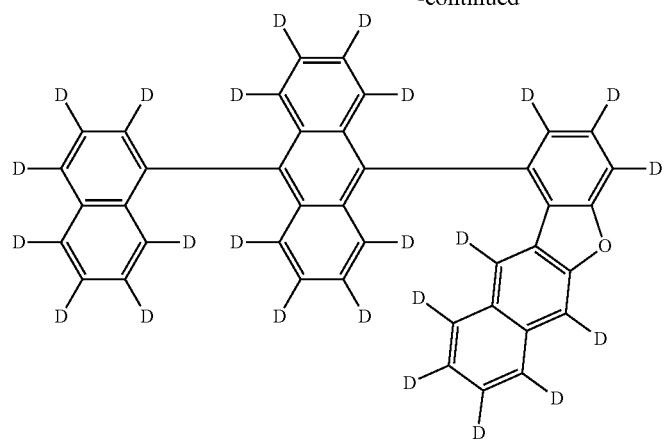
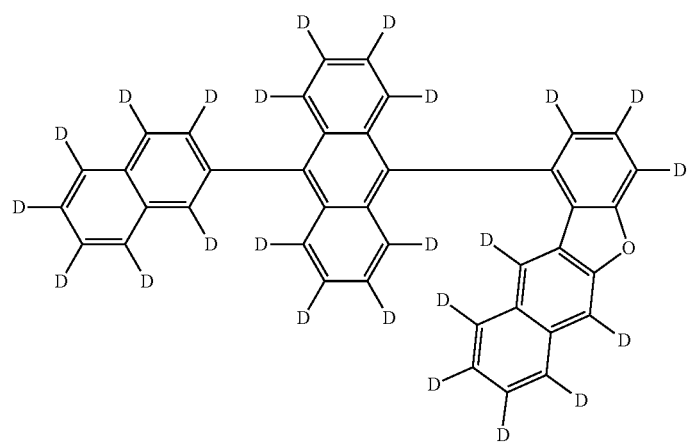
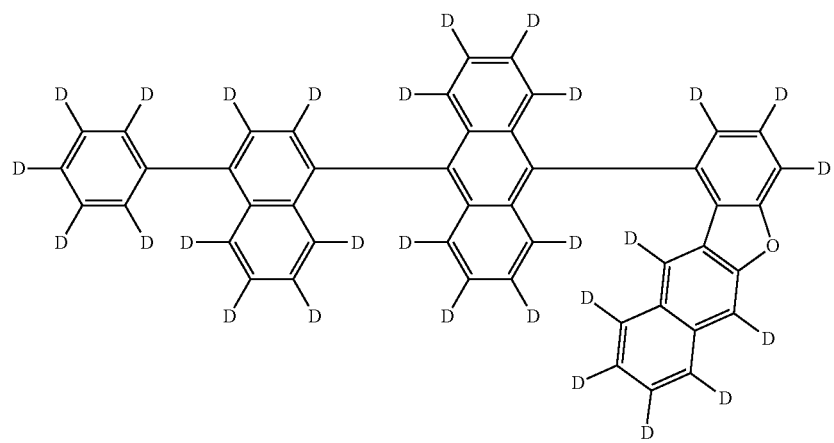

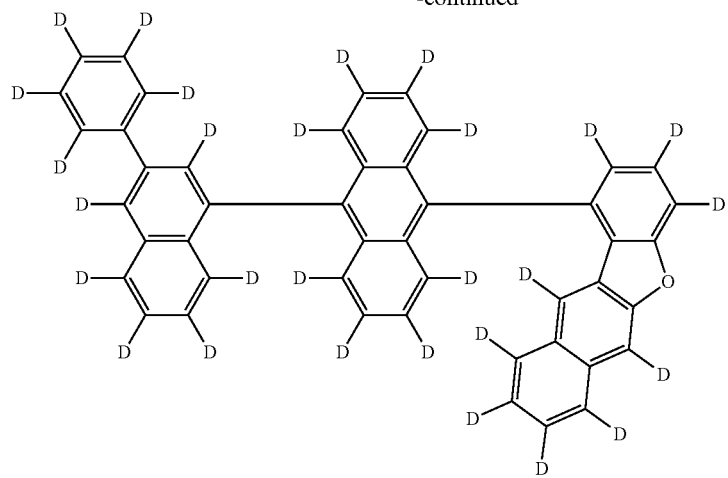
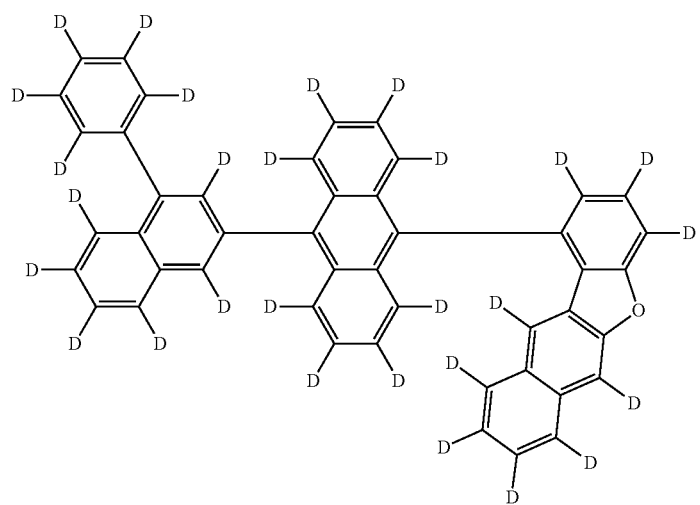
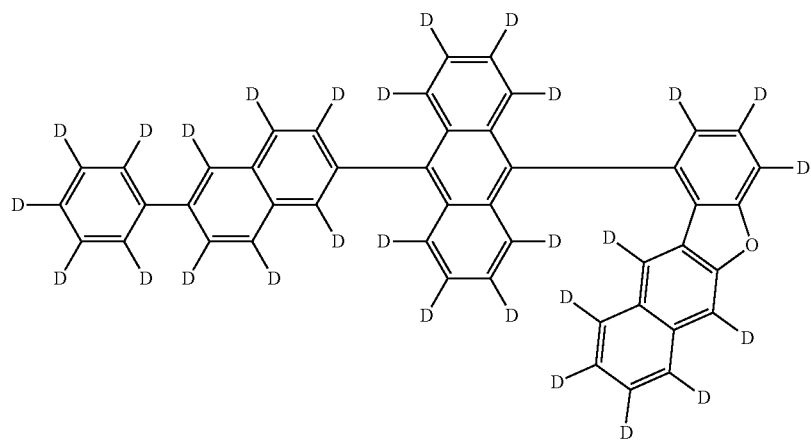

-continued
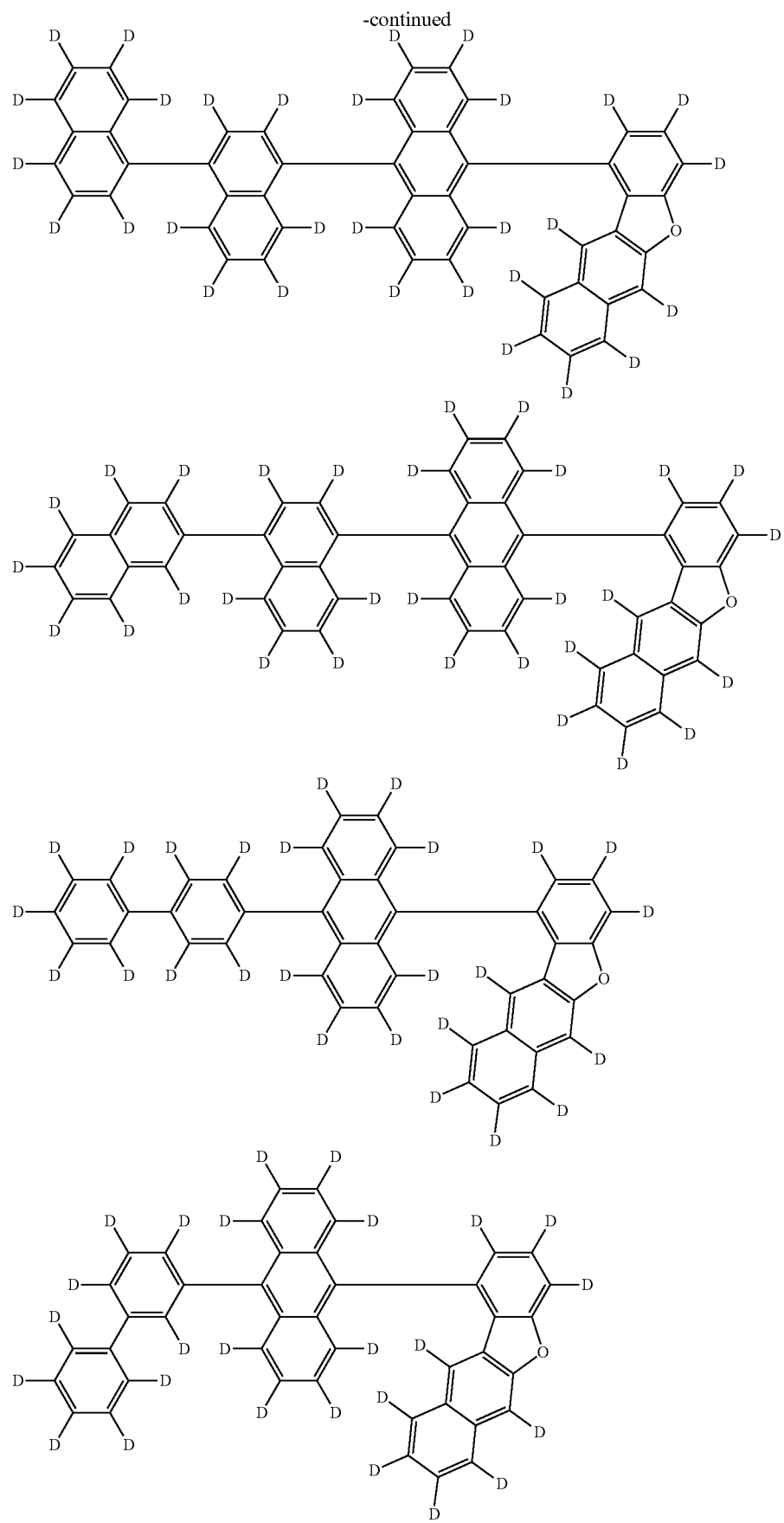

-continued
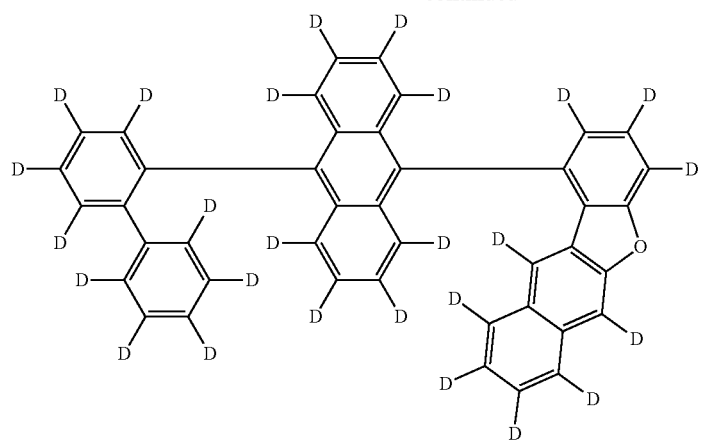
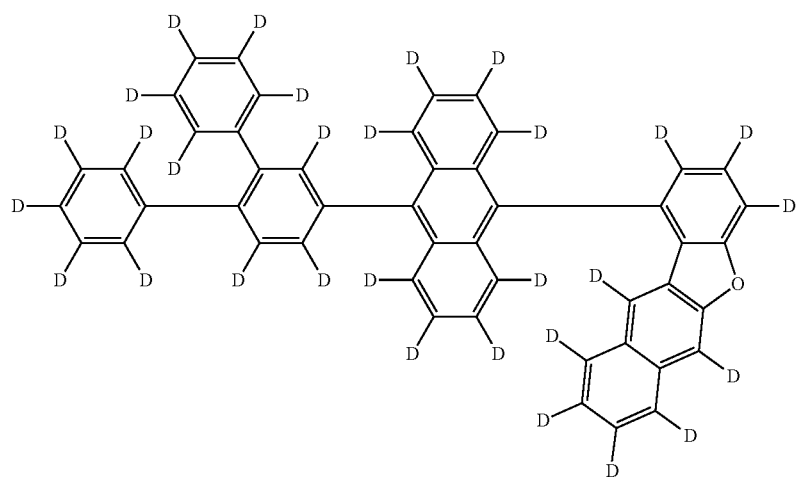
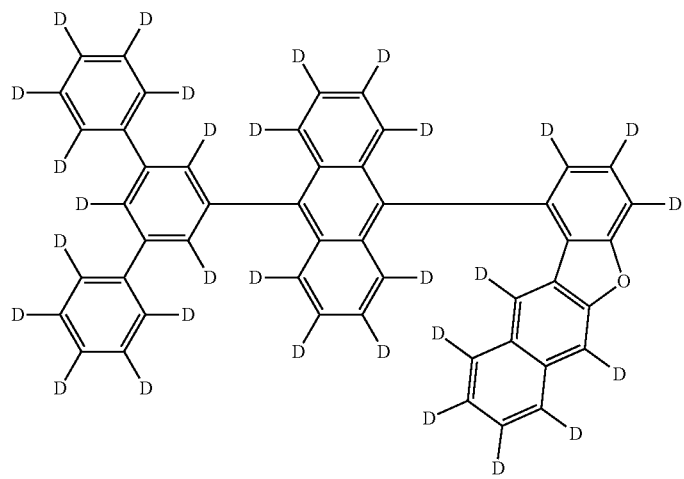

515
-continued
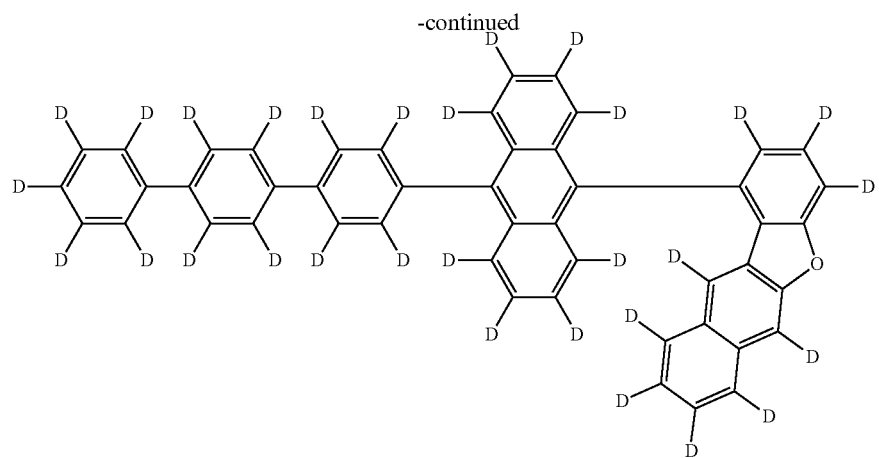
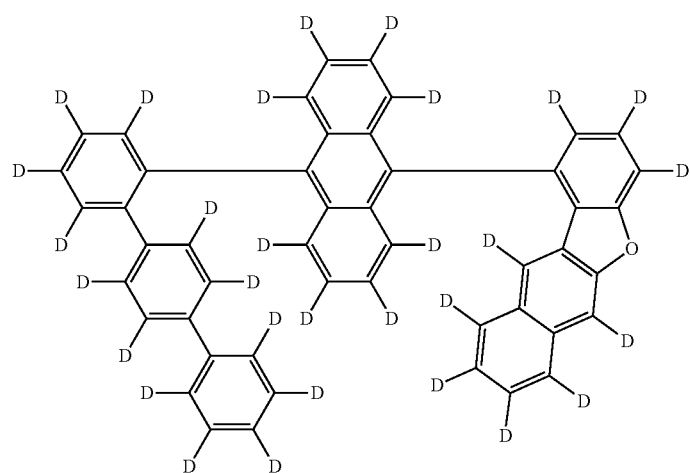 [SMILES: [2H]c1c([2H])c([2H])c(-c2c([2H])c([2H])c(-c3c([2H])c([2H])c([2H])c([2H])c3-c3c4c([2H])c([2H])c([2H])c([2H])c4c(-c4c([2H])c([2H])c([2H])c5oc6c([2H])c7c([2H])c([2H])c([2H])c([2H])c7c([2H])c6c45)c4c([2H])c([2H])c([2H])c([2H])c34)c([2H])c2[2H])c([2H])c1[2H]]
[Formula 234]
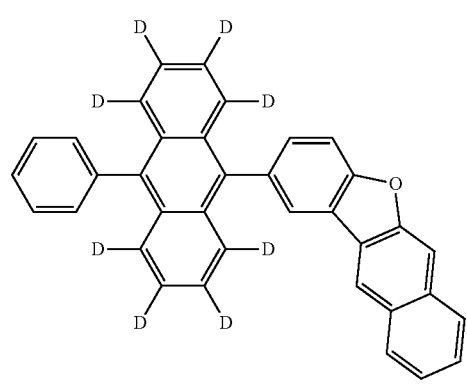
-continued
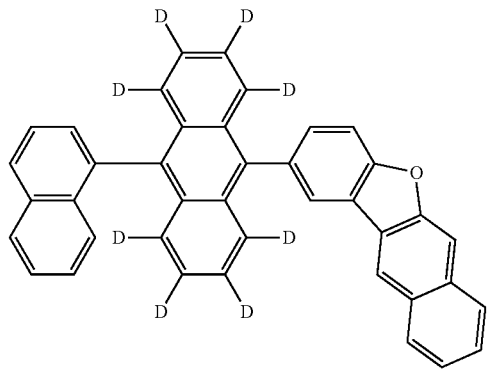

517
-continued
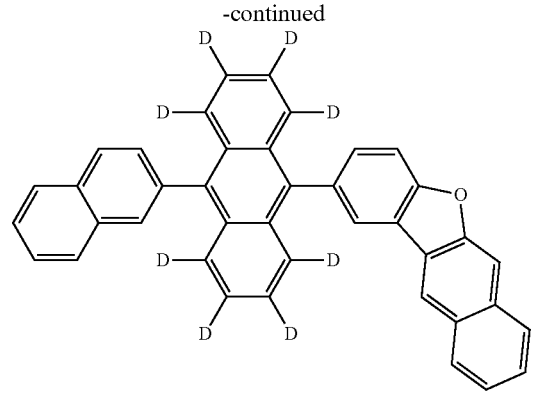
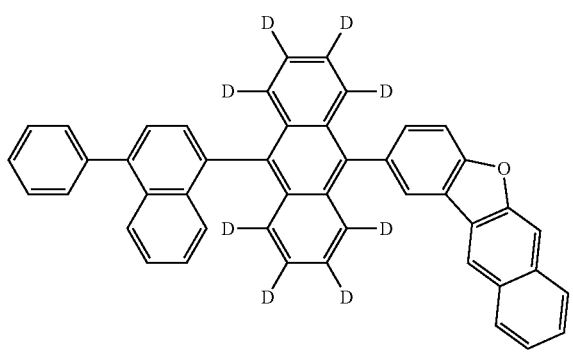
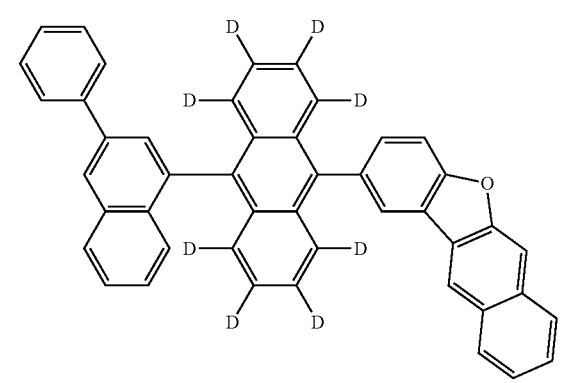
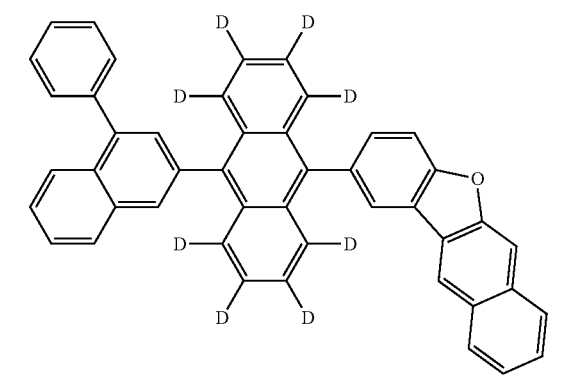
518
-continued
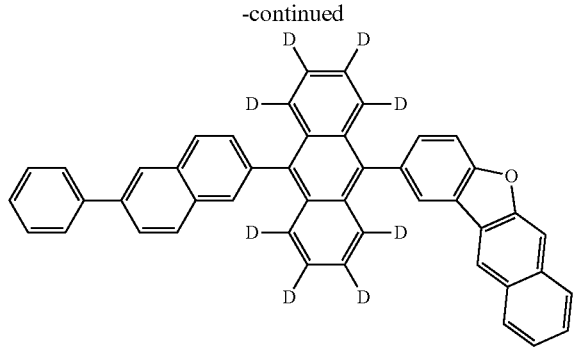
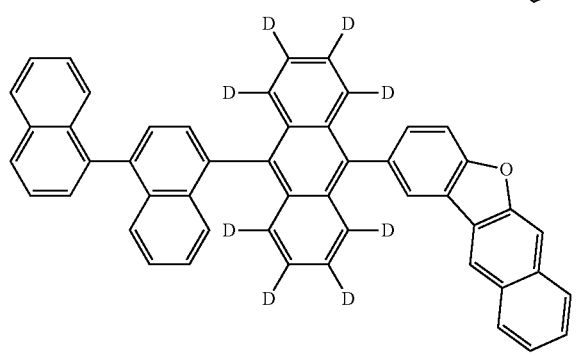
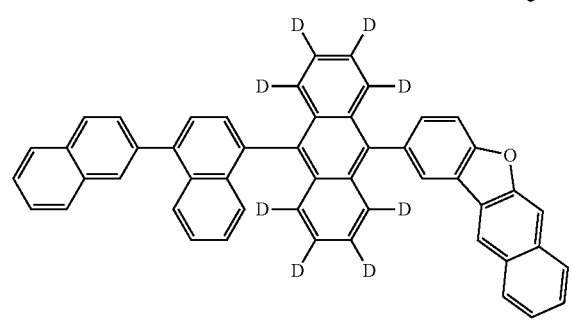
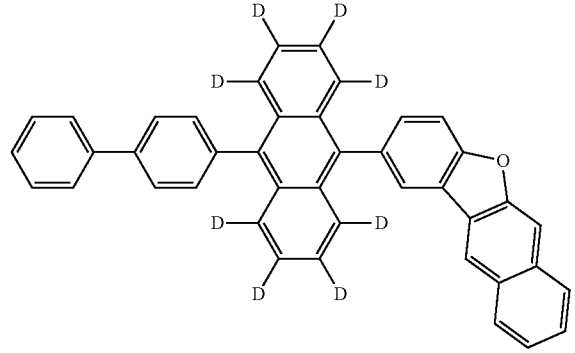
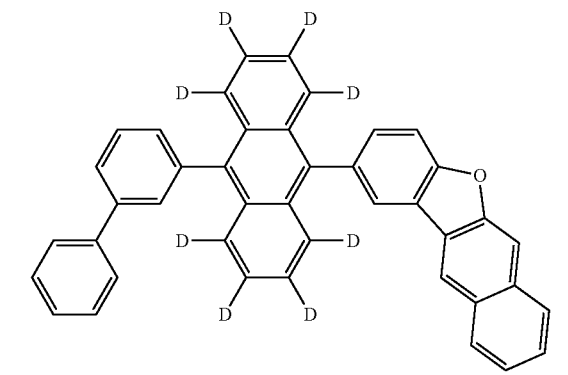

519
-continued
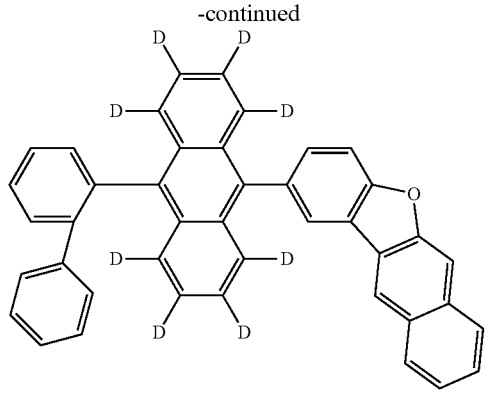
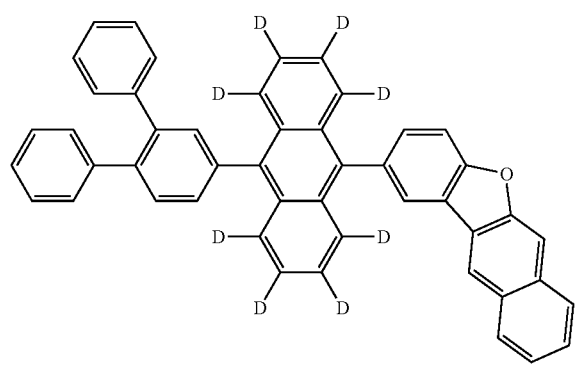
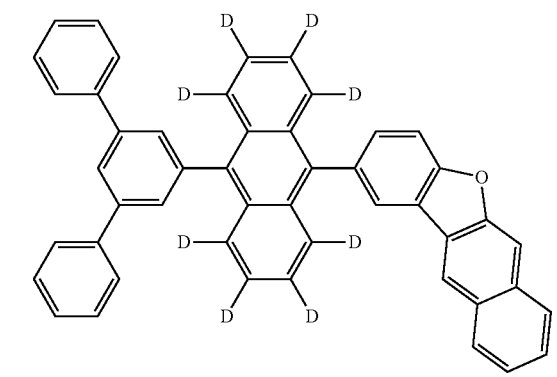
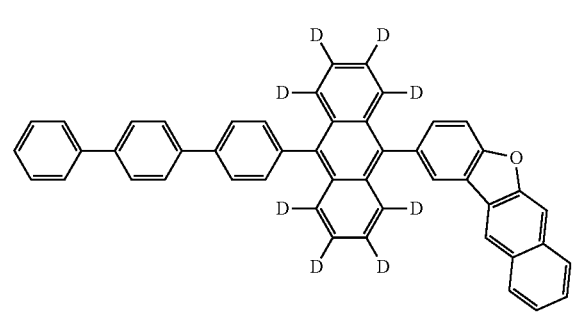
520
-continued
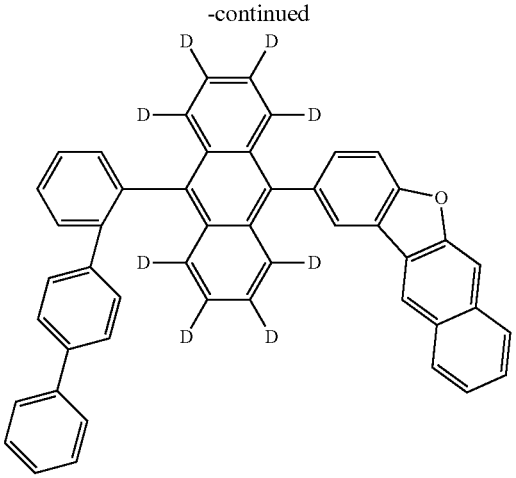
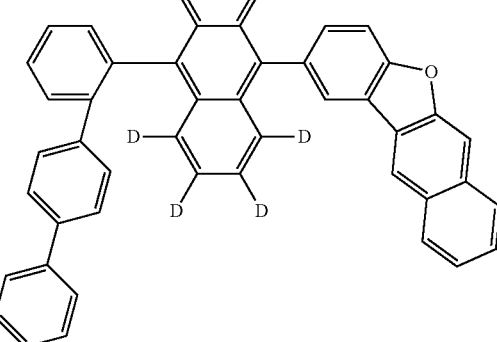
[Formula 235]
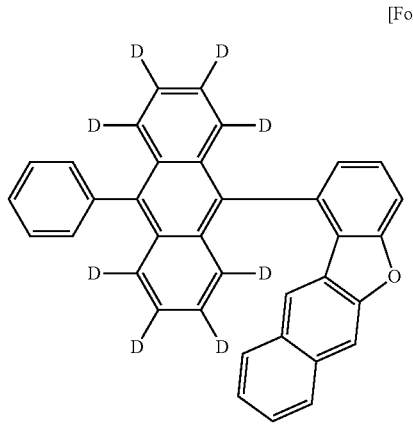
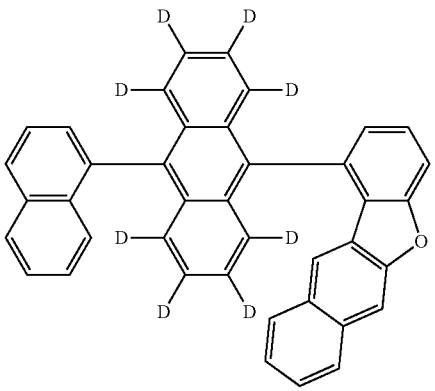

521    522
-continued    -continued
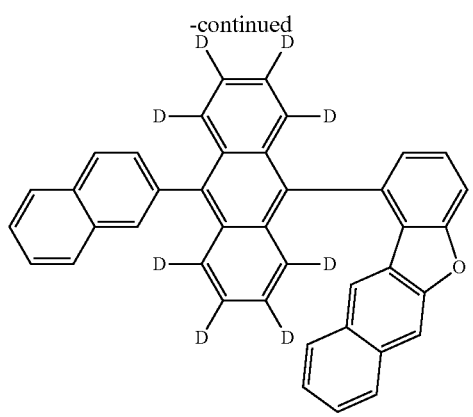
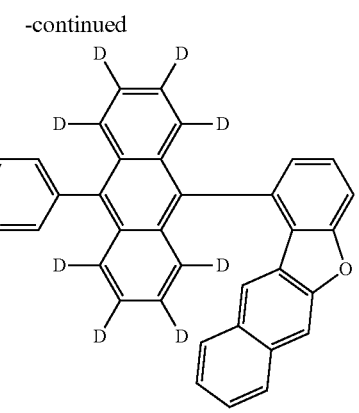
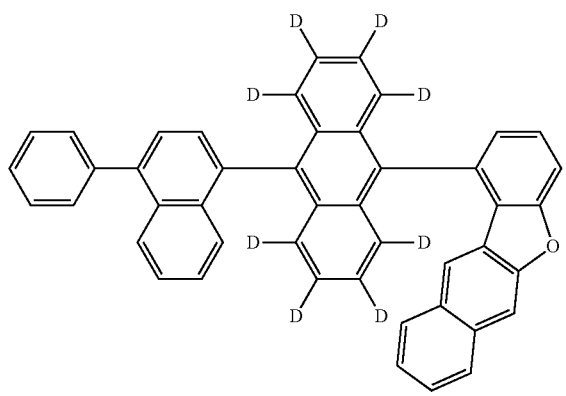
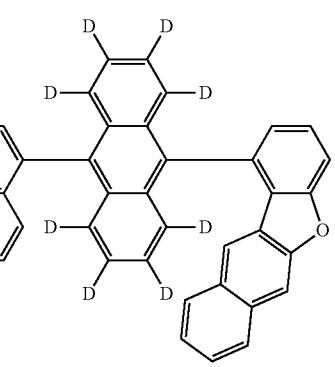
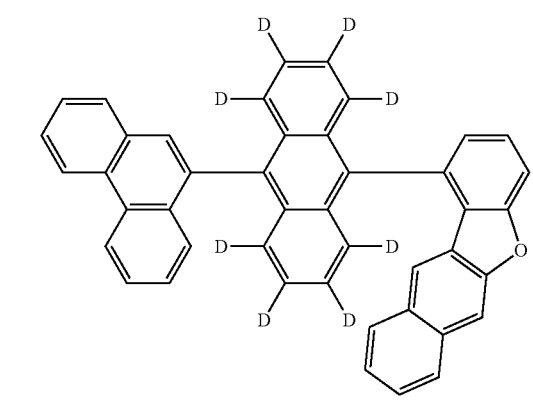
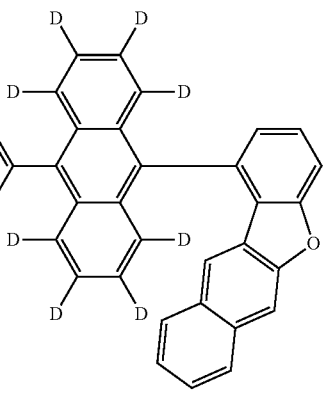
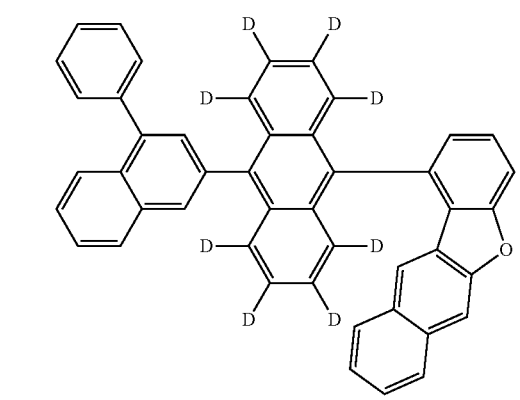

523
-continued
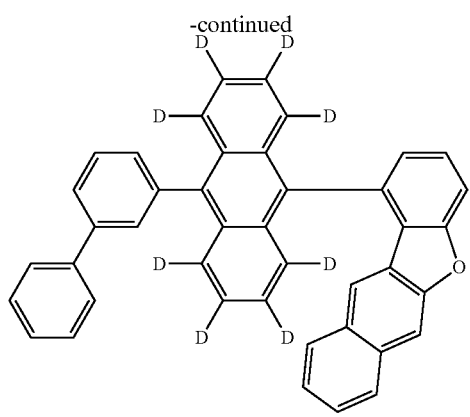
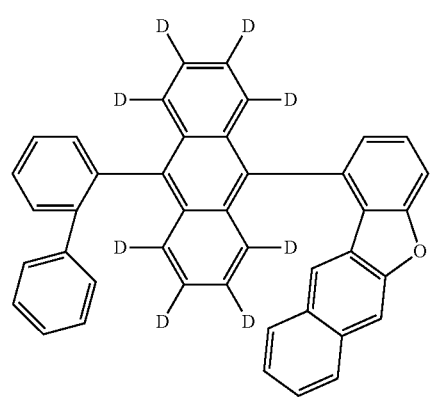
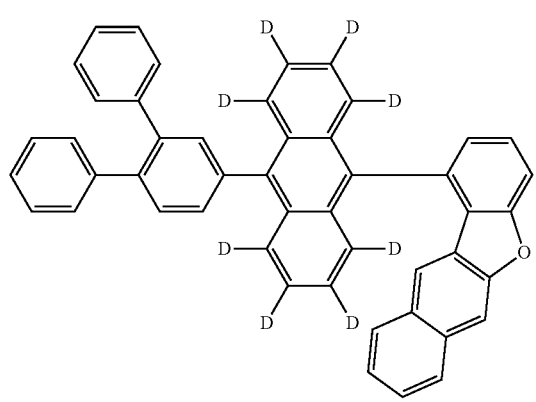
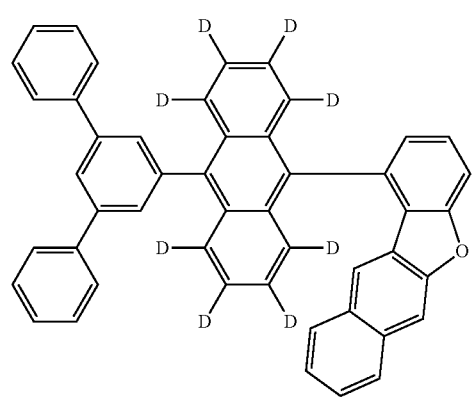
524
-continued
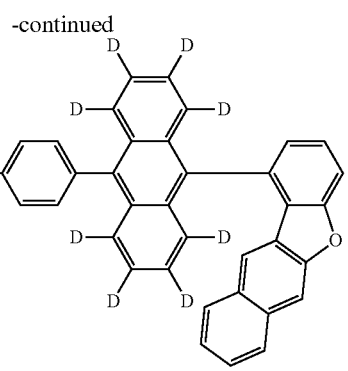
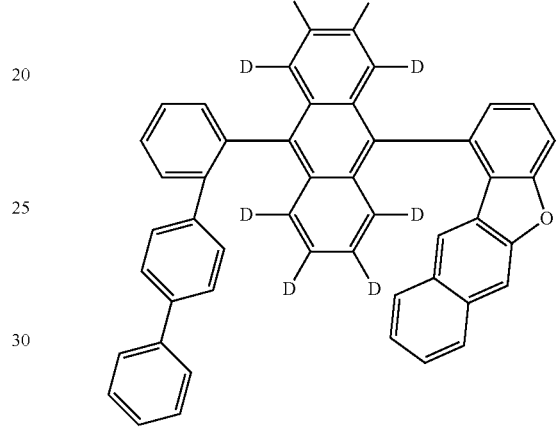
[Formula 236]
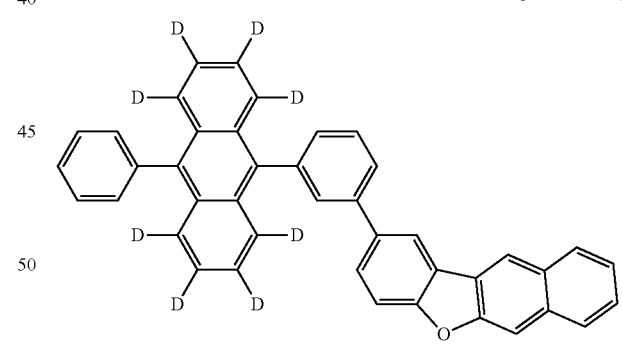
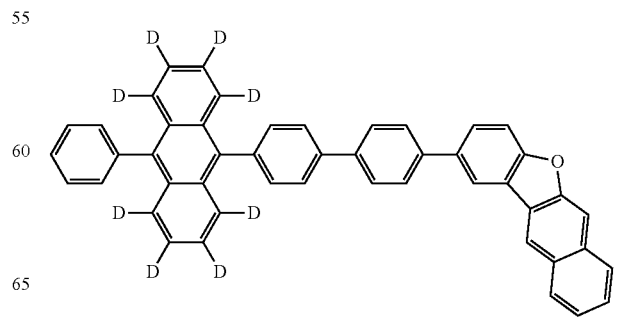

525
-continued
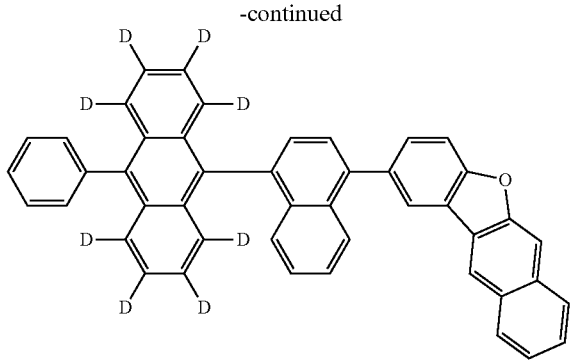
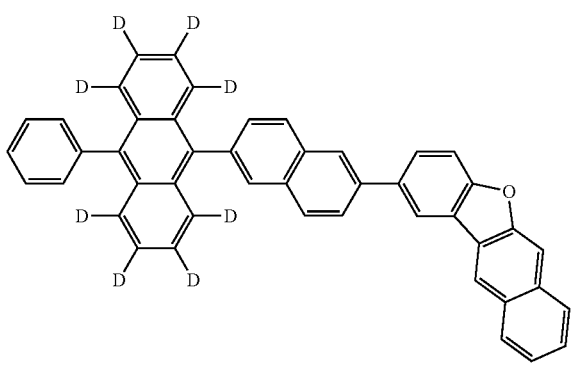
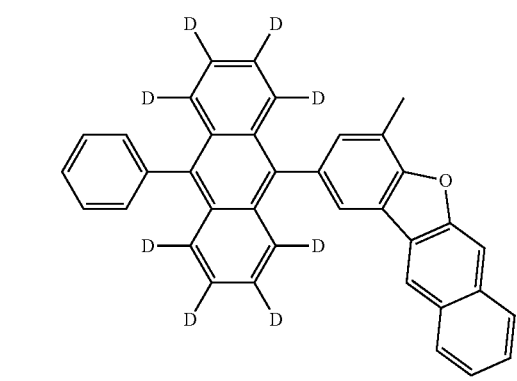
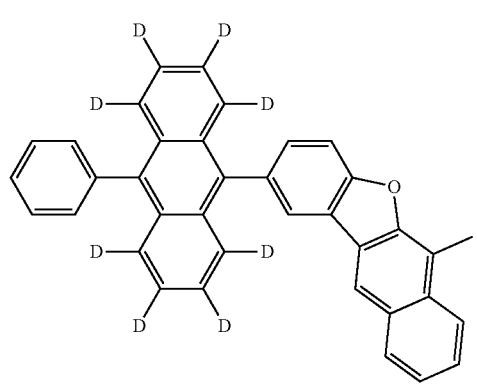
526
-continued
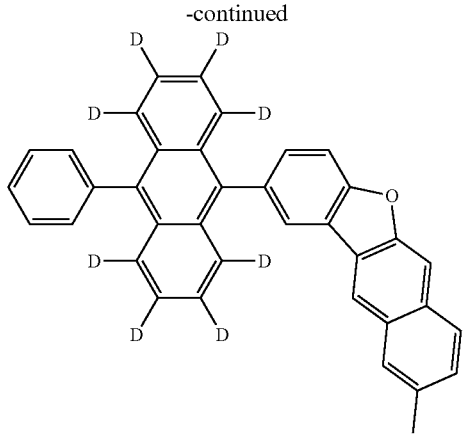
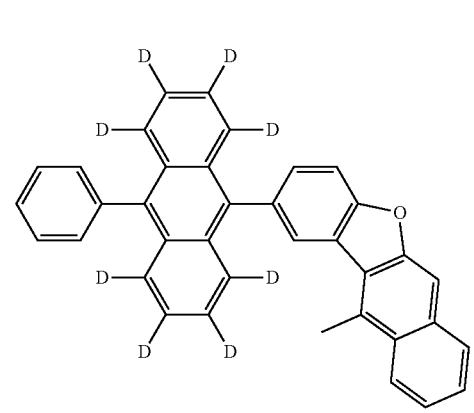
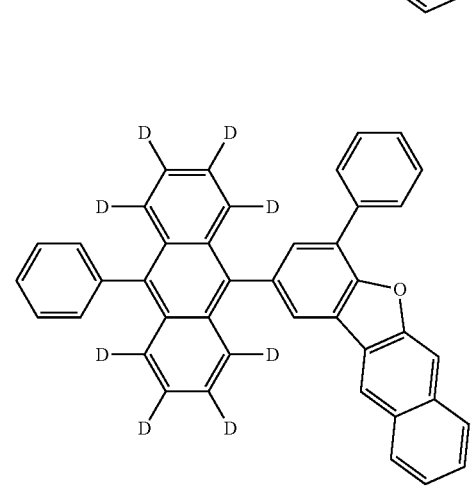
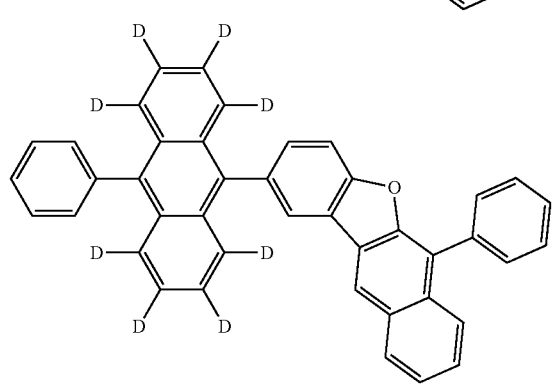

527
-continued
528
-continued
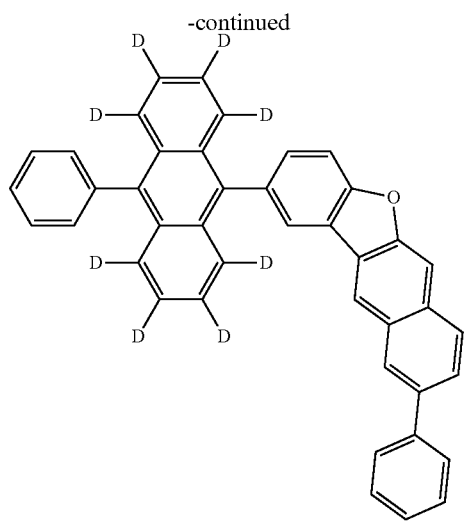
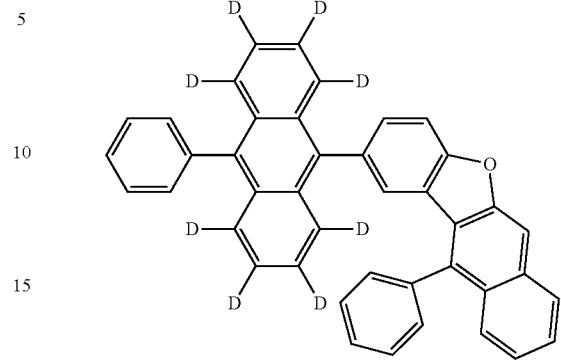
[Formula 237]
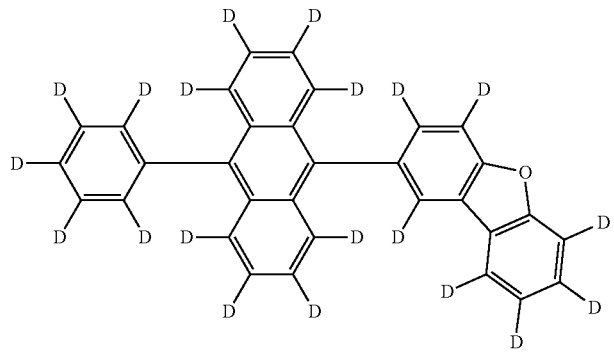
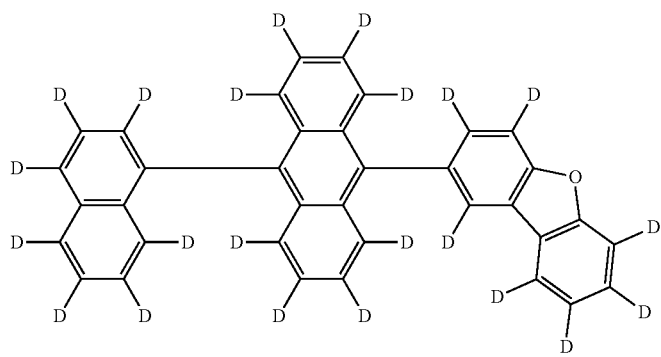
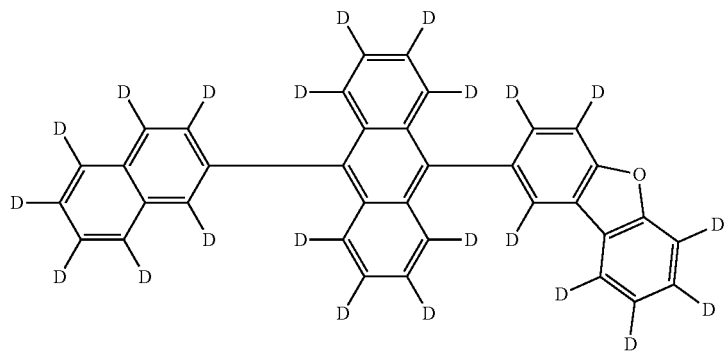

-continued
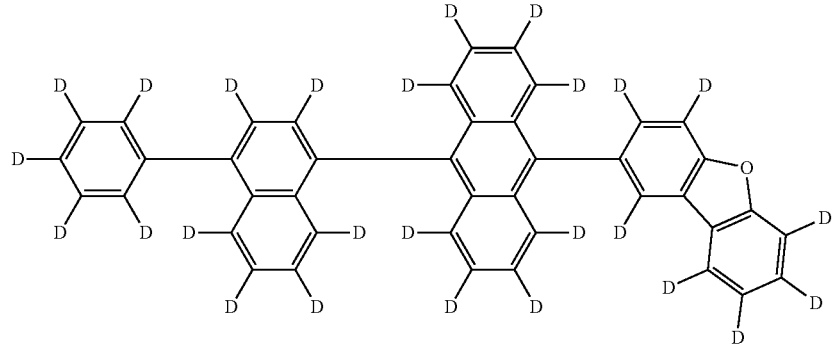
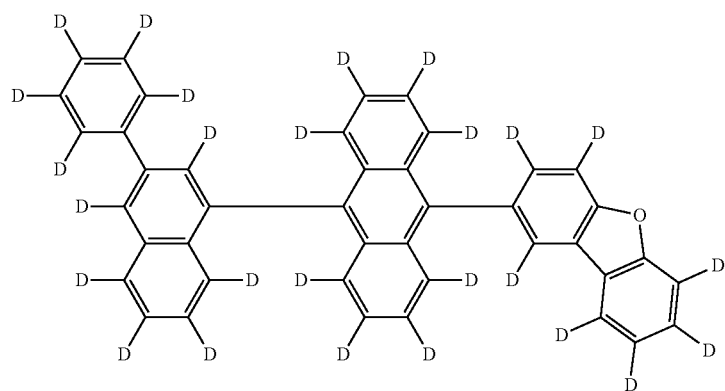
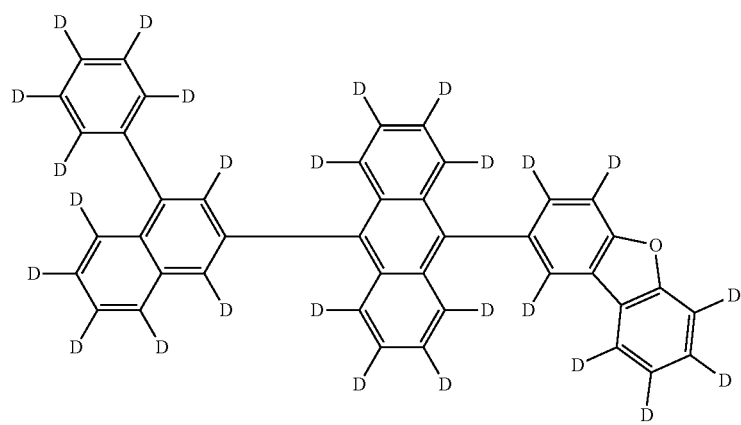
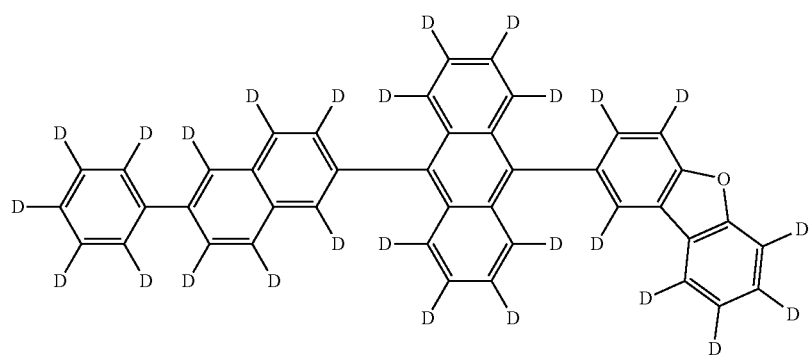

-continued
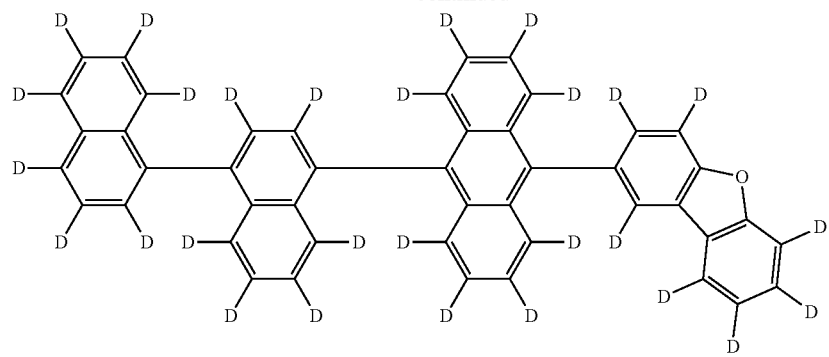
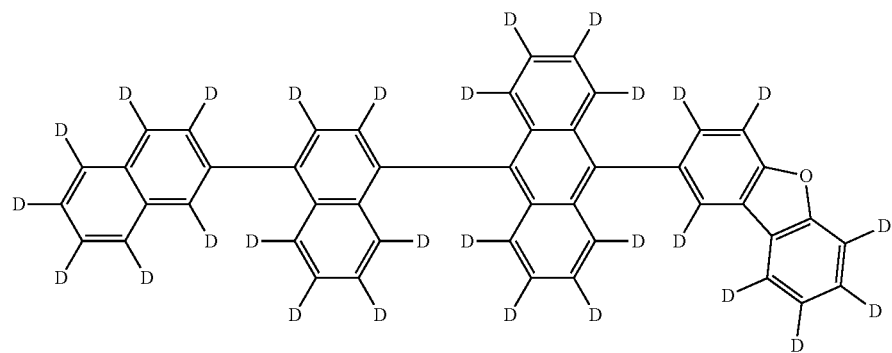
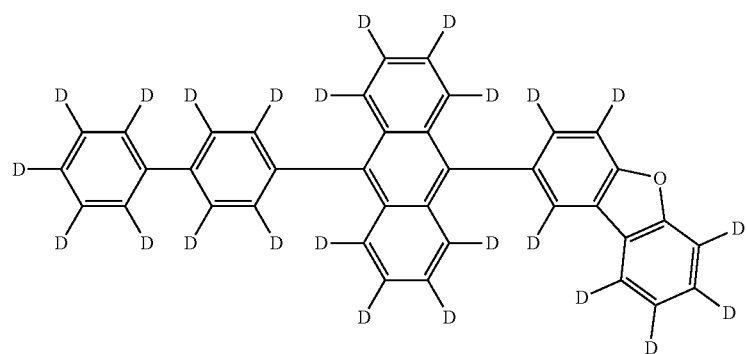
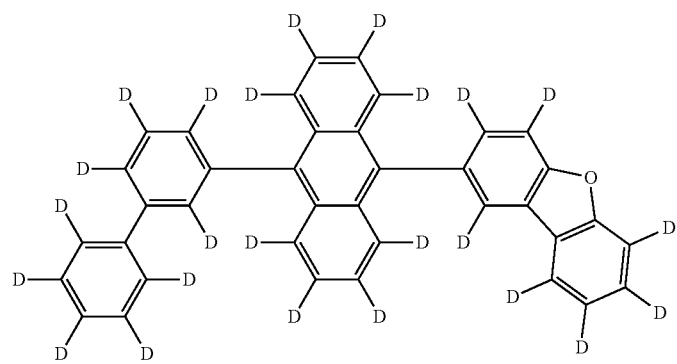

-continued
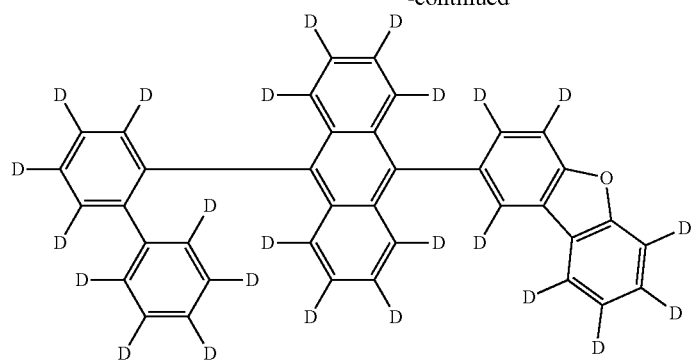
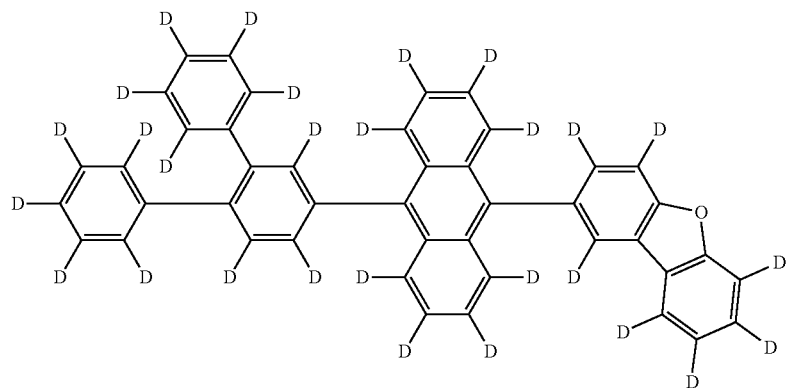
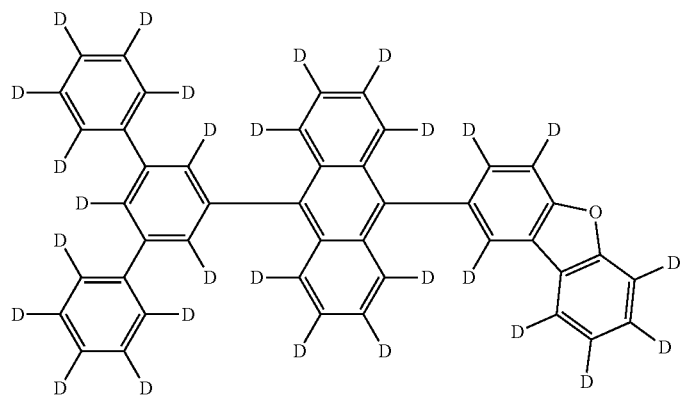
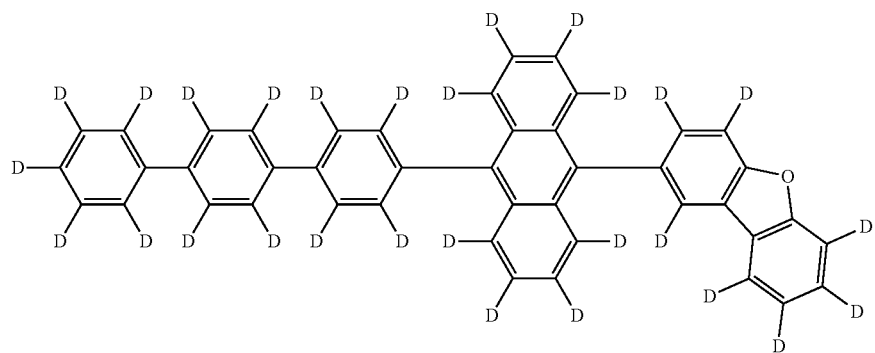

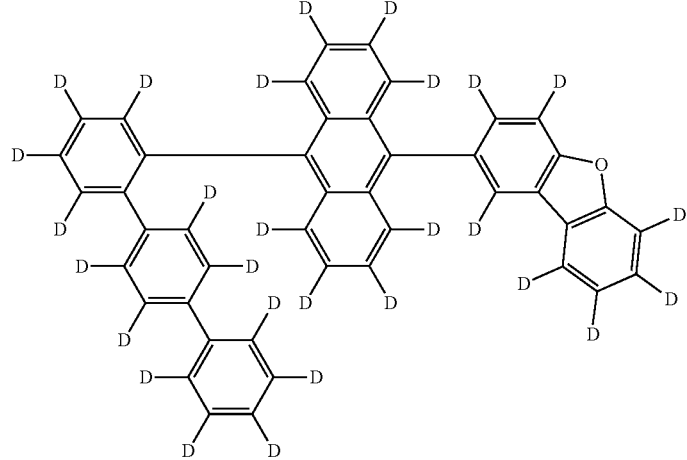
[Formula 238]

-continued
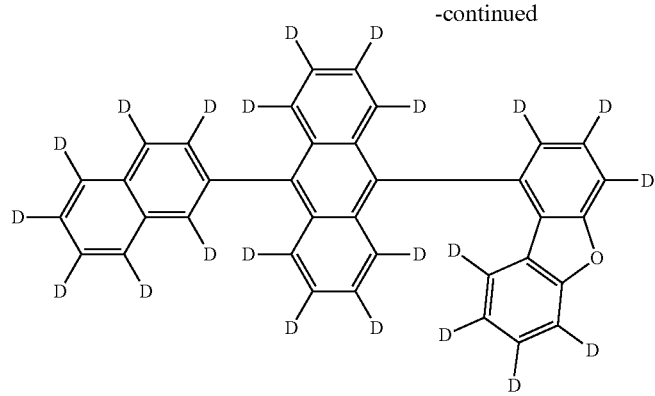
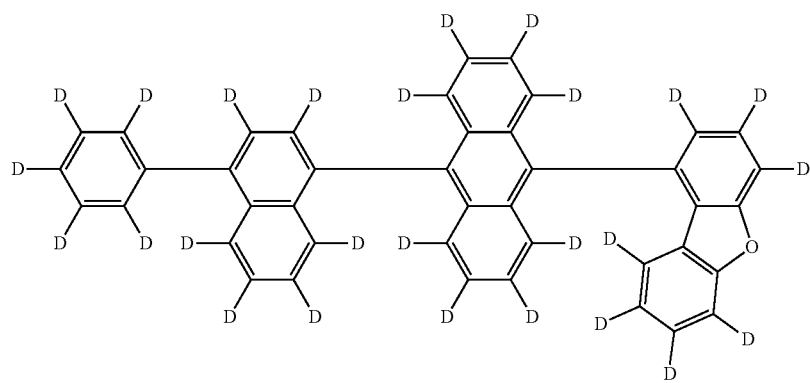
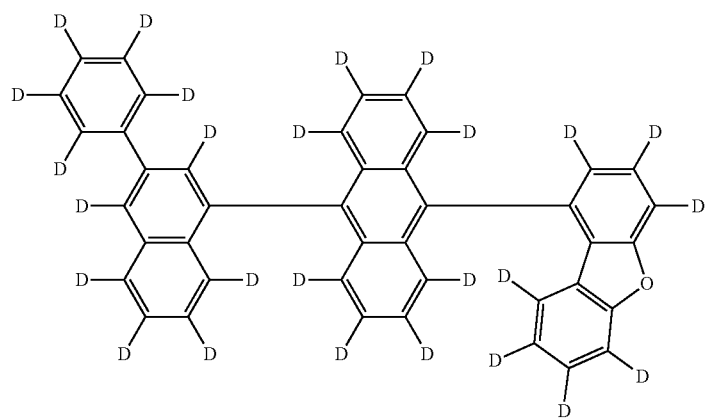
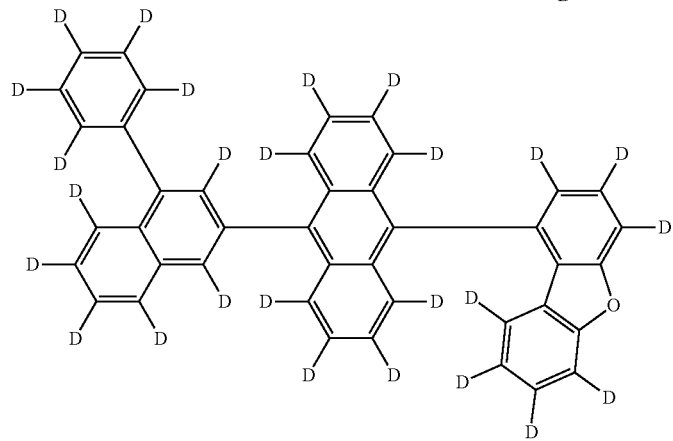

-continued
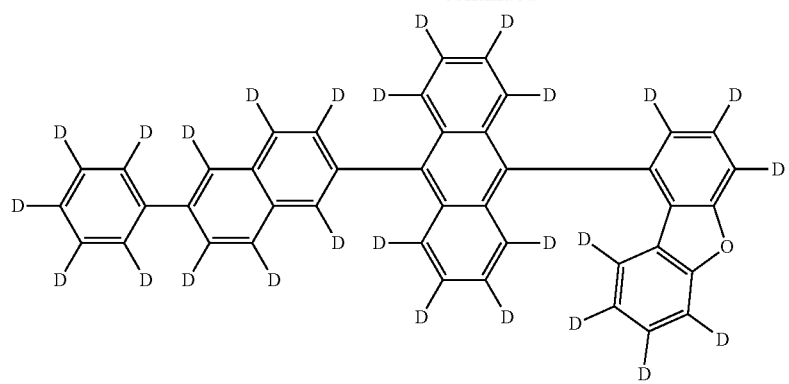
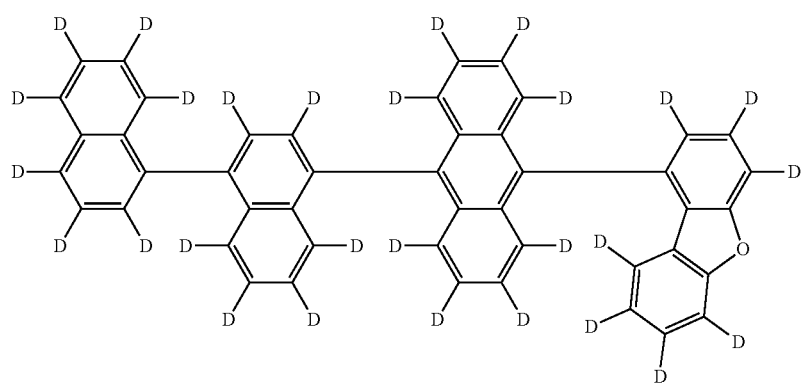
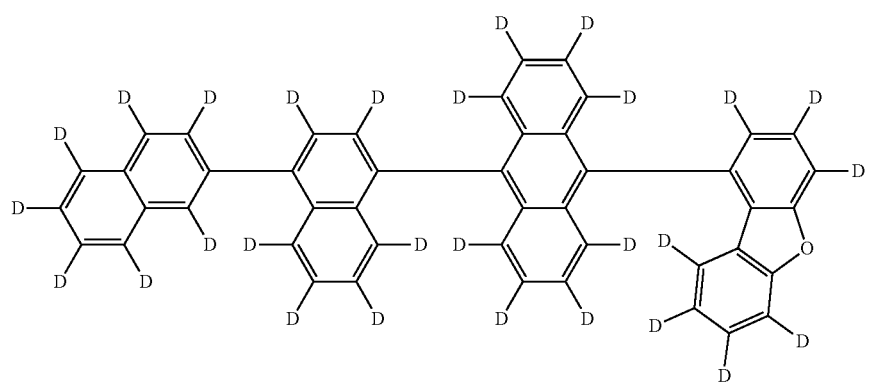
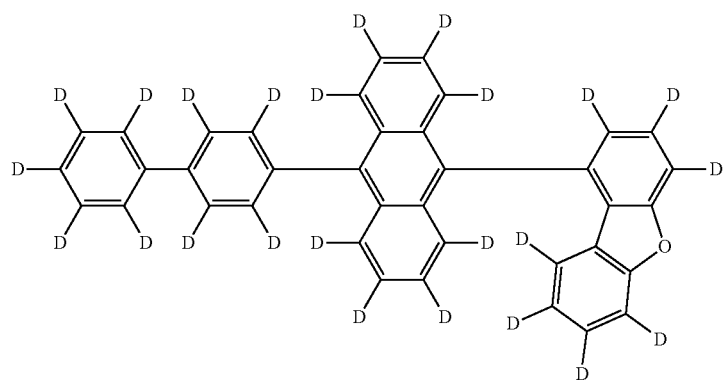

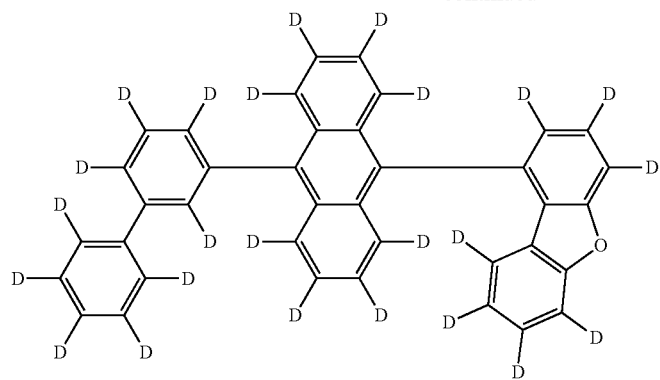
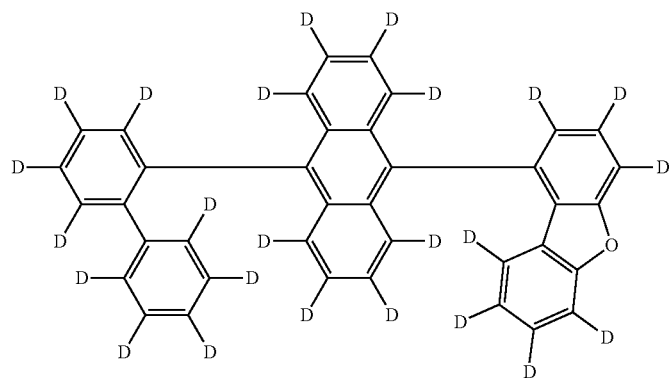
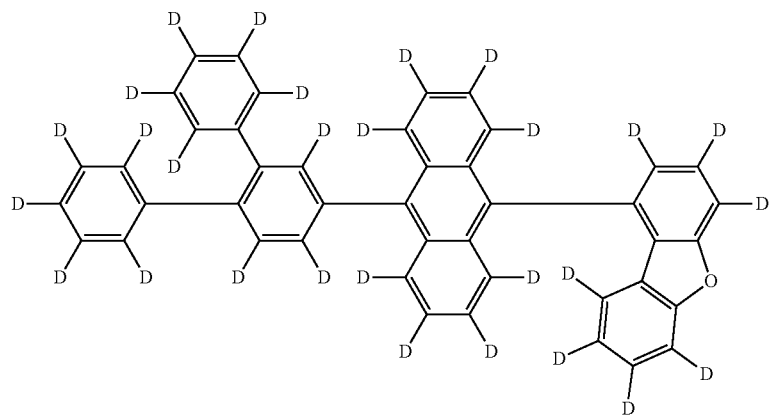
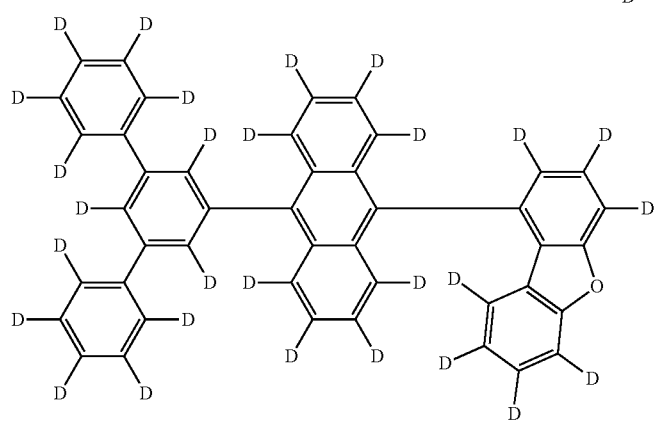

-continued
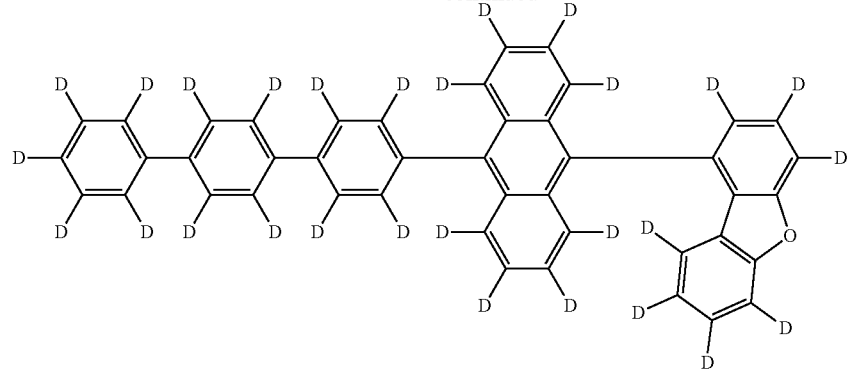
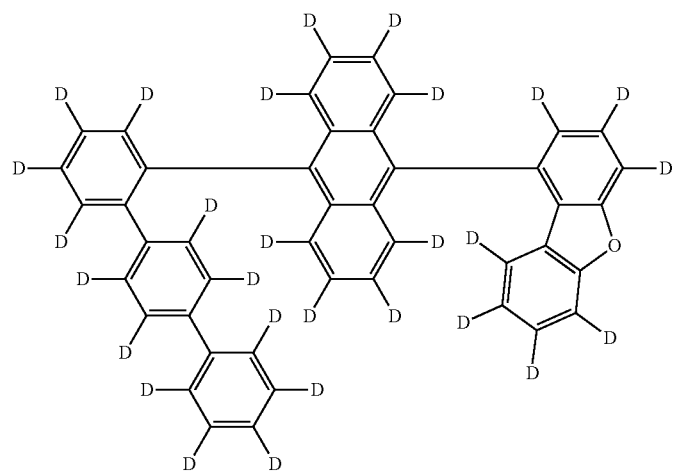
[Formula 239]
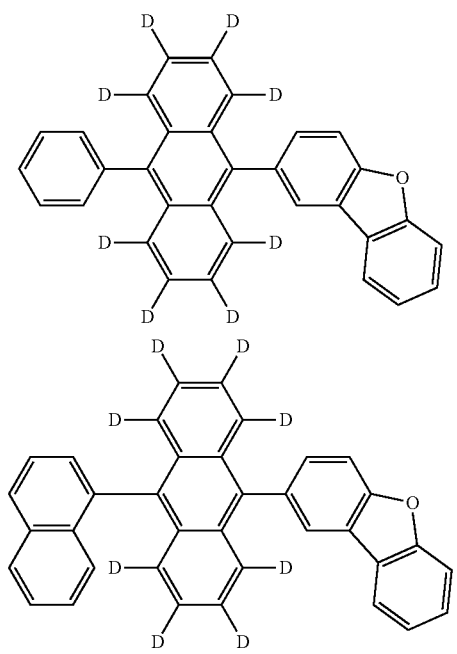
-continued
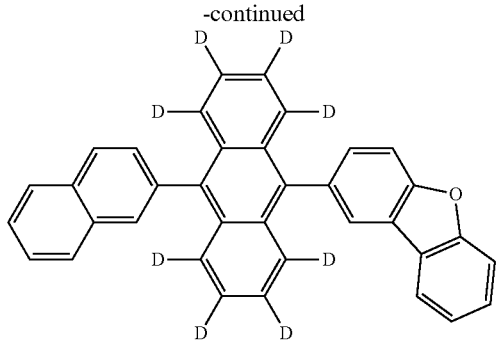
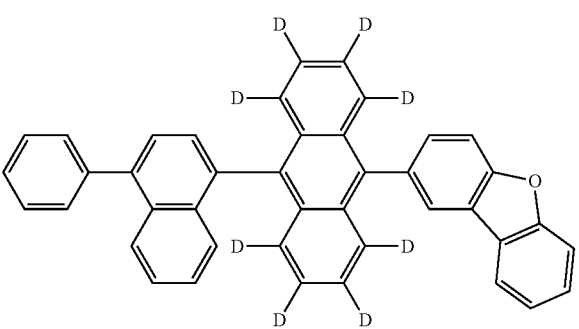

545
-continued
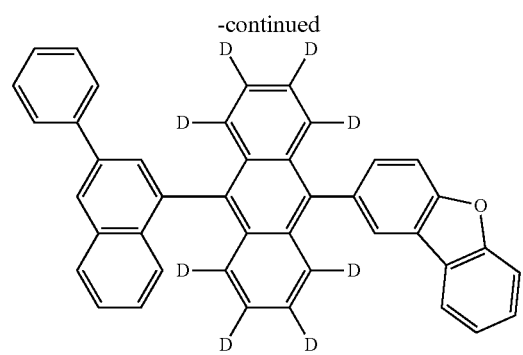
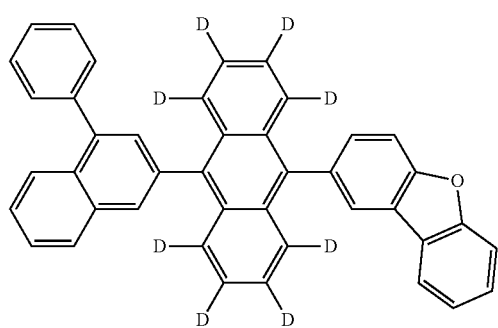
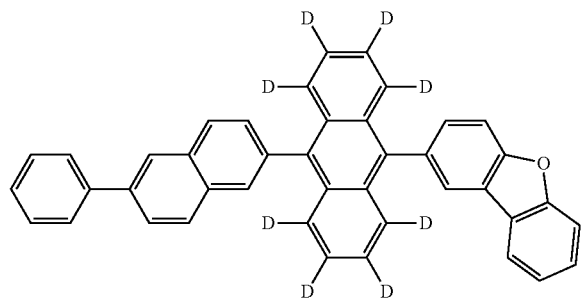
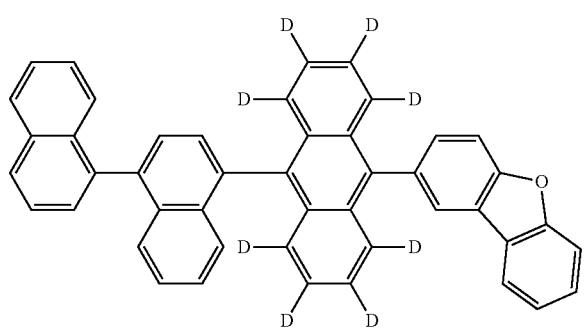
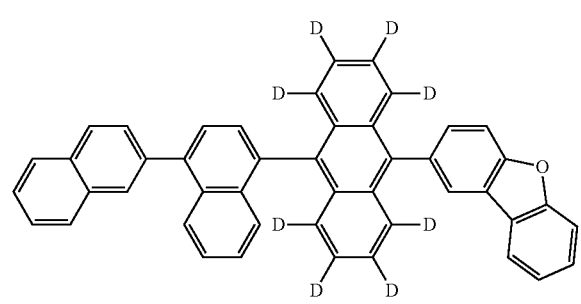
546
-continued
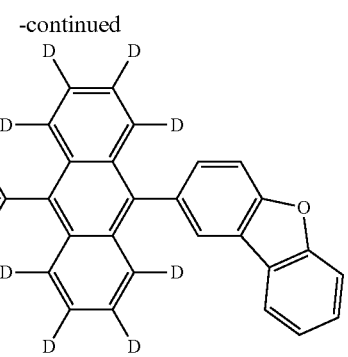
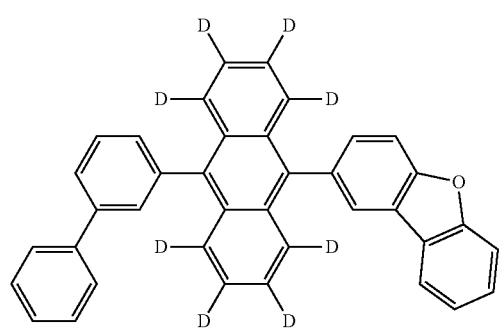
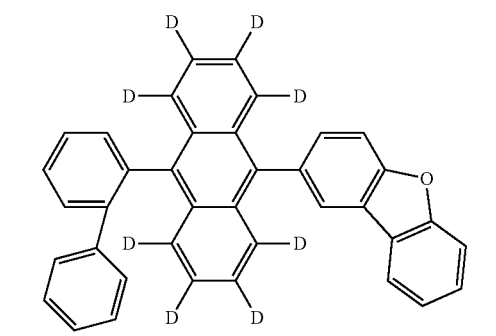
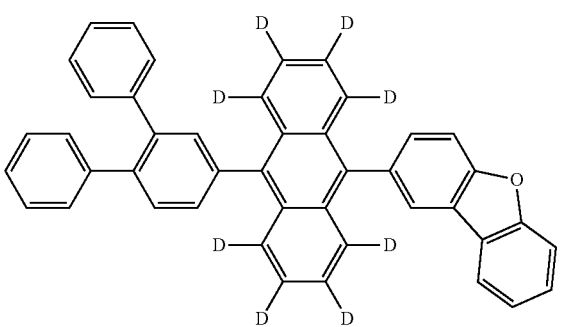
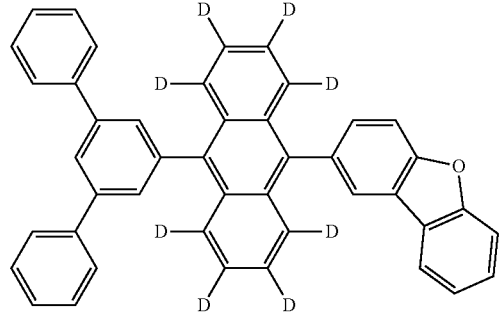

547
-continued
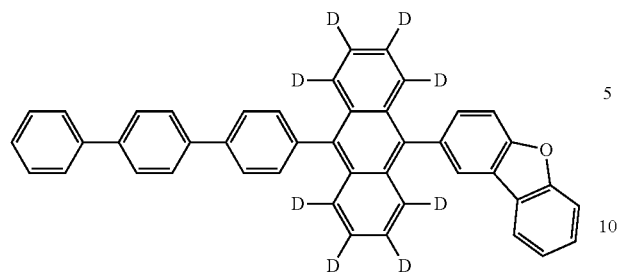
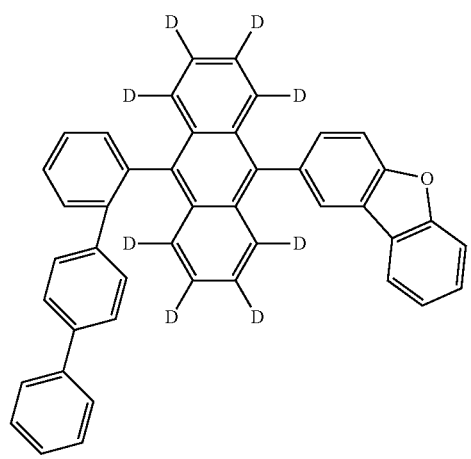
[Formula 240]
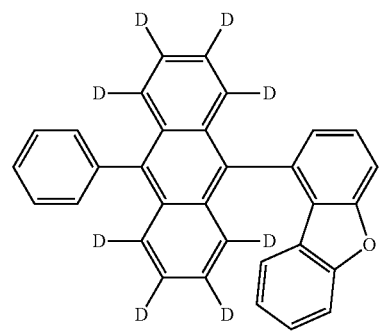
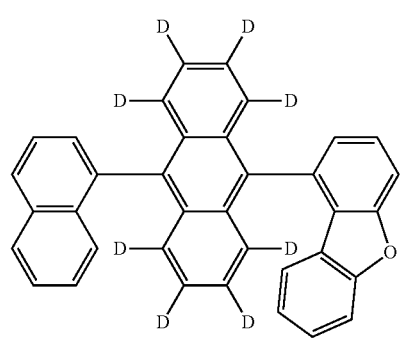
548
-continued
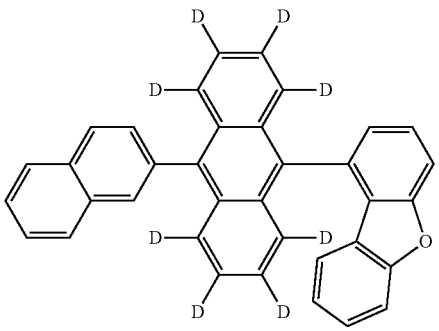
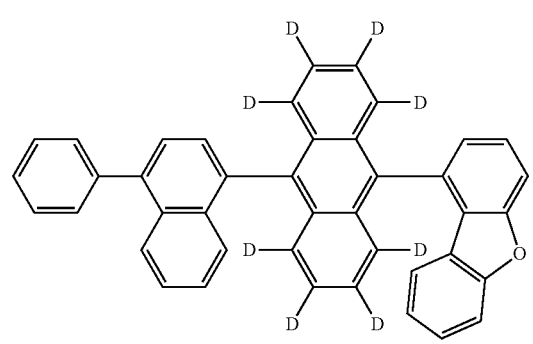
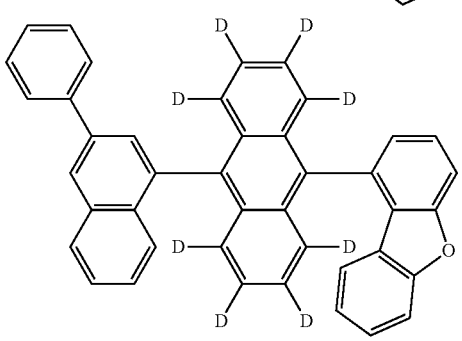
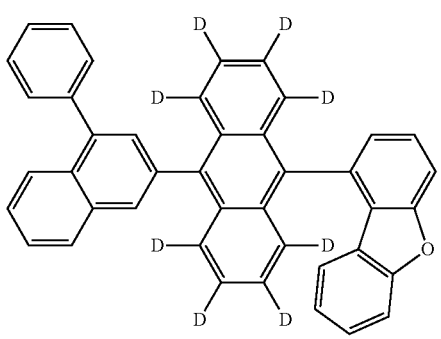
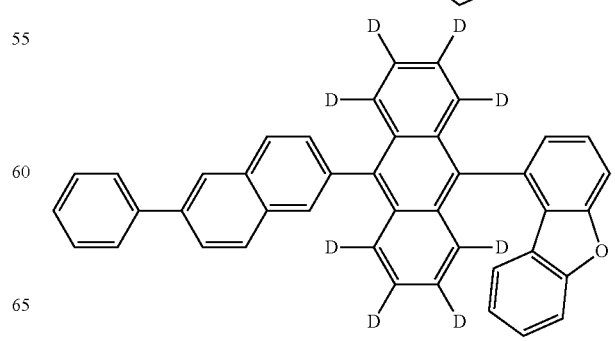

549
-continued
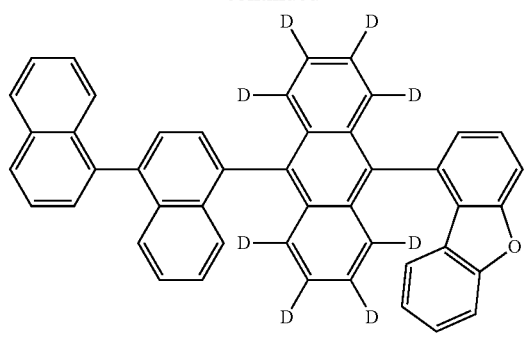
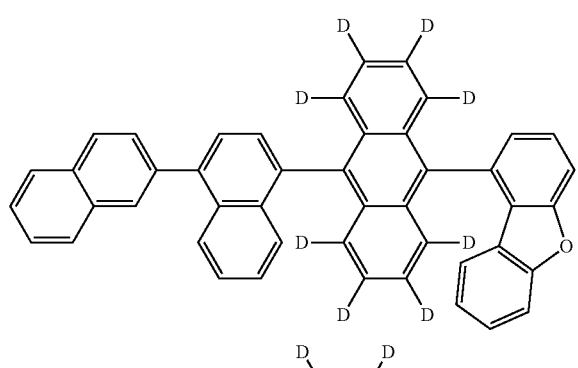
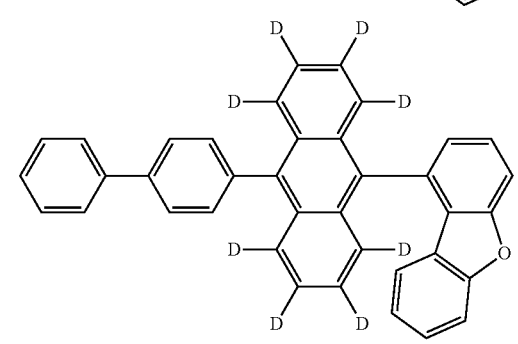
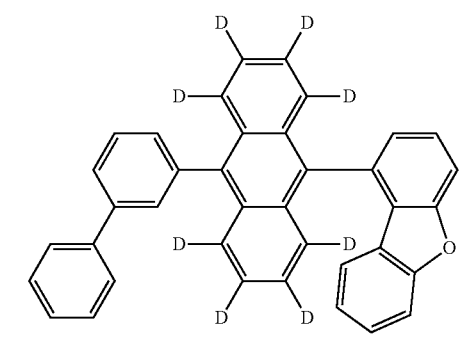
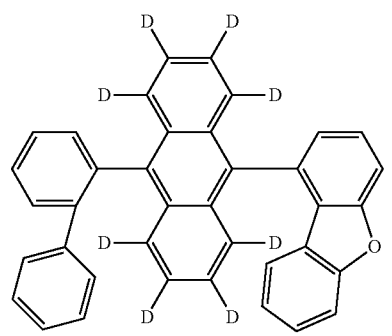
550
-continued
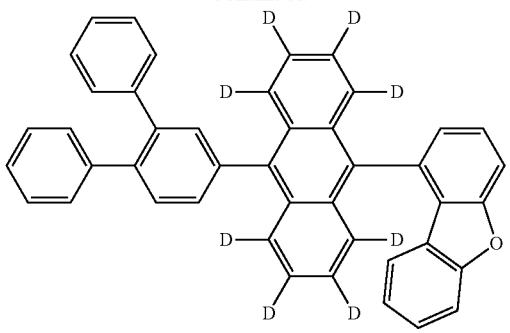
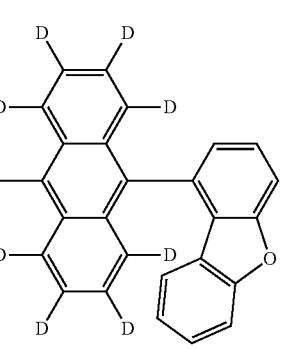
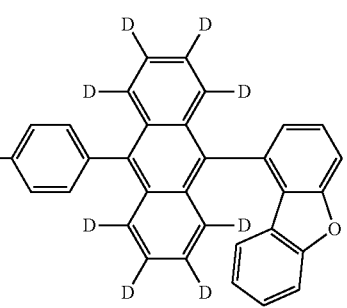
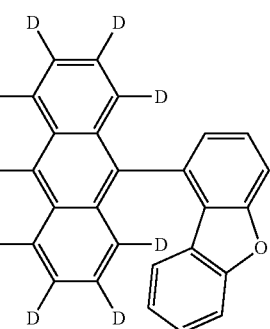

[Formula 241]
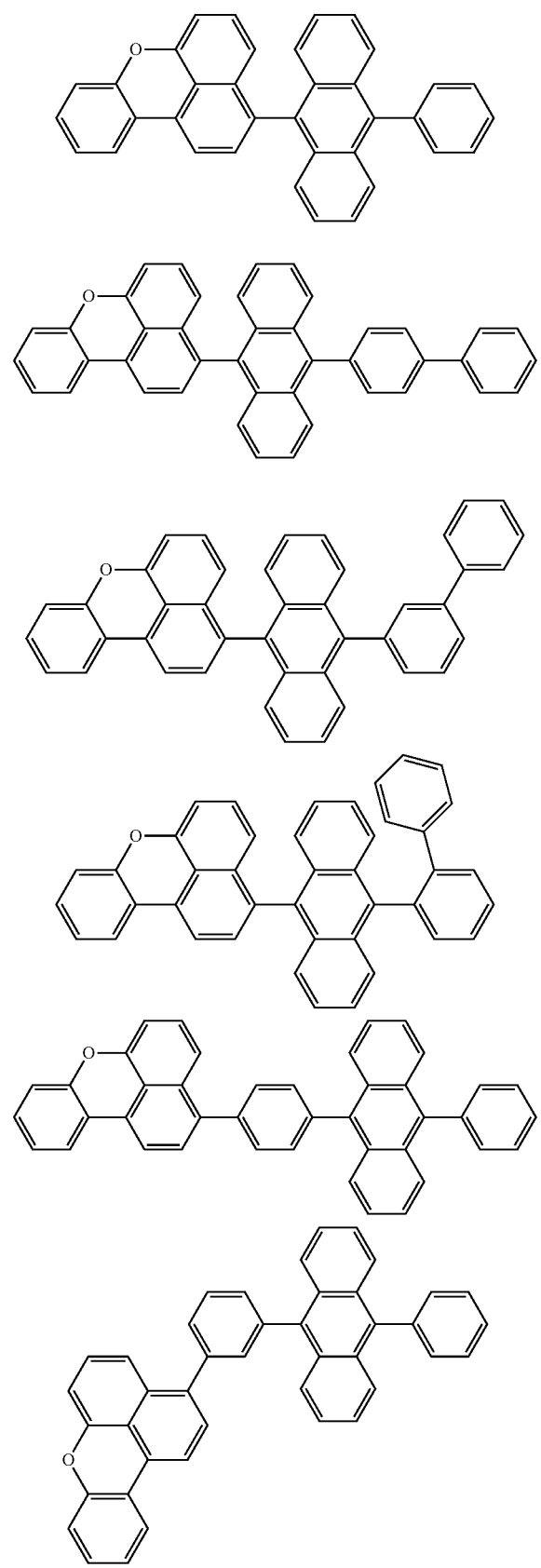
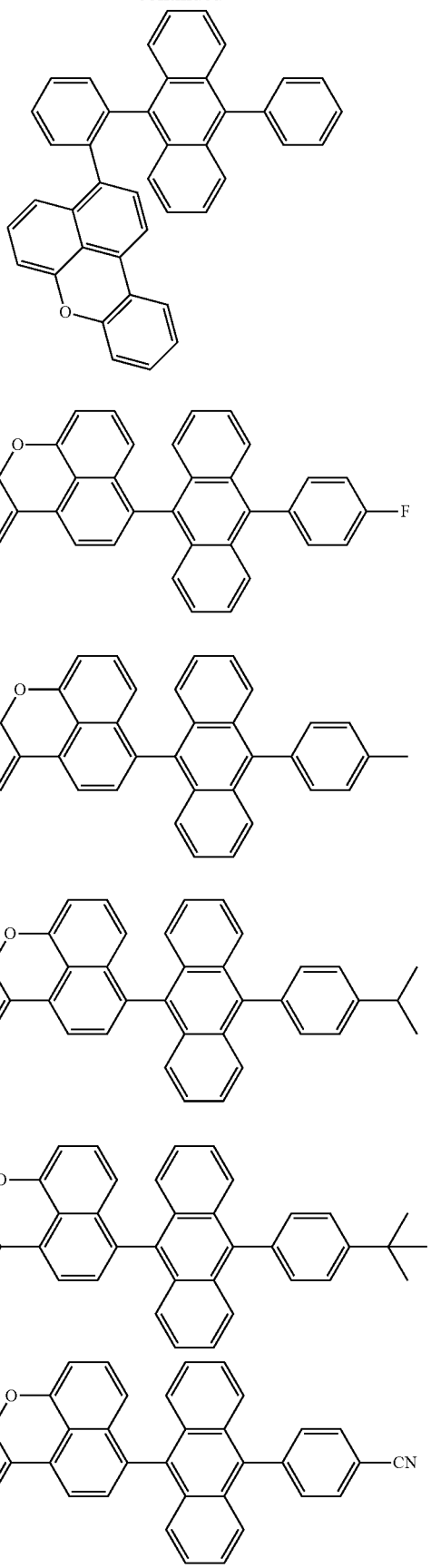
-continued

553
-continued
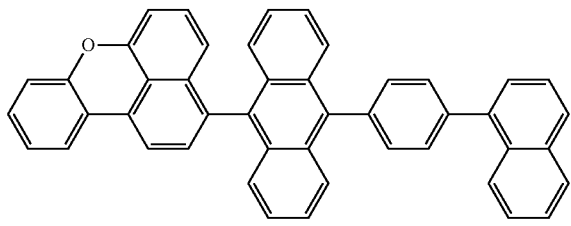
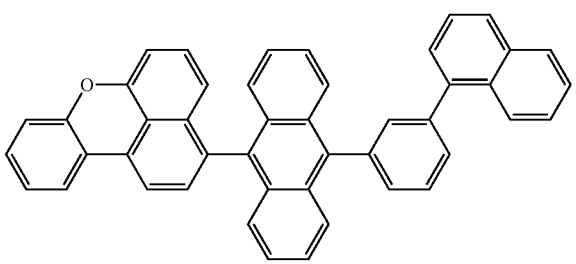
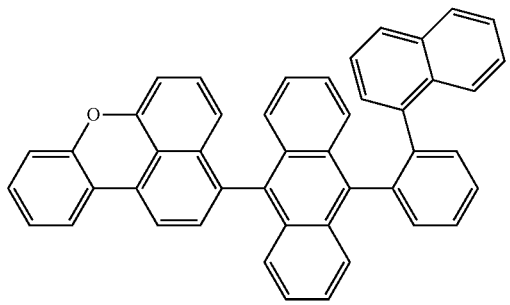
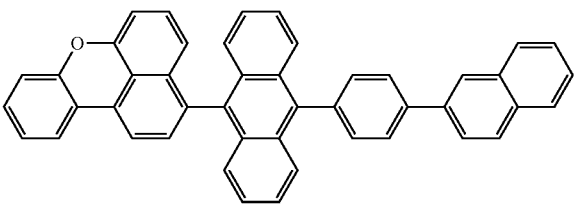
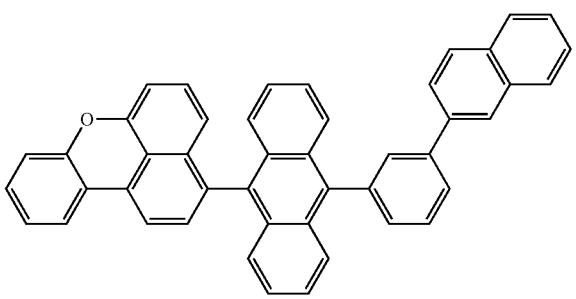
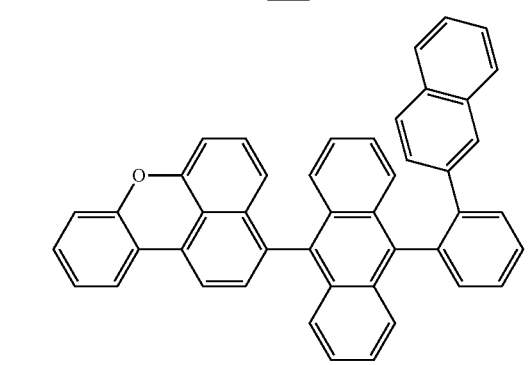
554
-continued
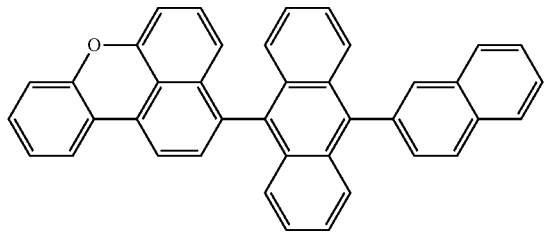
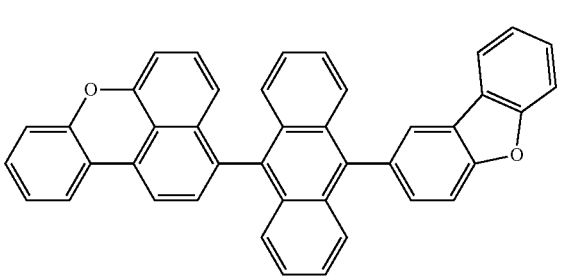
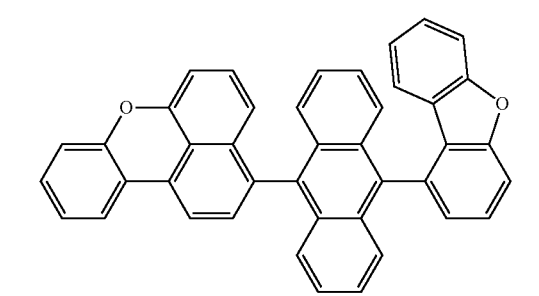
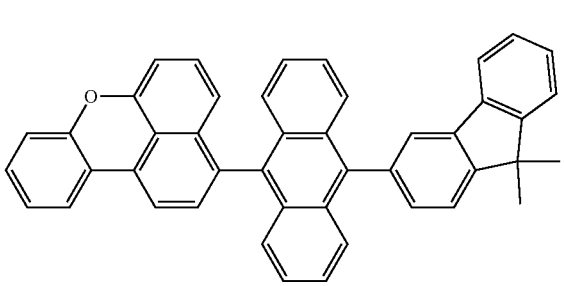
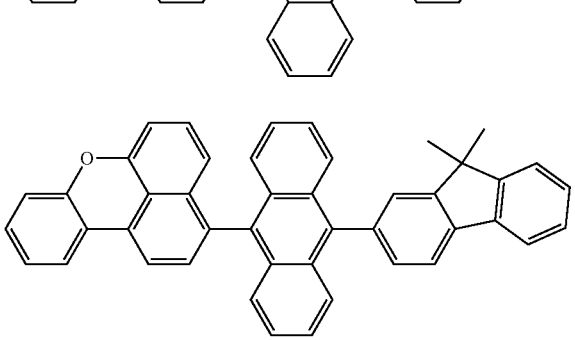
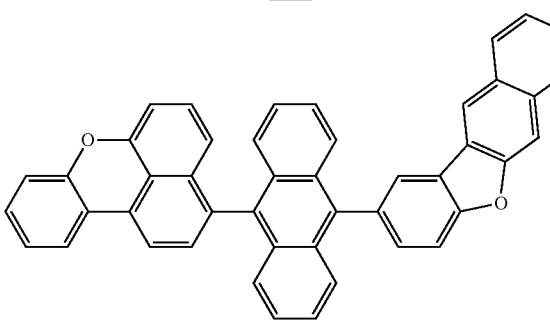

555
-continued
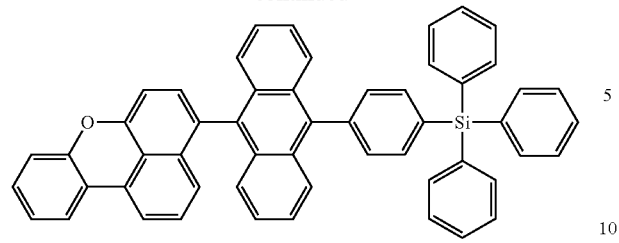
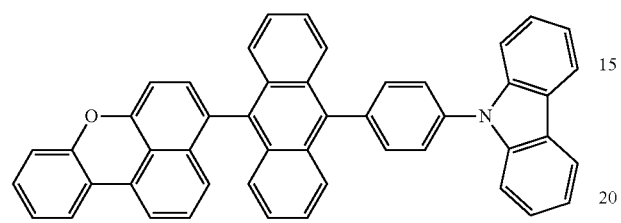
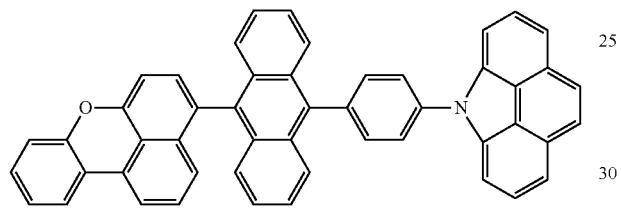
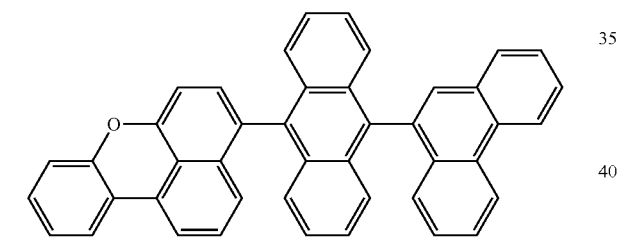
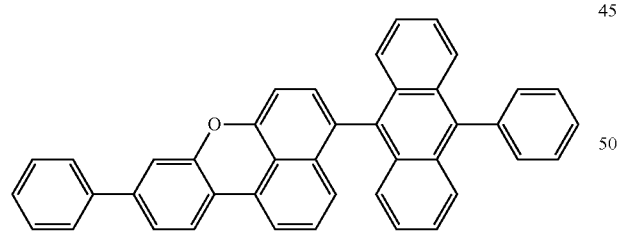
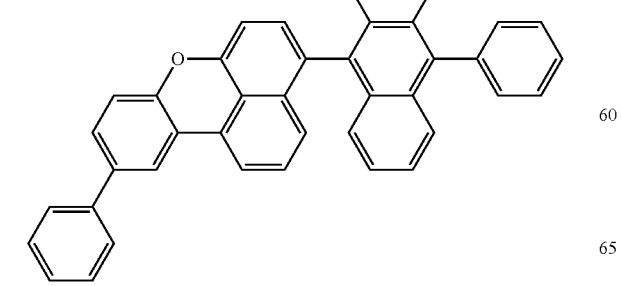
556
-continued
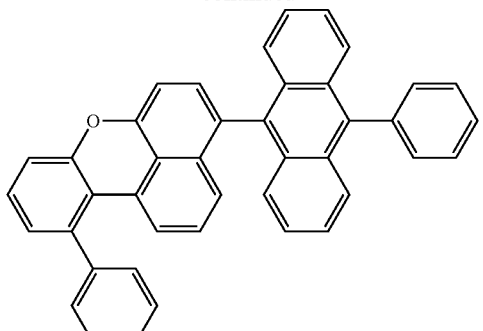
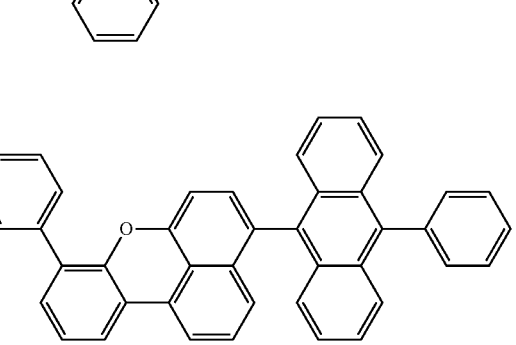
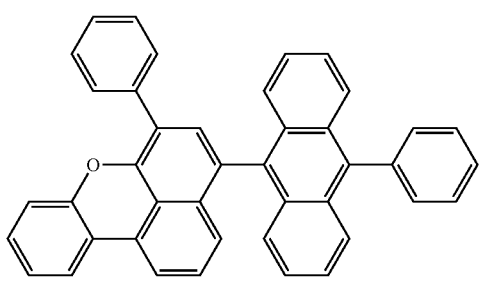
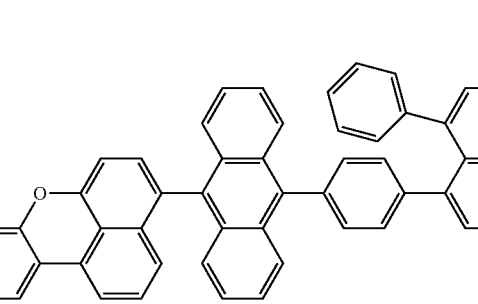
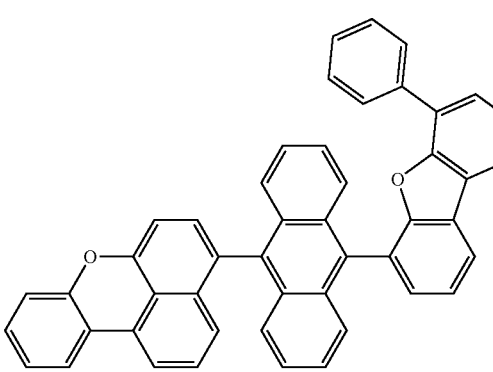

557 -continued
558 -continued
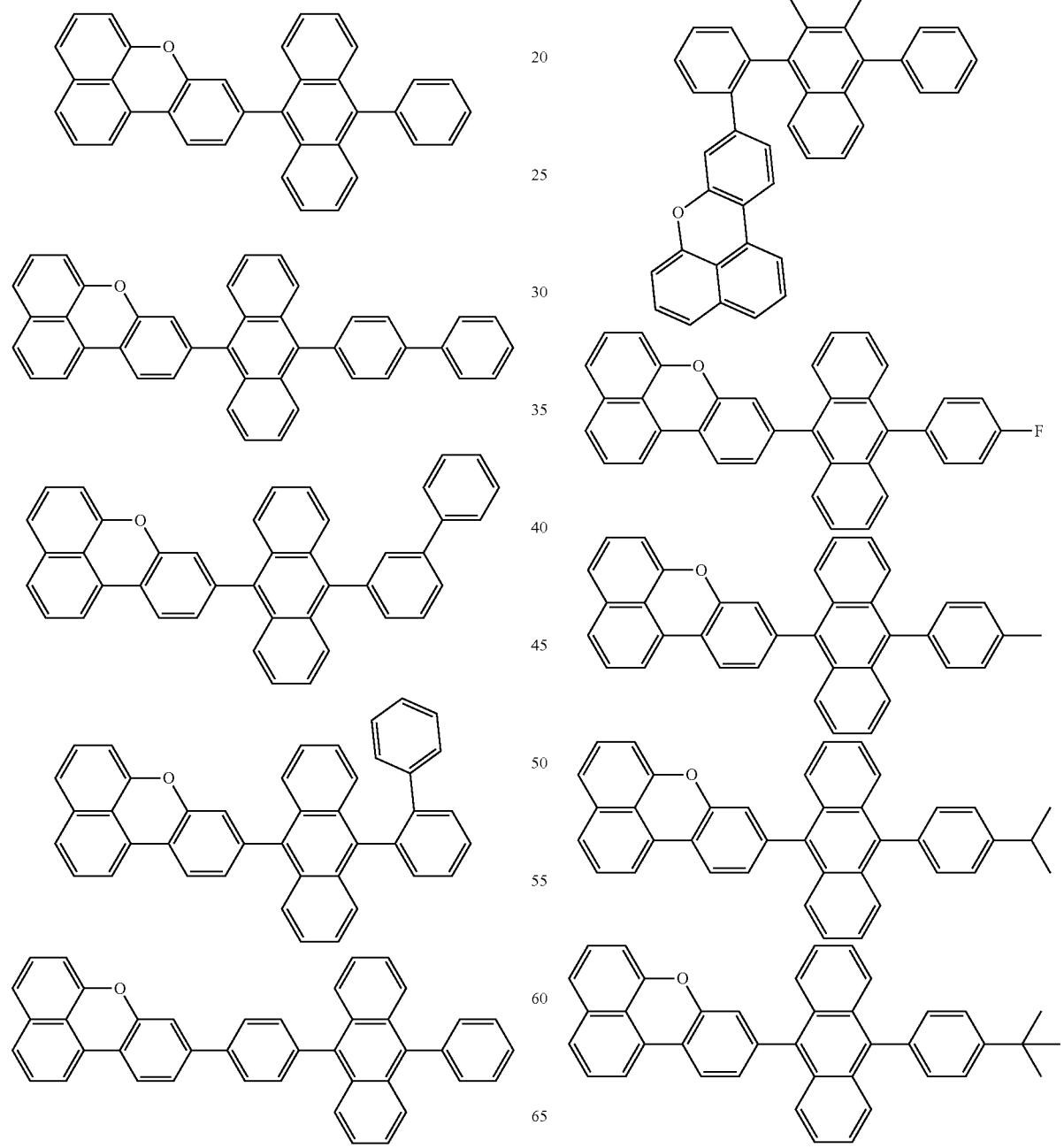

559
-continued
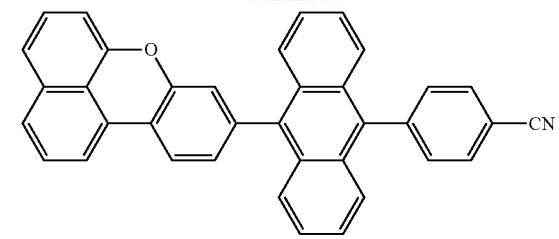
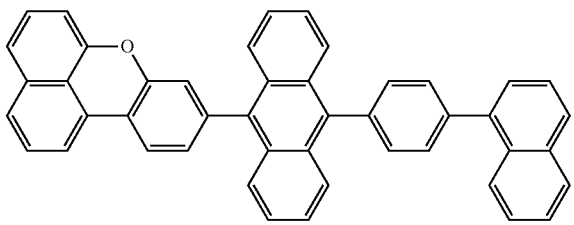
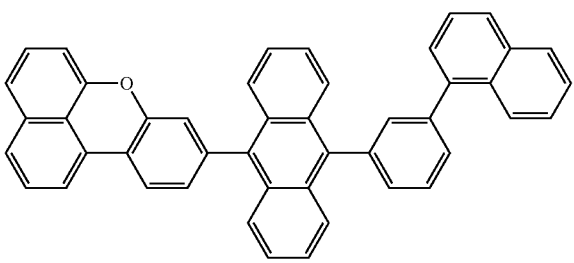
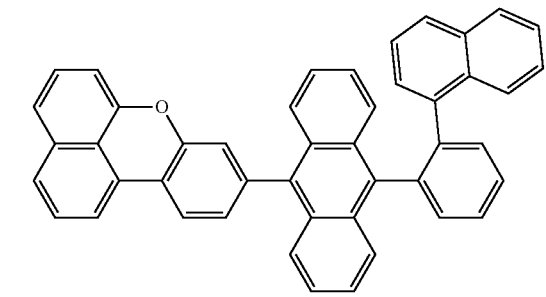
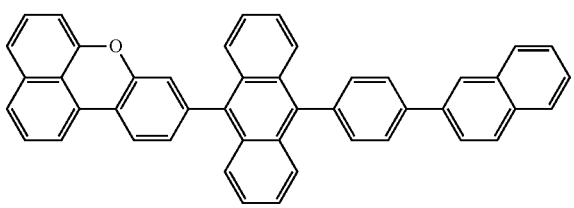
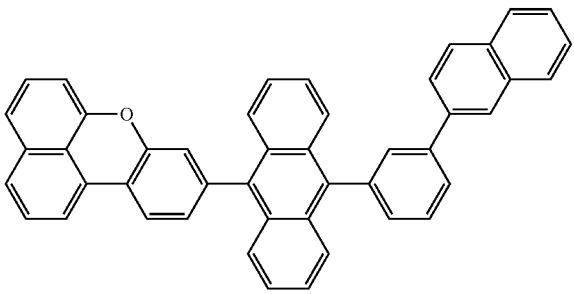
560
-continued
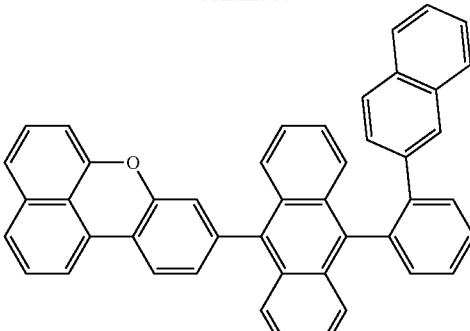
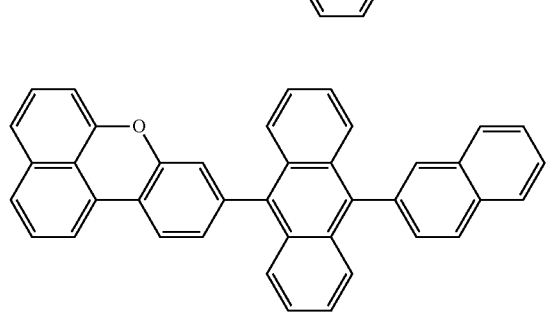
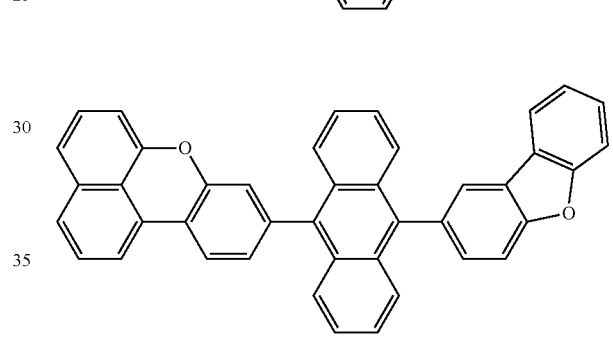
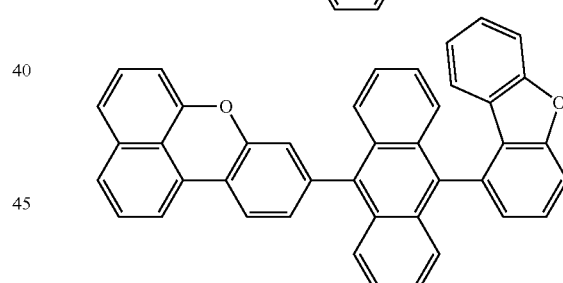
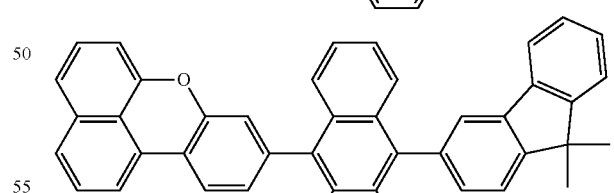
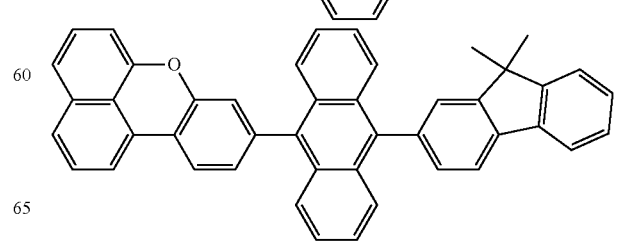

561
-continued
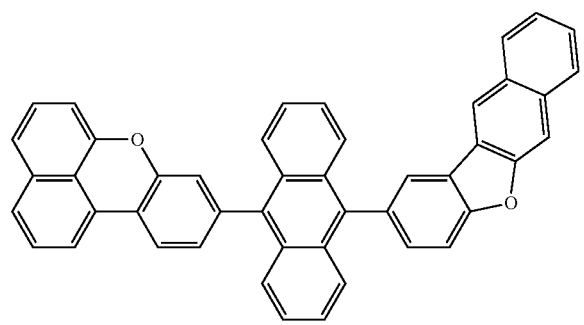
[Formula 243]
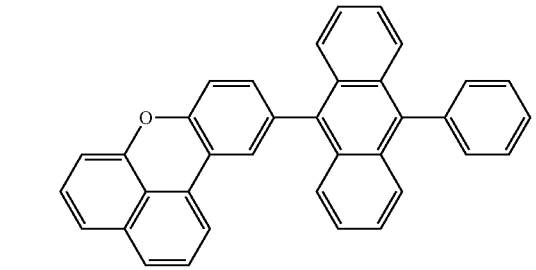
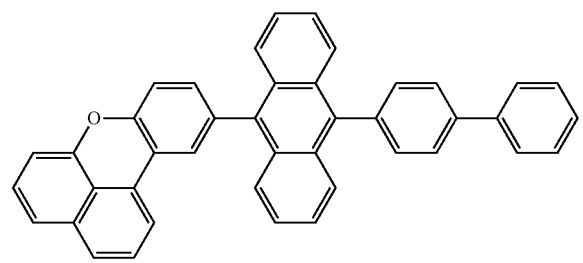
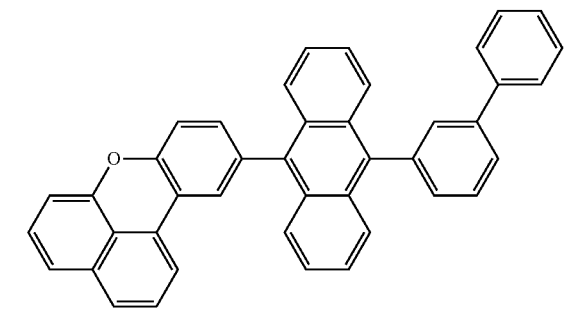
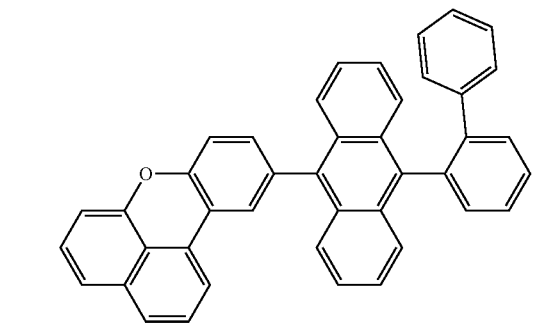
562
-continued
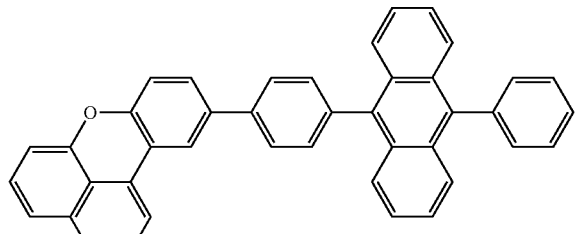
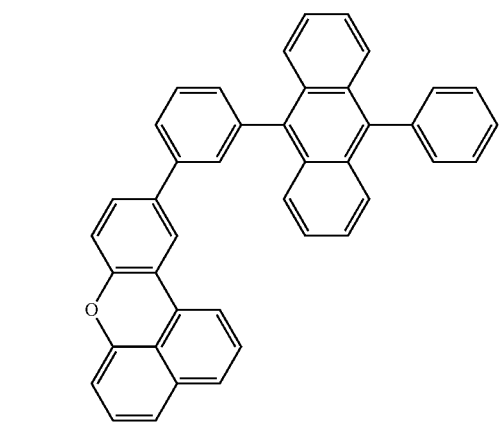
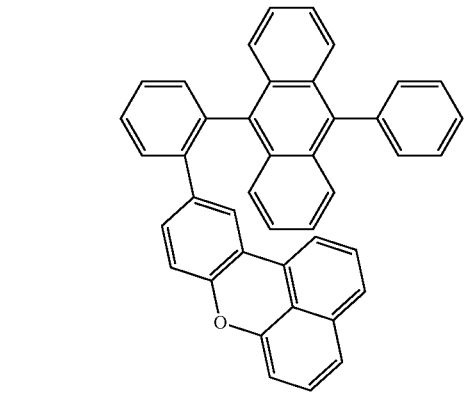
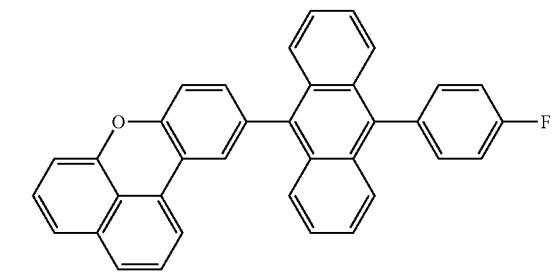
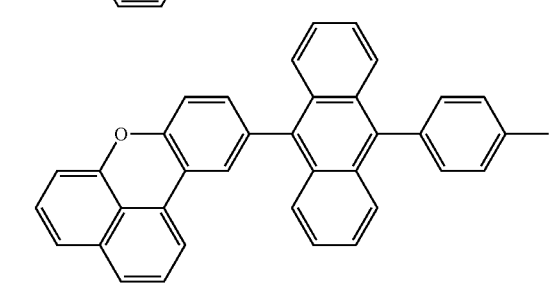

563
-continued
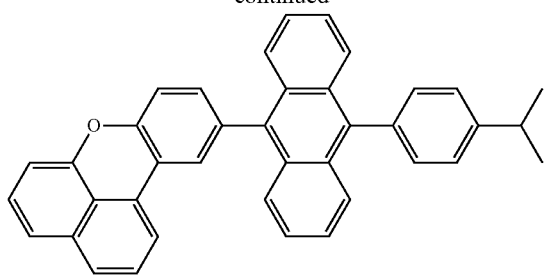
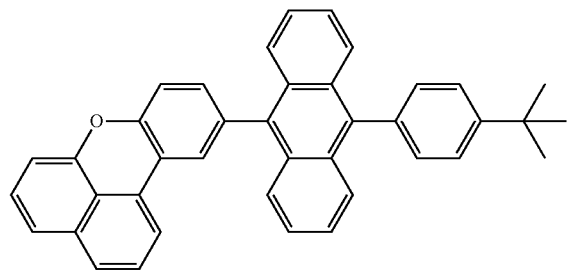
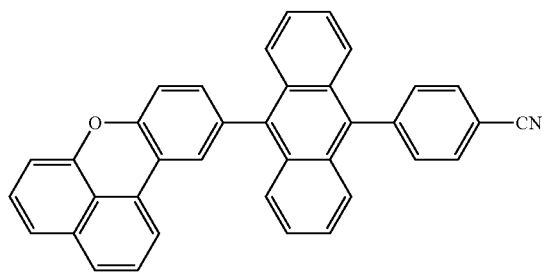
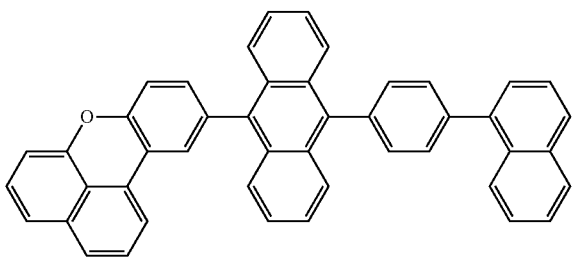
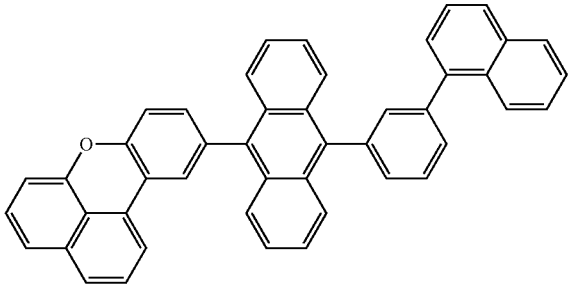
564
-continued
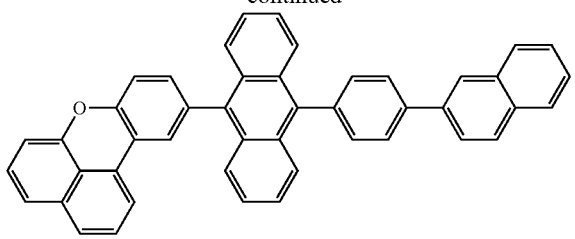
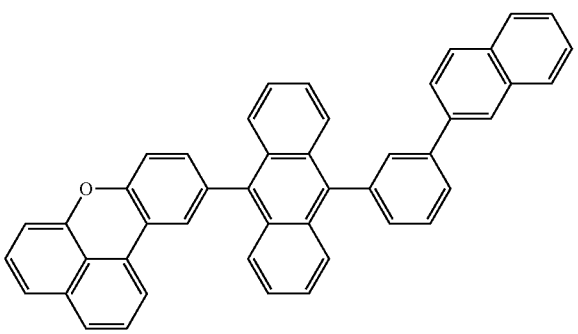
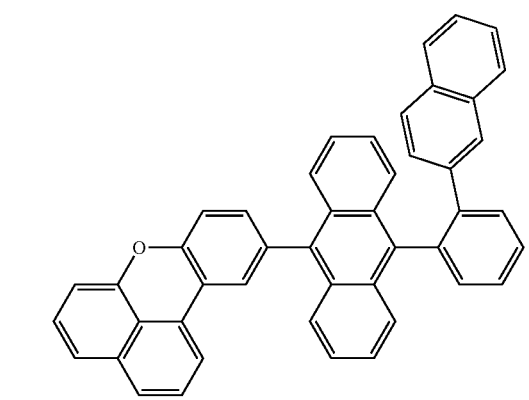
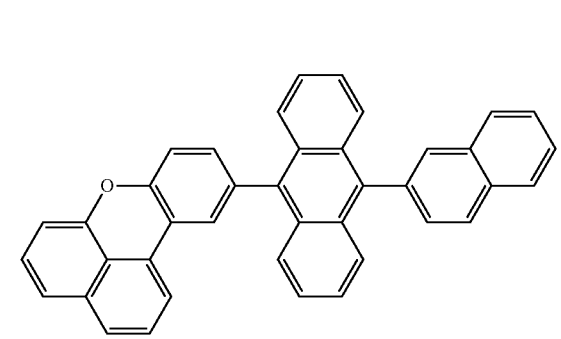
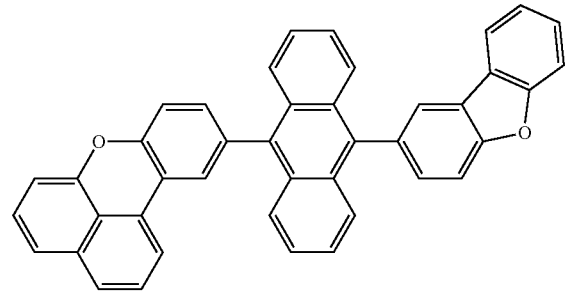

565
-continued
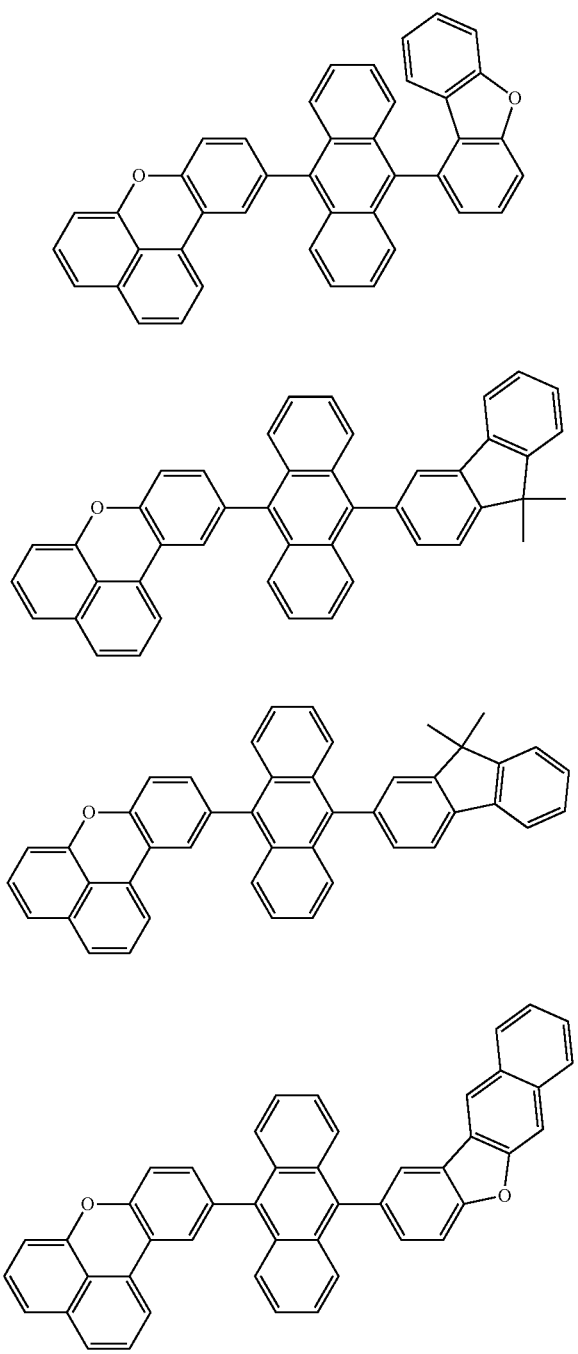
[Formula 244]
566
-continued
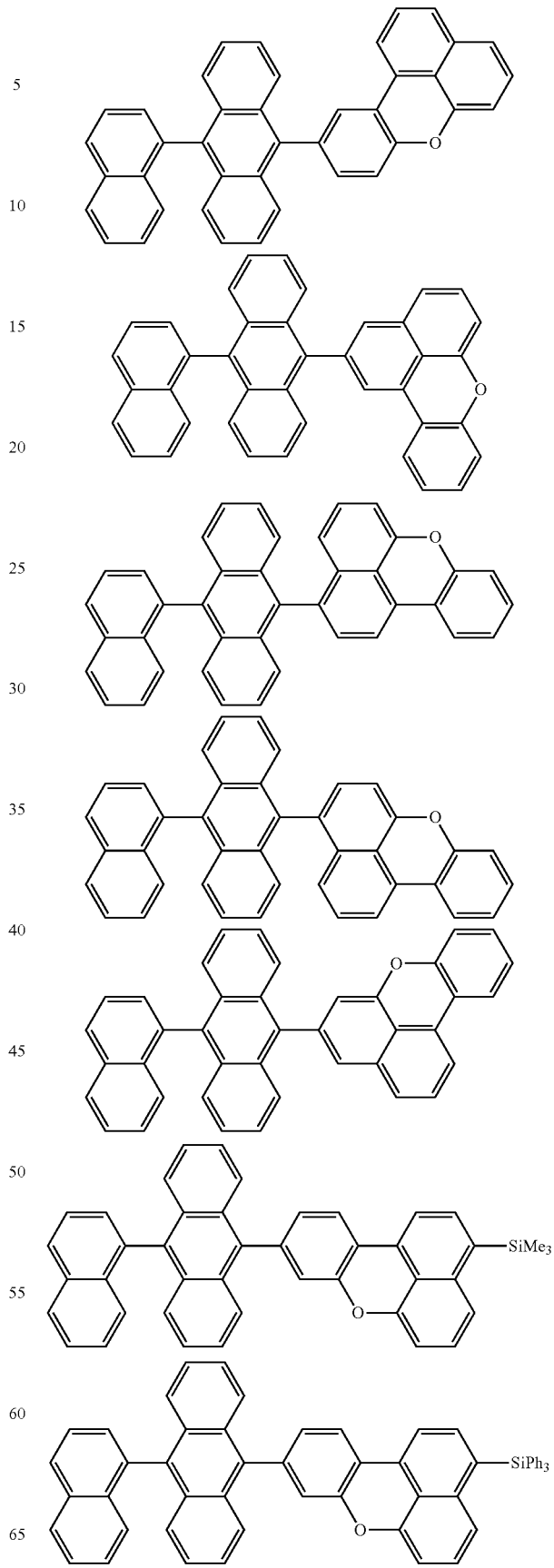

567
-continued
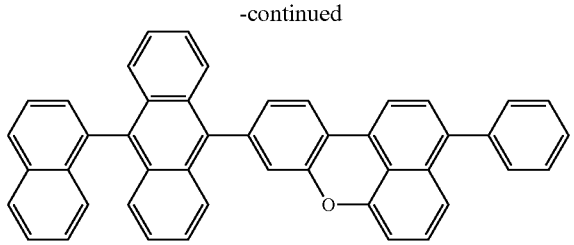
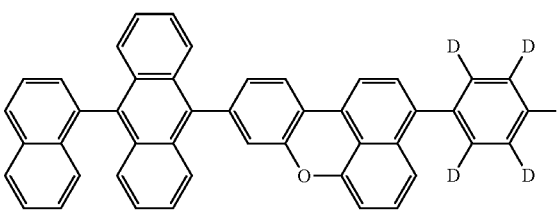
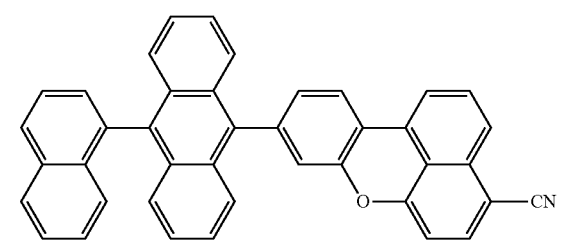
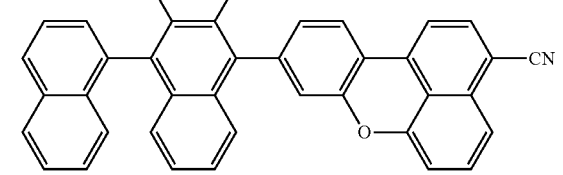
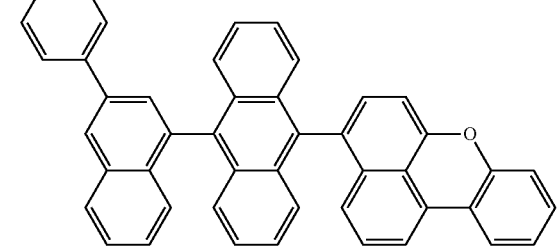
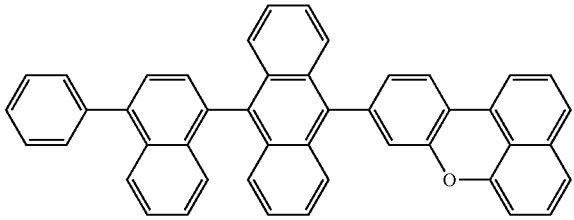
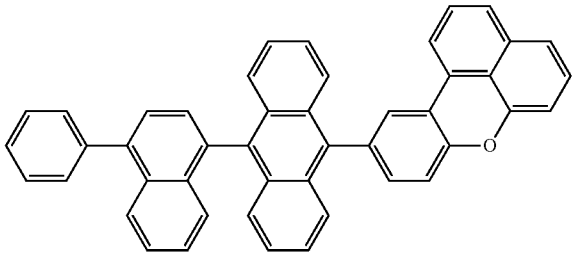
568
-continued
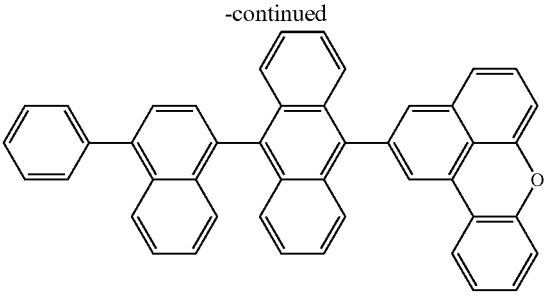
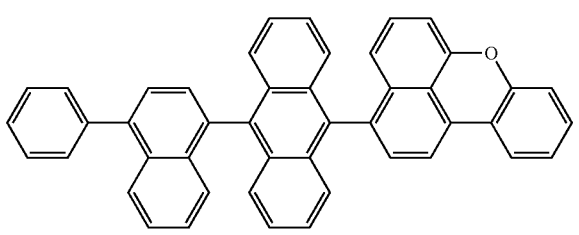
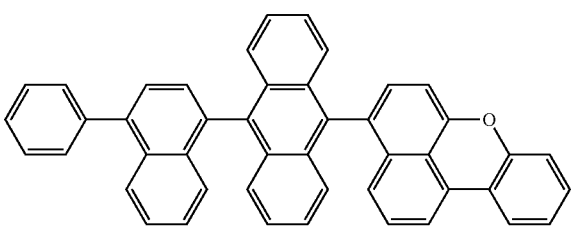
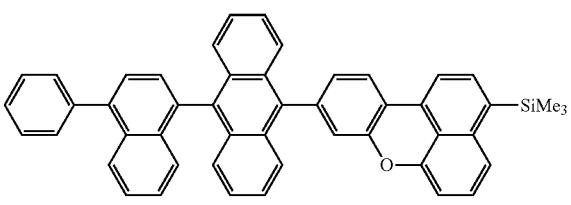
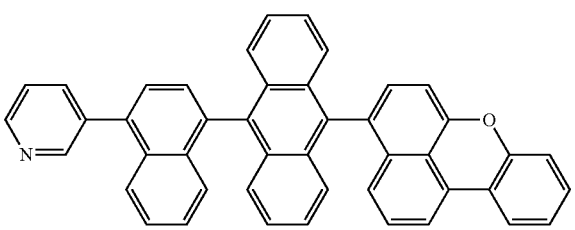
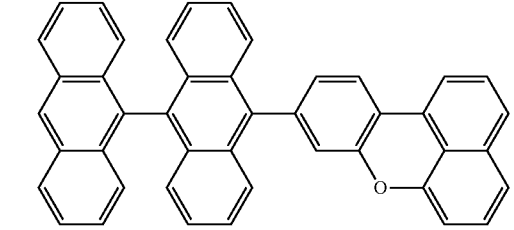

569
-continued
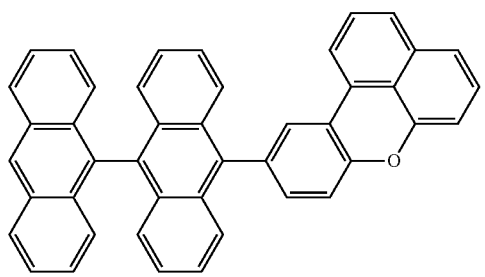
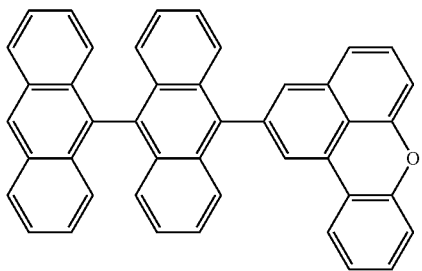
[Formula 245]
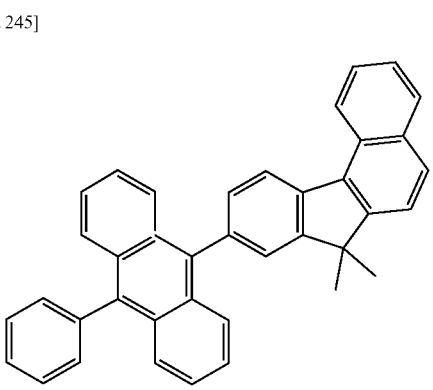
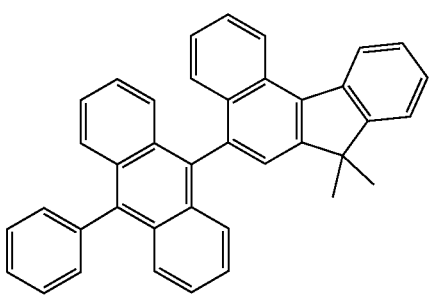
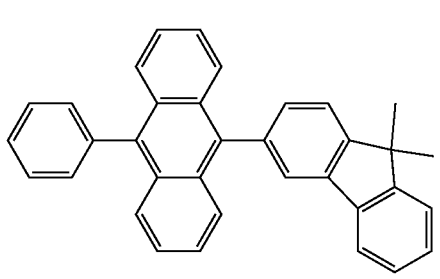
570
-continued
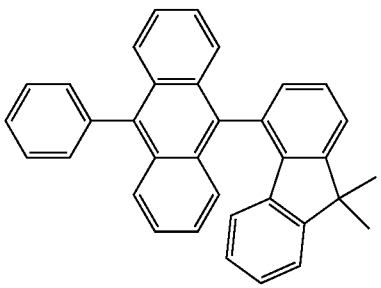
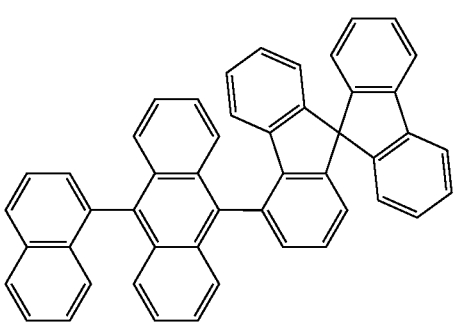
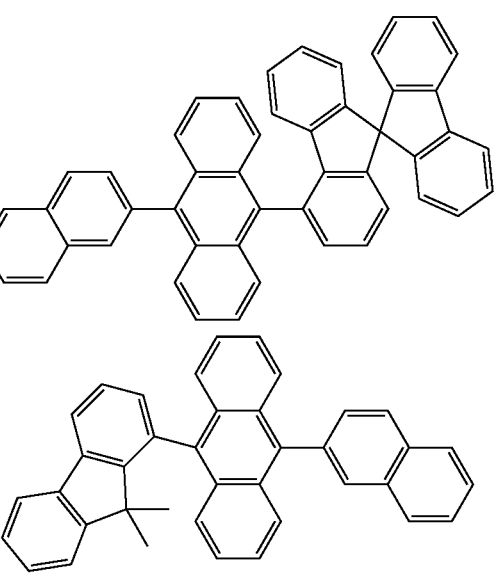
[Formula 246]
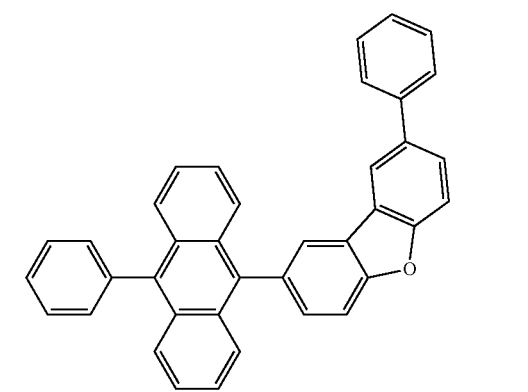

-continued

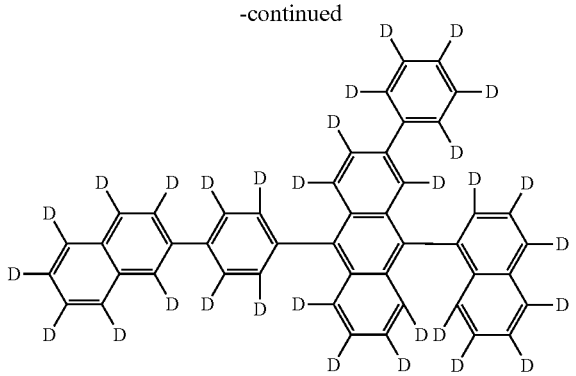

First Emitting Compound, Second Emitting Compound and Third Emitting Compound

In the organic EL device according to the exemplary embodiment, examples of the first emitting compound, the second emitting compound and the third emitting compound include a third compound and a fourth compound below. The third compound and the fourth compound are each independently at least one compound selected from the group consisting of a compound represented by a formula (3) below, a compound represented by a formula (4) below, a compound represented by a formula (5) below, a compound represented by a formula (6) below, a compound represented by a formula (7) below, a compound represented by a formula (8) below, a compound represented by a formula (9) below, and a compound represented by a formula (10) below.

Compound Represented by Formula (3)

The compound represented by the formula (3) will be described below.

[Formula 247]

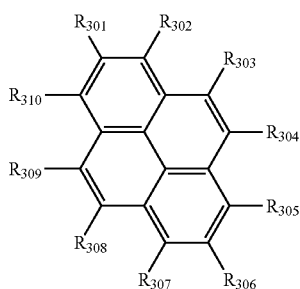

(3)

In the formula (3):

at least one combination of adjacent two or more of $R_{301}$ to $R_{310}$ are mutually bonded to form a substituted or unsubstituted monocyclic ring, mutually bonded to form a substituted or unsubstituted fused ring, or not mutually bonded;

at least one of $R_{301}$ to $R_{310}$ is a monovalent group represented by a formula (31) below; and $R_{301}$ to $R_{310}$ not forming the monocyclic ring, not forming the fused ring and not being the monovalent group represented by the formula (31) are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$) ($R_{903}$), a group represented by —O—($R_{904}$), a group represented by —S—($R_{905}$), a group represented by —N($R_{906}$) ($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

[Formula 248]

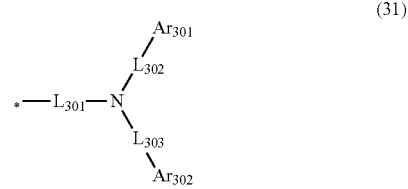

(31)

In the formula (31):

$Ar_{301}$ and $Ar_{302}$ are each independently a substituted or unsubstituted aryl group having 6 to 50 ring carbon atoms, or a substituted or unsubstituted heterocyclic group having 5 to 50 ring atoms;

$L_{301}$ to $L_{303}$ are each independently a single bond, a substituted or unsubstituted arylene group having 6 to 30 ring carbon atoms, or a substituted or unsubstituted divalent heterocyclic group having 5 to 30 ring atoms; and

* in the formula (3) represents a bonding position to a pyrene ring in the formula (3).

$R_{901}$, $R_{902}$, $R_{903}$, $R_{904}$, $R_{905}$, $R_{906}$, and $R_{907}$ in the third and fourth compounds are each dependently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, a substituted or unsubstituted heterocyclic group having 5 to 50 ring atoms, a substituted or unsubstituted alkyl group having 1 to 50 carbon atoms, or a substituted or unsubstituted aryl group having 6 to 50 ring carbon atoms;

when a plurality of $R_{901}$ are present, the plurality of $R_{901}$ are mutually the same or different;

when a plurality of $R_{902}$ are present, the plurality of $R_{902}$ are mutually the same or different;

when a plurality of $R_{903}$ are present, the plurality of $R_{903}$ are mutually the same or different;

when a plurality of $R_{904}$ are present, the plurality of $R_{904}$ are mutually the same or different;

when a plurality of $R_{905}$ are present, the plurality of $R_{905}$ are mutually the same or different;

when a plurality of $R_{906}$ are present, the plurality of $R_{906}$ are mutually the same or different; and when a plurality of $R_{907}$ are present, the plurality of $R_{907}$ are mutually the same or different.

In the formula (3), two of $R_{301}$ to $R_{310}$ are preferably groups represented by the formula (31).

In an exemplary embodiment, the compound represented by the formula (3) is represented by a formula (33) below.

[Formula 249]

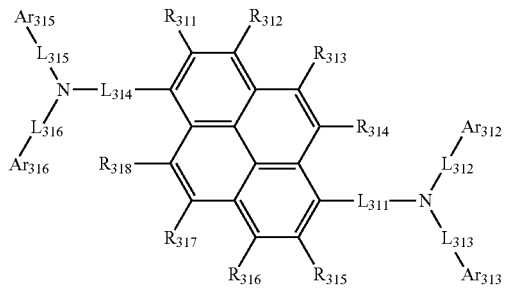

(33)

In the formula (33):

$R_{311}$ to $R_{318}$ each independently represent the same as $R_{301}$ to $R_{310}$ in the formula (3) that are not the monovalent group represented by the formula (31);

$L_{311}$ to $L_{316}$ are each independently a single bond, a substituted or unsubstituted arylene group having 6 to 30 ring carbon atoms, or a substituted or unsubstituted divalent heterocyclic group having 5 to 30 ring atoms; and $Ar_{312}$, $Ar_{313}$, $Ar_{315}$, and $Ar_{316}$ are each independently a substituted or unsubstituted aryl group having 6 to 50 ring carbon atoms, or a substituted or unsubstituted heterocyclic group having 5 to 50 ring atoms.

In the formula (31), $L_{301}$ is preferably a single bond, and $L_{302}$ and $L_{303}$ are each preferably a single bond.

In an exemplary embodiment, the compound represented by the formula (3) is represented by a formula (34) or a formula (35) below.

[Formula 250]

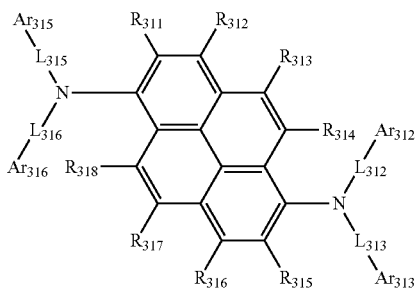

(34)

In the formula (34):

$R_{311}$ to $R_{318}$ each independently represent the same as $R_{301}$ to $R_{310}$ in the formula (3) that are not the monovalent group represented by the formula (31);

$L_{312}$, $L_{313}$, $L_{315}$ and $L_{316}$ each independently represent the same as $L_{312}$, $L_{313}$, $L_{315}$ and $L_{316}$ in the formula (33); and $Ar_{312}$, $Ar_{313}$, $Ar_{315}$ and $Ar_{316}$ each independently represent the same as $Ar_{312}$, $Ar_{313}$, $Ar_{315}$ and $Ar_{316}$ in the formula (33).

[Formula 251]

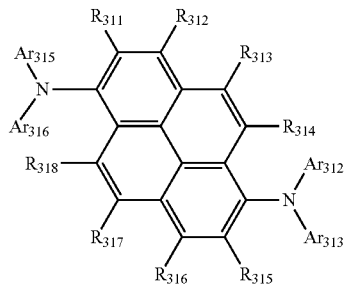

(35)

In the formula (35):

$R_{311}$ to $R_{318}$ each independently represent the same as $R_{301}$ to $R_{310}$ in the formula (3) that are not the monovalent group represented by the formula (31);

$Ar_{312}$, $Ar_{313}$, $Ar_{315}$ and $Ar_{316}$ each independently represent the same as $Ar_{312}$, $Ar_{313}$, $Ar_{315}$ and $Ar_{316}$ in the formula (33).

In the formula (31), at least one of $Ar_{301}$ or $Ar_{302}$ is preferably a group represented by a formula (36) below.

In the formulae (33) to (35), at least one of $Ar_{312}$ or $Ar_{313}$ is preferably a group represented by the formula (36) below.

In the formulae (33) to (35), at least one of $Ar_{315}$ or $Ar_{316}$ is preferably a group represented by the formula (36) below.

[Formula 252]

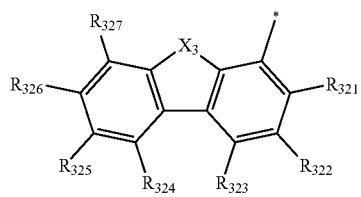

(36)

In the formula (36):

$X_3$ represents an oxygen atom or a sulfur atom;

at least one combination of adjacent two or more of $R_{321}$ to $R_{327}$ are mutually bonded to form a substituted or unsubstituted monocyclic ring, mutually bonded to form a substituted or unsubstituted fused ring, or not mutually bonded;

$R_{321}$ to $R_{327}$ not forming the monocyclic ring and not forming the fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$) ($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms; and

* represents a bonding position to $L_{302}$, $L_{303}$, $L_{312}$, $L_{313}$, $L_{315}$, or $L_{316}$.

$X_3$ is preferably an oxygen atom.

At least one of $R_{321}$ to $R_{327}$ is preferably a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

In the formula (31), it is preferable that $Ar_{301}$ is the group represented by the formula (36) and $Ar_{302}$ is a substituted or unsubstituted aryl group having 6 to 50 ring carbon atoms.

In the formulae (33) to (35), it is preferable that $Ar_{312}$ is the group represented by the formula (36) and $Ar_{313}$ is a substituted or unsubstituted aryl group having 6 to 50 ring carbon atoms.

In the formulae (33) to (35), it is preferable that $Ar_{315}$ is the group represented by the formula (36) and $Ar_{316}$ is a substituted or unsubstituted aryl group having 6 to 50 ring carbon atoms.

In an exemplary embodiment, the compound represented by the formula (3) is represented by a formula (37) below.

[Formula 253]

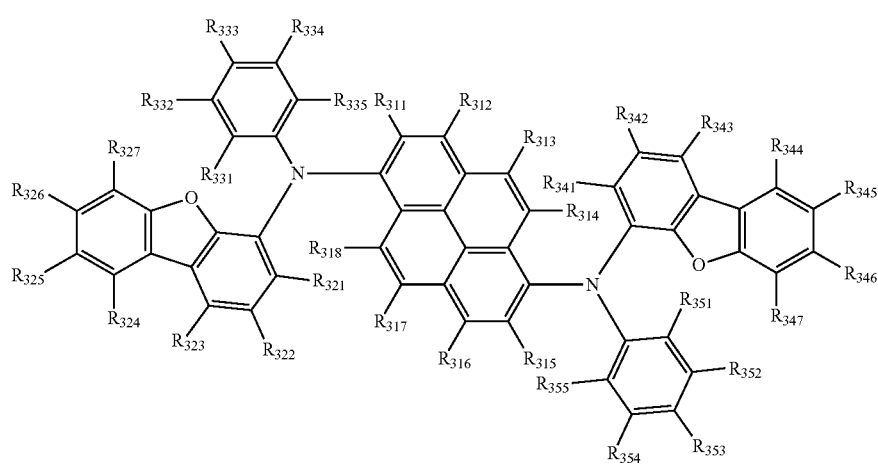

(37)

In the formula (37):

$R_{311}$ to $R_{318}$ each independently represent the same as $R_{301}$ to $R_{310}$ in the formula (3) that are not the monovalent group represented by the formula (31);

at least one combination of adjacent two or more of $R_{321}$ to $R_{327}$ are mutually bonded to form a substituted or unsubstituted monocyclic ring, mutually bonded to form a substituted or unsubstituted fused ring, or not mutually bonded;

at least one combination of adjacent two or more of $R_{341}$ to $R_{347}$ are mutually bonded to form a substituted or unsubstituted monocyclic ring, mutually bonded to form a substituted or unsubstituted fused ring, or not mutually bonded;

$R_{321}$ to $R_{327}$ and $R_{341}$ to $R_{347}$ not forming the monocyclic ring and not forming the fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $—Si(R_{901})(R_{902})(R_{903})$, a group represented by $—O—(R_{904})$, a group represented by $—S—(R_{905})$, a group represented by $—N(R_{906})(R_{907})$, a halogen atom, a cyano group, a nitro group, a substituted or unsubstituted aryl group having 6 to 50 ring carbon atoms, or a substituted or unsubstituted heterocyclic group having 5 to 50 ring atoms; and $R_{331}$ to $R_{335}$, and $R_{351}$ to $R_{335}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $—Si(R_{901})(R_{902})(R_{903})$, a group represented by $—O—(R_{904})$, a group represented by $—S—(R_{905})$, a group represented by $—N(R_{906})(R_{907})$, a halogen atom, a cyano group, a nitro group, a substituted or unsubstituted aryl group having 6 to 50 ring carbon atoms, or a substituted or unsubstituted heterocyclic group having 5 to 50 ring atoms.

Specific examples of the compound represented by the formula (3) include compounds shown below.

[Formula 254]

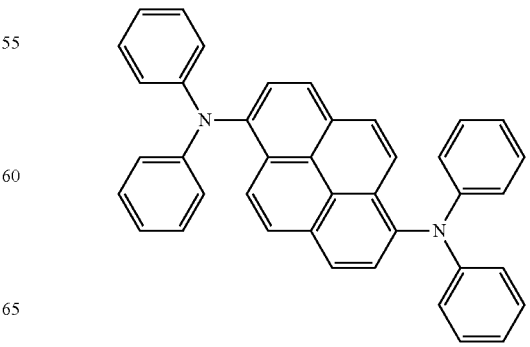

577
-continued
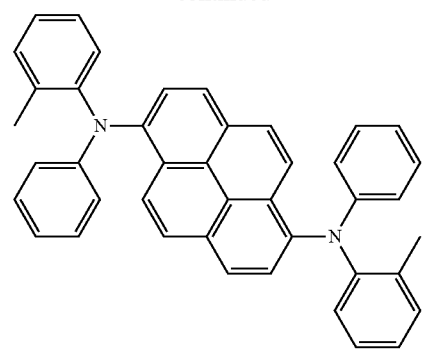
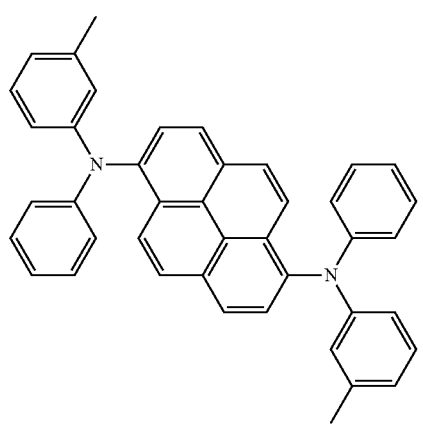
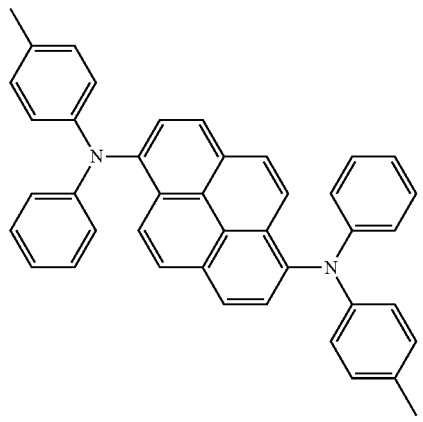
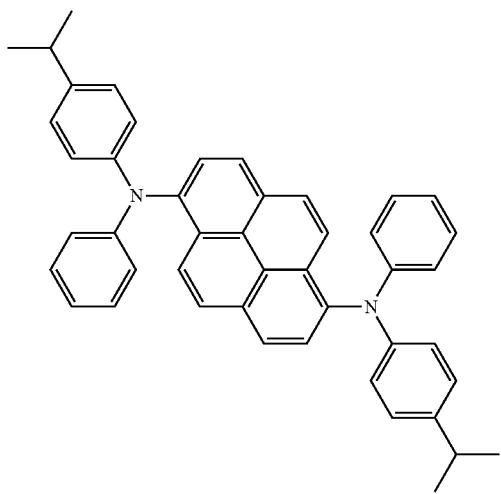
578
-continued
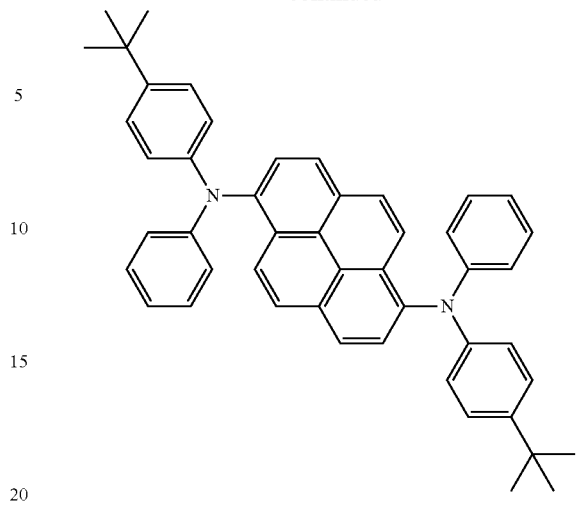
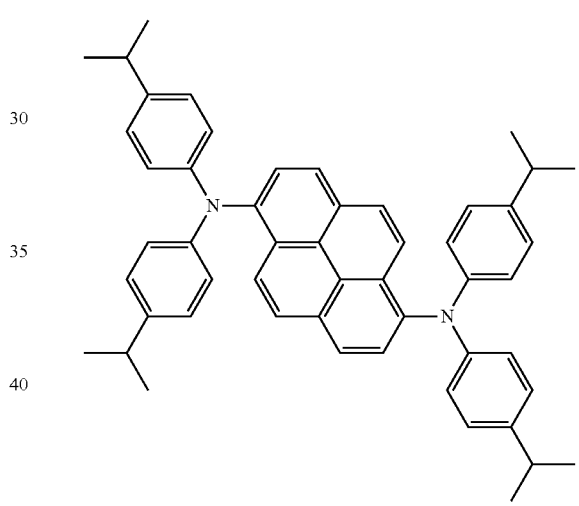
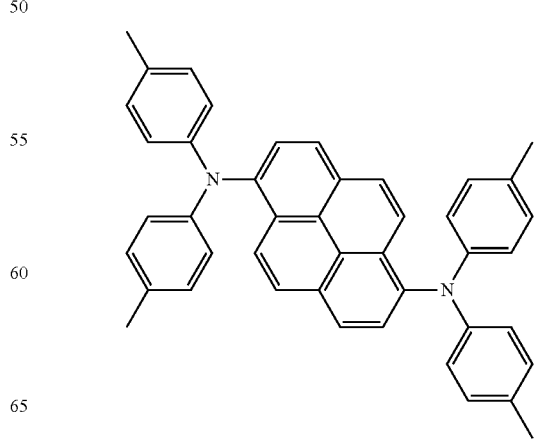

579
-continued
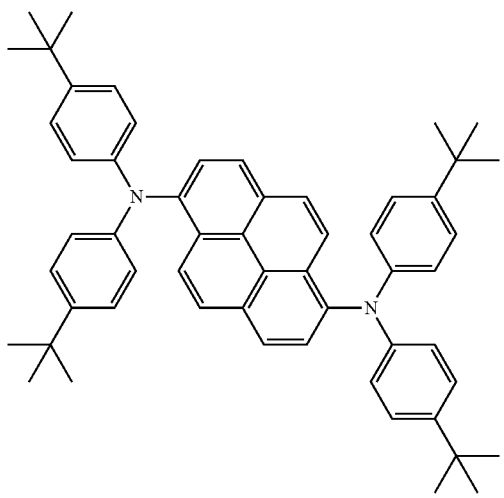
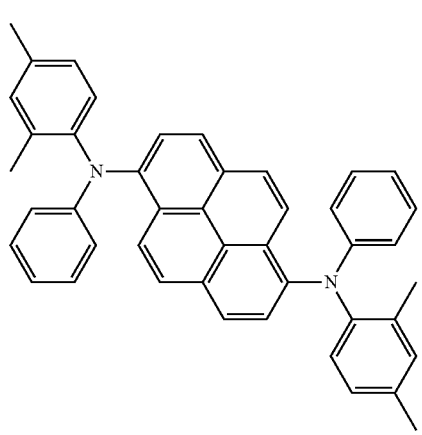
580
-continued
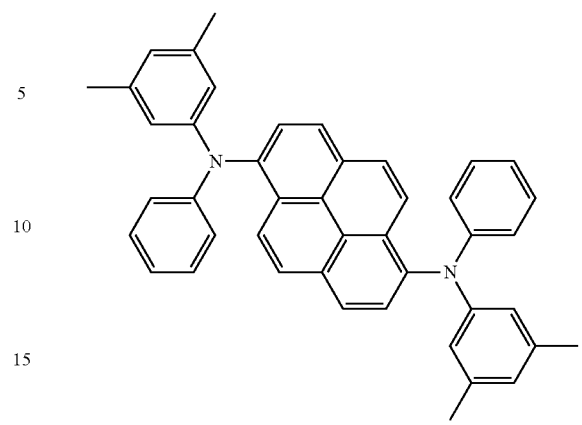
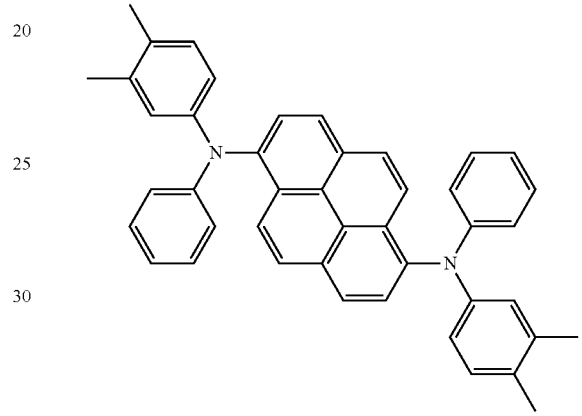
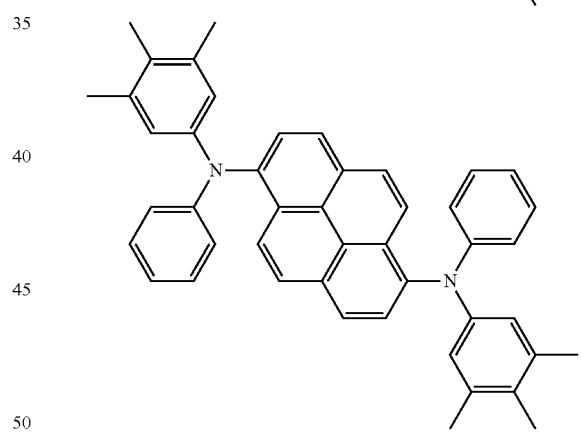

581
-continued
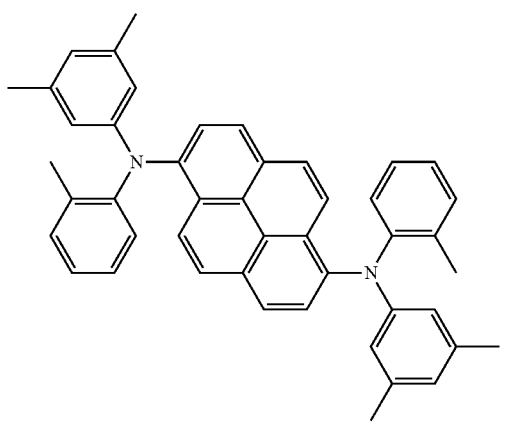
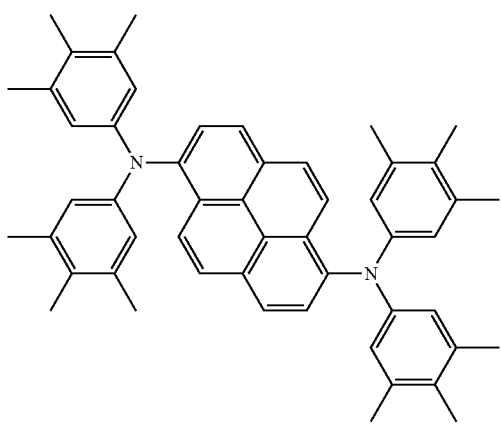
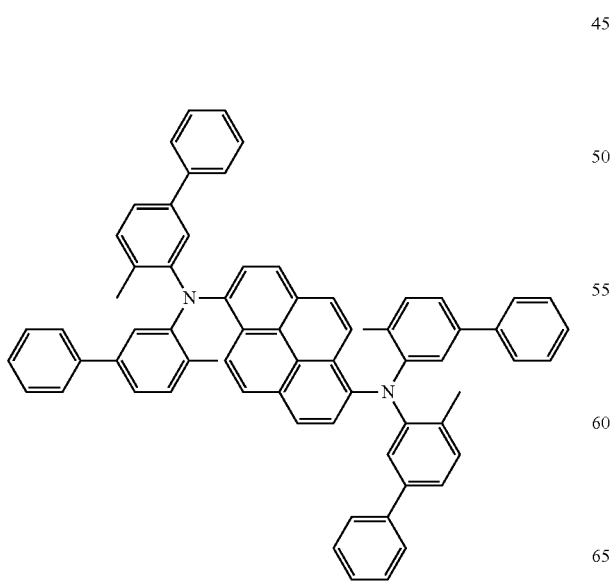
582
-continued
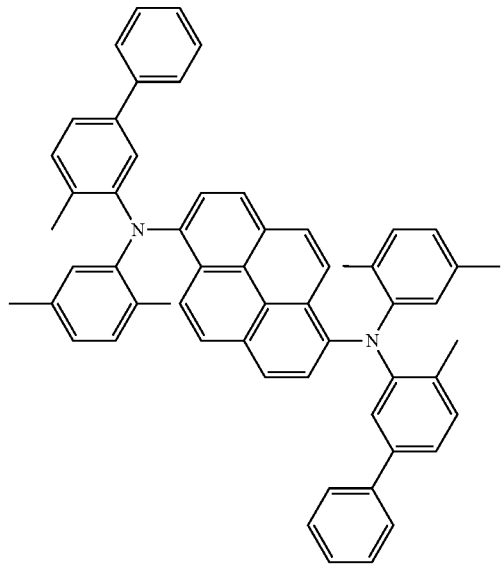
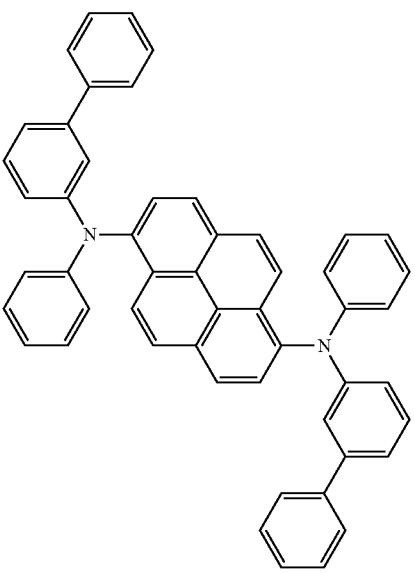

[Formula 255]
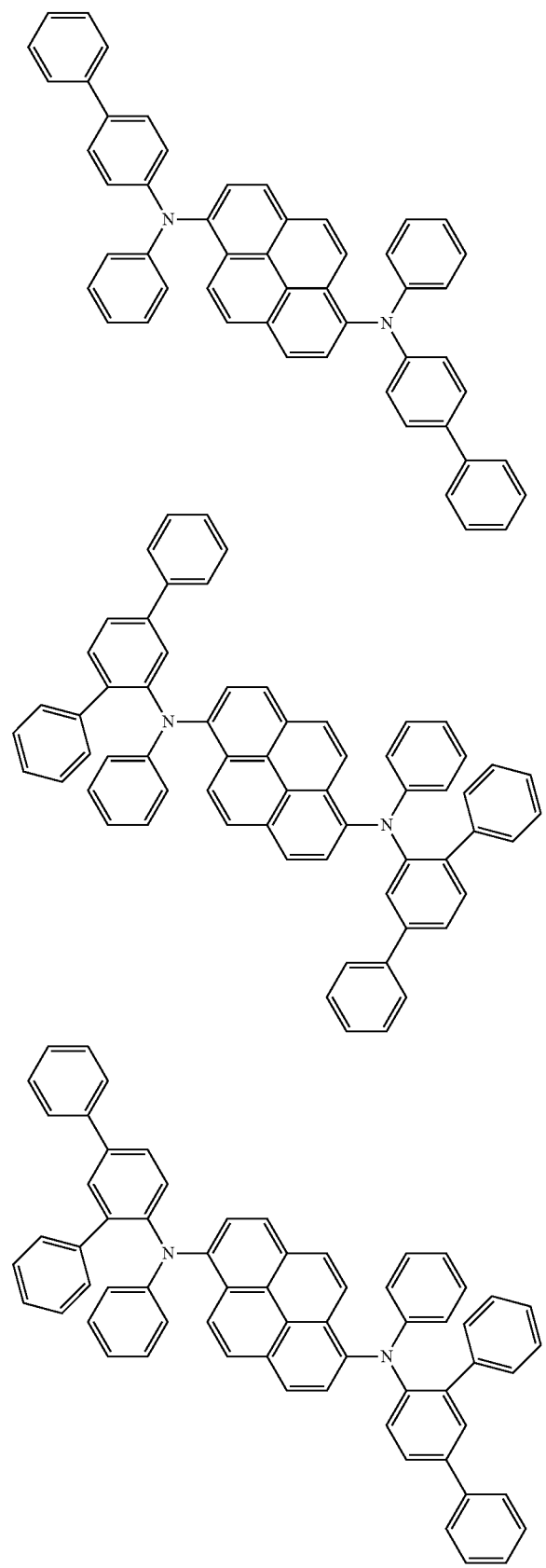
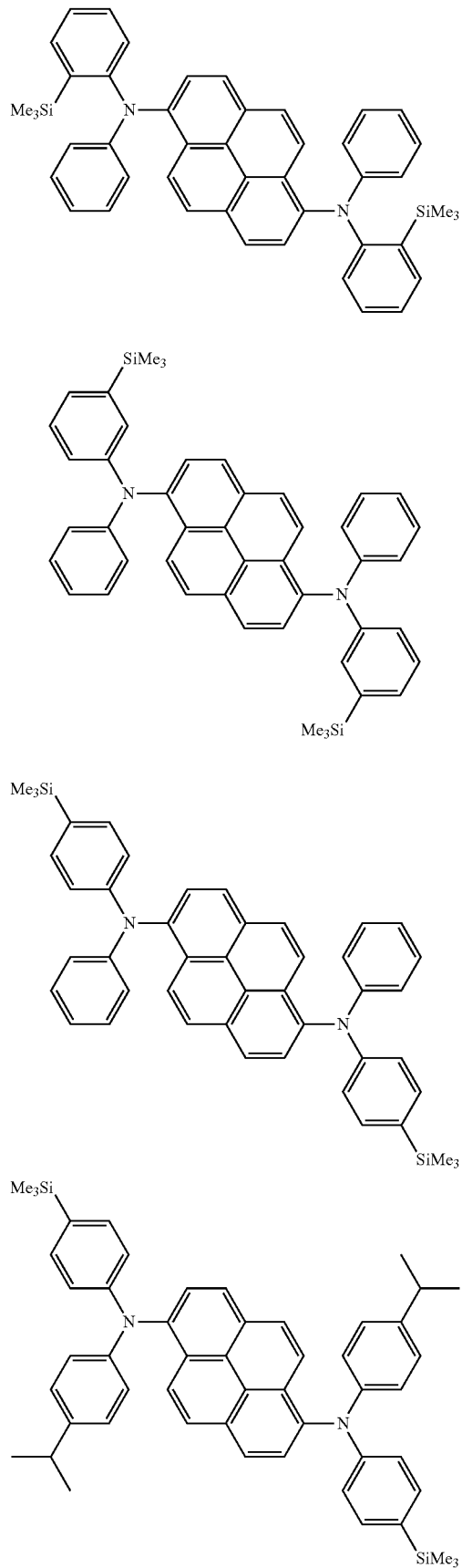

585
-continued
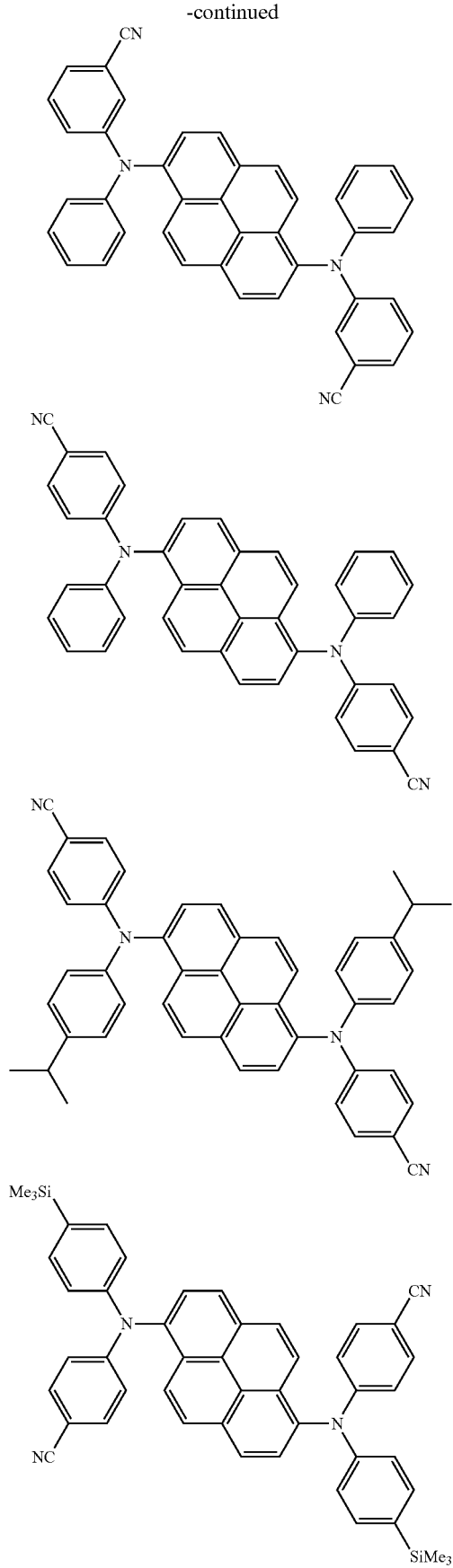
586
-continued
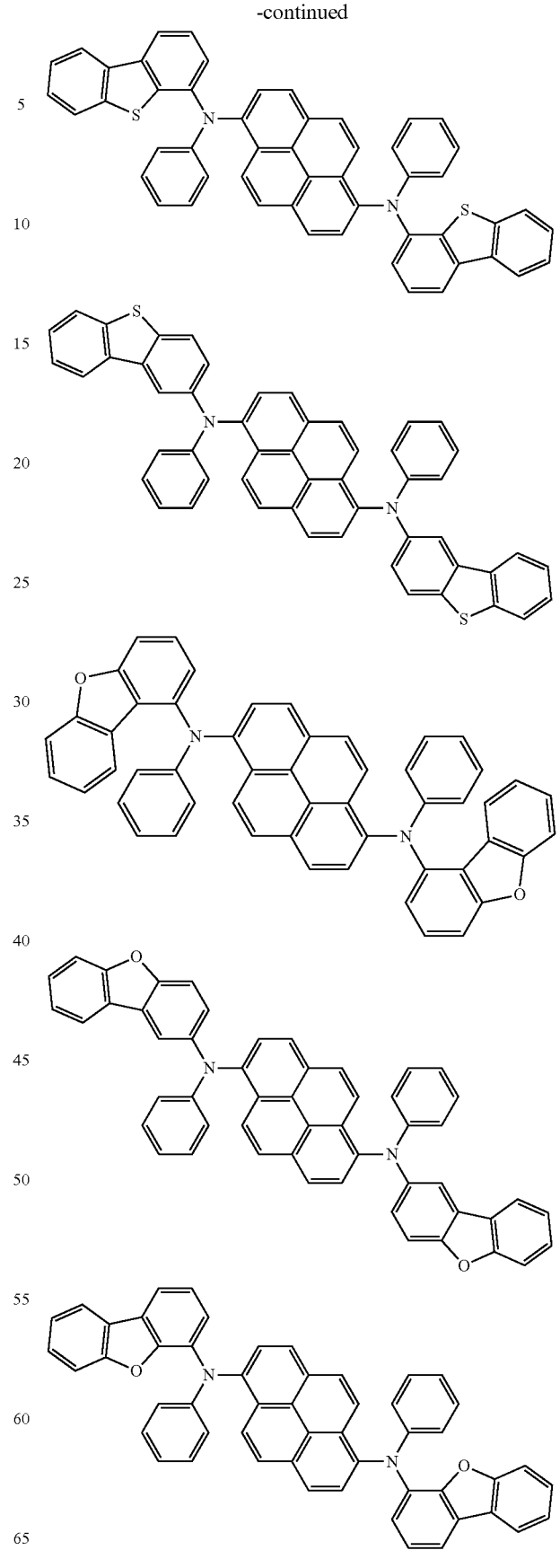

[Formula 256]
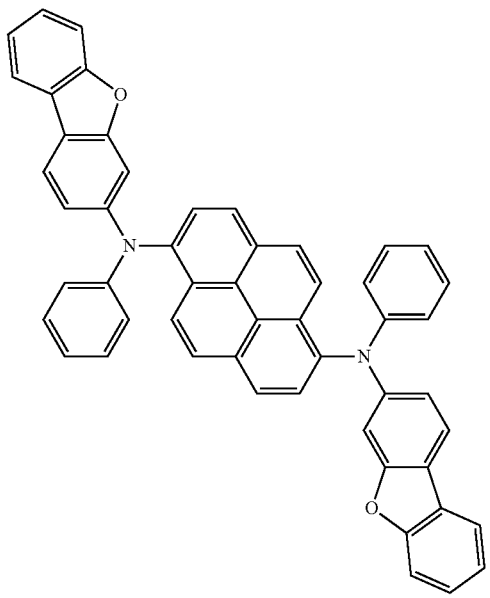
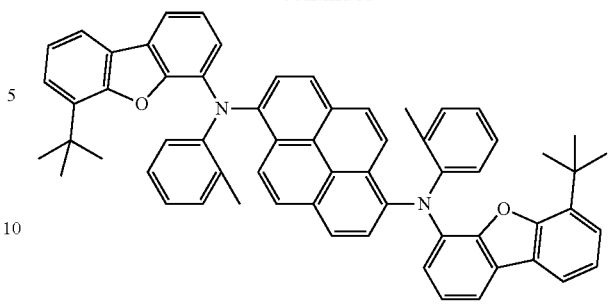
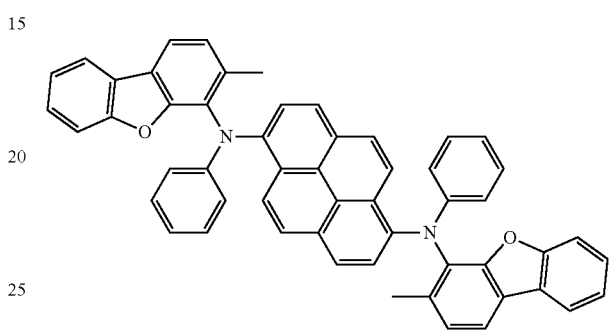
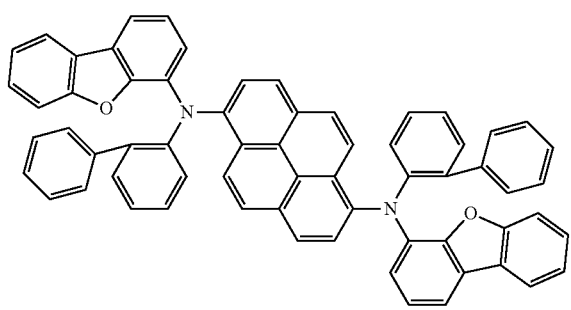
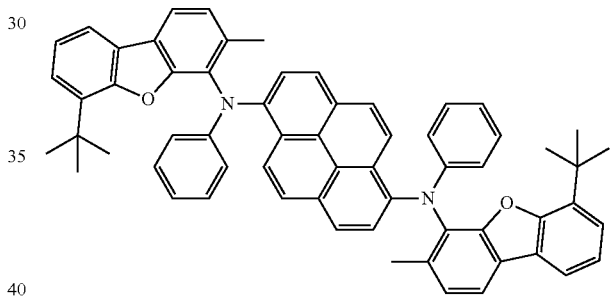
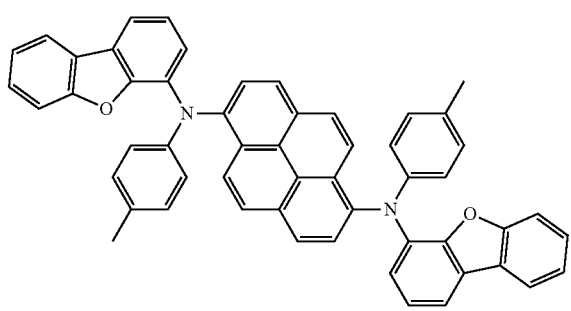 [SMILES: c1ccc(N(c2ccc3ccc4c(N(c5ccccc5)c5cccc6c5oc5ccccc56)ccc5ccc2c3c54)c2cccc3c2oc2ccccc23)cc1]
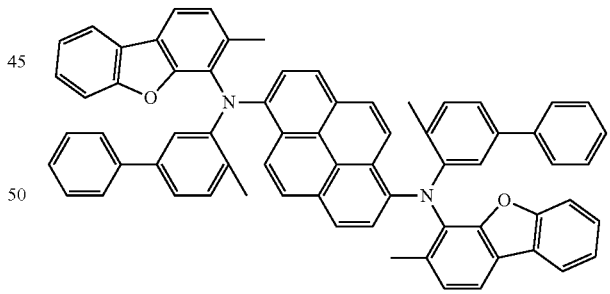
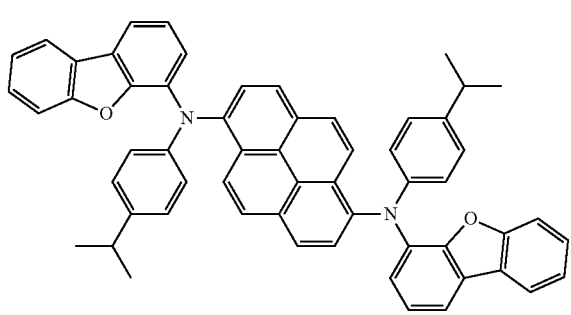
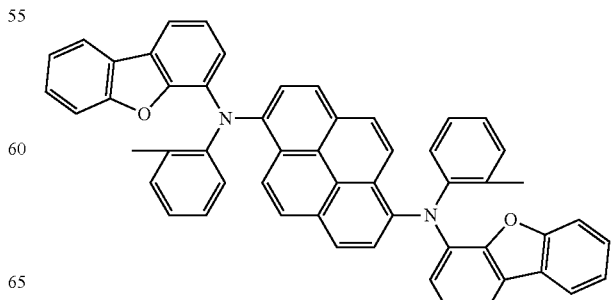

589
-continued
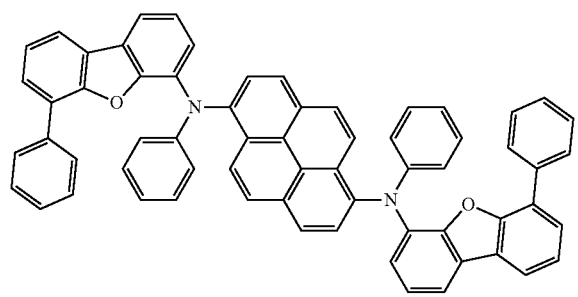
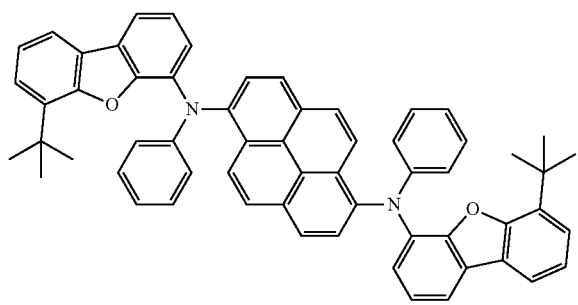 [SMILES: CC(C)c1cc(N(c2ccccc2)c2cccc3c2oc2c(C(C)(C)C)cccc23)c2ccc3c(C(C)C)cc(N(c4ccccc4)c4cccc5c4oc4c(C(C)(C)C)cccc45)c4ccc1c2c34]
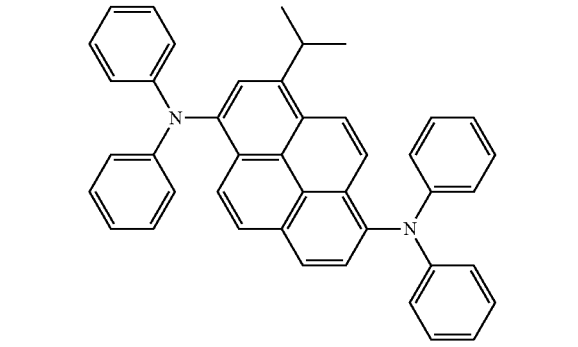
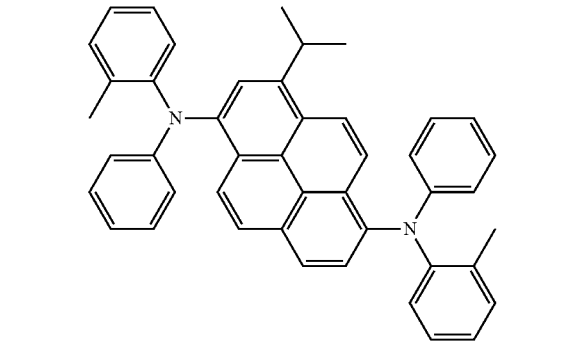
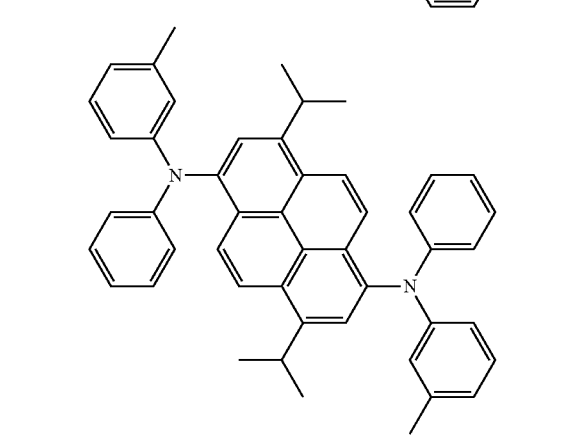
590
-continued
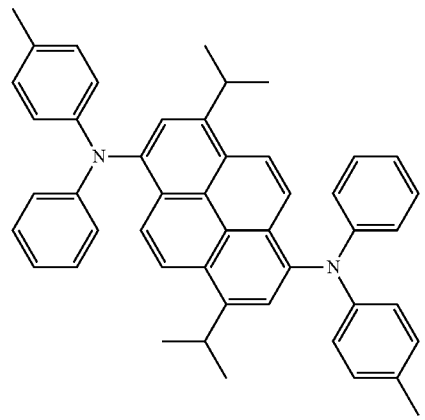
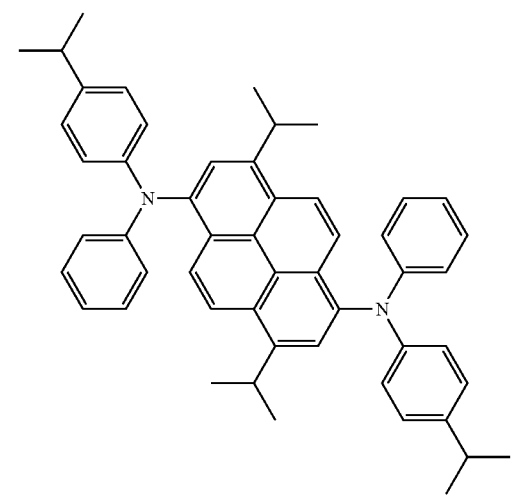

591
-continued
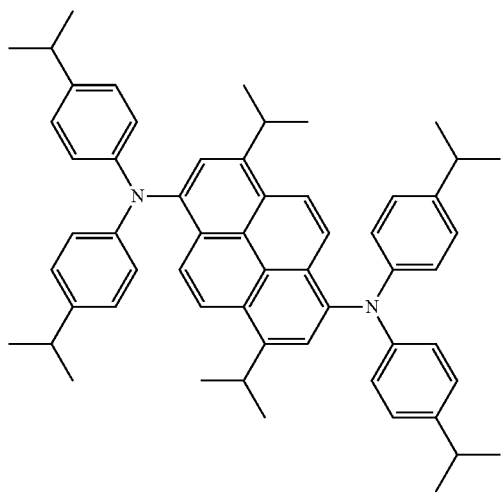
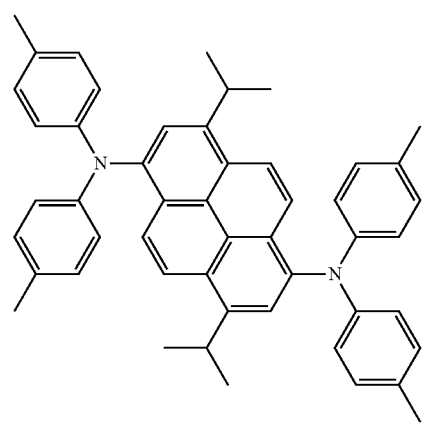
[Formula 257]
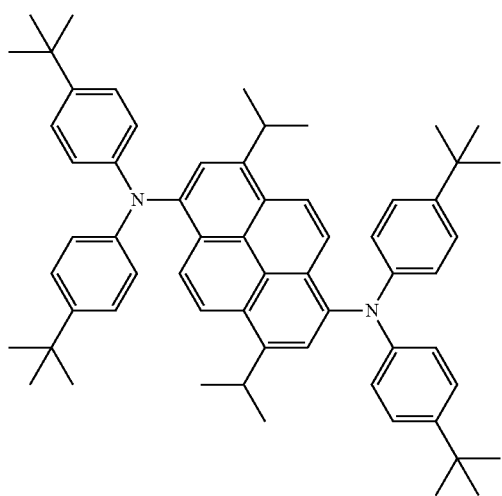
592
-continued
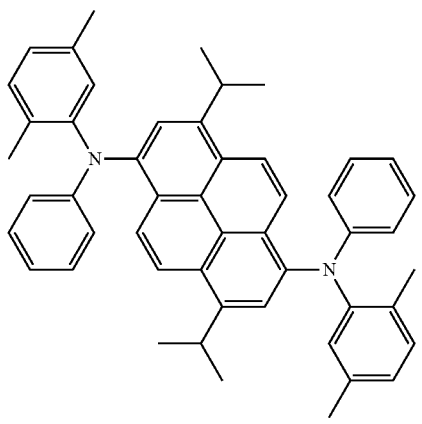
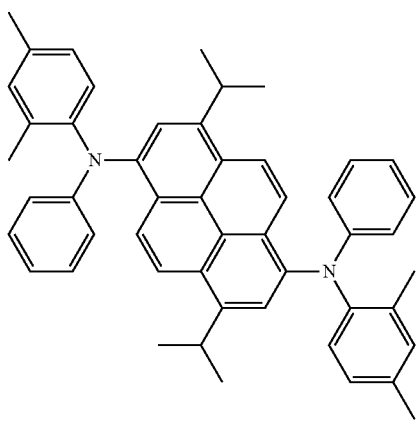
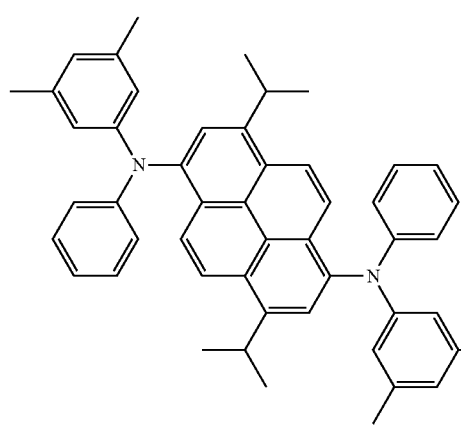
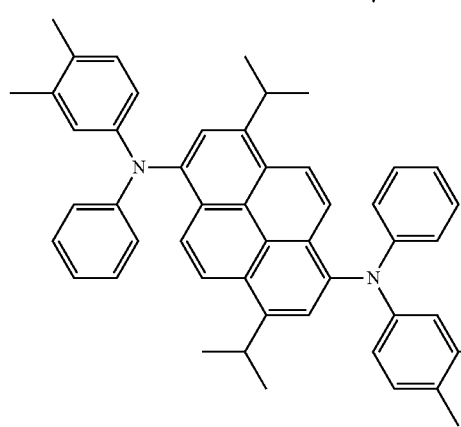

593
-continued
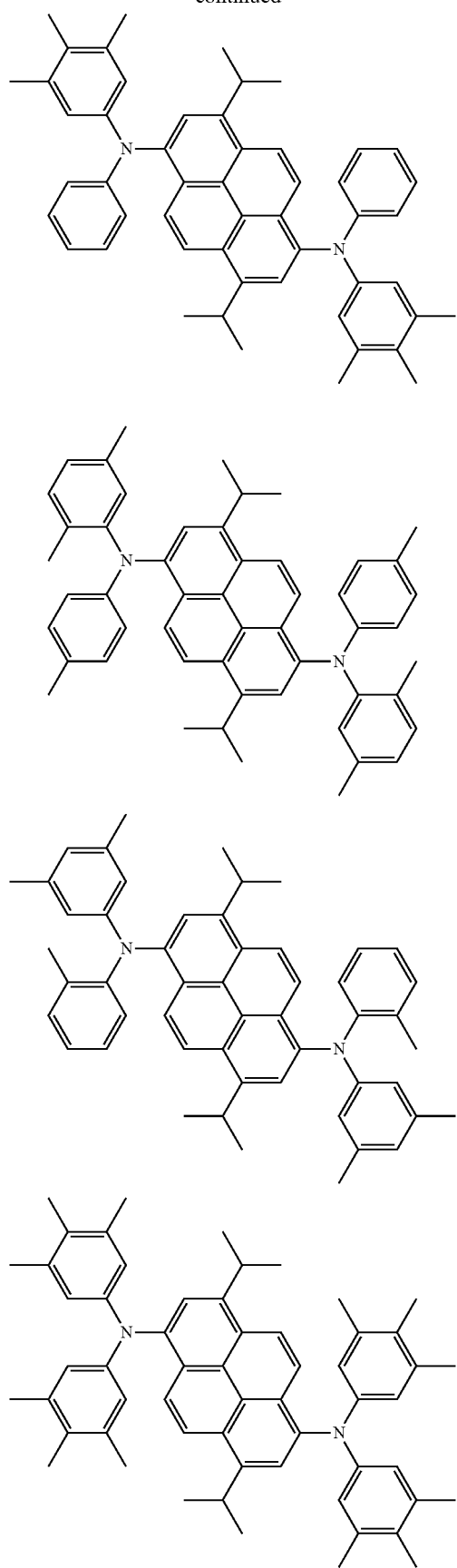
594
-continued
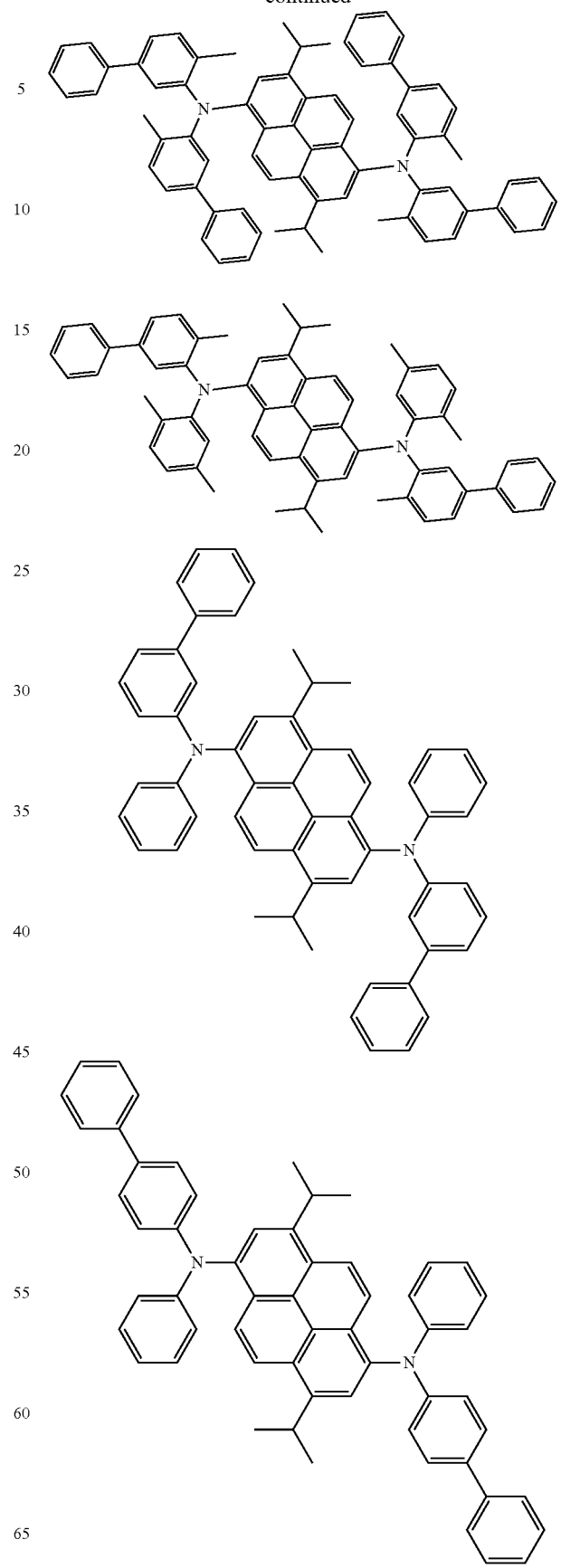

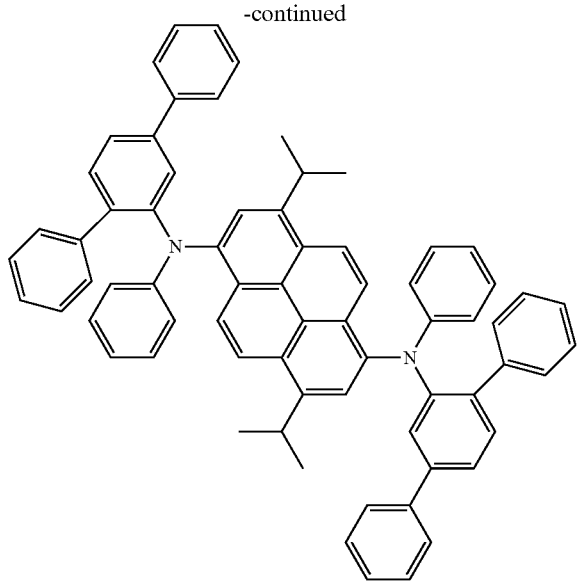
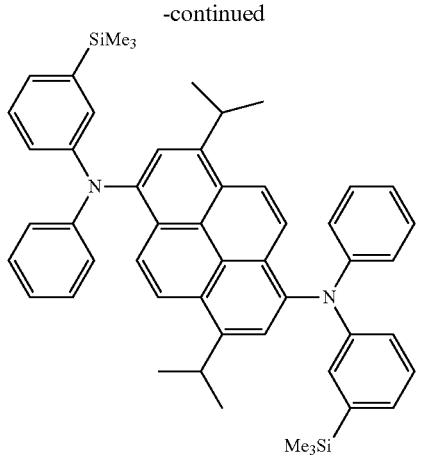
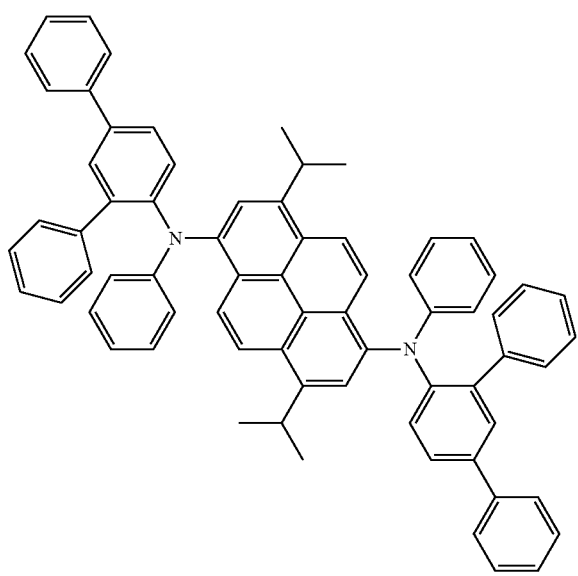
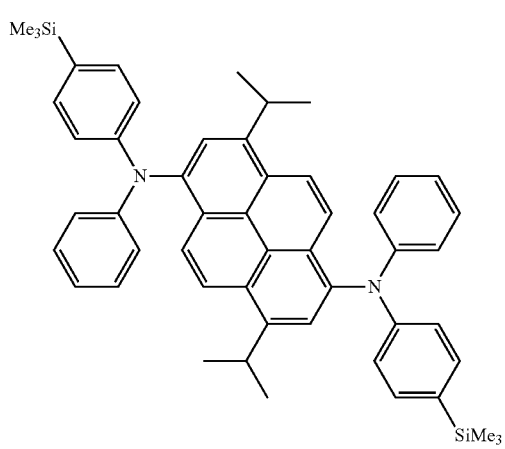
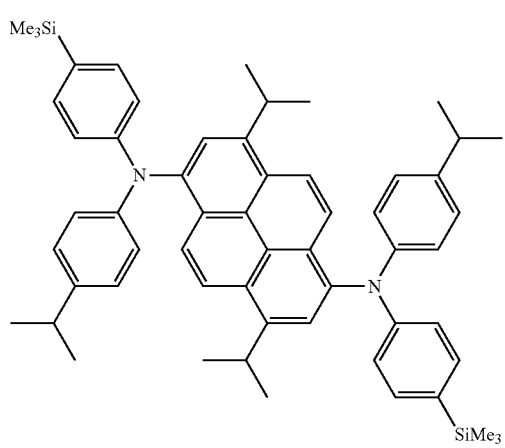
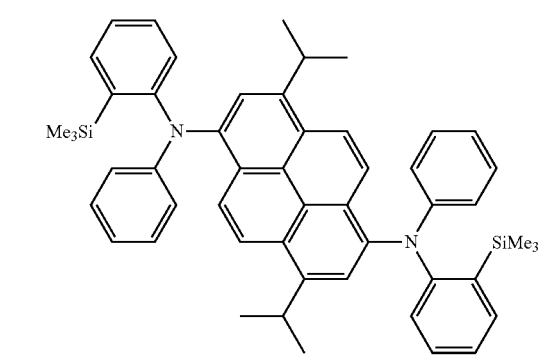
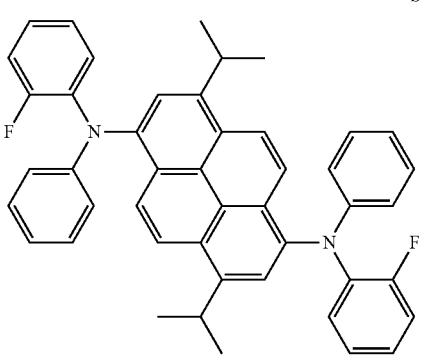

597
-continued
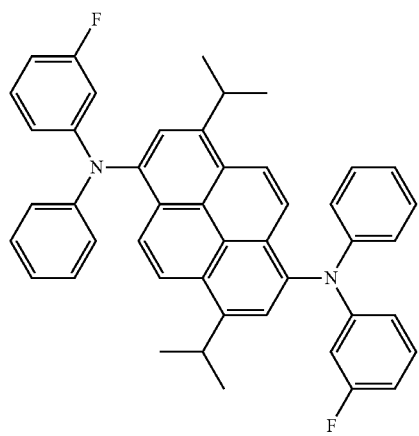
[Formula 258]
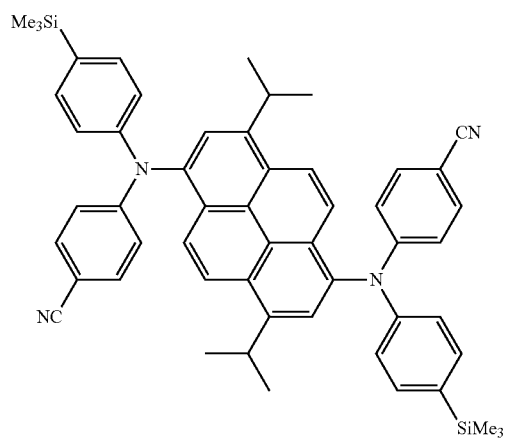
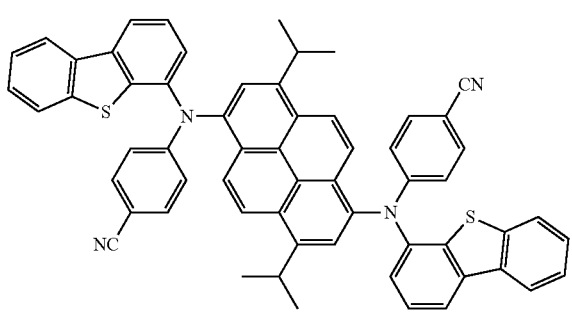
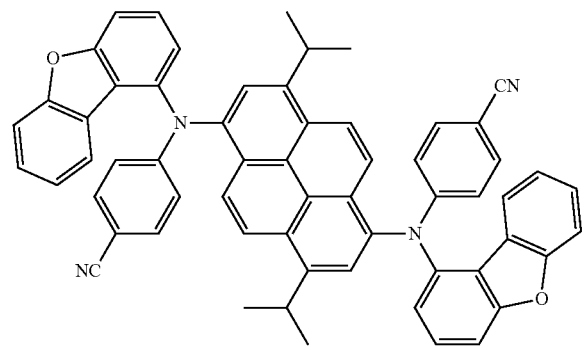
598
-continued
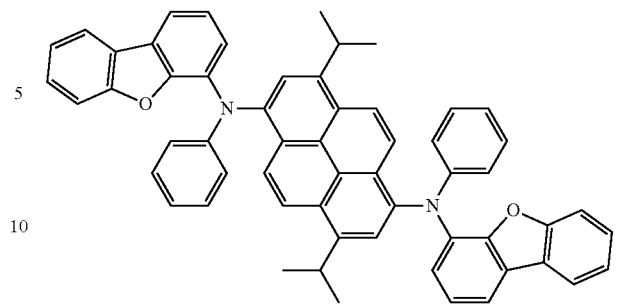
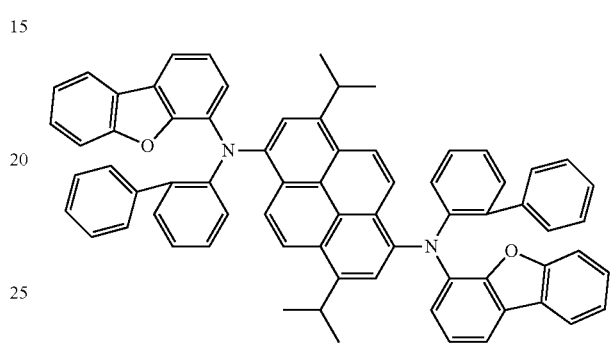
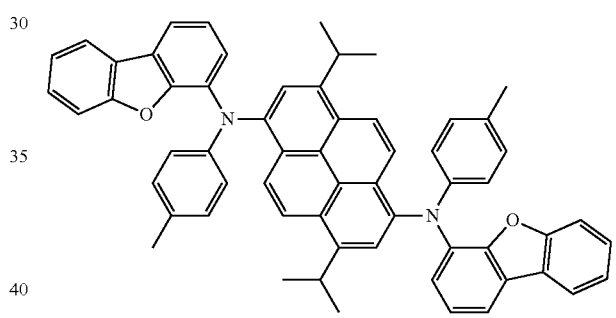
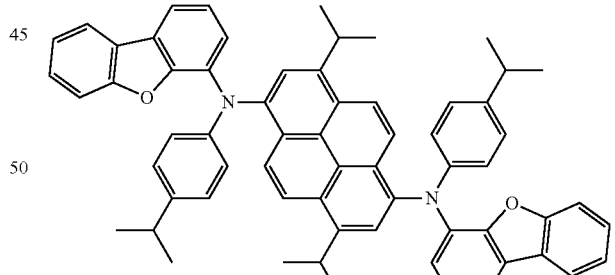
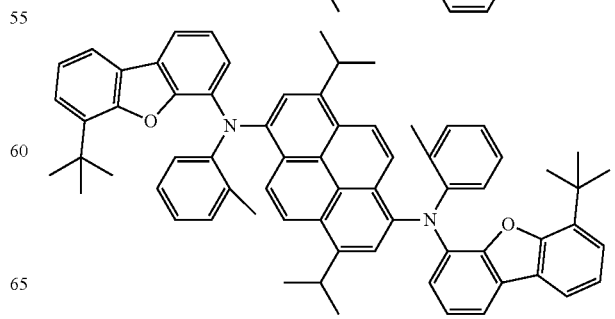

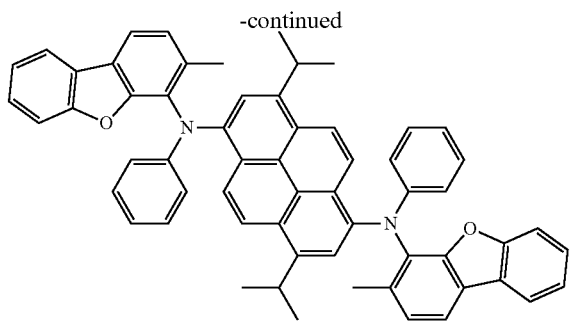

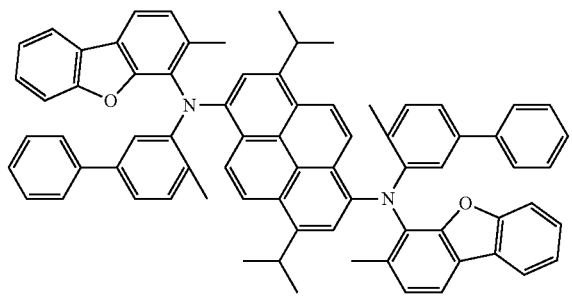

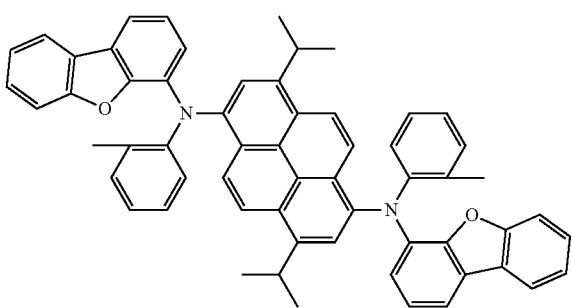

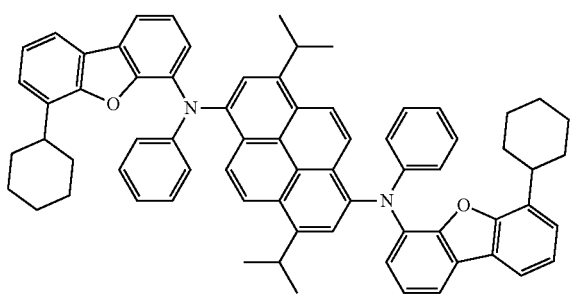

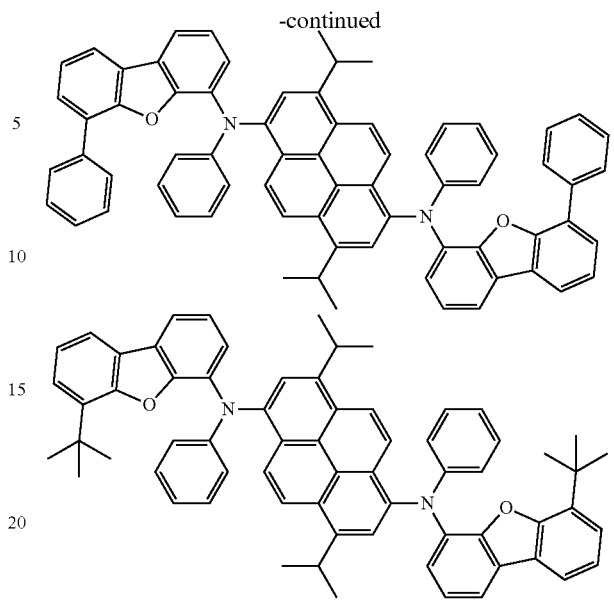

Compound Represented by Formula (4)

The compound represented by the formula (4) will be described below.

[Formula 259]

$$(4)$$

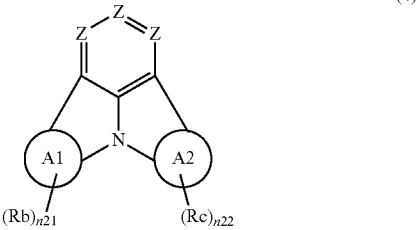

In the formula (4):

Z are each independently CRa or a nitrogen atom;

A1 ring and A2 ring are each independently a substituted or unsubstituted aromatic hydrocarbon ring having 6 to 50 ring carbon atoms, or a substituted or unsubstituted heterocycle having 5 to 50 ring atoms;

when a plurality of Ra are present, at least one combination of adjacent two or more of the plurality of Ra are mutually bonded to form a substituted or unsubstituted monocyclic ring, mutually bonded to form a substituted or unsubstituted fused ring, or not mutually bonded;

n21 and n22 are each independently 0, 1, 2, 3 or 4;

when a plurality of Rb are present, at least one combination of adjacent two or more of the plurality of Rb are mutually bonded to form a substituted or unsubstituted monocyclic ring, mutually bonded to form a substituted or unsubstituted fused ring, or not mutually bonded;

when a plurality of Rc are present, at least one combination of adjacent two or more of the plurality of Rc are mutually bonded to form a substituted or unsubstituted monocyclic ring, mutually bonded to form a substituted or unsubstituted fused ring, or not mutually bonded; and Ra, Rb, and Rc not forming the monocyclic ring and not forming the fused ring are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

The "aromatic hydrocarbon ring" for the A1 ring and A2 ring has the same structure as the compound formed by introducing a hydrogen atom to the "aryl group" described above.

Ring atoms of the "aromatic hydrocarbon ring" for the A1 ring and the A2 ring include two carbon atoms on a fused bicyclic structure at the center of the formula (4).

Specific examples of the "substituted or unsubstituted aromatic hydrocarbon ring having 6 to 50 ring carbon atoms" include a compound formed by introducing a hydrogen atom to the "aryl group" described in the specific example group G1.

The "heterocycle" for the A1 ring and A2 ring has the same structure as the compound formed by introducing a hydrogen atom to the "heterocyclic group" described above.

Ring atoms of the "heterocycle" for the A1 ring and the A2 ring include two carbon atoms on a fused bicyclic structure at the center of the formula (4).

Specific examples of the "substituted or unsubstituted heterocycle having 5 to 50 ring atoms" include a compound formed by introducing a hydrogen atom to the "heterocyclic group" described in the specific example group G2.

Rb is bonded to any one of carbon atoms forming the aromatic hydrocarbon ring as the A1 ring or any one of the atoms forming the heterocycle as the A1 ring.

Rc is bonded to any one of carbon atoms forming the aromatic hydrocarbon ring as the A2 ring or any one of the atoms forming the heterocycle as the A2 ring.

At least one of Ra, Rb, or Rc is preferably a group represented by the formula (4a) below. More preferably, at least two of Ra, Rb, and Rc are groups represented by the formula (4a).

[Formula 260]

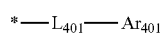

(4a)

In the formula (4a):

$L_{401}$ is a single bond, a substituted or unsubstituted arylene group having 6 to 30 ring carbon atoms, or a substituted or unsubstituted divalent heterocyclic group having 5 to 30 ring atoms; and $Ar_{401}$ is a substituted or unsubstituted aryl group having 6 to 50 ring carbon atoms, a substituted or unsubstituted heterocyclic group having 5 to 50 ring atoms, or a group represented by the formula (4b) below.

[Formula 261]

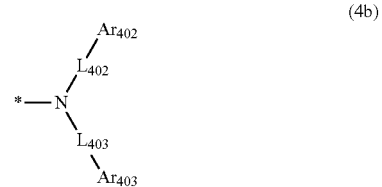

(4b)

In the formula (4b):

$L_{402}$ and $L_{403}$ are each independently a single bond, a substituted or unsubstituted arylene group having 6 to 30 ring carbon atoms, or a substituted or unsubstituted divalent heterocyclic group having 5 to 30 ring atoms;

a combination of $Ar_{402}$ and $Ar_{403}$ are mutually bonded to form a substituted or unsubstituted monocyclic ring, mutually bonded to form a substituted or unsubstituted fused ring, or not mutually bonded; and $Ar_{402}$ and $Ar_{403}$ not forming the monocyclic ring and not forming the fused ring are each independently a substituted or unsubstituted aryl group having 6 to 50 ring carbon atoms, or a substituted or unsubstituted heterocyclic group having 5 to 50 ring atoms.

In an exemplary embodiment, the compound represented by the formula (4) is represented by a formula (42) below.

[Formula 262]

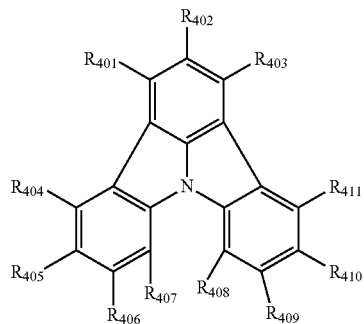

(42)

In the formula (42):

at least one combination of adjacent two or more of $R_{401}$ to $R_{411}$ are mutually bonded to form a substituted or unsubstituted monocyclic ring, mutually bonded to form a substituted or unsubstituted fused ring, or not mutually bonded; and $R_{401}$ to $R_{411}$ not forming the monocyclic ring and not forming the fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

At least one of $R_{401}$ to $R_{411}$ is preferably a group represented by the formula (4a). More preferably, at least two of $R_{401}$ to $R_{411}$ are groups represented by the formula (4a).

$R_{404}$ and $R_{411}$ are preferably groups represented by the formula (4a).

In an exemplary embodiment, the compound represented by the formula (4) is a compound formed by bonding a moiety represented by a formula (4-1) or a formula (4-2) below to the A1 ring.

Further, in an exemplary embodiment, the compound represented by the formula (42) is a compound formed by bonding the moiety represented by the formula (4-1) or the formula (4-2) to the ring bonded to $R_{404}$ to $R_{407}$.

[Formula 263]

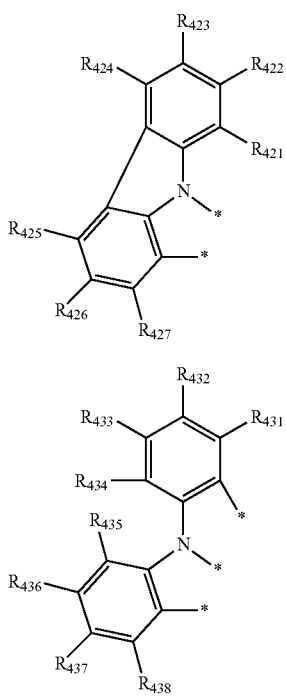

(4-1)

(4-2)

In the formula (4-1), two bonds * are each independently bonded to the ring-forming carbon atom of the aromatic hydrocarbon ring or the ring atom of the heterocycle as the A1 ring in the formula (4) or bonded to one of $R_{404}$ to $R_{407}$ in the formula (42);

in the formula (4-2), three bonds * are each independently bonded to the ring-forming carbon atom of the aromatic hydrocarbon ring or the ring atom of the heterocycle as the A1 ring in the formula (4) or bonded to one of $R_{404}$ to $R_{407}$ in the formula (42);

at least one combination of adjacent two or more of $R_{421}$ to $R_{427}$ are mutually bonded to form a substituted or unsubstituted monocyclic ring, mutually bonded to form a substituted or unsubstituted fused ring, or not mutually bonded;

at least one combination of adjacent two or more of $R_{431}$ to $R_{438}$ are mutually bonded to form a substituted or unsubstituted monocyclic ring, mutually bonded to form a substituted or unsubstituted fused ring, or not mutually bonded; and $R_{421}$ to $R_{427}$ and $R_{431}$ to $R_{438}$ not forming the monocyclic ring and not forming the fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

In an exemplary embodiment, the compound represented by the formula (4) is a compound represented by a formula (41-3), a formula (41-4) or a formula (41-5) below.

[Formula 264]

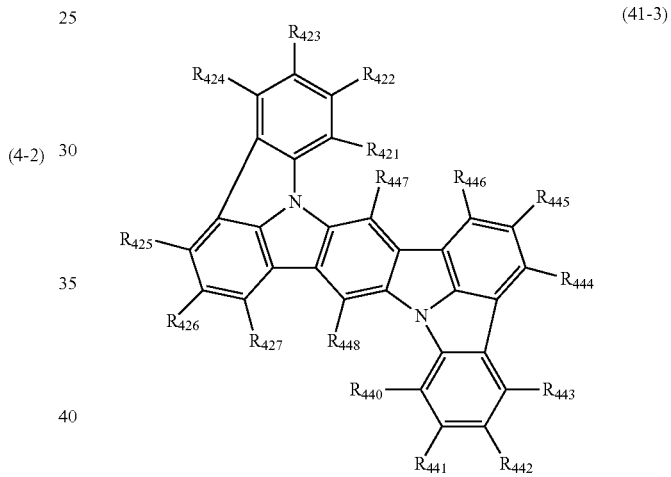

(41-3)

[Formula 265]

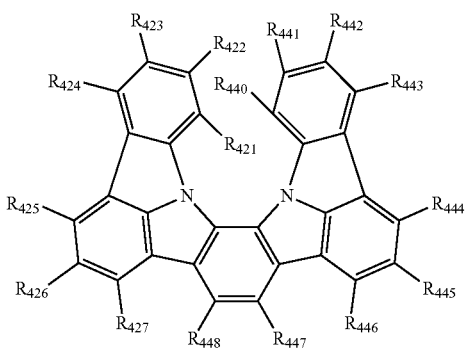

(41-4)

[Formula 266]

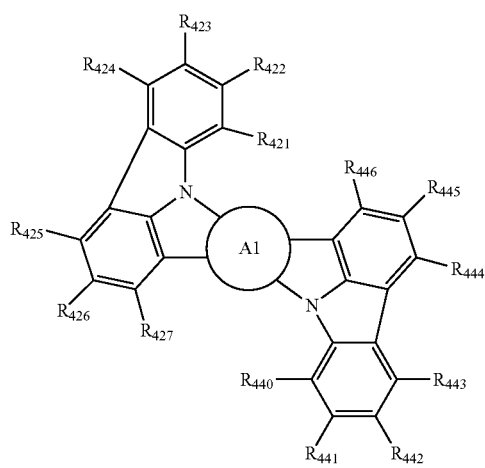

(41-5)

In the formulae (41-3), (41-4), and (41-5):

A1 ring is as defined for the formula (4);

$R_{421}$ to $R_{427}$ each independently represent the same as $R_{421}$ to $R_{427}$ in the formula (4-1); and $R_{440}$ to $R_{448}$ each independently represent the same as $R_{401}$ to $R_{411}$ in the formula (42).

In an exemplary embodiment, a substituted or unsubstituted aromatic hydrocarbon ring having 6 to 50 ring carbon atoms as the A1 ring in the formula (41-5) is a substituted or unsubstituted naphthalene ring, or a substituted or unsubstituted fluorene ring.

In an exemplary embodiment, a substituted or unsubstituted heterocycle having 5 to 50 ring atoms as the A1 ring in the formula (41-5) is a substituted or unsubstituted dibenzofuran ring, a substituted or unsubstituted carbazole ring, or a substituted or unsubstituted dibenzothiophene ring.

In an exemplary embodiment, the compound represented by the formula (4) or the formula (42) is a compound selected from the group consisting of compounds represented by formulae (461) to (467) below.

[Formula 267]

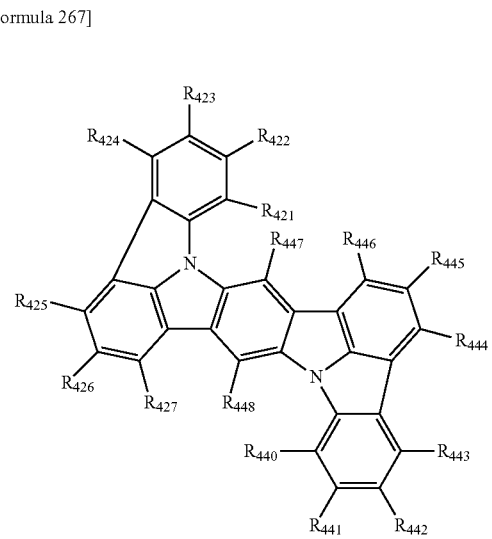

(461)

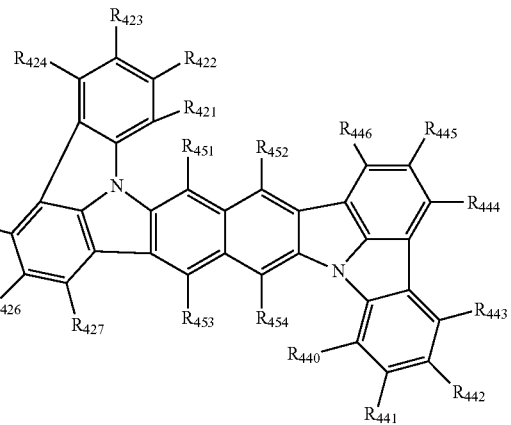

(462)

[Formula 268]

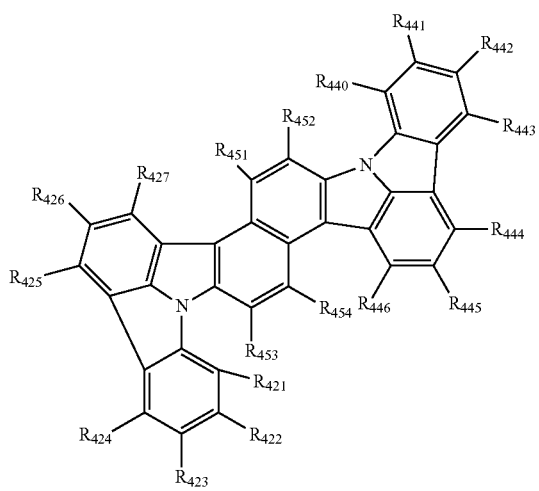

(463)

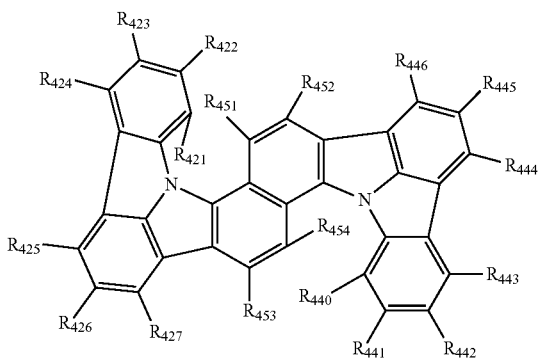

(464)

[Formula 269]

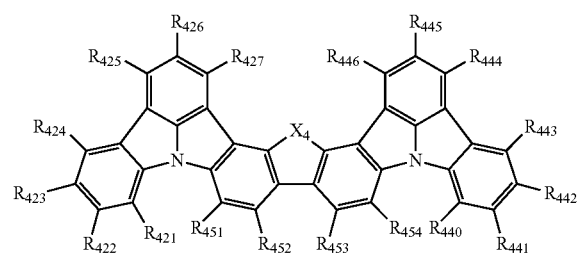

(465)

[Formula 270]

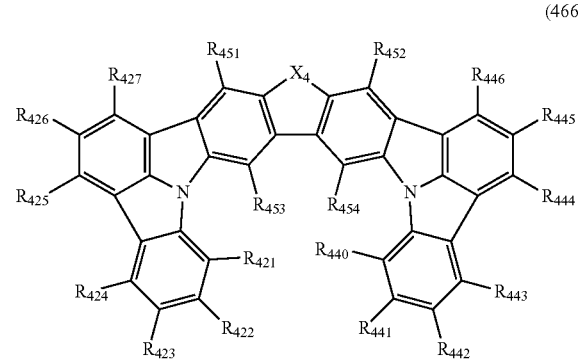

(466)

[Formula 271]

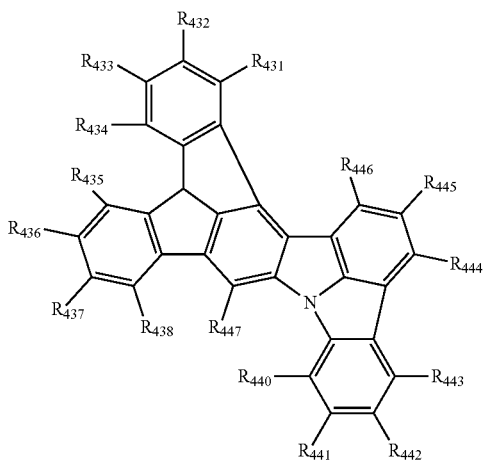

(467)

In the formulae (461), (462), (463), (464), (465), (466), and (467):

$R_{421}$ to $R_{427}$ each independently represent the same as $R_{421}$ to $R_{427}$ in the formula (4-1);

$R_{431}$ to $R_{438}$ each independently represent the same as $R_{431}$ to $R_{43}$ in the formula (4-2);

$R_{440}$ to $R_{448}$ and $R_{451}$ to $R_{454}$ each independently represent the same as $R_{401}$ to $R_{411}$ in the formula (42);

$X_4$ is an oxygen atom, $NR_{801}$, or $C(R_{802})(R_{803})$;

$R_{801}$, $R_{802}$, and $R_{803}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, a substituted or unsubstituted heterocyclic group having 5 to 50 ring atoms, a substituted or unsubstituted alkyl group having 1 to 50 carbon atoms, or a substituted or unsubstituted aryl group having 6 to 50 ring carbon atoms;

when a plurality of $R_{801}$ are present, the plurality of $R_{801}$ are mutually the same or different;

when a plurality of $R_{802}$ are present, the plurality of $R_{802}$ are mutually the same or different; and when a plurality of $R_{803}$ are present, the plurality of $R_{803}$ are mutually the same or different.

In an exemplary embodiment, at least one combination of adjacent two or more of $R_{401}$ to $R_{411}$ in the compound represented by the formula (42) are mutually bonded to form a substituted or unsubstituted monocyclic ring, or mutually bonded to form a substituted or unsubstituted fused ring. This exemplary embodiment will be described in detail below as a compound represented by a formula (45).

Compound Represented by Formula (45)

The compound represented by the formula (45) will be described below.

[Formula 272]

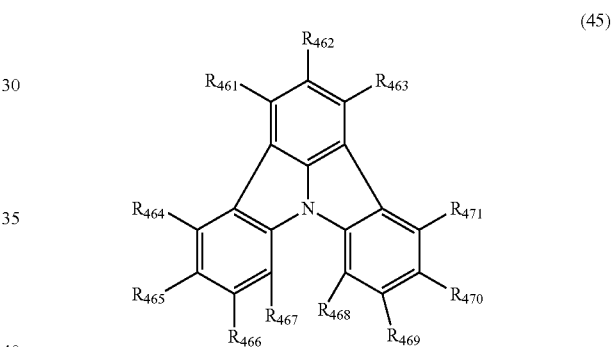

(45)

In the formula (45):

two or more of combinations selected from the group consisting of a combination of $R_{461}$ and $R_{462}$, a combination of $R_{462}$ and $R_{463}$, a combination of $R_{464}$ and $R_{465}$, a combination of $R_{465}$ and $R_{466}$, a combination of $R_{466}$ and $R_{467}$, a combination of $R_{468}$ and $R_{469}$, a combination of $R_{469}$ and $R_{470}$, and a combination of $R_{470}$ and $R_{471}$ are mutually bonded to form a substituted or unsubstituted monocyclic ring or mutually bonded to form a substituted or unsubstituted fused ring;

the combination of $R_{461}$ and $R_{462}$ and the combination of $R_{462}$ and $R_{463}$, the combination of $R_{464}$ and $R_{465}$ and the combination of $R_{465}$ and $R_{466}$, the combination of $R_{465}$ and $R_{466}$ and the combination of $R_{466}$ and $R_{467}$, the combination of $R_{468}$ and $R_{469}$ and the combination of $R_{469}$ and $R_{470}$, and the combination of $R_{469}$ and $R_{470}$ and the combination of $R_{470}$ and $R_{471}$ do not simultaneously form a ring;

the two or more rings formed by $R_{461}$ to $R_{471}$ are mutually the same or different; and $R_{461}$ to $R_{471}$ not forming the monocyclic ring and not forming the fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50

609 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

In the formula (45), $R_n$ and $R_{n+1}$ (n being an integer selected from 461, 462, 464 to 466, and 468 to 470) are mutually bonded to form a substituted or unsubstituted monocyclic ring or fused ring together with two ring-forming carbon atoms bonded to $R_n$ and $R_{n+1}$. The ring is preferably formed of atoms selected from the group consisting of a carbon atom, an oxygen atom, a sulfur atom, and a nitrogen atom, and is made of 3 to 7, more preferably 5 or 6 atoms.

The number of the above cyclic structures in the compound represented by the formula (45) is, for instance, 2, 3, or 4. The two or more of the cyclic structures may be present on the same benzene ring on the basic skeleton represented by the formula (45) or may be present on different benzene rings. For instance, when three cyclic structures are present, each of the cyclic structures may be present on corresponding one of the three benzene rings of the formula (45).

Examples of the above cyclic structures in the compound represented by the formula (45) include structures represented by formulae (451) to (460) below.

[Formula 273]

(451)
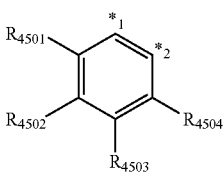

(452)
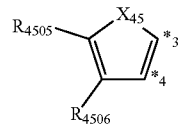

(453)
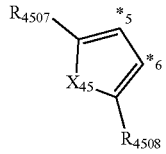

(454)
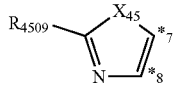

(455)
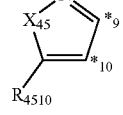

(456)
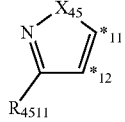

610

-continued (457)
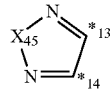

In the formulae (451) to (457):
each combination of *1 and *2, *3 and *4, *5 and *6, *7 and *8, *9 and *10, *11 and *12, and *13 and *14 represent the two ring-forming carbon atoms respectively bonded to $R_n$ and $R_{n+1}$;

the ring-forming carbon atom bonded to $R_n$ may be any one of the two ring-forming carbon atoms represented by *1 and *2, *3 and *4, *5 and *6, *7 and *8, *9 and *10, *11 and *12, and *13 and *14;

$X_{45}$ is C($R_{4512}$)($R_{4513}$), $NR_{4514}$, an oxygen atom, or a sulfur atom;

at least one combination of adjacent two or more of $R_{4501}$ to $R_{4506}$ and $R_{4512}$ to $R_{4513}$ are mutually bonded to form a substituted or unsubstituted monocyclic ring, mutually bonded to form a substituted or unsubstituted fused ring, or not mutually bonded; and $R_{4501}$ to $R_{4514}$ not forming the monocyclic ring and not forming the fused ring each independently represent the same as $R_{461}$ to $R_{471}$ in the formula (45).

[Formula 274]

(458)
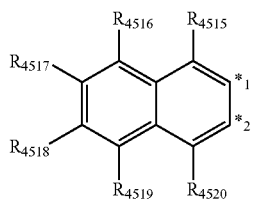

(459)
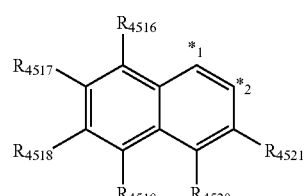

(460)
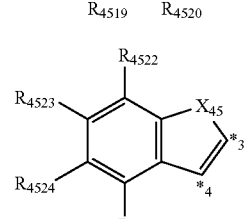

In the formulae (458) to (460):
each combination of *1 and *2, and *3 and *4 represent the two ring-forming carbon atoms each bonded to $R_n$ and $R_{n+1}$;

the ring-forming carbon atom bonded to $R_n$ may be any one of the two ring-forming carbon atoms represented by *1 and *2, or *3 and *4;

$X_{45}$ is C($R_{4512}$)($R_{4513}$), $NR_{4514}$, an oxygen atom, or a sulfur atom;

at least one combination of adjacent two or more of $R_{4512}$ to $R_{4513}$ and $R_{4515}$ to $R_{4525}$ are mutually bonded to form a substituted or unsubstituted monocyclic ring, mutually bonded to form a substituted or unsubstituted fused ring, or not mutually bonded; and $R_{4512}$ to $R_{4513}$, $R_{4515}$ to $R_{4521}$, $R_{4522}$ to $R_{4525}$, and $R_{4514}$ not forming the monocyclic ring and not forming the fused ring each independently represent the same as $R_{461}$ to $R_{471}$ in the formula (45).

In the formula (45), it is preferable that at least one of $R_{462}$, $R_{464}$, $R_{465}$, $R_{470}$ or $R_{471}$ (preferably, at least one of $R_{462}$, $R_{465}$ or $R_{470}$, more preferably $R_{462}$) is a group not forming the cyclic structure.

(i) A substituent, if present, of the cyclic structure formed by $R_n$ and $R_{n+1}$ of the formula (45), (ii) $R_{461}$ to $R_{471}$ not forming the cyclic structure in the formula (45), and (iii) $R_{4501}$ to $R_{4514}$, $R_{4515}$ to $R_{4525}$ in the formulae (451) to (460) are preferably each independently any one of groups selected from the group consisting of a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —N($R_{906}$)($R_{907}$), a substituted or unsubstituted aryl group having 6 to 50 ring carbon atoms, a substituted or unsubstituted heterocyclic group having 5 to 50 ring atoms, or a group represented by formulae (461) to (464) below.

[Formula 275]

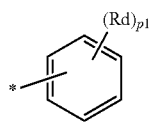

(461)

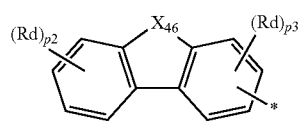

(462)

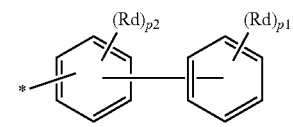

(463)

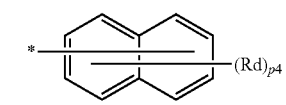

(464)

In the formulae (461) to (464):

$R_d$ is each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms;

$X_{46}$ is C($R_{801}$)($R_{802}$), $NR_{803}$, an oxygen atom or a sulfur atom;

$R_{801}$, $R_{802}$, and $R_{803}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, a substituted or unsubstituted heterocyclic group having 5 to 50 ring atoms, a substituted or unsubstituted alkyl group having 1 to 50 carbon atoms, or a substituted or unsubstituted aryl group having 6 to 50 ring carbon atoms;

when a plurality of $R_{801}$ are present, the plurality of $R_{801}$ are mutually the same or different;

when a plurality of $R_{802}$ are present, the plurality of $R_{802}$ are mutually the same or different;

when a plurality of $R_{803}$ are present, the plurality of $R_{803}$ are mutually the same or different;

p1 is 5;

p2 is 4;

p3 is 3;

p4 is 7; and

* in the formulae (461) to (464) each independently represent a bonding position to a cyclic structure.

$R_{901}$ to $R_{907}$ in the third compound and the fourth compound are as defined above.

In an exemplary embodiment, the compound represented by the formula (45) is represented by one of formulae (45-1) to (45-6) below.

[Formula 276]

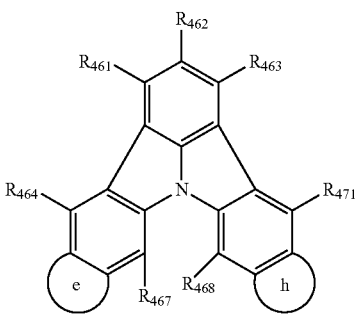

(45-1)

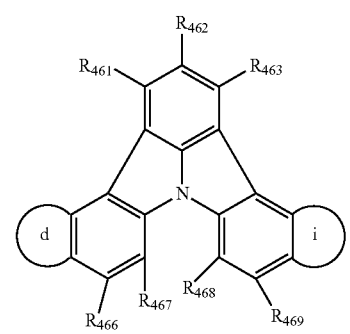

(45-2)

(45-3)

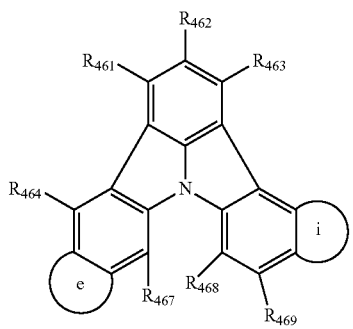

[Formula 277]

(45-4)

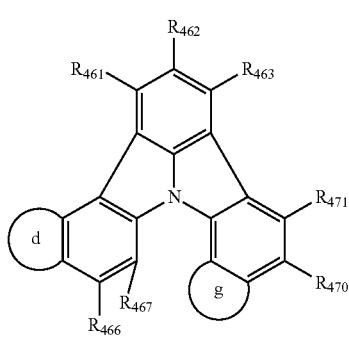

(45-5)

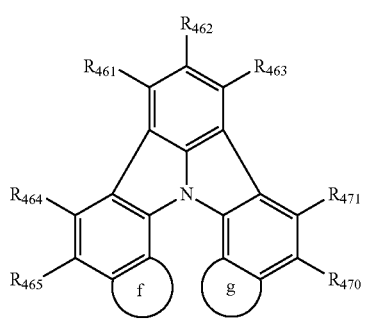

(45-6)

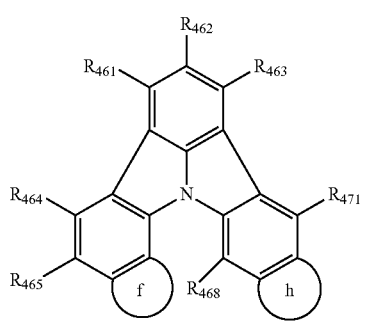

In the formulae (45-1) to (45-6):

rings d to i are each dependently a substituted or unsubstituted monocyclic ring or a substituted or unsubstituted fused ring; and $R_{461}$ to $R_{471}$ each independently represent the same as $R_{461}$ to $R_{471}$ in the formula (45).

In an exemplary embodiment, the compound represented by the formula (45) is represented by one of formulae (45-7) to (45-12) below.

[Formula 278]

(45-7)

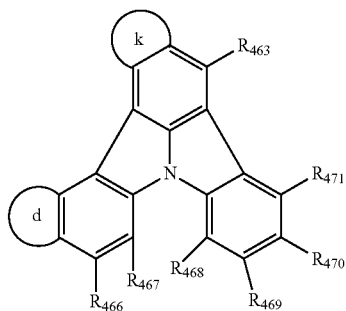

(45-8)

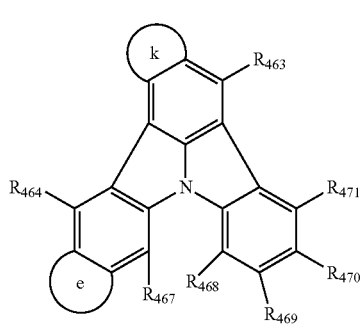

(45-9)

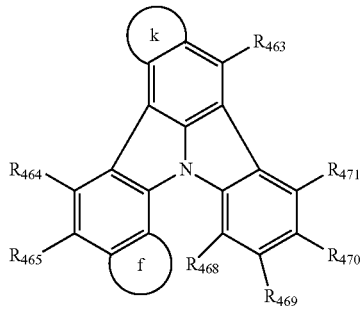

[Formula 279]

(45-10)

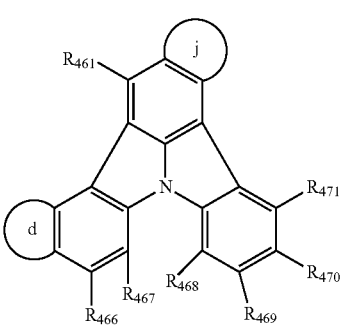

-continued (45-11)
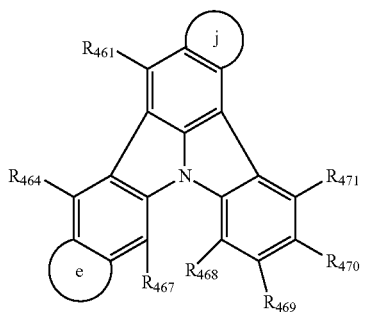

(45-12)
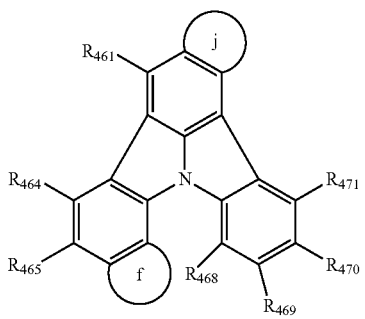

In the formulae (45-7) to (45-12):

rings d to f, k and j are each dependently a substituted or unsubstituted monocyclic ring or a substituted or unsubstituted fused ring; and $R_{461}$ to $R_{471}$ each independently represent the same as $R_{461}$ to $R_{471}$ in the formula (45).

In an exemplary embodiment, the compound represented by the formula (45) is represented by one of formulae (45-13) to (45-21) below.

[Formula 280]

(45-13)
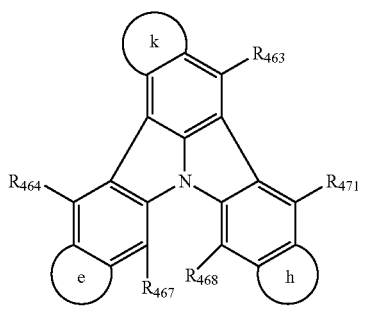

(45-14)
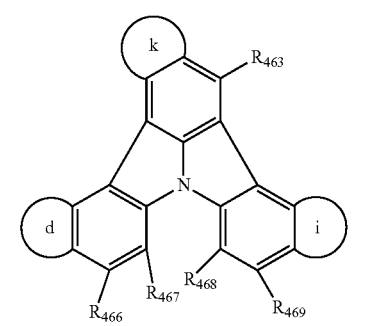

-continued (45-15)
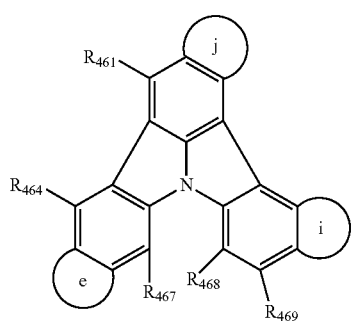

[Formula 281]

(45-16)
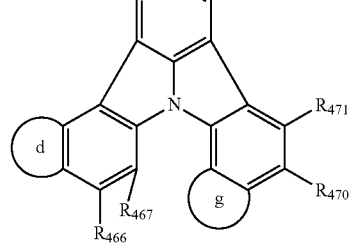

(45-17)
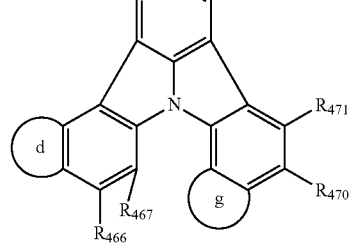

(45-18)
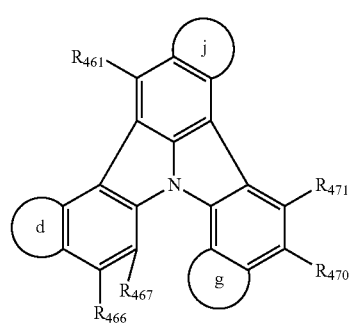

[Formula 282]

(45-19)
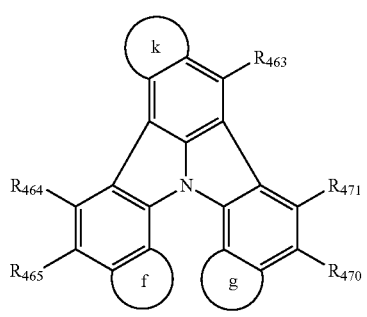

(45-20)
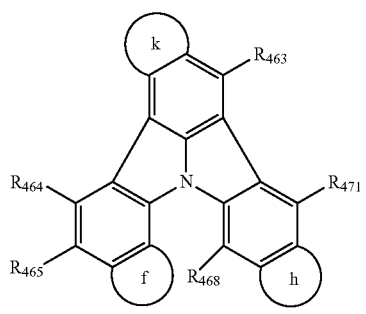

(45-21)
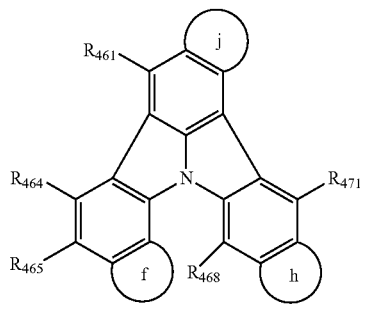

In the formulae (45-13) to (45-21):

rings d to k are each dependently a substituted or unsubstituted monocyclic ring or a substituted or unsubstituted fused ring; and $R_{461}$ to $R_{471}$ each independently represent the same as $R_{461}$ to $R_{471}$ in the formula (45).

When the ring g or the ring h further has a substituent, examples of the substituent include a substituted or unsubstituted alkyl group having 1 to 50 carbon atoms, a substituted or unsubstituted aryl group having 6 to 50 ring carbon atoms, a group represented by the formula (461), a group represented by the formula (463), and a group represented by the formula (464).

In an exemplary embodiment, the compound represented by the formula (45) is represented by one of formulae (45-22) to (45-25) below.

[Formula 283]

(45-22)
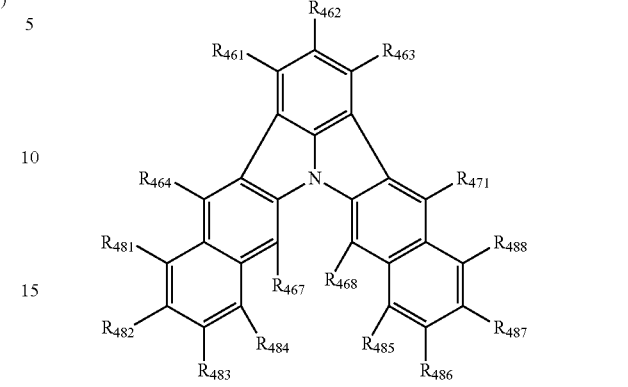

(45-23)
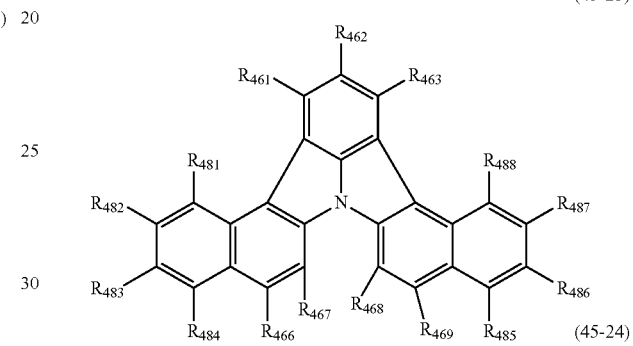

(45-24)
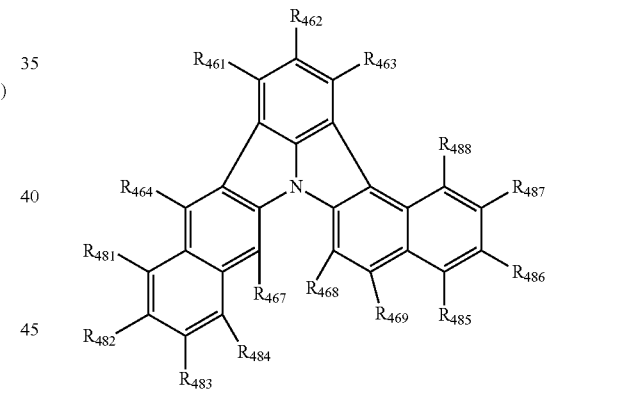

(45-25)
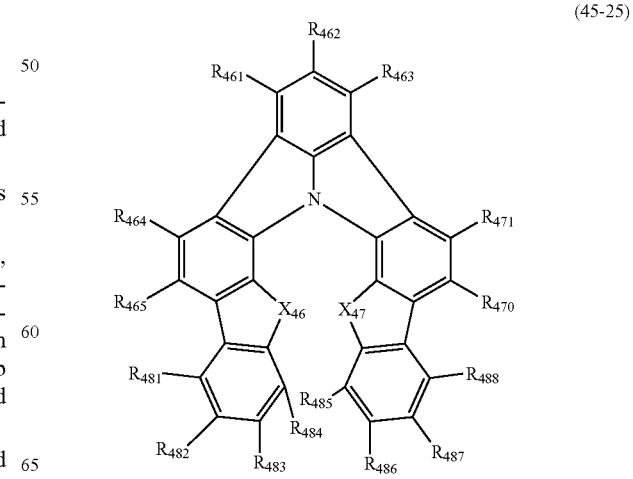

619

In the formulae (45-22) to (45-25):

$X_{46}$ and $X_{47}$ are each independently $C(R_{801})(R_{802})$, $NR_{803}$, an oxygen atom or a sulfur atom;

$R_{461}$ to $R_{471}$ and $R_{481}$ to $R_{488}$ each independently represent the same as $R_{461}$ to $R_{471}$ in the formula (45);

$R_{801}$, $R_{802}$, and $R_{803}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

a substituted or unsubstituted alkyl group having 1 to 50 carbon atoms, or a substituted or unsubstituted aryl group having 6 to 50 ring carbon atoms;

when a plurality of $R_{801}$ are present, the plurality of $R_{801}$ are mutually the same or different;

when a plurality of $R_{802}$ are present, the plurality of $R_{802}$ are mutually the same or different; and when a plurality of $R_{803}$ are present, the plurality of $R_{803}$ are mutually the same or different.

In an exemplary embodiment, the compound represented by the formula (45) is represented by a formula (45-26) below.

[Formula 284]

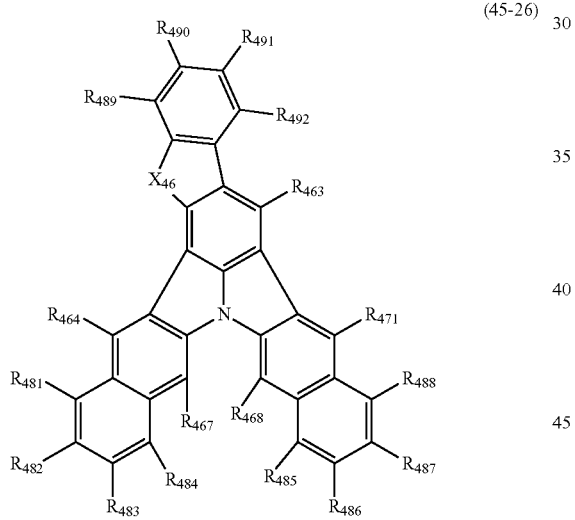

(45-26)

In the formula (45-26):

$X_{46}$ is $C(R_{801})(R_{802})$, $NR_{803}$, an oxygen atom or a sulfur atom;

$R_{463}$, $R_{464}$, $R_{467}$, $R_{468}$, $R_{471}$, and $R_{481}$ to $R_{492}$ each independently represent the same as $R_{461}$ to $R_{471}$ in the formula (45);

$R_{801}$, $R_{802}$, and $R_{803}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, a substituted or unsubstituted heterocyclic group having 5 to 50 ring atoms, a substituted or unsubstituted alkyl group having 1 to 50 carbon atoms, or a substituted or unsubstituted aryl group having 6 to 50 ring carbon atoms;

when a plurality of $R_{801}$ are present, the plurality of $R_{801}$ are mutually the same or different;

620 when a plurality of $R_{802}$ are present, the plurality of $R_{802}$ are mutually the same or different; and when a plurality of $R_{803}$ are present, the plurality of $R_{803}$ are mutually the same or different.

Specific examples of the compound represented by the formula (4) include compounds shown below. In the specific examples below, Ph represents a phenyl group, and D represents a deutrium atom.

[Formula 285]

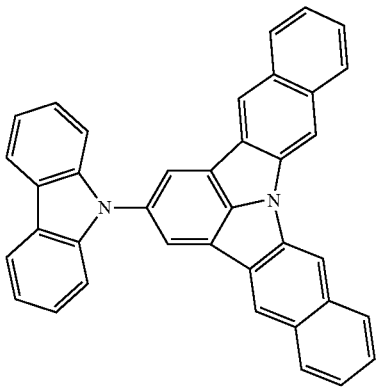

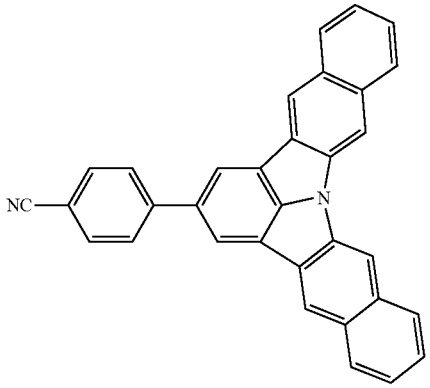

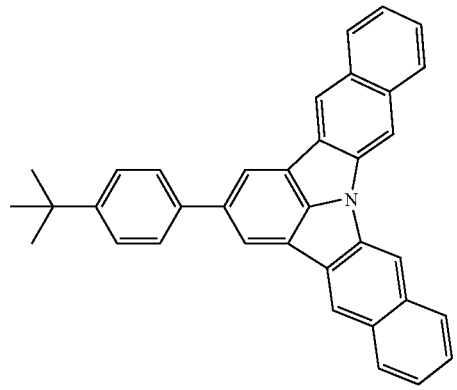

| 621 -continued | 622 -continued |
|---|---|
| 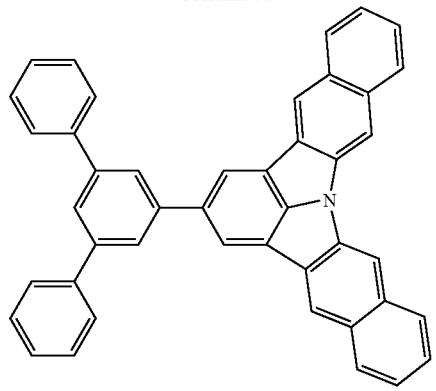 | 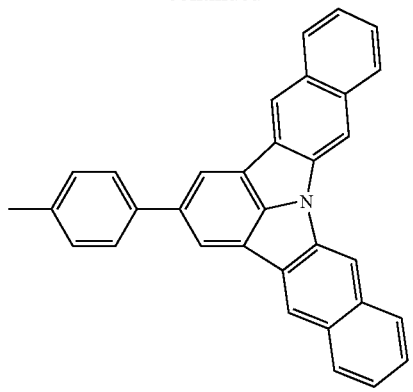 |
| 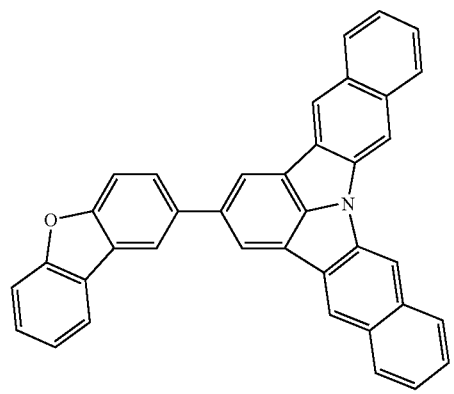 | 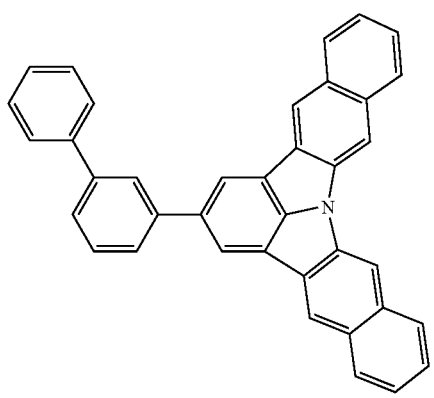 |
| 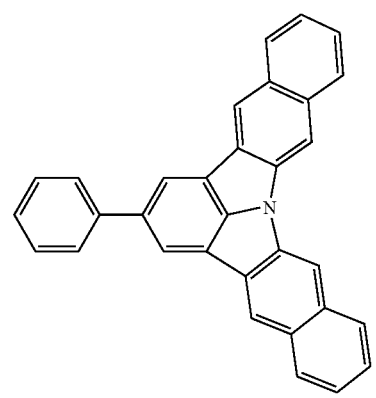 | 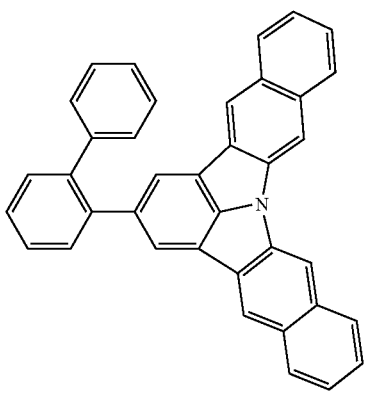 |
| 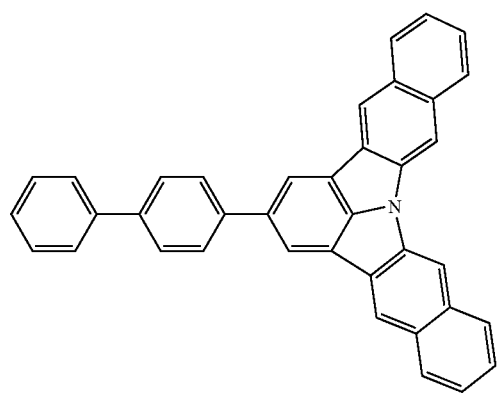 | 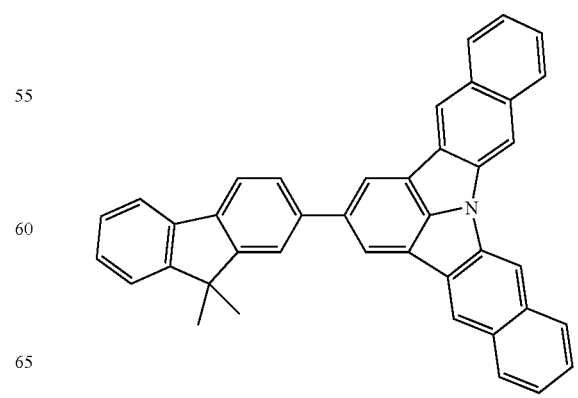 |

623
-continued
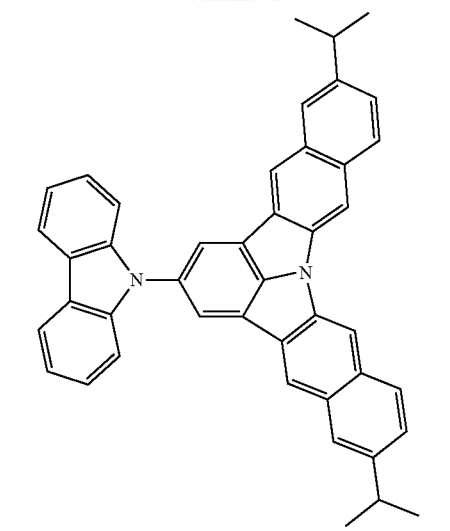
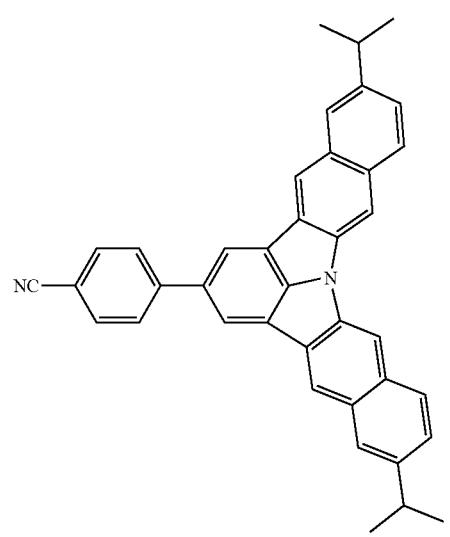
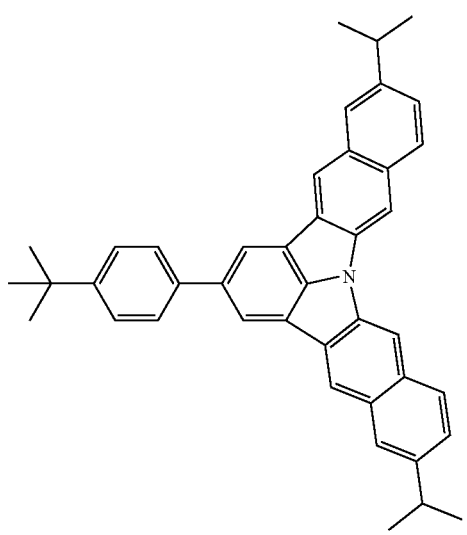
624
-continued
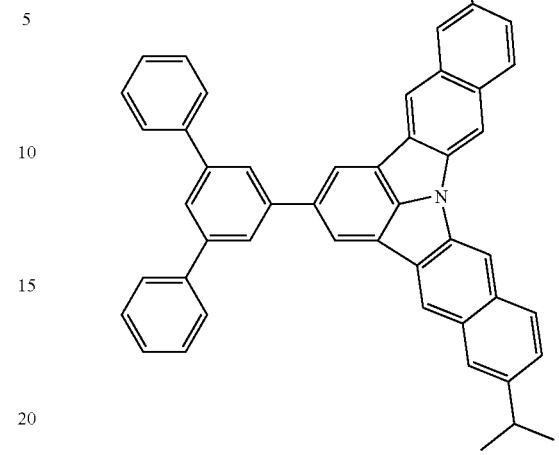
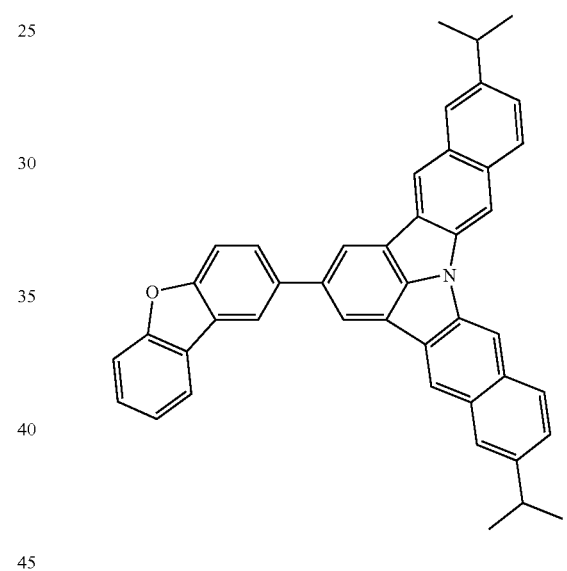
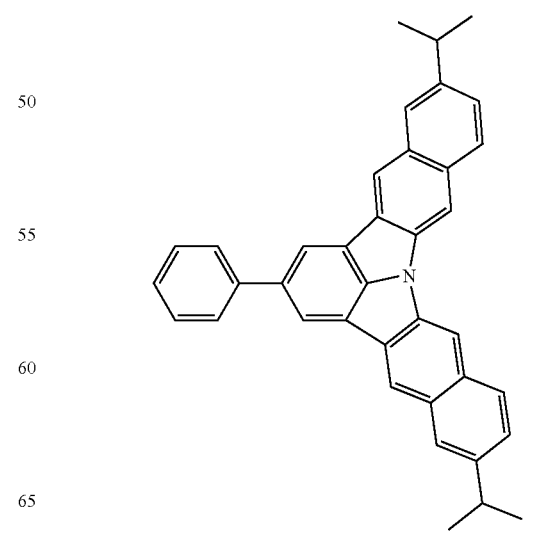

625
-continued
626
-continued
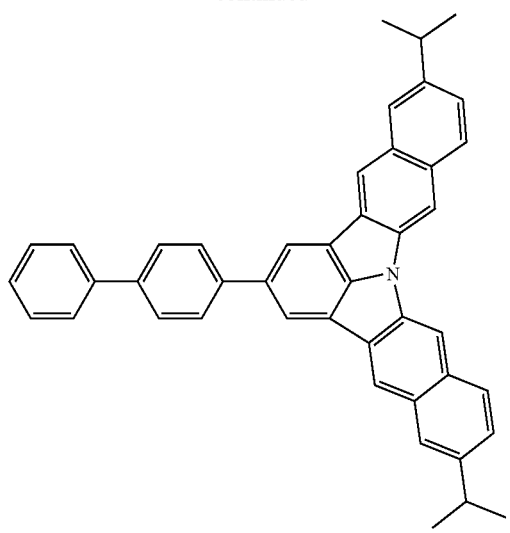
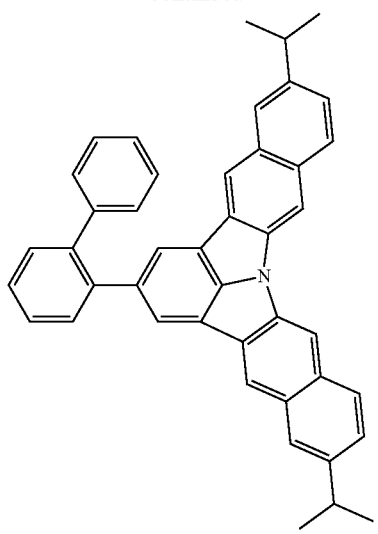
[Formula 286]
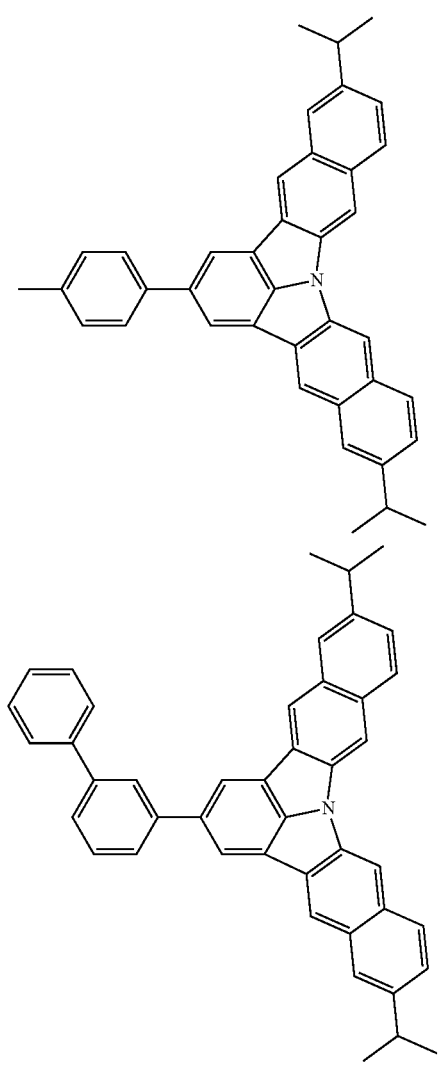
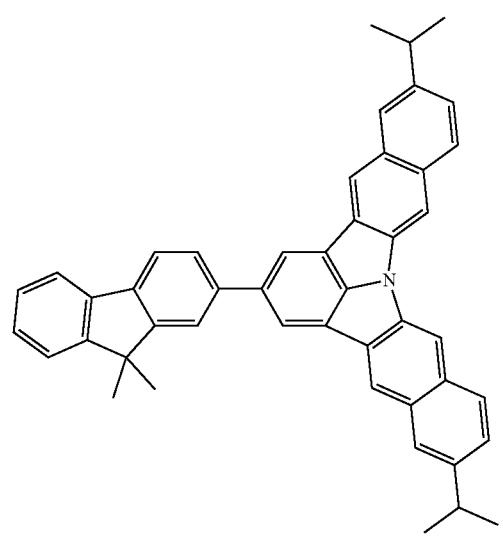
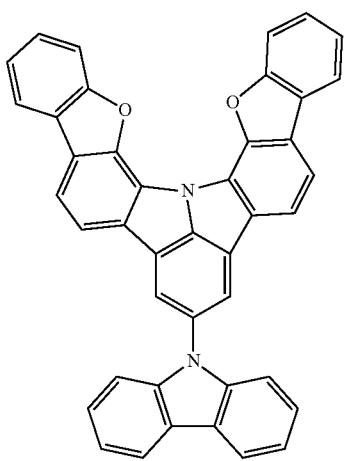

627
-continued
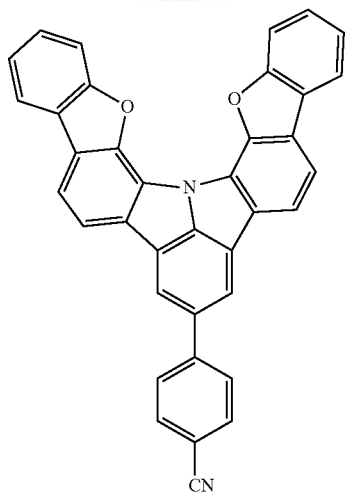
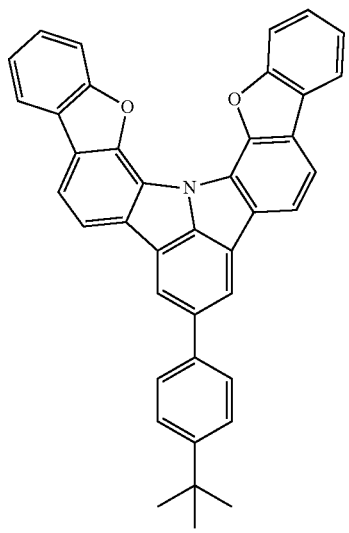 [SMILES: CC(C)(C)c1ccc(-c2cc3c4ccc5c6ccccc6oc5c4n4c3c(c2)c2ccc3c5ccccc5oc3c24)cc1]
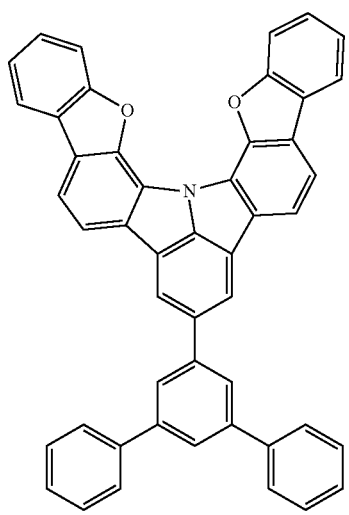
628
-continued
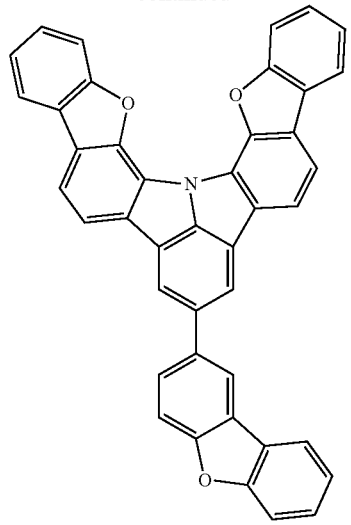
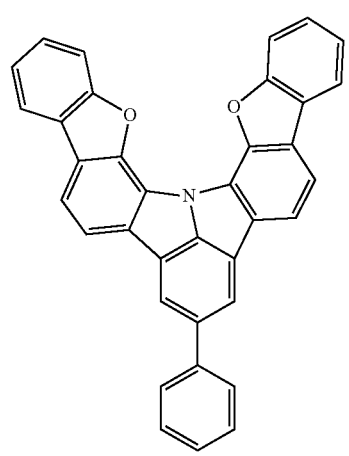
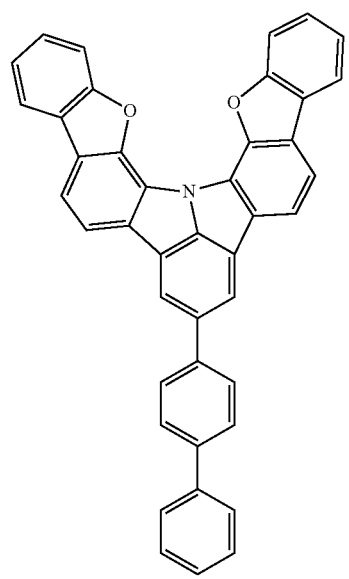

629
-continued
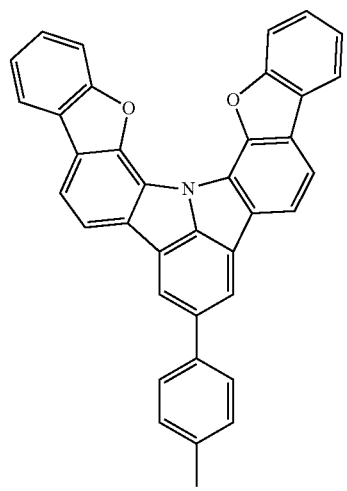
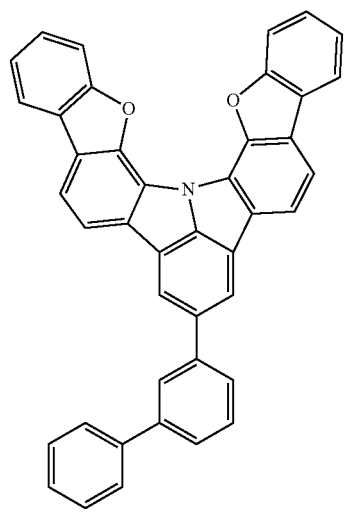
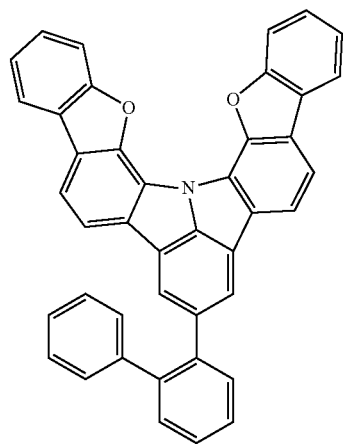
630
-continued
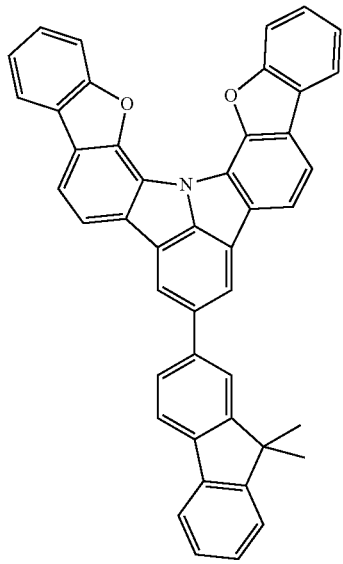
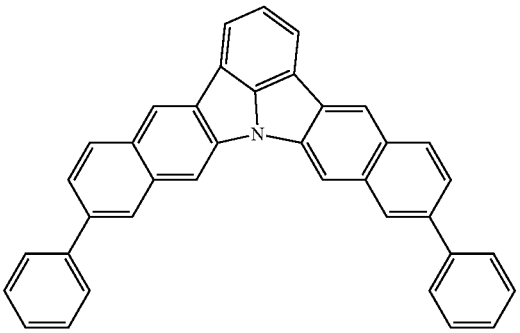
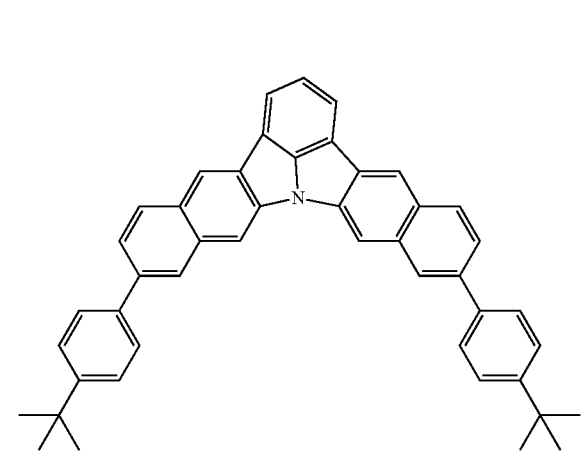

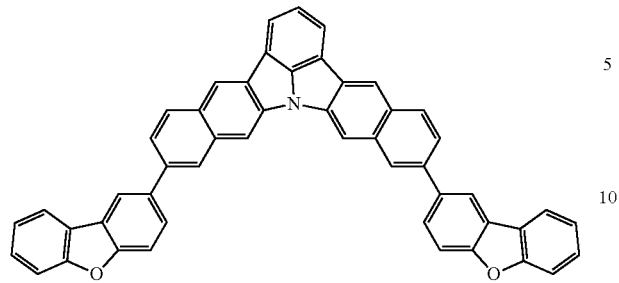
[Formula 287]
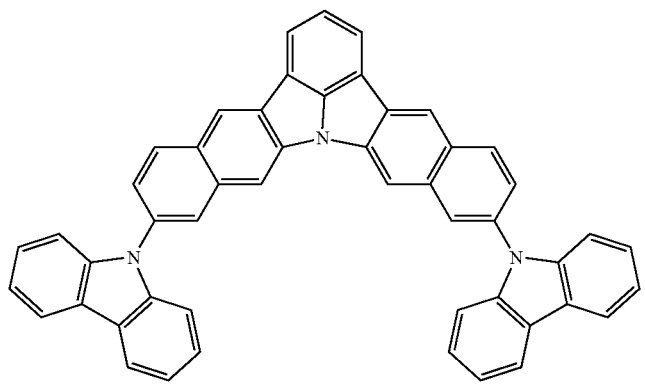
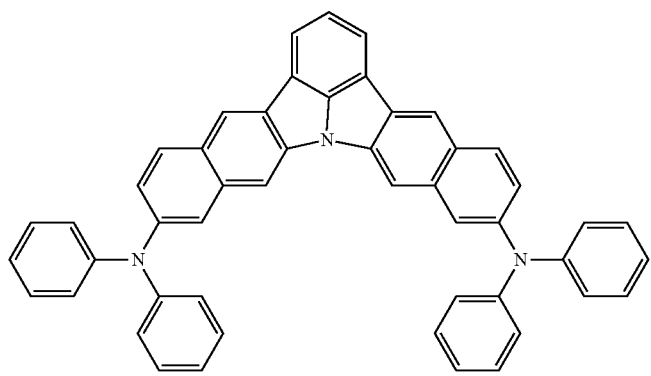
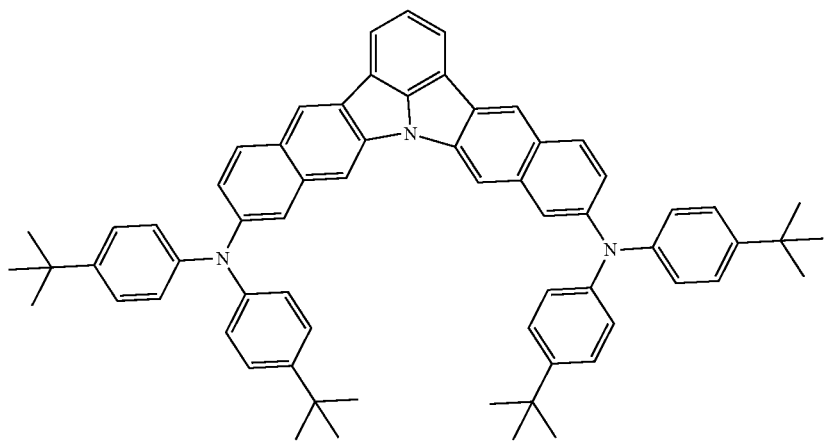

633
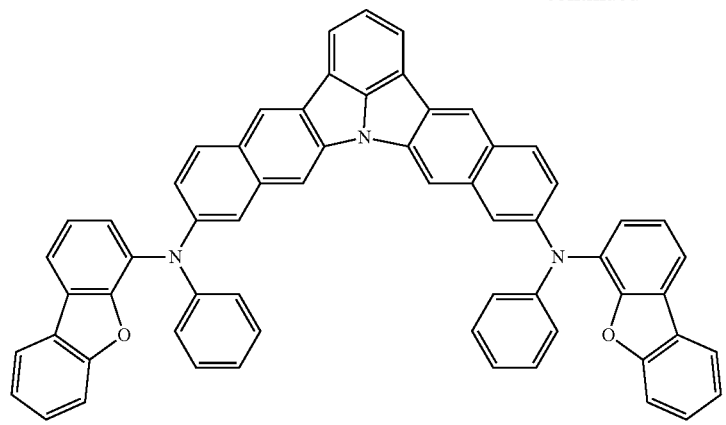
634
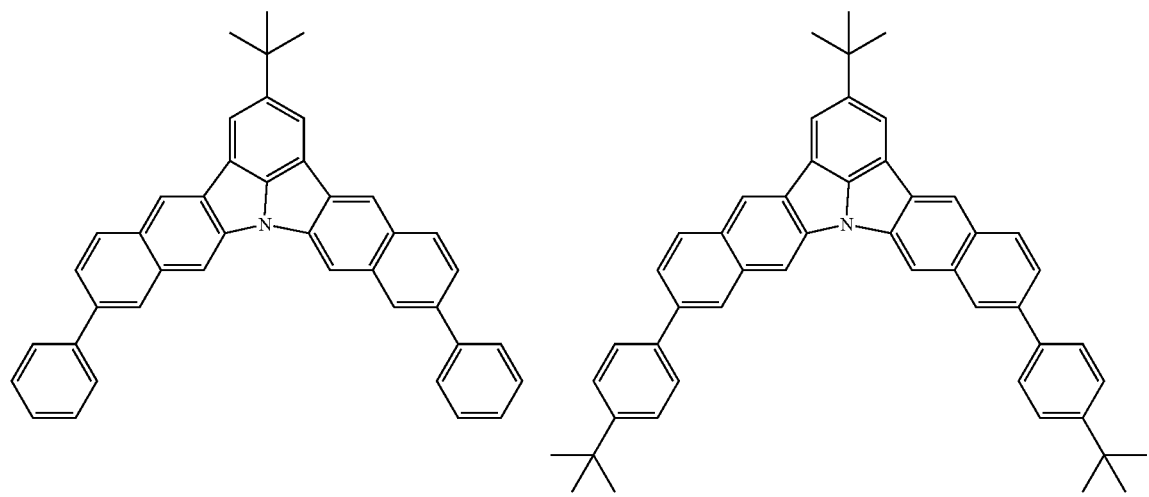
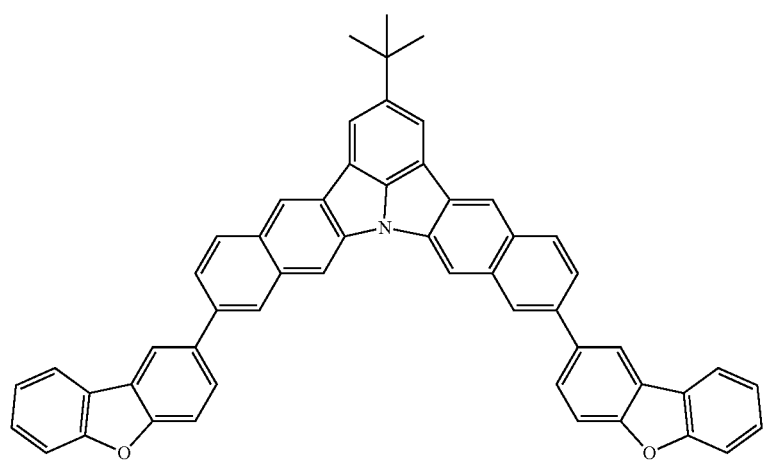

-continued
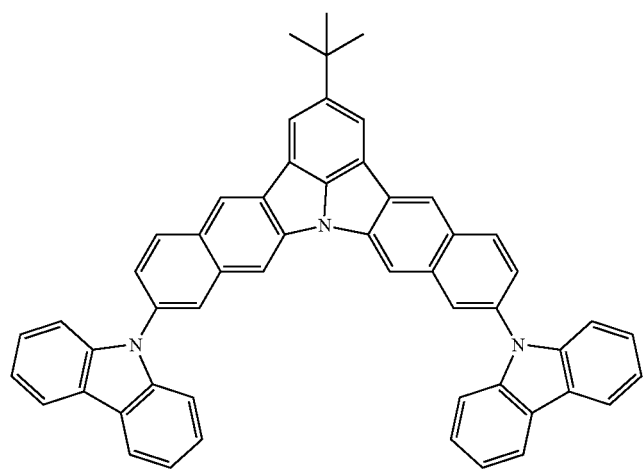
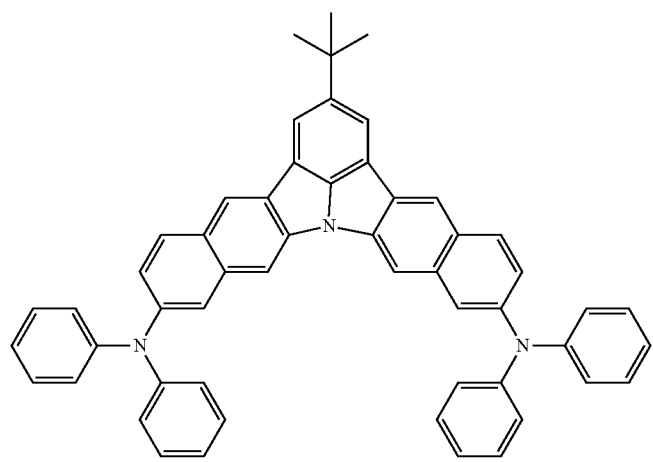
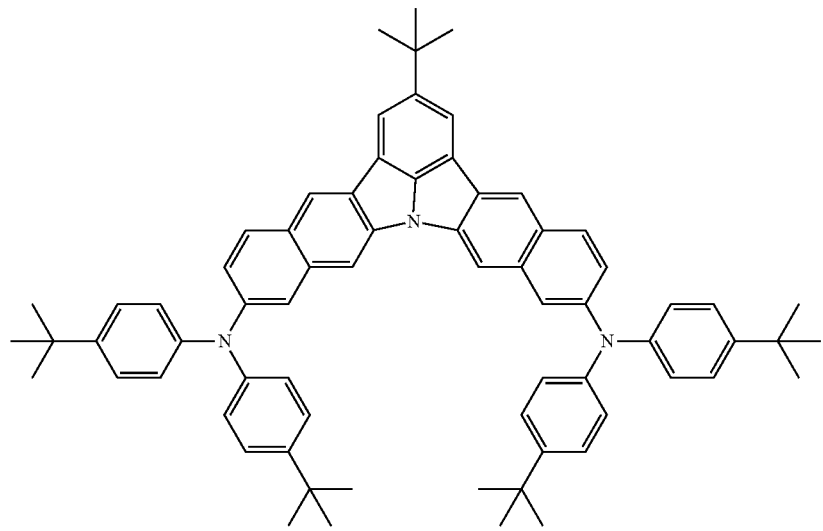

637 638
-continued
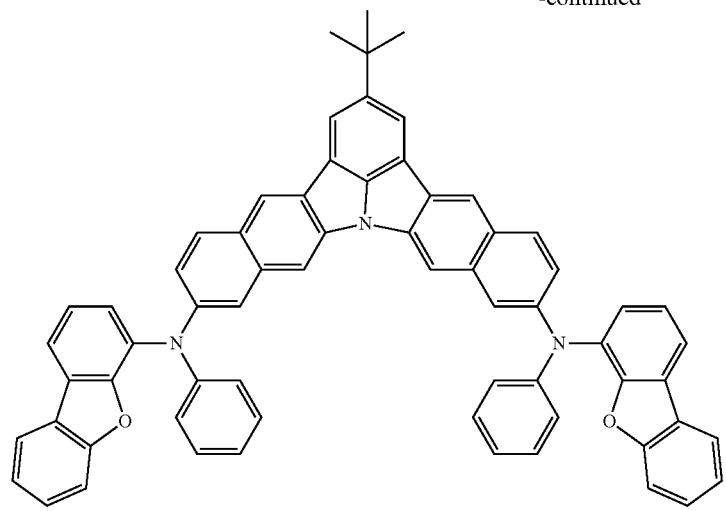
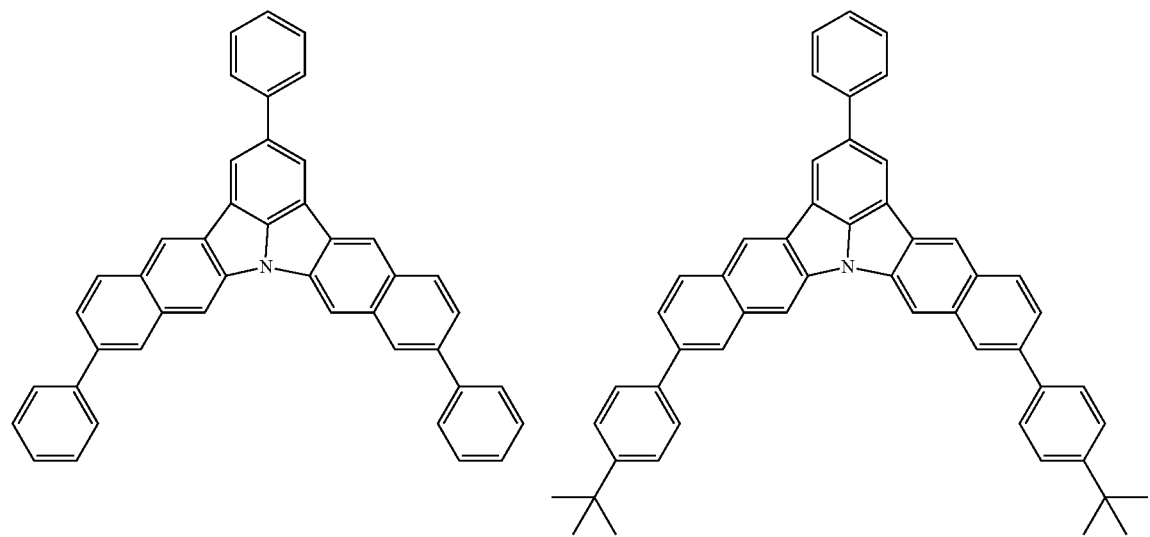
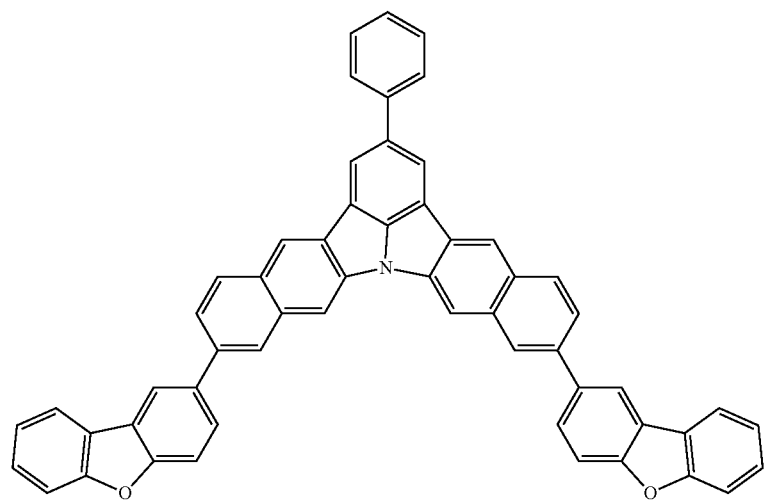

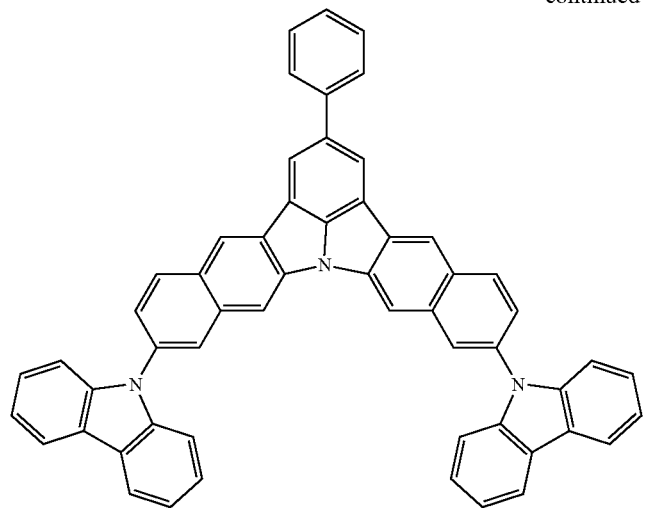
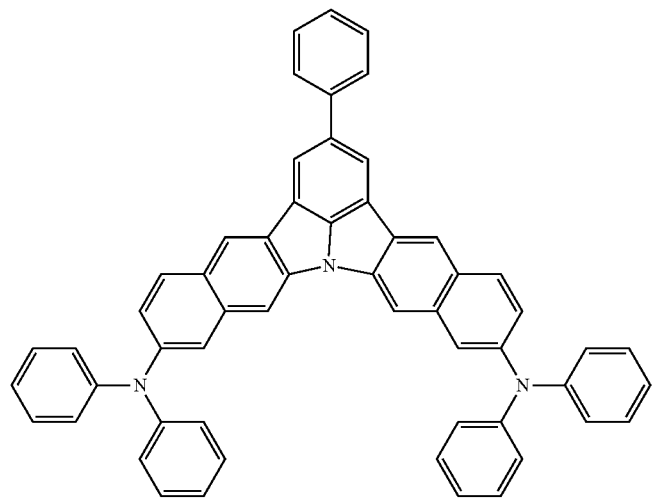
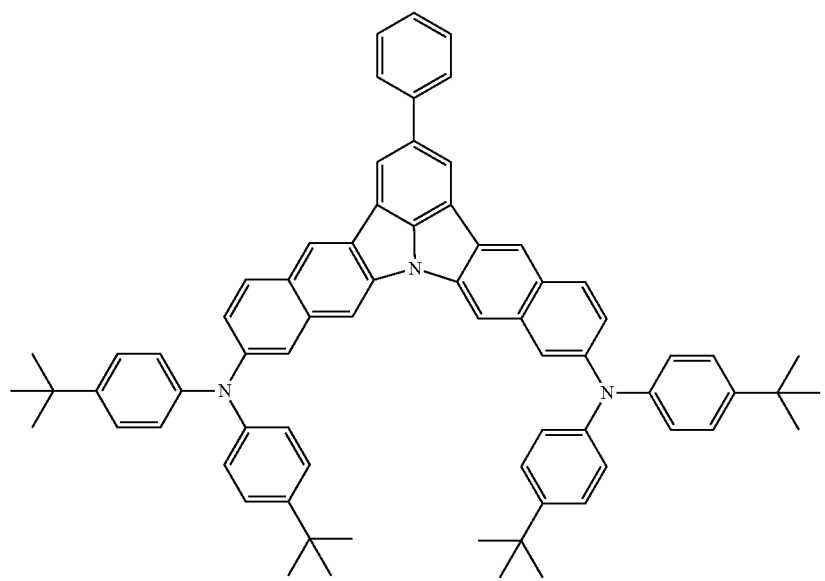 [SMILES: CC(C)(C)c1ccc(N(c2ccc(C(C)(C)C)cc2)c2ccc3cc4c5cc(-c6ccccc6)cc6c7cc8ccc(N(c9ccc(C(C)(C)C)cc9)c9ccc(C(C)(C)C)cc9)cc8cc7n(c4cc3c2)c56)cc1]

[Formula 288]
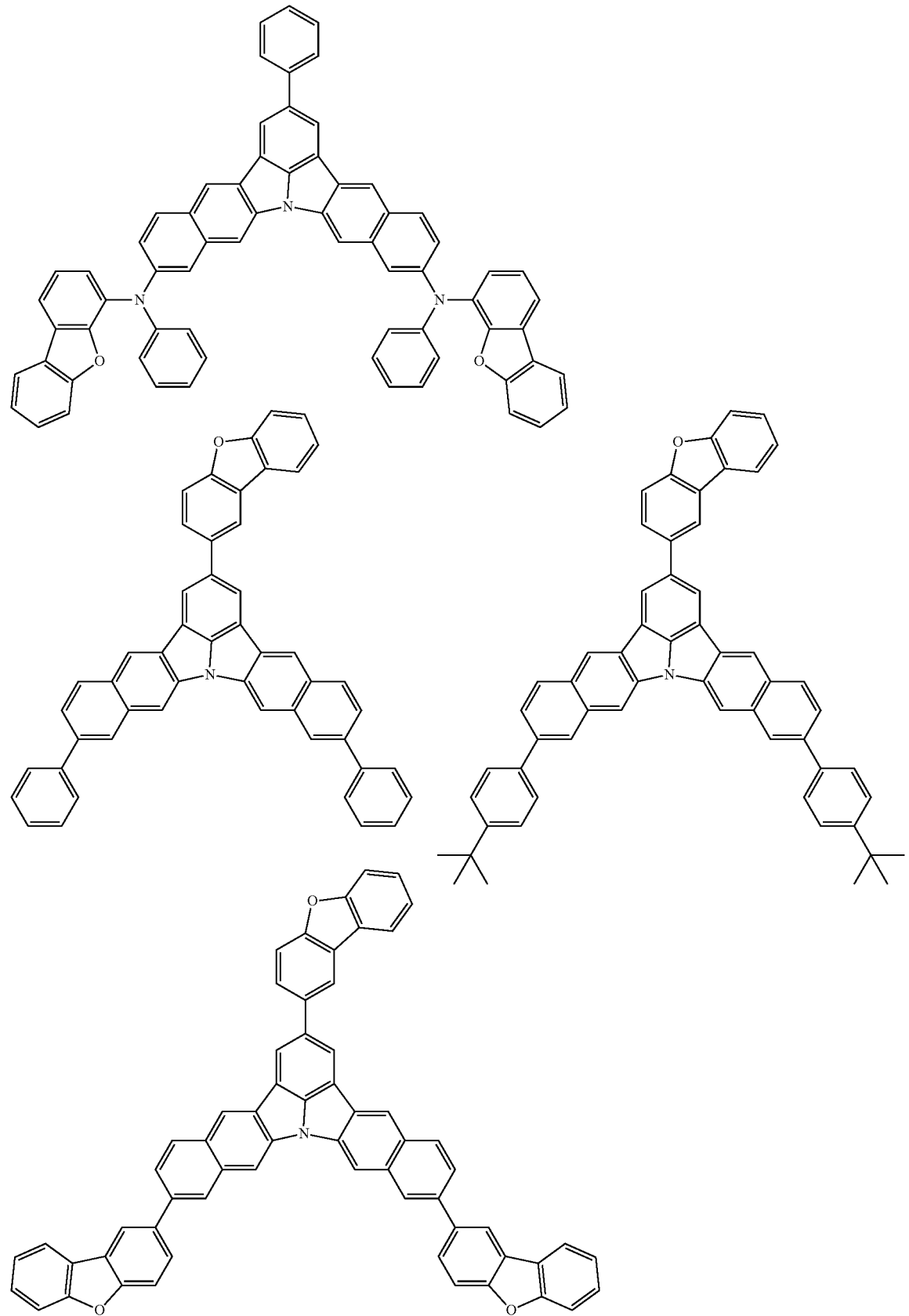

-continued
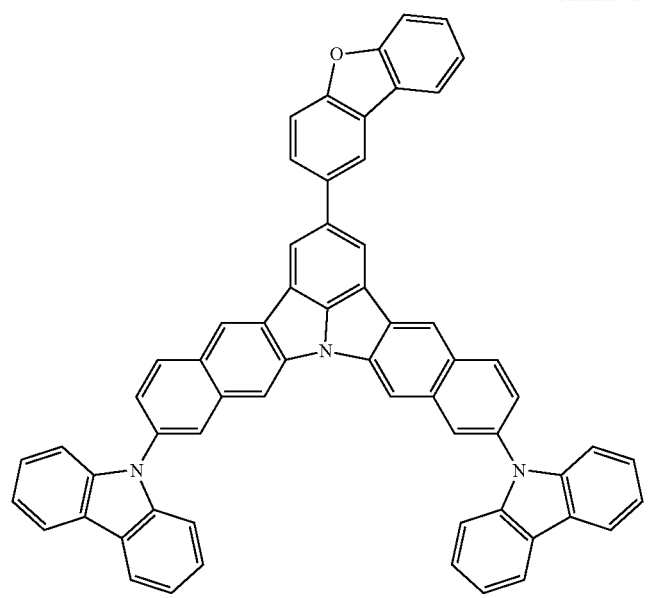
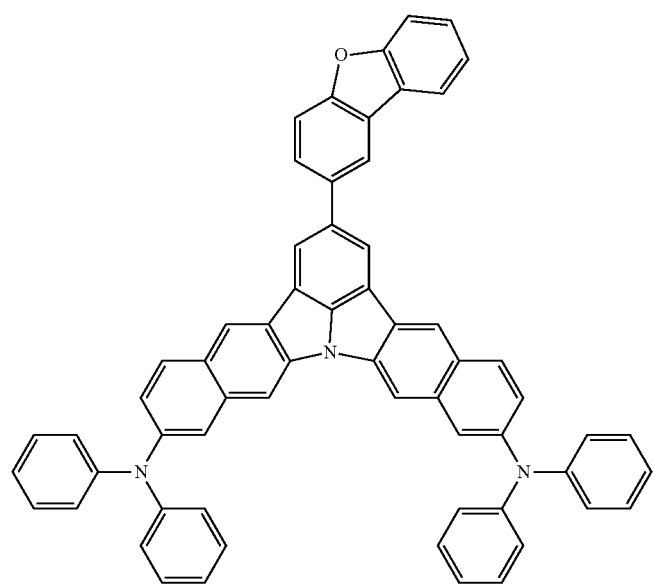

-continued
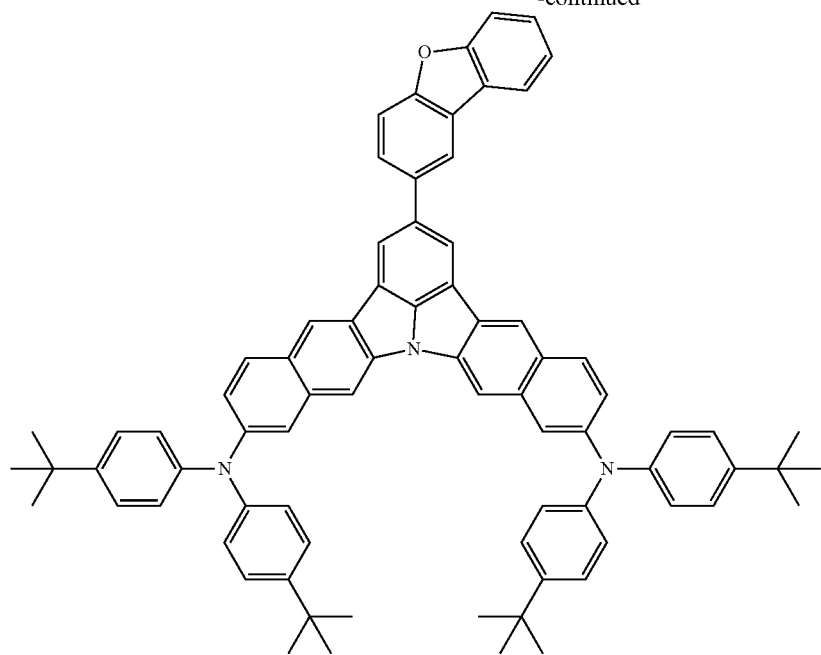
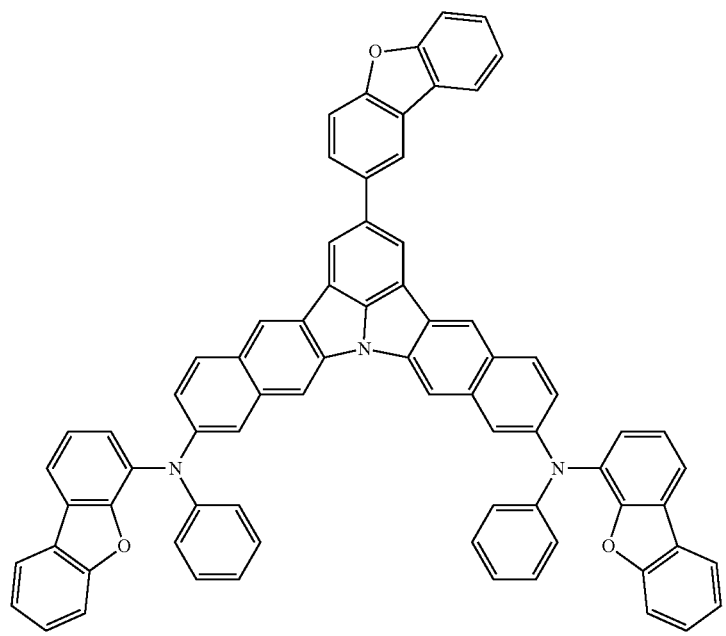

647
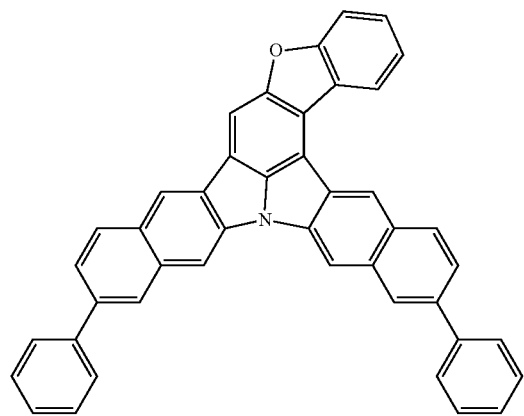
648
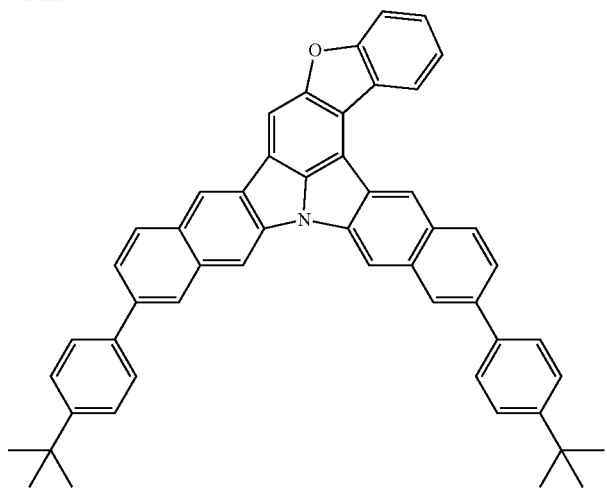
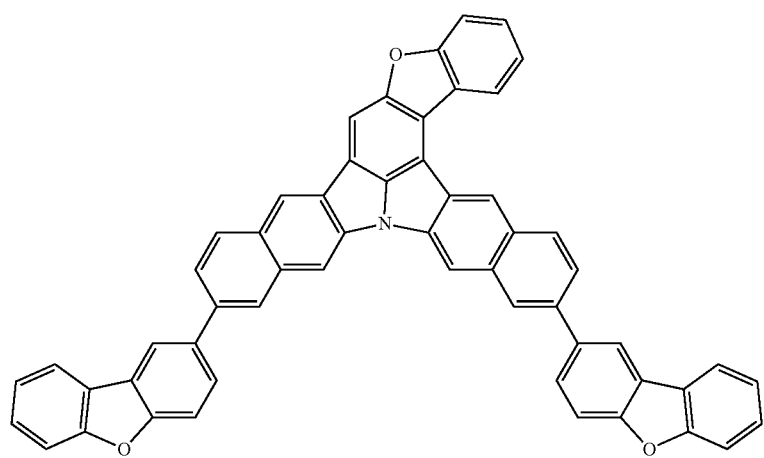
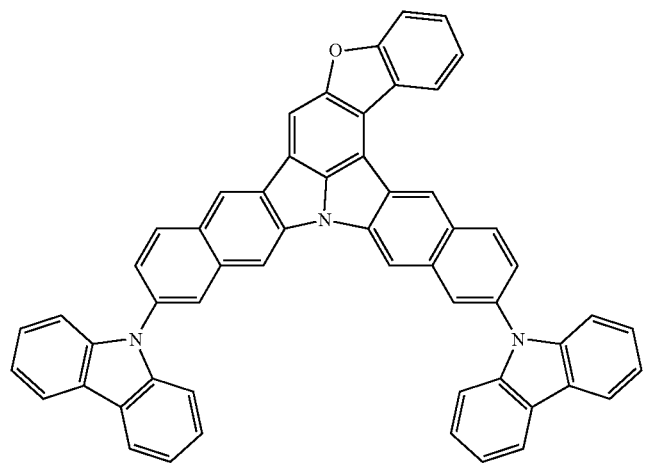

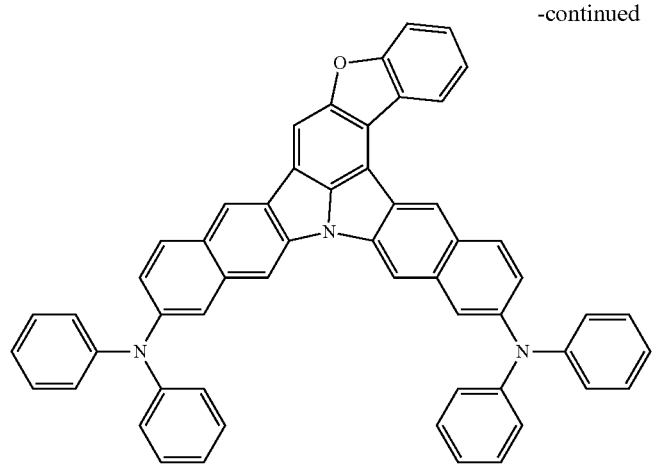
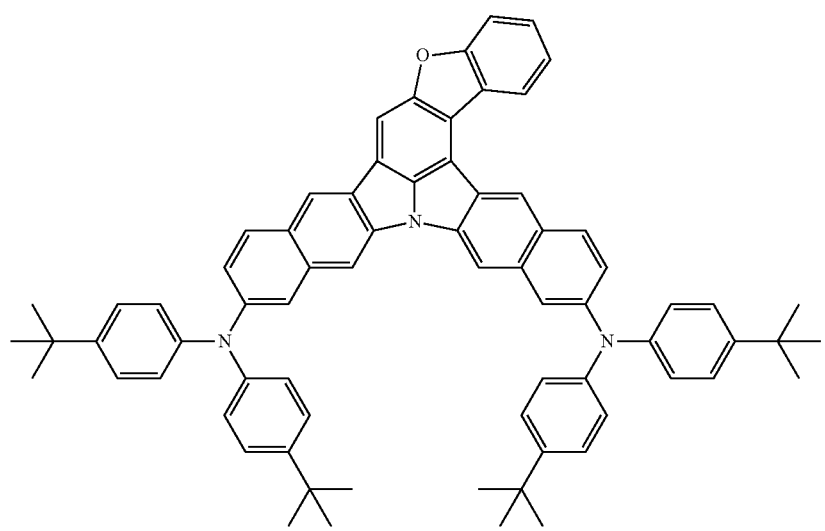 [SMILES: CC(C)(C)c1ccc(N(c2ccc(C(C)(C)C)cc2)c2ccc3cc4c5cc6oc7ccccc7c6c6c7cc8ccc(N(c9ccc(C(C)(C)C)cc9)c9ccc(C(C)(C)C)cc9)cc8cc7n(c4cc3c2)c56)cc1]
[Formula 289]
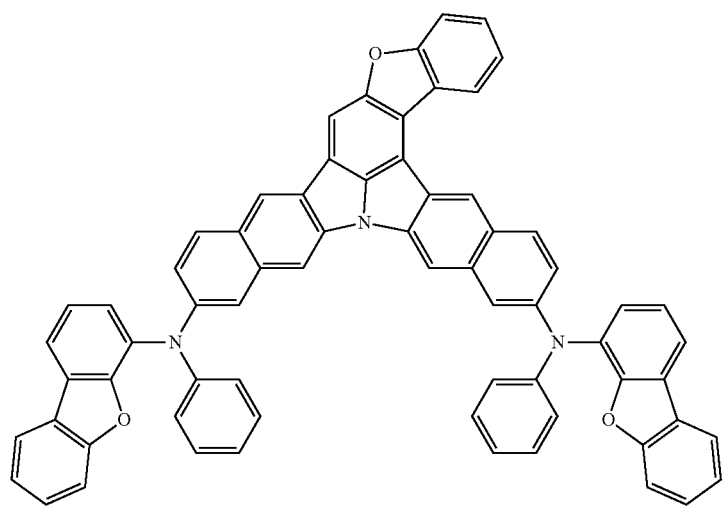

651 652
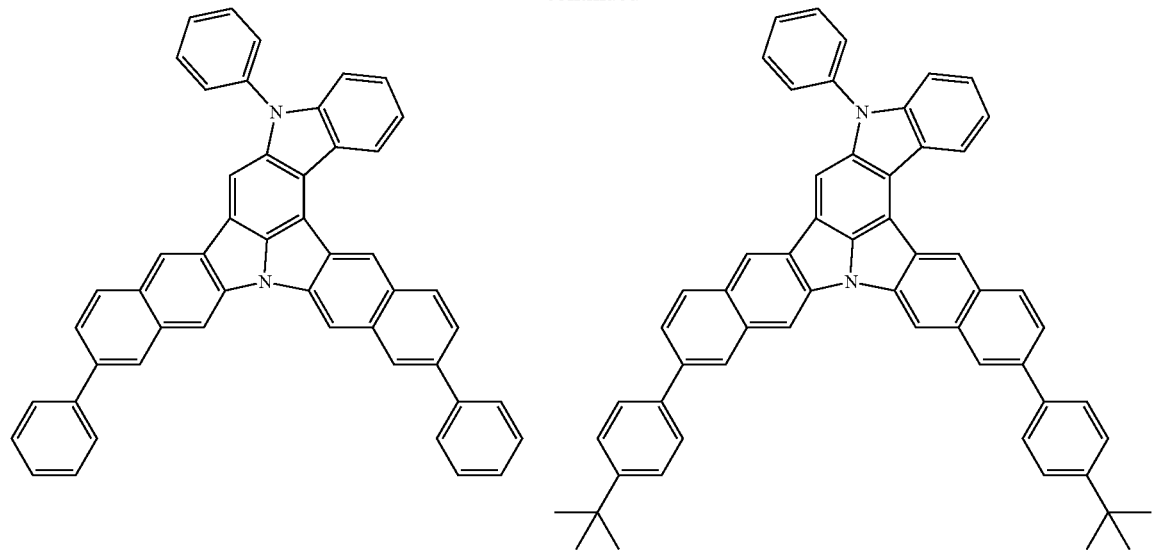
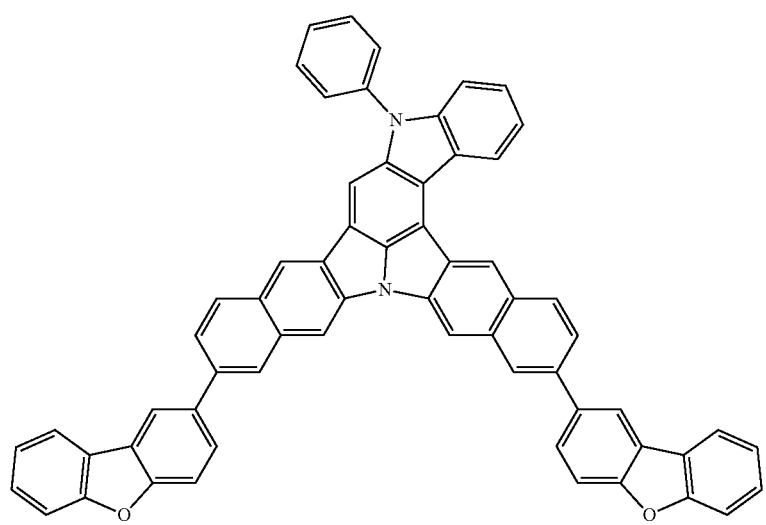
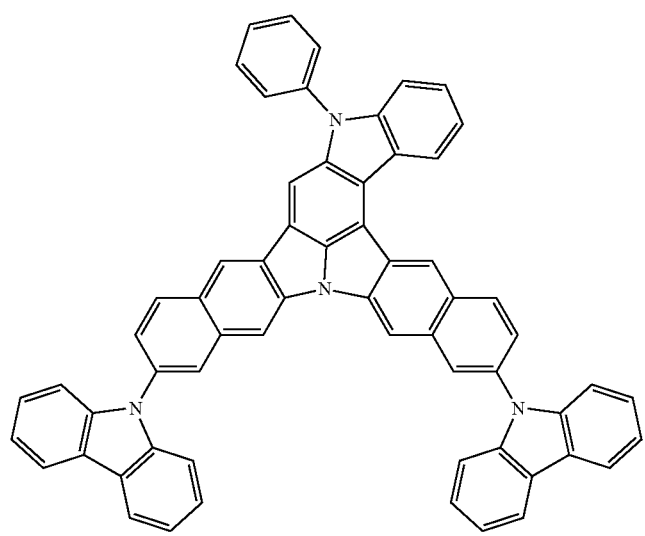

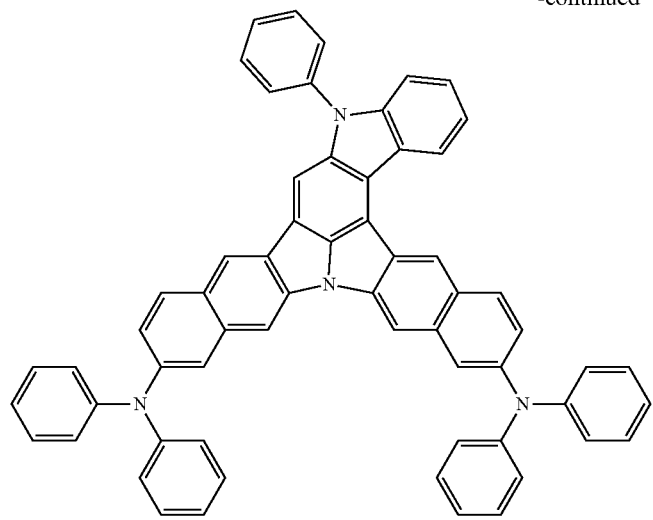
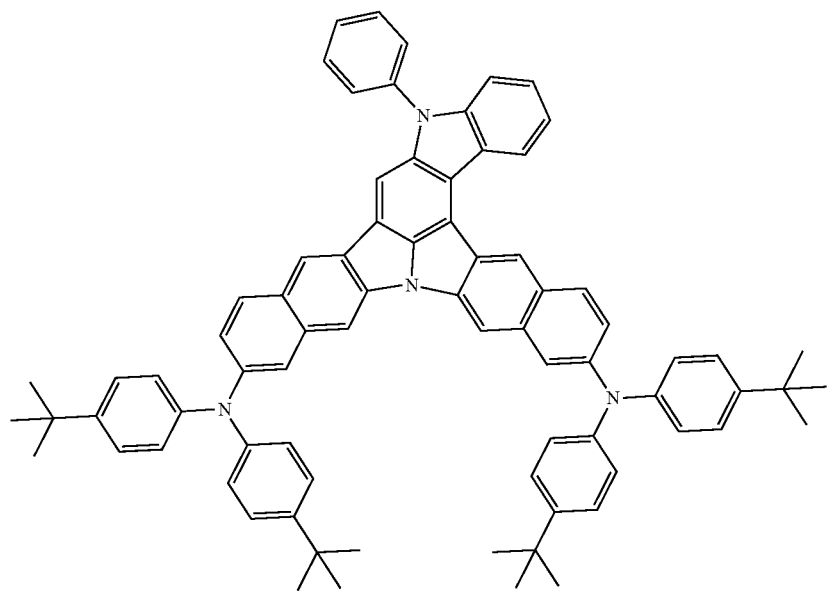
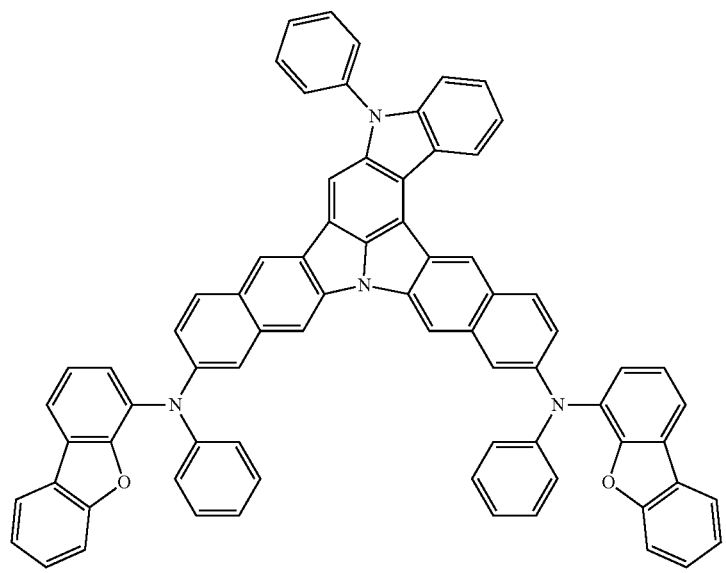

-continued
655 656
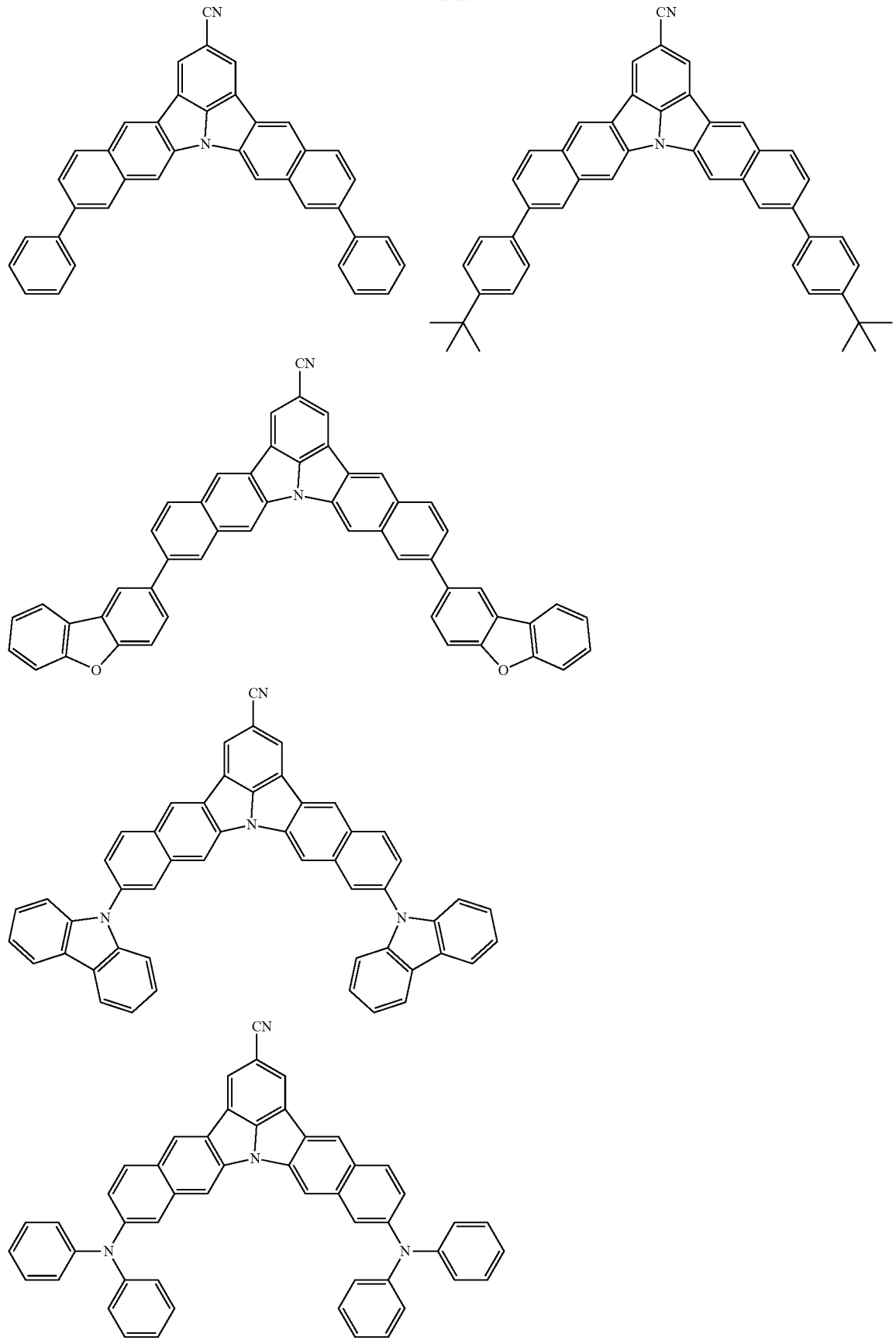

-continued
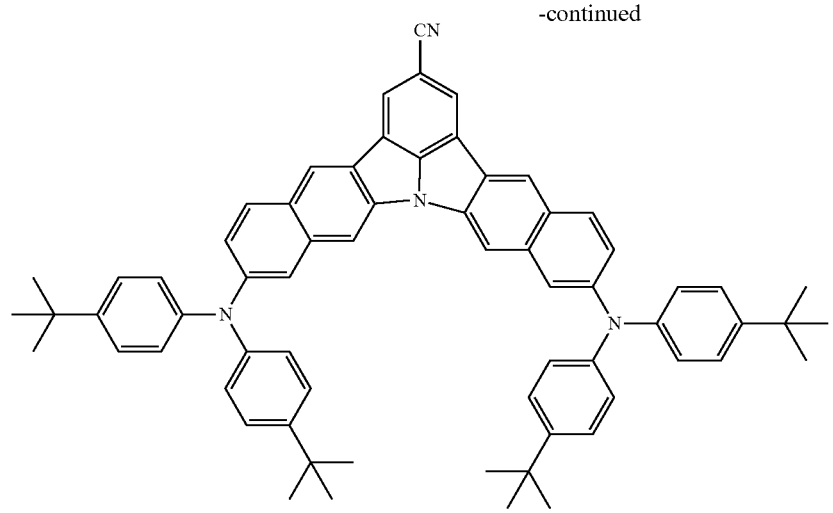
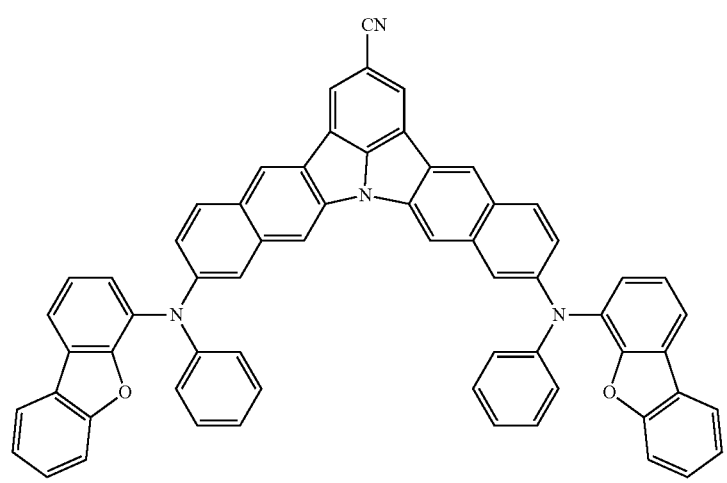
[Formula 290]
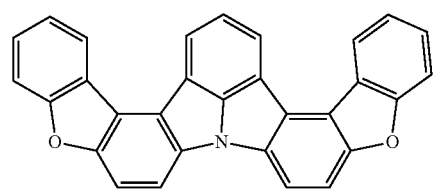
-continued
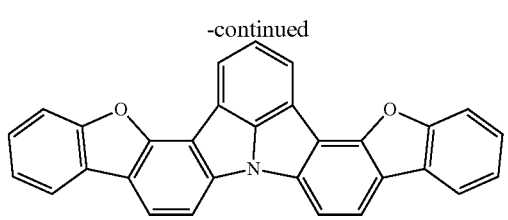
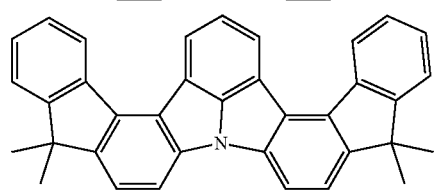
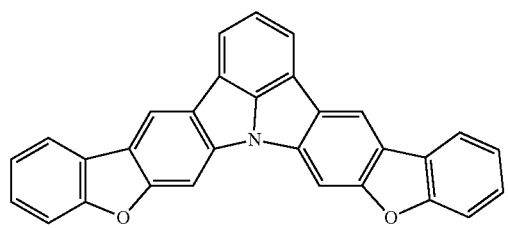
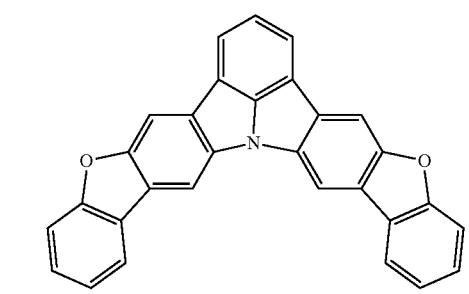

659
-continued
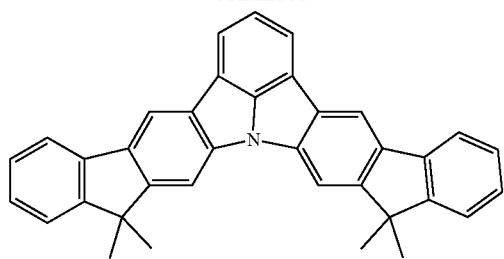
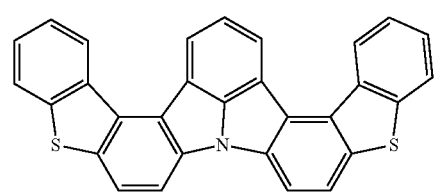
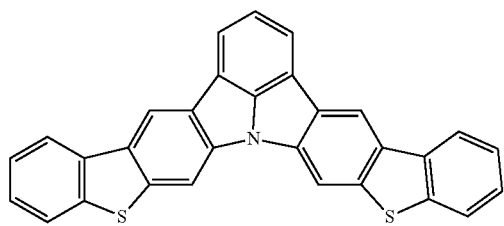
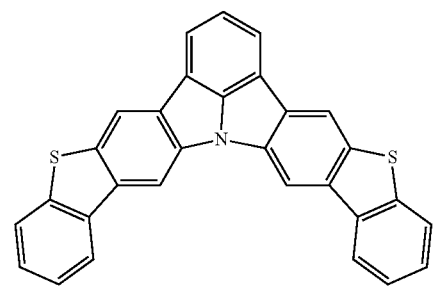
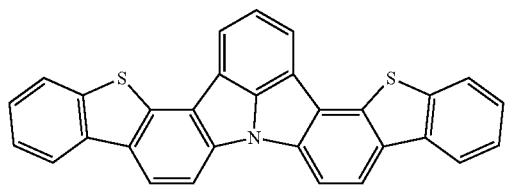
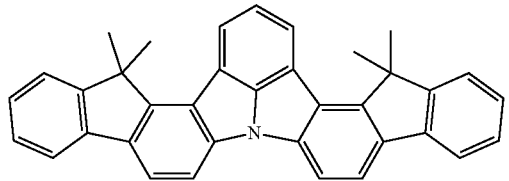
660
-continued
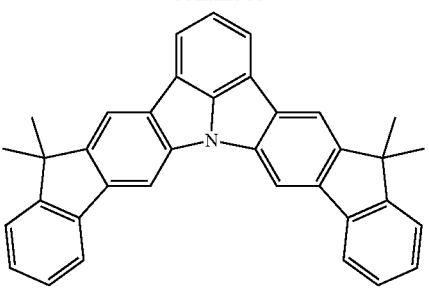
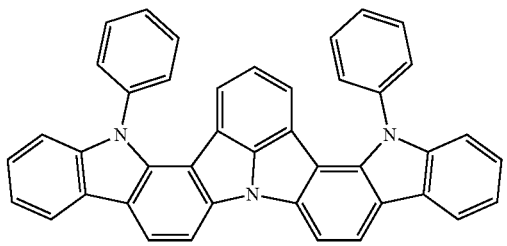
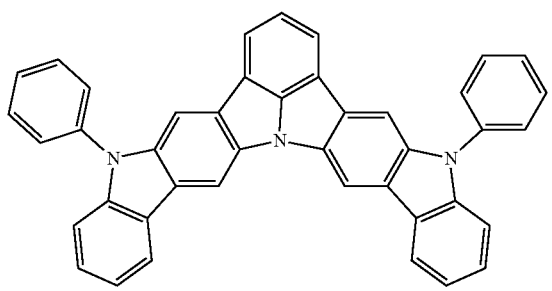
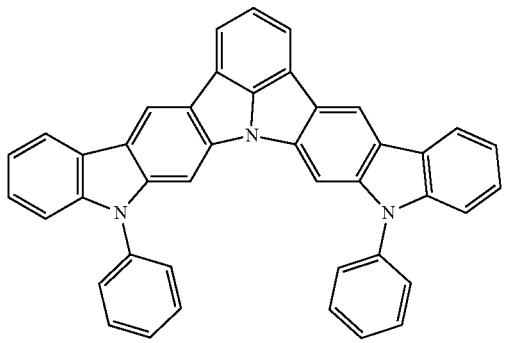
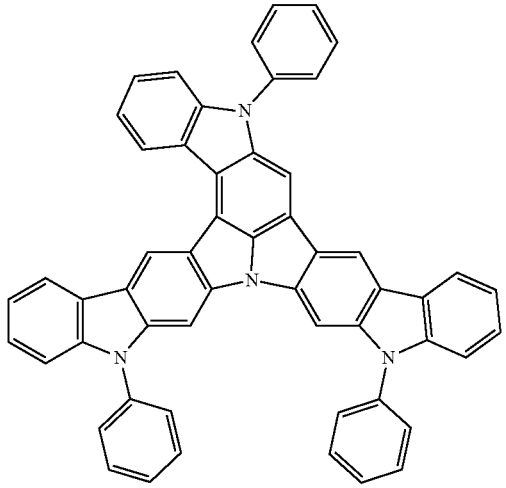

661
-continued
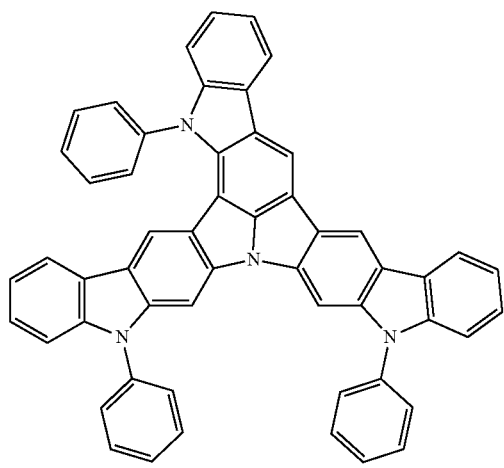
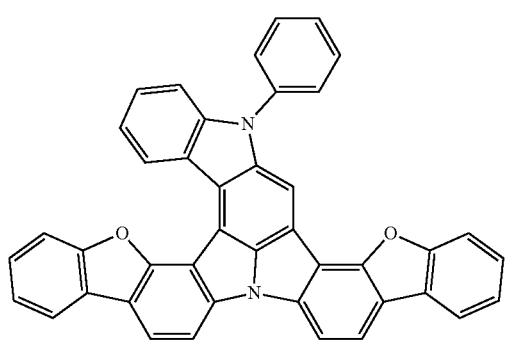
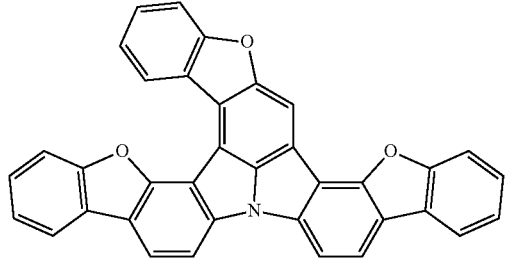
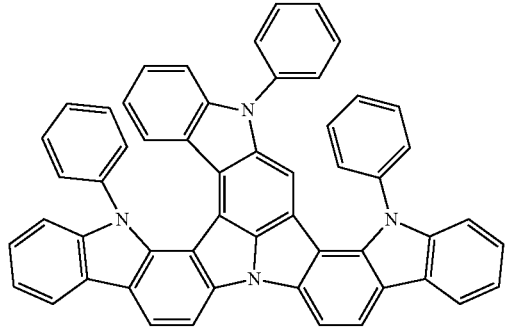
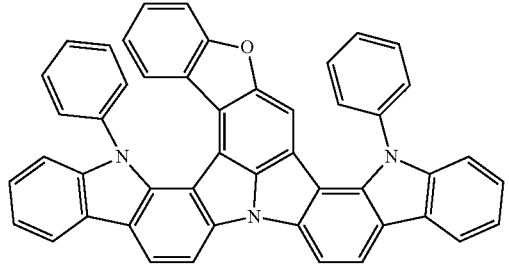
662
-continued
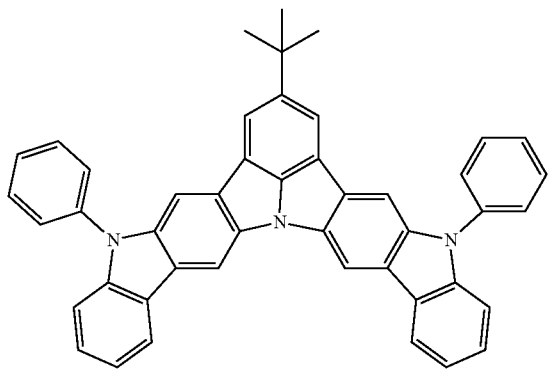
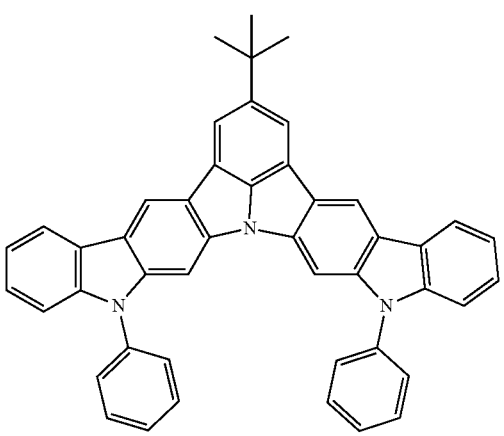
[Formula 291]
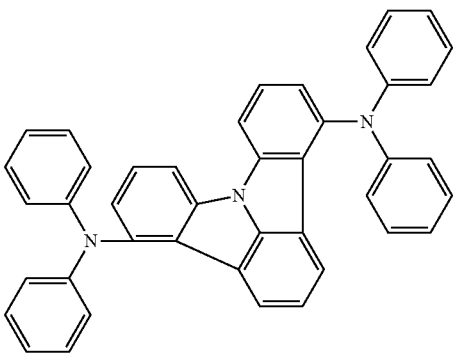
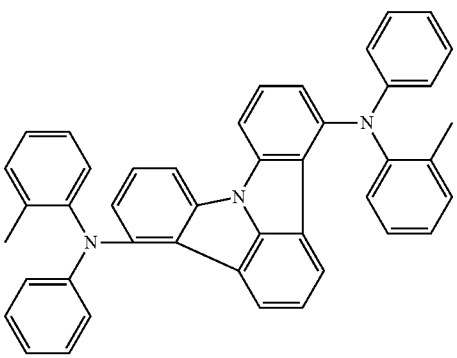

663
-continued
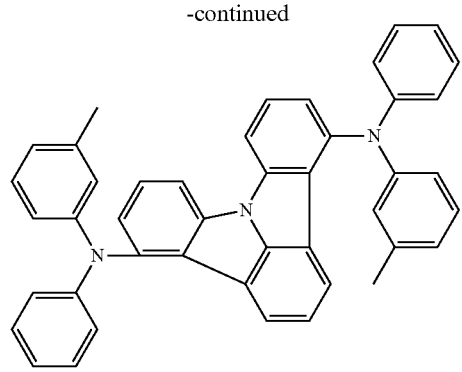
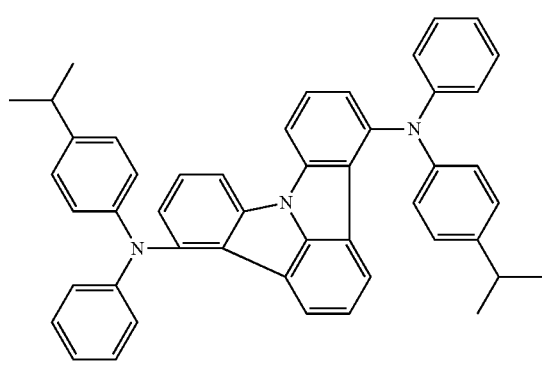
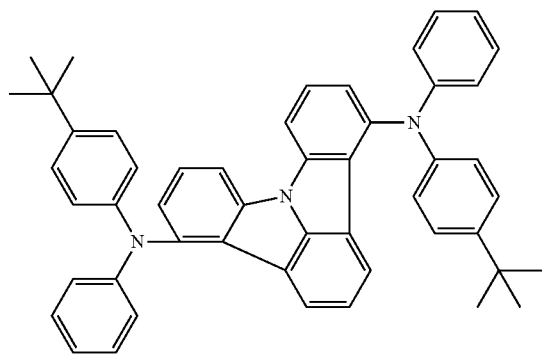
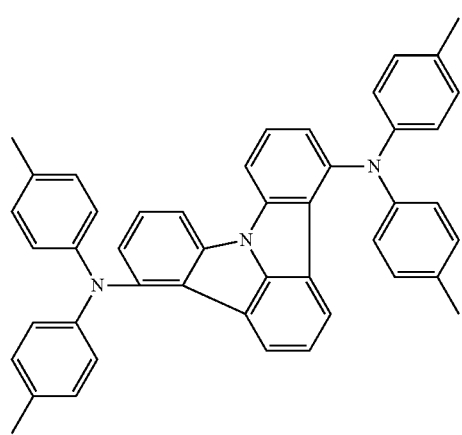
664
-continued
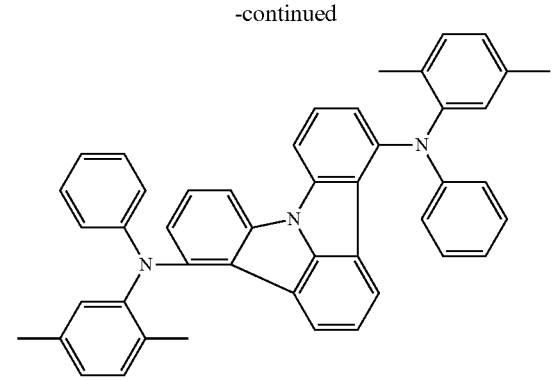
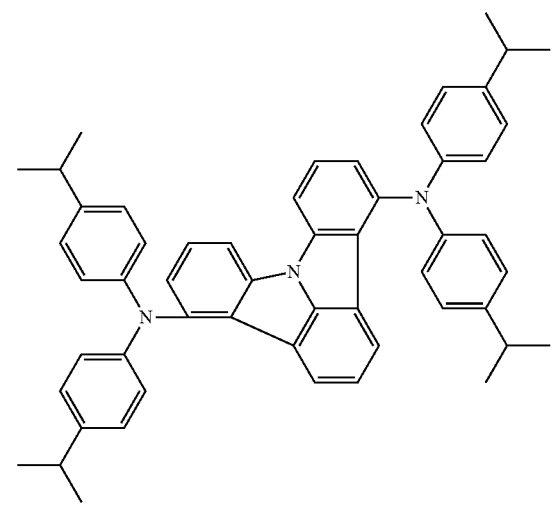
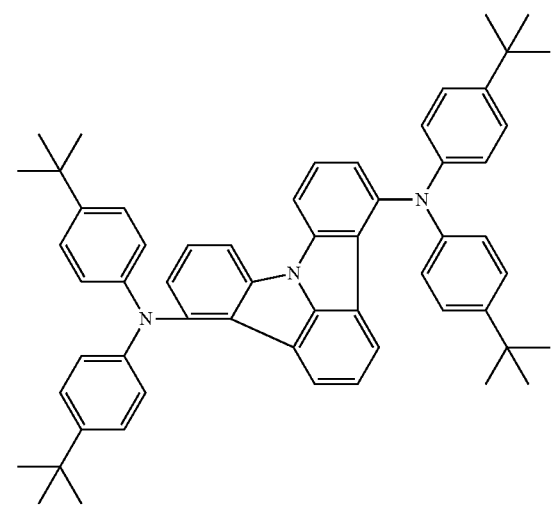
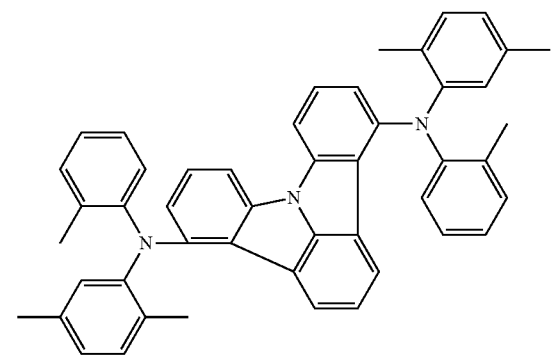

665
-continued
666
-continued
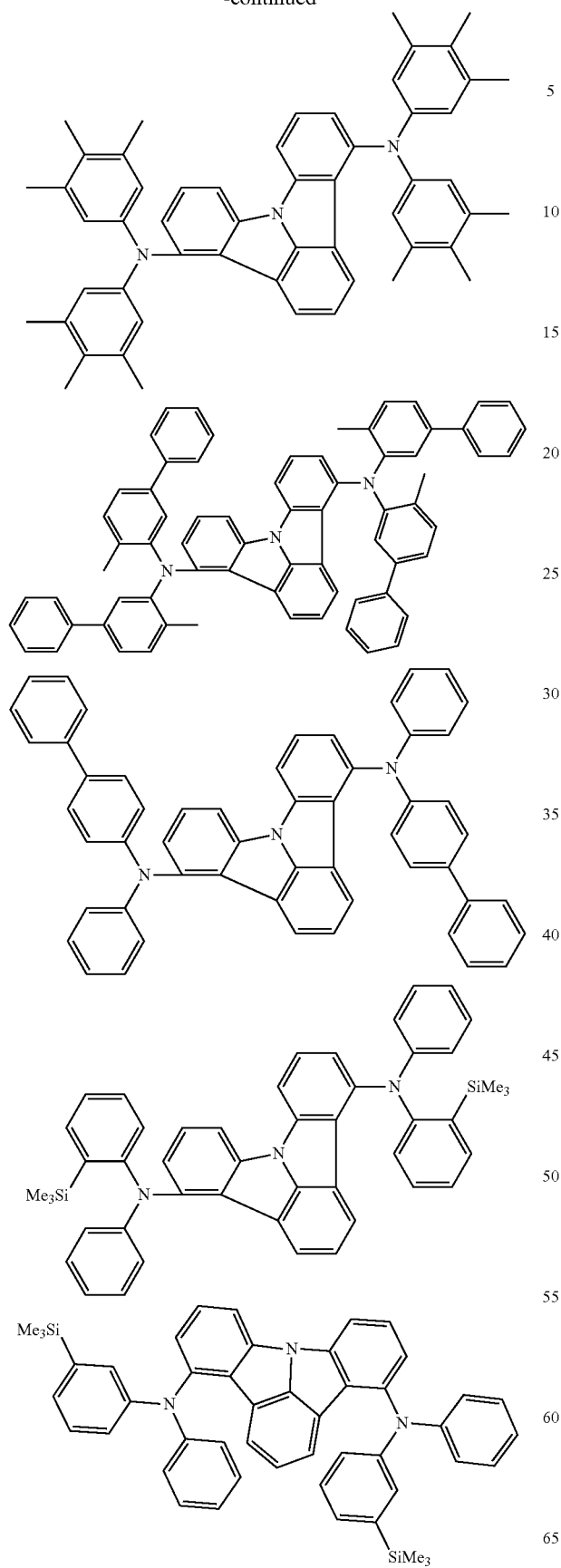
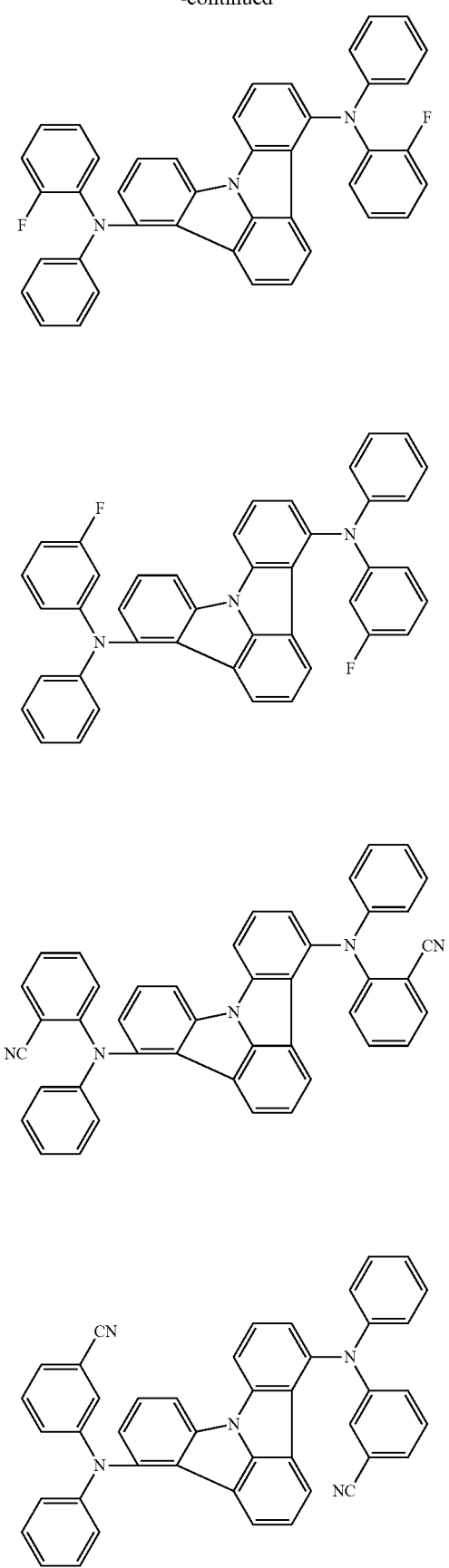

667
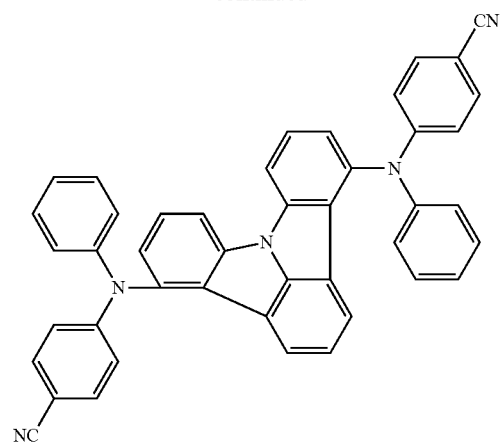
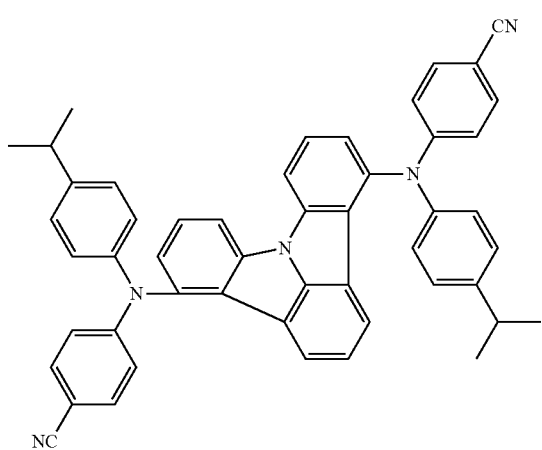 [SMILES: CC(C)c1ccc(N(c2ccc(C#N)cc2)c2cccc3c2c2cccc4c5c(N(c6ccc(C#N)cc6)c6ccc(C(C)C)cc6)cccc5n3c24)cc1]
[Formula 292]
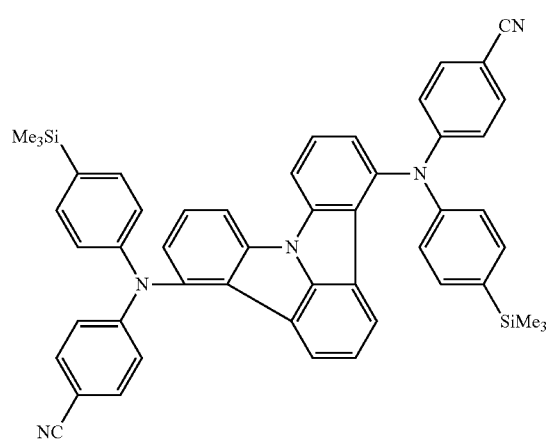
668
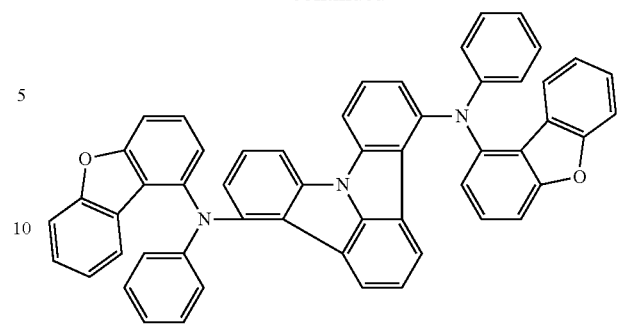
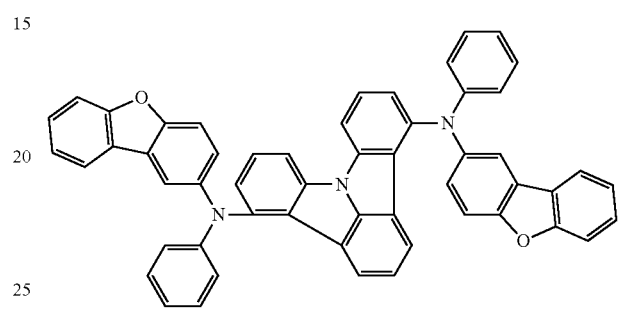
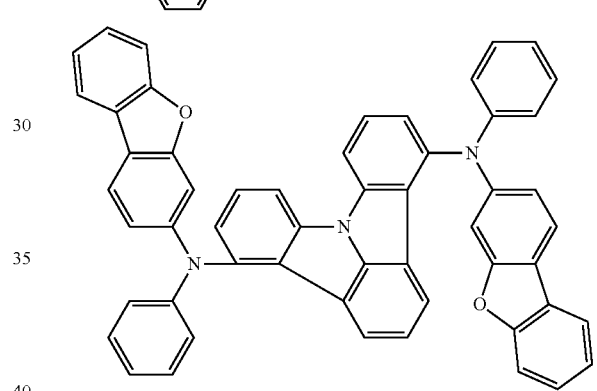
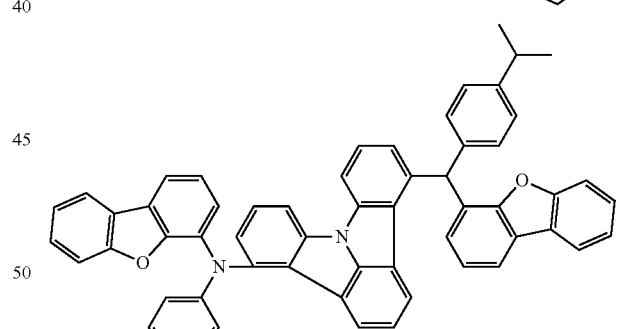
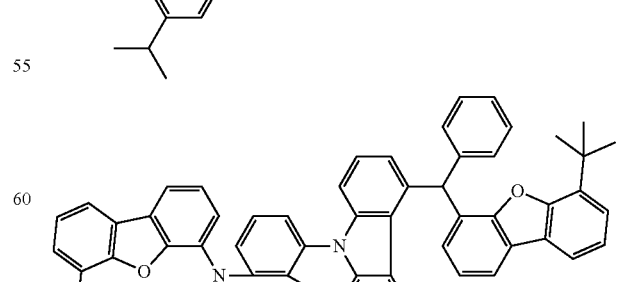

669
-continued
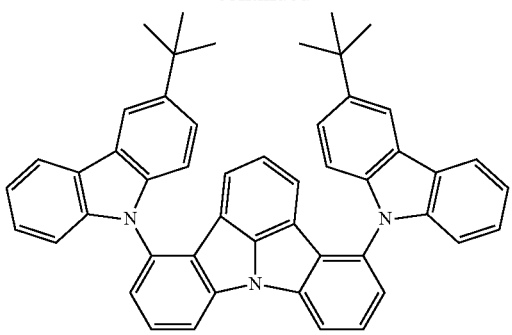
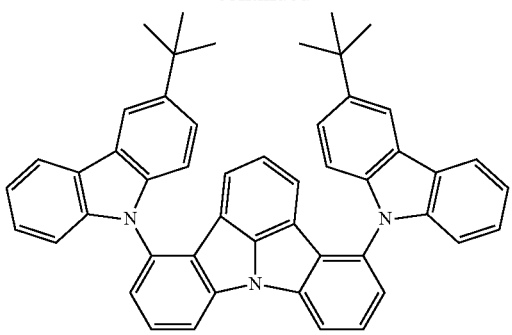
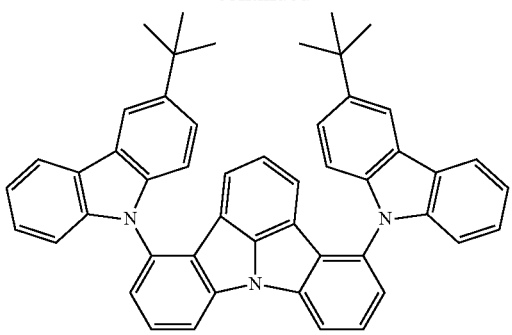
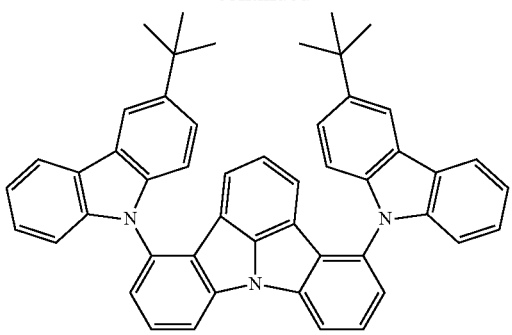
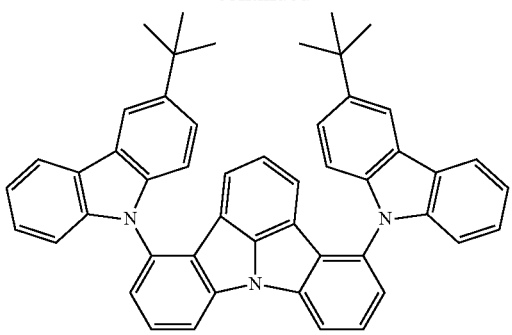
670
-continued
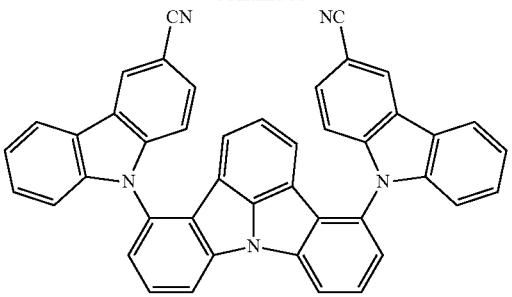
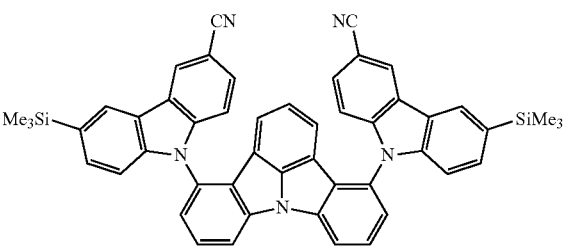
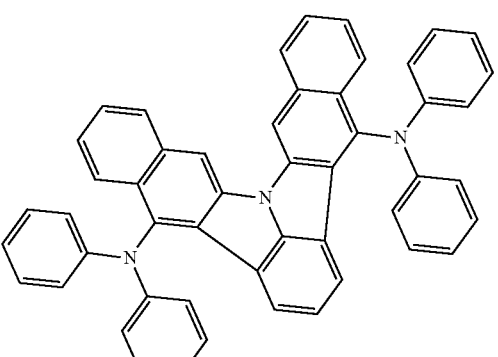
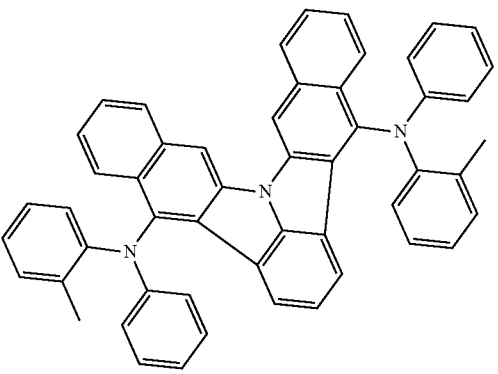
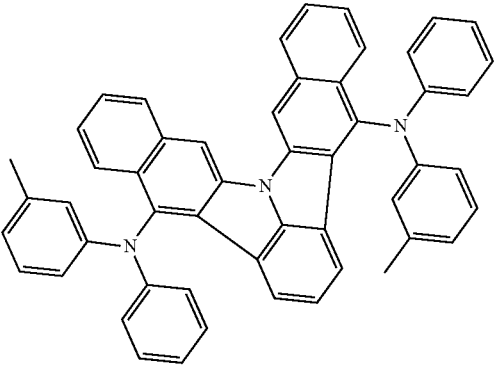

-continued
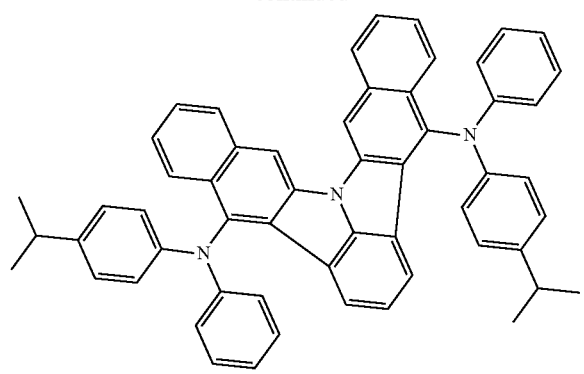
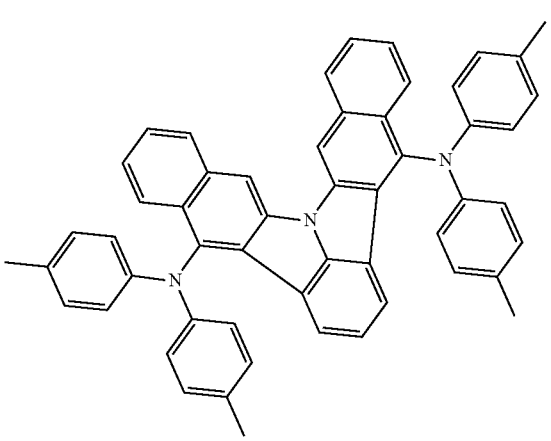
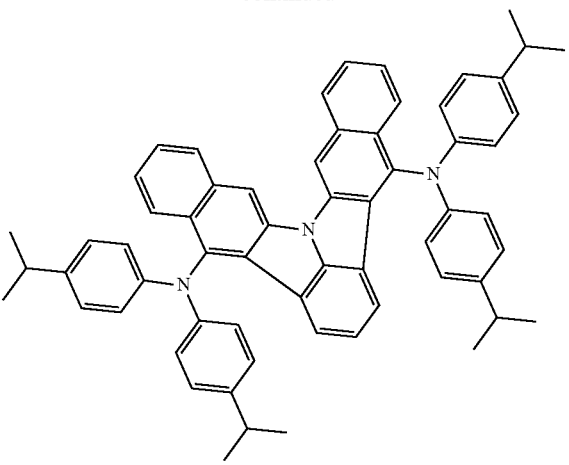
[Formula 293]
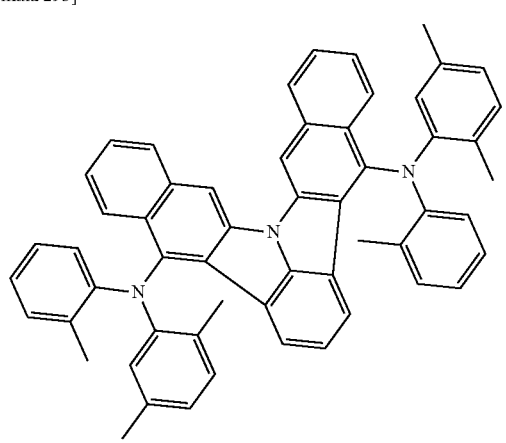

673
-continued
674
-continued
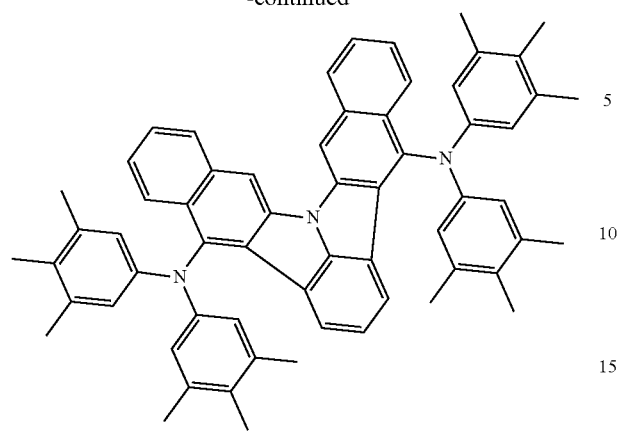
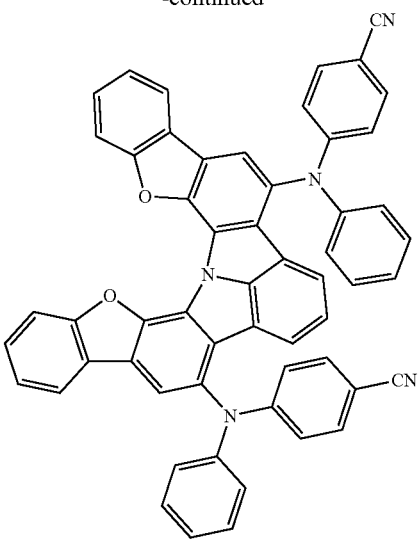
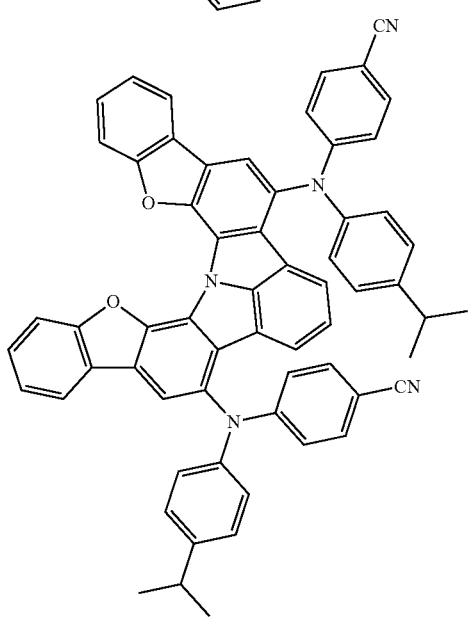
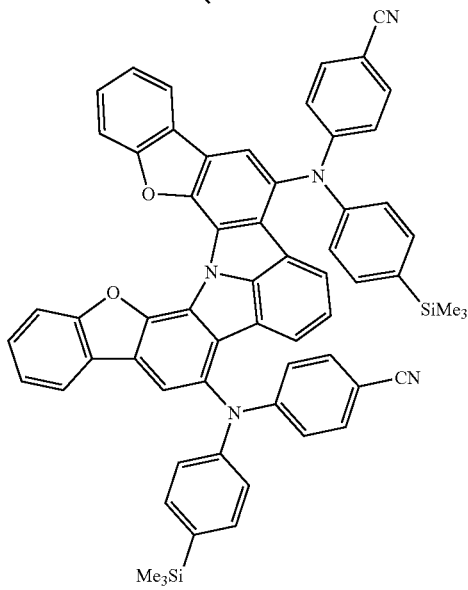

675
-continued
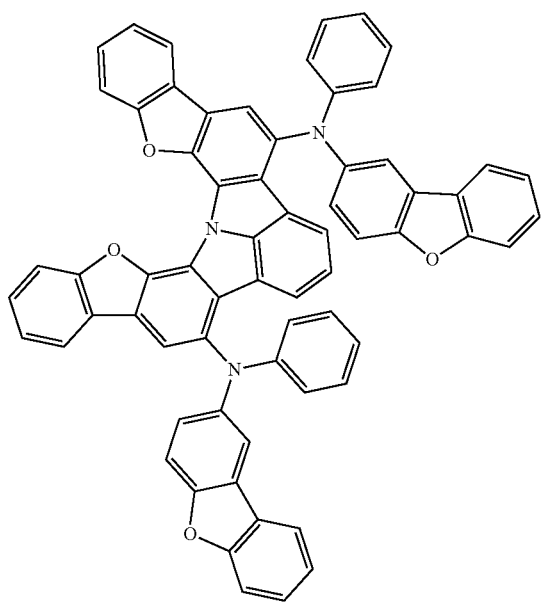
676
-continued
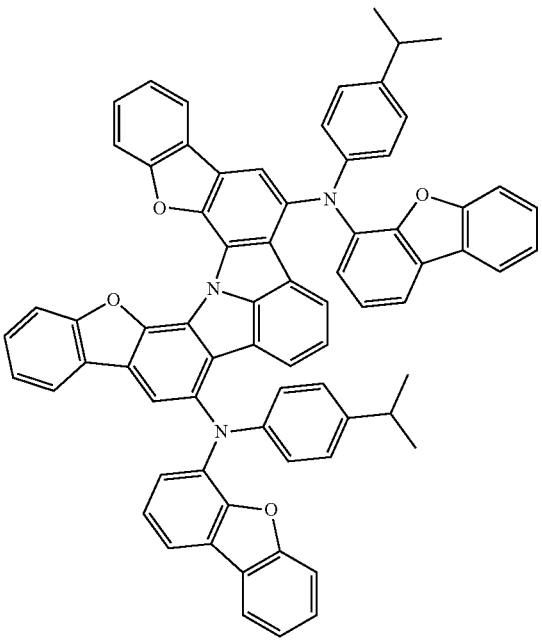
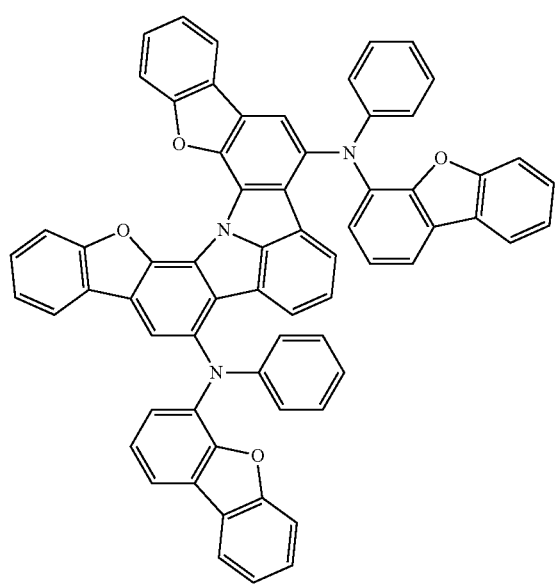
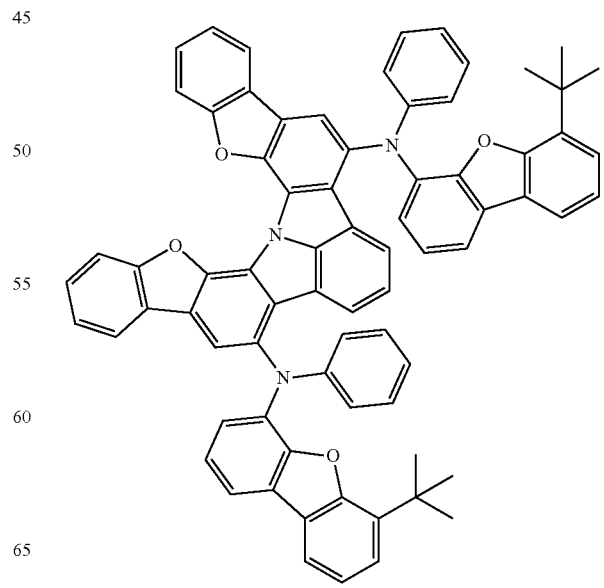

677
-continued
678
[Formula 294]
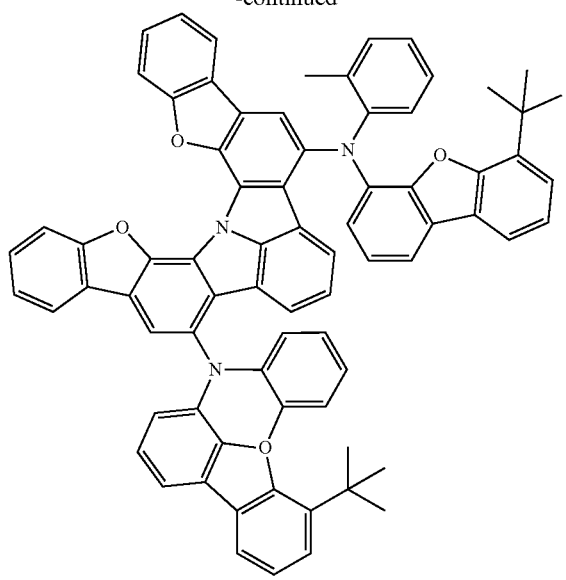
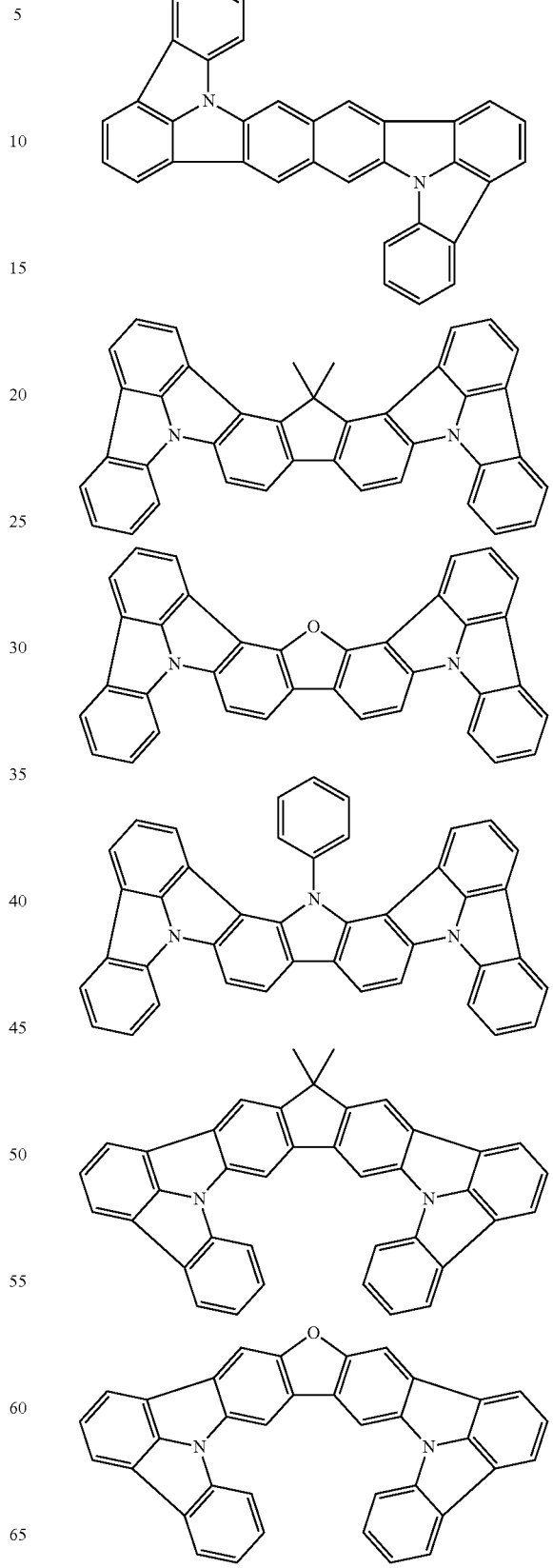

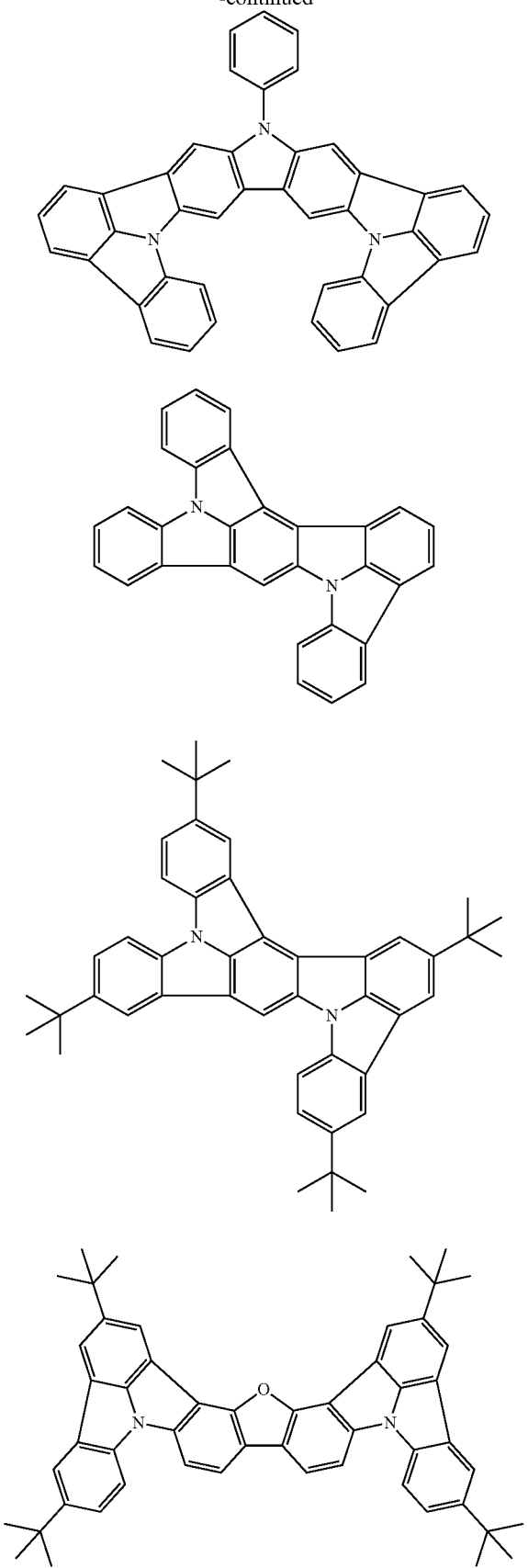

Compound Represented by Formula (5)

The compound represented by the formula (5) will be described below. The compound represented by the formula (5) corresponds to the compound represented by the above-described formula (41-3).

[Formula 295]

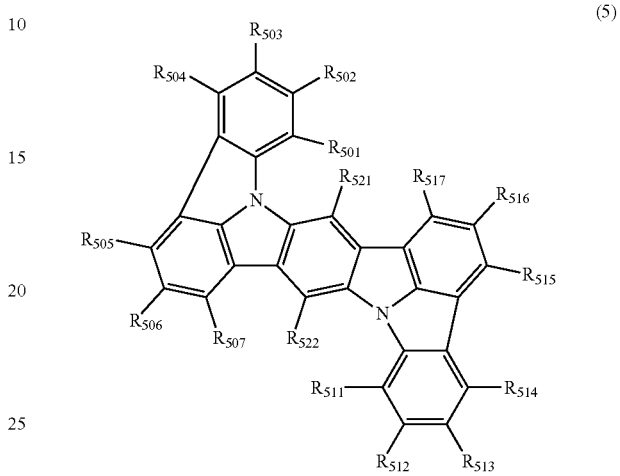

(5)

In the formula (5):

at least one combination of adjacent two or more of $R_{501}$ to $R_{507}$ and $R_{511}$ to $R_{517}$ are mutually bonded to form a substituted or unsubstituted monocyclic ring, mutually bonded to form a substituted or unsubstituted fused ring, or not mutually bonded;

$R_{501}$ to $R_{507}$ and $R_{511}$ to $R_{517}$ not forming the monocyclic ring and not forming the fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms; and $R_{521}$ and $R_{522}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

"A combination of adjacent two or more of $R_{501}$ to $R_{507}$ and $R_{511}$ to $R_{517}$" refers to, for instance, a combination of $R_{501}$ and $R_{502}$, a combination of $R_{502}$ and $R_{503}$, a combination of $R_{503}$ and $R_{504}$, a combination of $R_{505}$ and $R_{506}$, a combination of $R_{506}$ and $R_{507}$, and a combination of $R_{501}$, $R_{502}$, and $R_{503}$.

In an exemplary embodiment, at least one, preferably two of $R_{501}$ to $R_{507}$ and $R_{511}$ to $R_{517}$ are groups represented by —N($R_{906}$)($R_{907}$).

In an exemplary embodiment, $R_{501}$ to $R_{507}$ and $R_{511}$ to $R_{517}$ are each independently a hydrogen atom, a substituted or unsubstituted aryl group having 6 to 50 ring carbon atoms, or a substituted or unsubstituted heterocyclic group having 5 to 50 ring atoms.

In an exemplary embodiment, the compound represented by the formula (5) is represented by a formula (52) below.

[Formula 296]

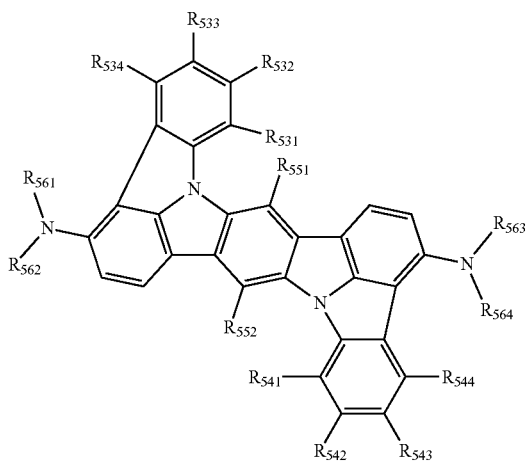

(52)

In the formula (52):
at least one combination of adjacent two or more of $R_{531}$ to $R_{534}$ and $R_{541}$ to $R_{544}$ are mutually bonded to form a substituted or unsubstituted monocyclic ring, mutually bonded to form a substituted or unsubstituted fused ring, or not mutually bonded;

$R_{531}$ to $R_{534}$, $R_{541}$ to $R_{544}$, and $R_{551}$ and $R_{552}$ not forming the monocyclic ring and not forming the fused ring are each independently a hydrogen atom, a substituted or unsubstituted aryl group having 6 to 50 ring carbon atoms, or a substituted or unsubstituted heterocyclic group having 5 to 50 ring atoms; and $R_{561}$ to $R_{564}$ are each independently a substituted or unsubstituted aryl group having 6 to 50 ring carbon atoms, or a substituted or unsubstituted heterocyclic group having 5 to 50 ring atoms.

In an exemplary embodiment, the compound represented by the formula (5) is represented by a formula (53) below.

[Formula 297]

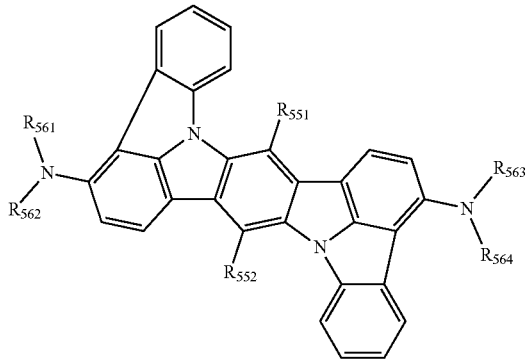

(53)

In the formula (53), $R_{551}$, $R_{552}$, and $R_{561}$ to $R_{564}$ each independently represent the same as $R_{551}$, $R_{552}$, and $R_{561}$ to $R_{564}$ in the formula (52).

In an exemplary embodiment, $R_{561}$ to $R_{564}$ in the formulae (52) and (53) are each independently a substituted or unsubstituted aryl group having 6 to 50 ring carbon atoms (preferably a phenyl group).

In an exemplary embodiment, $R_{521}$ and $R_{522}$ in the formula (5), and $R_{551}$ and $R_{552}$ in the formulae (52) and (53) are each a hydrogen atom.

In an exemplary embodiment, a substituent for the substituted or unsubstituted group in the formulae (5), (52) and (53) is a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

Specific examples of the compound represented by the formula (5) include compounds shown below.

[Formula 298]

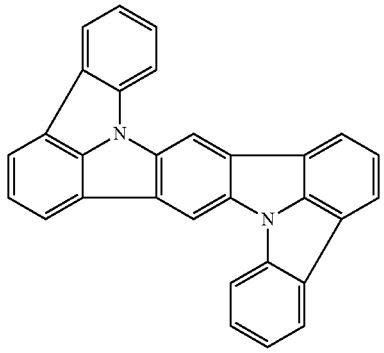

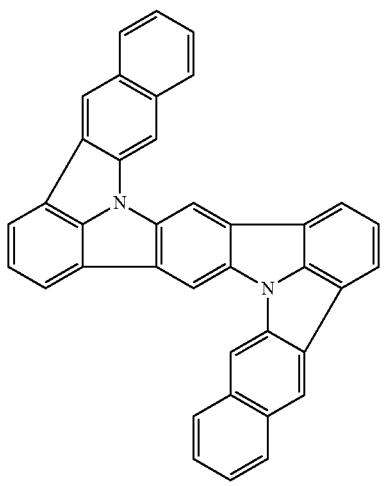

683
-continued
684
-continued
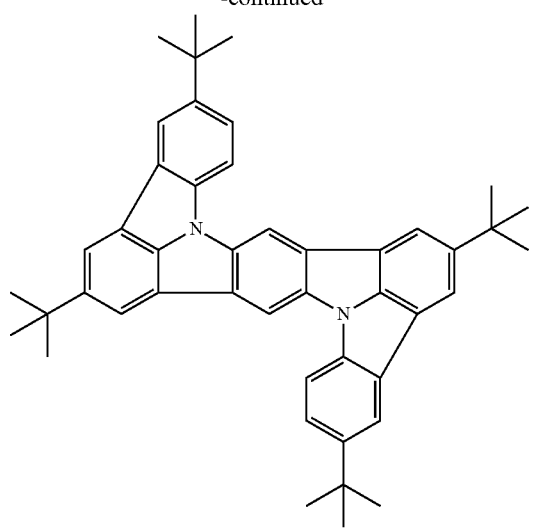
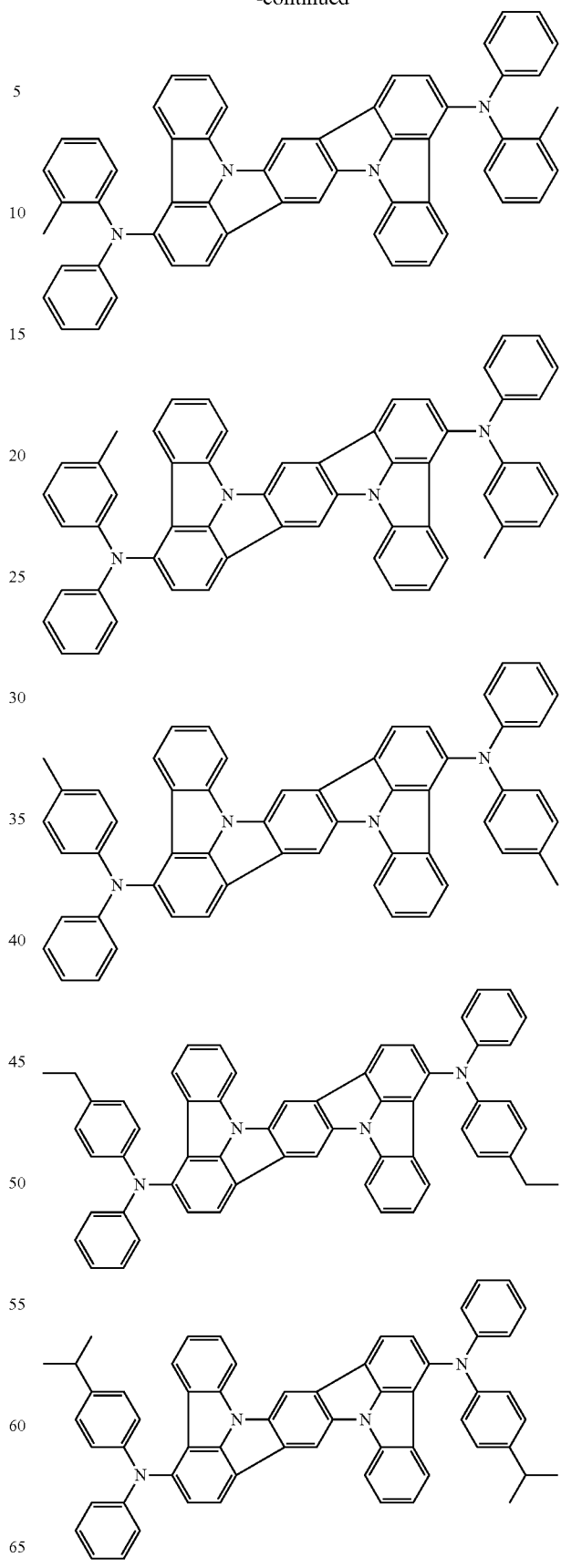

[Formula 299]
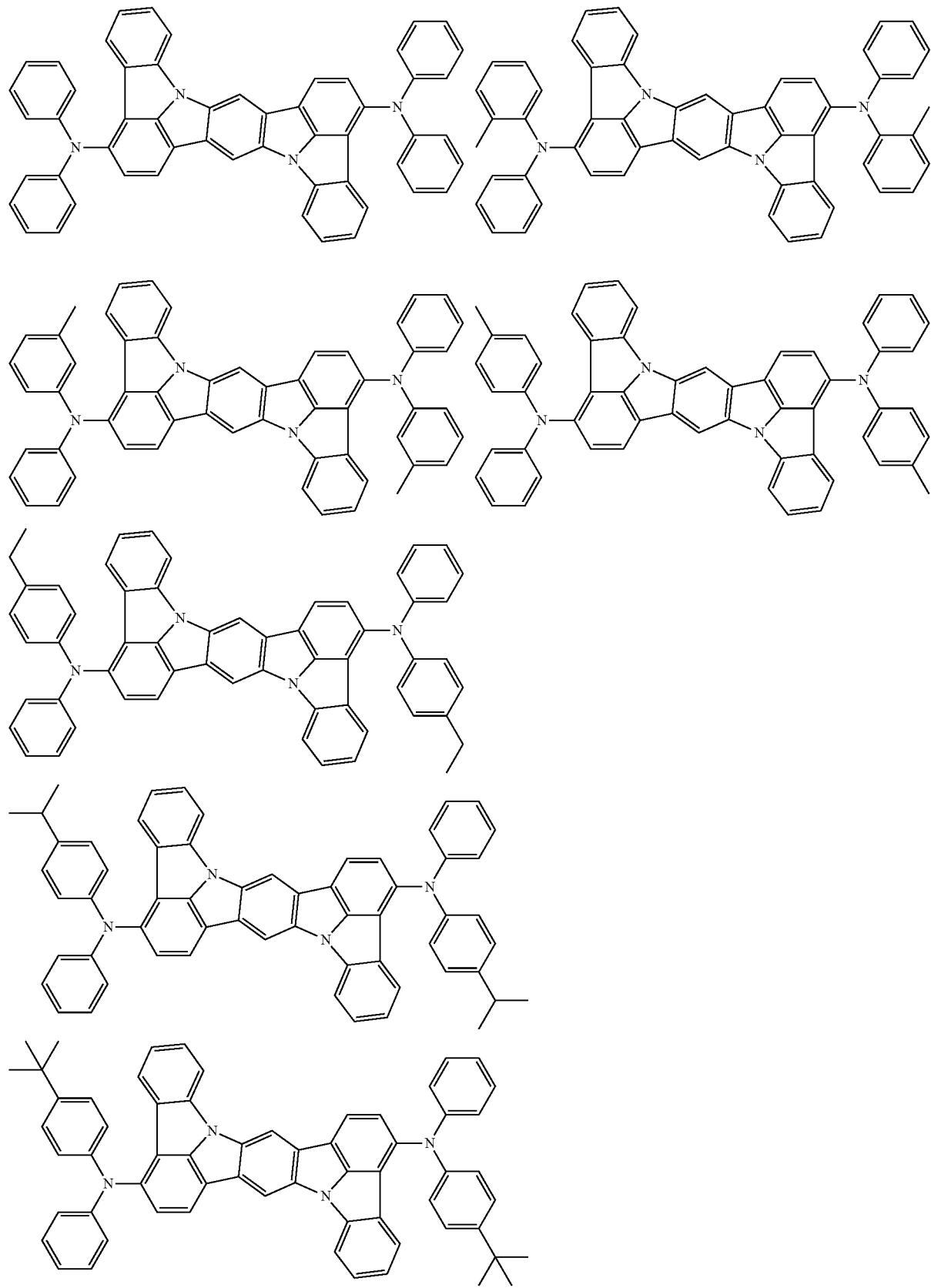

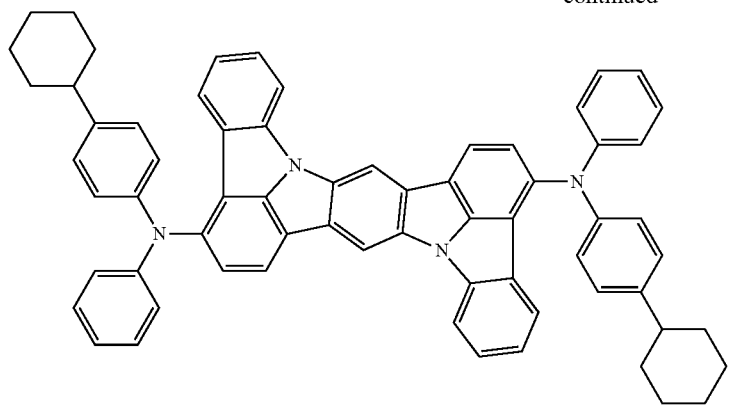
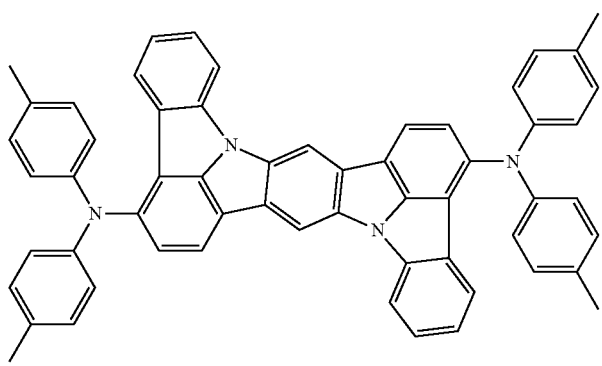
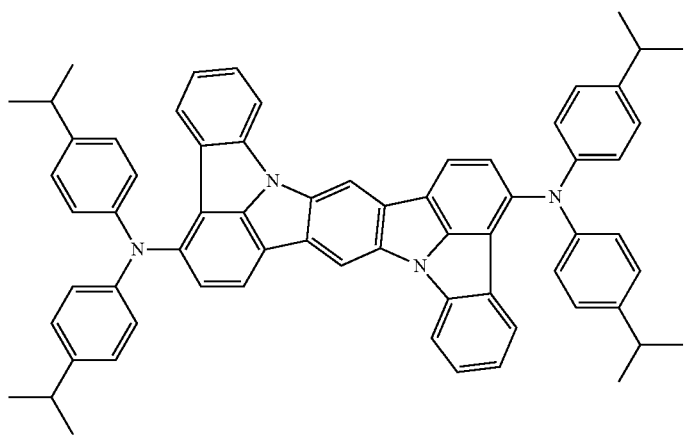
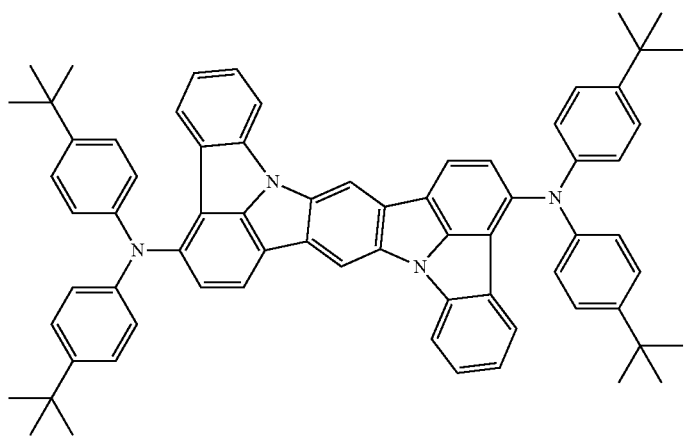

689
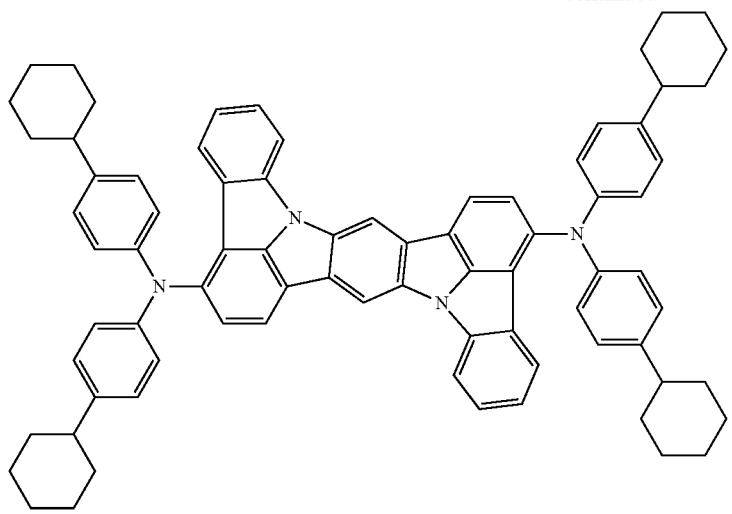
690
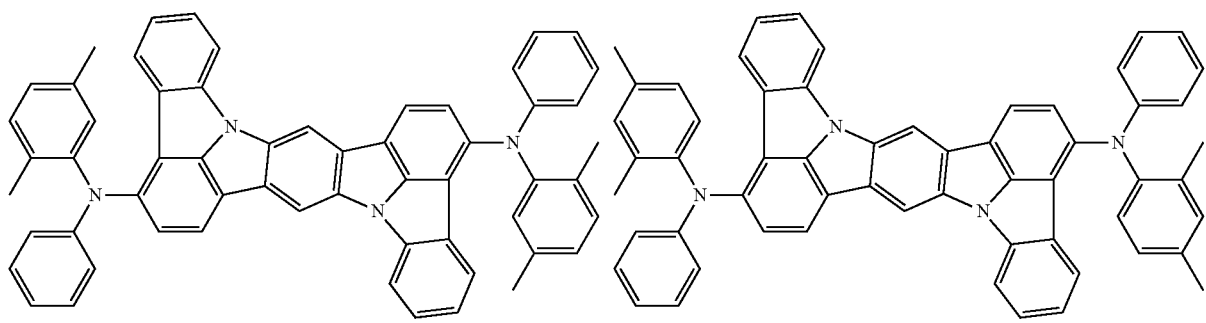
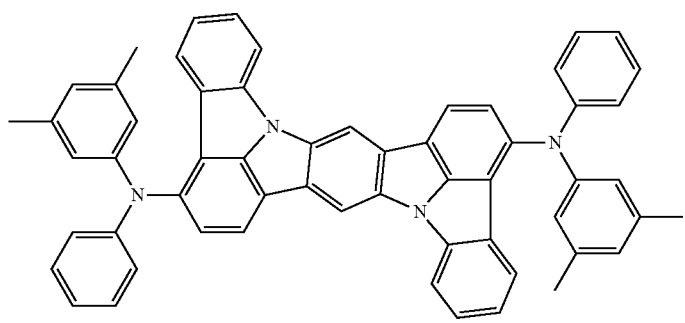
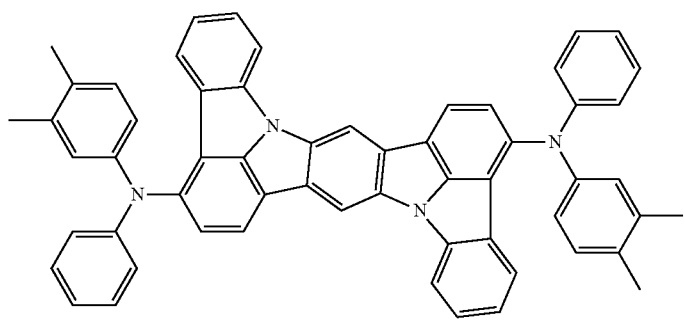

-continued
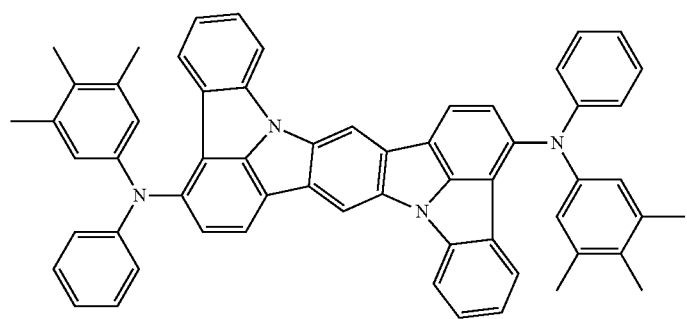
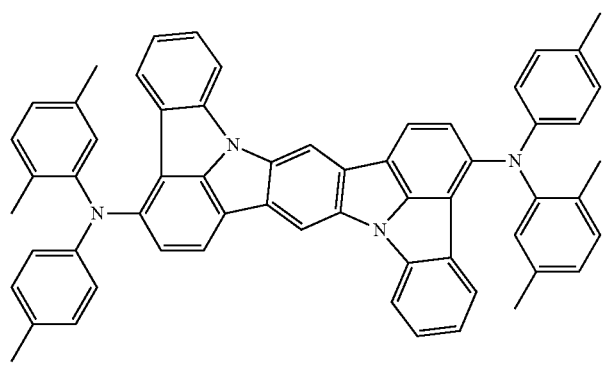
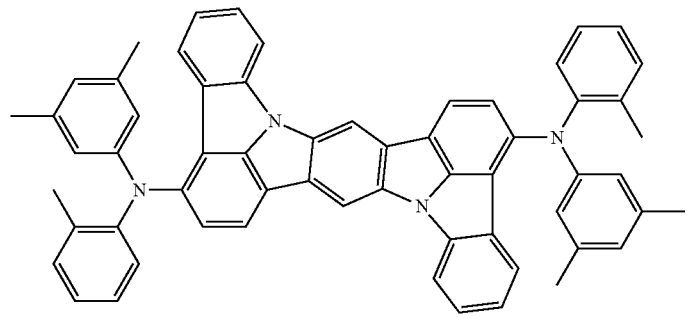
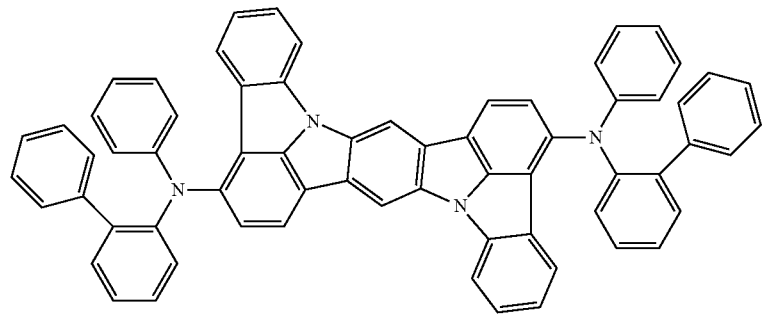
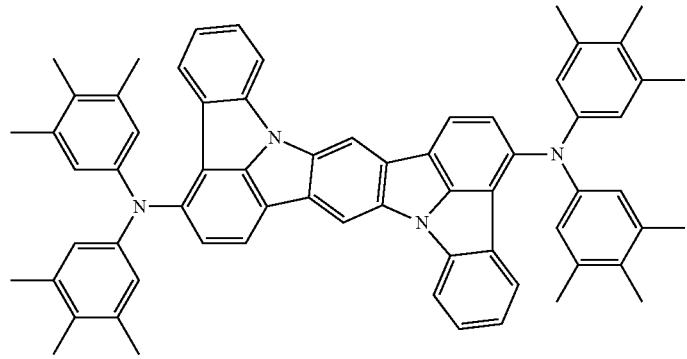

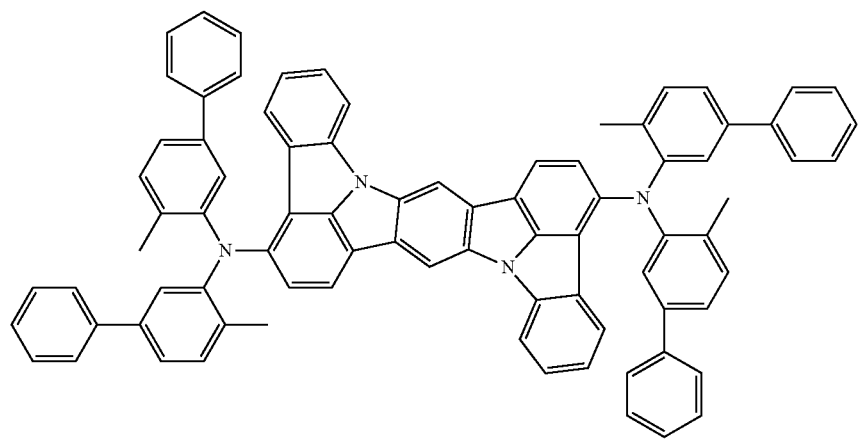
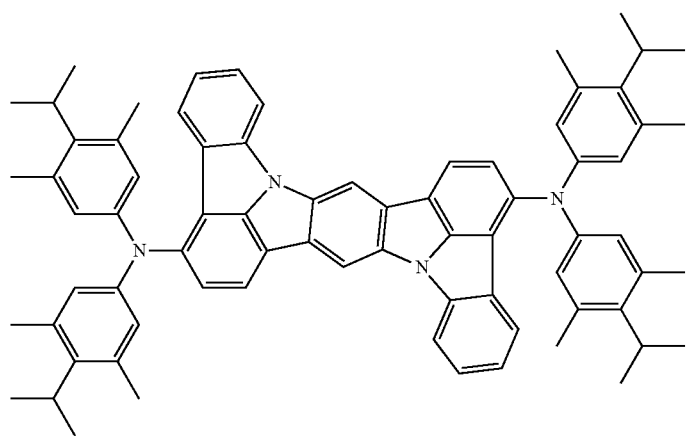
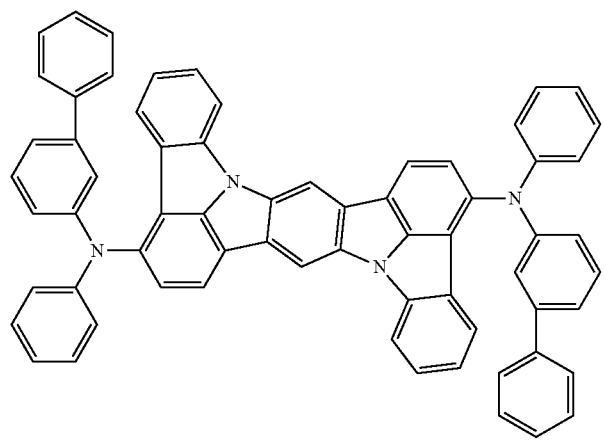

[Formula 300]
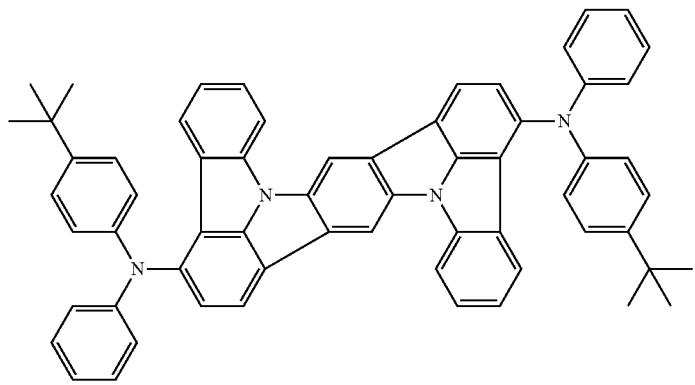 [SMILES: CC(C)c1ccc(N(c2ccccc2)c2ccc3c4cc5c(cc4n4c6ccccc6c2c34)c2ccc(N(c3ccccc3)c3ccc(C(C)C)cc3)c3c4ccccc4n5c23)cc1]
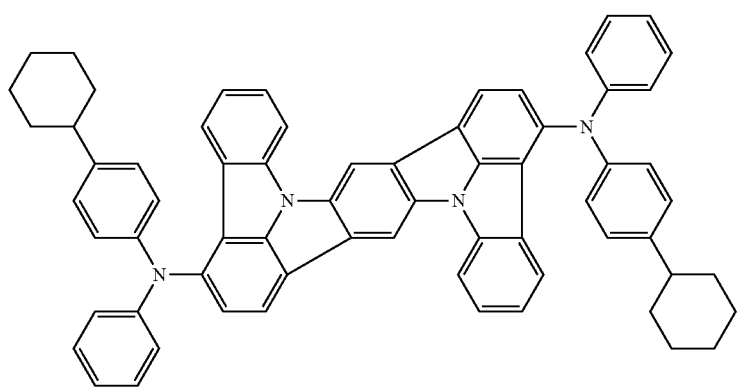
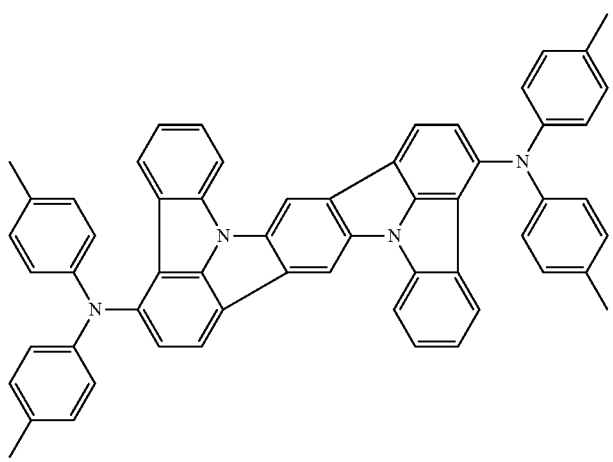
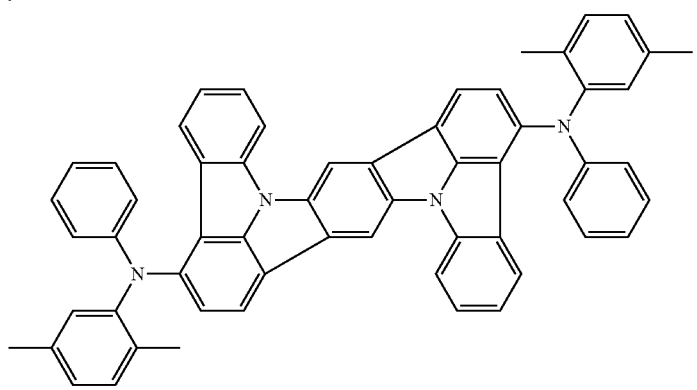

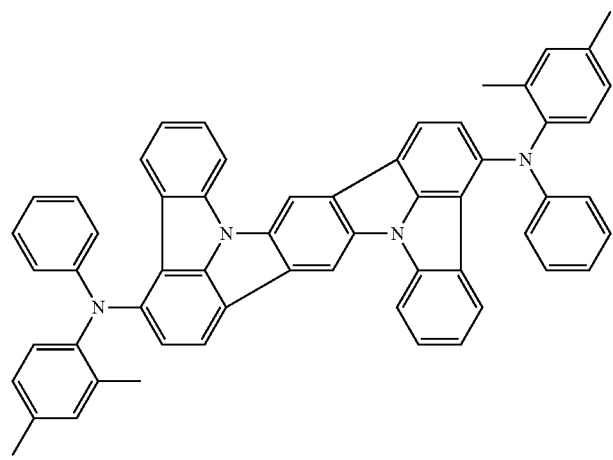
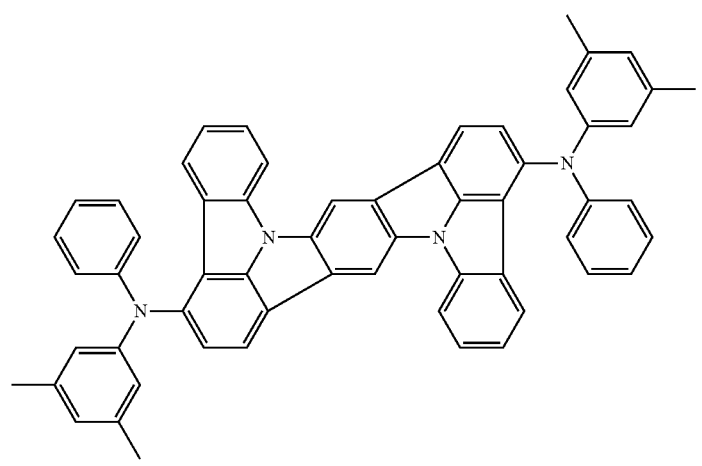
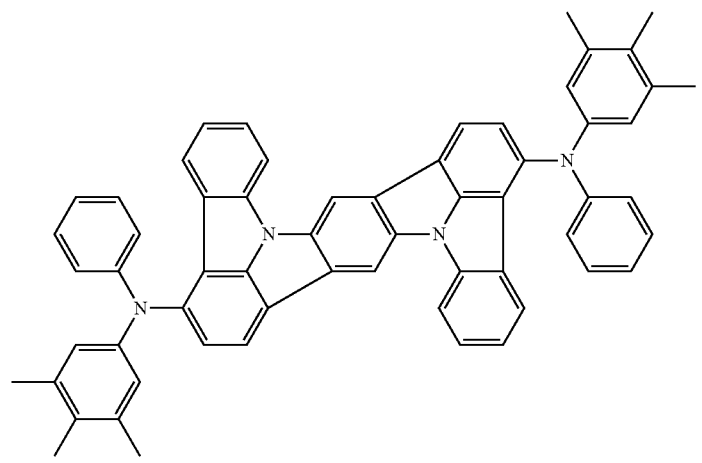

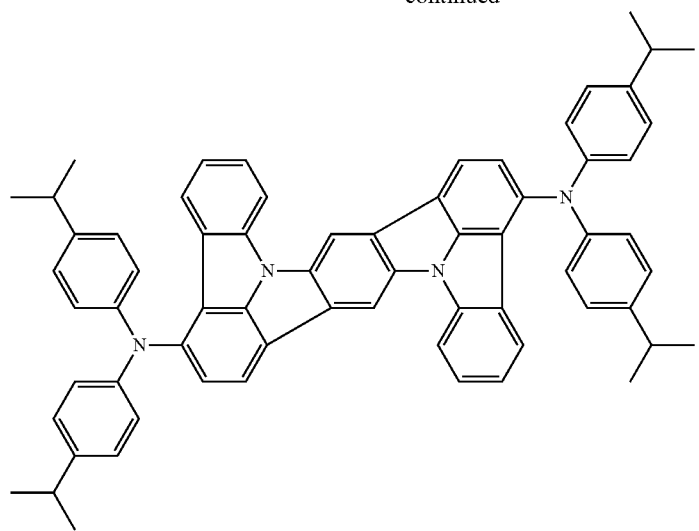
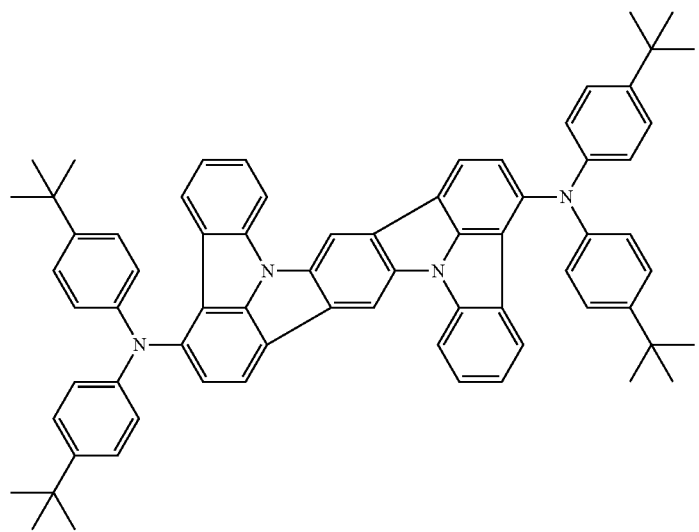
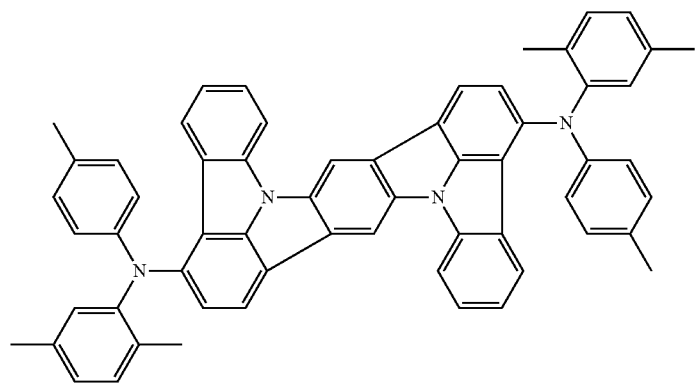

-continued
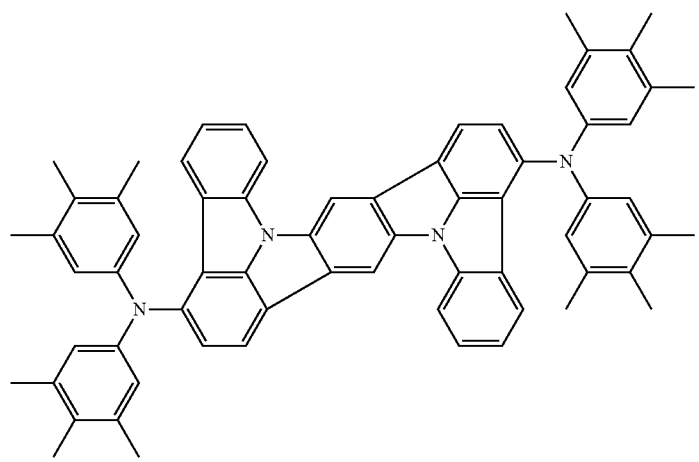
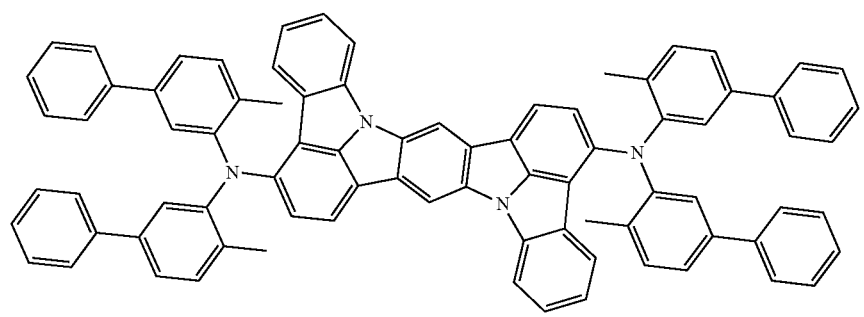
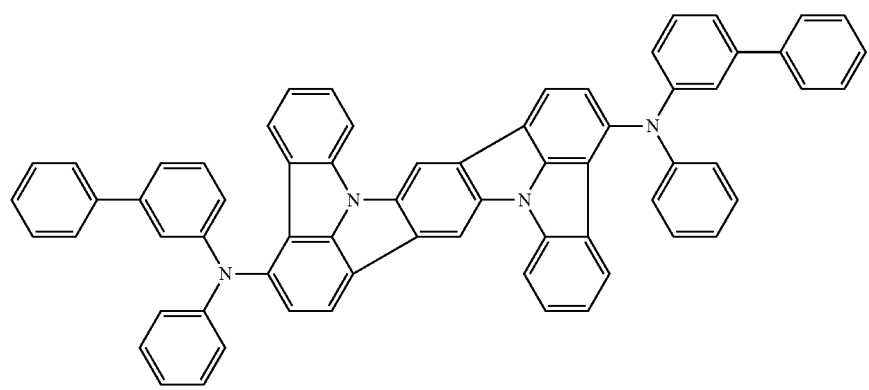
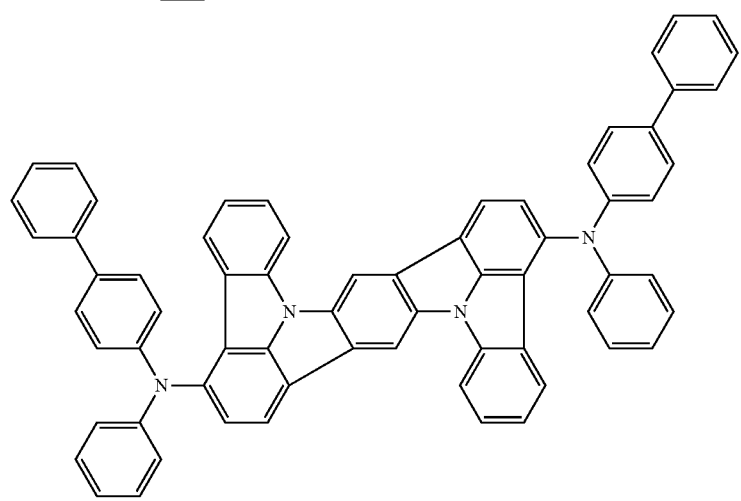

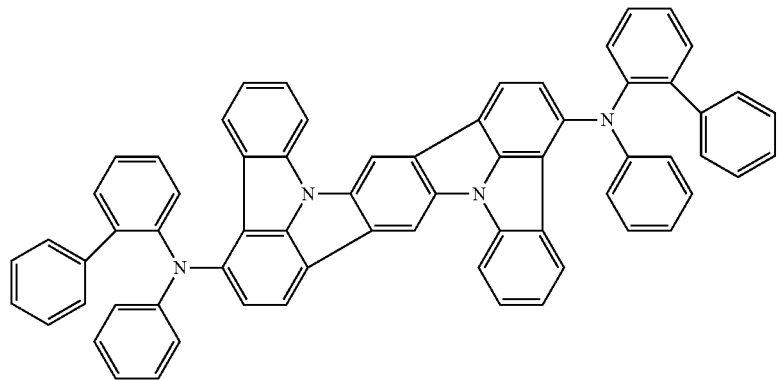
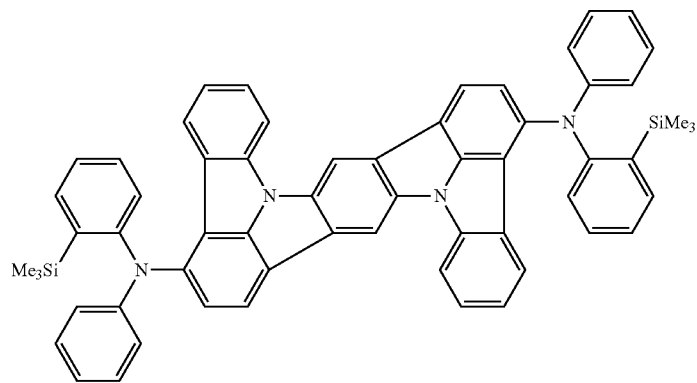
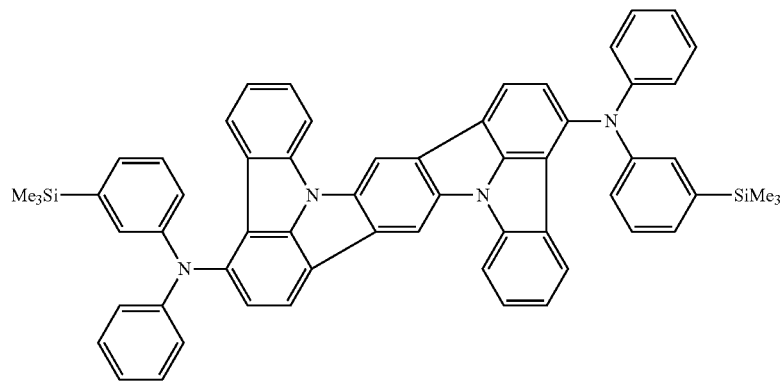
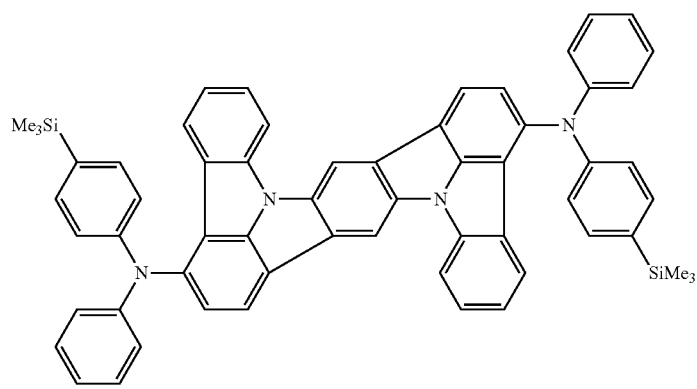

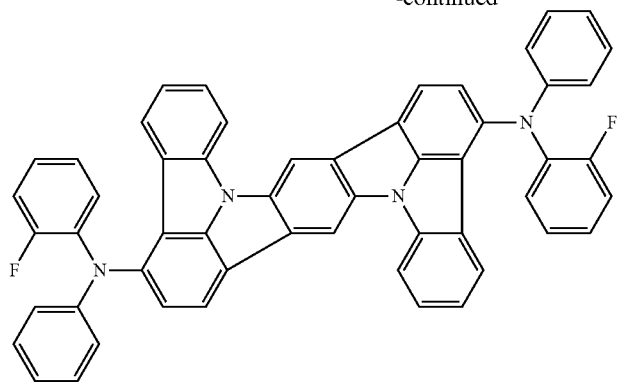
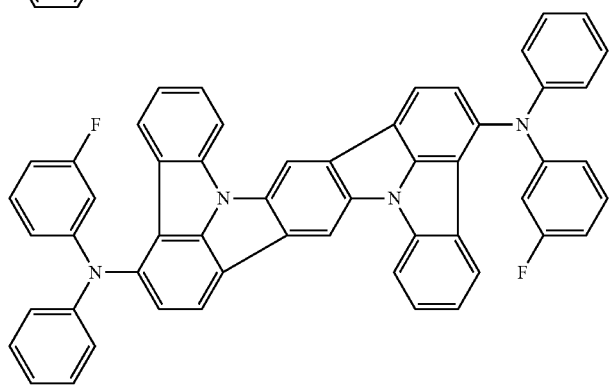
[Formula 301]
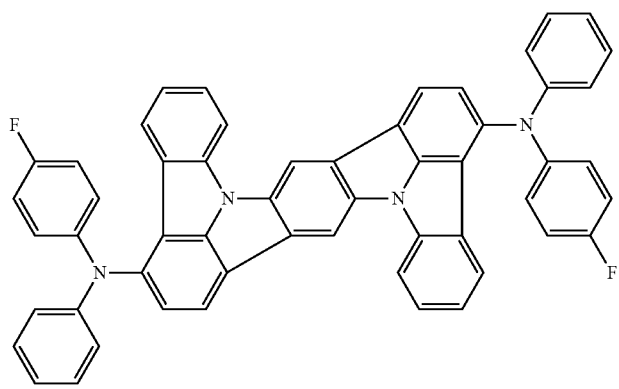
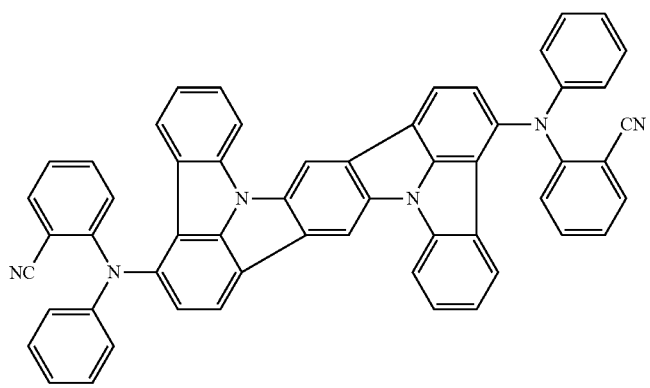

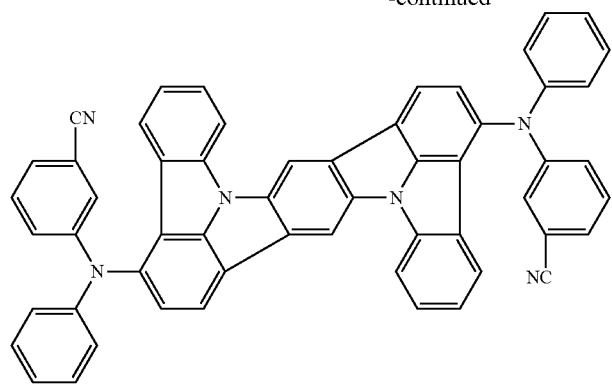
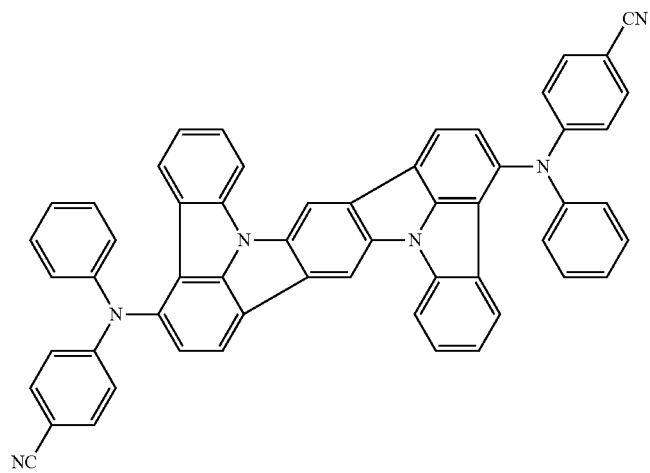
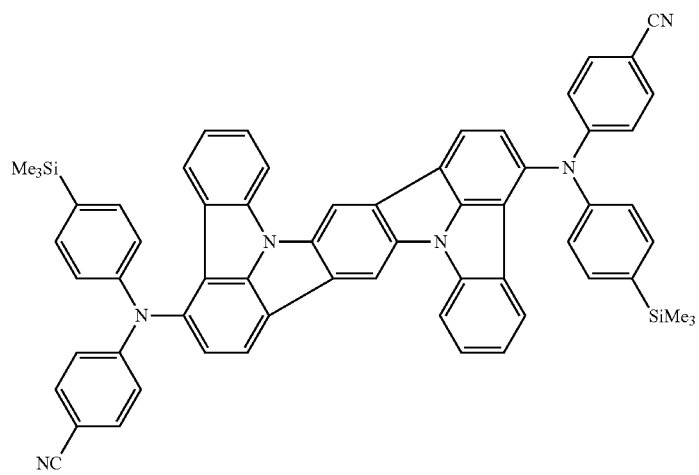

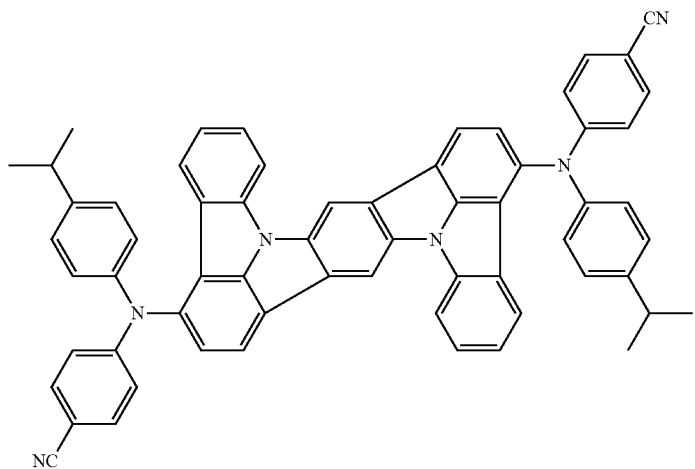
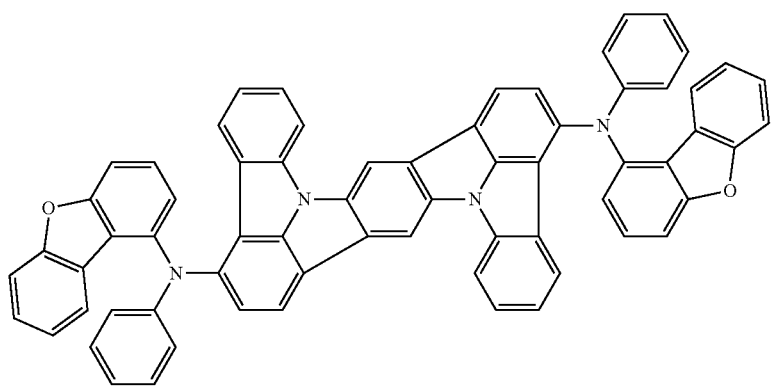
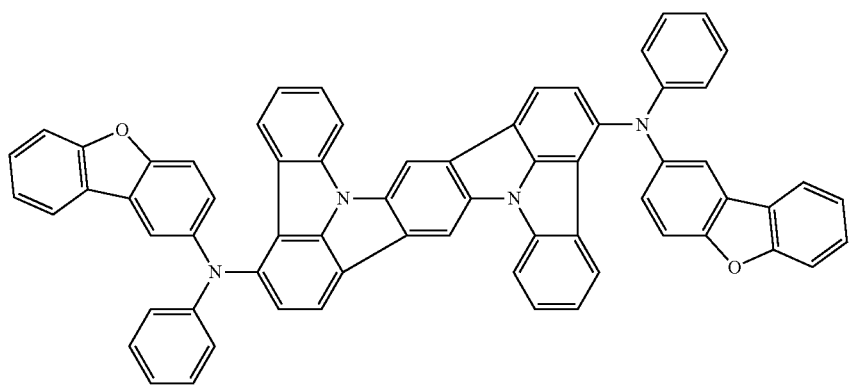
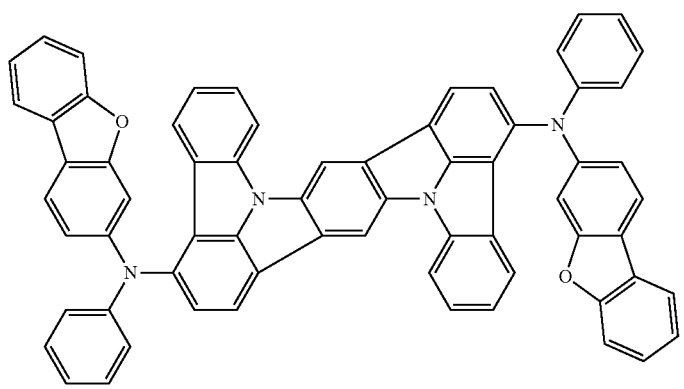

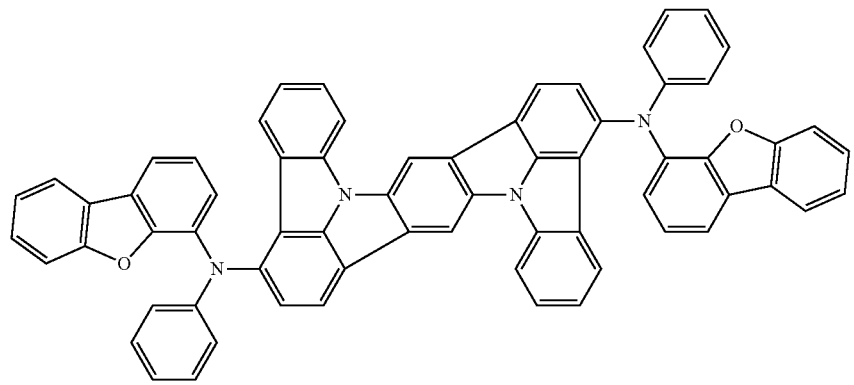
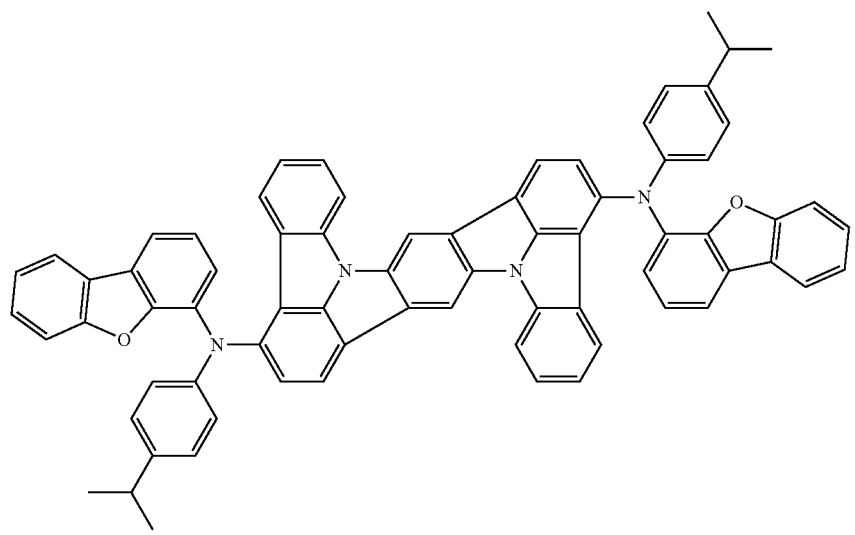
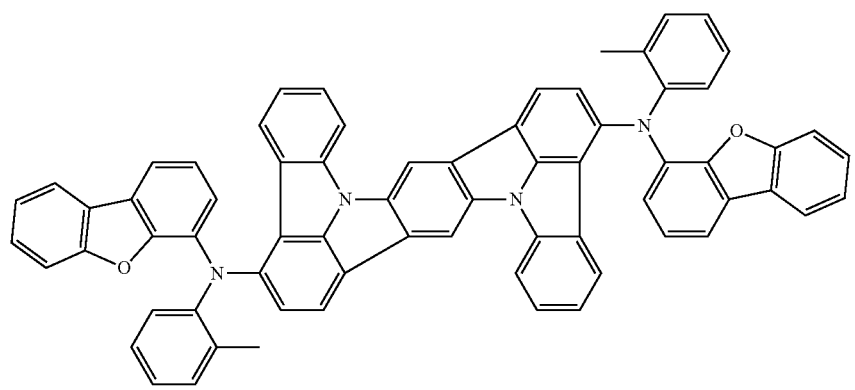

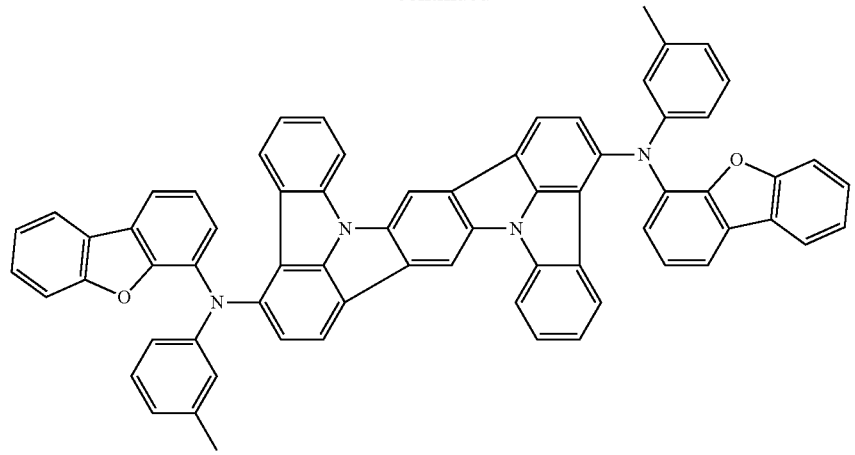
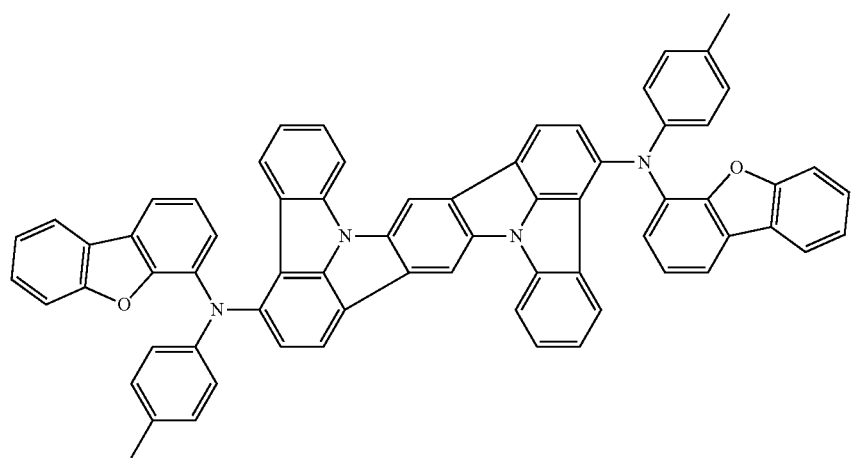
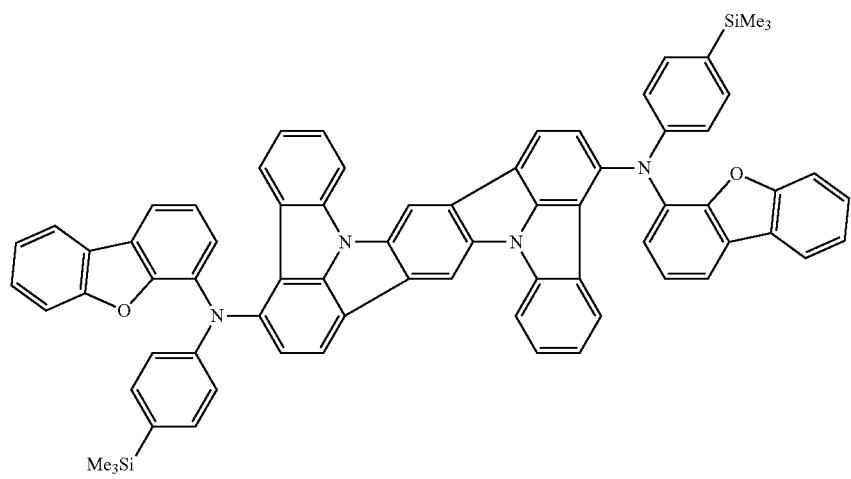

-continued
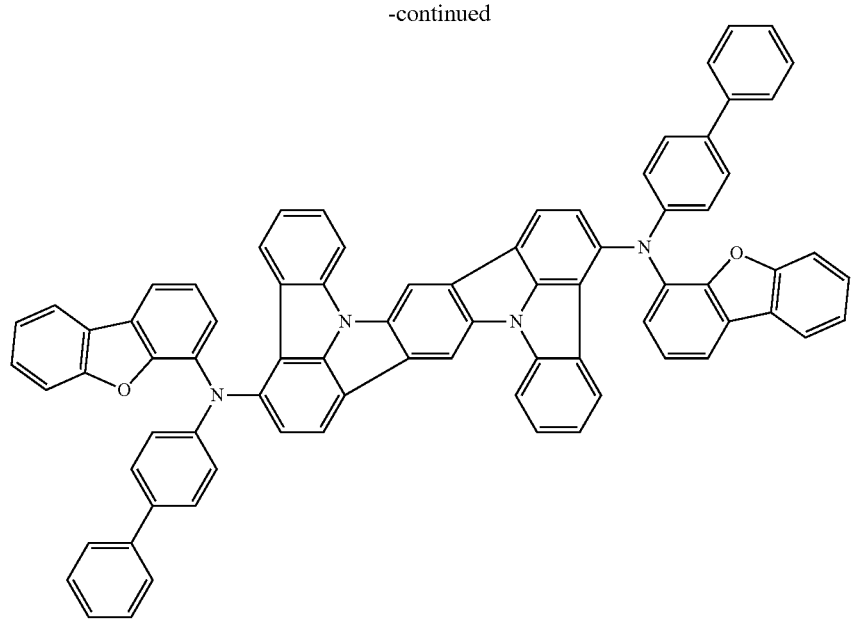
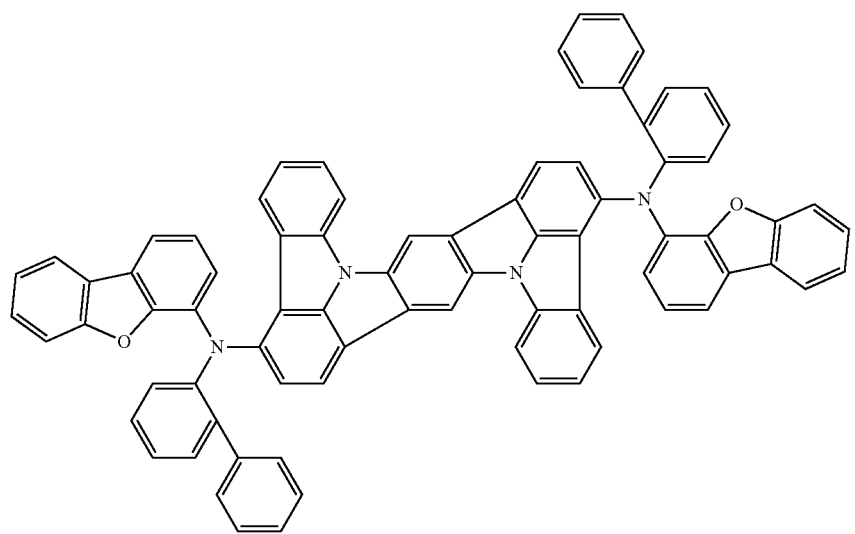
[Formula 302]
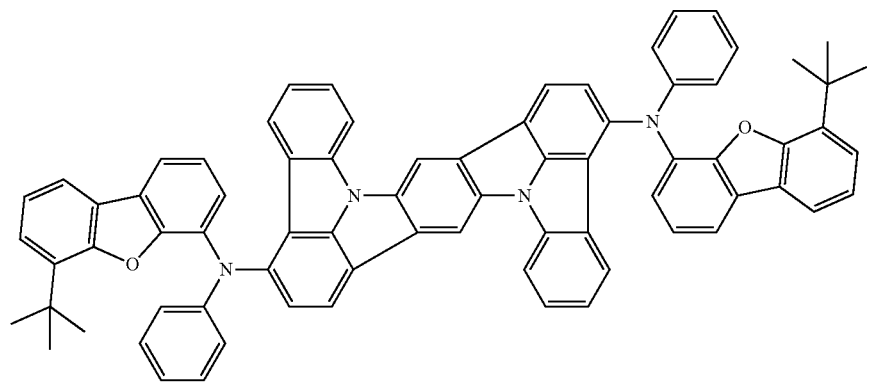

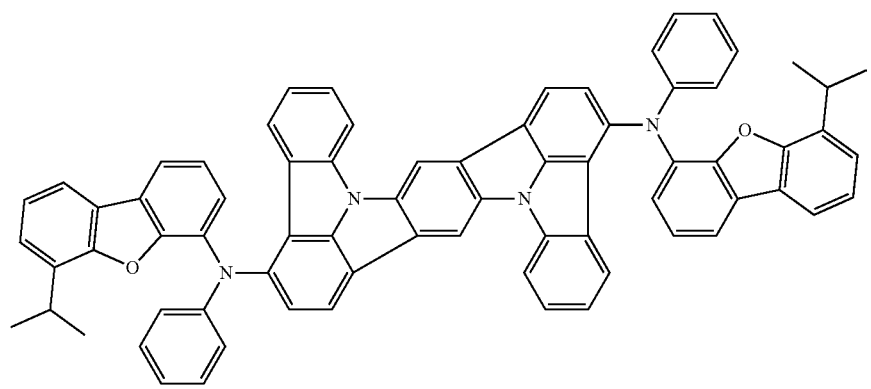
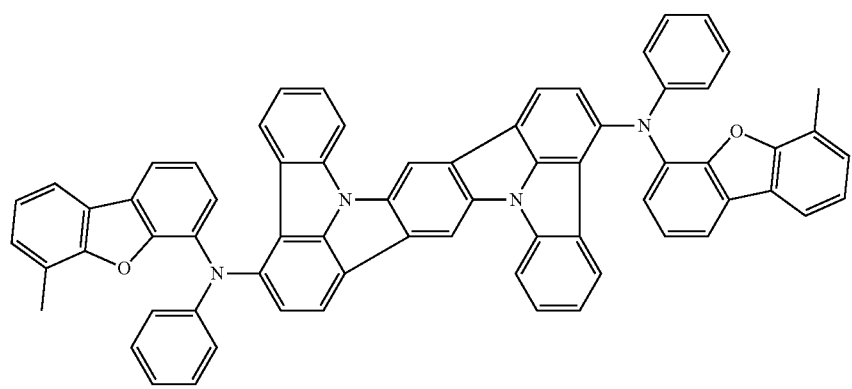
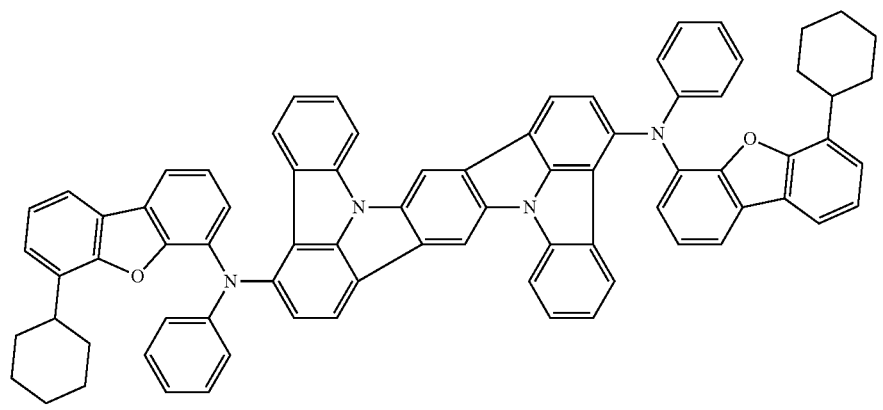
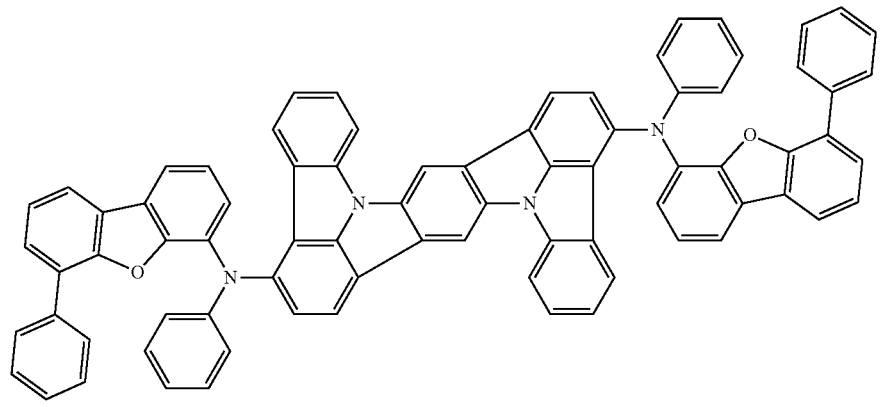

-continued
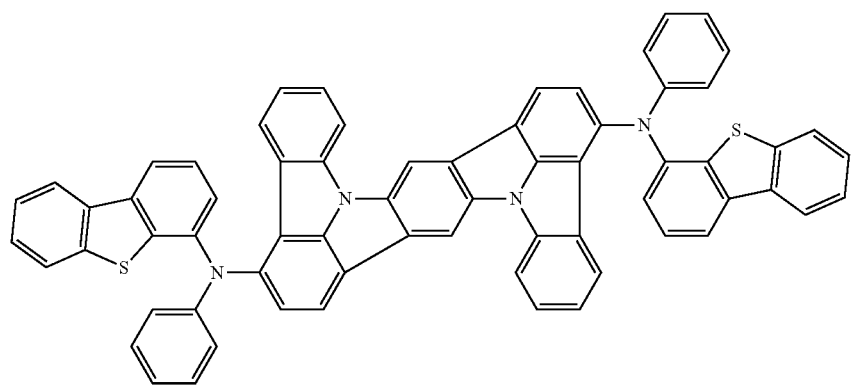
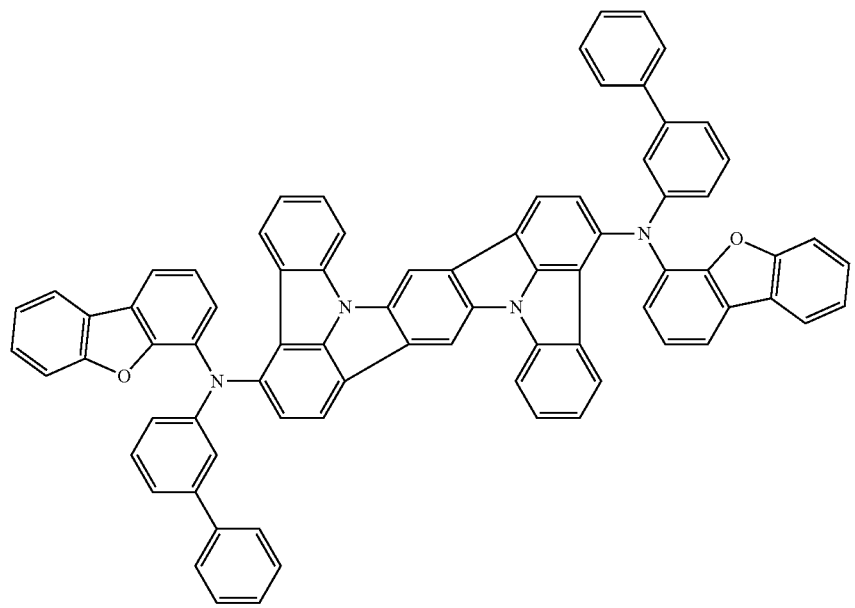
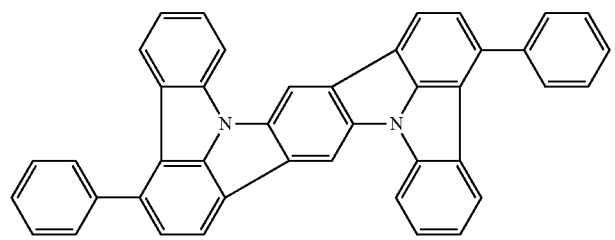
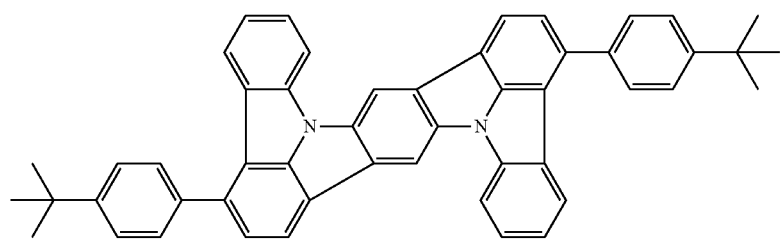
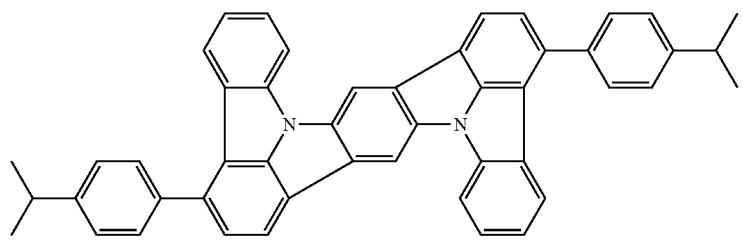

-continued
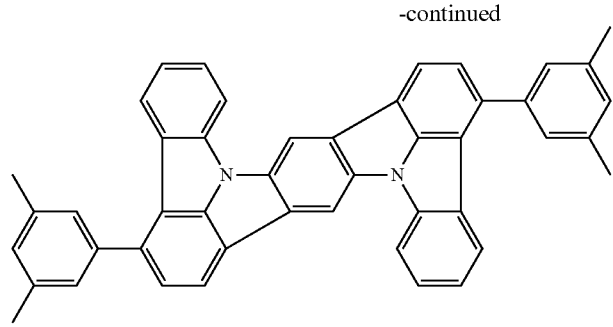
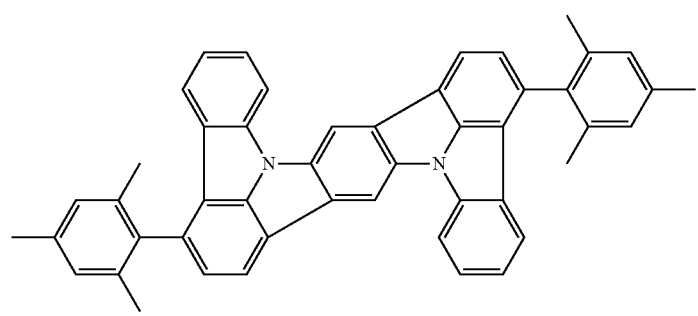
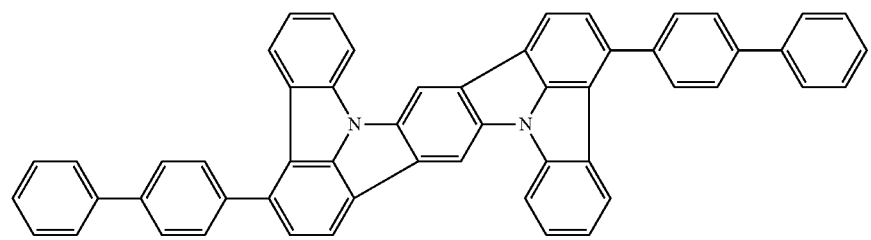
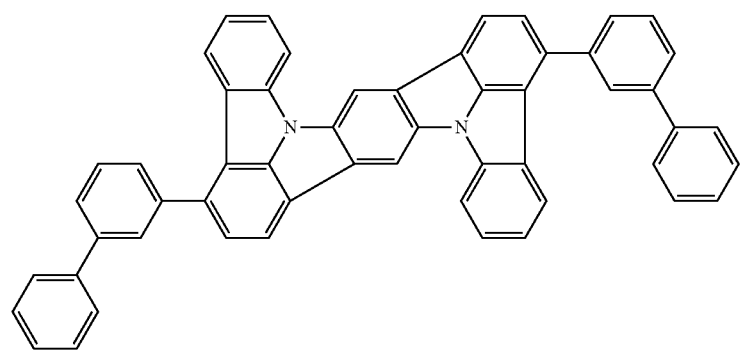
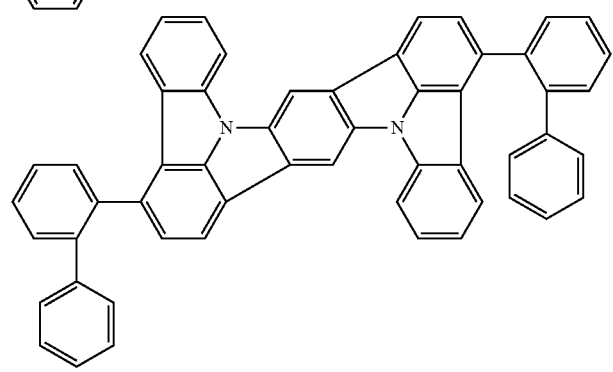

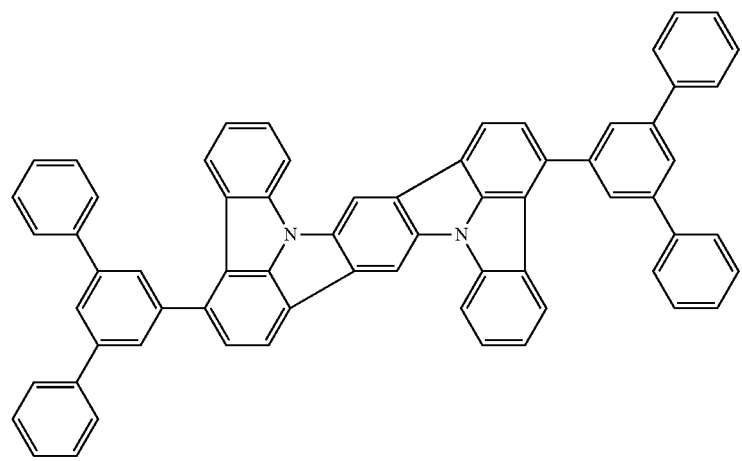
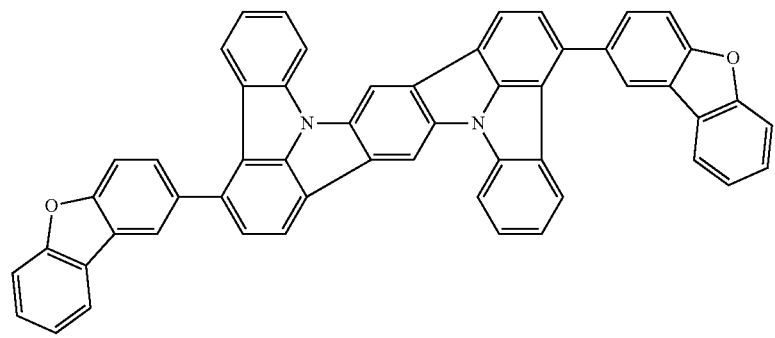
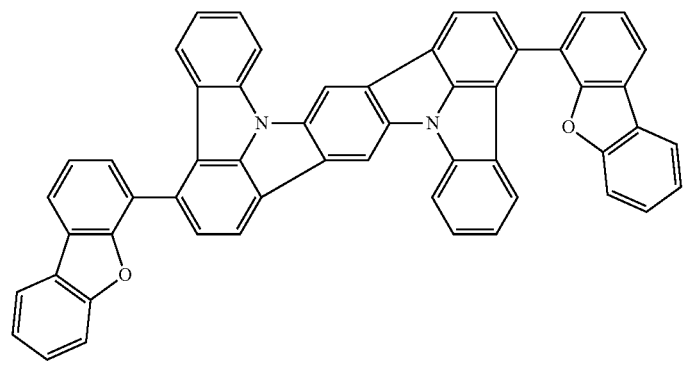
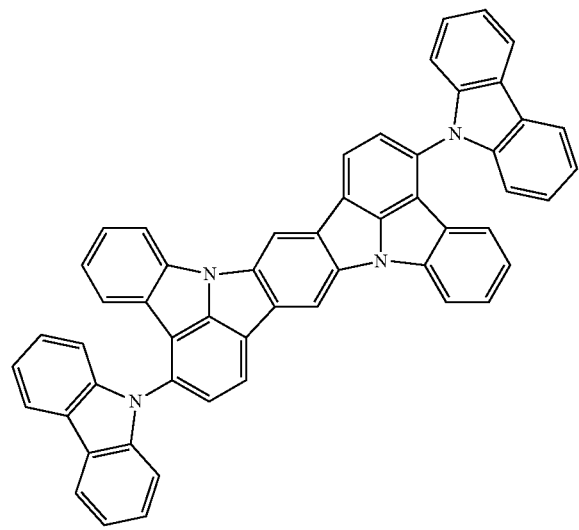 [SMILES: c1ccc2c(c1)c1ccccc1n2-c1ccc2c3cc4c(cc3n3c5ccccc5c1c23)c1ccc(-n2c3ccccc3c3ccccc32)c2c3ccccc3n4c12]

[Formula 303]
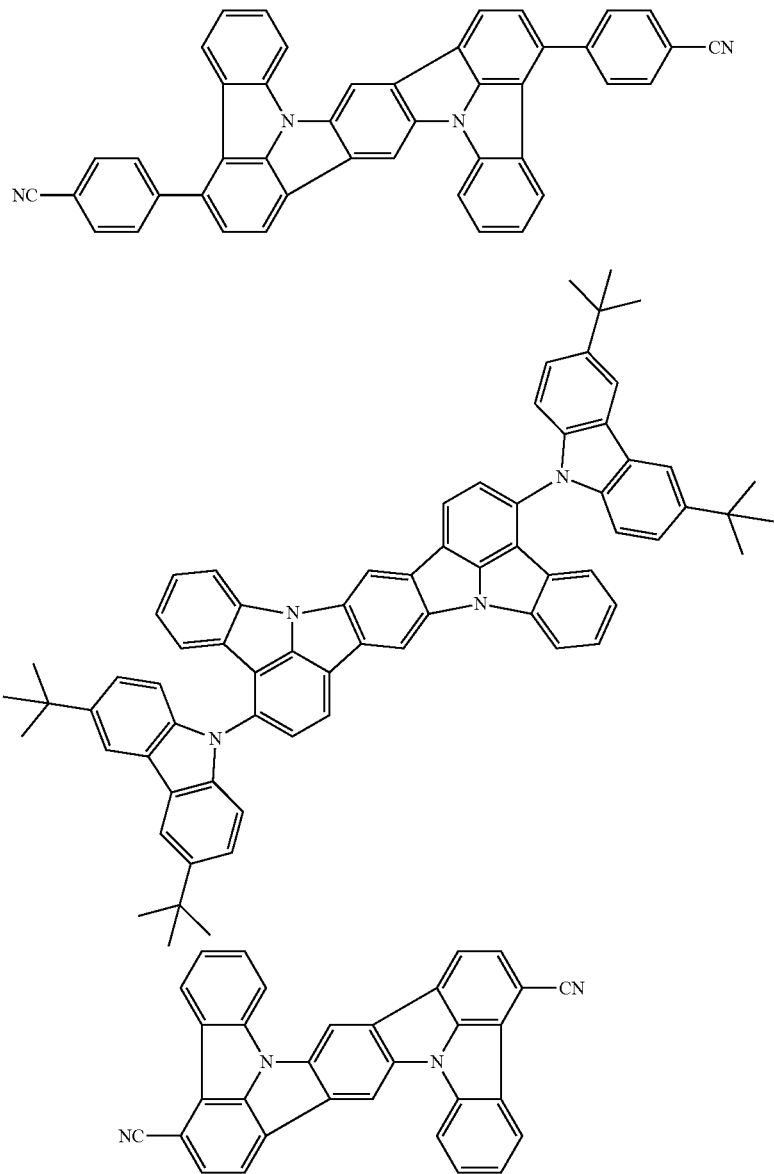
[Formula 304]
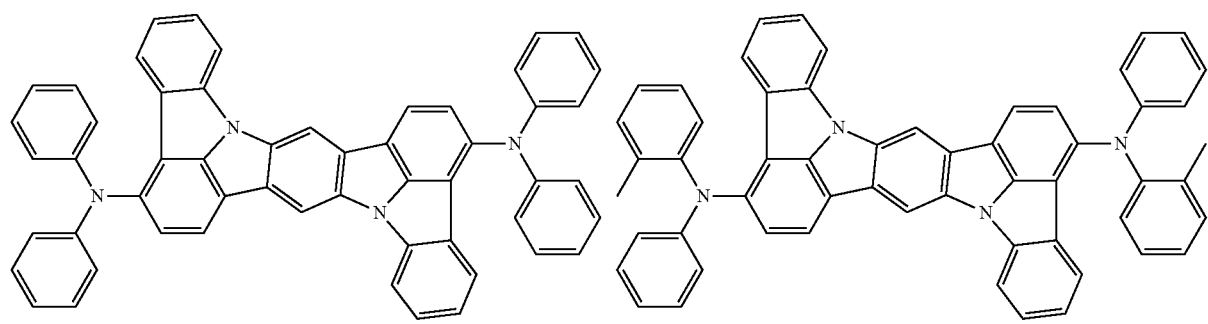

727 728
-continued
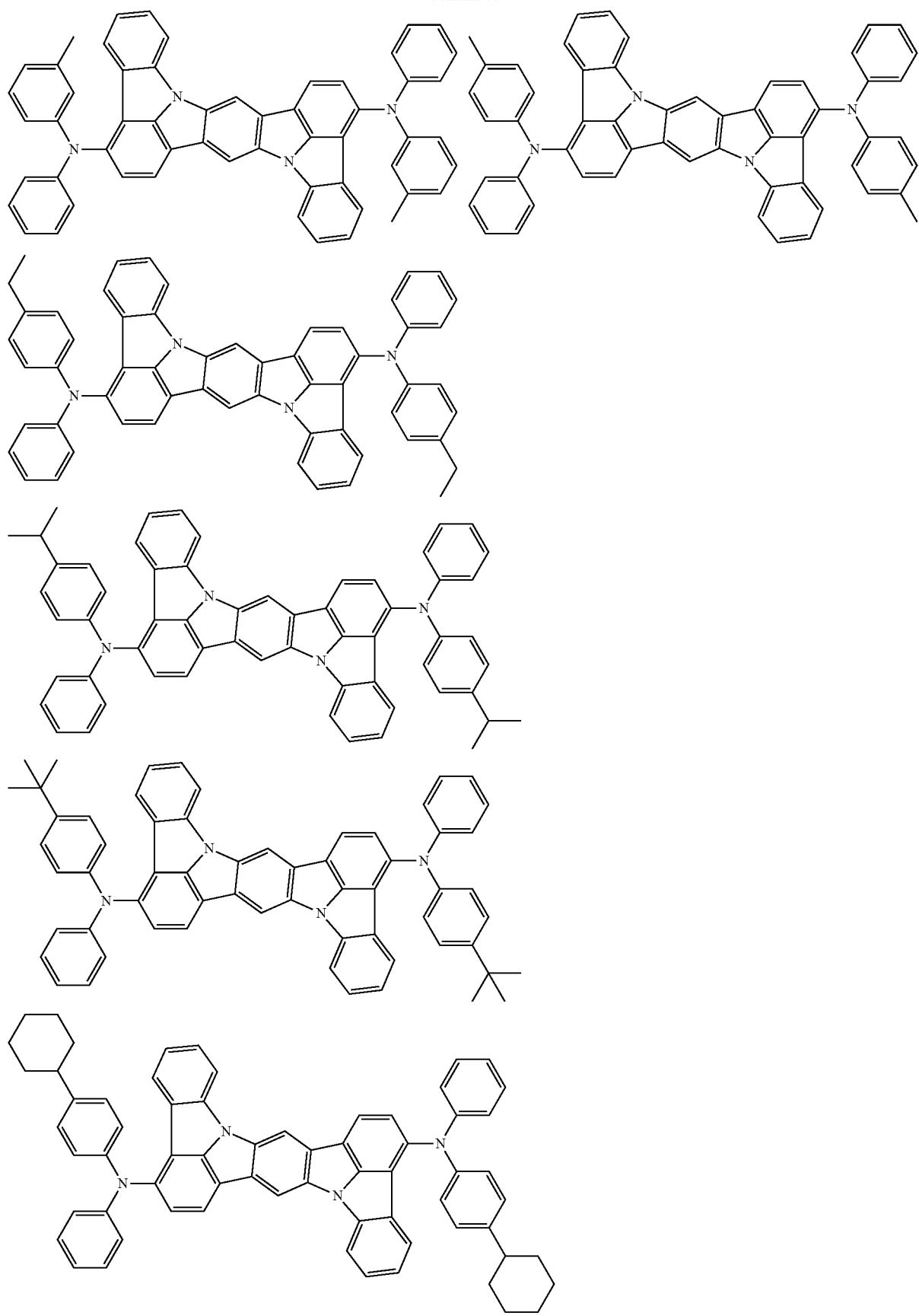

-continued
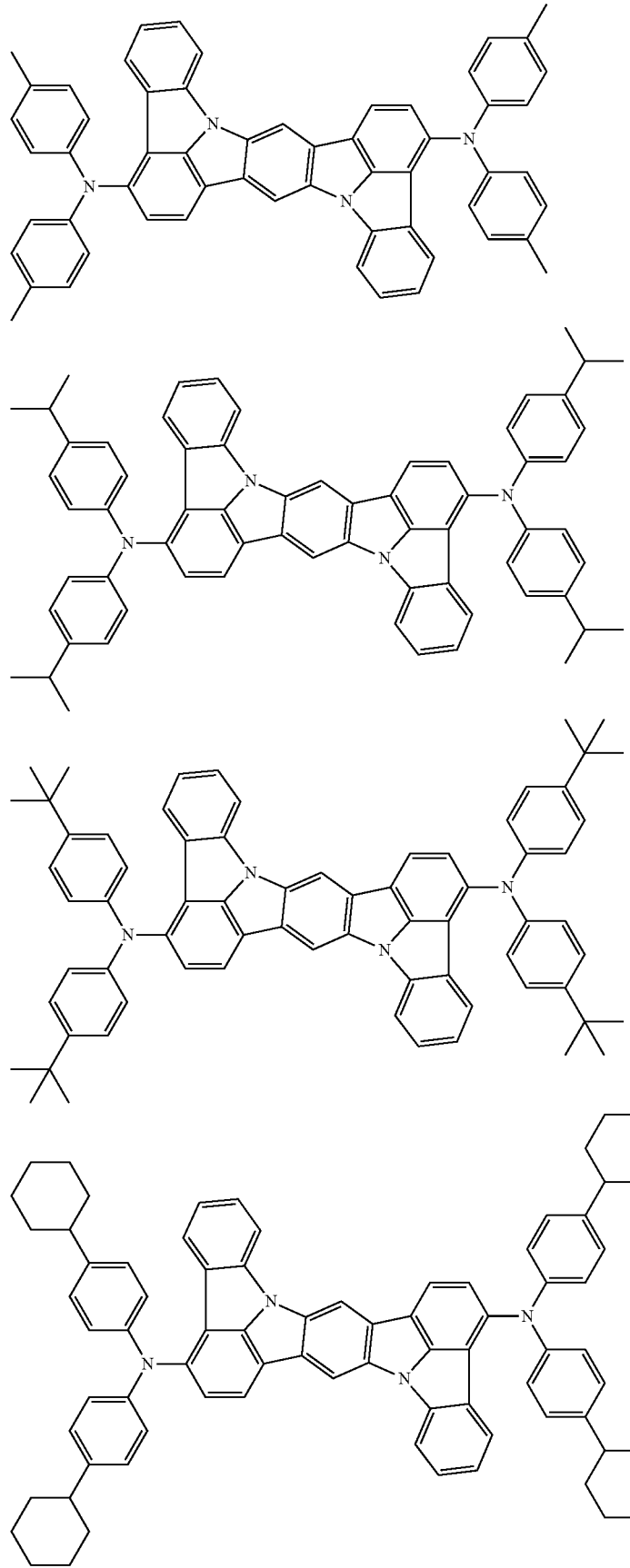

731 732
-continued
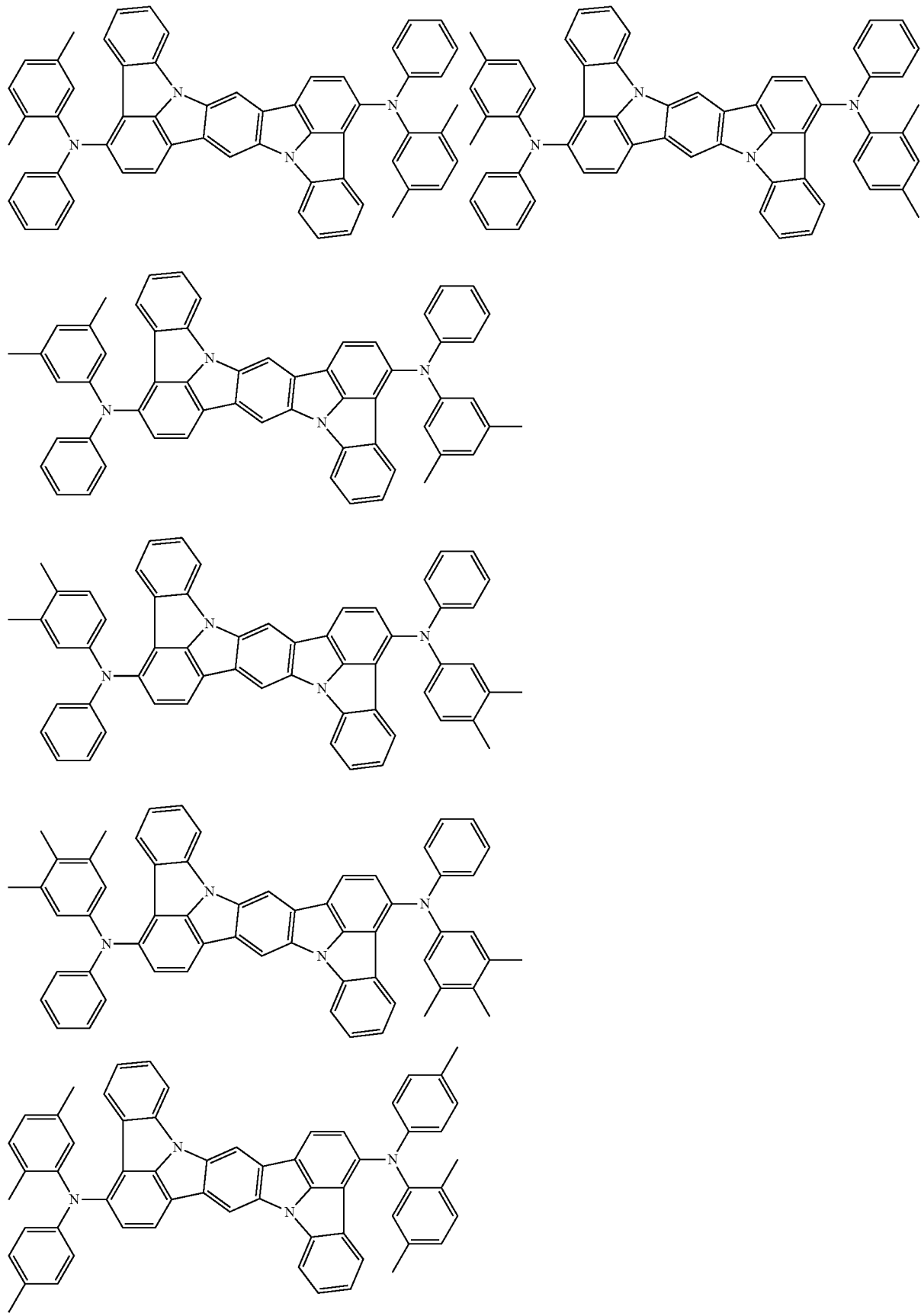

-continued
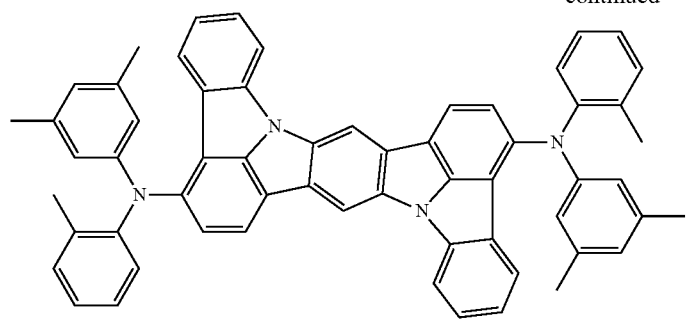
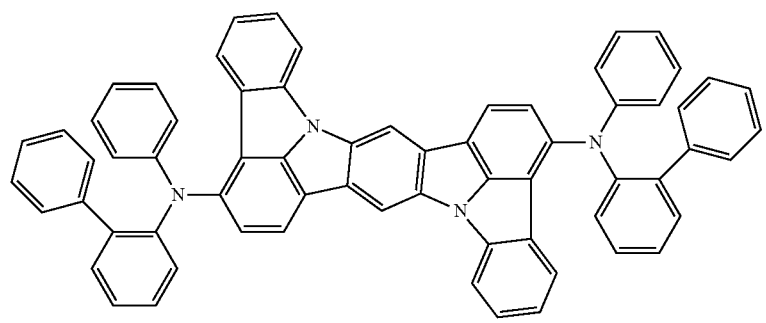
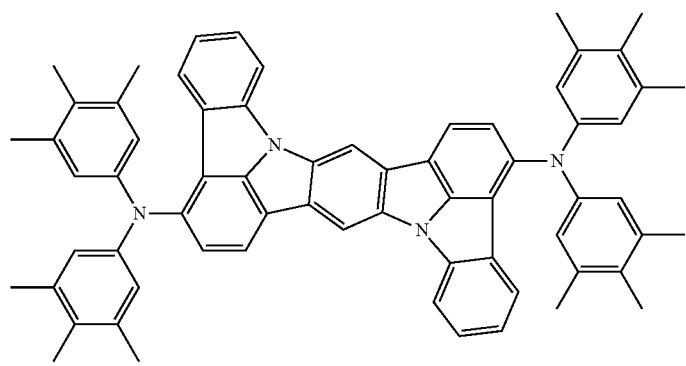
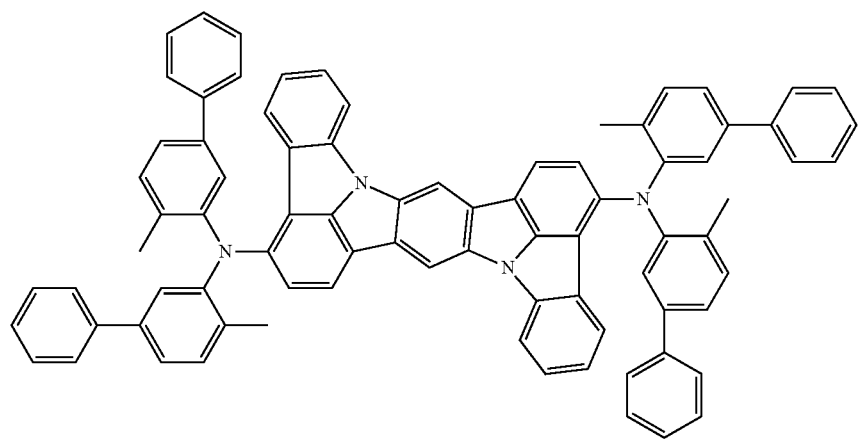

-continued
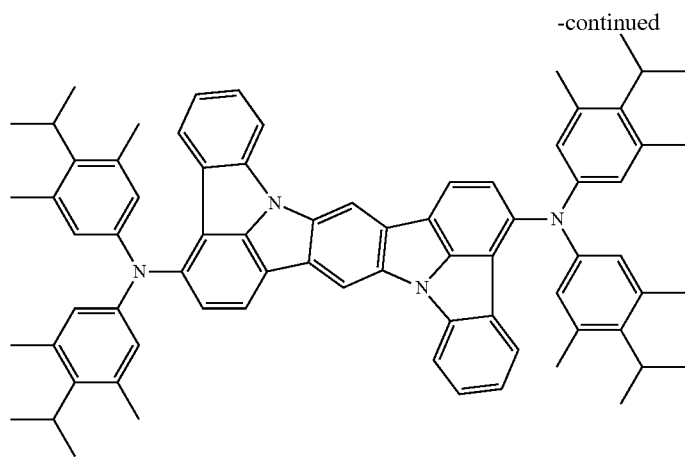
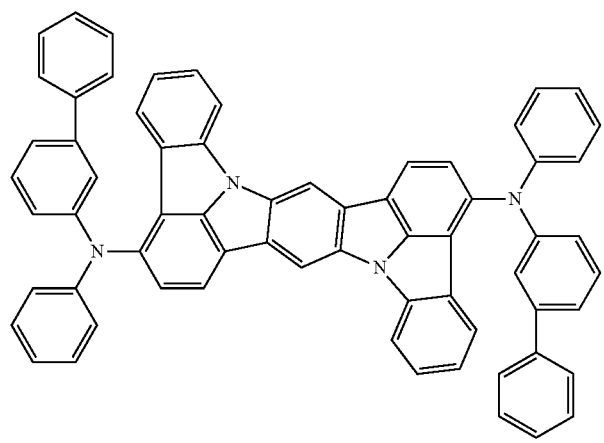
[Formula 305]
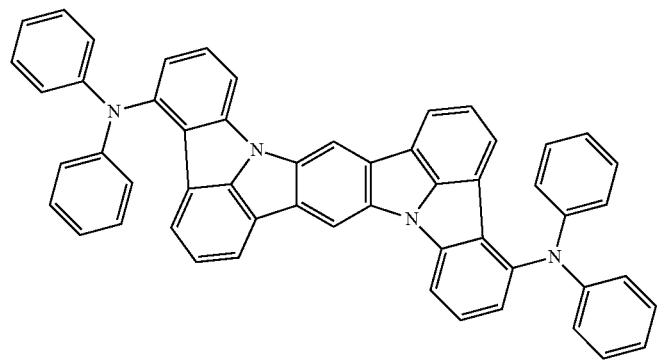

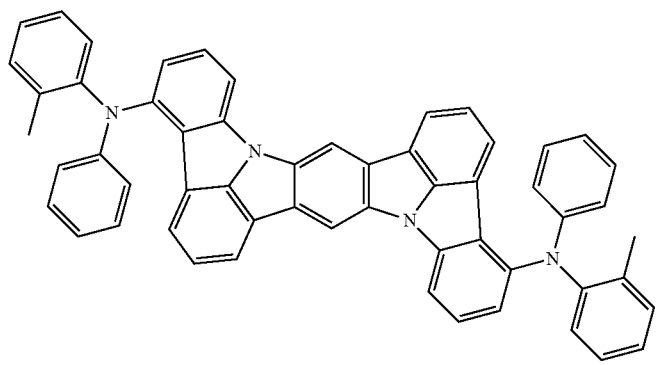
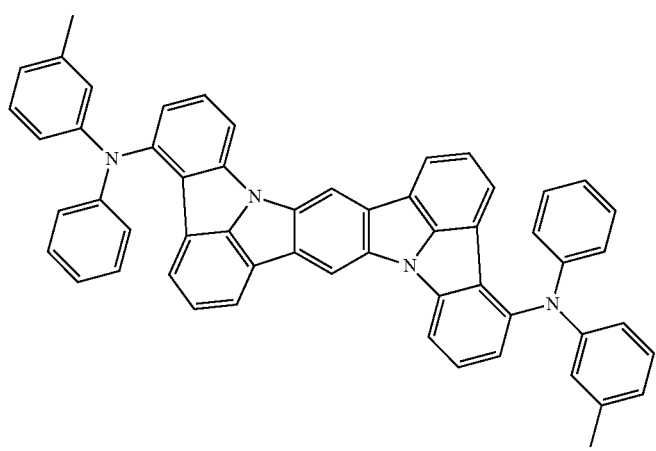
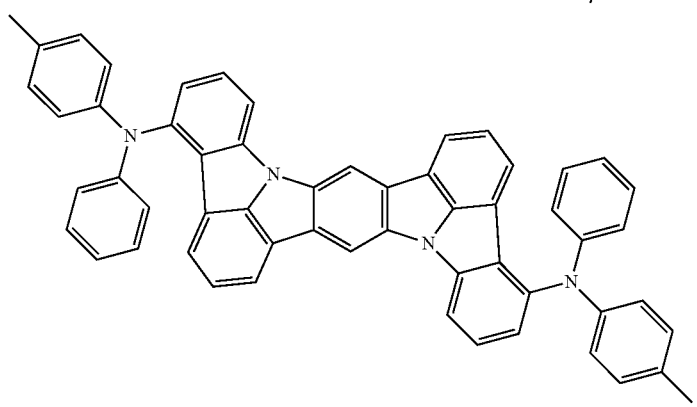
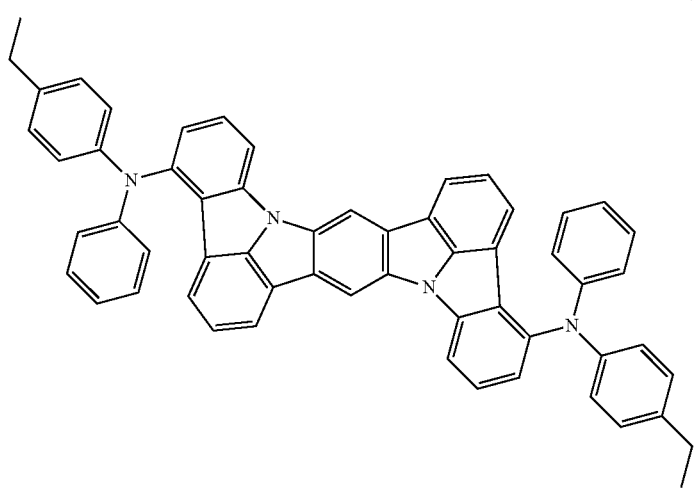

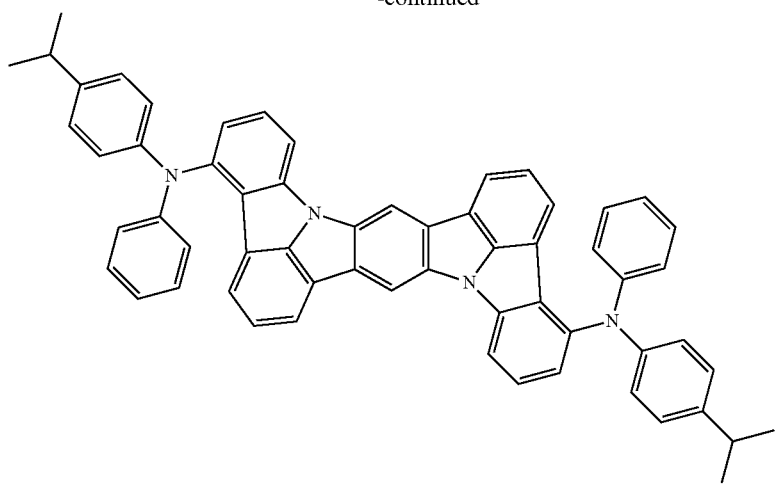
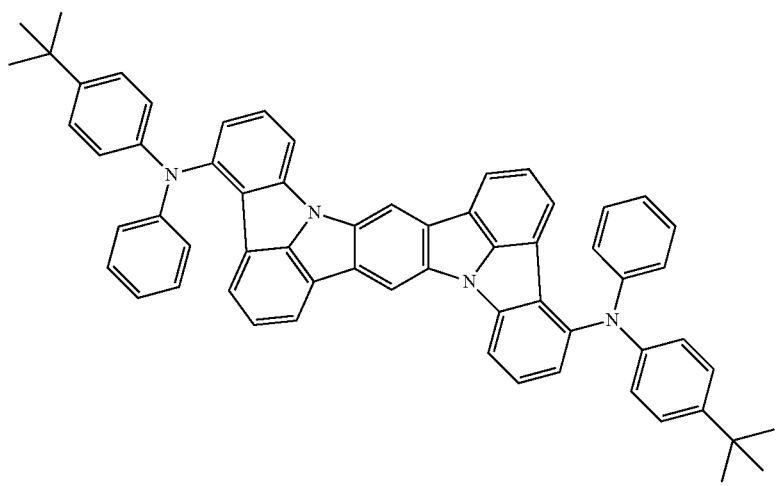
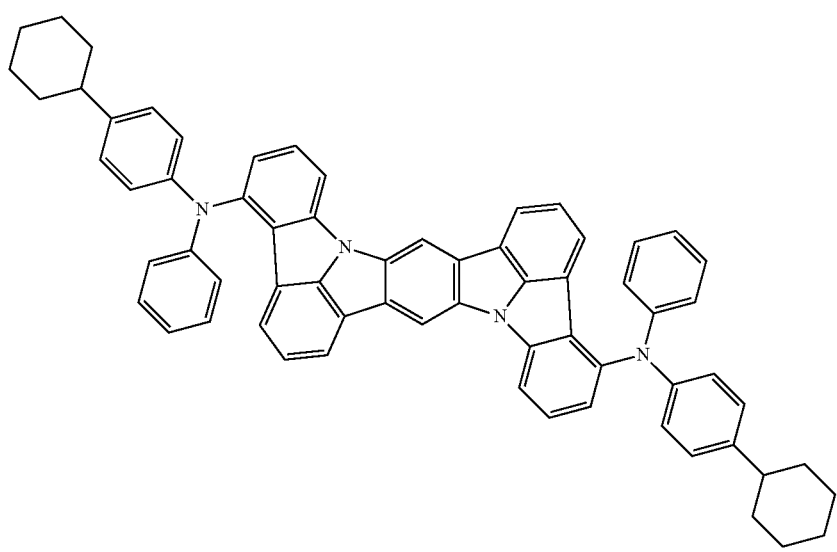

-continued
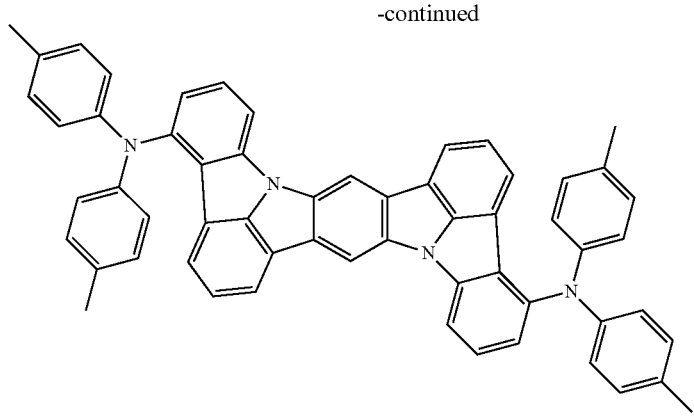
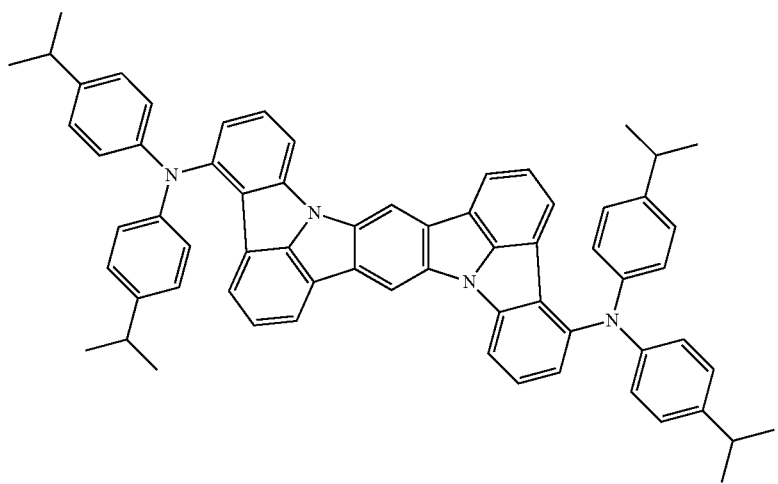
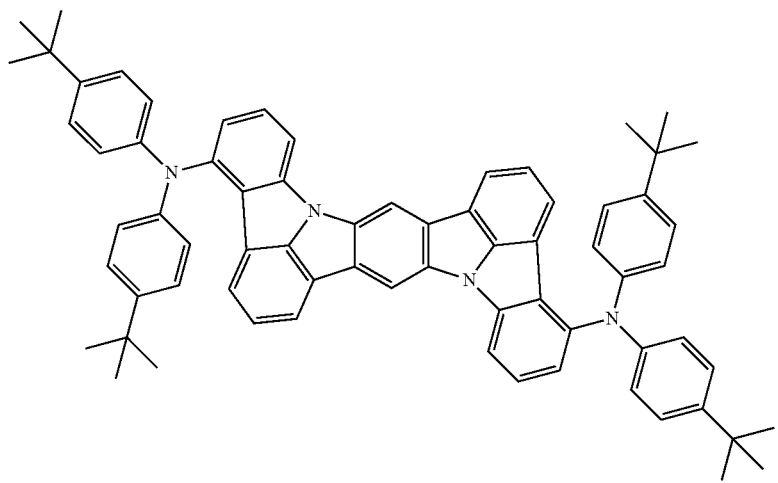

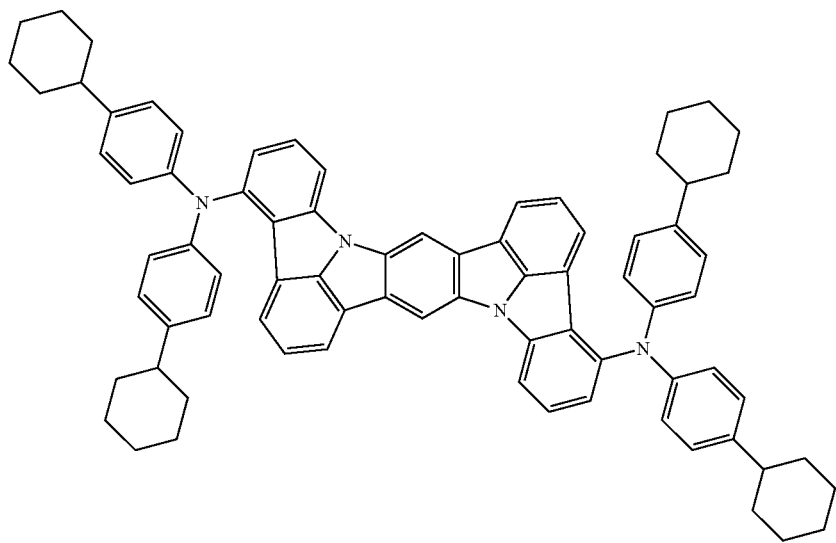
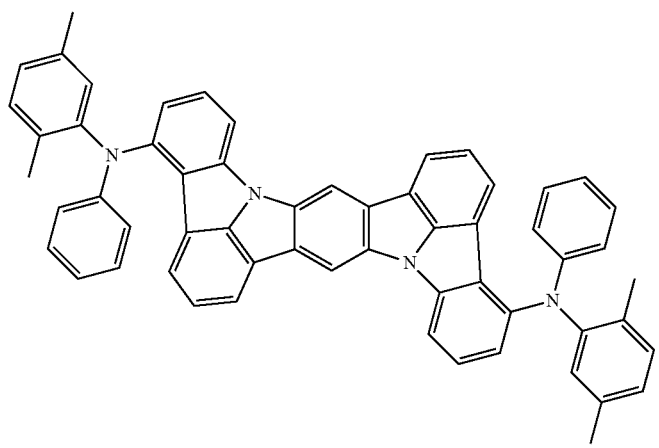
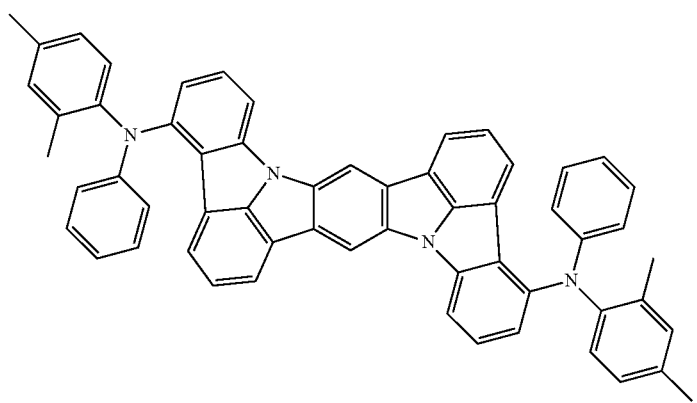

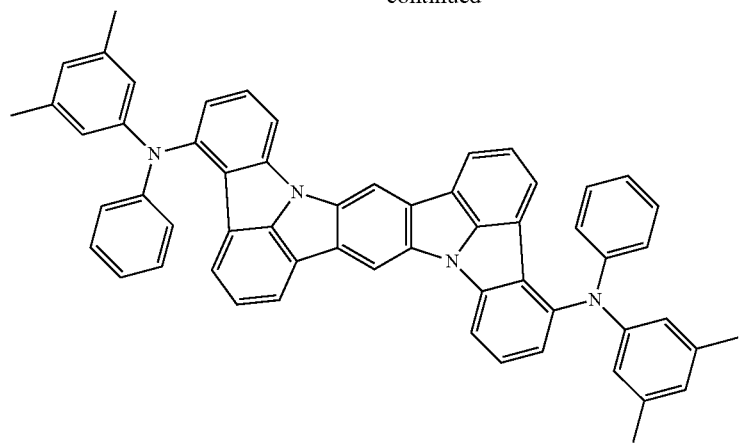
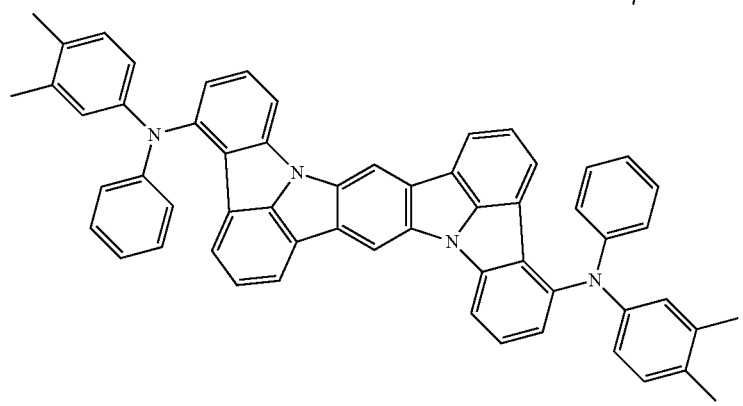
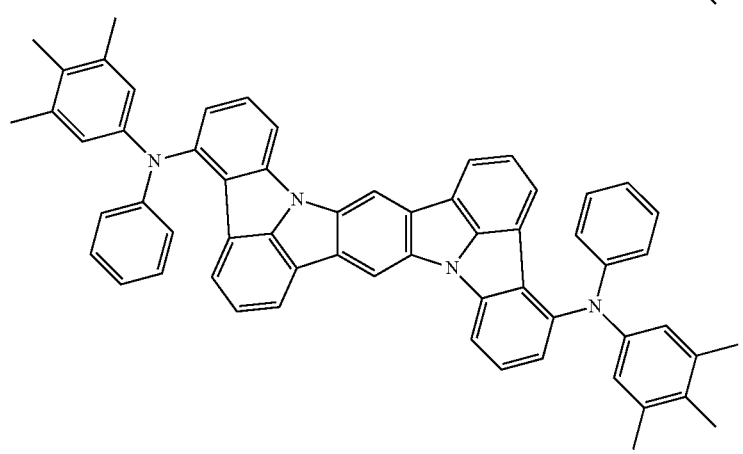
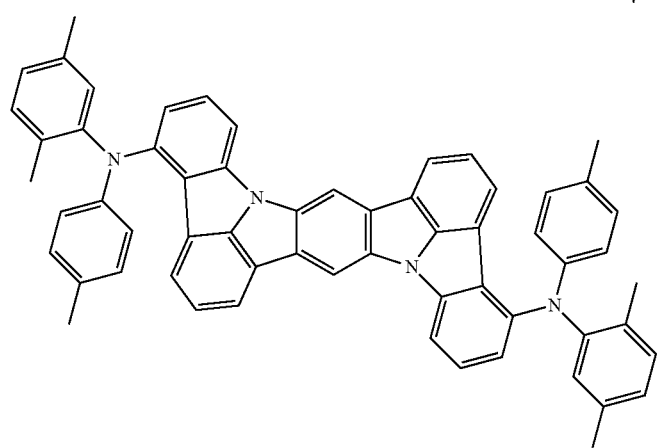

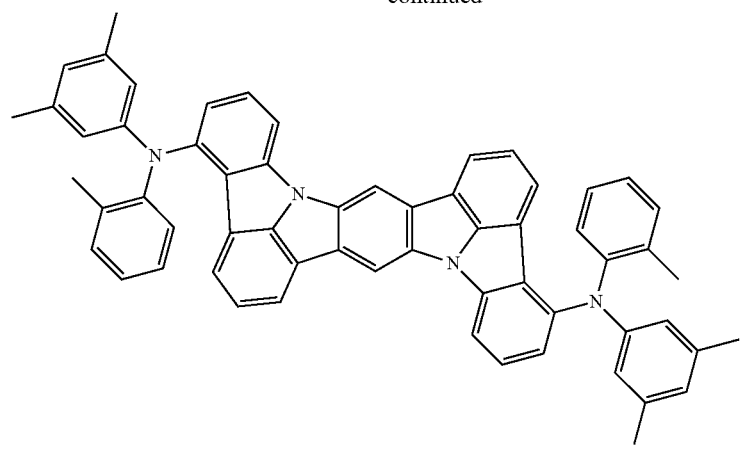
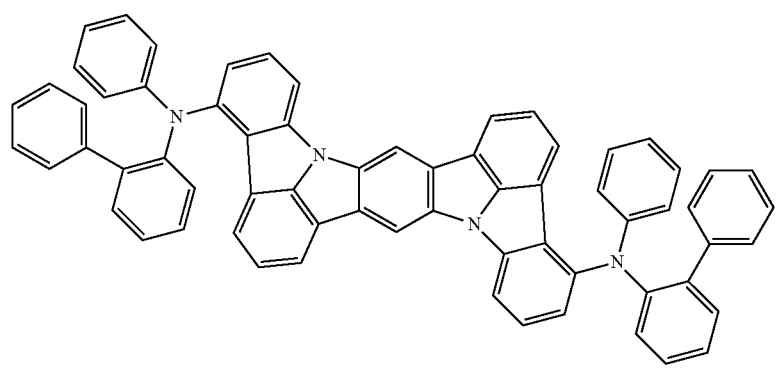
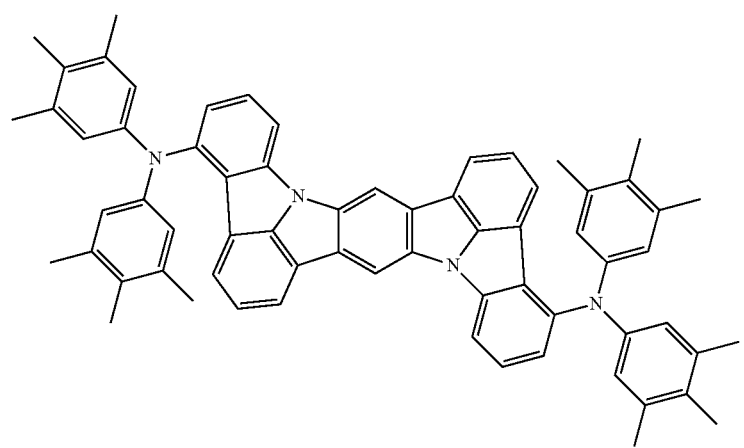

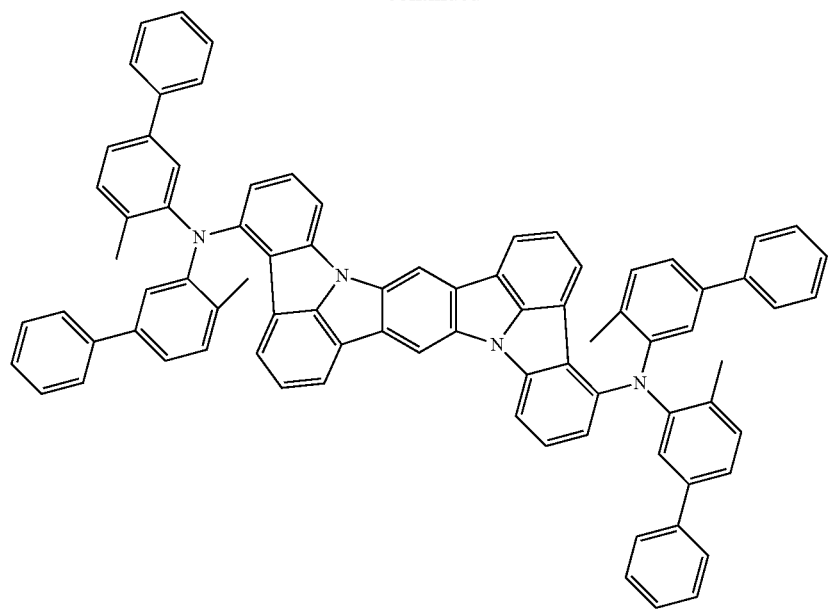
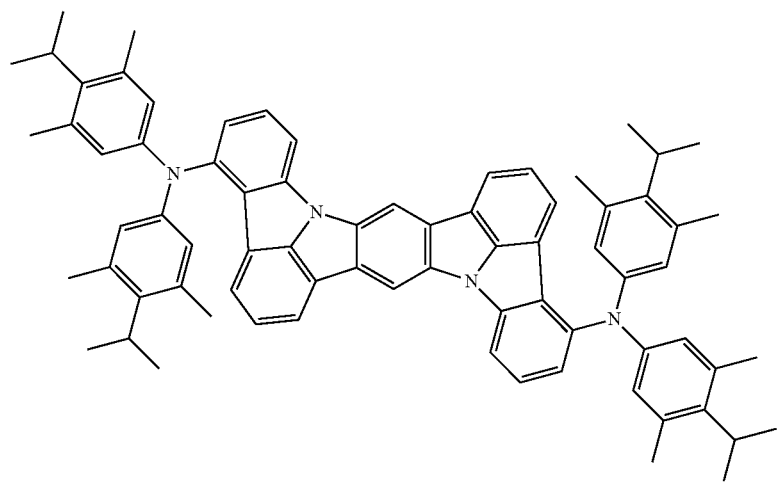
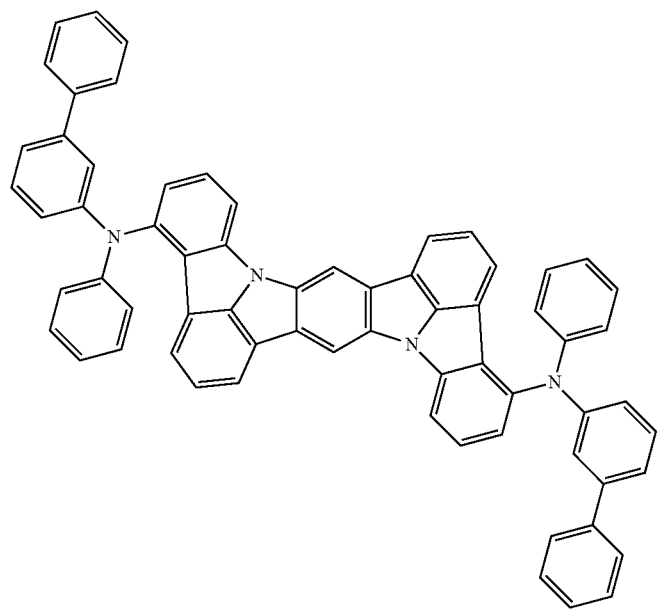

[Formula 306]
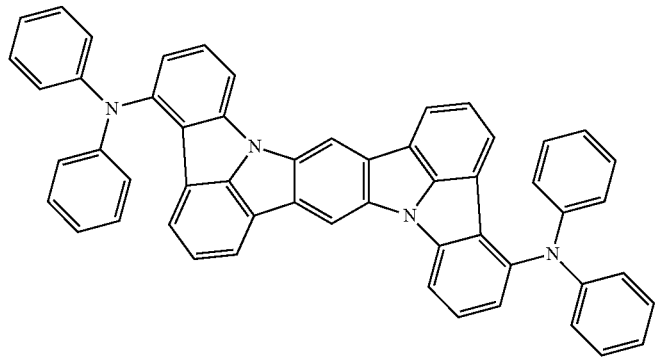
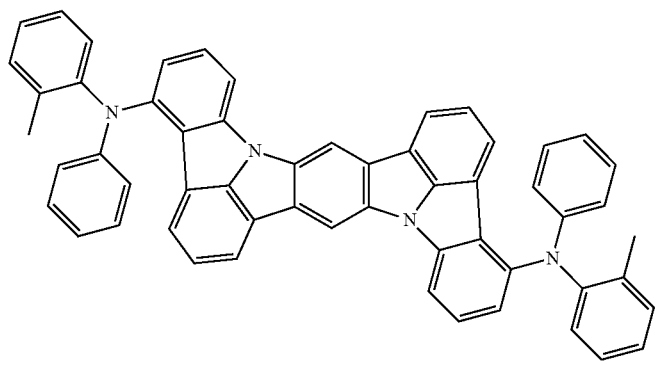
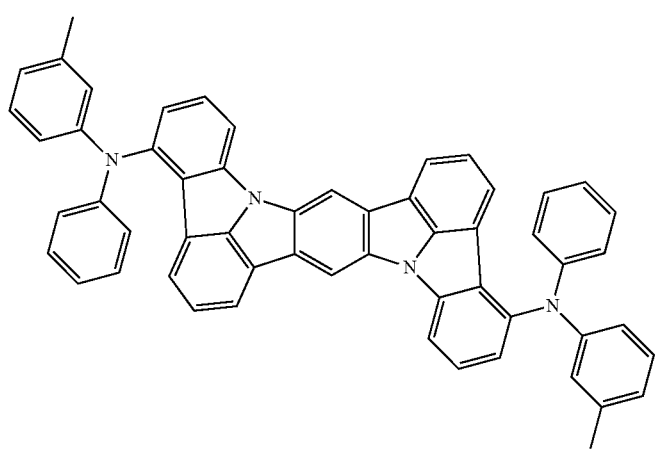
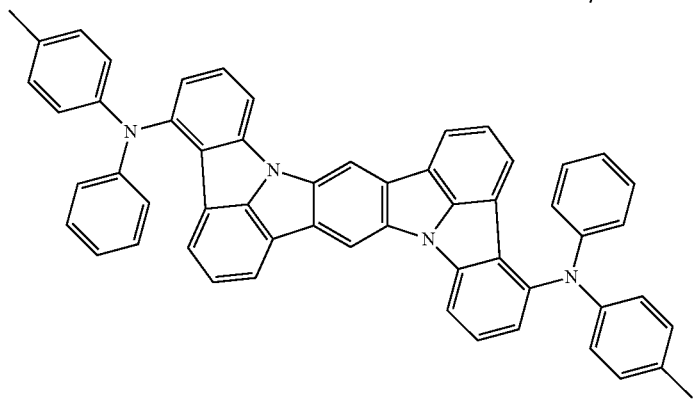

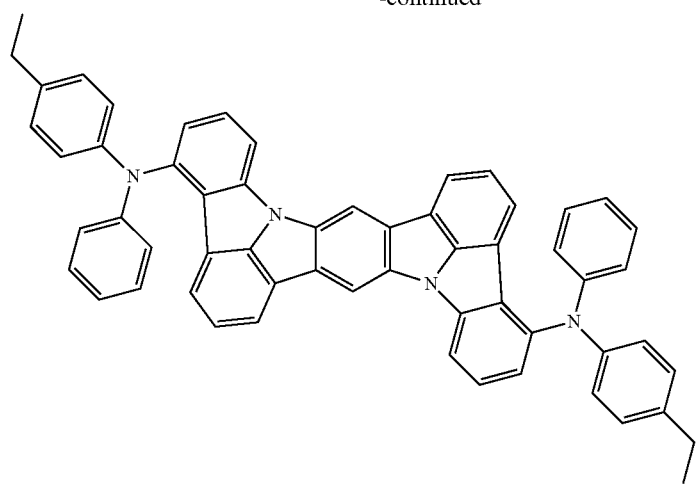
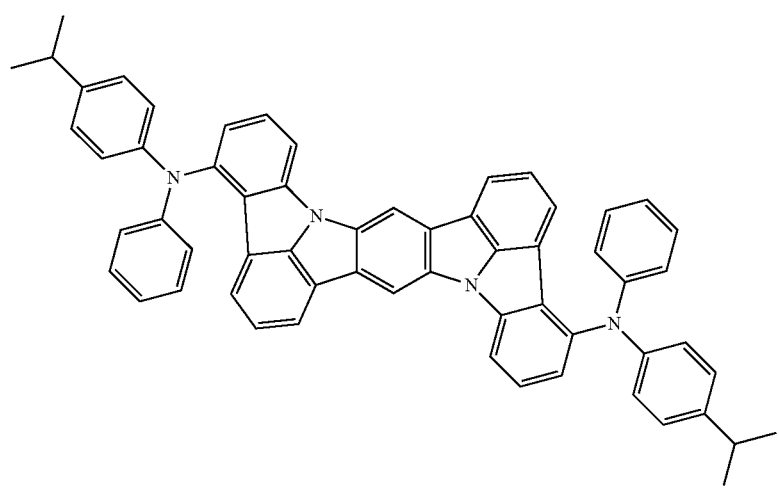
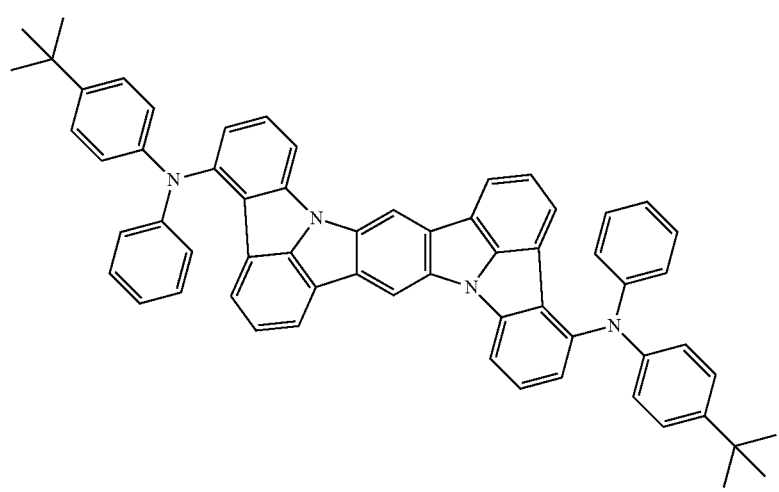

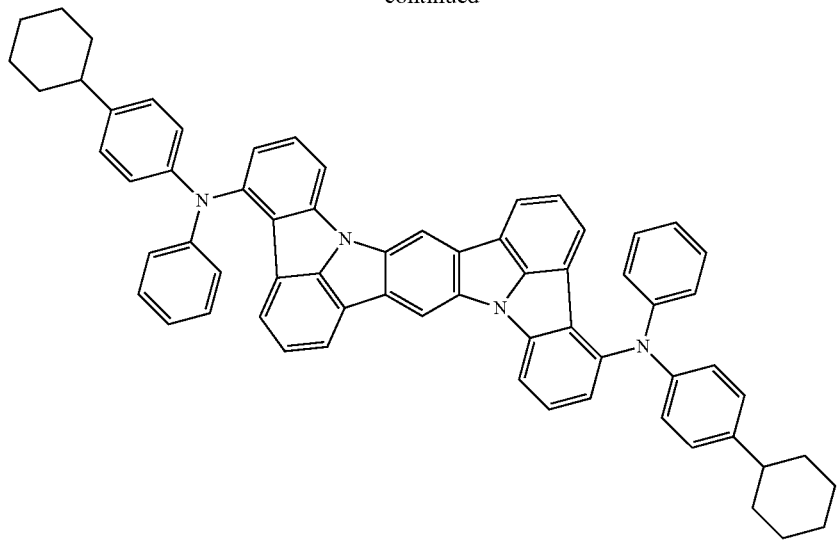
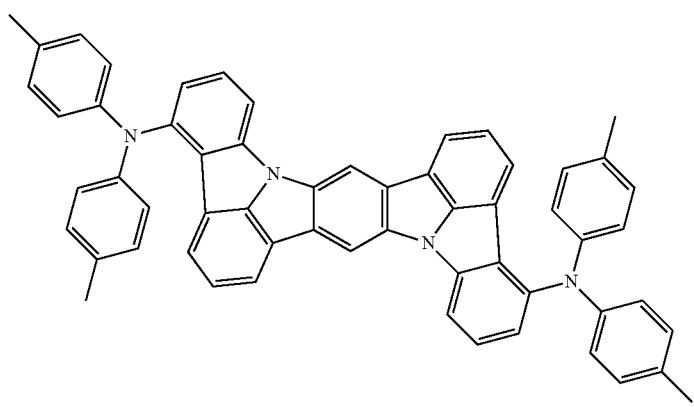
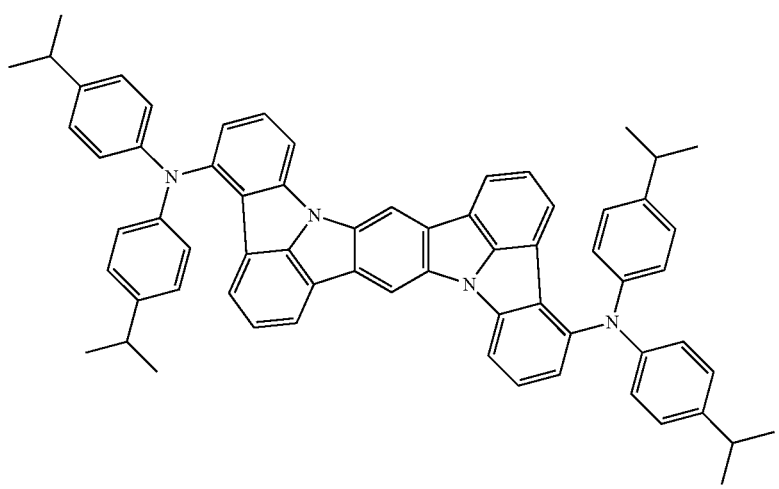

-continued
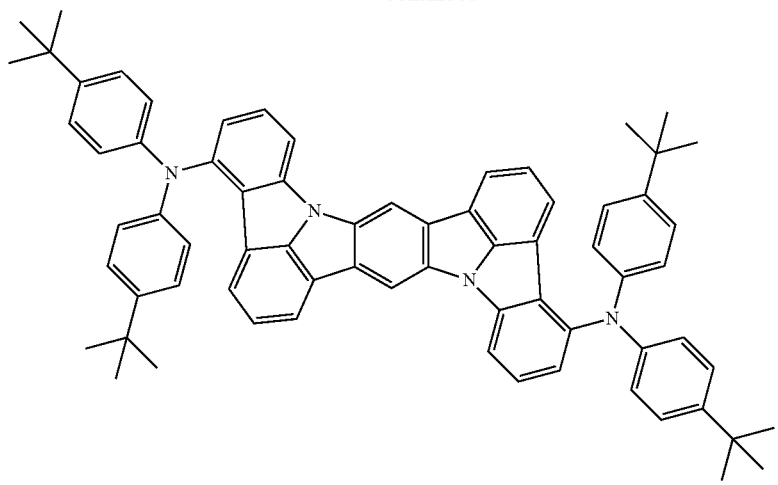
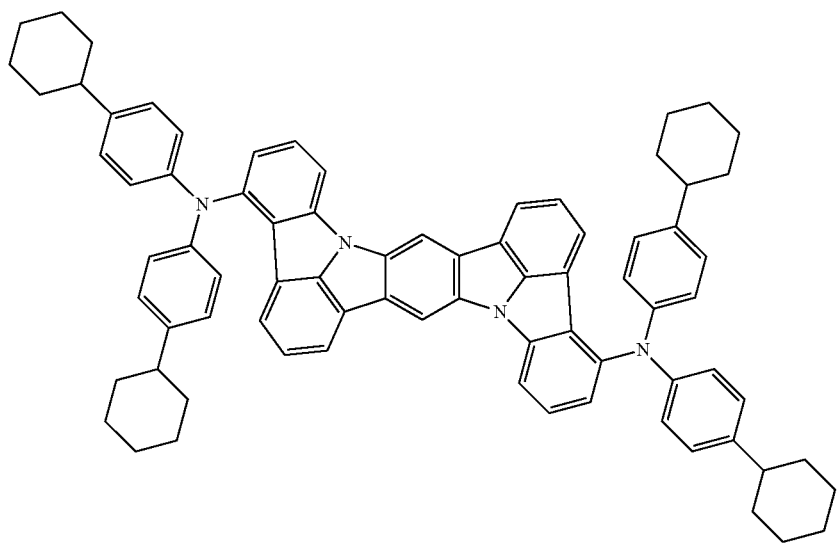
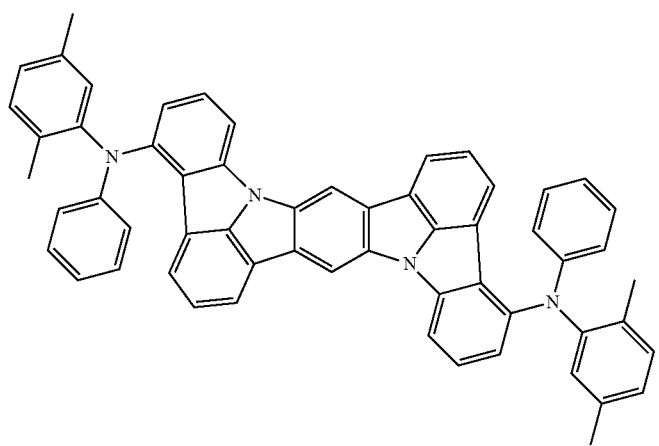

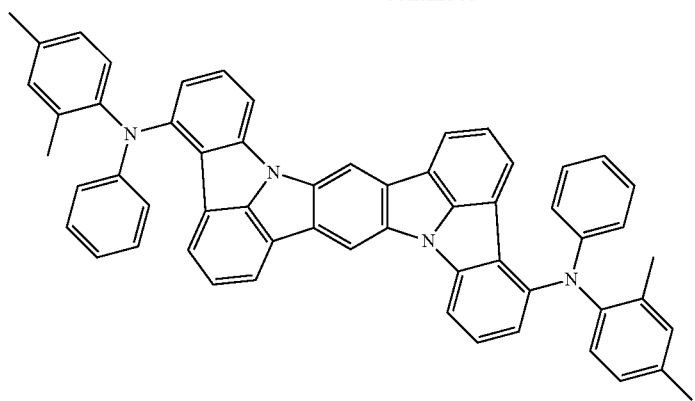
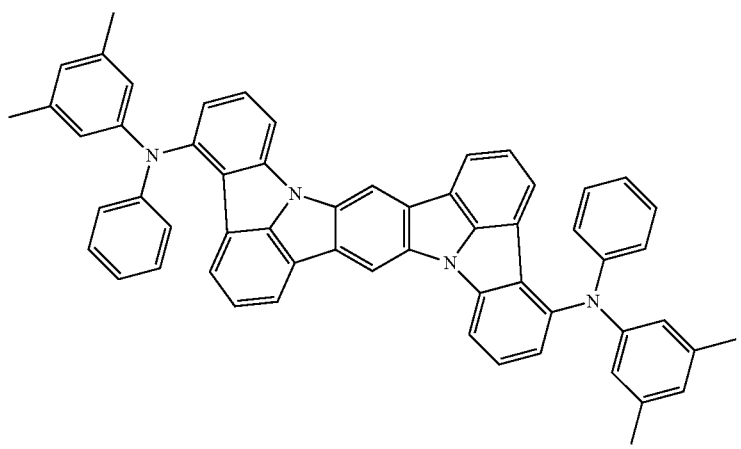
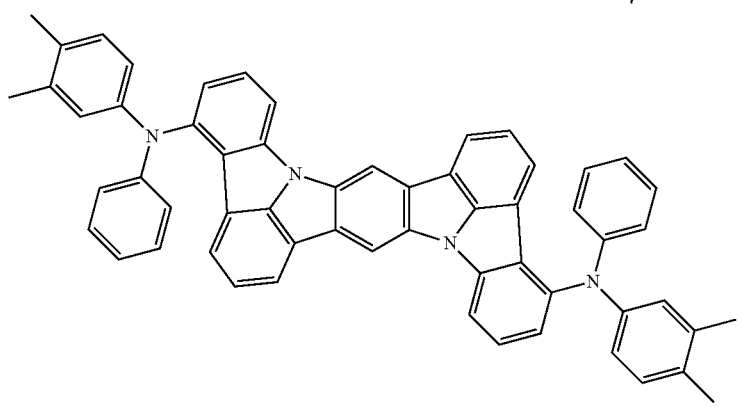
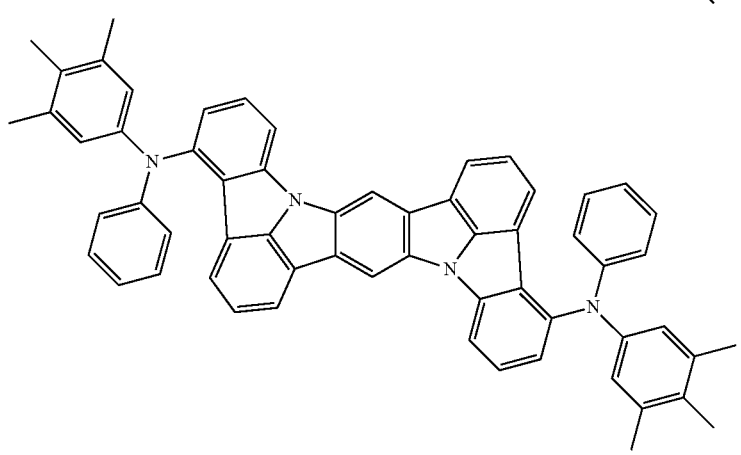

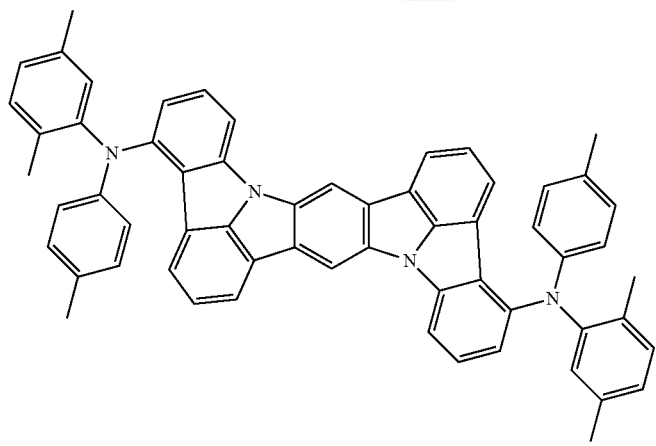
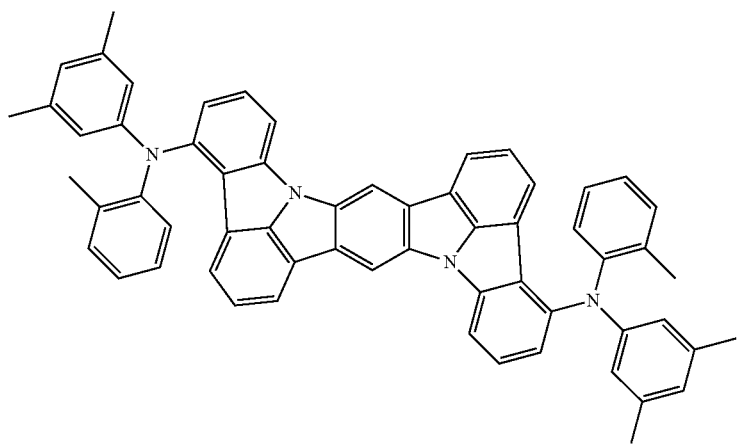
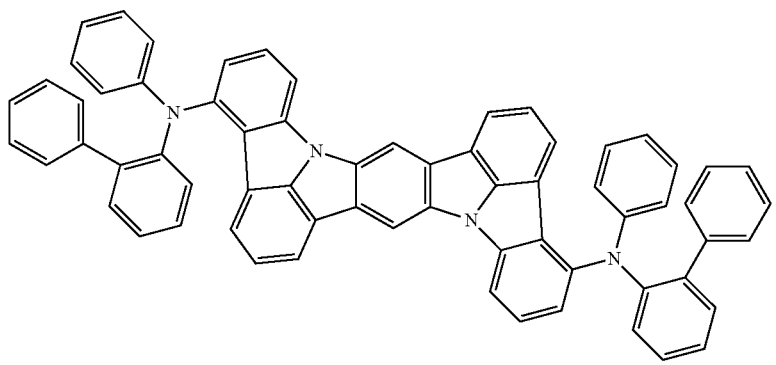
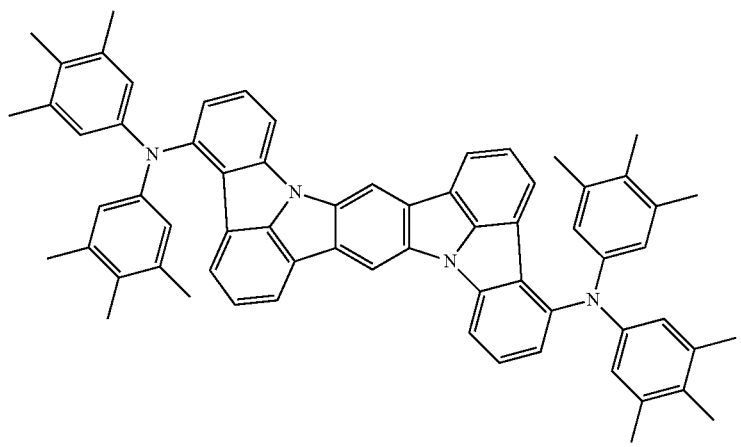

-continued
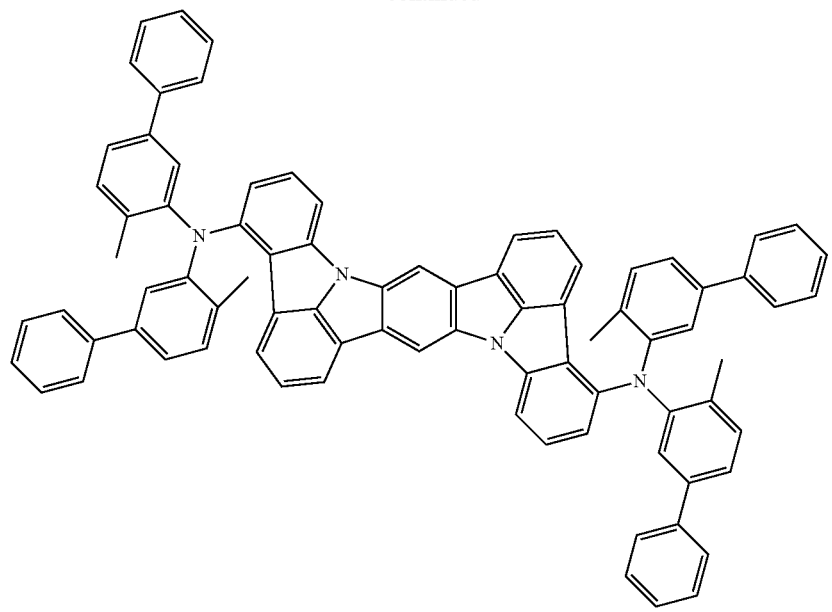
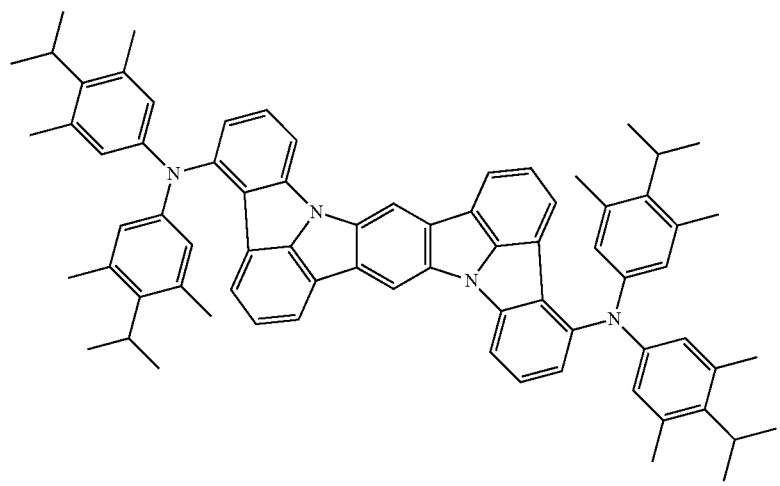
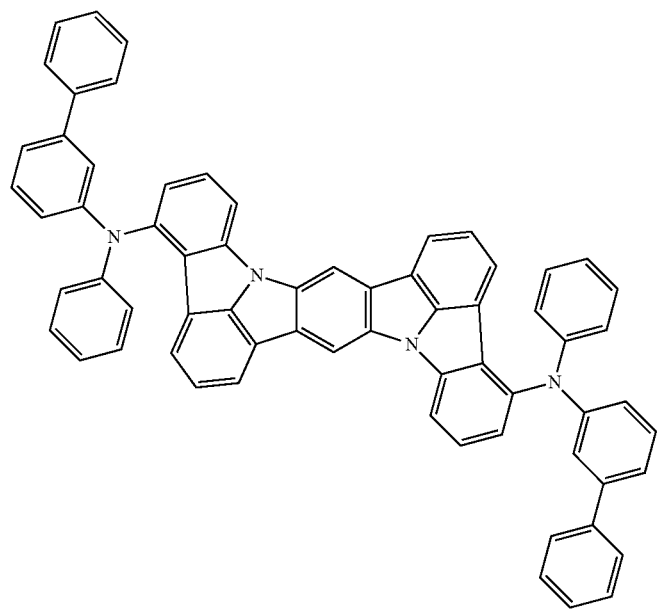

[Formula 307]
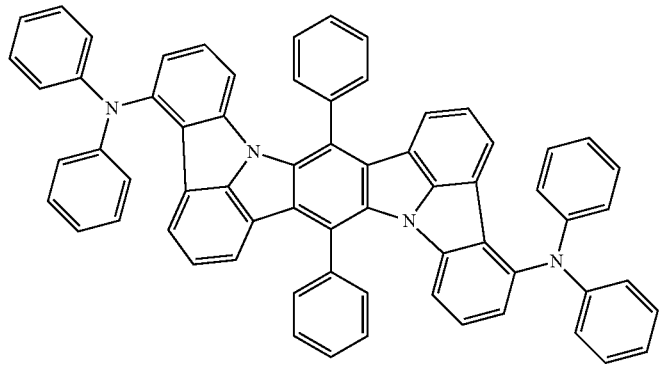
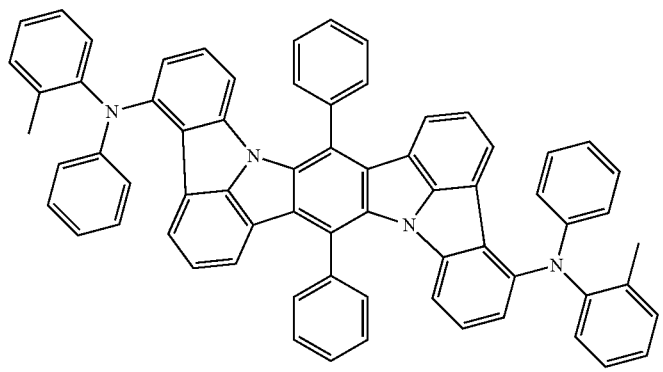
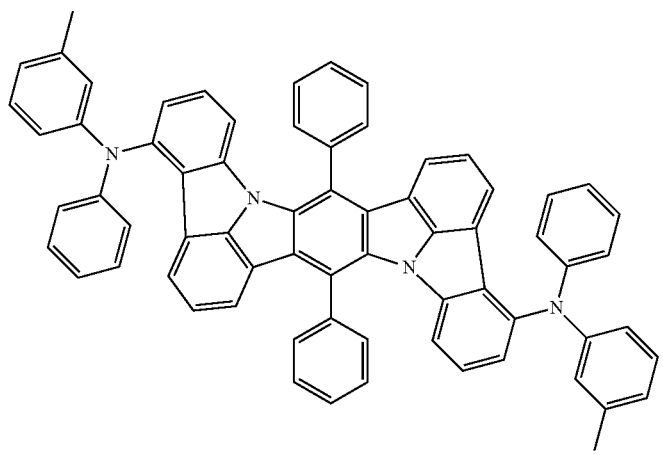
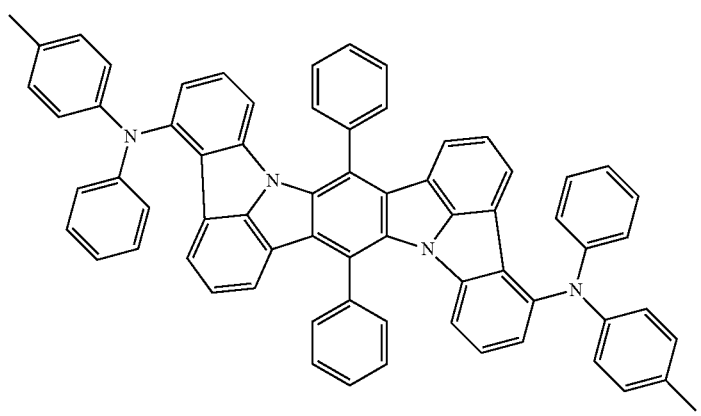

-continued
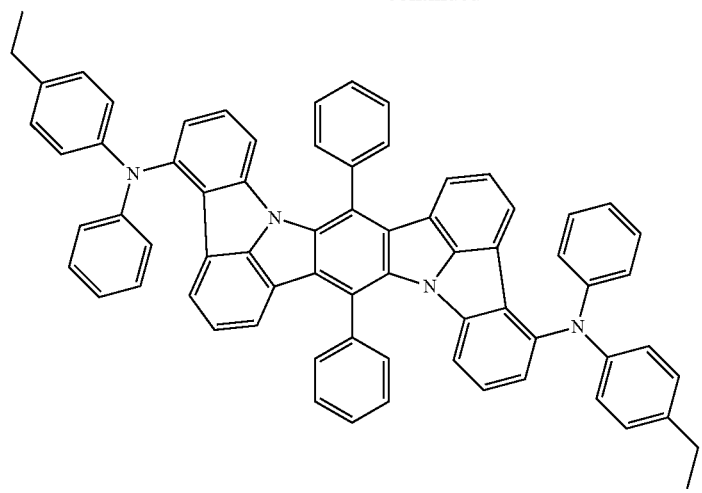
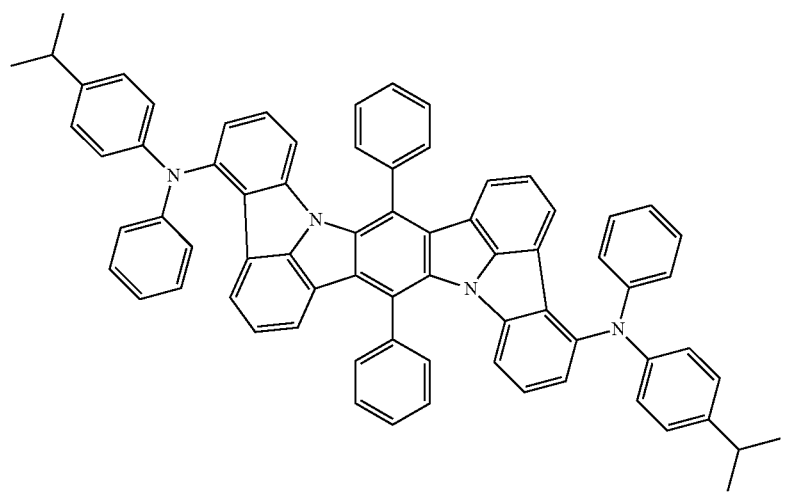
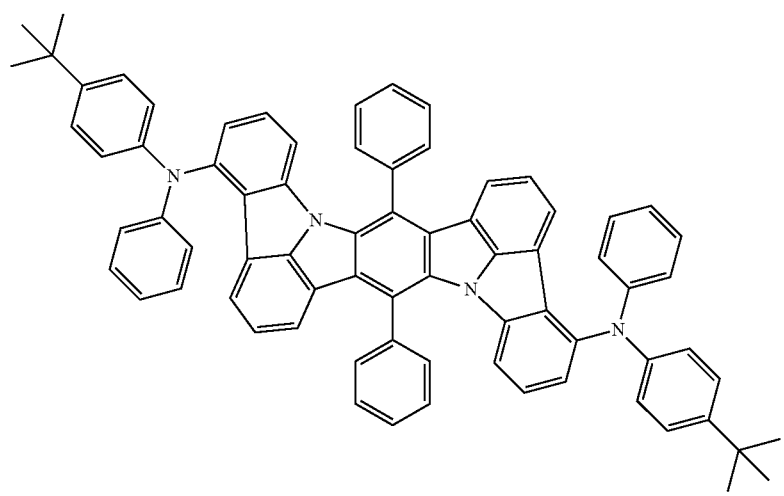

-continued
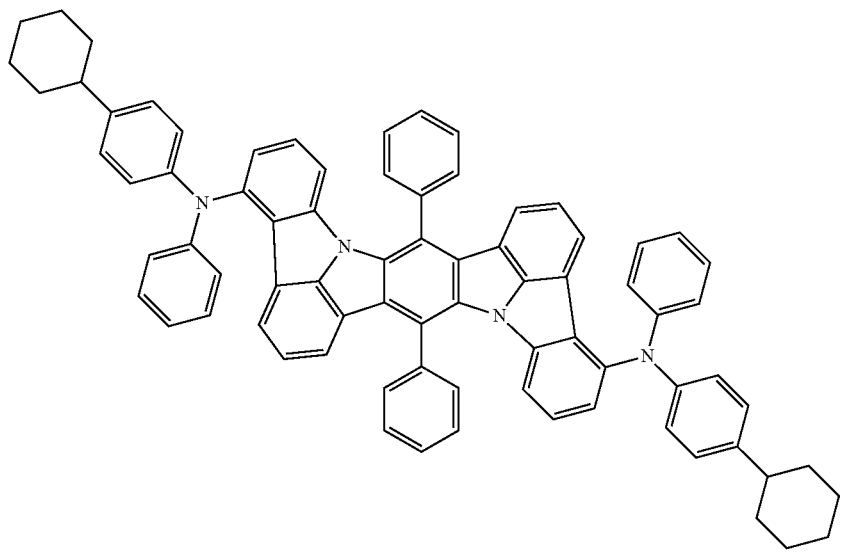
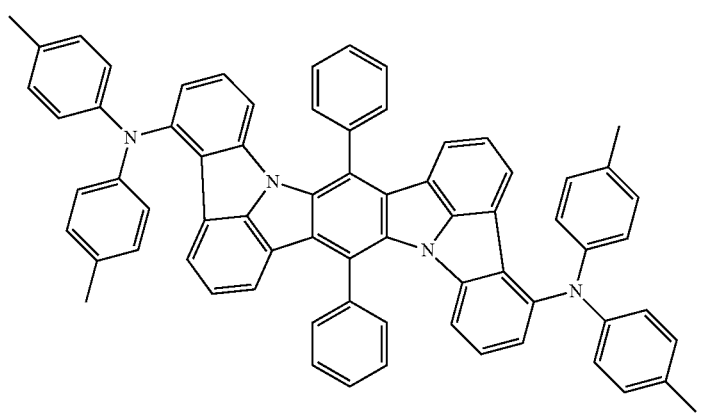
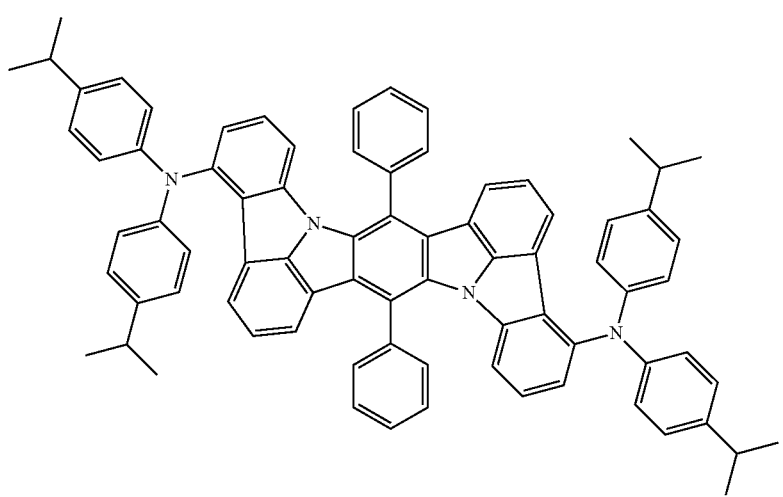

-continued
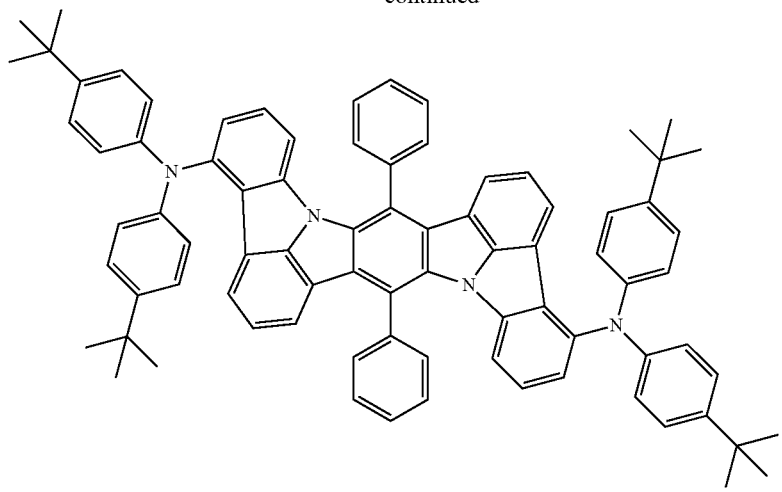
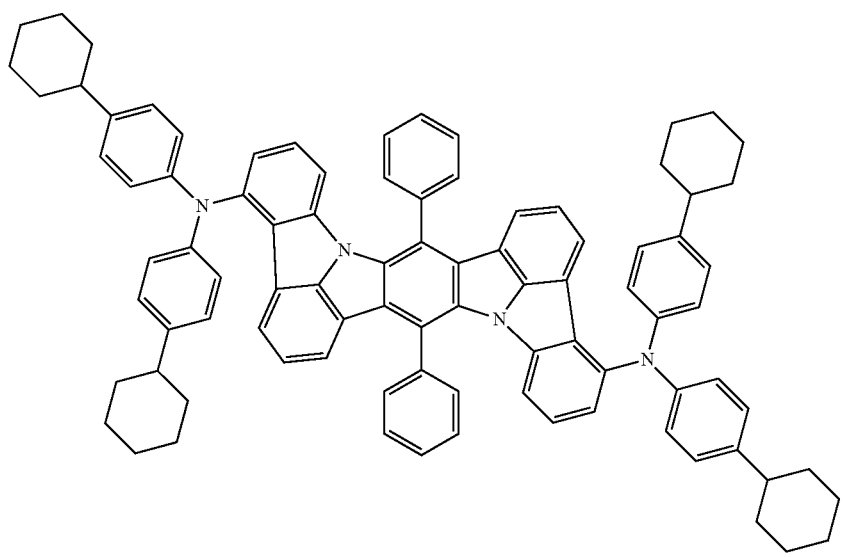
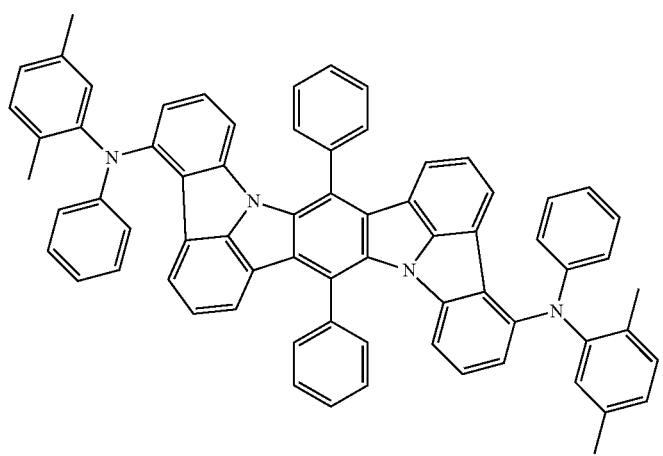

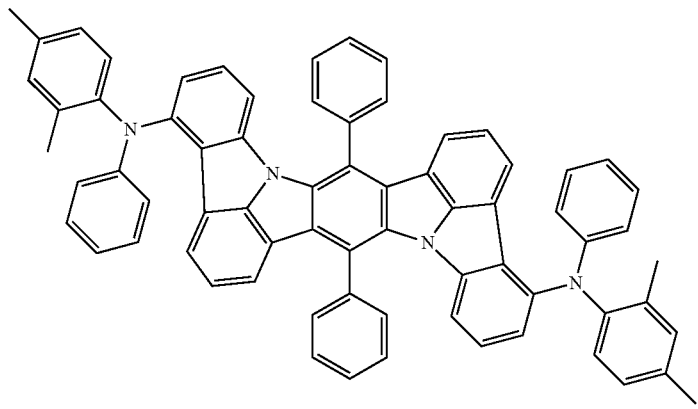
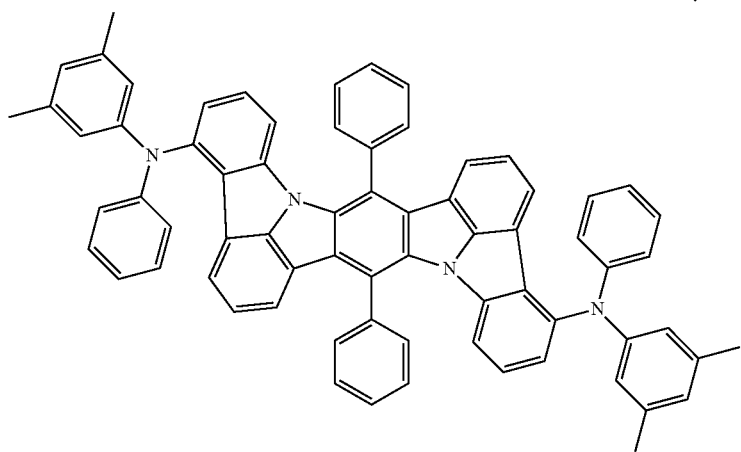
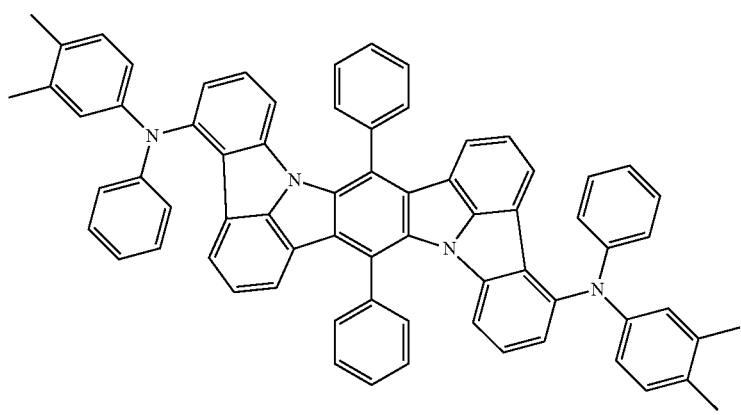
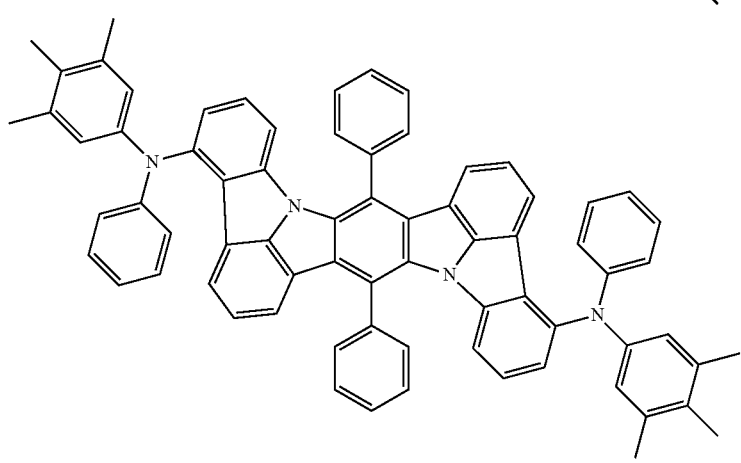

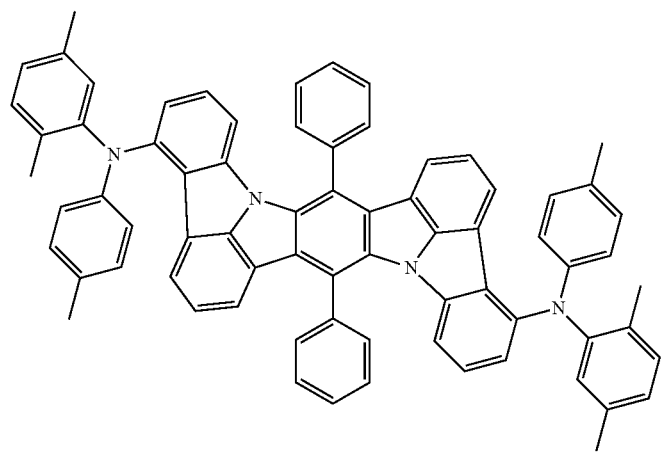
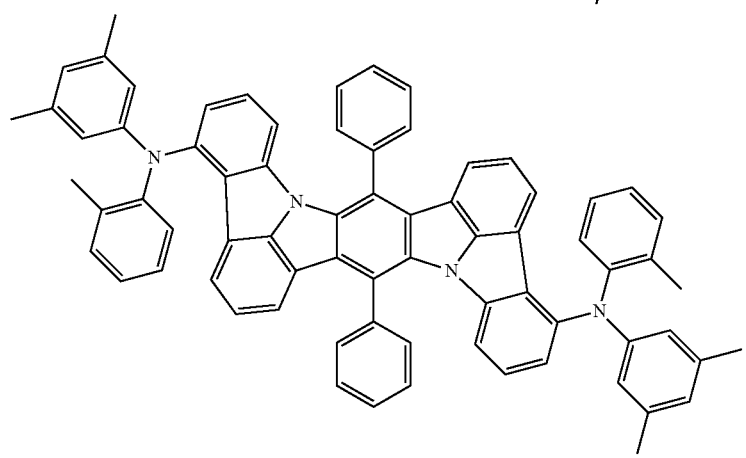
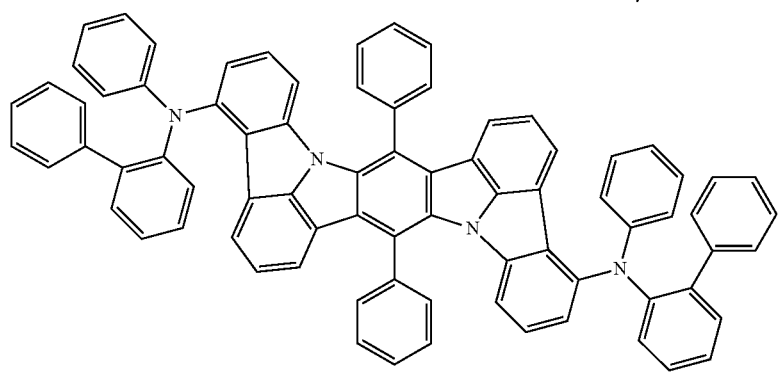
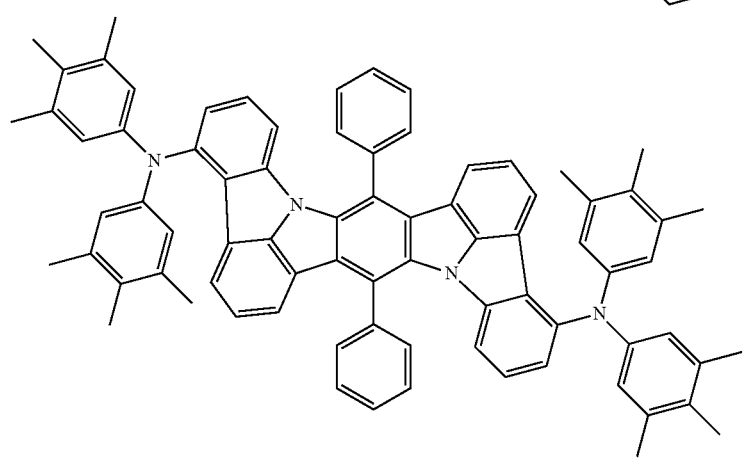

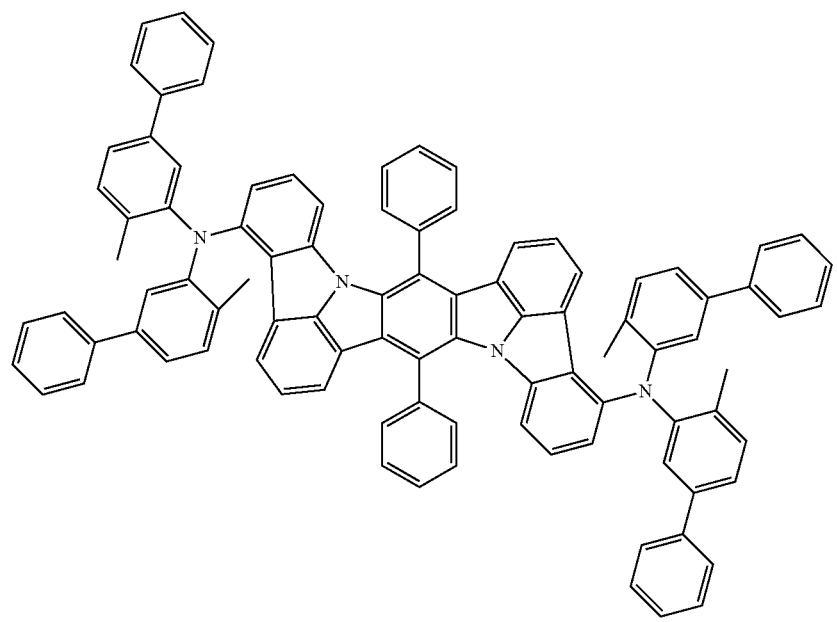
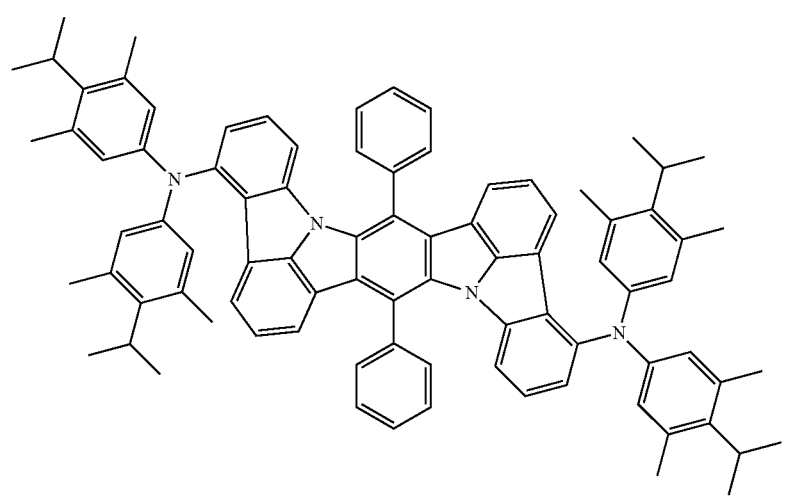

-continued
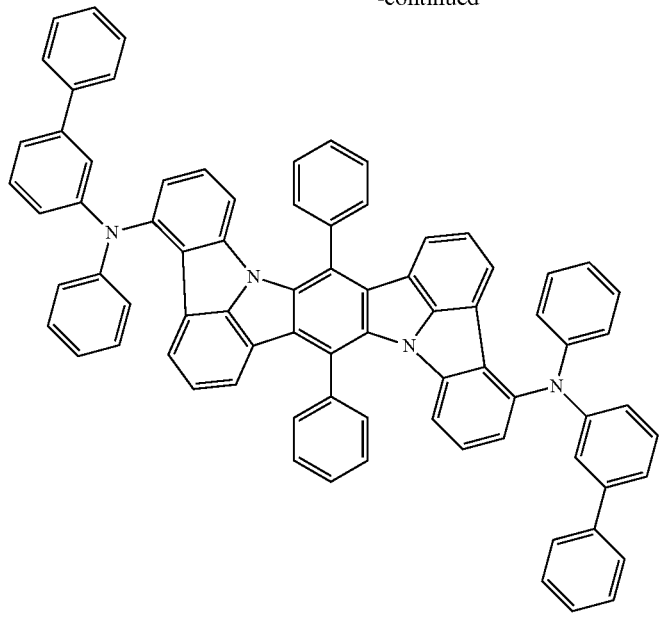
[Formula 308]
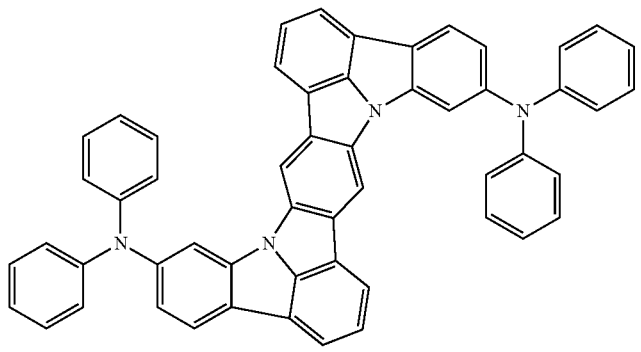
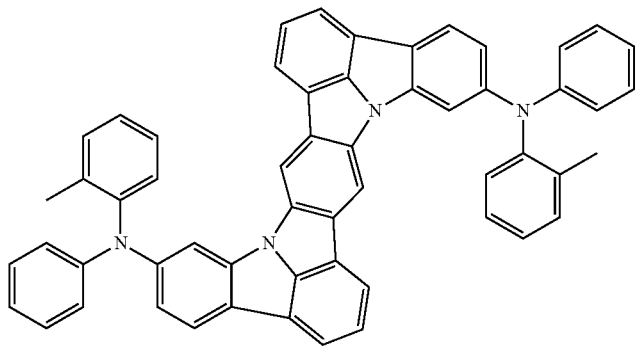

-continued
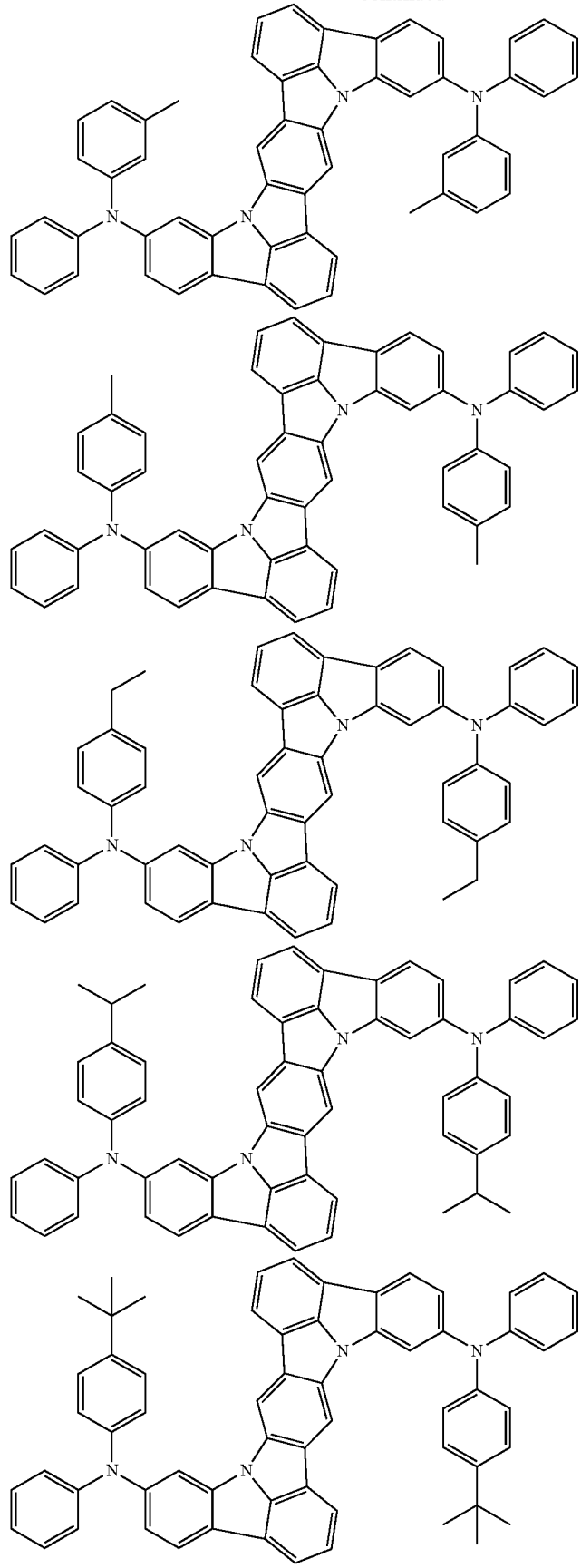

783
-continued
784
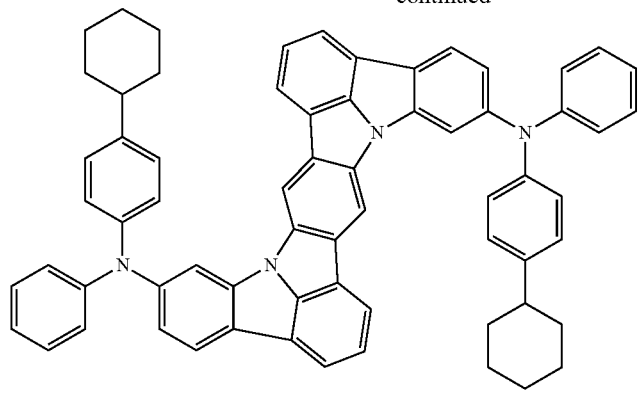
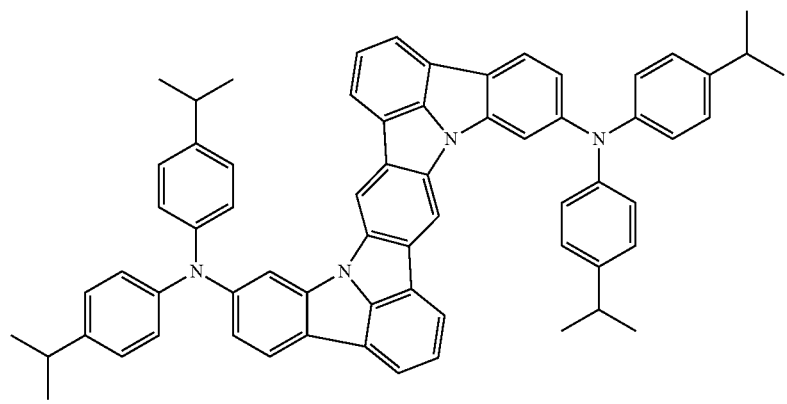
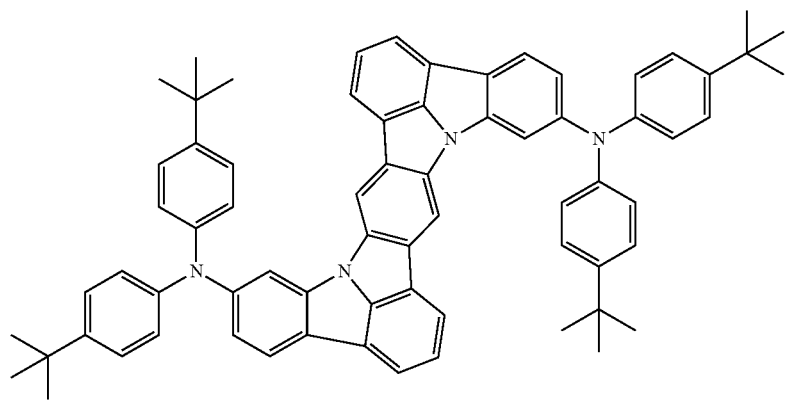

-continued
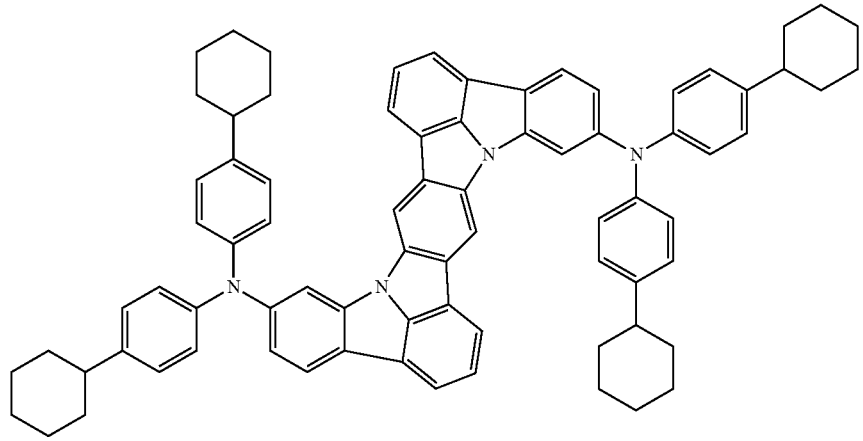
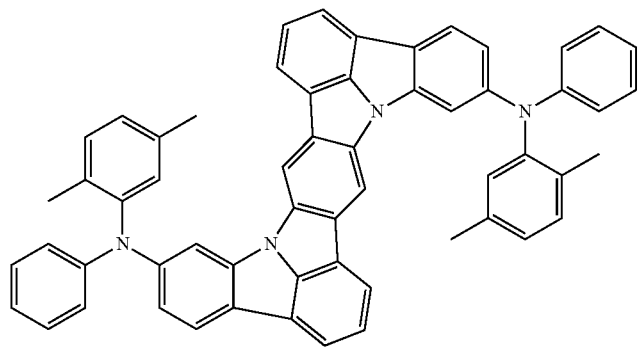
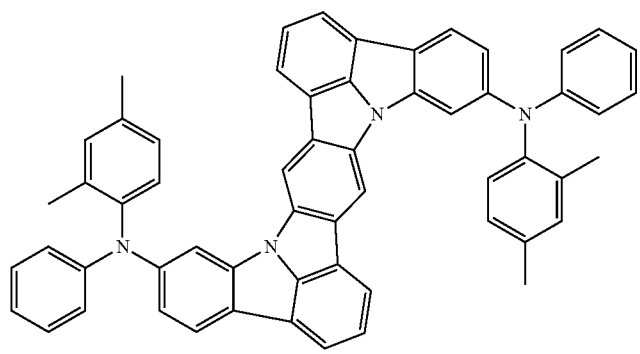
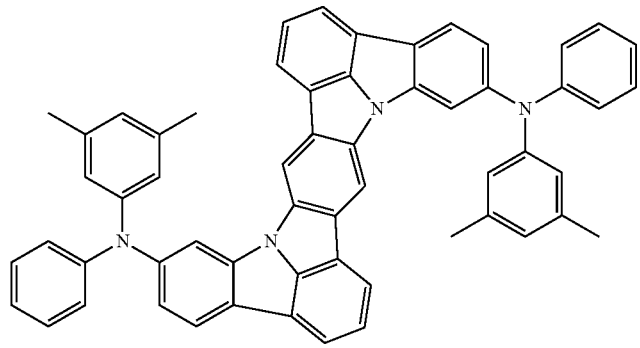

787
788
-continued
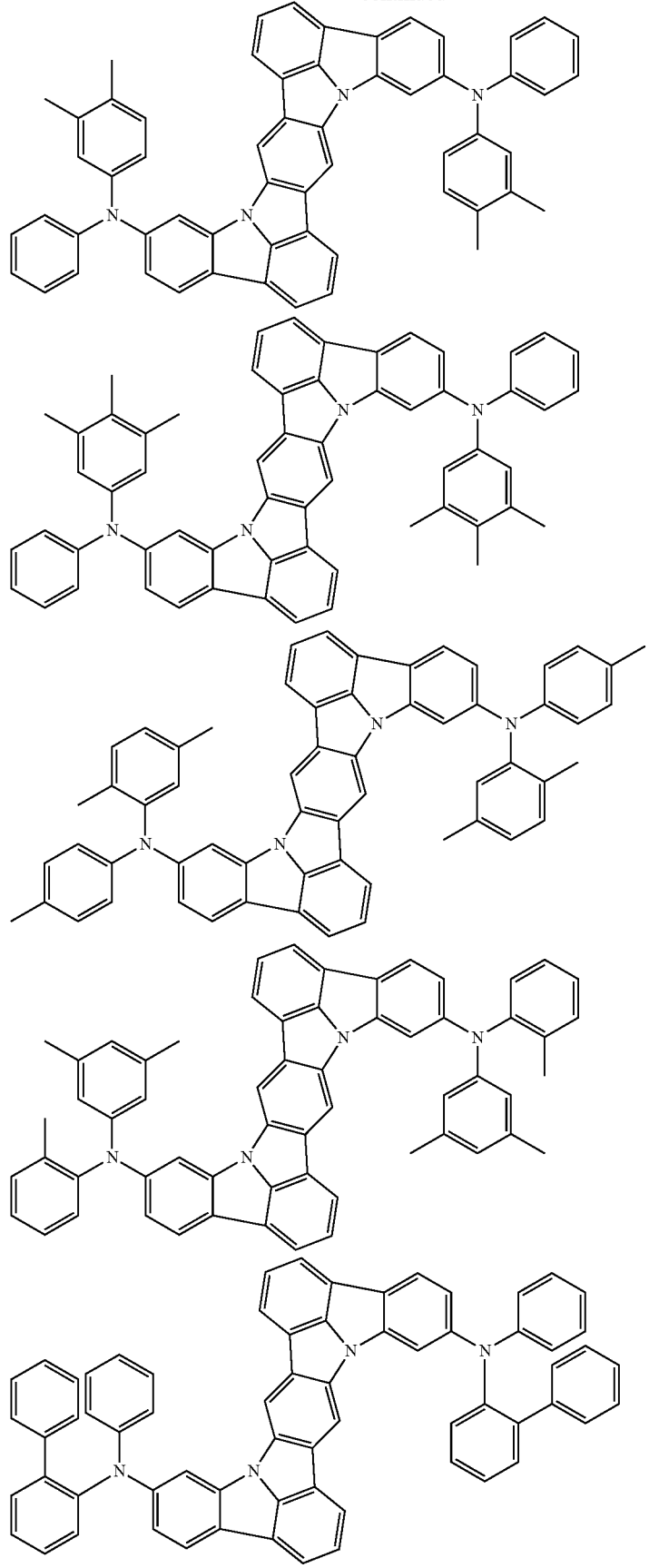

-continued
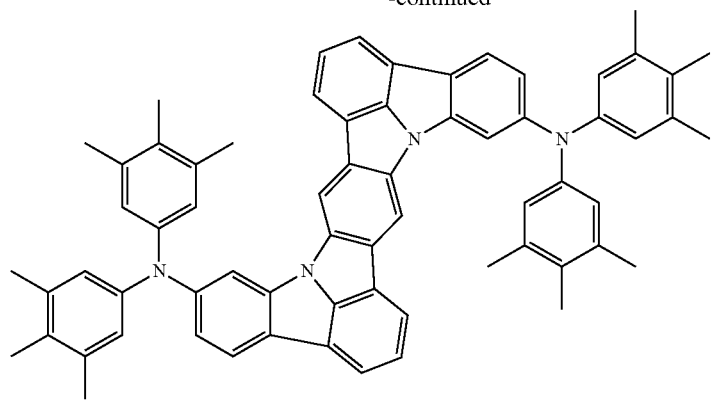
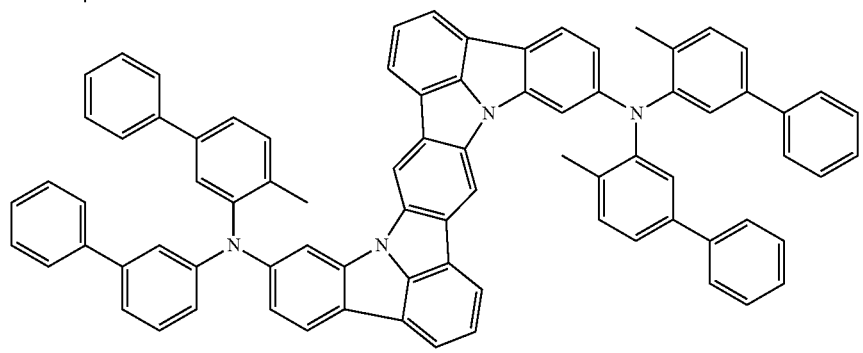
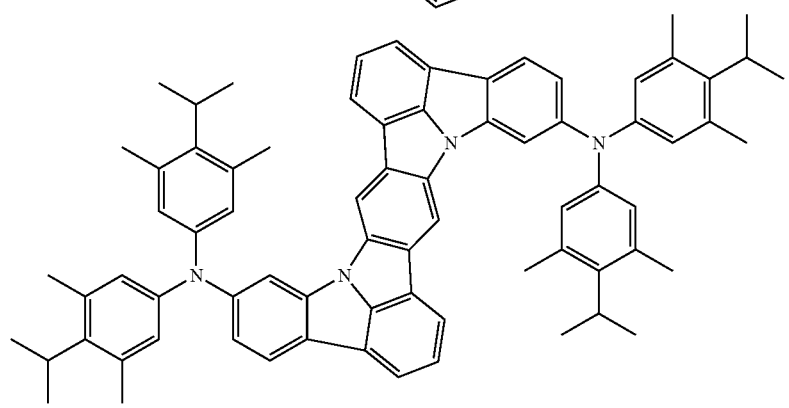
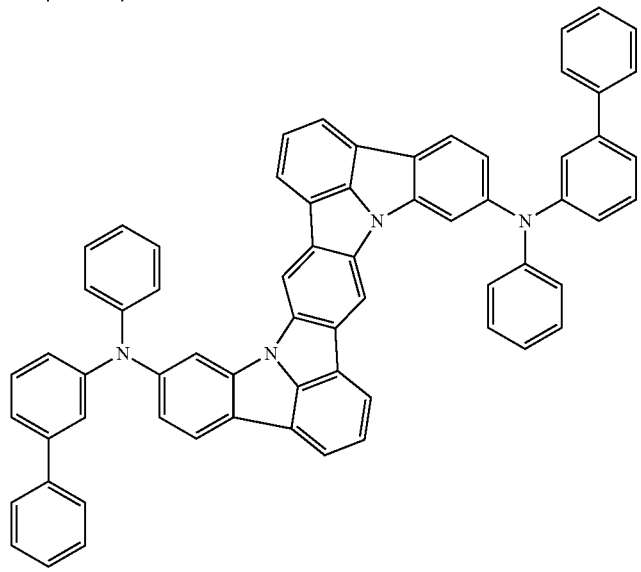

[Formula 309]
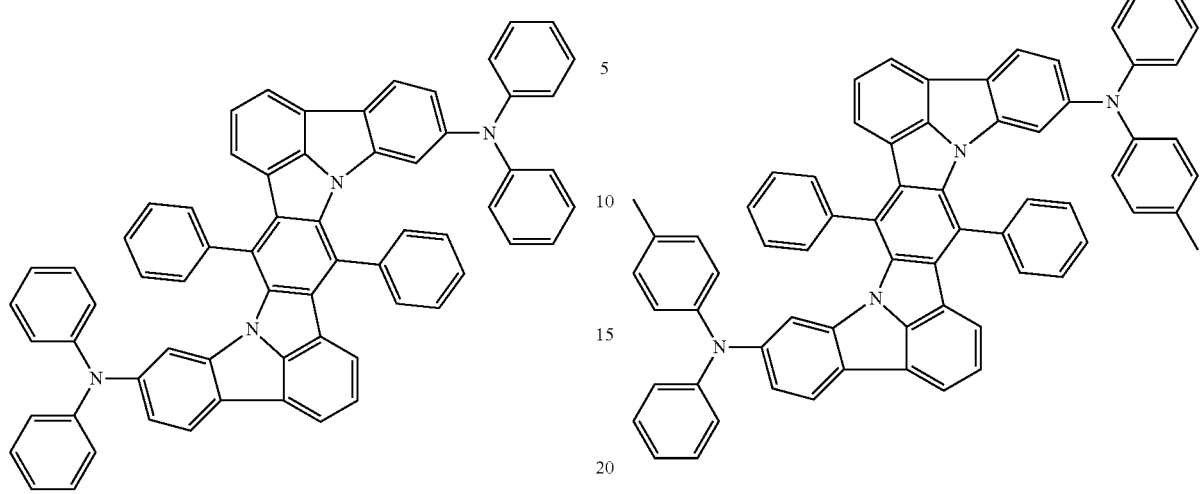
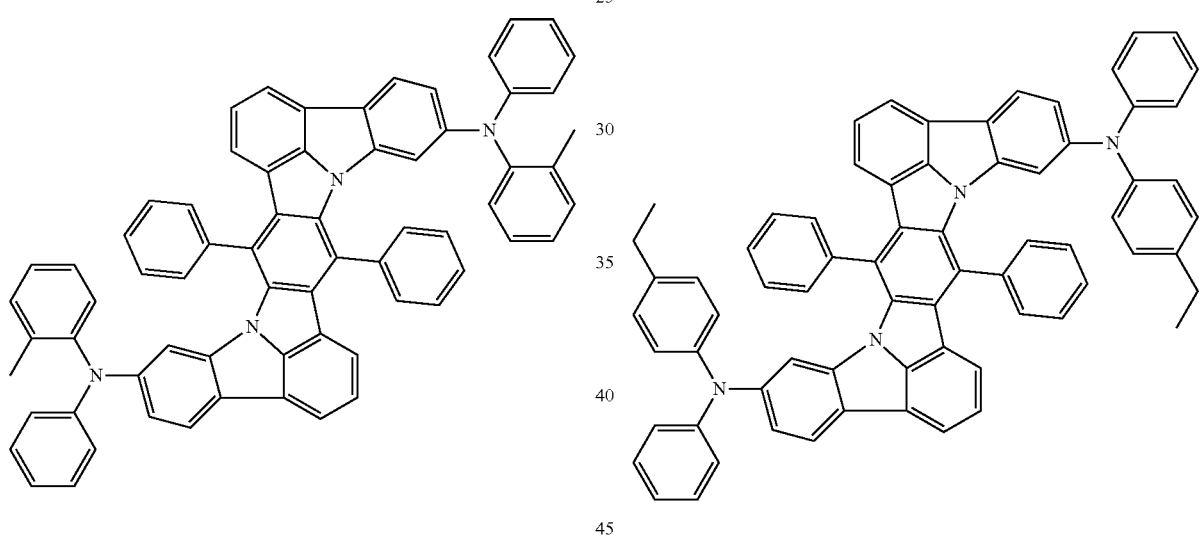
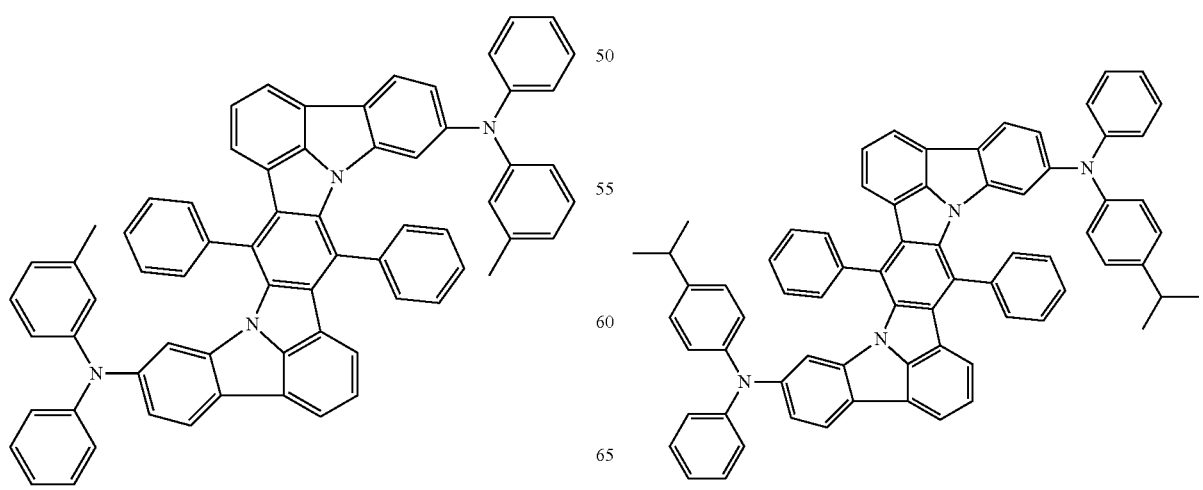

793
-continued
794
-continued
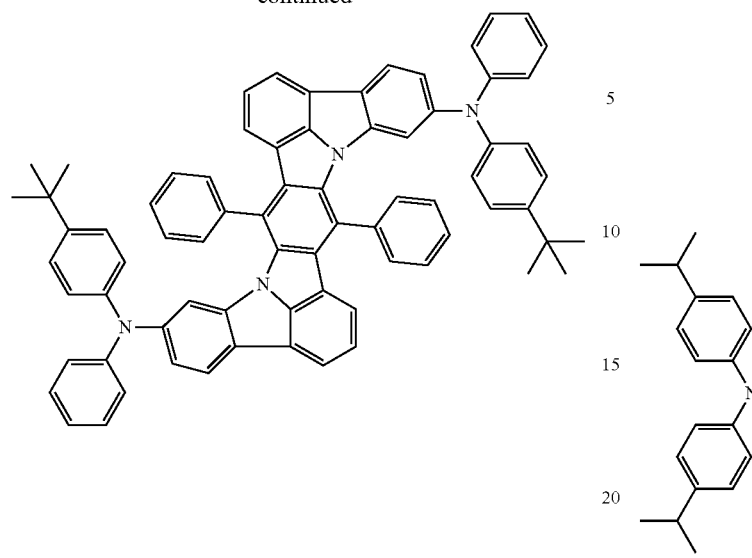
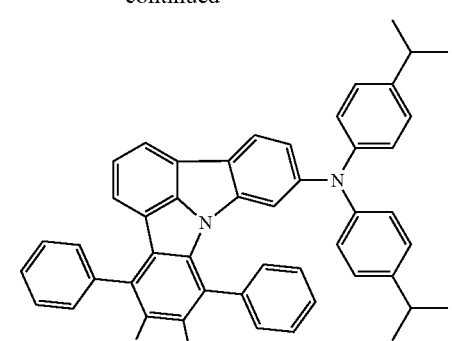
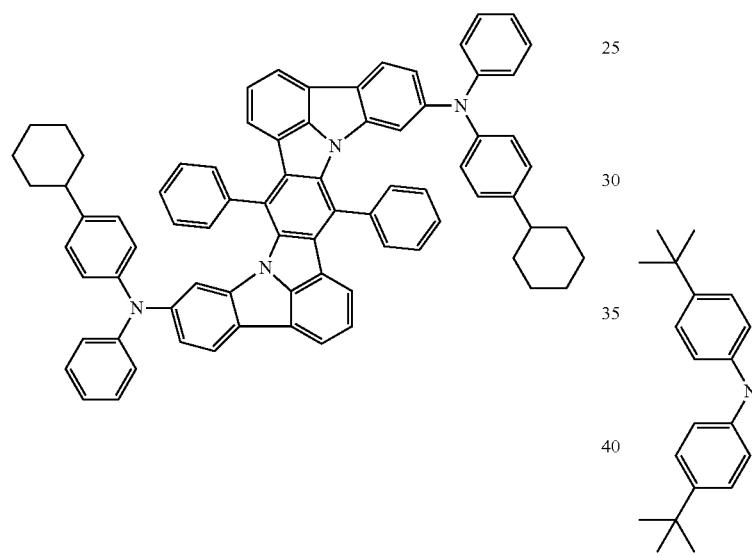

795
-continued
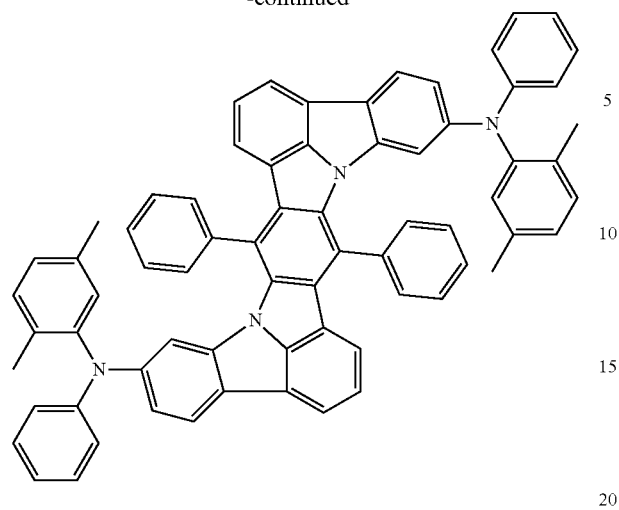
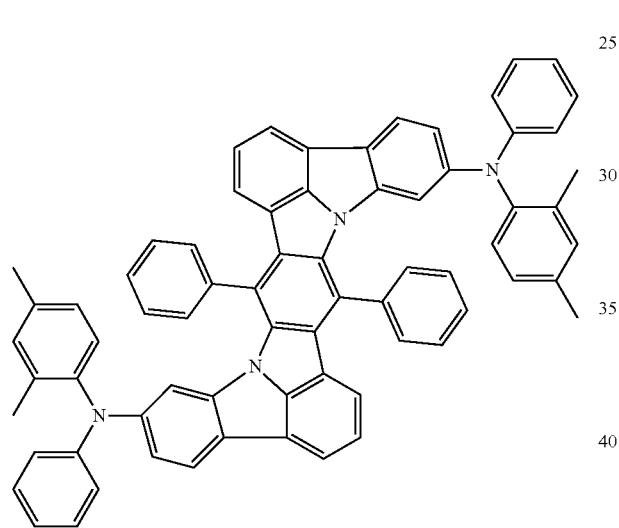
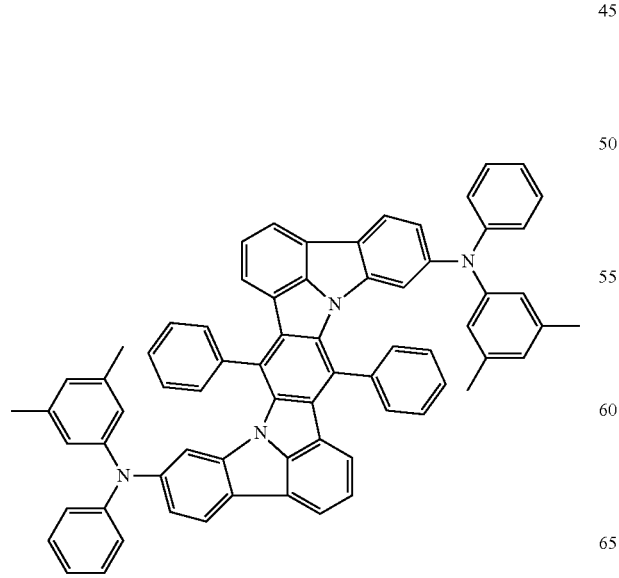
796
-continued
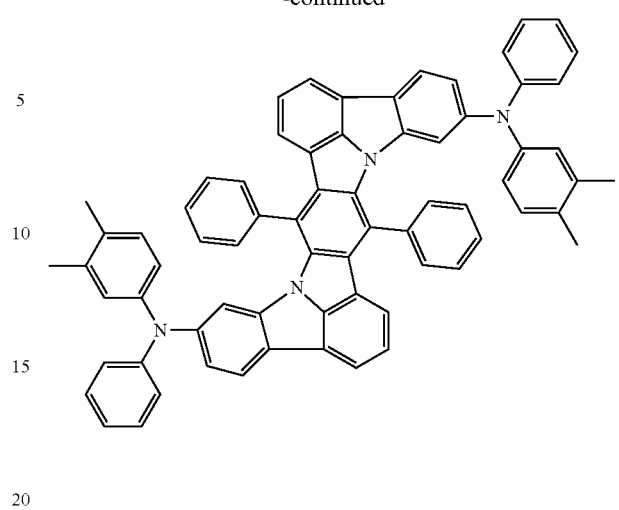
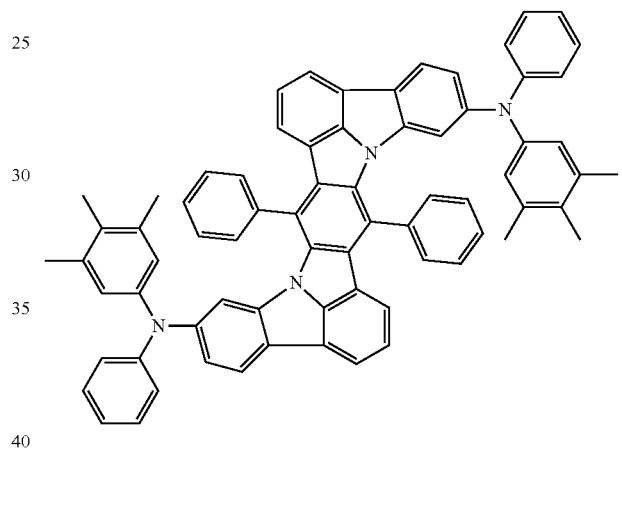
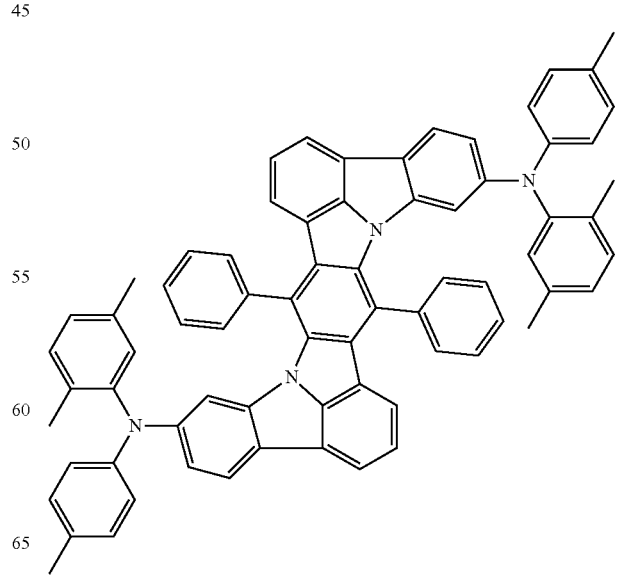

797
-continued
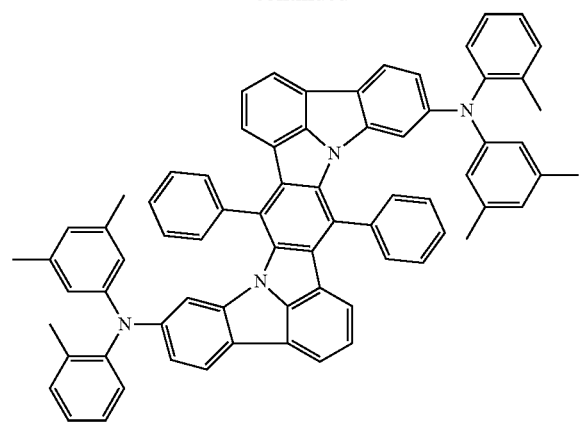
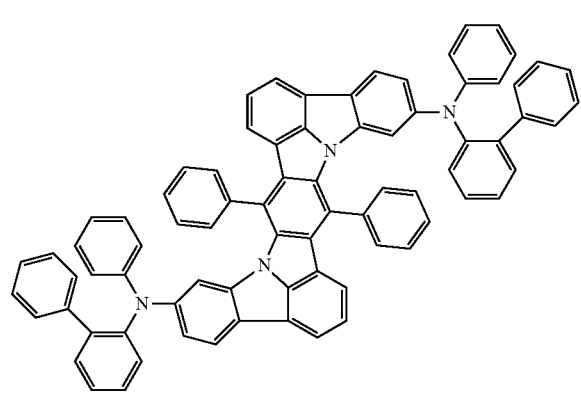
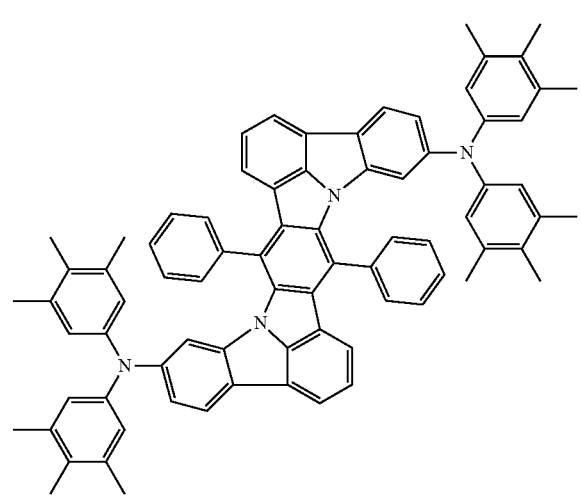
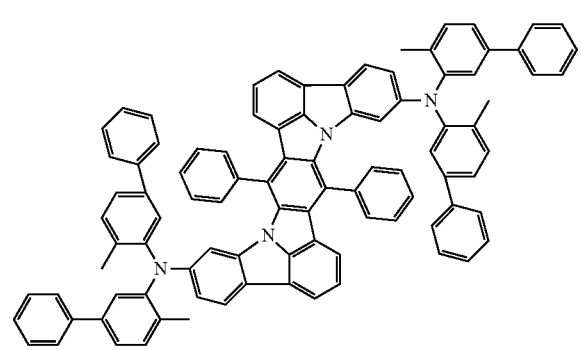
798
-continued
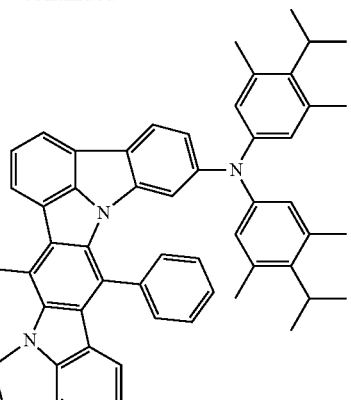
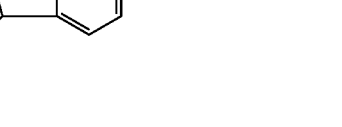
[Formula 310]

| 799 -continued | 800 -continued |
|---|---|
| 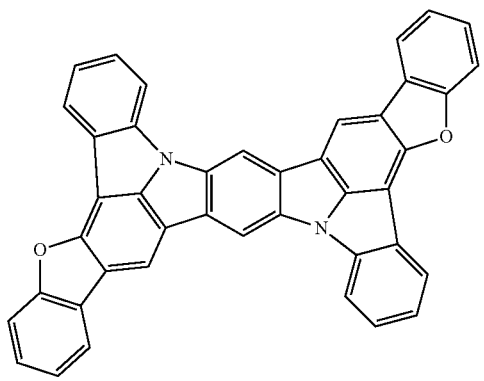 | 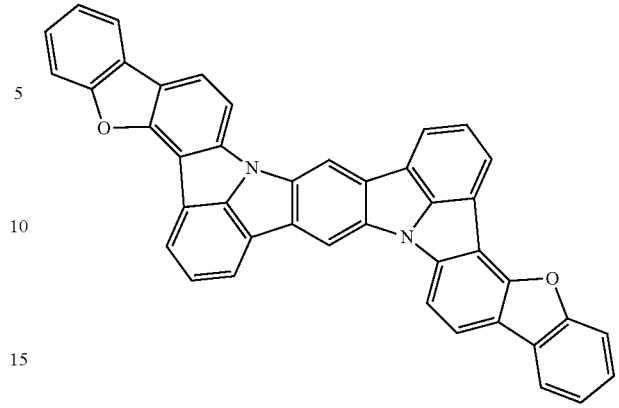 |
| 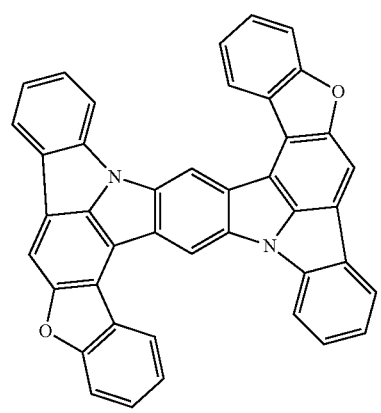 | 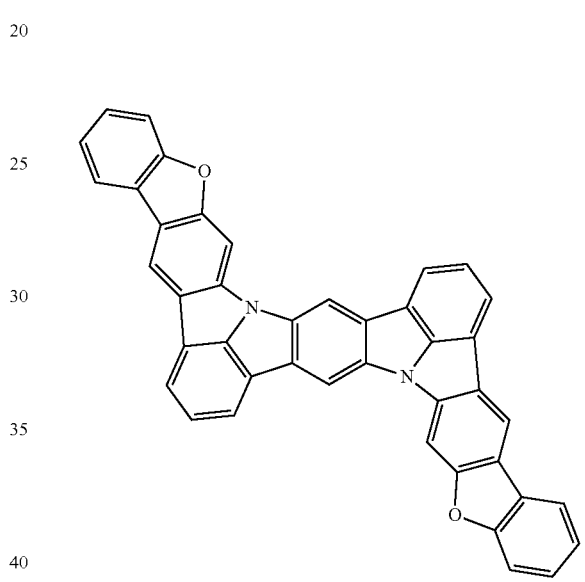 |
| 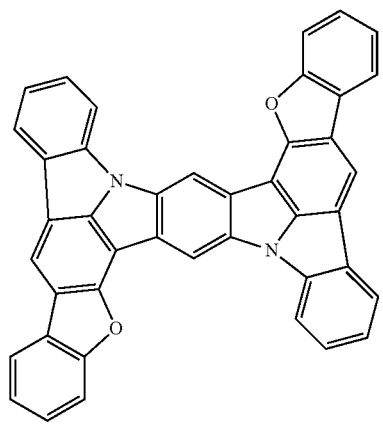 | |
| 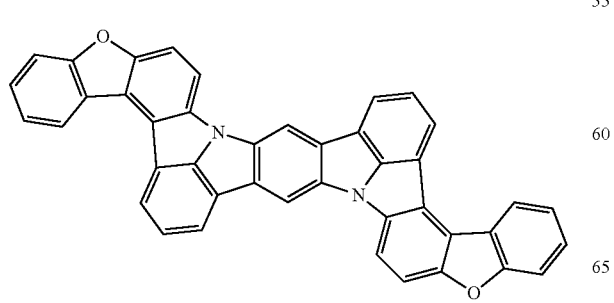 | 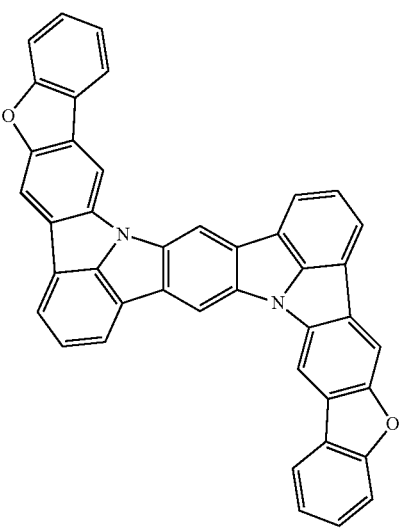 |

| 801 | 802 |
| --- | --- |
| -continued | -continued |
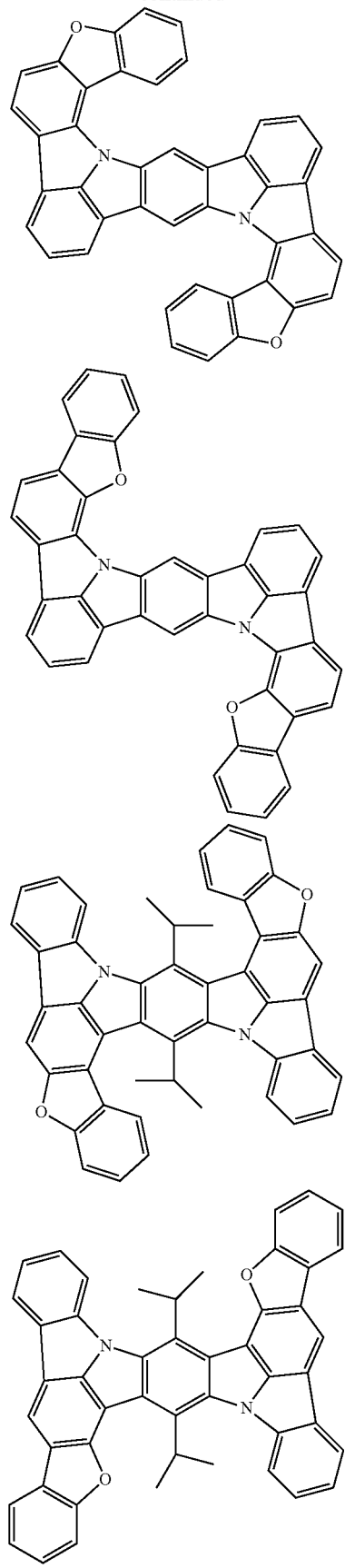
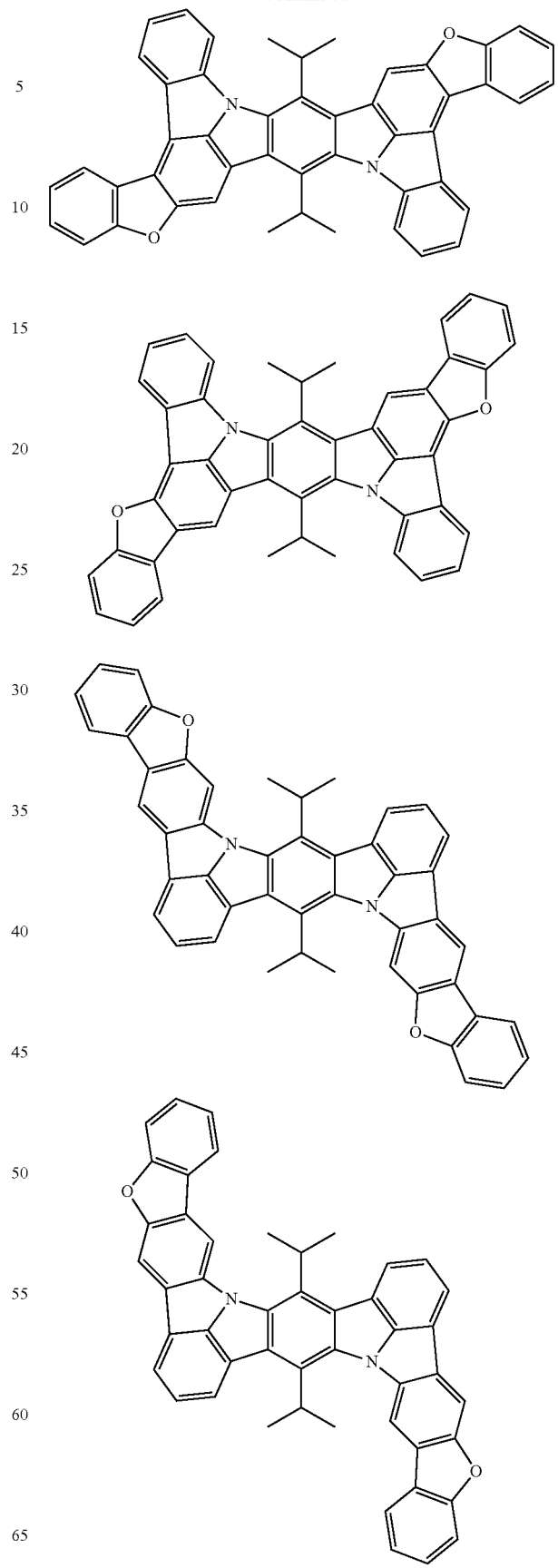

803
-continued
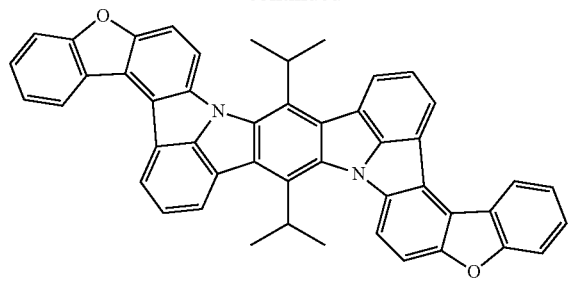
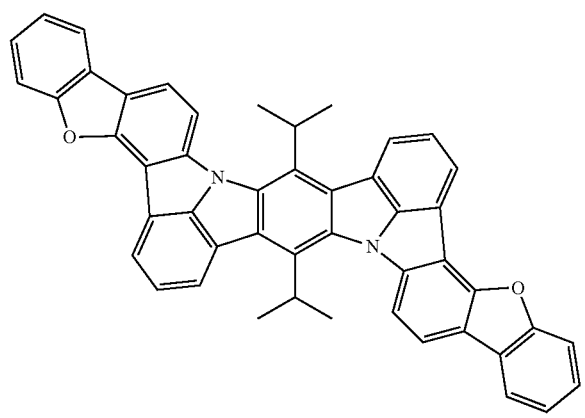
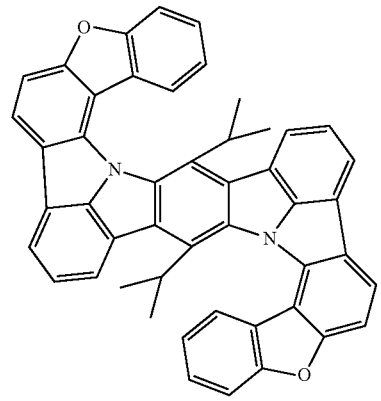
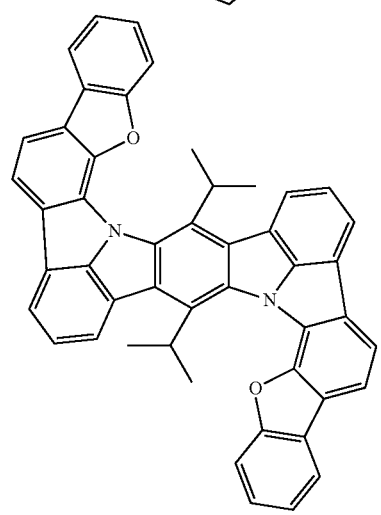
804
-continued
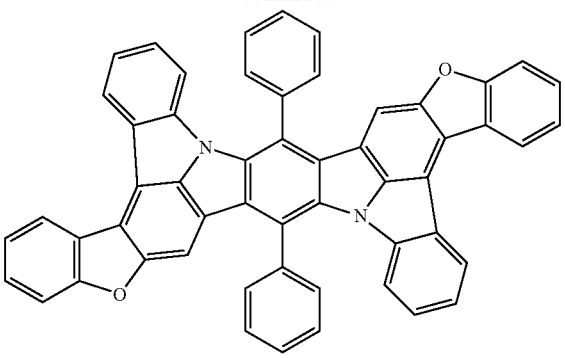
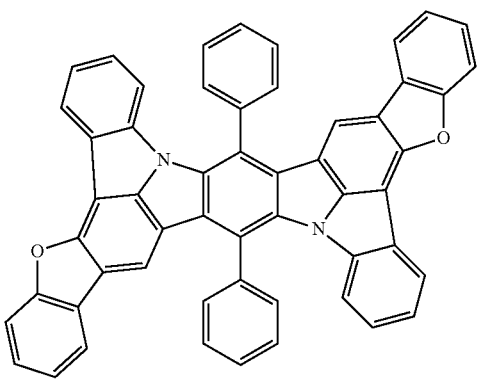
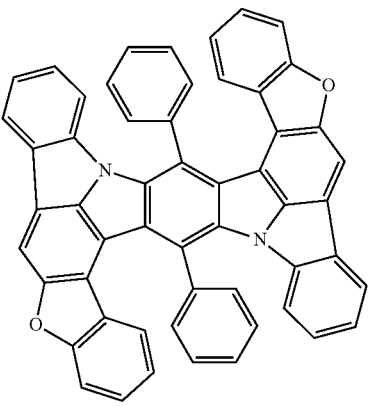
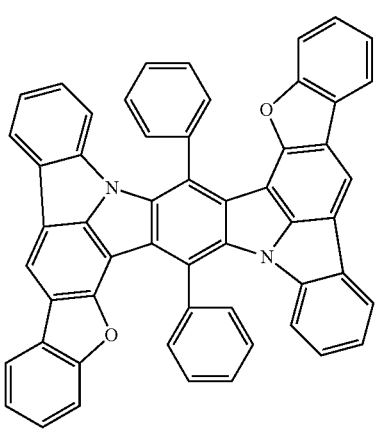

805
-continued
806
-continued
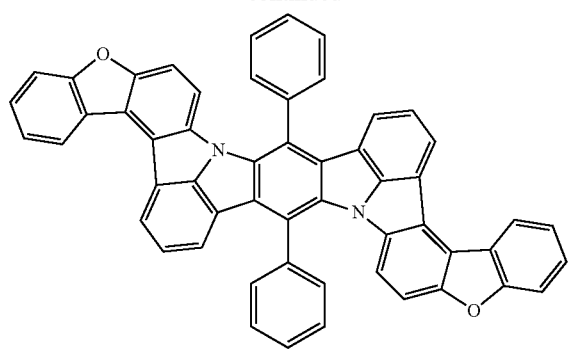
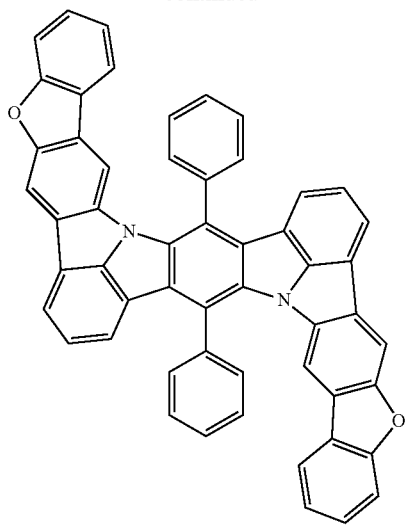
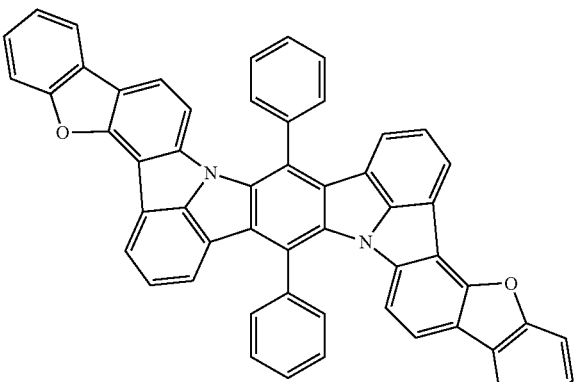
[Formula 311]
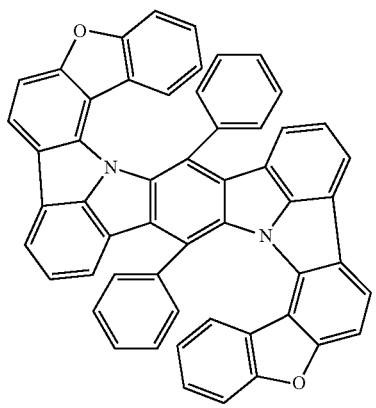
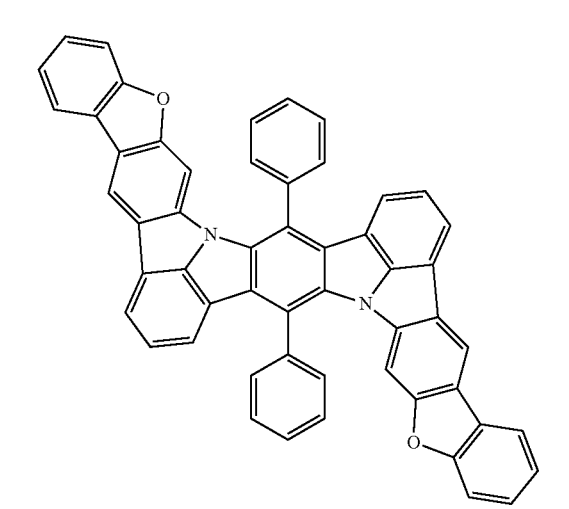
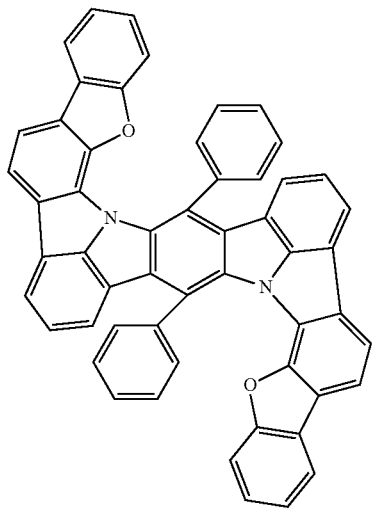

807
-continued
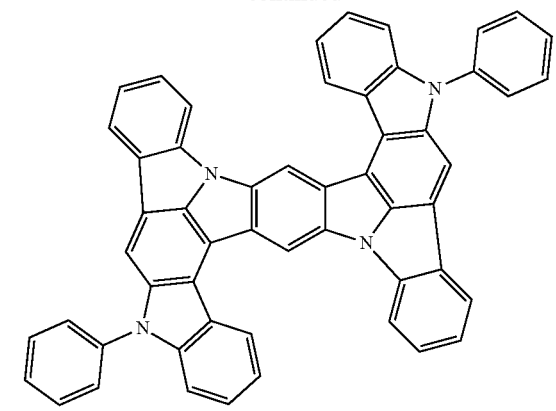
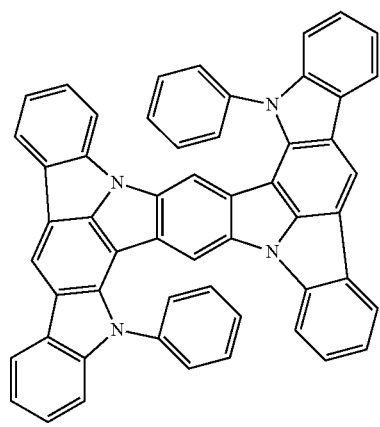
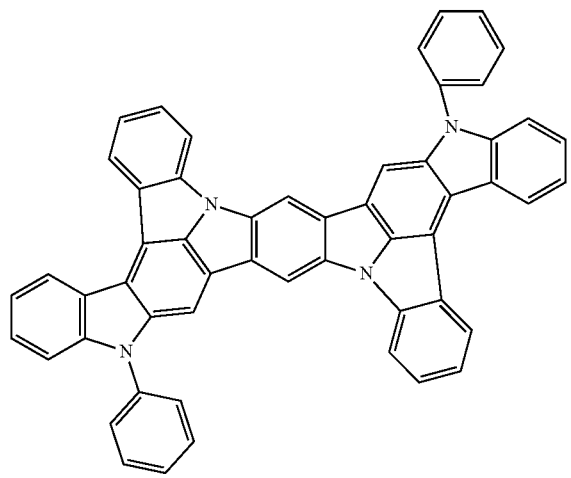
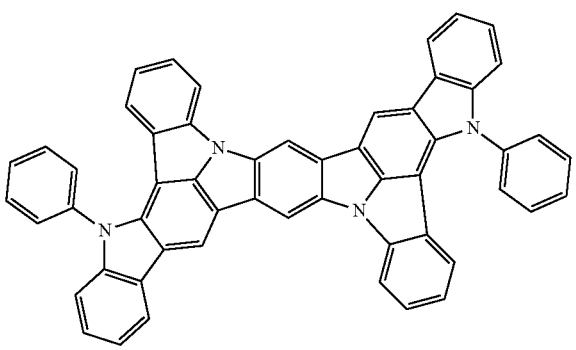
808
-continued
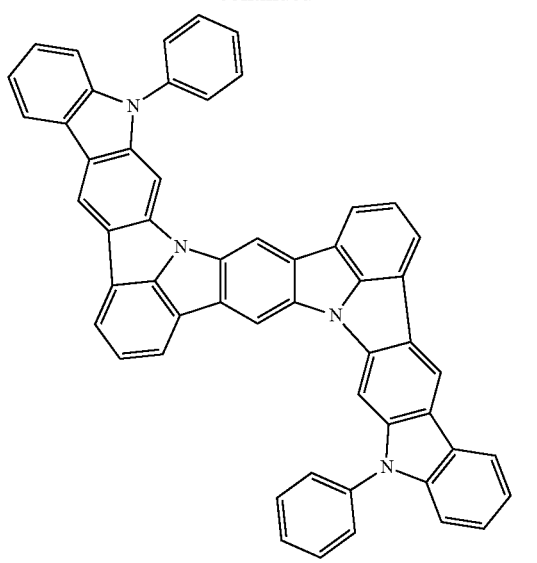
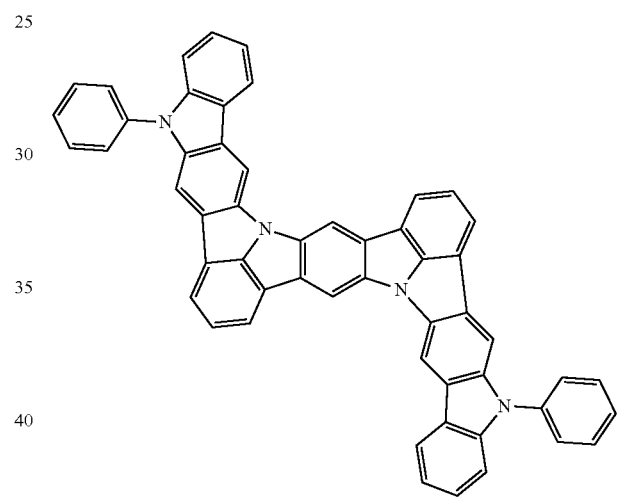
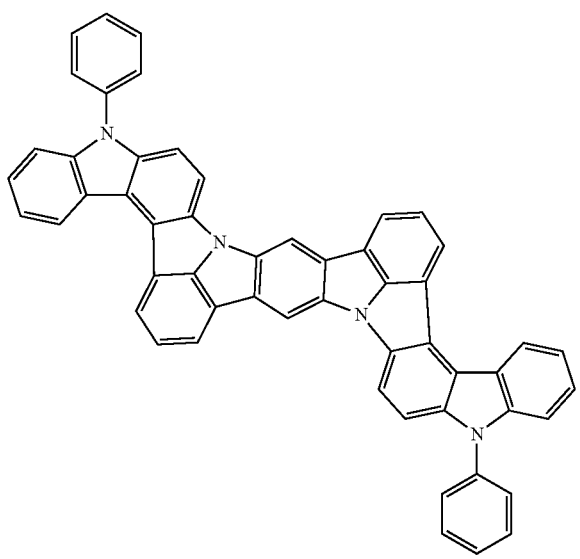

809
-continued
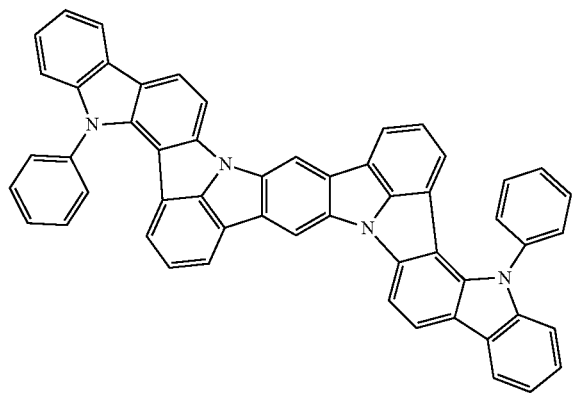
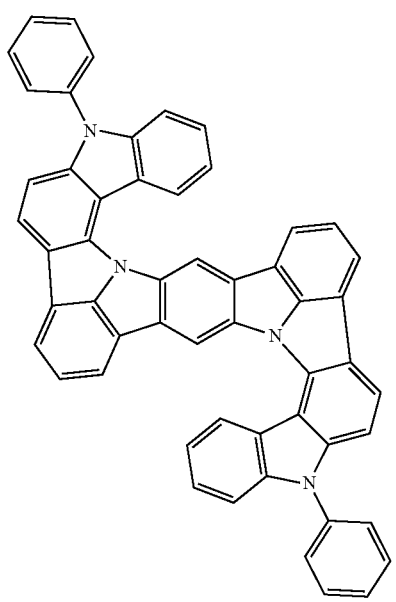
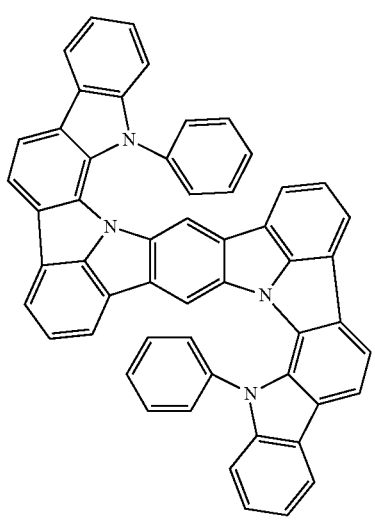
810
-continued
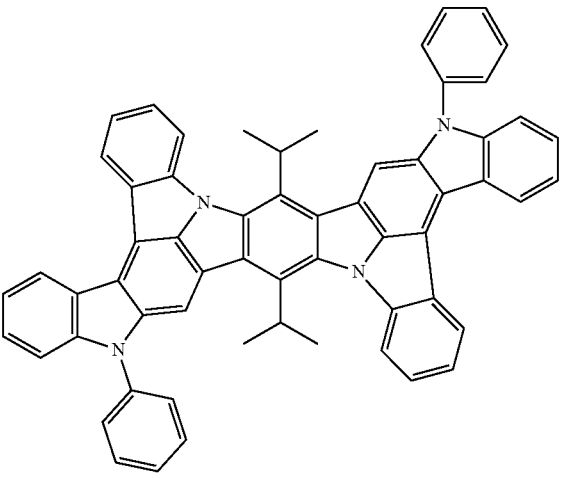
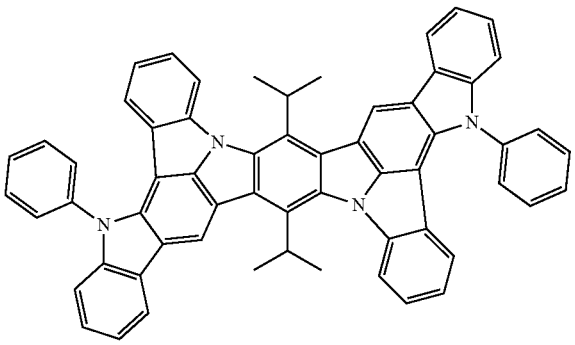

811
-continued
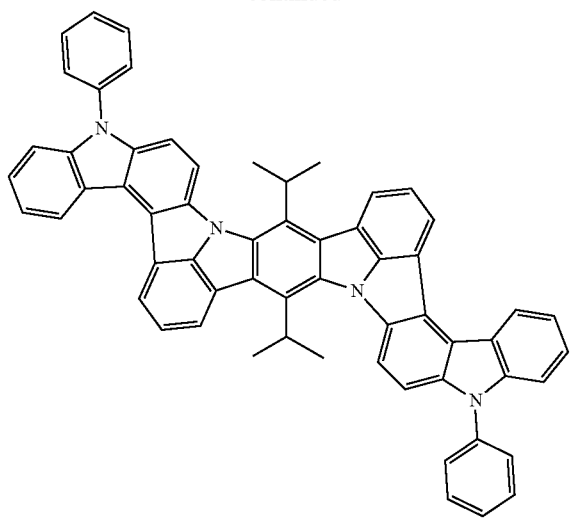
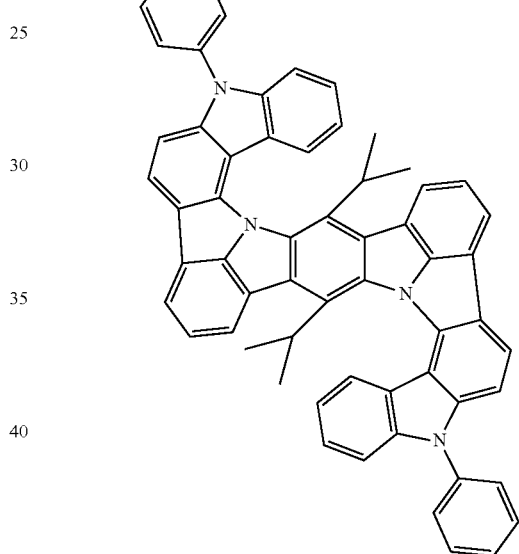
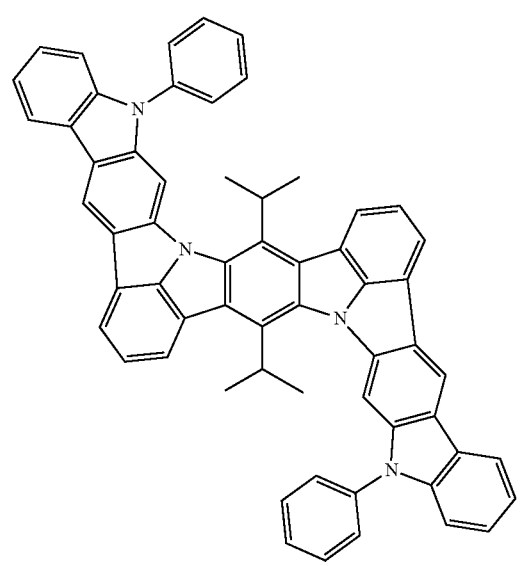
812
-continued
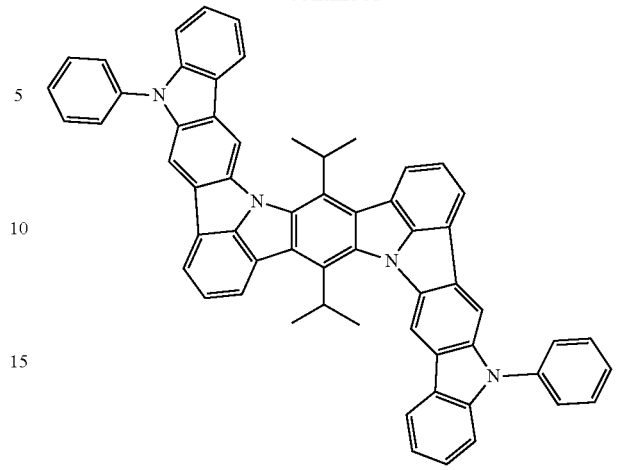
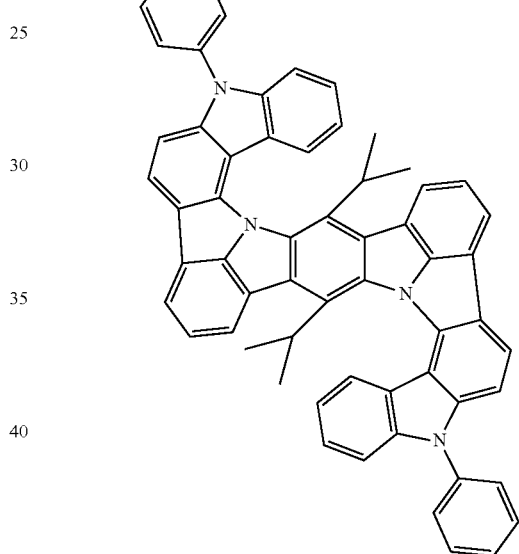
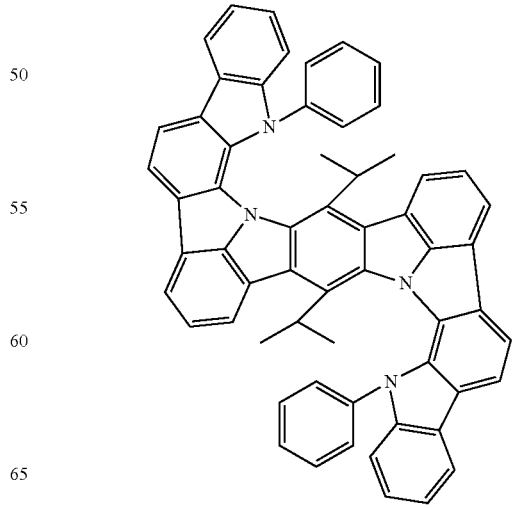

813
-continued
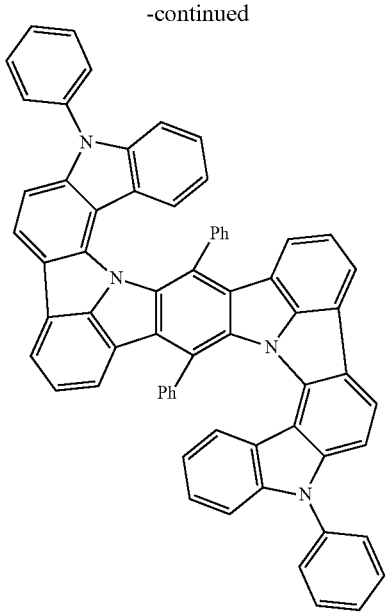
814
-continued
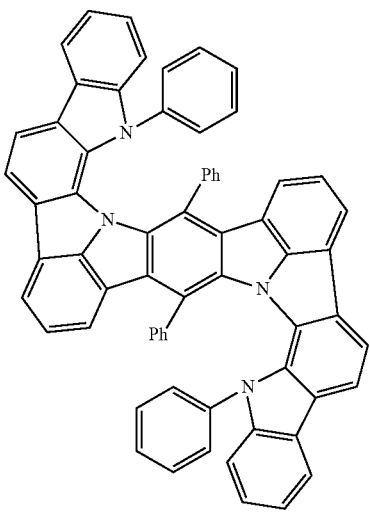
(In the formulae, Ph is a phenyl group.)
[Formula 312]
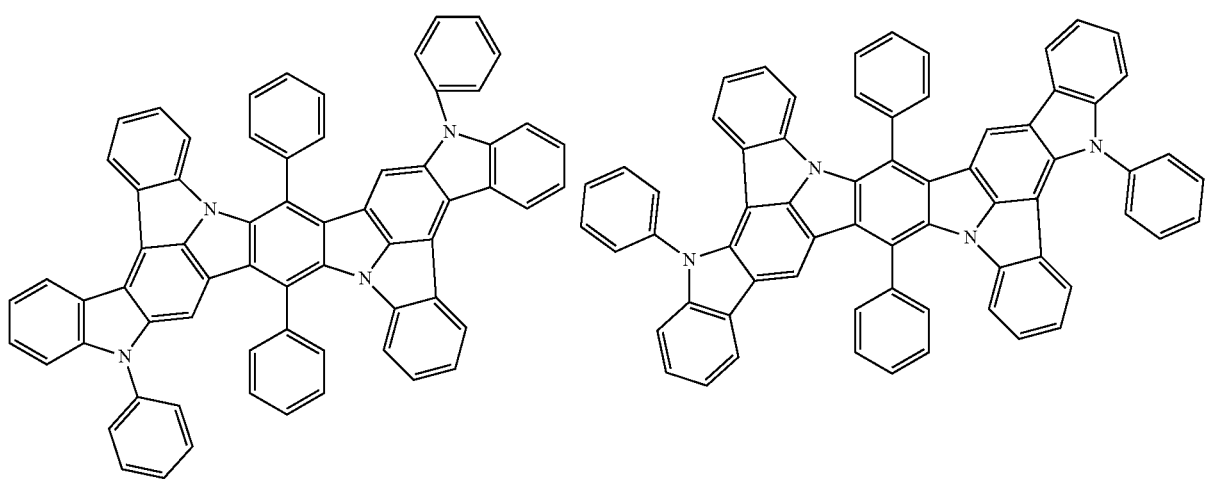
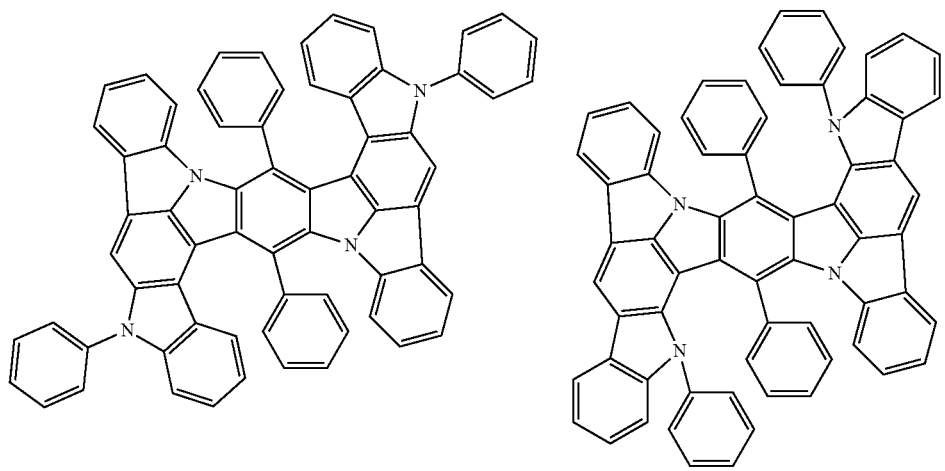

815
816
-continued
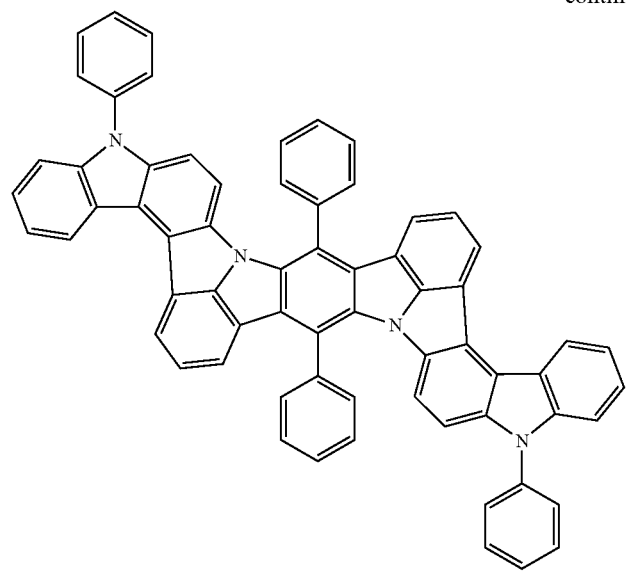
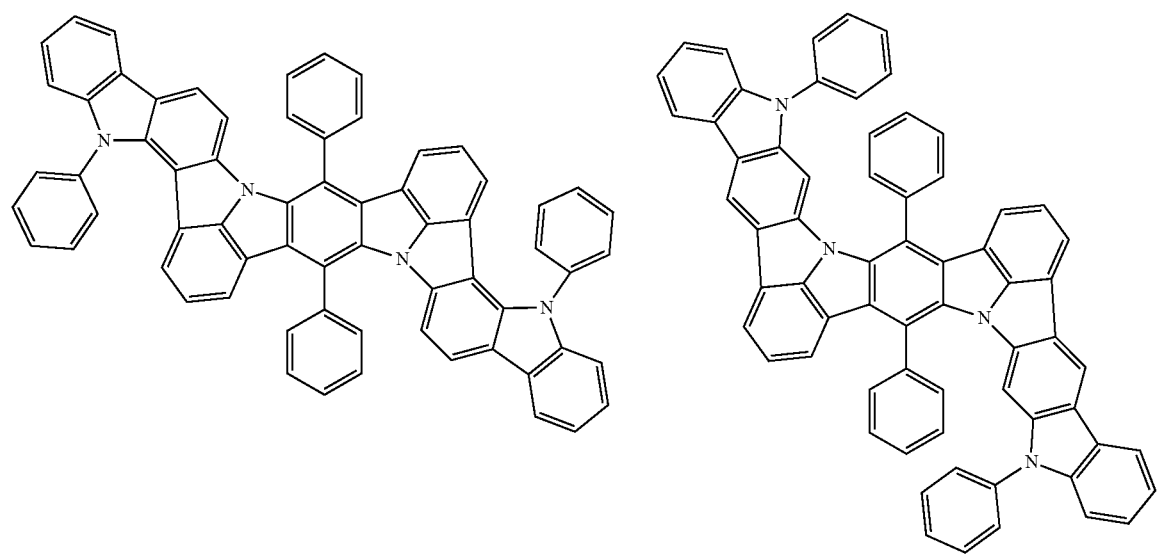
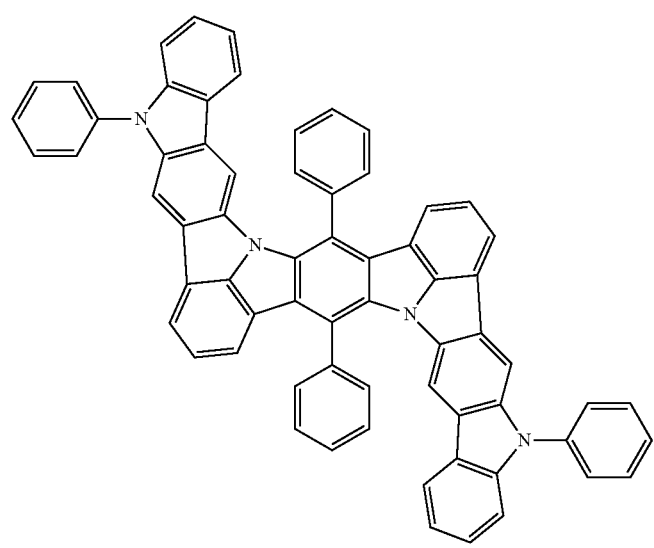

-continued
817 818
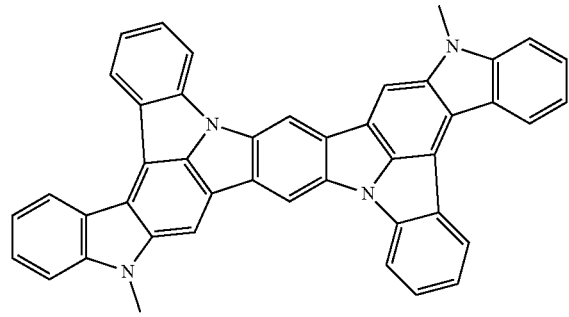 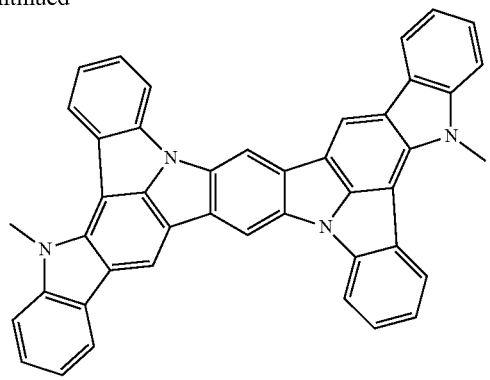
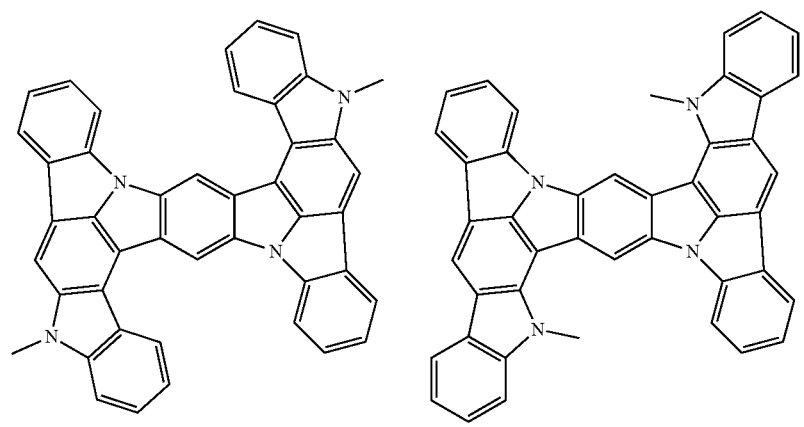
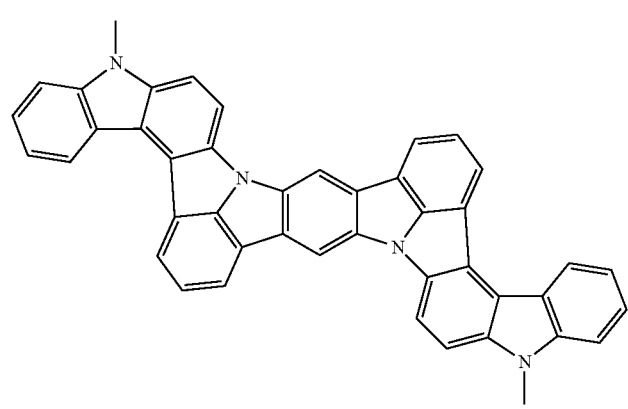 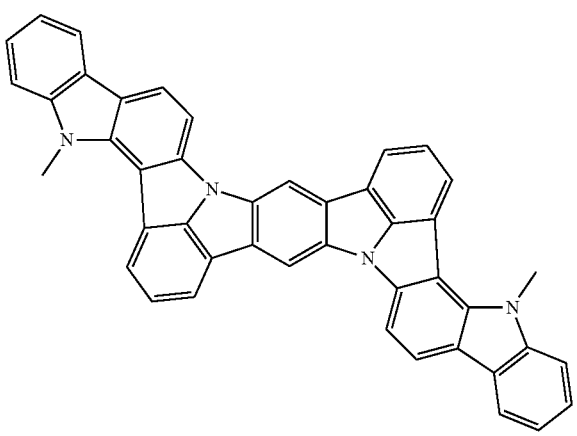

-continued
| 819 | 820 |
|---|---|
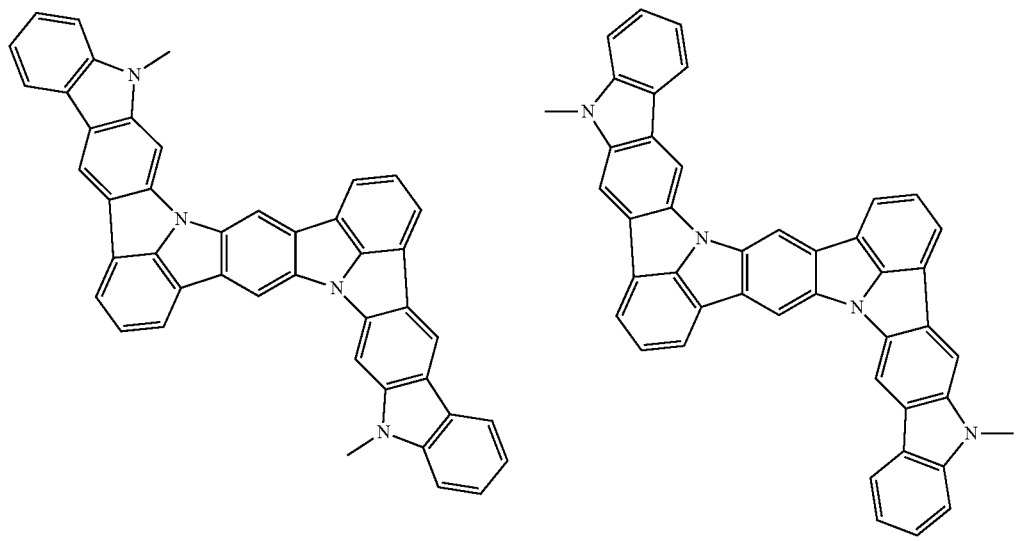
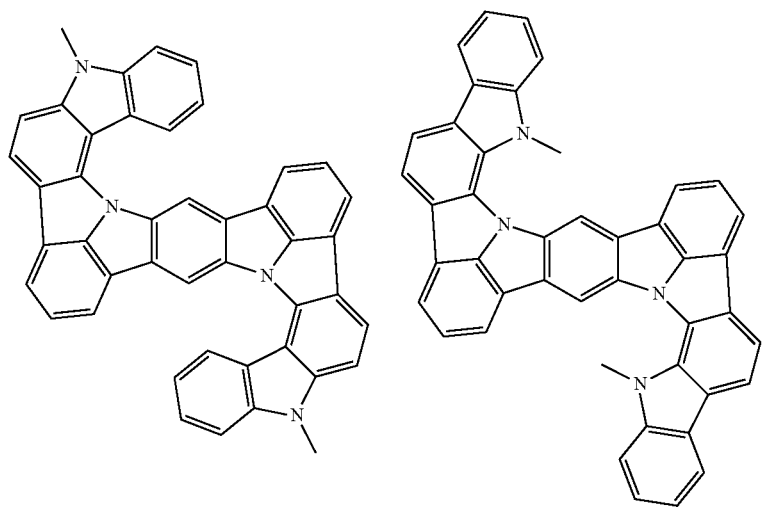
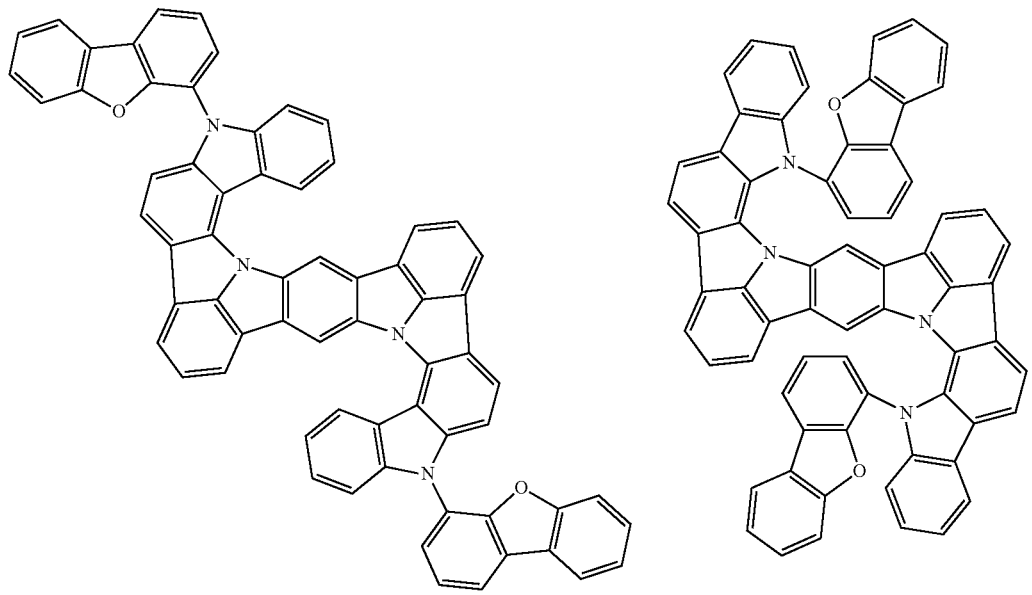

821
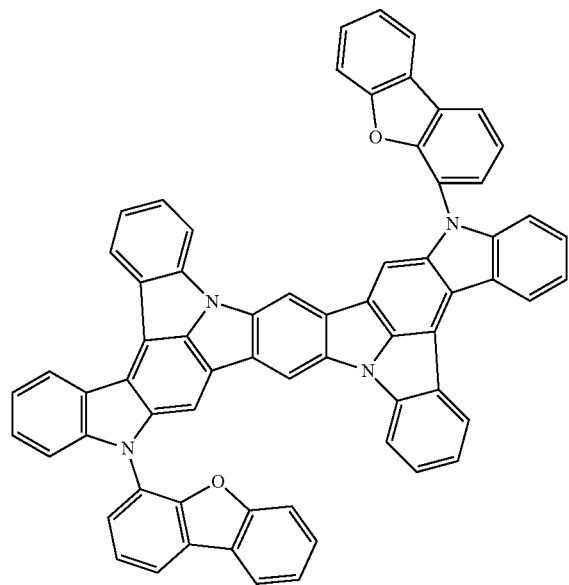
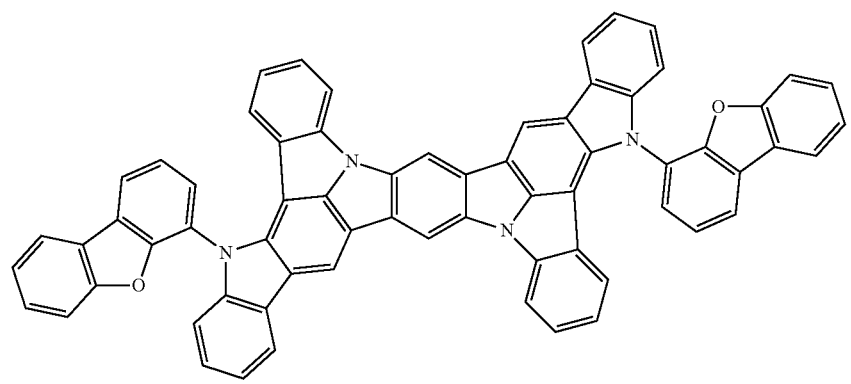
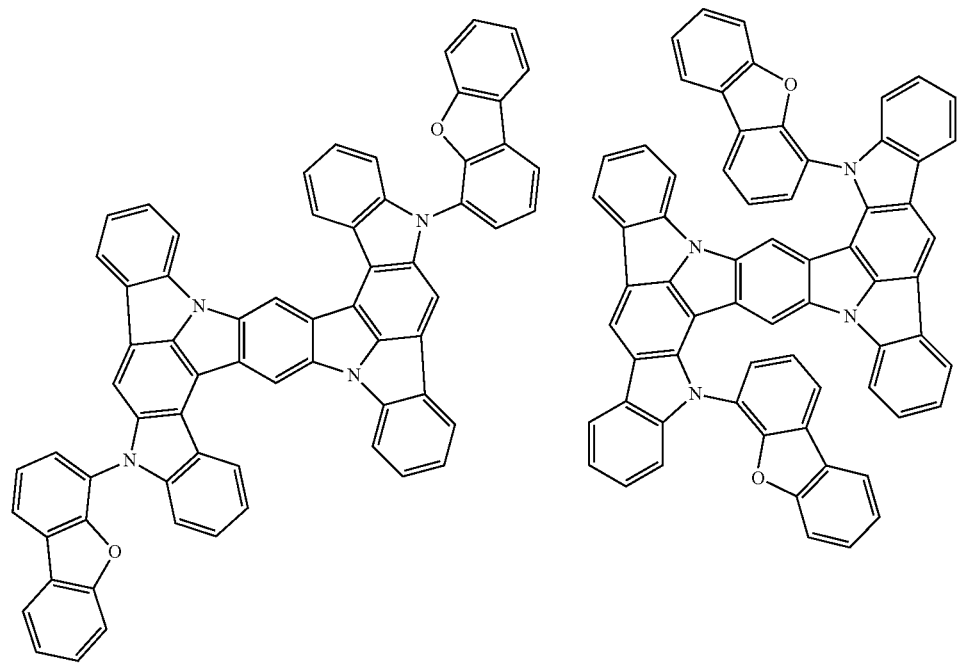
822

-continued
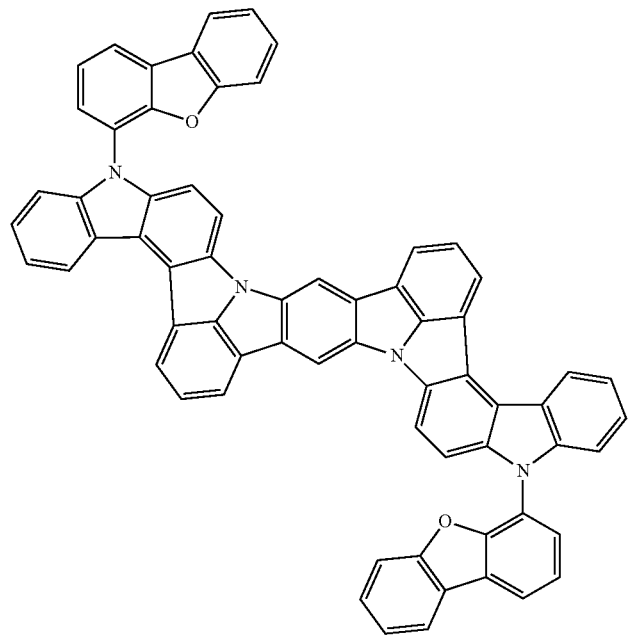
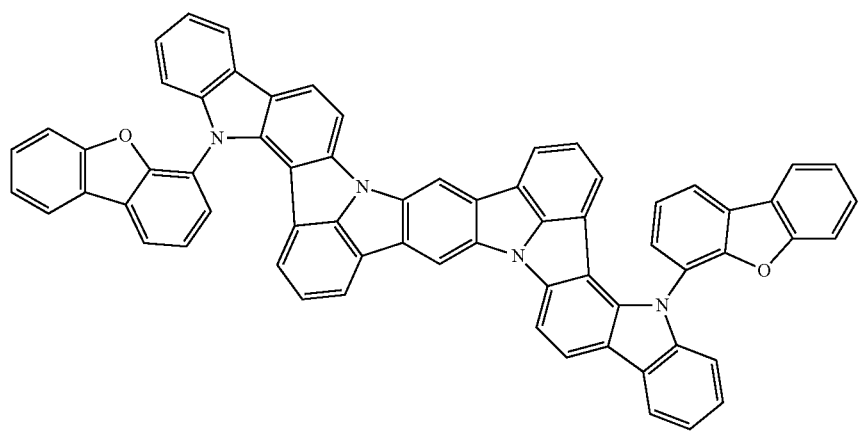
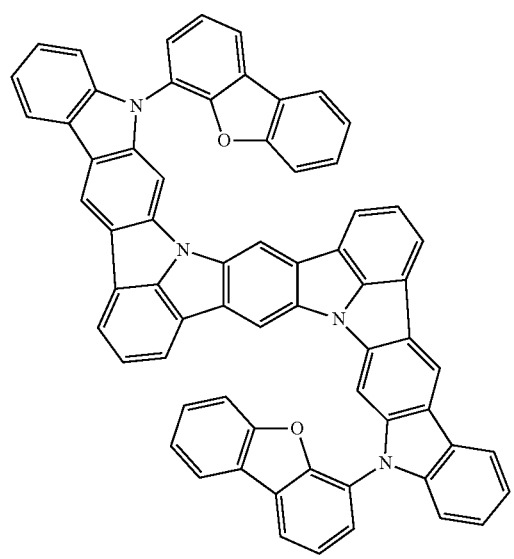

825
826
-continued
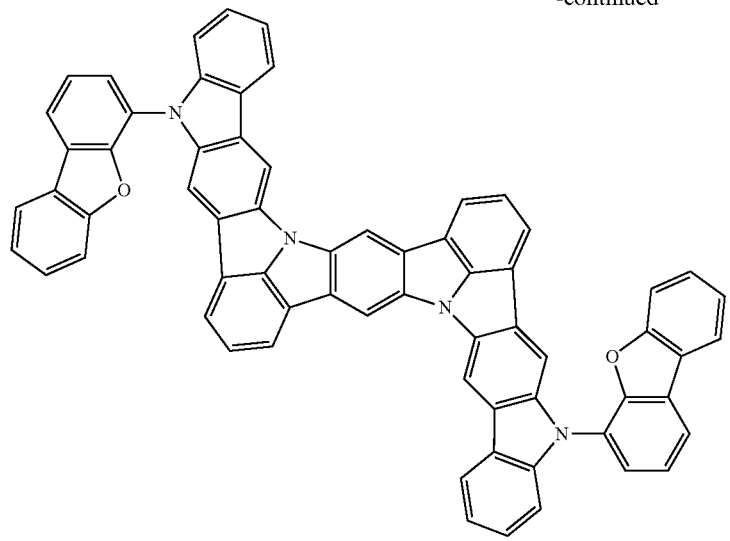
[Formula 313]
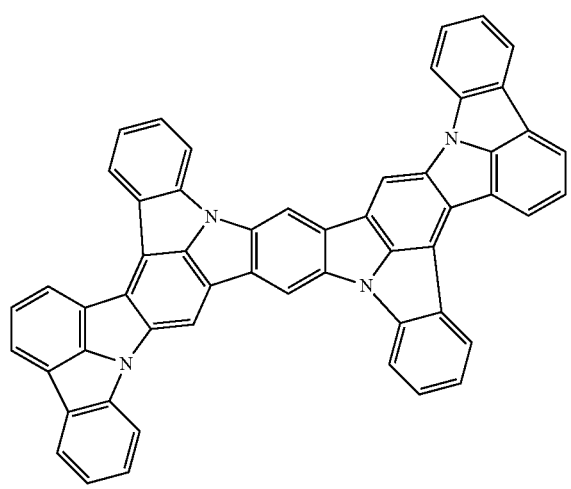
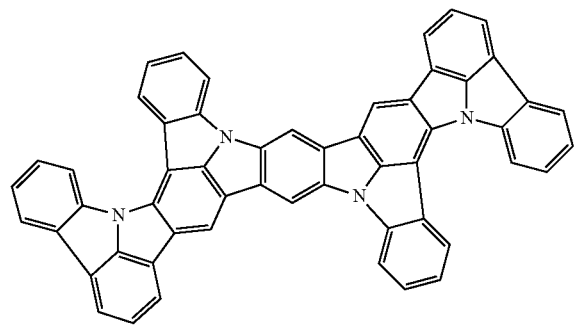

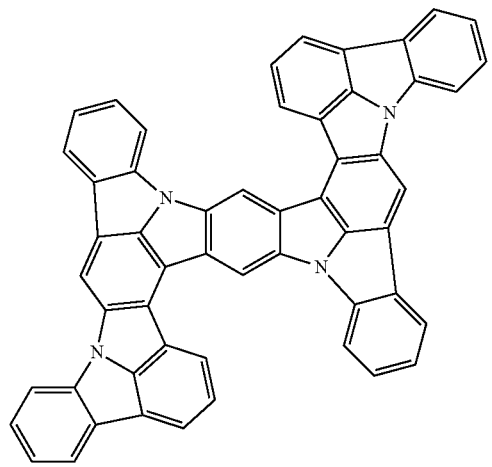
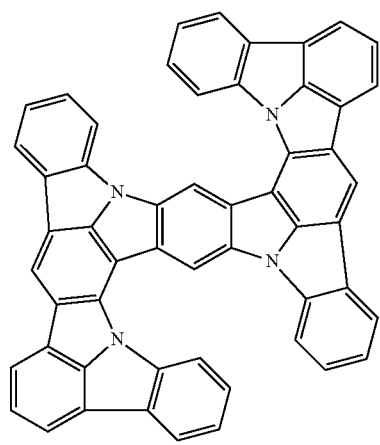
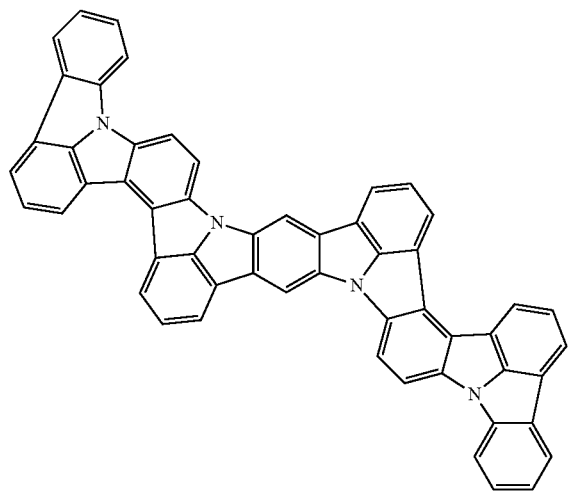

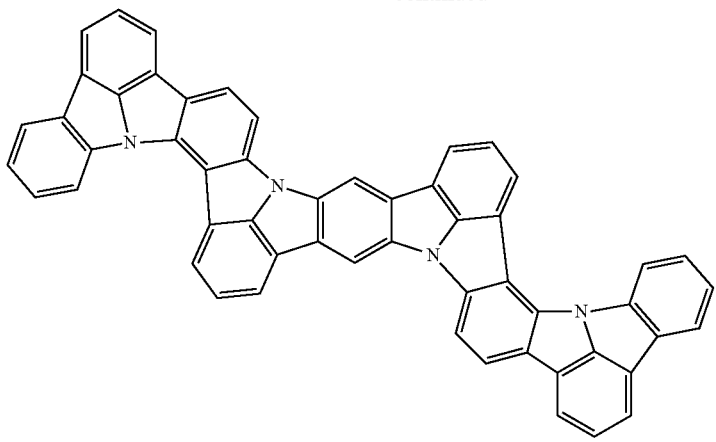
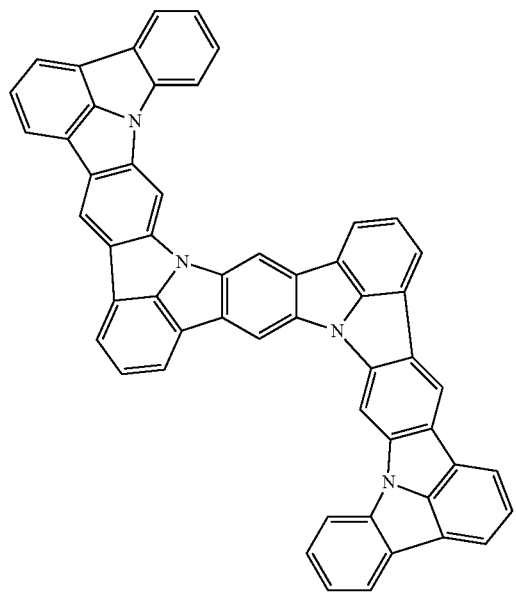
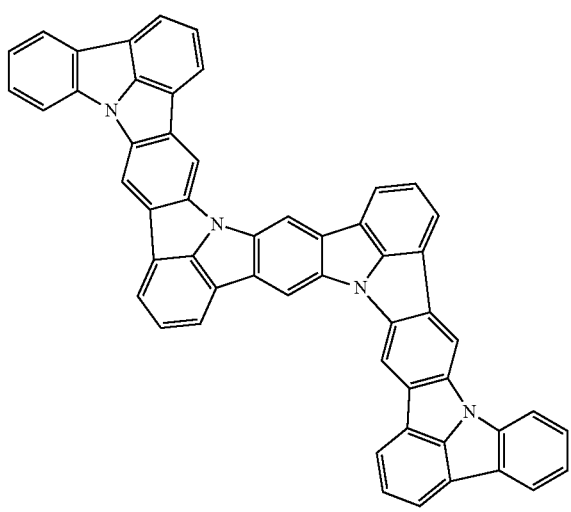

-continued
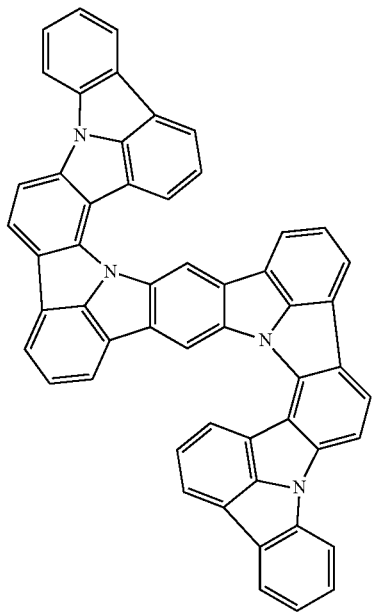
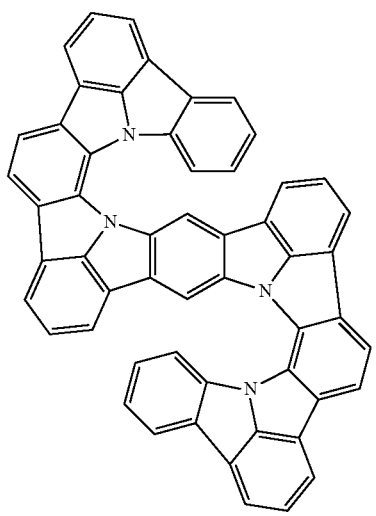
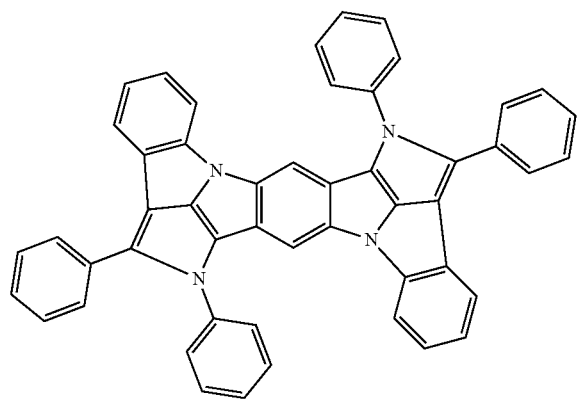

833
-continued
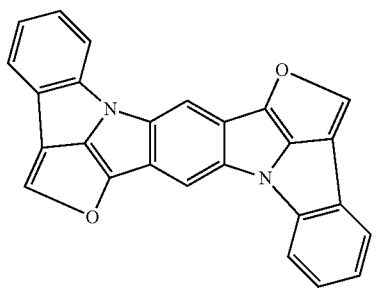
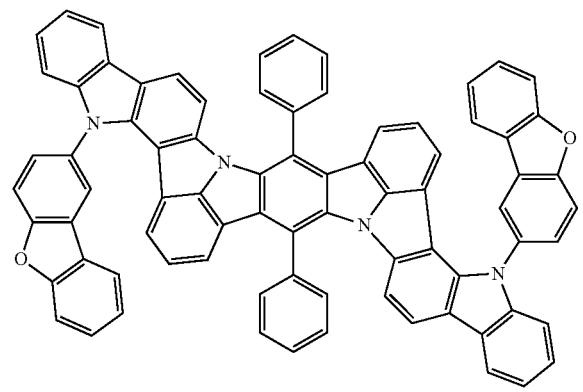
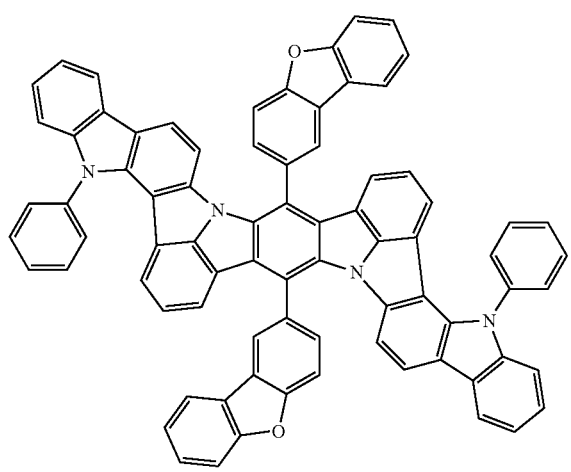
834
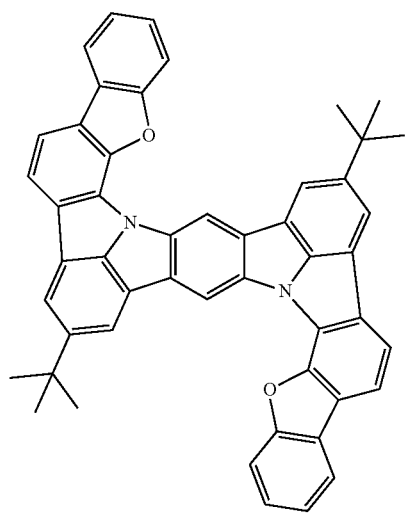

-continued
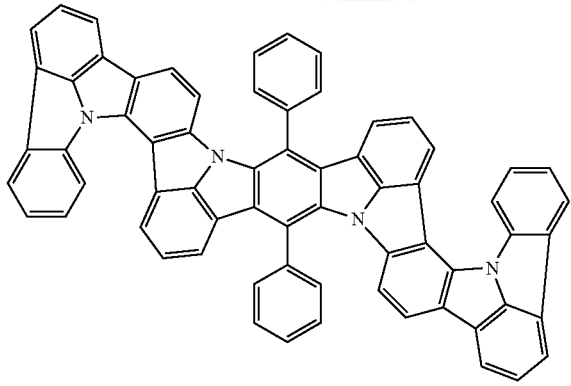
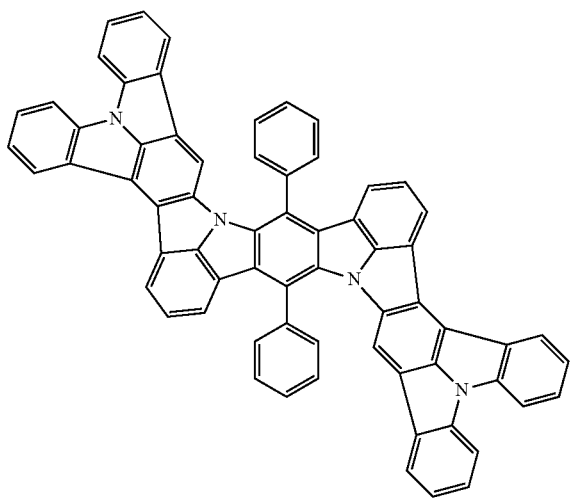
[Formula 314]
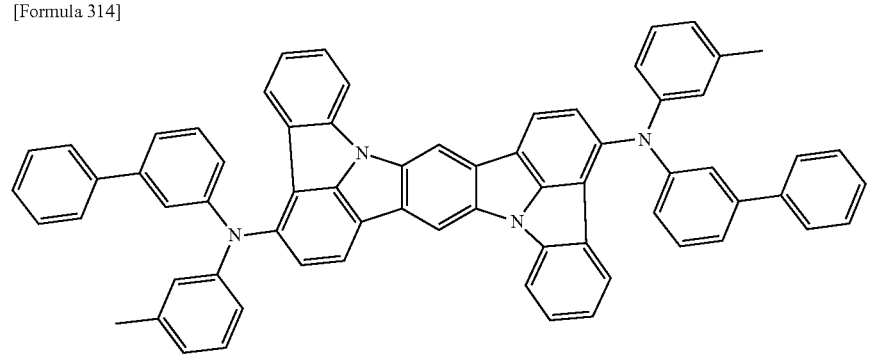

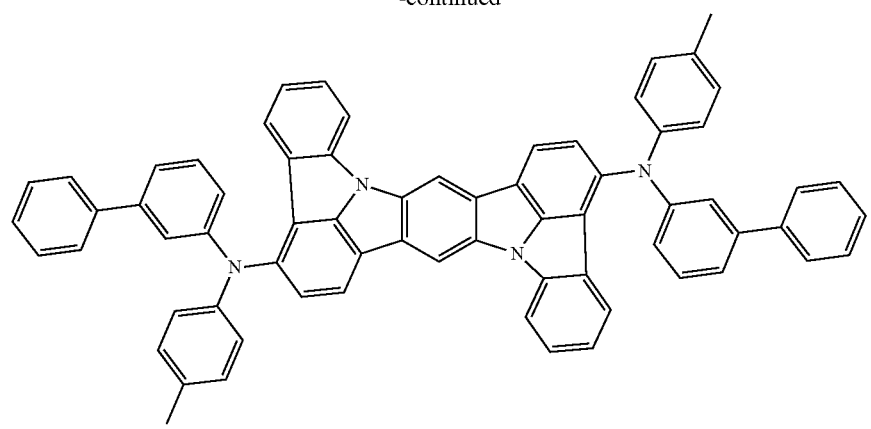
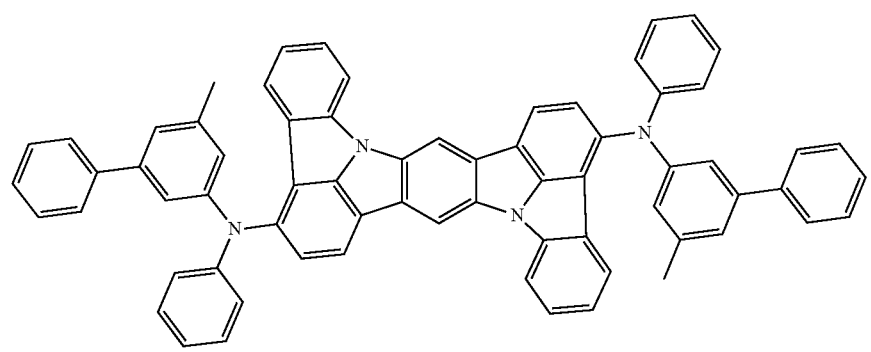
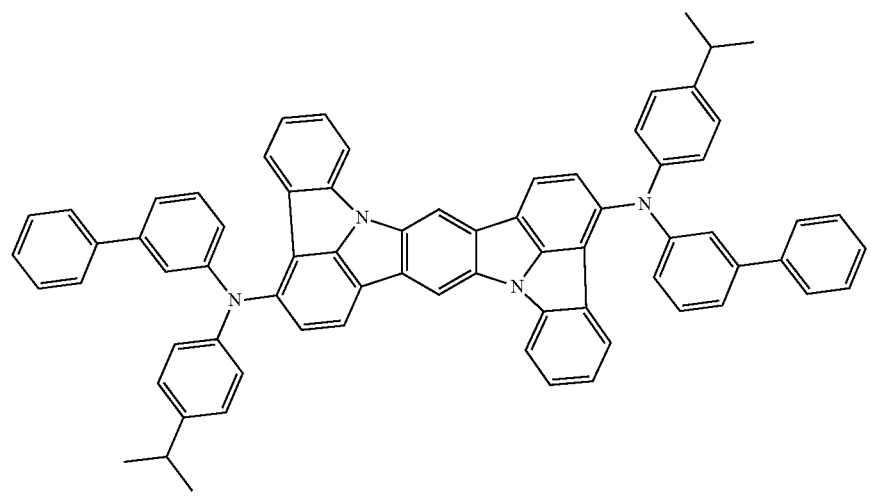
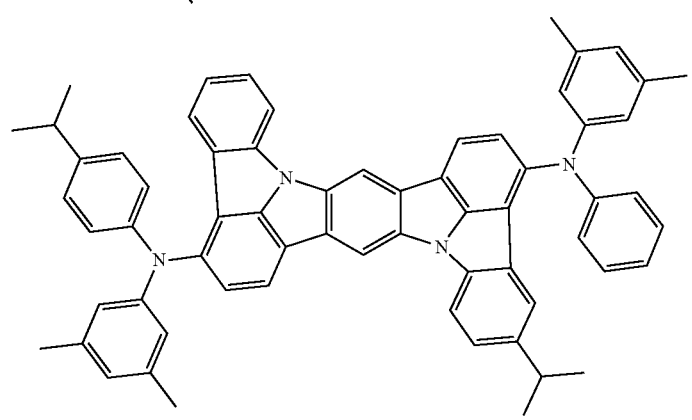

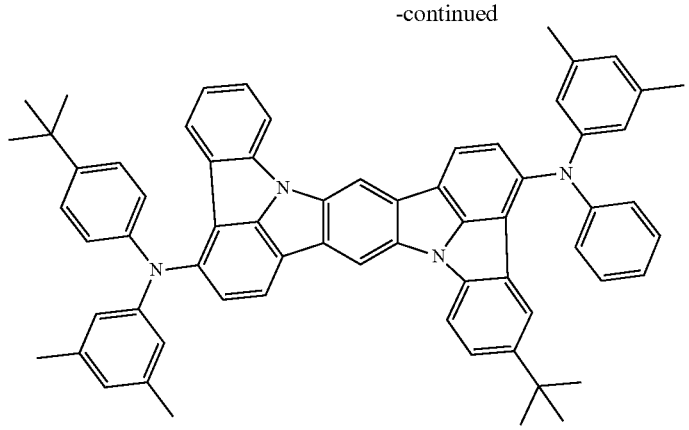

Compound Represented by Formula (6)

The compound represented by the formula (6) will be described below.

[Formula 315]

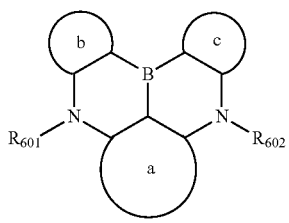

(6)

In the formula (6):

a ring, b ring and c ring are each independently a substituted or unsubstituted aromatic hydrocarbon ring having 6 to 50 ring carbon atoms, or a substituted or unsubstituted heterocycle having 5 to 50 ring atoms;

$R_{601}$ and $R_{602}$ are each independently bonded to the a ring, b ring, or a c ring to form a substituted or unsubstituted heterocycle or to form no substituted or unsubstituted heterocycle; and $R_{601}$ and $R_{602}$ not forming the substituted or unsubstituted heterocycle are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

The a ring, b ring and c ring are each a ring (a substituted or unsubstituted aromatic hydrocarbon ring having 6 to 50 ring carbon atoms, or a substituted or unsubstituted heterocycle having 5 to 50 ring atoms) fused with the fused bicyclic moiety formed of a boron atom and two nitrogen atoms at the center of the formula (6).

The "aromatic hydrocarbon ring" for the a, b, and c rings has the same structure as the compound formed by introducing a hydrogen atom to the "aryl group" described above.

Ring atoms of the "aromatic hydrocarbon ring" for the a ring include three carbon atoms on the fused bicyclic structure at the center of the formula (6).

Ring atoms of the "aromatic hydrocarbon ring" for the b ring and the c ring include two carbon atoms on a fused bicyclic structure at the center of the formula (6).

Specific examples of the "substituted or unsubstituted aromatic hydrocarbon ring having 6 to 50 ring carbon atoms" include a compound formed by introducing a hydrogen atom to the "aryl group" described in the specific example group G1.

The "heterocycle" for the a, b, and c rings has the same structure as the compound formed by introducing a hydrogen atom to the "heterocyclic group" described above.

Ring atoms of the "heterocycle" for the a ring include three carbon atoms on the fused bicyclic structure at the center of the formula (6). Ring atoms of the "heterocycle" for the b ring and the c ring include two carbon atoms on a fused bicyclic structure at the center of the formula (6). Specific examples of the "substituted or unsubstituted heterocycle having 5 to 50 ring atoms" include a compound formed by introducing a hydrogen atom to the "heterocyclic group" described in the specific example group G2.

$R_{601}$ and $R_{602}$ are optionally each independently bonded to the a ring, b ring, or c ring to form a substituted or unsubstituted heterocycle. The "heterocycle" in this arrangement includes the nitrogen atom on the fused bicyclic structure at the center of the formula (6). The heterocycle in the above arrangement optionally include a hetero atom other than the nitrogen atom. $R_{601}$ and $R_{602}$ bonded to the a ring, b ring, or c ring specifically means that atoms forming $R_{601}$ and $R_{602}$ are bonded to atoms forming the a ring, b ring, or c ring. For instance, $R_{601}$ may be bonded to the a ring to form a bicyclic (or tri-or-more cyclic) fused nitrogen-containing heterocycle, in which the ring including $R_{601}$ and the a ring are fused. Specific examples of the nitrogen-containing heterocycle include a compound corresponding to the nitrogen-containing bi(or-more)cyclic fused heterocyclic group in the specific example group G2.

The same applies to $R_{601}$ bonded to the b ring, $R_{602}$ bonded to the a ring, and $R_{602}$ bonded to the c ring.

In an exemplary embodiment, the a ring, b ring and c ring in the formula (6) are each independently a substituted or unsubstituted aromatic hydrocarbon ring having 6 to 50 ring carbon atoms.

In an exemplary embodiment, the a ring, b ring and c ring in the formula (6) are each independently a substituted or unsubstituted benzene ring or a substituted or unsubstituted naphthalene ring.

In an exemplary embodiment, $R_{601}$ and $R_{602}$ in the formula (6) are each independently a substituted or unsubstituted aryl group having 6 to 50 ring carbon atoms, or a substituted or unsubstituted heterocyclic group having 5 to 50 ring atoms, preferably a substituted or unsubstituted aryl group having 6 to 50 ring carbon atoms.

In an exemplary embodiment, the compound represented by the formula (6) is represented by a formula (62) below.

[Formula 316]

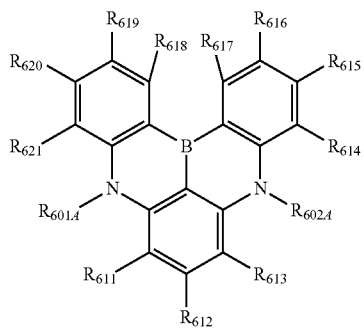

(62)

In the formula (62):

$R_{601A}$ is bonded to at least one of $R_{611}$ or $R_{621}$ to form a substituted or unsubstituted heterocycle or to form no substituted or unsubstituted heterocycle;

$R_{602A}$ is bonded to at least one of $R_{613}$ or $R_{614}$ to form a substituted or unsubstituted heterocycle or to form no substituted or unsubstituted heterocycle;

$R_{601A}$ and $R_{602A}$ not forming the substituted or unsubstituted heterocycle are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

at least one combination of adjacent two or more of $R_{611}$ to $R_{621}$ are mutually bonded to form a substituted or unsubstituted monocyclic ring, mutually bonded to form a substituted or unsubstituted fused ring, or not mutually bonded; and $R_{611}$ to $R_{621}$ not forming the substituted or unsubstituted heterocycle, not forming the monocyclic ring and not forming the fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

$R_{601A}$ and $R_{602A}$ in the formula (62) are groups corresponding to $R_{601}$ and $R_{602}$ in the formula (6), respectively.

For instance, $R_{601A}$ and $R_{611}$ are optionally bonded to each other to form a bicyclic (or tri-or-more cyclic) fused nitrogen-containing heterocycle, in which the ring including $R_{601A}$ and $R_{611}$ and a benzene ring corresponding to the a ring are fused. Specific examples of the nitrogen-containing heterocycle include a compound corresponding to the nitrogen-containing bi(or-more)cyclic fused heterocyclic group in the specific example group G2. The same applies to $R_{601A}$ bonded to $R_{621}$, $R_{602A}$ bonded to $R_{613}$, and $R_{602A}$ bonded to $R_{614}$.

At least one combination of adjacent two or more of $R_{611}$ to $R_{621}$ may be mutually bonded to form a substituted or unsubstituted monocyclic ring, or mutually bonded to form a substituted or unsubstituted fused ring.

For instance, $R_{611}$ and $R_{612}$ are optionally mutually bonded to form a structure in which a benzene ring, indole ring, pyrrole ring, benzofuran ring, benzothiophene ring or the like is fused to the six-membered ring bonded to $R_{611}$ and $R_{612}$, the resultant fused ring forming a naphthalene ring, carbazole ring, indole ring, dibenzofuran ring, or dibenzothiophene ring, respectively.

In an exemplary embodiment, $R_{611}$ to $R_{621}$, which do not contribute to ring formation, are each independently a hydrogen atom, a substituted or unsubstituted alkyl group having 1 to 50 carbon atoms, a substituted or unsubstituted aryl group having 6 to 50 ring carbon atoms, or a substituted or unsubstituted heterocyclic group having 5 to 50 ring atoms.

In an exemplary embodiment, $R_{611}$ to $R_{621}$, which do not contribute to ring formation, are each independently a hydrogen atom, a substituted or unsubstituted aryl group having 6 to 50 ring carbon atoms, or a substituted or unsubstituted heterocyclic group having 5 to 50 ring atoms.

In an exemplary embodiment, $R_{611}$ to $R_{621}$, which do not contribute to ring formation, are each independently a hydrogen atom, or a substituted or unsubstituted alkyl group having 1 to 50 carbon atoms.

In an exemplary embodiment: $R_{611}$ to $R_{621}$, which do not contribute to ring formation, are each independently a hydrogen atom, or a substituted or unsubstituted alkyl group having 1 to 50 carbon atoms; and at least one of $R_{611}$ to $R_{621}$ is a substituted or unsubstituted alkyl group having 1 to 50 carbon atoms.

In an exemplary embodiment, the compound represented by the formula (62) is represented by a formula (63) below.

[Formula 317]

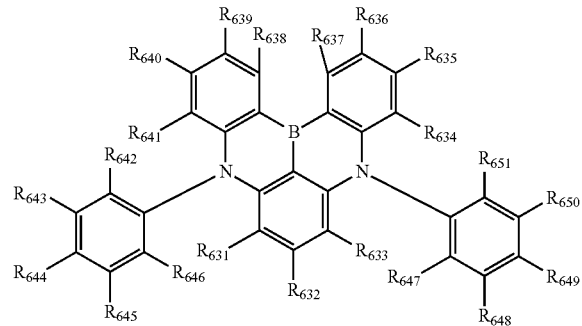

(63)

In the formula (63):

$R_{631}$ is bonded to $R_{646}$ to form a substituted or unsubstituted heterocycle or to form no substituted or unsubstituted heterocycle;

$R_{633}$ is bonded to $R_{647}$ to form a substituted or unsubstituted heterocycle or to form no substituted or unsubstituted heterocycle;

$R_{634}$ is bonded to $R_{651}$ to form a substituted or unsubstituted heterocycle or to form no substituted or unsubstituted heterocycle;

$R_{641}$ is bonded to $R_{642}$ to form a substituted or unsubstituted heterocycle or to form no substituted or unsubstituted heterocycle;

at least one combination of adjacent two or more of $R_{631}$ to $R_{651}$ are mutually bonded to form a substituted or unsubstituted monocyclic ring, mutually bonded to form a substituted or unsubstituted fused ring, or not mutually bonded; and $R_{631}$ to $R_{651}$ not forming the substituted or unsubstituted heterocycle, not forming the monocyclic ring and not forming the fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

$R_{631}$ are optionally mutually bonded to $R_{646}$ to form a substituted or unsubstituted heterocycle. For instance, $R_{631}$ and $R_{646}$ are optionally bonded to each other to form a tri-or-more cyclic fused nitrogen-containing heterocycle, in which a benzene ring bonded to $R_{646}$, a ring including a nitrogen atom, and a benzene ring corresponding to the a ring are fused. Specific examples of the nitrogen-containing heterocycle include a compound corresponding to the nitrogen-containing tri(-or-more)cyclic fused heterocyclic group in the specific example group G2. The same applies to $R_{633}$ bonded to $R_{647}$, $R_{634}$ bonded to $R_{651}$, and $R_{641}$ bonded to $R_{642}$.

In an exemplary embodiment, $R_{631}$ to $R_{651}$, which do not contribute to ring formation, are each independently a hydrogen atom, a substituted or unsubstituted alkyl group having 1 to 50 carbon atoms, a substituted or unsubstituted aryl group having 6 to 50 ring carbon atoms, or a substituted or unsubstituted heterocyclic group having 5 to 50 ring atoms.

In an exemplary embodiment, $R_{631}$ to $R_{651}$, which do not contribute to ring formation, are each independently a hydrogen atom, a substituted or unsubstituted aryl group having 6 to 50 ring carbon atoms, or a substituted or unsubstituted heterocyclic group having 5 to 50 ring atoms.

In an exemplary embodiment, $R_{631}$ to $R_{651}$, which do not contribute to ring formation, are each independently a hydrogen atom, or a substituted or unsubstituted alkyl group having 1 to 50 carbon atoms.

In an exemplary embodiment: $R_{631}$ to $R_{651}$, which do not contribute to ring formation, are each independently a hydrogen atom, or a substituted or unsubstituted alkyl group having 1 to 50 carbon atoms; and at least one of $R_{631}$ to $R_{651}$ is a substituted or unsubstituted alkyl group having 1 to 50 carbon atoms.

In an exemplary embodiment, the compound represented by the formula (63) is represented by a formula (63A) below.

[Formula 318]

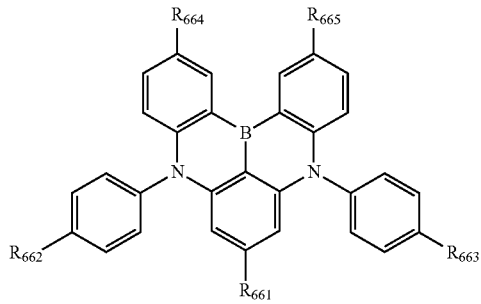

(63A)

In the formula (63A):

$R_{661}$ is a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, or a substituted or unsubstituted aryl group having 6 to 50 ring carbon atoms, and $R_{662}$ to $R_{665}$ are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, or a substituted or unsubstituted aryl group having 6 to 50 ring carbon atoms.

In an exemplary embodiment, $R_{661}$ to $R_{665}$, which do not contribute to ring formation, are each independently a substituted or unsubstituted alkyl group having 1 to 50 carbon atoms, or a substituted or unsubstituted aryl group having 6 to 50 ring carbon atoms.

In an exemplary embodiment, $R_{661}$ to $R_{665}$ are each independently a substituted or unsubstituted alkyl group having 1 to 50 carbon atoms.

In an exemplary embodiment, the compound represented by the formula (63) is represented by a formula (63B) below.

[Formula 319]

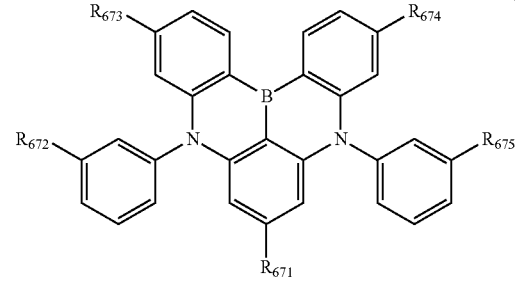

(63B)

In the formula (63B):

$R_{671}$ and $R_{672}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —N($R_{906}$)($R_{907}$), or a substituted or unsubstituted aryl group having 6 to 50 ring carbon atoms; and $R_{673}$ to $R_{675}$ are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —N($R_{906}$)($R_{907}$), or a substituted or unsubstituted aryl group having 6 to 50 ring carbon atoms.

In an exemplary embodiment, the compound represented by the formula (63) is represented by a formula (63B') below.

[Formula 320]

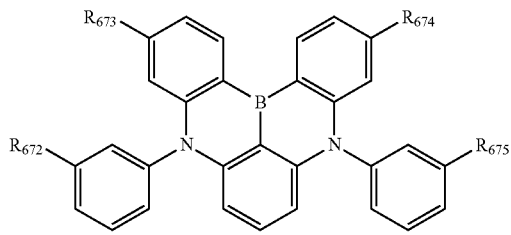

(63B')

In the formula (63B'), $R_{672}$ to $R_{675}$ each independently represent the same as $R_{672}$ to $R_{675}$ in the formula (63B).

In an exemplary embodiment: at least one of $R_{671}$ to $R_{675}$ is a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —N($R_{906}$)($R_{907}$), or a substituted or unsubstituted aryl group having 6 to 50 ring carbon atoms.

In an exemplary embodiment: $R_{672}$ is a hydrogen atom, a substituted or unsubstituted alkyl group having 1 to 50 carbon atoms, a group represented by —N($R_{906}$)($R_{907}$), or a substituted or unsubstituted aryl group having 6 to 50 ring carbon atoms, $R_{671}$, and $R_{673}$ to $R_{675}$ are each independently a substituted or unsubstituted alkyl group having 1 to 50 carbon atoms, a group represented by —N($R_{906}$)($R_{907}$), or a substituted or unsubstituted aryl group having 6 to 50 ring carbon atoms.

In an exemplary embodiment, the compound represented by the formula (63) is represented by a formula (63C) below.

[Formula 321]

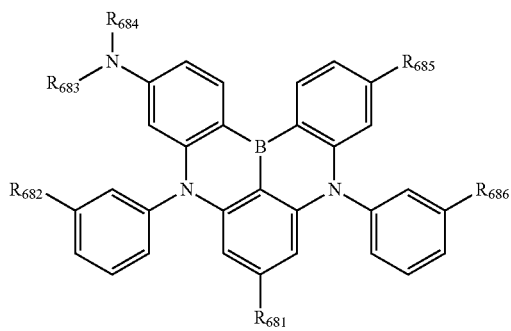

(63C)

In the formula (630):

$R_{681}$ and $R_{682}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, or a substituted or unsubstituted aryl group having 6 to 50 ring carbon atoms; and $R_{683}$ to $R_{686}$ are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, or a substituted or unsubstituted aryl group having 6 to 50 ring carbon atoms.

In an exemplary embodiment, the compound represented by the formula (63) is represented by a formula (63C') below.

[Formula 322]

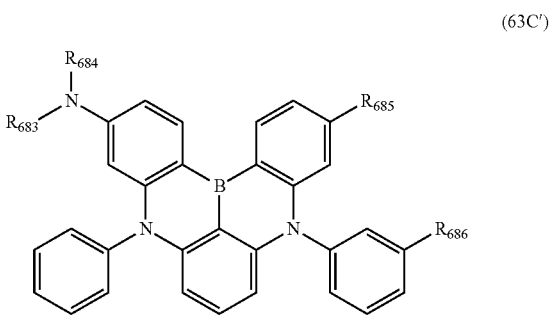

(63C')

In the formula (63C'), $R_{683}$ to $R_{686}$ each independently represent the same as $R_{683}$ to $R_{686}$ in the formula (63C).

In an exemplary embodiment, $R_{681}$ to $R_{686}$, which do not contribute to ring formation, are each independently a substituted or unsubstituted alkyl group having 1 to 50 carbon atoms, or a substituted or unsubstituted aryl group having 6 to 50 ring carbon atoms.

In an exemplary embodiment, $R_{681}$ to $R_{686}$ are each independently a substituted or unsubstituted aryl group having 6 to 50 ring carbon atoms.

The compound represented by the formula (6) is producible by initially bonding the a ring, b ring and c ring with linking groups (a group including N—$R_{601}$ and a group including N—$R_{602}$) to form an intermediate (first reaction), and bonding the a ring, b ring and c ring with a linking group (a group including a boron atom) to form a final product (second reaction). In the first reaction, an amination reaction (e.g. Buchwald-Hartwig reaction) is applicable. In the second reaction, Tandem Hetero-Friedel-Crafts Reactions or the like is applicable.

Specific examples of the compound represented by the formula (6) are shown below. It should however be noted that these specific examples are merely exemplary and do not limit the compound represented by the formula (6).

[Formula 323]
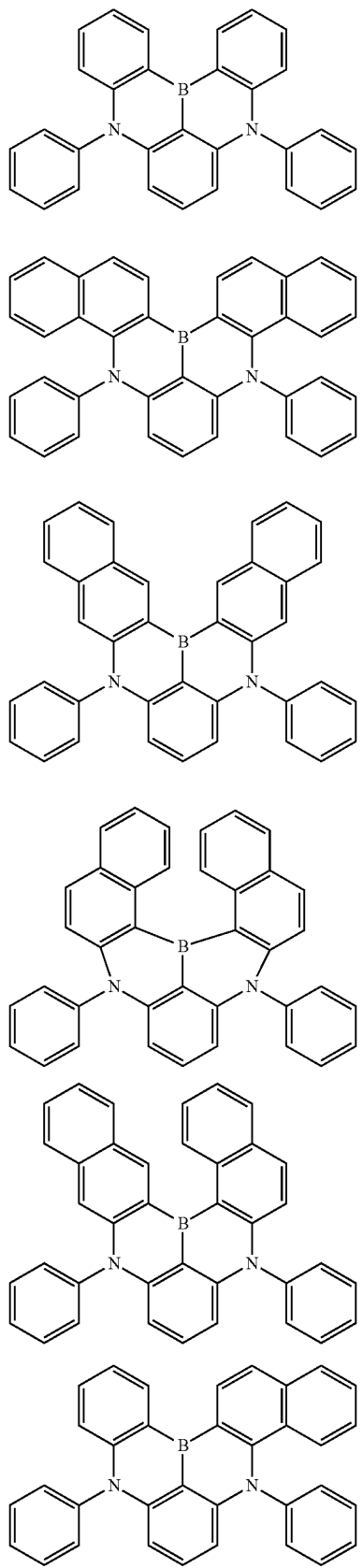
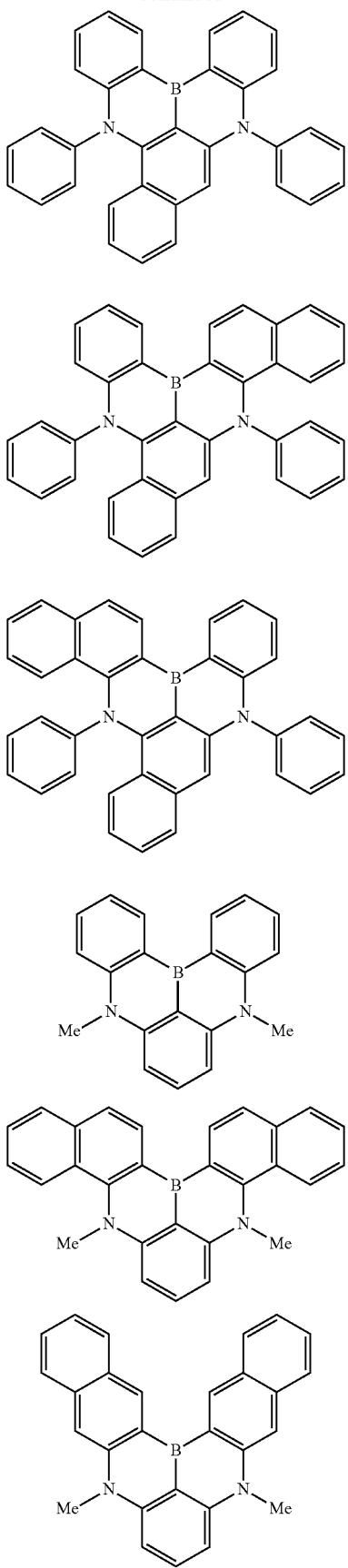

-continued
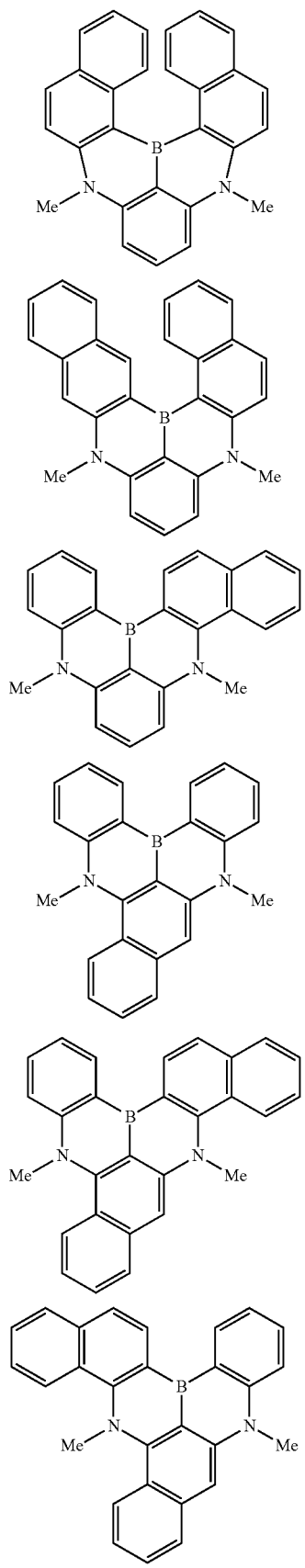
[Formula 324]
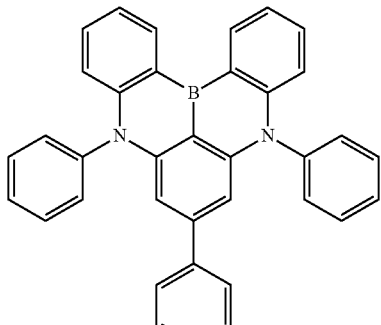
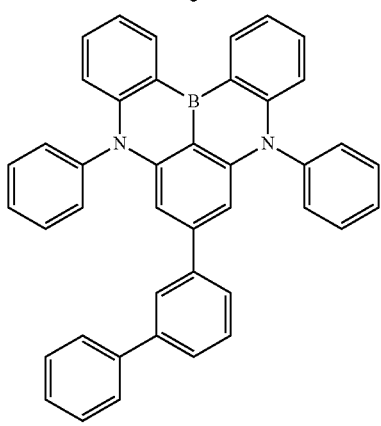
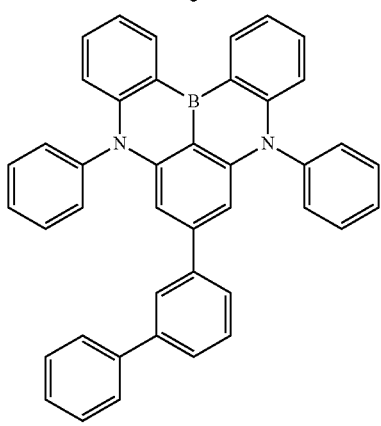
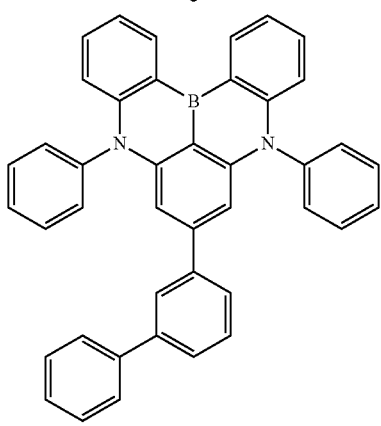
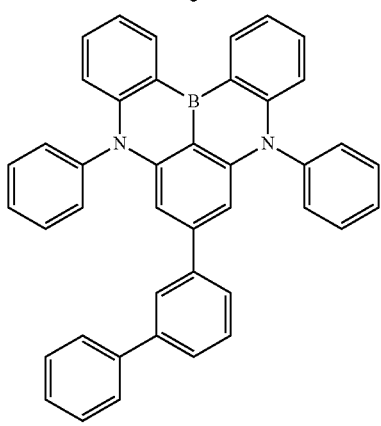
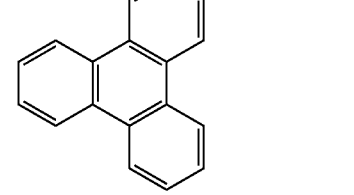

851
-continued
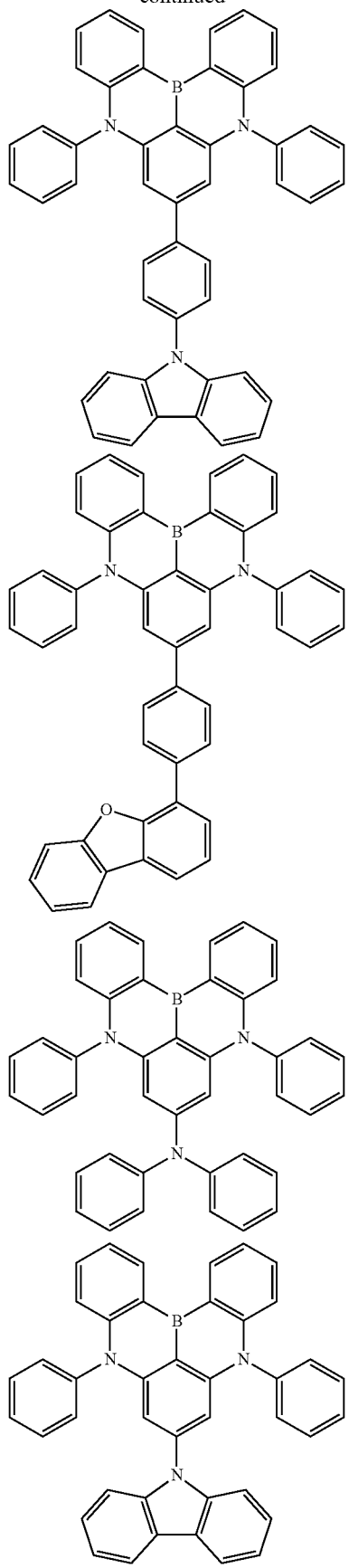
852
-continued
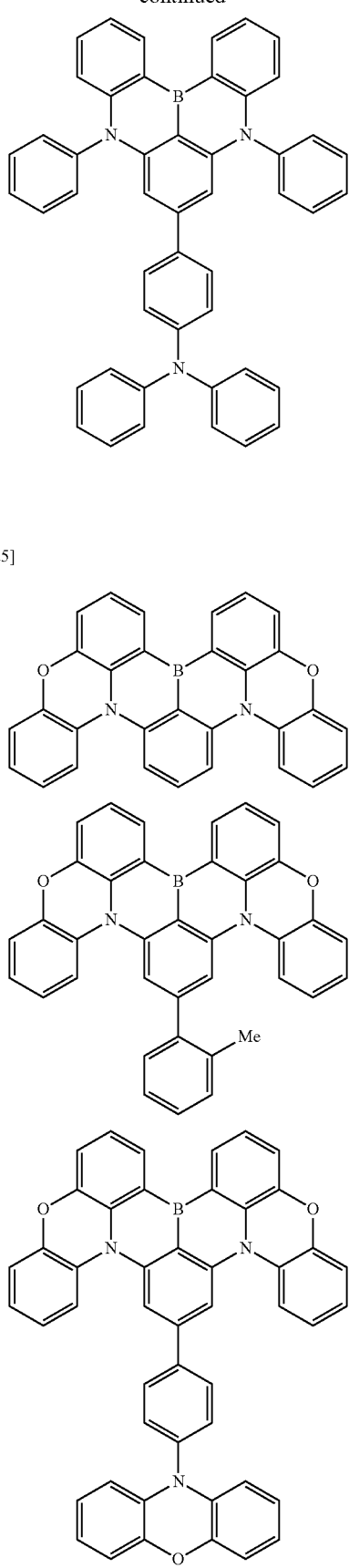
[Formula 325]

853
-continued
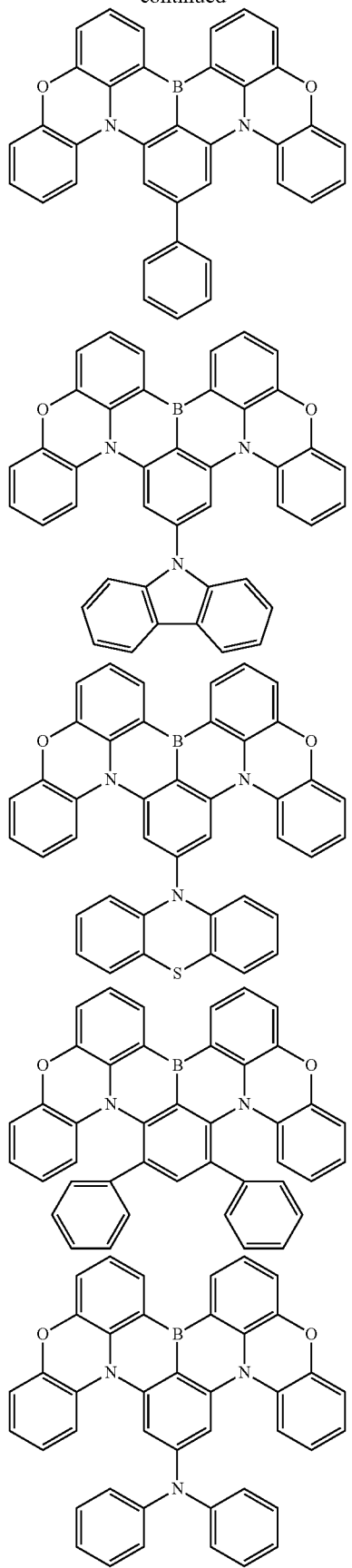
854
-continued
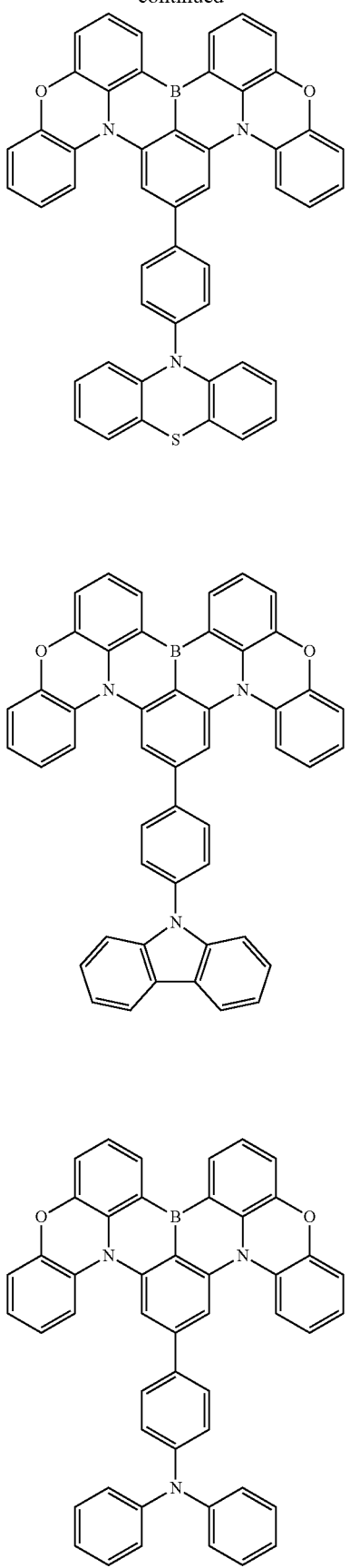

855
-continued
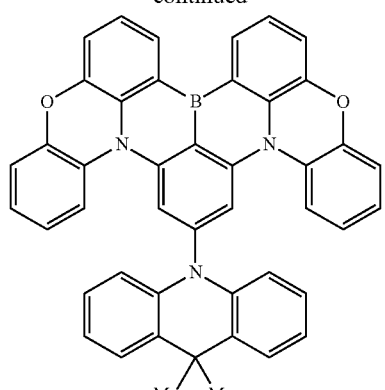
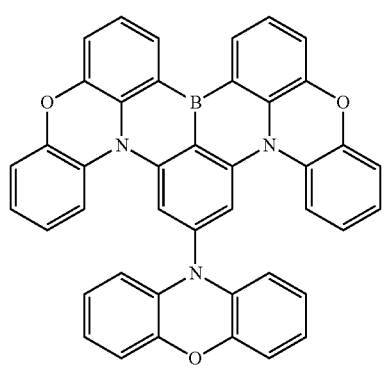
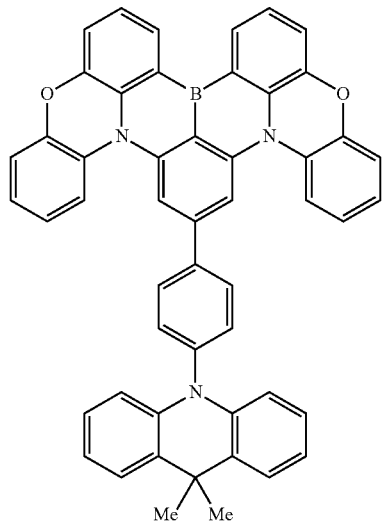
[Formula 326]
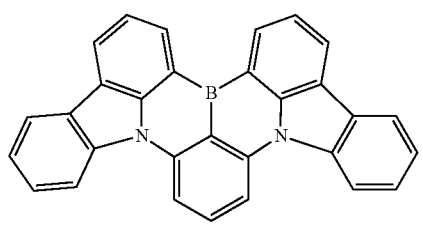
856
-continued
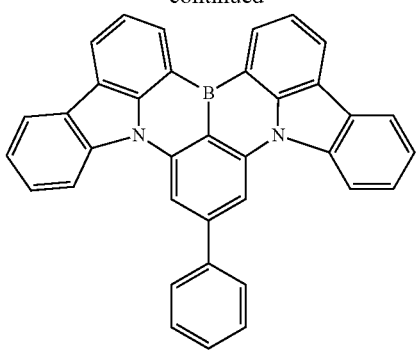
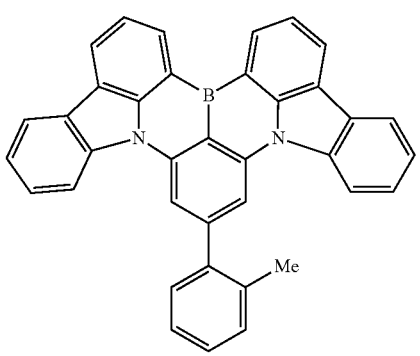
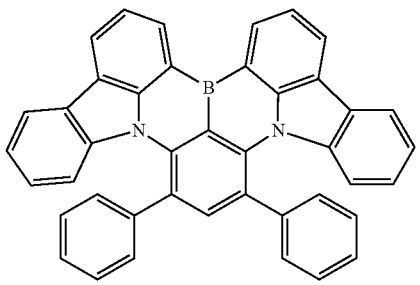
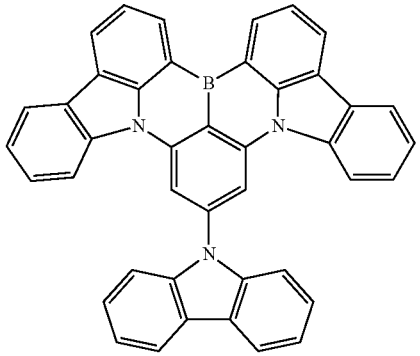
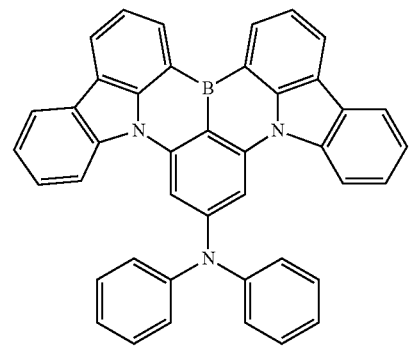

857
-continued
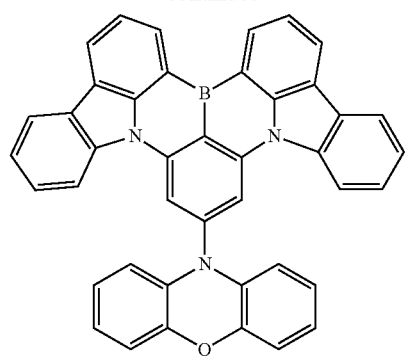
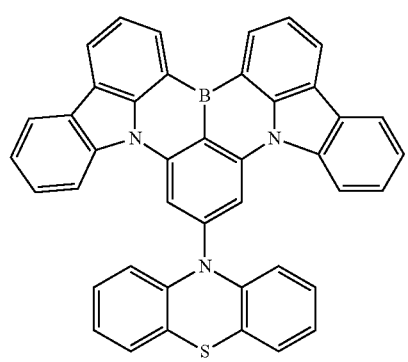
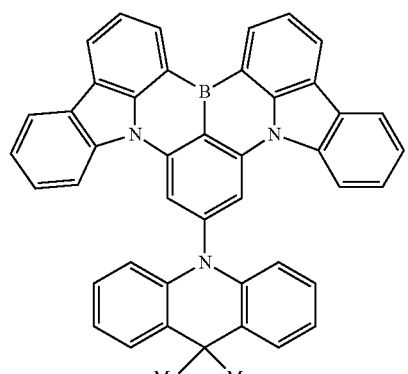
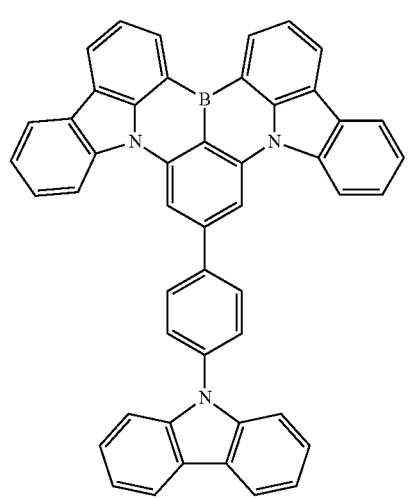
858
-continued
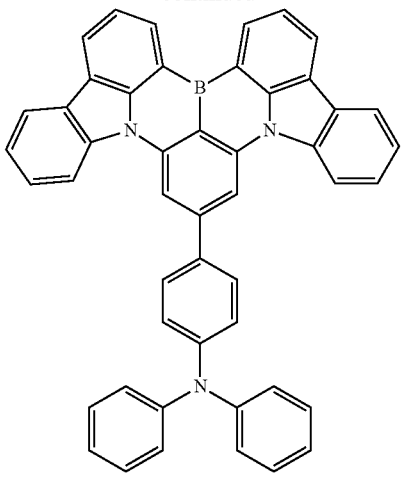
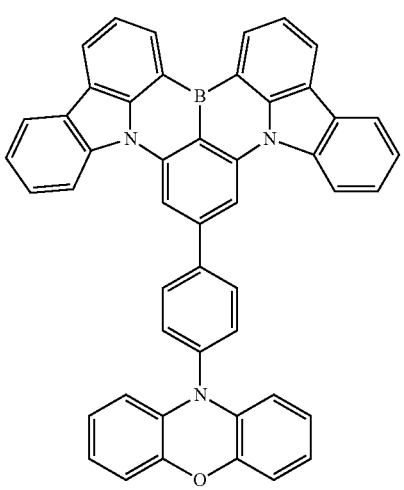
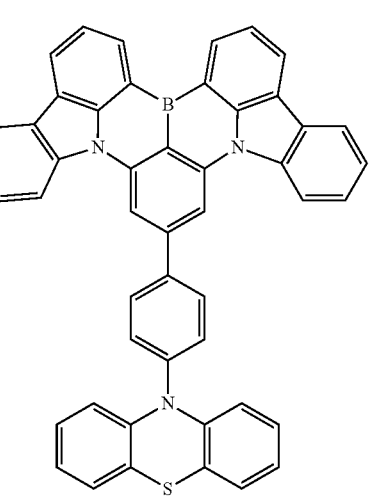

859
-continued
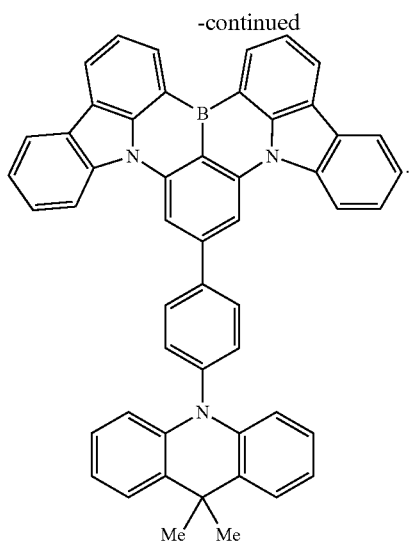
[Formula 327]
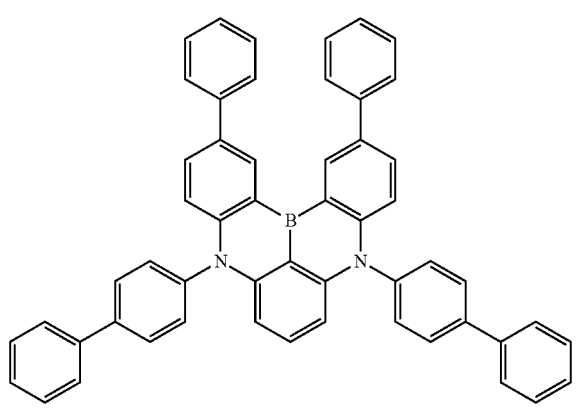
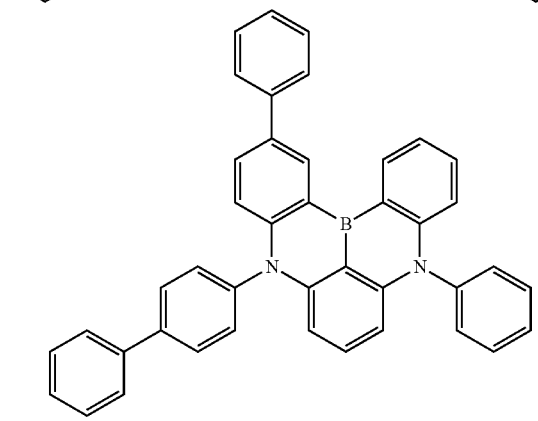
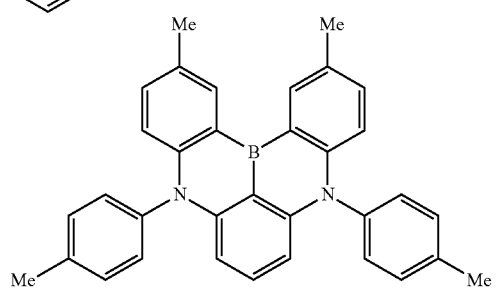
860
-continued
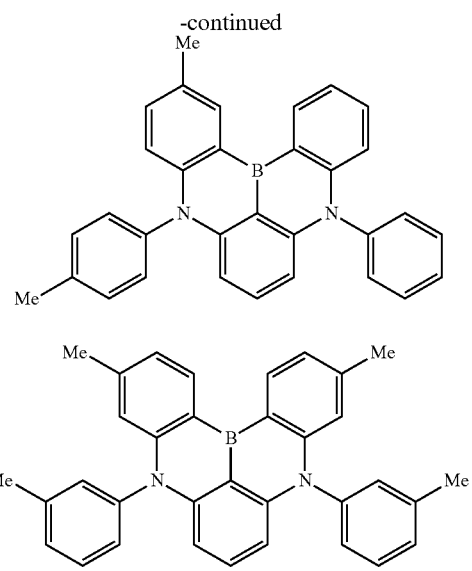
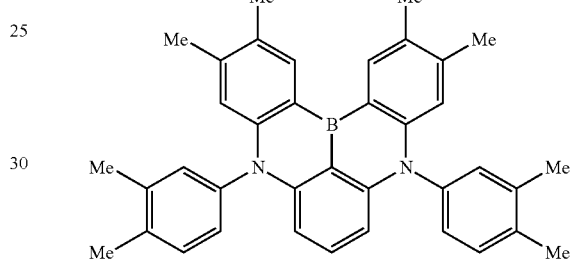
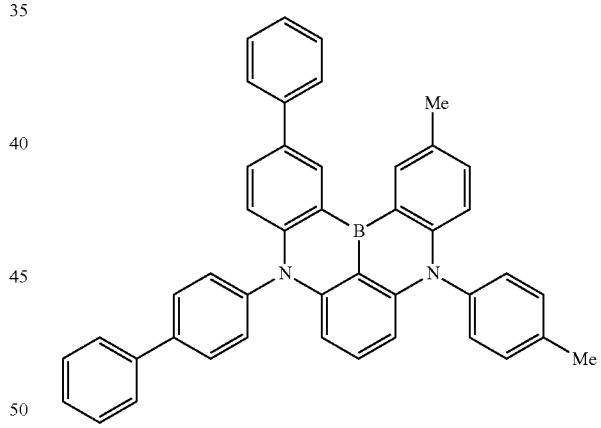
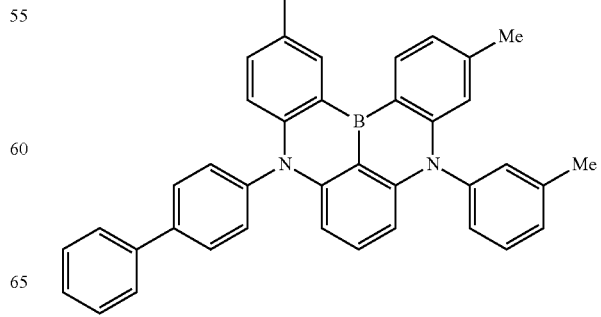

861
-continued
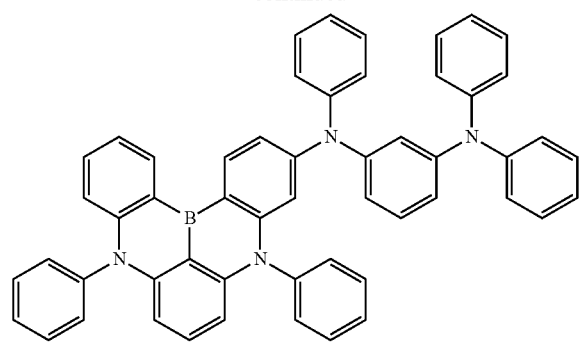
[Formula 328]
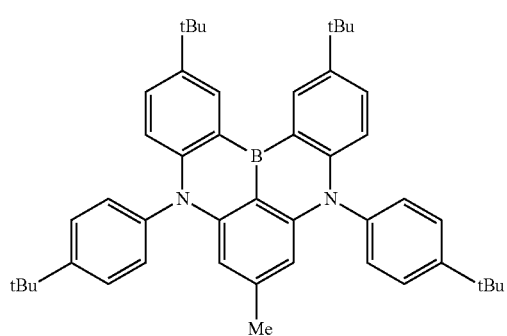 [SMILES: Cc1cc2c3c(c1)N(c1ccc(C(C)(C)C)cc1)c1ccc(C(C)(C)C)cc1B3c1cc(C(C)(C)C)ccc1N2c1ccc(C(C)(C)C)cc1]
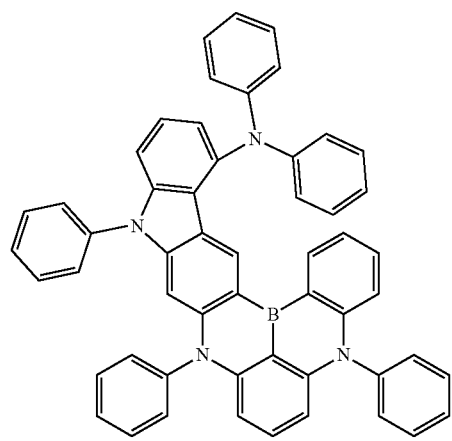
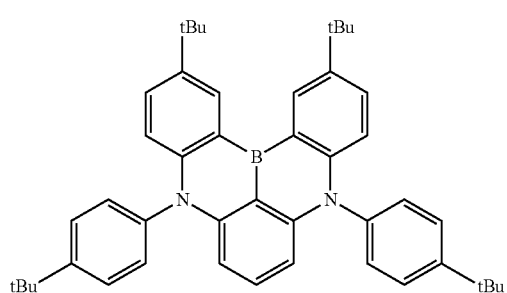
862
-continued
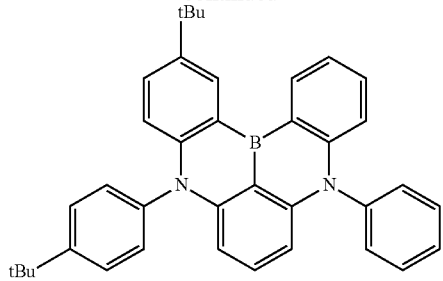
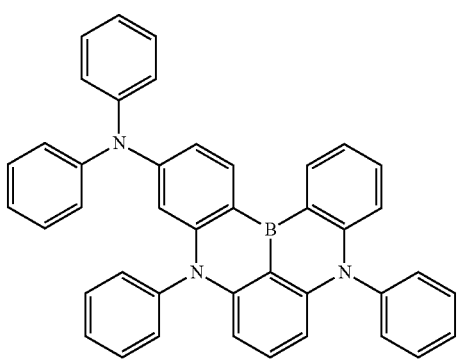
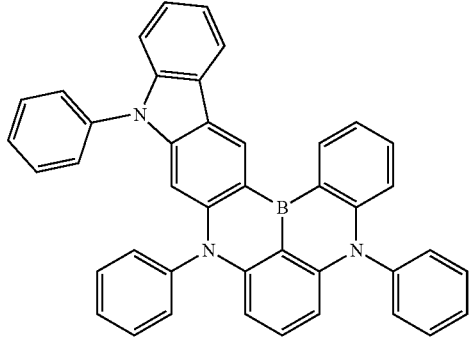
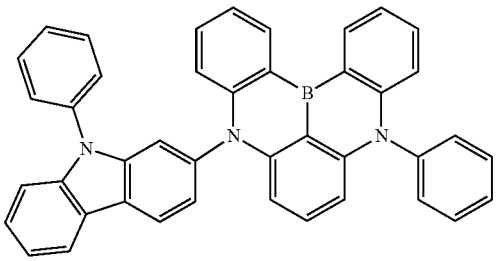
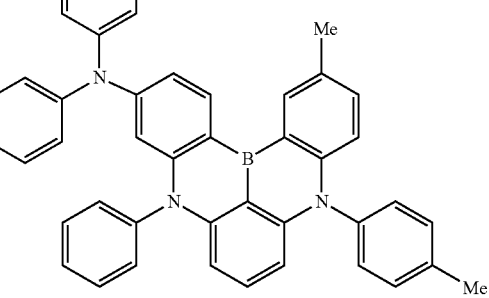

863
-continued
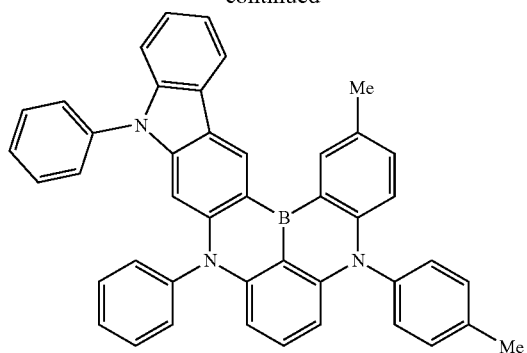
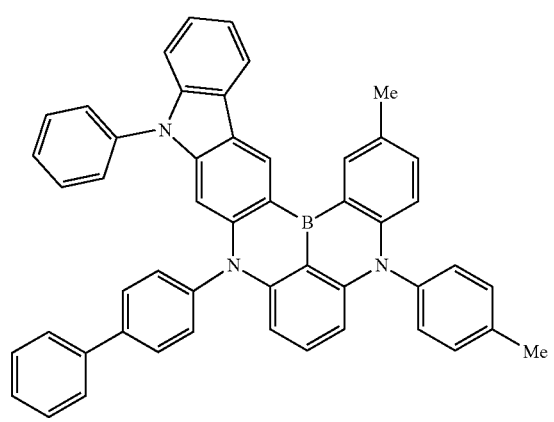
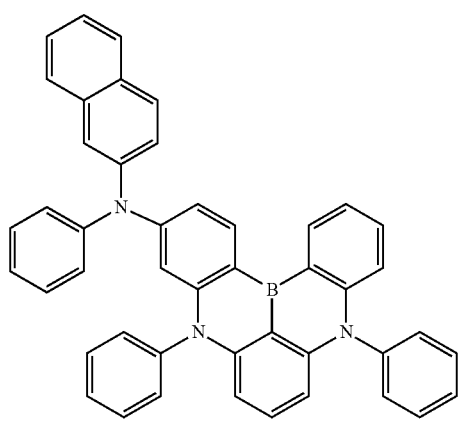
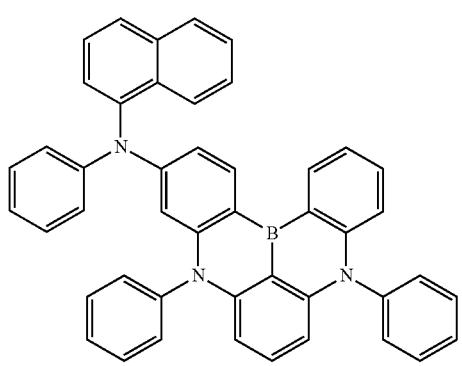
864
-continued
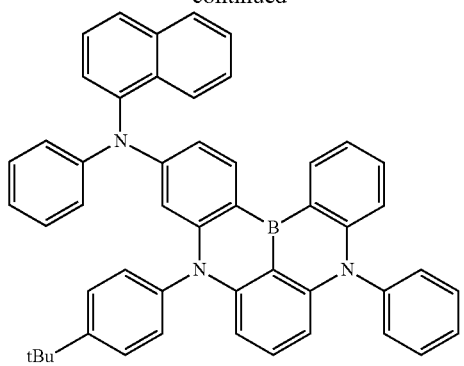
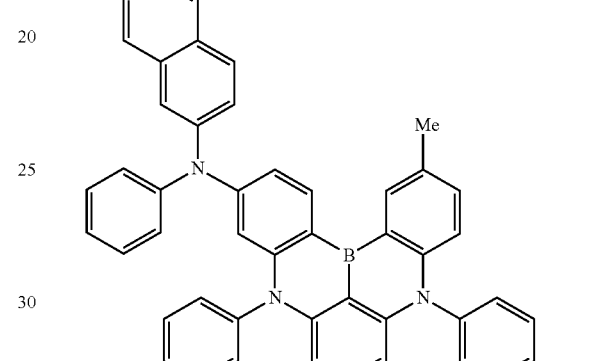
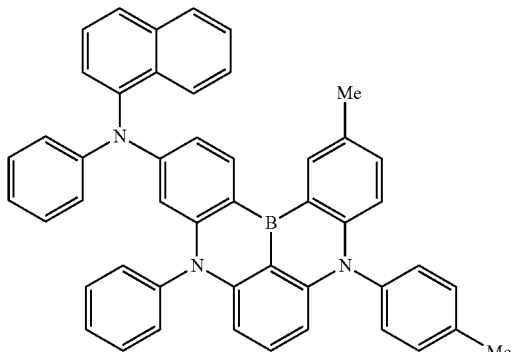
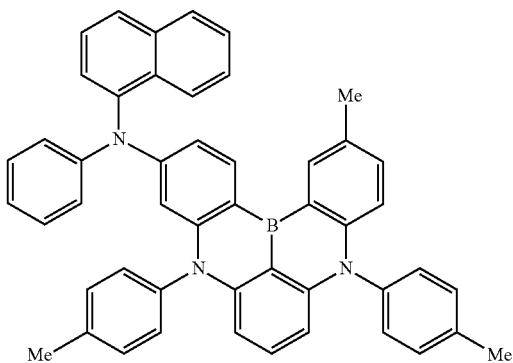

[Formula 329]
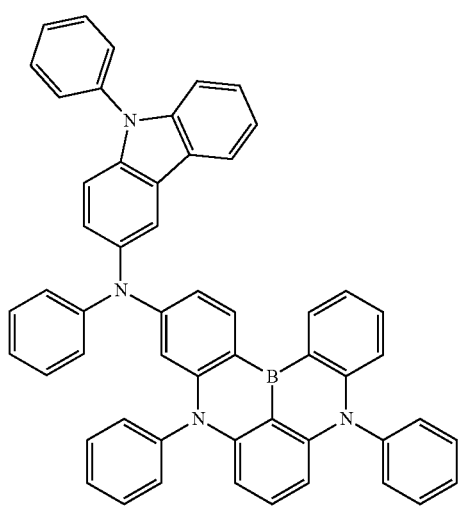
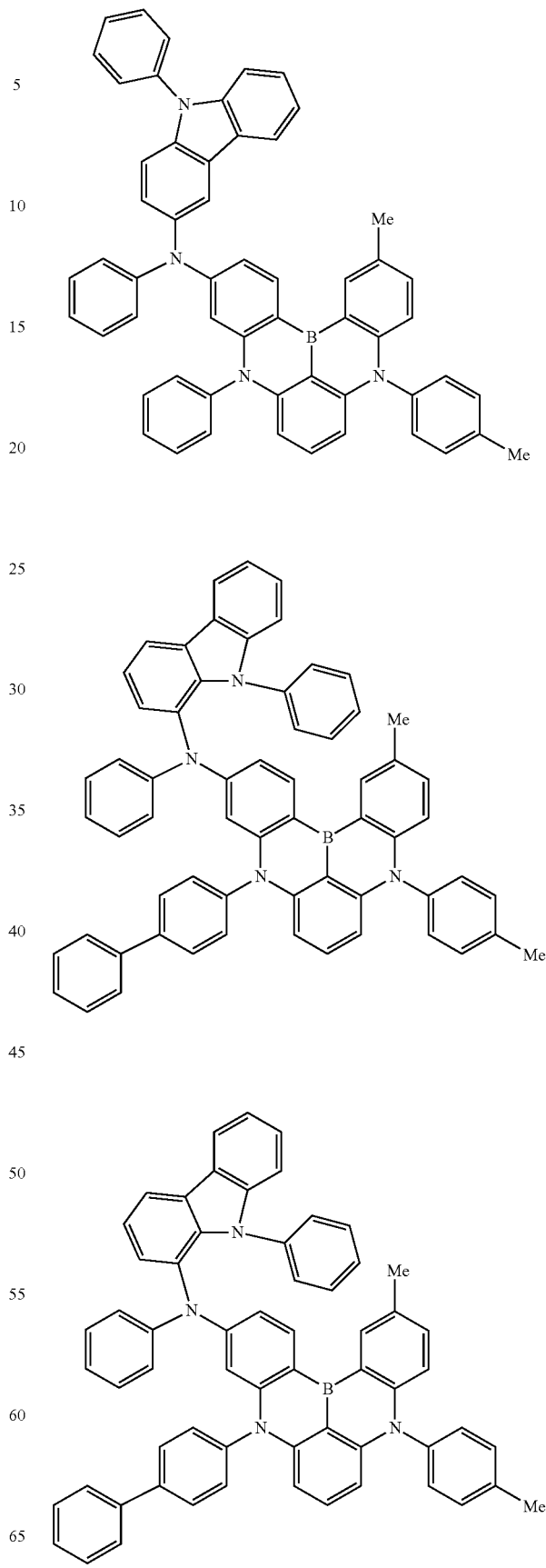

867
-continued
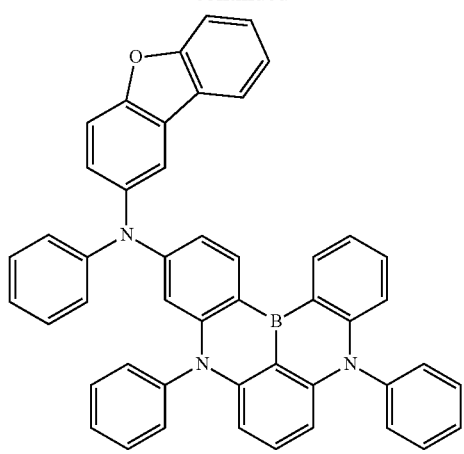
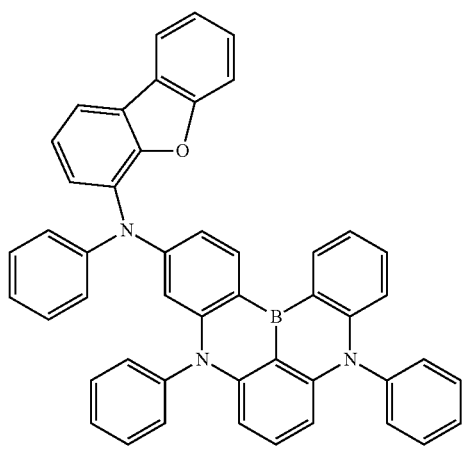
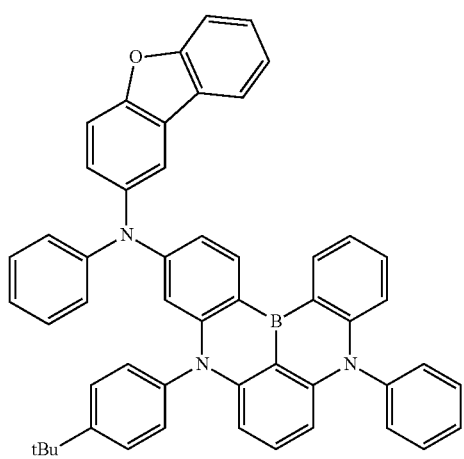
868
-continued
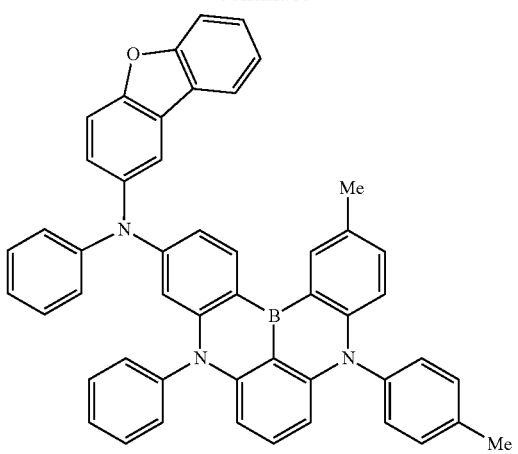
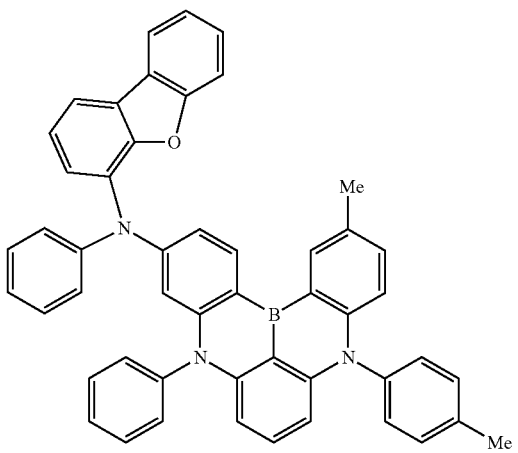
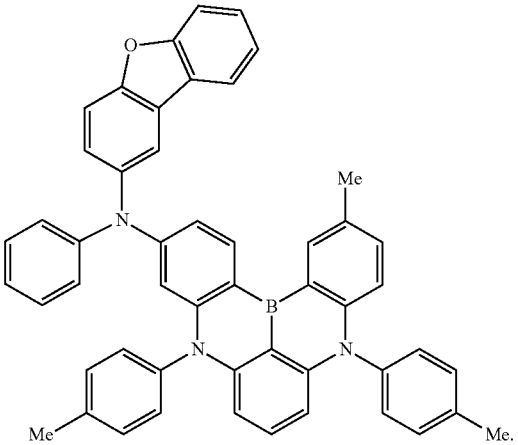

[Formula 330]
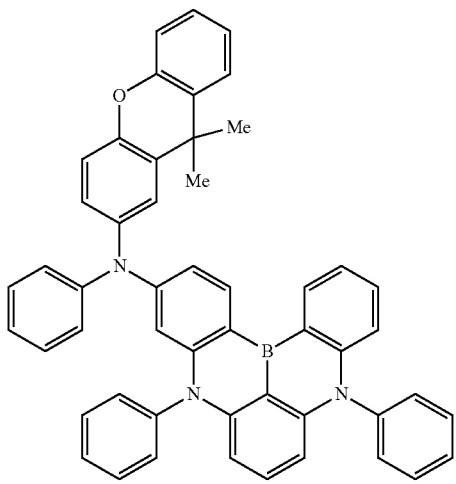
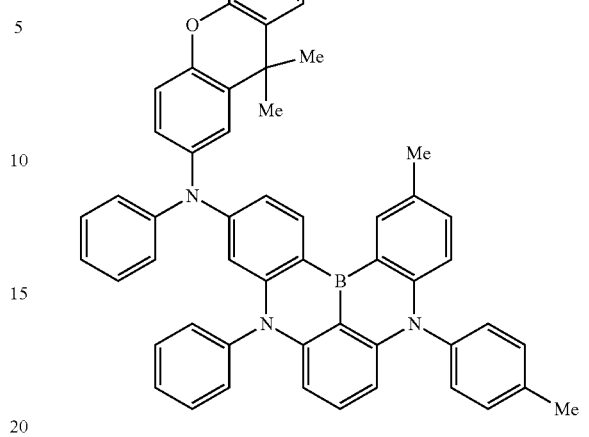
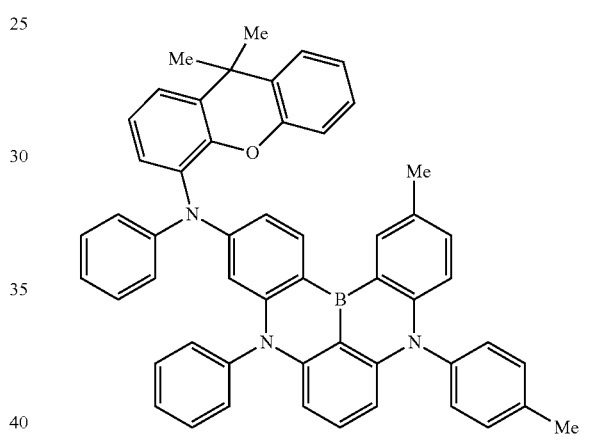
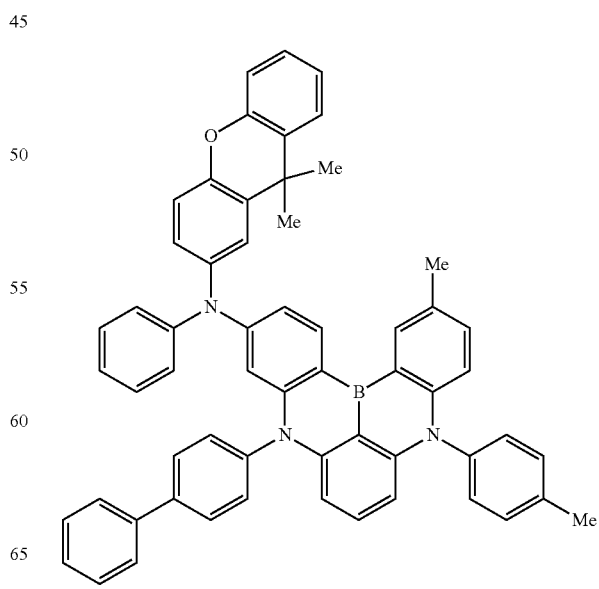

871
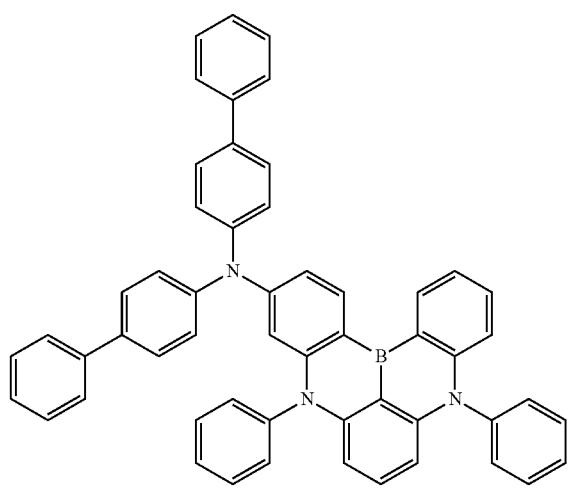
872
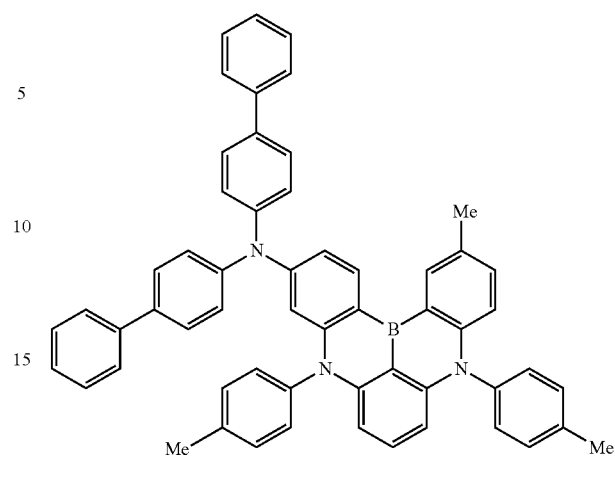
[Formula 331]
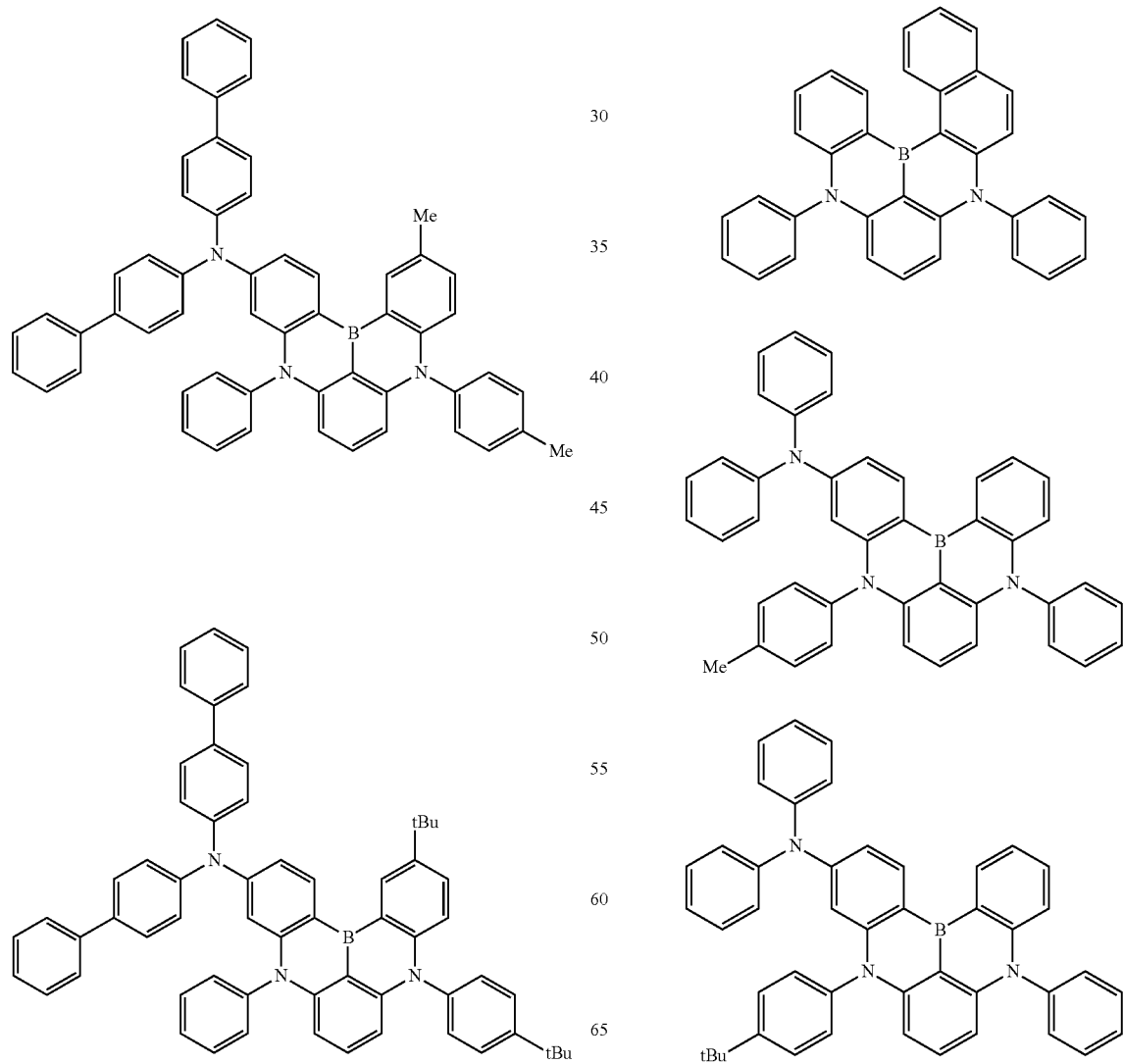

873
-continued
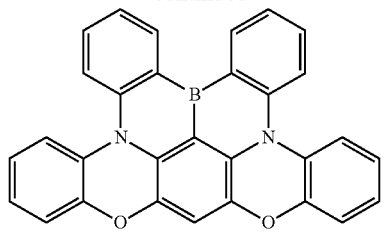
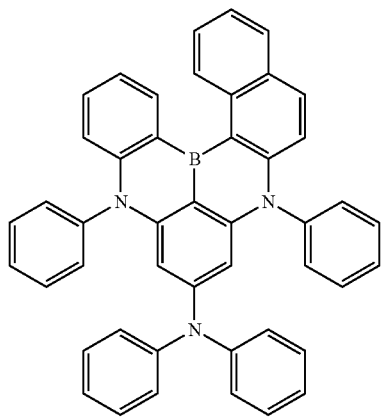
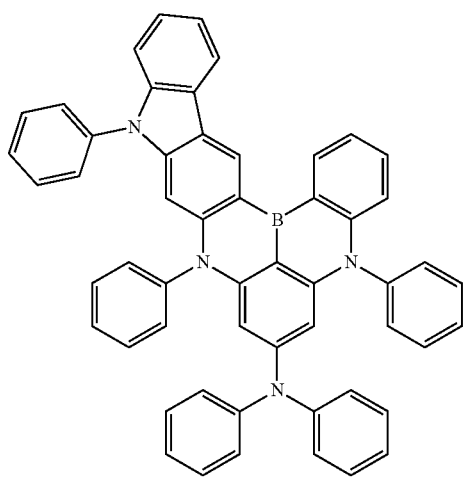
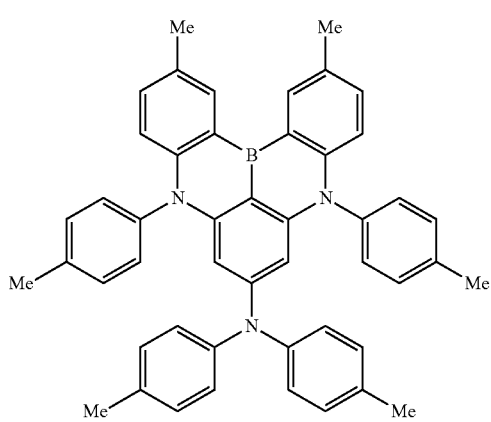
874
-continued
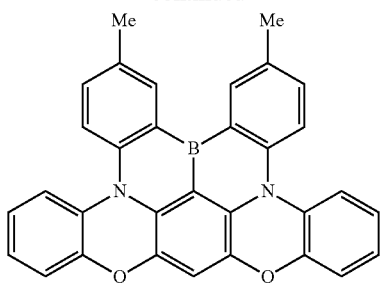
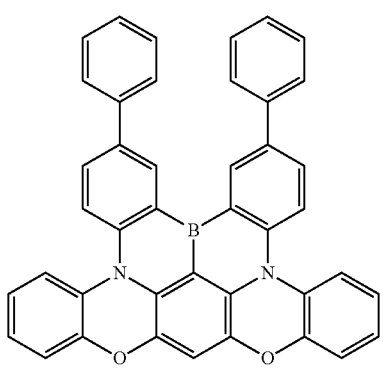
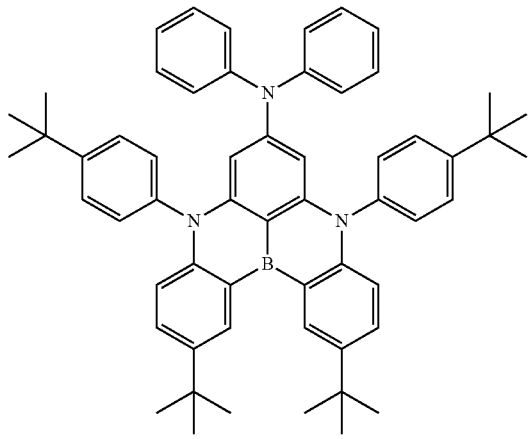 [SMILES: CC(C)(C)c1ccc(N2c3ccc(C(C)(C)C)cc3B3c4cc(C(C)(C)C)ccc4N(c4ccc(C(C)(C)C)cc4)c4cc(N(c5ccccc5)c5ccccc5)cc2c43)cc1]
[Formula 332]
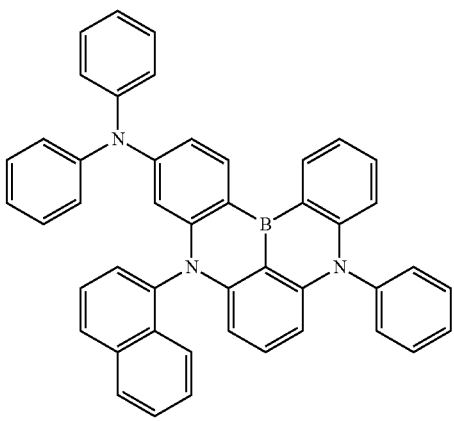

875
-continued

876
-continued

877
-continued
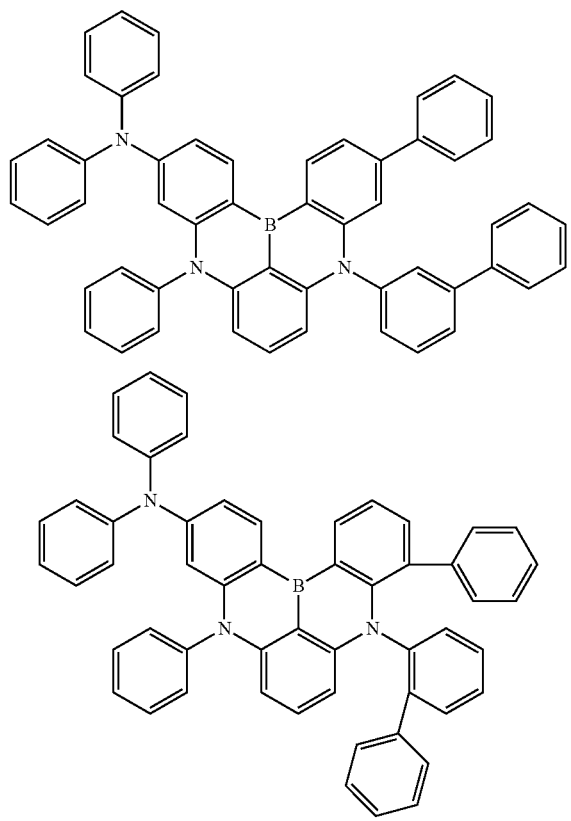
[Formula 333]
878
-continued
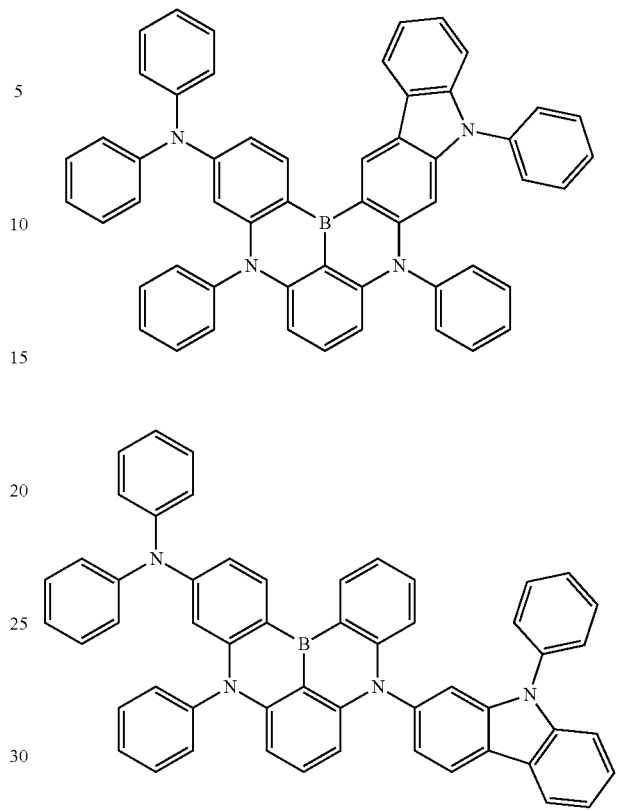
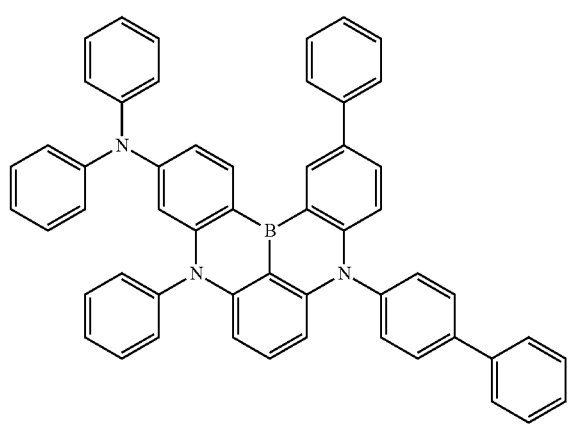
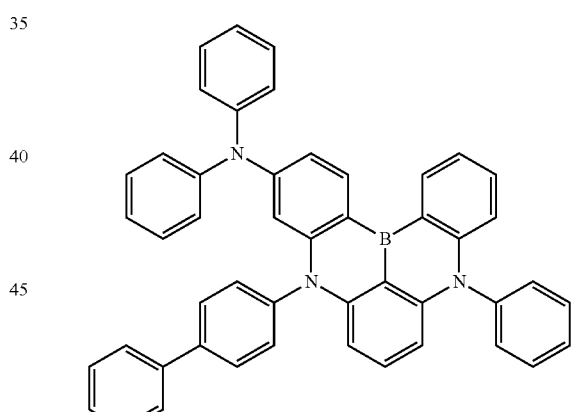
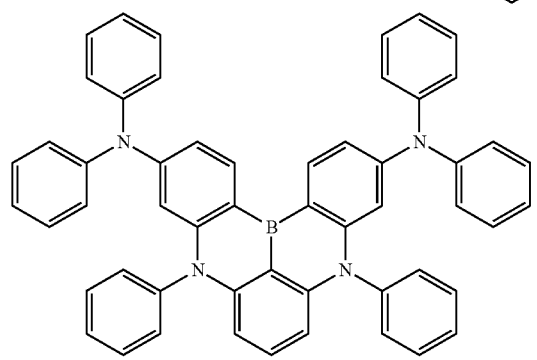
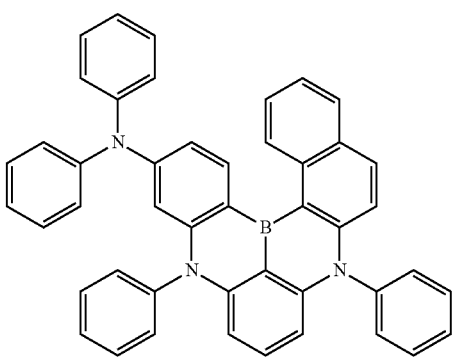

879
-continued
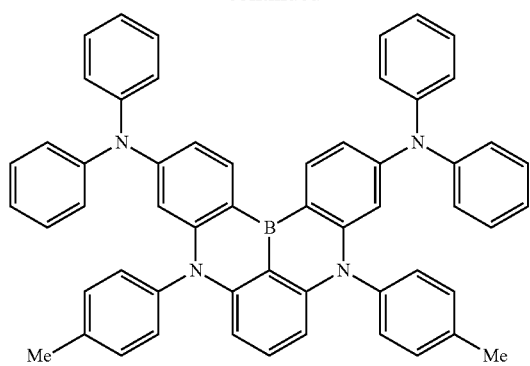
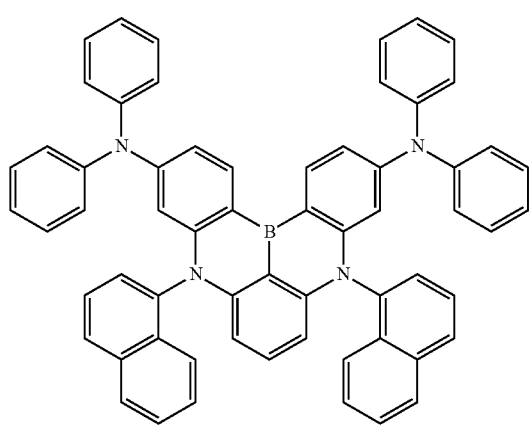
[Formula 334]
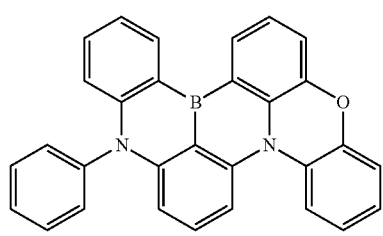
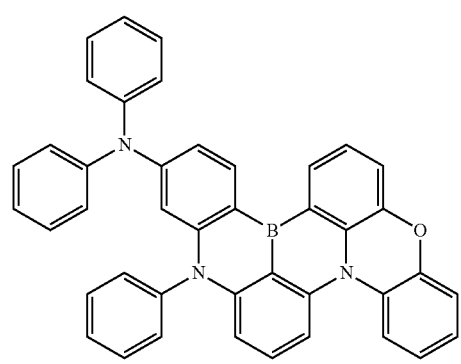
880
-continued
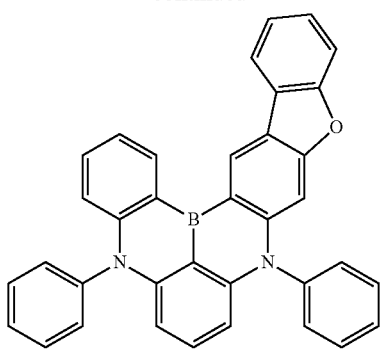
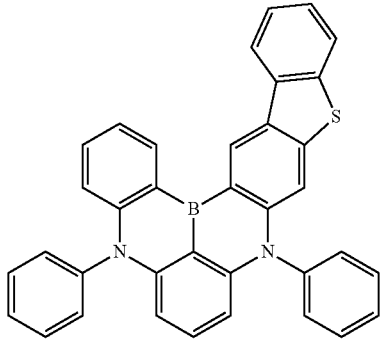
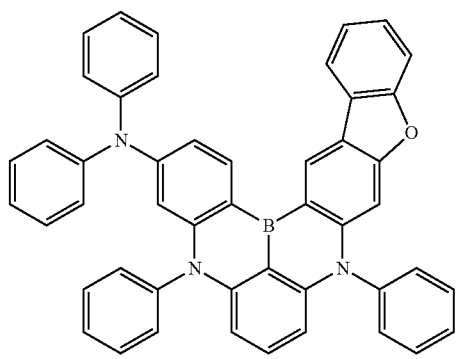
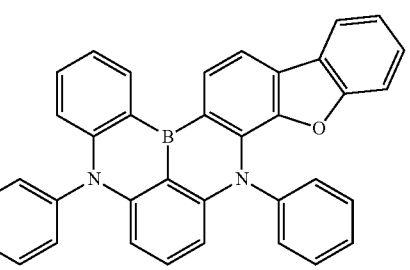
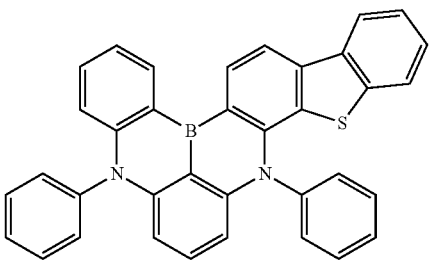

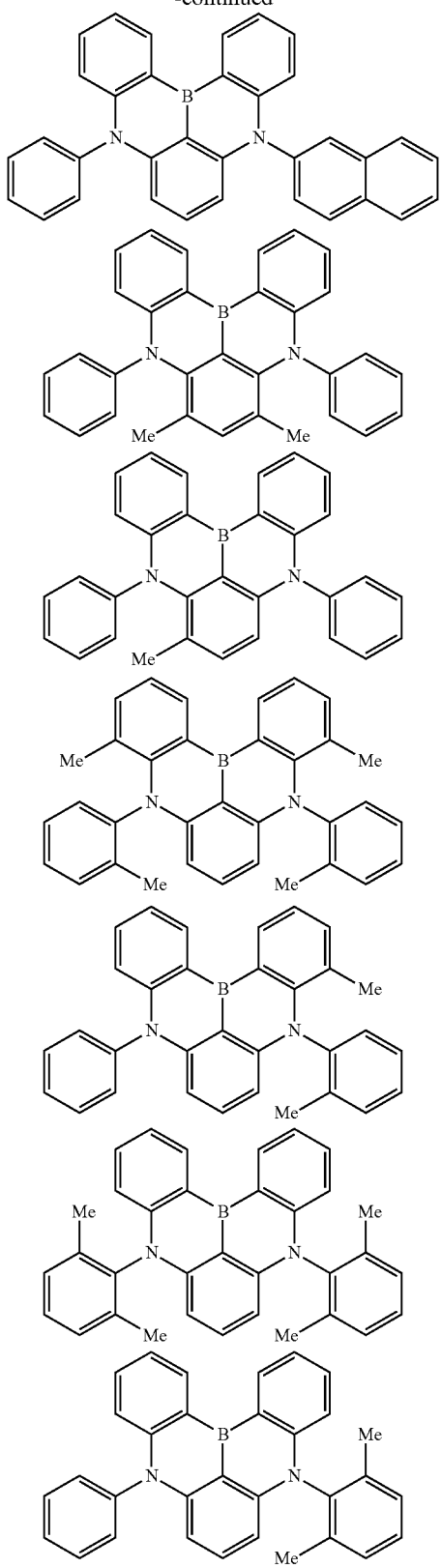

Compound Represented by Formula (7)

The compound represented by the formula (7) will be described below.

[Formula 335]

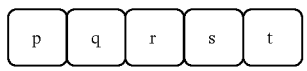

(7)

[Formula 336]

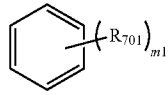

(72)

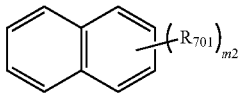

(73)

(74)

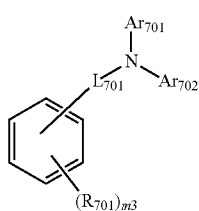

(75)

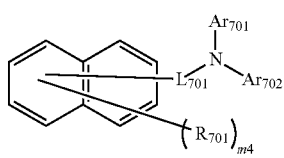

(76)

In the formula (7):
r ring is a ring represented by the formula (72) or the formula (73), the r ring being fused with at any position(s) of respective adjacent rings;
q ring and s ring are each independently a ring represented by the formula (74) and fused with any position(s) of respective adjacent rings;
p ring and t ring are each independently a moiety represented by the formula (75) or the formula (76) and fused with any position(s) of respective adjacent rings;
$X_7$ is an oxygen atom, a sulfur atom, or $NR_{702}$;
when a plurality of $R_{701}$ are present, adjacent ones of the plurality of $R_{701}$ are mutually bonded to form a substituted or unsubstituted monocyclic ring, mutually bonded to form a substituted or unsubstituted fused ring, or not mutually bonded;
$R_{701}$ and $R_{702}$ not forming the monocyclic ring and not forming the fused ring are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms;

$Ar_{701}$ and $Ar_{702}$ are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

$L_{701}$ is a substituted or unsubstituted alkylene group having 1 to 50 carbon atoms, a substituted or unsubstituted alkenylene group having 2 to 50 carbon atoms, a substituted or unsubstituted alkynylene group having 2 to 50 carbon atoms, a substituted or unsubstituted cycloalkylene group having 3 to 50 ring carbon atoms, a substituted or unsubstituted arylene group having 6 to 50 ring carbon atoms, or a substituted or unsubstituted divalent heterocyclic group having 5 to 50 ring atoms;

m1 is 0, 1, or 2;

m2 is 0, 1, 2, 3, or 4;

m3 is each independently 0, 1, 2, 3 or 3;

m4 is each independently 0, 1, 2, 3, 4, or 5;

when a plurality of $R_{701}$ are present, the plurality of $R_{701}$ are mutually the same or different;

when a plurality of $X_7$ are present, the plurality of $X_7$ are mutually the same or different;

when a plurality of $R_{702}$ are present, the plurality of $R_{702}$ are mutually the same or different;

when a plurality of $Ar_{701}$ are present, the plurality of $Ar_{701}$ are mutually the same or different;

when a plurality of $Ar_{702}$ are present, the plurality of $Ar_{702}$ are mutually the same or different; and when a plurality of $L_{701}$ are present, the plurality of $L_{701}$ are mutually the same or different.

In the formula (7), each of the p ring, q ring, r ring, s ring, and t ring is fused with an adjacent ring(s) sharing two carbon atoms. The fused position and orientation are not limited but may be defined as required.

In an exemplary embodiment, in the formula (72) or the formula (73) representing the r ring, m1=0 or m2=0.

In an exemplary embodiment, the compound represented by the formula (7) is represented by any one of formulae (71-1) to (71-6) below.

[Formula 337]

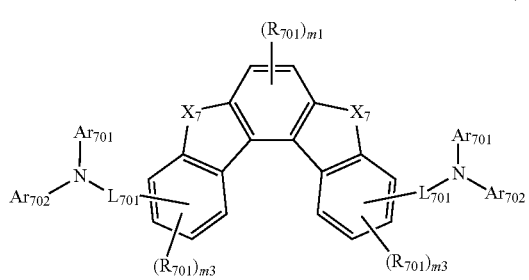

(71-1)

[Formula 338]

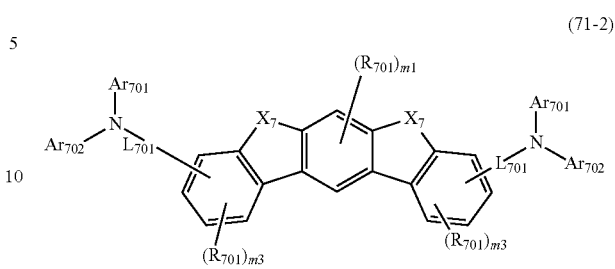

(71-2)

[Formula 339]

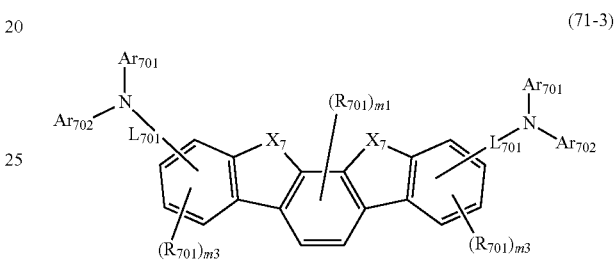

(71-3)

[Formula 340]

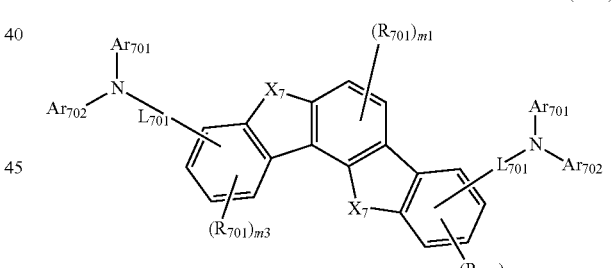

(71-4)

[Formula 341]

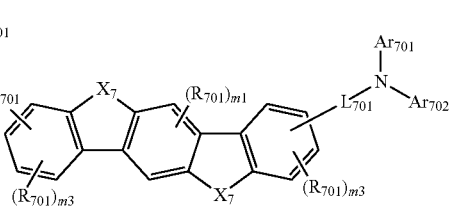

(71-5)

[Formula 342]

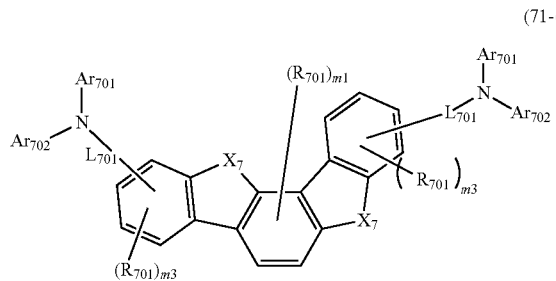

(71-6)

In the formulae (71-1) to (71-6), $R_{701}$, $X_7$, $Ar_{701}$, $Ar_{702}$, $L_{701}$, m1, and m3 respectively represent the same as $R_{701}$, $X_7$, $Ar_{701}$, $Ar_{702}$, $L_{701}$, m1, and m3 in the formula (7).

In an exemplary embodiment, the compound represented by the formula (7) is represented by any one of formulae (71-11) to (71-13) below.

[Formula 343]

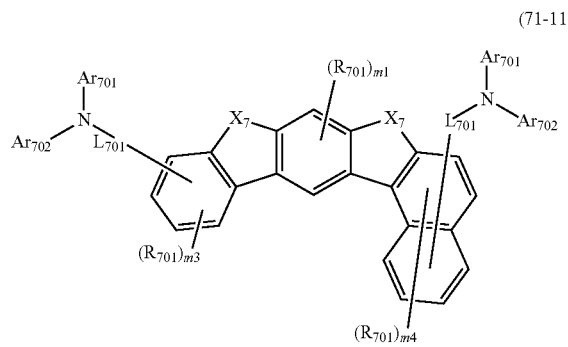

(71-11)

[Formula 344]

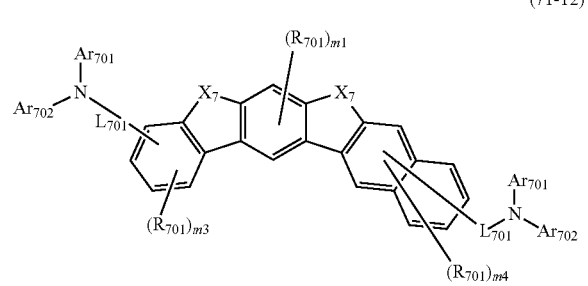

(71-12)

[Formula 345]

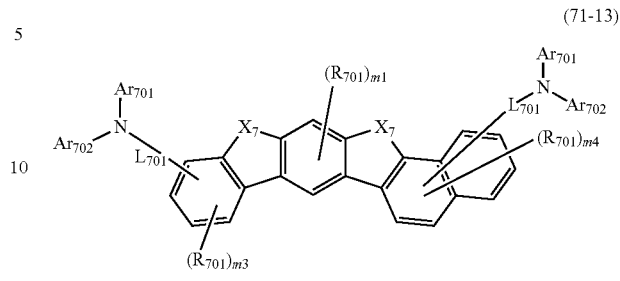

(71-13)

In the formulae (71-11) to (71-13), $R_{701}$, $X_7$, $Ar_{701}$, $Ar_{702}$, $L_{701}$, m1, m3 and m4 respectively represent the same as $R_{701}$, $X_7$, $Ar_{701}$, $Ar_{702}$, $L_{701}$, m1, m3 and m4 in the formula (7).

In an exemplary embodiment, the compound represented by the formula (7) is represented by any one of formulae (71-21) to (71-25) below.

[Formula 346]

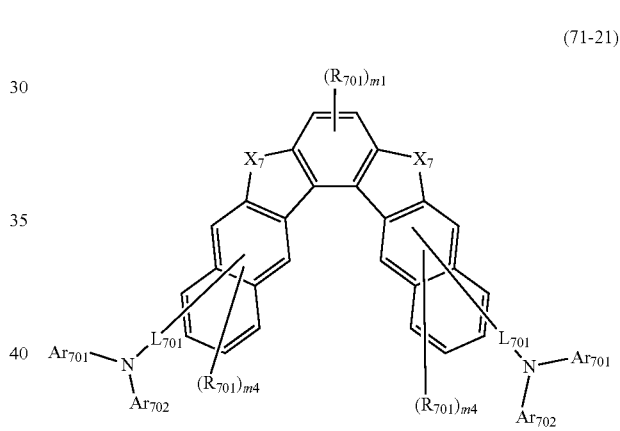

(71-21)

[Formula 347]

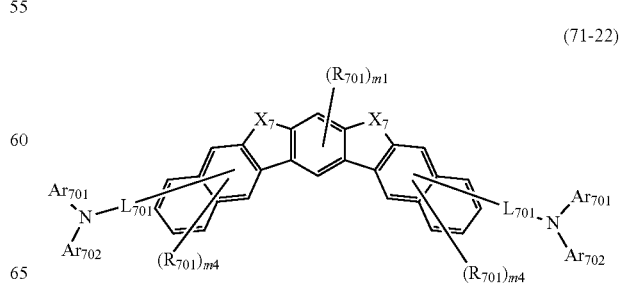

(71-22)

[Formula 348]
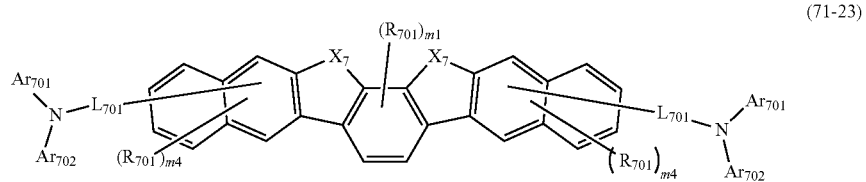
(71-23)
[Formula 349]
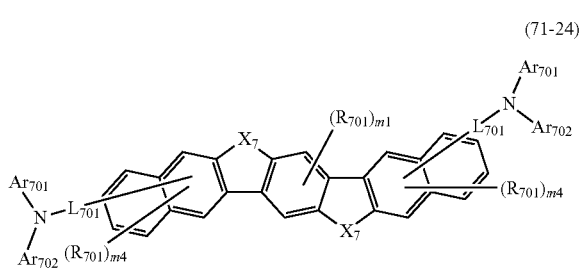
(71-24)
[Formula 350]
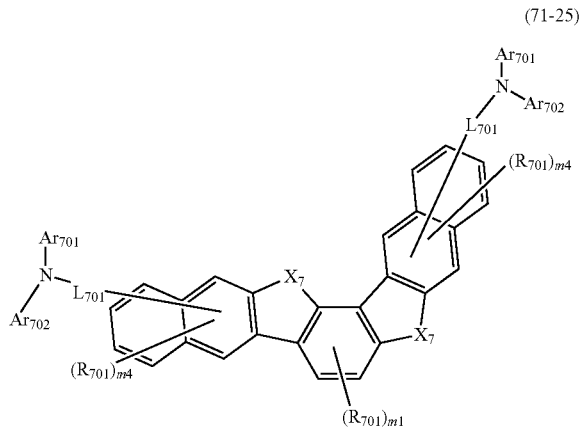
(71-25)
In the formulae (71-21) to (71-25), $R_{701}$, $X_7$, $Ar_{701}$, $Ar_{702}$, $L_{701}$, m1, and m4 respectively represent the same as $R_{701}$, $X_7$, $Ar_{701}$, $Ar_{702}$, $L_{701}$, m1, and m4 in the formula (7).
In an exemplary embodiment, the compound represented by the formula (7) is represented by any one of formulae (71-31) to (71-33) below.
[Formula 351]
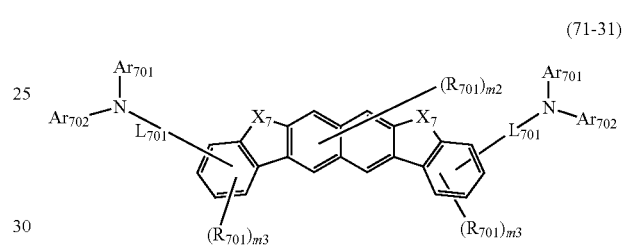
(71-31)
[Formula 352]
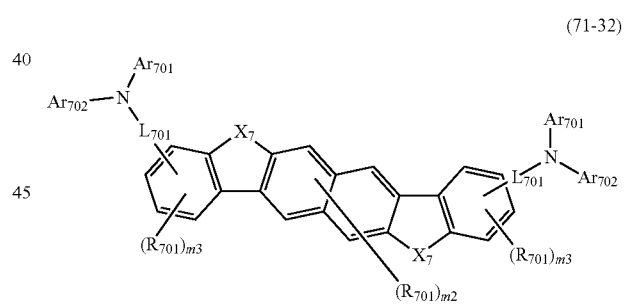
(71-32)
[Formula 353]
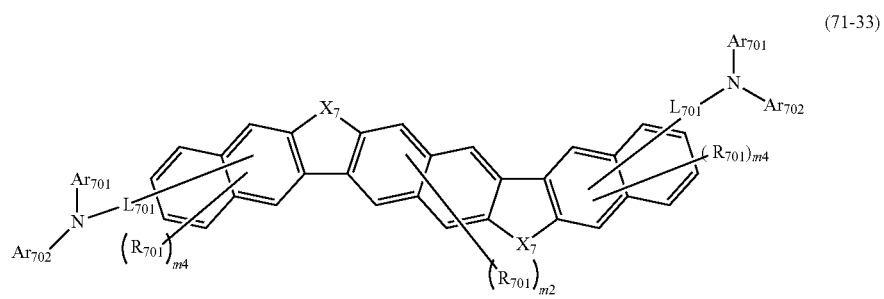
(71-33)

889

In the formulae (71-31) to (71-33), $R_{701}$, $X_7$, $Ar_{701}$, $Ar_{702}$, $L_{701}$, and m2 to m4 respectively represent the same as $R_{701}$, $X_7$, $Ar_{701}$, $Ar_{702}$, $L_{701}$, and m2 to m4 in the formula (7).

In an exemplary embodiment, $Ar_{701}$ and $Ar_{702}$ are each independently a substituted or unsubstituted aryl group having 6 to 50 ring carbon atoms.

890

In an exemplary embodiment, one of $Ar_{701}$ and $Ar_{702}$ is a substituted or unsubstituted aryl group having 6 to 50 ring carbon atoms, and the other of $Ar_{701}$ and $Ar_{702}$ is a substituted or unsubstituted heterocyclic group having 5 to 50 ring atoms.

Specific examples of the compound represented by the formula (7) include compounds shown below.

[Formula 354]

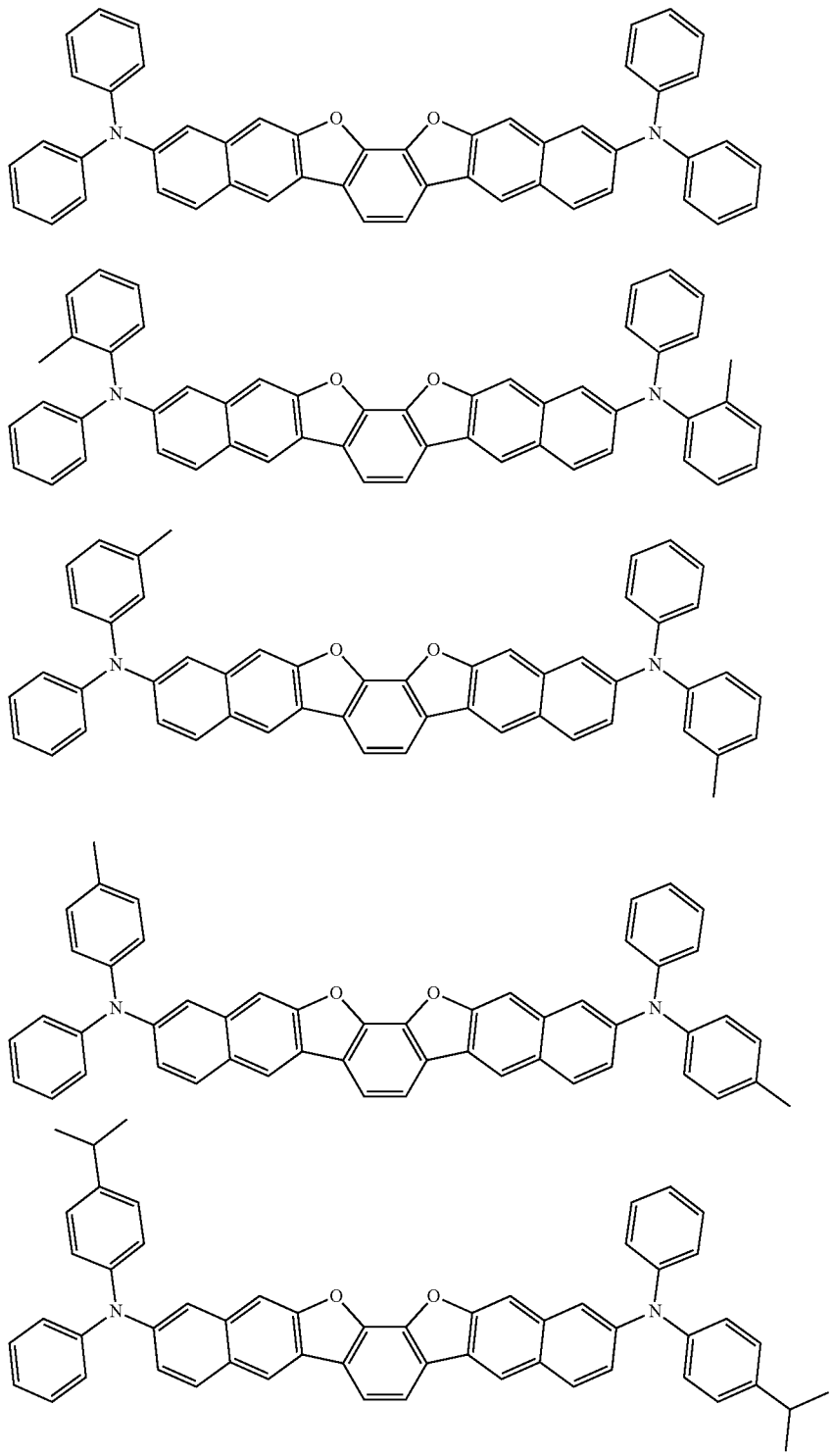

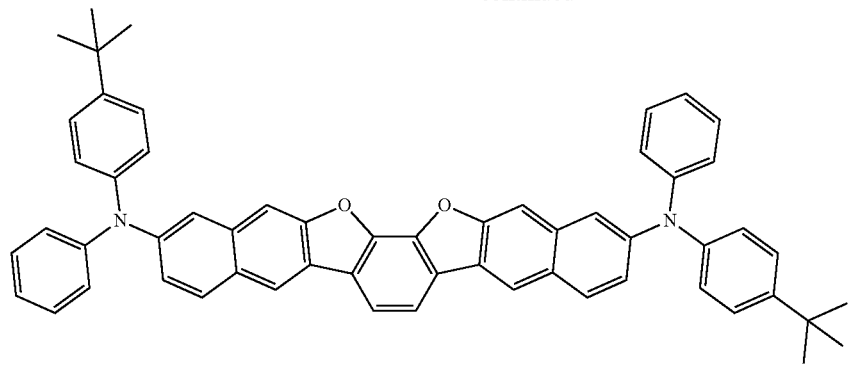
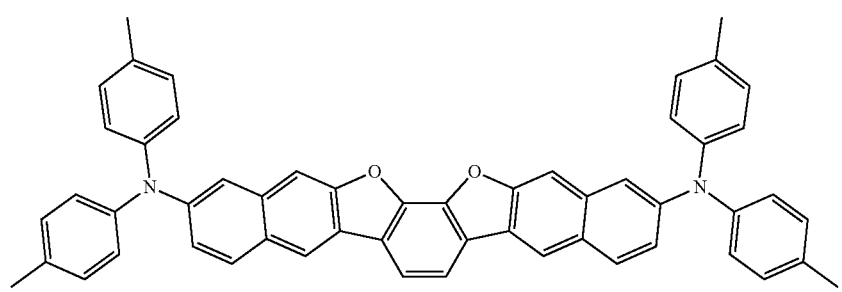
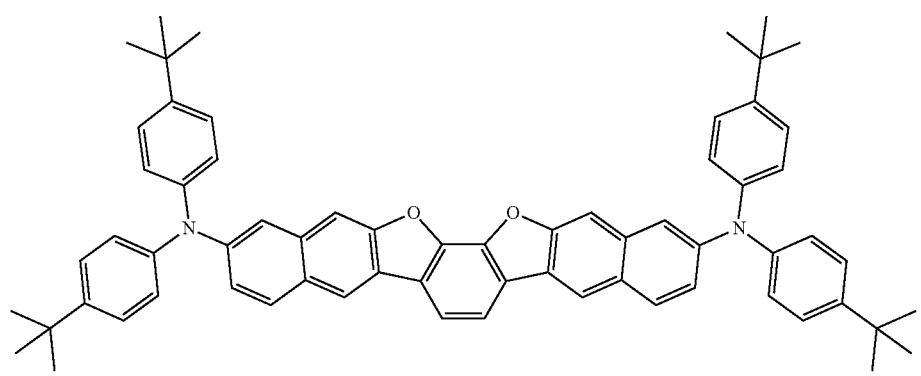
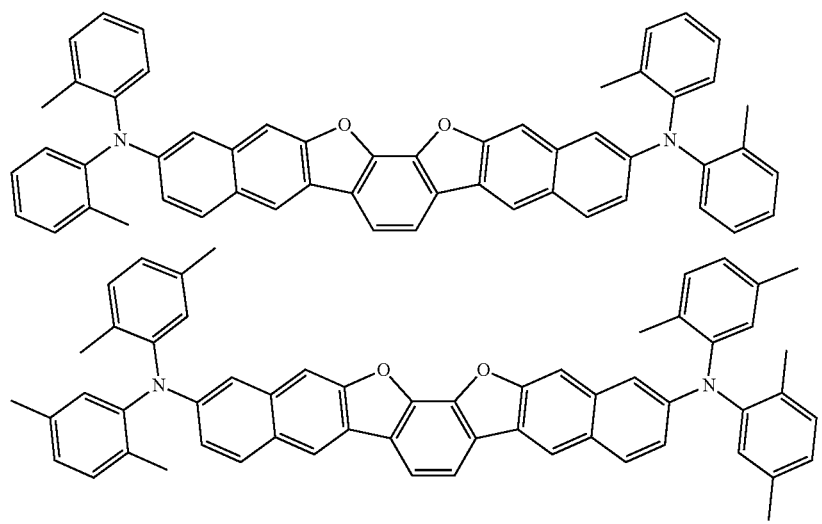

-continued
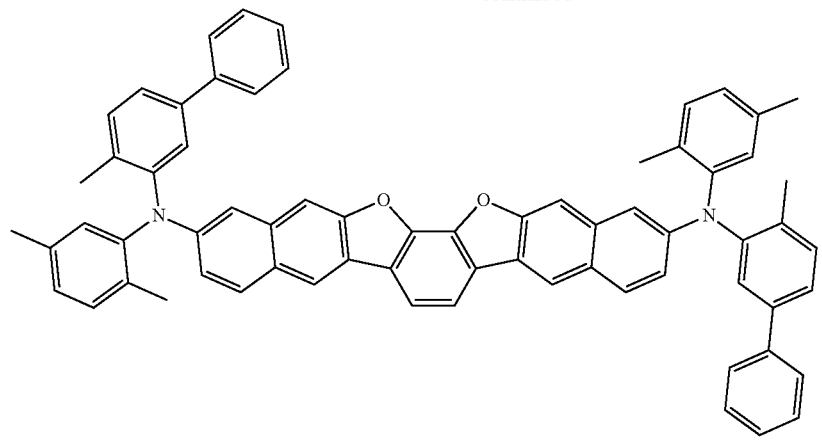
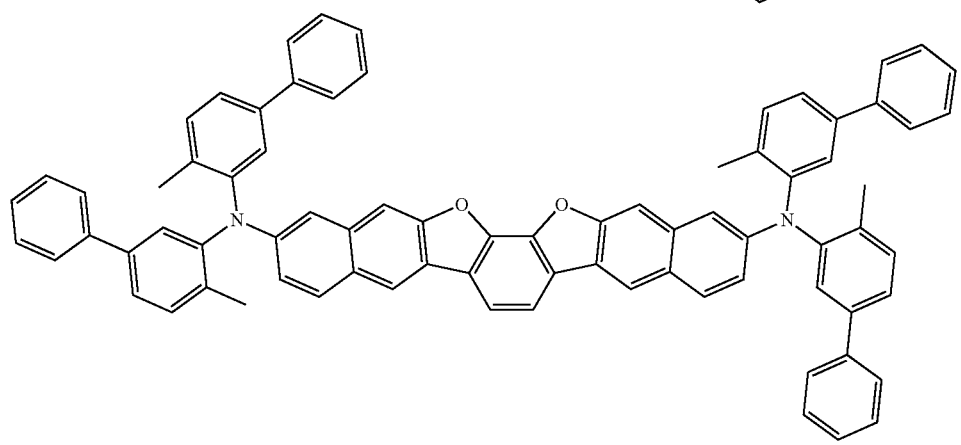
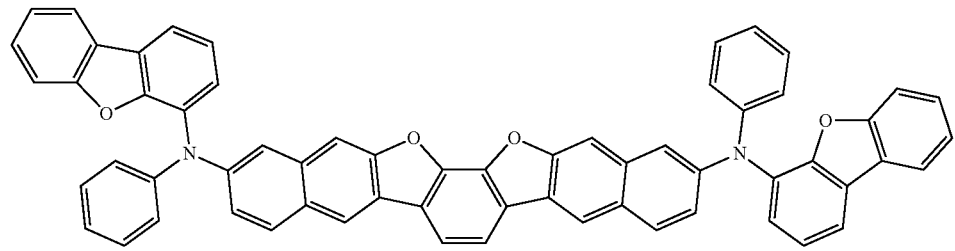
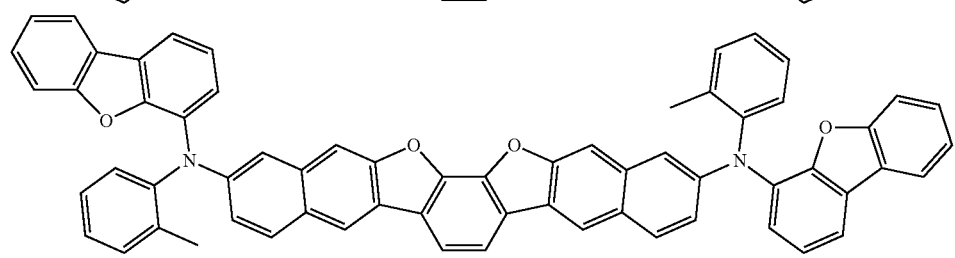
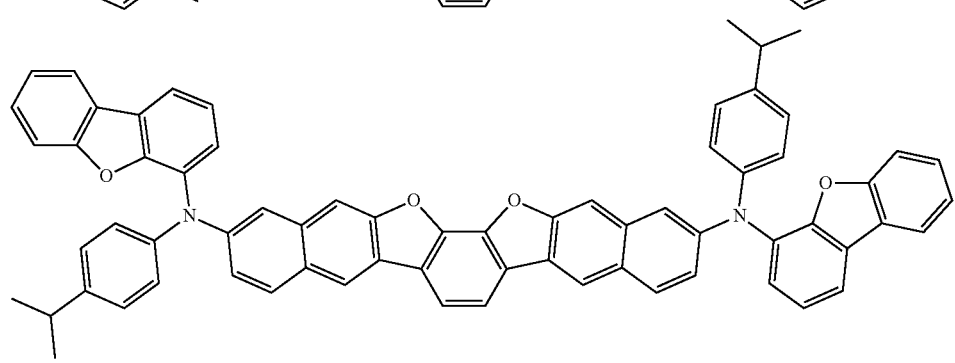

895    896
-continued
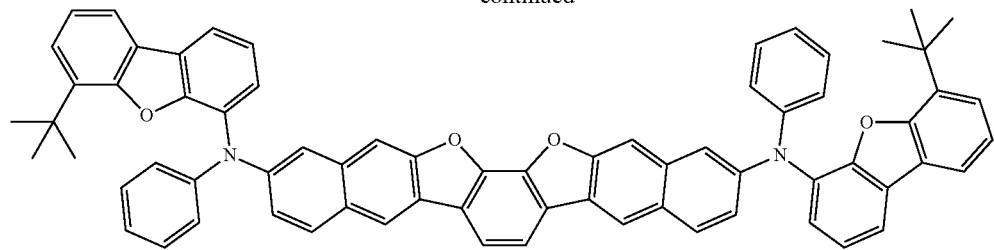
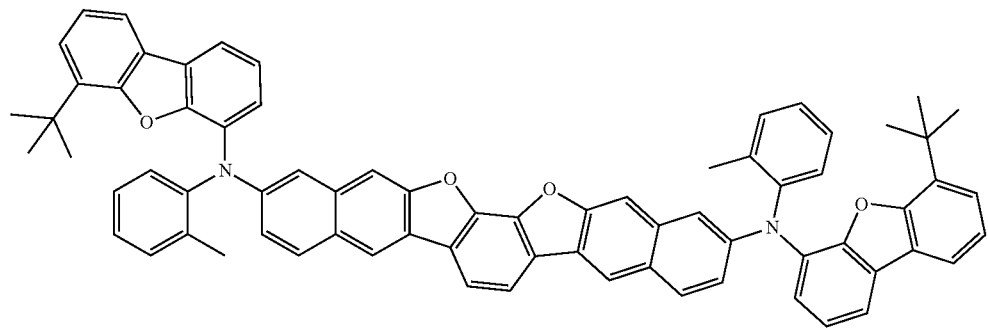
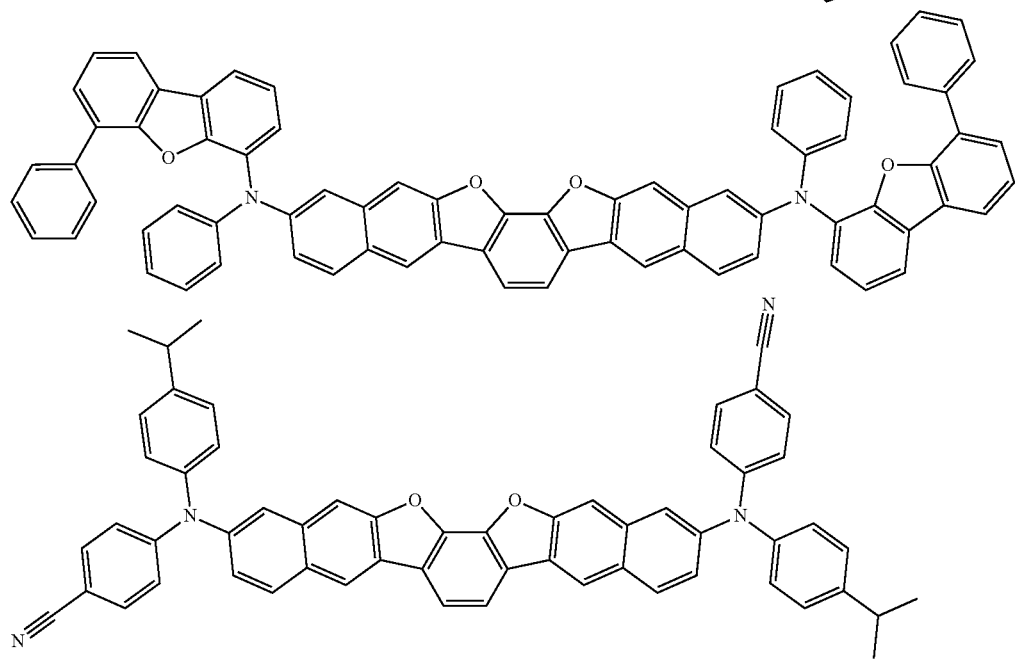
[Formula 355]
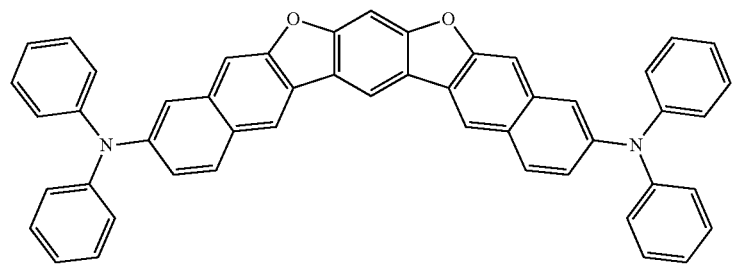

897 898
-continued
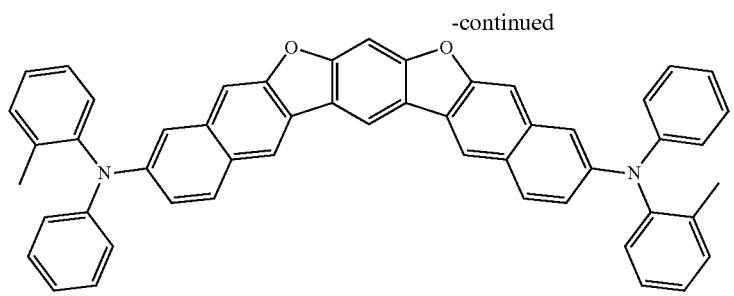
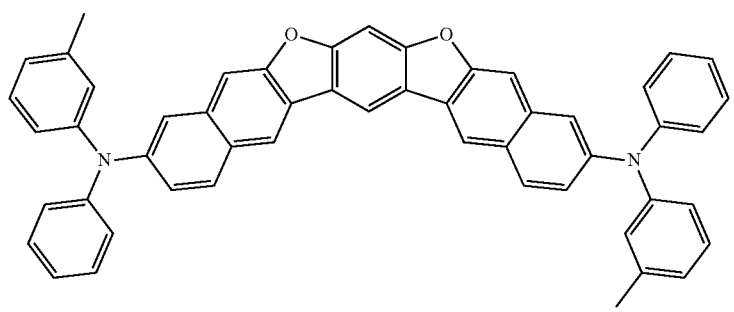
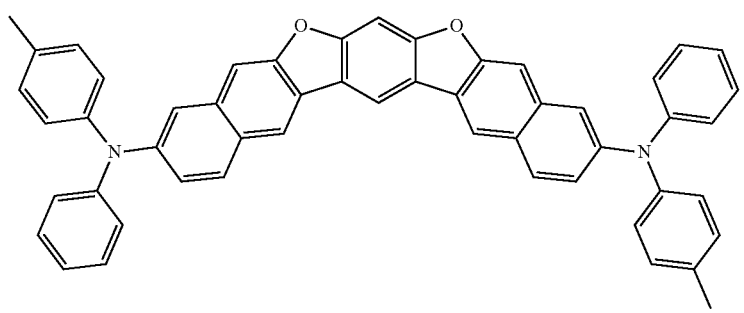
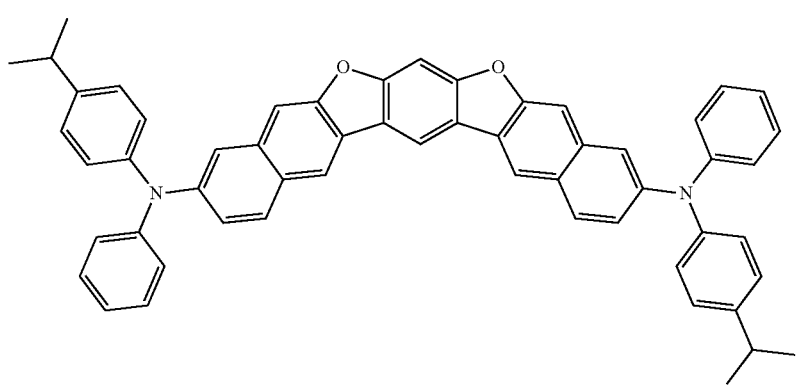
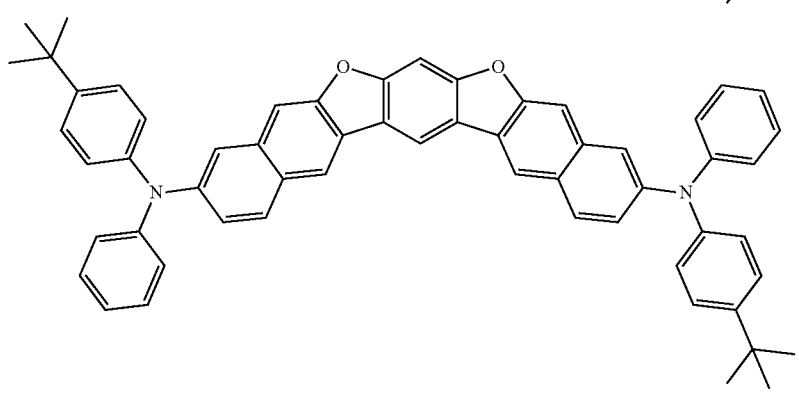

-continued
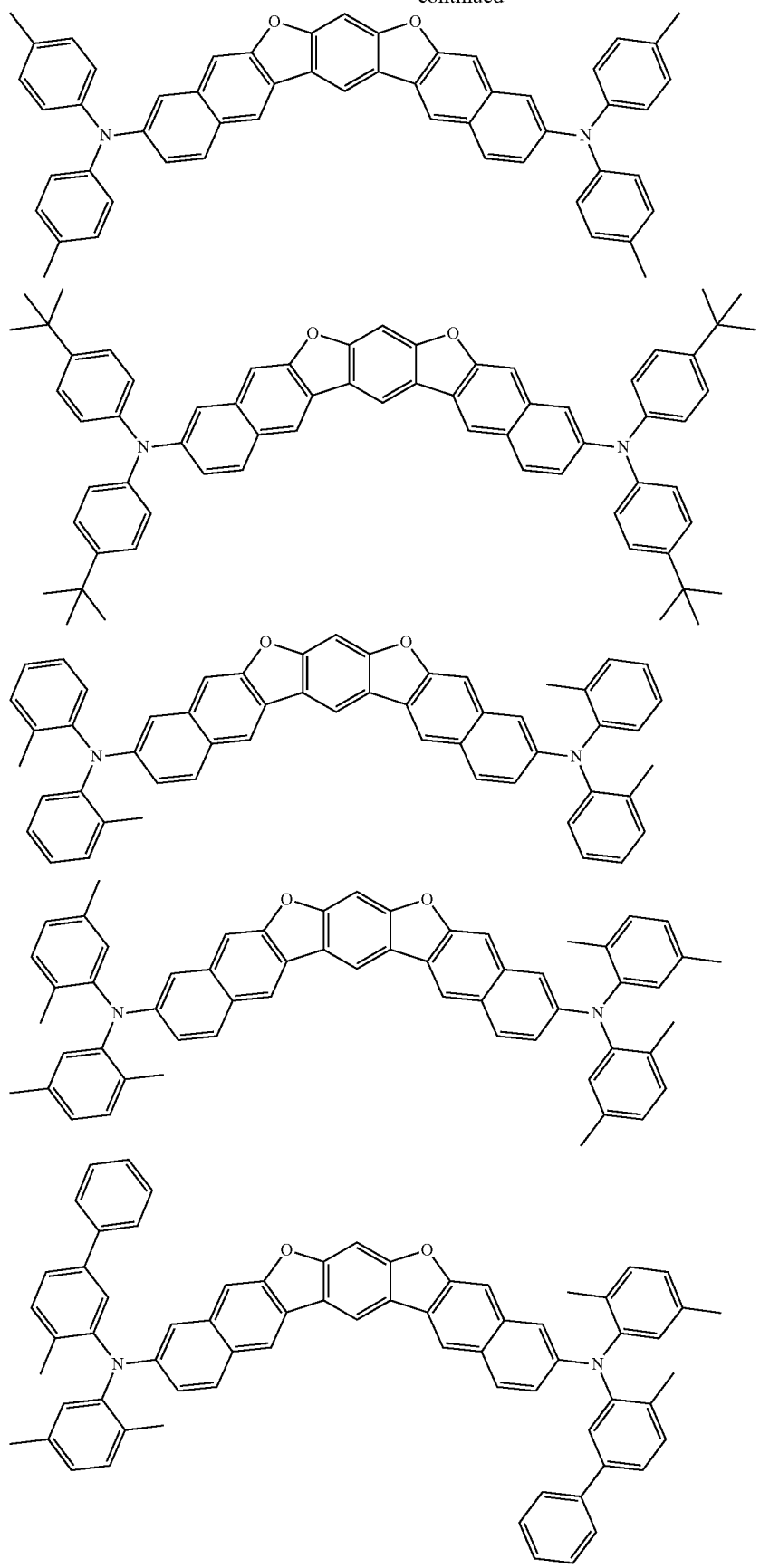

901    902
-continued
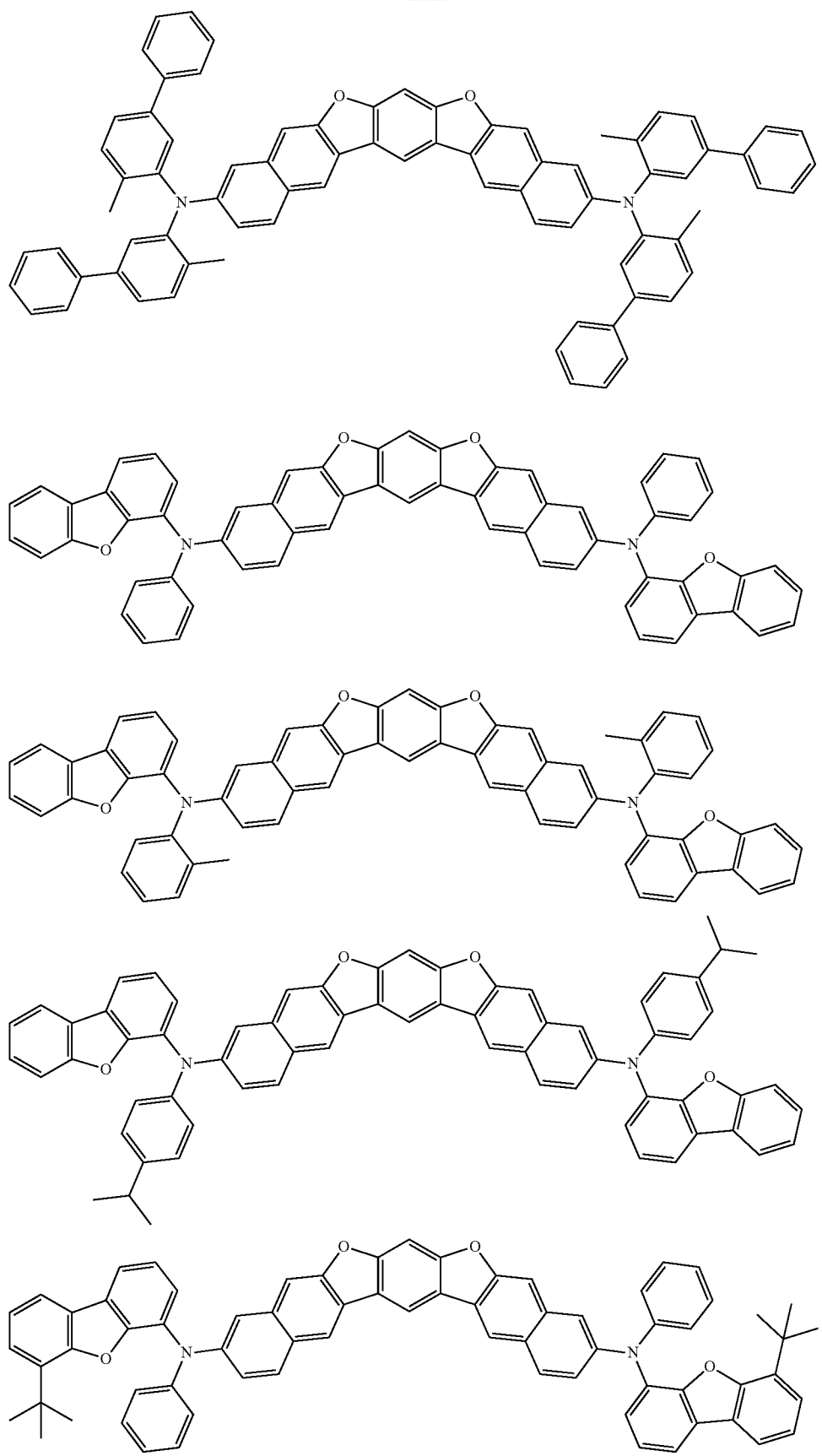

-continued
903  904
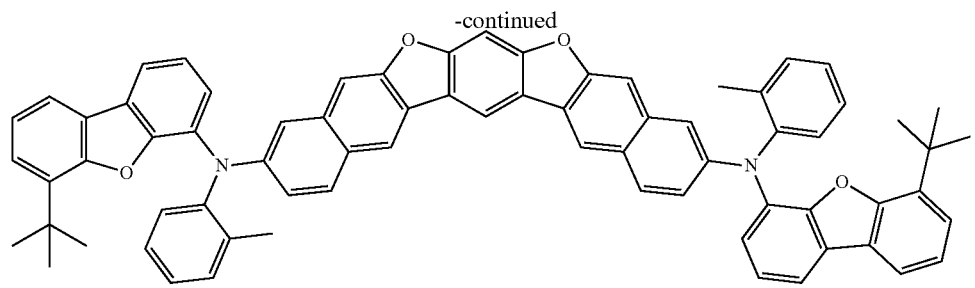
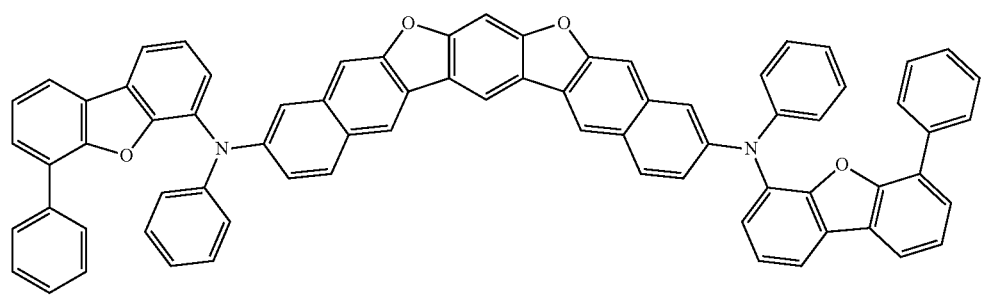
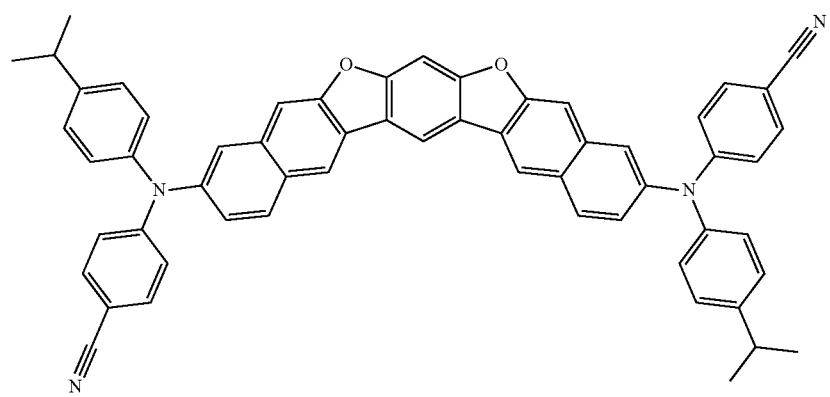 [SMILES: CC(C)c1ccc(N(c2ccc(C#N)cc2)c2ccc3cc4c(cc3c2)oc2cc3oc5cc6cc(N(c7ccc(C#N)cc7)c7ccc(C(C)C)cc7)ccc6cc5c3cc24)cc1]
[Formula 356]
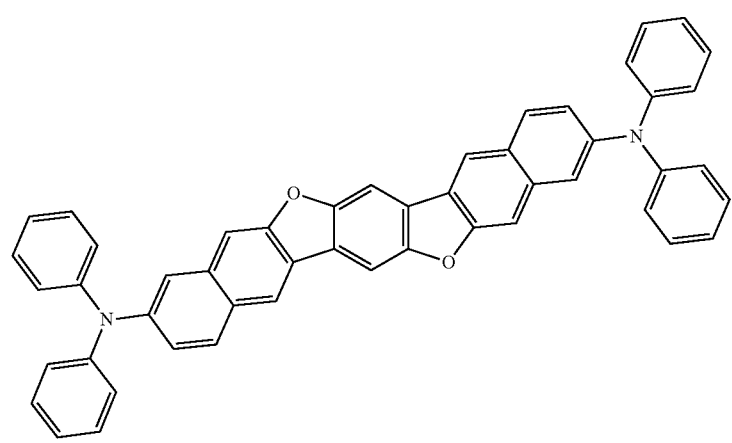

-continued
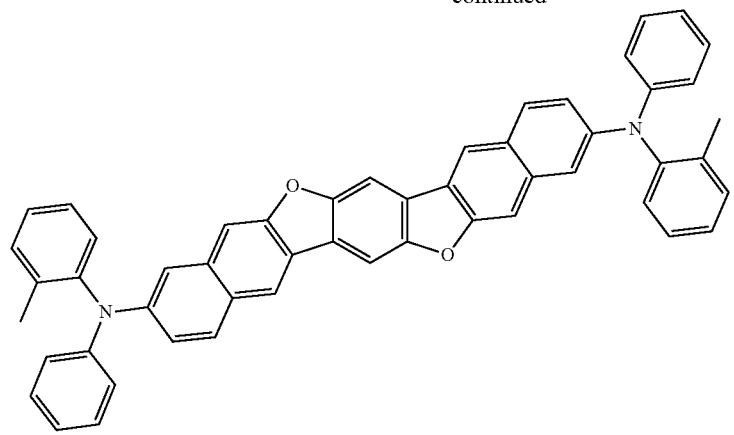
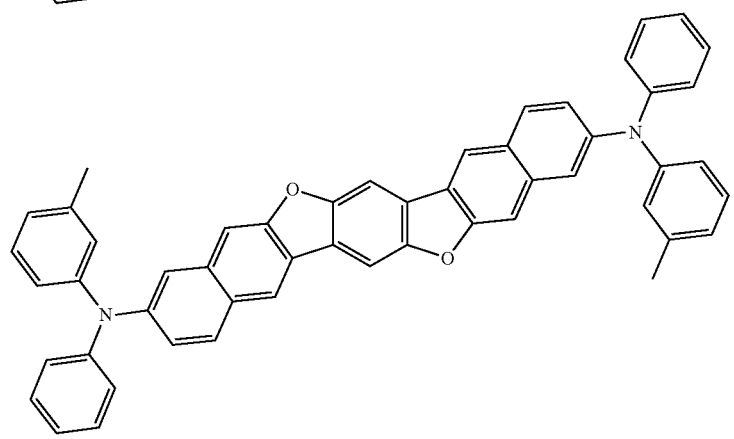
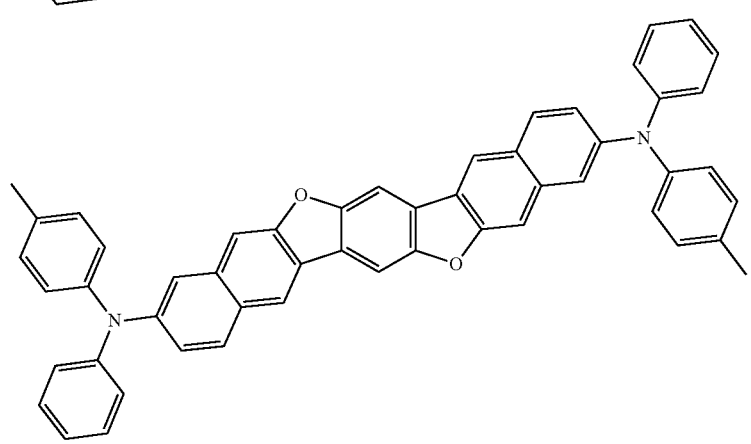
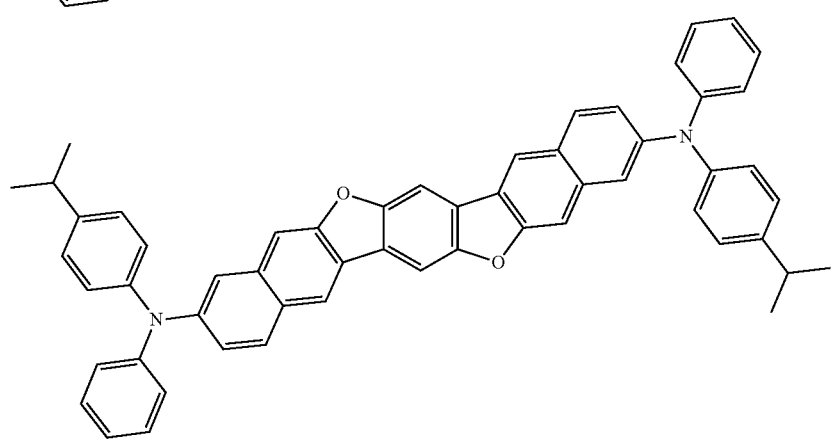

907                                                                                     908
-continued
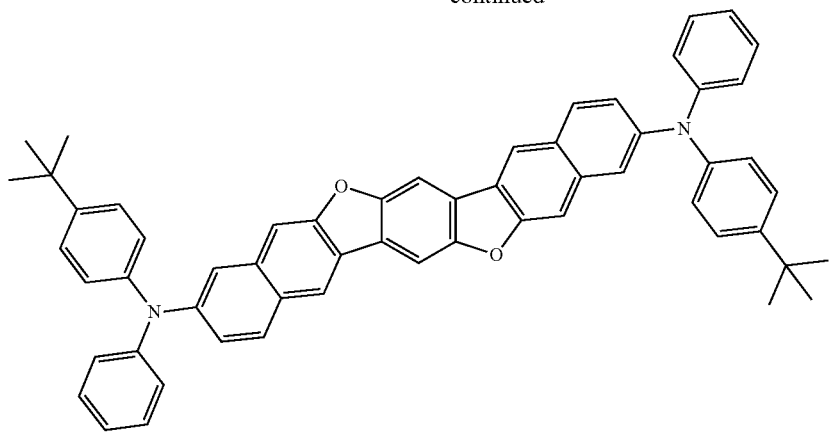
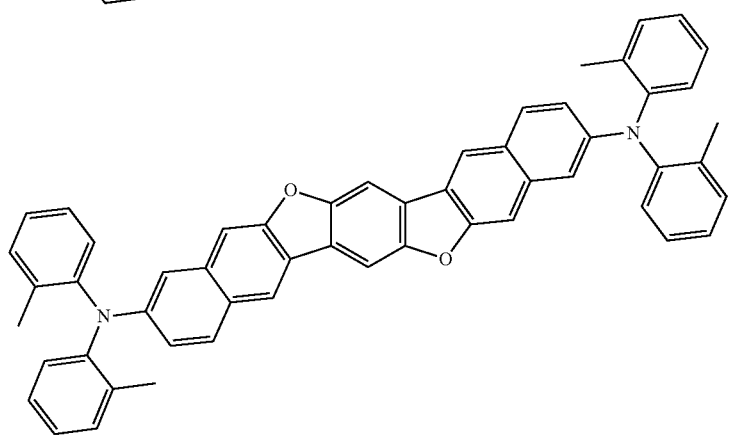
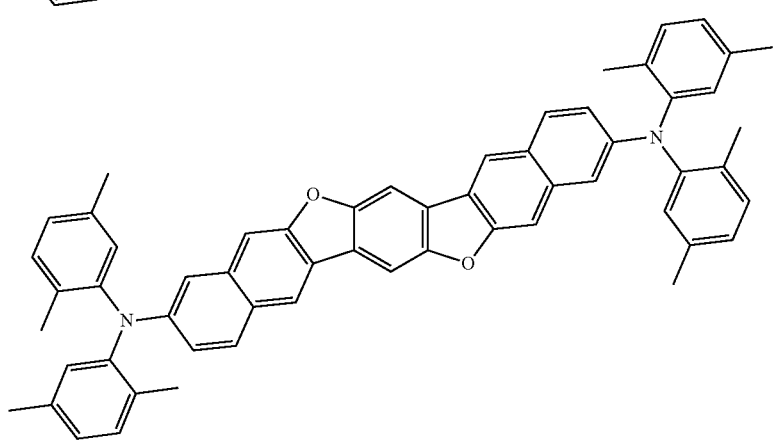
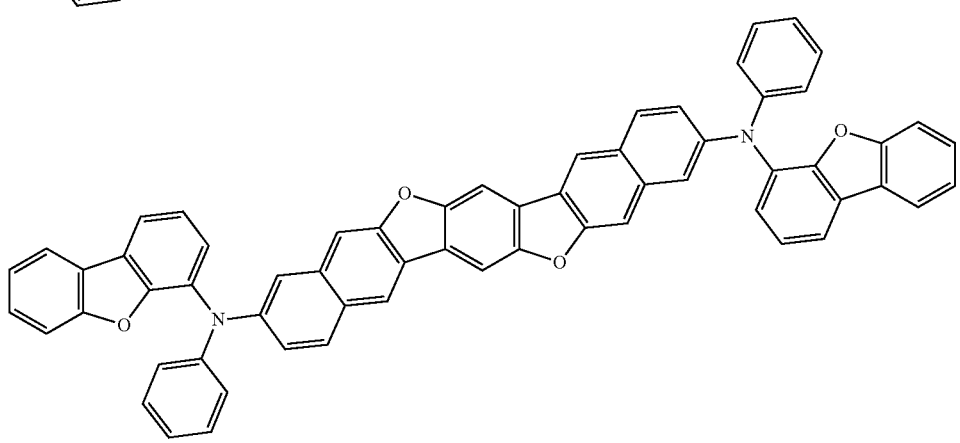

909
910
-continued
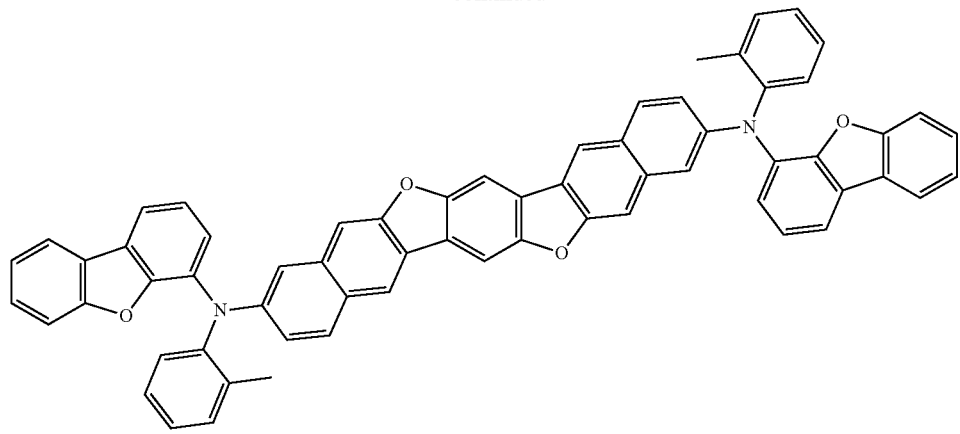
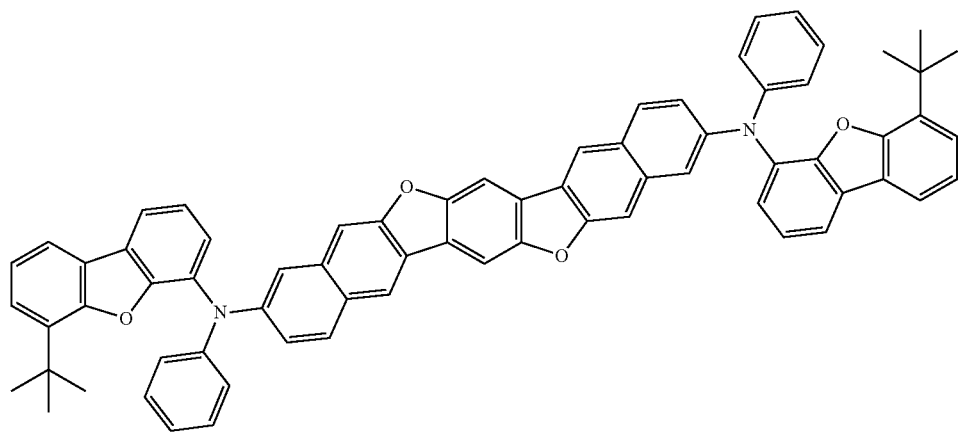
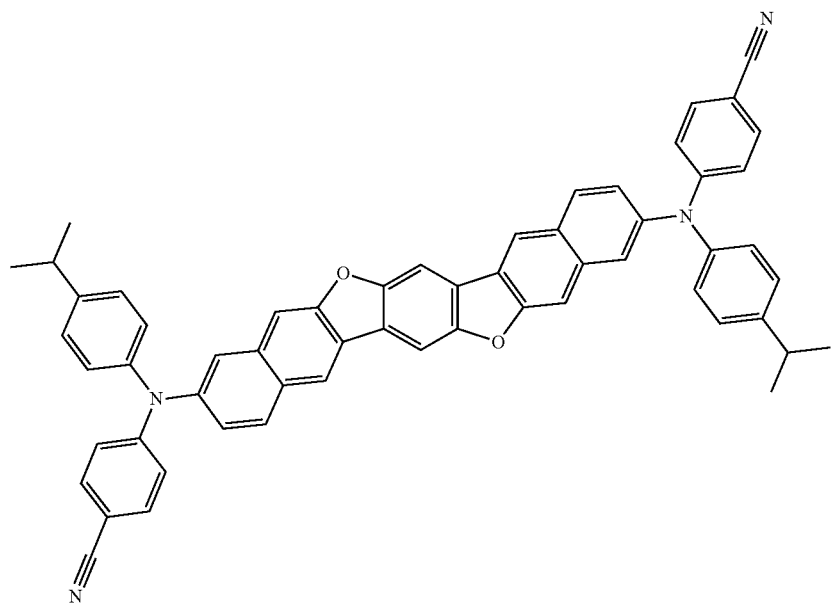

911
-continued
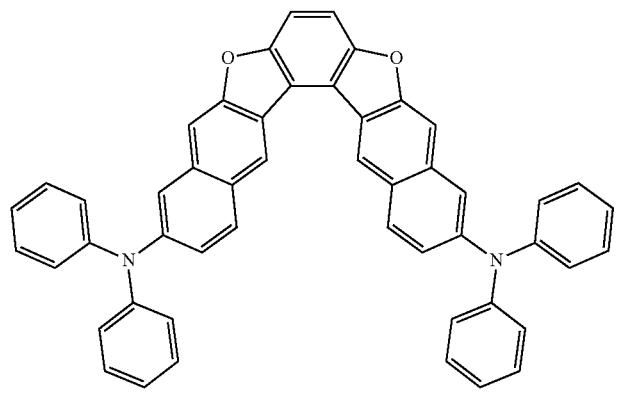
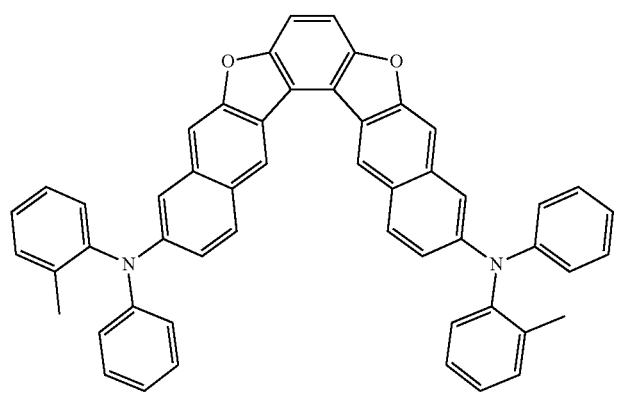
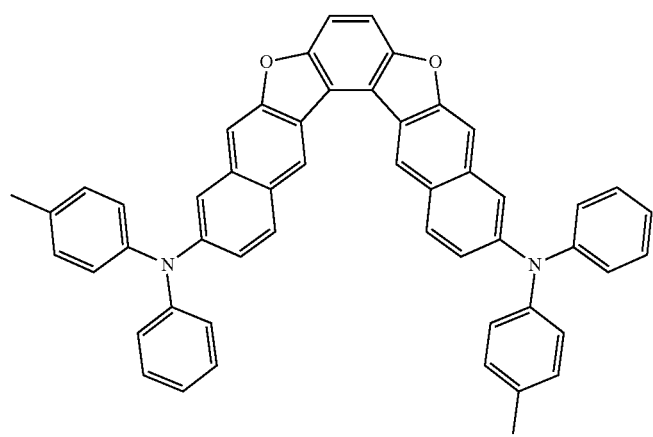

913 914
[Formula 357]
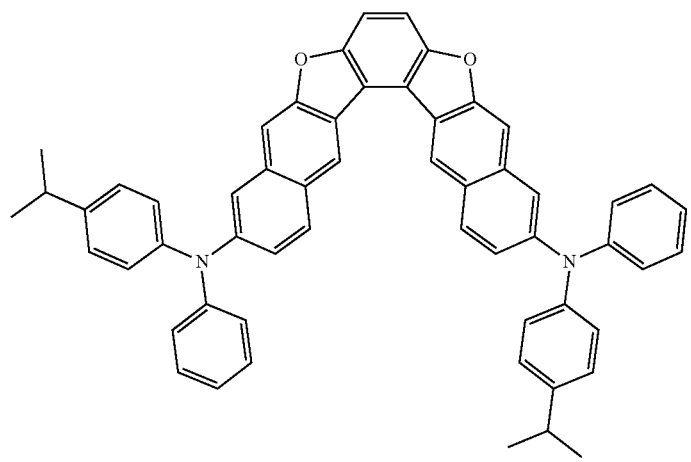
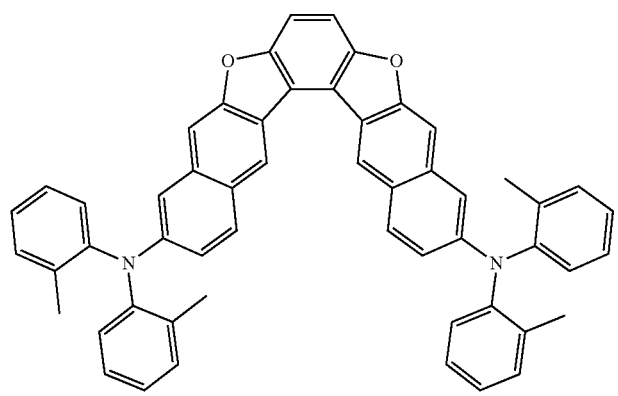
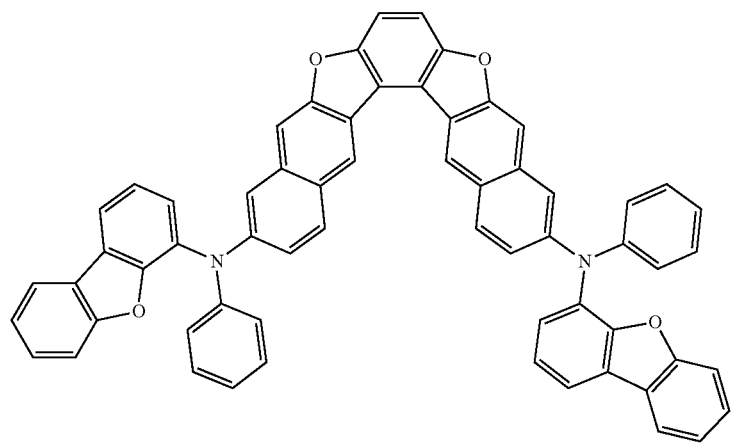

915
916
-continued
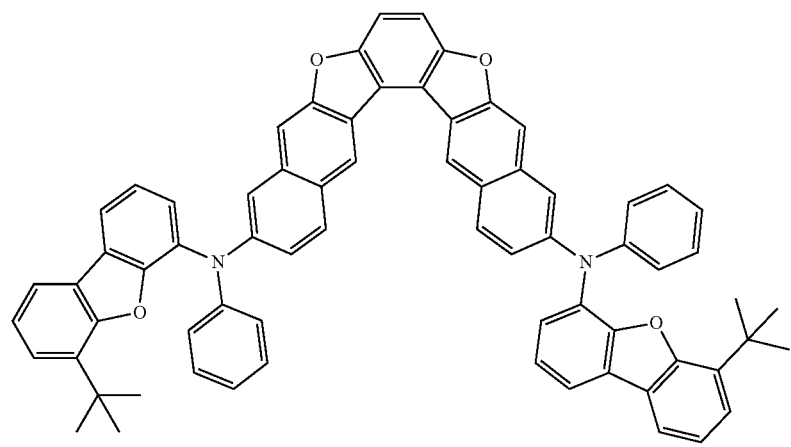
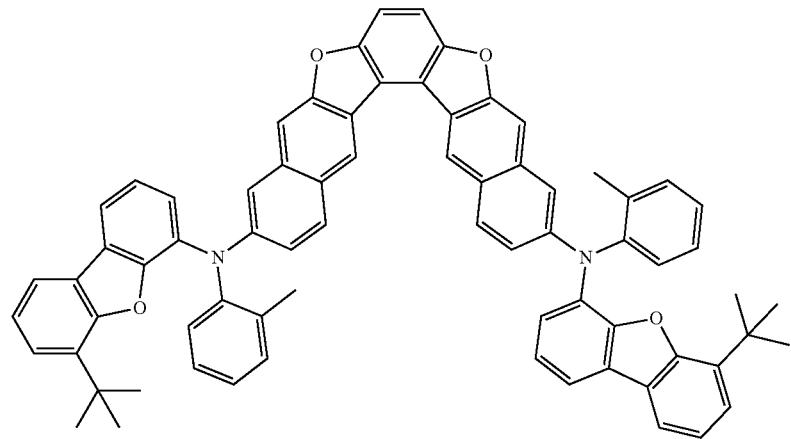
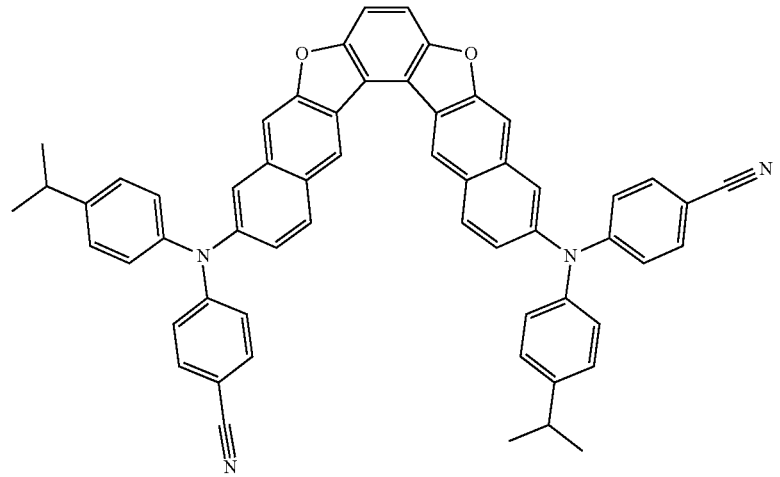
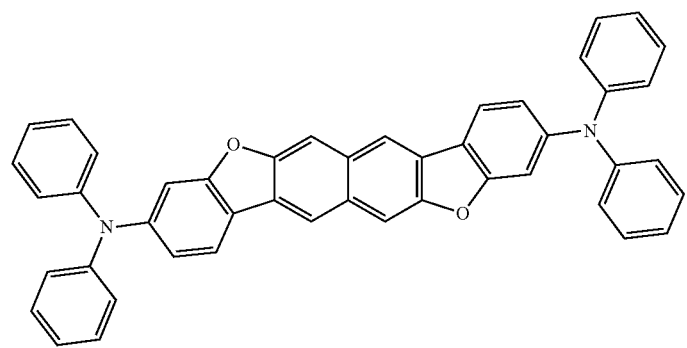

-continued
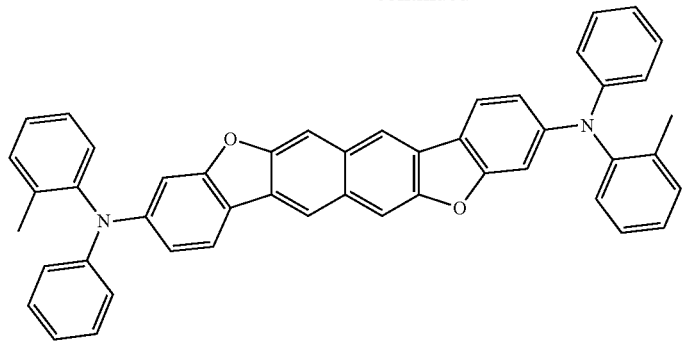
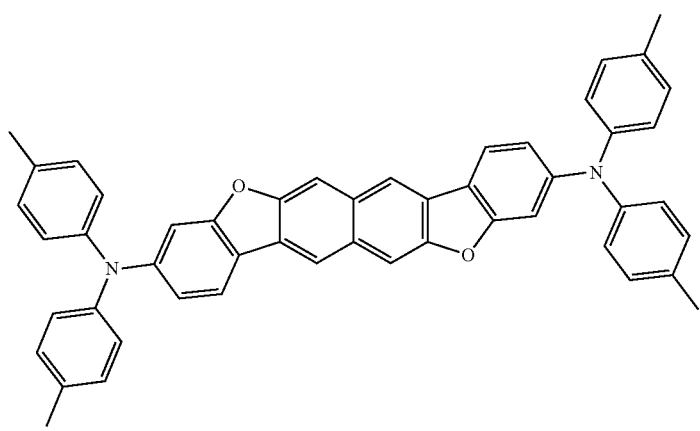
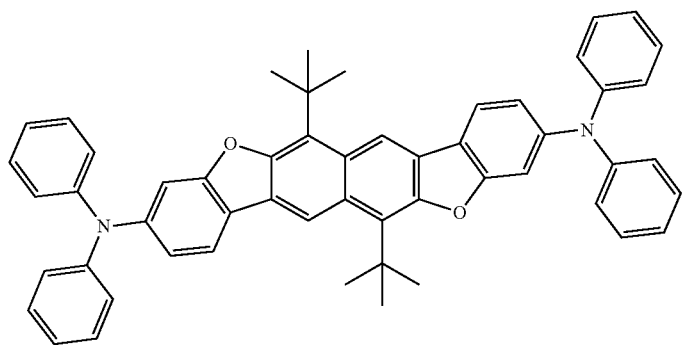
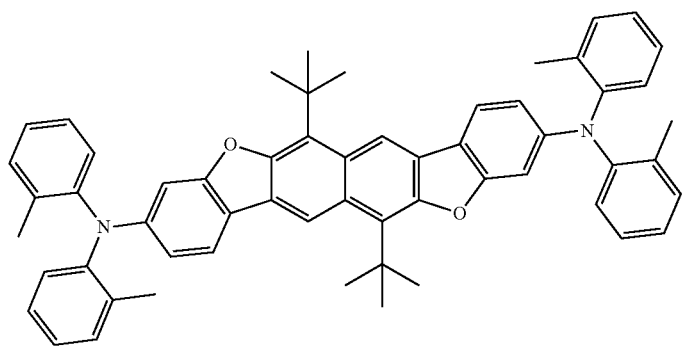

-continued
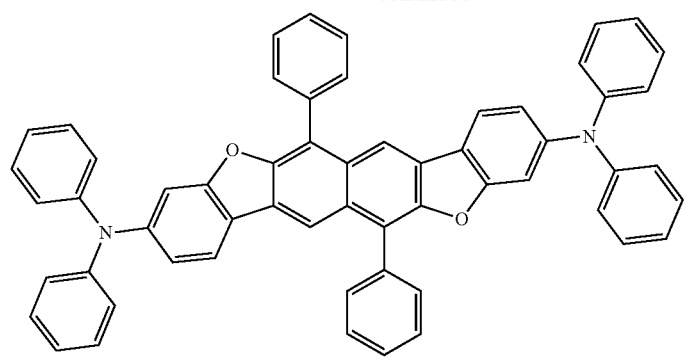
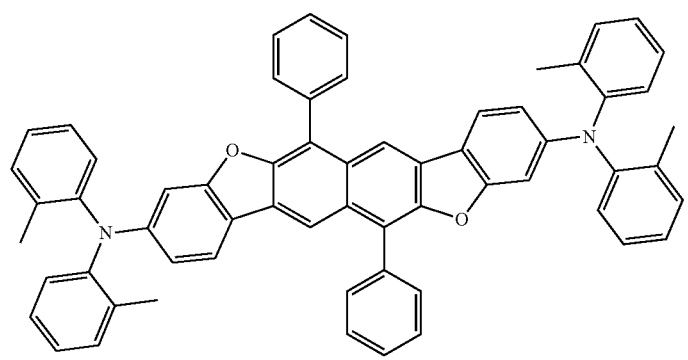
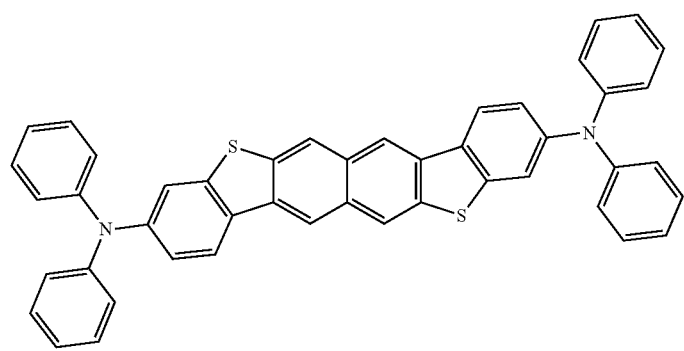
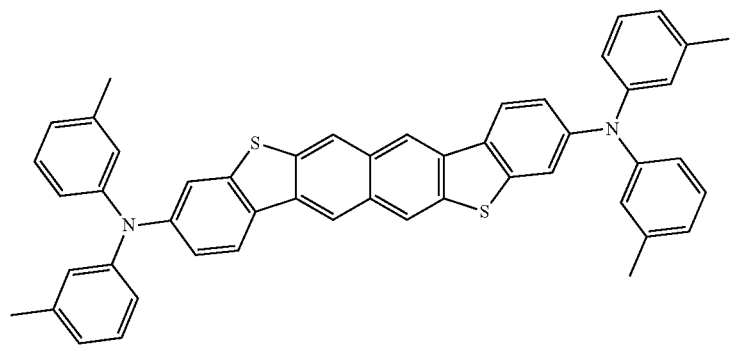
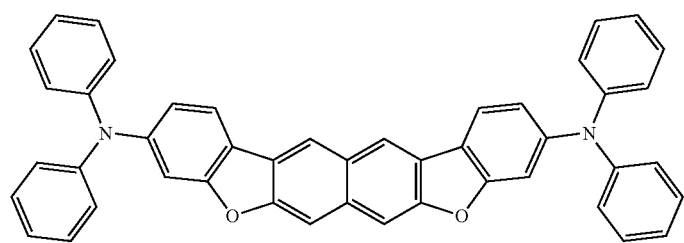

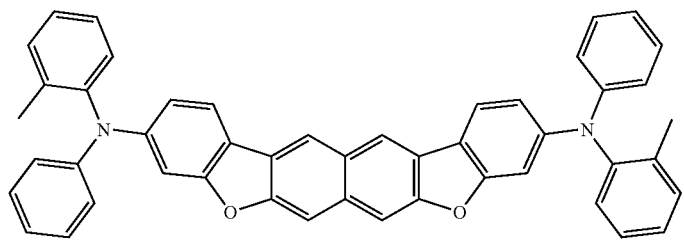
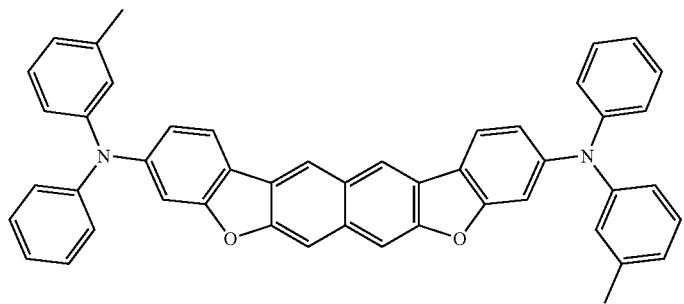
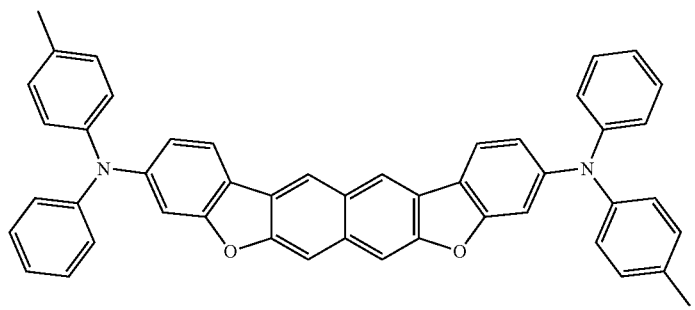
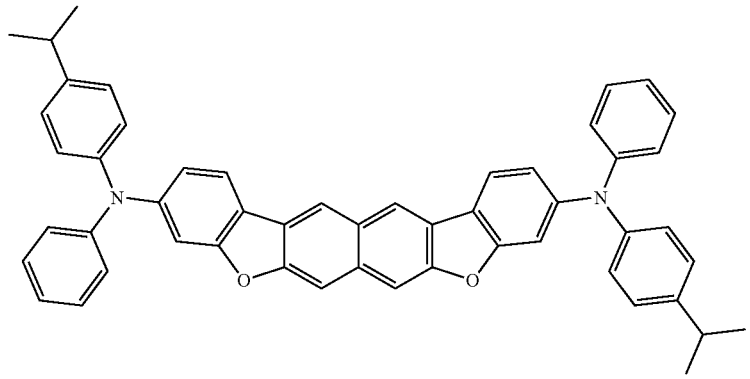
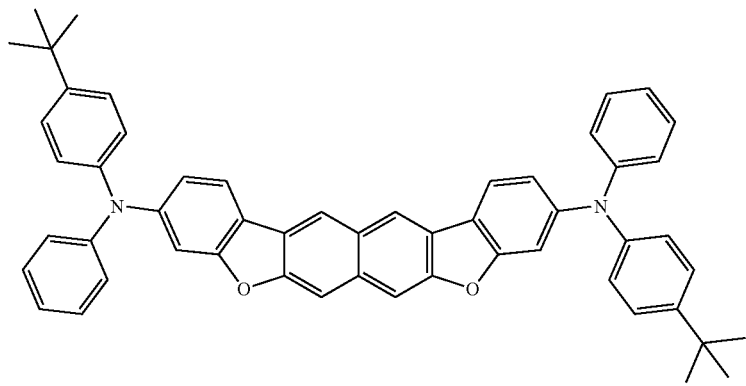 [SMILES: CC(C)(C)c1ccc(N(c2ccccc2)c2ccc3c(c2)oc2cc4cc5oc6cc(N(c7ccccc7)c7ccc(C(C)(C)C)cc7)ccc6c5cc4cc23)cc1]

[Formula 358]
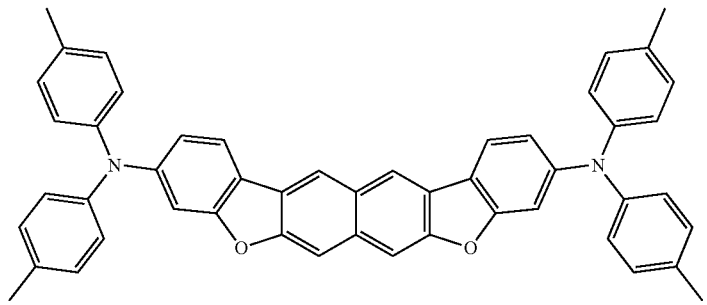
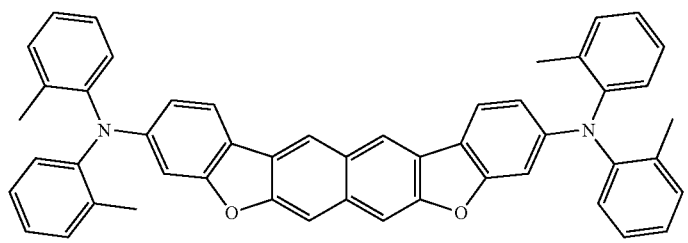
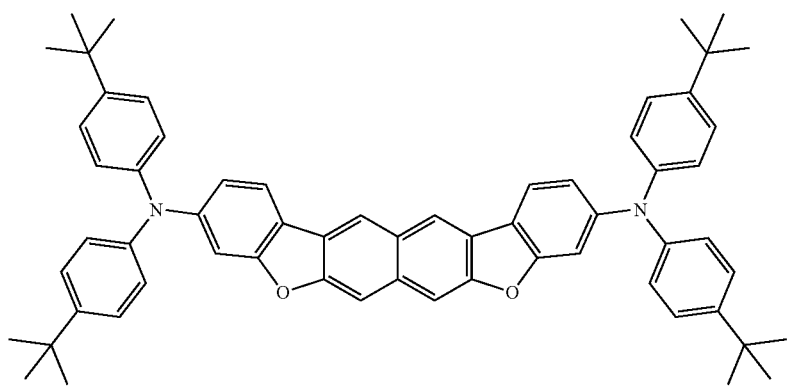
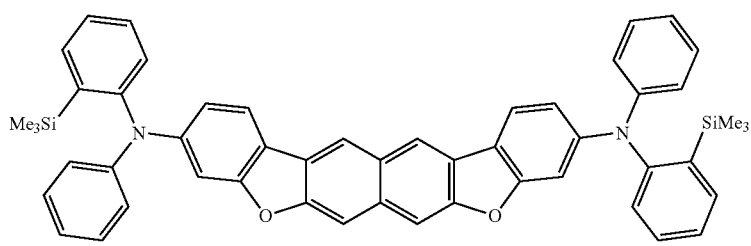
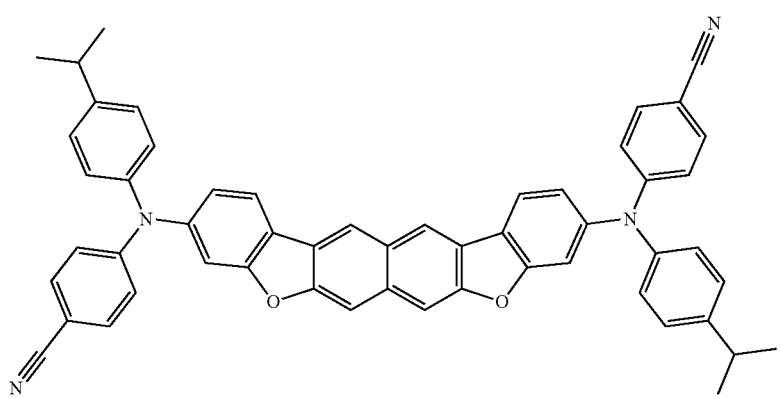

-continued
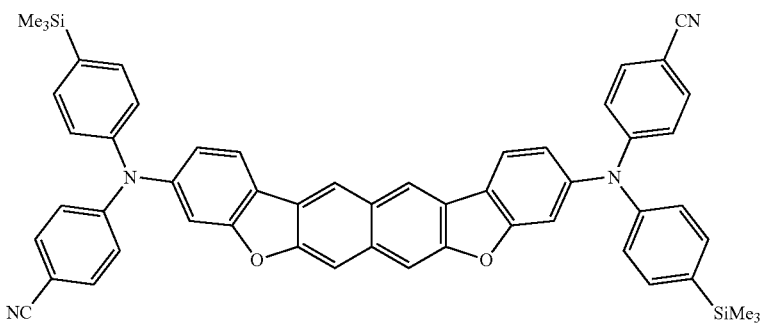
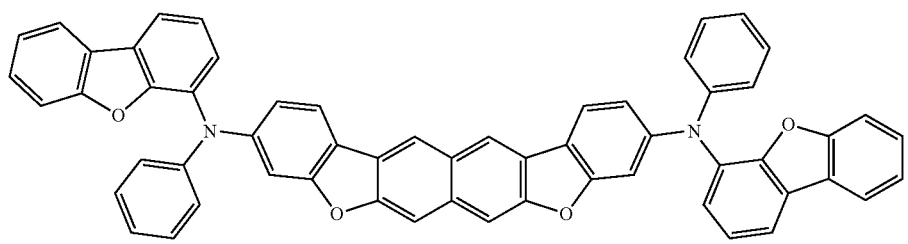
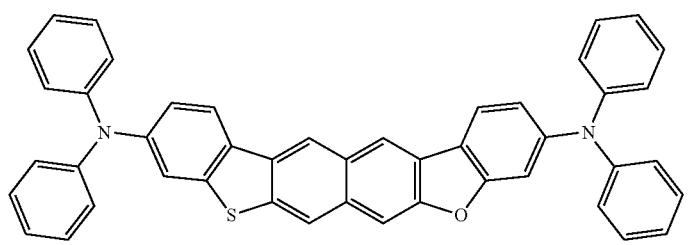
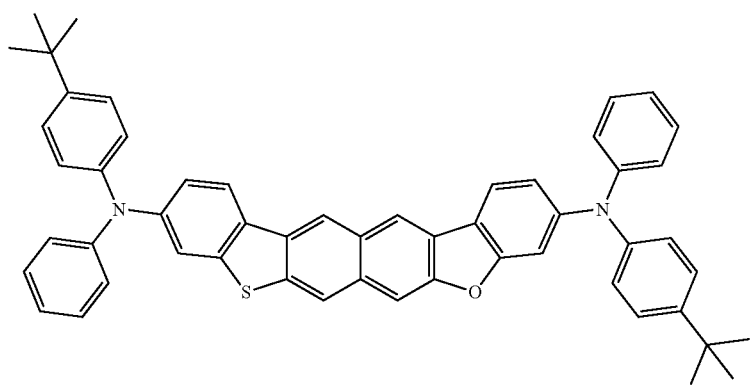
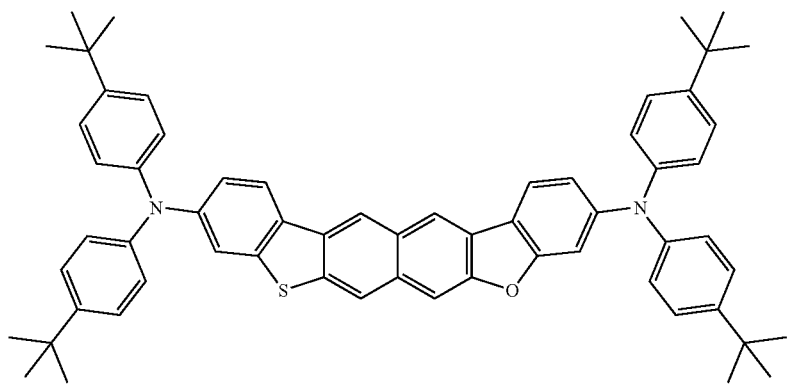

-continued
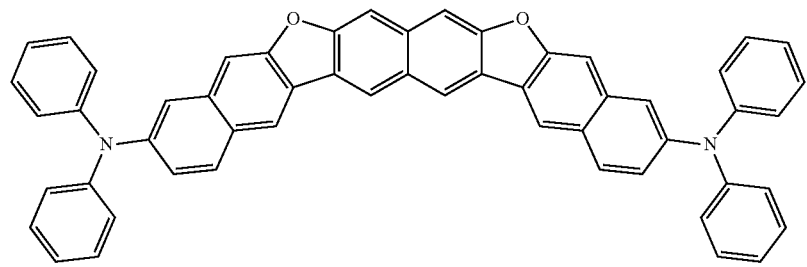
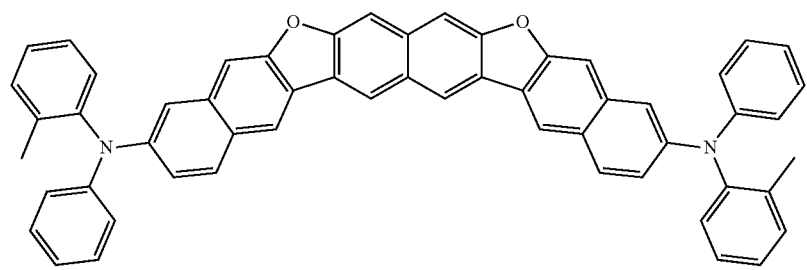
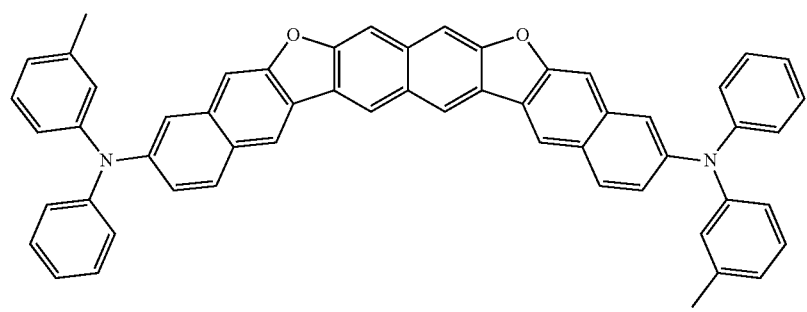
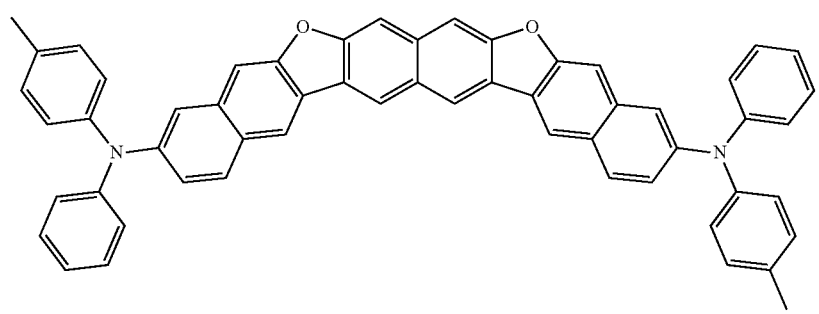
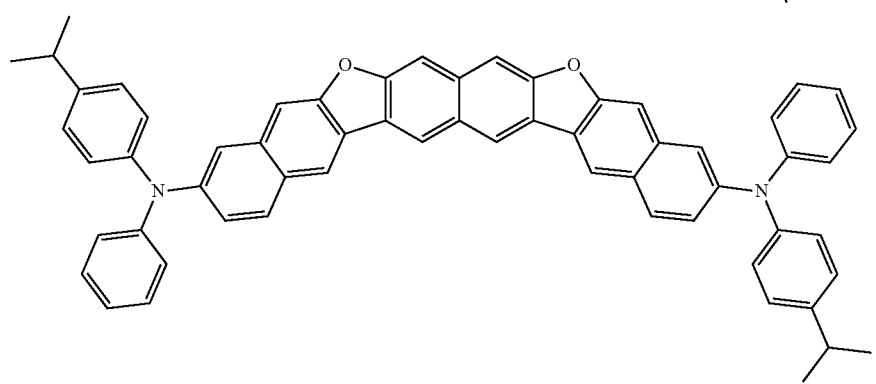

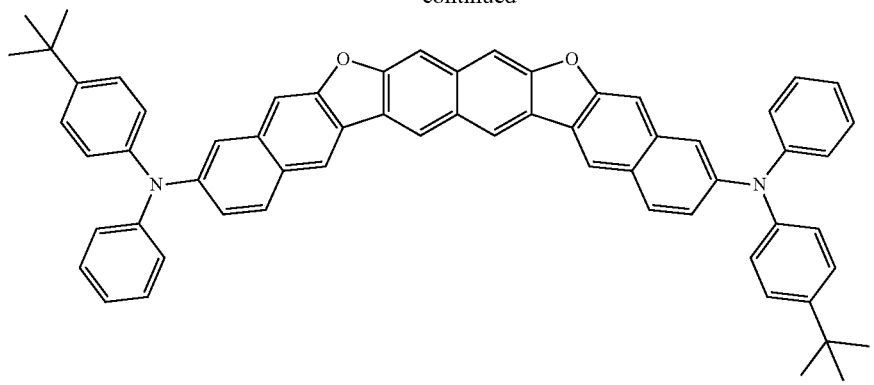
[Formula 359]
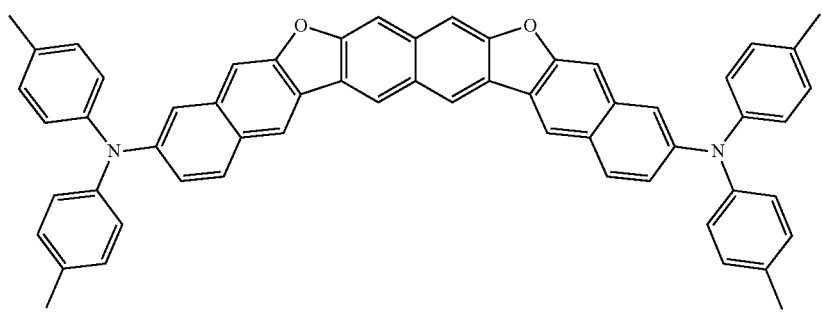
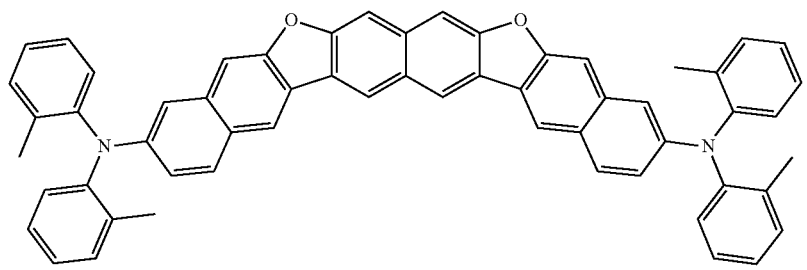
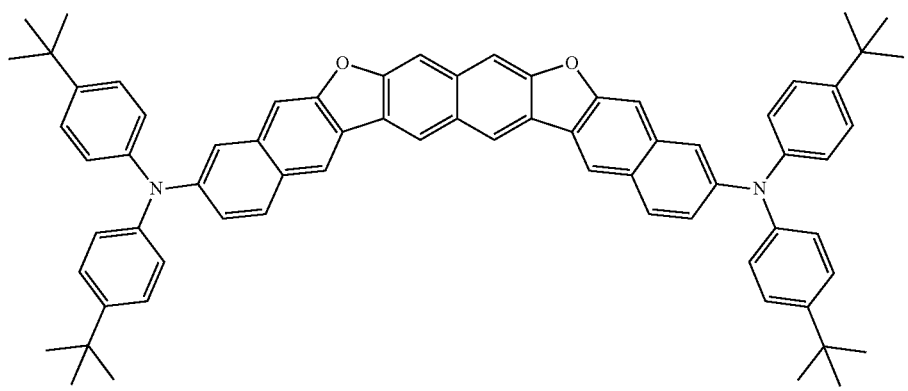

931

-continued

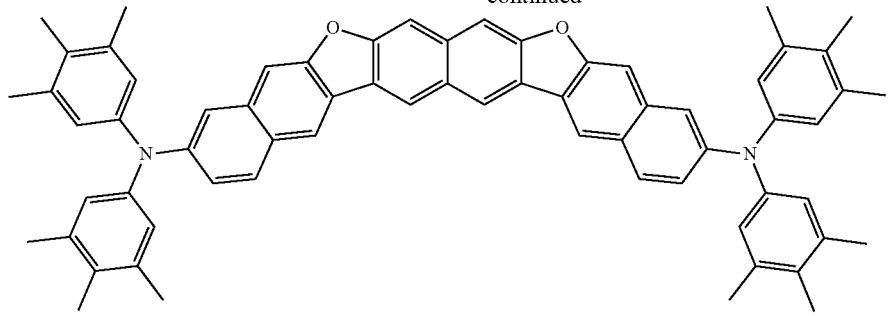

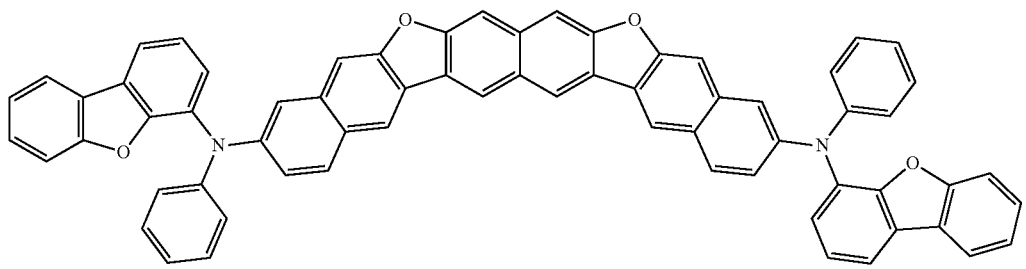

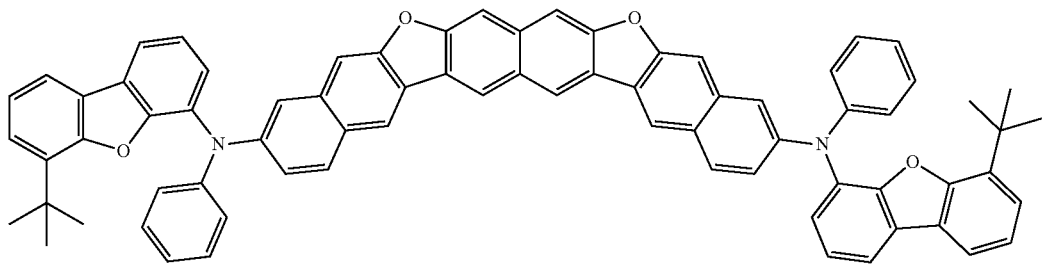

Compound Represented by Formula (8)

The compound represented by the formula (8) will be described below.

[Formula 360]

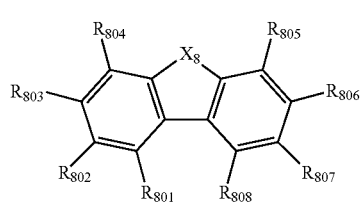

(8)

In the formula (8):

at least one combination of $R_{801}$ and $R_{802}$, $R_{802}$ and $R_{803}$, or $R_{803}$ and $R_{804}$ are mutually bonded to form a divalent group represented by a formula (82) below; and at least one combination of $R_{805}$ and $R_{806}$, $R_{806}$ and $R_{807}$, or $R_{807}$ and $R_{808}$ are mutually bonded to form a divalent group represented by a formula (83) below.

932

[Formula 361]

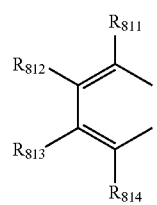

(82)

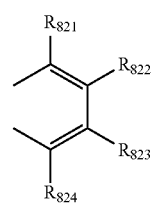

(83)

At least one of $R_{801}$ to $R_{804}$ or $R_{811}$ to $R_{814}$ not forming the divalent group represented by the formula (82) is a monovalent group represented by a formula (84) below;

at least one of $R_{805}$ to $R_{808}$ or $R_{821}$ to $R_{824}$ not forming the divalent group represented by the formula (83) is a monovalent group represented by a formula (84) below;

$X_8$ is an oxygen atom, a sulfur atom, or $NR_{809}$; and $R_{801}$ to $R_{808}$ not forming the divalent group represented by the formula (82) or (83) and not being the monovalent group represented by the formula (84), and $R_{811}$ to $R_{814}$, $R_{821}$ to $R_{824}$ and $R_{809}$ not being the monovalent group represented by the formula (84) are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

[Formula 362]

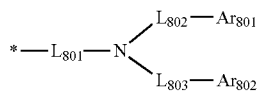

(84)

In the formula (84):

$Ar_{801}$ and $Ar_{802}$ are each independently a substituted or unsubstituted aryl group having 6 to 50 ring carbon atoms, or a substituted or unsubstituted heterocyclic group having 5 to 50 ring atoms;

$L_{801}$ to $L_{803}$ are each independently a single bond, a substituted or unsubstituted arylene group having 6 to 30 ring carbon atoms, a substituted or unsubstituted divalent heterocyclic group having 5 to 30 ring atoms, or a divalent linking group formed by bonding two, three or four groups selected from the group consisting of the substituted or unsubstituted arylene group having 6 to 30 ring carbon atoms and a substituted or unsubstituted divalent heterocyclic group having 5 to 30 ring atoms; and

* in the formula (84) represents a bonding position to the cyclic structure represented by the formula (8) or a bonding position to the group represented by the formula (82) or (83).

In the formula (8), the positions for the divalent group represented by the formula (82) and the divalent group represented by the formula (83) to be formed are not specifically limited but the divalent groups may be formed at any possible positions on $R_{801}$ to $R_{808}$.

In an exemplary embodiment, the compound represented by the formula (8) is represented by any one of formulae (81-1) to (81-6) below.

[Formula 363]

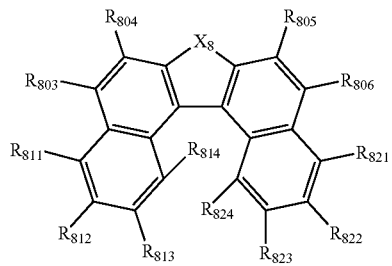

(81-1)

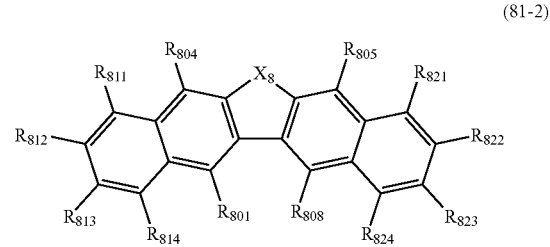

(81-2)

[Formula 364]

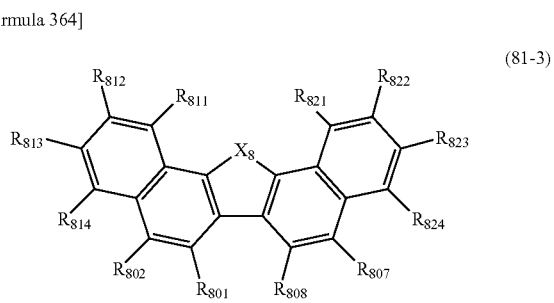

(81-3)

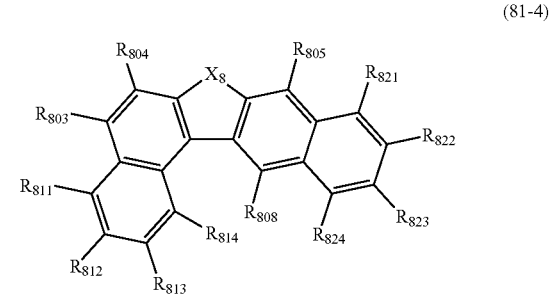

(81-4)

[Formula 365]

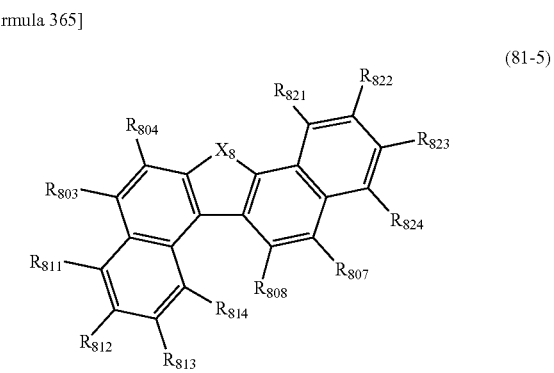

(81-5)

-continued (81-6)

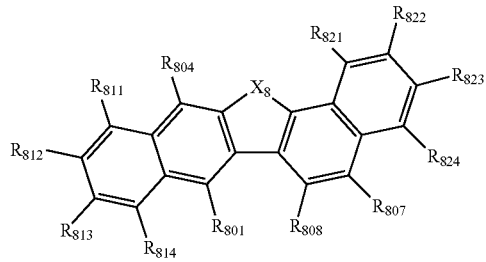

In the formulae (81-1) to (81-6):

$X_8$ represents the same as $X_8$ in the formula (8);

at least two of $R_{801}$ to $R_{824}$ are each a monovalent group represented by the formula (84); and $R_{801}$ to $R_{824}$ that are not the monovalent group represented by the formula (84) are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

In an exemplary embodiment, the compound represented by the formula (8) is represented by any one of formulae (81-7) to (81-18) below.

[Formula 366]

(81-7)

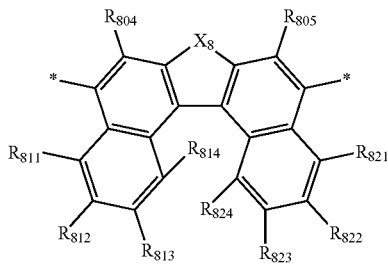

(81-8)

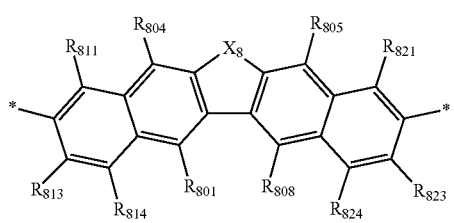

[Formula 367]

(81-9)

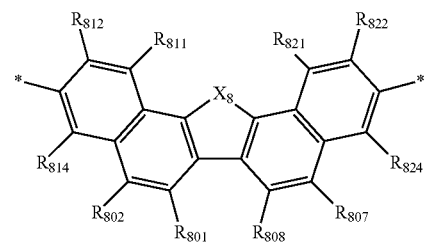

(81-10)

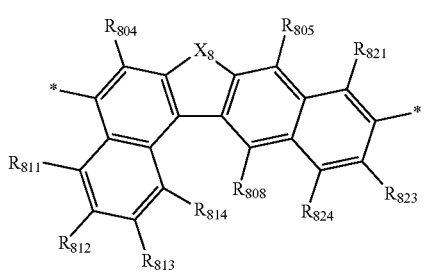

[Formula 368]

(81-11)

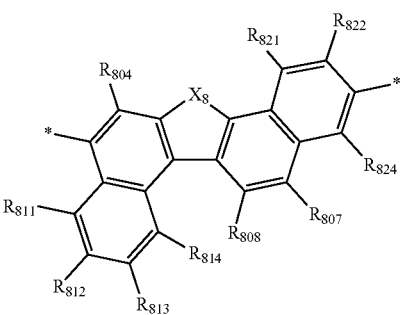

(81-12)

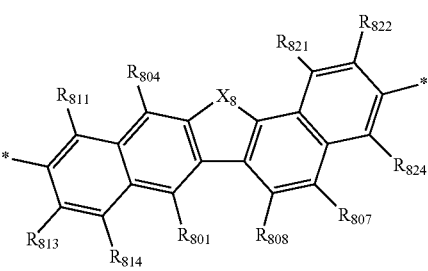

[Formula 369]

(81-13)
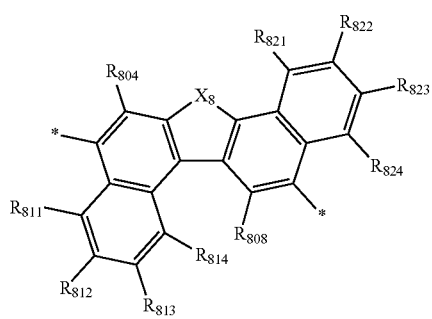

(81-14)
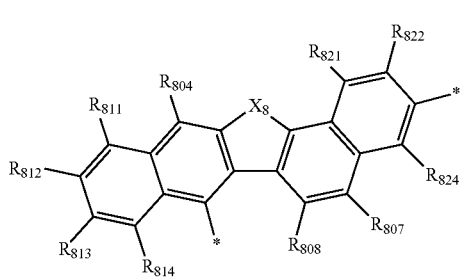

[Formula 370]

(81-15)
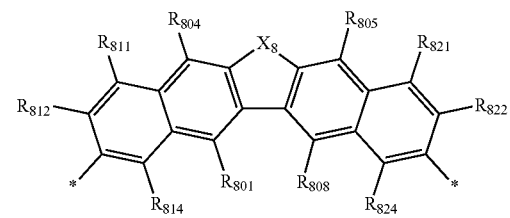

(81-16)
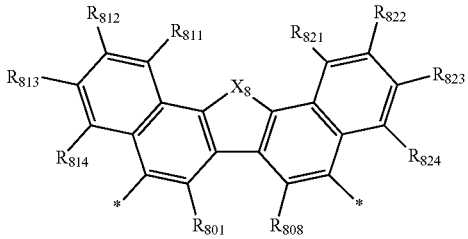

[Formula 371]

(81-17)
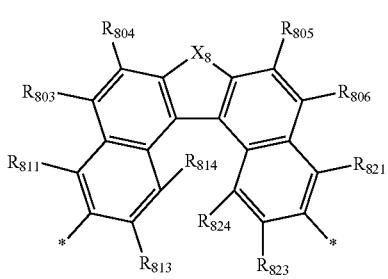

(81-18)
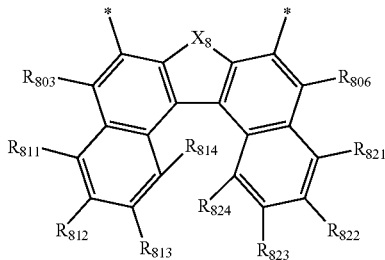

In the formulae (81-7) to (81-18):
$X_8$ represents the same as $X_8$ in the formula (8);
* is a single bond to be bonded to the monovalent group represented by the formula (84); and
$R_{801}$ to $R_{824}$ each independently represent the same as $R_{801}$ to $R_{824}$ in the formulae (81-1) to (81-6) that are not a monovalent group represented by the formula (84).

$R_{801}$ to $R_{808}$ not forming the divalent group represented by the formula (82) or (83) and not being the monovalent group represented by the formula (84), and $R_{811}$ to $R_{814}$ and $R_{821}$ to $R_{824}$ not being the monovalent group represented by the formula (84) are preferably each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

The monovalent group represented by the formula (84) is preferably represented by a formula (85) or (86) below.

[Formula 372]

(85)
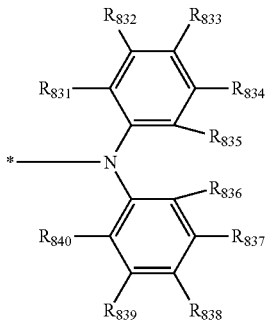

In the formula (85):
$R_{831}$ to $R_{840}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms; and

* in the formula (85) represents the same as * in the formula (84).

[Formula 373]

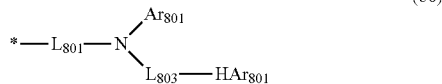

(86)

In the formula (86):

$Ar_{801}$, $L_{801}$, and $L_{803}$ represent the same as $Ar_{801}$, $L_{801}$, and $L_{803}$ in the formula (84); and $HAr_{801}$ is a moiety represented by a formula (87) below.

[Formula 374]

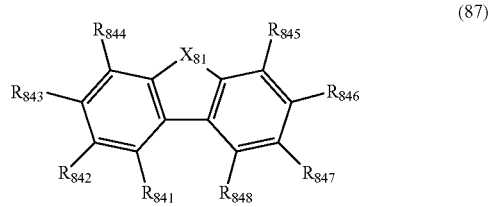

(87)

In the formula (87):

$X_{81}$ represents an oxygen atom or a sulfur atom;

one of $R_{841}$ to $R_{848}$ is a single bond with $L_{803}$; and $R_{841}$ to $R_{848}$ not being the single bond are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a group represented by $-N(R_{906})(R_{907})$, a halogen atom, a cyano group, a nitro group, a substituted or unsubstituted aryl group having 6 to 50 ring carbon atoms, or a substituted or unsubstituted heterocyclic group having 5 to 50 ring atoms.

Specific examples of the compound represented by the formula (8) include compounds shown below as well as the compounds disclosed in WO 2014/104144.

[Formula 375]

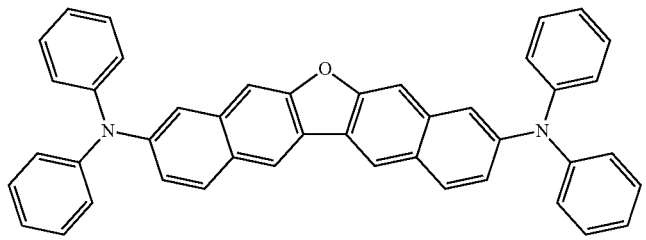

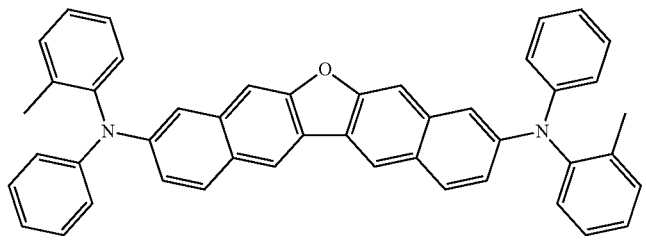

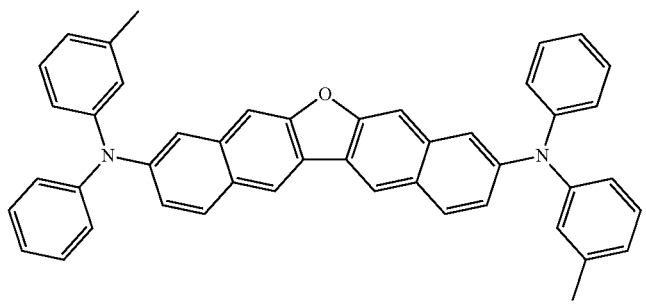

-continued
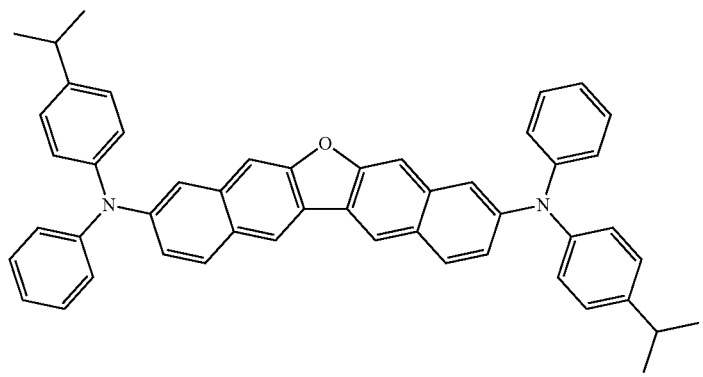
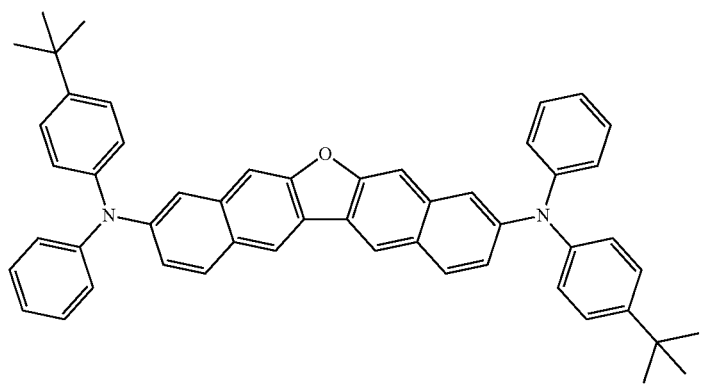
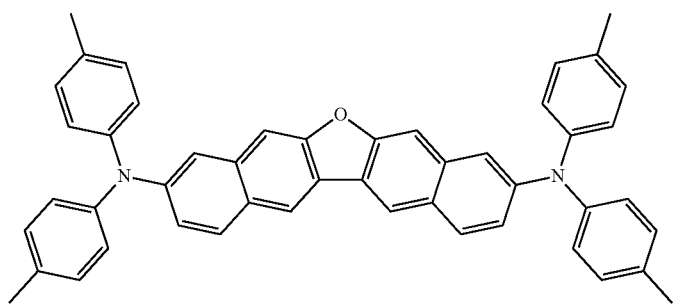
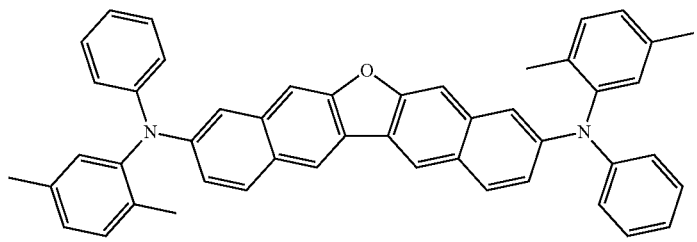
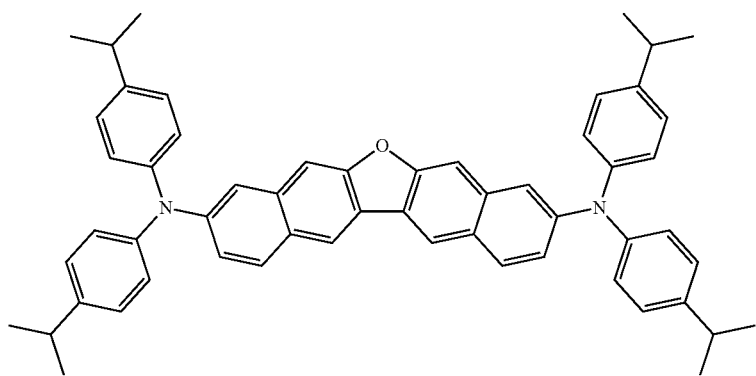

-continued
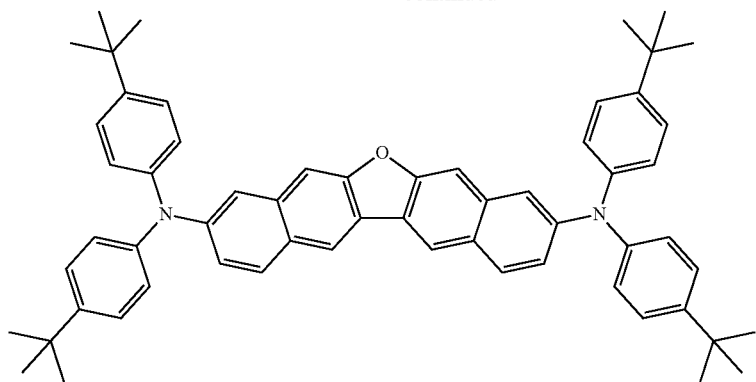
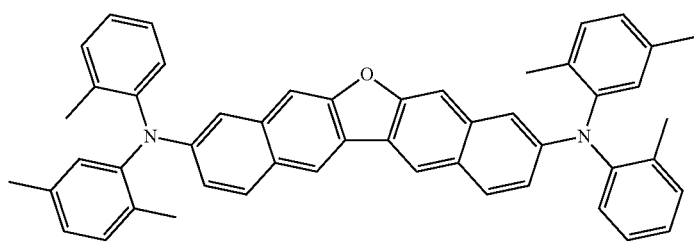
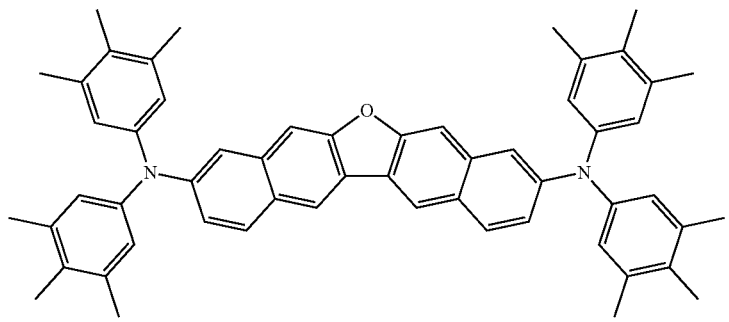
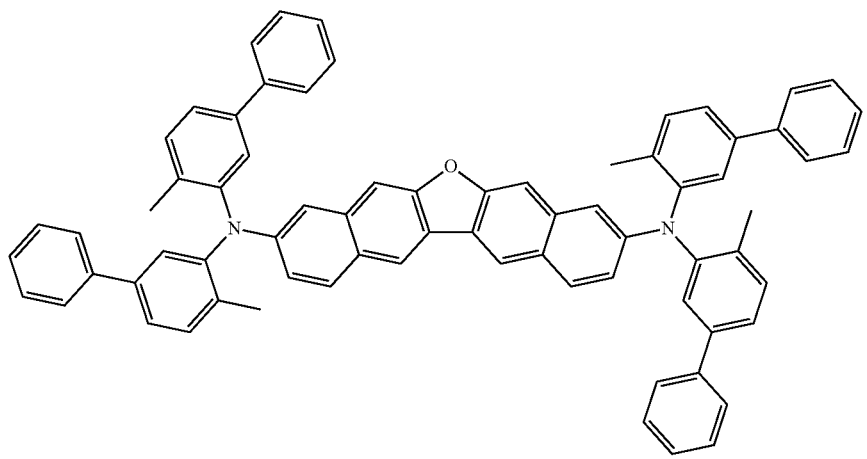

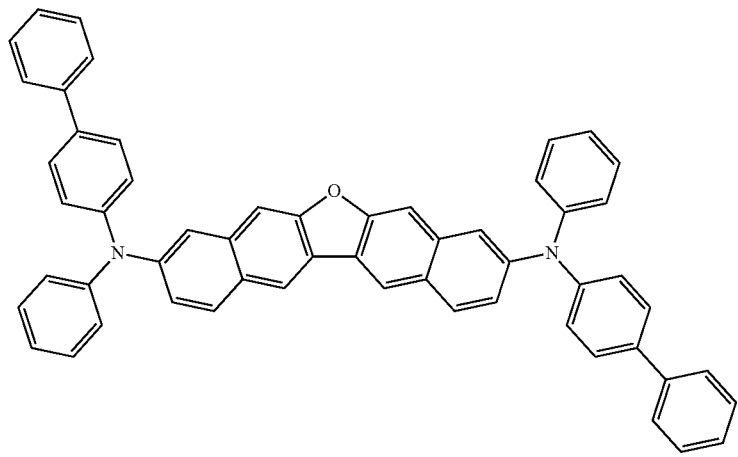
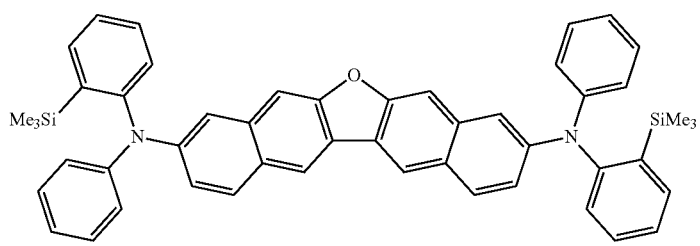
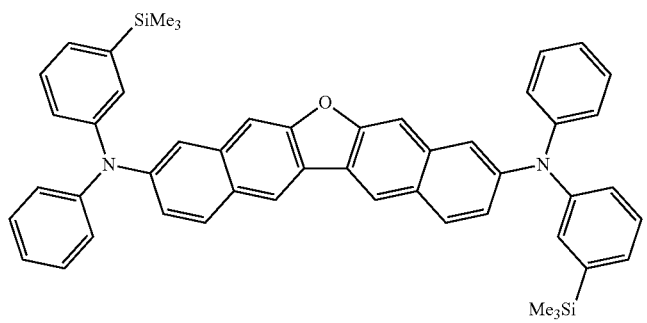
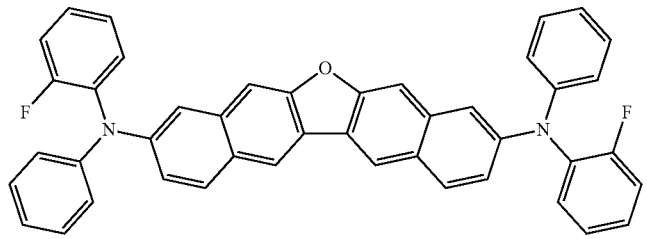
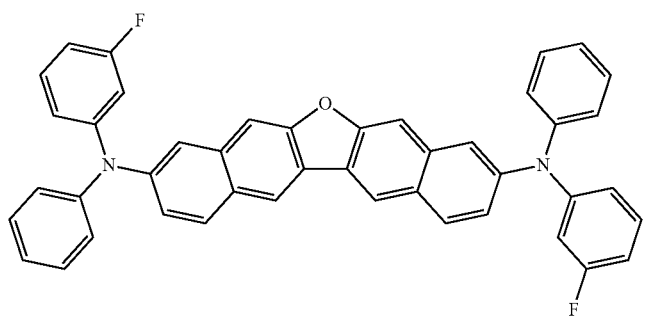

-continued
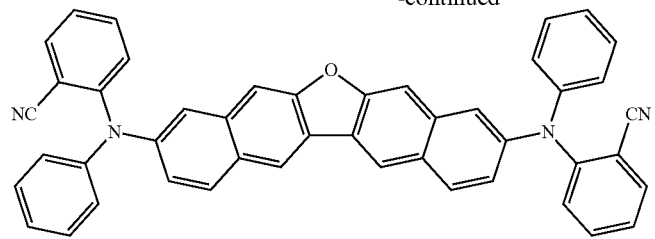
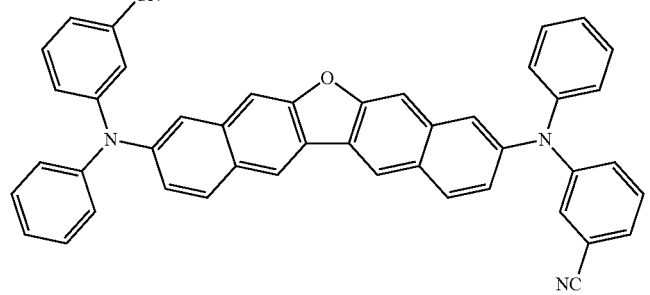
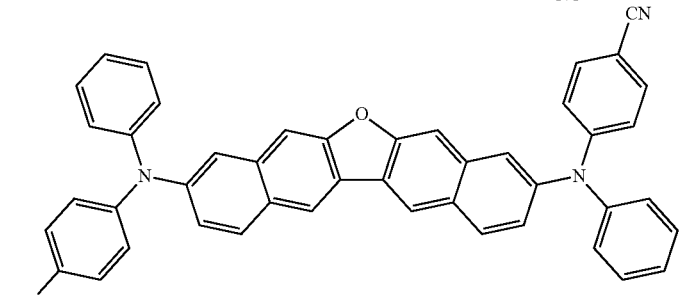
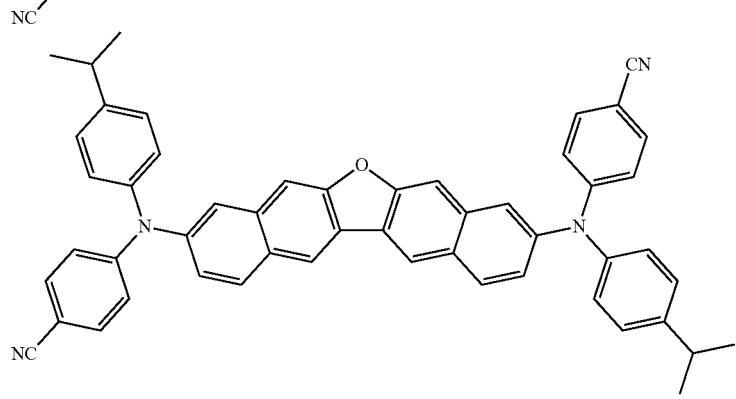
[Formula 376]
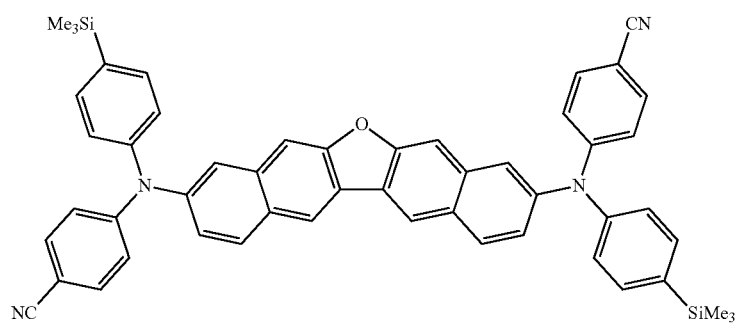

-continued
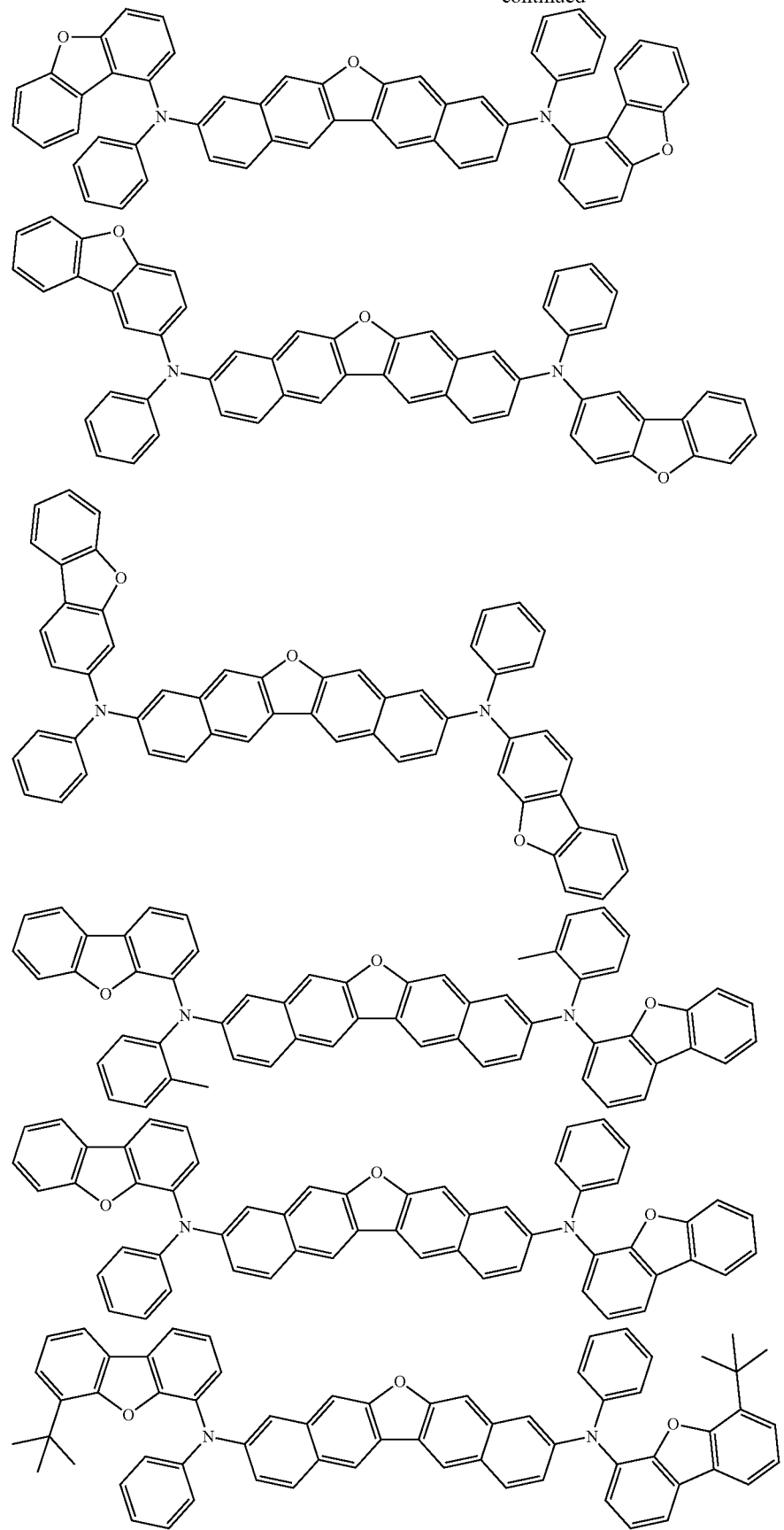

-continued
951
952
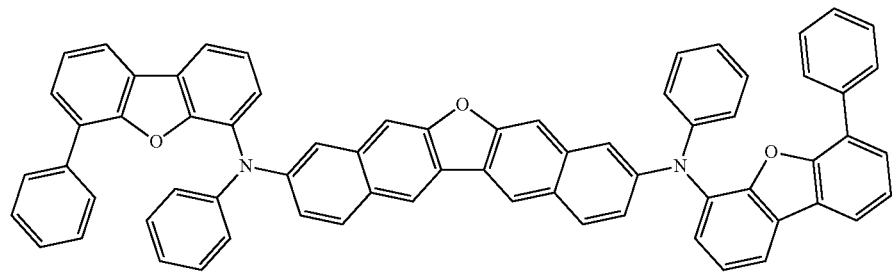
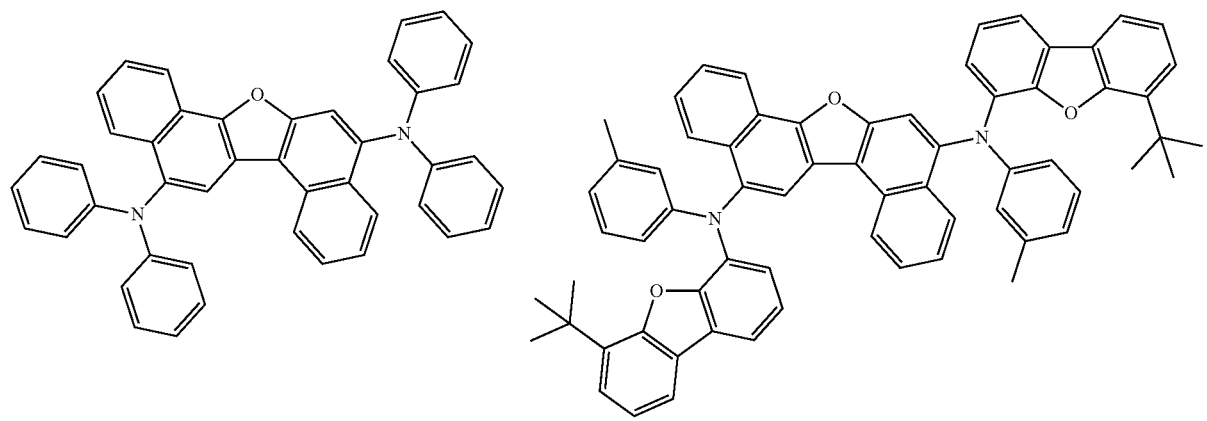
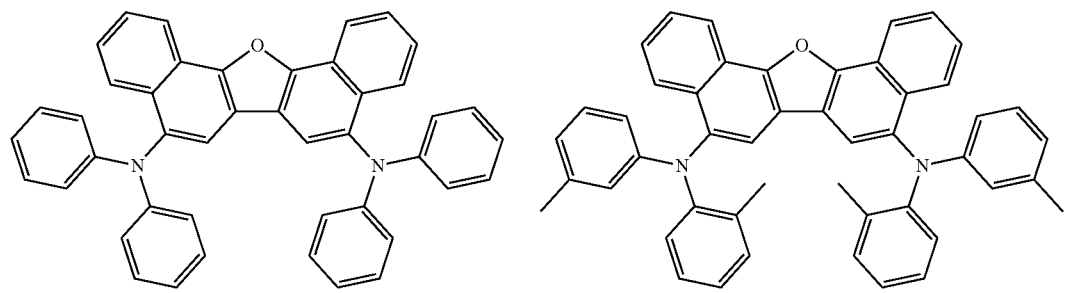
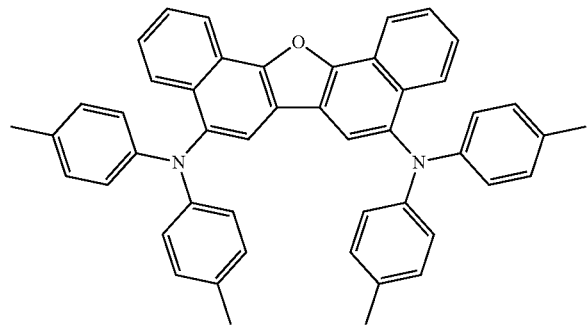

[Formula 377]
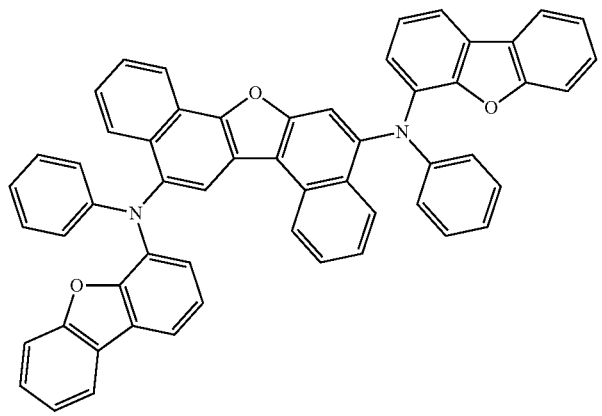
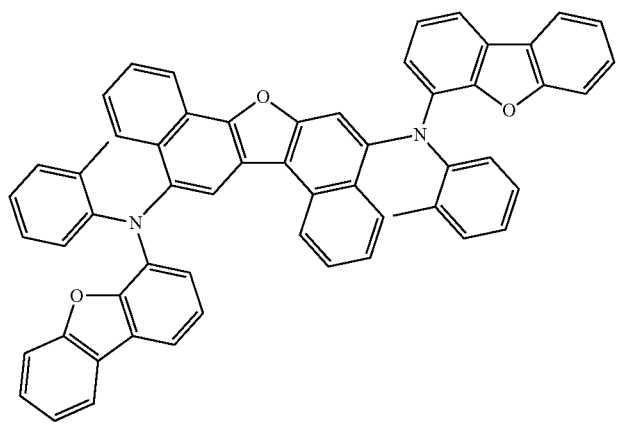
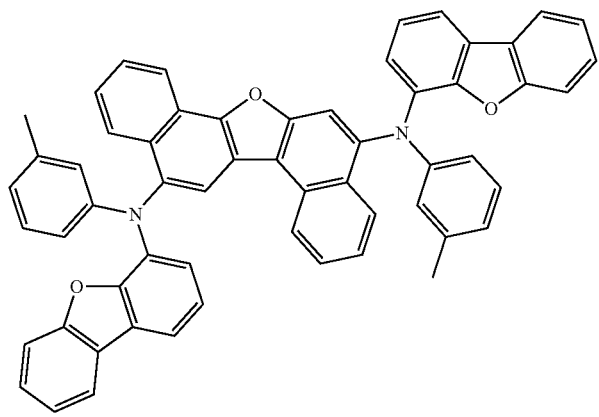
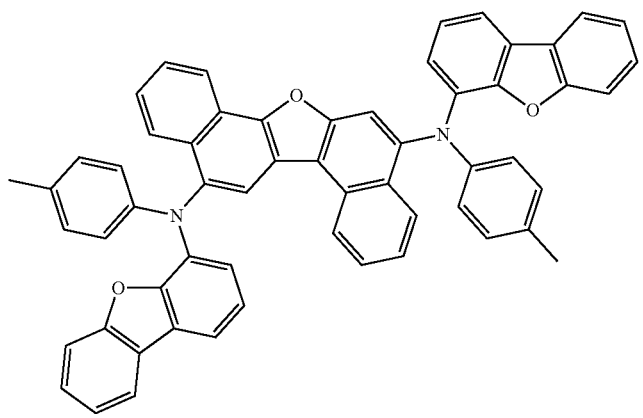

-continued
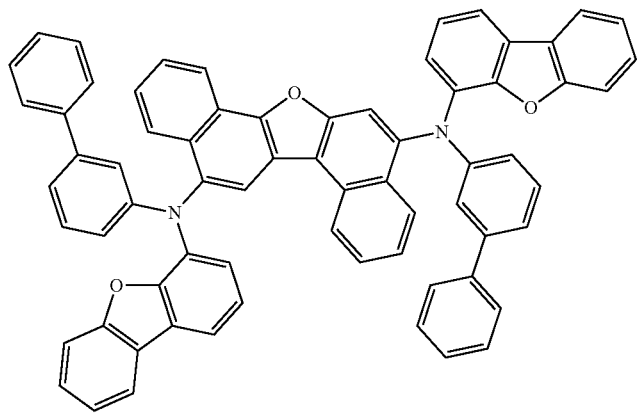
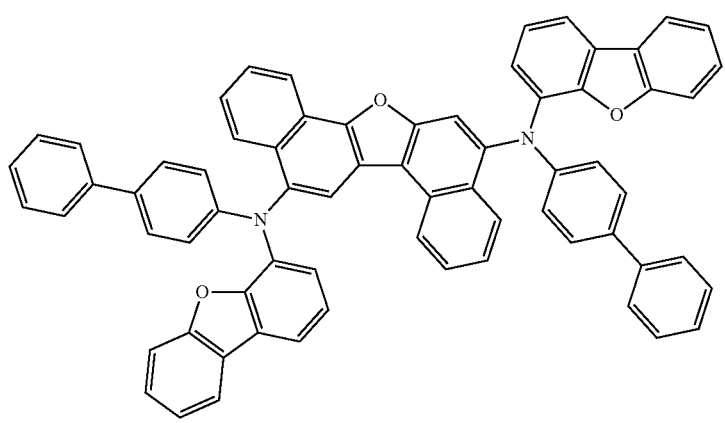
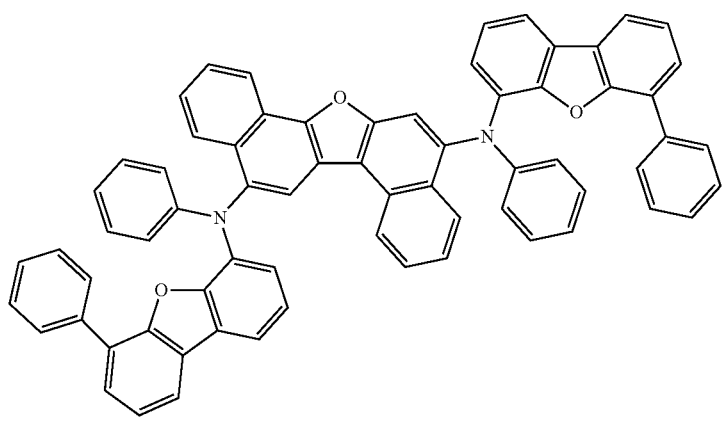

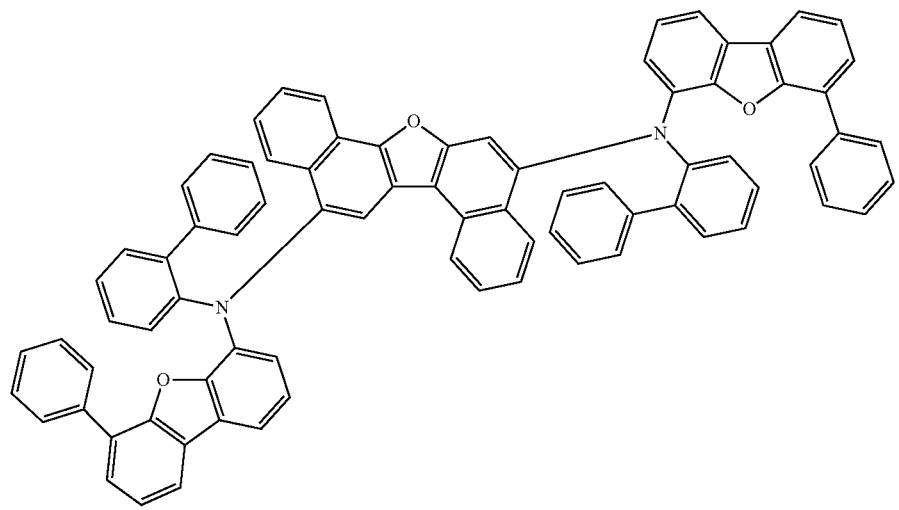
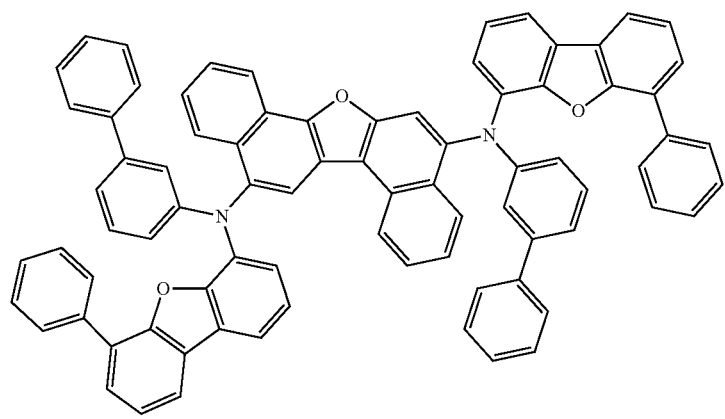
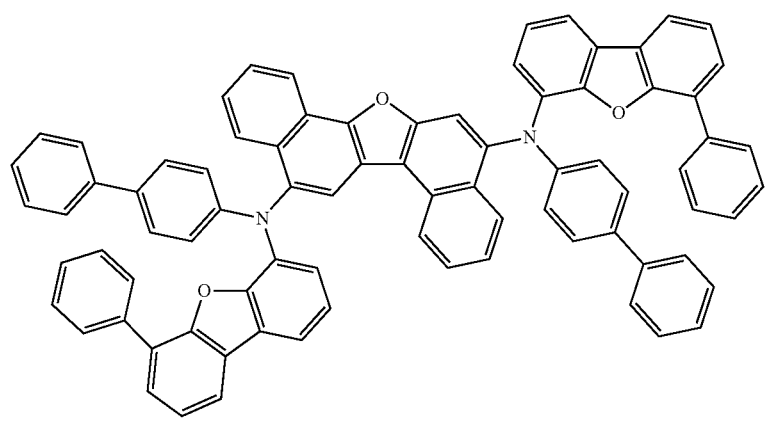

959
-continued
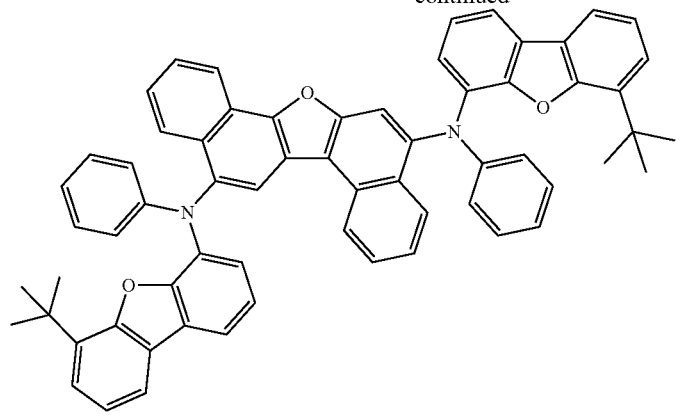
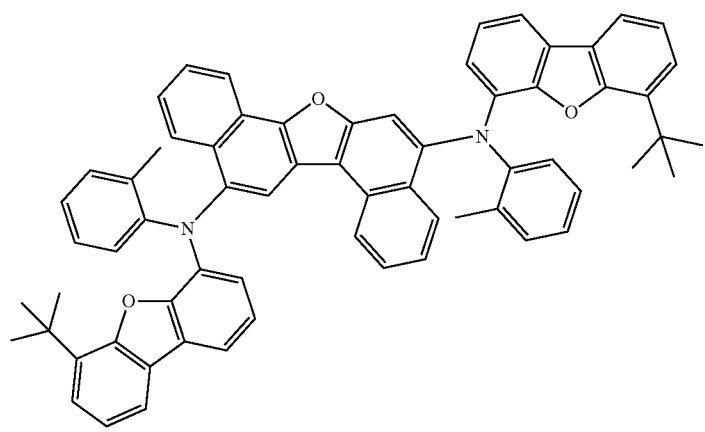
960
-continued
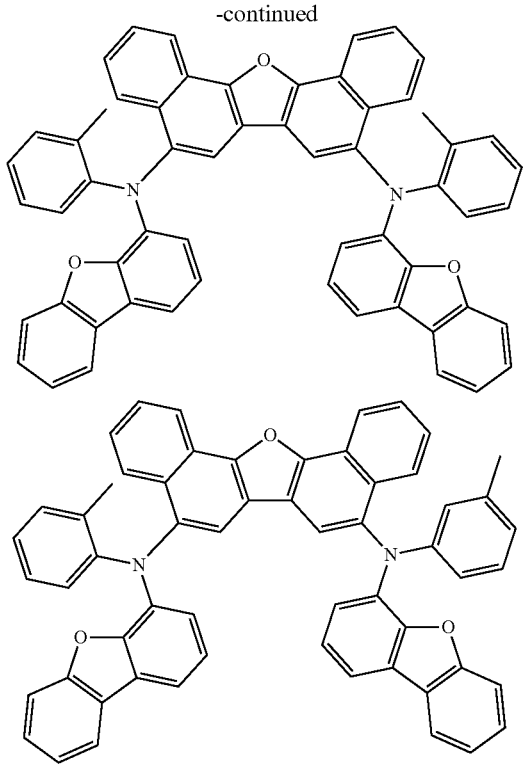
[Formula 378]
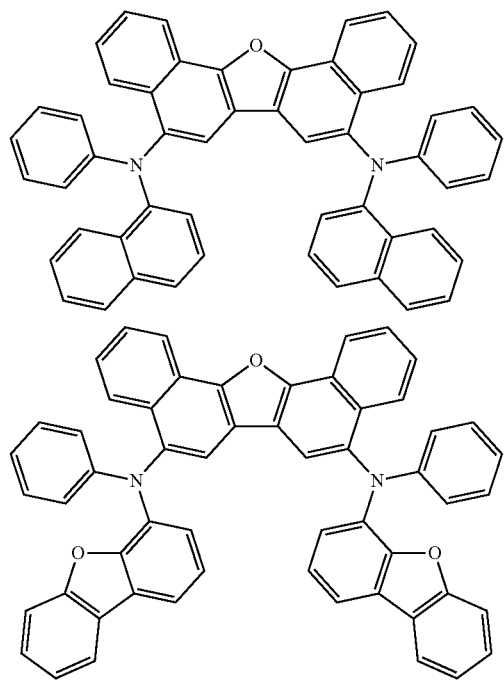

961
-continued
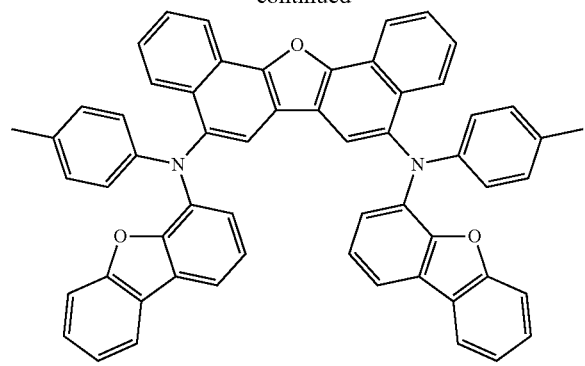
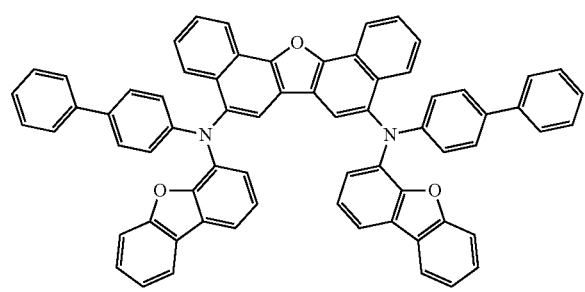
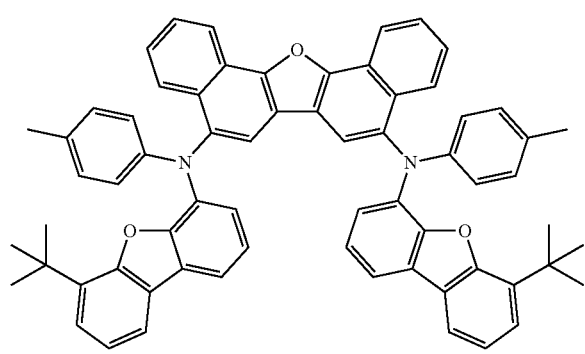
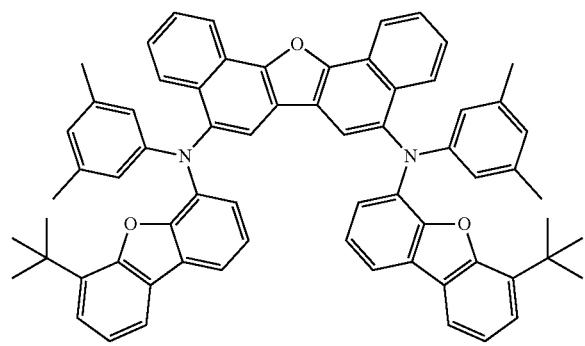
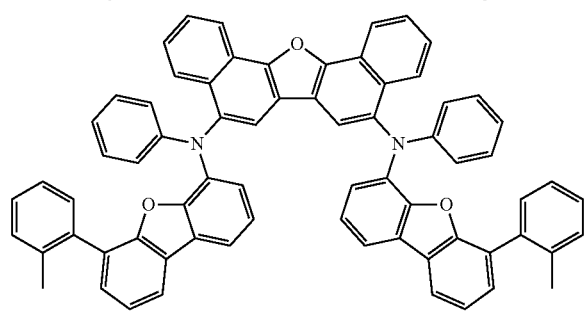
962
-continued
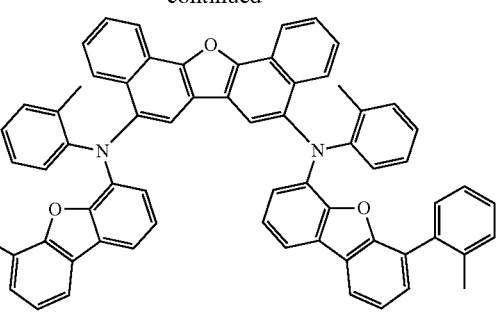
[Formula 379]
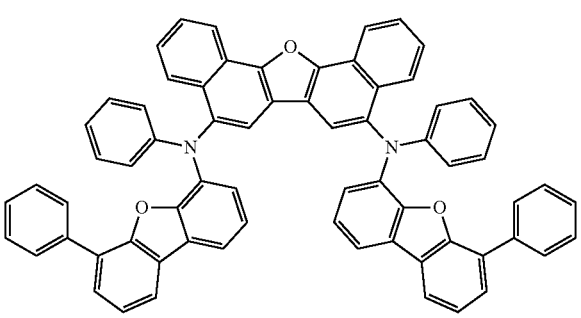
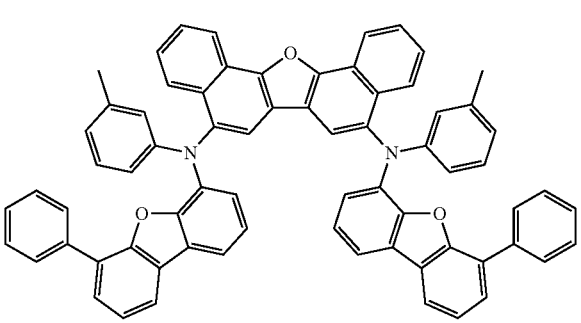
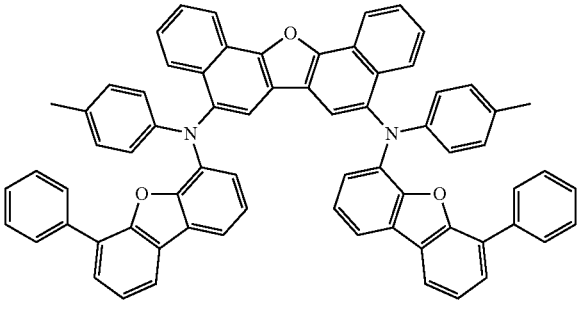
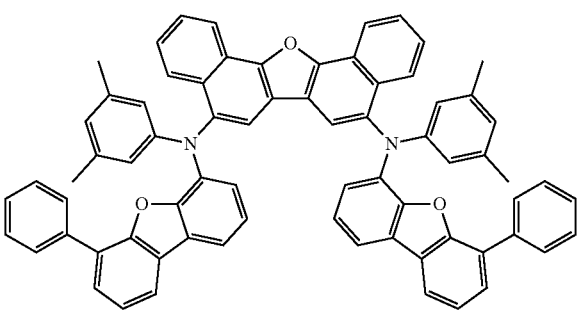

963
-continued
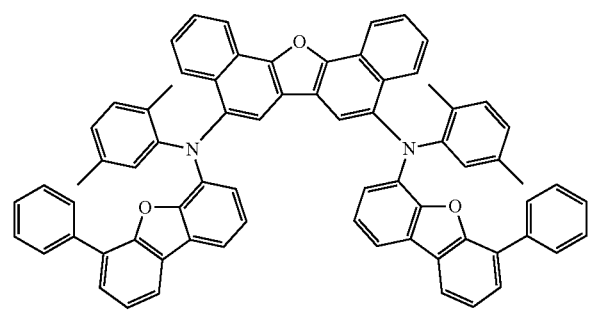
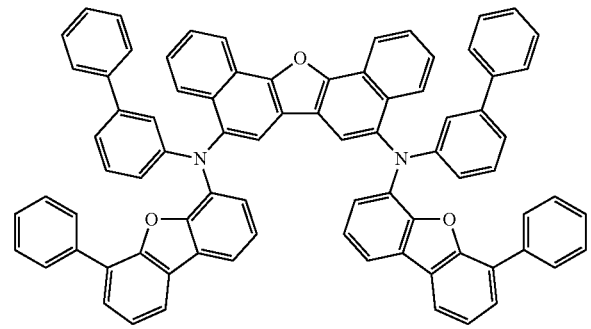
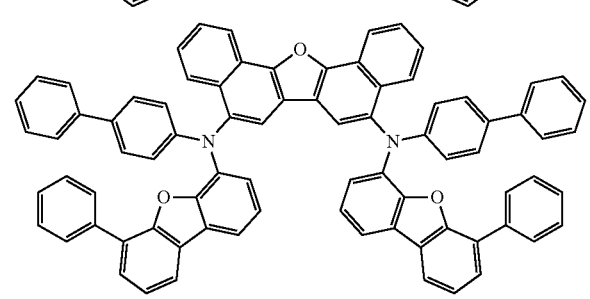
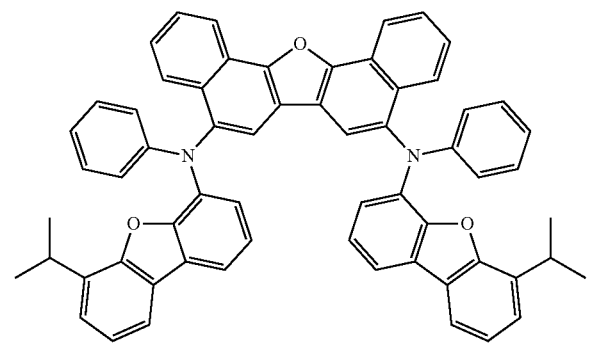
[Formula 380]
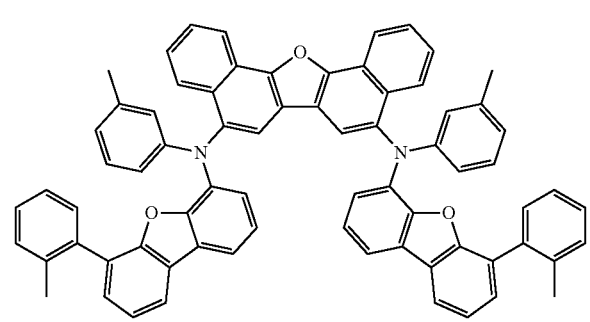
964
-continued
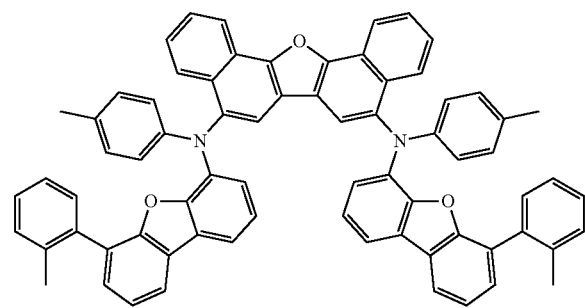
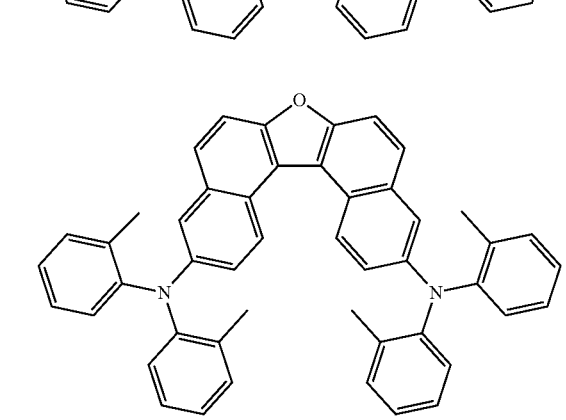
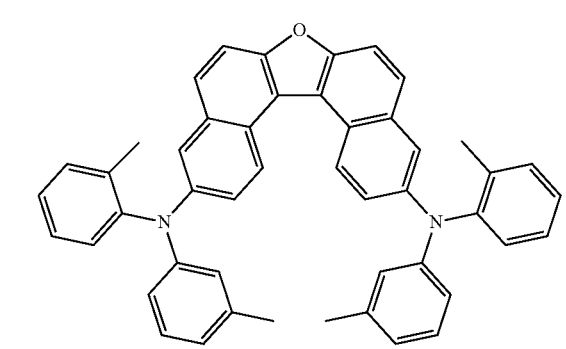

965
-continued
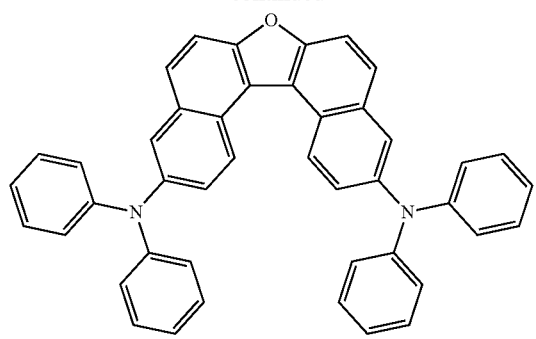
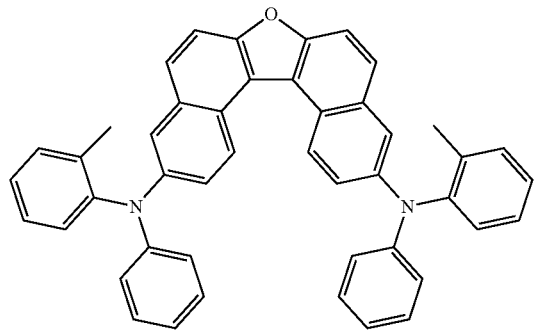
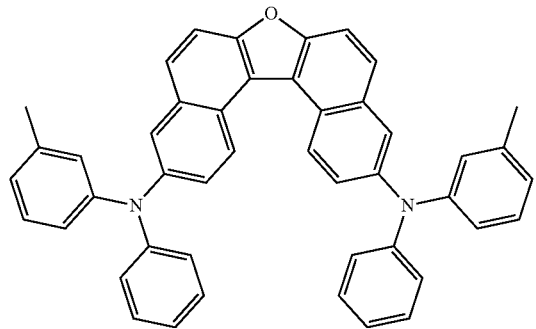
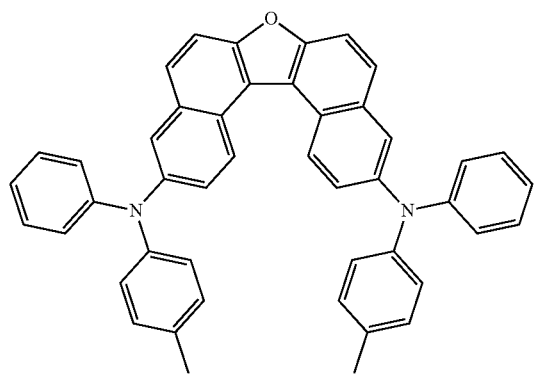
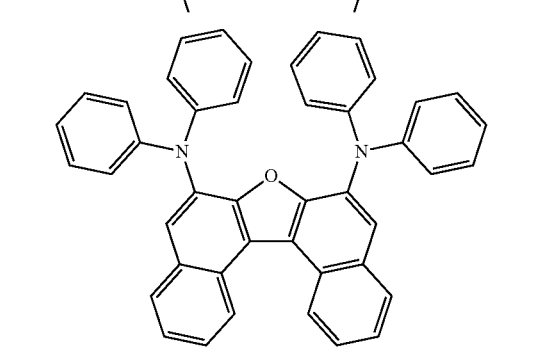
966
-continued
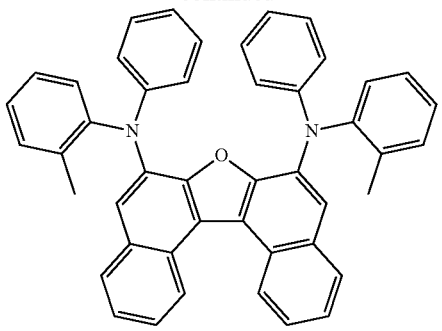
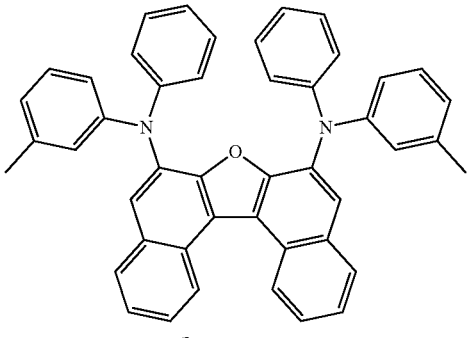
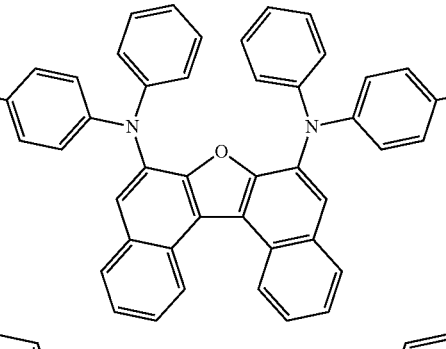
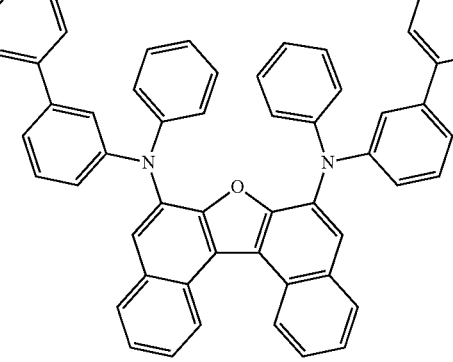
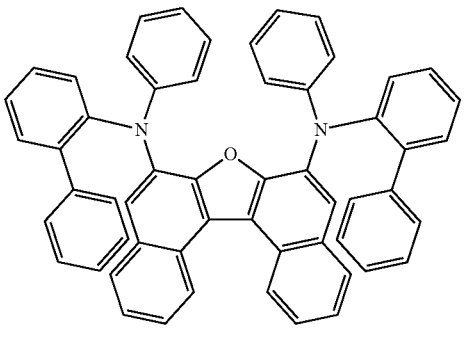

Compound Represented by Formula (9)

The compound represented by the formula (9) will be described below.

[Formula 381]

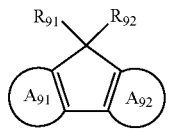
(9)

In the formula (9):

$A_{91}$ ring and $A_{92}$ ring are each independently a substituted or unsubstituted aromatic hydrocarbon ring having 6 to 50 ring carbon atoms, or a substituted or unsubstituted heterocycle having 5 to 50 ring atoms; and at least one of $A_{91}$ ring or $A_{92}$ ring is bonded to * in a moiety represented by a formula (92) below.

[Formula 382]

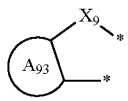
(92)

In the formula (92):

$A_{93}$ ring is a substituted or unsubstituted aromatic hydrocarbon ring having 6 to 50 ring carbon atoms or a substituted or unsubstituted heterocycle having 5 to 50 ring atoms;

$X_9$ is $NR_{93}$, $C(R_{94})(R_{95})$, $Si(R_{96})(R_{97})$, $Ge(R_{98})(R_{99})$, an oxygen atom, a sulfur atom, or a selenium atom;

$R_{91}$ and $R_{92}$ are mutually bonded to form a substituted or unsubstituted monocyclic ring, mutually bonded to form a substituted or unsubstituted fused ring, or not mutually bonded; and $R_{91}$ and $R_{92}$, and $R_{93}$ to $R_{99}$ not forming the monocyclic ring and not forming the fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —$Si(R_{901})(R_{902})(R_{903})$, a group represented by —O—$(R_{904})$, a group represented by —S—$(R_{905})$, a group represented by —$N(R_{906})(R_{907})$, a halogen atom, a cyano group, a nitro group, a substituted or unsubstituted aryl group having 6 to 50 ring carbon atoms, or a substituted or unsubstituted heterocyclic group having 5 to 50 ring atoms.

At least one ring selected from the group consisting of $A_{91}$ ring and $A_{92}$ ring is bonded to a bond * of the moiety represented by the formula (92). In other words, the ring-forming carbon atoms of the aromatic hydrocarbon ring or the ring atoms of the heterocycle of the $A_{91}$ ring in an exemplary embodiment are bonded to the bonds * in the moiety represented by the formula (92). Further, the ring-forming carbon atoms of the aromatic hydrocarbon ring or the ring atoms of the heterocycle of the $A_{92}$ ring in an exemplary embodiment are bonded to the bonds * in the moiety represented by the formula (92).

In an exemplary embodiment, the group represented by a formula (93) below is bonded to one or both of the $A_{91}$ ring and $A_{92}$ ring.

[Formula 383]

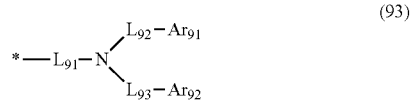
(93)

In the formula (93):

$Ar_{91}$ and $Ar_{92}$ are each independently a substituted or unsubstituted aryl group having 6 to 50 ring carbon atoms, or a substituted or unsubstituted heterocyclic group having 5 to 50 ring atoms;

$L_{91}$ to $L_{93}$ are each independently a single bond, a substituted or unsubstituted arylene group having 6 to 30 ring carbon atoms, a substituted or unsubstituted divalent heterocyclic group having 5 to 30 ring atoms, or a divalent linking group formed by bonding two, three or four groups selected from the group consisting of the substituted or unsubstituted arylene group having 6 to 30 ring carbon atoms and a substituted or unsubstituted divalent heterocyclic group having 5 to 30 ring atoms; and

* in the formula (93) represents a bonding position to one of $A_{91}$ ring and $A_{92}$ ring.

In an exemplary embodiment, in addition to the $A_{91}$ ring, the ring-forming carbon atoms of the aromatic hydrocarbon ring or the ring atoms of the heterocycle of the $A_{92}$ ring are bonded to * in the moiety represented by the formula (92). In this case, the moieties represented by the formula (92) are mutually the same or different.

In an exemplary embodiment, $R_{91}$ and $R_{92}$ are each independently a substituted or unsubstituted aryl group having 6 to 50 ring carbon atoms.

In an exemplary embodiment, $R_{91}$ and $R_{92}$ are mutually bonded to form a fluorene structure.

In an exemplary embodiment, the rings $A_{91}$ and $A_{92}$ are each independently a substituted or unsubstituted aromatic hydrocarbon ring having 6 to 50 ring carbon atoms, example of which is a substituted or unsubstituted benzene ring.

In an exemplary embodiment, the ring $A_{93}$ is a substituted or unsubstituted aromatic hydrocarbon ring having 6 to 50 ring carbon atoms, example of which is a substituted or unsubstituted benzene ring.

In an exemplary embodiment, $X_9$ is an oxygen atom or a sulfur atom.

Specific examples of the compound represented by the formula (9) include compounds shown below.

[Formula 384]

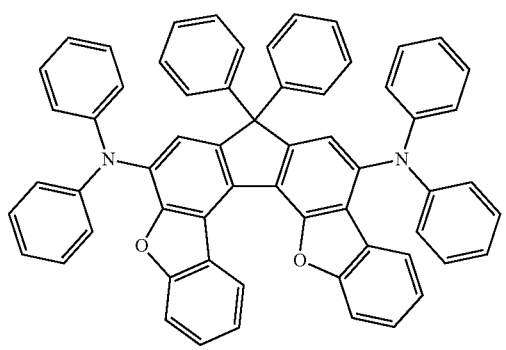

| 969 -continued | 970 -continued |
|---|---|
| 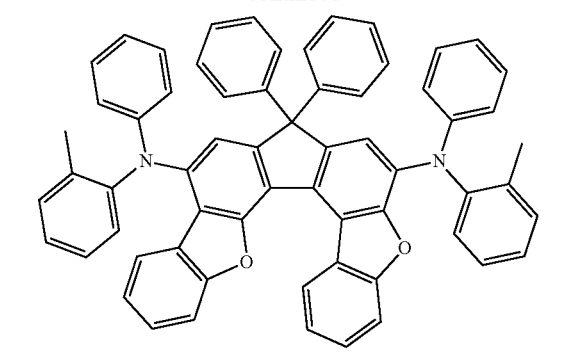 | 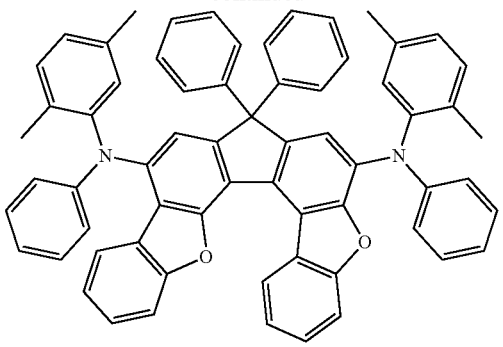 |
| 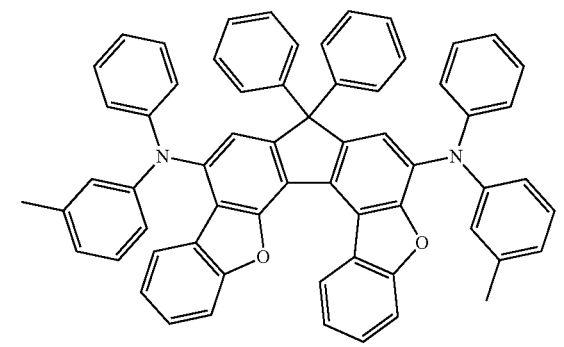 | 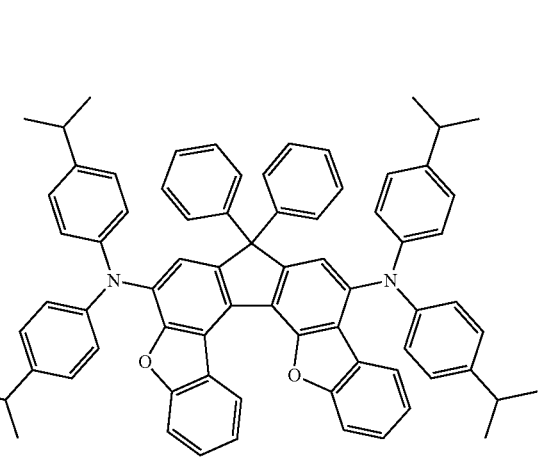 |
| 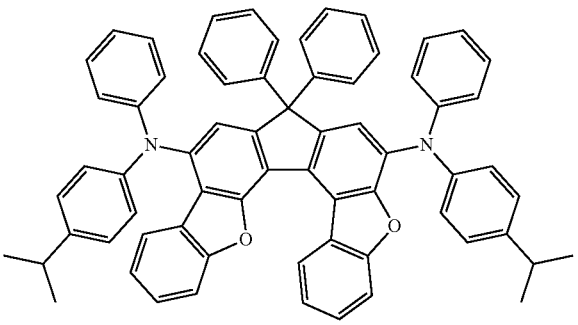 | |
| 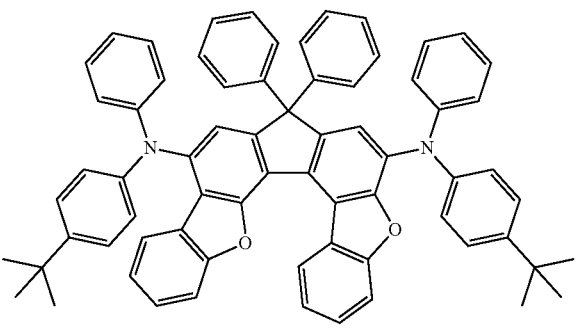 | 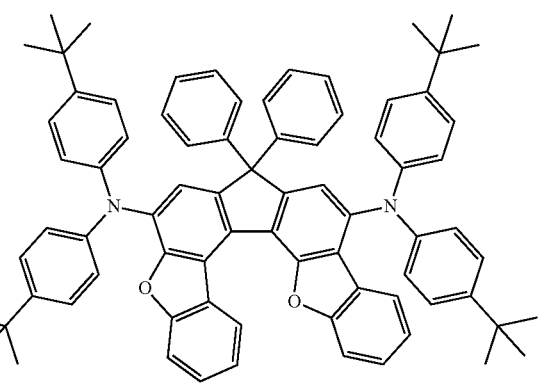 |
| 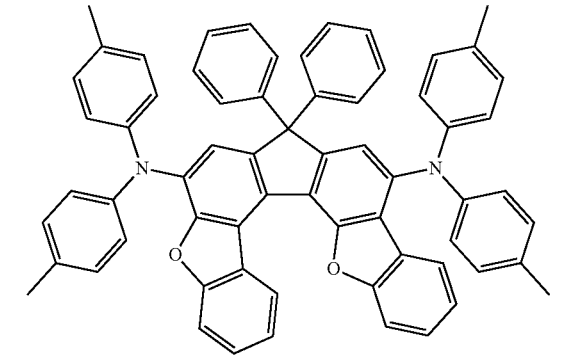 | 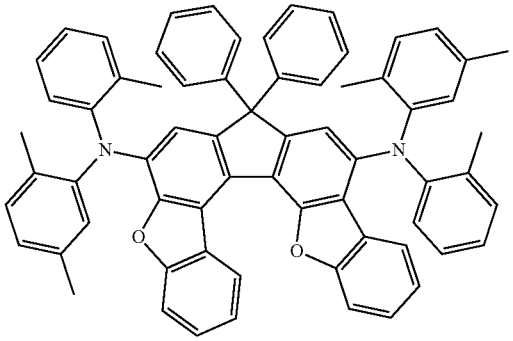 |

971
-continued
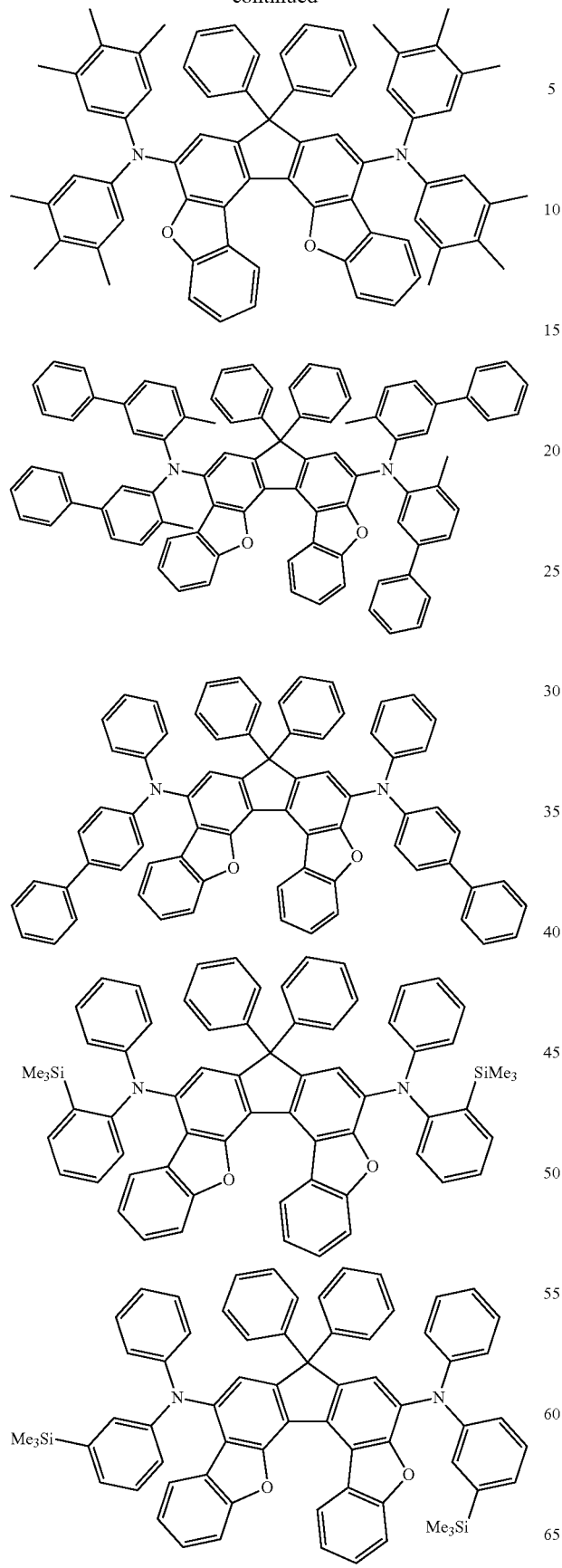
972
-continued
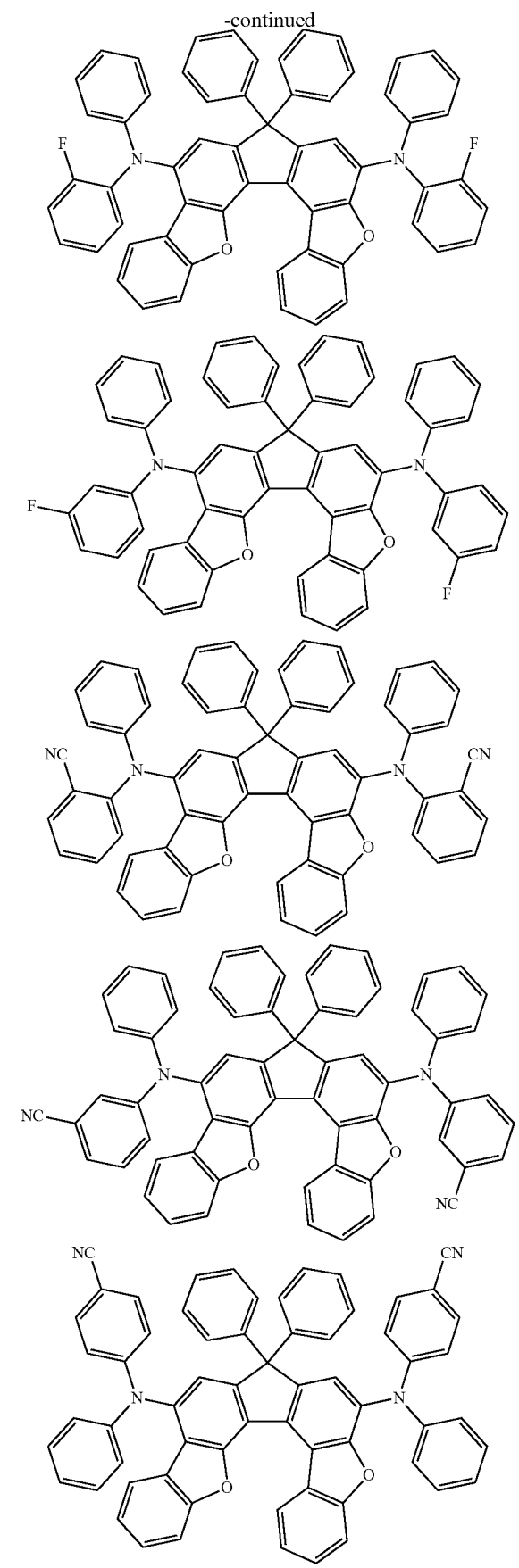

973
-continued
974
-continued
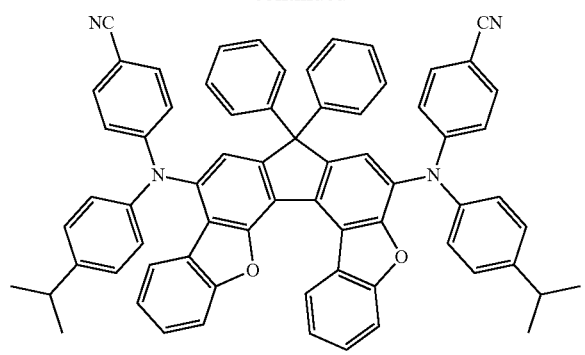 [SMILES: CC(C)c1ccc(N(c2ccc(C#N)cc2)c2cc3c(c4c2oc2ccccc24)-c2c(cc(N(c4ccc(C#N)cc4)c4ccc(C(C)C)cc4)c4c2oc2ccccc24)C3(c2ccccc2)c2ccccc2)cc1]
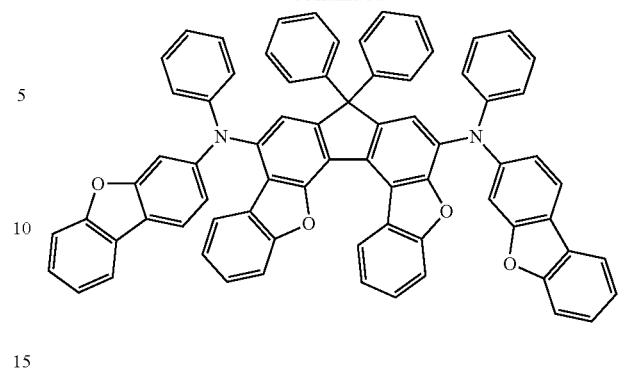
[Formula 385]
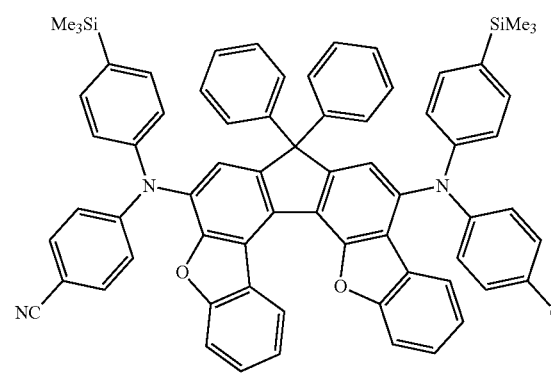
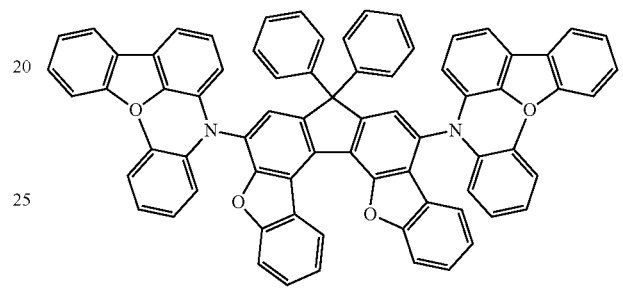
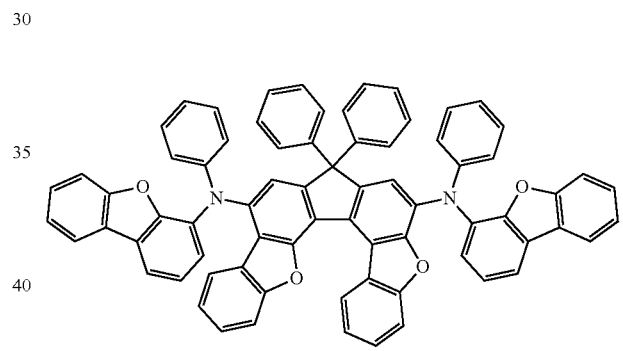
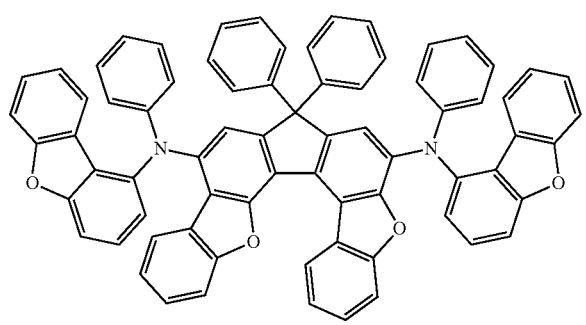
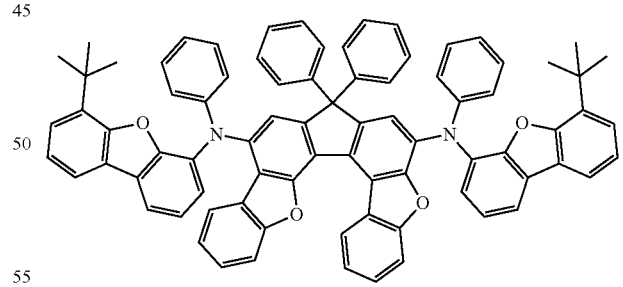
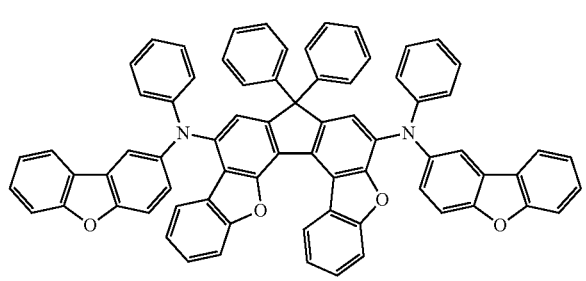
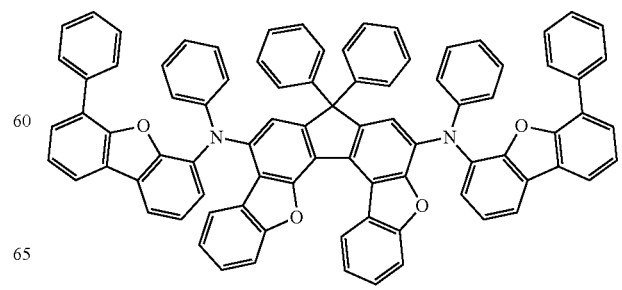

975
-continued
976
-continued
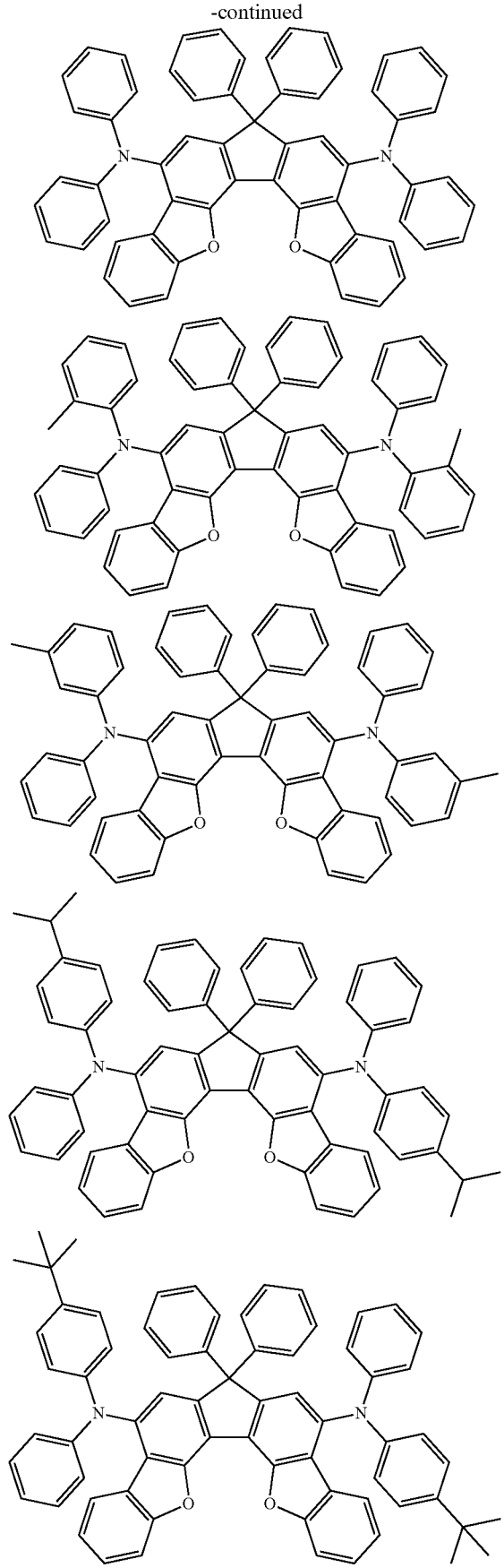
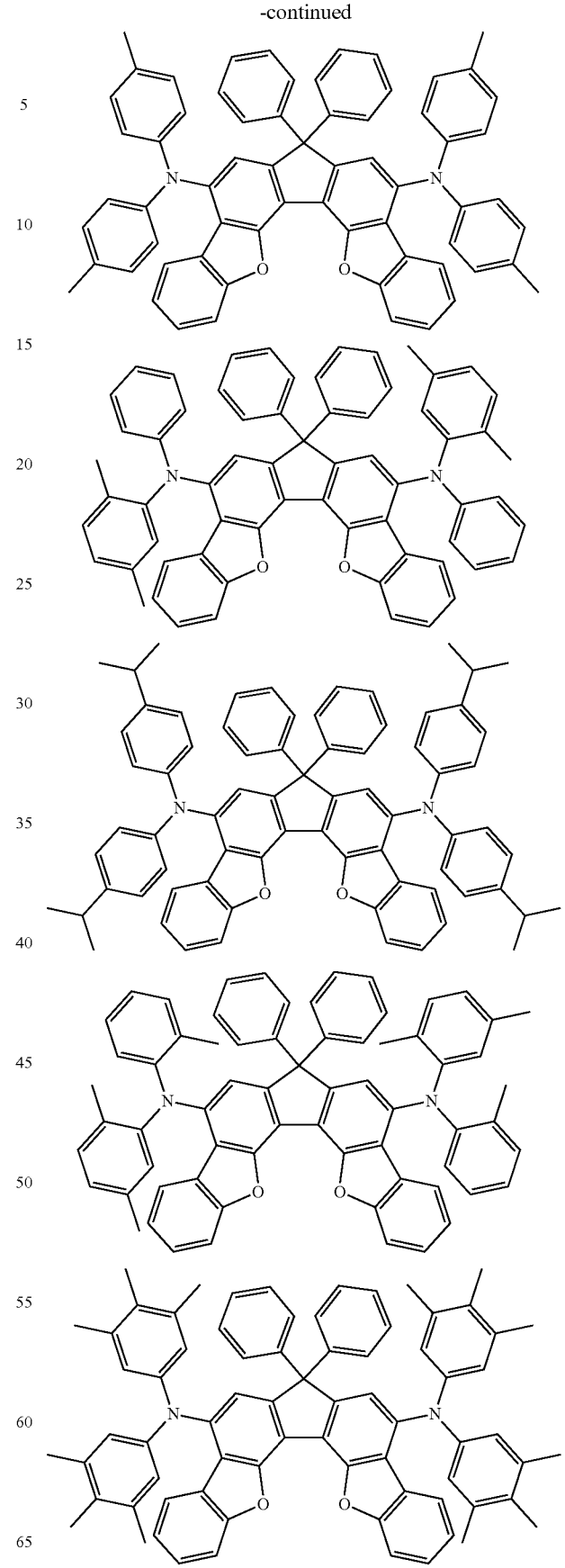

977 -continued
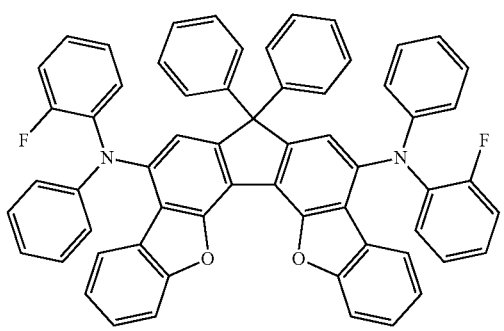
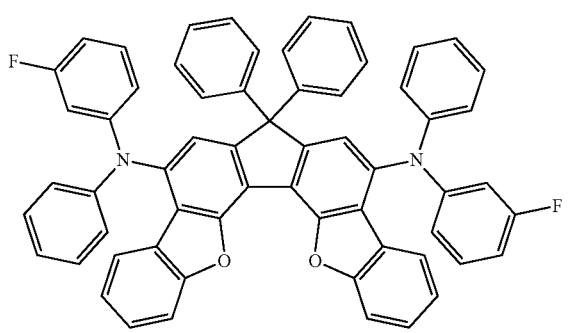
[Formula 386]
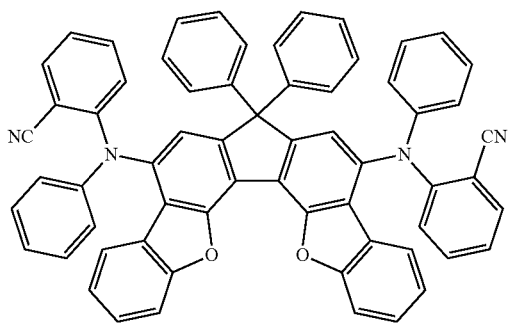
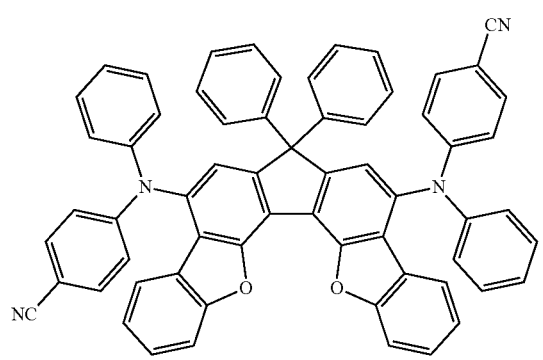
978 -continued
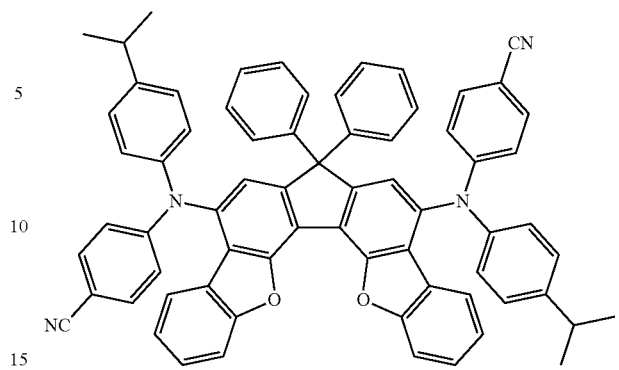
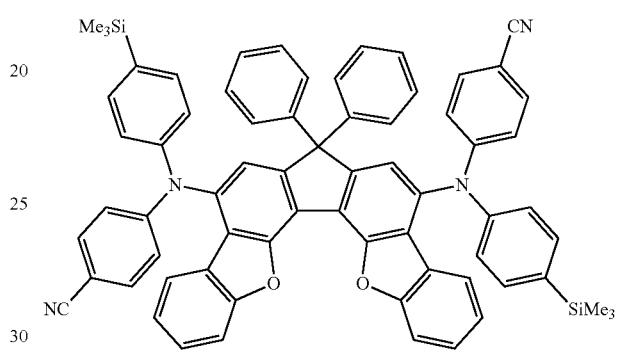
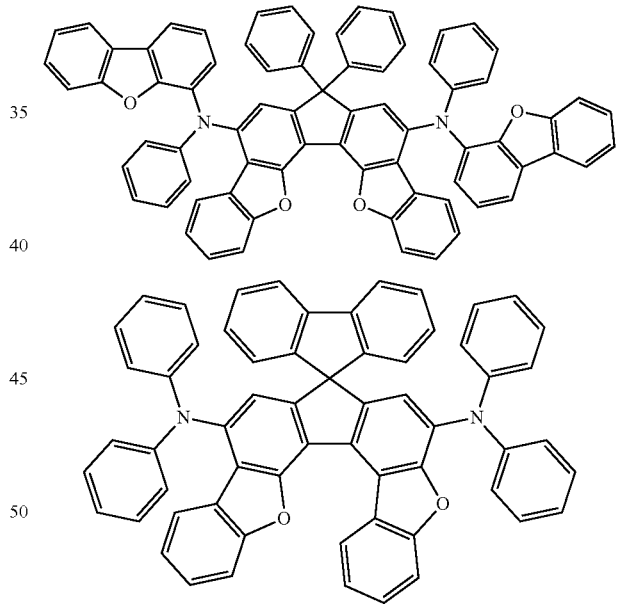
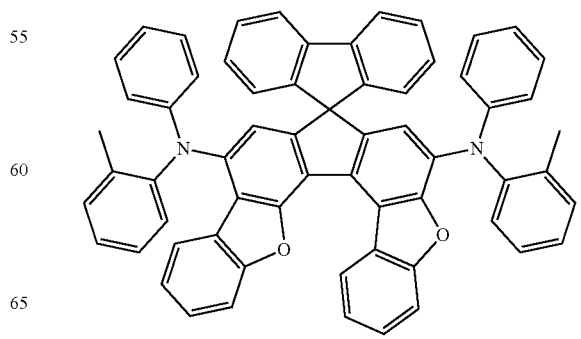

| 979 | 980 |
|---|---|
| -continued | -continued |
| 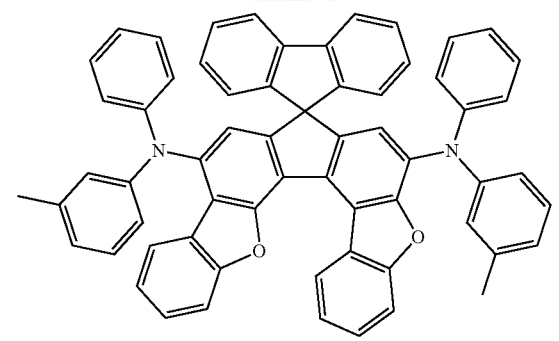 | 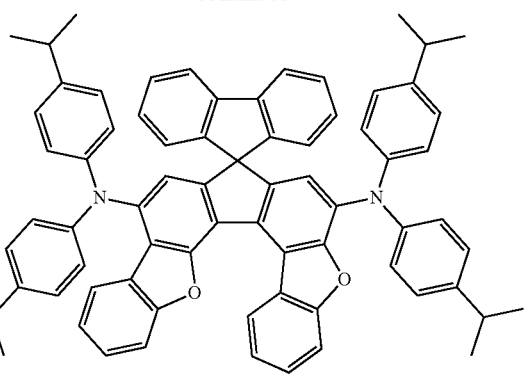 |
| 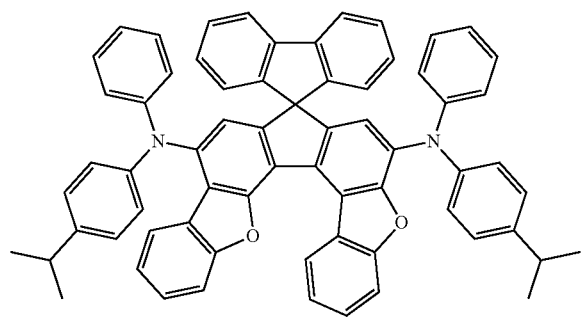 | 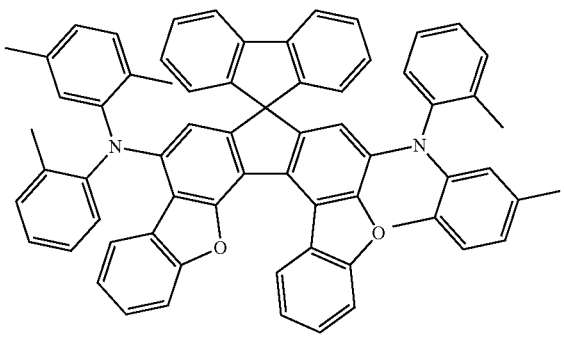 |
| 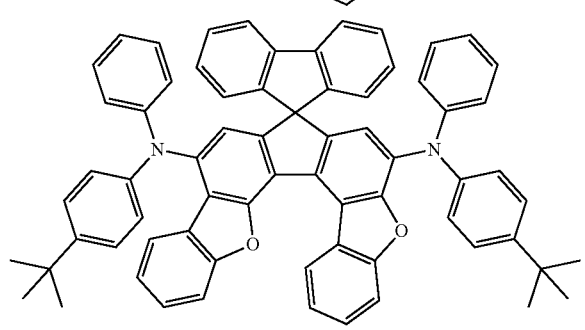 | 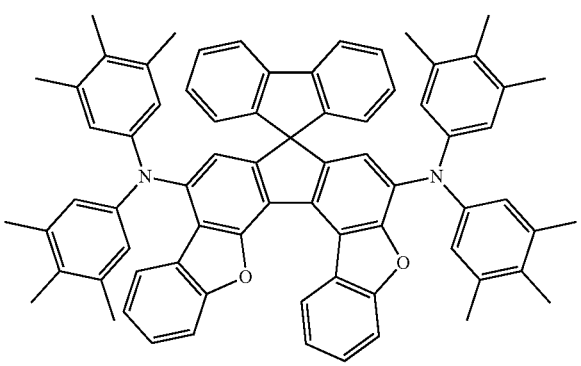 |
| 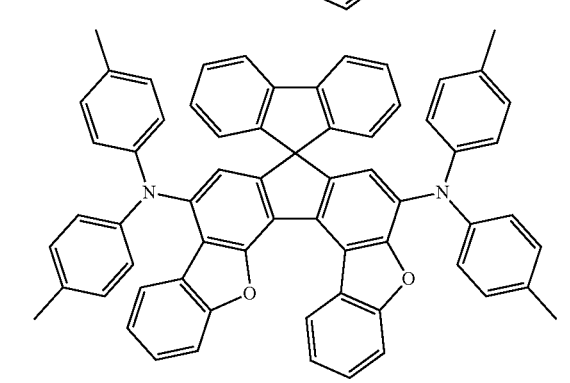 | 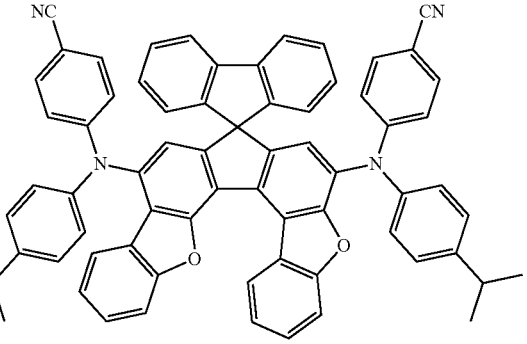 |
| 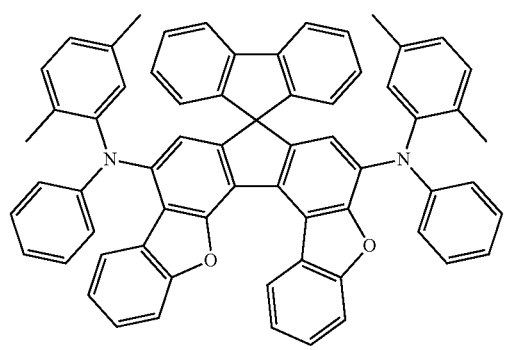 | |

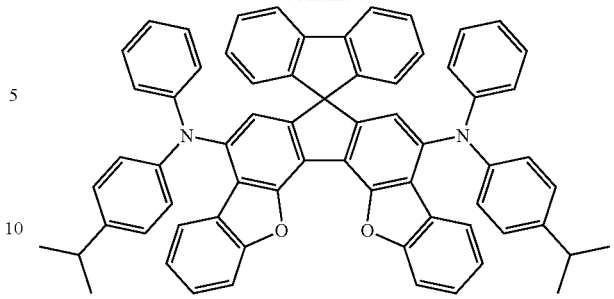
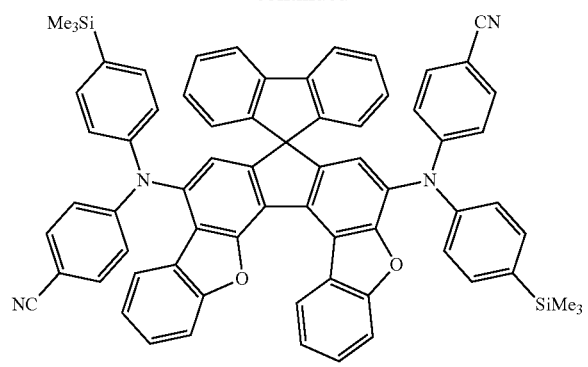
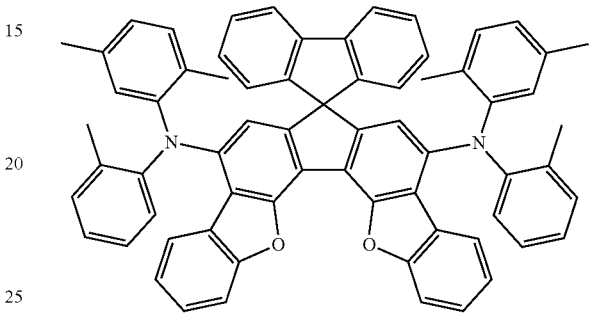
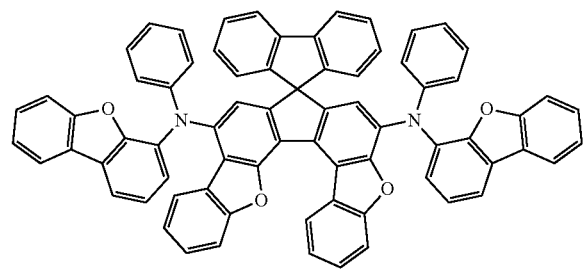
[Formula 387]
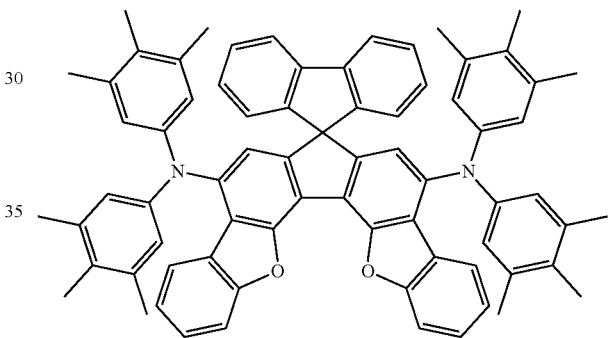
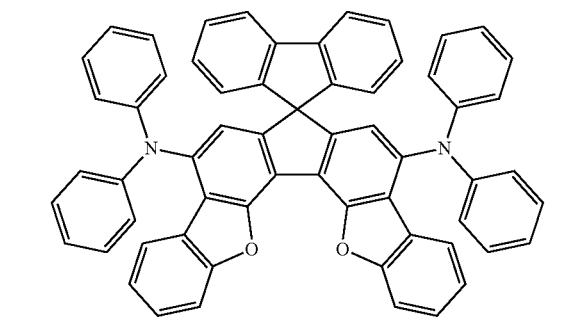
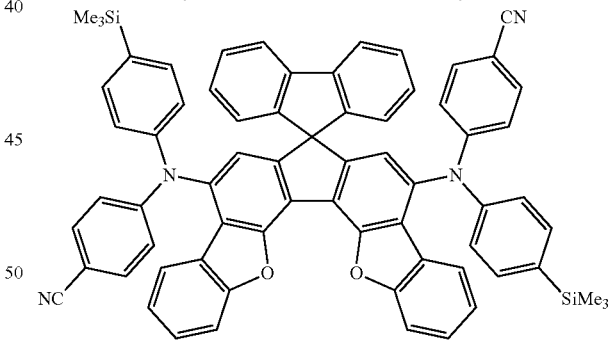
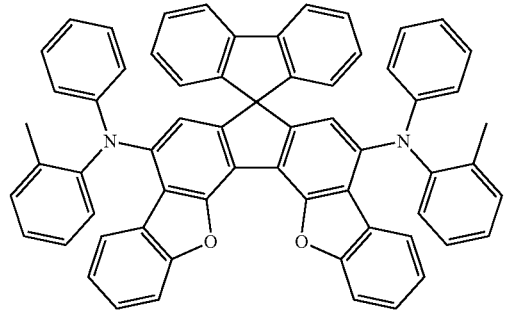
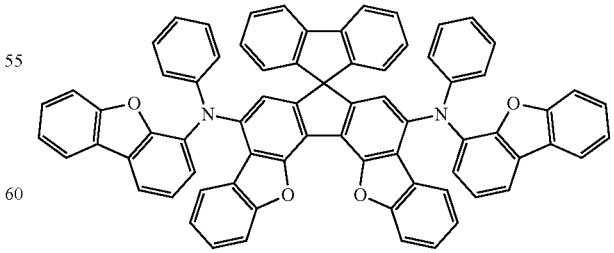
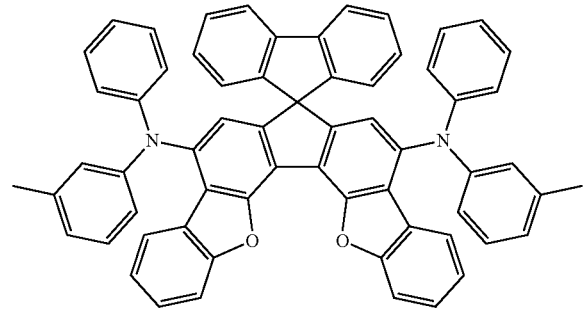
Compound Represented by Formula (10)
The compound represented by the formula (10) will be described below.

[Formula 388]

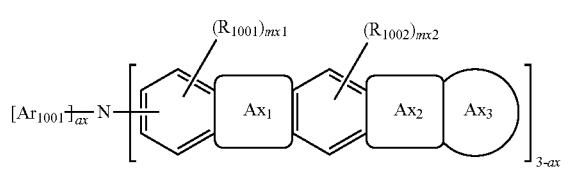

(10)

[Formula 389]

(10a)

(10b)

In the formula (10):

Ax$_1$ ring is a ring represented by the formula (10a) and fused with any positions of adjacent rings;

Ax$_2$ ring is a ring represented by the formula (10b) and fused with any positions of adjacent rings;

two * in the formula (10b) are bonded to any position of Ax$_3$ ring;

X$_A$ and X$_B$ are each independently C(R$_{1003}$)(R$_{1004}$), Si(R$_{1005}$)(R$_{1006}$), an oxygen atom or a sulfur atom;

Ax$_3$ ring is a substituted or unsubstituted aromatic hydrocarbon ring having 6 to 50 ring carbon atoms, or a substituted or unsubstituted heterocycle having 5 to 50 ring atoms;

Ar$_{1001}$ is a substituted or unsubstituted aryl group having 6 to 50 ring carbon atoms, or a substituted or unsubstituted heterocyclic group having 5 to 50 ring atoms;

R$_{1011}$ to R$_{1006}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si(R$_{901}$)(R$_{902}$)(R$_{903}$), a group represented by —O—(R$_{904}$), a group represented by —S—(R$_{905}$), a group represented by —N(R$_{906}$)(R$_{907}$), a halogen atom, a cyano group, a nitro group, a substituted or unsubstituted aryl group having 6 to 50 ring carbon atoms, or a substituted or unsubstituted heterocyclic group having 5 to 50 ring atoms;

mx1 is 3, mx2 is 2;

a plurality of R$_{1001}$ are mutually the same or different;

a plurality of R$_{1002}$ are mutually the same or different;

ax is 0, 1, or 2;

when ax is 0 or 1, the structures enclosed by brackets indicated by "3-ax" are mutually the same or different; and when ax is 2, a plurality of Ar$_{1001}$ are mutually the same or different.

In an exemplary embodiment, Ar$_{1001}$ is a substituted or unsubstituted aryl group having 6 to 50 ring carbon atoms.

In an exemplary embodiment, Ax$_3$ ring is a substituted or unsubstituted aromatic hydrocarbon ring having 6 to 50 ring carbon atoms, example of which is a substituted or unsubstituted benzene ring, a substituted or unsubstituted naphthalene ring, or a substituted or unsubstituted anthracene ring.

In an exemplary embodiment, R$_{1003}$ and R$_{1004}$ are each independently a substituted or unsubstituted alkyl group having 1 to 50 carbon atoms.

In an exemplary embodiment, ax is 1.

Specific examples of the compound represented by the formula (10) include compounds shown below.

[Formula 390]

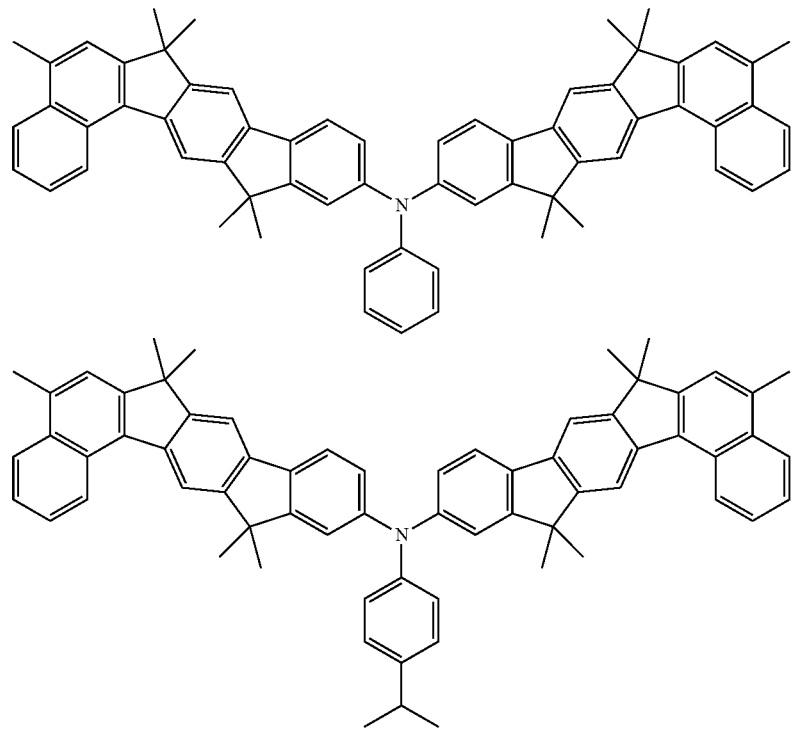

-continued
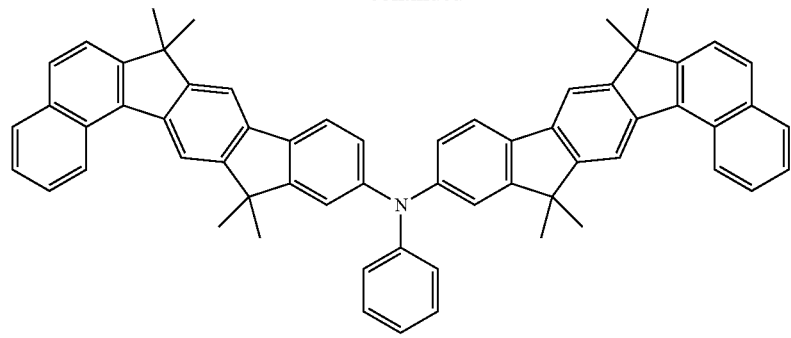
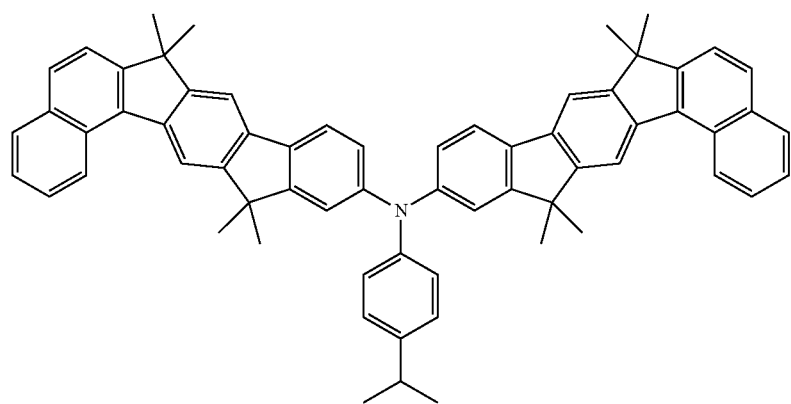
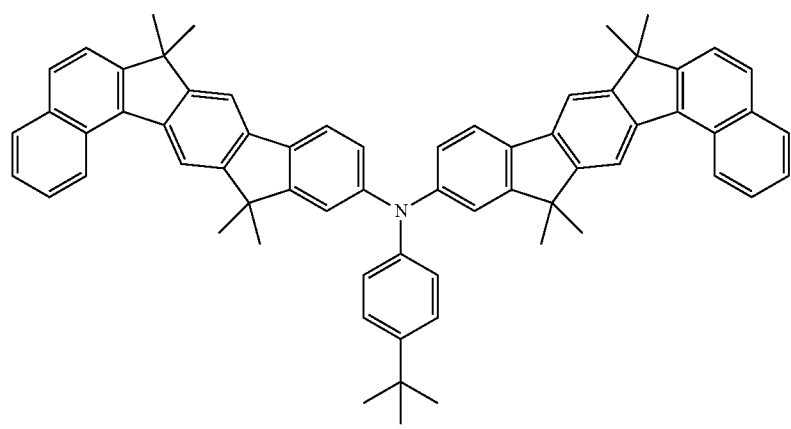
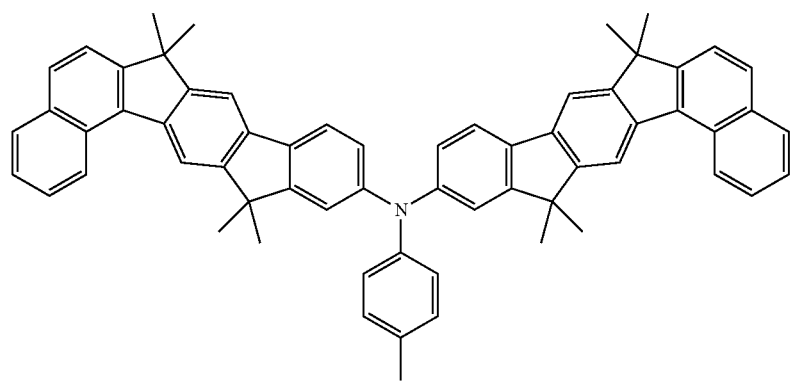

-continued
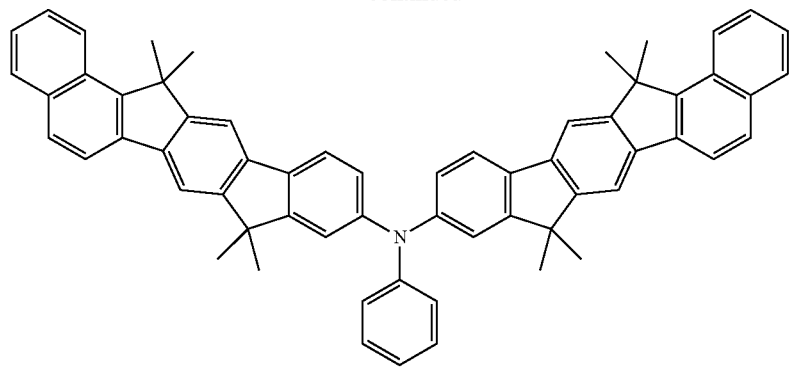
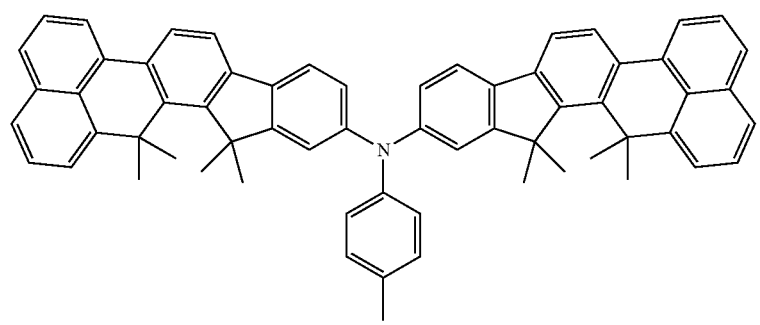
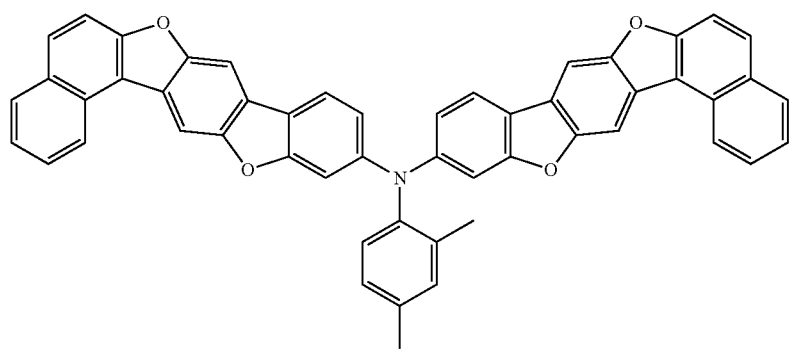
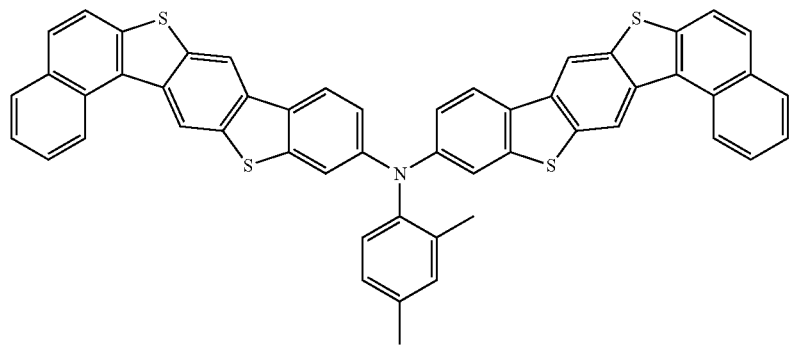

-continued

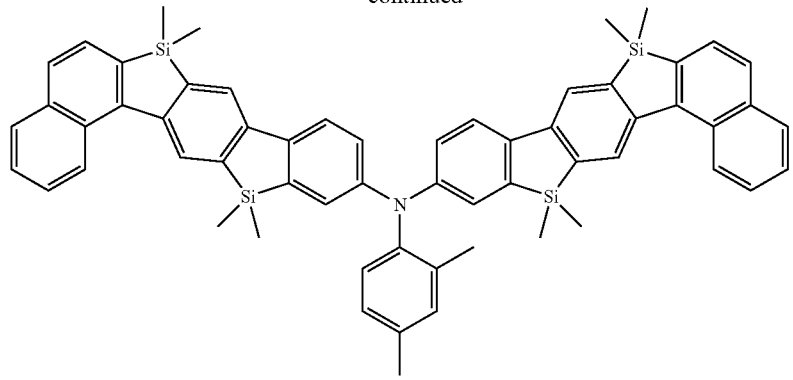

In an exemplary embodiment, the emitting layer contains, as at least one of the third compound or the fourth compound, at least one compound selected from the group consisting of the compound represented by the formula (4), the compound represented by the formula (5), the compound represented by the formula (7), the compound represented by the formula (8), the compound represented by the formula (9), and a compound represented by a formula (63a) below.

[Formula 391]

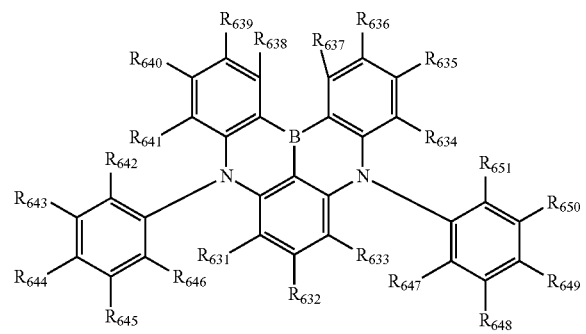

(63a)

In the formula (63a):

$R_{631}$ is bonded to $R_{646}$ to form a substituted or unsubstituted heterocycle or to form no substituted or unsubstituted heterocycle;

$R_{633}$ is bonded to $R_{647}$ to form a substituted or unsubstituted heterocycle or to form no substituted or unsubstituted heterocycle;

$R_{634}$ is bonded to $R_{651}$ to form a substituted or unsubstituted heterocycle or to form no substituted or unsubstituted heterocycle;

$R_{641}$ is bonded to $R_{642}$ to form a substituted or unsubstituted heterocycle or to form no substituted or unsubstituted heterocycle;

at least one combination of adjacent two or more of $R_{631}$ to $R_{651}$ are mutually bonded to form a substituted or unsubstituted monocyclic ring, mutually bonded to form a substituted or unsubstituted fused ring, or not mutually bonded;

$R_{631}$ to $R_{651}$ not forming the substituted or unsubstituted heterocycle, not forming the monocyclic ring and not forming the fused ring are each independently a hydrogen atom, a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a substituted or unsubstituted aryl group having 6 to 50 ring carbon atoms, or a substituted or unsubstituted heterocyclic group having 5 to 50 ring atoms;

at least one of $R_{631}$ to $R_{651}$ not forming the substituted or unsubstituted heterocycle, not forming the monocyclic ring and not forming the fused ring are a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

In an exemplary embodiment, the compound represented by the formula (4) is the compound represented by the formula (41-3), the formula (41-4) or the formula (41-5), the Al ring in the formula (41-5) being a substituted or unsubstituted fused aromatic hydrocarbon ring having 10 to 50 ring carbon atoms, or a substituted or unsubstituted fused heterocycle having 8 to 50 ring atoms.

In an exemplary embodiment: the substituted or unsubstituted fused aromatic hydrocarbon ring having 10 to 50 ring carbon atoms in the formulae (41-3), (41-4) and (41-5) is a substituted or unsubstituted naphthalene ring, a substituted or unsubstituted anthracene ring, or a substituted or unsubstituted fluorene ring; and the substituted or unsubstituted fused heterocycle having 8 to 50 ring atoms is a substituted or unsubstituted dibenzofuran ring, a substituted or unsubstituted carbazole ring, or a substituted or unsubstituted dibenzothiophene ring.

In an exemplary embodiment: the substituted or unsubstituted fused aromatic hydrocarbon ring having 10 to 50 ring carbon atoms in the formula (41-3), (41-4) or (41-5) is a substituted or unsubstituted naphthalene ring, or a substituted or unsubstituted fluorene ring; and the substituted or unsubstituted fused heterocycle having 8 to 50 ring atoms is a substituted or unsubstituted dibenzofuran ring, a substituted or unsubstituted carbazole ring, or a substituted or unsubstituted dibenzothiophene ring.

In an exemplary embodiment, the compound represented by the formula (4) is selected from the group consisting of a compound represented by the formula (461), a compound represented by the formula (462), a compound represented by the formula (463), a compound represented by the formula (464), a compound represented by the formula (465), a compound represented by the formula (466), and a compound represented by the formula (467).

[Formula 392]

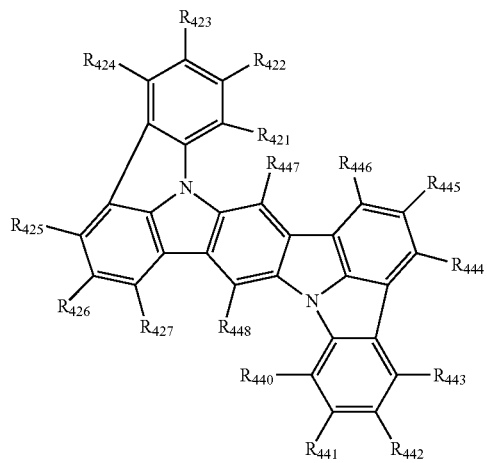

(461)

[Formula 393]

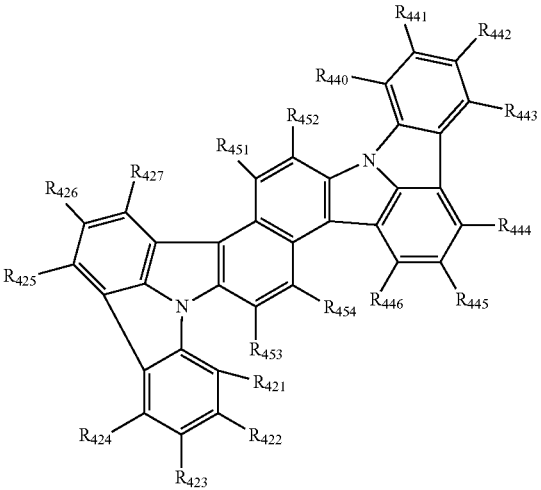

(463)

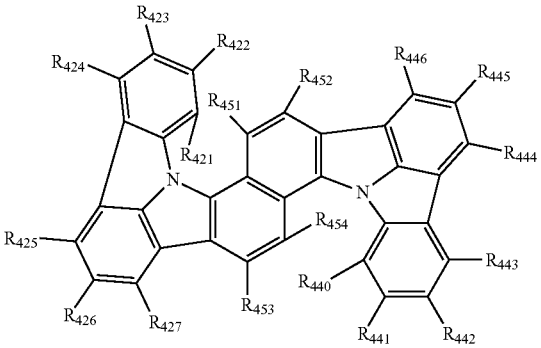

(464)

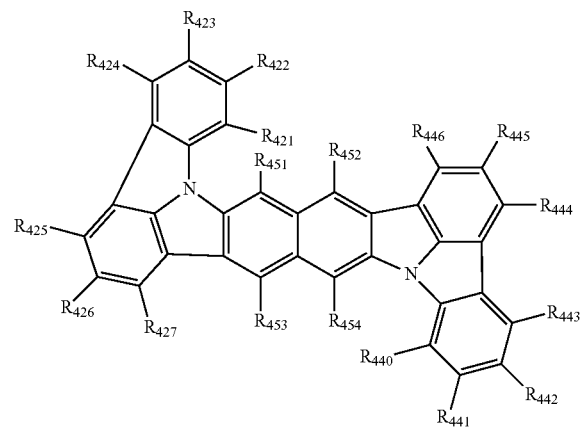

(462)

[Formula 394]

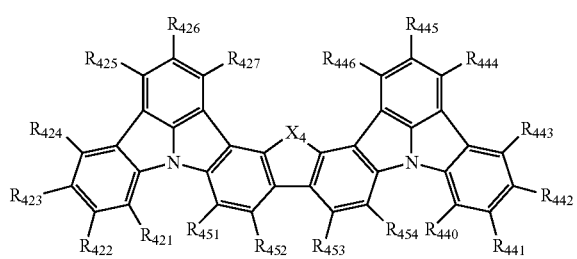

(465)

[Formula 395]

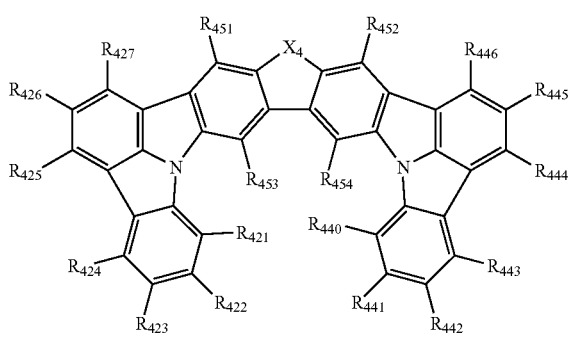

(466)

[Formula 396]

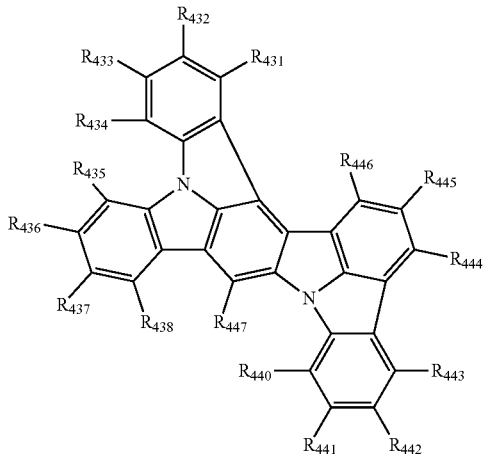

(467)

In the formulae (461) to (467):

at least one combination of adjacent two or more of $R_{421}$ to $R_{427}$, $R_{431}$ to $R_{436}$, $R_{440}$ to $R_{448}$, and $R_{451}$ to $R_{454}$ are mutually bonded to form a substituted or unsubstituted monocyclic ring, mutually bonded to form a substituted or unsubstituted fused ring, or not mutually bonded;

$R_{437}$, $R_{438}$, and $R_{421}$ to $R_{427}$, $R_{431}$ to $R_{436}$, $R_{440}$ to $R_{448}$ and $R_{451}$ to $R_{454}$ not forming the monocyclic ring and not forming the fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms;

$X_4$ is an oxygen atom, $NR_{801}$, or $C(R_{802})(R_{803})$;

$R_{801}$, $R_{802}$, and $R_{803}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, a substituted or unsubstituted heterocyclic group having 5 to 50 ring atoms, a substituted or unsubstituted alkyl group having 1 to 50 carbon atoms, or a substituted or unsubstituted aryl group having 6 to 50 ring carbon atoms;

when a plurality of $R_{801}$ are present, the plurality of $R_{801}$ are mutually the same or different;

when a plurality of $R_{802}$ are present, the plurality of $R_{802}$ are mutually the same or different; and when a plurality of $R_{803}$ are present, the plurality of $R_{803}$ are mutually the same or different.

In an exemplary embodiment, $R_{421}$ to $R_{427}$ and $R_{440}$ to $R_{448}$ are each independently a hydrogen atom, a substituted or unsubstituted aryl group having 6 to 50 ring carbon atoms, or a substituted or unsubstituted heterocyclic group having 5 to 50 ring atoms.

In an exemplary embodiment, $R_{421}$ to $R_{427}$ and $R_{440}$ to $R_{447}$ are each independently selected from the group consisting of a hydrogen atom, a substituted or unsubstituted aryl group having 6 to 18 ring carbon atoms, and a substituted or unsubstituted heterocyclic group having 5 to 18 ring atoms.

In an exemplary embodiment, the compound represented by the formula (41-3) is represented by a formula (41-3-1) below.

[Formula 397]

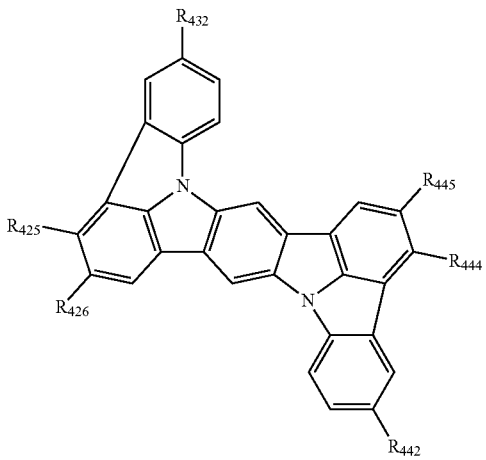

(41-3-1)

In the formula (41-3-1), $R_{423}$, $R_{425}$, $R_{426}$, $R_{442}$, $R_{444}$ and $R_{445}$ each independently represent the same as $R_{423}$, $R_{425}$, $R_{426}$, $R_{442}$, $R_{444}$ and $R_{445}$ in the formula (41-3).

In an exemplary embodiment, the compound represented by the formula (41-3) is represented by a formula (41-3-2) below.

[Formula 398]

(41-3-2)

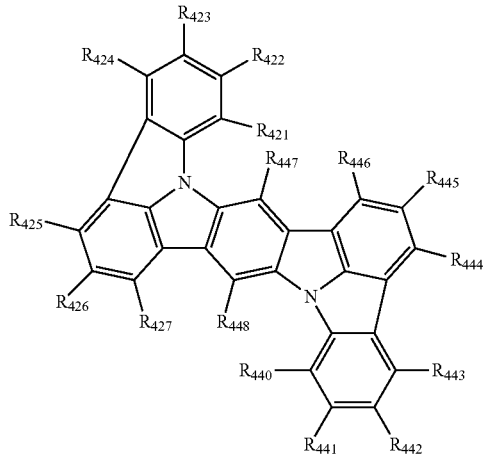

In the formula (41-3-2): $R_{421}$ to $R_{427}$ and $R_{440}$ to $R_{448}$ each independently represent the same as $R_{421}$ to $R_{427}$ and $R_{440}$ to $R_{448}$ in the formula (41-3); and at least one of $R_{421}$ to $R_{427}$ or $R_{440}$ to $R_{446}$ is a group represented by —N($R_{906}$)($R_{907}$).

In an exemplary embodiment, two of $R_{421}$ to $R_{427}$ and $R_{440}$ to $R_{446}$ in the formula (41-3-2) are groups represented by —N($R_{906}$)($R_{907}$).

In an exemplary embodiment, the compound represented by the formula (41-3-2) is represented by a formula (41-3-3) below.

[Formula 399]

(41-3-3)

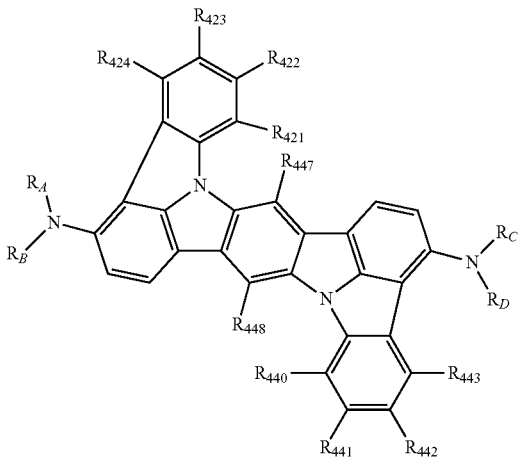

In the formula (41-3-3): $R_{421}$ to $R_{424}$, $R_{440}$ to $R_{443}$, $R_{447}$, and $R_{448}$ each independently represent the same as $R_{421}$ to $R_{424}$, $R_{440}$ to $R_{443}$, $R_{447}$, and $R_{448}$ in the formula (41-3); and $R_A$, $R_B$, $R_C$, and $R_D$ are each independently a substituted or unsubstituted aryl group having 6 to 18 ring carbon atoms, or a substituted or unsubstituted heterocyclic group having 5 to 18 ring atoms.

In an exemplary embodiment, the compound represented by the formula (41-3-3) is represented by a formula (41-3-4) below.

[Formula 400]

(41-3-4)

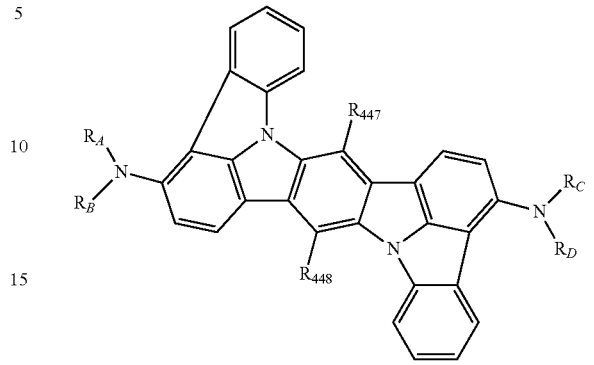

In the formula (41-3-4), $R_{447}$, $R_{448}$, $R_A$, $R_B$, $R_C$ and $R_D$ each independently represent the same as $R_{447}$, $R_{448}$, $R_A$, $R_B$, $R_C$ and $R_D$ in the formula (41-3-3).

In an exemplary embodiment, $R_A$, $R_B$, $R_C$, and $R_D$ are each independently a substituted or unsubstituted aryl group having 6 to 18 ring carbon atoms.

In an exemplary embodiment, $R_A$, $R_B$, $R_C$, and $R_D$ are each independently a substituted or unsubstituted phenyl group.

In an exemplary embodiment, $R_{447}$ and $R_{448}$ are each a hydrogen atom.

In an exemplary embodiment, a substituent for the substituted or unsubstituted group in each of the above formulae is an unsubstituted alkyl group having 1 to 50 carbon atoms, an unsubstituted alkenyl group having 2 to 50 carbon atoms, an unsubstituted alkynyl group having 2 to 50 carbon atoms, an unsubstituted cycloalkyl group having 3 to 50 ring carbon atoms, —Si($R_{901a}$)($R_{902a}$)($R_{903a}$), —O—($R_{904a}$), —S—($R_{905a}$), —N($R_{906a}$)($R_{907a}$), a halogen atom, a cyano group, a nitro group, an unsubstituted aryl group having 6 to 50 ring carbon atoms, or an unsubstituted heterocyclic group having 5 to 50 ring atoms;

$R_{901a}$ to $R_{907a}$ are each independently a hydrogen atom, an unsubstituted alkyl group having 1 to 50 carbon atoms, an unsubstituted aryl group having 6 to 50 ring carbon atoms, or an unsubstituted heterocyclic group having 5 to 50 ring atoms;

when two or more $R_{901a}$ are present, the two or more $R_{901a}$ are mutually the same or different;

when two or more $R_{902a}$ are present, the two or more $R_{902a}$ are mutually the same or different;

when two or more $R_{903a}$ are present, the two or more $R_{903a}$ are mutually the same or different;

when two or more $R_{904a}$ are present, the two or more $R_{904a}$ are mutually the same or different;

when two or more $R_{905a}$ are present, the two or more $R_{905a}$ are mutually the same or different;

when two or more $R_{906a}$ are present, the two or more $R_{906a}$ are mutually the same or different; and when two or more $R_{907a}$ are present, the two or more $R_{907a}$ are mutually the same or different.

In an exemplary embodiment, a substituent for the substituted or unsubstituted group in each of the above formulae is an unsubstituted alkyl group having 1 to 50 carbon atoms, an unsubstituted aryl group having 6 to 50 ring carbon atoms, or an unsubstituted heterocyclic group having 5 to 50 ring atoms.

In an exemplary embodiment, a substituent for the substituted or unsubstituted group in each of the above formulae is an unsubstituted alkyl group having 1 to 18 carbon atoms, an unsubstituted aryl group having 6 to 18 ring carbon atoms, or an unsubstituted heterocyclic group having 5 to 18 ring atoms.

In the organic EL device according to the exemplary embodiment, it is preferable that the second emitting layer contains the fluorescent fourth compound as the second emitting compound, and the fourth compound is a compound that emits light having a maximum peak wavelength in a range from 430 nm to 480 nm.

In the organic EL device according to the exemplary embodiment, it is preferable that the first emitting layer contains the fluorescent third compound as the first emitting compound, and the third compound is a compound that emits light having a maximum peak wavelength in a range from 430 nm to 480 nm.

A measurement method of the maximum peak wavelength of a compound is as follows. A toluene solution of a measurement target compound at a concentration ranging from $10^{-6}$ mol/L to $10^{-5}$ mol/L is prepared and put in a quartz cell. An emission spectrum (ordinate axis: luminous intensity, abscissa axis: wavelength) of the thus-obtained sample is measured at a normal temperature (300K). The emission spectrum can be measured using a spectrophotometer (machine name: F-7000) manufactured by Hitachi High-Tech Science Corporation. It should be noted that the machine for measuring the emission spectrum is not limited to the machine used herein.

A peak wavelength of the emission spectrum exhibiting the maximum luminous intensity is defined as the maximum emission peak wavelength. Herein, the maximum peak wavelength of fluorescence is sometimes referred to as the maximum fluorescence peak wavelength (FL-peak).

When the first emitting layer of the organic EL device according to the exemplary embodiment contains the first compound and the third compound, the first compound is preferably a host material (sometimes referred to as a matrix material) and the third compound is preferably a dopant material (sometimes referred to as a guest material, emitter, or luminescent material).

When the first emitting layer of the organic EL device according to the exemplary embodiment contains the first compound and the third compound as the first emitting compound, the singlet energy $S_1(H1)$ of the first compound and the singlet energy $S_1(D3)$ of the third compound preferably satisfy a relationship of a numerical formula (Numerical Formula 1) below.

$$S_1(H1) > S_1(D3) \qquad \text{(Numerical Formula 1)}$$

When the second emitting layer of the organic EL device according to the exemplary embodiment contains the second compound and the fourth compound as the second emitting compound, the second compound is preferably a host material (sometimes referred to as a matrix material) and the fourth compound is preferably a dopant material (sometimes referred to as a guest material, emitter, or luminescent material).

When the second emitting layer of the organic EL device according to the exemplary embodiment contains the second compound and the fourth compound, the singlet energy $S_1(H2)$ of the second compound and a singlet energy $S_1(D4)$ of the fourth compound preferably satisfy a relationship of a numerical formula (Numerical Formula 2) below.

$$S_1(H2) > S_1(D4) \qquad \text{(Numerical Formula 2)}$$

Singlet Energy $S_1$

A method of measuring the singlet energy $S_1$ with use of a solution (occasionally referred to as a solution method) is exemplified by a method below.

A toluene solution of a measurement target compound at a concentration ranging from $10^{-5}$ mol/L to $10^{-4}$ mol/L is prepared and put in a quartz cell. An absorption spectrum (ordinate axis: absorption intensity, abscissa axis: wavelength) of the thus-obtained sample is measured at a normal temperature (300K). A tangent is drawn to the fall of the absorption spectrum close to the long-wavelength region, and a wavelength value λedge (nm) at an intersection of the tangent and the abscissa axis is assigned to a conversion equation (F2) below to calculate singlet energy.

$$S_1 [\text{eV}] = 1239.85/\lambda_{edge} \qquad \text{Conversion Equation (F2):}$$

Any device for measuring absorption spectrum is usable. For instance, a spectrophotometer (U3310 manufactured by Hitachi, Ltd.) is usable.

The tangent to the fall of the absorption spectrum close to the long-wavelength region is drawn as follows. While moving on a curve of the absorption spectrum from the local maximum spectral value closest to the long-wavelength region in a long-wavelength direction, a tangent at each point on the curve is checked. An inclination of the tangent is decreased and increased in a repeated manner as the curve fell (i.e., a value of the ordinate axis is decreased). A tangent drawn at a point of the local minimum inclination closest to the long-wavelength region (except when absorbance is 0.1 or less) is defined as the tangent to the fall of the absorption spectrum on the long-wavelength region.

The local maximum absorbance of 0.2 or less is not included in the above-mentioned local maximum absorbance on the long-wavelength region.

Triplet Energy $T_1$

A method of measuring triplet energy $T_1$ is exemplified by a method below.

A measurement target compound is dissolved in EPA (diethylether:isopentane:ethanol=5:5:2 in volume ratio) so as to fall within a range from $10^{-5}$ mol/L to $10^{-4}$ mol/L, and the obtained solution is encapsulated in a quartz cell to provide a measurement sample. A phosphorescence spectrum (ordinate axis: phosphorescent luminous intensity, abscissa axis: wavelength) of the measurement sample is measured at a low temperature (77K). A tangent is drawn to the rise of the phosphorescent spectrum close to the short-wavelength region. An energy amount is calculated by a conversion equation (F1) below on a basis of a wavelength value $\lambda_{edge}$ [nm] at an intersection of the tangent and the abscissa axis. The calculated energy amount is defined as triplet energy $T_1$.

$$T_1 [\text{eV}] = 1239.85/\lambda_{edge} \qquad \text{Conversion Equation (F1):}$$

The tangent to the rise of the phosphorescence spectrum close to the short-wavelength region is drawn as follows. While moving on a curve of the phosphorescence spectrum from the short-wavelength region to the local maximum spectral value closest to the short-wavelength region among the local maximum spectral values, a tangent is checked at each point on the curve toward the long-wavelength region of the phosphorescence spectrum. An inclination of the tangent is increased along the rise of the curve (i.e., a value of the ordinate axis is increased). A tangent drawn at a point of the local maximum inclination (i.e., a tangent at an inflection point) is defined as the tangent to the rise of the phosphorescence spectrum close to the short-wavelength region.

The local maximum point where a peak intensity is 15% or less of the maximum peak intensity of the spectrum is not counted as the above-mentioned local maximum peak intensity closest to the short-wavelength region. The tangent drawn at a point that is closest to the local maximum peak intensity closest to the short-wavelength region and where the inclination of the curve is the local maximum is defined as a tangent to the rise of the phosphorescence spectrum close to the short-wavelength region.

For phosphorescence measurement, a spectrophotofluorometer body F-4500 (manufactured by Hitachi High-Technologies Corporation) is usable. The measurement instrument is not limited to this arrangement. A combination of a cooling unit, a low temperature container, an excitation light source and a light-receiving unit may be used for measurement.

It is preferable that the first emitting layer and the second emitting layer do not contain a phosphorescent material (dopant material).

Further, it is preferable that the first emitting layer and the second emitting layer do not contain a heavy-metal complex and a phosphorescent rare-earth metal complex. Examples of the heavy-metal complex herein include iridium complex, osmium complex, and platinum complex.

Further, it is also preferable that the first emitting layer and the second emitting layer do not contain a metal complex.

Film Thickness of Emitting Layer

Except for the cases particularly described above (e.g., the film thickness of each of the first emitting layer and the second emitting layer of the laminated emitting unit), a film thickness of the emitting layer of the organic EL device according to the exemplary embodiment is preferably in a range from 5 nm to 50 nm, more preferably in a range from 7 nm to 50 nm, further preferably in a range from 10 nm to 50 nm. When the film thickness of the emitting layer is 5 nm or more, the formation of the emitting layer and adjustment of chromaticity are likely to be facilitated. When the film thickness of the emitting layer is 50 nm or less, an increase in the drive voltage is likely to be inhibited.

Content Ratio of Compound in Emitting Layer

When the first emitting layer contains the first compound and the third compound, the content ratios of the first and third compounds in the first emitting layer also preferably fall, for instance, within a range below.

The content ratio of the first compound is preferably in a range from 80 mass % to 99 mass %, also preferably in a range from 90 mass % to 99 mass %, and also preferably in a range from 95 mass % to 99 mass %.

The content ratio of the third compound is also preferably in a range from 1 mass % to 10 mass %, also preferably in a range from 1 mass % to 7 mass %, and also preferably in a range from 1 mass % to 5 mass %.

An upper limit of the total of the respective content ratios of the first and third compounds in the first emitting layer is 100 mass %.

It should be noted that the first emitting layer of the exemplary embodiment may further contain material(s) other than the first and third compounds.

The first emitting layer may include a single type of the first compound or may include two or more types of the first compound. The first emitting layer may include a single type of the third compound or may include two or more types of the third compound.

An example of the organic EL device whose first emitting layer contains mutually different two or more types of the first compound is as follows.

An organic EL device including: an anode; a cathode; a first emitting layer disposed between the anode and the cathode; and a second emitting layer disposed between the first emitting layer and the cathode, in which the first emitting layer contains a first host material in a form of the first compound including at least one group represented by the formula (11), the first compound being represented by the formula (1), the first emitting layer contains mutually different two or more types of the first compound, the second emitting layer contains a second host material in a form of the second compound represented by the formula (2), and the first emitting layer and the second emitting layer are in direct contact with each other.

When the second emitting layer contains the second compound and the fourth compound, the content ratios of the second and fourth compounds in the second emitting layer also preferably fall, for instance, within a range below.

The content ratio of the second compound is also preferably in a range from 80 mass % to 99 mass %, also preferably in a range from 90 mass % to 99 mass %, and also preferably in a range from 95 mass % to 99 mass %.

The content ratio of the fourth compound is also preferably in a range from 1 mass % to 10 mass %, also preferably in a range from 1 mass % to 7 mass %, and also preferably in a range from 1 mass % to 5 mass %.

An upper limit of the total of the respective content ratios of the second and fourth compounds in the second emitting layer is 100 mass %.

It should be noted that the second emitting layer of the exemplary embodiment may further contain material(s) other than the second and fourth compounds.

The second emitting layer may include a single type of the second compound or may include two or more types of the second compound. The second emitting layer may include a single type of the fourth compound or may include two or more types of the fourth compound.

An example of the organic EL device whose second emitting layer contains mutually different two or more types of the second compound is as follows.

An organic EL device including: an anode; a cathode; a first emitting layer disposed between the anode and the cathode; and a second emitting layer disposed between the first emitting layer and the cathode, in which the first emitting layer contains a first host material in a form of the first compound including at least one group represented by the formula (11), the first compound being represented by the formula (1), the second emitting layer contains a second host material in a form of the second compound represented by the formula (2), the second emitting layer contains mutually different two or more types of the second compound, and the first emitting layer and the second emitting layer are in direct contact with each other.

An arrangement of an organic EL device will be further described below. It should be noted that the reference numerals will be sometimes omitted below.

Substrate

The substrate is used as a support for the organic EL device. For instance, glass, quartz, plastics and the like are usable for the substrate. A flexible substrate is also usable. The flexible substrate refers to a bendable substrate, example of which is a plastic substrate or the like. Examples of the material for the plastic substrate include polycarbonate, polyarylate, polyethersulfone, polypropylene, polyester, polyvinyl fluoride, polyvinyl chloride, polyimide, and polyethylene naphthalate. Moreover, an inorganic vapor deposition film is also usable.

Anode

Metal, an alloy, an electrically conductive compound, a mixture thereof, or the like having a large work function (specifically, 4.0 eV or more) is preferably used as the anode formed on the substrate. Specific examples of the material include ITO (Indium Tin Oxide), indium oxide-tin oxide containing silicon or silicon oxide, indium oxide-zinc oxide, indium oxide containing tungsten oxide and zinc oxide, and graphene. In addition, gold (Au), platinum (Pt), nickel (Ni), tungsten (W), chrome (Cr), molybdenum (Mo), iron (Fe), cobalt (Co), copper (Cu), palladium (Pd), titanium (Ti), and nitrides of a metal material (e.g., titanium nitride) are usable.

The material is typically formed into a film by a sputtering method. For instance, the indium oxide-zinc oxide can be formed into a film by the sputtering method using a target in which zinc oxide in a range from 1 mass % to 10 mass % is added to indium oxide. Moreover, for instance, the indium oxide containing tungsten oxide and zinc oxide can be formed by the sputtering method using a target in which tungsten oxide in a range from 0.5 mass % to 5 mass % and zinc oxide in a range from 0.1 mass % to 1 mass % are added to indium oxide. In addition, the anode may be formed by a vacuum deposition method, a coating method, an inkjet method, a spin coating method or the like.

Among the organic layers formed on the anode, since the hole injecting layer adjacent to the anode is formed of a composite material into which holes are easily injectable irrespective of the work function of the anode, a material usable as an electrode material (e.g., metal, an alloy, an electroconductive compound, a mixture thereof, and the elements belonging to the group 1 or 2 of the periodic table) is also usable for the anode.

A material having a small work function such as elements belonging to Groups 1 and 2 in the periodic table of the elements, specifically, an alkali metal such as lithium (Li) and cesium (Cs), an alkaline earth metal such as magnesium (Mg), calcium (Ca) and strontium (Sr), alloys (e.g., MgAg and AlLi) including the alkali metal or the alkaline earth metal, a rare earth metal such as europium (Eu) and ytterbium (Yb), alloys including the rare earth metal are also usable for the anode. It should be noted that the vacuum deposition method and the sputtering method are usable for forming the anode using the alkali metal, alkaline earth metal and the alloy thereof. Further, when a silver paste is used for the anode, the coating method and the inkjet method are usable.

When the organic EL device is of a bottom emission type, the anode is preferably formed of a light-transmissive or semi-transmissive metallic material that transmits light from the emitting layer. Herein, the light-transmissive or semi-transmissive property means the property of allowing transmissivity of 50% or more (preferably 80% or more) of the light emitted from the emitting layer. The light-transmissive or semi-transmissive metallic material can be selected in use as needed from the above materials listed in the description about the anode.

When the organic EL device is of a top emission type, the anode is a reflective electrode having a reflective layer. The reflective layer is preferably formed of a metallic material having light reflectivity. Herein, the light reflectivity means the property of reflecting 50% or more (preferably 80% or more) of the light emitted from the emitting layer. The metallic material having light reflectivity can be selected in use as needed from the above materials listed in the description about the anode.

The anode may be formed only of the reflective layer, but may be a multilayer structure having the reflective layer and a conductive layer (preferably a transparent conductive layer). When the anode has the reflective layer and the conductive layer, the conductive layer is preferably disposed between the reflective layer and the hole transporting zone. A material of the conductive layer can be selected in use as needed from the above materials listed in the description about the anode.

Cathode

Metal, an alloy, an electrically conductive compound, a mixture thereof, or the like having a small work function (specifically, 3.8 eV or less) is preferably used as the cathode. Examples of the material for the cathode include elements belonging to Groups 1 and 2 in the periodic table of the elements, specifically, the alkali metal such as lithium (Li) and cesium (Cs), the alkaline earth metal such as magnesium (Mg), calcium (Ca) and strontium (Sr), alloys (e.g., MgAg and AlLi) including the alkali metal or the alkaline earth metal, the rare earth metal such as europium (Eu) and ytterbium (Yb), and alloys including the rare earth metal.

It should be noted that the vacuum deposition method and the sputtering method are usable for forming the cathode using the alkali metal, alkaline earth metal and the alloy thereof. Further, when a silver paste is used for the cathode, the coating method and the inkjet method are usable.

By providing the electron injecting layer, various conductive materials such as Al, Ag, ITO, graphene, and indium oxide-tin oxide containing silicon or silicon oxide may be used for forming the cathode regardless of the work function. The conductive materials can be formed into a film using the sputtering method, inkjet method, spin coating method and the like.

When the organic EL device is of a bottom emission type, the cathode is a reflective electrode. The reflective layer is preferably formed of a metallic material having light reflectivity. The metallic material having light reflectivity can be selected in use as needed from the above materials listed in the description about the cathode.

When the organic EL device is of a top emission type, the cathode is preferably formed of a light-transmissive or semi-transmissive metallic material that transmits light from the emitting layer. The light-transmissive or semi-transmissive metallic material can be selected in use as needed from the above materials listed in the description about the cathode.

Capping Layer

The top emission type organic EL device typically has a capping layer on the top of the cathode.

A capping layer may contain at least one compound selected from the group consisting of, for instance, a high polymer compound, metal oxide, metal fluoride, metal boride, silicon nitride, and silicon compound (silicon oxide or the like).

In addition, the capping layer may contain at least one compound selected from the group consisting of, for instance, an aromatic amine derivative, an anthracene derivative, a pyrene derivative, a fluorene derivative, and a dibenzofuran derivative.

Moreover, a laminate obtained by laminating layers containing these substances is also usable as a capping layer.

Hole Injecting Layer

The hole injecting layer is a layer containing a high hole injectable substance. Examples of the high hole injectable substance include molybdenum oxide, titanium oxide, vanadium oxide, rhenium oxide, ruthenium oxide, chrome oxide, zirconium oxide, hafnium oxide, tantalum oxide, silver oxide, tungsten oxide, and manganese oxide.

In addition, the examples of the high hole injectable substance further include: an aromatic amine compound, which is a low-molecule organic compound, such as 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazole-3-yl)-N-phenylamino]-9-phenylcarbazole (abbreviation: PCzPCA1), 3,6-bis[N-(9-phenylcarbazole-3-yl)-N-phenylamino]-9-phenylcarbazole (abbreviation: PCzPCA2), and 3-[N-(1-naphthyl)-N-(9-phenylcarbazole-3-yl)amino]-9-phenylcarbazole (abbreviation: PCzPCN1); and dipyrazino[2,3-f:20,30-h]quinoxaline-2,3,6,7,10,11-hexacarbonitrile (HAT-CN).

In addition, a high polymer compound (e.g., oligomer, dendrimer and polymer) is usable as the high hole injectable substance. Examples of the high-molecule compound include poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide](abbreviation: PTPDMA), and poly[N,N'-bis(4-butylphenyl)-N,N'-bis(phenyl)benzidine] (abbreviation: Poly-TPD). Moreover, an acid-added high polymer compound such as poly(3,4-ethylenedioxythiophene)/poly(styrene sulfonic acid) (PEDOT/PSS) and polyaniline/poly(styrene sulfonic acid) (PAni/PSS) is also usable.

Hole Transporting Layer

The hole transporting layer is a layer containing a highly hole-transporting substance. An aromatic amine compound, carbazole derivative, anthracene derivative and the like are usable for the hole transporting layer. Specific examples of a material for the hole transporting layer include 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4-phenyl-4'-(9-phenylfluorene-9-yl)triphenylamine (abbreviation: BAFLP), 4,4'-bis[N-(9,9-dimethylfluorene-2-yl)-N-phenylamino]biphenyl (abbreviation: DFLDPBi), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), and 4,4'-bis[N-(spiro-9,9'-bifluorene-2-yl)-N-phenylamino]biphenyl (abbreviation: BSPB). The above-described substances mostly have a hole mobility of $10^{-6}$ cm$^2$/(V·s) or more.

For the hole transporting layer, a carbazole derivative such as CBP, 9-[4-(N-carbazolyl)]phenyl-10-phenylanthracene (CzPA), and 9-phenyl-3-[4-(10-phenyl-9-anthryl)phenyl]-9H-carbazole (PCzPA) and an anthracene derivative such as t-BuDNA, DNA, and DPAnth may be used. A high polymer compound such as poly(N-vinylcarbazole) (abbreviation: PVK) and poly(4-vinyltriphenylamine) (abbreviation: PVTPA) is also usable.

However, in addition to the above substances, any substance exhibiting a higher hole transportability than an electron transportability may be used. It should be noted that the layer containing the substance exhibiting a high hole transportability may be not only a single layer but also a laminate of two or more layers formed of the above substance(s).

Electron Transporting Layer

The electron transporting layer is a layer containing a highly electron-transporting substance. For the electron transporting layer, 1) a metal complex such as an aluminum complex, beryllium complex, and zinc complex, 2) a hetero aromatic compound such as imidazole derivative, benzimidazole derivative, azine derivative, carbazole derivative, and phenanthroline derivative, and 3) a high polymer compound are usable. Specifically, as a low-molecule organic compound, a metal complex such as Alq, tris(4-methyl-8-quinolinolato)aluminum (abbreviation: Almq$_3$), bis(10-hydroxybenzo[h]quinolinato)beryllium (abbreviation: BeBq$_2$), BAlq, Znq, ZnPBO and ZnBTZ is usable. In addition to the metal complex, a heteroaromatic compound such as 2-(4-biphenylyl)-5-(4-tert-butylphenyl)-1,3,4-oxadiazole (abbreviation: PBD), 1,3-bis[5-(ptert-butylphenyl)-1,3,4-oxadiazole-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), and 4,4'-bis(5-methylbenzoxazole-2-yl)stilbene (abbreviation: BzOs) is usable. In the exemplary embodiment, a benzimidazole compound is preferably usable. The above-described substances mostly have an electron mobility of $10^{-6}$ cm$^2$/(V·s) or more. It should be noted that any substance other than the above substance may be used for the electron transporting layer as long as the substance exhibits a higher electron transportability than the hole transportability. The electron transporting layer may be provided in the form of a single layer or a laminate of two or more layers of the above substance(s).

Specific examples of the compound usable for the electron transporting layer is exemplified by compounds below. It should however be noted that the invention is not limited by the specific examples of the compound.

[Formula 401]

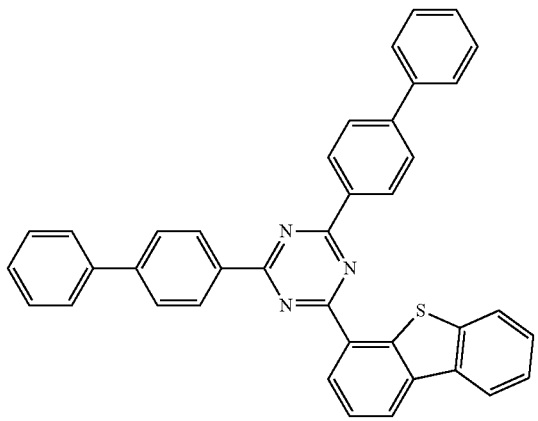

1005
-continued
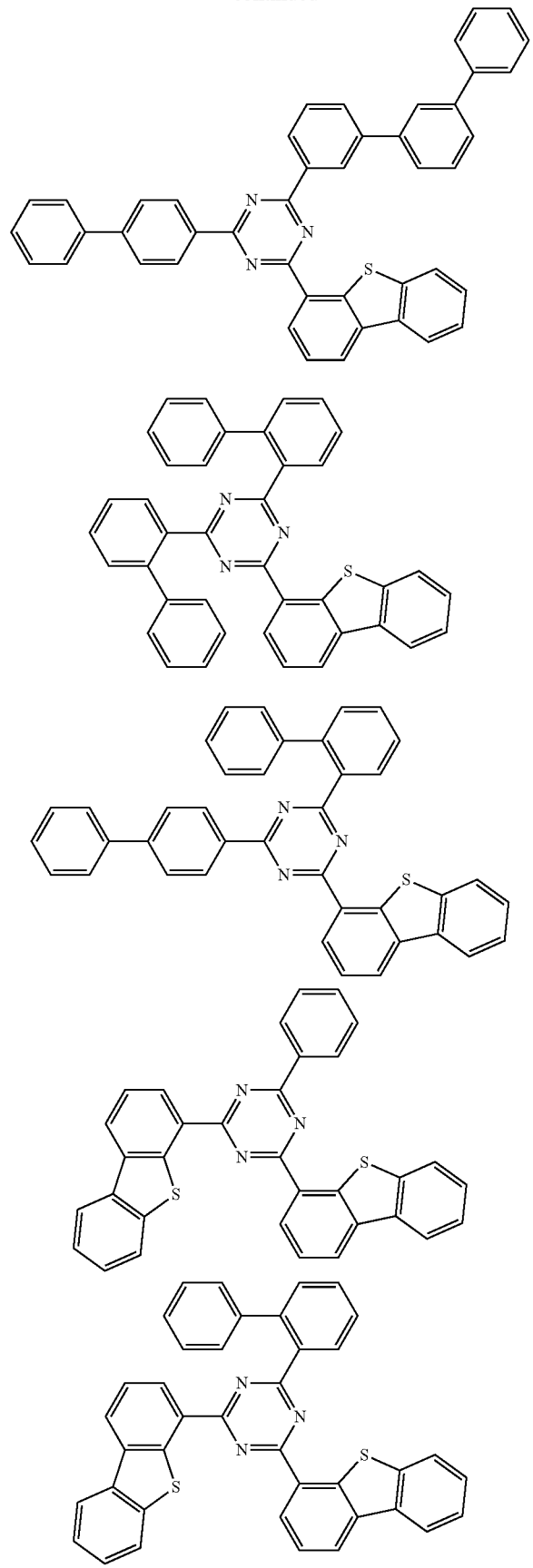
1006
-continued
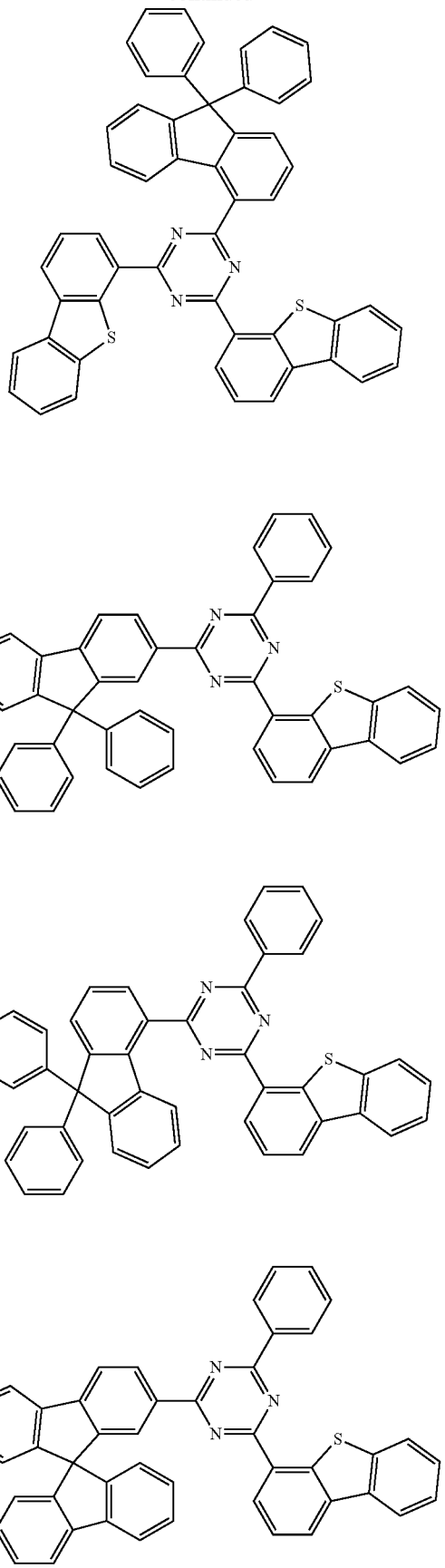

-continued

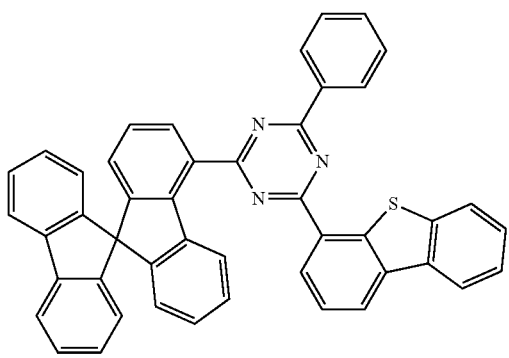

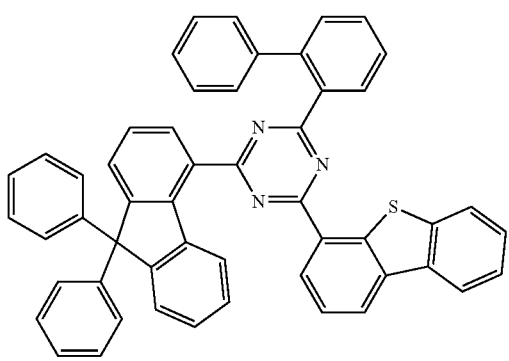

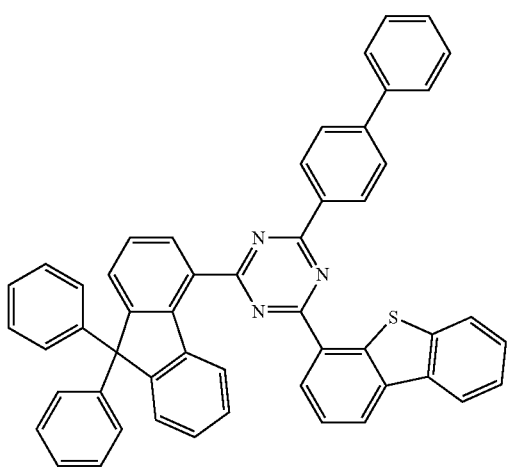

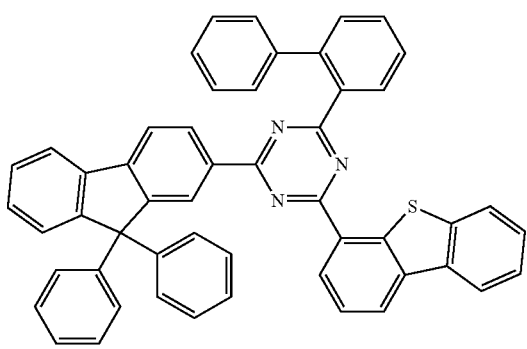

-continued

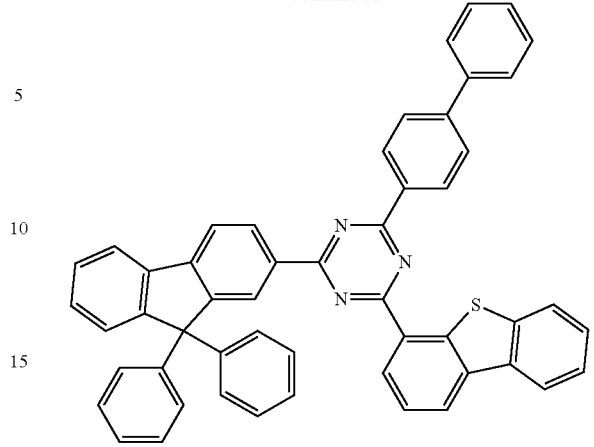

Moreover, a high polymer compound is usable for the electron transporting layer. For instance, poly[(9,9-dihexylfluorene-2,7-diyl)-co-(pyridine-3,5-diyl)](abbreviation: PF-Py), poly[(9,9-dioctylfluorene-2,7-diyl)-co-(2,2'-bipyridine-6,6'-diyl)](abbreviation: PF-BPy) and the like are usable.

Electron Injecting Layer

The electron injecting layer is a layer containing a highly electron-injectable substance. Examples of a material for the electron injecting layer include an alkali metal, alkaline earth metal and a compound thereof, examples of which include lithium (Li), cesium (Cs), calcium (Ca), lithium fluoride (LiF), cesium fluoride (CsF), calcium fluoride ($CaF_2$), and lithium oxide (LiOx). In addition, the alkali metal, alkaline earth metal or the compound thereof may be added to the substance exhibiting the electron transportability in use. Specifically, for instance, magnesium (Mg) added to Alq may be used. In this case, the electrons can be more efficiently injected from the cathode.

Alternatively, the electron injecting layer may be provided by a composite material in a form of a mixture of the organic compound and the electron donor. Such a composite material exhibits excellent electron injectability and electron transportability since electrons are generated in the organic compound by the electron donor. In this case, the organic compound is preferably a material excellent in transporting the generated electrons. Specifically, the above examples (e.g., the metal complex and the hetero aromatic compound) of the substance forming the electron transporting layer are usable. As the electron donor, any substance exhibiting electron donating property to the organic compound is usable. Specifically, the electron donor is preferably alkali metal, alkaline earth metal and rare earth metal such as lithium, cesium, magnesium, calcium, erbium and ytterbium. The electron donor is also preferably alkali metal oxide and alkaline earth metal oxide such as lithium oxide, calcium oxide, and barium oxide. Moreover, a Lewis base such as magnesium oxide is usable. Further, the organic compound such as tetrathiafulvalene (abbreviation: TTF) is usable.

Layer Formation Method(s)

A method for forming each layer of the organic EL device in the exemplary embodiment is subject to no limitation except for the above particular description. However, known methods of dry film-forming such as vacuum deposition, sputtering, plasma or ion plating and wet film-forming such as spin coating, dipping, flow coating or ink jet printing are applicable.

Layer Thickness

The film thickness of the organic layers of the organic EL device in the exemplary embodiment is not limited unless otherwise specified in the above. In general, since excessively small film thickness is likely to cause defects (e.g. pin holes) and excessively large thickness leads to the necessity of applying high voltage and consequent reduction in efficiency, the thickness of the organic layer of the organic EL device typically preferably ranges from several nanometers to 1 μm.

Color Conversion Portion 5

The organic EL device according to the exemplary embodiment preferably has a color conversion portion 5 provided on a side of the organic EL device through which light is extracted. The color conversion portion 5 is not particularly limited, but examples of the color conversion portion include a color filter and a quantum dot. The side of the organic EL device through which light is extracted may be close to the anode or the cathode.

The color conversion portion 5 is provided on the side of the organic EL device through which light is extracted, and serves as converting the light extracted through the side through which light is extracted to desired color light.

The color conversion portion 5 is preferably disposed on an electrode (transparent electrode) that is either the anode or the cathode, which is provided on the side through which light is extracted. Moreover, when the side through which light is extracted is close to the anode of the organic EL device, the color conversion portion 5 may be disposed between the substrate and the anode, or may be disposed on the side of the substrate, which is opposite to a side on which the anode is provided.

In addition, when the side through which light is extracted is close to the cathode of the organic EL device, the color conversion portion 5 may be disposed on the cathode.

The color conversion portion 5 is exemplified by a color filter and a material including a quantum dot.

Color Filter

A material for the color filter is exemplified by the following dyes only and the dyes in a solid state in which the dyes are dissolved or dispersed in a binder resin.

Red (R) Dye

One or a mixture of at least two or more of a perylene pigment, lake pigment, azo pigment, quinacridone pigment, anthraquinone pigment, anthracene pigment, isoindoline pigment, isoindolinone pigment and the like are usable.

Green (G) Dye

One or a mixture of at least two or more of a halogen polysubstituted phthalocyanine pigment, halogen polysubstituted copper phthalocyanine pigment, triphenylmethane basic dyes, isoindoline pigment, isoindolinone pigment and the like are usable.

Blue (B) Dye

One or a mixture of at least two or more of a copper phthalocyanine pigment, indanthrone pigment, indophenol pigment, cyanine pigment, dioxazine pigment and the like are usable.

The binder resin used as the material for the color filter is preferably a transparent material. For instance, a material having transmittance of 50% or more in a visible light region is preferably used.

Examples of the binder resin used as the material for the color filter include a transparent resin (polymer) such as polymethyl methacrylate, polyacrylate, polycarbonate, polyvinyl alcohol, polyvinyl pyrrolidone, hydroxyethyl cellulose, and carboxymethyl cellulose, among which one or a mixture of two or more thereof are usable.

Quantum Dot

A material for the quantum dot is exemplified by a material in which quantum dots are dispersed in a resin. CdSe, ZnSe, CdS, CdSeS/ZnS, InP, InP/ZnS, CdS/CdSe, CdS/ZnS, PbS, CdTe and the like are usable as the quantum dot.

The color filter and the material including a quantum dot may be used in combination for the color conversion portion.

The organic EL device according to the exemplary embodiment is also preferably an organic EL device for a display device. The tandem organic EL device is suitably used for a display device particularly in terms of a longer lifetime. Examples of the display device for which the tandem organic EL device is used include a TV, a personal computer, a tablet (sometimes referred to as a tablet computer), a display for a moving body (i.e., a display installed in a moving body), a display component (e.g., an organic EL panel module), a mobile phone (sometimes referred to as a cell phone) and a smartphone (sometimes referred to as a mobile phone). The tandem organic EL device can be suitably used as a medium- and large-sized panel such as a TV, a personal computer, a tablet, and a display for a moving body, for which a longer lifetime is important. The moving body with which a display device is installed is exemplified by an automobile and an aircraft.

The device of the invention, which is an improved tandem organic EL device, is suitably used for any display devices for which the tandem organic EL device can be suitably used.

According to the exemplary embodiment, an organic electroluminescence device having improved luminous efficiency and a longer lifetime can be provided.

Second Exemplary Embodiment

Electronic Device

An electronic device according to the exemplary embodiment is installed with any one of the organic EL devices according to the above exemplary embodiment. Examples of the electronic device include a display device and an emitting unit. Examples of the display device include a TV, a personal computer, a tablet, a display for a moving body, a display component (e.g., an organic EL panel module), a mobile phone and a smartphone. A display device installed with any one of the organic EL devices according to the above exemplary embodiment is preferably a TV, a personal computer, a tablet, and a display for a moving body. Examples of the emitting unit include an illuminator and a vehicle light.

Modification of Exemplary Embodiment(s)

The scope of the invention is not limited by the above-described exemplary embodiments but includes any modification and improvement as long as such modification and improvement are compatible with the invention.

For instance, only two emitting layers are not necessarily provided, but more than two emitting layers are provided and laminated with each other. When the organic EL device includes a plurality of (more than two) emitting layers, it is only necessary that at least two of the plurality of emitting layers should satisfy the requirements mentioned in the above exemplary embodiments. The rest of the emitting layers is, for instance, a fluorescent emitting layer or a phosphorescent emitting layer with use of emission caused by electron transfer from the triplet excited state directly to the ground state, in an exemplary embodiment.

When the organic EL device includes a plurality of emitting layers, these emitting layers may be mutually adjacently provided, or form a so-called tandem organic EL device, in which a plurality of emitting units are layered via an intermediate layer.

An example of the organic EL device including three or more emitting layers is as follows.

An organic EL device including: an anode; a cathode; a first emitting layer disposed between the anode and the cathode; a second emitting layer disposed between the first emitting layer and the cathode; and a fourth emitting layer disposed between the anode and the cathode and not being in direct contact with both of the first emitting layer and the second emitting layer, in which the first emitting layer contains a first host material in a form of the first compound including at least one group represented by the formula (11), the first compound being represented by the formula (1), the second emitting layer contains a second host material in a form of the second compound represented by the formula (2), and the first emitting layer and the second emitting layer are in direct contact with each other.

The fourth emitting layer also preferably contains the first compound.

The fourth emitting layer also preferably contains the second compound.

The organic electroluminescence device preferably includes an intermediate layer between the fourth emitting layer, and the first emitting layer and the second emitting layer.

For instance, in an exemplary embodiment, a blocking layer is provided adjacent to at least one of a side close to the anode or a side close to the cathode of the emitting layer. The blocking layer is preferably provided in contact with the emitting layer to block at least any of holes, electrons, or excitons.

For instance, when the blocking layer is provided in contact with the side close to the cathode of the emitting layer, the blocking layer permits transport of electrons, and blocks holes from reaching a layer provided closer to the cathode (e.g., the electron transporting layer) beyond the blocking layer. When the organic EL device includes the electron transporting layer, the blocking layer is preferably disposed between the emitting layer and the electron transporting layer.

When the blocking layer is provided in contact with the side close to the anode of the emitting layer, the blocking layer permits transport of holes, and blocks electrons from reaching a layer provided closer to the anode (e.g., the hole transporting layer) beyond the blocking layer. When the organic EL device includes the hole transporting layer, the blocking layer is preferably disposed between the emitting layer and the hole transporting layer.

Alternatively, the blocking layer may be provided adjacent to the emitting layer so that the excitation energy does not leak out from the emitting layer toward neighboring layer(s). The blocking layer blocks excitons generated in the emitting layer from being transferred to a layer(s) (e.g., the electron transporting layer and the hole transporting layer) closer to the electrode(s) beyond the blocking layer.

The emitting layer is preferably bonded to the blocking layer.

Specific structure, shape and the like of the components in the invention may be designed in any manner as long as an object of the invention can be achieved.

EXAMPLES

The invention will be described in further detail with reference to Examples. It should be noted that the scope of the invention is by no means limited by Examples.

Compounds

Structures of the compound represented by the formula (20) and used for manufacturing organic EL devices in Examples and Comparatives are shown below.

[Formula 402]

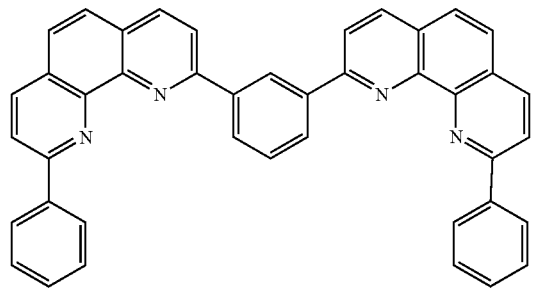

ET9

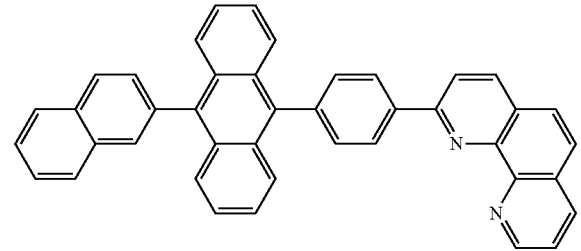

ET10

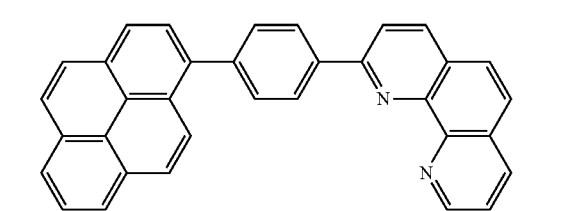

ET11

A structure of the compound represented by the formula (1) and used for manufacturing organic EL devices in Examples and Comparatives is shown below.

[Formula 403]

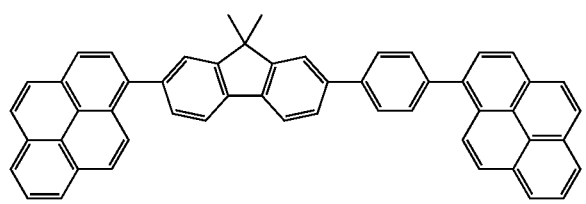

BH1

Structures of the compound represented by the formula (1X), (14X) or (15X) and used for manufacturing organic EL devices in Examples and Comparatives are shown below.

[Formula 404]

BH1-2

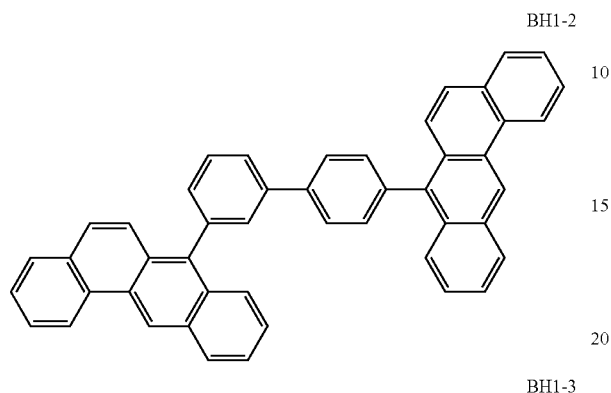

BH1-3

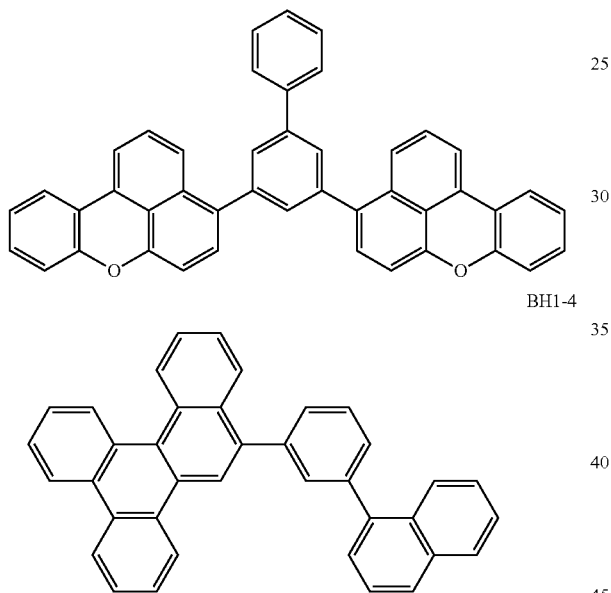

BH1-4

Structures of the compound represented by the formula (2) and used for manufacturing organic EL devices in Examples and Comparatives are shown below.

[Formula 405]

BH2-8

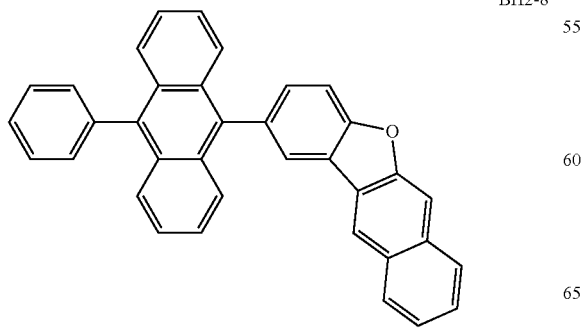

BH2-19

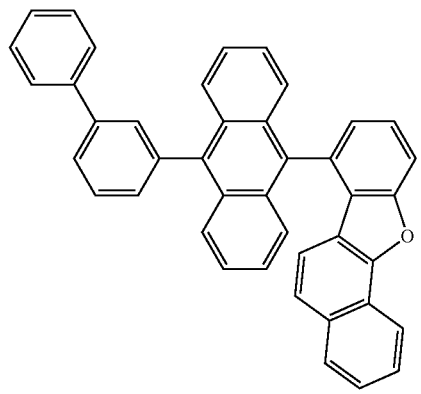

BH2-30

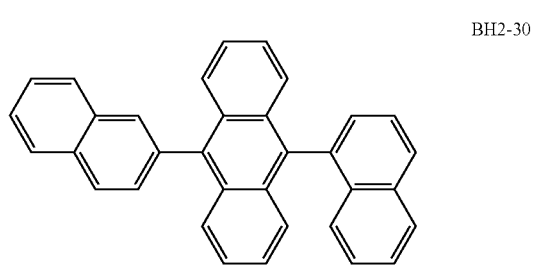

Structures of other compounds used for manufacturing organic EL devices in Examples and Comparatives are shown below.

[Formula 406]

HA2

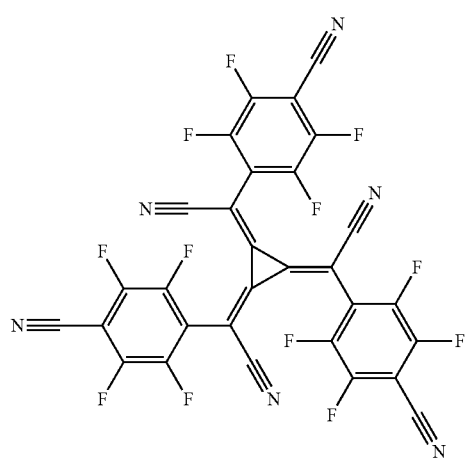

[Formula 407]
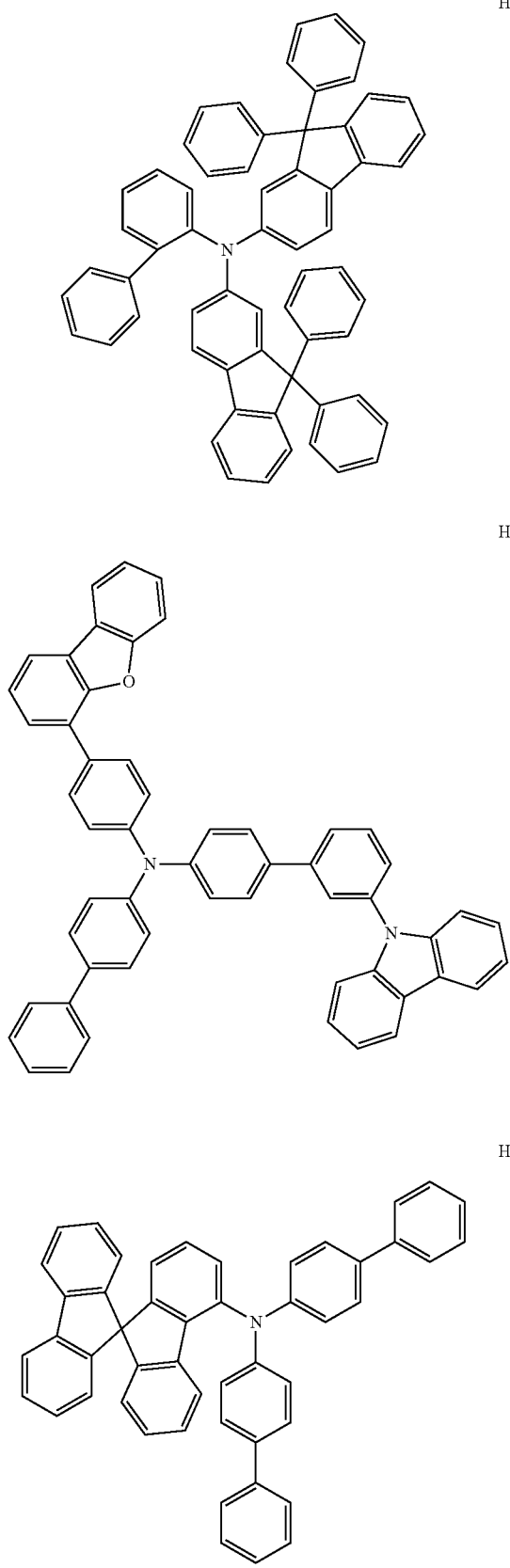
HT3
HT6
HT7
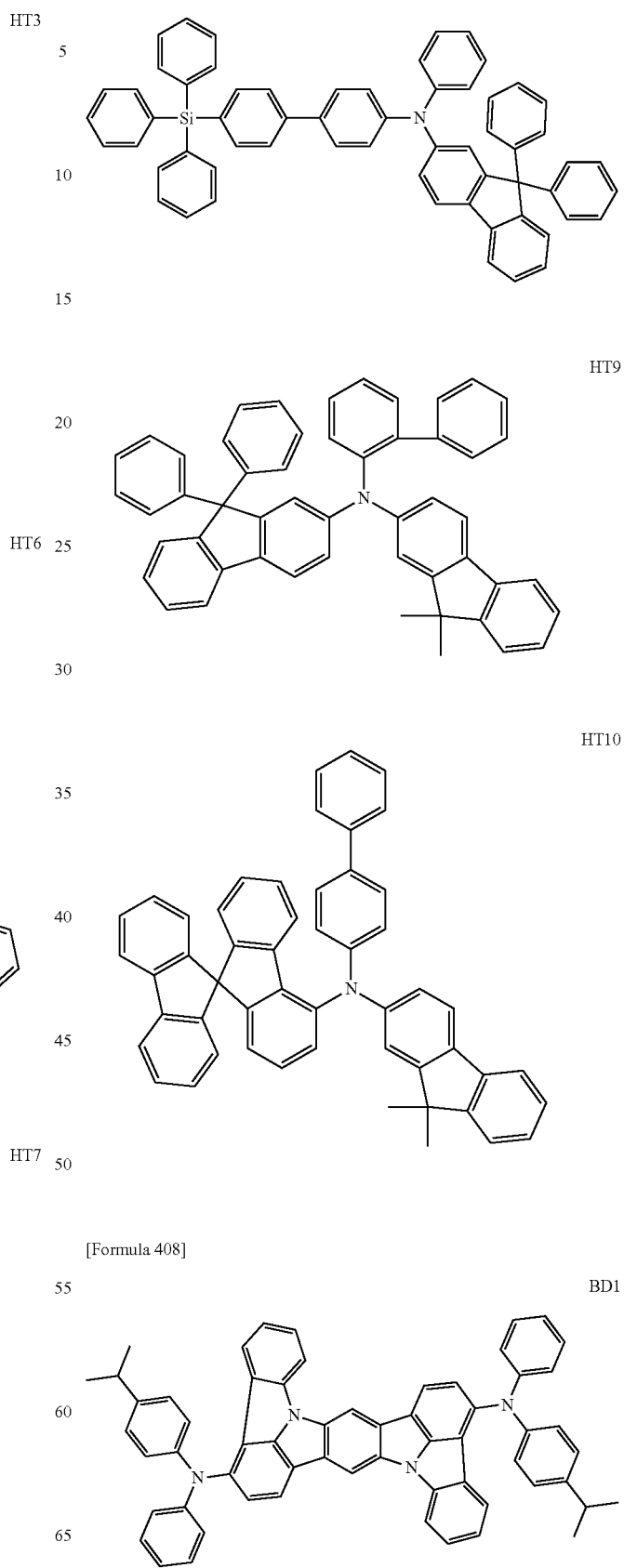
HT8
HT9
HT10
[Formula 408]
BD1

BD2
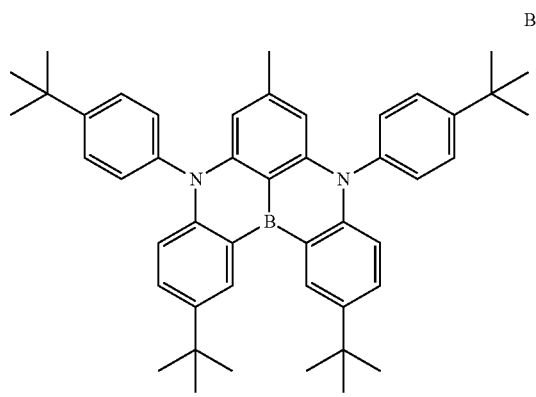
ET7
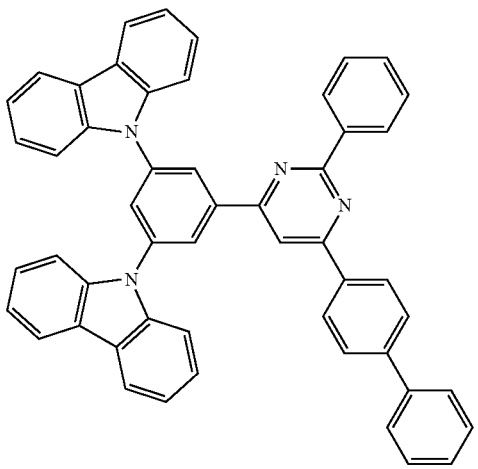
[Formula 409]
ET1
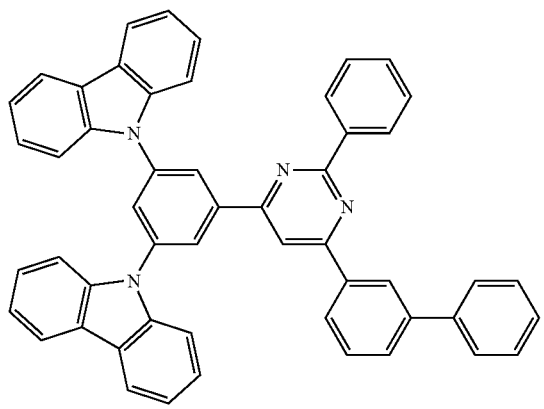
ET8
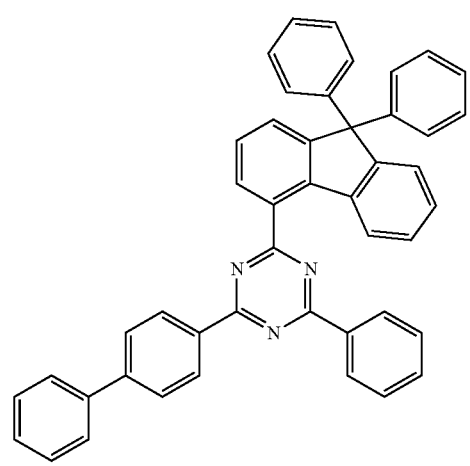
Liq
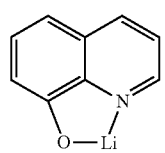
ET2
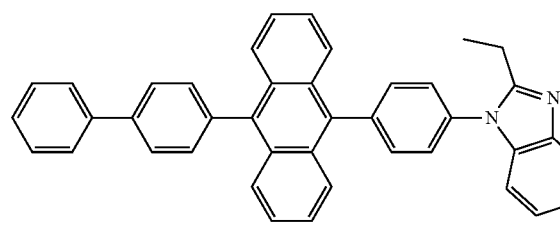
Cap1
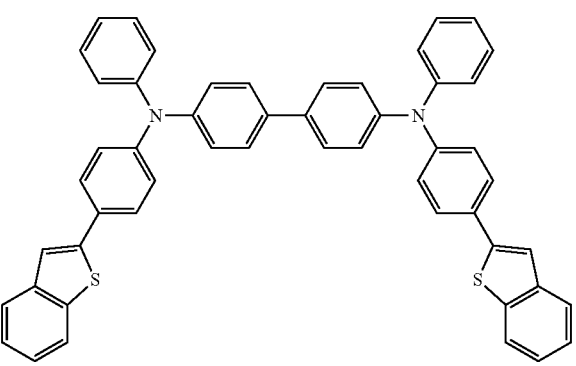
ET3
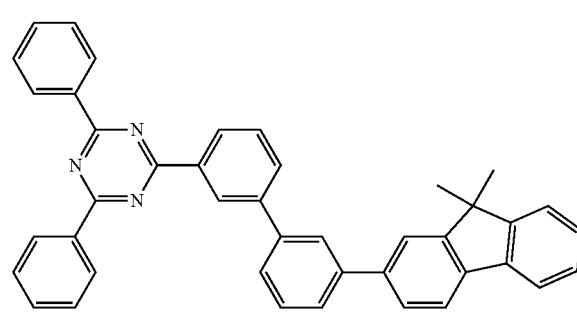
Manufacturing 1 of Organic EL Device
Example 1
An APC (Ag—Pd—Cu) layer (reflective layer) having a film thickness of 100 nm, which was silver alloy layer, and an indium zinc oxide (IZO: registered trademark) film (transparent conductive layer) having a thickness of 10 nm were sequentially formed by sputtering on a glass substrate (25 mm×75 mm×0.7 mm thickness) to be a substrate for manufacturing a device. By this operation, a conductive material layer of the APC layer and the IZO film was obtained.

Subsequently, the conductive material layer was patterned by etching using a resist pattern as a mask using a normal lithography technique to form a lower electrode (anode).

Formation of First Emitting Unit

Next, the compound HT9 and the compound HA2 were co-deposited on the lower electrode by vacuum deposition to form a hole injecting layer having a film thickness of 10 nm. The concentrations of the compound HT9 and the compound HA2 in the hole injecting layer were 90 mass % and 10 mass %, respectively.

Next, the compound HT9 was vapor-deposited on the hole injecting layer to form a first hole transporting layer having a thickness of 22 nm.

Next, the compound HT8 was vapor-deposited on the first hole injecting layer to form a second hole transporting layer having a thickness of 5 nm.

The compound BH1 (first host material (BH)) and the compound BD2 (dopant material (BD)) were co-deposited on the second hole transporting layer to form a 3.5-nm-thick first emitting layer (UT1-EM1) of a first emitting unit. The concentrations of the compound BH1 and the compound BD2 in the first emitting layer (UT1-EM1) were 99 mass % and 1 mass %, respectively.

The compound BH2-19 (second host material (BH)) and the compound BD2 (dopant material (BD)) were co-deposited on the first emitting layer (UT1-EM1) to form a 13.5-nm-thick second emitting layer (UT1-EM2) of the first emitting unit. The concentrations of the compound BH2-19 and the compound BD2 in the second emitting layer (UT1-EM2) were 99 mass % and 1 mass %, respectively.

The compound ET1 was vapor-deposited on the second emitting layer (UT1-EM2) to form a 5-nm-thick first electron transporting layer (also referred to as a hole blocking layer (HBL)).

Formation of Intermediate Unit (First Charge Generating Layer)

Subsequently, the compound ET8 and Liq were co-deposited on the first electron transporting layer of the first emitting unit to form a 25-nm-thick first N layer. The concentrations of the compound ET8 and Liq in the first N layer were both 50 mass %. It should be noted that Liq is an abbreviation for (8-quinolinolato)lithium((8-Quinolinolato) lithium).

Then, the compound ET9 and lithium (Li) were co-deposited on the first N layer to form a 15-nm-thick second N layer. The concentrations of the compound ET9 and Li in the second N layer were 96 mass % and 4 mass %, respectively.

Thereafter, the compound HT9 and the compound HA2 were co-deposited on the second N layer to form a 10-nm-thick first P layer. The concentrations of the compound HT9 and the compound HA2 in the first P layer were 90 mass % and 10 mass %, respectively.

Formation of Second Emitting Unit

Next, the compound HT9 was vapor-deposited on the first P layer to form a 45-nm-thick first hole transporting layer.

Next, the compound HT8 was vapor-deposited on the first hole transporting layer to form a 5-nm-thick second hole transporting layer.

The compound BH1 and the compound BD2 were then co-deposited on the second hole transporting layer to form a 3.5-nm-thick first emitting layer (UT2-EM1) of a second emitting unit. The concentrations of the compound BH1 and the compound BD2 in the first emitting layer (UT2-EM1) were 99 mass % and 1 mass %, respectively.

Subsequently, the compound BH2-19 (second host material (BH)) and the compound BD2 (dopant material (BD)) were co-deposited on the first emitting layer (UT2-EM1) to form a 13.5-nm-thick second emitting layer (UT2-EM2) of the second emitting unit. The concentrations of the compound BH2-19 and the compound BD2 in the second emitting layer (UT2-EM2) were 99 mass % and 1 mass %, respectively.

Thereafter, the compound ET1 was vapor-deposited on the second emitting layer (UT2-EM2) to form a 5-nm-thick first electron transporting layer (also referred to as a hole blocking layer (HBL)).

Formation of Intermediate Unit (Second Charge Generating Layer)

Subsequently, the compound ET8 and Liq were co-deposited on the first electron transporting layer of the second emitting unit to form a 25-nm-thick third N layer. The concentrations of the compound ET8 and Liq in the third N layer were both 50 mass %.

Then, the compound ET9 and lithium (Li) were co-deposited on the third N layer to form a 15-nm-thick fourth N layer. The concentrations of the compound ET9 and Li in the fourth N layer were 96 mass % and 4 mass %, respectively.

Thereafter, the compound HT9 and the compound HA2 were co-deposited on the fourth N layer to form a 10-nm-thick second P layer. The concentrations of the compound HT9 and the compound HA2 in the second P layer were 90 mass % and 10 mass %, respectively.

Formation of Third Emitting Unit

Subsequently, the compound HT9 was vapor-deposited on the second P layer to form a 35-nm-thick first hole transporting layer on the second P layer.

Next, the compound HT8 was vapor-deposited on the first hole injecting layer to form a 5-nm-thick second hole transporting layer.

The compound BH1 and the compound BD2 were then co-deposited on the second hole transporting layer to form a 3.5-nm-thick first emitting layer (UT3-EM1) of a third emitting unit. The concentrations of the compound BH1 and the compound BD2 in the first emitting layer (UT3-EM1) were 99 mass % and 1 mass %, respectively.

Next, the compound BH2-19 (the second host material (BH)) and the compound BD2 (the dopant material (BD)) were co-deposited on the first emitting layer (UT3-EM1) to form a 13.5-nm-thick second emitting layer (UT3-EM2) of the third emitting unit. The concentrations of the compound BH2-19 and the compound BD2 in the second emitting layer (UT3-EM2) were 99 mass % and 1 mass %, respectively.

Thereafter, the compound ET1 was vapor-deposited on the second emitting layer (UT3-EM2) to form a 5-nm-thick first electron transporting layer (also referred to as a hole blocking layer (HBL)).

Subsequently, the compound ET8 and Liq were co-deposited on the first electron transporting layer of the third emitting unit to form a 38-nm-thick second electron transporting layer. The concentrations of the compound ET8 and Liq in the second electron transporting layer were both 50 mass %.

Thereafter, ytterbium (Yb) was vapor-deposited on the second electron transporting layer of the third emitting unit to form a 1.5-nm-thick electron injecting layer.

Then, Mg and Ag were co-deposited on the electron injecting layer of the third emitting unit so as to have a mixing ratio (mass % ratio) of 15%:85%, so that an upper electrode (cathode) made of a semi-transparent MgAg alloy (total film thickness 12 nm) was formed.

Next, the compound Cap1 was deposited on the entire surface of the upper electrode to form a 50-nm-thick capping layer.

A top emission type organic EL device according to Example 1 was manufactured as described above.

A device arrangement of the organic EL device of Example 1 is roughly shown as follows. APC(100)/IZO(10)/HT9: HA2(10,90%:10%)/HT9(22)/HT8(5)/BH1:BD2(3.5, 99%:1%)/BH2-19:BD2(13.5, 99%:1%)/ET1(5)/ET8:Liq(25,50%:50%)/ET9:Li(15,96%:4%)/HT9:HA2(10,90%:10%)/HT9(45)/HT8(5)/BH1:BD2(3.5, 99%:1%)/BH2-19:BD2(13.5, 99%:1%)/ET1(5)/ET8:Liq(25,50%:50%)/ET9:Li(15,96%:4%)/HT9:HA2(10,90%:10%)/HT9(35)/HT8(5)/BH1:BD2(3.5, 99%:1%)/BH2-19:BD2(13.5, 99%:1%)/ET1(5)/ET8:Liq(38,50%:50%)/Yb(1.5)/Mg:Ag(12,15%:85%)/Cap1(50)

Comparative 1

A top emission type organic EL device in Comparative 1 was manufactured in the same manner as in Example 1 except that the first emitting layer was not formed, and a 17-nm-thick second emitting layer was formed on the second hole transporting layer in the first emitting unit, the second emitting unit and the third emitting unit as shown in Table 1.

TABLE 1

|  | Emitting Unit | First Emitting Layer | | | Second Emitting Layer | | | First Electron Transporting Layer | Voltage [V] | EQE [%] | LT95 [hr] |
|---|---|---|---|---|---|---|---|---|---|---|---|
|  |  | First Compound | Third Compound | Film Thickness [nm] | Second Compound | Fourth Compound | Film Thickness [nm] |  |  |  |  |
| Example 1 | First | BH1 | BD2 | 3.5 | BH2-19 | BD2 | 13.5 | ET1 | 9.67 | 29.6 | 102 |
|  | Second | BH1 | BD2 | 3.5 | BH2-19 | BD2 | 13.5 | ET1 |  |  |  |
|  | Third | BH1 | BD2 | 3.5 | BH2-19 | BD2 | 13.5 | ET1 |  |  |  |
| Comparative 1 | First | — | — | — | BH2-19 | BD2 | 17.0 | ET1 | 10.09 | 24.7 | 42 |
|  | Second | — | — | — | BH2-19 | BD2 | 17.0 | ET1 |  |  |  |
|  | Third | — | — | — | BH2-19 | BD2 | 17.0 | ET1 |  |  |  |

Example 2

A top emission type organic EL device of Example 2 was manufactured in the same manner as in Example 1 except that the compound BH2-19 (the second host material) in the second emitting layer was changed to the second compound shown in Table 2, and the compound ET1 in the first electron transporting layer was changed to the compound ET3 shown in Table 2 in the first emitting unit, the second emitting unit and the third emitting unit.

Comparative 2

A top emission type organic EL device in Comparative 2 was manufactured in the same manner as in Example 2 except that the first emitting layer was not formed, and a 17-nm-thick second emitting layer was formed on the second hole transporting layer in the first emitting unit, the second emitting unit and the third emitting unit as shown in Table 2.

TABLE 2

|  | Emitting Unit | First Emitting Layer | | | Second Emitting Layer | | | First Electron Transporting Layer | Voltage [V] | EQE [%] | LT95 [hr] |
|---|---|---|---|---|---|---|---|---|---|---|---|
|  |  | First Compound | Third Compound | Film Thickness [nm] | Second Compound | Fourth Compound | Film Thickness [nm] |  |  |  |  |
| Example 2 | First | BH1 | BD2 | 3.5 | BH2-8 | BD2 | 13.5 | ET3 | 9.33 | 29.8 | 85 |
|  | Second | BH1 | BD2 | 3.5 | BH2-8 | BD2 | 13.5 | ET3 |  |  |  |
|  | Third | BH1 | BD2 | 3.5 | BH2-8 | BD2 | 13.5 | ET3 |  |  |  |
| Comparative 2 | First | — | — | — | BH2-8 | BD2 | 17.0 | ET3 | 9.43 | 26.2 | 49 |
|  | Second | — | — | — | BH2-8 | BD2 | 17.0 | ET3 |  |  |  |
|  | Third | — | — | — | BH2-8 | BD2 | 17.0 | ET3 |  |  |  |

It should be noted that the values of voltage, EQE and LT95 shown in Tables 1, 2, 3 and 4 are not measured for each of the emitting units but for the entire organic EL device including the first emitting unit, the second emitting unit and the third emitting unit.

Example 3

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

Formation of First Emitting Unit

Next, the compound HT9 and the compound HA2 were co-deposited on the ITO transparent electrode by vacuum deposition to form a 10-nm-thick hole injecting layer. The concentrations of the compound HT9 and the compound HA2 in the hole injecting layer were 90 mass % and 10 mass %, respectively.

Next, the compound HT9 was vapor-deposited on the hole injecting layer to form a 80-nm-thick first hole transporting layer.

Next, the compound HT7 was vapor-deposited on the first hole transporting layer to form a 10-nm-thick second hole transporting layer.

Next, the compound BH1-2 (the first host material (BH)) and the compound BD1 (the dopant material (BD)) were co-deposited on the second hole transporting layer to form a 5-nm-thick first emitting layer (UT1-EM1) of the first emitting unit. The concentrations of the compound BH1-2 and the compound BD1 in the first emitting layer (UT1-EM1) were 98 mass % and 2 mass %, respectively.

Next, the compound BH2-30 (the second host material (BH)) and the compound BD1 (the dopant material (BD)) were co-deposited on the first emitting layer (UT1-EM1) to form a 20-nm-thick second emitting layer (UT1-EM2) of the first emitting unit. The concentrations of the compound BH2-30 and the compound BD1 in the second emitting layer (UT1-EM2) were 98 mass % and 2 mass %, respectively.

Next, the compound ET1 was vapor-deposited on the second emitting layer (UT1-EM2) to form a 10-nm-thick first electron transporting layer (also referred to as the hole blocking layer (HBL)).

Formation of Intermediate Unit (First Charge Generating Layer)

Next, the compound ET10 and lithium (Li) were co-deposited on the first electron transporting layer in the first emitting unit to form a 20-nm-thick first N layer. The concentrations of the compound ET10 and Li in the first N layer were 97 mass % and 3 mass %, respectively.

Next, the compound HT10 and the compound HA2 were co-deposited on the first N layer to form a 10-nm-thick first P layer. The concentrations of the compound HT10 and the compound HA2 in the first P layer were 90 mass % and 10 mass %, respectively.

Formation of Second Emitting Unit

Next, the compound HT10 was vapor-deposited on the first P layer to form a 80-nm-thick first hole transporting layer.

Next, the compound HT7 was vapor-deposited on the first hole transporting layer to form a 10-nm-thick second hole transporting layer.

Next, the compound BH1-2 (the first host material (BH)) and the compound BD1 (the dopant material (BD)) were co-deposited on the second hole transporting layer to form a 5-nm-thick first emitting layer (UT2-EM1) of the second emitting unit. The concentrations of the compound BH1-2 and the compound BD1 in the first emitting layer (UT2-EM1) were 98 mass % and 2 mass %, respectively.

Next, the compound BH2-30 (the second host material (BH)) and the compound BD1 (the dopant material (BD)) were co-deposited on the first emitting layer (UT2-EM1) to form a 20-nm-thick second emitting layer (UT2-EM2) of the second emitting unit. The concentrations of the compound BH2-30 and the compound BD1 in the second emitting layer (UT2-EM2) were 98 mass % and 2 mass %, respectively.

Next, the compound ET1 was vapor-deposited on the second emitting layer (UT2-EM2) to form a 10-nm-thick first electron transporting layer (also referred to as the hole blocking layer (HBL)).

Next, the compound ET2 was vapor-deposited on the first electron transporting layer in the second emitting unit to form a 20-nm-thick second electron transporting layer.

Next, LiF was vapor-deposited on the second electron transporting layer in the second emitting unit to form a 1-nm-thick electron injecting layer.

In addition, metal Al was vapor-deposited on the electron injecting layer in the second emitting unit to form an 80-nm-thick cathode.

A bottom emission type organic EL device according to Example 3 was manufactured as described above.

A device arrangement of an organic EL device of Example 3 is roughly shown as follows. ITO(130)/HT9:HA2(10,97%:3%)/HT9(80)/HT7(10)/BH1-2:BD1(5,98%:2%)/BH2-30:BD1(20,98%:2%)/ET1(10)/ET10:Li(20,97%:3%)/HT10:HA2(10,90%:10%)/HT10(80)/HT7(10)/BH1-2:BD1(5,98%:2%)/BH2-30:BD1(20,98%:2%)/ET1(10)/ET2(20)/LiF(1)/Al(80)

Example 4

A bottom emission type organic EL device in Example 4 was manufactured in the same manner as in Example 3 except that the compound BH1-2 in the first emitting layer was changed to the compound BH1-3 in the first emitting unit and the second emitting unit as shown in Table 3.

Comparative 3

A bottom emission type organic EL device in Comparative 3 was manufactured in the same manner as in Example 3 except that the first emitting layer was not formed, and a 25-nm-thick second emitting layer was formed on the second hole transporting layer in the first emitting unit and the second emitting unit as shown in Table 3.

TABLE 3

|  | | First Emitting Layer | | | Second Emitting Layer | | | | |
| --- | --- | --- | --- | --- | --- | --- | --- | --- | --- |
|  | Emitting Unit | First Compound | Third Compound | Film Thickness [nm] | Second Compound | Fourth Compound | Film Thickness [nm] | EQE [%] | LT95 [hr] |
| Example 3 | First | BH1-2 | BD1 | 5 | BH2-30 | BD1 | 20 | 19.2 | 150 |
|  | Second | BH1-2 | BD1 | 5 | BH2-30 | BD1 | 20 |  |  |
| Example 4 | First | BH1-3 | BD1 | 5 | BH2-30 | BD1 | 20 | 17.8 | 180 |
|  | Second | BH1-3 | BD1 | 5 | BH2-30 | BD1 | 20 |  |  |
| Comparative 3 | First | — | — | — | BH2-30 | BD1 | 25 | 17.5 | 80 |
|  | Second | — | — | — | BH2-30 | BD1 | 25 |  |  |

Example 5

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

Formation of First Emitting Unit

Next, the compound HT3 and the compound HA2 were co-deposited on the ITO transparent electrode by vacuum deposition to form a 10-nm-thick hole injecting layer. The concentrations of the compound HT3 and the compound HA2 in the hole injecting layer were 97 mass % and 3 mass %, respectively.

Next, the compound HT3 was vapor-deposited on the hole injecting layer to form a 80-nm-thick first hole transporting layer.

Next, the compound HT6 was vapor-deposited on the first hole transporting layer to form a 10-nm-thick second hole transporting layer.

Next, the compound BH1-4 (the first host material (BH)) and the compound BD2 (the dopant material (BD)) were co-deposited on the second hole transporting layer to form a 5-nm-thick first emitting layer (UT1-EM1) of the first emitting unit. The concentrations of the compound BH1-4 and the compound BD2 in the first emitting layer (UT1-EM1) were 98 mass % and 2 mass %, respectively.

Next, the compound BH2-30 (the second host material (BH)) and the compound BD2 (the dopant material (BD)) were co-deposited on the first emitting layer (UT1-EM1) to form a 20-nm-thick second emitting layer (UT1-EM2) of the first emitting unit. The concentrations of the compound BH2-30 and the compound BD2 in the second emitting layer (UT1-EM2) were 98 mass % and 2 mass %, respectively.

Next, the compound ET7 was vapor-deposited on the second emitting layer (UT1-EM2) to form a 10-nm-thick first electron transporting layer (also referred to as the hole blocking layer (HBL)).

Formation of Intermediate Unit (First Charge Generating Layer)

Next, the compound ET11 and lithium (Li) were co-deposited on the first electron transporting layer in the first emitting unit to form a 20-nm-thick first N layer. The concentrations of the compound ET11 and Li in the first N layer were 97 mass % and 3 mass %, respectively.

Next, the compound HT3 and the compound HA2 were co-deposited on the first N layer to form a 10-nm-thick first P layer. The concentrations of the compound HT3 and the compound HA2 in the first P layer were 90 mass % and 10 mass %, respectively.

Formation of Second Emitting Unit

Next, the compound HT3 was vapor-deposited on the first P layer to form a 80-nm-thick first hole transporting layer.

Next, the compound HT6 was vapor-deposited on the first hole transporting layer to form a 10-nm-thick second hole transporting layer.

Next, the compound BH1-4 (the first host material (BH)) and the compound BD2 (the dopant material (BD)) were co-deposited on the second hole transporting layer to form a 5-nm-thick first emitting layer (UT2-EM1) of the second emitting unit. The concentrations of the compound BH1-4 and the compound BD2 in the first emitting layer (UT2-EM1) were 98 mass % and 2 mass %, respectively.

Next, the compound BH2-30 (the second host material (BH)) and the compound BD2 (the dopant material (BD)) were co-deposited on the first emitting layer (UT2-EM1) to form a 20-nm-thick second emitting layer (UT2-EM2) of the second emitting unit. The concentrations of the compound BH2-30 and the compound BD2 in the second emitting layer (UT2-EM2) were 98 mass % and 2 mass %, respectively.

Next, the compound ET7 was vapor-deposited on the second emitting layer (UT2-EM2) to form a 10-nm-thick first electron transporting layer (also referred to as the hole blocking layer (HBL)).

Next, the compound ET2 was vapor-deposited on the first electron transporting layer in the second emitting unit to form a 20-nm-thick second electron transporting layer.

Next, LiF was vapor-deposited on the second electron transporting layer in the second emitting unit to form a 1-nm-thick electron injecting layer.

In addition, metal Al was vapor-deposited on the electron injecting layer in the second emitting unit to form an 80-nm-thick cathode.

A bottom emission type organic EL device according to Example 5 was manufactured as described above.

A device arrangement of an organic EL device of Example 5 is roughly shown as follows. ITO(130)/HT3: HA2(10,97%:3%)/HT3(80)/HT6(10)/BH1-4:BD2(5,98%: 2%)/BH2-30:BD2(20,98%:2%)/ET7(10)/ET11:Li(20,97%: 3%)/HT3:HA2(10,90%:10%)/HT3(80)/HT6(10)/BH1-4: BD2(5,98%:2%)/BH2-30:BD2(20,98%:2%)/ET7(10)/ET2 (20)/LiF(1)/Al(80)

Comparative 4

A bottom emission type organic EL device in Comparative 4 was manufactured in the same manner as in Example 5 except that the first emitting layer was not formed, and a 25-nm-thick second emitting layer was formed on the second hole transporting layer in the first emitting unit and the second emitting unit as shown in Table 4.

TABLE 4

|  | | First Emitting Layer | | | Second Emitting Layer | | | | |
| --- | --- | --- | --- | --- | --- | --- | --- | --- | --- |
|  | Emitting Unit | First Compound | Third Compound | Film Thickness [nm] | Second Compound | Fourth Compound | Film Thickness [nm] | EQE [%] | LT95 [hr] |
| Example 5 | First | BH1-4 | BD2 | 5 | BH2-30 | BD2 | 20 | 18.6 | 100 |
|  | Second | BH1-4 | BD2 | 5 | BH2-30 | BD2 | 20 | | |
| Comparative 4 | First | — | — | — | BH2-30 | BD2 | 25 | 15.5 | 40 |
|  | Second | — | — | — | BH2-30 | BD2 | 25 | | |

Evaluation of Organic EL Device

The organic EL devices manufactured by Examples and Comparatives were evaluated as follows. Evaluation results are shown in Tables 1 to 4.

External Quantum Efficiency EQE

Voltage was applied on the organic EL devices such that a current density was 10 mA/cm$^2$, where spectral radiance spectrum was measured by a spectroradiometer (CS-2000 manufactured by Konica Minolta, Inc.). The external quantum efficiency EQE (unit: %) was calculated based on the obtained spectral-radiance spectra, assuming that the spectra was provided under a Lambertian radiation.

Lifetime LT95

Voltage was applied on the resultant devices such that a current density was 50 mA/cm$^2$, where a time (LT95 (unit: hr)) elapsed before a luminance intensity was reduced to 95% of the initial luminance intensity was measured.

Drive Voltage

The voltage (unit: V) when electric current was applied between the anode and the cathode such that the current density was 10 mA/cm² was measured.

Evaluation of Compounds

Preparation of Toluene Solution

The compound BD1 was dissolved in toluene at a concentration of $4.9 \times 10^{-6}$ mol/L to prepare a toluene solution of the compound BD1. A toluene solution of the compound BD2 was prepared in the same manner.

Measurement of Maximum Fluorescence Peak Wavelength (FL-peak)

A maximum fluorescence peak wavelength of the toluene solution of the compound BD1 excited at 390 nm was measured using a fluorescence spectrometer (spectrophotofluorometer F-7000 manufactured by Hitachi High-Tech Science Corporation). A maximum fluorescence peak wavelength of the toluene solution of the compound BD2 was measured in the same manner as the compound BD1.

The maximum fluorescence peak wavelength of the compound BD1 was 453 nm.

The maximum fluorescence peak wavelength of the compound BD2 was 455 nm.

Triplet Energy $T_1$

A measurement target compound was dissolved in EPA (diethylether isopentane: ethanol=5:5:2 in volume ratio) at a concentration of 10 μmol/L, and the obtained solution was encapsulated in a quartz cell to provide a measurement sample. A phosphorescence spectrum (ordinate axis: phosphorescent luminous intensity, abscissa axis: wavelength) of the measurement sample was measured at a low temperature (77K). A tangent was drawn to the rise of the phosphorescent spectrum close to the short-wavelength region. An energy amount was calculated by a conversion equation (F1) below on a basis of a wavelength value $\lambda_{edge}$ [nm] at an intersection of the tangent and the abscissa axis. The calculated energy amount was defined as triplet energy $T_1$. It should be noted that the triplet energy $T_1$ has an error of about plus or minus 0.02 eV depending on measurement conditions.

$$T_1[eV]=1239.85/\lambda_{edge} \quad \text{Conversion Equation (F1):}$$

The tangent to the rise of the phosphorescence spectrum close to the short-wavelength region is drawn as follows. While moving on a curve of the phosphorescence spectrum from the short-wavelength region to the local maximum spectral value closest to the short-wavelength region among the local maximum spectral values, a tangent is checked at each point on the curve toward the long-wavelength region of the phosphorescence spectrum. An inclination of the tangent is increased along the rise of the curve (i.e., a value of the ordinate axis is increased). A tangent drawn at a point of the local maximum inclination (i.e., a tangent at an inflection point) is defined as the tangent to the rise of the phosphorescence spectrum close to the short-wavelength region.

A local maximum point where a peak intensity is 15% or less of the maximum peak intensity of the spectrum is not counted as the above-mentioned local maximum peak intensity closest to the short-wavelength region. The tangent drawn at a point that is closest to the local maximum peak intensity closest to the short-wavelength region and where the inclination of the curve is the local maximum is defined as a tangent to the rise of the phosphorescence spectrum close to the short-wavelength region.

For phosphorescence measurement, a spectrophotofluorometer body F-4500 manufactured by Hitachi High-Technologies Corporation was used.

Singlet Energy $S_1$

A toluene solution of a measurement target compound at a concentration of 10 μmol/L was prepared and put in a quartz cell. An absorption spectrum (ordinate axis: absorption intensity, abscissa axis: wavelength) of the thus-obtained sample was measured at a normal temperature (300K). A tangent was drawn to the fall of the absorption spectrum on the long-wavelength region, and a wavelength value $\lambda_{edge}$ (nm) at an intersection of the tangent and the abscissa axis was assigned to a conversion equation (F2) below to calculate the singlet energy.

$$S_1[eV]=1239.85/\lambda_{edge} \quad \text{Conversion Equation (F2):}$$

A spectrophotometer (U3310 manufactured by Hitachi, Ltd.) was used for measuring absorption spectrum.

The tangent to the fall of the absorption spectrum on the long-wavelength region is drawn as follows. While moving on a curve of the absorption spectrum from the local maximum spectral value closest to the long-wavelength region in a long-wavelength direction, a tangent at each point on the curve is checked. An inclination of the tangent is decreased and increased in a repeated manner as the curve fell (i.e., a value of the ordinate axis is decreased). A tangent drawn at a point of the local minimum inclination closest to the long-wavelength region (except when absorbance is 0.1 or less) is defined as the tangent to the fall of the absorption spectrum on the long-wavelength region.

The local maximum absorbance of 0.2 or less is not included in the above-mentioned local maximum absorbance on the long-wavelength region.

Measurement values of the singlet energy $S_1$ and the triplet energy $T_1$ of the compound are shown in the table.

TABLE 5

| | $S_1$ [eV] | $T_1$ [eV] |
|---|---|---|
| BH1 | 3.12 | 2.10 |
| BH1-2 | 3.20 | 2.07 |
| BH1-3 | 3.03 | 2.16 |
| BH1-4 | 3.13 | 2.35 |
| BH2-19 | 3.01 | 1.82 |
| BH2-8 | 3.02 | 1.89 |
| BH2-30 | 3.01 | 1.80 |
| BD1 | 2.73 | 2.29 |
| BD2 | 2.71 | 2.64 |

What is claimed is:

1. An organic electroluminescence device comprising:
   an anode;
   a cathode;
   two or more emitting units disposed between the anode and the cathode; and
   an intermediate layer disposed between the anode and the cathode, wherein
   at least one emitting unit of the two or more emitting units is a laminated emitting unit,
   the intermediate layer contains a phenanthroline compound having a phenanthroline skeleton,
   the laminated emitting unit comprises a first emitting layer and a second emitting layer,
   the first emitting layer contains a first host material,
   the second emitting layer contains a second host material,
   the first host material and the second host material are mutually different,
   the first emitting layer at least contains a first emitting compound that emits light having a maximum peak wavelength of 500 nm or less, the second emitting layer at least contains a second emitting compound that emits light having a maximum peak wavelength of 500 nm or less, the first emitting compound and the second emitting compound are mutually the same or different, and a triplet energy $T_1(H1)$ of the first host material and a triplet energy $T_1(H2)$ of the second host material satisfy a relationship of a numerical formula (Numerical Formula 3) below, $T_1(H1) > T_1(H2)$ ... (Numerical Formula 3), wherein the phenanthroline compound is a compound that has at least one group represented by a formula (21) below and is represented by a formula (20) below, $$\begin{array}{c} X_{24}=X_{25} \\ X_{23} \diagup \diagdown X_{26} \\ X_{22} \diagdown \diagup X_{27} \\ X_{21}=N \quad N=X_{28} \end{array} \quad (20)$$

$$* \!-\! L_2 \!\!-\!\! (Ar_2)_p \quad (21)$$

where: in the formula (20), $X_{21}$ to $X_{28}$ are each independently a nitrogen atom, $CR_{21}$, or a carbon atom bonded to the group represented by the formula (21), at least one of $X_{21}$ to $X_{28}$ is a carbon atom bonded to the group represented by the formula (21), when a plurality of groups represented by the formula (21) are present, the plurality of groups represented by the formula (21) are mutually the same or different, at least one combination of adjacent two or more of a plurality of $R_{21}$ are mutually bonded to form a substituted or unsubstituted monocyclic ring, mutually bonded to form a substituted or unsubstituted fused ring, or not mutually bonded, and $R_{21}$ not forming the substituted or unsubstituted monocyclic ring and not forming the substituted or unsubstituted fused ring are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R)(R_{902})(R_{903})$, a group represented by $-O-(R_{904})$, a group represented by $-S-(R_{905})$, a group represented by $-N(R_{906})(R_{907})$, a substituted or unsubstituted aralkyl group having 7 to 50 carbon atoms, a group represented by $-C(=O)R_{931}$, a group represented by $-COOR_{932}$, a group represented by $-S(=O)_2R_{933}$, a group represented by $-B(R_{934})(R_{935})$, a group represented by $-P(=O)(R_{936})(R_{937})$, a halogen atom, a cyano group, a nitro group, a substituted or unsubstituted aryl group having 6 to 50 ring carbon atoms, or a substituted or unsubstituted heterocyclic group having 5 to 50 ring atoms, in the formula (21), $Ar_2$ is a substituted or unsubstituted aryl group having 6 to 50 ring carbon atoms, or a substituted or unsubstituted heterocyclic group having 5 to 50 ring atoms, p is 1, 2, 3, 4 or 5, when two or more $Ar_2$ are present, the two or more $Ar_2$ are mutually the same or different, $L_2$ is a single bond or a linking group, $L_2$ as the linking group is a substituted or unsubstituted polyvalent linear, branched or cyclic aliphatic hydrocarbon group having 1 to 50 carbon atoms, a substituted or unsubstituted polyvalent aromatic hydrocarbon group having 6 to 50 ring carbon atoms, a substituted or unsubstituted polyvalent heterocyclic group having 5 to 50 ring atoms, or a polyvalent multiple linking group provided by bonding two or three groups selected from the polyvalent aromatic hydrocarbon ring group and the polyvalent heterocyclic group, the aromatic hydrocarbon ring group and the heterocyclic group forming $L_2$ as the multiple linking group are mutually the same or different, and adjacent ones thereof are mutually bonded to form a ring, or not mutually bonded, $Ar_2$ and $L_2$ as the linking group are mutually bonded to form a ring, or not mutually bonded, $L_2$ as the linking group, and a carbon atom in one of $X_{21}$ to $X_{28}$ adjacent to a carbon atom bonded to $L_2$, or $R_{21}$ in $CR_{21}$ are mutually bonded to form a ring, or not mutually bonded, and

* in the formula (21) represents a bonding position to a ring represented by the formula 20), and in the phenanthroline compound, $R_{901}$, $R_{902}$, $R_{903}$, $R_{904}$, $R_{905}$, $R_{906}$, $R_{907}$, $R_{931}$, $R_{932}$, $R_{933}$, $R_{934}$, $R_{935}$, $R_{936}$ and $R_{937}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms, when a plurality of $R_{901}$ are present, the plurality of $R_{901}$ are mutually the same or different, when a plurality of $R_{902}$ are present, the plurality of $R_{902}$ are mutually the same or different, when a plurality of $R_{903}$ are present, the plurality of $R_{903}$ are mutually the same or different, when a plurality of $R_{904}$ are present, the plurality of $R_{904}$ are mutually the same or different, when a plurality of $R_{905}$ are present, the plurality of $R_{905}$ are mutually the same or different, when a plurality of $R_{906}$ are present, the plurality of $R_{906}$ are mutually the same or different, when a plurality of $R_{907}$ are present, the plurality of $R_{907}$ are mutually the same or different, when a plurality of $R_{931}$ are present, the plurality of $R_{931}$ are mutually the same or different, when a plurality of $R_{932}$ are present, the plurality of $R_{932}$ are mutually the same or different, when a plurality of $R_{933}$ are present, the plurality of $R_{933}$ are mutually the same or different, when a plurality of $R_{934}$ are present, the plurality of $R_{934}$ are mutually the same or different, when a plurality of $R_{935}$ are present, the plurality of $R_{935}$ are mutually the same or different, when a plurality of $R_{936}$ are present, the plurality of $R_{936}$ are mutually the same or different, and when a plurality of $R_{937}$ are present, the plurality of $R_{937}$ are mutually the same or different.

2. The organic electroluminescence device according to claim 1, wherein the intermediate layer is disposed close to the cathode with respect to the at least one laminated emitting unit.

3. The organic electroluminescence device according to claim 1, wherein
the first host material has a structure of Condition (i) or a structure of Condition (ii) below in a molecule, and
the second host material is an anthracene derivative,
Condition (i): a biphenyl structure comprising a first benzene ring and a second benzene ring that are linked to each other with a single bond, the first benzene ring and the second benzene ring in the biphenyl structure being further linked to each other by cross-linking at at least one site other than the single bond,
Condition (ii): a linking structure comprising a benzene ring and a naphthalene ring that are linked to each other with a single bond, the benzene ring and the naphthalene ring in the linking structure being each independently further fused or not fused with a monocyclic ring or fused ring, the benzene ring and the naphthalene ring in the linking structure being further linked to each other by cross-linking at at least one site other than the single bond.

4. The organic electroluminescence device according to claim 3, wherein
the intermediate layer is disposed close to the cathode with respect to the at least one laminated emitting unit.

5. The organic electroluminescence device according to claim 3, wherein
the first host material has the structure of Condition (i) in a molecule, and
the first benzene ring and the second benzene ring in the biphenyl structure are further linked to each other by the cross-linking at one site other than the single bond.

6. The organic electroluminescence device according to claim 3, wherein
the first host material has the structure of Condition (i) in a molecule, and
the first benzene ring and the second benzene ring in the biphenyl structure are further linked to each other by the cross-linking at two sites other than the single bond.

7. Withdrawn The organic electroluminescence device according to claim 3, wherein
the cross-linking comprises a double bond.

8. The organic electroluminescence device according to claim 1, wherein
the first host material is a first compound that has at least one group represented by a formula (11) below and is represented by a formula (1) below,

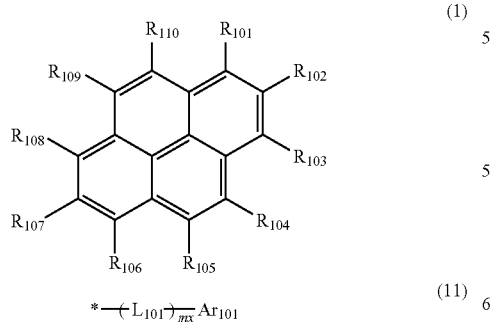

where: in the formula (1),
$R_{101}$ to $R_{110}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(=O)$R_{801}$, a group represented by —COOR$_{802}$, a halogen atom, a cyano group, a nitro group, a substituted or unsubstituted aryl group having 6 to 50 ring carbon atoms, a substituted or unsubstituted heterocyclic group having 5 to 50 ring atoms, or the group represented by the formula (11),
at least one of $R_{101}$ to $R_{110}$ is the group represented by the formula (11),
when a plurality of groups represented by the formula (11) are present, the plurality of groups represented by the formula (11) are mutually the same or different,
$L_{101}$ is a single bond, a substituted or unsubstituted arylene group having 6 to 50 ring carbon atoms, or a substituted or unsubstituted divalent heterocyclic group having 5 to 50 ring atoms,
$Ar_{101}$ is a substituted or unsubstituted aryl group having 6 to 50 ring carbon atoms, or a substituted or unsubstituted heterocyclic group having 5 to 50 ring atoms,
mx is 0, 1, 2, 3, 4, or 5,
when two or more $L_{101}$ are present, the two or more $L_{101}$ are mutually the same or different,
when two or more $Ar_{101}$ are present, the two or more $Ar_{101}$ are mutually the same or different, and
* n the formula (11) represents a bonding position to a pyrene ring in the formula (1), and
in the first compound, $R_{901}$, $R_{902}$, $R_{903}$, $R_{904}$, $R_{905}$, $R_{801}$ and $R_{802}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms,
when a plurality of $R_{901}$ are present, the plurality of $R_{901}$ are mutually the same or different,
when a plurality of $R_{902}$ are present, the plurality of $R_{902}$ are mutually the same or different,
when a plurality of $R_{903}$ are present, the plurality of $R_{903}$ are mutually the same or different,
when a plurality of $R_{904}$ are present, the plurality of $R_{904}$ are mutually the same or different,
when a plurality of $R_{905}$ are present, the plurality of $R_{905}$ are mutually the same or different,
when a plurality of $R_{801}$ are present, the plurality of $R_{801}$ are mutually the same or different, and
when a plurality of $R_{802}$ are present, the plurality of $R_{802}$ are mutually the same or different.

9. The organic electroluminescence device according to claim 3, wherein
the first host material has the structure of Condition (i) in a molecule,
the first benzene ring and the second benzene ring in the biphenyl structure are further linked to each other by the cross-linking at two sites other than the single bond, and
the cross-linking does not comprise a double bond.

10. The organic electroluminescence device according to claim 3, wherein
the first host material has the structure of Condition (ii) in a molecule.

11. The organic electroluminescence device according to claim 10, wherein
the cross-linking comprises a double bond.

12. An organic electroluminescence device comprising,
an anode;
a cathode;
two or more emitting units disposed between the anode and the cathode; and
an intermediate layer disposed between the anode and the cathode, wherein
at least one emitting unit of the two or more emitting units is a laminated emitting unit,
the intermediate layer contains a phenanthroline compound having a phenanthroline skeleton,
the laminated emitting unit comprises a first emitting layer and a second emitting layer,
the first emitting layer contains a first host material,
the second emitting layer contains a second host material,
the first host material and the second host material are mutually different,
the first emitting layer at least contains a first emitting compound that emits light having a maximum peak wavelength of 500 nm or less,
the second emitting layer at least contains a second emitting compound that emits light having a maximum peak wavelength of 500 nm or less,
the first emitting compound and the second emitting compound are mutually the same or different, and
a triplet energy $T_1(H1)$ of the first host material and a triplet energy $T_1(H2)$ of the second host material satisfy a relationship of a numerical formula (Numerical Formula 3) below, $$T_1(H1) > T_1(H2) \quad \text{(Numerical Formula 3)}$$ wherein the second host material is a second compound represented by a formula (2) below,

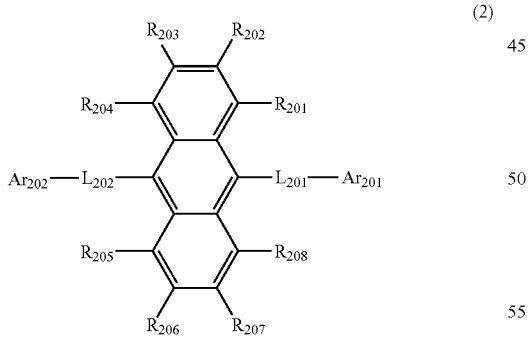

(2)

where: in the formula (2),
$R_{201}$ to $R_{208}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a group represented by $-N(R_{906})(R_{907})$, a substituted or unsubstituted aralkyl group having 7 to 50 carbon atoms, a group represented by $-C(=O)R_{801}$, a group represented by $-COOR_{802}$, a halogen atom, a cyano group, a nitro group, a substituted or unsubstituted aryl group having 6 to 50 ring carbon atoms, or a substituted or unsubstituted heterocyclic group having 5 to 50 ring atoms,
$L_{201}$ and $L_{202}$ are each independently a single bond, a substituted or unsubstituted arylene group having 6 to 50 ring carbon atoms, or a substituted or unsubstituted divalent heterocyclic group having 5 to 50 ring atoms, and
$Ar_{201}$ and $Ar_{202}$ are each independently a substituted or unsubstituted aryl group having 6 to 50 ring carbon atoms, or a substituted or unsubstituted heterocyclic group having 5 to 50 ring atoms, and
in the second compound, $R_{901}$, $R_{902}$, $R_{903}$, $R_{904}$, $R_{905}$, $R_{906}$, $R_{907}$, $R_{801}$ and $R_{802}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms,
when a plurality of $R_{901}$ are present, the plurality of $R_{901}$ are mutually the same or different,
when a plurality of $R_{902}$ are present, the plurality of $R_{902}$ are mutually the same or different,
when a plurality of $R_{903}$ are present, the plurality of $R_{903}$ are mutually the same or different,
when a plurality of $R_{904}$ are present, the plurality of $R_{904}$ are mutually the same or different,
when a plurality of $R_{905}$ are present, the plurality of $R_{905}$ are mutually the same or different,
when a plurality of $R_{906}$ are present, the plurality of $R_{906}$ are mutually the same or different,
when a plurality of $R_{907}$ are present, the plurality of $R_{907}$ are mutually the same or different,
when a plurality of $R_{801}$ are present, the plurality of $R_{801}$ are mutually the same or different, and
when a plurality of $R_{802}$ are present, the plurality of $R_{802}$ are mutually the same or different.

13. The organic electroluminescence device according to claim 1, wherein the second emitting layer of the laminated emitting unit is disposed between the first emitting layer and the intermediate layer.

14. The organic electroluminescence device according to claim 1, wherein the first emitting layer of the laminated emitting unit is disposed between the second emitting layer and the intermediate layer.

15. The organic electroluminescence device according to claim 14, wherein a second cathode side organic layer is disposed between the first emitting layer and the intermediate layer.

16. The organic electroluminescence device according to claim 15, wherein the second cathode side organic layer does not contain a phenanthroline compound having a phenanthroline skeleton.

17. The organic electroluminescence device according to claim 1, wherein the first emitting layer is disposed 30 nm or more apart from the intermediate layer.

18. The organic electroluminescence device according to claim 1, wherein the two or more emitting units comprise the laminated emitting unit and at least one phosphorescent emitting unit, which is different from the laminated emitting unit, and the phosphorescent emitting unit contains a phosphorescent compound that exhibits phosphorescence.

19. The organic electroluminescence device according to claim 1, wherein the intermediate layer is disposed between the laminated emitting unit and another emitting unit, which is different from the laminated emitting unit.

20. The organic electroluminescence device according to claim 1, wherein a hole mobility $\mu h(H1)$ of the first host material and a hole mobility $\mu h(H2)$ of the second host material satisfy a relationship of a numerical formula (Numerical Formula 31) below, $$\mu h(H1) > \mu h(H2) \qquad \text{(Numerical Formula 31).}$$

21. The organic electroluminescence device according to claim 1, wherein a hole mobility $\mu h(H1)$ of the first host material, an electron mobility $\mu e(H1)$ of the first host material, a hole mobility $\mu h(H2)$ of the second host material, and an electron mobility $\mu e(H2)$ of the second host material satisfy a relationship of a numerical formula (Numerical Formula 32) below, $$(\mu e(H1)/\mu h(H1)) < (\mu e(H2)/\mu h(H2)) \qquad \text{(Numerical Formula 32).}$$

22. The organic electroluminescence device according to claim 1, wherein an electron mobility $\mu e(H1)$ of the first host material and an electron mobility $\mu e(H2)$ of the second host material satisfy a relationship of a numerical formula (Numerical Formula 33) below, $$\mu e(H1) < \mu e(H2) \qquad \text{(Numerical Formula 33).}$$

23. The organic electroluminescence device according to claim 1, further comprising a color conversion portion disposed on a side of the organic electroluminescence device through which light is extracted.

24. An electronic device comprising the organic electroluminescence device according to claim 1.

25. The electronic device according to claim 24, wherein the electronic device is a TV, a personal computer, a tablet, or a display for a moving body.

26. The organic electroluminescence device according to claim 1, wherein the first emitting layer contains the first emitting compound at 10 mass % or less relative to the total mass of the first emitting layer, and the second emitting layer contains the second emitting compound at 10 mass % or less relative to the total mass of the second emitting layer.

27. The organic electroluminescence device according to claim 12, wherein the first emitting layer contains the first emitting compound at 10 mass % or less relative to the total mass of the first emitting layer, and the second emitting layer contains the second emitting compound at 10 mass % or less relative to the total mass of the second emitting layer.

\* \* \* \* \*

UNITED STATES PATENT AND TRADEMARK OFFICE
CERTIFICATE OF CORRECTION

PATENT NO. : 11,552,259 B1
APPLICATION NO. : 17/463266
DATED : January 10, 2023
INVENTOR(S) : Satomi Tasaki, Kazuki Nishimura and Hiroaki Toyoshima It is certified that error appears in the above-identified patent and that said Letters Patent is hereby corrected as shown below:

In the Claims

Claim 1, Column 1029, Lines 50-51:
Please delete:
"carbon atoms, a group represented by -Si($R_{902}$)($R_{903}$), a group represented by -O-($R_{904}$), a group"
Please replace with:
carbon atoms, a group represented by -Si($R_{901}$)($R_{902}$)($R_{903}$), a group represented by -O-($R_{904}$), a group Claim 7, Column 1031, Line 39:
Please delete:
"Withdrawn The organic electroluminescence device"
Please replace with:
The organic electroluminescence device Claim 8, Column 1032, Line 34:
Please delete:
"* n the formula (11) represents a bonding position to a"
Please replace with:
* in the formula (11) represents a bonding position to a Signed and Sealed this
Eighteenth Day of April, 2023

Katherine Kelly Vidal
*Director of the United States Patent and Trademark Office*